(12) United States Patent
Vandeusen et al.

(10) Patent No.: US 11,753,403 B2
(45) Date of Patent: Sep. 12, 2023

(54) EIF4E INHIBITORS AND USES THEREOF

(71) Applicant: PIC Therapeutics, Inc., Natick, MA (US)

(72) Inventors: Christopher L. Vandeusen, Hopkinton, MA (US); Alan E. Walts, Charlestown, MA (US); Yat Sun Or, Waltham, MA (US)

(73) Assignee: PIC Therapeutics, Inc., Natick, MA (US)

( * ) Notice: Subject to any disclaimer, the term of this patent is extended or adjusted under 35 U.S.C. 154(b) by 0 days.

(21) Appl. No.: 17/191,072

(22) Filed: Mar. 3, 2021

(65) Prior Publication Data

US 2022/0356178 A1    Nov. 10, 2022

Related U.S. Application Data

(60) Provisional application No. 62/984,543, filed on Mar. 3, 2020.

(51) Int. Cl.
| | | |
|---|---|---|
| *C07D 417/04* | (2006.01) | |
| *C07D 277/42* | (2006.01) | |
| *C07D 417/06* | (2006.01) | |
| *C07D 417/10* | (2006.01) | |
| *C07D 417/12* | (2006.01) | |

(52) U.S. Cl.
CPC ......... *C07D 417/04* (2013.01); *C07D 277/42* (2013.01); *C07D 417/06* (2013.01); *C07D 417/10* (2013.01); *C07D 417/12* (2013.01)

(58) Field of Classification Search
None
See application file for complete search history.

(56) References Cited

U.S. PATENT DOCUMENTS

| 5,463,071 A | 10/1995 | Himmelsbach et al. |
|---|---|---|
| 2022/0356178 A1 | 11/2022 | Vandeusen et al. |

FOREIGN PATENT DOCUMENTS

| CN | 109232467 A | 1/2019 |
|---|---|---|
| CN | 109320473 A | 2/2019 |
| CN | 109456279 A | 3/2019 |
| JP | H07149745 A | 6/1995 |
| WO | WO-2000047194 A2 | 8/2000 |
| WO | WO-2003062215 A1 | 7/2003 |
| WO | 2005103022 A1 | 11/2005 |
| WO | WO-2006078942 A2 | 7/2006 |
| WO | WO-2007118149 A2 | 10/2007 |
| WO | 2010025142 | 3/2010 |
| WO | WO-2010079239 A1 | 7/2010 |
| WO | WO-2013041468 A1 | 3/2013 |
| WO | WO-2015050984 A1 | 4/2015 |
| WO | WO-2016196644 A1 | 12/2016 |
| WO | WO-2020051424 A1 | 3/2020 |
| WO | WO-2021178488 A1 | 9/2021 |

OTHER PUBLICATIONS

Database Registry Chemical Abstracts Service, Columbus, Ohio, Accession No. RN 1181268-76-7, Entered STN: Sep. 8, 2009.*
Database Registry Chemical Abstracts Service, Columbus, Ohio, Accession No. RN 1348427-33-7, 1347990-03-7, Entered STN: Dec. 4, 2011.*
Database Registry Chemical Abstracts Service, Columbus, Ohio, Accession No. RN 256471-38-2, Entered STN: Feb. 23, 2000.*
Bestgen et al., "2-Aminothiazole Derivatives as Selective Allosteric Modulators of the Protein Kinase CK2. 2. Structure-Based Optimization and Investigation of Effects Specific to the Allosteric Mode of Action," J Med Chem. Feb. 28, 2019;62(4):1817-1836.
Makam and Kannan, "2-Aminothiazole derivatives as antimycobacterial agents: Synthesis, characterization, in vitro and in silico studies," Eur J Med Chem. Nov. 24, 2014;87:643-56.
PCT International Search Report from PCT/US2021/020597 dated Apr. 14, 2021.
Tsuno et al., "Pharmacological evaluation of novel (6-aminopyridin-3-yl)(4-(pyridin-2-yl)piperazin-1-yl) methanone derivatives as TRPV4 antagonists for the treatment of pain," Bioorg Med Chem. Apr. 1, 2017;25(7):2177-2190.
Dai et al., "A novel series of histone deacetylase inhibitors incorporating hetero aromatic ring systems as connection units," Bioorg Med Chem Lett. Nov. 3, 2003;13(21):3817-20.
Moerke et al., "Small-molecule inhibition of the interaction between the translation initiation factors eIF4E and eIF4G," Cell. Jan. 26, 2007;128(2):257-67.
Pubchem SID 112504174, 2-[4-(4-phenylphenyl)-1,3-thiazol-2-yl]acetic acid, 2011.
U.S. Appl. No. 17/822,337, filed Aug. 25, 2022 (not attached).
U.S. Appl. No. 17/822,344, filed Aug. 25, 2022 (not attached).

* cited by examiner

*Primary Examiner* — Samantha L Shterengarts
(74) *Attorney, Agent, or Firm* — Dechert LLP; Andrea L. C. Reid; Gang Wang

(57) ABSTRACT

The present invention provides compounds inhibiting eIF4E activity, and compositions and methods of using thereof.

21 Claims, No Drawings

EIF4E INHIBITORS AND USES THEREOF

TECHNICAL FIELD OF THE INVENTION

The present invention relates to compounds and methods useful for inhibition of Eukaryotic initiation factor 4E (eIF4E). The invention also provides pharmaceutically acceptable compositions comprising compounds of the present invention and methods of using said compositions in the treatment of various disorders.

BACKGROUND OF THE INVENTION

Eukaryotic initiation factor 4E (eIF4E) is a 24 kDa protein that plays a key role in the initiation of translation of select mRNAs. At the initiation of mRNA translation, eIF4E binds to the 7-methylguanosine cap at the 5' end of mRNAs, and forms a complex (called eIF4F) with proteins including the scaffolding protein eIF4G and the helicase eIF4A. The formation of the 4F complex is required for the initiation of cap-dependent translation, and therefore the binding of eIF4E to its cognate partners is a critical event in eIF4E mediated translation.

A number of studies have suggested that dysregulated eIF4E is important in some cancer phenotypes, and therefore eIF4E is a potential target in the field of oncology.

SUMMARY OF THE INVENTION

It has now been found that compounds of the present invention, and pharmaceutically acceptable compositions thereof, are effective as eIF4E inhibitors. In one aspect, the present invention provides a compound of Formula (I):

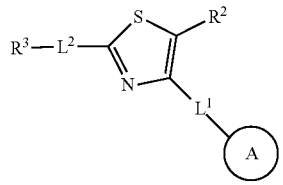

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with eIF4E. Such diseases, disorders, or conditions include cellular proliferative disorders (e.g., cancer) such as those described herein.

DETAILED DESCRIPTION OF CERTAIN EMBODIMENTS

1. General Description of Certain Embodiments of the Invention

Compounds of the present invention, and pharmaceutical compositions thereof, are useful as inhibitors of eIF4E. Without wishing to be bound by any particular theory, it is believed that compounds of the present invention, and pharmaceutical compositions thereof, may inhibit the activity of eIF4E and thus treat certain diseases, such as cancer.

It has now been found that compounds of this invention, and pharmaceutically acceptable compositions thereof, are effective as eIF4E inhibitors. In one aspect, the present invention provides a compound of Formula I:

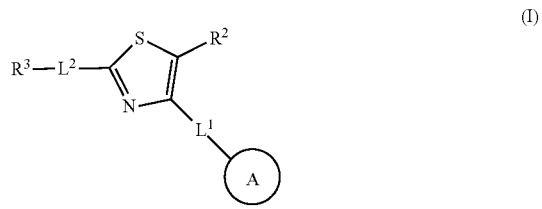

or a pharmaceutically acceptable salt thereof, wherein:

Ring A is an optionally substituted ring selected from phenyl, a 5-6 membered monocyclic heteroaromatic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur;

$L^1$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, or —S(O)$_2$—;

$R^2$ is halogen, R, —OR, —SR, —C(O)R, —C(O)OR, —C(O)N(R)$_2$, —S(O)$_2$R, —S(O)$_2$OR, or —S(O)$_2$N(R)$_2$;

$L^2$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, —S(O)$_2$—, or -Cy-;

$R^3$ is —CN, —C(O)R, —C(O)OR, —C(O)N(R)$_2$, —N(R)—C(O)—R, —N(R)—C(O)—OR, —S(O)$_2$—N(R)$_2$, —S(O)$_2$—N(R)—C(O)R, —C(O)—N(R)—S(O)$_2$R, —C(=NR)—N(R)$_2$, —N(R)—C(=NR)—N(R)$_2$, or a 5-6 membered monocyclic heteroaromatic ring having 1-4 heteroatoms independently selected from nitrogen, oxygen, and sulfur;

-Cy- is an optionally substituted bivalent ring selected from phenylene, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, a 3-6 membered monocyclic, saturated or partially unsaturated, heterocyclic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur; and R is hydrogen, optionally substituted —$C_{1-6}$ aliphatic, or an optionally substituted ring selected from phenyl, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, or a 3-6 membered monocyclic, saturated or partially unsaturated, heterocyclic ring having 1-4 heteroatoms independently selected from nitrogen, oxygen, and sulfur.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

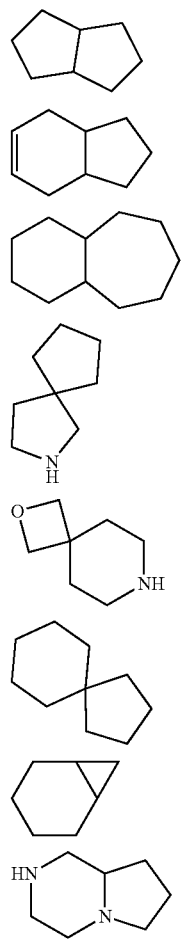

Exemplary bridged bicyclics include:

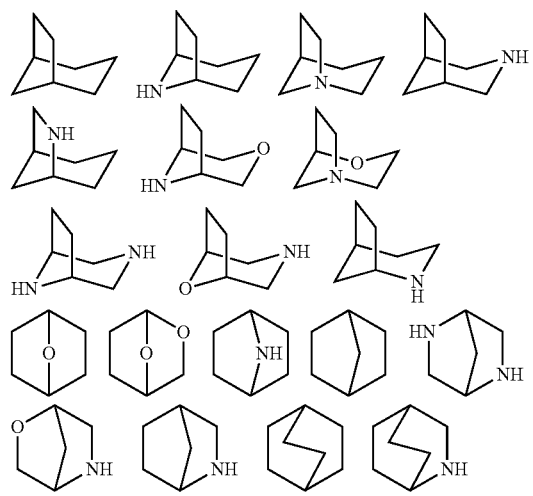

-continued

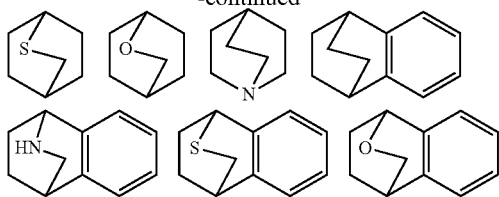

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

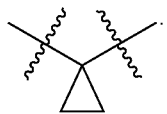

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)(NR^\circ)R^\circ$; $-S(O)_2N=C(NR^\circ_2)_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$.

Each $R^\circ$ is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from $=O$ and $=S$; or each $R^\circ$ is optionally substituted with a monovalent substituent independently selected from halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$.

Each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, or a divalent substituent bound to vicinal substitutable carbons of an "optionally substituted" group is $-O(CR^*_2)_{2-3}O-$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic, unsubstituted $-OPh$, or an unsubstituted 5-6-membered saturated, partially unsaturated, or aryl ring having 0-4 heteroatoms independently selected from nitrogen, oxygen, or sulfur, or, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-4}$ aliphatic, $R^\dagger$ is optionally substituted with halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "inhibitor" is defined as a compound that binds to and/or inhibits eIF4E with measurable affinity. In certain embodiments, an inhibitor has an $IC_{50}$ and/or binding constant of less than about 100 μM, less than about 50 μM, less than about 22.5 uM, less than about 15 uM, or less than about 7.5 uM.

The terms "measurable affinity" and "measurably inhibit," as used herein, means a measurable change in eIF4E activity between a sample comprising a compound of the present invention, or composition thereof, and eIF4E, and an equivalent sample comprising eIF4E, in the absence of said compound, or composition thereof.

3. Description of Exemplary Embodiments

In one aspect, the present invention provides a compound of Formula I:

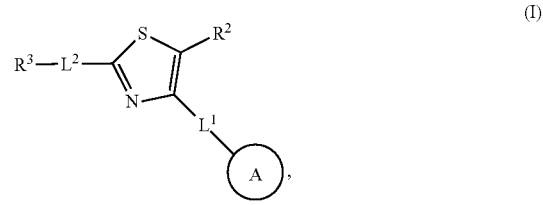

or a pharmaceutically acceptable salt thereof, wherein:
  Ring A is an optionally substituted ring selected from phenyl, a 5-6 membered monocyclic heteroaromatic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur;
  $L^1$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, or —S(O)$_2$—;
  $R^2$ is halogen, R, —OR, —SR, —C(O)R, —C(O)OR, —C(O)N(R)$_2$, —S(O)$_2$R, —S(O)$_2$OR, or —S(O)$_2$N(R)$_2$;
  $L^2$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, —S(O)$_2$—, or -Cy-;
  $R^3$ is —CN, —C(O)R, —C(O)OR, —C(O)N(R)$_2$, —N(R)—C(O)—R, —N(R)—C(O)—OR, —S(O)$_2$—N(R)$_2$, —S(O)$_2$—N(R)—C(O)R, —C(O)—N(R)—S(O)$_2$R, —C(=NR)—N(R)$_2$, —N(R)—C(=NR)—N(R)$_2$, or a 5-6 membered monocyclic heteroaromatic ring having 1-4 heteroatoms independently selected from nitrogen, oxygen, and sulfur;
  -Cy- is an optionally substituted bivalent ring selected from phenylene, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, a 3-6 membered monocyclic, saturated or partially unsaturated, heterocyclic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur; and
  R is hydrogen, optionally substituted —$C_{1-6}$ aliphatic, or an optionally substituted ring selected from phenyl, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, or a 3-6 membered monocyclic, saturated or partially unsaturated, heterocyclic ring having 1-4 heteroatoms independently selected from nitrogen, oxygen, and sulfur.

As defined generally above, Ring A is an optionally substituted ring selected from phenyl, a 5-6 membered monocyclic heteroaromatic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur.

In some embodiments, Ring A is optionally substituted phenyl.

In some embodiments, Ring A is

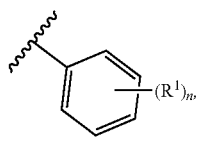

wherein each $R^1$ is independently halogen, R, —N(R)$_2$, —OR, —SR, —C(O)OR, or —S(O)$_2$R; n is 0, 1, 2, 3, 4, or 5; and each R is independently as described herein.

In some embodiments, $R^1$ is halogen. In some embodiments, $R^1$ is —Cl. In some embodiments, $R^1$ is —F.

In some embodiments, $R^1$ is R, as described herein. In some embodiments, $R^1$ is —N(R)$_2$, wherein each R is independently as described herein. In some embodiments, $R^1$ is —OR, wherein R is as described herein. In some embodiments, $R^1$ is —SR, wherein R is as described herein. In some embodiments, $R^1$ is —C(O)OR, wherein R is as described herein. In some embodiments, $R^1$ is —S(O)$_2$R, wherein R is as described herein.

In some embodiments, $R^1$ is hydrogen, —Cl, —CH$_3$, —F, —CF$_3$, —OCH$_3$,

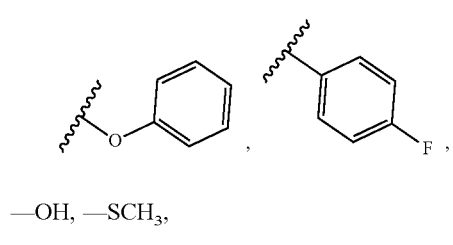

—OH, —SCH$_3$,

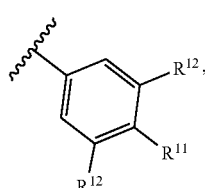, or

In some embodiments, $R^1$ is

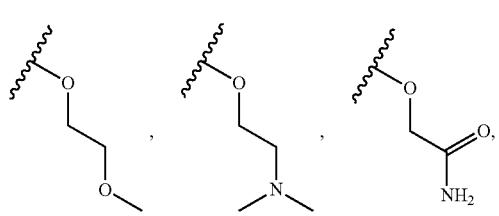

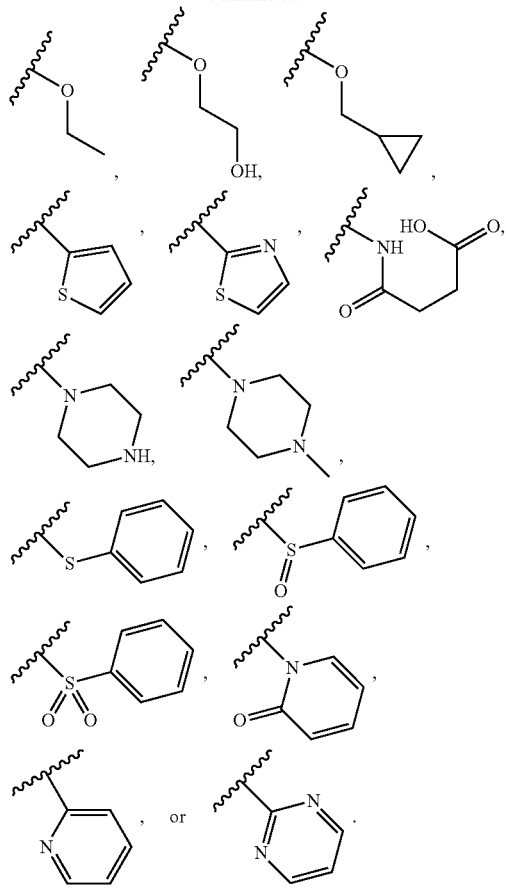

In some embodiments, $R^1$ is selected from those depicted in Table 1, below.

In some embodiments, n is 0. In some embodiments, n is 1. In some embodiments, n is 2. In some embodiments, n is 3. In some embodiments, n is 4. In some embodiments, n is 5.

In some embodiments, Ring A is

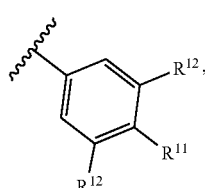

wherein each of $R^{11}$ and $R^{12}$ is independently halogen, R, —N(R)$_2$, —OR, —SR, —C(O)OR, or —S(O)$_2$, wherein each R is independently as described herein R.

In some embodiments, Ring A is

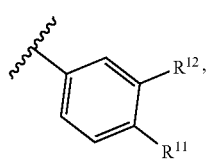

wherein each of $R^{11}$ and $R^{12}$ is independently halogen, R, —N(R)$_2$, —OR, —SR, —C(O)OR, or —S(O)$_2$R, wherein each R is independently as described herein.

In some embodiments, $R^{11}$ is halogen. In some embodiments, $R^{11}$ is R, as described herein. In some embodiments, $R^{11}$ is —N(R)$_2$, wherein each R is independently as described herein. In some embodiments, $R^{11}$ is —OR, wherein R is as described herein. In some embodiments, $R^{11}$ is —SR, wherein R is as described herein. In some embodiments, $R^{11}$ is —C(O)OR, wherein R is as described herein. In some embodiments, $R^{11}$ is —S(O)$_2$R, wherein R is as described herein.

In some embodiments, $R^{12}$ is halogen. In some embodiments, $R^{12}$ is R, as described herein. In some embodiments, $R^{12}$ is —N(R)$_2$, wherein each R is independently as described herein. In some embodiments, $R^{12}$ is —OR, wherein R is as described herein. In some embodiments, $R^{12}$ is —SR, wherein R is as described herein. In some embodiments, $R^{12}$ is —C(O)OR, wherein R is as described herein. In some embodiments, $R^{12}$ is —S(O)$_2$R, wherein R is as described herein.

In some embodiments, $R^{11}$ is hydrogen, —Cl, —CH$_3$, —F, —OCH$_3$,

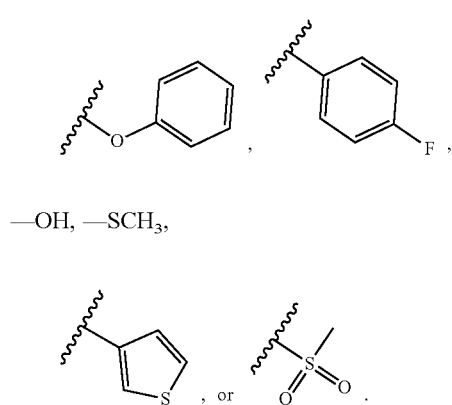

—OH, —SCH$_3$,

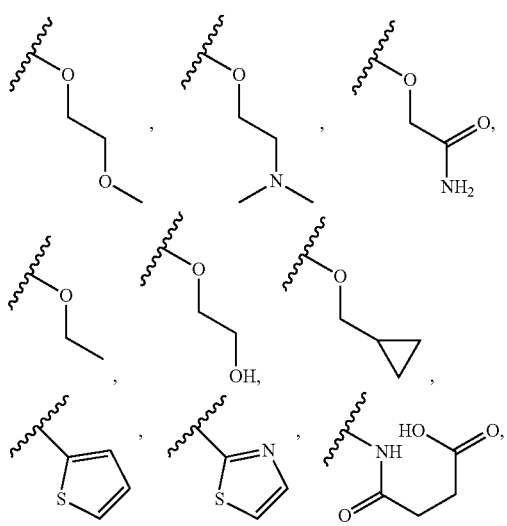

In some embodiments, $R^{11}$ is —CF$_3$,

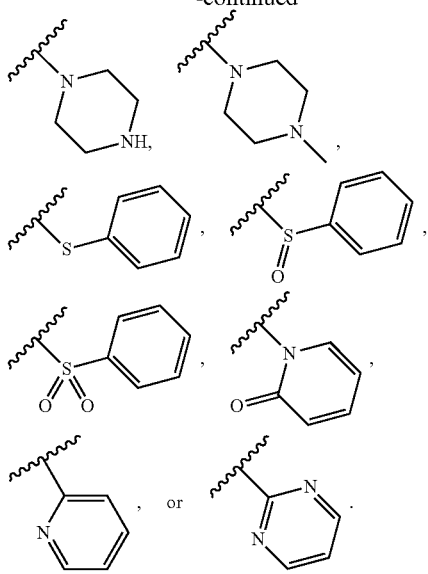

In some embodiments, at least one of $R^{12}$ is not hydrogen. In some embodiments, $R^{12}$ is —Cl, —OCH$_3$, H, —CH$_3$, —F, or —CF$_3$.

In some embodiments, Ring A is an optionally substituted 5-6 membered monocyclic heteroaromatic ring having 1-4 heteroatoms independently selected from nitrogen, oxygen, and sulfur. In some embodiments, Ring A is an optionally substituted 5-membered monocyclic heteroaromatic ring having 1, 2, or 3 heteroatoms independently selected from nitrogen, oxygen, and sulfur. In some embodiments, Ring A is an optionally substituted 6-membered monocyclic heteroaromatic ring having 1, 2, or 3 heteroatoms independently selected from nitrogen, oxygen, and sulfur. In some embodiments, Ring A is optionally substituted phenyl. In some embodiments, Ring A is optionally substituted

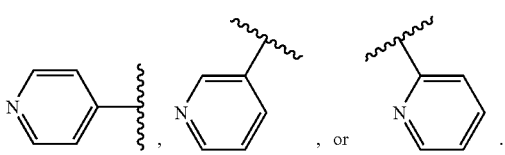

In some embodiments, Ring A is optionally substituted

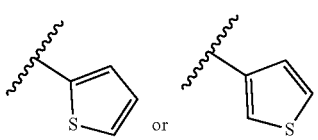

In some embodiments, Ring A is an optionally substituted 8-10 membered bicyclic aromatic carbocyclic ring. In some embodiments, Ring A is an optionally substituted 8-membered bicyclic aromatic carbocyclic ring. In some embodiments, Ring A is an optionally substituted 9-membered bicyclic aromatic carbocyclic ring. In some embodiments, Ring A is an optionally substituted 10-membered bicyclic aromatic carbocyclic ring. In some embodiments, Ring A is optionally substituted or

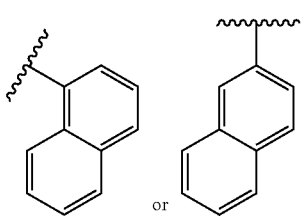

In some embodiments, Ring A is an optionally substituted 8-10 membered bicyclic heteroaromatic ring having 1-4 heteroatoms independently selected from nitrogen, oxygen, and sulfur. In some embodiments, Ring A is an optionally substituted 8-membered bicyclic heteroaromatic ring having 1, 2, or 3 heteroatoms independently selected from nitrogen, oxygen, and sulfur. In some embodiments, Ring A is an optionally substituted 9-membered bicyclic heteroaromatic ring having 1, 2, or 3 heteroatoms independently selected from nitrogen, oxygen, and sulfur. In some embodiments, Ring A is an optionally substituted 10-membered bicyclic heteroaromatic ring having 1, 2, or 3 heteroatoms independently selected from nitrogen, oxygen, and sulfur. In some embodiments, Ring A is optionally substituted indole. In some embodiments, Ring A is optionally substituted

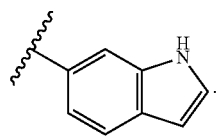 [SMILES: *c1ccc2cc[nH]c2c1]

In some embodiments, Ring A is optionally substituted

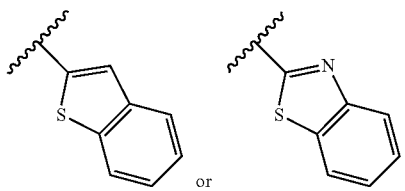

In some embodiments, Ring A is selected from those depicted in Table 1, below.

As defined generally above, $L^1$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, or —S(O)$_2$—.

In some embodiments, $L^1$ is a bond.

In some embodiments, $L^1$ is an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, —C(O)—, or —S(O)$_2$—. In some embodiments, $L^1$ is an unsubstituted $C_{1-8}$ bivalent straight or branched hydrocarbon chain. In some embodiments, $L^1$ is a $C_{1-8}$ bivalent straight or branched hydrocarbon chain, wherein 1 methylene unit of the hydrocarbon chain is replaced with —O—, —S—, —N(R)—, —C(O)—, or —S(O)$_2$—. In some embodiments, $L^1$ is a $C_{1-8}$ bivalent straight or branched hydrocarbon chain, wherein 2 methylene units of the hydrocarbon chain are independently replaced with —O—, —S—, —N(R)—, —C(O)—, or —S(O)$_2$—.

In some embodiments, $L^1$ is —CH$_2$—.

In some embodiments, $L^1$ is selected from those depicted in Table 1, below.

As defined generally above, $R^2$ is halogen, R, —OR, —SR, —C(O)R, —C(O)OR, —C(O)N(R)$_2$, —S(O)$_2$R, —S(O)$_2$OR, or —S(O)$_2$N(R)$_2$.

In some embodiments, $R^2$ is halogen. In some embodiments, $R^2$ is R. In some embodiments, $R^2$ is —OR. In some embodiments, $R^2$ is —SR. In some embodiments, $R^2$ is —C(O)R. In some embodiments, $R^2$ is —C(O)OR. In some embodiments, $R^2$ is —C(O)N(R)$_2$. In some embodiments, $R^2$ is —S(O)$_2$R. In some embodiments, $R^2$ is —S(O)$_2$OR. In some embodiments, $R^2$ is —S(O)$_2$N(R)$_2$.

In some embodiments, $R^2$ is not hydrogen.

In some embodiments, $R^2$ is H,

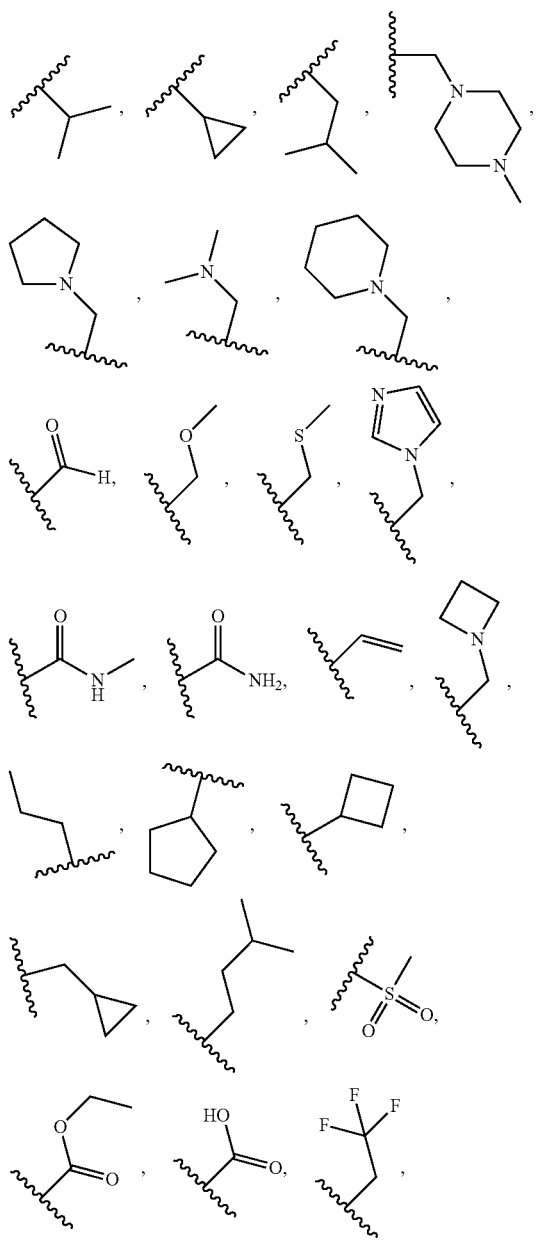

-continued

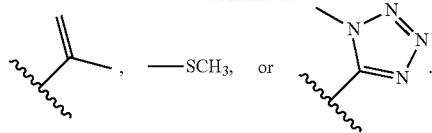

In embodiments, R² is

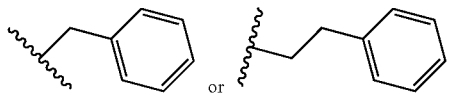

In some embodiments, R² is selected from those depicted in Table 1, below.

As defined generally above, L² is a bond, or an optionally substituted C₁₋₈ bivalent straight or branched hydrocarbon chain, wherein 1, 2, 3, or 4 methylene units of the hydrocarbon chain are optionally and independently replaced with —O—, —S—, —N(R)—, —C(O)—, —S(O)₂—, or -Cy-.

In some embodiments, L² is a bond.

In some embodiments, L² is an optionally substituted C₁₋₈ bivalent straight or branched hydrocarbon chain, wherein 1, 2, 3, or 4 methylene units of the hydrocarbon chain are optionally and independently replaced with —O—, —S—, —N(R)—, —C(O)—, —S(O)₂—, or -Cy-. In some embodiments, L² is an unsubstituted C₁₋₈ bivalent straight or branched hydrocarbon chain. In some embodiments, L² is an optionally substituted C₁₋₈ bivalent straight or branched hydrocarbon chain, wherein 1 methylene unit of the hydrocarbon chain is replaced with —O—, —S—, —N(R)—, —C(O)—, —S(O)₂—, or -Cy-. In some embodiments, L² is an optionally substituted C₁₋₈ bivalent straight or branched hydrocarbon chain, wherein 2 methylene units of the hydrocarbon chain are independently replaced with —O—, —S—, —N(R)—, —C(O)—, —S(O)₂—, or -Cy-. In some embodiments, L² is an optionally substituted C₁₋₈ bivalent straight or branched hydrocarbon chain, wherein 3 methylene units of the hydrocarbon chain are independently replaced with —O—, —S—, —N(R)—, —C(O)—, —S(O)₂—, or -Cy-. In some embodiments, L² is an optionally substituted C₁₋₈ bivalent straight or branched hydrocarbon chain, wherein 4 methylene units of the hydrocarbon chain are independently replaced with —O—, —S—, —N(R)—, —C(O)—, —S(O)₂—, or -Cy-.

In some embodiments, L² does not attach to the thiazole moiety through a carboxamide or sulfonamide moiety.

In some embodiments, L² does not attach to the thiazole moiety through a diazole moiety.

In some embodiments, L² is an optionally substituted C₁₋₈ bivalent straight or branched hydrocarbon chain, wherein 2 methylene units of the hydrocarbon chain are independently replaced with —N(R)— and -Cy-.

In some embodiments, L² is -Cy-N(R)—, wherein -Cy- and R is independently as described herein.

In some embodiments, L² is

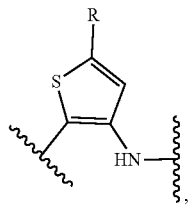

wherein R is as described herein. In some embodiments, L² is

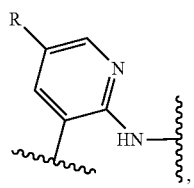

wherein R is as described herein.

In some embodiments, L² is

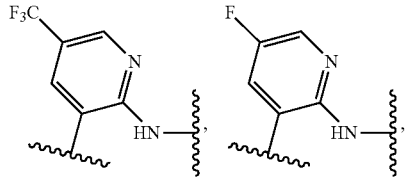

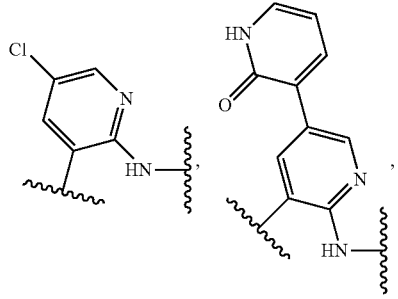

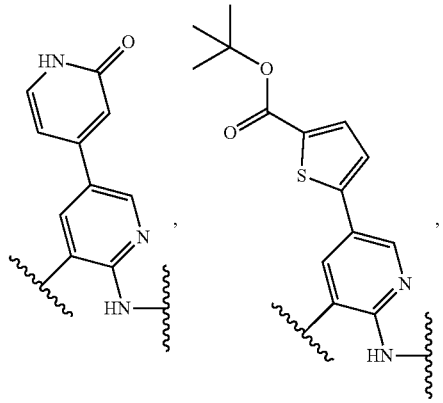

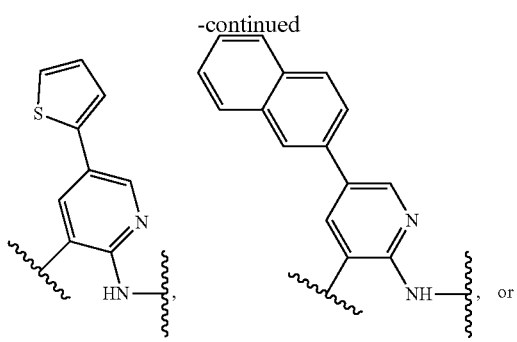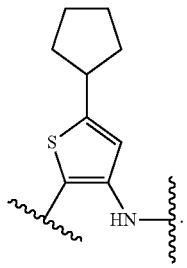
In some embodiments, L² is selected from the following:
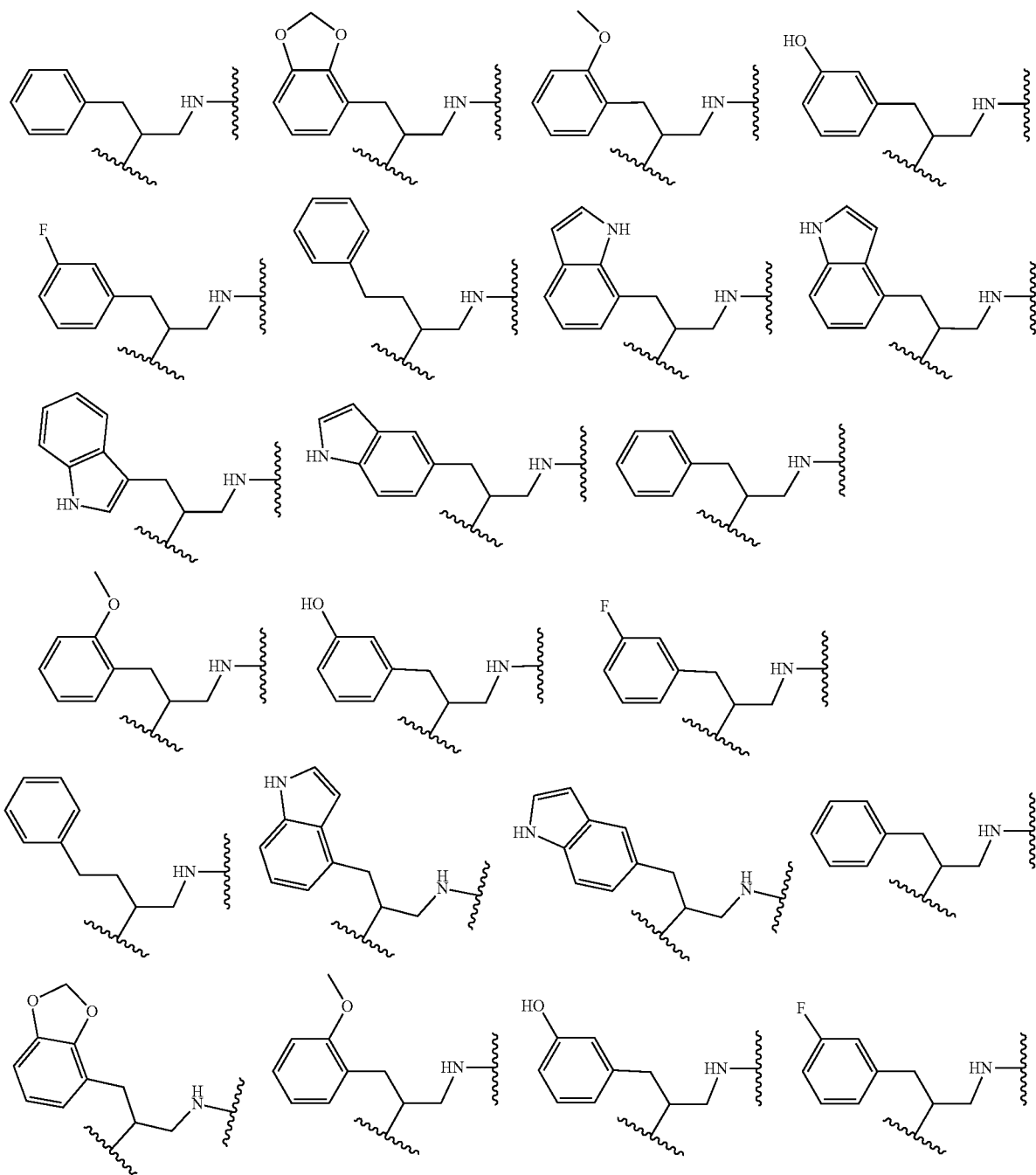

-continued
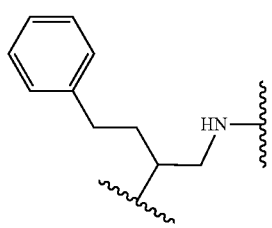 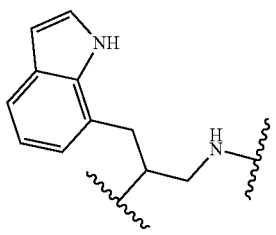 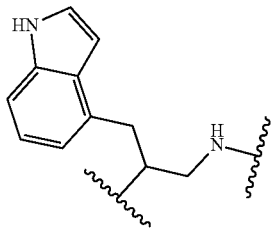
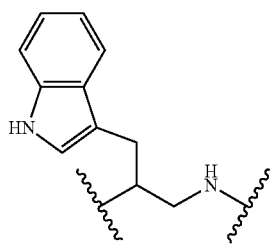 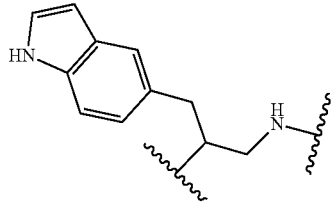 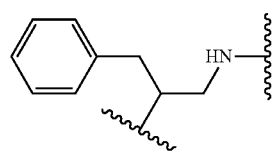
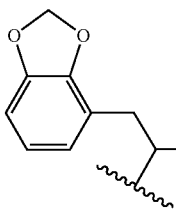 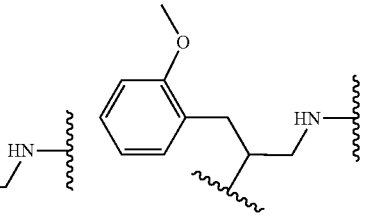 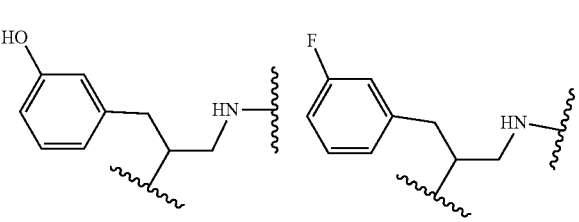
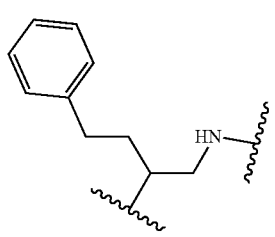 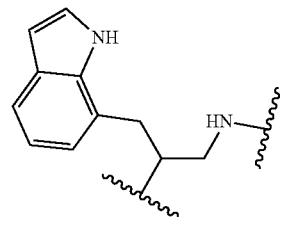 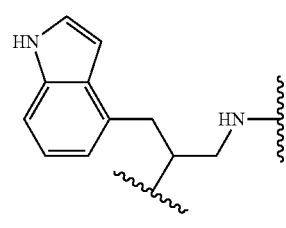
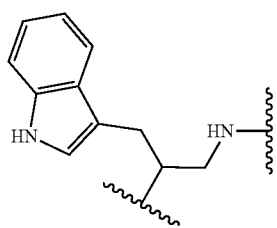 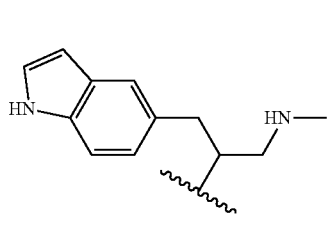 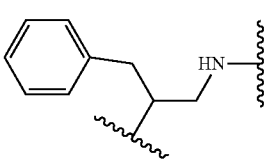
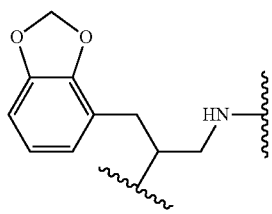 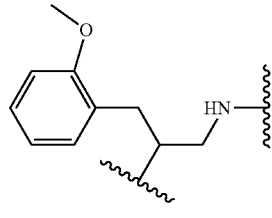 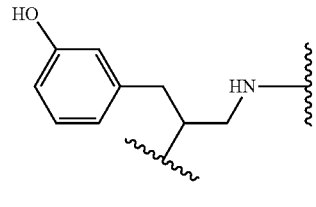
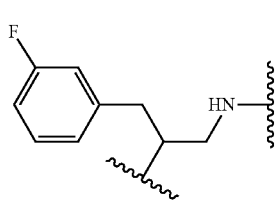 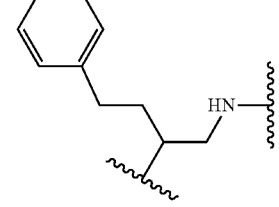 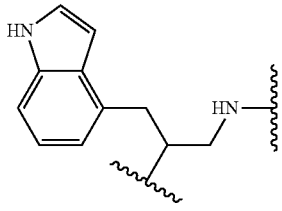

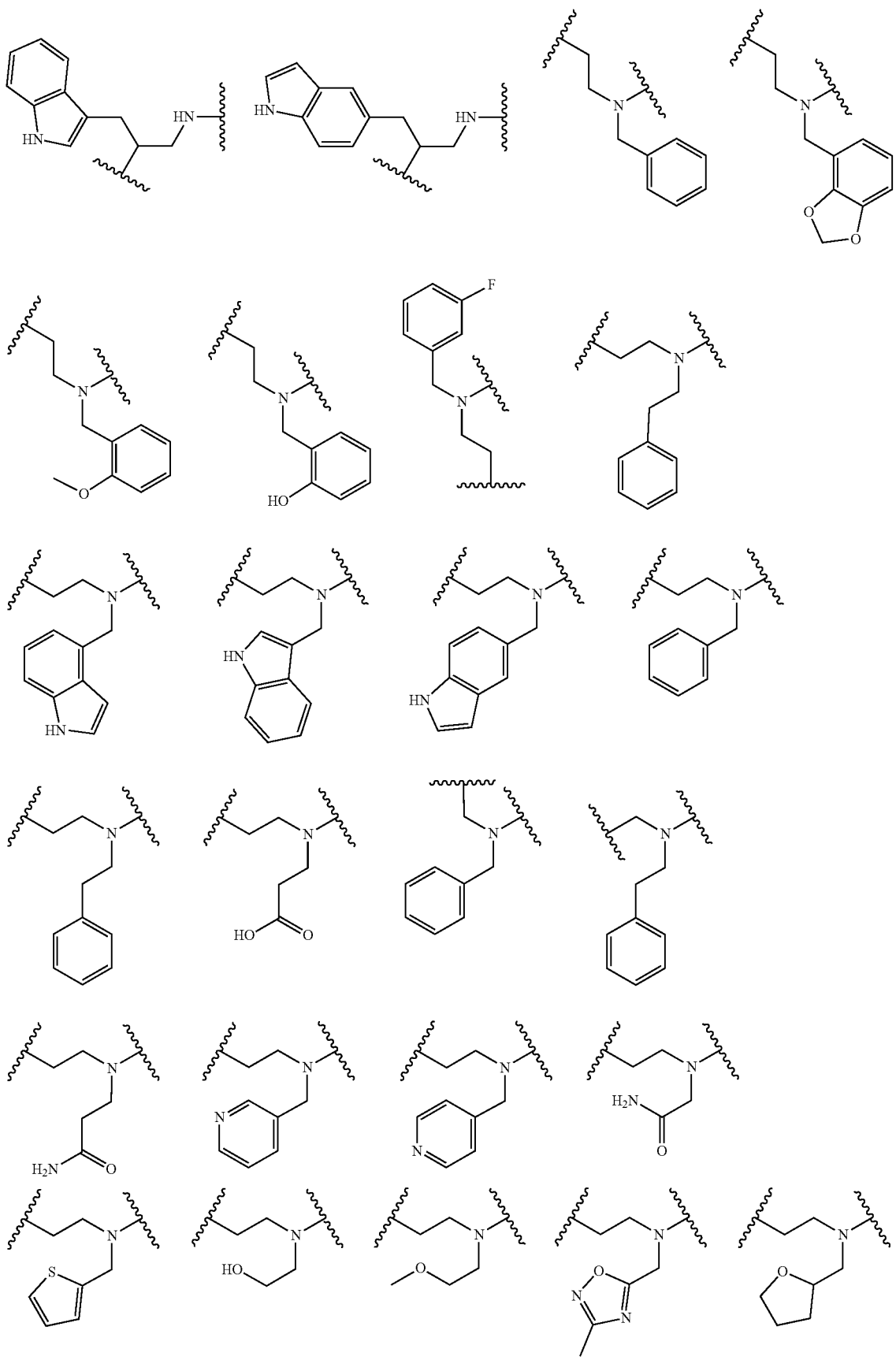

-continued
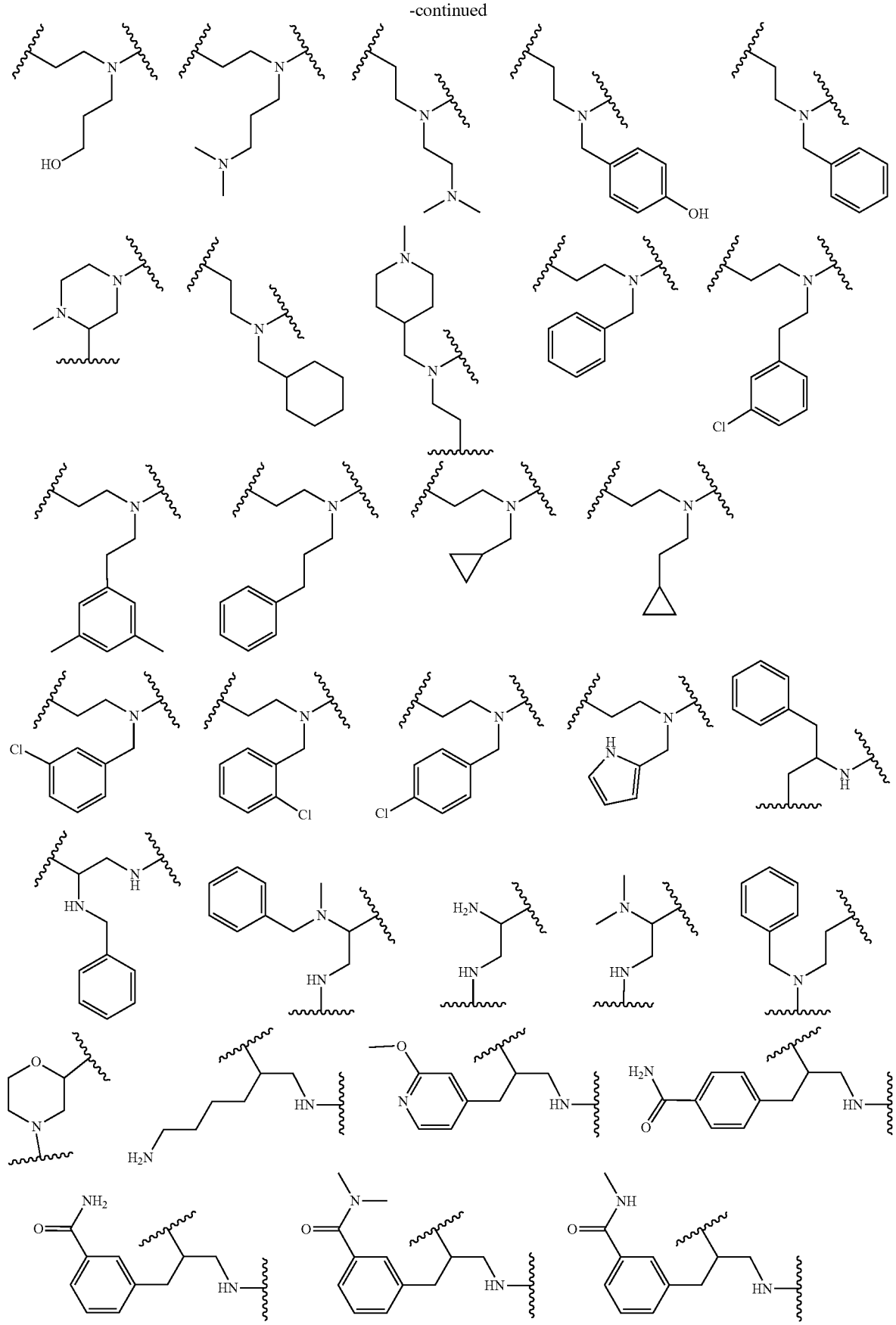

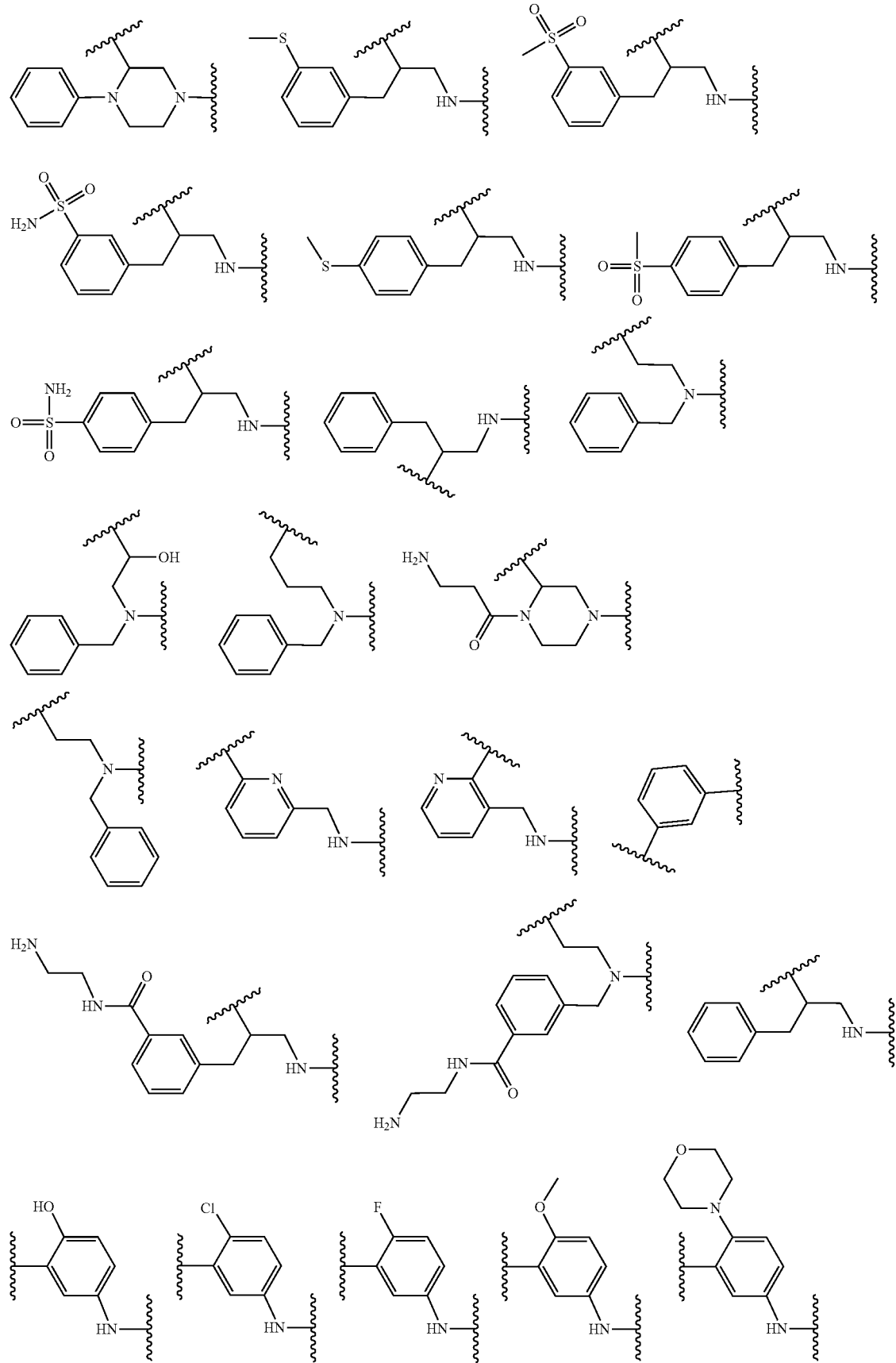

-continued
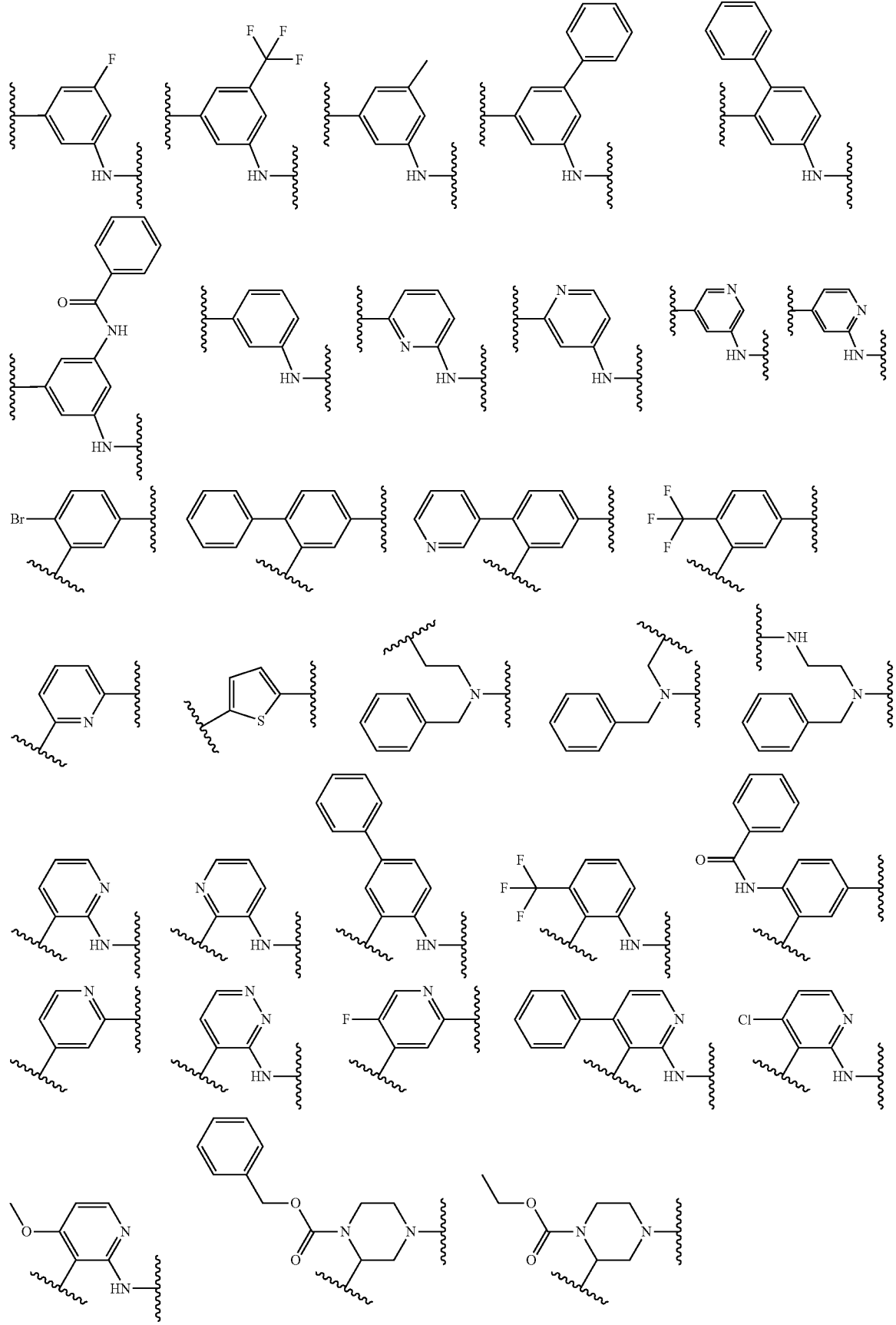

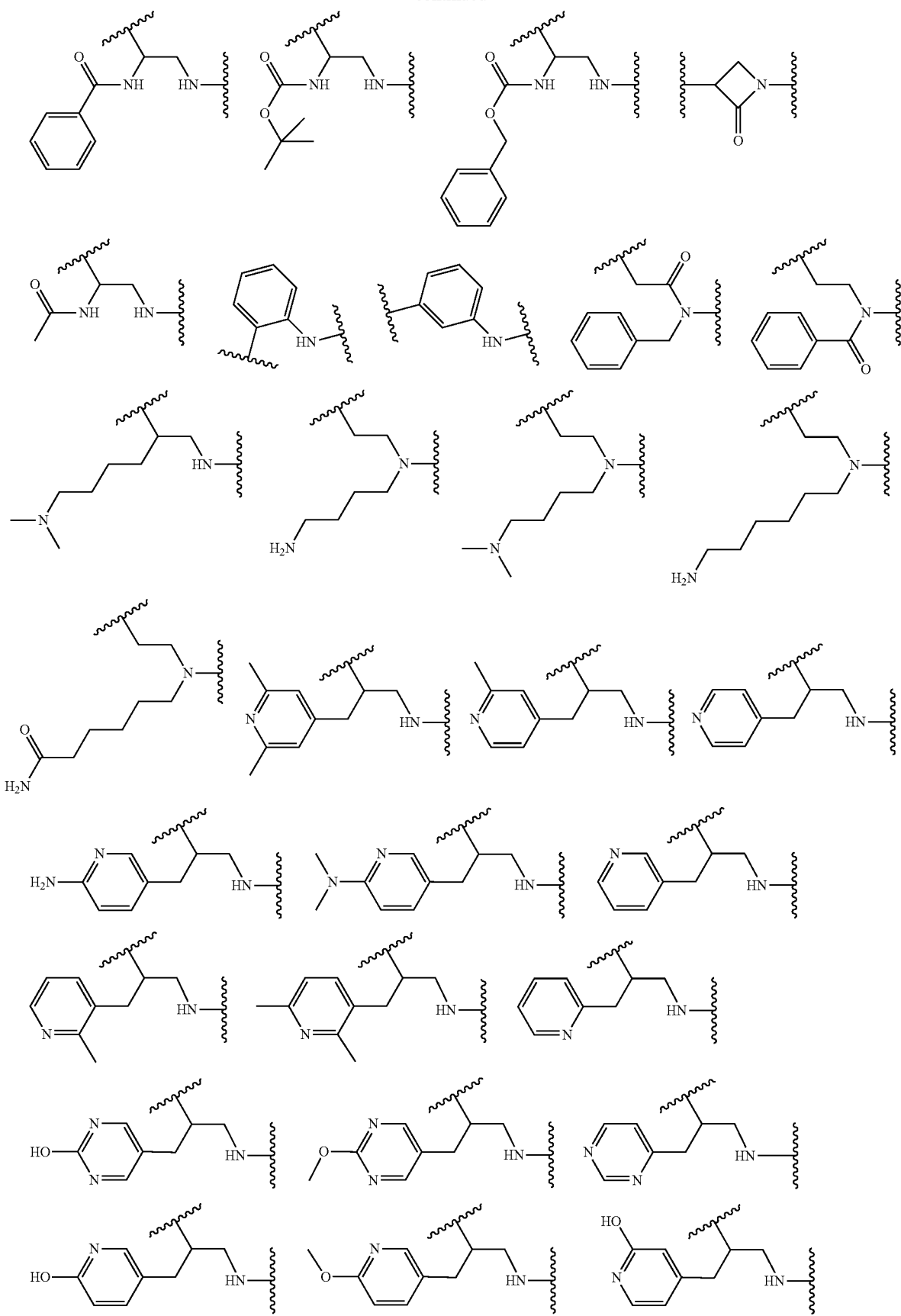

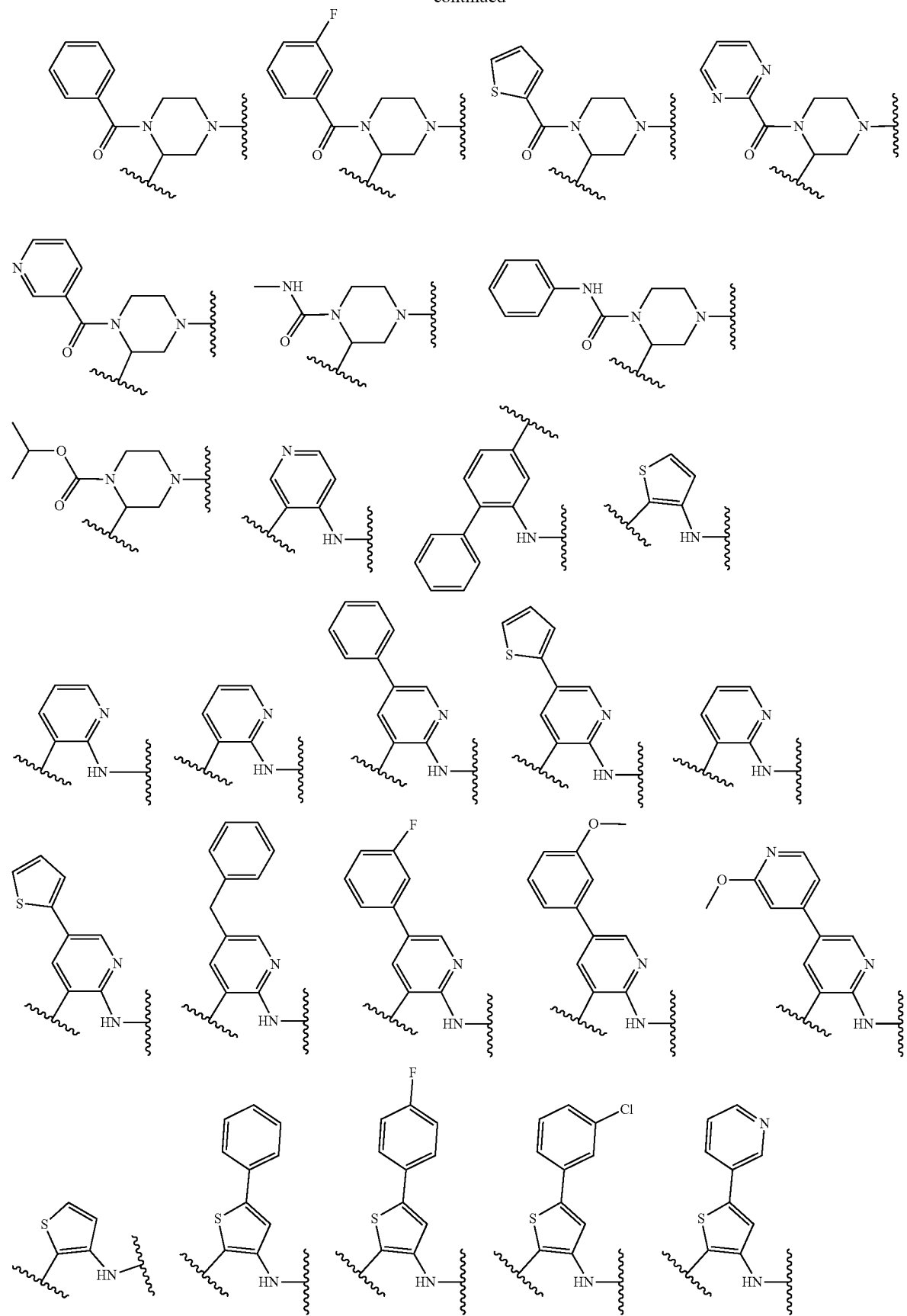

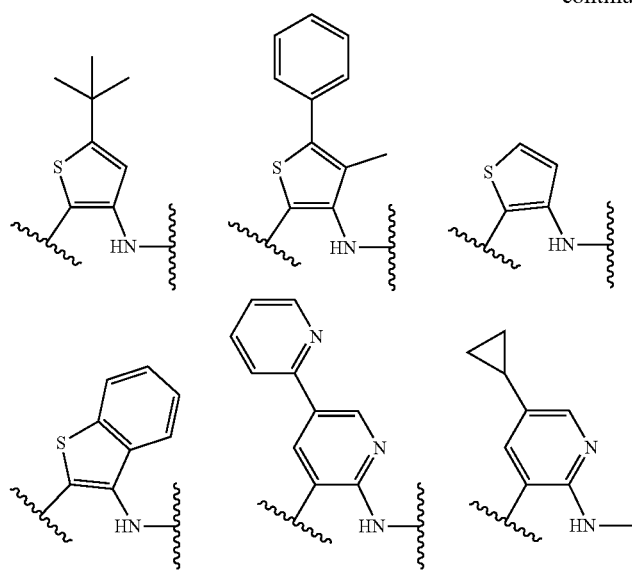
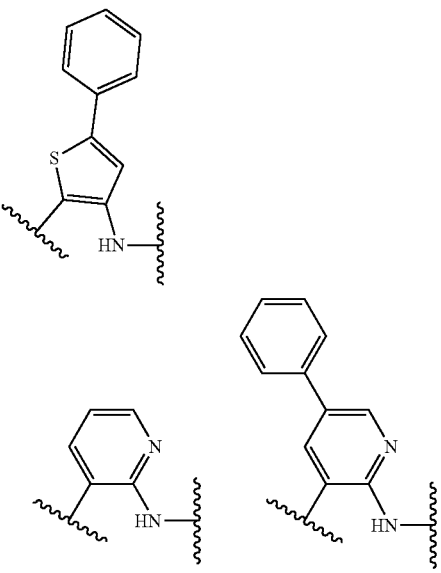

In some embodiments, $L^2$ is selected from those depicted in Table 1, below.

As defined generally above, $R^3$ is —CN, —C(O)R, —C(O)OR, —C(O)N(R)$_2$, —N(R)—C(O)—R, —N(R)—C(O)—OR, —S(O)$_2$—N(R)$_2$, —S(O)$_2$—N(R)—C(O)R, —C(O)—N(R)—S(O)$_2$R, —C(=NR)—N(R)$_2$, —N(R)—C(=NR)—N(R)$_2$, or a 5-6 membered monocyclic heteroaromatic ring having 1-4 heteroatoms independently selected from nitrogen, oxygen, and sulfur.

In some embodiments, $R^3$ is —CN. In some embodiments, $R^3$ is —C(O)R. In some embodiments, $R^3$ is —C(O)OR. In some embodiments, $R^3$ is —C(O)N(R)$_2$. In some embodiments, $R^3$ is —N(R)—C(O)—R. In some embodiments, $R^3$ is —N(R)—C(O)—OR. In some embodiments, $R^3$ is —S(O)$_2$—N(R)$_2$. In some embodiments, $R^3$ is —S(O)$_2$—N(R)—C(O)R. In some embodiments, $R^3$ is —C(O)—N(R)—S(O)$_2$R. In some embodiments, $R^3$ is —C(=NR)—N(R)$_2$. In some embodiments, $R^3$ is —N(R)—C(=NR)—N(R)$_2$. In some embodiments, $R^3$ is a 5-6 membered monocyclic heteroaromatic ring having 1, 2, 3, or 4 heteroatoms independently selected from nitrogen, oxygen, and sulfur.

In some embodiments, $R^3$ is —COOH. In some embodiments, $R^3$ is —CN,

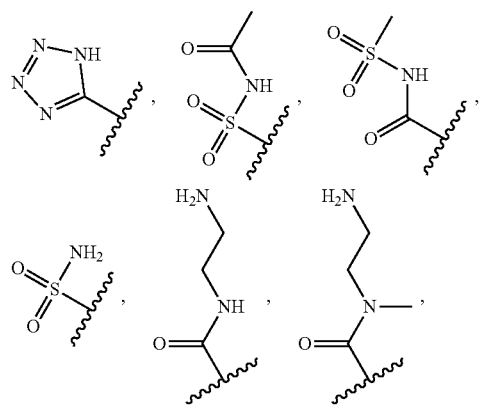

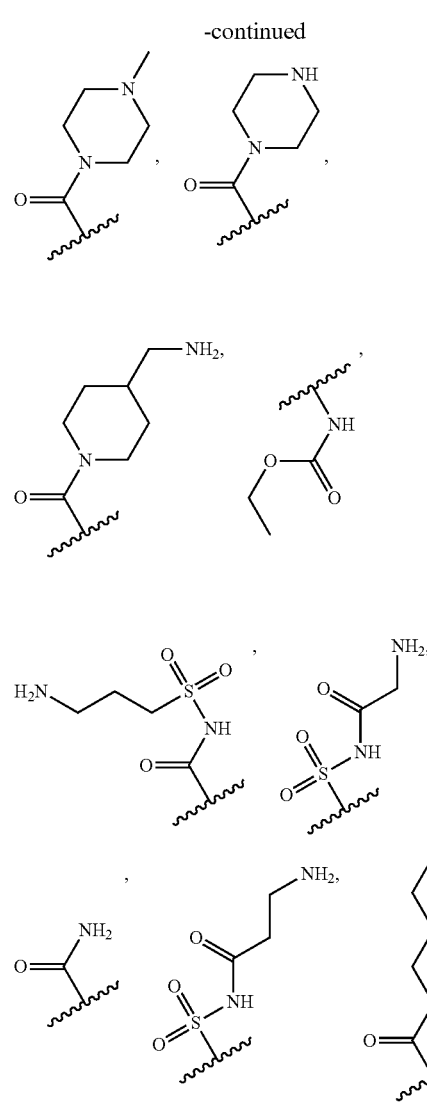

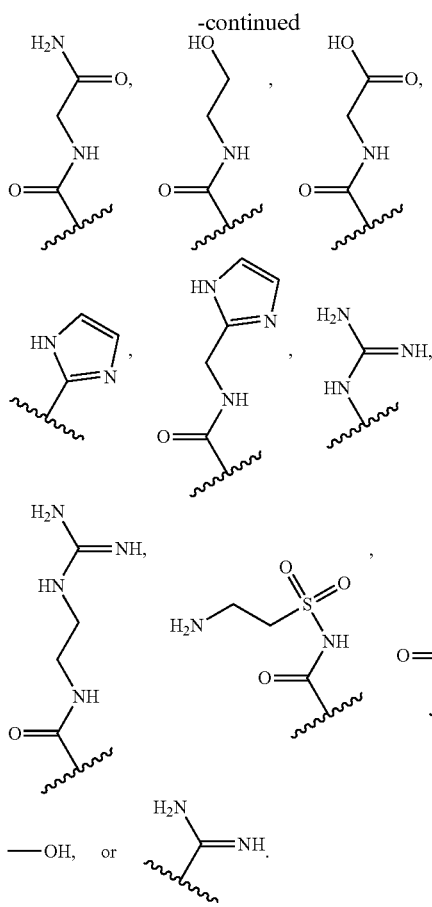

In some embodiments, R³ is selected from those depicted in Table 1, below.

As defined generally above, -Cy- is an optionally substituted bivalent ring selected from phenylene, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, a 3-6 membered monocyclic, saturated or partially unsaturated, heterocyclic ring having 1-4 heteroatoms independently selected from nitrogen, oxygen, and sulfur, an 8-10 membered bicyclic aromatic carbocyclic ring, or an 8-10 membered bicyclic heteroaromatic ring having 1-4 heteroatoms independently selected from nitrogen, oxygen, and sulfur.

In some embodiments, -Cy- is optionally substituted phenylene.

In some embodiments, -Cy- is an optionally substituted bivalent 5-6 membered monocyclic heteroaromatic ring having 1, 2, 3, or 4 heteroatoms independently selected from nitrogen, oxygen, and sulfur. In some embodiments, -Cy- is an optionally substituted bivalent pyridine ring. In some embodiments, -Cy- is an optionally substituted bivalent pyridazine ring. In some embodiments, -Cy- is an optionally substituted bivalent thiophene ring.

In some embodiments, -Cy- is an optionally substituted bivalent 3, 4, 5, or 6 membered monocyclic, saturated or partially unsaturated, carbocyclic ring.

In some embodiments, -Cy- is an optionally substituted bivalent 3, 4, 5, or 6 membered monocyclic, saturated or partially unsaturated, heterocyclic ring having 1, 2, 3, or 4 heteroatoms independently selected from nitrogen, oxygen, and sulfur. In some embodiments, -Cy- is an optionally substituted bivalent morpholine ring. In some embodiments, -Cy- is an optionally substituted bivalent piperazine ring.

In some embodiments, -Cy- is an optionally substituted bivalent 8, 9, or 10 membered bicyclic aromatic carbocyclic ring. In some embodiments, -Cy- is an optionally substituted bivalent benzothiophene ring.

In some embodiments, -Cy- is an optionally substituted bivalent 8, 9, or 10 membered bicyclic heteroaromatic ring having 1, 2, 3, or 4 heteroatoms independently selected from nitrogen, oxygen, and sulfur.

In some embodiments, -Cy- is

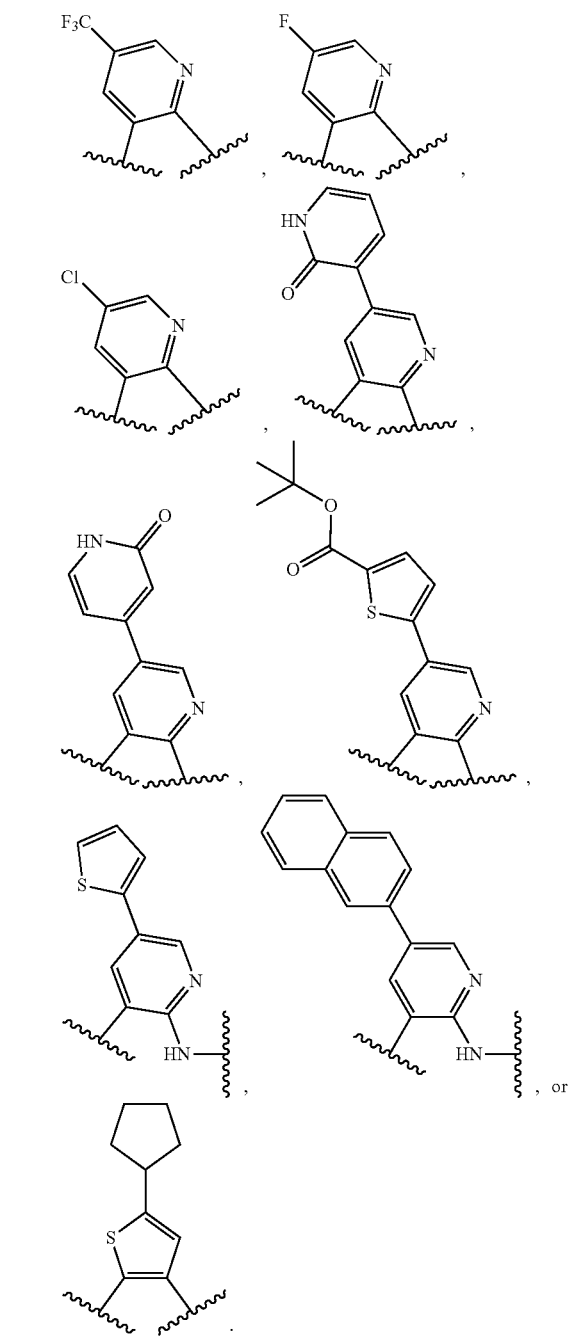

In some embodiments, -Cy- is selected from those depicted in Table 1, below.

As defined generally above, R is hydrogen, optionally substituted —$C_{1-6}$ aliphatic, or an optionally substituted ring selected from phenyl, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, or a 3-6 membered monocyclic, saturated or partially unsaturated, heterocyclic ring having 1-4 heteroatoms independently selected from nitrogen, oxygen, and sulfur.

In some embodiments, R is hydrogen.

In some embodiments, R is optionally substituted —$C_{1-6}$ aliphatic. In some embodiments, R is optionally substituted —$C_{1-6}$ alkyl. In some embodiments, R is unsubstituted —$C_{1-6}$ alkyl. In some embodiments, R is —$C_{1-6}$ alkyl substituted 1, 2, 3, 4, 5, or 6 times by halogen. In some embodiments, R is —$C_{1-6}$ alkyl substituted by a phenyl group, wherein the phenyl group is optionally substituted. In some embodiments, R is —$C_{1-6}$ alkyl substituted by a phenyl group, wherein the phenyl group is substituted 1, 2, 3, 4, or 5 times by halogen. In some embodiments, R is —$CH_3$. In some embodiments, R is —$CH_2CH_3$. In some embodiments, R is —$CF_3$. In some embodiments, R is

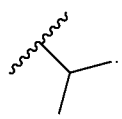 [SMILES: *C(C)C]

In some embodiments, R is

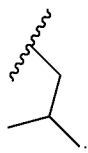

In some embodiments, R is

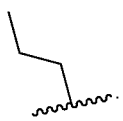

In some embodiments, R is

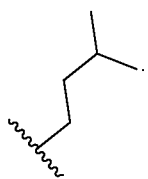 [SMILES: *CCC(C)C]

In some embodiments, R is

In some embodiments, R is

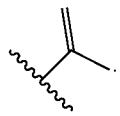 [SMILES: *C(=C)C]

In some embodiments, R is optionally substituted phenyl. In some embodiments, R is unsubstituted phenyl. In some embodiments, R is phenyl substituted 1, 2, 3, 4, or 5 times by halogen. In some embodiments, R is phenyl substituted 1, 2, 3, 4, or 5 times by —$C_{1-6}$ alkyl, wherein —$C_{1-6}$ alkyl is optionally substituted 1, 2, 3, 4, 5, or 6 times by halogen.

In some embodiments, R is an optionally substituted 8-10 membered bicyclic aromatic carbocyclic ring. In some embodiments, R is an optionally substituted 8-membered bicyclic aromatic carbocyclic ring. In some embodiments, R is an optionally substituted 9-membered bicyclic aromatic carbocyclic ring. In some embodiments, R is an optionally substituted 10-membered bicyclic aromatic carbocyclic ring. In some embodiments, R is optionally substituted

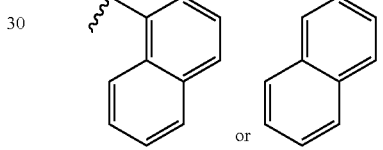

In some embodiments, R is an optionally substituted 5-6 membered monocyclic heteroaromatic ring having 1-4 heteroatoms independently selected from nitrogen, oxygen, and sulfur. In some embodiments, R is an optionally substituted 5-6 membered monocyclic heteroaromatic ring having 1, 2, or 3 heteroatoms independently selected from nitrogen, oxygen, and sulfur. In some embodiments, R is a 5-6 membered monocyclic heteroaromatic ring having 1, 2, or 3 heteroatoms independently selected from nitrogen, oxygen, and sulfur, which is optionally substituted 1, 2, 3, 4, 5, or 6 times by halogen. In some embodiments, R is optionally substituted

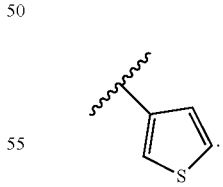

In some embodiments, R is optionally substituted

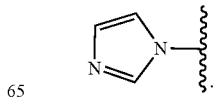

In some embodiments, R is optionally substituted

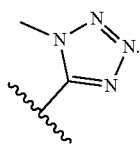 [SMILES: *c1nnnn1C]

In some embodiments, R is optionally substituted

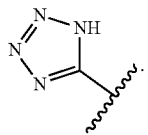 [SMILES: *c1nnn[nH]1]

In some embodiments, R is optionally substituted

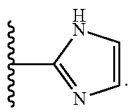

In some embodiments, R is an optionally substituted 3, 4, 5, or 6 membered monocyclic, saturated or partially unsaturated, carbocyclic ring. In some embodiments, R is a 3, 4, 5, or 6 membered monocyclic, saturated or partially unsaturated, carbocyclic ring substituted 1, 2, 3, 4, 5, or 6 times by halogen. In some embodiments, R is a 3, 4, 5, or 6 membered monocyclic, saturated or partially unsaturated, carbocyclic ring substituted 1, 2, 3, 4, 5, or 6 times by 1, 2, 3, 4, or 5 times by —$C_{1-6}$ alkyl, wherein —$C_{1-6}$ alkyl is optionally substituted 1, 2, 3, 4, 5, or 6 times by halogen. In some embodiments, R is optionally substituted

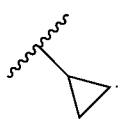 [SMILES: *C1CC1]

In some embodiments, R is optionally substituted

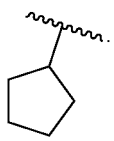

In some embodiments, R is optionally substituted

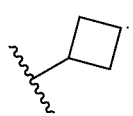

In some embodiments, R is an optionally substituted 3, 4, 5, or 6 membered monocyclic, saturated or partially unsaturated, heterocyclic ring having 1, 2, 3, or 4 heteroatoms independently selected from nitrogen, oxygen, and sulfur. In some embodiments, R is a 3, 4, 5, or 6 membered monocyclic, saturated or partially unsaturated, heterocyclic ring having 1, 2, 3, or 4 heteroatoms independently selected from nitrogen, oxygen, and sulfur, which is substituted 1, 2, 3, 4, 5, or 6 times by halogen. In some embodiments, R is a 3, 4, 5, or 6 membered monocyclic, saturated or partially unsaturated, heterocyclic ring having 1, 2, 3, or 4 heteroatoms independently selected from nitrogen, oxygen, and sulfur, which is substituted 1, 2, 3, 4, 5, or 6 times by —$C_{1-6}$ alkyl, wherein —$C_{1-6}$ alkyl is optionally substituted 1, 2, 3, 4, 5, or 6 times by halogen. In some embodiments, R is optionally substituted

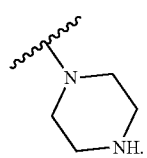

In some embodiments, R is optionally substituted

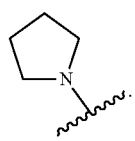 [SMILES: *N1CCCC1]

In some embodiments, R is optionally substituted

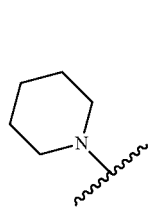

In some embodiments, R is optionally substituted

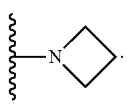

In some embodiments, R is optionally substituted

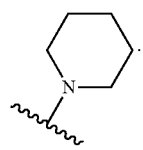 [SMILES: *N1CCCCC1]

In some embodiments, R is

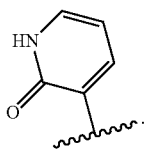

In some embodiments, R is

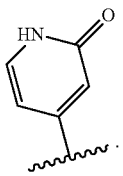

In some embodiments, R is

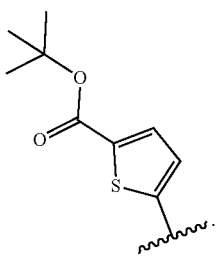 [SMILES: *c1ccc(C(=O)OC(C)(C)C)s1]

In some embodiments, R is

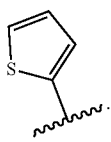 [SMILES: *c1cccs1]

In some embodiments, R is —CF$_3$. In some embodiments, R is F. In some embodiments, R is Cl.

In some embodiments, R is selected from those depicted in Table 1, below.

In some embodiments, the present invention provides a compound of Formula II.

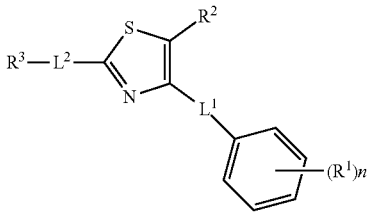

or a pharmaceutically acceptable salt thereof, wherein each of $R^1$, $R^2$, $R^3$, $L^1$, $L^2$, and n is as defined above and described in embodiments herein, both singly and in combination.

In some embodiments, the present invention provides a compound of Formulae II-a to II-d:

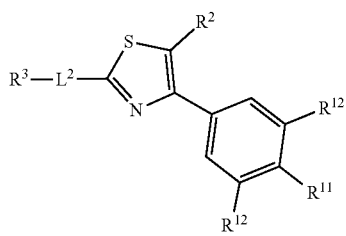

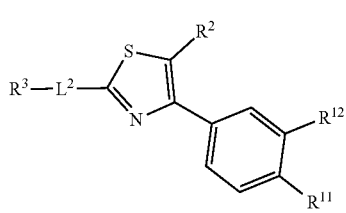

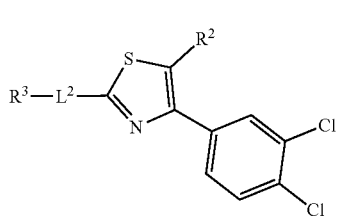

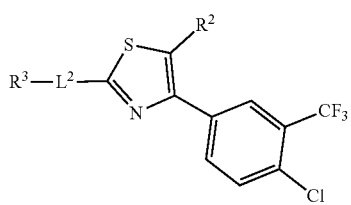

or a pharmaceutically acceptable salt thereof, wherein each of $R^{11}$, $R^{12}$, $R^2$, $R^3$, and $L^2$ is as defined above and described in embodiments herein, both singly and in combination.

In some embodiments, the present invention provides a compound of Formula III:

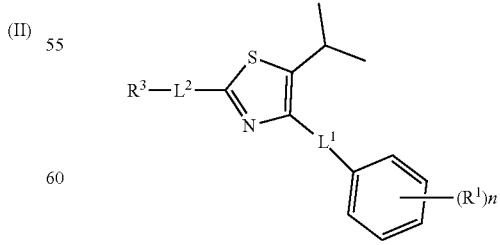

or a pharmaceutically acceptable salt thereof, wherein each of $R^1$, $R^3$, $L^1$, $L^2$, and n is as defined above and described in embodiments herein, both singly and in combination.

In some embodiments, the present invention provides a compound of Formulae III-a to III-d:

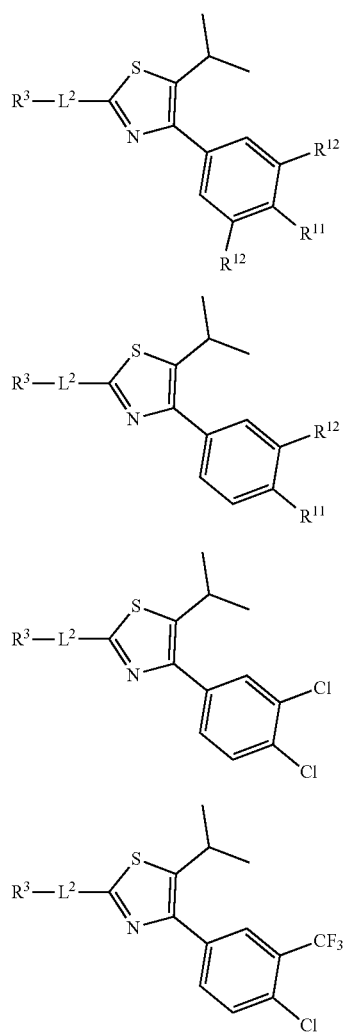

(III-a)
(III-b)
(III-c)
(III-d)

or a pharmaceutically acceptable salt thereof, wherein each of $R^{11}$, $R^{12}$, $R^3$, and $L^2$ is as defined above and described in embodiments herein, both singly and in combination.

In some embodiments, the present invention provides a compound of Formula IV:

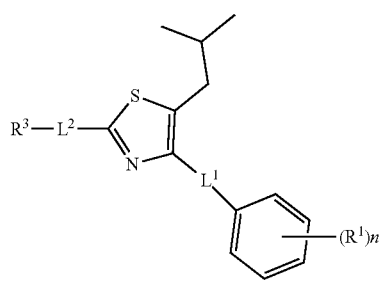

(IV)

or a pharmaceutically acceptable salt thereof, wherein each of $R^1$, $R^3$, $L^1$, $L^2$, and n is as defined above and described in embodiments herein, both singly and in combination.

In some embodiments, the present invention provides a compound of Formulae IV-a to IV-d:

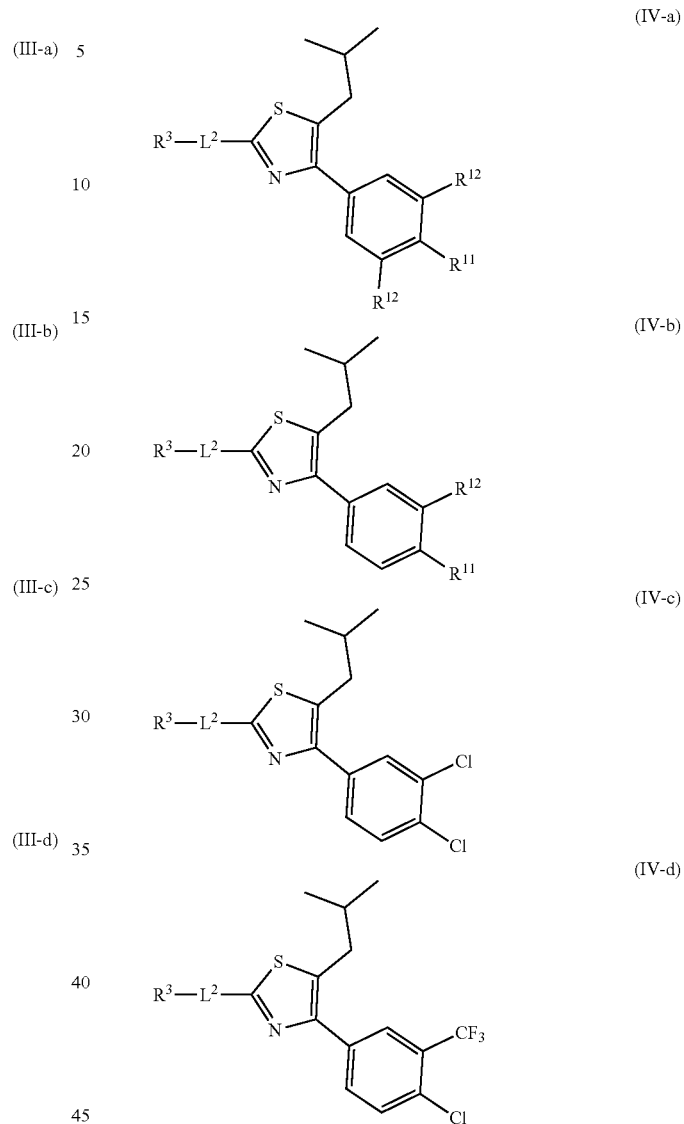

(IV-a)
(IV-b)
(IV-c)
(IV-d)

or a pharmaceutically acceptable salt thereof, wherein each of $R^{11}$, $R^{12}$, $R^3$, and $L^2$ is as defined above and described in embodiments herein, both singly and in combination.

In some embodiments, the present invention provides a compound of Formula V:

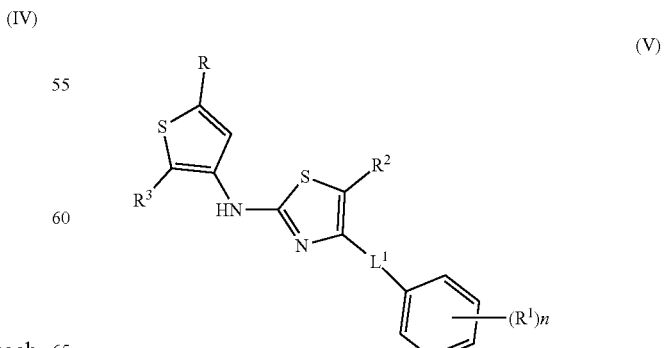

(V)

or a pharmaceutically acceptable salt thereof, wherein each of $R^1$, $R^2$, $R^3$, R, $L^1$, and n is as defined above and described in embodiments herein, both singly and in combination.

In some embodiments, the present invention provides a compound of Formulae V-a to V-d:

(V-a)

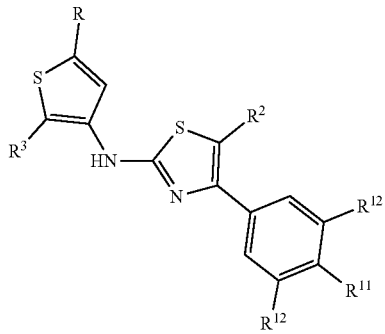

(V-b)

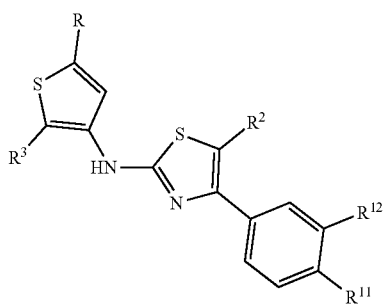

(V-c)

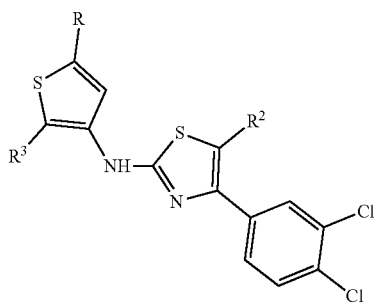

(V-d)

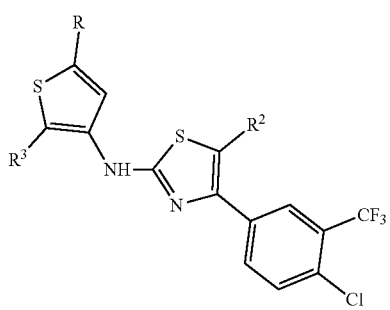

or a pharmaceutically acceptable salt thereof, wherein each of $R^{11}$, $R^{12}$, $R^2$, $R^3$, and R is as defined above and described in embodiments herein, both singly and in combination.

In some embodiments, the present invention provides a compound of Formula VI:

(VI)

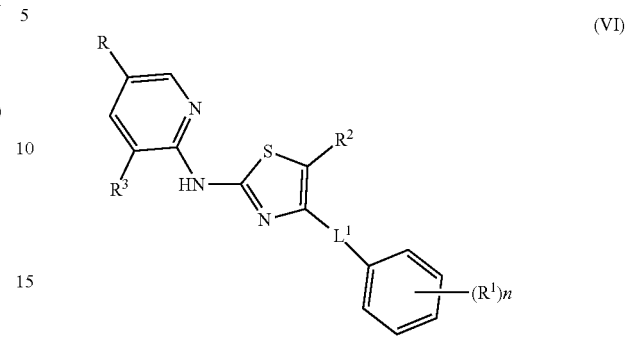

or a pharmaceutically acceptable salt thereof, wherein each of $R^1$, $R^2$, $R^3$, R, $L^1$, and n is as defined above and described in embodiments herein, both singly and in combination.

In some embodiments, the present invention provides a compound of Formulae VI-a to VI-d:

(VI-a)

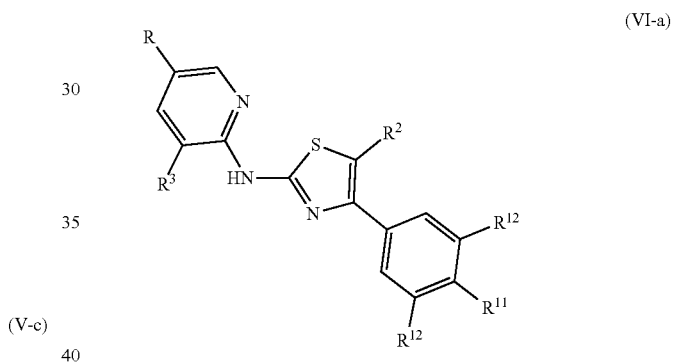

(VI-b)

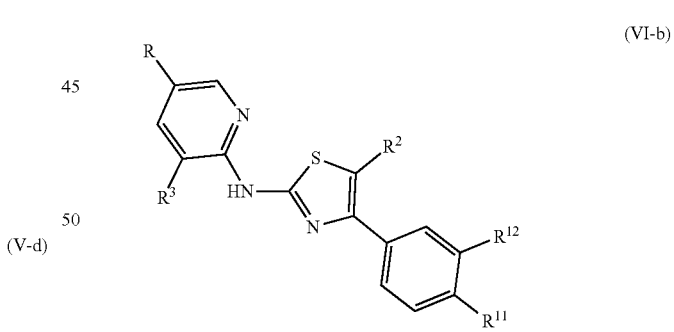

(VI-c)

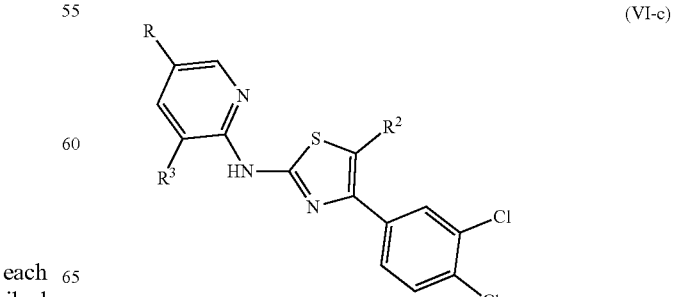

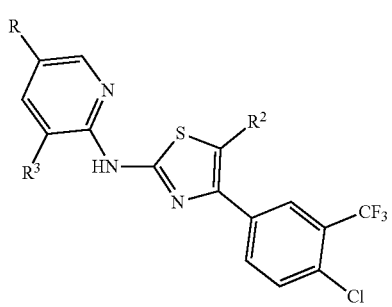
(VI-d)

or a pharmaceutically acceptable salt thereof, wherein each of $R^{11}$, $R^{12}$, $R^2$, $R^3$, and R is as defined above and described in embodiments herein, both singly and in combination.

In some embodiments, the present invention provides a compound of Formula VII:

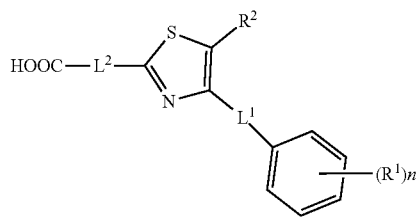
(VII)

or a pharmaceutically acceptable salt thereof, wherein each of $R^1$, $R^2$, $L^1$, $L^2$, and n is as defined above and described in embodiments herein, both singly and in combination.

In some embodiments, the present invention provides a compound of Formulae VII-a to VII-d:

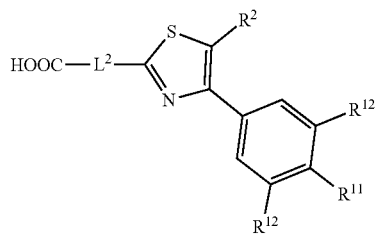
(VII-a)

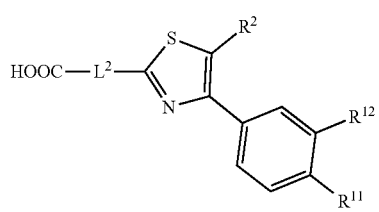
(VII-b)

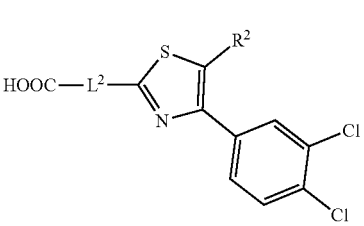
(VII-c)

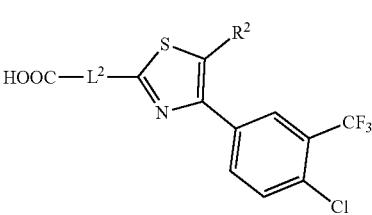
(VII-d)

or a pharmaceutically acceptable salt thereof, wherein each of $R^{11}$, $R^{12}$, $R^2$, and $L^2$ is as defined above and described in embodiments herein, both singly and in combination.

In some embodiments, the present invention provides a compound of Formula VIII:

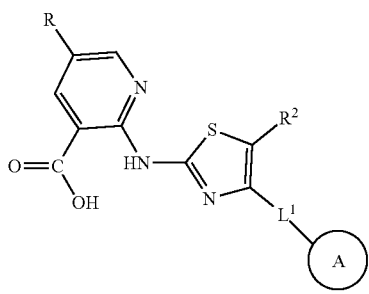
(VIII)

or a pharmaceutically acceptable salt thereof, wherein each of R, $R^2$, $L^1$, and Ring A is as defined above and described in embodiments herein, both singly and in combination.

In some embodiments, the present invention provides a compound of Formula VIII-a:

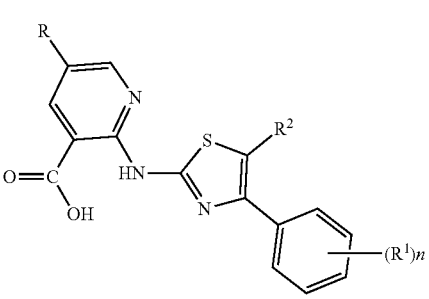
(VIII-a)

or a pharmaceutically acceptable salt thereof, wherein each of R, $R^2$, $R^1$, and n is as defined above and described in embodiments herein, both singly and in combination.

In some embodiments, the present invention provides a compound of Formulae VIII-b or VIII-C:

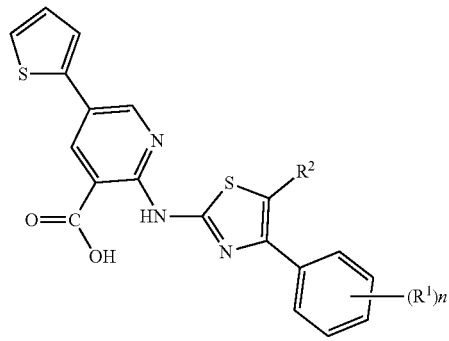

(VIII-b)

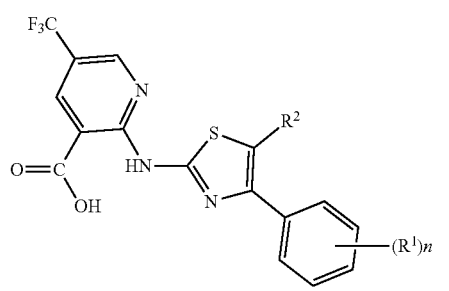

(VIII-c)

or a pharmaceutically acceptable salt thereof, wherein each of $R^2$, $R^1$, and n is as defined above and described in embodiments herein, both singly and in combination.

In some embodiments, the present invention provides a compound of Formula VIII-d:

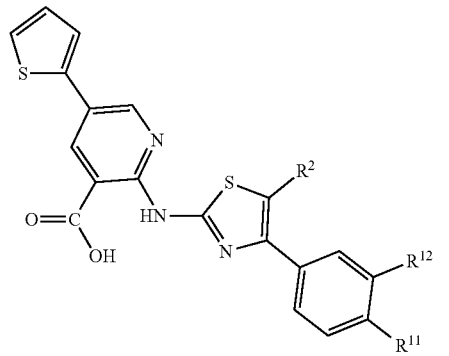

(VIII-d)

or a pharmaceutically acceptable salt thereof, wherein each of $R^2$, $R^{11}$, and $R^{12}$ is as defined above and described in embodiments herein, both singly and in combination. In some embodiments, $R^{11}$ is halogen. In some embodiments, $R^{12}$ is —OR, wherein R is as described herein. In some embodiments, $R^{12}$ is —OR, wherein R is optionally substituted —$C_{1-6}$ aliphatic. In some embodiments, $R^{12}$ is —OR, wherein R is optionally substituted —$C_{1-6}$ alkyl. In some embodiments, $R^{12}$ is —OR, wherein R is unsubstituted —$C_{1-6}$ alkyl, or —$C_{1-6}$ alkyl substituted 1, 2, 3, 4, 5, or 6 times by halogen. In some embodiments, $R^{12}$ is —OR, wherein R is —$C_{1-6}$ alkyl wherein as least one methylene unit is replaced by —O—.

Exemplary compounds of the invention are set forth in Table 1, below.

In some embodiments, the present invention provides a compound of Table 1, or a pharmaceutically acceptable salt thereof.

In some embodiments, the present invention provides a compound selected from those depicted in the Exemplification section, or a pharmaceutically acceptable salt thereof.

TABLE 1

Exemplary Compounds

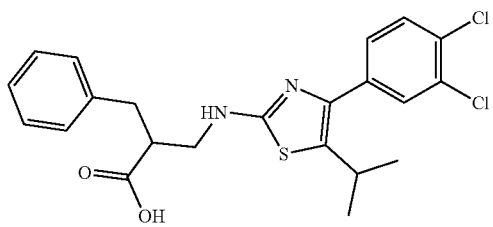 [SMILES: CC(C)c1sc(NCC(Cc2ccccc2)C(=O)O)nc1-c1ccc(Cl)c(Cl)c1]

I-1

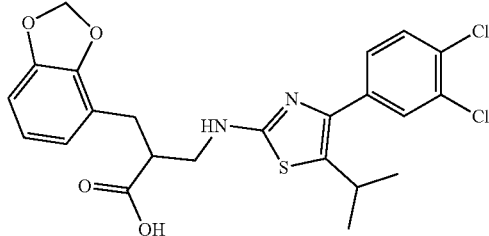 [SMILES: CC(C)c1sc(NCC(Cc2cccc3c2OCO3)C(=O)O)nc1-c1ccc(Cl)c(Cl)c1]

I-2

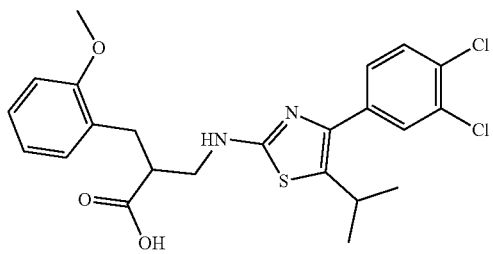 [SMILES: COc1ccccc1CC(CNc1nc(-c2ccc(Cl)c(Cl)c2)c(C(C)C)s1)C(=O)O]

I-3

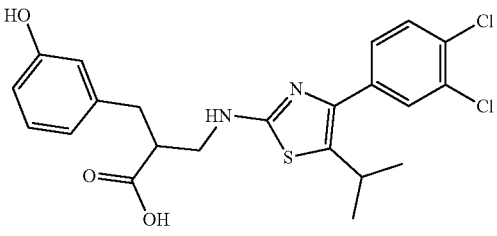 [SMILES: CC(C)c1sc(NCC(Cc2cccc(O)c2)C(=O)O)nc1-c1ccc(Cl)c(Cl)c1]

I-4

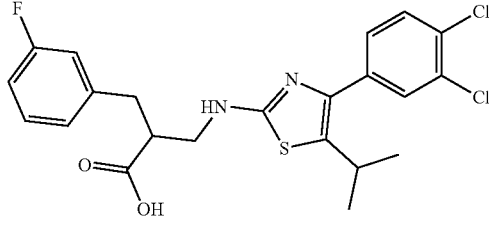 [SMILES: CC(C)c1sc(NCC(Cc2cccc(F)c2)C(=O)O)nc1-c1ccc(Cl)c(Cl)c1]

I-5

TABLE 1-continued
Exemplary Compounds
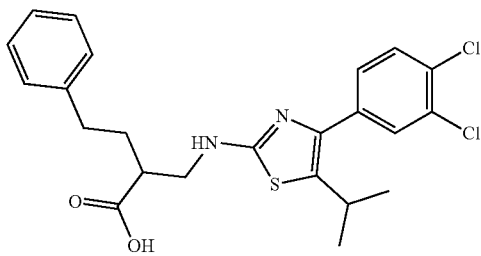 [SMILES: CC(C)c1sc(NCC(CCc2ccccc2)C(=O)O)nc1-c1ccc(Cl)c(Cl)c1]
I-6
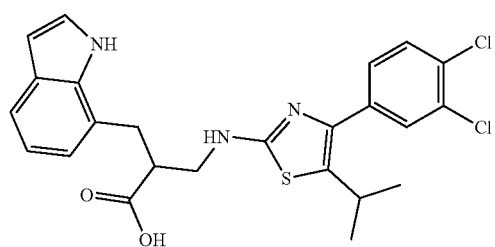 [SMILES: CC(C)c1sc(NCC(Cc2cccc3cc[nH]c23)C(=O)O)nc1-c1ccc(Cl)c(Cl)c1]
I-7
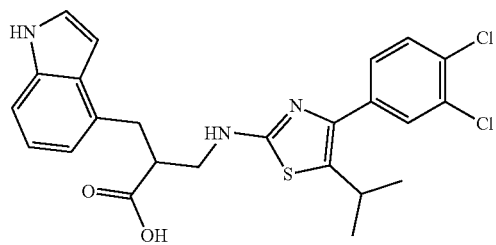 [SMILES: CC(C)c1sc(NCC(Cc2cccc3[nH]ccc23)C(=O)O)nc1-c1ccc(Cl)c(Cl)c1]
I-8

I-9
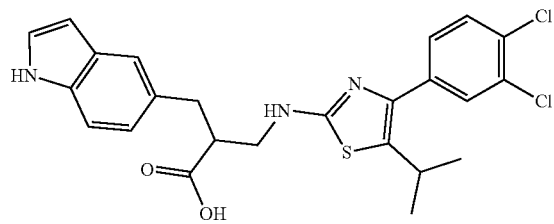 [SMILES: CC(C)c1sc(NCC(Cc2ccc3[nH]ccc3c2)C(=O)O)nc1-c1ccc(Cl)c(Cl)c1]
I-10
TABLE 1-continued
Exemplary Compounds
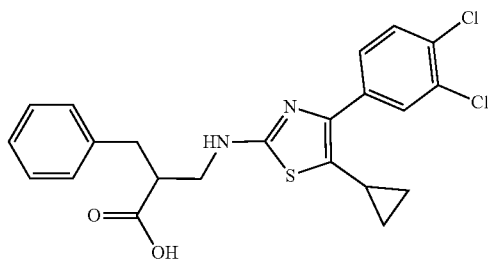 [SMILES: O=C(O)C(CNc1nc(-c2ccc(Cl)c(Cl)c2)c(C2CC2)s1)Cc1ccccc1]
I-11
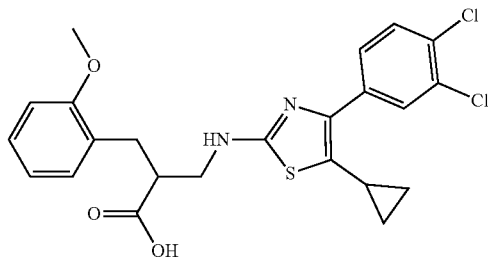 [SMILES: COc1ccccc1CC(CNc1nc(-c2ccc(Cl)c(Cl)c2)c(C2CC2)s1)C(=O)O]
I-12
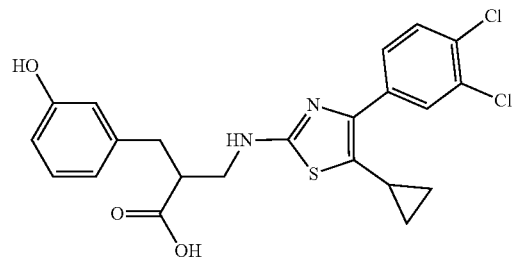 [SMILES: O=C(O)C(CNc1nc(-c2ccc(Cl)c(Cl)c2)c(C2CC2)s1)Cc1cccc(O)c1]
I-13
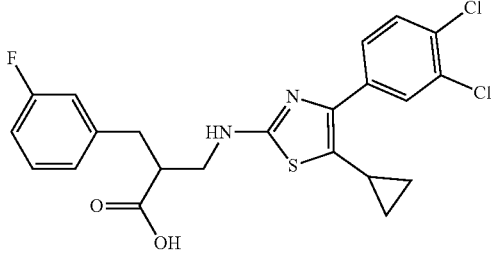 [SMILES: O=C(O)C(CNc1nc(-c2ccc(Cl)c(Cl)c2)c(C2CC2)s1)Cc1cccc(F)c1]
I-14
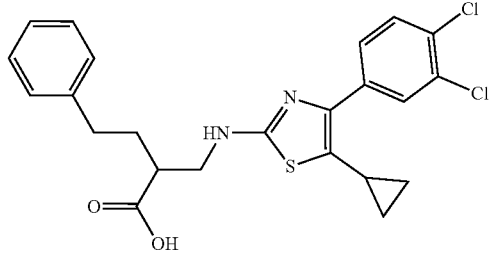 [SMILES: O=C(O)C(CCc1ccccc1)CNc1nc(-c2ccc(Cl)c(Cl)c2)c(C2CC2)s1]
I-15

TABLE 1-continued
Exemplary Compounds
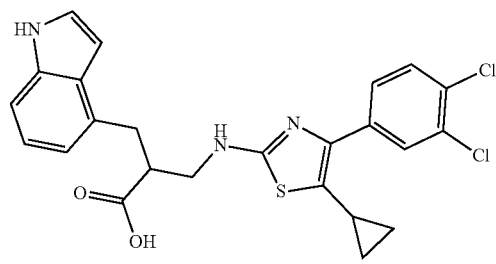 [SMILES: O=C(O)C(CNc1nc(-c2ccc(Cl)c(Cl)c2)c(C2CC2)s1)Cc1cccc2[nH]ccc12]
I-16
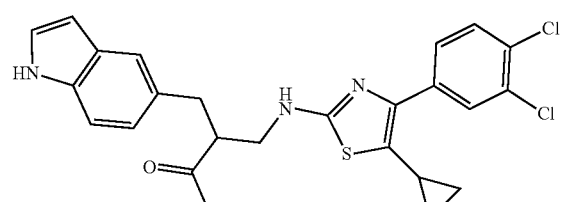
I-17
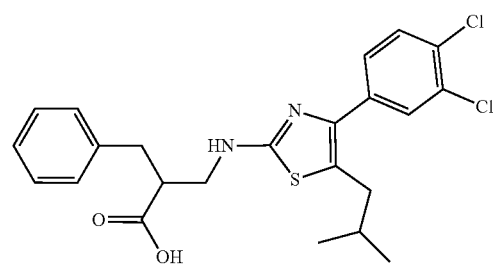 [SMILES: CC(C)Cc1sc(NCC(Cc2ccccc2)C(=O)O)nc1-c1ccc(Cl)c(Cl)c1]
I-18
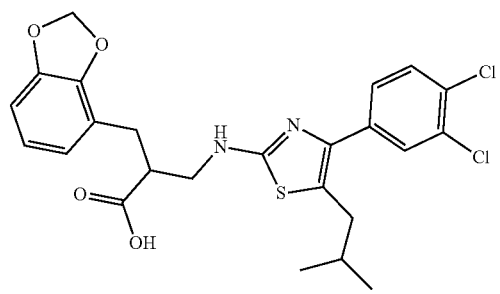 [SMILES: CC(C)Cc1sc(NCC(Cc2cccc3c2OCO3)C(=O)O)nc1-c1ccc(Cl)c(Cl)c1]
I-19
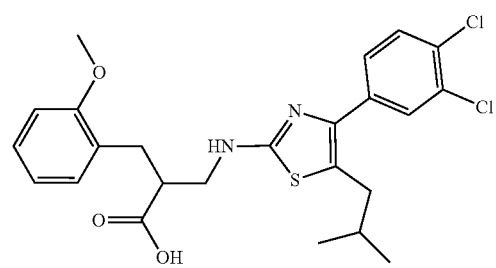 [SMILES: COc1ccccc1CC(CNc1nc(-c2ccc(Cl)c(Cl)c2)c(CC(C)C)s1)C(=O)O]
I-20
TABLE 1-continued
Exemplary Compounds
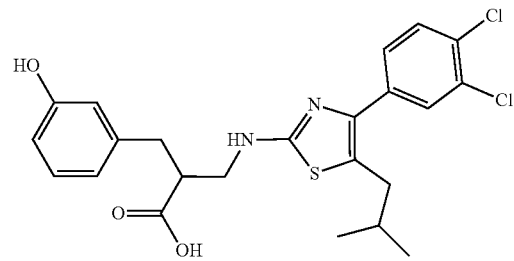 [SMILES: CC(C)Cc1sc(NCC(Cc2cccc(O)c2)C(=O)O)nc1-c1ccc(Cl)c(Cl)c1]
I-21
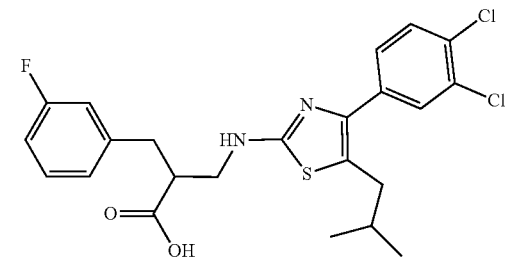 [SMILES: CC(C)Cc1sc(NCC(Cc2cccc(F)c2)C(=O)O)nc1-c1ccc(Cl)c(Cl)c1]
I-22
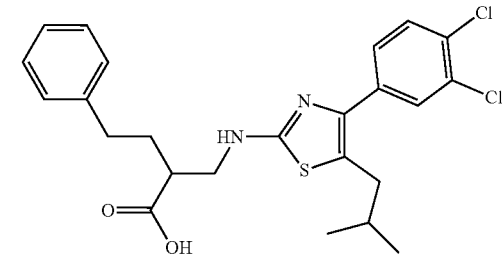 [SMILES: CC(C)Cc1sc(NCC(CCc2ccccc2)C(=O)O)nc1-c1ccc(Cl)c(Cl)c1]
I-23
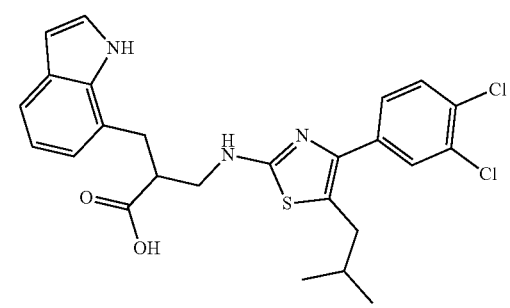 [SMILES: CC(C)Cc1sc(NCC(Cc2cccc3cc[nH]c23)C(=O)O)nc1-c1ccc(Cl)c(Cl)c1]
I-24
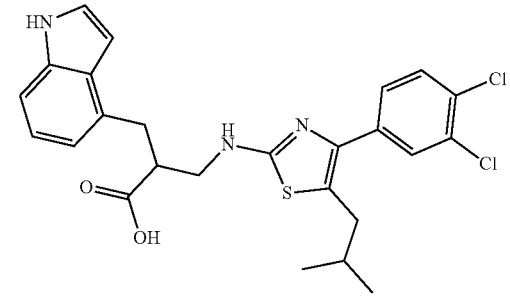 [SMILES: CC(C)Cc1sc(NCC(Cc2cccc3[nH]ccc23)C(=O)O)nc1-c1ccc(Cl)c(Cl)c1]
I-25

TABLE 1-continued
Exemplary Compounds
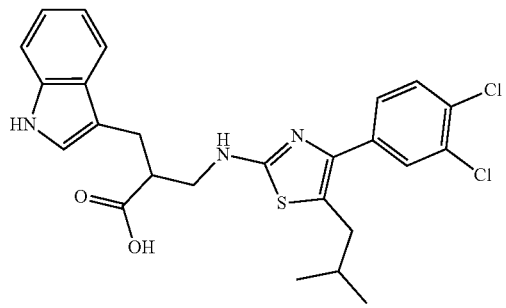 [SMILES: CC(C)Cc1sc(NCC(Cc2c[nH]c3ccccc23)C(=O)O)nc1-c1ccc(Cl)c(Cl)c1]
I-26
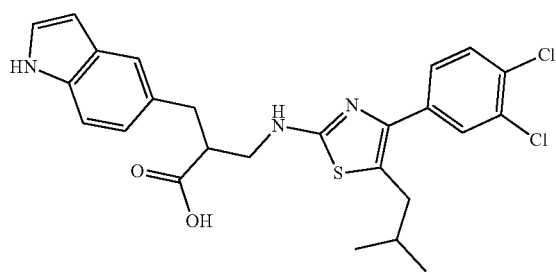 [SMILES: CC(C)Cc1sc(NCC(Cc2ccc3[nH]ccc3c2)C(=O)O)nc1-c1ccc(Cl)c(Cl)c1]
I-27
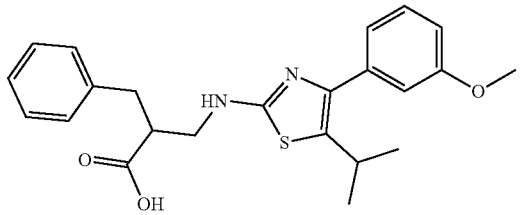 [SMILES: COc1cccc(-c2nc(NCC(Cc3ccccc3)C(=O)O)sc2C(C)C)c1]
I-28
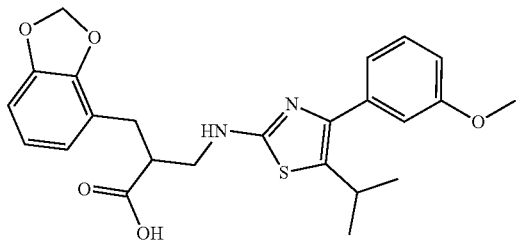 [SMILES: COc1cccc(-c2nc(NCC(Cc3cccc4c3OCO4)C(=O)O)sc2C(C)C)c1]
I-29
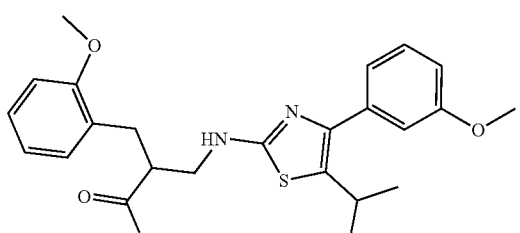
I-30
TABLE 1-continued
Exemplary Compounds
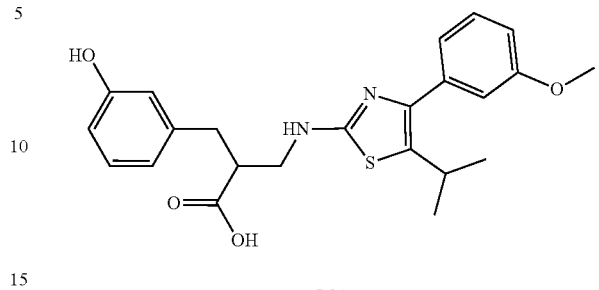
I-31
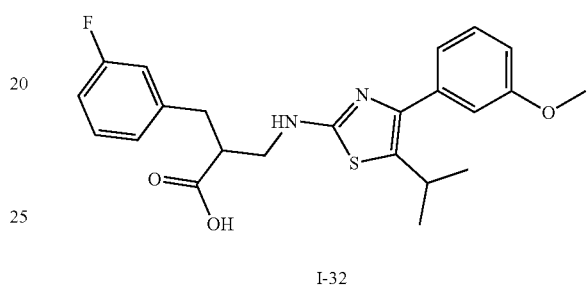
I-32
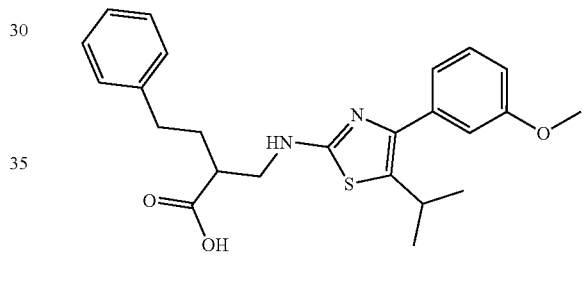
I-33
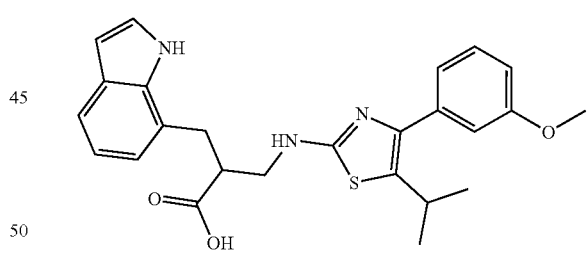
I-34
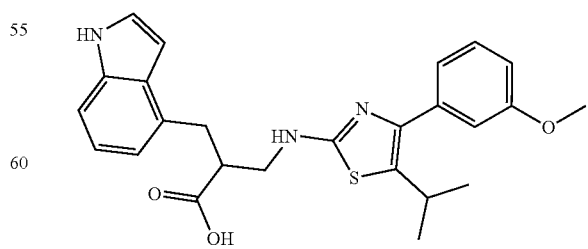
I-35

TABLE 1-continued
Exemplary Compounds
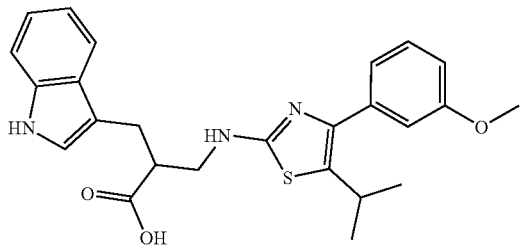 [SMILES: COc1cccc(-c2nc(NCC(Cc3c[nH]c4ccccc34)C(=O)O)sc2C(C)C)c1]
I-36
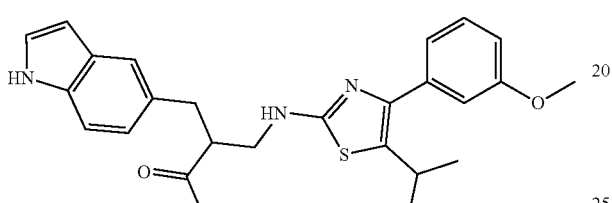
I-37
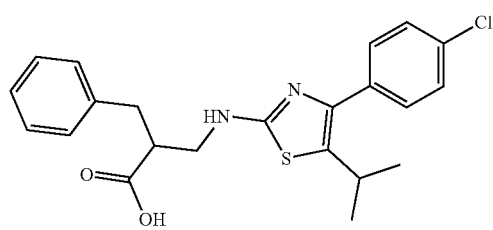 [SMILES: CC(C)c1sc(NCC(Cc2ccccc2)C(=O)O)nc1-c1ccc(Cl)cc1]
I-38
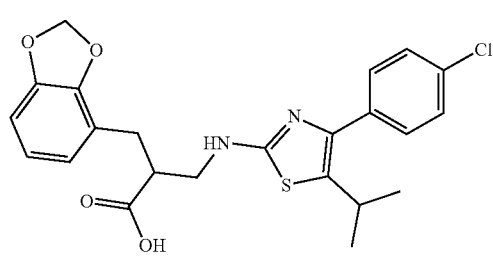 [SMILES: CC(C)c1sc(NCC(Cc2cccc3c2OCO3)C(=O)O)nc1-c1ccc(Cl)cc1]
I-39
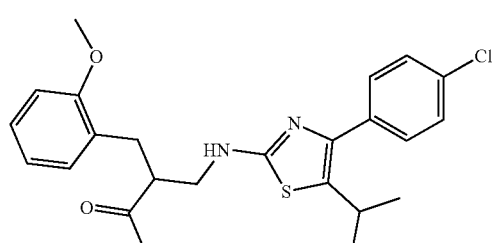
I-40
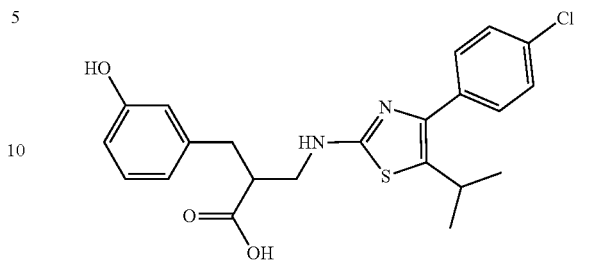
I-41
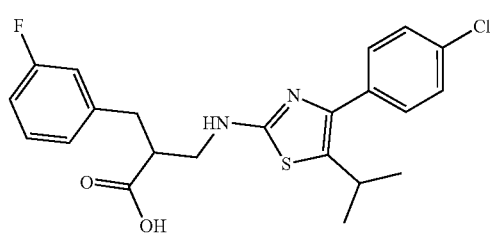 [SMILES: CC(C)c1sc(NCC(Cc2cccc(F)c2)C(=O)O)nc1-c1ccc(Cl)cc1]
I-42
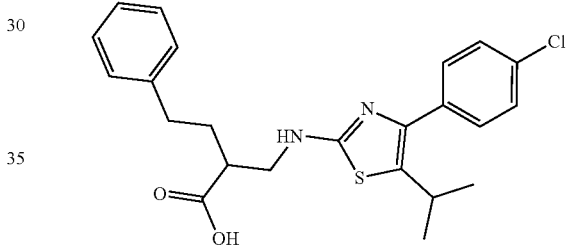
I-43
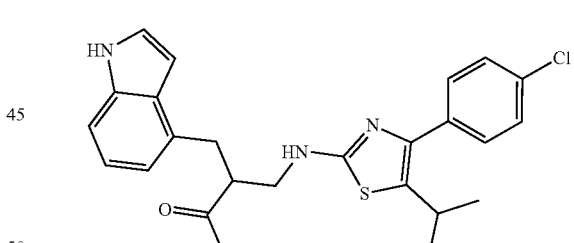
I-44
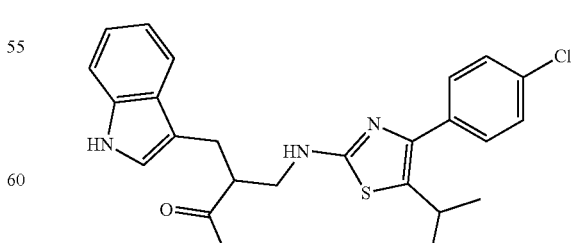
I-45

TABLE 1-continued
Exemplary Compounds
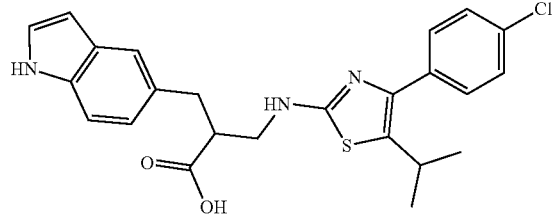 [SMILES: CC(C)c1sc(NCC(Cc2ccc3[nH]ccc3c2)C(=O)O)nc1-c1ccc(Cl)cc1]
I-46
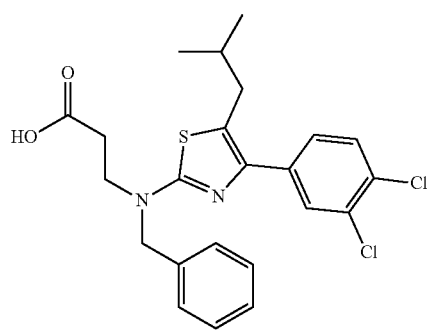 [SMILES: CC(C)Cc1sc(N(CCC(=O)O)Cc2ccccc2)nc1-c1ccc(Cl)c(Cl)c1]
I-47
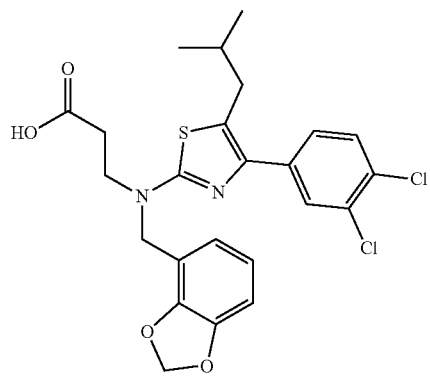 [SMILES: CC(C)Cc1sc(N(CCC(=O)O)Cc2cccc3c2OCO3)nc1-c1ccc(Cl)c(Cl)c1]
I-48
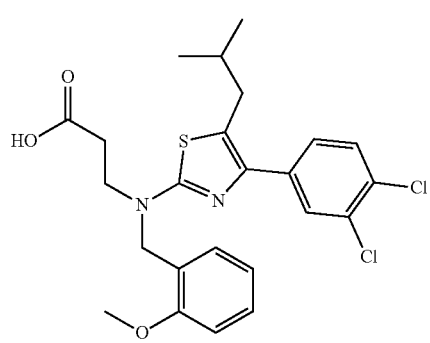 [SMILES: COc1ccccc1CN(CCC(=O)O)c1nc(-c2ccc(Cl)c(Cl)c2)c(CC(C)C)s1]
I-49
TABLE 1-continued
Exemplary Compounds
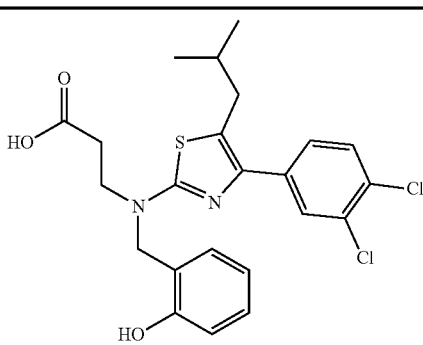
I-50
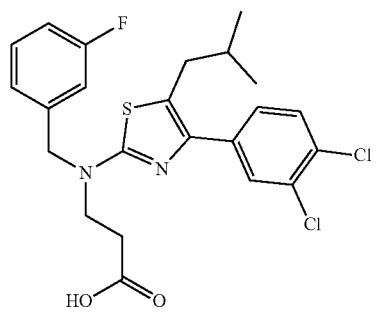 [SMILES: CC(C)Cc1sc(N(CCC(=O)O)Cc2cccc(F)c2)nc1-c1ccc(Cl)c(Cl)c1]
I-51
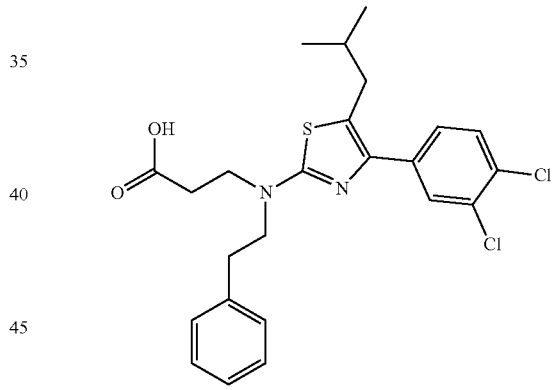
I-52
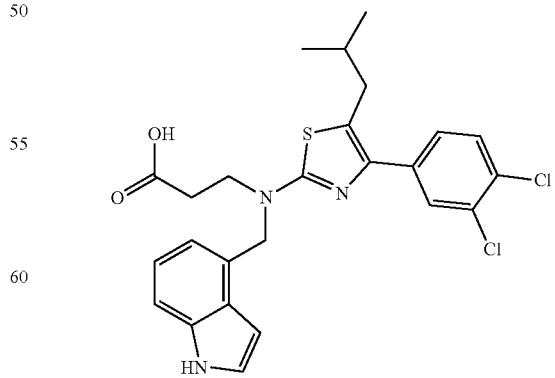
I-53

TABLE 1-continued
Exemplary Compounds
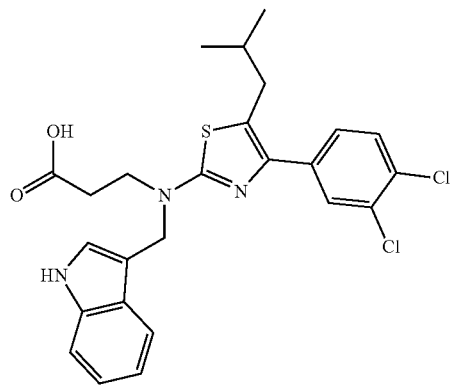 [SMILES: CC(C)Cc1sc(N(CCC(=O)O)Cc2c[nH]c3ccccc23)nc1-c1ccc(Cl)c(Cl)c1]
I-54
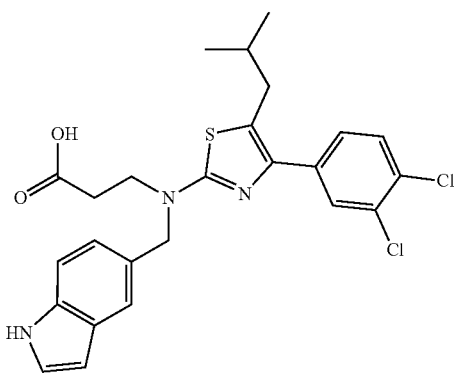 [SMILES: CC(C)Cc1sc(N(CCC(=O)O)Cc2ccc3[nH]ccc3c2)nc1-c1ccc(Cl)c(Cl)c1]
I-55
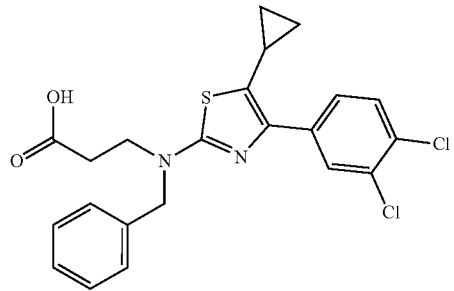 [SMILES: O=C(O)CCN(Cc1ccccc1)c1nc(-c2ccc(Cl)c(Cl)c2)c(C2CC2)s1]
I-56
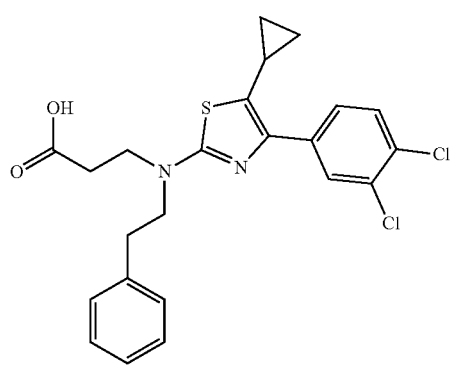 [SMILES: O=C(O)CCN(CCc1ccccc1)c1nc(-c2ccc(Cl)c(Cl)c2)c(C2CC2)s1]
I-57
TABLE 1-continued
Exemplary Compounds
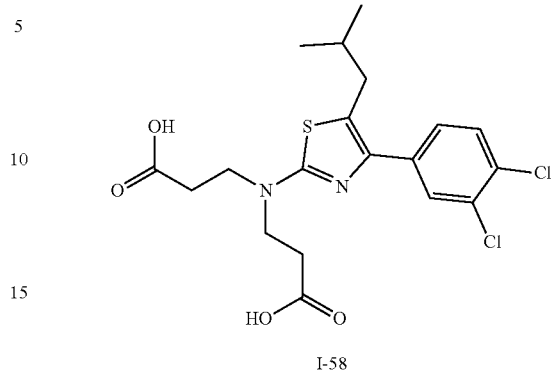
I-58
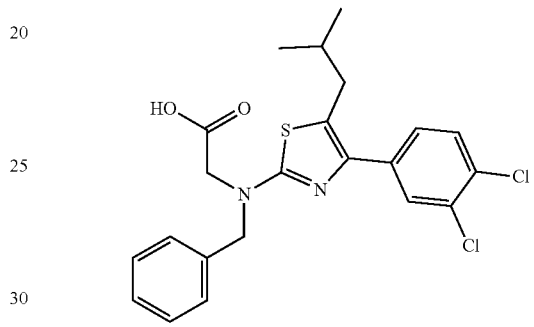
I-59
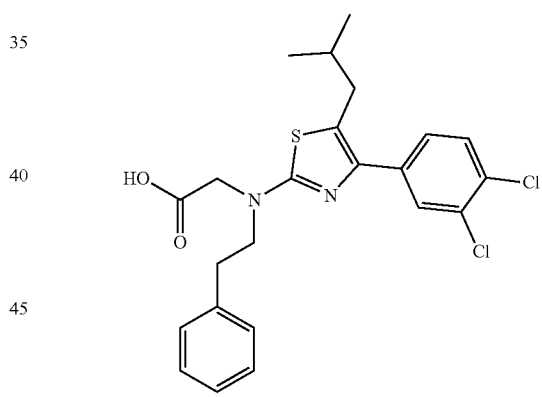
I-60
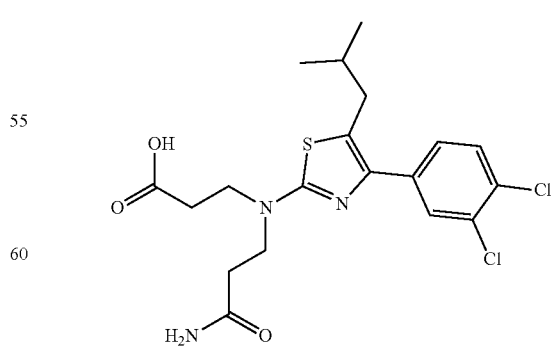
I-61

TABLE 1-continued
Exemplary Compounds
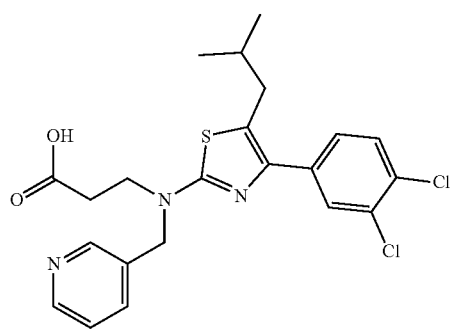 [SMILES: CC(C)Cc1sc(N(CCC(=O)O)Cc2cccnc2)nc1-c1ccc(Cl)c(Cl)c1]
I-62
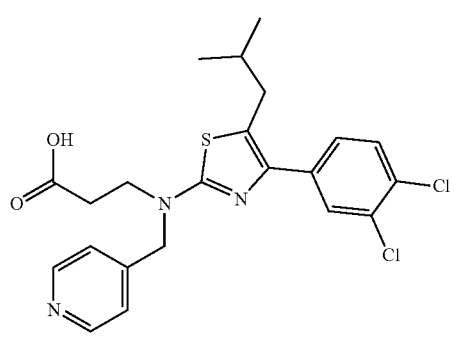 [SMILES: CC(C)Cc1sc(N(CCC(=O)O)Cc2ccncc2)nc1-c1ccc(Cl)c(Cl)c1]
I-63
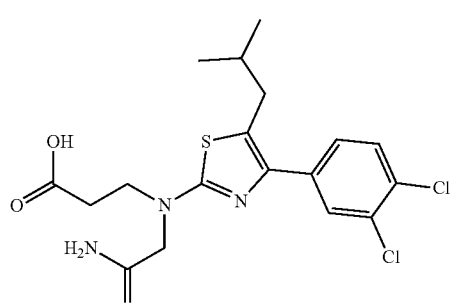
I-64
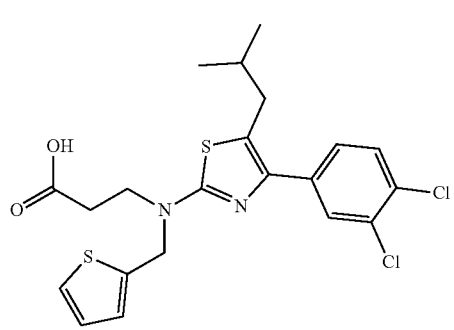 [SMILES: CC(C)Cc1sc(N(CCC(=O)O)Cc2cccs2)nc1-c1ccc(Cl)c(Cl)c1]
I-65
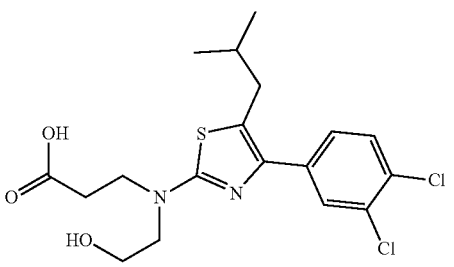 [SMILES: CC(C)Cc1sc(N(CCO)CCC(=O)O)nc1-c1ccc(Cl)c(Cl)c1]
I-66
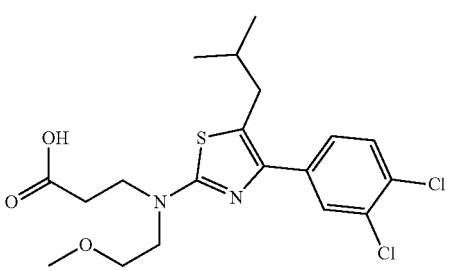 [SMILES: COCCN(CCC(=O)O)c1nc(-c2ccc(Cl)c(Cl)c2)c(CC(C)C)s1]
I-67
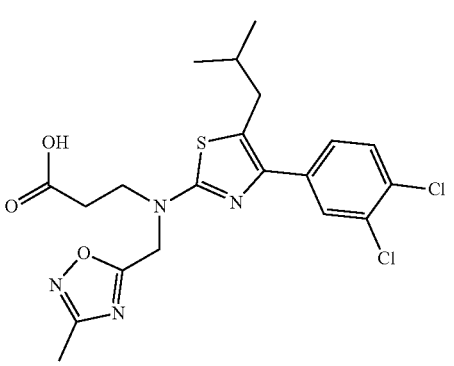 [SMILES: Cc1noc(CN(CCC(=O)O)c2nc(-c3ccc(Cl)c(Cl)c3)c(CC(C)C)s2)n1]
I-68
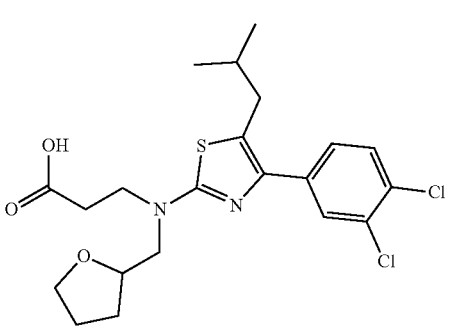 [SMILES: CC(C)Cc1sc(N(CCC(=O)O)CC2CCCO2)nc1-c1ccc(Cl)c(Cl)c1]
I-69

TABLE 1-continued
Exemplary Compounds
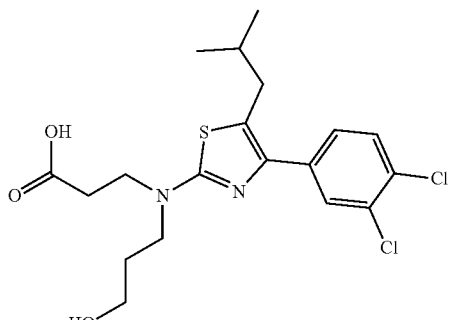
I-70
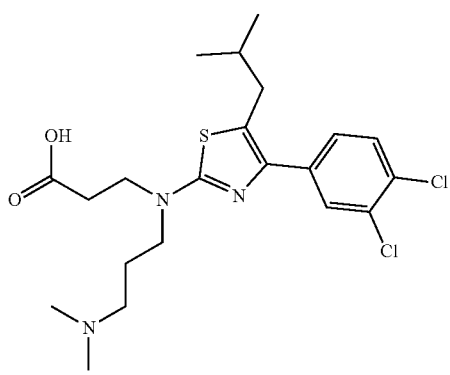 [SMILES: CC(C)Cc1sc(N(CCCN(C)C)CCC(=O)O)nc1-c1ccc(Cl)c(Cl)c1]
I-71
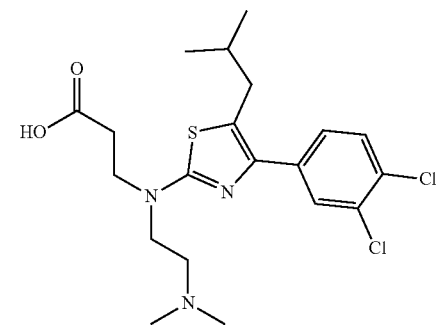 [SMILES: CC(C)Cc1sc(N(CCC(=O)O)CCN(C)C)nc1-c1ccc(Cl)c(Cl)c1]
I-72
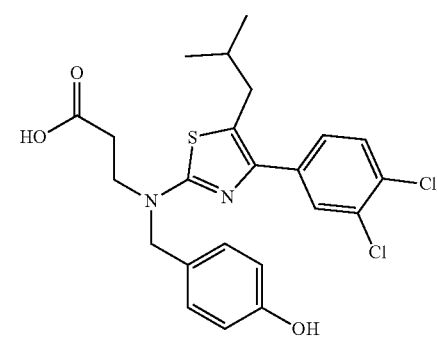 [SMILES: CC(C)Cc1sc(N(CCC(=O)O)Cc2ccc(O)cc2)nc1-c1ccc(Cl)c(Cl)c1]
I-73
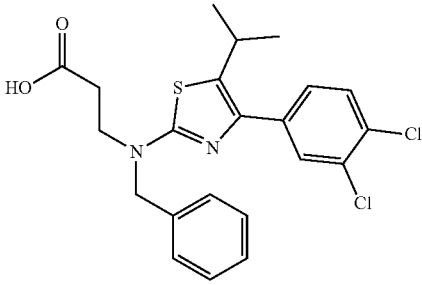 [SMILES: CC(C)c1sc(N(CCC(=O)O)Cc2ccccc2)nc1-c1ccc(Cl)c(Cl)c1]
I-74
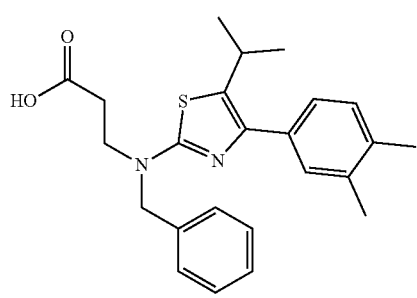 [SMILES: Cc1ccc(-c2nc(N(CCC(=O)O)Cc3ccccc3)sc2C(C)C)cc1C]
I-75
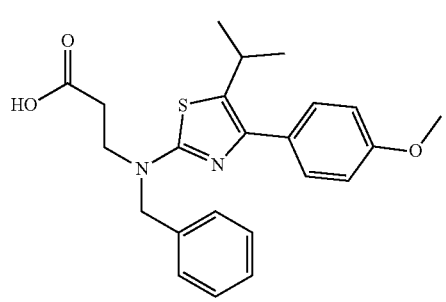 [SMILES: COc1ccc(-c2nc(N(CCC(=O)O)Cc3ccccc3)sc2C(C)C)cc1]
I-76
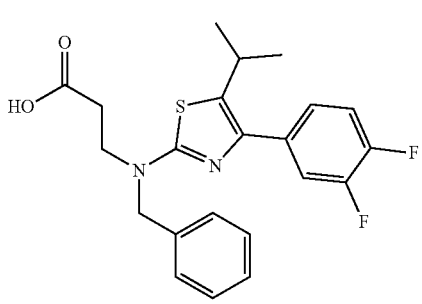
I-77

TABLE 1-continued
Exemplary Compounds
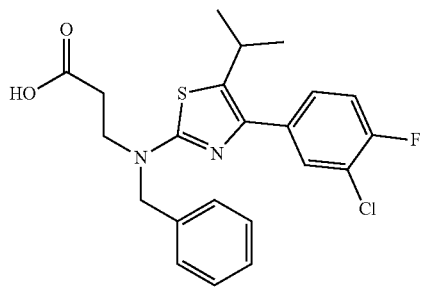 [SMILES: CC(C)c1sc(N(CCC(=O)O)Cc2ccccc2)nc1-c1ccc(F)c(F)c1]
I-78
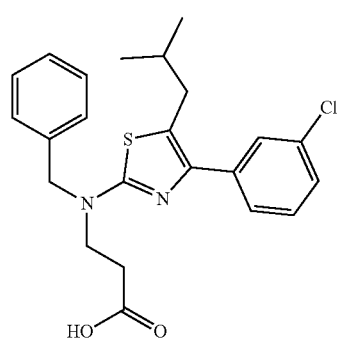 [SMILES: CC(C)Cc1sc(N(CCC(=O)O)Cc2ccccc2)nc1-c1cccc(Cl)c1]
I-79
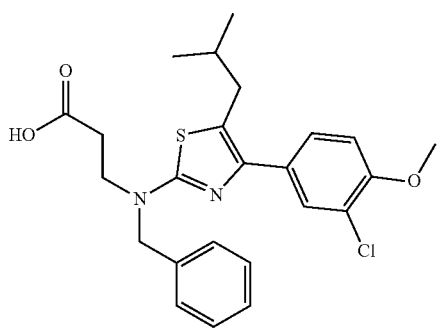 [SMILES: COc1ccc(-c2nc(N(CCC(=O)O)Cc3ccccc3)sc2CC(C)C)cc1Cl]
I-80
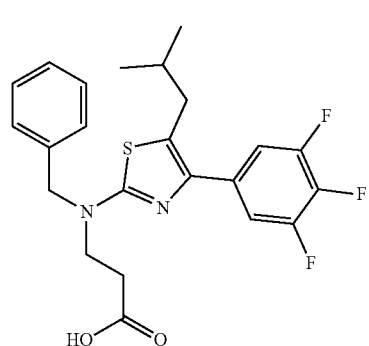 [SMILES: CC(C)Cc1sc(N(CCC(=O)O)Cc2ccccc2)nc1-c1cc(F)c(F)c(F)c1]
I-81
TABLE 1-continued
Exemplary Compounds
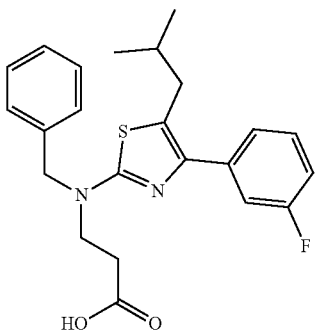 [SMILES: CC(C)Cc1sc(N(CCC(=O)O)Cc2ccccc2)nc1-c1cccc(F)c1]
I-82
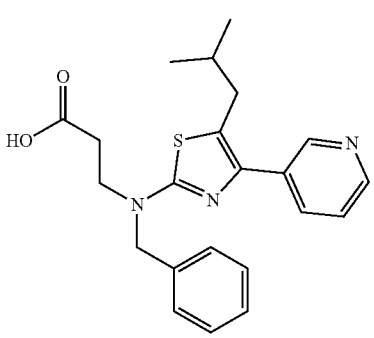 [SMILES: CC(C)Cc1sc(N(CCC(=O)O)Cc2ccccc2)nc1-c1cccnc1]
I-83
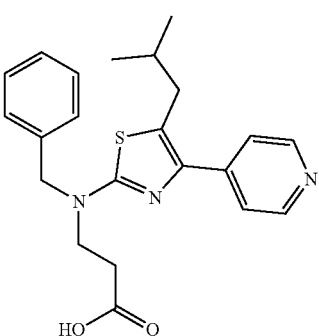 [SMILES: CC(C)Cc1sc(N(CCC(=O)O)Cc2ccccc2)nc1-c1ccncc1]
I-84
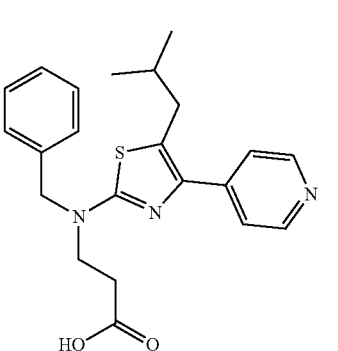
I-85

TABLE 1-continued
Exemplary Compounds
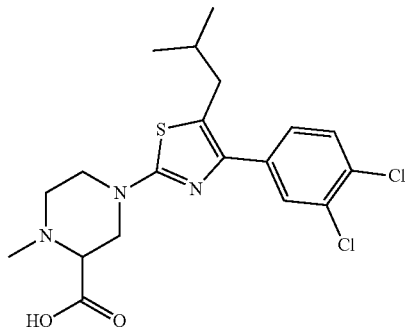 [SMILES: CC(C)Cc1sc(N2CCN(C)C(C(=O)O)C2)nc1-c1ccc(Cl)c(Cl)c1]
I-86
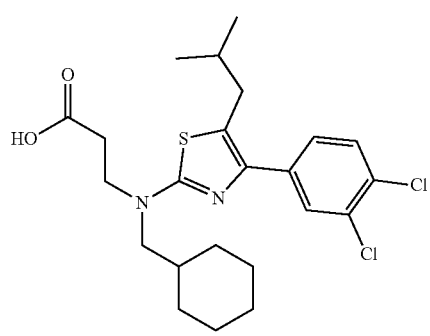 [SMILES: CC(C)Cc1sc(N(CCC(=O)O)CC2CCCCC2)nc1-c1ccc(Cl)c(Cl)c1]
I-87
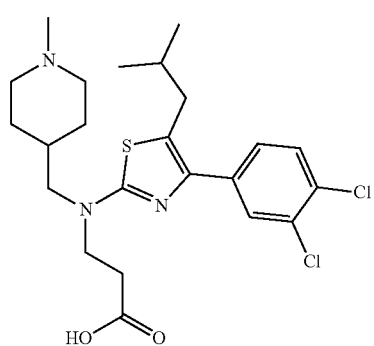 [SMILES: CC(C)Cc1sc(N(CCC(=O)O)CC2CCN(C)CC2)nc1-c1ccc(Cl)c(Cl)c1]
I-88
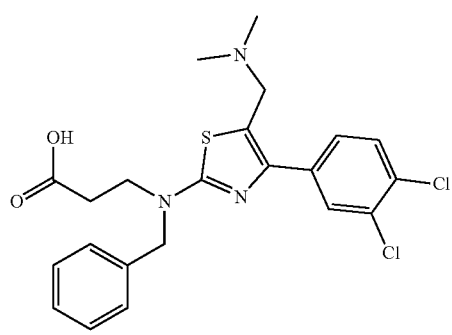 [SMILES: CN(C)Cc1sc(N(CCC(=O)O)Cc2ccccc2)nc1-c1ccc(Cl)c(Cl)c1]
I-89
TABLE 1-continued
Exemplary Compounds
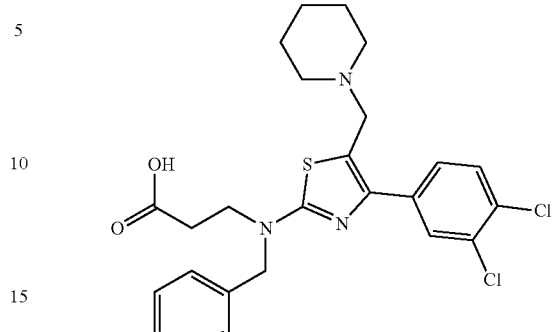
I-90
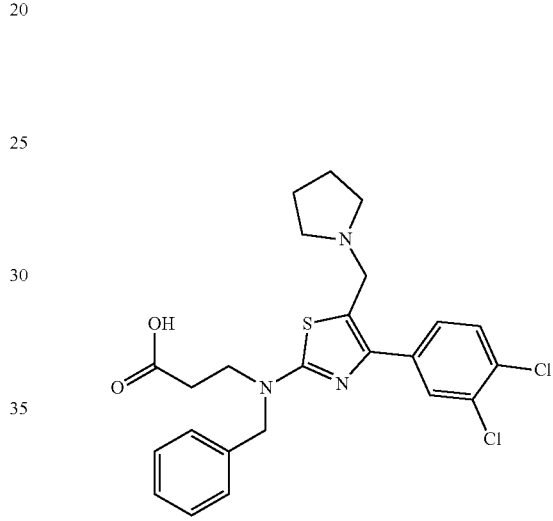
I-91
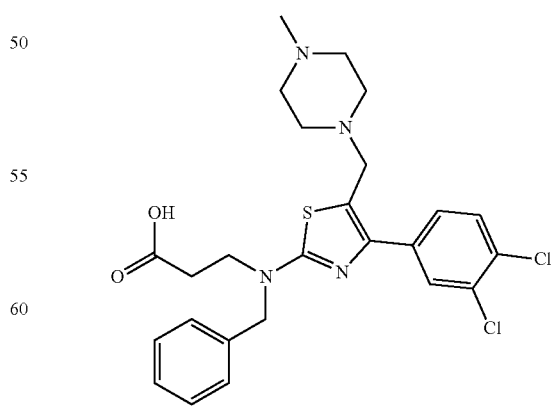
I-92

TABLE 1-continued
Exemplary Compounds
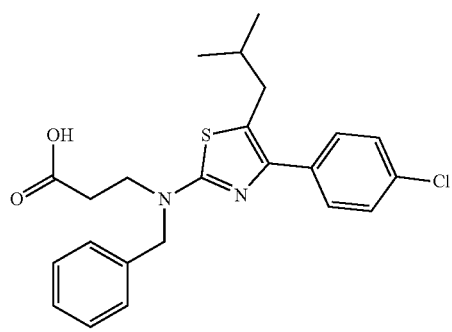 [SMILES: CC(C)Cc1sc(N(CCC(=O)O)Cc2ccccc2)nc1-c1ccc(Cl)cc1]
I-93
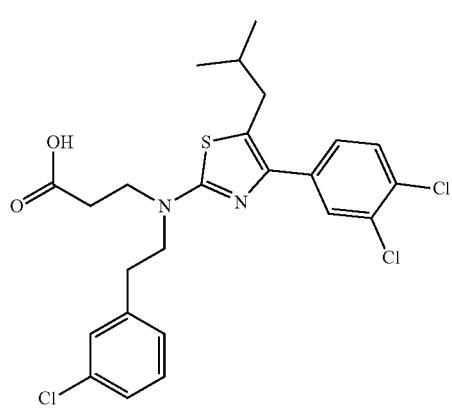 [SMILES: CC(C)Cc1sc(N(CCC(=O)O)CCc2cccc(Cl)c2)nc1-c1ccc(Cl)c(Cl)c1]
I-94
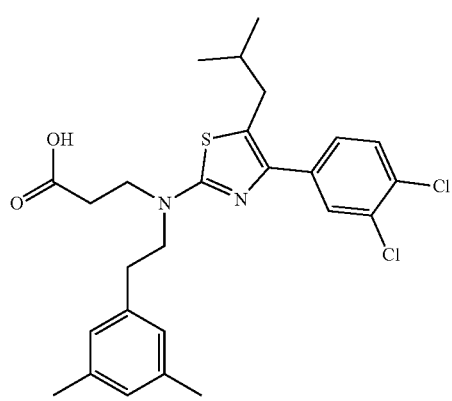 [SMILES: Cc1cc(C)cc(CCN(CCC(=O)O)c2nc(-c3ccc(Cl)c(Cl)c3)c(CC(C)C)s2)c1]
I-95
TABLE 1-continued
Exemplary Compounds
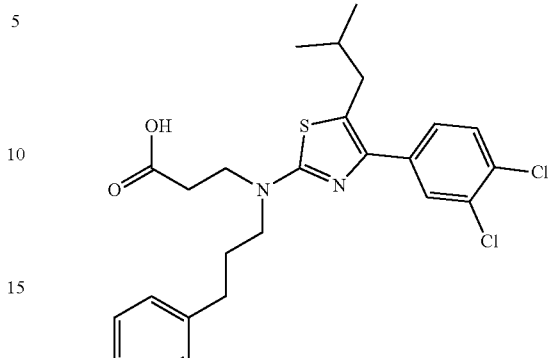
I-96
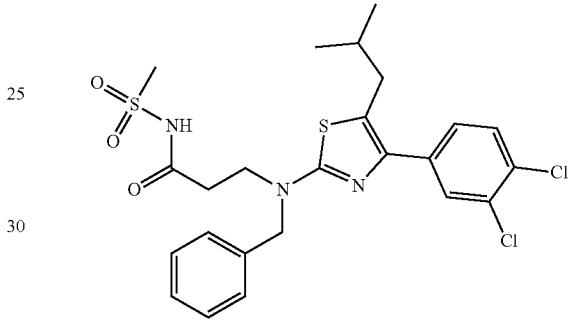
I-97
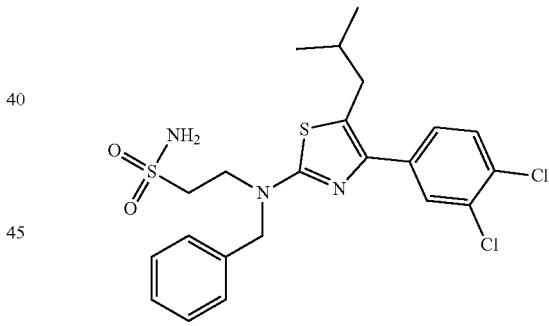
I-98
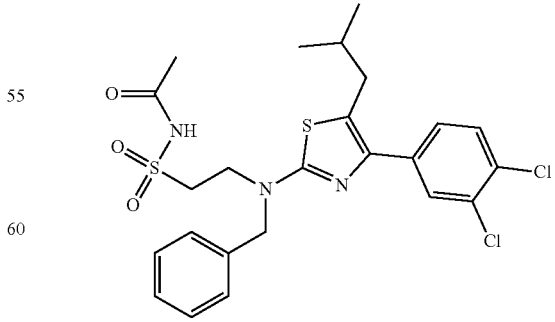
I-99

TABLE 1-continued
Exemplary Compounds
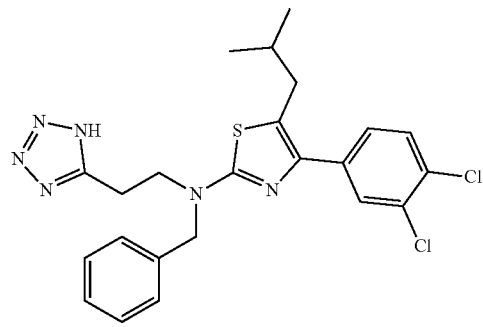 [SMILES: CC(C)Cc1sc(N(CCc2nnn[nH]2)Cc2ccccc2)nc1-c1ccc(Cl)c(Cl)c1]
I-100
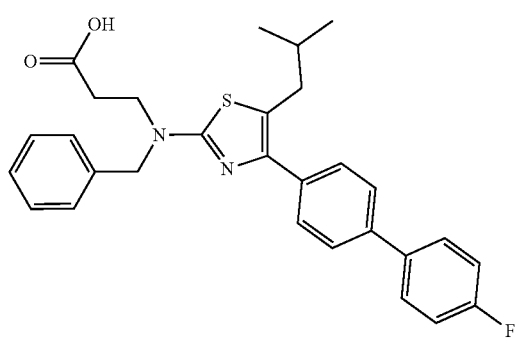 [SMILES: CC(C)Cc1sc(N(CCC(=O)O)Cc2ccccc2)nc1-c1ccc(-c2ccc(F)cc2)cc1]
I-101
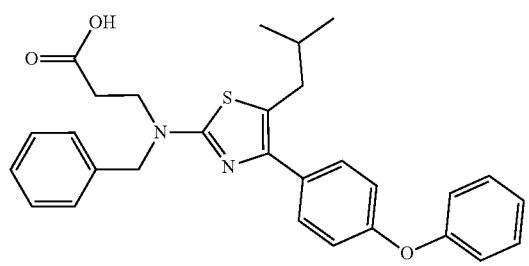 [SMILES: CC(C)Cc1sc(N(CCC(=O)O)Cc2ccccc2)nc1-c1ccc(Oc2ccccc2)cc1]
I-102
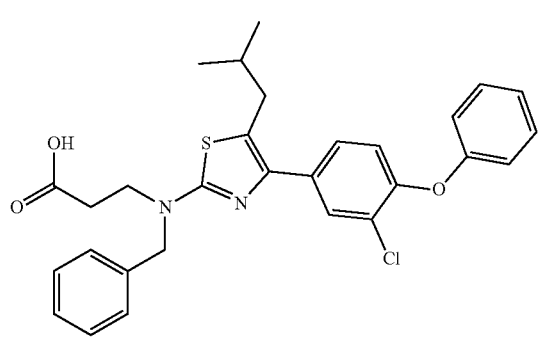 [SMILES: CC(C)Cc1sc(N(CCC(=O)O)Cc2ccccc2)nc1-c1ccc(Oc2ccccc2)c(Cl)c1]
I-103
TABLE 1-continued
Exemplary Compounds
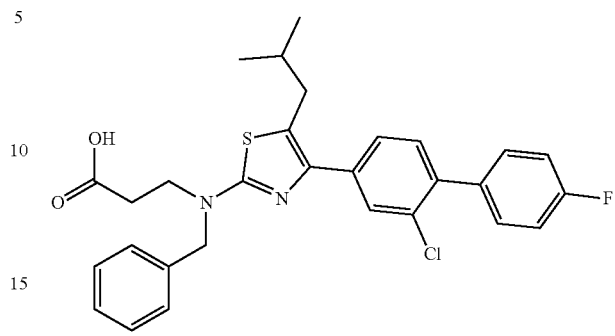
I-104
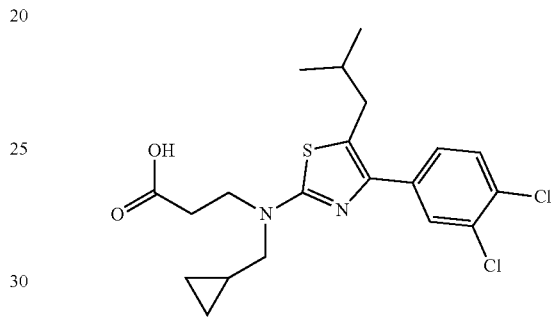
I-105
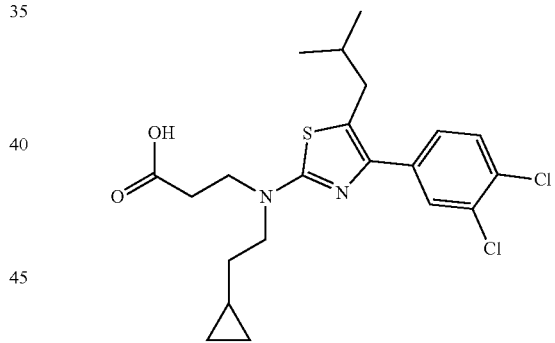
I-106
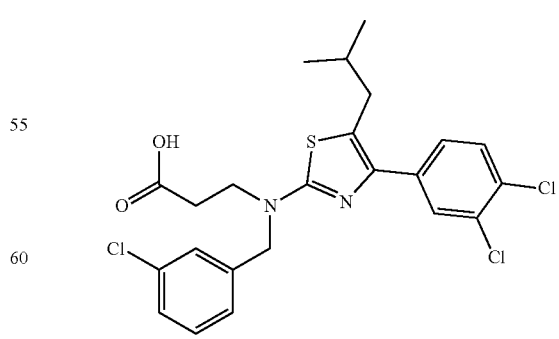
I-107

TABLE 1-continued
Exemplary Compounds
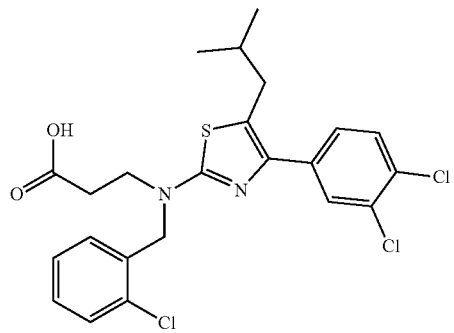 [SMILES: CC(C)Cc1sc(N(CCC(=O)O)Cc2ccccc2Cl)nc1-c1ccc(Cl)c(Cl)c1]
I-108
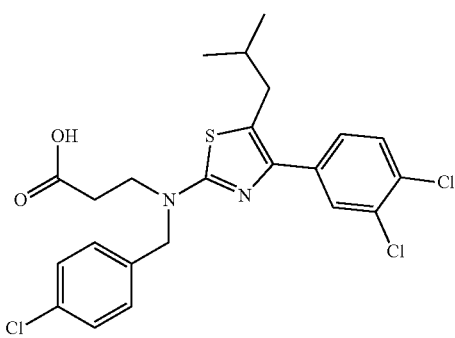 [SMILES: CC(C)Cc1sc(N(CCC(=O)O)Cc2ccc(Cl)cc2)nc1-c1ccc(Cl)c(Cl)c1]
I-109
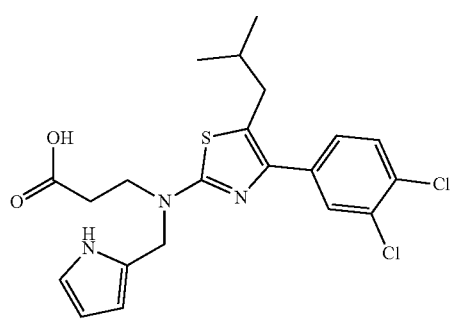 [SMILES: CC(C)Cc1sc(N(CCC(=O)O)Cc2ccc[nH]2)nc1-c1ccc(Cl)c(Cl)c1]
I-110
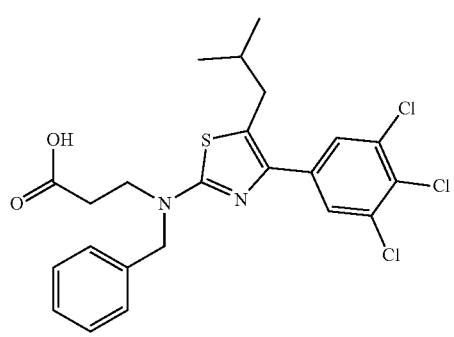 [SMILES: CC(C)Cc1sc(N(CCC(=O)O)Cc2ccccc2)nc1-c1cc(Cl)c(Cl)c(Cl)c1]
I-111
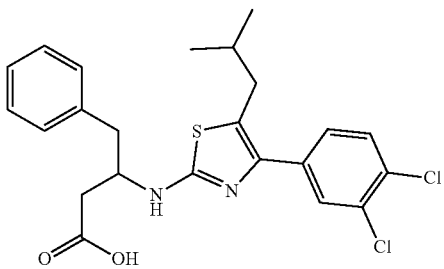 [SMILES: CC(C)Cc1sc(NC(CC(=O)O)Cc2ccccc2)nc1-c1ccc(Cl)c(Cl)c1]
I-112
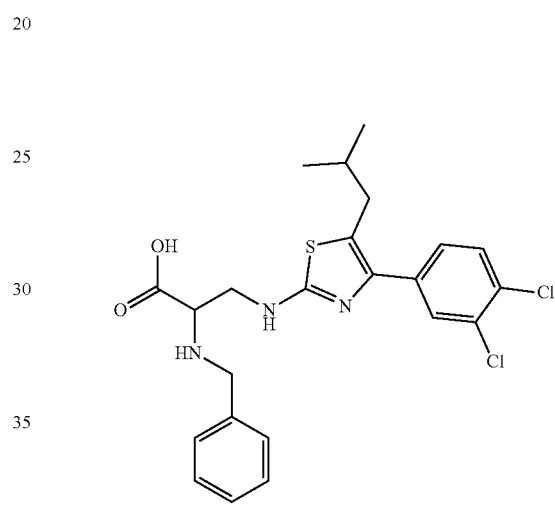
I-113
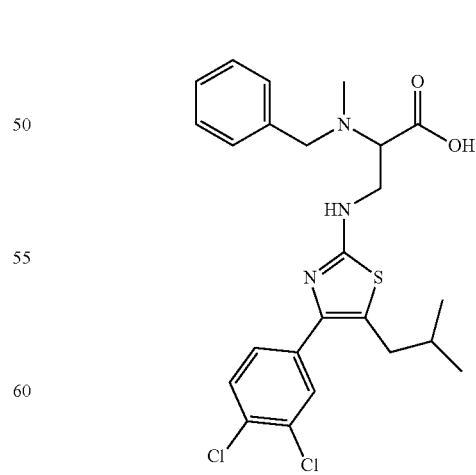
I-114

TABLE 1-continued
Exemplary Compounds
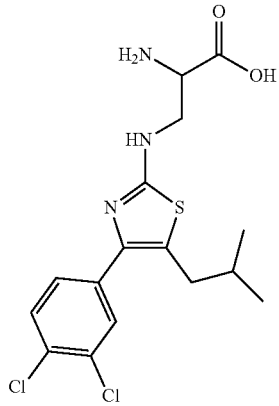 [SMILES: CC(C)Cc1sc(NCC(N)C(=O)O)nc1-c1ccc(Cl)c(Cl)c1]
I-115
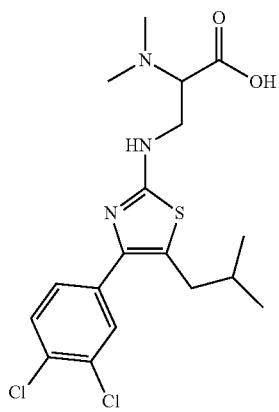 [SMILES: CC(C)Cc1sc(NCC(C(=O)O)N(C)C)nc1-c1ccc(Cl)c(Cl)c1]
I-116
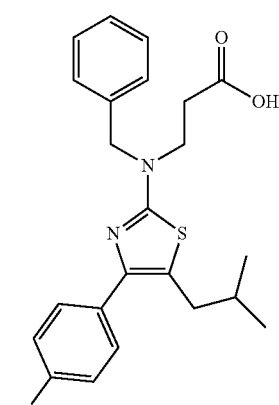
I-117
TABLE 1-continued
Exemplary Compounds
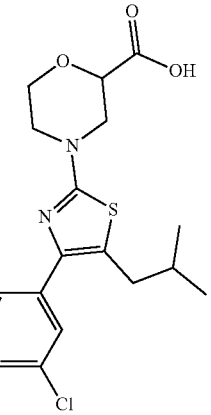
I-118
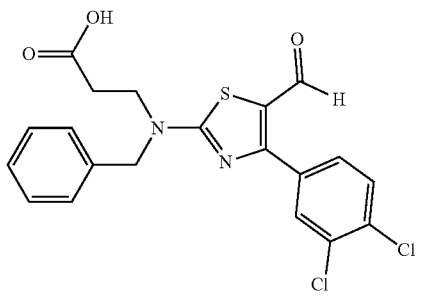 [SMILES: O=Cc1sc(N(CCC(=O)O)Cc2ccccc2)nc1-c1ccc(Cl)c(Cl)c1]
I-119
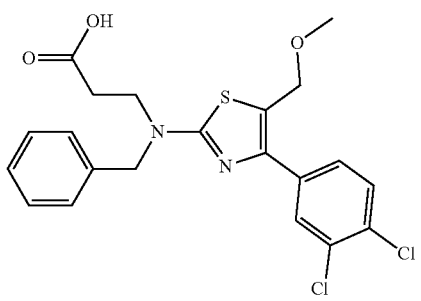 [SMILES: COCc1sc(N(CCC(=O)O)Cc2ccccc2)nc1-c1ccc(Cl)c(Cl)c1]
I-120
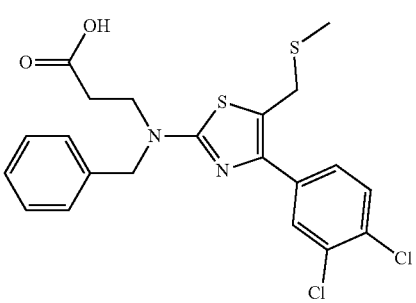
I-121

TABLE 1-continued
Exemplary Compounds
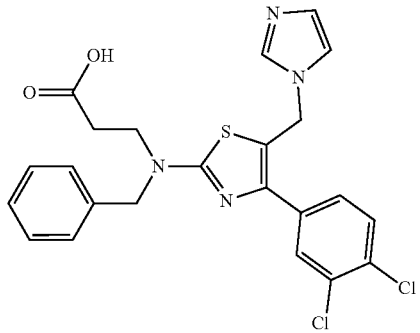 [SMILES: O=C(O)CCN(Cc1ccccc1)c1nc(-c2ccc(Cl)c(Cl)c2)c(Cn2ccnc2)s1]
I-122
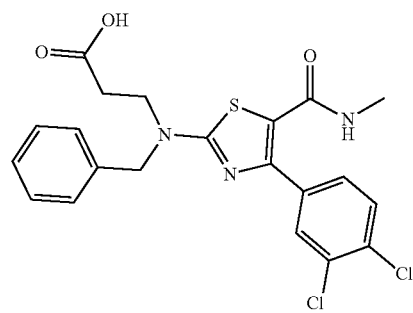 [SMILES: CNC(=O)c1sc(N(CCC(=O)O)Cc2ccccc2)nc1-c1ccc(Cl)c(Cl)c1]
I-123
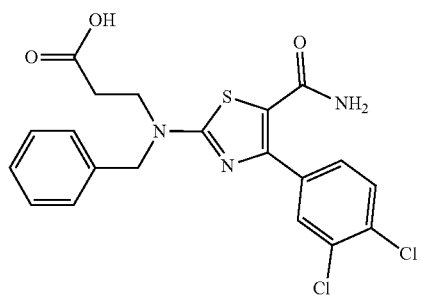 [SMILES: NC(=O)c1sc(N(CCC(=O)O)Cc2ccccc2)nc1-c1ccc(Cl)c(Cl)c1]
I-124
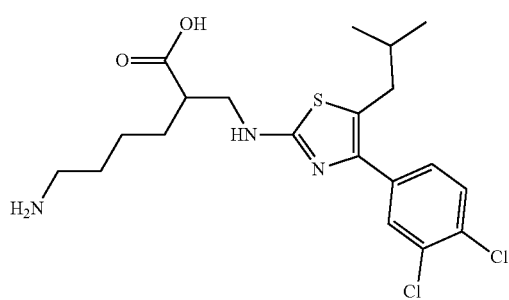 [SMILES: CC(C)Cc1sc(NCC(CCCCN)C(=O)O)nc1-c1ccc(Cl)c(Cl)c1]
I-125
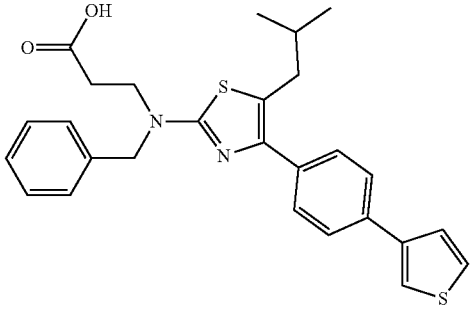 [SMILES: CC(C)Cc1sc(N(CCC(=O)O)Cc2ccccc2)nc1-c1ccc(-c2ccsc2)cc1]
I-126
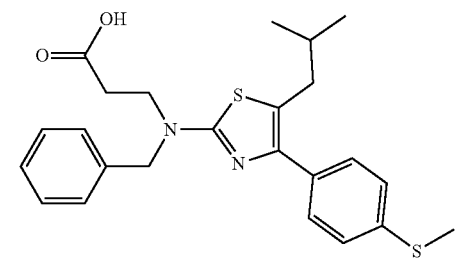 [SMILES: CSc1ccc(-c2nc(N(CCC(=O)O)Cc3ccccc3)sc2CC(C)C)cc1]
I-127
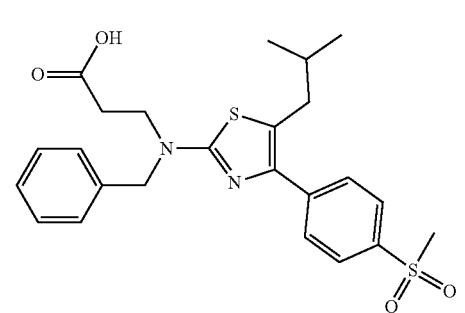 [SMILES: CC(C)Cc1sc(N(CCC(=O)O)Cc2ccccc2)nc1-c1ccc(S(C)(=O)=O)cc1]
I-128
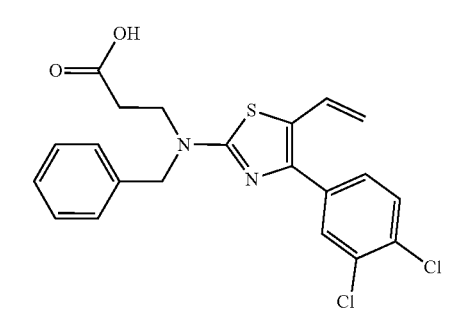 [SMILES: C=Cc1sc(N(CCC(=O)O)Cc2ccccc2)nc1-c1ccc(Cl)c(Cl)c1]
I-129

TABLE 1-continued
Exemplary Compounds
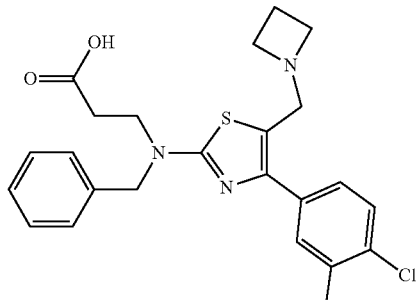
I-130
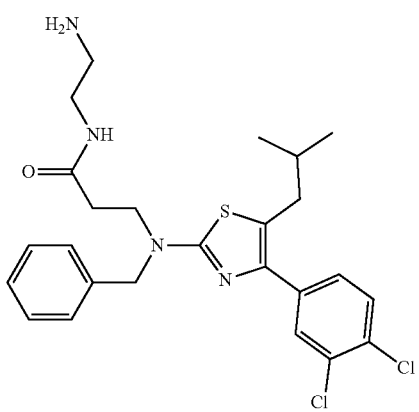 [SMILES: CC(C)Cc1sc(N(CCC(=O)NCCN)Cc2ccccc2)nc1-c1ccc(Cl)c(Cl)c1]
I-131
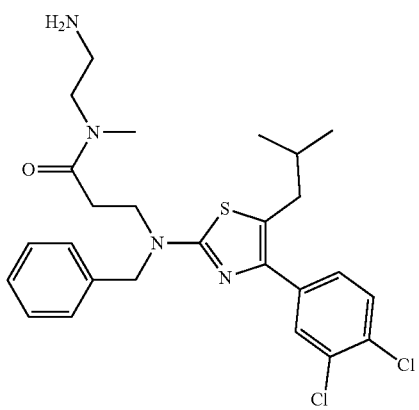 [SMILES: CC(C)Cc1sc(N(CCC(=O)N(C)CCN)Cc2ccccc2)nc1-c1ccc(Cl)c(Cl)c1]
I-132
TABLE 1-continued
Exemplary Compounds
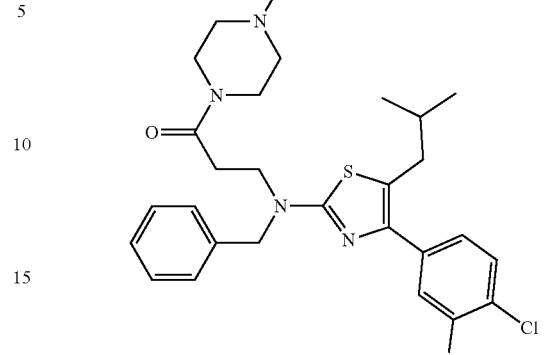
I-133
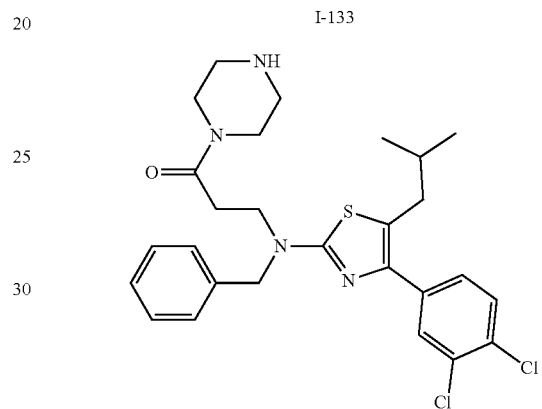
I-134
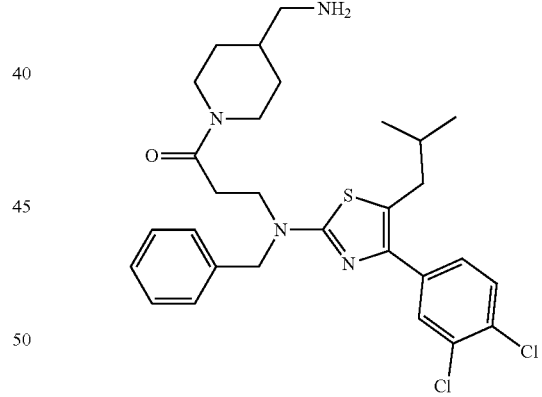
I-135
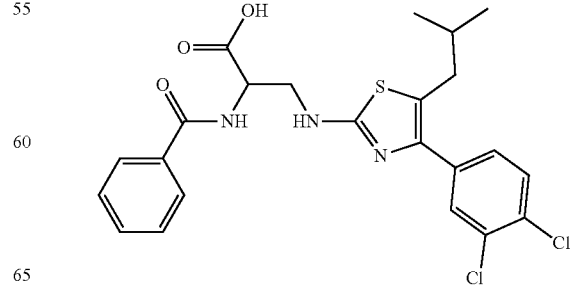

TABLE 1-continued
Exemplary Compounds
I-136
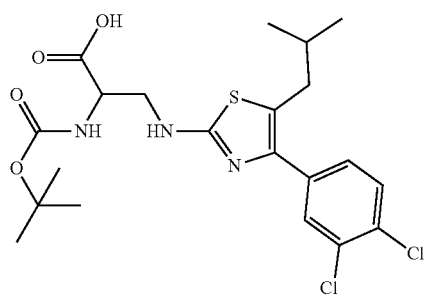 [SMILES: CC(C)Cc1sc(NCC(NC(=O)OC(C)(C)C)C(=O)O)nc1-c1ccc(Cl)c(Cl)c1]
I-137
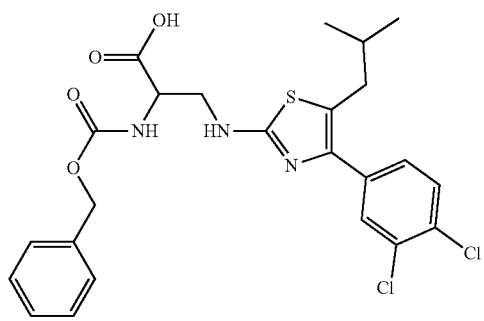 [SMILES: CC(C)Cc1sc(NCC(NC(=O)OCc2ccccc2)C(=O)O)nc1-c1ccc(Cl)c(Cl)c1]
I-138
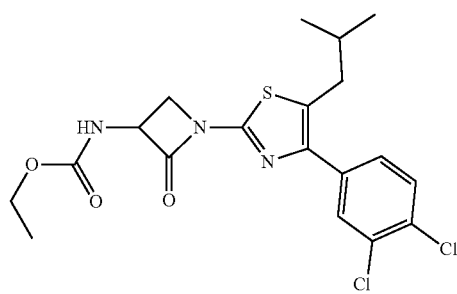 [SMILES: CCOC(=O)NC1CN(c2nc(-c3ccc(Cl)c(Cl)c3)c(CC(C)C)s2)C1=O]
I-140
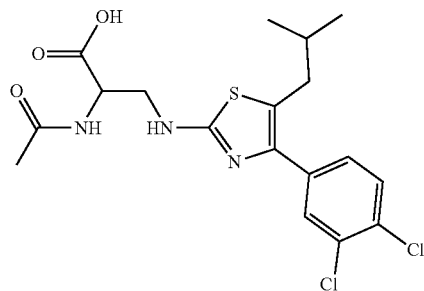 [SMILES: CC(=O)NC(CNc1nc(-c2ccc(Cl)c(Cl)c2)c(CC(C)C)s1)C(=O)O]
TABLE 1-continued
Exemplary Compounds
I-141
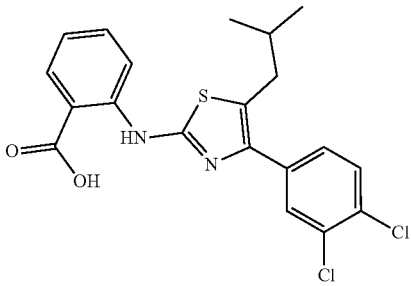 [SMILES: CC(C)Cc1sc(Nc2ccccc2C(=O)O)nc1-c1ccc(Cl)c(Cl)c1]
I-142
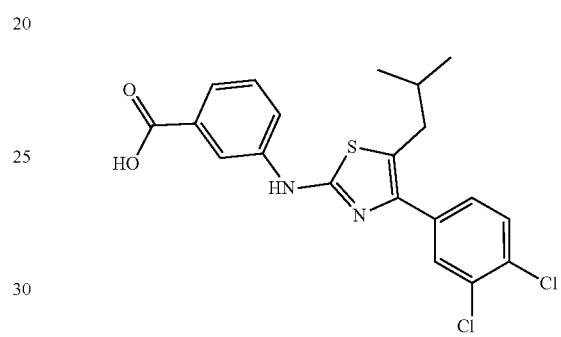
I-143
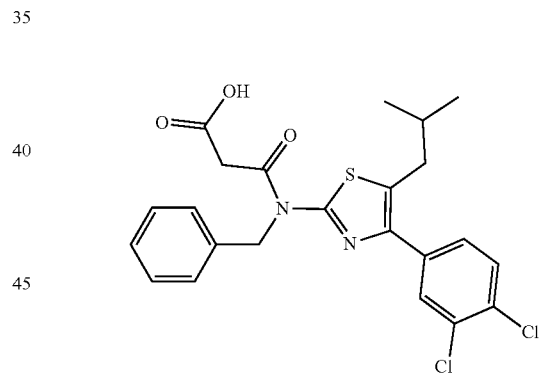
I-144
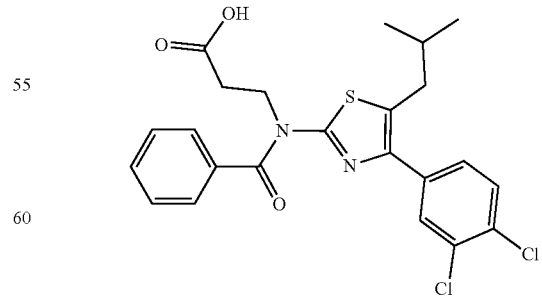

TABLE 1-continued
Exemplary Compounds
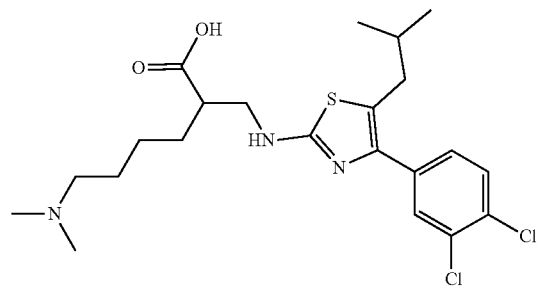 [SMILES: CC(C)Cc1sc(NCC(CCCCN(C)C)C(=O)O)nc1-c1ccc(Cl)c(Cl)c1]
I-145
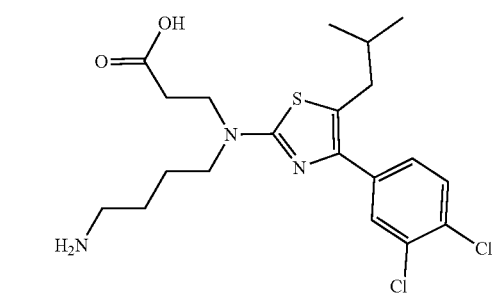 [SMILES: CC(C)Cc1sc(N(CCCCN)CCC(=O)O)nc1-c1ccc(Cl)c(Cl)c1]
I-146
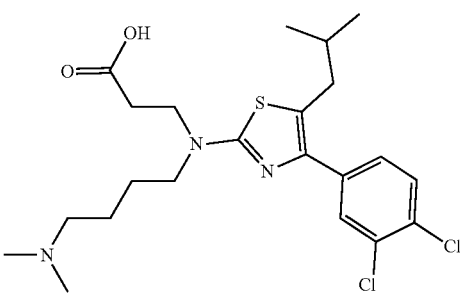 [SMILES: CC(C)Cc1sc(N(CCCCN(C)C)CCC(=O)O)nc1-c1ccc(Cl)c(Cl)c1]
I-147
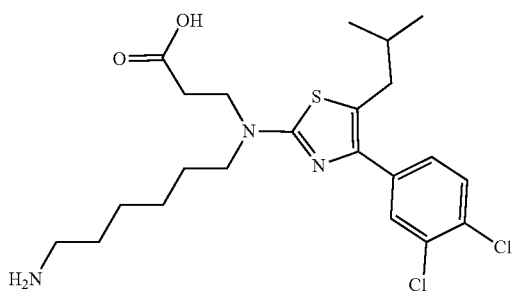 [SMILES: CC(C)Cc1sc(N(CCCCCCN)CCC(=O)O)nc1-c1ccc(Cl)c(Cl)c1]
I-148
TABLE 1-continued
Exemplary Compounds
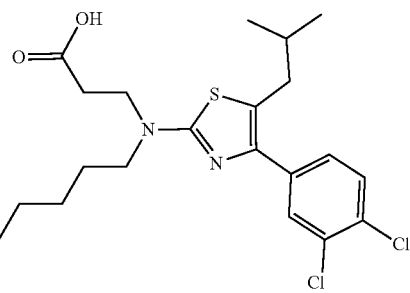
I-149
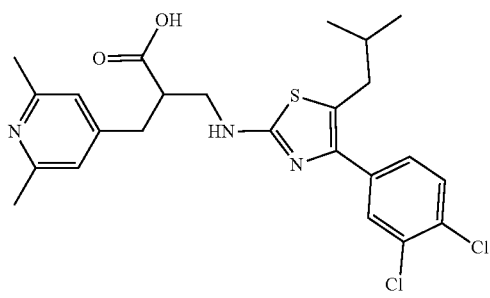 [SMILES: Cc1cc(CC(CNc2nc(-c3ccc(Cl)c(Cl)c3)c(CC(C)C)s2)C(=O)O)cc(C)n1]
I-150
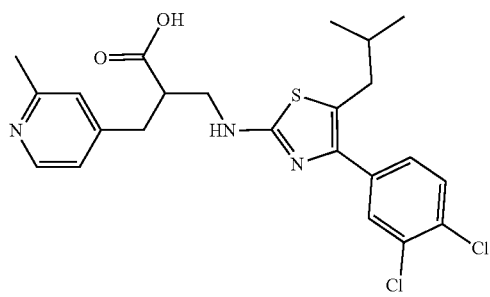 [SMILES: Cc1cc(CC(CNc2nc(-c3ccc(Cl)c(Cl)c3)c(CC(C)C)s2)C(=O)O)ccn1]
I-151
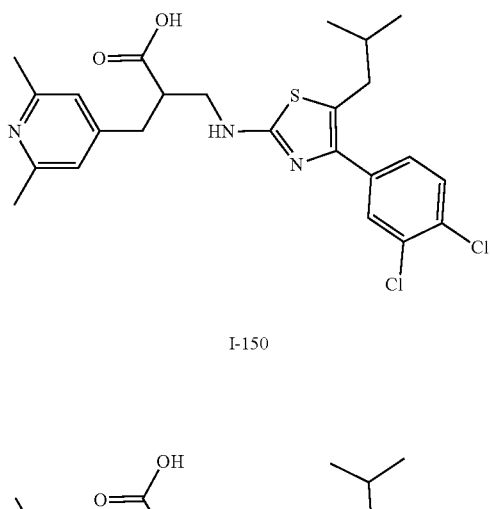
I-152

TABLE 1-continued
Exemplary Compounds
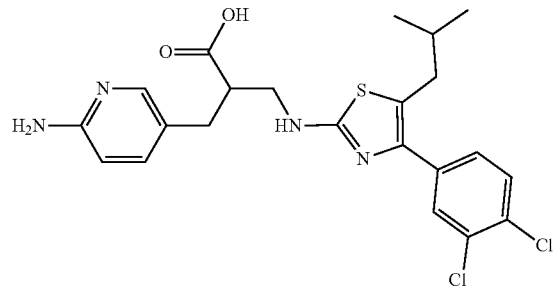 [SMILES: CC(C)Cc1sc(NCC(Cc2ccc(N)nc2)C(=O)O)nc1-c1ccc(Cl)c(Cl)c1]
I-153
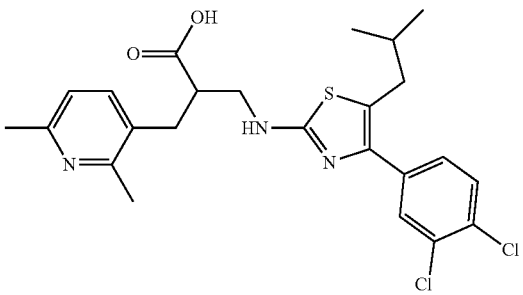
I-157
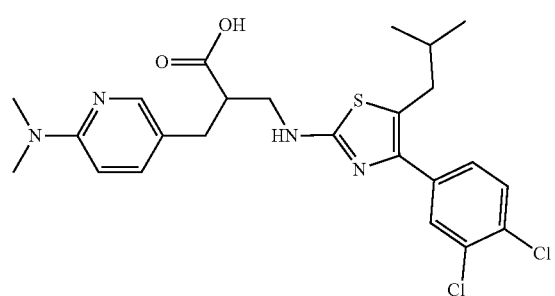 [SMILES: CC(C)Cc1sc(NCC(Cc2ccc(N(C)C)nc2)C(=O)O)nc1-c1ccc(Cl)c(Cl)c1]
I-154
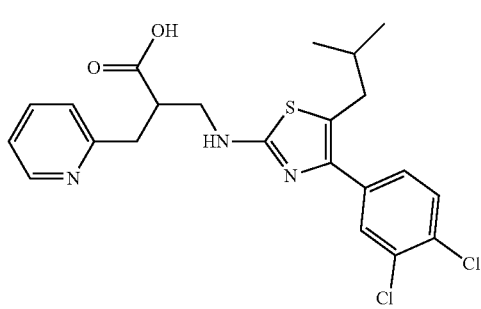
I-158
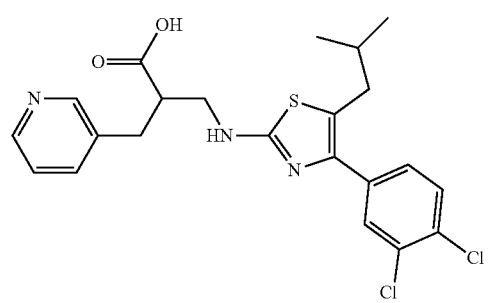 [SMILES: CC(C)Cc1sc(NCC(Cc2cccnc2)C(=O)O)nc1-c1ccc(Cl)c(Cl)c1]
I-155
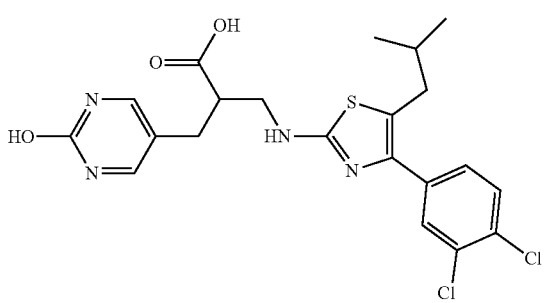
I-159
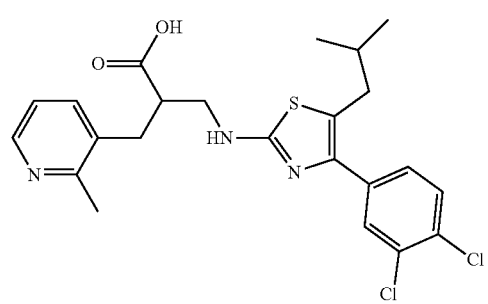 [SMILES: Cc1ncccc1CC(CNc1nc(-c2ccc(Cl)c(Cl)c2)c(CC(C)C)s1)C(=O)O]
I-156
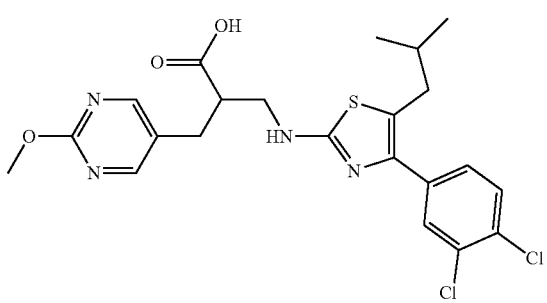 [SMILES: COc1ncc(CC(CNc2nc(-c3ccc(Cl)c(Cl)c3)c(CC(C)C)s2)C(=O)O)cn1]
I-160

TABLE 1-continued
Exemplary Compounds
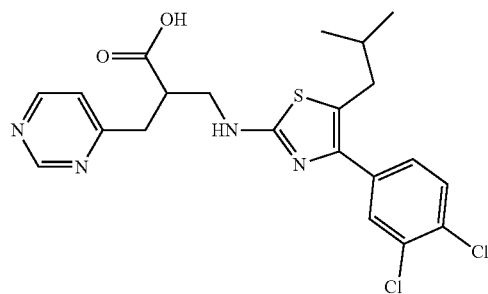 [SMILES: CC(C)Cc1sc(NCC(Cc2ccncn2)C(=O)O)nc1-c1ccc(Cl)c(Cl)c1]
I-161
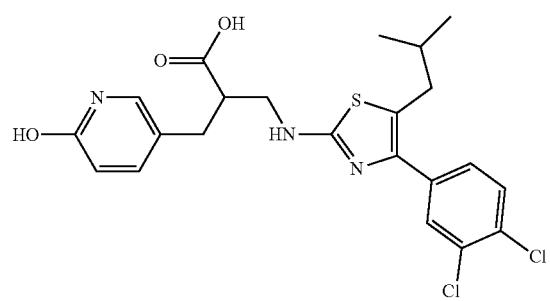 [SMILES: CC(C)Cc1sc(NCC(Cc2ccc(O)nc2)C(=O)O)nc1-c1ccc(Cl)c(Cl)c1]
I-162
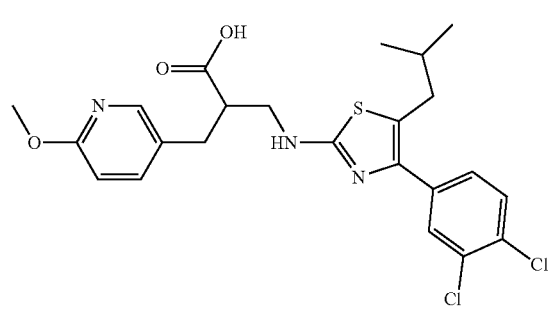
I-163
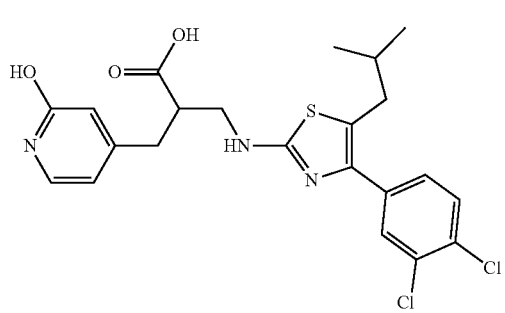 [SMILES: CC(C)Cc1sc(NCC(Cc2ccnc(O)c2)C(=O)O)nc1-c1ccc(Cl)c(Cl)c1]
I-164
TABLE 1-continued
Exemplary Compounds
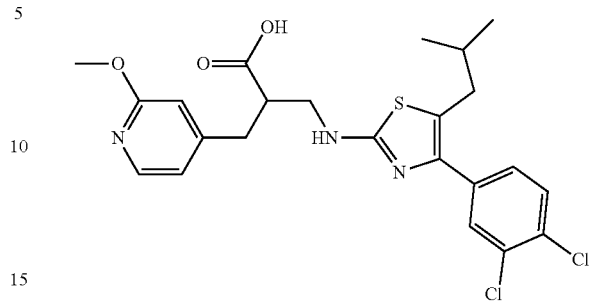
I-165
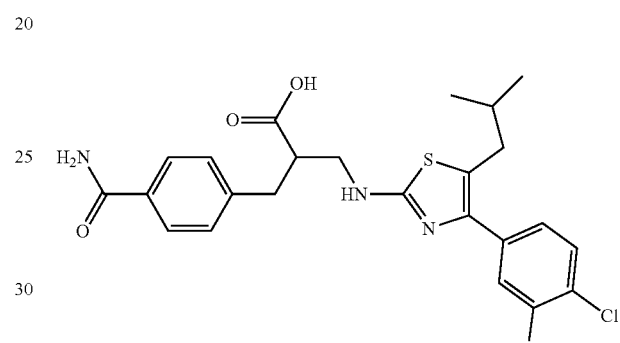
I-166
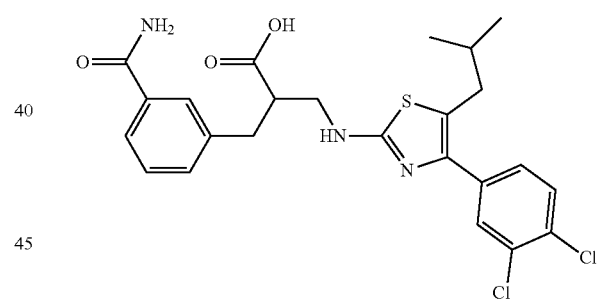
I-167
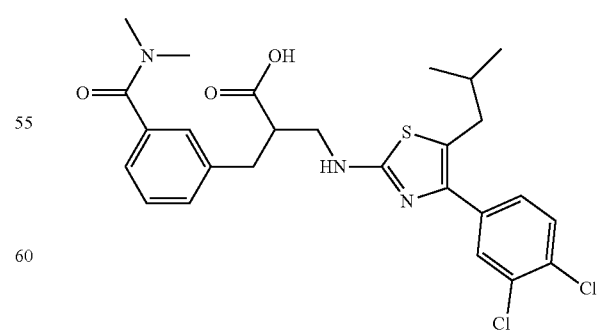
I-168

TABLE 1-continued
Exemplary Compounds
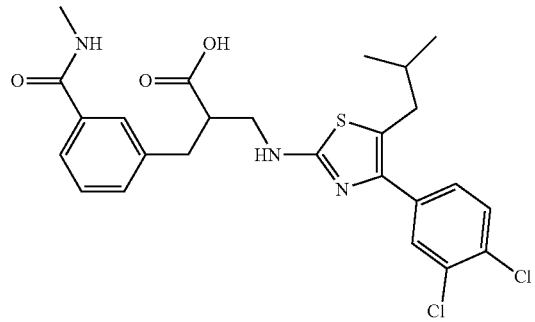 [SMILES: CNC(=O)c1cccc(CC(CNc2nc(-c3ccc(Cl)c(Cl)c3)c(CC(C)C)s2)C(=O)O)c1]
I-169
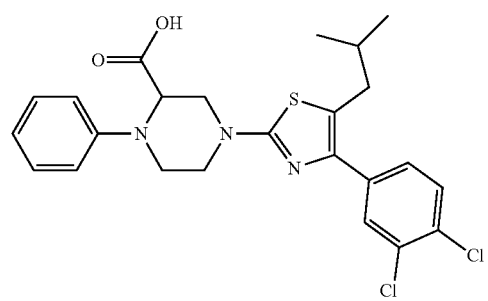 [SMILES: CC(C)Cc1sc(N2CCN(c3ccccc3)C(C(=O)O)C2)nc1-c1ccc(Cl)c(Cl)c1]
I-170
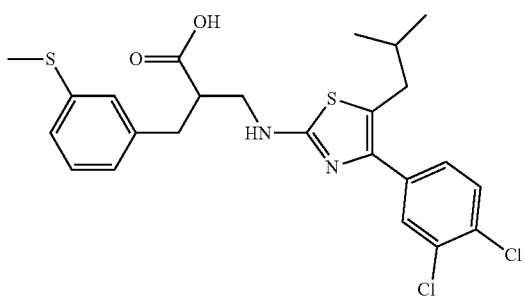 [SMILES: CSc1cccc(CC(CNc2nc(-c3ccc(Cl)c(Cl)c3)c(CC(C)C)s2)C(=O)O)c1]
I-171
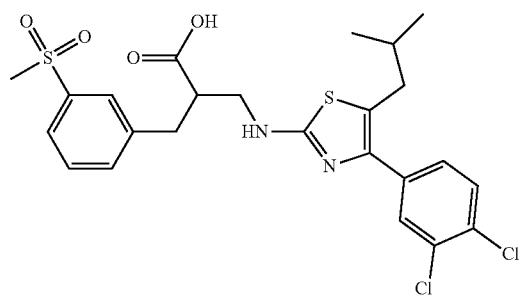 [SMILES: CC(C)Cc1sc(NCC(Cc2cccc(S(C)(=O)=O)c2)C(=O)O)nc1-c1ccc(Cl)c(Cl)c1]
I-172
TABLE 1-continued
Exemplary Compounds
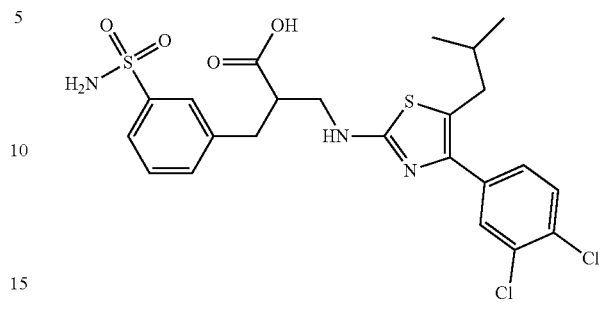
I-173
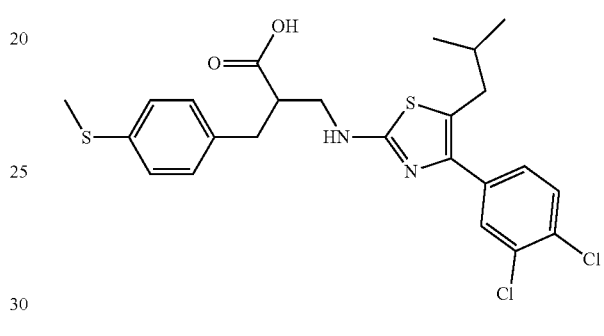
I-174
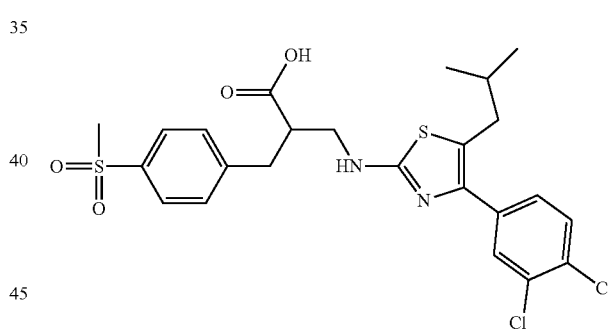
I-175
I-176

TABLE 1-continued
Exemplary Compounds
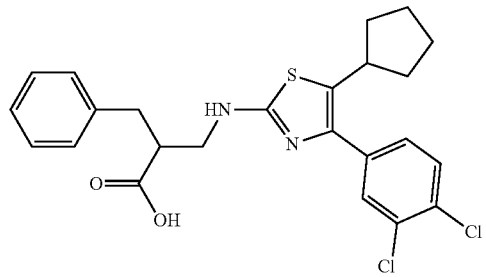 [SMILES: O=C(O)C(CNc1nc(-c2ccc(Cl)c(Cl)c2)c(C2CCCC2)s1)Cc1ccccc1]
I-177
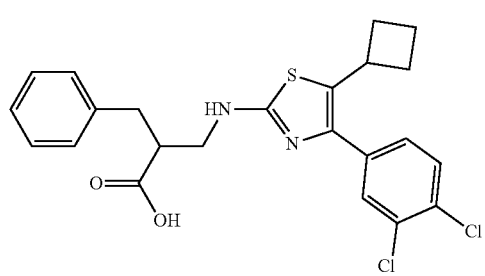 [SMILES: O=C(O)C(CNc1nc(-c2ccc(Cl)c(Cl)c2)c(C2CCC2)s1)Cc1ccccc1]
I-178
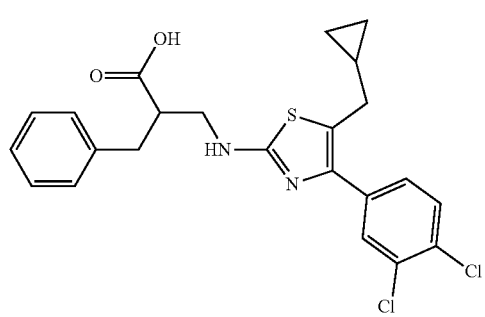 [SMILES: O=C(O)C(CNc1nc(-c2ccc(Cl)c(Cl)c2)c(CC2CC2)s1)Cc1ccccc1]
I-179
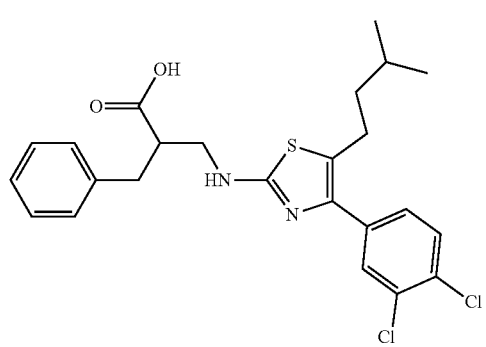 [SMILES: CC(C)CCc1sc(NCC(Cc2ccccc2)C(=O)O)nc1-c1ccc(Cl)c(Cl)c1]
I-180
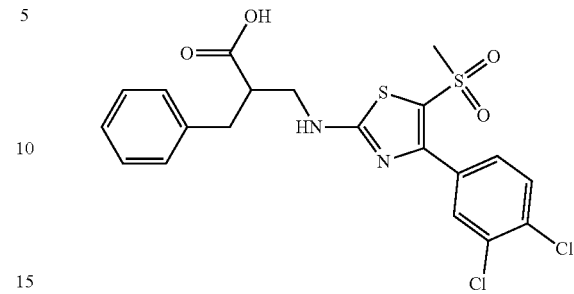
I-181
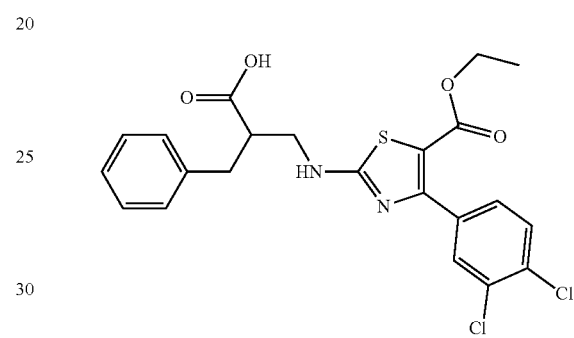
I-182
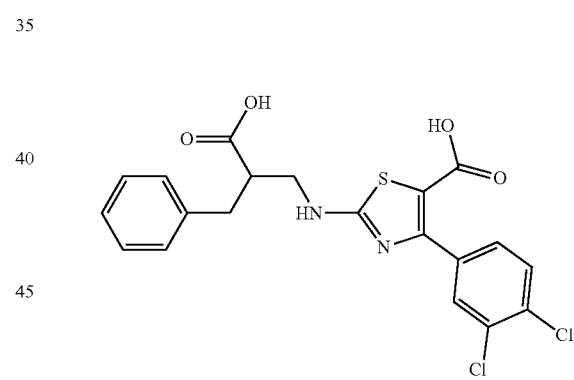
I-183
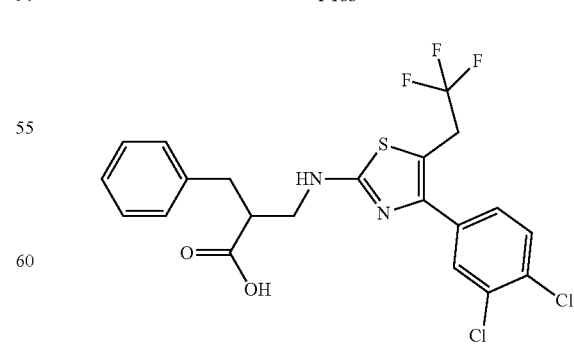
I-184

TABLE 1-continued
Exemplary Compounds
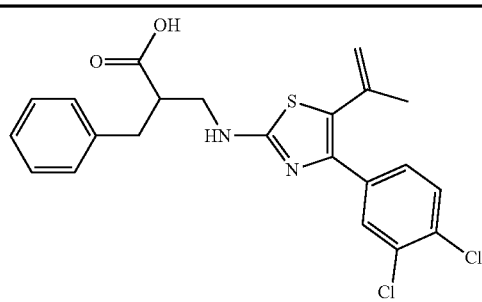
I-185
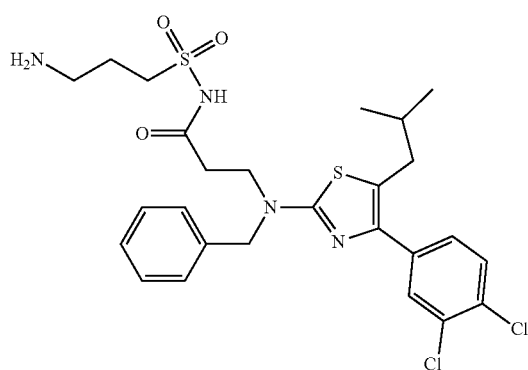 [SMILES: CC(C)Cc1sc(N(CCC(=O)NS(=O)(=O)CCCN)Cc2ccccc2)nc1-c1ccc(Cl)c(Cl)c1]
I-186
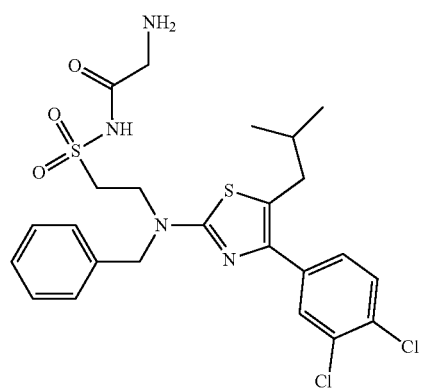 [SMILES: CC(C)Cc1sc(N(CCS(=O)(=O)NC(=O)CN)Cc2ccccc2)nc1-c1ccc(Cl)c(Cl)c1]
I-187
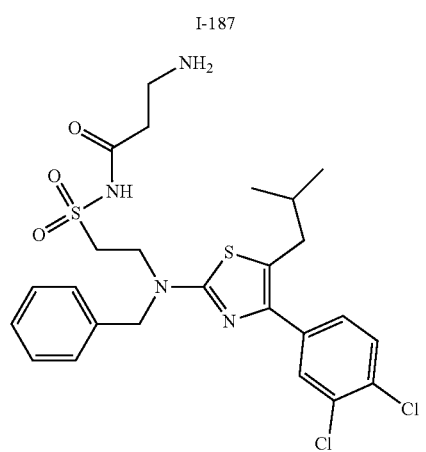
I-188
TABLE 1-continued
Exemplary Compounds
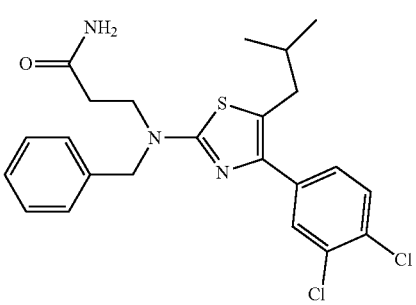 [SMILES: CC(C)Cc1sc(N(CCC(N)=O)Cc2ccccc2)nc1-c1ccc(Cl)c(Cl)c1]
I-189
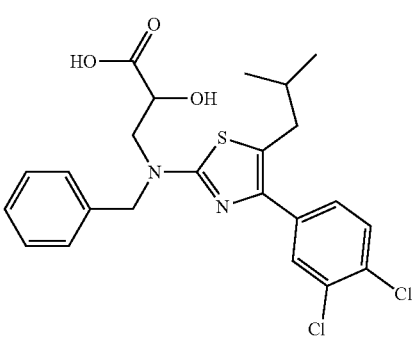 [SMILES: CC(C)Cc1sc(N(Cc2ccccc2)CC(O)C(=O)O)nc1-c1ccc(Cl)c(Cl)c1]
I-190
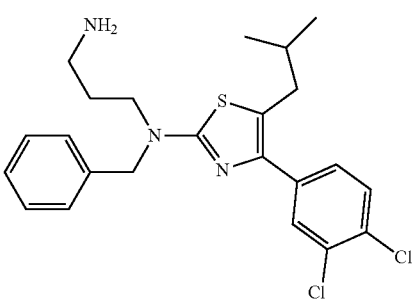 [SMILES: CC(C)Cc1sc(N(CCCN)Cc2ccccc2)nc1-c1ccc(Cl)c(Cl)c1]
I-191
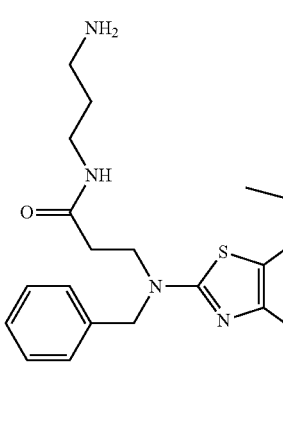
I-192

TABLE 1-continued
Exemplary Compounds
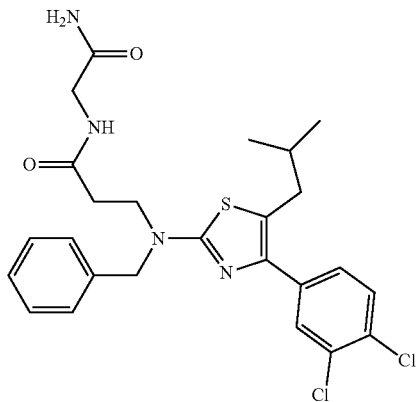 [SMILES: CC(C)Cc1sc(N(CCC(=O)NCC(N)=O)Cc2ccccc2)nc1-c1ccc(Cl)c(Cl)c1]
I-193
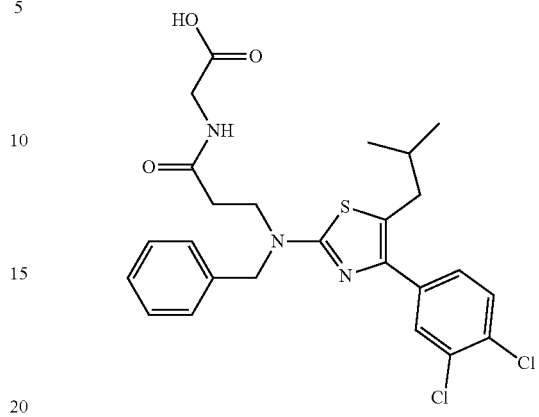
I-196
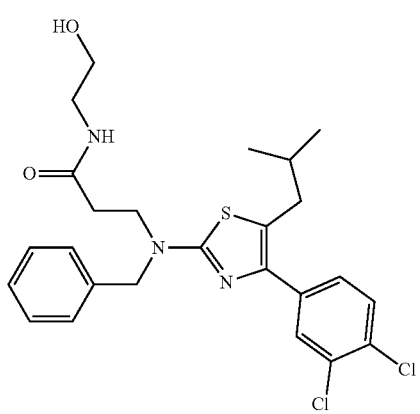 [SMILES: CC(C)Cc1sc(N(CCC(=O)NCCO)Cc2ccccc2)nc1-c1ccc(Cl)c(Cl)c1]
I-194
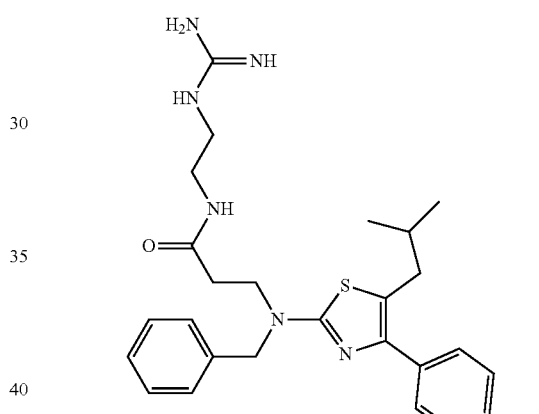
I-197
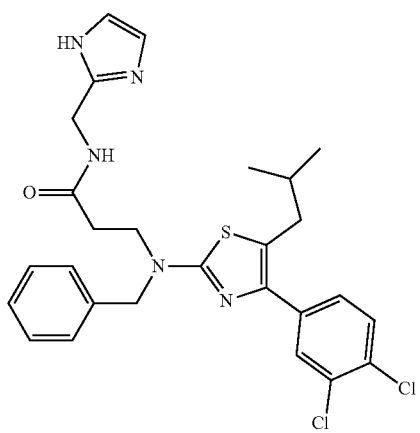 [SMILES: CC(C)Cc1sc(N(CCC(=O)NCc2ncc[nH]2)Cc2ccccc2)nc1-c1ccc(Cl)c(Cl)c1]
I-195
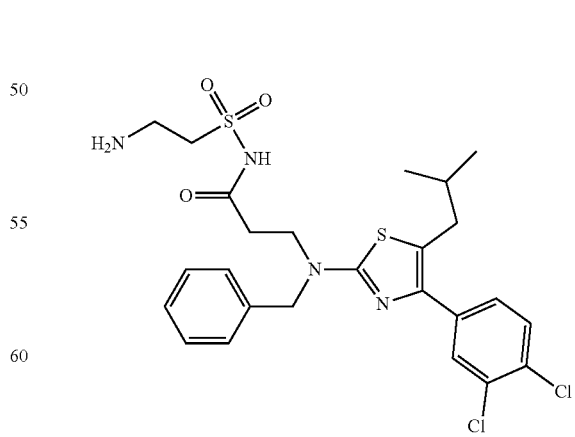
I-198

TABLE 1-continued
Exemplary Compounds
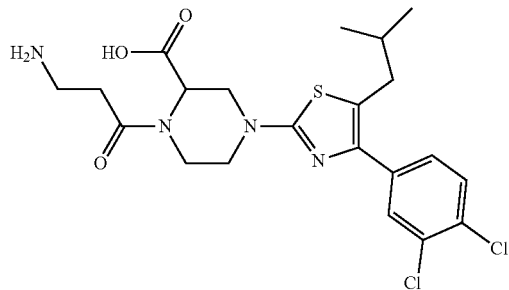 [SMILES: CC(C)Cc1sc(N2CCN(C(=O)CCN)C(C(=O)O)C2)nc1-c1ccc(Cl)c(Cl)c1]
I-199
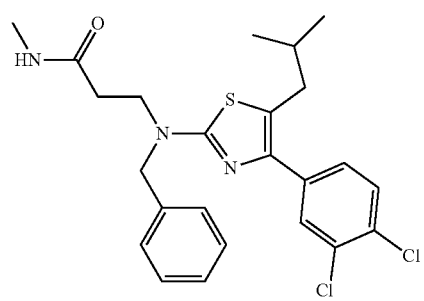 [SMILES: CNC(=O)CCN(Cc1ccccc1)c1nc(-c2ccc(Cl)c(Cl)c2)c(CC(C)C)s1]
I-200
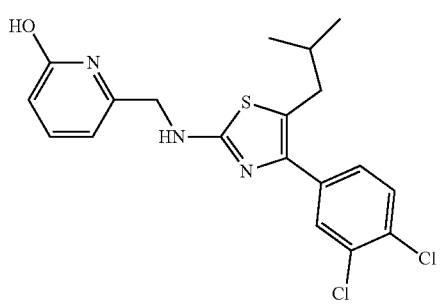 [SMILES: CC(C)Cc1sc(NCc2cccc(O)n2)nc1-c1ccc(Cl)c(Cl)c1]
I-201
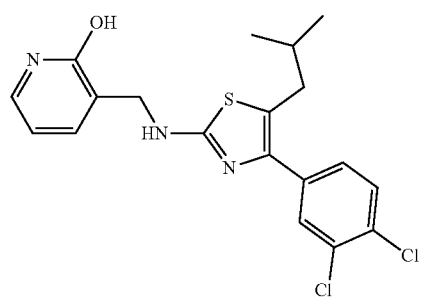 [SMILES: CC(C)Cc1sc(NCc2cccnc2O)nc1-c1ccc(Cl)c(Cl)c1]
I-202
TABLE 1-continued
Exemplary Compounds
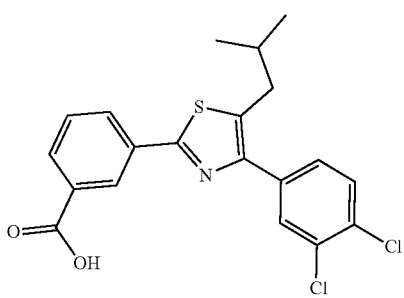 [SMILES: CC(C)Cc1sc(-c2cccc(C(=O)O)c2)nc1-c1ccc(Cl)c(Cl)c1]
I-203
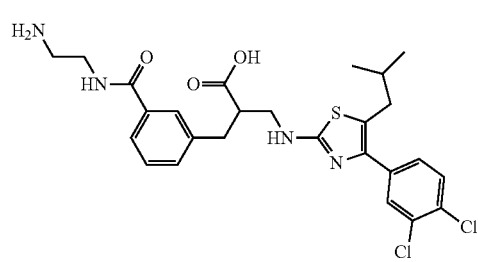 [SMILES: CC(C)Cc1sc(NCC(Cc2cccc(C(=O)NCCN)c2)C(=O)O)nc1-c1ccc(Cl)c(Cl)c1]
I-204
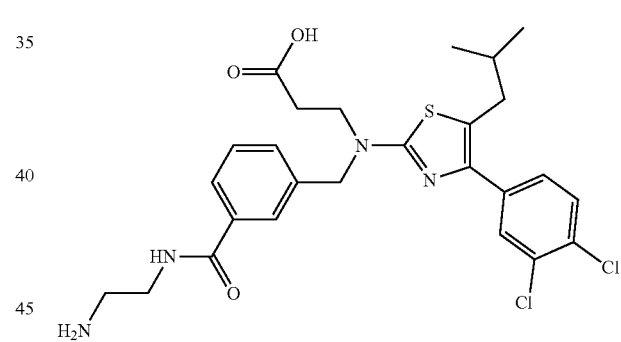
I-205
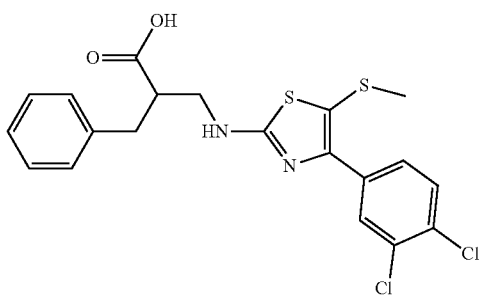 [SMILES: CSc1sc(NCC(Cc2ccccc2)C(=O)O)nc1-c1ccc(Cl)c(Cl)c1]
I-206

TABLE 1-continued
Exemplary Compounds
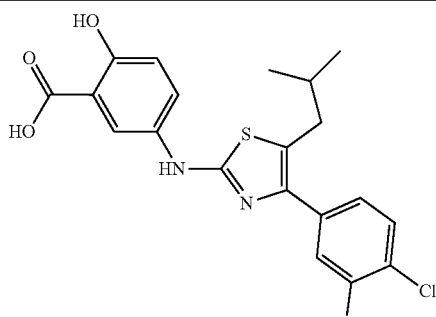
I-207
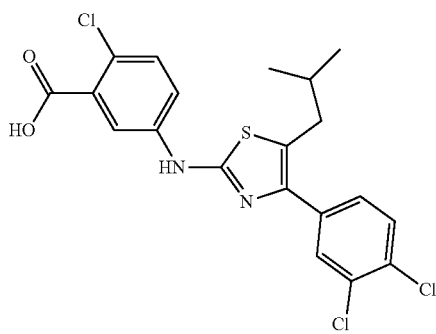 [SMILES: CC(C)Cc1sc(Nc2ccc(Cl)c(C(=O)O)c2)nc1-c1ccc(Cl)c(Cl)c1]
I-208
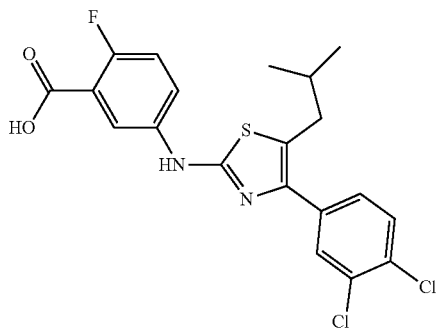 [SMILES: CC(C)Cc1sc(Nc2ccc(F)c(C(=O)O)c2)nc1-c1ccc(Cl)c(Cl)c1]
I-209
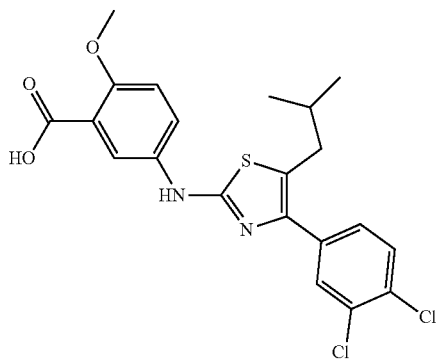 [SMILES: COc1ccc(Nc2nc(-c3ccc(Cl)c(Cl)c3)c(CC(C)C)s2)cc1C(=O)O]
I-210
TABLE 1-continued
Exemplary Compounds
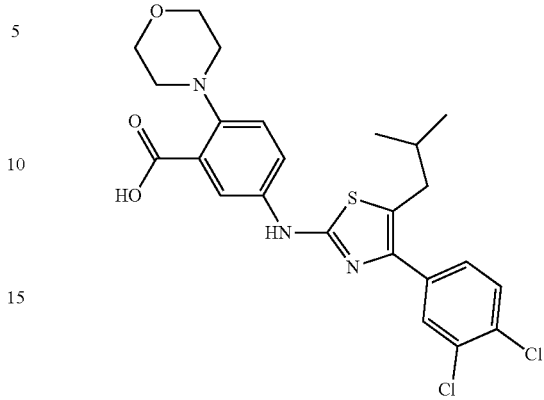
I-211
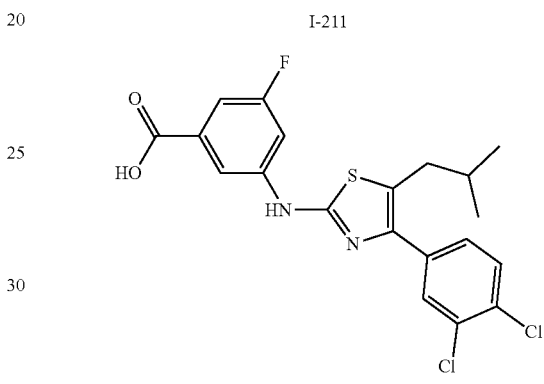
I-212
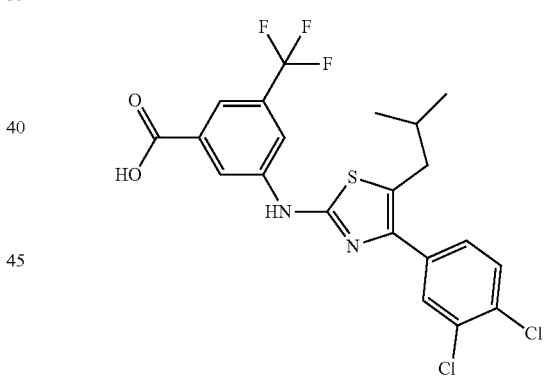
I-213
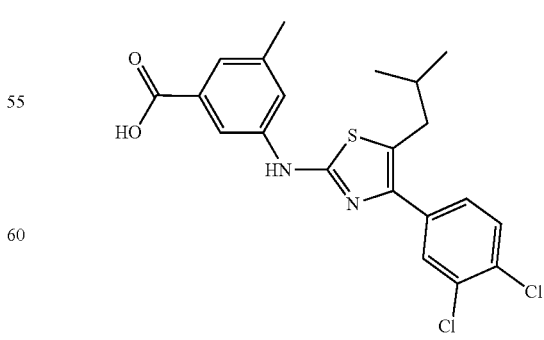
I-214

TABLE 1-continued
Exemplary Compounds
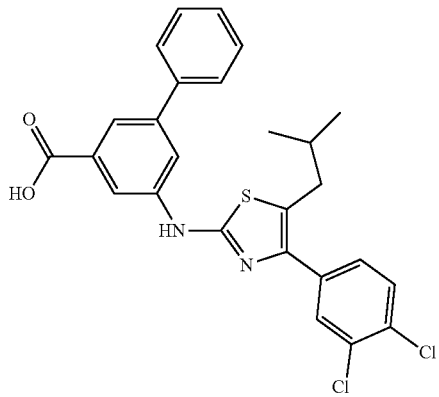 [SMILES: CC(C)Cc1sc(Nc2cc(C(=O)O)cc(-c3ccccc3)c2)nc1-c1ccc(Cl)c(Cl)c1]
I-215
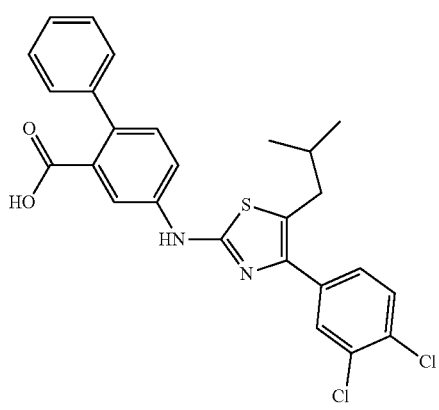 [SMILES: CC(C)Cc1sc(Nc2ccc(-c3ccccc3)c(C(=O)O)c2)nc1-c1ccc(Cl)c(Cl)c1]
I-216
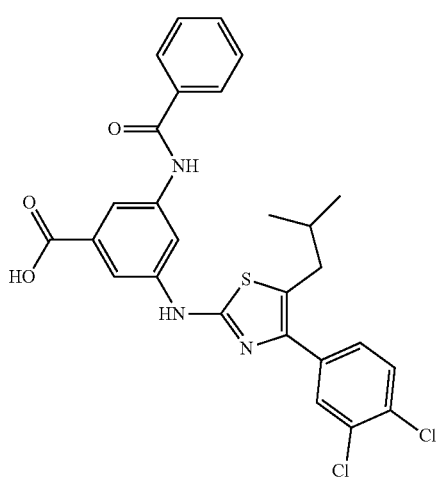 [SMILES: CC(C)Cc1sc(Nc2cc(NC(=O)c3ccccc3)cc(C(=O)O)c2)nc1-c1ccc(Cl)c(Cl)c1]
I-217
TABLE 1-continued
Exemplary Compounds
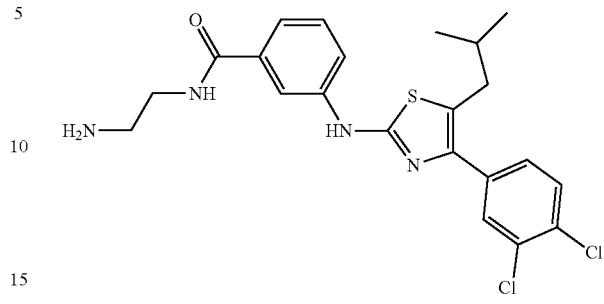
I-218
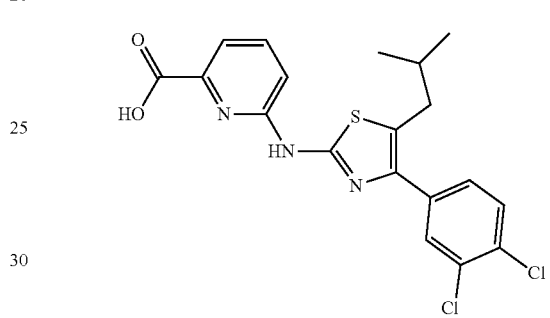
I-219
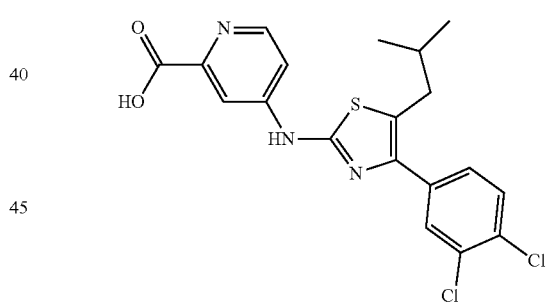
I-220
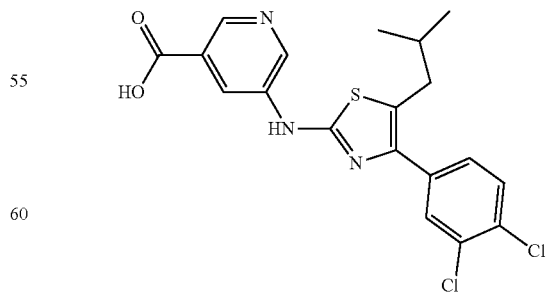
I-221

TABLE 1-continued
Exemplary Compounds
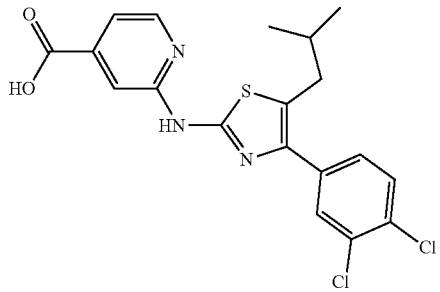 [SMILES: CC(C)Cc1sc(Nc2cc(C(=O)O)ccn2)nc1-c1ccc(Cl)c(Cl)c1]
I-222
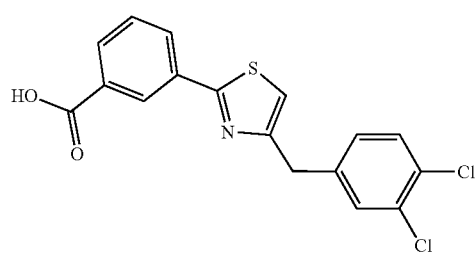 [SMILES: O=C(O)c1cccc(-c2nc(Cc3ccc(Cl)c(Cl)c3)cs2)c1]
I-223
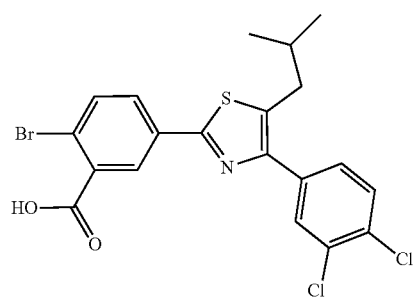 [SMILES: CC(C)Cc1sc(-c2ccc(Br)c(C(=O)O)c2)nc1-c1ccc(Cl)c(Cl)c1]
I-224
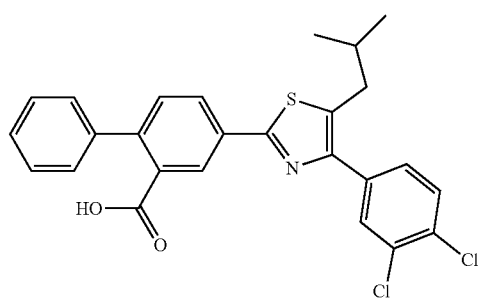 [SMILES: CC(C)Cc1sc(-c2ccc(-c3ccccc3)c(C(=O)O)c2)nc1-c1ccc(Cl)c(Cl)c1]
I-225
TABLE 1-continued
Exemplary Compounds
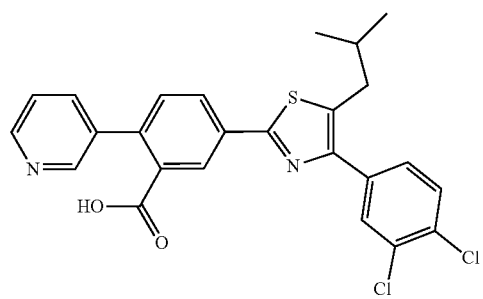
I-226
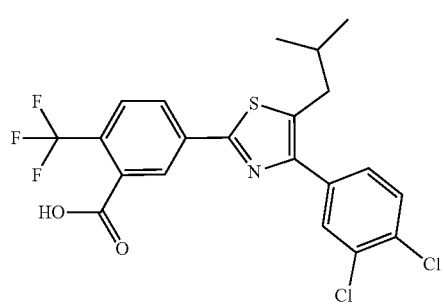 [SMILES: CC(C)Cc1sc(-c2ccc(C(F)(F)F)c(C(=O)O)c2)nc1-c1ccc(Cl)c(Cl)c1]
I-227
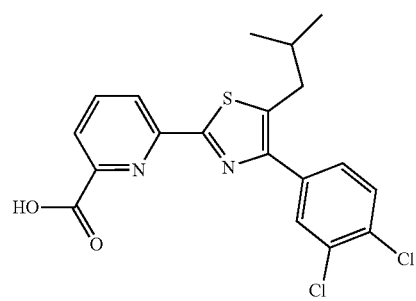 [SMILES: CC(C)Cc1sc(-c2cccc(C(=O)O)n2)nc1-c1ccc(Cl)c(Cl)c1]
I-228
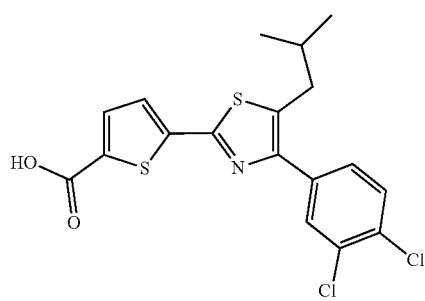 [SMILES: CC(C)Cc1sc(-c2ccc(C(=O)O)s2)nc1-c1ccc(Cl)c(Cl)c1]
I-229

TABLE 1-continued
Exemplary Compounds
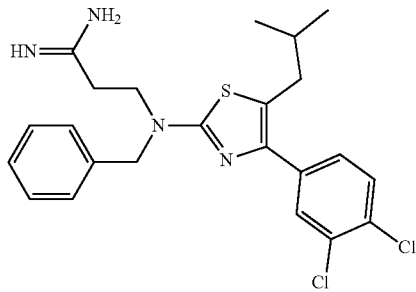 [SMILES: CC(C)Cc1sc(N(CCC(=N)N)Cc2ccccc2)nc1-c1ccc(Cl)c(Cl)c1]
I-230
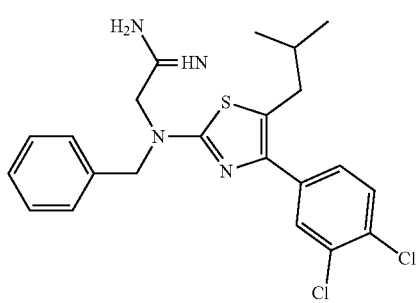 [SMILES: CC(C)Cc1sc(N(CC(=N)N)Cc2ccccc2)nc1-c1ccc(Cl)c(Cl)c1]
I-231
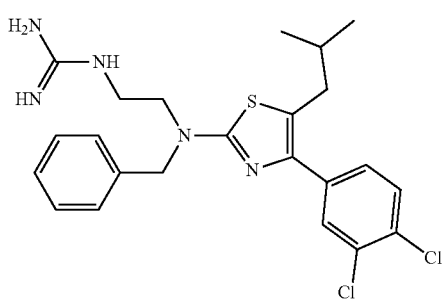 [SMILES: CC(C)Cc1sc(N(CCNC(=N)N)Cc2ccccc2)nc1-c1ccc(Cl)c(Cl)c1]
I-232
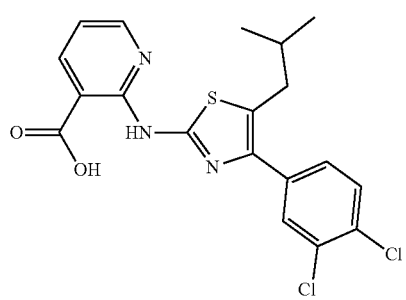 [SMILES: CC(C)Cc1sc(Nc2ncccc2C(=O)O)nc1-c1ccc(Cl)c(Cl)c1]
I-233
TABLE 1-continued
Exemplary Compounds
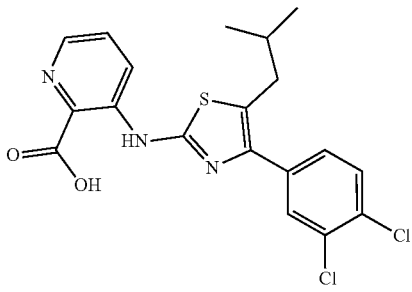 [SMILES: CC(C)Cc1sc(Nc2cccnc2C(=O)O)nc1-c1ccc(Cl)c(Cl)c1]
I-234
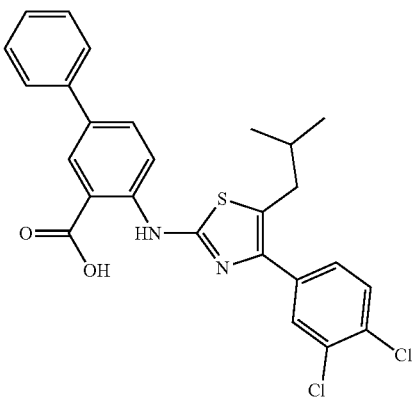 [SMILES: CC(C)Cc1sc(Nc2ccc(-c3ccccc3)cc2C(=O)O)nc1-c1ccc(Cl)c(Cl)c1]
I-235
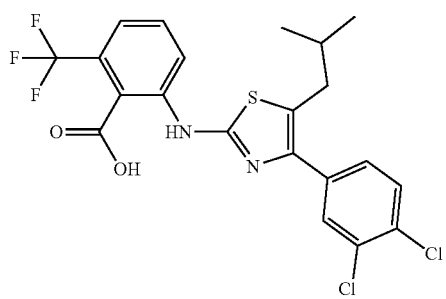 [SMILES: CC(C)Cc1sc(Nc2cccc(C(F)(F)F)c2C(=O)O)nc1-c1ccc(Cl)c(Cl)c1]
I-236
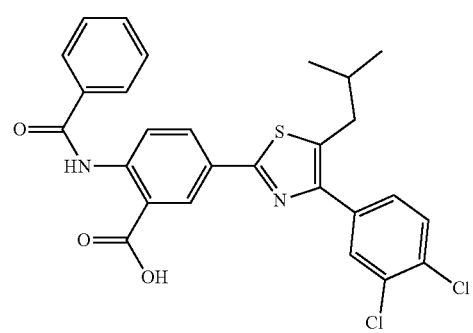 [SMILES: CC(C)Cc1sc(-c2ccc(NC(=O)c3ccccc3)c(C(=O)O)c2)nc1-c1ccc(Cl)c(Cl)c1]
I-237

TABLE 1-continued
Exemplary Compounds
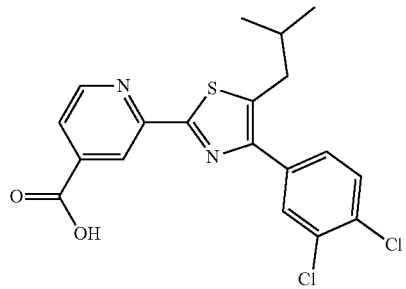 [SMILES: CC(C)Cc1sc(-c2cc(C(=O)O)ccn2)nc1-c1ccc(Cl)c(Cl)c1]
I-238
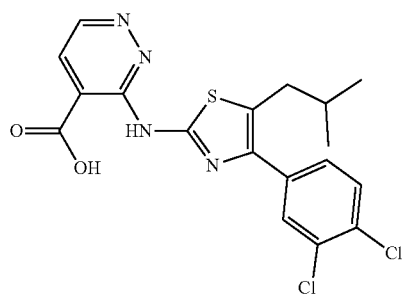 [SMILES: CC(C)Cc1sc(Nc2nnccc2C(=O)O)nc1-c1ccc(Cl)c(Cl)c1]
I-239
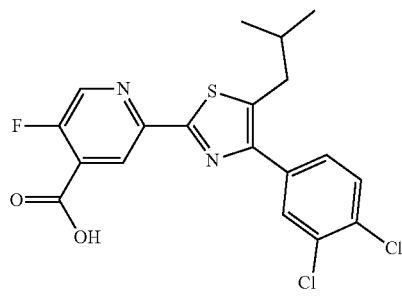 [SMILES: CC(C)Cc1sc(-c2cc(C(=O)O)c(F)cn2)nc1-c1ccc(Cl)c(Cl)c1]
I-240
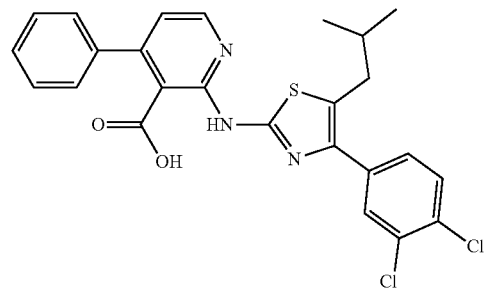 [SMILES: CC(C)Cc1sc(Nc2nccc(-c3ccccc3)c2C(=O)O)nc1-c1ccc(Cl)c(Cl)c1]
I-241
TABLE 1-continued
Exemplary Compounds
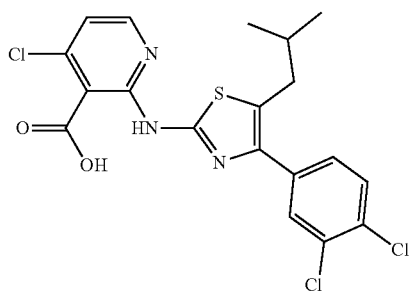 [SMILES: CC(C)Cc1sc(Nc2nccc(Cl)c2C(=O)O)nc1-c1ccc(Cl)c(Cl)c1]
I-242
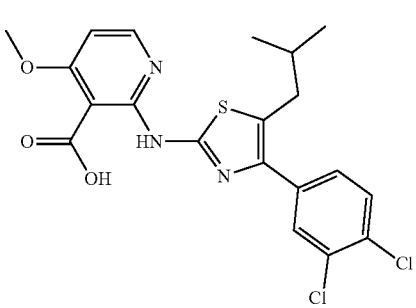 [SMILES: COc1ccnc(Nc2nc(-c3ccc(Cl)c(Cl)c3)c(CC(C)C)s2)c1C(=O)O]
I-243
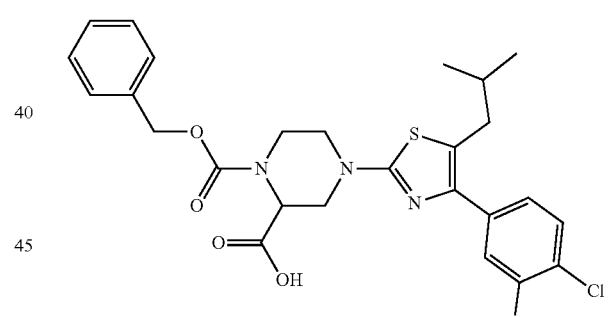
I-244
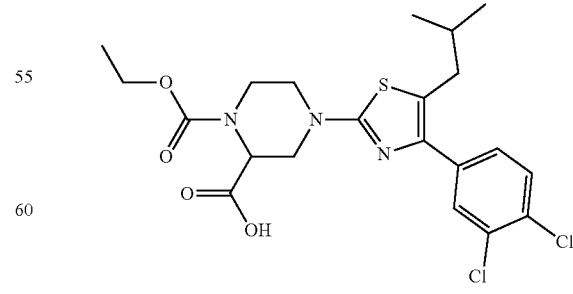
I-245

TABLE 1-continued
Exemplary Compounds
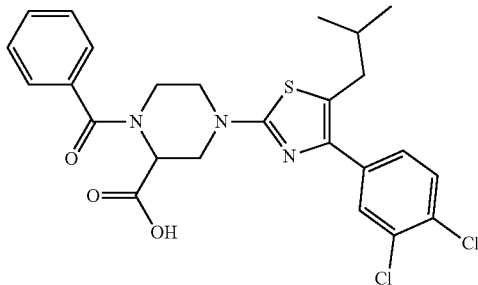 [SMILES: CC(C)Cc1sc(N2CCN(C(=O)c3ccccc3)C(C(=O)O)C2)nc1-c1ccc(Cl)c(Cl)c1]
I-246
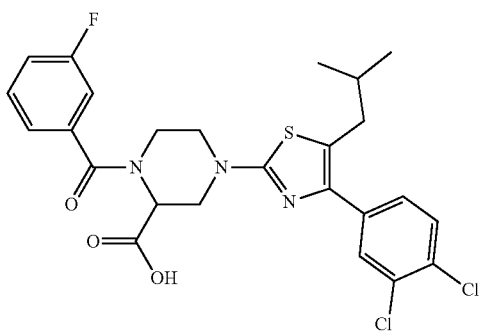 [SMILES: CC(C)Cc1sc(N2CCN(C(=O)c3cccc(F)c3)C(C(=O)O)C2)nc1-c1ccc(Cl)c(Cl)c1]
I-247
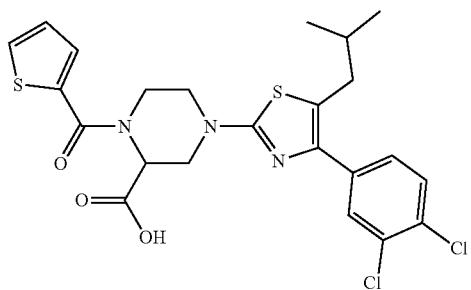 [SMILES: CC(C)Cc1sc(N2CCN(C(=O)c3cccs3)C(C(=O)O)C2)nc1-c1ccc(Cl)c(Cl)c1]
I-248
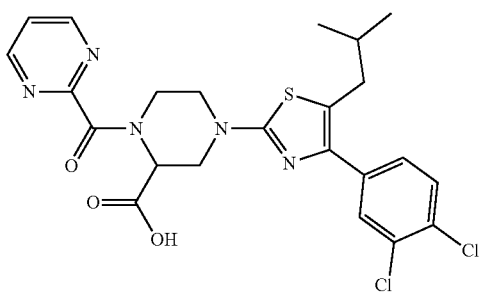 [SMILES: CC(C)Cc1sc(N2CCN(C(=O)c3ncccn3)C(C(=O)O)C2)nc1-c1ccc(Cl)c(Cl)c1]
I-249
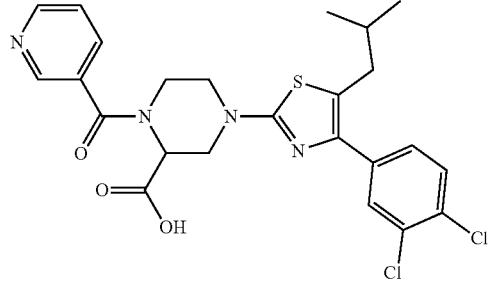 [SMILES: CC(C)Cc1sc(N2CCN(C(=O)c3cccnc3)C(C(=O)O)C2)nc1-c1ccc(Cl)c(Cl)c1]
I-250
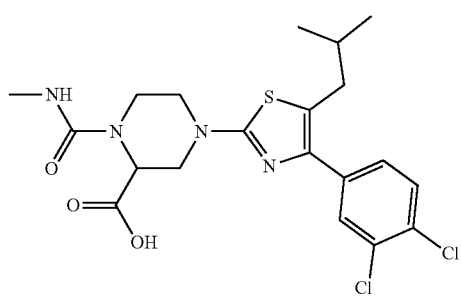 [SMILES: CNC(=O)N1CCN(c2nc(-c3ccc(Cl)c(Cl)c3)c(CC(C)C)s2)CC1C(=O)O]
I-251
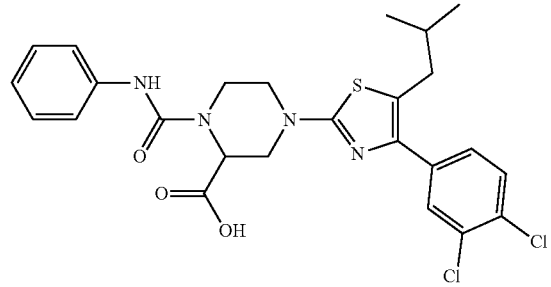 [SMILES: CC(C)Cc1sc(N2CCN(C(=O)Nc3ccccc3)C(C(=O)O)C2)nc1-c1ccc(Cl)c(Cl)c1]
I-252
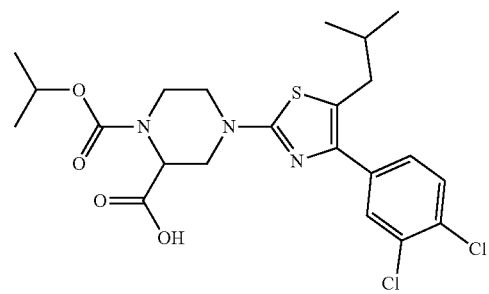 [SMILES: CC(C)Cc1sc(N2CCN(C(=O)OC(C)C)C(C(=O)O)C2)nc1-c1ccc(Cl)c(Cl)c1]
I-253

TABLE 1-continued
Exemplary Compounds
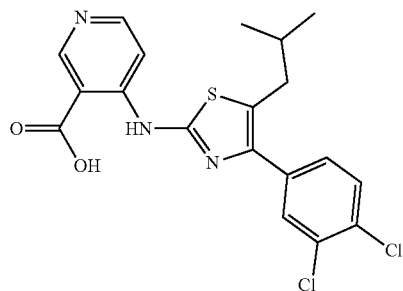 [SMILES: CC(C)Cc1sc(Nc2ccncc2C(=O)O)nc1-c1ccc(Cl)c(Cl)c1]
I-254
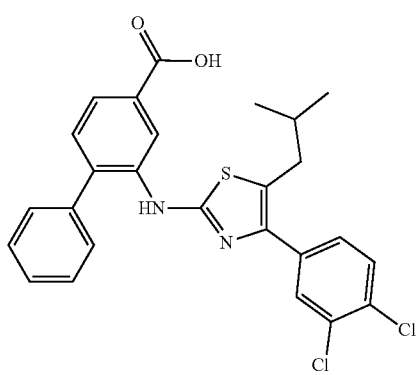 [SMILES: CC(C)Cc1sc(Nc2cc(C(=O)O)ccc2-c2ccccc2)nc1-c1ccc(Cl)c(Cl)c1]
I-255
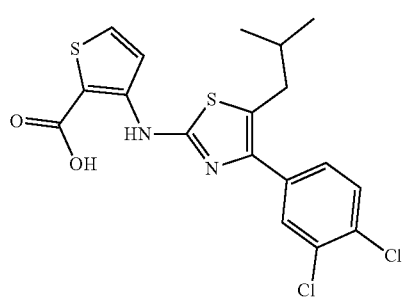 [SMILES: CC(C)Cc1sc(Nc2ccsc2C(=O)O)nc1-c1ccc(Cl)c(Cl)c1]
I-256
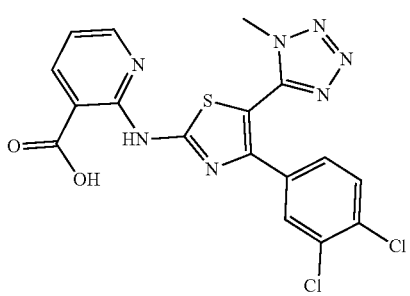 [SMILES: Cn1nnnc1-c1sc(Nc2ncccc2C(=O)O)nc1-c1ccc(Cl)c(Cl)c1]
I-257
TABLE 1-continued
Exemplary Compounds
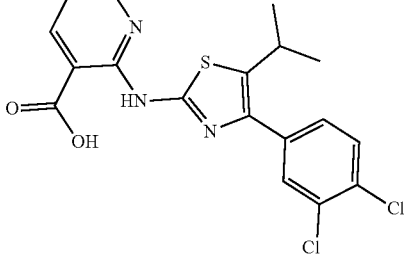
I-258
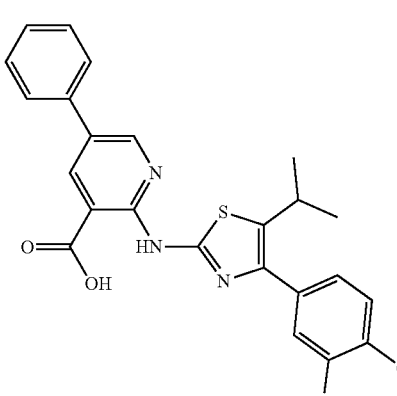
I-259
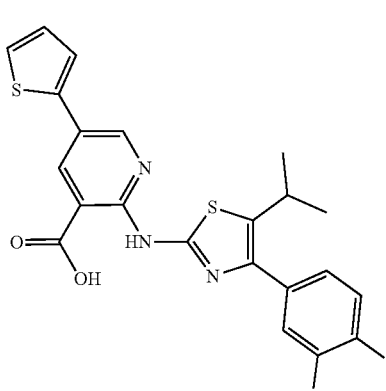
I-260
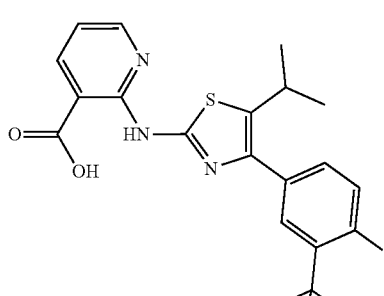
I-261

TABLE 1-continued
Exemplary Compounds
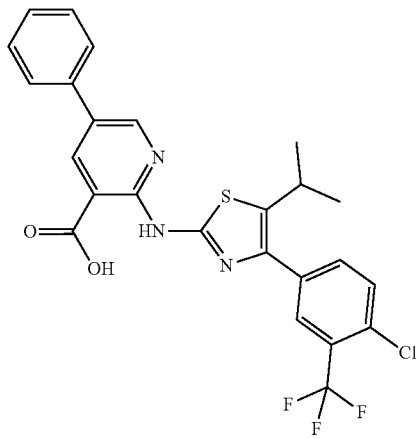 [SMILES: CC(C)c1sc(Nc2ncc(-c3ccccc3)cc2C(=O)O)nc1-c1ccc(Cl)c(C(F)(F)F)c1]
I-262
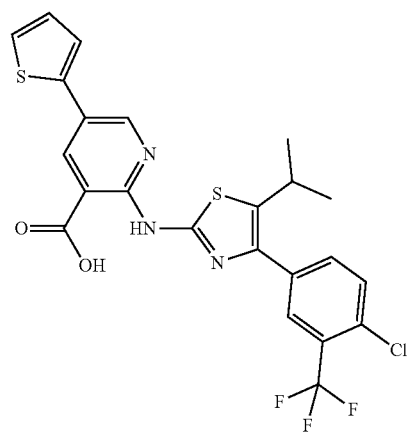 [SMILES: CC(C)c1sc(Nc2ncc(-c3cccs3)cc2C(=O)O)nc1-c1ccc(Cl)c(C(F)(F)F)c1]
I-263
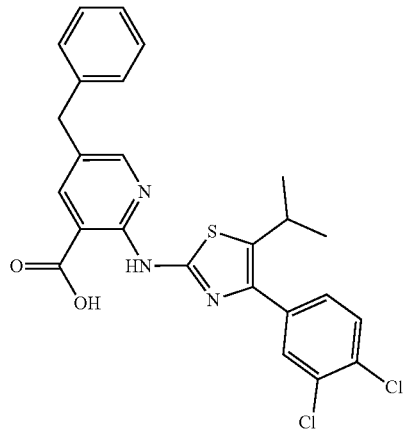 [SMILES: CC(C)c1sc(Nc2ncc(Cc3ccccc3)cc2C(=O)O)nc1-c1ccc(Cl)c(Cl)c1]
I-264
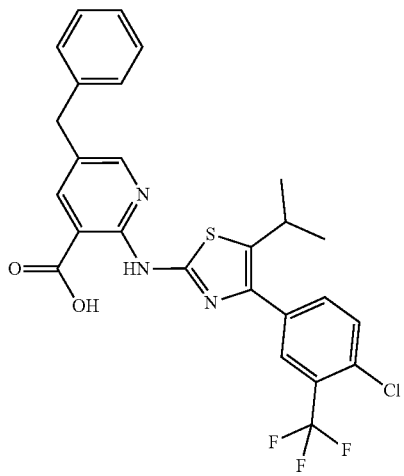 [SMILES: CC(C)c1sc(Nc2ncc(Cc3ccccc3)cc2C(=O)O)nc1-c1ccc(Cl)c(C(F)(F)F)c1]
I-265
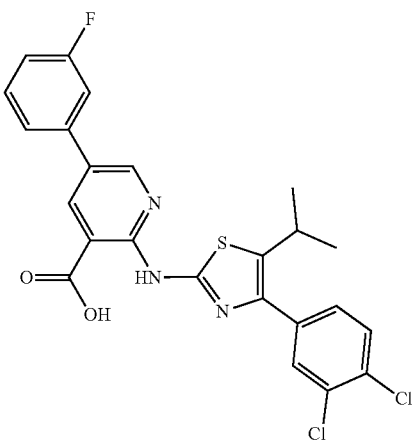 [SMILES: CC(C)c1sc(Nc2ncc(-c3cccc(F)c3)cc2C(=O)O)nc1-c1ccc(Cl)c(Cl)c1]
I-266
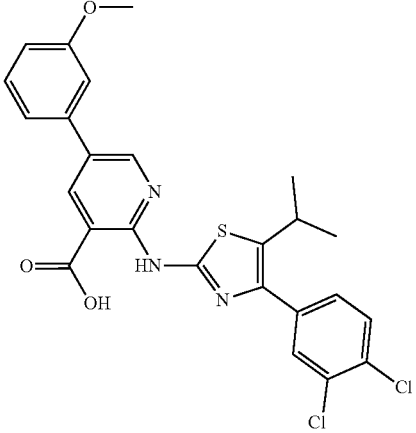 [SMILES: COc1cccc(-c2cnc(Nc3nc(-c4ccc(Cl)c(Cl)c4)c(C(C)C)s3)c(C(=O)O)c2)c1]
I-267

TABLE 1-continued
Exemplary Compounds
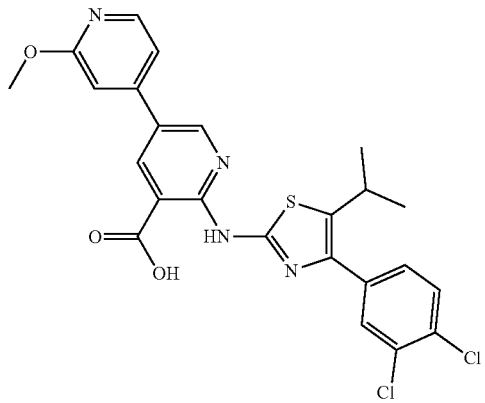 [SMILES: COc1cc(-c2cnc(Nc3nc(-c4ccc(Cl)c(Cl)c4)c(C(C)C)s3)c(C(=O)O)c2)ccn1]
I-268
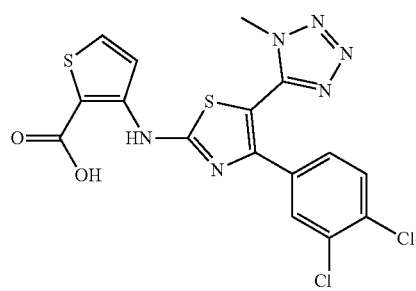 [SMILES: Cn1nnnc1-c1sc(Nc2ccsc2C(=O)O)nc1-c1ccc(Cl)c(Cl)c1]
I-269
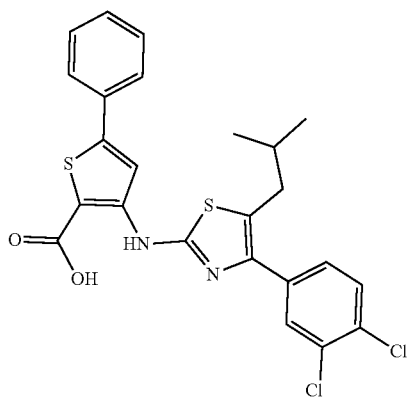 [SMILES: CC(C)Cc1sc(Nc2cc(-c3ccccc3)sc2C(=O)O)nc1-c1ccc(Cl)c(Cl)c1]
I-270
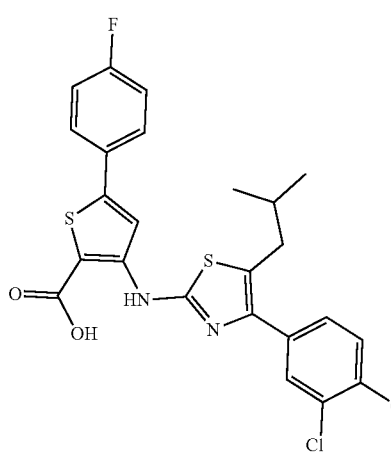
I-271
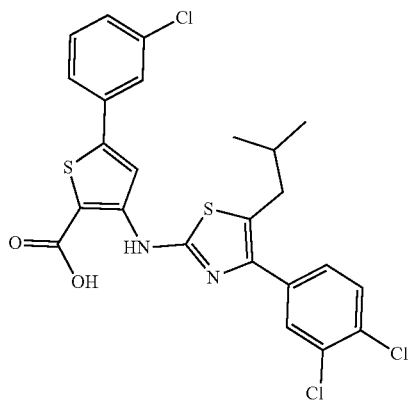 [SMILES: CC(C)Cc1sc(Nc2cc(-c3cccc(Cl)c3)sc2C(=O)O)nc1-c1ccc(Cl)c(Cl)c1]
I-272
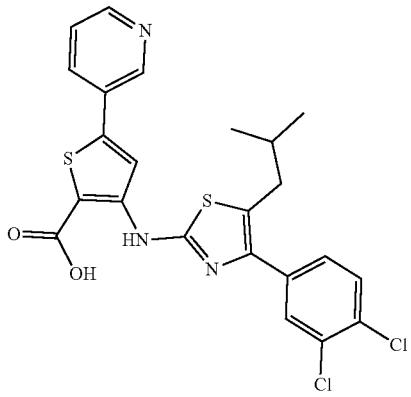 [SMILES: CC(C)Cc1sc(Nc2cc(-c3cccnc3)sc2C(=O)O)nc1-c1ccc(Cl)c(Cl)c1]
I-273

TABLE 1-continued
Exemplary Compounds
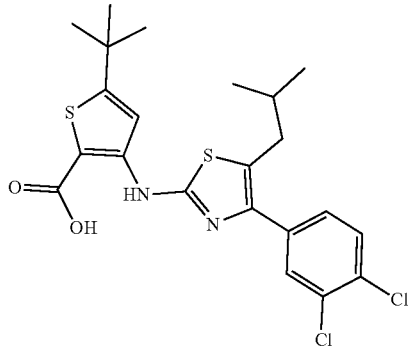 [SMILES: CC(C)Cc1sc(Nc2cc(C(C)(C)C)sc2C(=O)O)nc1-c1ccc(Cl)c(Cl)c1]
I-274
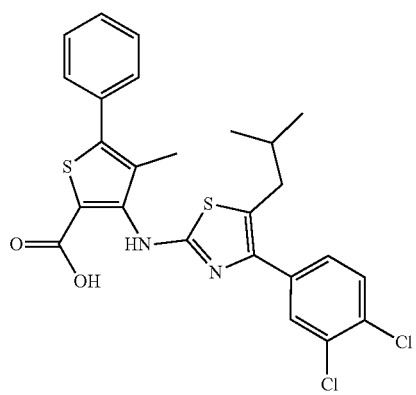 [SMILES: Cc1c(-c2ccccc2)sc(C(=O)O)c1Nc1nc(-c2ccc(Cl)c(Cl)c2)c(CC(C)C)s1]
I-275
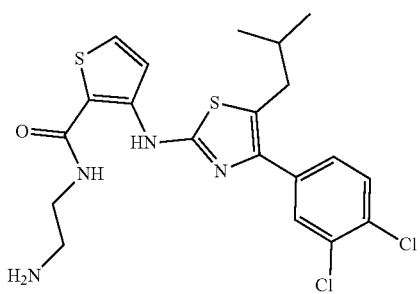 [SMILES: CC(C)Cc1sc(Nc2ccsc2C(=O)NCCN)nc1-c1ccc(Cl)c(Cl)c1]
I-276
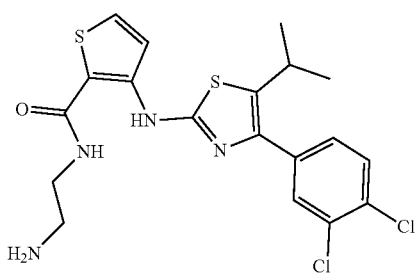 [SMILES: CC(C)c1sc(Nc2ccsc2C(=O)NCCN)nc1-c1ccc(Cl)c(Cl)c1]
I-277
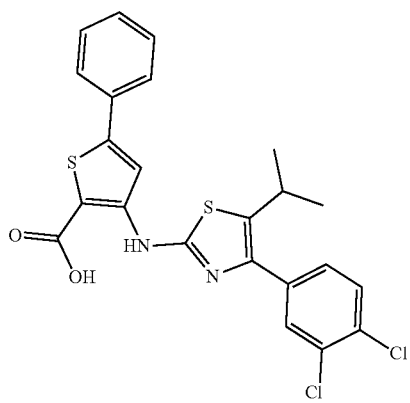 [SMILES: CC(C)c1sc(Nc2cc(-c3ccccc3)sc2C(=O)O)nc1-c1ccc(Cl)c(Cl)c1]
I-278
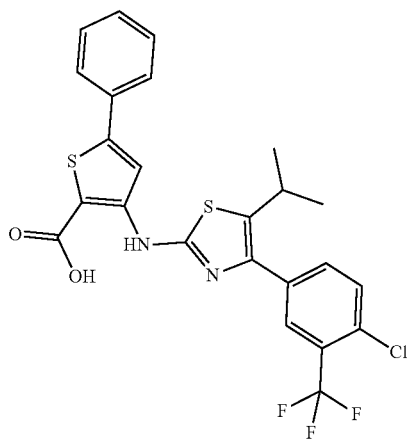 [SMILES: CC(C)c1sc(Nc2cc(-c3ccccc3)sc2C(=O)O)nc1-c1ccc(Cl)c(C(F)(F)F)c1]
I-279
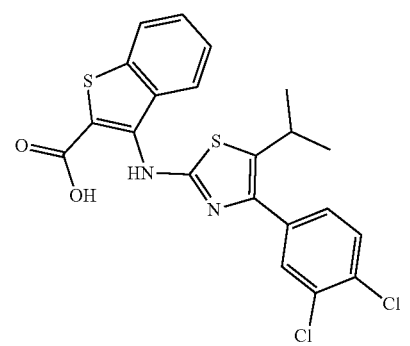 [SMILES: CC(C)c1sc(Nc2c(C(=O)O)sc3ccccc23)nc1-c1ccc(Cl)c(Cl)c1]
I-280

TABLE 1-continued
Exemplary Compounds
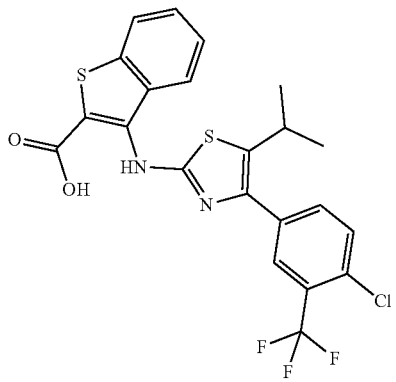 [SMILES: CC(C)c1sc(Nc2c(C(=O)O)sc3ccccc23)nc1-c1ccc(Cl)c(C(F)(F)F)c1]
I-281
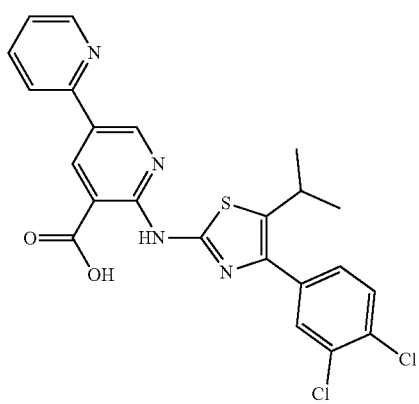 [SMILES: CC(C)c1sc(Nc2ncc(-c3ccccn3)cc2C(=O)O)nc1-c1ccc(Cl)c(Cl)c1]
I-282
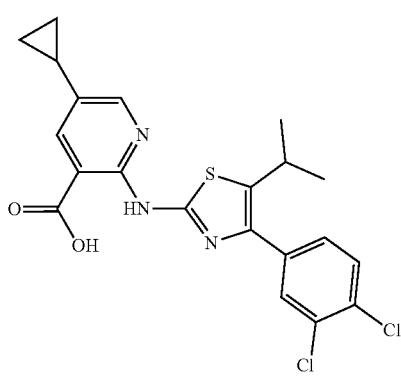 [SMILES: CC(C)c1sc(Nc2ncc(C3CC3)cc2C(=O)O)nc1-c1ccc(Cl)c(Cl)c1]
I-283
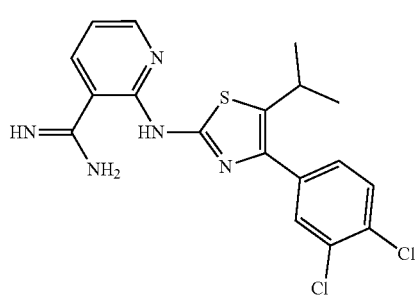 [SMILES: CC(C)c1sc(Nc2ncccc2C(=N)N)nc1-c1ccc(Cl)c(Cl)c1]
I-284
TABLE 1-continued
Exemplary Compounds
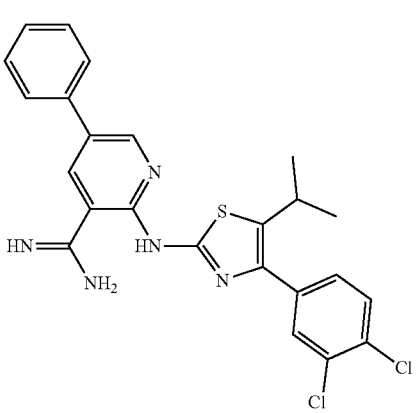 [SMILES: CC(C)c1sc(Nc2ncc(-c3ccccc3)cc2C(=N)N)nc1-c1ccc(Cl)c(Cl)c1]
I-285
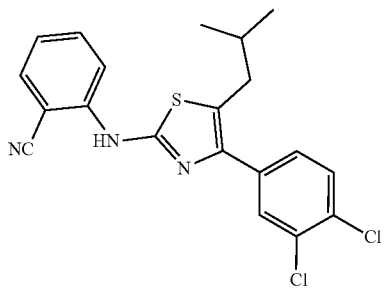 [SMILES: CC(C)Cc1sc(Nc2ccccc2C#N)nc1-c1ccc(Cl)c(Cl)c1]
I-286
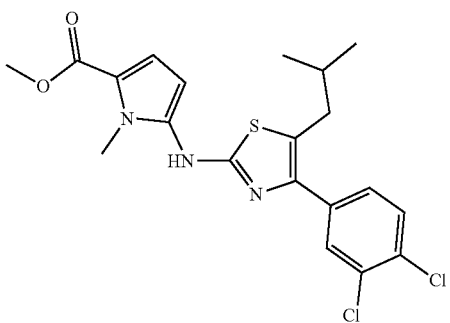 [SMILES: COC(=O)c1ccc(Nc2nc(-c3ccc(Cl)c(Cl)c3)c(CC(C)C)s2)n1C]
I-287
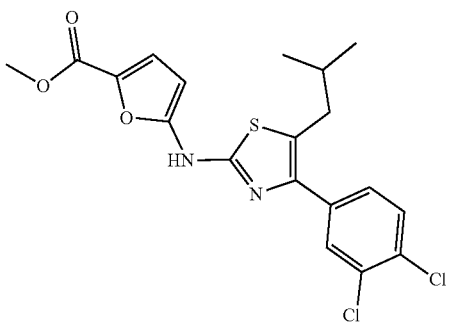 [SMILES: COC(=O)c1ccc(Nc2nc(-c3ccc(Cl)c(Cl)c3)c(CC(C)C)s2)o1]
I-288

TABLE 1-continued
Exemplary Compounds
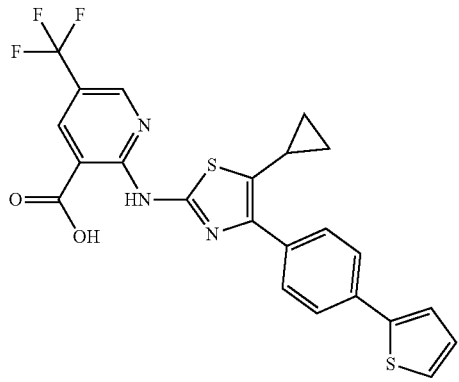 [SMILES: O=C(O)c1cc(C(F)(F)F)cnc1Nc1nc(-c2ccc(-c3cccs3)cc2)c(C2CC2)s1]
I-289
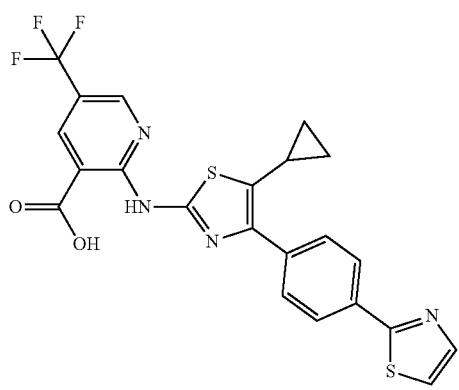 [SMILES: O=C(O)c1cc(C(F)(F)F)cnc1Nc1nc(-c2ccc(-c3nccs3)cc2)c(C2CC2)s1]
I-290
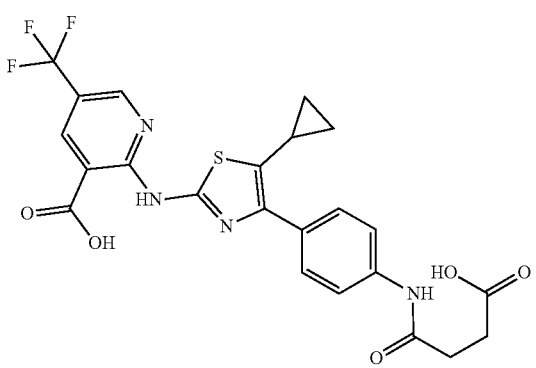 [SMILES: O=C(O)CCC(=O)Nc1ccc(-c2nc(Nc3ncc(C(F)(F)F)cc3C(=O)O)sc2C2CC2)cc1]
I-291
TABLE 1-continued
Exemplary Compounds
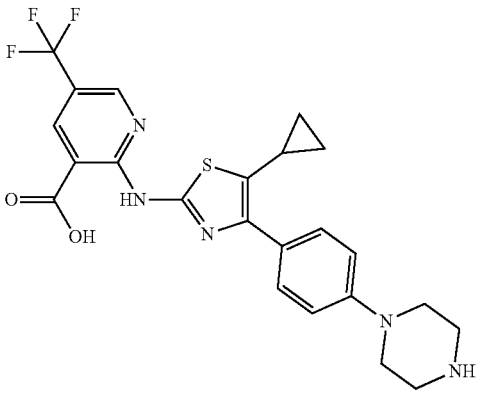 [SMILES: O=C(O)c1cc(C(F)(F)F)cnc1Nc1nc(-c2ccc(N3CCNCC3)cc2)c(C2CC2)s1]
I-292
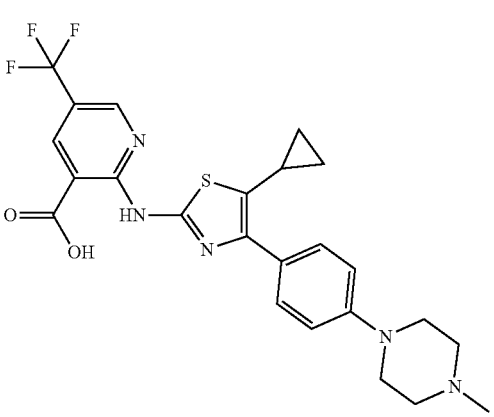 [SMILES: CN1CCN(c2ccc(-c3nc(Nc4ncc(C(F)(F)F)cc4C(=O)O)sc3C3CC3)cc2)CC1]
I-293
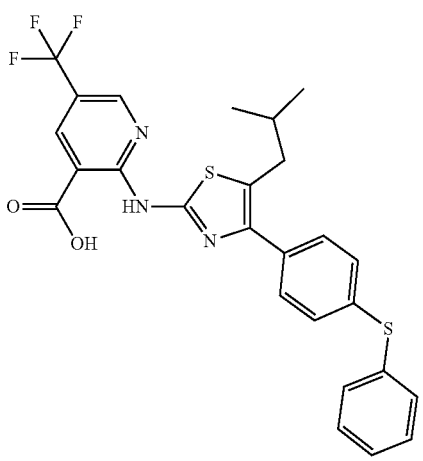 [SMILES: CC(C)Cc1sc(Nc2ncc(C(F)(F)F)cc2C(=O)O)nc1-c1ccc(Sc2ccccc2)cc1]
I-294

TABLE 1-continued
Exemplary Compounds
I-295
I-296
I-297
I-298
I-299
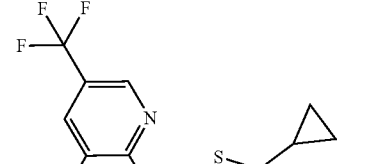
I-300

TABLE 1-continued
Exemplary Compounds
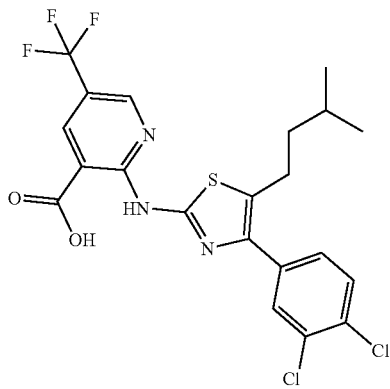 [SMILES: CC(C)CCc1sc(Nc2ncc(C(F)(F)F)cc2C(=O)O)nc1-c1ccc(Cl)c(Cl)c1]
I-301
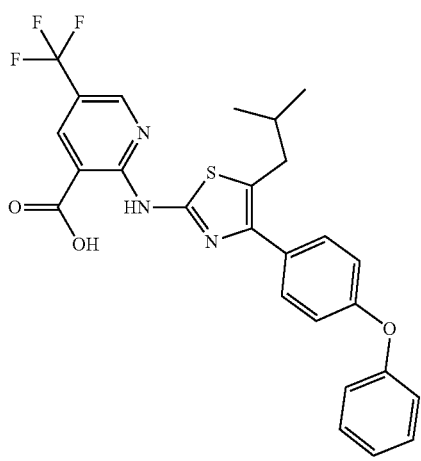 [SMILES: CC(C)Cc1sc(Nc2ncc(C(F)(F)F)cc2C(=O)O)nc1-c1ccc(Oc2ccccc2)cc1]
I-302
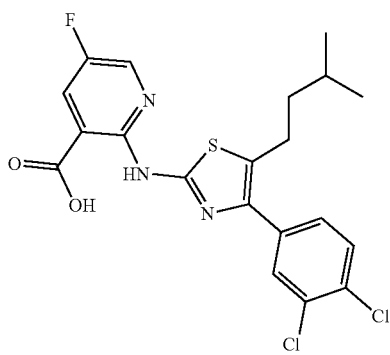 [SMILES: CC(C)CCc1sc(Nc2ncc(F)cc2C(=O)O)nc1-c1ccc(Cl)c(Cl)c1]
I-303
TABLE 1-continued
Exemplary Compounds
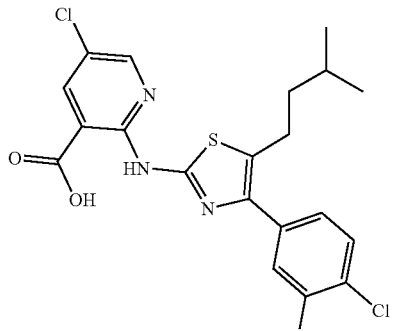
I-304
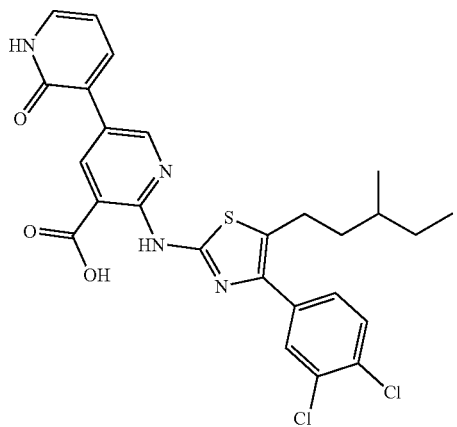 [SMILES: CCC(C)CCc1sc(Nc2ncc(-c3ccc[nH]c3=O)cc2C(=O)O)nc1-c1ccc(Cl)c(Cl)c1]
I-305
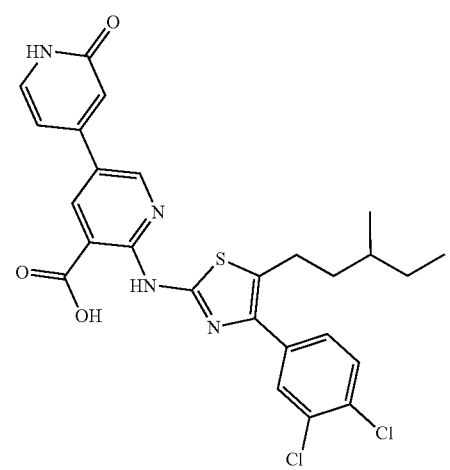 [SMILES: CCC(C)CCc1sc(Nc2ncc(-c3cc[nH]c(=O)c3)cc2C(=O)O)nc1-c1ccc(Cl)c(Cl)c1]
I-306

TABLE 1-continued
Exemplary Compounds
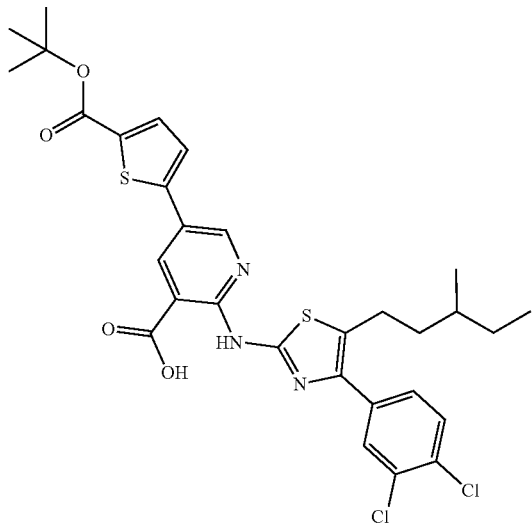 [SMILES: CCC(C)CCc1sc(Nc2ncc(-c3ccc(C(=O)OC(C)(C)C)s3)cc2C(=O)O)nc1-c1ccc(Cl)c(Cl)c1]
I-307
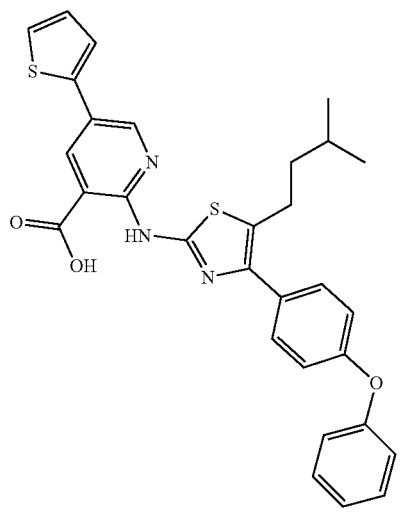 [SMILES: CC(C)CCc1sc(Nc2ncc(-c3cccs3)cc2C(=O)O)nc1-c1ccc(Oc2ccccc2)cc1]
I-308
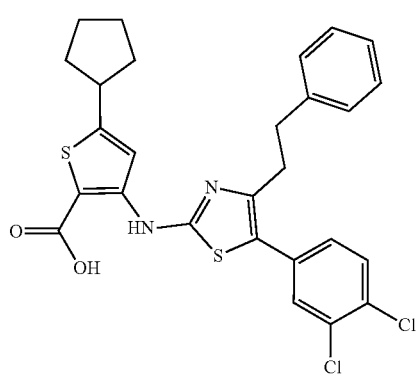 [SMILES: O=C(O)c1sc(C2CCCC2)cc1Nc1nc(CCc2ccccc2)c(-c2ccc(Cl)c(Cl)c2)s1]
I-309
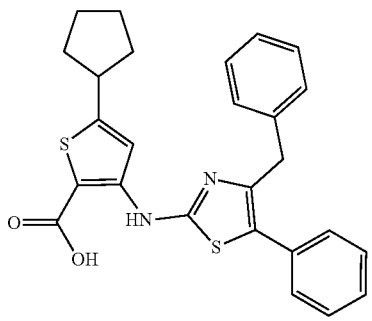 [SMILES: O=C(O)c1sc(C2CCCC2)cc1Nc1nc(Cc2ccccc2)c(-c2ccccc2)s1]
I-310
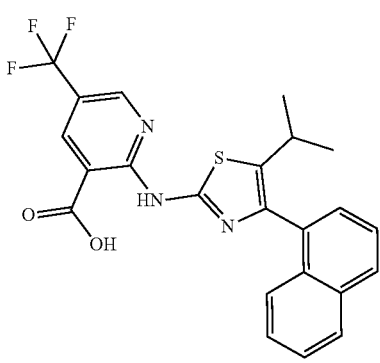 [SMILES: CC(C)c1sc(Nc2ncc(C(F)(F)F)cc2C(=O)O)nc1-c1cccc2ccccc12]
I-311
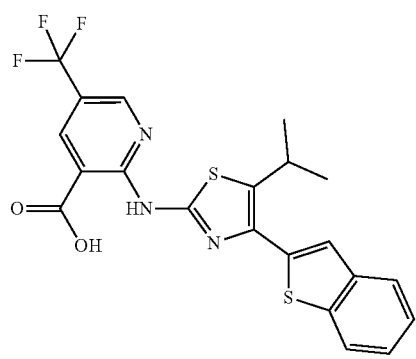 [SMILES: CC(C)c1sc(Nc2ncc(C(F)(F)F)cc2C(=O)O)nc1-c1cc2ccccc2s1]
I-312
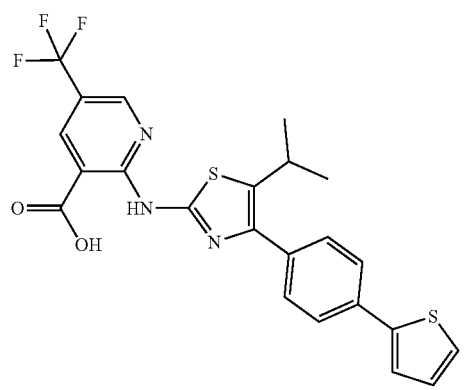 [SMILES: CC(C)c1sc(Nc2ncc(C(F)(F)F)cc2C(=O)O)nc1-c1ccc(-c2cccs2)cc1]
I-313

TABLE 1-continued
Exemplary Compounds
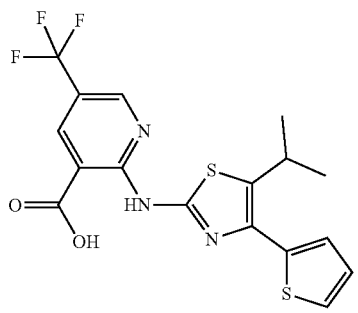 [SMILES: CC(C)c1sc(Nc2ncc(C(F)(F)F)cc2C(=O)O)nc1-c1cccs1]
I-314
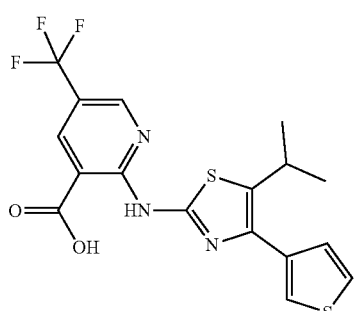
I-315
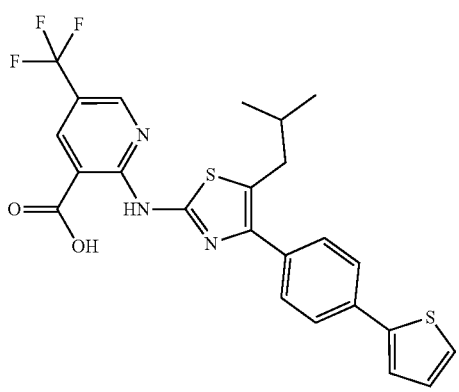 [SMILES: CC(C)Cc1sc(Nc2ncc(C(F)(F)F)cc2C(=O)O)nc1-c1ccc(-c2cccs2)cc1]
I-316
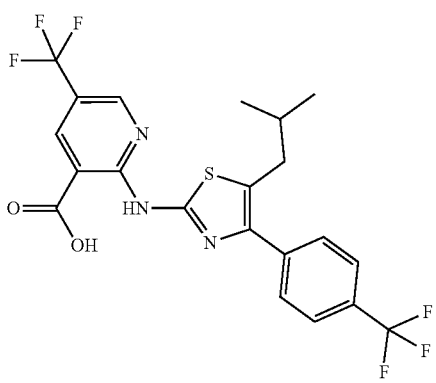 [SMILES: CC(C)Cc1sc(Nc2ncc(C(F)(F)F)cc2C(=O)O)nc1-c1ccc(C(F)(F)F)cc1]
I-317
TABLE 1-continued
Exemplary Compounds
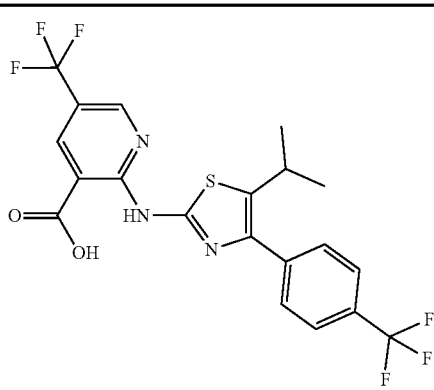
I-318
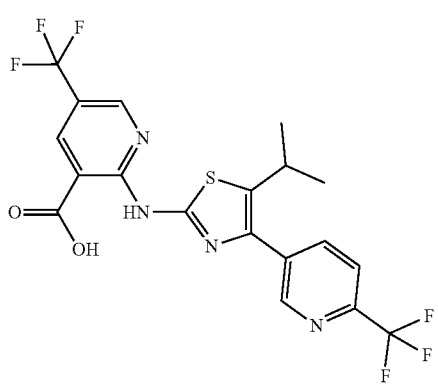 [SMILES: CC(C)c1sc(Nc2ncc(C(F)(F)F)cc2C(=O)O)nc1-c1ccc(C(F)(F)F)nc1]
I-319
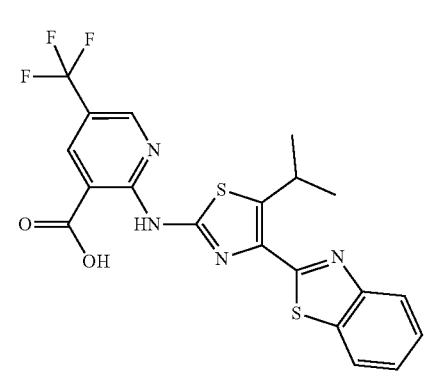 [SMILES: CC(C)c1sc(Nc2ncc(C(F)(F)F)cc2C(=O)O)nc1-c1nc2ccccc2s1]
I-320

TABLE 1-continued

Exemplary Compounds

I-321

I-322

I-323

I-324

I-325

I-326

TABLE 1-continued
Exemplary Compounds
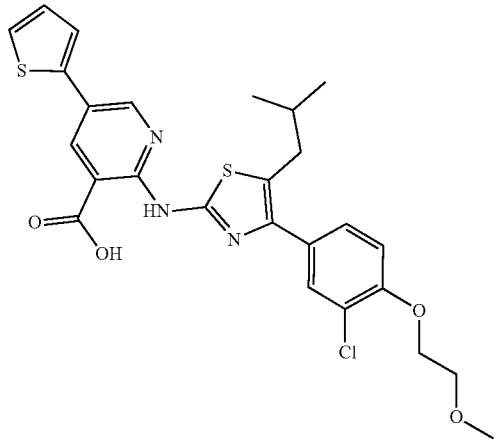 [SMILES: COCCOc1ccc(-c2nc(Nc3ncc(-c4cccs4)cc3C(=O)O)sc2CC(C)C)cc1Cl]
I-327
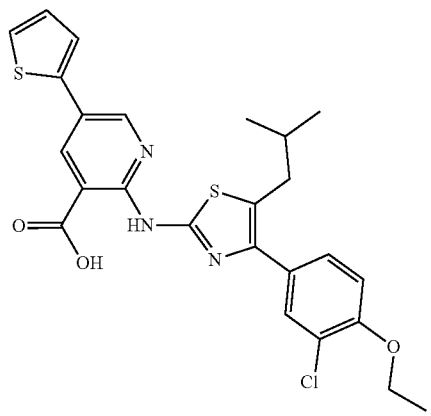
I-330
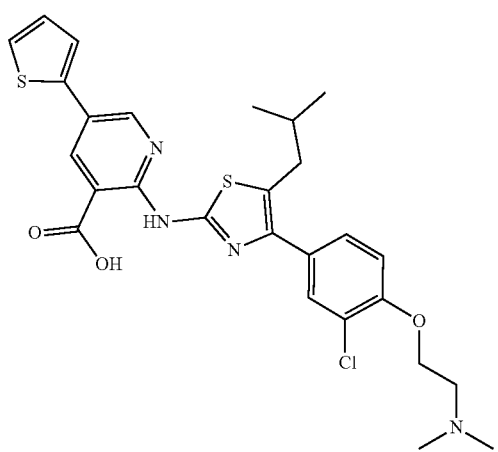 [SMILES: CC(C)Cc1sc(Nc2ncc(-c3cccs3)cc2C(=O)O)nc1-c1ccc(OCCN(C)C)c(Cl)c1]
I-328
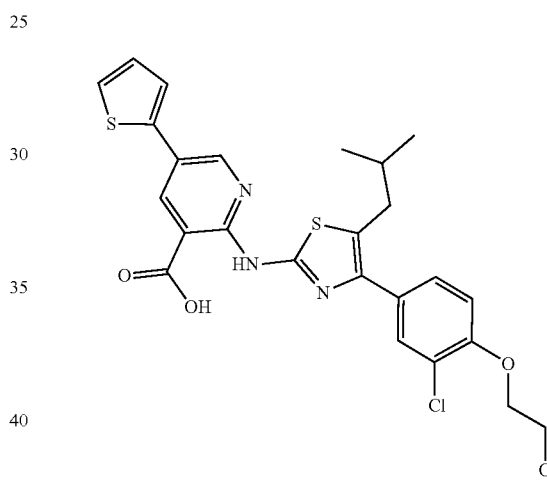
I-331
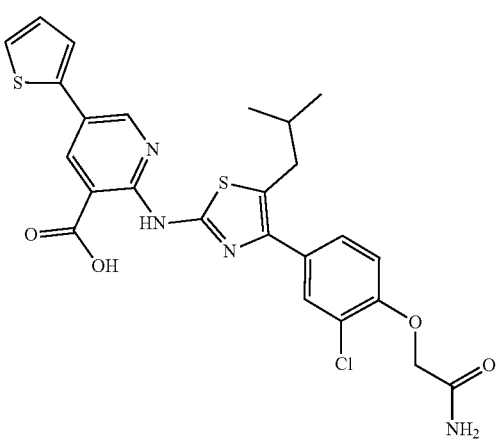 [SMILES: CC(C)Cc1sc(Nc2ncc(-c3cccs3)cc2C(=O)O)nc1-c1ccc(OCC(N)=O)c(Cl)c1]
I-329
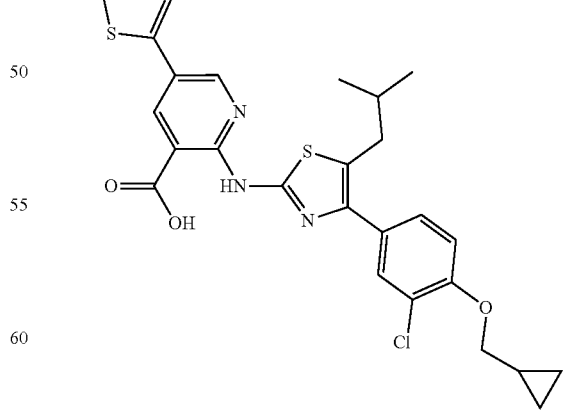
I-332

TABLE 1-continued

Exemplary Compounds

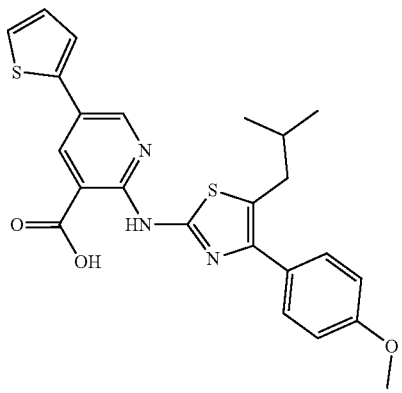 [SMILES: COc1ccc(-c2nc(Nc3ncc(-c4cccs4)cc3C(=O)O)sc2CC(C)C)cc1]

I-333

4. Formulation and Administration 4.1 Pharmaceutically Acceptable Compositions

According to another embodiment, the invention provides a composition comprising a compound of this invention, or a pharmaceutically acceptable derivative thereof, and a pharmaceutically acceptable carrier, adjuvant, or vehicle. The amount of compound in compositions of this invention is such that is effective to measurably inhibit eIF4E, or a mutant thereof, in a biological sample or in a patient. In certain embodiments, the amount of compound in compositions of this invention is such that is effective to measurably inhibit eIF4E, or a mutant thereof, in a biological sample or in a patient. In certain embodiments, a composition of this invention is formulated for administration to a patient in need of such composition. In some embodiments, a composition of this invention is formulated for oral administration to a patient.

In some embodiments, the invention provides a pharmaceutical composition comprising a compound of Formula (I), or a pharmaceutically acceptable salt thereof, and a pharmaceutically acceptable carrier, adjuvant, or vehicle.

In some embodiments, the invention provides a pharmaceutical composition comprising a compound of Formulae (II) to (VII), (II-a) to (VII-a), (II-b) to (VII-b), or a pharmaceutically acceptable salt thereof, and a pharmaceutically acceptable carrier, adjuvant, or vehicle.

In some embodiments, the invention provides a pharmaceutical composition comprising a compound of Table 1, or a pharmaceutically acceptable salt thereof, and a pharmaceutically acceptable carrier, adjuvant, or vehicle.

In some embodiments, a compound of the invention, or a pharmaceutically acceptable derivative or composition thereof, is administered in a single composition as a single dosage form.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of eIF4E, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

4.2. Co-Administration with One or More Other Therapeutic Agent

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 20, 21, 22, 23, or 24 hours from one another. In some embodiments, one or more other therapeutic agent and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention may be administered with one or more other therapeutic agent simultaneously or sequentially in separate unit dosage forms or together in a single unit dosage form. Accordingly, the present invention provides a single unit dosage form comprising a compound of the current invention, one or more other therapeutic agent, and a pharmaceutically acceptable carrier, adjuvant, or vehicle.

The amount of a compound of the invention and one or more other therapeutic agent (in those compositions which comprise an additional therapeutic agent as described above) that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent, the one or more other therapeutic agent and a compound of the invention may act synergistically. Therefore, the amount of the one or more other therapeutic agent in such compositions may be less than that required in a monotherapy utilizing only that therapeutic agent. In such compositions a dosage of between 0.01-1,000 µg/kg body weight/day of the one or more other therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

4.2.1. Exemplary Other Therapeutic Agents

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); nedaplatin (Aqupla@, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaeceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgGI antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal©); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-10}33$, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; $Zd_6474$; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

4.2.2. Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fni4, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgGI, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO09/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase– (TK–) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCTO2124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiments, the bystander cells comprise tumor-associated antigen (TAA) negative cancer cells. In some embodiments, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, T6, and memory CD8$^+$ (ap) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgGI anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgGl Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KTR) inhibitors. KTR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgGl, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

5. Uses

Compounds and compositions described herein are generally useful for the inhibition of eIF4E or a mutant thereof.

The activity of a compound utilized in this invention as an inhibitor of eIF4E, or a mutant thereof, may be assayed in vitro, in vivo or in a cell line. In vitro assays include assays that determine inhibition of eIF4E, or a mutant thereof. Alternate in vitro assays quantitate the ability of the inhibitor to bind to eIF4E. Detailed conditions for assaying a compound utilized in this invention as an inhibitor of eIF4E, or a mutant thereof, are set forth in the Examples below.

Provided compounds are inhibitors of eIF4E and are therefore useful for treating one or more disorders associated with activity of eIF4E. Thus, in certain embodiments, the present invention provides a method for treating an eIF4E-mediated disorder comprising the step of administering to a patient in need thereof a compound of the present invention, or pharmaceutically acceptable composition thereof. In certain embodiments, an eIF4E-mediated disorder is an eIF4E-mediated cancer. In some embodiments, an eIF4E-mediated cancer is selected from breast cancer, colorectal cancer, lung caner, glioblastoma, sarcomas, melanoma, prostate cancer, and lymphomas. In some embodiments, an eIF4E-mediated cancer is breast cancer.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "eIF4E-mediated" disorders, diseases, and/or conditions as used herein means any disease or other deleterious condition in which eIF4E, or a mutant thereof, is known to play a role, including, but is not limited to, a cellular proliferative disorder. In some embodiments, a cellular proliferative disorder is cancer as described herein. Cancer Cancer includes, in some embodiments, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrom Macroglobulinemia, or Wilms Tumor.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

In some embodiments, the cancer is small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In some embodiments, the cancer is small cell lung cancer, non-small cell lung cancer, colorectal cancer, multiple myeloma, or AML.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a tumor in a patient in need thereof, comprising administering to the patient compound II, or a pharmaceutical salt or composition thereof, and an immuno-oncology agent as described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments, the tumor comprises small cell lung cancer (SCLC). In some embodiments, the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

The compounds and compositions, according to the method of the present invention, may be administered using any amount and any route of administration effective for treating or lessening the severity of a cancer. The exact amount required will vary from subject to subject, depending on the species, age, and general condition of the subject, the severity of the disease or condition, the particular agent, its mode of administration, and the like. The compounds and compositions, according to the method of the present invention, are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The following examples are provided for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of Compounds I-1 to I-48

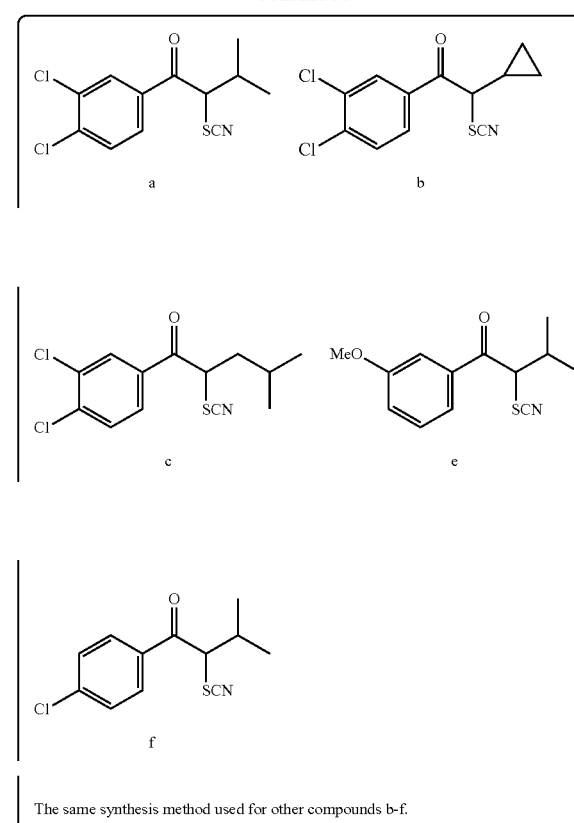

The same synthesis method used for other compounds b-f.

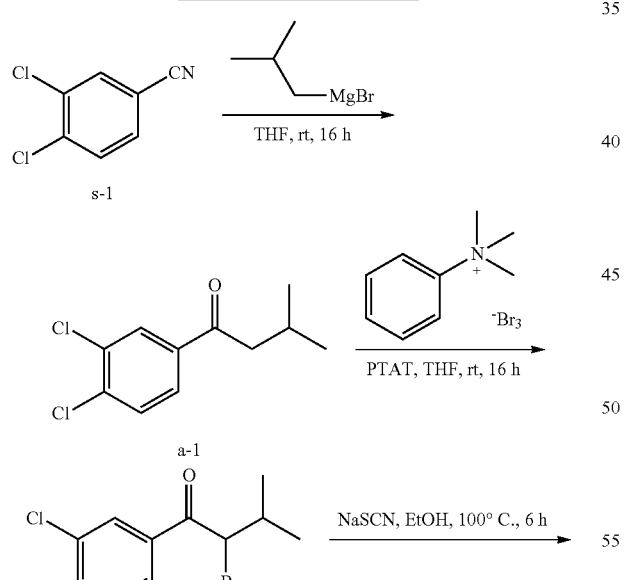

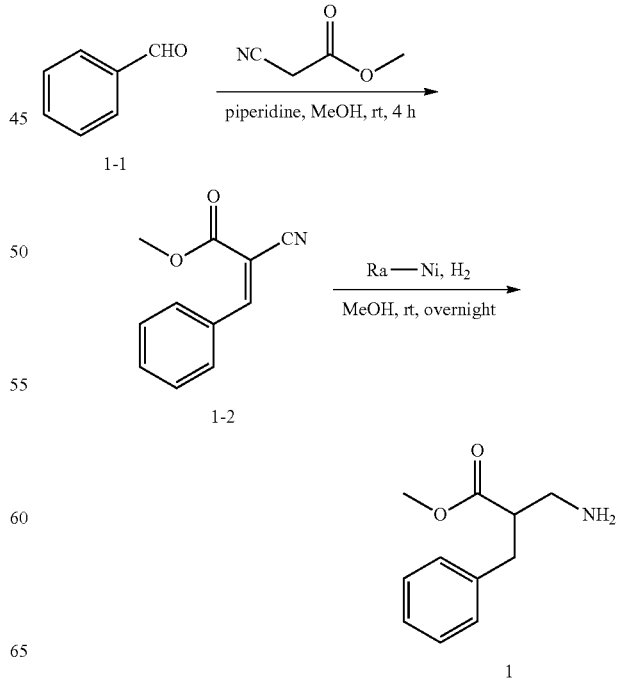

175
-continued
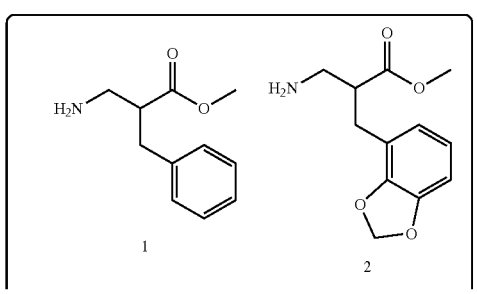
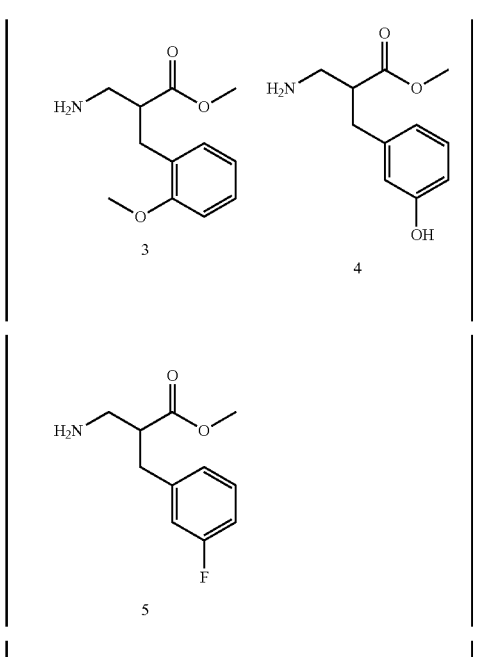
The same synthesis method used for other compounds 2-5.
Scheme 3: Route for compound 6
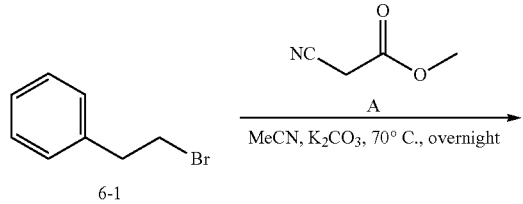
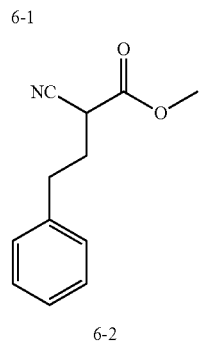
176
-continued
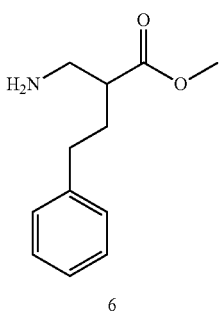
Scheme 4: Route for 7, 8, 9, 10
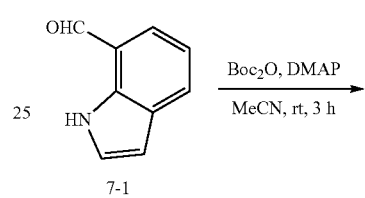
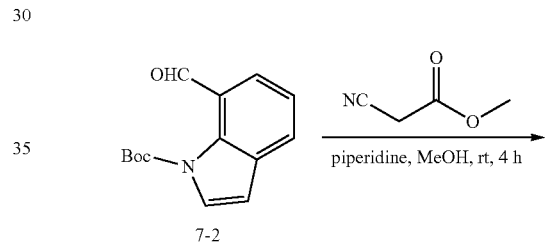
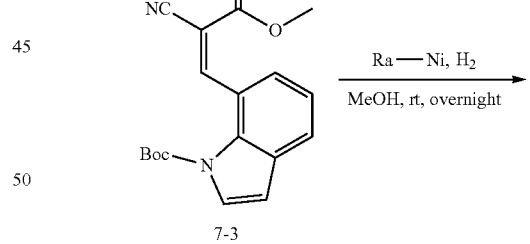
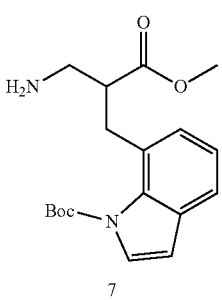

-continued
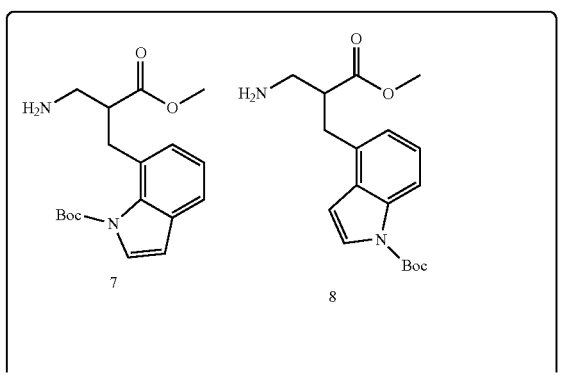
The same synthesis method used for other three compounds 8-10.
Scheme 5: Route for I-1 to I-6, I-11 to I-15, I-18 to I-23, I-28 to I-33, I-38 to I-43
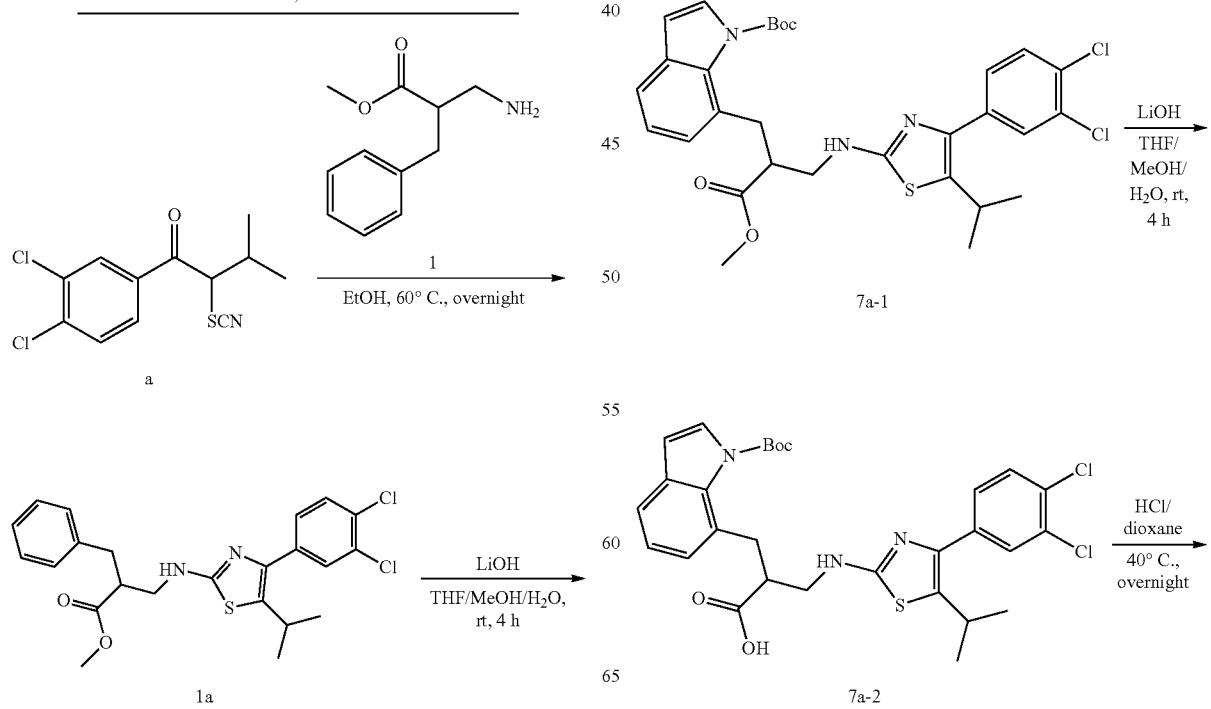
-continued
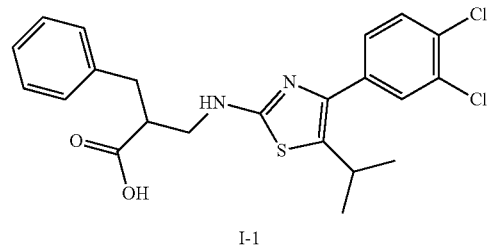
The same synthesis method used for other cmopounds I-2 to I-6, I-11 to I-15, I-18 to I-23, I-28 to I-33, I-38 to I-43
Scheme 6: Route for I-7 to I-10, I-16, I-17, I-24 to I-27, I-34 to I-37, I-44 to I-46
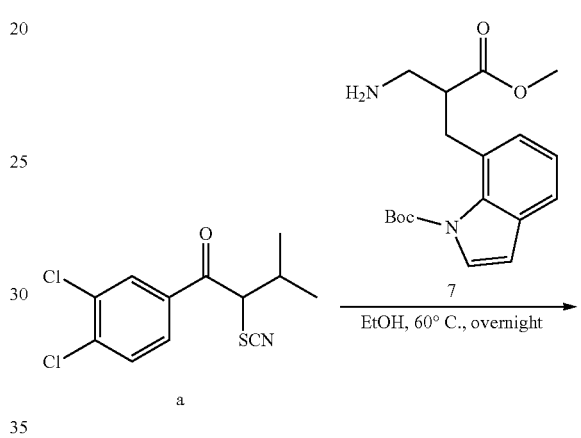

179

-continued

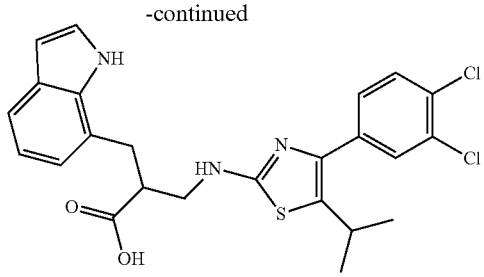

I-7

The same synthesis method used for other compounds I-8 to I-10, I-16, I-17, I-24 to I-27, I-34 to I-37, I-44 to I-46

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [$CH_3CN$+0.05% TFA] to 0% [water+0.05% TFA] and 100% [$CH_3CN$+0.05% TFA] in 0.8 min, then under this condition for 0.4 min, finally changed to 95% [water+0.05% TFA] and 5% [$CH_3CN$+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.)

180

Synthesis of 1-(3,4-dichlorophenyl)-3-methylbutan-1-one (a-1)

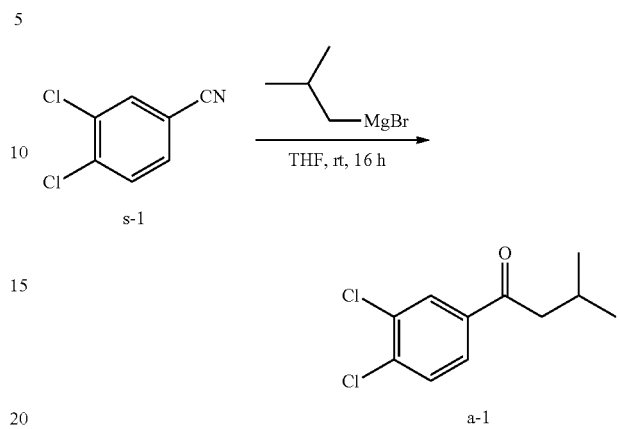

To a solution of s-1 (10.0 g, 58.1 mmol) in THF (100 mL) was added isobutyl magnesium bromide (1.0 M in THF, 87.1 mL, 87.1 mmol). The reaction was stirred at room temperature for 16 h. When the reaction was completed, it was poured into aq.$NH_4Cl$ (sat., 500 mL) and extracted with EtOAc (100 mL×3). The organic phase was combined, and washed with $H_2O$ (100 mL) and brine (80 mL), then dried with anhydrous $Na_2SO_4$, concentrated and purified by silica gel column chromatography (petrol ether/ethyl acetate=20/1) to afford a-1 (7.50 g, 55.8% yield) as a yellow oil.

Synthesis of 2-bromo-1-(3,4-dichlorophenyl)-3-methylbutan-1-one (a-2)

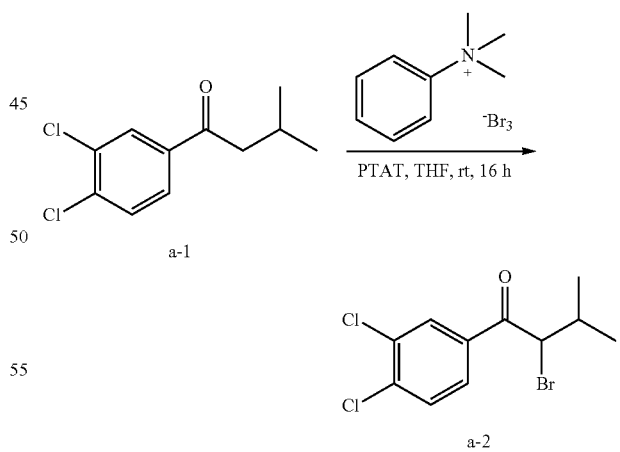

A mixture of a-1 (7.50 g, 32.5 mmol) and PTAT (18.3 g, 48.7 mmol) in THF (150 mL) was stirred at room temperature overnight. When the reaction was completed, it was concentrated, and the residual was dissolved in $H_2O$ (100 mL), and then extracted with EtOAc (100 mL×2). The organic layer was combined, and washed with $H_2O$ (60 mL×2) and Brine (80 mL), then dried by anhydrous $Na_2SO_4$.

The solution was concentrated to give the crude product, which was used directly in next step without farther purification to afford a-2 (10.1 g, 100% yield) as brown oil.

Synthesis of 1-(3,4-dichlorophenyl)-3-methyl-2-thiocyanatobutan-1-one (a)

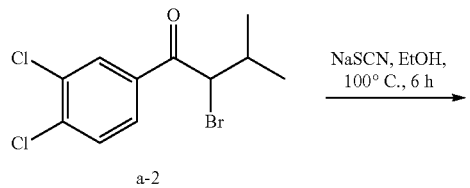

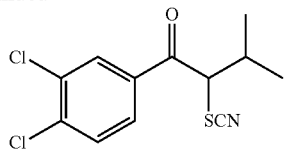

A mixture of a-2 (10.1 g, 32.5 mmol) and NaSCN (5.26 g, 64.9 mmol) in EtOH (100.0 mL) was stirred at 100° C. for 6 h. When the reaction was completed, it was concentrated and purified by silica gel column chromatography (petrol ether/ethyl acetate=10/1) to afford a (5.32 g, 57.00% yield) as a white solid.

TABLE 1-1

Characterization Data for Compounds a-f

| Compounds | Chemical Structure | LCMS |
|---|---|---|
| a | 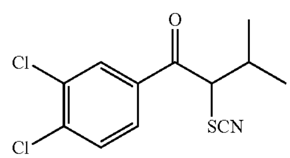 | Method B, Purity is 81.7%, Rt = 2.283 min; MS Calcd.: 287.0; MS Found: 288.0 [M + H]⁺. |
| b | 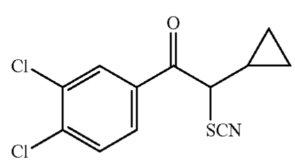 | Method B, Purity is 100%, Rt = 2.053 min; MS Calcd.: 284.98; No MS Found. |
| c | 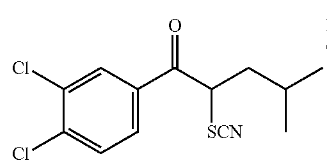 | Method B, Purity is 75.2%, Rt = 2.480 min; MS Calcd.: 301.0; MS Found: 324.1 [M + Na]⁺. |
| e | 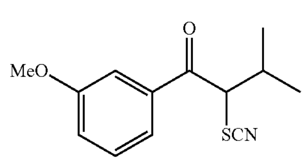 | Method B, Purity is 90.1%, Rt = 1.947 min; MS Calcd.: 249.1; MS Found: 250.2 [M + H]⁺. |
| f | 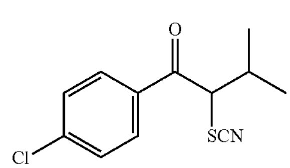 | Method B, Purity is 97.7%, Rt = 2.296 min; MS Calcd.: 253.03; No MS Found. |

Synthesis of (Z)-methyl 2-cyano-3-phenylacrylate (1-2)

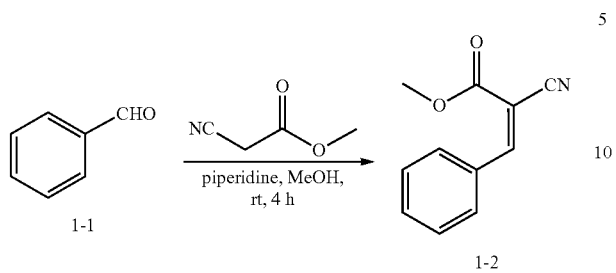

To a mixture of 1-1 (5.00 g, 47.2 mmol) and methyl 2-cyanoacetate (5.61 g, 56.6 mmol) in MeOH (100 mL) was added piperidine (5 drops). The reaction was stirred at room temperature for 4 h. When the reaction was completed, the reaction mixture was filtered, and the residue was washed with MeOH (2.0 mL×2), dried to afford 1-2 (6.50 g, 73.7% yield) as a white solid.

Synthesis of methyl 3-amino-2-benzylpropanoate (1)

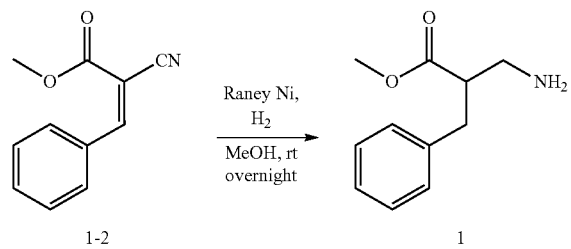

A mixture of 1-2 (6.50 g, 34.7 mmol) and Raney Ni (2.00 g) in MeOH (800 mL) was stirred under $H_2$ atmosphere at room temperature overnight. When the reaction was completed, the mixture was filtered, and the filtrate was concentrated to give a crude product, which was purified by silica gel column chromatography ($CH_2Cl_2/CH_3OH$=50/1) to afford 1 (550 mg, 7.5% yield) as a colorless oil.

Synthesis of methyl 2-cyano-4-phenylbutanoate (6-2)

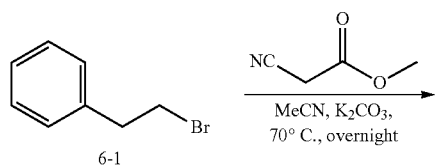

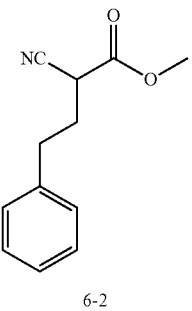

A mixture of 6-1 (4.00 g, 21.6 mmol), methyl 2-cyanoacetate (10.7 g, 108.1 mmol) and $K_2CO_3$ (8.95 g, 64.8 mmol) in MeCN (200 mL) was stirred at 70° C. overnight. When the reaction was completed, the mixture was concentrated and purified by silica gel column chromatography (petrol ether/ethyl acetate=30/1) to afford 6-2 (3.20 g, 72.8% yield) as a yellow oil.

Synthesis of methyl 2-(aminomethyl)-4-phenylbutanoate (6)

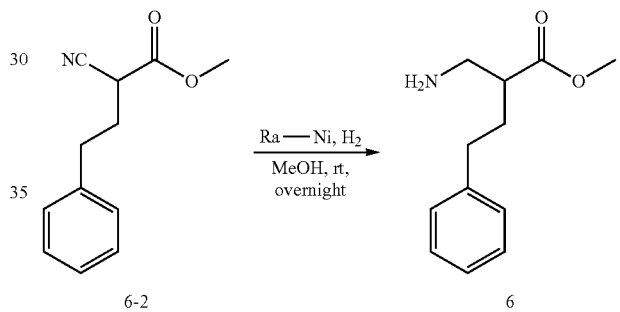

A mixture of 6-2 (3.20 g, 34.7 mmol) and Raney Ni (2.00 g) in MeOH (1000 mL) was stirred under $H_2$ atmosphere at room temperature overnight. When the reaction was completed, the mixture was filtered, and the filtrate was concentrated to give a crude product, which was purified by silica gel column chromatography ($CH_2Cl_2/CH_3OH$=30/1) to afford 6 (2.00 g, 61.3% yield) as a colorless oil.

Synthesis of tert-butyl 7-formyl-1H-indole-1-carboxylate (7-2)

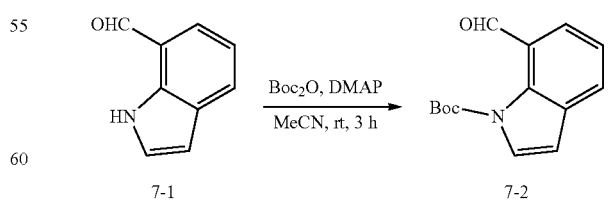

To a mixture of 7-1 (4.00 g, 27.6 mmol) and DMAP (5.05 g, 41.3 mmol) in MeCN (150 mL) was added $Boc_2O$ (6.61 g, 30.3 mmol). The reaction was stirred at room temperature for 3 h. When the reaction was completed, the reaction mixture was filtered, and the residue was washed with MeCN (2.0 mL×2), dried to afford 7-2 (3.60 g, 53.3% yield) as a white solid.

Synthesis of (Z)-tert-butyl 7-(2-cyano-3-methoxy-3-oxoprop-1-enyl)-1H-indole-1-carboxylate (7-3)

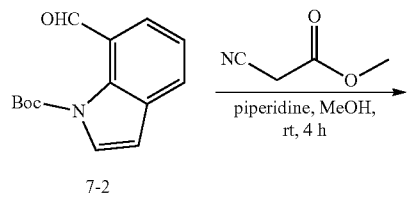

Synthesis of tert-butyl 7-(2-(aminomethyl)-3-methoxy-3-oxopropyl)-1H-indole-1-carboxylate (7)

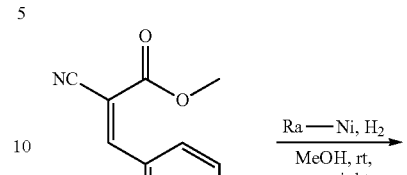

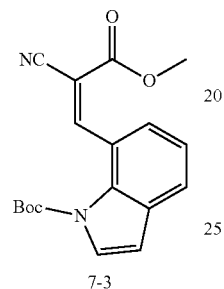

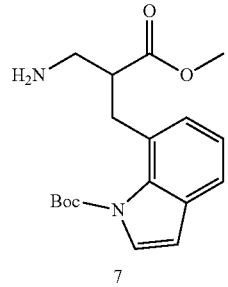

To a mixture of 7-2 (3.60 g, 14.7 mmol) and methyl 2-cyanoacetate (1.75 g, 17.6 mmol) in MeOH (80 mL) was added piperidine (3 drops). The reaction was stirred at room temperature for 4 h. When the reaction was completed, the reaction mixture was filtered, and the residue was washed with MeOH (2.0 mL×2), dried to afford 7-3 (4.00 g, 83.5% yield) as a white solid.

A mixture of 7-3 (4.00 g, 12.3 mmol) and Raney Ni (2.00 g) in MeOH (1000 mL) was stirred under $H_2$ atmosphere at room temperature overnight. When the reaction was completed, the mixture was filtered, and the filtrate was concentrated to give a crude product, which was purified by silica gel column chromatography ($CH_2Cl_2/CH_3OH=30/1$) to afford 7 (1.40 g, 34.4% yield) as a colorless oil.

TABLE 1-2

Characterization Data for Compounds 1-10

| Compounds | Chemical Structure | LCMS |
|---|---|---|
| 1 | 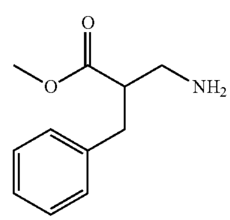 | Method B, Purity is 41.3%, Rt = 1.285 min; MS Calcd.: 193.1; MS Found: 194.3 [M + H]+. |
| 2 | 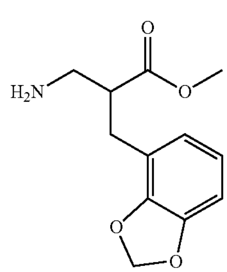 [SMILES: COC(=O)C(CN)Cc1cccc2c1OCO2] | Method B, Purity is 55.4%, Rt = 1.251 min; MS Calcd.: 237.1; MS Found: 238.3 [M + H]+. |

TABLE 1-2-continued

Characterization Data for Compounds 1-10

| Compounds | Chemical Structure | LCMS |
| --- | --- | --- |
| 3 | methyl 3-amino-2-(2-methoxybenzyl)propanoate | Method B, Purity is 98.7%, Rt = 1.316 min; MS Calcd.: 223.1; MS Found: 224.3 [M + H]$^+$. |
| 4 | methyl 3-amino-2-(3-hydroxybenzyl)propanoate | Method B, Purity is 39.0%, Rt = 1.144 min; MS Calcd.: 209.1; MS Found: 210.3 [M + H]$^+$. |
| 5 | methyl 3-amino-2-(3-fluorobenzyl)propanoate | Method B, Purity is 42.8%, Rt = 1.254 min; MS Calcd.: 211.1; MS Found: 212.2 [M + H]$^+$. |
| 6 | methyl 2-(aminomethyl)-4-phenylbutanoate | Method B, Purity is 88.0%, Rt = 1.421 min; MS Calcd.: 207.1; MS Found: 208.3 [M + H]$^+$. |

TABLE 1-2-continued

Characterization Data for Compounds 1-10

| Compounds | Chemical Structure | LCMS |
|---|---|---|
| 7 | (structure: methyl 2-(aminomethyl)-3-(1-Boc-indol-7-yl)propanoate) | Method B, Purity is 55.6%, Rt = 1.602 min; MS Calcd.: 332.2; MS Found: 333.3 [M + H]+. |
| 8 | (structure: methyl 2-(aminomethyl)-3-(1-Boc-indol-4-yl)propanoate) | Method B, Purity is 97.0%, Rt = 1.590 min; MS Calcd.: 332.2; MS Found: 333.3 [M + H]+. |
| 9 | (structure: methyl 2-(aminomethyl)-3-(1-Boc-indol-3-yl)propanoate) | Method A, Purity is 69.5%, Rt = 0.648 min; MS Calcd.: 332.2; MS Found: 333.0 [M + H]+. |
| 10 | (structure: methyl 2-(aminomethyl)-3-(1-Boc-indol-5-yl)propanoate) | Method B, Purity is 93.3%, Rt = 1.580 min; MS Calcd.: 332.2; MS Found: 333.3 [M + H]+. |

191

Synthesis of methyl 2-benzyl-3-(4-(3,4-dichlorophenyl)-5-isopropylthiazol-2-ylamino)propanoate (1a)

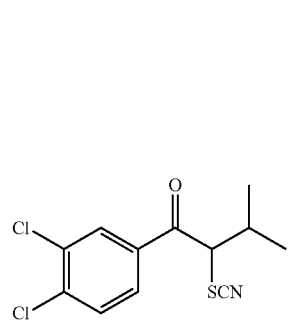

a

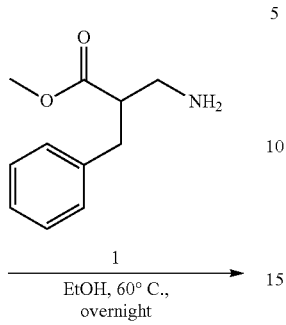

1

EtOH, 60° C., overnight

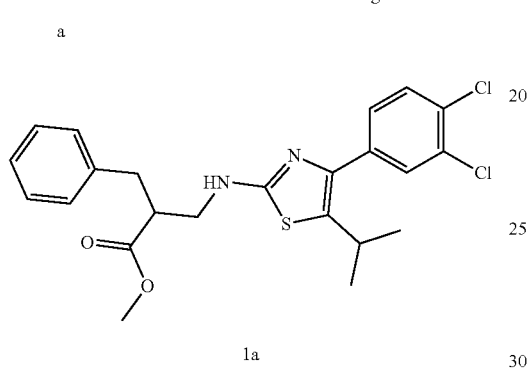

1a

A mixture of a (100 mg, 0.347 mmol) and 1 (80.5 mg, 0.416 mmol) in EtOH (4.00 mL) was stirred at 60° C. overnight. When the reaction was completed, the mixture was purified by prep-TLC (CH$_2$Cl$_2$/CH$_3$OH=120/1) to afford 1a (80.0 mg, 49.8% yield) as a yellow solid.

192

Synthesis of 2-benzyl-3-(4-(3,4-dichlorophenyl)-5-isopropylthiazol-2-ylamino)propanoic acid (I-1)

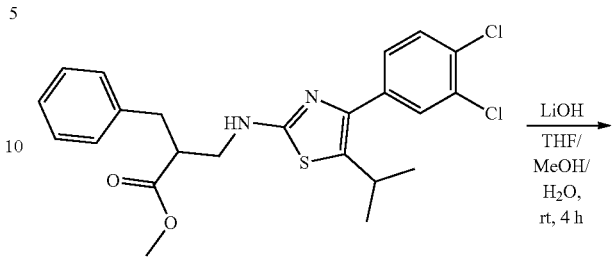

1a

LiOH
THF/
MeOH/
H$_2$O,
rt, 4 h

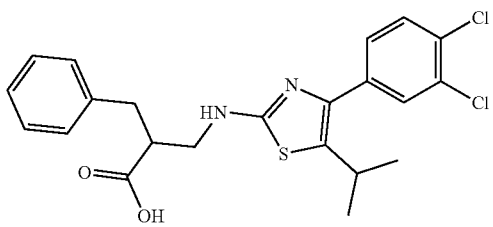

I-1

To a solution of 1a (80.0 mg, 0.173 mmol) in THF/MeOH/H$_2$O (v/v/v=4/1/1, 10 mL) was added LiOH (2.0 M in H$_2$O, 0.22 mL). The reaction was stirred at room temperature for 4 h. When the reaction was completed, the resulting reaction was concentrated, then it was diluted with H$_2$O (10 mL) and adjusted pH to 4-5 with HCl (1.0 M). The mixture was extracted with EtOAc (40 mL×2), and the combined organic phase washed with brine (30 mL), dried by anhydrous Na$_2$SO$_4$, and concentrated, the residue was purified by prep-HPLC to afford I-1 (30.0 mg, 38.7% yield) as a white solid.

TABLE 1-3

| | Characterization Data for Compounds | | |
|---|---|---|---|
| I-# | Chemical Structure | LCMS | $^1$H NMR (400 MHz, DMSO-d$_6$) |
| 1 | | Method C, Purity is 95.6%, Rt = 2.055 min; MS Calcd.: 448.1; MS Found: 449.2 [M + H]$^+$. | δ: 1.21 (6H, dd, J = 6.8, 3.6 Hz), 2.79-2.90 (2H, m), 2.98-3.02 (1H, m), 3.25 (1H, t, J = 6.8 Hz), 3.36-3.40 (2H, m), 7.18-7.30 (5H, m), 7.45 (1H, dd, J = 8.4, 2.0 Hz), 7.65-7.73 (3H, m), 12.34 (1H, brs). |
| 2 | | Method C, Purity is 94.1%, Rt = 2.049 min; MS Calcd.: 492.1; MS Found: 493.0 [M + H]$^+$. | δ: 1.20 (6H, dd, J = 6.4, 4.4 Hz), 2.75-2.80 (2H, m), 3.05-3.08 (1H, m), 3.25 (1H, t, J = 6.8 Hz), 3.37-3.42 (2H, m), 5.94 (2H, d, J = 12.8 Hz), 6.71-6.80 (3H, m), 7.44 (1H, dd, J = 8.4, 2.0 Hz), 7.65-7.71 (3H, m), 12.36 (1H, s). |

TABLE 1-3-continued

Characterization Data for Compounds

| I-# | Chemical Structure | LCMS | $^1$H NMR (400 MHz, DMSO-d$_6$) |
|---|---|---|---|
| 3 | 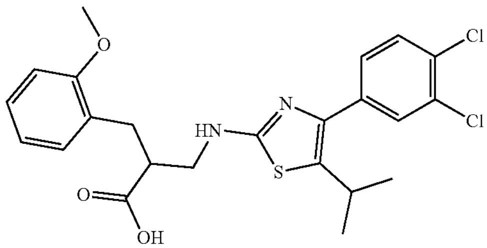 [SMILES: COc1ccccc1CC(CNc1nc(-c2ccc(Cl)c(Cl)c2)c(C(C)C)s1)C(=O)O] | Method C, Purity is 93.8%, Rt = 2.082 min; MS Calcd.: 478.1; MS Found: 479.0 [M + H]$^+$. | δ: 1.20 (6H, dd, J = 6.8, 2.4 Hz), 2.78 (2H, d, J = 7.6 Hz), 3.03-3.07 (1H, m), 3.23-3.29 (2H, m), 3.36-3.40 (1H, m), 3.73 (3H, s), 6.84 (1H, t, J = 7.6 Hz), 6.95 (1H, d, J = 8.0 Hz), 7.14-7.22 (2H, m), 7.44 (1H, dd, J = 8.4, 2.0 Hz), 7.66-7.70 (2H, m), 12.22 (1 H, s). |
| 4 | 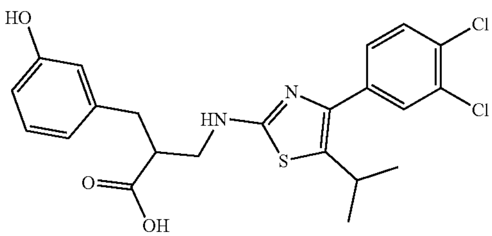 [SMILES: CC(C)c1sc(NCC(Cc2cccc(O)c2)C(=O)O)nc1-c1ccc(Cl)c(Cl)c1] | Method C, Purity is 100%, Rt = 1.857 min; MS Calcd.: 464.1; MS Found: 465.2 [M + H]$^+$. | δ: 1.19 (6H, dd, J = 6.8, 3.2 Hz), 2.64-2.68 (2H, m), 2.74-2.84 (2H, m), 3.20-3.26 (2H, m), 3.31-3.33 (1H, m), 6.55-6.62 (3H, m), 7.02 (1H, t, J = 8.0 Hz), 7.43 (1H, dd, J = 8.4, 2.0 Hz), 7.62-7.66 (3H, m), 9.26 (1H, brs). |
| 5 | 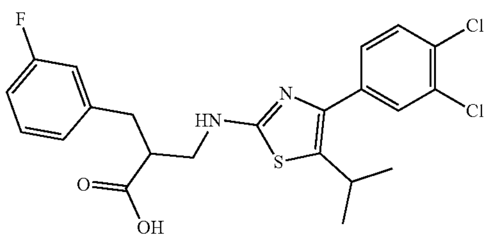 [SMILES: CC(C)c1sc(NCC(Cc2cccc(F)c2)C(=O)O)nc1-c1ccc(Cl)c(Cl)c1] | Method C, Purity is 94.2%, Rt = 2.076 min; MS Calcd.: 466.1; MS Found: 467.0 [M + H]$^+$. | δ: 1.21 (6H, dd, J = 6.8, 2.8 Hz), 2.85-2.89 (2H, m), 3.00-3.01 (1H, m), 3.23 (1H, t, J = 6.8 Hz), 3.36-3.42 (2H, m), 7.03-7.09 (3H, m), 7.29-7.33 (1H, m), 7.45 (1H, dd, J = 8.4, 2.0 Hz), 7.65-7.73 (3H, m), 12.41 (1H, s). |
| 6 | 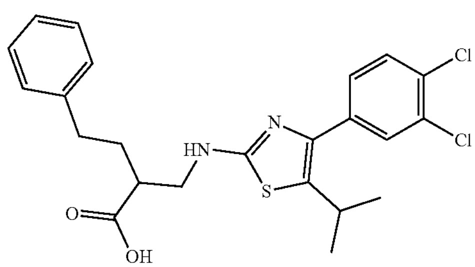 [SMILES: CC(C)c1sc(NCC(CCc2ccccc2)C(=O)O)nc1-c1ccc(Cl)c(Cl)c1] | Method C, Purity is 94.9%, Rt = 2.801 min; MS Calcd.: 462.1; MS Found: 463.0 [M + H]$^+$. | δ: 1.21 (6H, d, J = 6.8 Hz), 1.81-1.82 (2H, m), 2.58-2.67 (3H, m), 3.24 (1H, t, J = 6.8 Hz), 3.38-3.40 (1H, m), 3.45-3.47 (1H, m), 7.16-7.26 (5H, m), 7.44 (1H, dd, J = 8.4, 2.0 Hz), 7.65-7.69 (3H, m), 12.38 (1H, brs). |
| 11 | 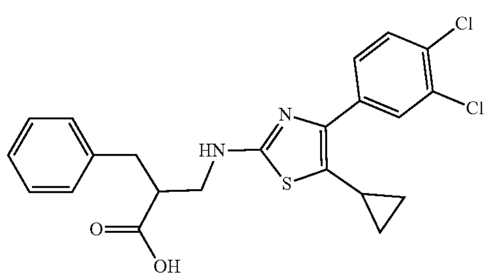 [SMILES: O=C(O)C(CNc1nc(-c2ccc(Cl)c(Cl)c2)c(C2CC2)s1)Cc1ccccc1] | Method C, Purity is 97.0%, Rt = 1.981 min; MS Calcd.: 446.1; MS Found: 447.2 [M + H]$^+$. | δ: 2.80-2.91 (2H, m), 3.00-3.03 (1H, m), 3.33-3.42 (2H, m), 3.49 (2H, d, J = 6.0 Hz), 5.10-5.14 (2H, m), 5.94-6.00 (1H, m), 7.19-7.31 (5H, m), 7.49 (1H, dd, J = 8.4, 2.0 Hz), 7.66 (1H, d, J = 8.4 Hz), 7.73-7.76 (2H, m), 12.34 (1H, brs). |
| 12 | 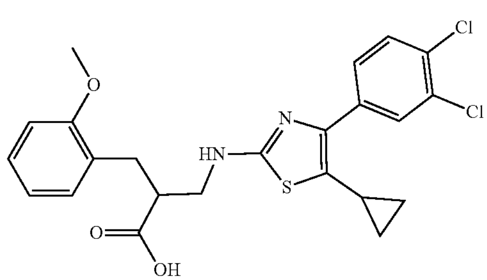 [SMILES: COc1ccccc1CC(CNc1nc(-c2ccc(Cl)c(Cl)c2)c(C2CC2)s1)C(=O)O] | Method C, Purity is 95.3%, Rt = 1.997 min; MS Calcd.: 476.1; MS Found: 477.2 [M + H]$^+$. | δ: 2.77 (2H, d, J = 6.8 Hz), 3.04 (1H, t, J = 5.8 Hz), 3.34-3.47 (4H, m), 3.72 (3H, s), 5.10 (2H, d, J = 12.8 Hz), 5.90-5.98 (1H, m), 6.81-6.94 (2H, m), 7.12-7.20 (2H, m), 7.46 (1H, d, J = 8.0 Hz), 7.63-7.70 (3H, m), 12.22 (1H, brs). |

TABLE 1-3-continued

Characterization Data for Compounds

| I-# | Chemical Structure | LCMS | $^1$H NMR (400 MHz, DMSO-d$_6$) |
|---|---|---|---|
| 13 | 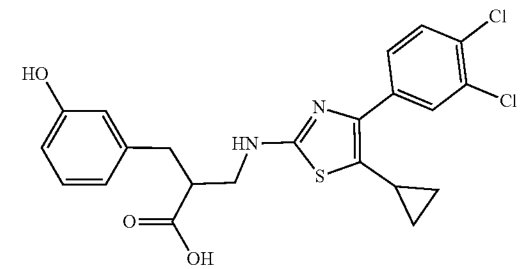 [SMILES: O=C(O)C(CNc1nc(-c2ccc(Cl)c(Cl)c2)c(C2CC2)s1)Cc1cccc(O)c1] | Method C, Purity is 93.6%, Rt = 1.849 min; MS Calcd.: 462.1; MS Found: 463.2 [M + H]$^+$. | δ: 2.68-2.78 (2H, m), 2.91-2.94 (1H, m), 3.34-3.40 (2H, m), 3.46 (2H, d, J = 6.0 Hz), 5.10 (2H, dd, J = 13.2, 1.6 Hz), 5.92-5.98 (1H, m), 6.57-6.62 (3H, m), 7.04 (1H, t, J = 8.0 Hz), 7.48 (1H, dd, J = 8.4, 2.0 Hz), 7.63 (1H, d, J = 8.4 Hz), 7.71-7.73 (2H, m), 9.26 (1H, s), 12.27 (1H, brs). |
| 14 | 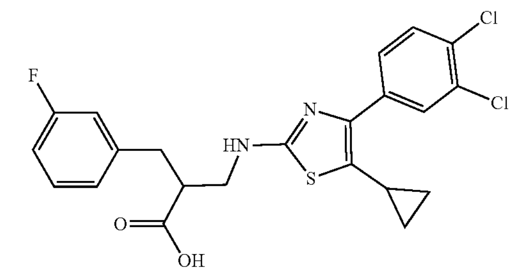 [SMILES: O=C(O)C(CNc1nc(-c2ccc(Cl)c(Cl)c2)c(C2CC2)s1)Cc1cccc(F)c1] | Method C, Purity is 96.4%, Rt = 2.103 min; MS Calcd.: 464.0; MS Found: 465.0 [M + H]$^+$. | δ: 2.81-2.91 (2H, m), 2.98-3.01 (1H, m), 3.36-3.41 (2H, m), 3.46 (2H, d, J = 6.0 Hz), 5.10 (2H, dd, J = 13.2, 1.6 Hz), 5.91-5.98 (1H, m), 6.99-7.07 (3H, m), 7.30 (1H, d, J = 8.0 Hz), 7.47 (1H, dd, J = 8.8, 2.0 Hz), 7.63 (1H, d, J = 8.4 Hz), 7.70-7.73 (2H, m), 12.38 (1H, brs). |
| 15 | 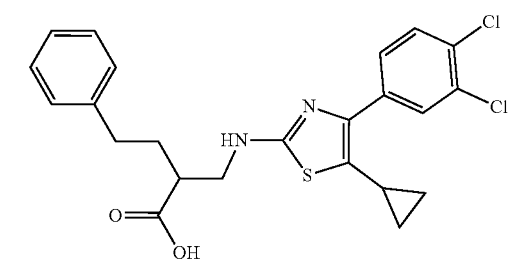 [SMILES: O=C(O)C(CCc1ccccc1)CNc1nc(-c2ccc(Cl)c(Cl)c2)c(C2CC2)s1] | Method C, Purity is 97.1%, Rt = 2.028 min; MS Calcd.: 460.1; MS Found: 461.2 [M + H]$^+$. | δ: 1.71-1.86 (2H, m), 2.52-2.68 (3H, m), 3.35-3.46 (4H, m), 5.10 (2H, dd, J = 13.2, 1.6 Hz), 5.90-6.00 (1H, m), 7.12-7.24 (5H, m), 7.46 (1H, dd, J = 8.4, 2.0 Hz), 7.62 (1H, d, J = 8.4 Hz), 7.70-7.71 (2H, m), 12.45 (1H, brs). |
| 16 | 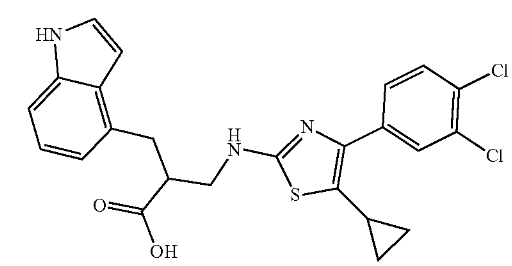 [SMILES: O=C(O)C(CNc1nc(-c2ccc(Cl)c(Cl)c2)c(C2CC2)s1)Cc1cccc2[nH]ccc12] | Method C, Purity is 97.5%, Rt = 1.994 min; MS Calcd.: 485.1; MS Found: 486.2 [M + H]$^+$. | δ: 2.99-3.17 (3H, m), 3.41-3.47 (4H, m), 5.09 (1H, dd, J = 6.0, 1.2 Hz), 5.12 (1H, s), 5.90-6.00 (1H, m), 6.44 (1H, s), 6.82 (1H, d, J = 6.8 Hz), 6.97 (1H, t, J = 7.6 Hz), 7.23 (1H, d, J = 8.0 Hz), 7.27 (1H, t, J = 2.8 Hz), 7.41 (1H, dd, J = 8.4, 2.0 Hz), 7.63 (1H, d, J = 8.4 Hz), 7.71 (1H, d, J = 2.0 Hz), 7.77(1H, brs), 11.06(1H, s). |
| 17 | 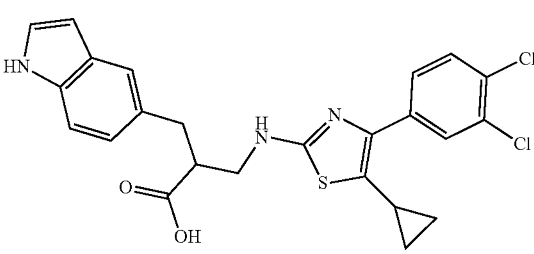 [SMILES: O=C(O)C(CNc1nc(-c2ccc(Cl)c(Cl)c2)c(C2CC2)s1)Cc1ccc2[nH]ccc2c1] | Method C, Purity is 100%, Rt = 1.804 min; MS Calcd.: 485.1; MS Found: 486.1 [M + H]$^+$. | δ: 2.82 (1H, q, J = 6.8 Hz), 2.90-3.01 (2H, m), 3.35-3.41 (2H, m), 3.46 (2H, d, J = 6.0 Hz), 5.10 (2H, dd, J = 13.2, 2.0 Hz), 5.90-5.99 (1H, m), 6.30 (1H, s), 6.93 (1H, dd, J = 8.4, 1.6 Hz), 7.26-7.29 (2H, m), 7.33 (1H, s), 7.45 (1H, dd, J = 8.4, 2.0 Hz), 7.60 (1H, d, J = 8.4 Hz), 7.71-7.72 (2H, m), 10.96 (1H, s). |

TABLE 1-3-continued

Characterization Data for Compounds

| I-# | Chemical Structure | LCMS | ¹H NMR (400 MHz, DMSO-d₆) |
|---|---|---|---|
| 18 | | Method C, Purity is 95.6%, Rt = 2.055 min; MS Calcd.: 448.1; MS Found: 449.2 [M + H]⁺. | δ: 1.21 (6H, dd, J = 6.8, 3.6 Hz), 2.79-2.90 (2H, m), 2.98-3.02 (1H, m), 3.25 (1H, t, J = 6.8 Hz), 3.36-3.40 (2H, m), 7.18-7.30 (5H, m), 7.45 (1H, dd, J = 8.4, 2.0 Hz), 7.65-7.73 (3H, m), 12.34 (1H, brs). |
| 18 | | Method B, Purity is 100%, Rt = 2.803 min; MS Calcd.: 506.1; MS Found: 507.1 [M + H]⁺. | δ: 0.88 (6H, d, J = 6.8 Hz), 1.67-1.80 (1H, m), 2.58-2.60 (2H, d, J = 6.8 Hz), 2.70-2.86 (2H, m), 3.00-3.11 (1H, m), 3.35-3.47 (2H, m), 5.92-5.96 (2H, dd, J = 13.2, 0.8 Hz), 6.69-6.81 (3H, m), 7.47 (1H, dd, J = 8.4, 2.8 Hz), 7.63-7.73 (3H, m), 12.36 (1H, brs). |
| 20 | 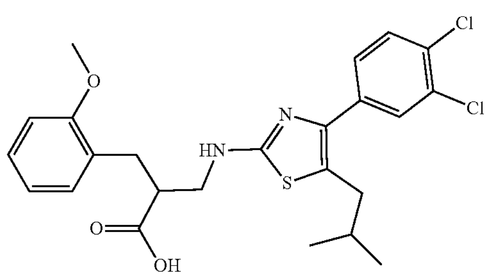 [SMILES: COc1ccccc1CC(CNc1nc(-c2ccc(Cl)c(Cl)c2)c(CC(C)C)s1)C(=O)O] | Method B, Purity is 100%, Rt = 3.076 min; MS Calcd.: 492.1; MS Found: 493.1 [M + H]⁺. | δ: 0.88 (6H, d, J = 6.8 Hz), 1.70-1.77 (1H, m), 2.58-2.60 (2H, d, J = 6.8 Hz), 2.77-2.79 (2H, d, J = 7.6 Hz), 3.01-3.08 (1H, m), 3.39-3.43 (2H, m), 3.74 (3H, s), 6.82-6.86 (1H, t, J = 7.2 Hz), 6.93-6.95 (1H, d, J = 8 Hz), 7.13-7.22 (2H, m), 7.48 (1H, dd, J = 8.4, 2.0 Hz), 7.65-7.70 (3H, m), 12.22 (1H, brs). |
| 21 | 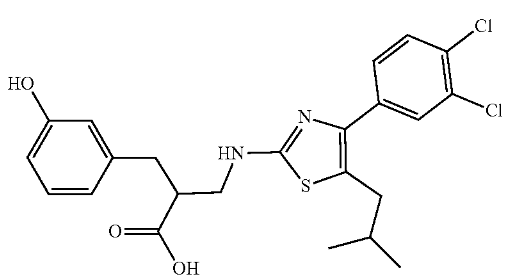 [SMILES: CC(C)Cc1sc(NCC(Cc2cccc(O)c2)C(=O)O)nc1-c1ccc(Cl)c(Cl)c1] | Method C, Purity is 100%, Rt = 1.946 min; MS Calcd.: 478.1; MS Found: 479.2 [M + H]⁺. | δ: 0.86 (6H, d, J = 6.4 Hz), 1.69-1.74 (1H, m), 2.57 (2H, d, J = 12 Hz), 2.66-2.78 (2H, m), 2.89-2.93 (1H, m), 3.32-3.38 (2H, m), 6.55-6.62 (3H, m), 7.03 (1H, t, J = 8.0 Hz), 7.47 (1H, dd, J = 8.4, 2.0 Hz), 7.62-7.69 (3H, m), 9.24 (1H, s), 12.26 (1H, brs). |
| 22 | 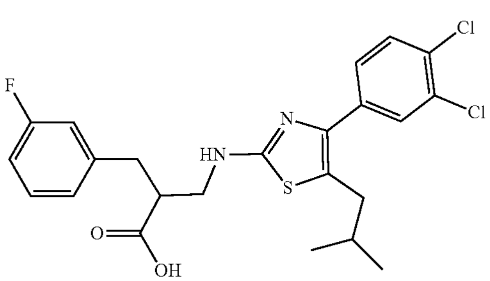 [SMILES: CC(C)Cc1sc(NCC(Cc2cccc(F)c2)C(=O)O)nc1-c1ccc(Cl)c(Cl)c1] | Method B, Purity is 100%, Rt = 2.043 min; MS Calcd.: 480.2; MS Found: 481.1 [M + H]⁺. | δ: 0.88 (6H, d, J = 6.8 Hz), 1.71-1.77 (1H, m), 2.59 (2H, d, J = 6.8 Hz), 2.81-2.92 (2H, m), 2.97-3.03 (1H, m), 3.38-3.44 (2H, m), 7.01-7.08 (3H, m), 7.32 (1H, q, J = 8.0 Hz), 7.48 (1H, dd, J = 8.4, 2.0 Hz), 7.64-7.72 (3H, m), 12.42 (1H, brs). |

TABLE 1-3-continued

Characterization Data for Compounds

| I-# | Chemical Structure | LCMS | $^1$H NMR (400 MHz, DMSO-d$_6$) |
|---|---|---|---|
| 23 | 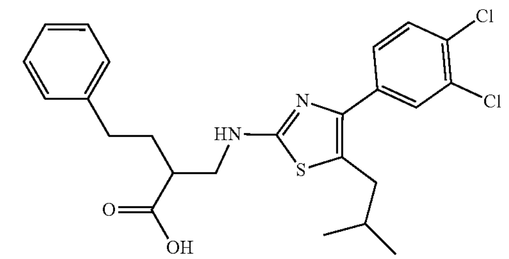 [SMILES: CC(C)Cc1sc(NCC(CCc2ccccc2)C(=O)O)nc1-c1ccc(Cl)c(Cl)c1] | Method C, Purity is 99.6%, Rt = 2.017 min; MS Calcd.: 476.0; MS Found: 477.0 [M + H]$^+$. | δ: 0.88 (6H, d, J = 6.8 Hz), 1.72-1.84 (3H, m), 2.54-2.68 (5H, m), 3.39-3.50 (2H, m), 7.13-7.26 (5H, m), 7.47(1H, dd, J = 8.4, 1.6 Hz), 7.68 (2H, d, J = 18.0 Hz), 7.71 (1H, s), 12.28 (1H, brs). |
| 28 | 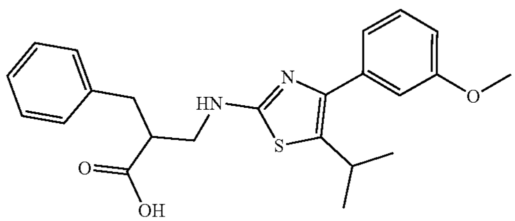 [SMILES: COc1cccc(-c2nc(NCC(Cc3ccccc3)C(=O)O)sc2C(C)C)c1] | Method C, Purity is 100%, Rt = 1.710 min; MS Calcd.: 410.2; MS Found: 411.1 [M + H]$^+$. | δ: 1.21 (6H, dd, J = 6.8, 3.2 Hz), 2.50-2.51 (2H, m), 3.23-3.32 (2H, m), 3.39-3.44 (2H, m), 3.78 (1H, s), 8.90 (1H, dd, J = 8.0, 2.4 Hz), 7.02-7.06 (2H, m), 7.18-7.29 (4H, m), 7.33 (1H, t, J = 8.0 Hz), 7.63 (1H, t, J = 5.2Hz), 12.34 (1H, brs). |
| 29 | 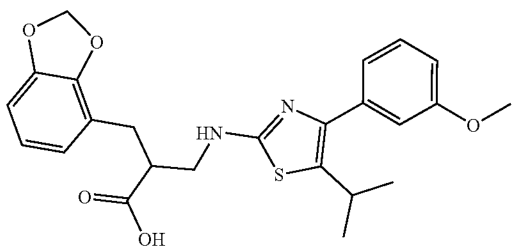 [SMILES: COc1cccc(-c2nc(NCC(Cc3cccc4c3OCO4)C(=O)O)sc2C(C)C)c1] | Method C, Purity is 100%, Rt = 1.699 min; MS Calcd.: 454.2; MS Found: 455.2 [M + H]$^+$. | δ: 1.21 (6H, dd, J = 6.8, 4.8 Hz), 2.73-2.84 (2H, m), 3.08 (1H, dd, J = 8.4, 5.6 Hz), 3.25-3.30 (2H, m), 3.38-3.44 (2H, m), 3.77 (3H, s), 5.94 (2H, d, J = 15.2 Hz), 6.71-6.80 (3H, m), 6.90 (1H, dd, J = 8.0, 2.4 Hz), 7.01-7.05 (2H, m), 7.32 (1H, t, J = 8.0 Hz), 7.60 (1H, t, J = 5.6 Hz), 12.37 (1H, brs). |
| 30 | 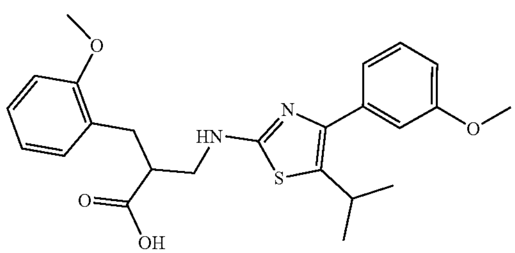 [SMILES: COc1cccc(-c2nc(NCC(Cc3ccccc3OC)C(=O)O)sc2C(C)C)c1] | Method C, Purity is 100%, Rt = 1.787 min; MS Calcd.: 440.2; MS Found: 441.1 [M + H]$^+$. | δ: 1.20 (6H, dd, J = 6.8, 3.2 Hz), 2.73-2.83 (2H, m), 3.03-3.10 (1H, m), 3.25-3.32 (2H, m), 3.36-3.43 (1H, m), 3.73 (3H, s), 3.77 (3H, s), 6.83 (1H, t, J = 7.2 Hz), 6.89 (1H, dd, J = 8.0, 2.4 Hz), 6.94 (1H, d, J = 8.0 Hz), 7.01-7.05 (2H, m), 7.14-7.21 (2H, m), 7.32 (1H, t, J = 8.0 Hz), 7.58 (1H, t, J = 5.6 Hz), 12.20 (1H, s). |
| 31 | 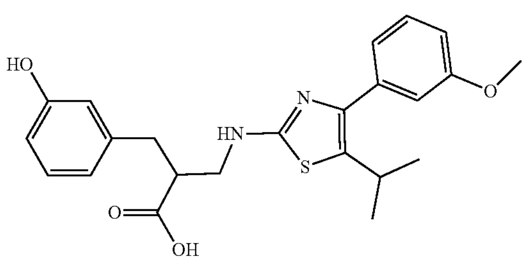 [SMILES: COc1cccc(-c2nc(NCC(Cc3cccc(O)c3)C(=O)O)sc2C(C)C)c1] | Method C, Purity is 100%, Rt = 1.593 min; MS Calcd.: 426.2; MS Found: 427.1 [M + H]$^+$. | δ: 1.21 (6H, dd, J = 6.8, 3.2 Hz), 2.74 (2H, d, J = 6.8 Hz), 2.91-2.98 (1H, m), 3.24-3.32 (2H, m), 3.37-3.44 (1H, m), 3.77 (3H, s), 6.57-6.64 (3H, m), 6.89 (1H, dd, J = 8.0, 2.4 Hz), 7.02-7.07 (3H, m), 7.32 (1H, t, J = 8.0 Hz), 7.58-7.61 (1H, m), 9.27 (1H, s), 12.28 (1H, brs). |
| 32 | 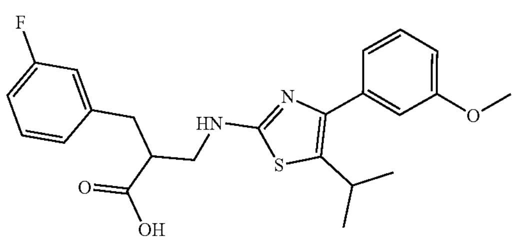 [SMILES: COc1cccc(-c2nc(NCC(Cc3cccc(F)c3)C(=O)O)sc2C(C)C)c1] | Method C, Purity is 96.3%, Rt = 1.813 min; MS Calcd.: 428.2; MS Found: 429.1 [M + H]$^+$. | δ: 1.20 (6H, dd, J = 6.8, 3.6 Hz), 2.82-2.97 (3H, m), 3.24-3.29 (2H, m), 3.36-3.40 (2H, m), 3.77 (3H, s), 6.89 (1H, dd, J = 8.0, 2.4 Hz), 6.99-7.08 (5H, m), 7.27-7.33 (2H, m), 7.61 (1H, brs). |

TABLE 1-3-continued

Characterization Data for Compounds

| I-# | Chemical Structure | LCMS | ¹H NMR (400 MHz, DMSO-d$_6$) |
|---|---|---|---|
| 33 | 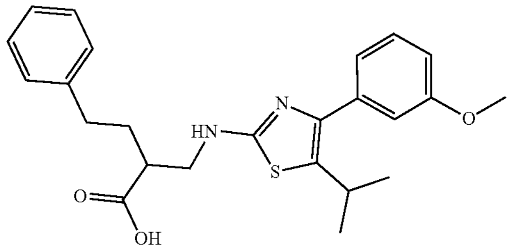 [SMILES: COc1cccc(-c2nc(NCC(CCc3ccccc3)C(=O)O)sc2C(C)C)c1] | Method C, Purity is 100%, Rt = 1.757 min; MS Calcd.: 424.2; MS Found: 425.2 [M + H]⁺. | δ: 1.17 (6H, d, J = 6.8 Hz), 1.70-1.85 (2H, m), 2.54-2.69 (3H, m), 3.20-3.30 (2H, m), 3.39-3.47 (2H, m), 3.75 (3H, s), 6.88 (1H, dd, J = 8.0, 2.0 Hz), 7.00-7.04 (2H, m), 7.12-7.25 (5H, m), 7.30 (1H, t, J = 8.0 Hz), 7.48 (1H, brs). |
| 38 | 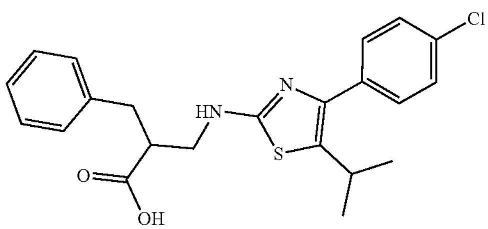 [SMILES: CC(C)c1sc(NCC(Cc2ccccc2)C(=O)O)nc1-c1ccc(Cl)cc1] | Method C, Purity is 97.1%, Rt = 1.903 min; MS Calcd.: 414.1; MS Found: 415.2 [M + H]⁺. | δ: 1.20 (6H, dd, J = 6.4, 2.0 Hz), 2.78-2.89 (2H, m), 2.95-3.02 (1H, m), 3.21-3.28 (1H, m), 3.37-3.43 (2H, m), 7.18-7.30 (5H, m), 7.45-7.50 (4H, m), 7.65 (1H, brs), 12.35 (1H, s). |
| 39 | 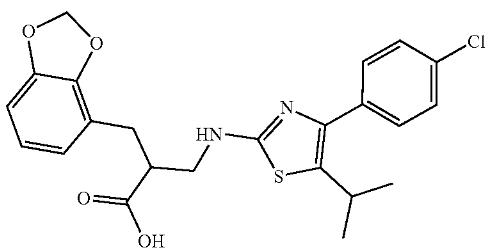 [SMILES: CC(C)c1sc(NCC(Cc2cccc3c2OCO3)C(=O)O)nc1-c1ccc(Cl)cc1] | Method C, Purity is 94.1%, Rt = 1.898 min; MS Calcd.: 458.1; MS Found: 459.0 [M + H]⁺. | δ: 1.20 (6H, t, J = 6.0 Hz), 2.67-2.84 (2H, m), 3.02-3.09 (1H, m), 3.21-3.28 (1H, m), 3.36-3.44 (2H, m), 5.95 (2H, d, J = 11.2 Hz), 6.71-6.80 (3H, m), 7.44-7.50 (4H, m), 7.64 (1H, t, J = 4.8 Hz), 12.36 (1H, s). |
| 40 | 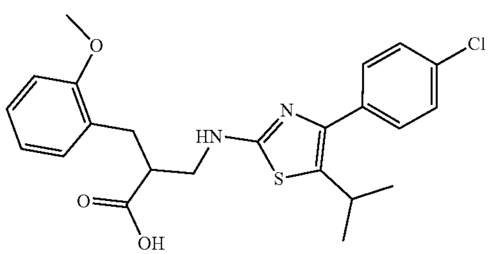 [SMILES: COc1ccccc1CC(CNc1nc(-c2ccc(Cl)cc2)c(C(C)C)s1)C(=O)O] | Method C, Purity is 91.4%, Rt = 1.921 min; MS Calcd.: 444.1; MS Found: 445.0 [M + H]⁺. | δ: 1.20 (6H, dd, J = 6.0, 4.0 Hz), 2.77 (2H, d, J = 12 Hz), 3.01-3.07 (1H, m), 3.19-3.30 (3H, m), 3.73 (3H, s), 6.84 (1H, t, J = 12 Hz), 6.95 (1H, d, J = 8.4Hz), 7.14 (1H, d, J = 6.8 Hz), 7.20 (1H, t, J = 12 Hz), 7.45-7.50 (4H, m), 7.63 (1H, t, J = 4.8 Hz), 12.23(1H, s). |
| 41 | 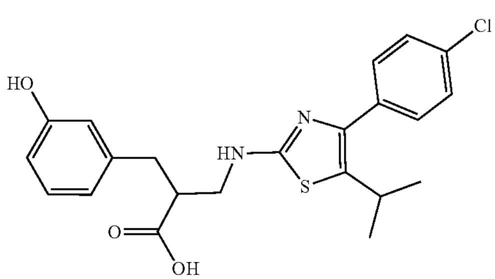 [SMILES: CC(C)c1sc(NCC(Cc2cccc(O)c2)C(=O)O)nc1-c1ccc(Cl)cc1] | Method C, Purity is 98.6%, Rt = 1.822 min; MS Calcd.: 430.1; MS Found: 431.2 [M + H]⁺. | δ: 1.19 (6H, q, J = 3.2 Hz), 2.65-2.77 (2H, m), 2.88-2.95 (1H, m), 3.19-3.26 (1H, m), 3.32-3.40 (2H, m), 6.57-6.62 (3H, m), 7.03 (1H, t, J = 7.6 Hz), 7.45 (4H, q, J = 8.8 Hz), 7.60 (1H, t, J = 5.6 Hz), 9.26 (1H, s), 12.26 (1H, brs). |
| 42 | 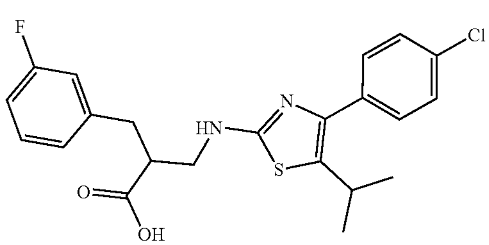 [SMILES: CC(C)c1sc(NCC(Cc2cccc(F)c2)C(=O)O)nc1-c1ccc(Cl)cc1] | Method C, Purity is 95.5%, Rt = 1.912 min; MS Calcd.: 432.1; MS Found: 433.0 [M + H]⁺. | δ: 1.20 (6H, dd, J = 6.8, 2.8 Hz), 2.81-2.91 (2H, m), 2.97-3.04 (1H, m), 3.21-3.28 (1H, m), 3.36-3.44 (2H, m), 7.01-7.08 (3H, m), 7.29-7.35 (1H, m), 7.47 (4H, q, J = 8.8 Hz), 7.65 (1H, t, J = 5.6 Hz), 12.41 (1H, s). |

TABLE 1-3-continued

Characterization Data for Compounds

| I-# | Chemical Structure | LCMS | $^1$H NMR (400 MHz, DMSO-$d_6$) |
|---|---|---|---|
| 43 | 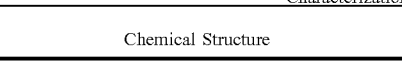 | Method B, Purity is 94.8%, Rt = 1.850 min; MS Calcd.: 428.1; MS Found: 429.2 [M + H]$^+$. | δ: 1.20 (6H, d, J = 6.4 Hz), 1.76-1.85 (2H, m), 2.53-2.71 (3H, m), 3.19-3.26 (1H, m), 3.35-3.49 (2H, m), 7.15-7.26 (5H, m), 7.46 (4H, q, J = 4.8 Hz), 7.62 (IH, t, J = 4.4 Hz), 12.40 (1H, brs). |

Synthesis of tert-butyl 7-(2-((4-(3,4-dichlorophenyl)-5-isopropylthiazol-2-ylamino)methyl)-3-methoxy-3-oxopropyl)-1H-indole-1-carboxylate (7a-1)

Synthesis of 3-(1-(tert-butoxycarbonyl)-1H-indol-7-yl)-2-((4-(3,4-dichlorophenyl)-5-isopropylthiazol-2-ylamino)methyl)propanoic acid (7a-2)

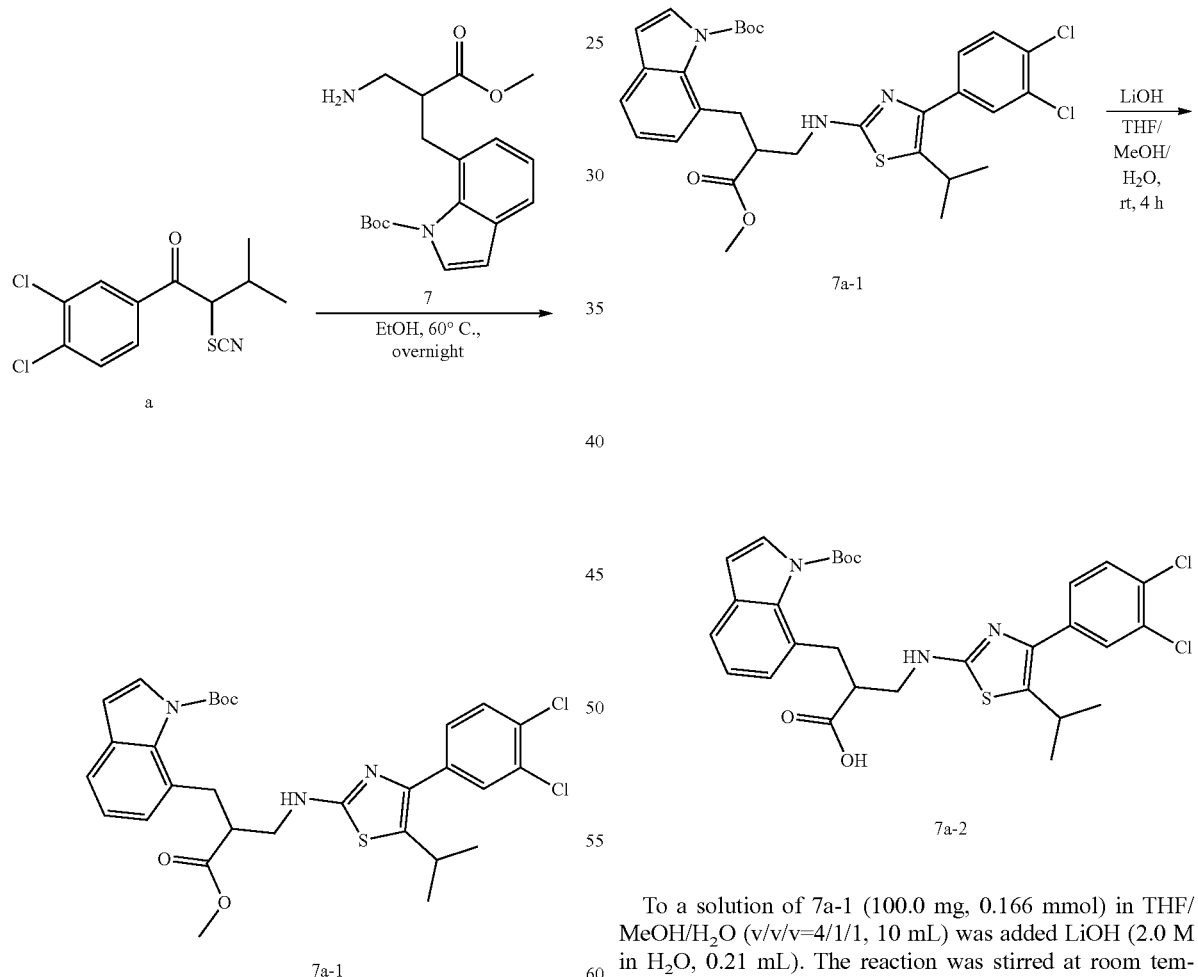

A mixture of a (100 mg, 0.347 mmol) and 7 (138 mg, 0.416 mmol) in EtOH (4.00 mL) was stirred at 60° C. overnight. When the reaction was completed, the mixture was purified by prep-TLC (CH$_2$Cl$_2$/CH$_3$OH=120/1) to afford 7a-1 (100.0 mg, 47.8% yield) as a yellow solid.

To a solution of 7a-1 (100.0 mg, 0.166 mmol) in THF/MeOH/H$_2$O (v/v/v=4/1/1, 10 mL) was added LiOH (2.0 M in H$_2$O, 0.21 mL). The reaction was stirred at room temperature for 4 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated to afford 7a-2 (80.0 mg, 81.9% yield) as a white solid.

Synthesis of 2-((1H-indol-7-yl)methyl)-3-(4-(3,4-dichlorophenyl)-5-isopropylthiazol-2-ylamino) propanoic acid (I-7)

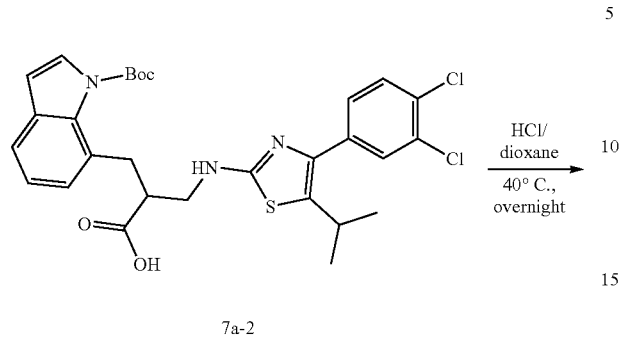

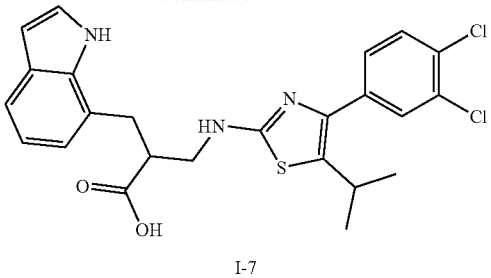

A mixture of 7a-2 (80.0 mg, 0.136 mmol) in HCl (4.0 M in dioxane, 5.00 mL) was stirred at 40° C. overnight. When the reaction was completed, it was concentrated to give a crude product, which was purified by prep-TPLC to afford I-7 (15.0 mg, 22.62 yield) as an off-white solid.

TABLE 1-4

Characterization Data for Compounds

| I-# | Chemical Structure | LCMS | $^1$H NMR (400 MHz, DMSO-$d_6$) |
|---|---|---|---|
| 7 | 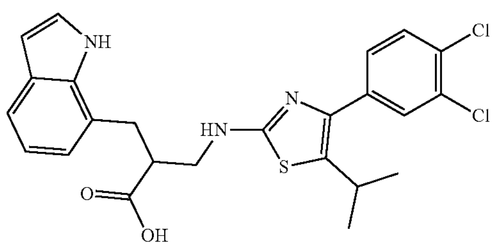 [SMILES: CC(C)c1sc(NCC(Cc2cccc3cc[nH]c23)C(=O)O)nc1-c1ccc(Cl)c(Cl)c1] | Method C, Purity is 99.1%, Rt = 2.082 min; MS Calcd.: 487.1; MS Found: 488.2 [M + H]$^+$. | δ: 1.18 (6H, dd, J = 6.8, 2.8 Hz), 3.08-3.12 (3H, m), 3.20-3.23 (1H, m), 3.40-3.41 (2H, m), 6.39-6.40 (1H, m), 6.86-6.90 (1H, m), 6.94-6.96 (1H, m), 7.29 (1H, t, J = 2.4 Hz), 7.36-7.41 (2H, m), 7.62-7.66 (3H, m), 11.14 (1H, brs). |
| 8 | 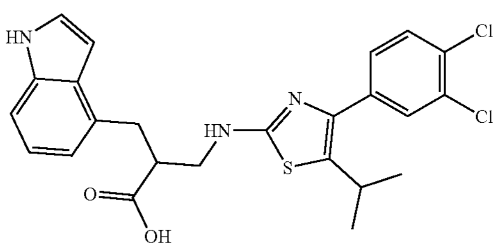 [SMILES: CC(C)c1sc(NCC(Cc2cccc3[nH]ccc23)C(=O)O)nc1-c1ccc(Cl)c(Cl)c1] | Method C, Purity is 99.3%, Rt = 1.936 min; MS Calcd.: 487.1; MS Found: 488.2 [M + H]$^+$. | δ: 1.20 (6H, t, J = 6.4 Hz), 2.99-3.02 (1H, m), 3.06-3.14 (2H, m), 3.22-3.26 (2H, m), 3.41-3.42 (1H, m), 6.45 (1H, s), 6.83 (1H, d, J = 7.2 Hz), 6.94-6.96 (1H, m), 7.23-7.28 (2H, m), 7.40 (1H, dd, J = 4.4, 2.0 Hz), 7.65-7.68 (2H, m), 7.76 (1H, brs), 11.07 (1H, brs). |
| 9 | 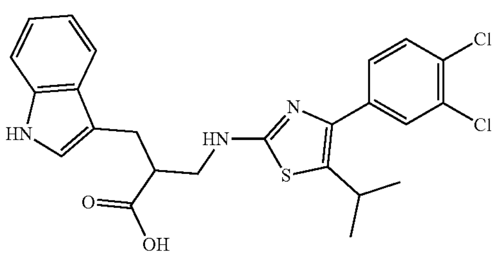 [SMILES: CC(C)c1sc(NCC(Cc2c[nH]c3ccccc23)C(=O)O)nc1-c1ccc(Cl)c(Cl)c1] | Method C, Purity is 95.7%, Rt = 1.991 min; MS Calcd.: 487.1; MS Found: 488.2 [M + H]$^+$. | δ: 1.20 (6H, dd, J = 6.8, 3.2 Hz), 2.90-2.98 (2H, m), 3.05-3.08 (1H, m), 3.21-3.28 (1H, m), 3.40-3.45 (2H, m), 6.92 (1H, t, J = 7.2 Hz), 7.05 (1H, t, J = 7.6 Hz), 7.13 (1H, d, J = 1.2 Hz), 7.32 (1H, d, J = 8.0 Hz), 7.42-7.44 (1H, m), 7.49 (1H, d, J = 6.8 Hz), 7.64-7.68 (2H, m), 7.72 (1H, brs), 10.80 (1H, brs). |
| 10 | 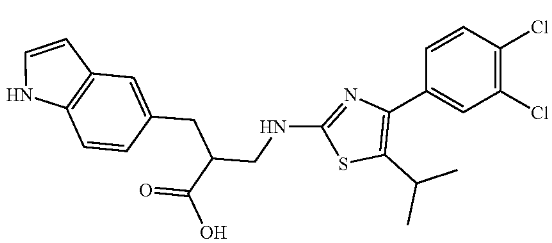 [SMILES: CC(C)c1sc(NCC(Cc2ccc3[nH]ccc3c2)C(=O)O)nc1-c1ccc(Cl)c(Cl)c1] | Method C, Purity is 99.4%, Rt = 1.916 min; MS Calcd.: 487.1; MS Found: 488.2 [M + H]$^+$. | δ: 1.18 (6H, t, J = 6.4 Hz), 2.80-2.83 (1H, m), 2.89-2.96 (2H, m), 3.20-3.24 (1H, m), 3.32-3.35 (2H, m), 6.29 (1H, t, J = 2.0 Hz), 6.93 (1H, dd, J = 8.4, 1.2 Hz), 7.26-7.28 (2H, m), 7.33 (1H, s), 7.41 (1H, dd, J = 8.4, 2.0 Hz), 7.60-7.63 (1H, m), 7.66-7.67 (2H, m), 10.96 (1H, brs). |

TABLE 1-4-continued

Characterization Data for Compounds

| I-# | Chemical Structure | LCMS | ¹H NMR (400 MHz, DMSO-d$_6$) |
|---|---|---|---|
| 16 | 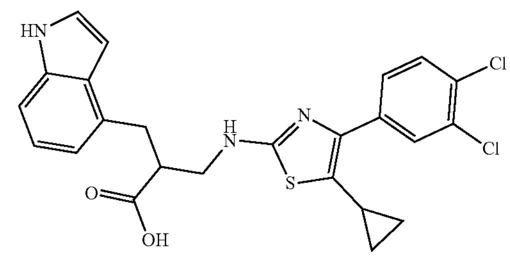 [SMILES: O=C(O)C(CNc1nc(-c2ccc(Cl)c(Cl)c2)c(C2CC2)s1)Cc1cccc2[nH]ccc12] | Method C, Purity is 97.5%, Rt = 1.994 min; MS Calcd.: 485.1; MS Found: 486.2 [M + H]⁺. | δ: 2.99-3.17 (3H, m), 3.41-3.47 (4H, m), 5.09 (1H, dd, J = 6.0, 1.2 Hz), 5.12 (1H, s), 5.90-6.00 (1H, m), 6.44 (1H, s), 6.82 (1H, d, J = 6.8 Hz), 6.97 (1H, t, J = 7.6 Hz), 7.23 (1H, d, J = 8.0 Hz), 7.27 (1H, t, J = 2.8 Hz), 7.41 (1H, dd, J = 8.4, 2.0 Hz), 7.63 (1H, d, J = 8.4 Hz), 7.71 (1H, d, J = 2.0 Hz), 7.77 (1H, brs), 11.06 (1H, s). |
| 17 | 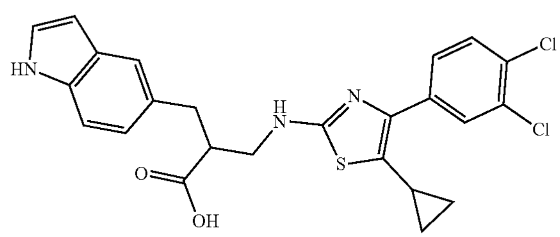 [SMILES: O=C(O)C(CNc1nc(-c2ccc(Cl)c(Cl)c2)c(C2CC2)s1)Cc1ccc2[nH]ccc2c1] | Method C, Purity is 100%, Rt = 1.804 min; MS Calcd.: 485.1; MS Found: 486.1 [M + H]⁺. | δ: 2.82 (1H, q, J = 6.8 Hz), 2.90-3.01 (2H, m), 3.35-3.41 (2H, m), 3.46 (2H, d, J = 6.0 Hz), 5.10 (2H, dd, J = 13.2, 2.0 Hz), 5.90-5.99 (1H, m), 6.30 (1H, s), 6.93 (1H, dd, J = 8.4, 1.6 Hz), 7.26-7.29 (2H, m), 7.33 (1H, s), 7.45 (1H, dd, J = 8.4, 2.0 Hz), 7.60 (1H, d, J = 8.4 Hz), 7.71-7.72 (2H, m), 10.96 (1H, s). |
| 24 | 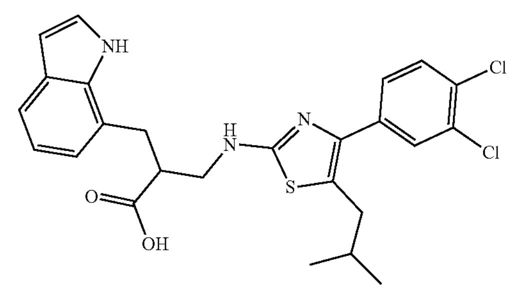 [SMILES: CC(C)Cc1sc(NCC(Cc2cccc3cc[nH]c23)C(=O)O)nc1-c1ccc(Cl)c(Cl)c1] | Method C, Purity is 99.1%, Rt = 2.166 min; MS Calcd.: 501.1; MS Found: 502.2 [M + H]⁺. | δ: 0.85 (6H, d, J = 6.4 Hz), 1.69-1.73 (1H, m), 2.56 (2H, d, J = 6.8 Hz), 3.08-3.13 (3H, m), 3.42 (2H, s), 6.39 (1H, q, J = 1.7 Hz), 6.88 (1H, t, J = 7.2 Hz), 6.94 (1H, d, J = 6.8 Hz), 7.29 (1H, t, J = 2.8 Hz), 7.36 (1H, d, J = 8..0 Hz), 7.44 (1H, dd, J = 8.4, 1.6 Hz), 7.62 (2H, d, J = 8.4 Hz), 7.69 (1H, d, J = 2.0 Hz), 12.12 (1H, brs) |
| 25 | 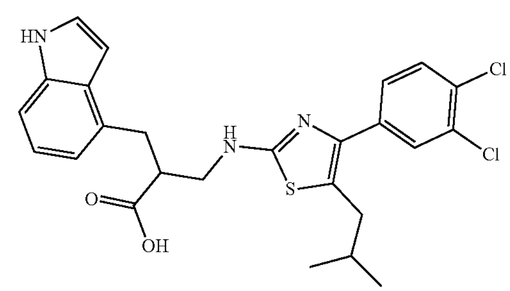 [SMILES: CC(C)Cc1sc(NCC(Cc2cccc3[nH]ccc23)C(=O)O)nc1-c1ccc(Cl)c(Cl)c1] | Method C, Purity is 99.5%, Rt = 2.008 min; MS Calcd.: 501.1; MS Found: 502.2 [M + H]⁺. | δ: 0.86 (6H, d, J = 6.8 Hz), 1.69-1.73 (1H, m), 2.57 (2H, d, J = 7.2 Hz), 2.99-3.15 (3H, m), 3.36-3.44 (2H, m), 6.41 (1H, s), 6.80 (1 H, d, J = 12 Hz), 6.95 (1H, t, J = 8.0 Hz), 7.23 (2H, dd, J = 17.2, 7.2 Hz), 7.41 (1H, dd, J = 8.6, 2.0 Hz), 7.62 (1H, dd, J = 8.4 Hz), 7.68-7.72 (2H, m), 11.05 (1H, brs) |
| 26 | 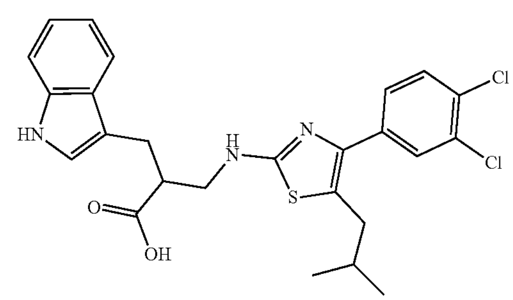 [SMILES: CC(C)Cc1sc(NCC(Cc2c[nH]c3ccccc23)C(=O)O)nc1-c1ccc(Cl)c(Cl)c1] | Method C, Purity is 100%, Rt = 1.959 min; MS Calcd.: 501.1; MS Found: 502.2 [M + H]⁺. | δ: 0.88 (6H, d, J = 6.4 Hz), 1.72-1.75 (1H, m), 2.59 (2H, d, J = 7.2 Hz), 2.93-2.97 (2H, m), 3.07-3.09 (2H, m), 3.42-3.47 (2H, m), 6.91 (1H, d, J = 12 Hz), 7.05 (1H, d, J = 7.2 Hz), 7.13 (1H, d, J = 2.0 Hz), 7.30 (1H, d, J = 8.0 Hz), 7.45-7.49 (2H, m), 7.64 (1H, dd, J = 8.4 Hz), 7.71-7.74 (2H, m), 10.82 (1H, s), 12.24 (1H, brs) |

TABLE 1-4-continued

Characterization Data for Compounds

| I-# | Chemical Structure | LCMS | ¹H NMR (400 MHz, DMSO-$d_6$) |
|---|---|---|---|
| 27 | 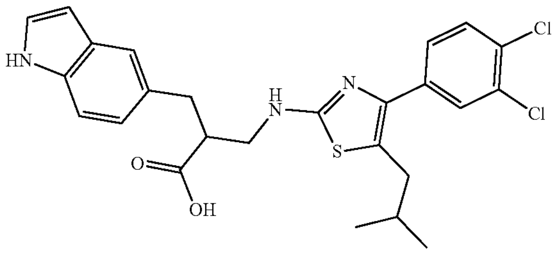 [SMILES: CC(C)Cc1sc(NCC(Cc2ccc3[nH]ccc3c2)C(=O)O)nc1-c1ccc(Cl)c(Cl)c1] | Method C, Purity is 98.8%, Rt = 2.029 min; MS Calcd.: 501.1; MS Found: 502.2 [M + H]⁺. | δ: 0.85 (6H, d, J = 6.4 Hz), 1.69-1.73 (1H, m), 2.56 (2H, d, J = 12 Hz), 2.75-2.80 (1H, m), 2.87-2.95 (2H, m), 3.28-3.32 (2H, m), 6.28 (1H, s), 6.92 (1H, dd, J = 8.4, 1.2 Hz), 7.25-7.27 (2H, m), 7.32 (1H, s), 7.44 (1H, dd, J = 8.6, 1.6 Hz), 7.60 (1H, d, J = 8.4 Hz, ), 7.68 (1H, d, J = 2.0 Hz), 10.95 (1H, brs). |
| 34 | 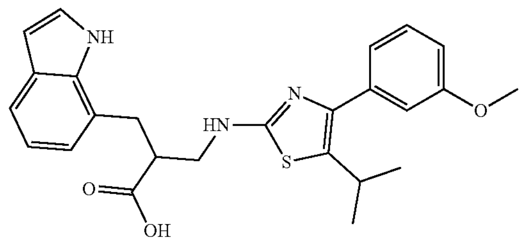 [SMILES: COc1cccc(-c2nc(NCC(Cc3cccc4cc[nH]c34)C(=O)O)sc2C(C)C)c1] | Method C, Purity is 97.2%, Rt = 1.773 min; MS Calcd.: 449.2; MS Found: 450.1 [M + H]⁺. | δ: 1.17 (6H, dd, J = 6.8, 2.4 Hz), 2.95-3.02 (2H, m), 3.08-3.15 (1H, m), 3.21-3.26 (2H, m), 3.37-3.42 (2H, m), 3.74 (3H, s), 6.38 (1H, d, J = 2.8 Hz), 6.84-6.88 (2H, m), 6.92-6.94 (1H, m), 6.98-7.02 (2H, m), 7.24-7.25 (1H, m), 7.29 (1H, t, J = 8.0 Hz), 7.35 (1H, d, J = 8.0 Hz), 7.51-7.54 (1H, m), 11.36 (1H, brs). |
| 35 | 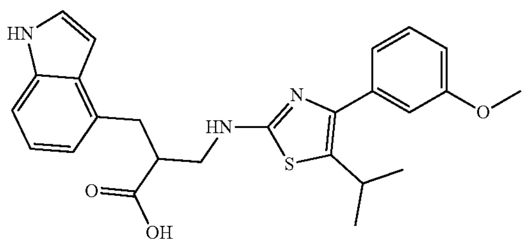 [SMILES: COc1cccc(-c2nc(NCC(Cc3cccc4[nH]ccc34)C(=O)O)sc2C(C)C)c1] | Method C, Purity is 91.9%, Rt = 1.628 min; MS Calcd.: 449.2; MS Found: 450.2 [M + H]⁺. | δ: 1.19 (6H, dd, J = 6.8, 4.0 Hz), 2.98-3.02 (1H, m), 3.08-3.13 (2H, m), 3.23-3.30 (2H, m), 3.38-3.51 (2H, m), 3.76 (3H, s), 6.45 (1H, brs), 6.83 (1H, d, J = 6.8 Hz), 6.86-6.90 (1H, m), 6.96 (1H, t, J = 7.6 Hz), 7.00-7.03 (2H, m), 7.23 (1H, d, J = 8.4 Hz), 7.26 (1H, t, J = 2.8 Hz), 7.31 (1H, t, J = 8.4 Hz), 7.64 (1H, brs), 12.37 (1H, brs). |
| 36 | 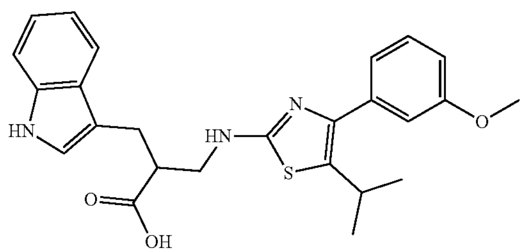 [SMILES: COc1cccc(-c2nc(NCC(Cc3c[nH]c4ccccc34)C(=O)O)sc2C(C)C)c1] | Method C, Purity is 100%, Rt = 1.681 min; MS Calcd.: 449.2; MS Found: 450.3 [M + H]⁺. | δ: 1.20 (6H, dd, J = 6.8, 4.0 Hz), 2.91-2.97 (2H, m), 3.08-3.12 (1H, m), 3.24-3.29 (2H, m), 3.42-3.45 (2H, m), 3.76 (3H, s), 6.88-6.94 (2H, m), 7.02-7.07 (3H, m), 7.13 (1H, d, J = 2.4 Hz), 7.29-7.33 (2H, m), 7.49 (1H, d, J = 8.0 Hz), 7.64 (1H, brs), 10.81 (1H, brs). |
| 37 | 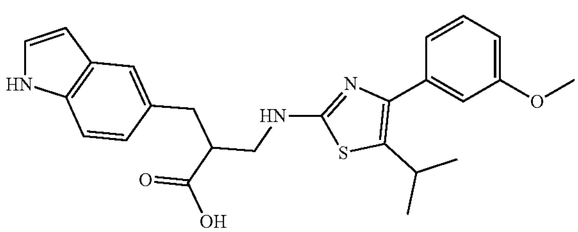 [SMILES: COc1cccc(-c2nc(NCC(Cc3ccc4[nH]ccc4c3)C(=O)O)sc2C(C)C)c1] | Method C, Purity is 100%, Rt = 1.625 min; MS Calcd.: 449.2; MS Found: 450.3 [M + H]⁺. | δ: 1.17 (6H, t, J = 6.8 Hz), 2.82-2.96 (3H, m), 3.21-3.27 (2H, m), 3.35-3.39 (2H, m), 3.74 (3H, s), 6.29 (1H, brs), 6.86 (1H, dd, J = 8.0, 2.0 Hz), 6.92 (1H, d, J = 8.4 Hz), 7.00-7.02 (2H, m), 7.24-7.33 (4H, m), 7.58 (1H, brs), 10.95 (1H, brs). |
| 44 | 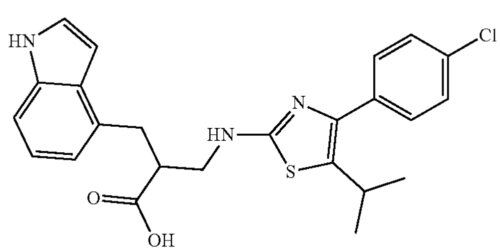 [SMILES: CC(C)c1sc(NCC(Cc2cccc3[nH]ccc23)C(=O)O)nc1-c1ccc(Cl)cc1] | Method C, Purity is 96.9%, Rt = 1.833 min; MS Calcd.: 453.1; MS Found: 454.3 [M + H]⁺. | δ: 1.19 (6H, t, J = 6.8 Hz), 2.94-3.00 (1H, m), 3.08-3.12 (2H, m), 3.20-3.26 (2H, m), 3.38-3.43 (1H, m), 6.45 (1H, brs), 6.82 (1H, d, J = 7.2 Hz), 6.97 (1H, t, J = 6.0 Hz), 7.24 (1H, d, J = 8.0 Hz), 7.28 (1H, t, J = 2.8 Hz), 7.41-7.46 (4H, m), 7.69 (1H, brs), 11.08 (1H, s). |

TABLE 1-4-continued
Characterization Data for Compounds
| I-# | Chemical Structure | LCMS | $^1$H NMR (400 MHz, DMSO-$d_6$) |
|---|---|---|---|
| 45 | 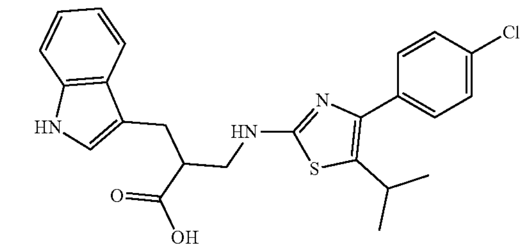 [SMILES: CC(C)c1sc(NCC(Cc2c[nH]c3ccccc23)C(=O)O)nc1-c1ccc(Cl)cc1] | Method C, Purity is 96.7%, Rt = 1.909 min; MS Calcd.: 453.1; MS Found: 454.3 [M + H]$^+$. | δ: 1.19 (6H, dd, J = 6.8, 4.4 Hz), 2.87-3.08 (3H, m), 3.20-3.27 (1H, m), 3.37-3.40 (2H, m), 6.93 (1H, t, J = 7.6 Hz), 7.06 (1H, t, J = 7.2 Hz), 7.14 (1H, d, J = 1.6 Hz), 7.33 (1H, d, J = 8.0 Hz), 7.43-7.50 (5H, m), 7.67 (1H, brs), 10.81 (1H, s). |
| 46 | 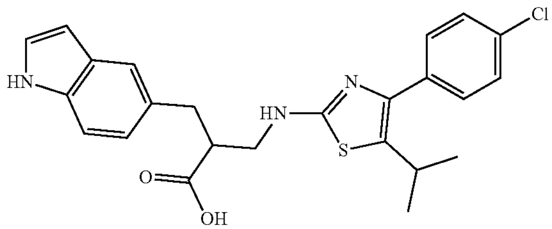 [SMILES: CC(C)c1sc(NCC(Cc2ccc3[nH]ccc3c2)C(=O)O)nc1-c1ccc(Cl)cc1] | Method C, Purity is 97.0%, Rt = 1.874 min; MS Calcd.: 453.1; MS Found: 454.2 [M + H]$^+$. | δ: 1.17 (6H, dd, J = 6.8, 5.6 Hz), 2.79-2.84 (1H, m), 2.88-2.98 (2H, m), 3.18-3.25 (1H, m), 3.34-3.38 (2H, m), 6.30 (1H, brs), 6.92 (1H, d, J = 8.0 Hz), 7.27 (2H, t, J = 2.8 Hz), 7.33 (1H, s), 7.43 (4H, q, J = 8.8 Hz), 7.60 (1H, brs), 10.96 (1H, s), 12.21 (1H, brs). |
Example 2. Synthesis of Compounds I-49 to I-118
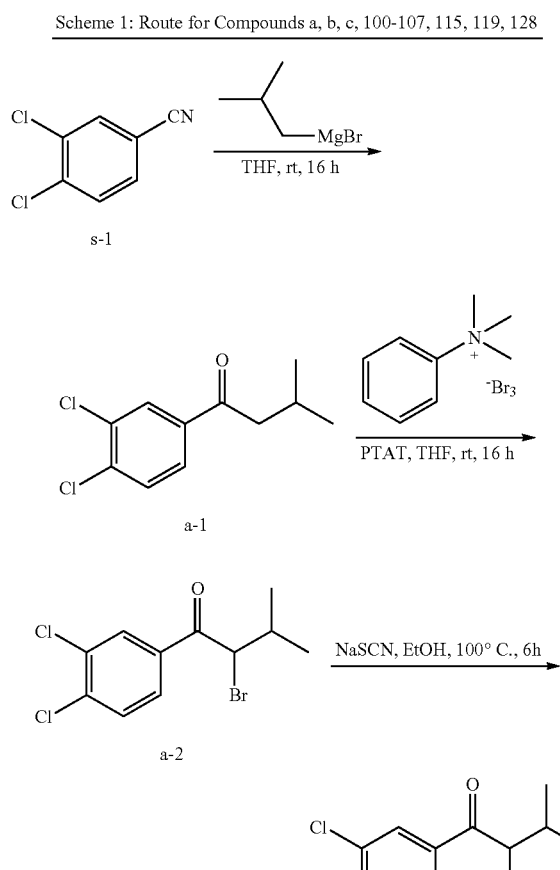
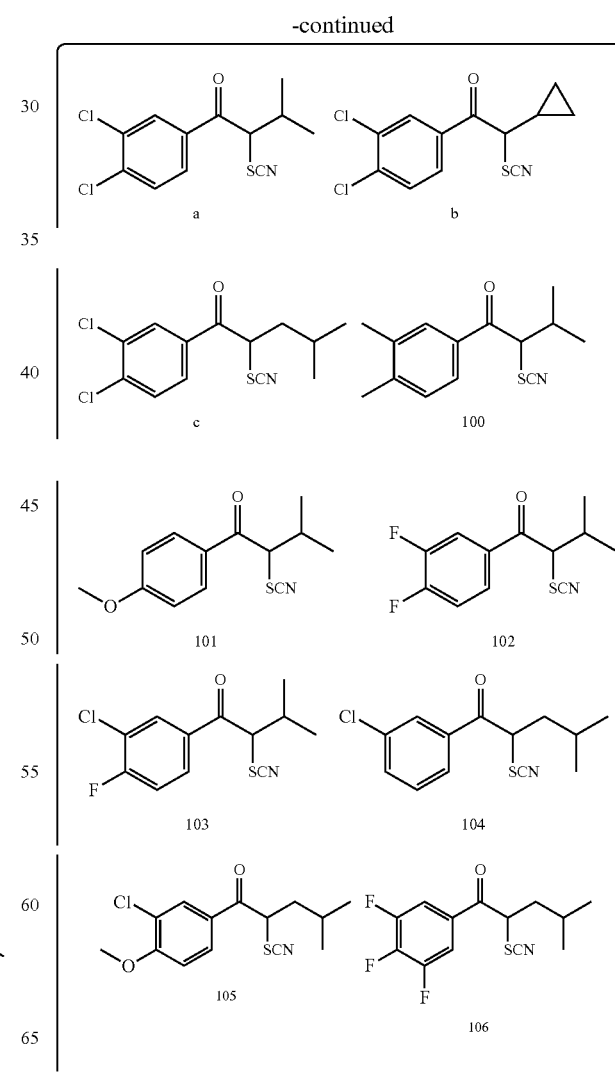

-continued
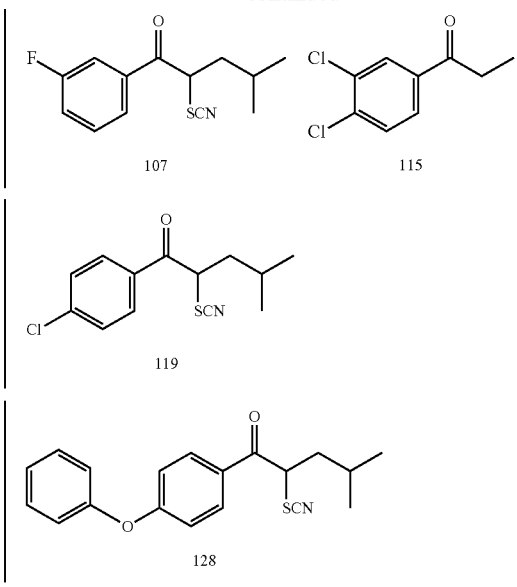
The same synthesis method used for other compounds b-c, 100-107, 115, 119, 128.
Scheme 2: Route for Compounds 108, 109
-continued
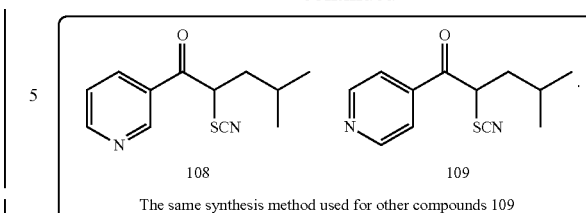
The same synthesis method used for other compounds 109
Scheme 3: Route for Compound 110
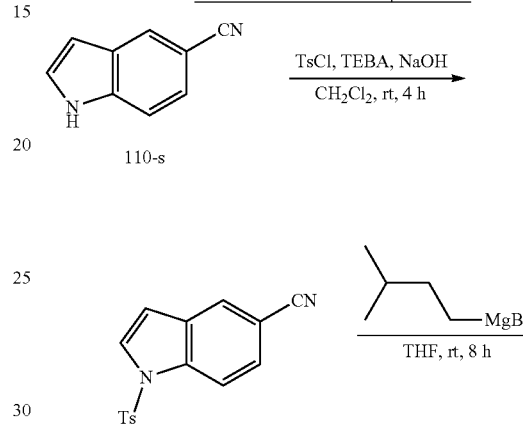
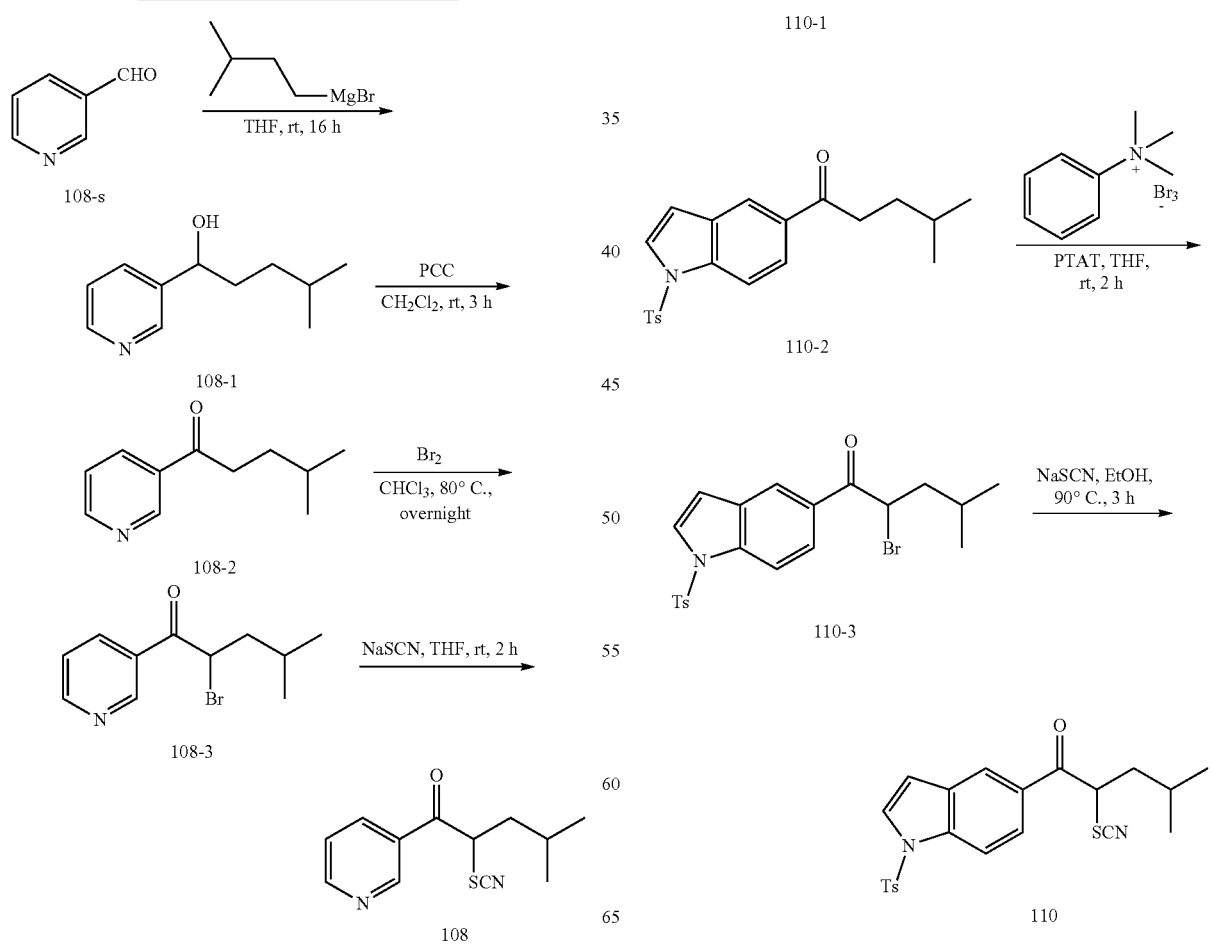

Scheme 4: Route for Compound 129
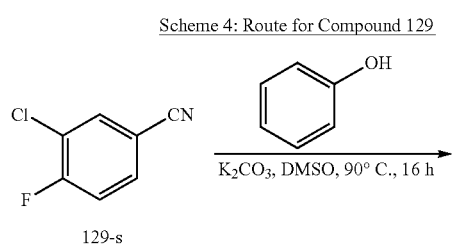
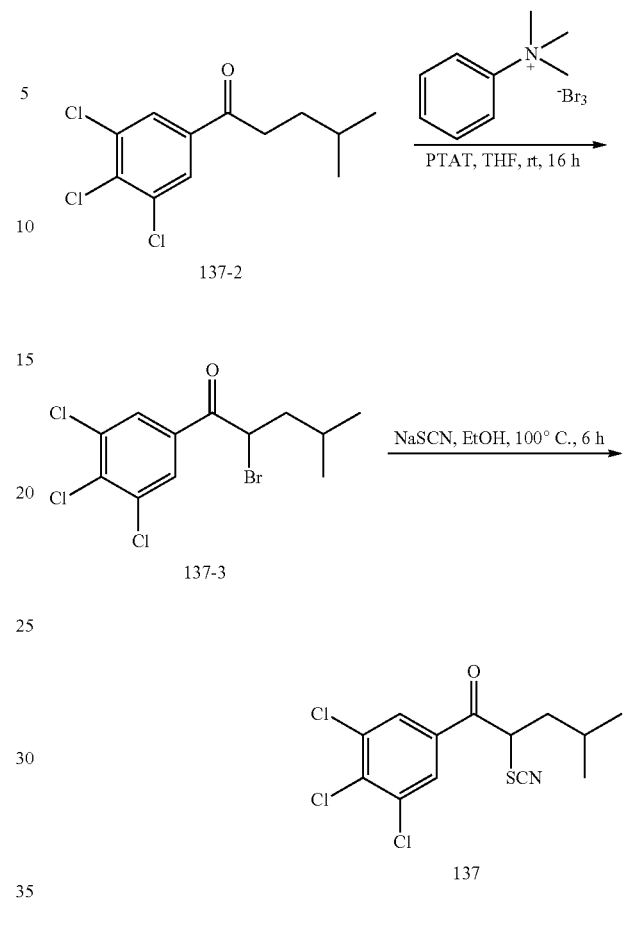
Scheme 5: Route for Compound 137
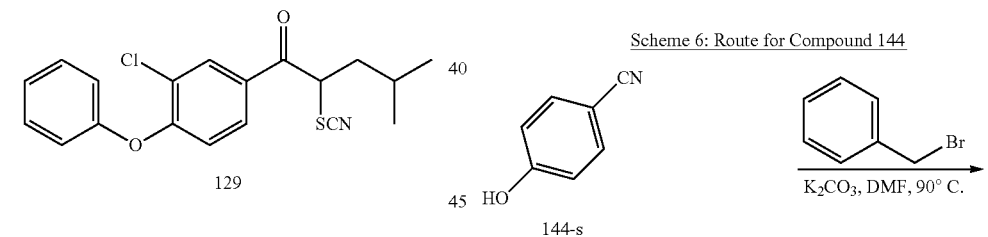
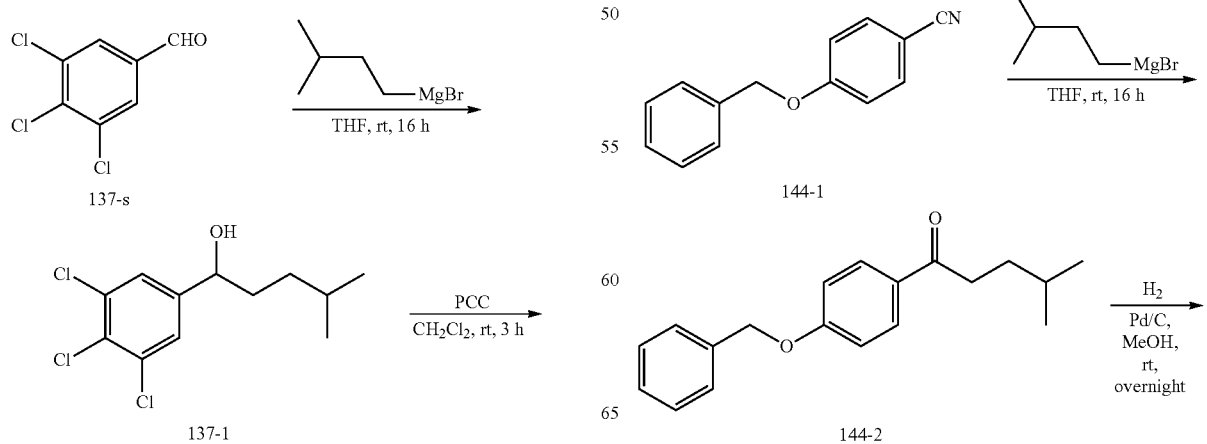

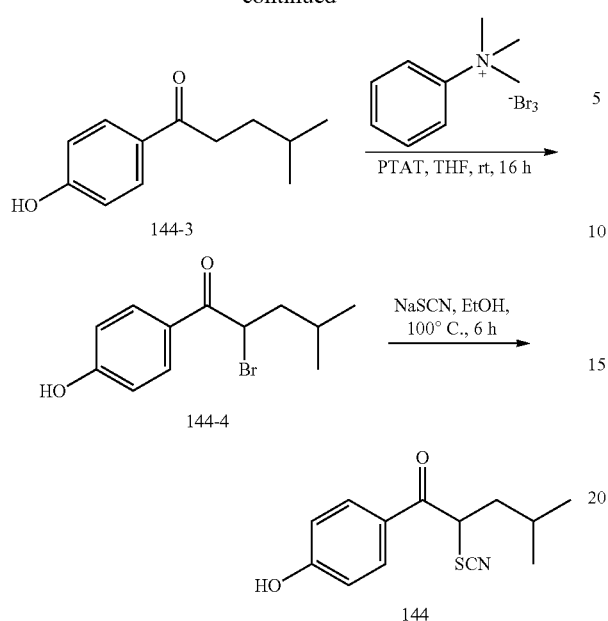
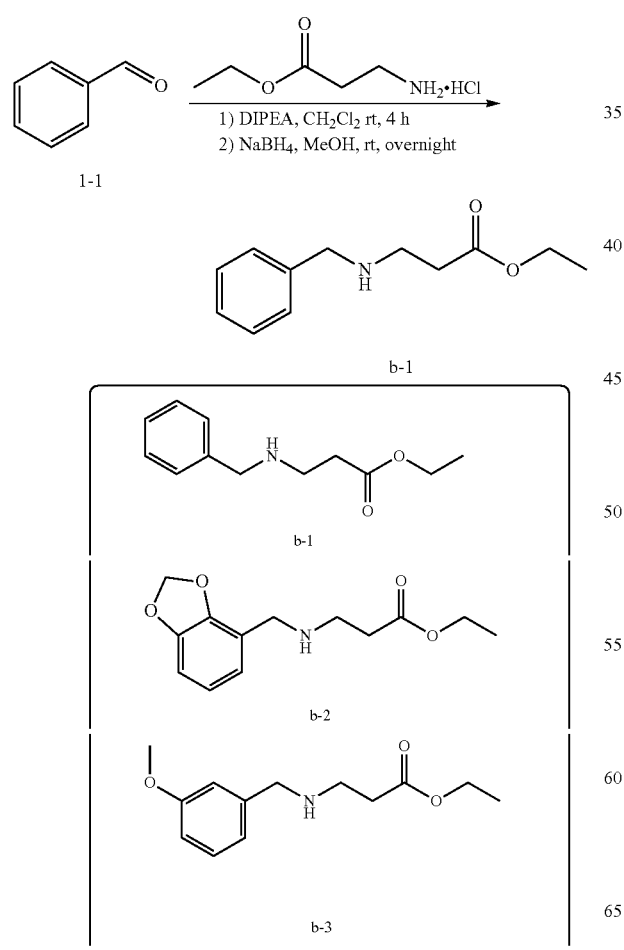
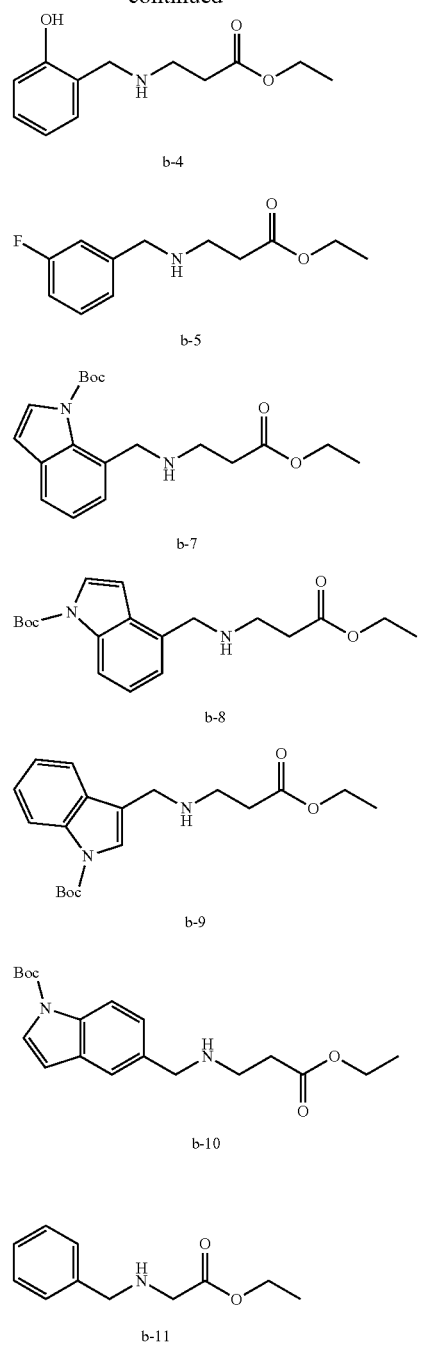

-continued
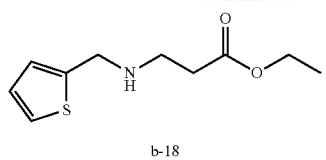
b-18
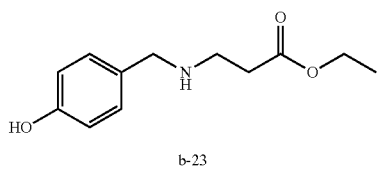
b-23
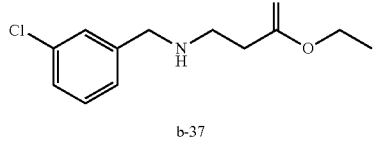
b-37
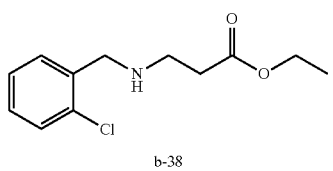
b-38
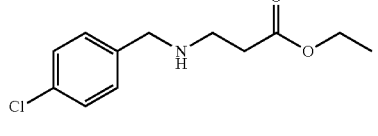
b-39
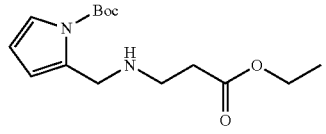
b-40
The same synthesis method used for other compounds b-2 ~ b-5, b-7 ~ b-11, b-16 ~ b-18, b-23, b-37 ~ b-40
Scheme 8: Route for Compounds b-6, b-12, b-14, b-15, b-22, b-26, b-29, b-31, b-32, b-35
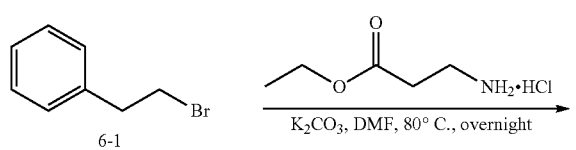
-continued
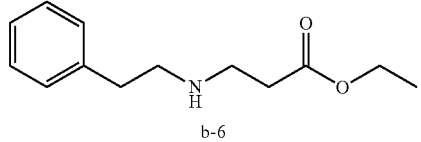
b-6
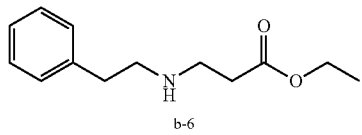
b-6
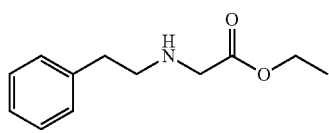
b-12
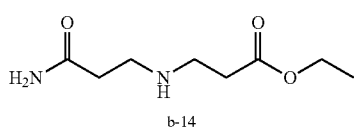
b-14
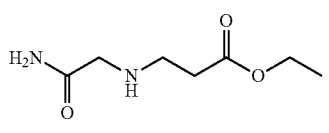
b-15
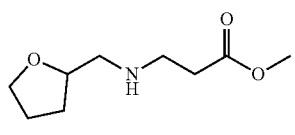
b-22
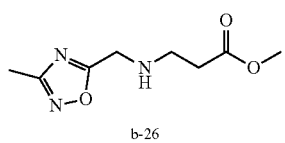
b-26
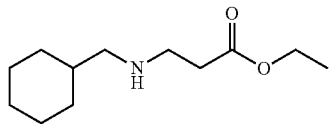
b-29
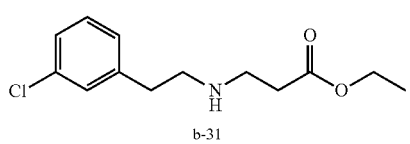
b-31
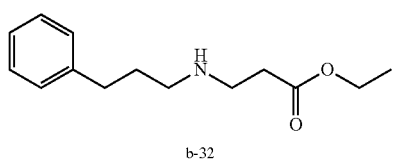
b-32

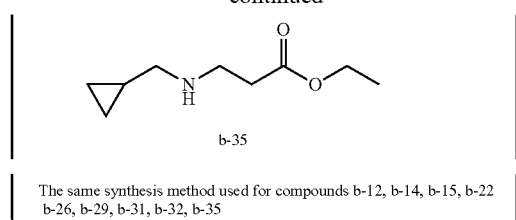
The same synthesis method used for compounds b-12, b-14, b-15, b-22, b-26, b-29, b-31, b-32, b-35
Scheme 9: Route for Compounds b-19, b-20
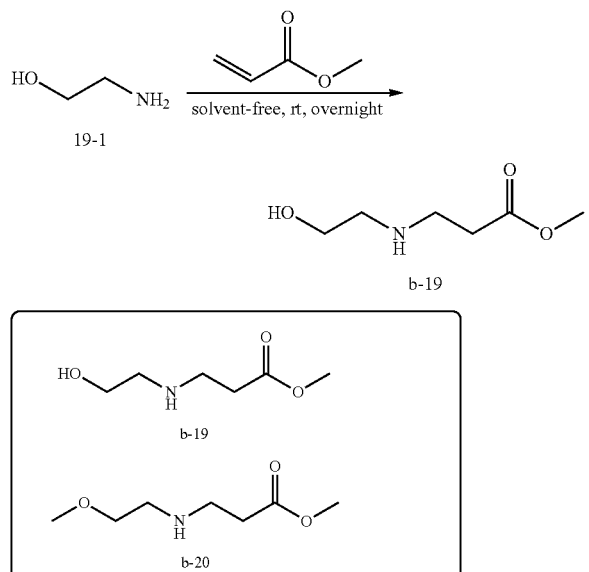
Scheme 10: Route for Compounds b-21, b-24
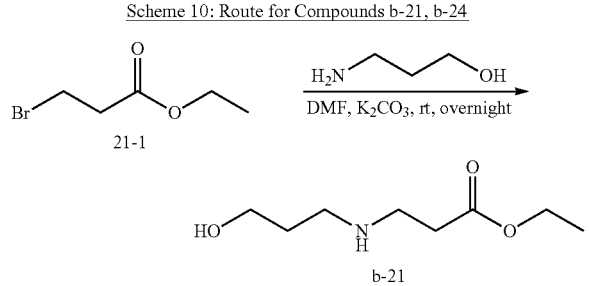
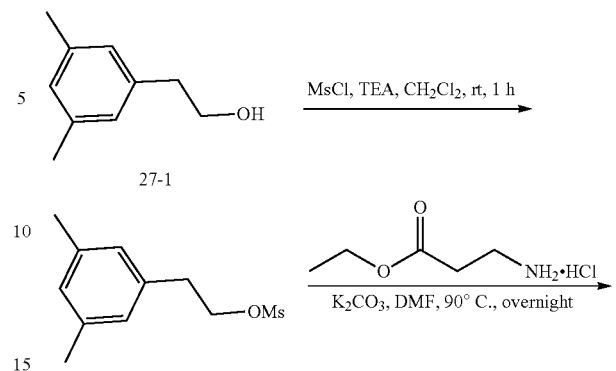
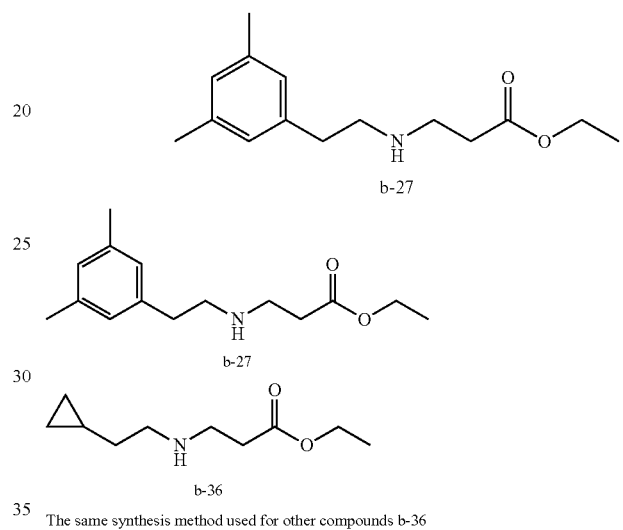
The same synthesis method used for other compounds b-36
Scheme 11: Route for Compounds b-28
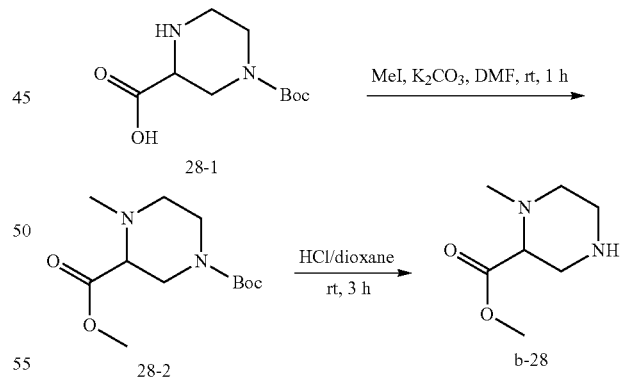
Scheme 12: Route for Compounds b-30
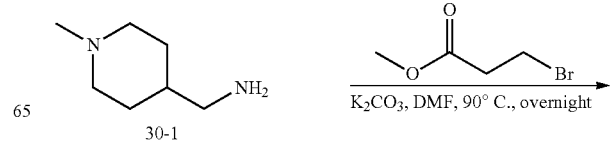

223
-continued

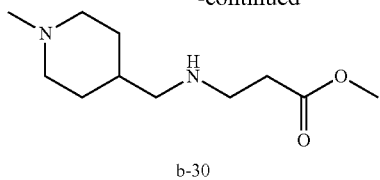

b-30

Scheme 13: Route for Compounds b-33

[structure of benzaldehyde] + H$_2$N-CH$_2$CH$_2$-S(O)$_2$NH$_2$
33-1
→ EtOH, NaBH$_3$CN, 90° C., 2 h →

[structure of N-benzyl-2-aminoethanesulfonamide]
b-33

Scheme 13: Route for Compounds b-34

[structure of 5-(2-chloroethyl)-1H-tetrazole] + benzylamine
34-1
→ K$_2$CO$_3$, DMF, 90° C., overnight →

[structure of N-benzyl-2-(1H-tetrazol-5-yl)ethylamine]
b-34

224

Scheme 14: Route for I-47 to I-52, I-56, I-57, I-59 to I-109, I-86 to I-88, I-93 to I-96, I-98, I-100, I-103, I-105 to I-109, I-111, I-112, I-117

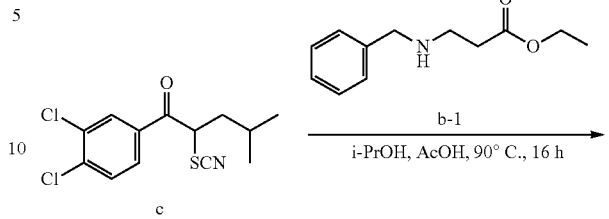

b-1
i-PrOH, AcOH, 90° C., 16 h

[structure 061-1: ethyl ester thiazole with 3,4-dichlorophenyl, isobutyl, and N-benzyl substituents]
061-1

LiOH
THF/
MeOH/
H$_2$O,
rt, 4 h

[structure I-47: carboxylic acid thiazole with 3,4-dichlorophenyl, isobutyl, and N-benzyl substituents]
I-47

The same synthesis method used for other compounds I-48 to I-52, I-56, I-57, I-59 to I-84, I-86 to I-88, I-93 to I-96, I-98, I-100, I-103, I-105 to I-109, I-111, I-112

Scheme 15: Route for I-53 to I-55, I-110

[structure: Boc-indole-CH$_2$-NH-CH$_2$CH$_2$-CO$_2$Et]
b-8

[structure c: 3,4-dichlorophenyl ketone with SCN and isobutyl]
c

→ i-PrOH, AcOH, 90° C., 16 h →

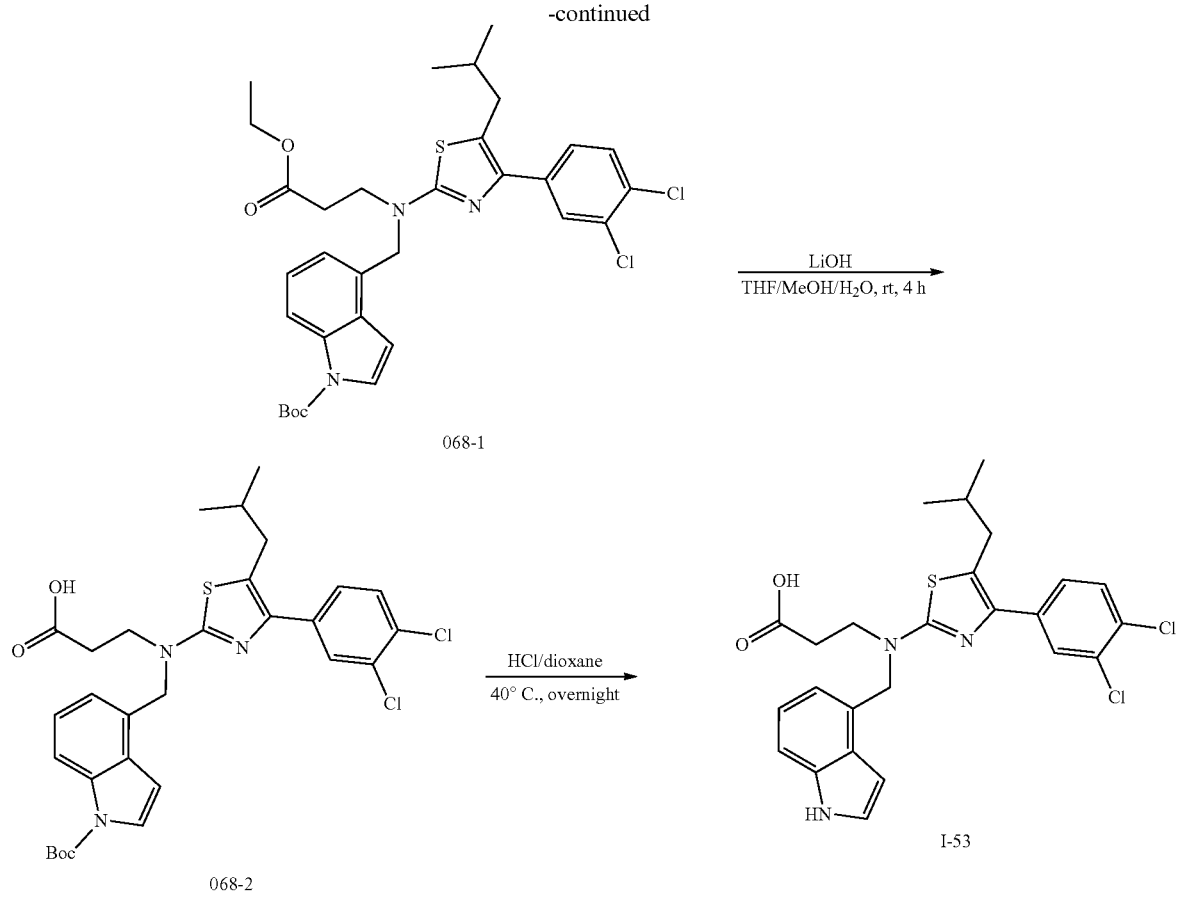
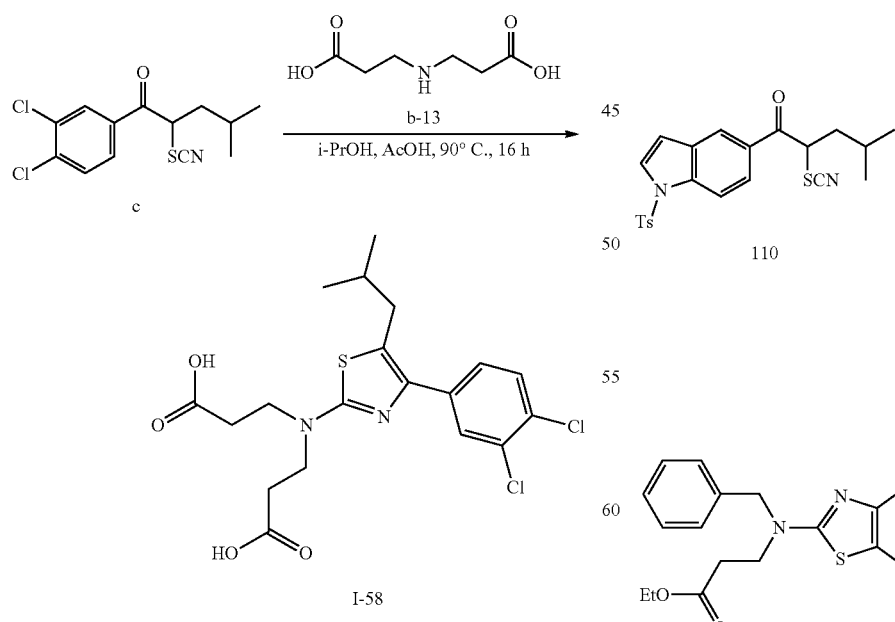
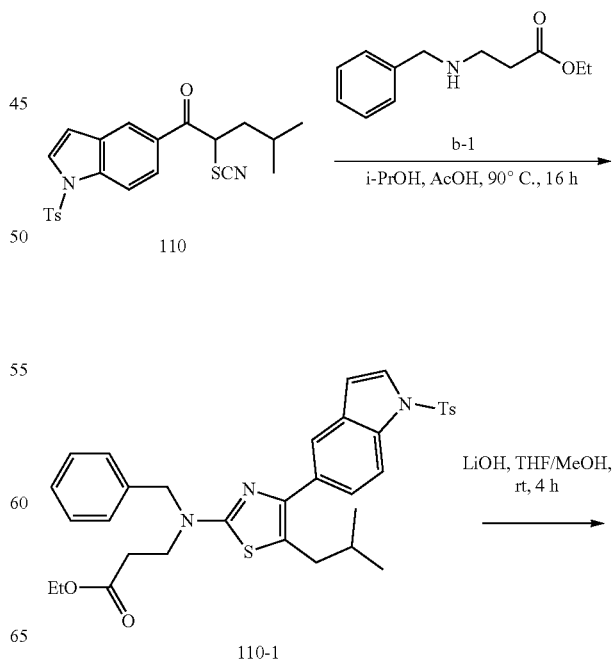

227
-continued
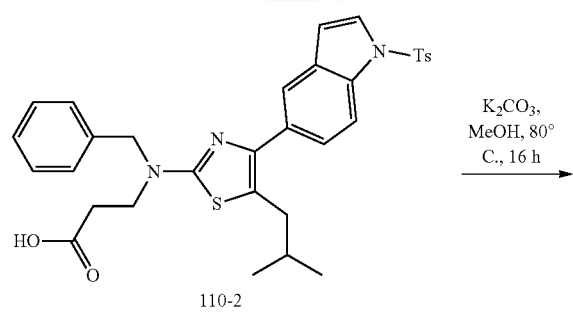
110-2
K₂CO₃, MeOH, 80° C., 16 h →
228
-continued
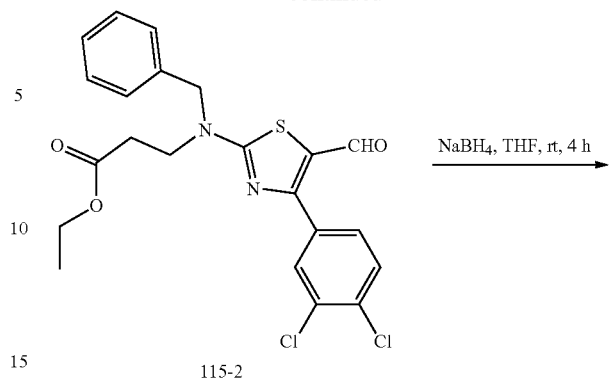
115-2
NaBH₄, THF, rt, 4 h →
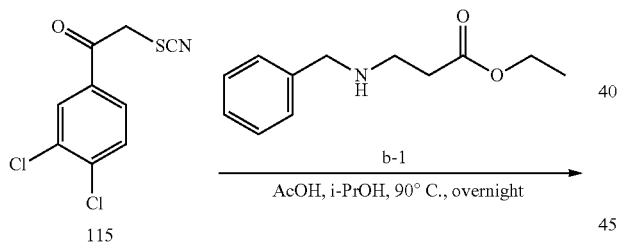
I-85
Scheme 18: Route for I-89 to I-92
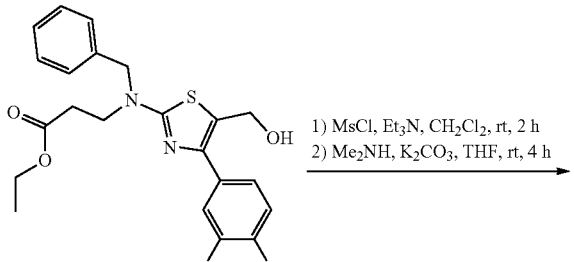
115-3
1) MsCl, Et₃N, CH₂Cl₂, rt, 2 h
2) Me₂NH, K₂CO₃, THF, rt, 4 h →
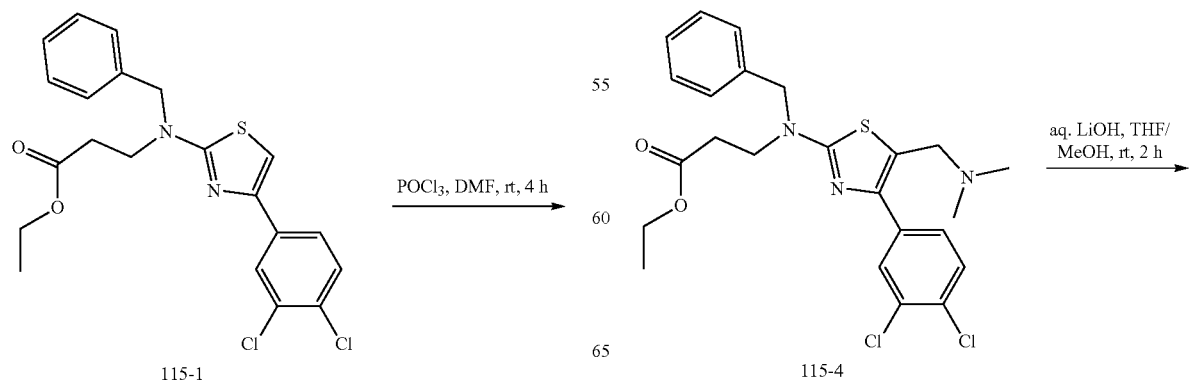
115
b-1
AcOH, i-PrOH, 90° C., overnight →
115-1
POCl₃, DMF, rt, 4 h →
115-4
aq. LiOH, THF/ MeOH, rt, 2 h →

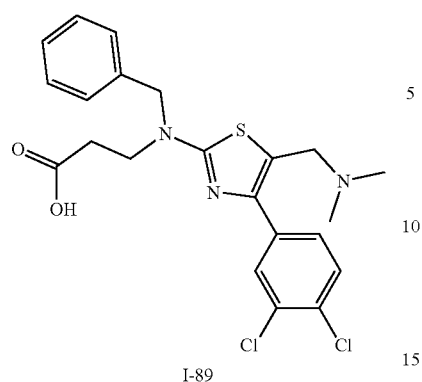
I-89
The same synthesis method used for other compounds I-90 to I-92
Scheme 19: Route for I-97
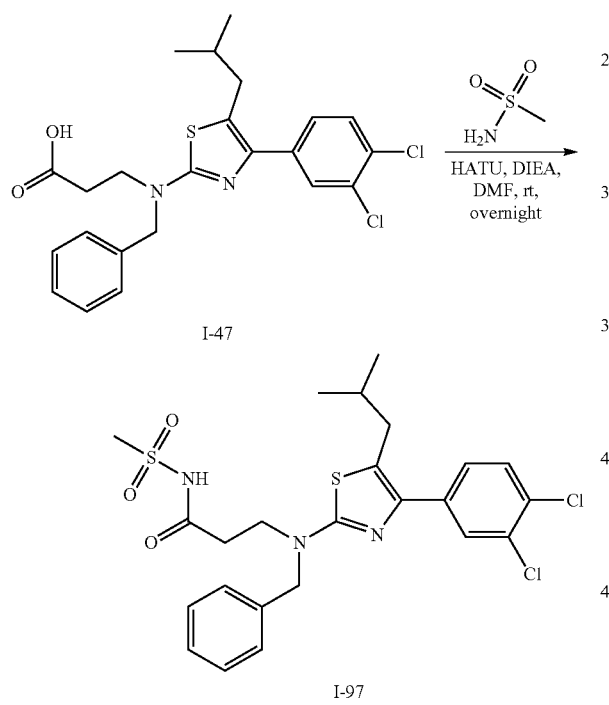
Scheme 20: Route I-99
Scheme 20: Route for I-101
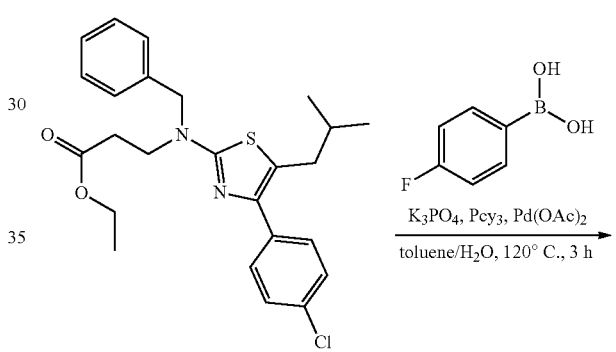
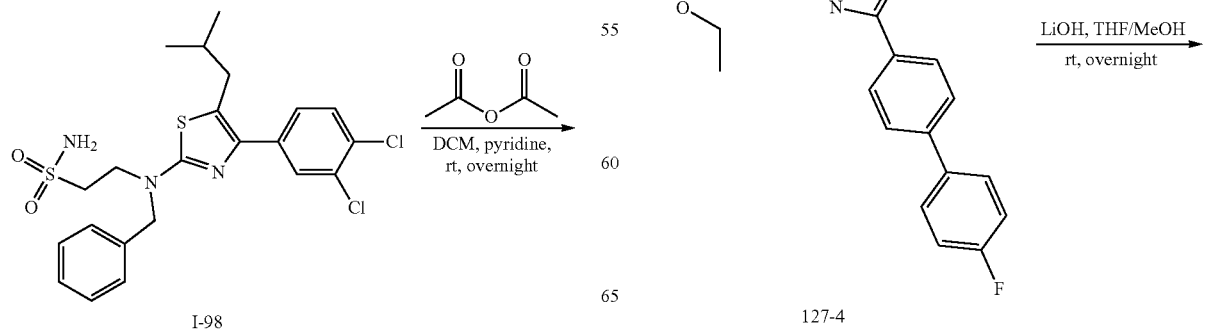

231
-continued
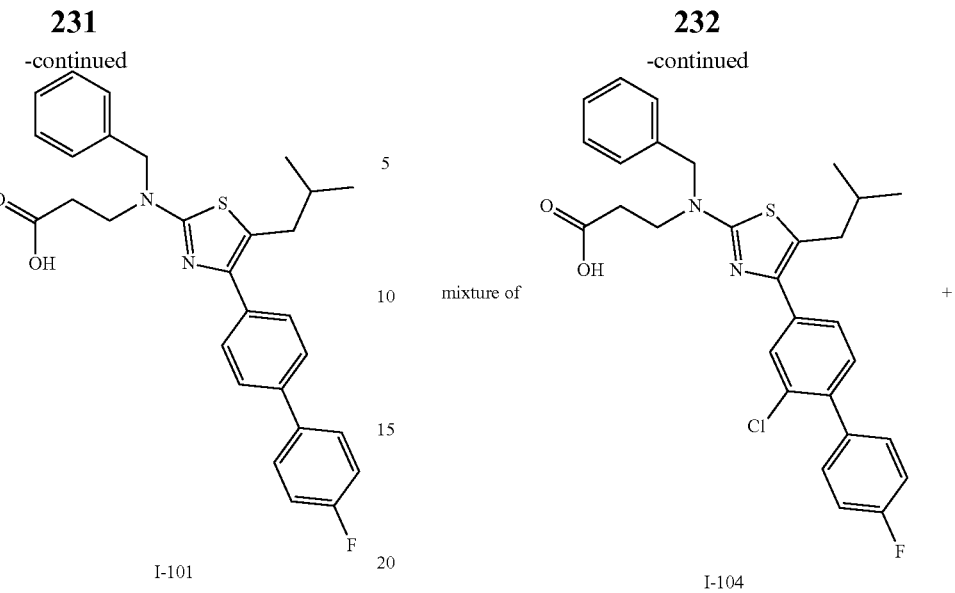
I-101
mixture of
232
-continued
I-104
+
Scheme 21: Route for I-104
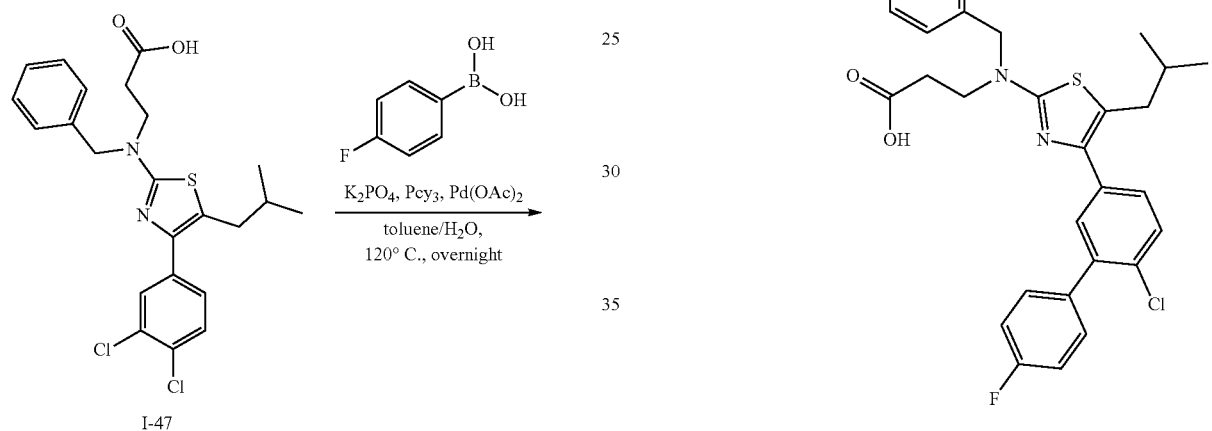
I-47
Scheme 22: Route for I-113 to I-116
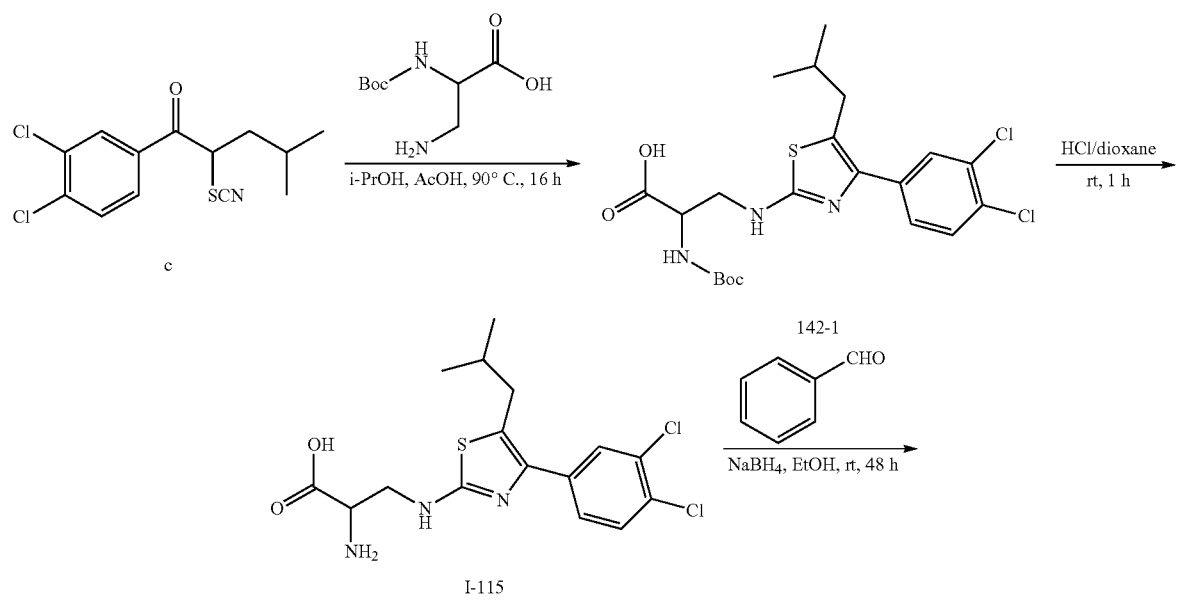
142-1
I-115

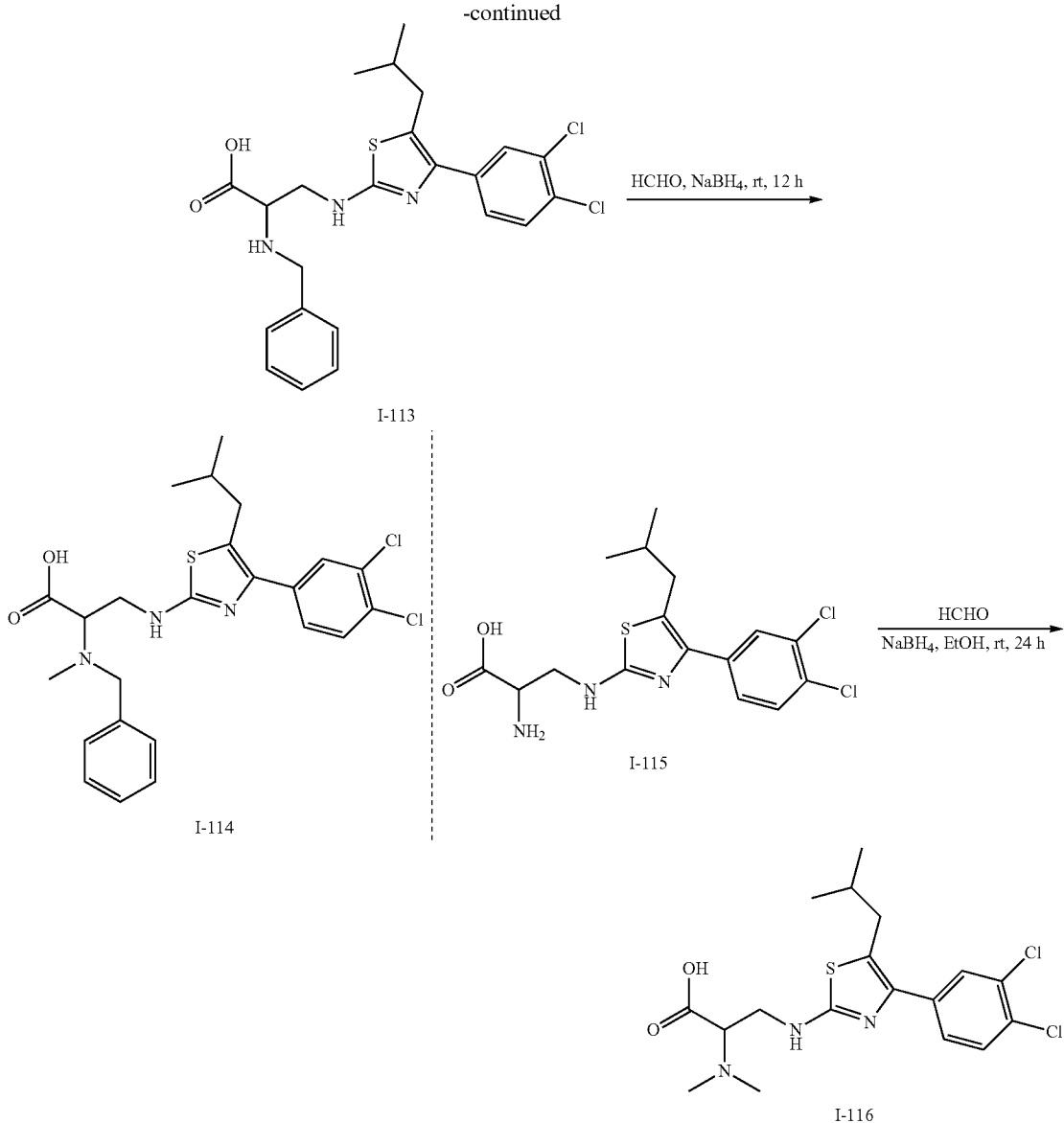

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [$CH_3CN$+0.05% TFA] to 0% [water+0.05% TFA] and 100% [$CH_3CN$+0.05% TFA] in 0.8 min, then under this condition for 0.4 min, finally changed to 95% [water+0.05% TFA] and 5% [$CH_3CN$+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95%

[water+10 mM NH₄HCO₃] and 5% [CH₃CN] in 0.1 min and under this condition for 0.7 min.)

Synthesis of 1-(3,4-dichlorophenyl)-3-methylbutan-1-one (a-1)

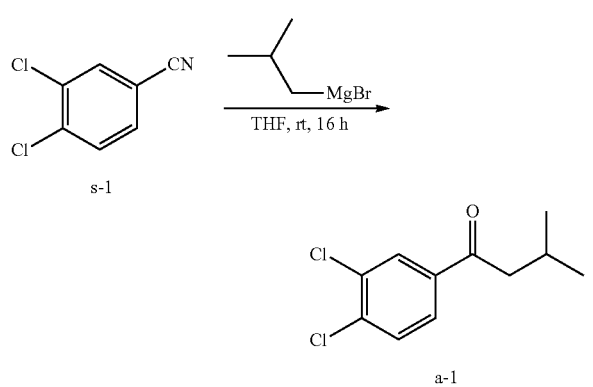

s-1 a-1

To a solution of s-1 (10.0 g, 58.1 mmol) in THF (100 mL) was added isobutyl magnesium bromide (1.0 M in THF, 87.1 mL, 87.1 mmol). The reaction was stirred at room temperature for 16 h. When the reaction was completed, it was poured into aq.NH₄Cl (sat., 500 mL) and extracted with EtOAc (100 mL×3). The organic phase was combined, and washed with H₂O (100 mL) and brine (80 mL), then dried with anhydrous Na₂SO₄, concentrated and purified by silica gel column chromatography (petrol ether/ethyl acetate=20/1) to afford a-1 (7.50 g, 56% yield) as yellow oil.

Synthesis of 2-bromo-1-(3,4-dichlorophenyl)-3-methylbutan-1-one (a-2)

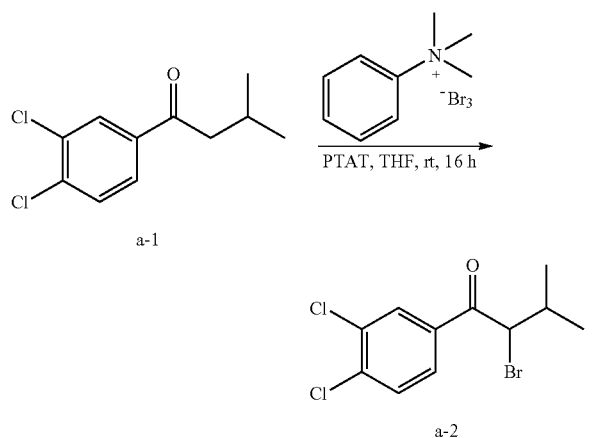

a-1 a-2

A mixture of a-1 (7.50 g, 32.5 mmol) and PTAT (18.3 g, 48.7 mmol) in THF (150 mL) was stirred at room temperature overnight. When the reaction was completed, it was concentrated, and the residual was dissolved in H₂O (100 mL), and then extracted with EtOAc (100 mL×2). The organic layer was combined, and washed with H₂O (60 mL×2) and Brine (80 mL), then dried by anhydrous Na₂SO₄. The solution was concentrated to give the crude product, which was used directly in next step without farther purification to afford a-2 (10.1 g, 100% yield) as brown oil.

Synthesis of 1-(3,4-dichlorophenyl)-3-methyl-2-thiocyanatobutan-1-one (a)

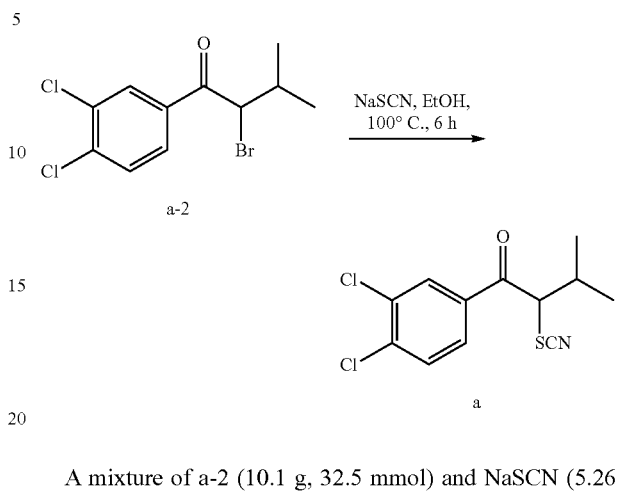

a-2 a

A mixture of a-2 (10.1 g, 32.5 mmol) and NaSCN (5.26 g, 64.9 mmol) in EtOH (100.0 mL) was stirred at 100° C. for 6 h. When the reaction was completed, it was concentrated and purified by silica gel column chromatography (petrol ether/ethyl acetate=10/1) to afford a (5.32 g, 57% yield) as a white solid.

Synthesis of 4-methyl-1-(pyridin-3-yl)pentan-1-ol (108-1)

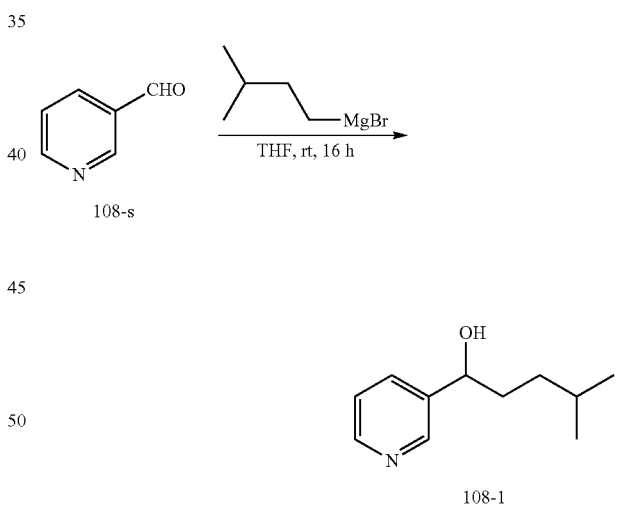

108-s 108-1

To a solution of 108-s (2.14 g, 20.0 mmol) in THF (50 mL) was added isobutyl magnesium bromide (1.0 M in THF, 40.0 mL, 40.0 mmol). The reaction was stirred at room temperature for 16 h. When the reaction was completed, it was poured into aq.NH₄Cl (sat., 200 mL) and extracted with EtOAc (100 mL×3). The organic phase was combined, and washed with H₂O (100 mL) and brine (80 mL), then dried with anhydrous Na₂SO₄, concentrated to afford 108-1 (2.10 g, 59% yield) as yellow oil, which was used directly in next step without farther purification.

Synthesis of 4-methyl-1-(pyridin-3-yl)pentan-1-one (108-2)

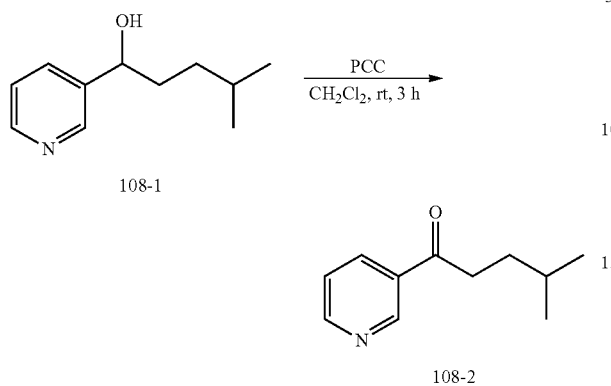

To a solution of 108-1 (2.10 g, 11.7 mmol) in CH₂Cl₂ (150 mL) was added PCC (3.79 g, 17.6 mmol). The reaction was stirred at room temperature for 3 h. When the reaction was completed, it was concentrated, and purified by silica gel column chromatography (petrol ether/ethyl acetate=300/1) to afford 108-2 (800 mg, 39% yield) as yellow oil.

Synthesis of 2-bromo-4-methyl-1-(pyridin-3-yl)pentan-1-one (108-3)

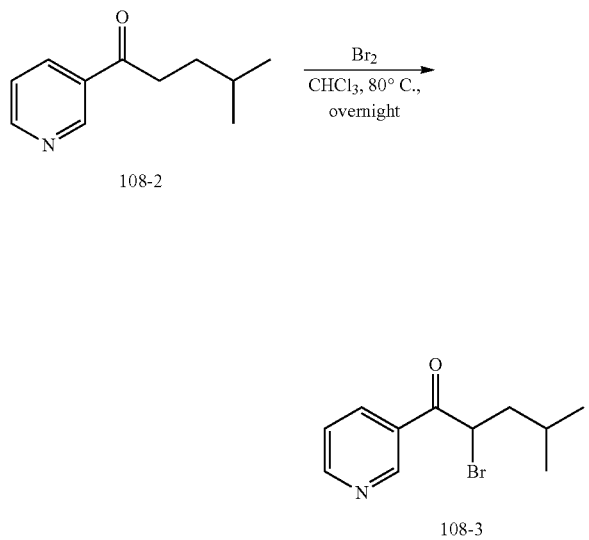

To a solution of 108-2 (800 mg, 4.52 mmol) in CHCl₃ (150 mL) was added Br₂ (867 mg, 5.42 mmol). The reaction was stirred at 80° C., overnight. When the reaction was completed, it was concentrated, and washed with H₂O (100 mL) and brine (80 mL), then dried with anhydrous Na₂SO₄, concentrated to afford 108-3 (1.0 g, 100% yield) as brown oil, which was used directly in next step without farther purification.

Synthesis of 4-methyl-1-(pyridin-3-yl)-2-thiocyanatopentan-1-one (108)

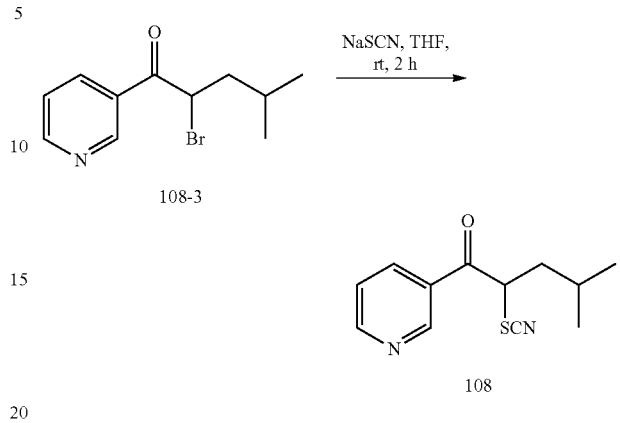

A mixture of 108-3 (1.0 g, 3.91 mmol) and NaSCN (633 mg, 7.81 mmol) in THF (100.0 mL) was stirred at room temperature for 2 h. When the reaction was completed, it was concentrated and purified by silica gel column chromatography (petrol ether/ethyl acetate=50/1) to afford 108 (400 mg, 44% yield) as brown oil.

Synthesis of 1-tosyl-1H-indole-5-carbonitrile (110-1)

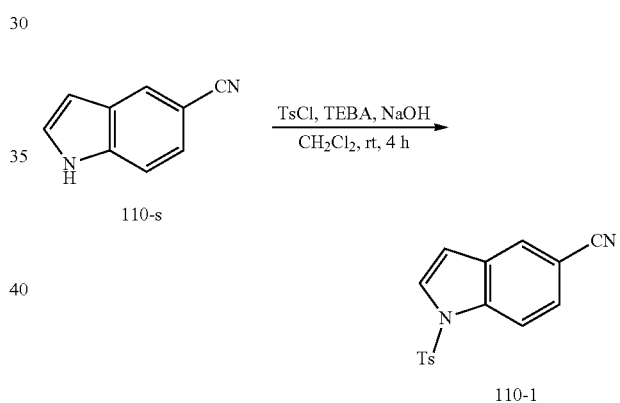

To a mixture of 110-s (5.0 g, 35.2 mmol), TEBA (800 mg, 3.52 mmol) and NaOH (2.54 g, 63.4 mmol) in CH₂Cl₂ (100.0 mL) was added TsCl (8.0 g, 42.3 mmol). The reaction was stirred at room temperature for 4 h. When the reaction was completed, it was concentrated and purified by silica gel column chromatography (petrol ether/ethyl acetate=80/1) to afford 110-1 (2.50 g, 71% yield) as a white solid.

Synthesis of 4-methyl-1-(1-tosyl-1H-indol-5-yl)pentan-1-one (110-2)

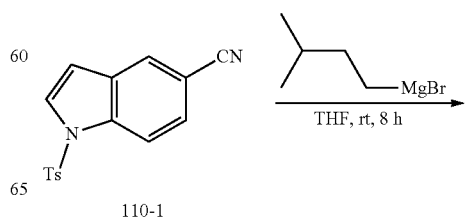

-continued

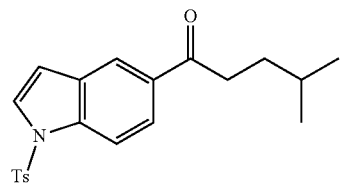

110-2

To a solution of 110-1 (4.0 g, 13.5 mmol) in THF (30 mL) was added isobutyl magnesium bromide (1.0 M in THF, 27 mL, 27.0 mmol). The reaction was stirred at room temperature for 8 h. When the reaction was completed, it was poured into aq.NH$_4$Cl (sat., 500 mL) and extracted with EtOAc (100 mL×3). The organic phase was combined, and washed with H$_2$O (100 mL) and brine (80 mL), then dried with anhydrous Na$_2$SO$_4$, concentrated and purified by silica gel column chromatography (petrol ether/ethyl acetate=100/1) to afford 110-2 (1.0 g, 37% yield) as a white solid.

Synthesis of 2-bromo-4-methyl-1-(1-tosyl-1H-indol-5-yl)pentan-1-one (110-3)

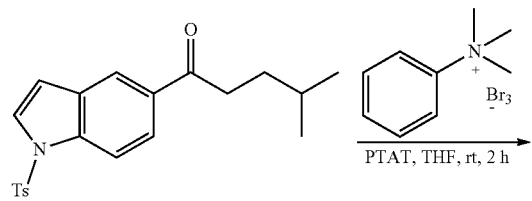

110-2

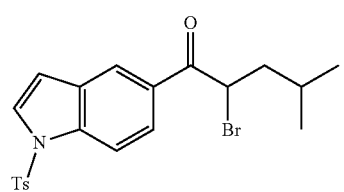

110-3

A mixture of 110-2 (0.60 g, 1.52 mmol) and PTAT (682 mg, 1.82 mmol) in THF (50 mL) was stirred at room temperature for 2 h. When the reaction was completed, it was concentrated, and the residual was dissolved in H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was used directly in next step without farther purification to afford 110-3 (677 mg, 100% yield) as yellow oil.

Synthesis of 4-methyl-2-thiocyanato-1-(1-tosyl-1H-indol-5-yl)pentan-1-one (110)

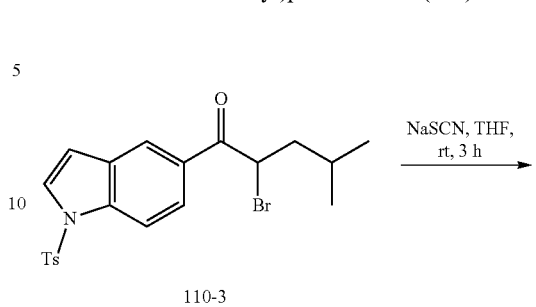

110-3

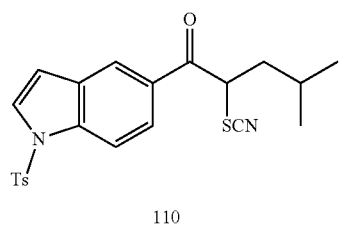

110

A mixture of 110-3 (677 mg, 1.52 mmol) and NaSCN (245 mg, 3.03 mmol) in EtOH (50.0 mL) was stirred at 100° C. for 3 h. When the reaction was completed, it was concentrated and purified by silica gel column chromatography (petrol ether/ethyl acetate=30/1) to afford 110 (320 mg, 47% yield) as a white solid.

Synthesis of 3-chloro-4-phenoxybenzonitrile (129-1)

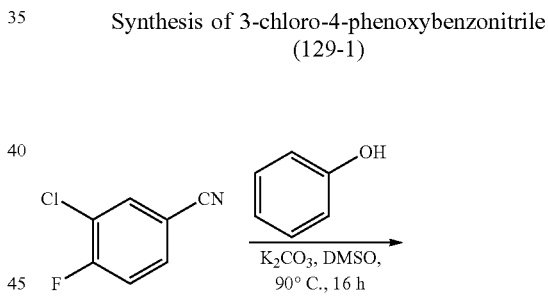

129-s

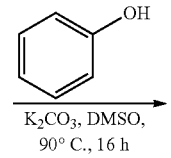

129-1

A mixture of 129-s (5.0 g, 32.3 mmol), phenol (3.34 g, 35.5 mmol) and K$_2$CO$_3$ (5.30 g, 38.7 mmol) in DMSO (50.0 mL) was stirred at 90° C. for 16 h. When the reaction was completed, it was concentrated and purified by silica gel column chromatography (petrol ether/ethyl acetate=100/1) to afford 129-1 (1.80 g, 45% yield) as yellow oil.

Synthesis of 1-(3-chloro-4-phenoxyphenyl)-4-methylpentan-1-one (129-2)

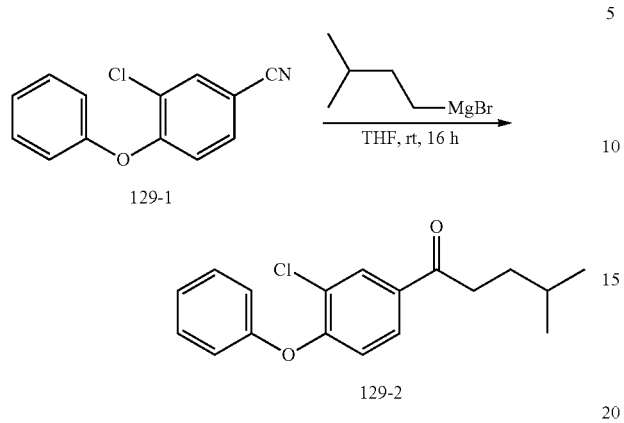

To a solution of 129-1 (2.50 g, 10.9 mmol) in THF (30 mL) was added isobutyl magnesium bromide (1.0 M in THF, 21.8 mL, 21.8 mmol). The reaction was stirred at room temperature for 16 h. When the reaction was completed, it was poured into aq.NH$_4$Cl (sat., 500 mL) and extracted with EtOAc (100 mL×3). The organic phase was combined, and washed with H$_2$O (100 mL) and brine (80 mL), then dried with anhydrous Na$_2$SO$_4$, concentrated and purified by silica gel column chromatography (petrol ether/ethyl acetate=20/1) to afford 129-2 (0.70 g, 47% yield) as yellow oil.

Synthesis of 2-bromo-1-(3-chloro-4-phenoxyphenyl)-4-methylpentan-1-one (129-3)

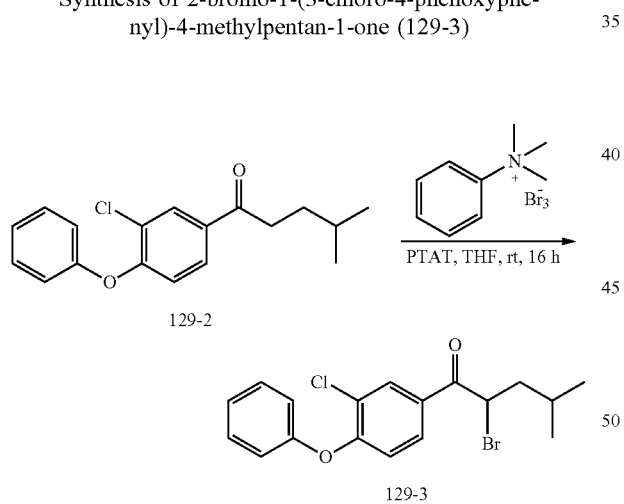

A mixture of 129-2 (1.10 g, 3.64 mmol) and PTAT (1.64 g, 4.37 mmol) in THF (50 mL) was stirred at room temperature overnight. When the reaction was completed, it was concentrated, and the residual was dissolved in H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was used directly in next step without farther purification to afford 129-3 (1.40 g, 100% yield) as brown oil.

Synthesis of 1-(3-chloro-4-phenoxyphenyl)-4-methyl-2-thiocyanatopentan-1-one (129)

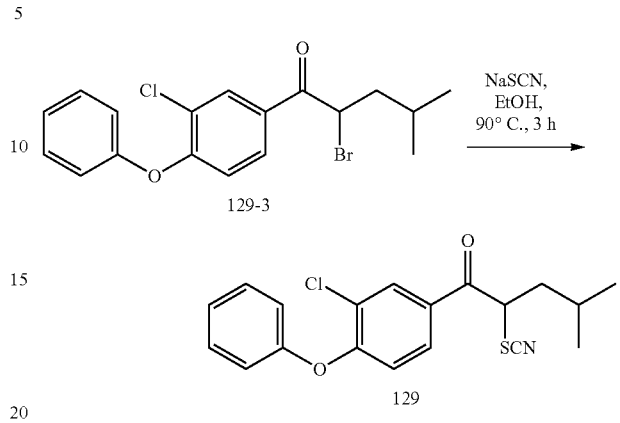

A mixture of 129-3 (1.40 g, 3.64 mmol) and NaSCN (590 mg, 7.28 mmol) in EtOH (20.0 mL) was stirred at 90° C. for 3 h. When the reaction was completed, it was concentrated and purified by silica gel column chromatography (petrol ether/ethyl acetate=10/1) to afford 129 (1.30 g, 78% yield) as a yellow solid.

Synthesis of 4-methyl-1-(3,4,5-trichlorophenyl)pentan-1-ol (137-1)

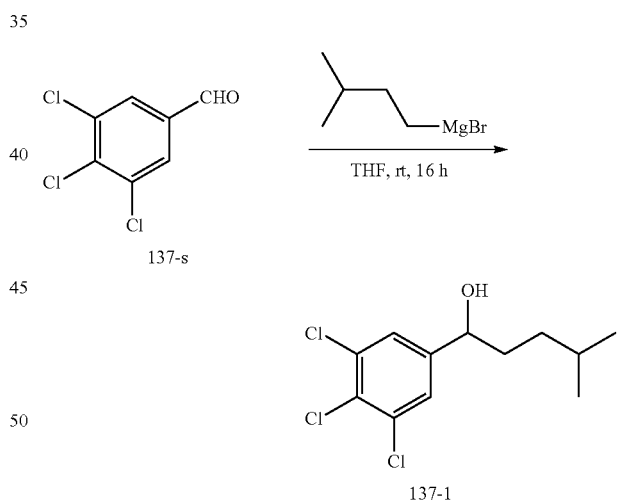

To a solution of 137-s (750 mg, 3.60 mmol) in THF (10 mL) was added isobutyl magnesium bromide (1.0 M in THF, 7.2 mL, 7.20 mmol). The reaction was stirred at room temperature for 16 h. When the reaction was completed, it was poured into aq.NH$_4$Cl (sat., 50 mL) and extracted with EtOAc (20 mL×3). The organic phase was combined, and washed with H$_2$O (20 mL) and brine (20 mL), then dried with anhydrous Na$_2$SO$_4$ and concentrated to afford 137-1 (800 mg, 100% yield) as yellow oil, which was used directly in next step without farther purification.

243

Synthesis of 4-methyl-1-(3,4,5-trichlorophenyl)pentan-1-one (137-2)

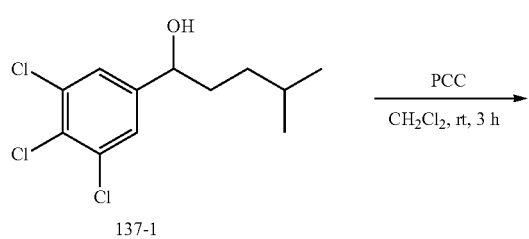

To a solution of 137-1 (800 mg, 3.60 mmol) in CH₂Cl₂ (30 mL) was added PCC (930 mg, 4.30 mmol). The reaction was stirred at room temperature for 3 h. When the reaction was completed, it was concentrated, and purified by silica gel column chromatography (petrol ether/ethyl acetate=20/1) to afford 137-2 (190 mg, 23% yield) as yellow oil.

Synthesis of 2-bromo-4-methyl-1-(3,4,5-trichlorophenyl)pentan-1-one (137-3)

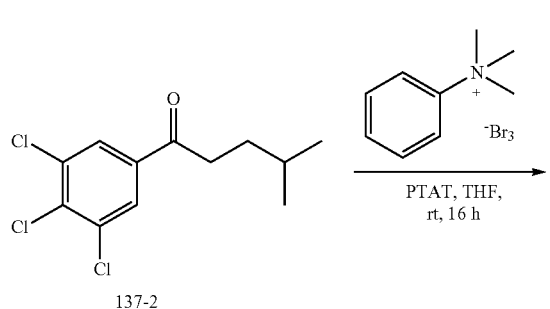

A mixture of 137-2 (190 mg, 0.68 mmol) and PTAT (310 mg, 0.82 mmol) in THF (20 mL) was stirred at room temperature for 16 h. When the reaction was completed, it was concentrated, and the residual was dissolved in H₂O (20 mL), and then extracted with EtOAc (30 mL×2). The organic layer was combined, and washed with H₂O (20 mL×2) and Brine (20 mL), then dried by anhydrous Na₂SO₄. The solution was concentrated to give the crude product, which was used directly in next step without farther purification to afford 137-3 (241 mg, 100% yield) as a yellow solid.

244

Synthesis of 4-methyl-2-thiocyanato-1-(3,4,5-trichlorophenyl)pentan-1-one (137)

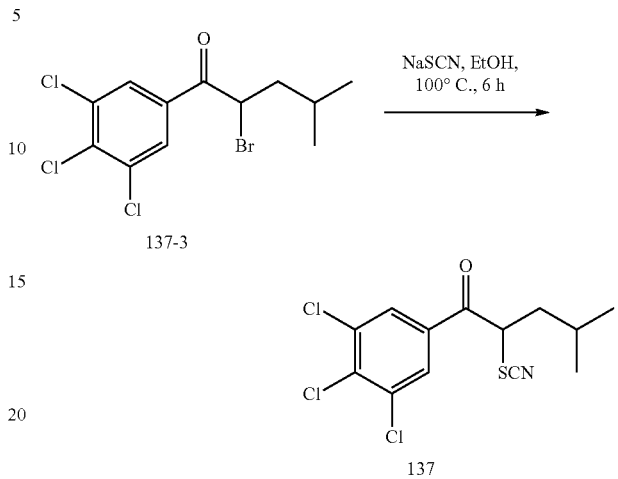

A mixture of 137-3 (241 mg, 0.68 mmol) and NaSCN (110 mg, 1.36 mmol) in EtOH (10.0 mL) was stirred at 100° C. for 6 h. When the reaction was completed, it was concentrated and purified by silica gel column chromatography (petrol ether/ethyl acetate=20/1) to afford 137 (130 mg, 28% yield) as a white solid.

Synthesis of 4-(benzyloxy)benzonitrile (144-1)

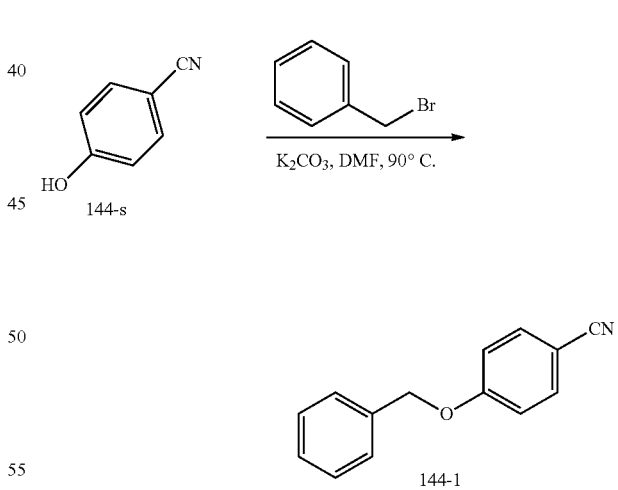

A mixture of 144-s (10.0 g, 9.50 mmol), (bromomethyl)benzene (13.0 g, 12.0 mmol) and K₂CO₃ (11.0 g, 18.0 mmol) in DMSO (50.0 mL) was stirred at 90° C. for 6 h. When the reaction was completed, it was concentrated and purified by silica gel column chromatography (petrol ether/ethyl acetate=10/1) to afford 144-1 (8.0 g, 67% yield) as a white solid.

Synthesis of 1-(4-(benzyloxy)phenyl)-4-methylpentan-1-one (144-2)

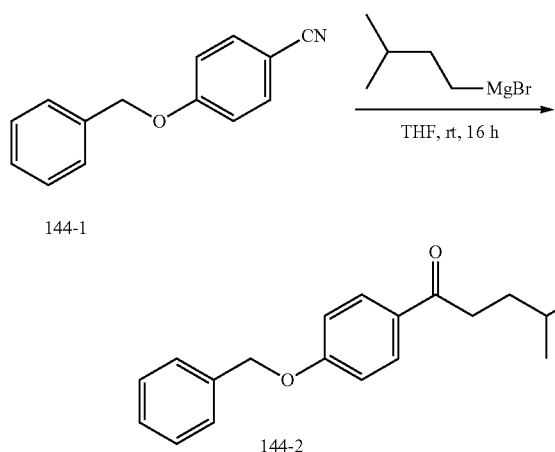

To a solution of 144-1 (5.0 g, 17.8 mmol) in THF 50 mL) was added isobutyl magnesium bromide (1.0 M in THF, 26.0 mL, 26.0 mmol). The reaction was stirred at room temperature for 16 h. When the reaction was completed, it was poured into aq.NH$_4$Cl (sat., 500 mL) and extracted with EtOAc (100 mL×3). The organic phase was combined, and washed with H$_2$O (100 mL) and brine (80 mL), then dried with anhydrous Na$_2$SO$_4$, concentrated and purified by silica gel column chromatography (petrol ether/ethyl acetate=60/1) to afford 144-2 (4.0 g, 46% yield) as colorless oil.

Synthesis of 1-(4-hydroxyphenyl)-4-methylpentan-1-one (144-3)

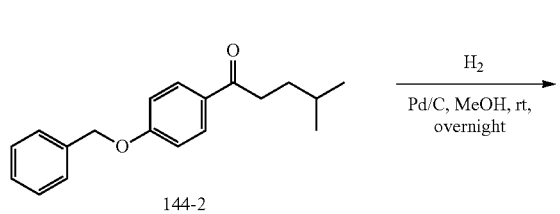

A mixture of 144-2 (2.0 g, 7.08 mmol) and Pd/C (200 mg) in MeOH (100 mL) was stirred under H$_2$ atmosphere at room temperature overnight. When the reaction was completed, it was filtered and the filtrate wad concentrated and purified by silica gel column chromatography (petrol ether/ethyl acetate=20/1) to afford 144-3 (400 mg, 29% yield) as colorless oil.

Synthesis of 2-bromo-1-(4-hydroxyphenyl)-4-methylpentan-1-one (144-4)

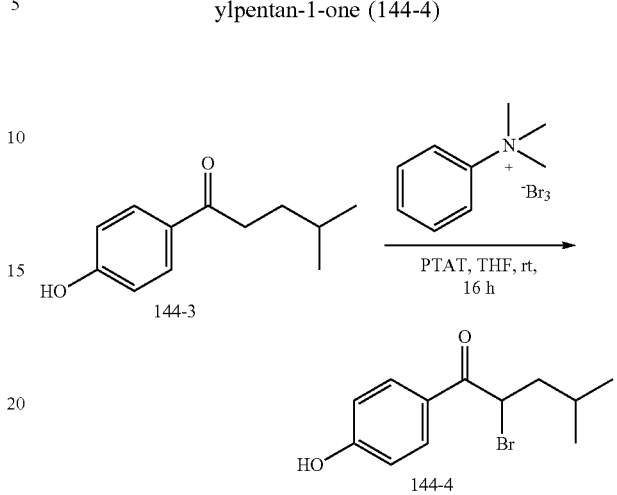

A mixture of 144-3 (400 mg, 2.08 mmol) and PTAT (1.17 g, 3.12 mmol) in THE (50 mL) was stirred at room temperature overnight. When the reaction was completed, it was concentrated, and the residual was dissolved in H$_2$O (50 mL), and then extracted with EtOAc (50 mL×2). The organic layer was combined, and washed with H$_2$O (30 mL×2) and Brine (30 mL), then dried by anhydrous Na$_2$SO$_4$. The solution was concentrated to give the crude product, which was used directly in next step without farther purification to afford 144-4 (600 mg, 1000 yield) as brown oil.

Synthesis of 1-(4-hydroxyphenyl)-4-methyl-2-thiocyanatopentan-1-one (144)

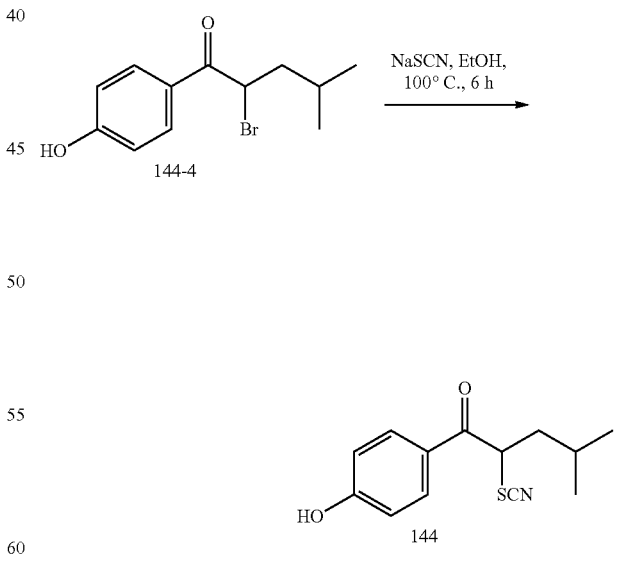

A mixture of 144-4 (600 mg, 2.21 mmol) and NaSCN (359 mg, 4.43 mmol) in EtOH (20.0 mL) was stirred at 100° C. for 6 h. When the reaction was completed, it was concentrated and purified by silica gel column chromatography (petrol ether/ethyl acetate=10/1) to afford 144 (200 mg, 36% yield) as a white solid.

TABLE 2-1

| Compounds | Chemical Structure | LCMS |
|---|---|---|
| A | 3,4-dichlorophenyl C(=O)CH(SCN)CH(CH3)2 | Method B, Purity is 81.7%, Rt = 2.283 min; MS Calcd.: 287.0; MS Found: 288.0 [M + H]+. |
| B | 3,4-dichlorophenyl C(=O)CH(SCN)-cyclopropyl | Method B, Purity is 100%, Rt = 2.053 min; MS Calcd.: 284.98; No MS Found. |
| C | 3,4-dichlorophenyl C(=O)CH(SCN)CH2CH(CH3)2 | Method B, Purity is 75.2%, Rt = 2.480 min; MS Calcd.: 301.0; MS Found: 324.1 [M + Na]+. |
| 100 | 3,4-dimethylphenyl C(=O)CH(SCN)CH(CH3)2 | Method B, Purity is 71.4%, Rt = 2.043 min; MS Calcd.: 247.1; MS Found: 248.3 [M + H]+. |
| 101 | 4-methoxyphenyl C(=O)CH(SCN)CH(CH3)2 | Method C, Purity is 64.8%, Rt = 2.153 min; MS Calcd.: 249.1; MS Found: 250.4 [M + H]+. |
| 102 | 3,4-difluorophenyl C(=O)CH(SCN)CH(CH3)2 | No MS Data. |
| 103 | 3-chloro-4-fluorophenyl C(=O)CH(SCN)CH(CH3)2 | Method B, Purity is 72.0%, Rt = 2.038 min; MS Calcd.: 271.0; MS Found: 272.0 [M + H]+. |
| 104 | 3-chlorophenyl C(=O)CH(SCN)CH2CH(CH3)2 | Method B, Purity is 94.0%, Rt = 2.070 min; MS Calcd.: 267.1; No MS Found. |
| 105 | 3-chloro-4-methoxyphenyl C(=O)CH(SCN)CH2CH(CH3)2 | Method B, Purity is 93.8%, Rt = 2.038 min; MS Calcd.: 297.1; MS Found: 298.1 [M + H]+. |

TABLE 2-1-continued

Characterization Data for Compounds

| Compounds | Chemical Structure | LCMS |
|---|---|---|
| 106 | 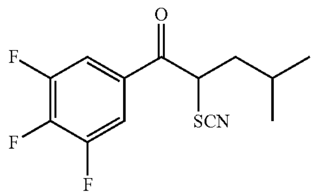 | Method B, Purity is 86.5%, Rt = 2.060 min; MS Calcd.: 287.1; MS Found: 288.2 [M + H]+. |
| 107 | 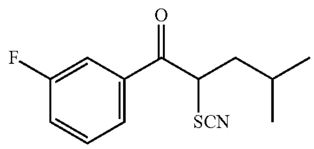 | Method B, Purity is 75.0%, Rt = 1.998 min; MS Calcd.: 251.1; MS Found: 252.3 [M + H]+. |
| 108 | 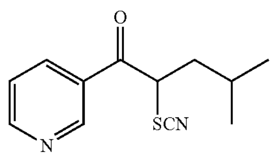 | Method B, Purity is 43.8%, Rt = 1.668 min; MS Calcd.: 234.1; MS Found: 235.1 [M + H]+. |
| 109 | 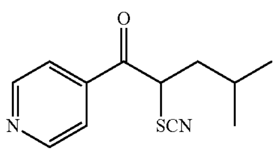 | Method B, Purity is 50.3%, Rt = 1.648 min; MS Calcd.: 234.1; MS Found: 235.1 [M + H]+. |
| 110 | 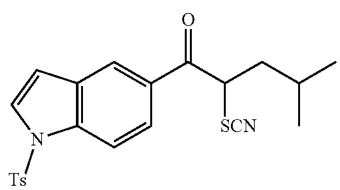 | Method B, Purity is 88.0%, Rt = 2.149 min; MS Calcd.: 426.1; MS Found: 427.1 [M + H]+. |
| 115 | 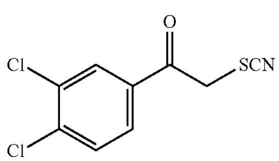 | No MS Data. |
| 119 | 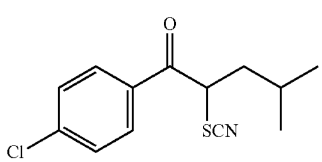 | Method B, Purity is 89.5%, Rt = 2.072 min; MS Calcd.: 267.1; No MS Found. |
| 128 | 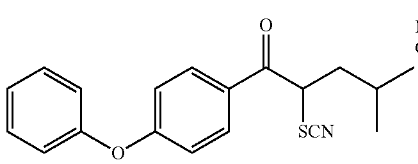 | Method B, Purity is 98.0%, Rt = 2.157 min; MS Calcd.: 325.1; MS Found: 326.2 [M + H]+. |
| 129 | 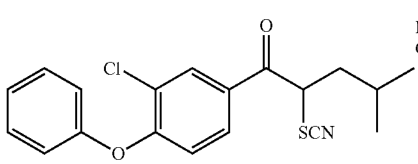 | Method B, Purity is 39.8%, Rt = 2.211 min; MS Calcd.: 359.1; MS Found: 360.1 [M + H]+. |

TABLE 2-1-continued

Characterization Data for Compounds

| Compounds | Chemical Structure | LCMS |
|---|---|---|
| 137 | 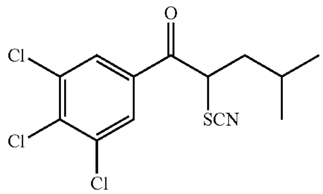 | Method B, Purity is 78.5%, Rt = 2.232 min; MS Calcd.: 335.0; No MS Found. |
| 144 | 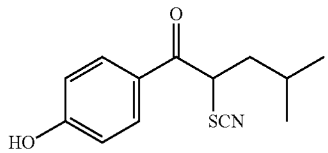 | Method B, Purity is 39.8%, Rt = 1.799 min; MS Calcd.: 249.1; MS Found: 250.1 [M + H]⁺. |

Synthesis of ethyl 3-(benzylamino)propanoate (b-1)

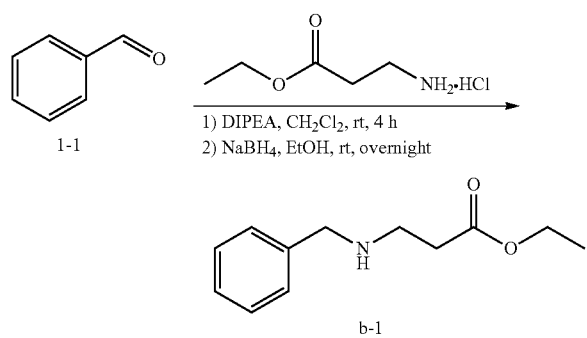

To a mixture of 1-1 (3.0 g, 28.3 mmol) and ethyl 3-aminopropanoate hydrochloride (4.50 g, 31.0 mmol) in CH$_2$Cl$_2$ (100 mL) was added DIPEA (4.50 g, 33 mmol). The reaction was stirred at room temperature for 4 h. When the reaction was completed, it was filtered, and the residue was concentrated and dissolved with EtOH (100 mL). To the reaction was added NaBH$_4$ (1.10 g, 28.3 mmol). The reaction was stirred at room temperature overnight. When the reaction was completed, it was concentrated and purified by silica gel column chromatography (CH$_2$Cl$_2$/CH$_3$OH=50/1) to afford b-1 (1.20 g, 61% yield) as colorless oil.

Synthesis of ethyl 3-(phenethylamino)propanoate (b-6)

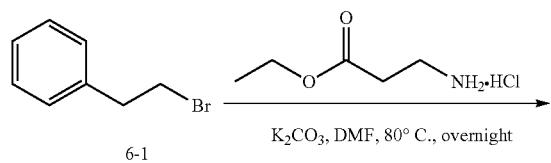

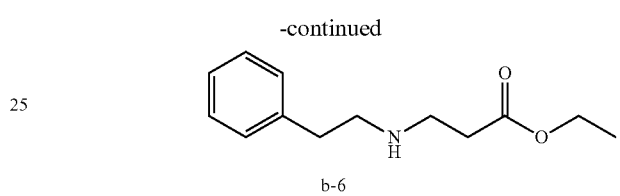

A mixture of 6-1 (1.0 g, 5.40 mmol), ethyl 3-aminopropanoate hydrochloride (1.60 g, 10.8 mmol) and K$_2$CO$_3$ (2.20 g, 16.2 mmol) in DMF (10 mL) was stirred at 80° C. overnight. When the reaction was completed, it was poured into H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was purified by silica gel column chromatography (CH$_2$Cl$_2$/CH$_3$OH=50/1) to afford b-6 (800 mg, 63% yield) as colorless oil.

Synthesis of methyl 3-(2-hydroxyethylamino)propanoate (b-19)

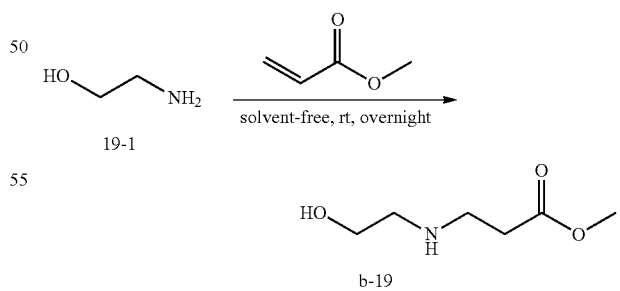

A mixture of 19-1 (1.0 g, 16.4 mmol) and methyl acrylate (1.96 g, 19.6 mmol) was stirred at room temperature overnight. When the reaction was completed, the mixture was concentrated and purified by silica gel column chromatography (petrol ether/ethyl acetate=8/1) to afford b-19 (600 mg, 25% yield) as colorless oil.

Synthesis of ethyl 3-(3-hydroxypropylamino)propanoate (b-21)

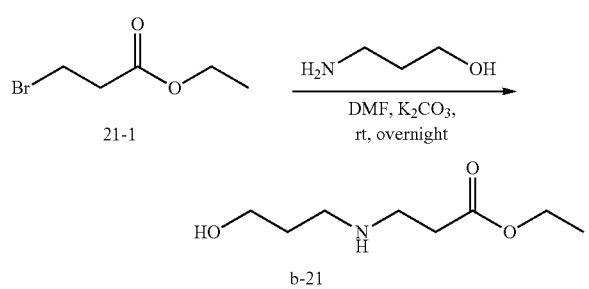

A mixture of 21-1 (1.0 g, 5.50 mmol), 3-aminopropan-1-ol (830 mg, 11.0 mmol) and K$_2$CO$_3$ (2.30 g, 16.5 mmol) in DMF (20 mL) was stirred at room temperature overnight. When the reaction was completed, it was poured into H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was purified by silica gel column chromatography (CH$_2$Cl$_2$/CH$_3$OH=5/1) to afford b-21 (320 mg, 33% yield) as colorless oil.

Synthesis of 3,5-dimethylphenethyl methanesulfonate (27-2)

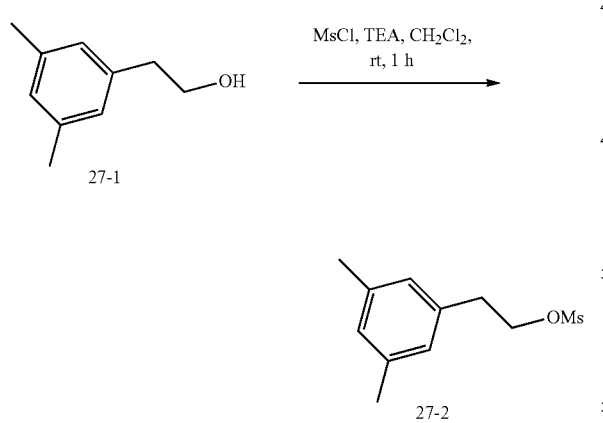

To a mixture of 27-1 (1.50 g, 10.0 mmol) and TEA (2.0 g, 20.0 mmol) in CH$_2$Cl$_2$ (150 mL) was added MsCl (1.70 g, 15.0 mmol) at 0° C. The reaction was stirred at room temperature for 1 h. When the reaction was completed, the reaction mixture was concentrated to afford 27-2 (2.20 g, 96% yield) as a white solid, which was used directly in next step without farther purification

Synthesis of ethyl 3-(3,5-dimethylphenethylamino)propanoate (b-27)

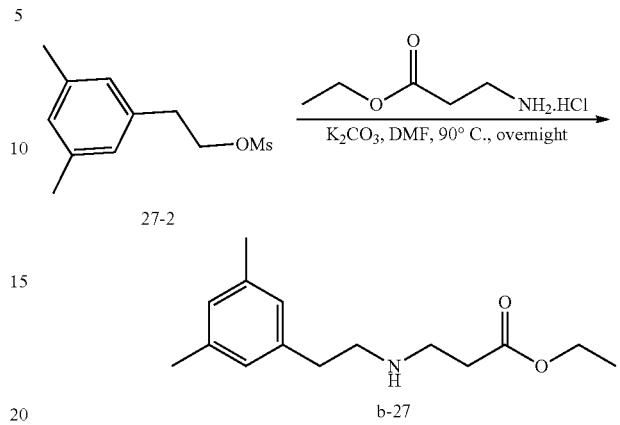

A mixture of 27-2 (2.20 g, 9.60 mmol), ethyl 3-amino-propanoate hydrochloride (2.90 g, 19.2 mmol) and K$_2$CO$_3$ (3.90 g, 28.2 mmol) in DMF (30 mL) was stirred at 90° C. overnight. When the reaction was completed, it was poured into H$_2$O (50 mL), and then extracted with EtOAc (50 mL×2). The organic layer was combined, and washed with H$_2$O (30 mL×2) and Brine (20 mL), then dried by anhydrous Na$_2$SO$_4$. The solution was concentrated to give the crude product, which was purified by silica gel column chromatography (CH$_2$Cl$_2$/CH$_3$OH=50/1) to afford b-27 (1.50 g, 63% yield) as colorless oil.

Synthesis of 1-tert-butyl 3-methyl 4-methylpiperazine-1,3-dicarboxylate (28-2)

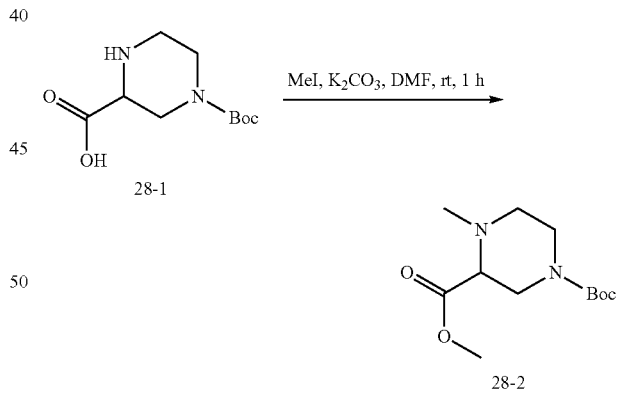

To a mixture of 28-1 (1.0 g, 4.30 mmol) and K$_2$CO$_3$ (1.80 g, 12.9 mmol) in DMF (15 mL) was added iodomethane (1.50 g, 10.8 mmol). The reaction was stirred at room temperature for 1 h. When the reaction was completed, it was poured into H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was purified by silica gel column chromatography (CH$_2$Cl$_2$/CH$_3$OH=50/1) to afford 28-2 (500 mg, 61% yield) as colorless oil.

Synthesis of methyl 1-methylpiperazine-2-carboxylate (b-28)

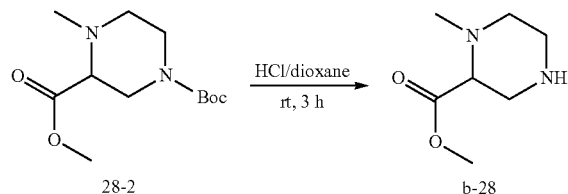 [SMILES: COC(=O)C1CN(C(=O)OC(C)(C)C)CCN1C ; COC(=O)C1CNCCN1C]

A mixture of 28-2 (500 mg, 1.94 mmol) in HCl (4.0 M in dioxane, 3.00 mL) was stirred at room temperature for 3 h. When the reaction was completed, it was concentrated to give a crude product, which was purified by silica gel column chromatography (CH$_2$Cl$_2$/CH$_3$OH=20/1) to afford b-28 (100 mg, 33% yield) as yellow oil.

Synthesis of methyl 3-((1-methylpiperidin-4-yl)methylamino)propanoate (b-30)

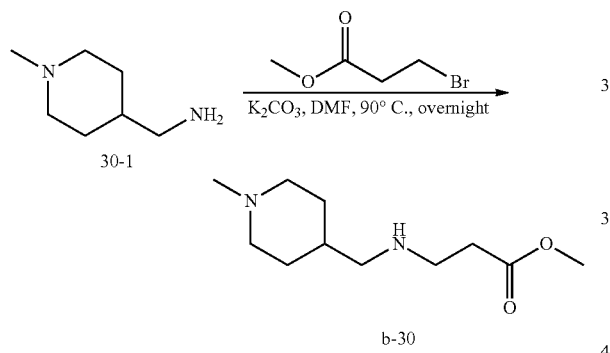

A mixture of 30-1 (1.0 g, 7.80 mmol), methyl 3-bromopropanoate (644 mg, 3.90 mmol) and K$_2$CO$_3$ (2.20 g, 15.6 mmol) in DMF (10 mL) was stirred at 90° C. overnight. When the reaction was completed, it was poured into H$_2$O (100 mL), and then extracted with EtOAc (80 mL×2). The organic layer was combined, and washed with H$_2$O (60 mL×2) and Brine (80 mL), then dried by anhydrous Na$_2$SO$_4$. The solution was concentrated to give the crude product, which was purified by silica gel column chromatography (CH$_2$Cl$_2$/CH$_3$OH=20/1) to afford b-30 (600 mg, 51% yield) as yellow oil.

Synthesis of 2-(benzylamino)ethanesulfonamide (b-33)

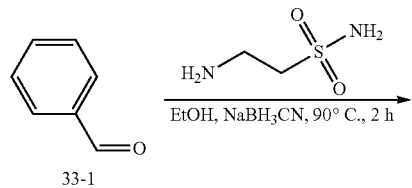

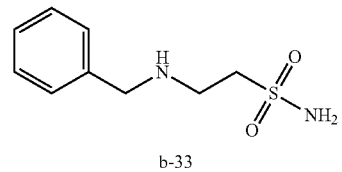

A mixture of 33-1 (2.0 g, 18.8 mmol), 2-aminoethanesulfonamide (2.5 g, 20 mmol) and NaBH$_3$CN (2.3 g, 37.6 mmol) in EtOH (25 mL) was stirred at 90° C. for 2 h. When the reaction was completed, it was concentrated to give a crude product, which was purified by silica gel column chromatography (CH$_2$Cl$_2$/CH$_3$OH=30/1) to afford b-33 (1.40 g, 34% yield) as colorless oil.

Synthesis of N-benzyl-2-(1H-tetrazol-5-yl)ethanamine (b-34)

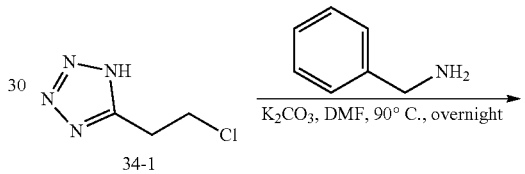

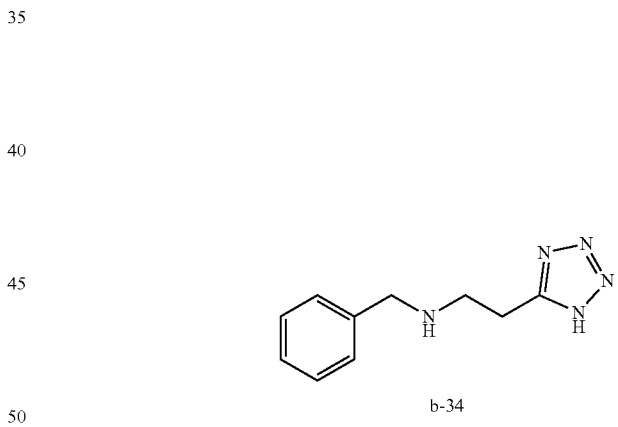

A mixture of 34-1 (150 mg, 1.10 mmol), phenylmethanamine (243 mg, 2.20 mmol) and K$_2$CO$_3$ (379 mg, 2.70 mmol) in DMF (30 mL) was stirred at 90° C. overnight. When the reaction was completed, it was poured into H$_2$O (50 mL), and then extracted with EtOAc (50 mL×2). The organic layer was combined, and washed with H$_2$O (30 mL×2) and Brine (20 mL), then dried by anhydrous Na$_2$SO$_4$. The solution was concentrated to give the crude product, which was purified by silica gel column chromatography (CH$_2$Cl$_2$/CH$_3$OH=5/1) to afford b-34 (100 mg, 4900 yield) as a white solid.

Scheme 2: Characterization Data for Compounds

| Compounds | Chemical Structure | LCMS |
|---|---|---|
| b-1 | 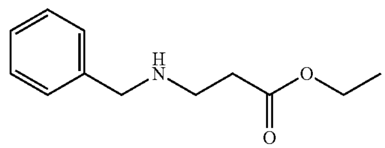 | Method B, Purity is 70.1%, Rt = 1.210 min; MS Calcd.: 249.1; MS Found: 194.3 [M + H]$^+$. |
| b-2 | 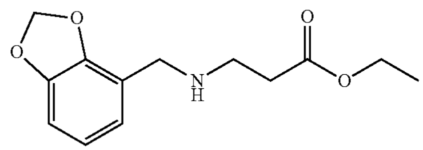 [SMILES: CCOC(=O)CCNCc1cccc2c1OCO2] | Method B, Purity is 79.7%, Rt = 1.307 min; MS Calcd.: 249.1; MS Found: 252.3 [M + H]$^+$. |
| b-3 | 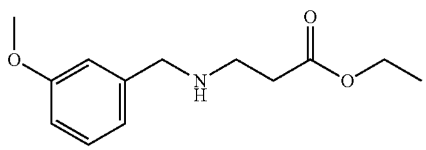 [SMILES: CCOC(=O)CCNCc1cccc(OC)c1] | Method B, Purity is 69.5%, Rt = 1.383 min; MS Calcd.: 249.1; MS Found: 238.3 [M + H]$^+$. |
| b-4 | 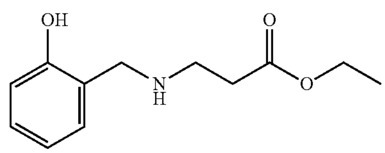 [SMILES: CCOC(=O)CCNCc1ccccc1O] | Method B, Purity is 81.2%, Rt = 1.296 min; MS Calcd.: 249.1; MS Found: 224.2 [M + H]$^+$. |
| b-5 | 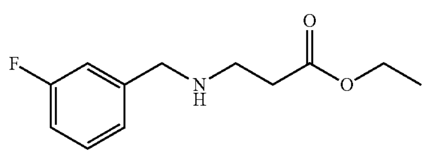 [SMILES: CCOC(=O)CCNCc1cccc(F)c1] | Method B, Purity is 50.2%, Rt = 1.357 min; MS Calcd.: 249.1; MS Found: 226.2 [M + H]$^+$. |
| b-6 | 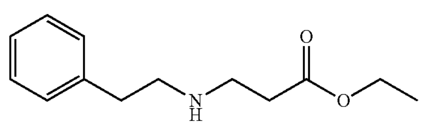 [SMILES: CCOC(=O)CCNCCc1ccccc1] | Method C, Purity is 86.5%, Rt = 1.644 min; MS Calcd.: 249.1; MS Found: 222.3 [M + H]$^+$. |
| b-7 | 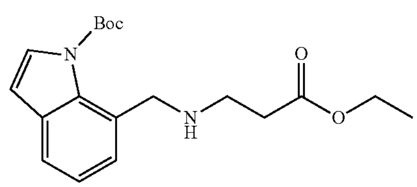 [SMILES: CCOC(=O)CCNCc1cccc2ccn(C(=O)OC(C)(C)C)c12] | Method B, Purity is 88.2%, Rt = 2.131 min; MS Calcd.: 249.1; MS Found: 347.2 [M + H]$^+$. |
| b-8 | 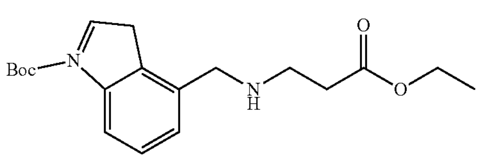 | Method B, Purity is 94.6%, Rt = 1.648 min; MS Calcd.: 249.1; MS Found: 347.2 [M + H]$^+$. |
| b-9 | 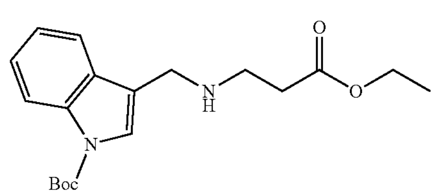 [SMILES: CCOC(=O)CCNCc1cn(C(=O)OC(C)(C)C)c2ccccc12] | Method B, Purity is 85.7%, Rt = 1.625 min; MS Calcd.: 249.1; MS Found: 347.2 [M + H]$^+$. |

-continued

| Scheme 2: Characterization Data for Compounds ||| 
| Compounds | Chemical Structure | LCMS |
| --- | --- | --- |
| b-10 | 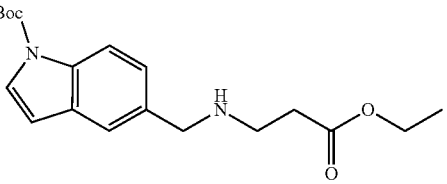 | Method C, Purity is 80.8%, Rt = 2.340 min; MS Calcd.: 249.1; MS Found: 347.3 [M + H]+. |
| b-11 | 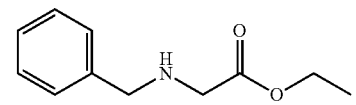 | Method C, Purity is 60.4%, Rt = 1.802 min; MS Calcd.: 249.1; MS Found: 194.2 [M + H]+. |
| b-12 | 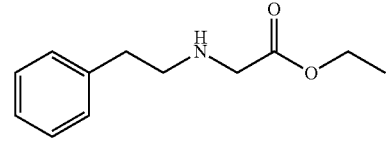 | Method C, Purity is 92.9%, Rt = 1.761 min; MS Calcd.: 249.1; MS Found: 208.2 [M + H]+. |
| b-14 | 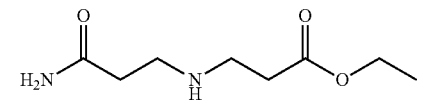 | Method C, No Purity, No Rt; MS Calcd.: 249.1; MS Found: 189.2 [M + H]+. |
| b-15 | 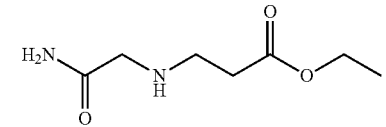 | Method C, No Purity, No Rt; MS Calcd.: 249.1; MS Found: 175.2 [M + H]+. |
| b-16 | 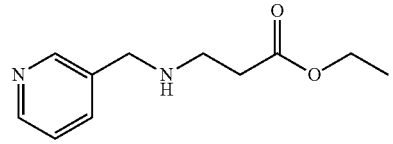 | Method C, Purity is 63.0%, Rt = 1.334 min; MS Calcd.: 249.1; MS Found: 209.4 [M + H]+. |
| b-17 | 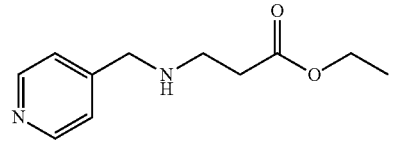 | Method C, Purity is 43.6%, Rt = 1.331 min; MS Calcd.: 249.1; MS Found: 209.4 [M + H]+. |
| b-18 | 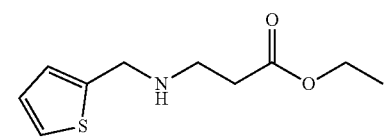 | Method C, Purity is 93.8%, Rt = 1.807 min; MS Calcd.: 249.1; MS Found: 214.3 [M + H]+. |
| b-19 | 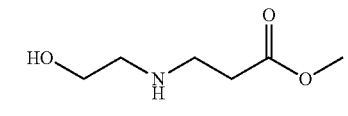 | Method C, Purity is 78.4%, Rt = 1.303 min; MS Calcd.: 249.1; MS Found: 234.2 [M + H]+. |
| b-20 | 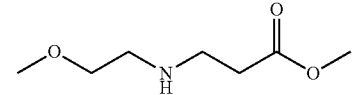 | Method C, Purity is 54.8%, Rt = 1.570 min; MS Calcd.: 249.1; MS Found: 248.4 [M + H]+. |
| b-21 | 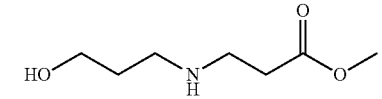 | Method B, Purity is 64.0%, Rt = 1.683 min; MS Calcd.: 249.1; MS Found: 281.3 [M + H]+. |

-continued

| Compounds | Chemical Structure | LCMS |
|---|---|---|
| b-22 | 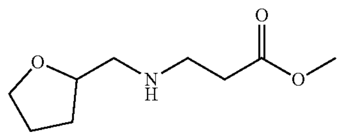 | Method B, No Purity, No Rt; MS Calcd.: 249.1; MS Found: 202.2 [M + H]+. |
| b-23 | 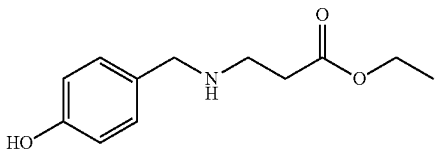 [SMILES: CCOC(=O)CCNCc1ccc(O)cc1] | Method B, Purity is 66.4%, Rt = 1.079 min; MS Calcd.: 249.1; MS Found: 224.3 [M + H]+. |
| b-24 | 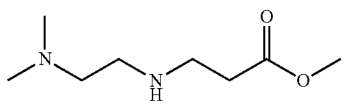 | Method B, No Purity, No Rt; MS Calcd.: 249.1; MS Found: 175.3 [M + H]+. |
| b-26 | 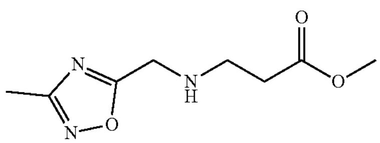 | Method C, Purity is 21.0%, Rt = 1.132 min; MS Calcd.: 249.1; MS Found: 200.3 [M + H]+. |
| b-27 | 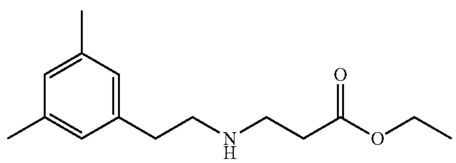 [SMILES: CCOC(=O)CCNCCc1cc(C)cc(C)c1] | Method B, Purity is 60.6%, Rt = 1.476 min; MS Calcd.: 249.1; MS Found: 250.3 [M + H]+. |
| b-28 | 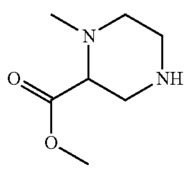 | Method C, Purity is 91.9%, Rt = 0.979 min; MS Calcd.: 249.1; MS Found: 159.2 [M + H]+. |
| b-29 | 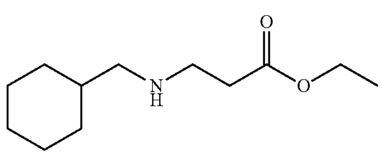 | Method B, No Purity, No Rt; MS Calcd.: 249.1; MS Found: 214.3 [M + H]+. |
| b-30 | 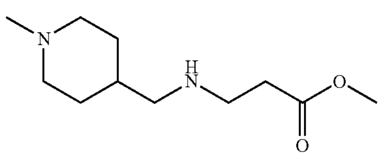 | Method B, No Purity, No Rt; MS Calcd.: 249.1; MS Found: 215.3 [M + H]+. |
| b-31 | 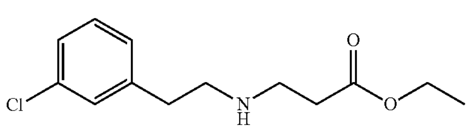 | Method B, No Purity, Rt = 1.423 min; MS Calcd.: 249.1; MS Found: 242.2 [M + H]+. |
| b-32 | 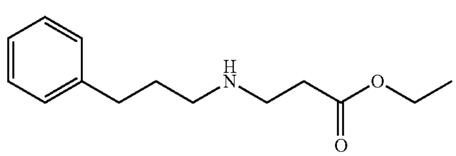 [SMILES: CCOC(=O)CCNCCCc1ccccc1] | Method A, Purity is 66.3%, Rt = 0.505 min; MS Calcd.: 249.1; MS Found: 236.2 [M + H]+. |

Scheme 2: Characterization Data for Compounds

| Compounds | Chemical Structure | LCMS |
|---|---|---|
| b-33 | (benzyl-NH-CH₂CH₂-SO₂NH₂) | Method C, Purity is 82.6%, Rt = 1.406 min; MS Calcd.: 249.1; MS Found: 215.1 [M + H]⁺. |
| b-34 | (benzyl-NH-CH₂CH₂-tetrazole) | Method C, Purity is 39.6%, Rt = 1.043 min; MS Calcd.: 249.1; MS Found: 204.2 [M + H]⁺. |
| b-35 | (cyclopropylmethyl-NH-CH₂CH₂-CO₂Et) | Method C, No Purity, No Rt; MS Calcd.: 249.1; MS Found: 172.1 [M + H]⁺. |
| b-36 | (cyclopropylethyl-NH-CH₂CH₂-CO₂Et) | Method B, No Purity, No Rt; MS Calcd.: 249.1; MS Found: 186.3 [M + H]⁺. |
| b-37 | (3-Cl-benzyl-NH-CH₂CH₂-CO₂Et) | Method B, Purity is 95.1%, Rt = 1.250 min; MS Calcd.: 249.1; MS Found: 242.2 [M + H]⁺. |
| b-38 | (2-Cl-benzyl-NH-CH₂CH₂-CO₂Et) | Method B, Purity is 100%, Rt = 1.286 min; MS Calcd.: 249.1; MS Found: 242.2 [M + H]⁺. |
| b-39 | (4-Cl-benzyl-NH-CH₂CH₂-CO₂Et) | Method B, Purity is 59.2%, Rt = 1.358 min; MS Calcd.: 249.1; MS Found: 242.2 [M + H]⁺. |
| b-40 | (N-Boc-pyrrole-2-CH₂-NH-CH₂CH₂-CO₂Et) | Method B, Purity is 96.5%, Rt = 1.489 min; MS Calcd.: 249.1; MS Found: 297.3 [M + H]⁺. |

265

Synthesis of ethyl 3-(benzyl(4-(3,4-dichlorophenyl)-5-isobutylthiazol-2-yl)amino)propanoate (061-1)

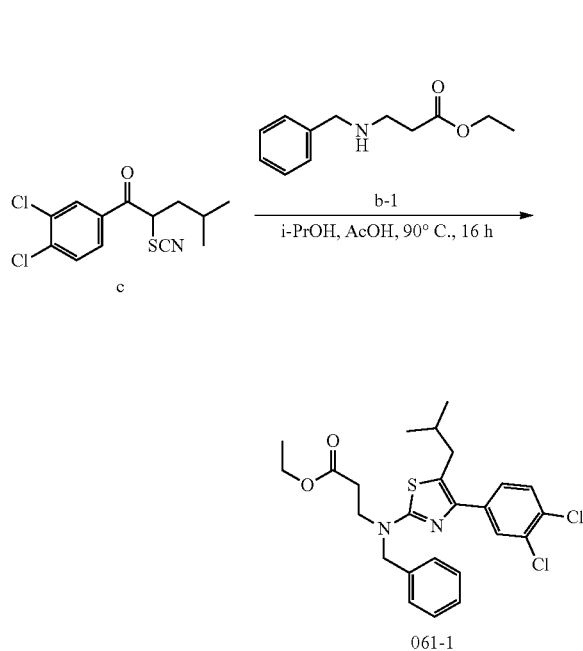

A mixture of c (150 mg, 0.50 mmol), b-1 (144 mg, 0.75 mmol) and AcOH (60 mg, 1.0 mmol) in i-PrOH (3.00 mL) was stirred at 90° C. for 16 h. When the reaction was completed, the mixture was purified by prep-TLC ($CH_2Cl_2$/$CH_3OH$=120/1) to afford 061-1 (80.0 mg, 3300 yield) as a yellow solid.

266

Synthesis of 3-(benzyl(4-(3,4-dichlorophenyl)-5-isobutylthiazol-2-yl)amino)propanoic acid (I-47)

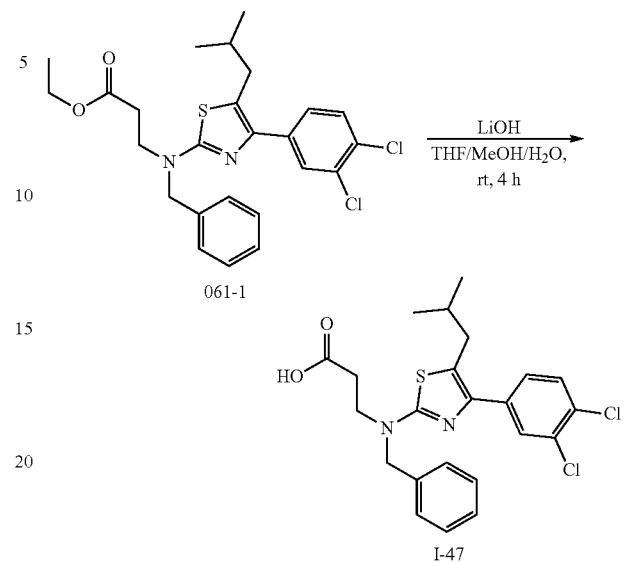

To a solution of 061-1 (80.0 mg, 0.163 mmol) in THF/MeOH/$H_2O$ (v/v/v=4/1/1, 8 mL) was added LiOH (2.0 M in $H_2O$, 0.22 mL). The reaction was stirred at room temperature for 4 h. When the reaction was completed, the resulting reaction was concentrated, then it was diluted with $H_2O$ (10 mL) and adjusted pH to 4-5 with HCl (1.0 M). The mixture was extracted with EtOAc (40 mL×2), and the combined organic phase washed with brine (30 mL), dried by anhydrous $Na_2SO_4$, and concentrated, the residue was purified by prep-HPLC to afford I-47 (30.0 mg, 40% yield) as a white solid.

Synthesis of tert-butyl 4-(((4-(3,4-dichlorophenyl)-5-isobutylthiazol-2-yl)(3-ethoxy-3-oxopropyl)amino)methyl)-1H-indole-1-carboxylate (068-1)

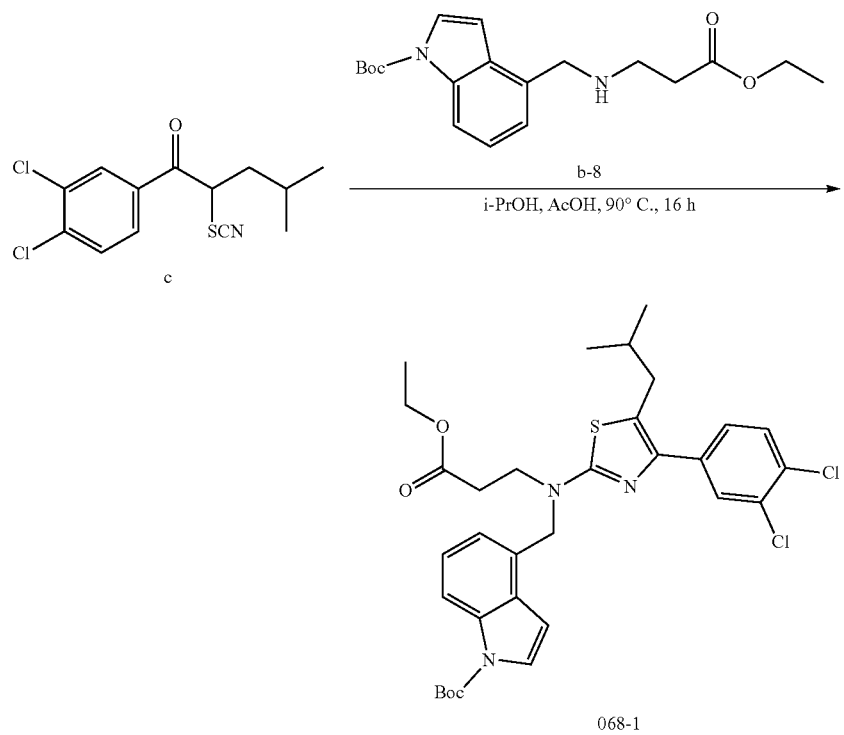

A mixture of c (100 mg, 0.33 mmol), b-8 (138 mg, 0.39 mmol) and AcOH (40 mg, 0.66 mmol) in i-PrOH (4.00 mL) was stirred at 90° C. for 16 h. When the reaction was completed, the mixture was purified by prep-TLC (CH$_2$Cl$_2$/ CH$_3$OH=120/1) to afford 068-1 (95.0 mg, 45% yield) as a yellow solid.

Synthesis of 3-(((1-(tert-butoxycarbonyl)-1H-indol-4-yl)methyl)(4-(3,4-dichlorophenyl)-5-isobutylthiazol-2-yl)amino)propanoic acid (068-2)

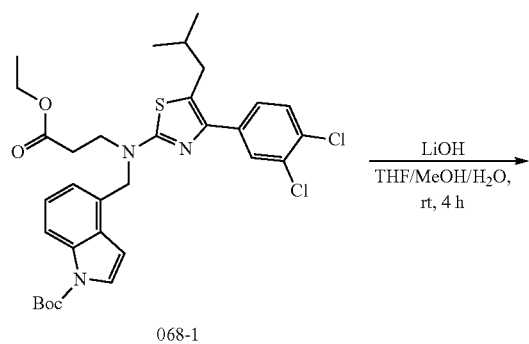

To a solution of 068-1 (95.0 mg, 0.151 mmol) in THF/ MeOH/H$_2$O (v/v/v=4/1/1, 8 mL) was added LiOH (2.0 M in H$_2$O, 0.21 mL). The reaction was stirred at room temperature for 4 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated to afford 068-2 (60.0 mg, 66% yield) as a white solid.

Synthesis of 3-(((1H-indol-4-yl)methyl)(4-(3,4-dichlorophenyl)-5-isobutylthiazol-2-yl)amino)propanoic acid (I-53)

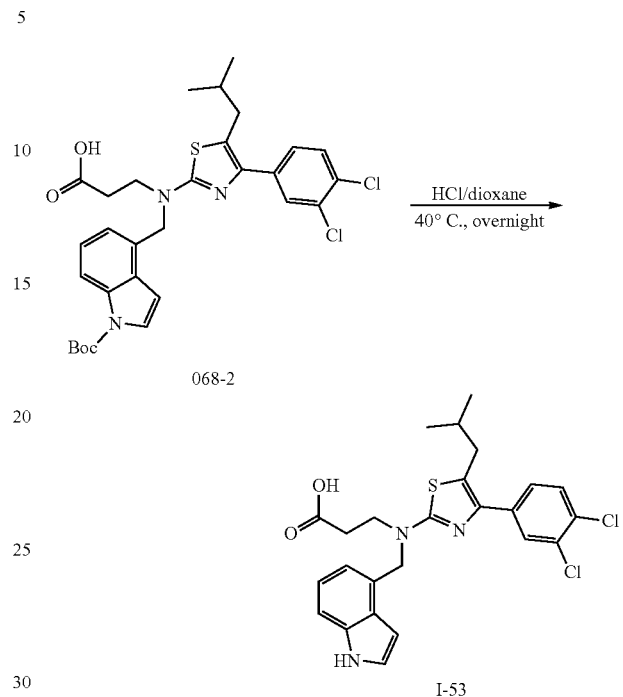

A mixture of 068-2 (60.0 mg, 0.10 mmol) in HCl (4.0 M in dioxane, 5.00 mL) was stirred at 40° C. overnight. When the reaction was completed, it was concentrated to give a crude product, which was purified by prep-HPLC to afford I-53 (13.0 mg, 26% yield) as a white solid.

Synthesis of 3,3'-(4-(3,4-dichlorophenyl)-5-isobutylthiazol-2-ylazanediyl)dipropanoic acid (I-58)

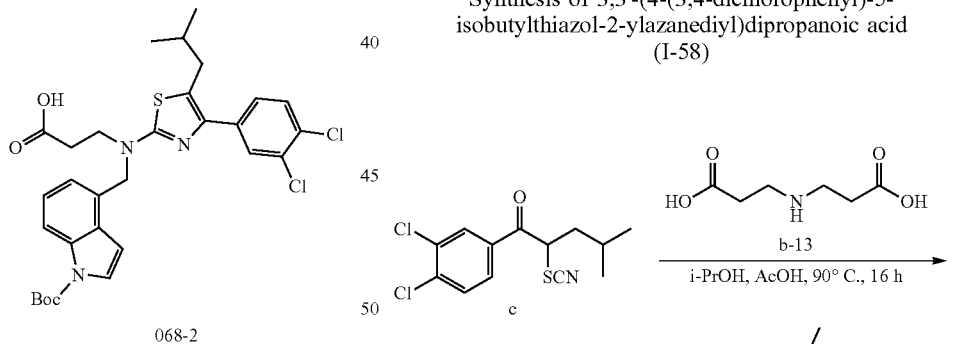

A mixture of c (120 mg, 0.399 mmol), b-13 (77.2 mg, 0.479 mmol) and AcOH (47.9 mg, 0.798 mmol) in i-PrOH (2.00 mL) was stirred at 90° C. for 16 h. When the reaction was completed, the mixture was purified by prep-HPLC to afford I-58 (10.0 mg, 5.6% yield) as a white solid.

Synthesis of ethyl 3-(benzyl(5-isobutyl-4-(1-tosyl-1H-indol-5-yl)thiazol-2-yl)amino)propanoate (110-1)

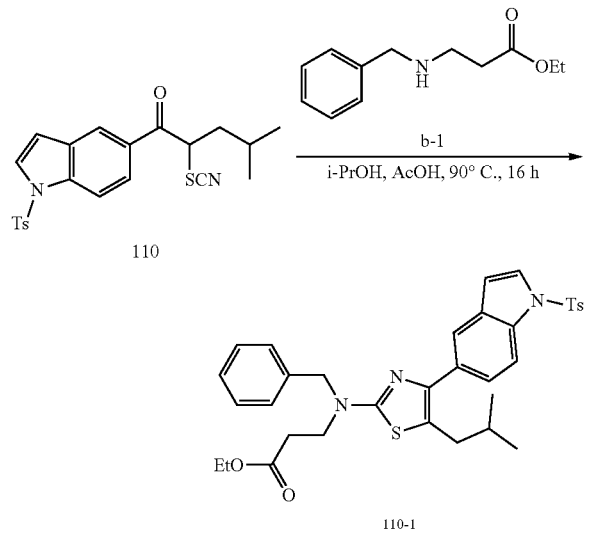

A mixture of 110 (200 mg, 0.44 mmol), b-1 (110 mg, 0.53 mmol) and AcOH (53.0 mg, 0.88 mmol) in i-PrOH (3.00 mL) was stirred at 90° C. for 16 h. When the reaction was completed, the mixture was purified by prep-TLC (CH$_2$Cl$_2$/CH$_3$OH=120/1) to afford 110-1 (110 mg, 49% yield) as a yellow solid.

Synthesis of 3-(benzyl(5-isobutyl-4-(1-tosyl-1H-indol-5-yl)thiazol-2-yl)amino)propanoic acid (110-2)

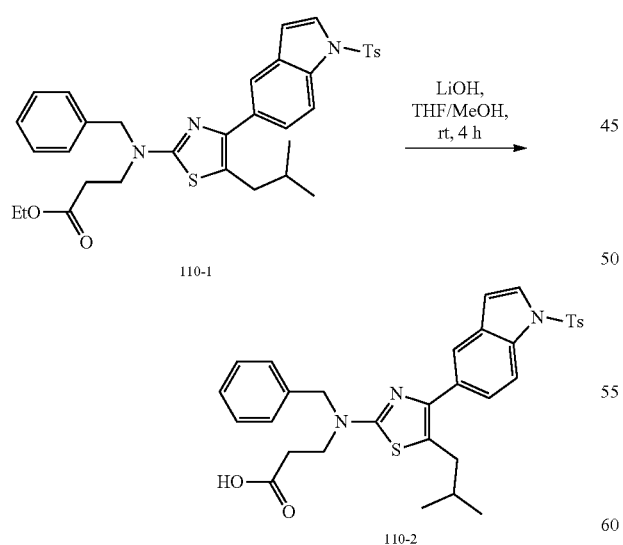

To a solution of 110-1 (110 mg, 0.179 mmol) in THF/MeOH/H$_2$O (v/v/v=4/1/1, 10 mL) was added LiOH (2.0 M in H$_2$O, 0.21 mL). The reaction was stirred at room temperature for 4 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated to afford 110-2 (90.0 mg, 86% yield) as a white solid.

Synthesis of 3-((4-(1H-indol-5-yl)-5-isobutylthiazol-2-yl)(benzyl)amino)propanoic acid (I-85)

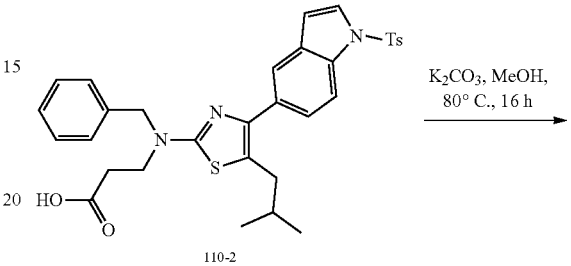

A mixture of 110-2 (90.0 mg, 0.153 mmol) and K$_2$CO$_3$ (42.3 mg 0.306 mmol) in MeOH (10 mL) was stirred at 80° C. for 16 h. When the reaction was completed, it was concentrated to give the crude product, which was purified by prep-HPLC to afford I-85 (20.0 mg, 30% yield) as a white solid.

Synthesis of ethyl 3-(benzyl(4-(3,4-dichlorophenyl)thiazol-2-yl)amino)propanoate (115-1)

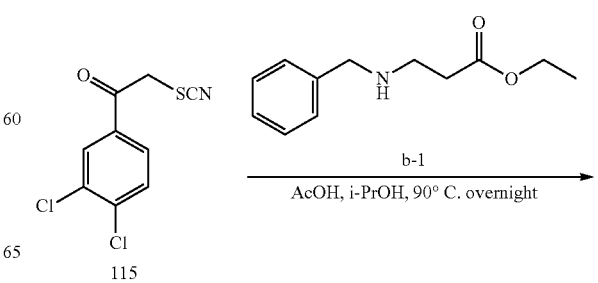

-continued

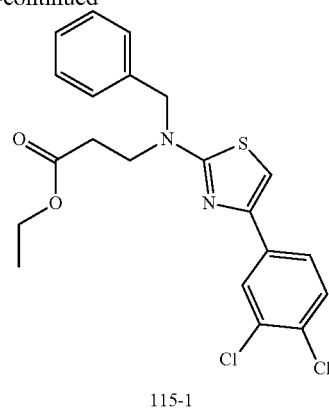

115-1

A mixture of 115 (500 mg, 2.03 mmol), b-1 (505 mg, 2.44 mmol) and AcOH (244 mg, 4.06 mmol) in i-PrOH (10.0 mL) was stirred at 90° C. overnight. When the reaction was completed, the mixture was purified by silica gel column chromatography (petrol ether/ethyl acetate=15/1) to afford 115-1 (190 mg, 22% yield) as a yellow solid.

Synthesis of ethyl 3-(benzyl(4-(3,4-dichlorophenyl)-5-formylthiazol-2-yl)amino)propanoate (115-2)

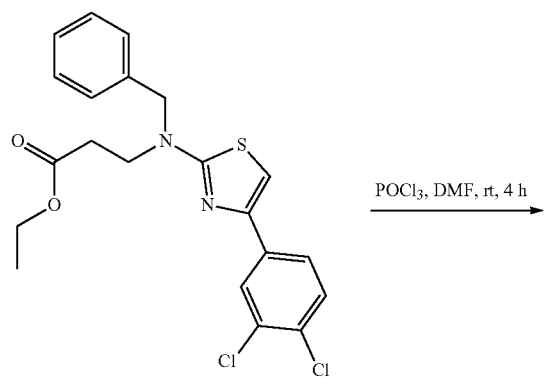

A mixture of 115-1 (200 mg, 0.46 mmol) and POCl₃ (177 mg, 1.16 mmol) in DMF (15 mL) was stirred at room temperature for 4 h. When the reaction was completed, the mixture was purified by prep-TLC (CH₂Cl₂/CH₃OH=100/1) to afford 115-2 (120 mg, 62% yield) as a yellow solid.

Synthesis of ethyl 3-(benzyl(4-(3,4-dichlorophenyl)-5-(hydroxymethyl)thiazol-2-yl)amino)propanoate (115-3)

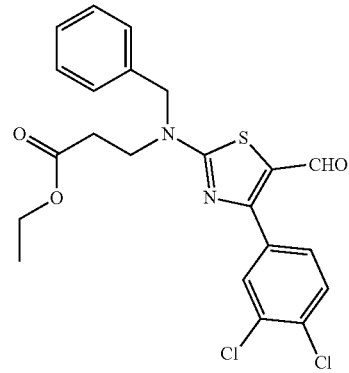

115-2

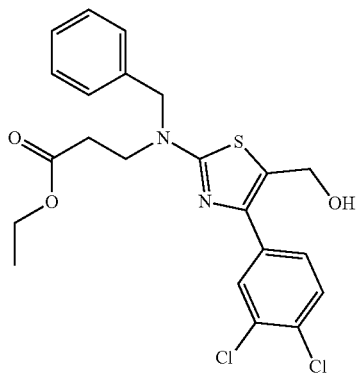

115-3

A mixture of 115-2 (1.0 g, 0.45 mmol) and NaBH₄ (380 mg, 0.88 mmol) in THF (30 mL) was stirred at room temperature for 4 h. When the reaction was completed, the mixture was purified by prep-TLC (CH₂Cl₂/CH₃OH=60/1) to afford 115-3 (700 mg, 87% yield) as yellow oil.

Synthesis of ethyl 3-(benzyl(4-(3,4-dichlorophenyl)-5-((dimethylamino)methyl)thiazol-2-yl)amino)propanoate (115-4)

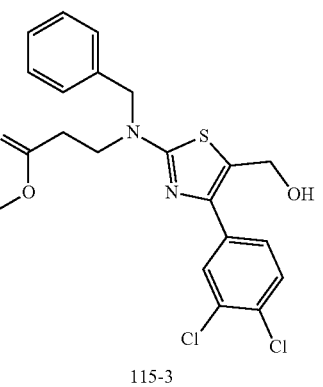

115-3

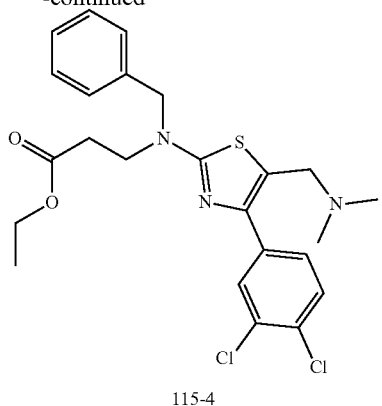

115-4

A mixture of 115-3 (200 mg, 0.43 mmol), MsCl (100 mg, 0.86 mmol) and Et₃N (109 mg, 1.08 mmol) in CH₂Cl₂ (5 mL) was stirred at room temperature for 2 h. When the reaction was completed, the mixture was concentrated and dissolved with THF (10 mL). To the reaction was added dimethylamine (1.0 M in THF, 0.65 mL, 0.65 mmol) and K₂CO₃ (119 mg, 0.86 mmol). The reaction was stirred at room temperature for 4 h. When the reaction was completed, it was purified by prep-TLC (CH₂Cl₂/CH₃OH=100/1) to afford 115-4 (130 mg, 61% yield) as a white solid.

Synthesis of 3-(benzyl(4-(3,4-dichlorophenyl)-5-((dimethylamino)methyl)thiazol-2-yl)amino)propanoic acid (I-89)

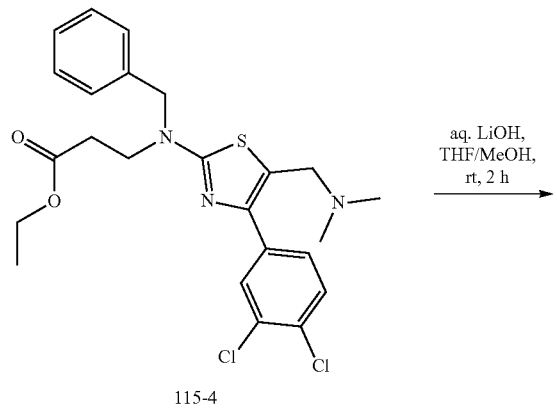

115-4 aq. LiOH,
THF/MeOH,
rt, 2 h

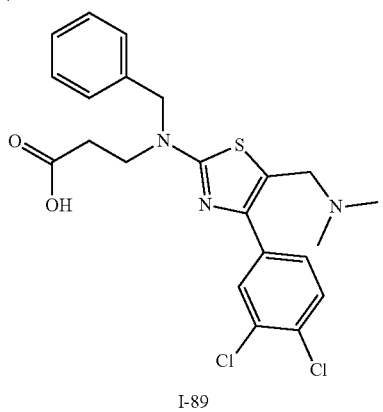

I-89

To a solution of 115-4 (130 mg, 0.263 mmol) in THF/MeOH/H₂O (v/v/v=4/1/1, 10 mL) was added LiOH (2.0 M in H₂O, 0.25 mL). The reaction was stirred at room temperature for 2 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, concentrated and purified by prep-HPLC to afford I-89 (80.0 mg, 65% yield) as a white solid.

Synthesis of 3-(benzyl(4-(3,4-dichlorophenyl)-5-isobutylthiazol-2-yl)amino)-N-(methylsulfonyl)propanamide (I-97)

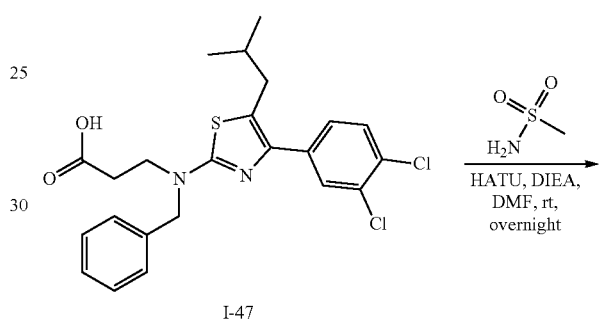

I-47

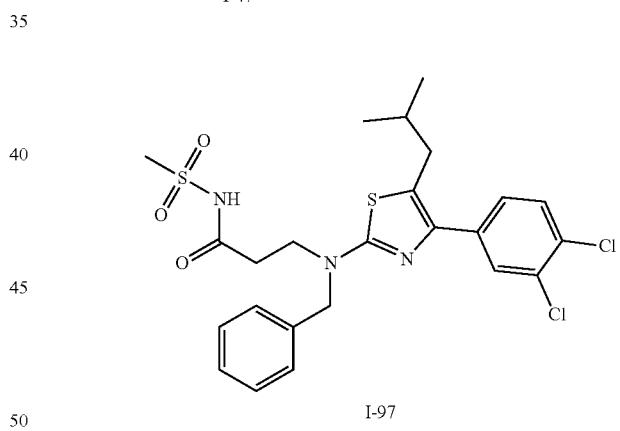

I-97

A mixture of I-47 (25.0 mg, 0.054 mmol), methanesulfonamide (6.18 mg, 0.065 mmol), HATU (41.1 mg, 0.108 mmol) and DIPEA (20.9 mg, 0.162 mmol) in DMF (2.0 mL) was stirred at room temperature overnight. When the reaction was completed, it was poured into H₂O (100 mL), and then extracted with EtOAc (100 mL×2). The organic layer was combined, and washed with H₂O (60 mL×2) and Brine (80 mL), then dried by anhydrous Na₂SO₄. The solution was concentrated to give the crude product, which was purified by prep-HPLC to afford I-97 (5.0 mg, 16% yield) as a yellow solid.

Synthesis of N-(2-(benzyl(4-(3,4-dichlorophenyl)-5-isobutylthiazol-2-yl)amino)ethylsulfonyl)acetamide (I-99)

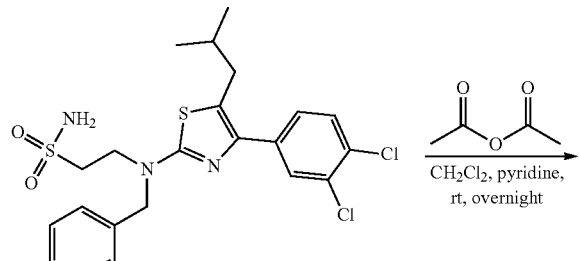

I-98

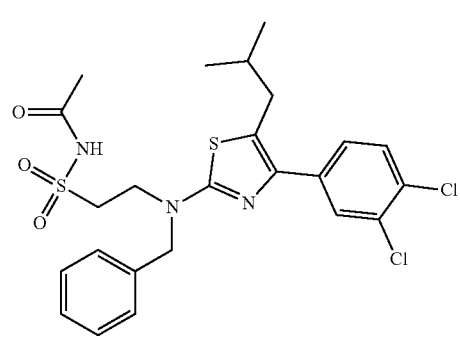

I-99

To a mixture of I-98 (60.0 mg, 0.120 mmol) and pyridine (0.2 mL) in CH$_2$Cl$_2$ (1.0 mL) was added acetic anhydride (36.0 mg, 0.360 mmol). The reaction was stirred at room temperature overnight. When the reaction was completed, the mixture was purified by prep-HPLC to afford I-99 (15.0 mg, 36% yield) as a white solid.

Synthesis of ethyl 3-(benzyl(4-(4'-fluorobiphenyl-4-yl)-5-isobutylthiazol-2-yl)amino)propanoate (127-4)

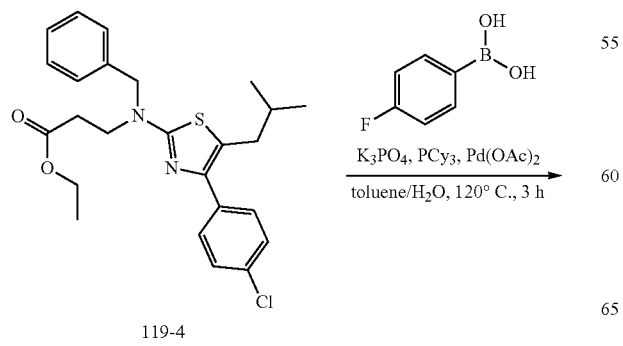

119-4

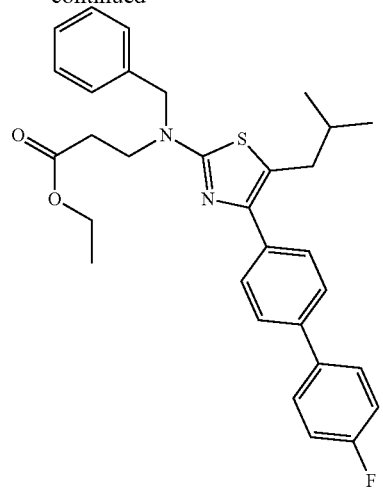

127-4

A mixture of 119-4 (350 mg, 0.76 mmol), 4-fluorophenylboronic acid (160 mg, 1.14 mmol), Pd(OAc)$_2$ (17 mg, 0.076 mmol), PCy$_3$ (43 mg, 0.152 mmol) and K$_3$PO$_4$ (484 mg, 2.28 mmol) in toluene/H$_2$O (v/v=10/1, 22.0 mL) was stirred under N$_2$ atmosphere at 120° C. for 3 h. When the reaction was completed, the mixture was purified by silica gel column chromatography (petrol ether/ethyl acetate=10/1) to afford 127-4 (160 mg, 53% yield) as a yellow solid.

Synthesis of 3-(benzyl(4-(4'-fluorobiphenyl-4-yl)-5-isobutylthiazol-2-yl)amino)propanoic acid (I-101)

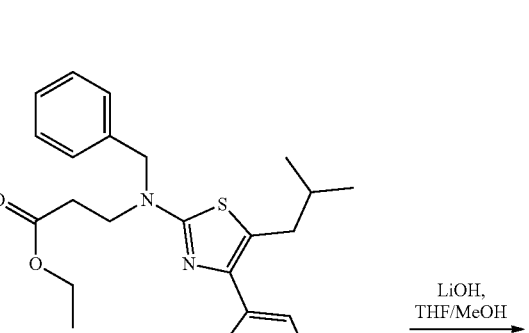

127-4

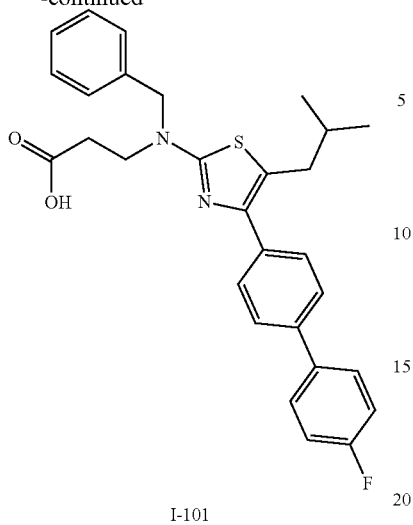

I-101

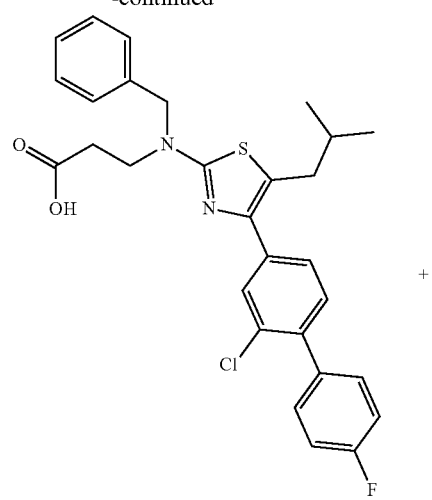

I-104

+

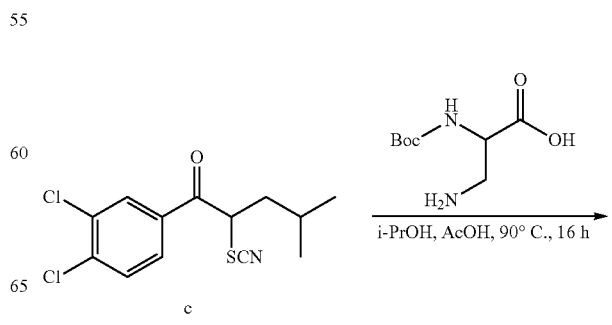

To a solution of 127-4 (160 mg, 0.310 mmol) in THF/MeOH/H$_2$O (v/v/v=4/1/1, 10 mL) was added LiOH (2.0 M in H$_2$O, 0.30 mL). The reaction was stirred at room temperature for 4 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, concentrated and purified by prep-HPLC to afford I-101 (34.0 mg, 28% yield) as a white solid.

Synthesis of the mixture of 3-(benzyl(4-(2-chloro-4'-fluorobiphenyl-4-yl)-5-isobutylthiazol-2-yl)amino)propanoic acid and 3-(benzyl(4-(6-chloro-4'-fluorobiphenyl-3-yl)-5-isobutylthiazol-2-yl)amino)propanoic acid (I-104)

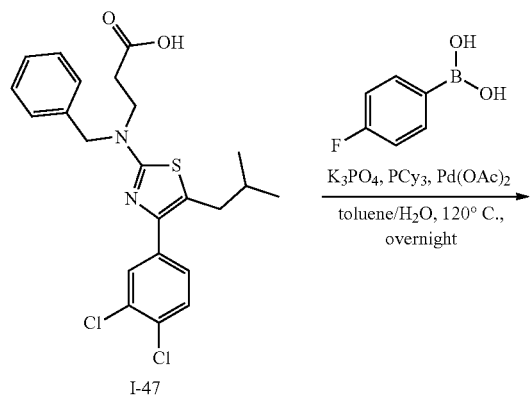

A mixture of I-47 (200 mg, 0.432 mmol), 4-fluorophenylboronic acid (121 mg, 0.866 mmol), Pd(OAc)$_2$ (9.7 mg, 0.0433 mmol), PCy$_3$ (25.2 mg, 0.0866 mmol) and K$_3$PO$_4$ (184 mg, 0.866 mmol) in toluene/H$_2$O (v/v=10/1, 2.20 mL) was stirred under N$_2$ atmosphere at 120° C. overnight. When the reaction was completed, the mixture was purified by prep-HPLC to afford I-104 (60.0 mg, 27% yield) as a white solid.

Synthesis of 2-(tert-butoxycarbonylamino)-3-(4-(3,4-dichlorophenyl)-5-isobutylthiazol-2-ylamino)propanoic acid (142-1)

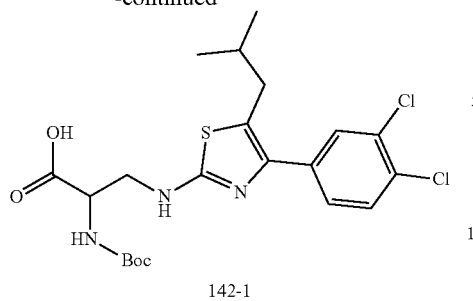

142-1

A mixture of c (600 mg, 1.99 mmol), 3-amino-2-(tert-butoxycarbonylamino)propanoic acid (448 mg, 2.19 mmol) and AcOH (239 mg, 3.99 mmol) in i-PrOH (5.0 mL) was stirred at 90° C. for 16 h. When the reaction was completed, it was concentrated to afford 142-1 (800 mg, 82% yield) as yellow oil, which was used directly in next step without farther purification.

Synthesis of 2-amino-3-(4-(3,4-dichlorophenyl)-5-isobutylthiazol-2-ylamino)propanoic acid (I-115)

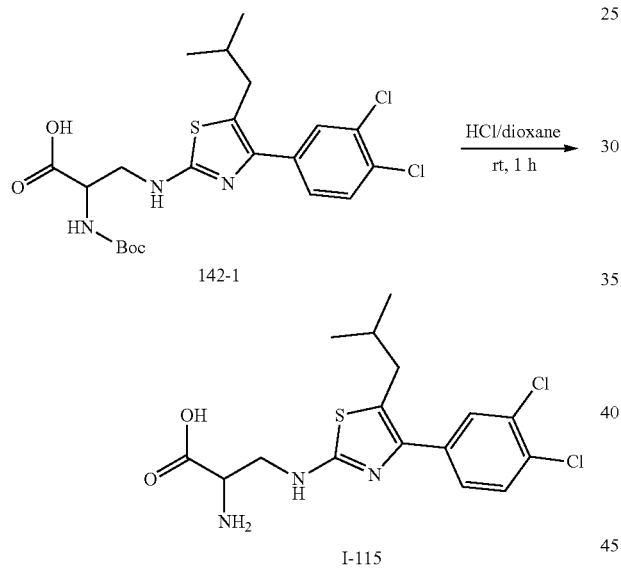

I-115

A mixture of 142-1 (800 mg, 1.64 mmol) in HCl (4.0 M in dioxane, 10.0 mL) was stirred at room temperature for 1 h. When the reaction was completed, it was concentrated to give a crude product, which was purified by prep-HPLC to afford I-115 (600 mg, 94% yield) as a white solid.

Synthesis of 2-(benzylamino)-3-(4-(3,4-dichlorophenyl)-5-isobutylthiazol-2-ylamino)propanoic acid (I-113)

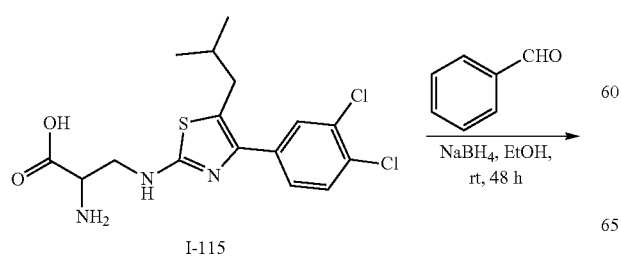

I-115

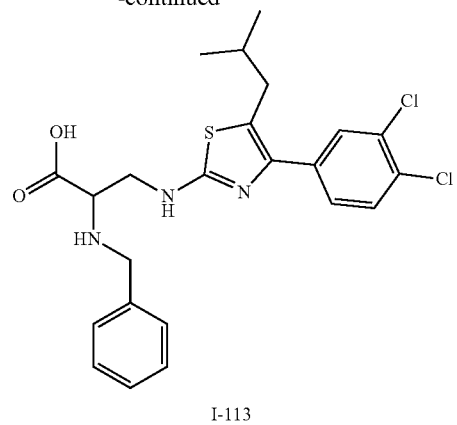

I-113

A mixture of I-115 (100 mg, 0.26 mmol), benzaldehyde (30.2 mg, 0.28 mmol) and NaBH$_4$ (9.82 mg, 0.26 mmol) in EtOH (5.0 mL) was stirred at room temperature for 48 h. When the reaction was completed, it was concentrated to give a crude product, which was purified by prep-HPLC to afford I-113 (30 mg, 24% yield) as a white solid.

Synthesis of 2-(benzyl(methyl)amino)-3-(4-(3,4-dichlorophenyl)-5-isobutylthiazol-2-ylamino)propanoic acid (I-114)

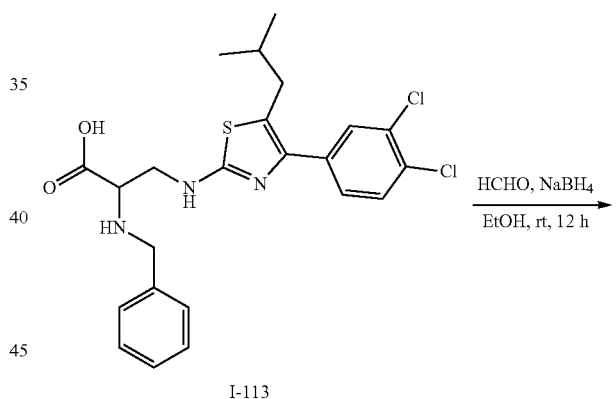

I-113

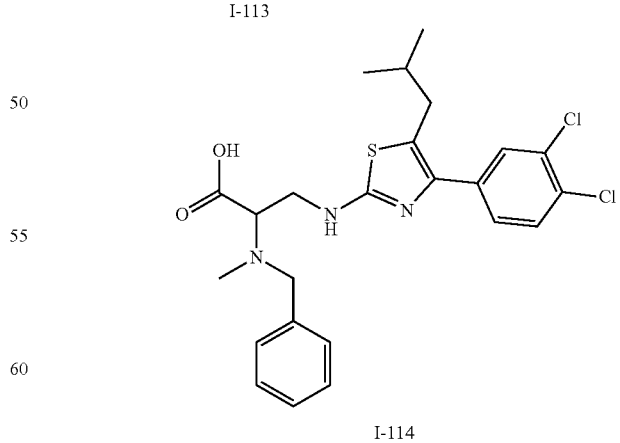

I-114

A mixture of I-113 (180 mg, 0.377 mmol), formaldehyde (37% in H$_2$O, 34 mg, 0.414 mmol) and NaBH$_4$ (14.3 mg, 0.377 mmol) in EtOH (5.0 mL) was stirred at room temperature for 12 h. When the reaction was completed, it was concentrated to give a crude product, which was purified by prep-HPLC to afford I-114 (20 mg, 11% yield) as a white solid.

Synthesis of 3-(4-(3,4-dichlorophenyl)-5-isobutylthiazol-2-ylamino)-2-(dimethylamino)propanoic acid (I-116)

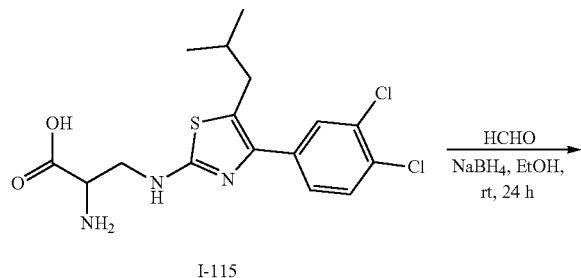

I-115

I-116

A mixture of I-115 (200 mg, 0.517 mmol), formaldehyde (37% in $H_2O$, 105 mg, 1.29 mmol) and $NaBH_4$ (39.3 mg, 1.03 mmol) in EtOH (15.0 mL) was stirred at room temperature for 24 h. When the reaction was completed, it was concentrated to give a crude product, which was purified by prep-HPLC to afford I-116 (110 mg, 51% yield) as a white solid.

TABLE 2-3

Characterization Data for Compounds

| I-# | Chemical Structure | LCMS | $^1$H NMR (400 MHz, DMSO-$d_6$) |
|---|---|---|---|
| 47 | 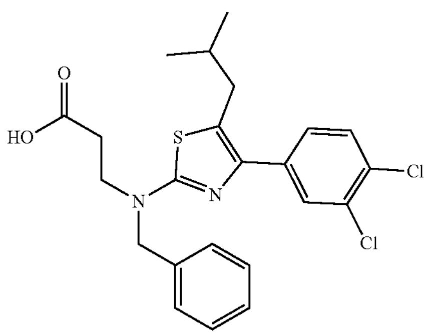 [SMILES: CC(C)Cc1sc(N(CCC(=O)O)Cc2ccccc2)nc1-c1ccc(Cl)c(Cl)c1] | Method C, Purity is 98.9%, Rt = 2.132 min; MS Calcd.: 462.1; MS Found: 463.2 [M + H]$^+$. | δ: 0.86 (6H, d, J = 6.4 Hz), 1.70-1.72 (1H, m), 2.58-2.62 (4 H, m), 3.64 (2 H, t, J = 7.2 Hz), 4.65 (2H, s), 7.26-7.36 (5 H, m), 7.50 (1 H, dd, J = 8.4, 2.0 Hz), 7.65 (1H, d, J = 8.4 Hz), 7.71 (1H, d, J = 2.0 Hz), 12.32 (1 H, brs). |
| 48 | 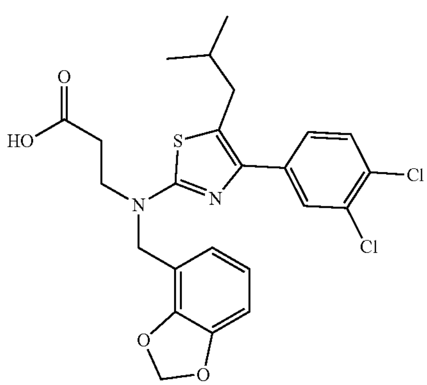 [SMILES: CC(C)Cc1sc(N(CCC(=O)O)Cc2cccc3c2OCO3)nc1-c1ccc(Cl)c(Cl)c1] | Method C, Purity is 100%, Rt = 2.030 min; MS Calcd.: 506.1; MS Found: 507.0 [M + H]$^+$. | δ: 0.88 (6H, d, J = 6.4 Hz), 1.73-1.77 (1H, m), 2.62 (4H, d, J = 7.2 Hz), 4.61 (2H, s), 6.04 (2H, s), 6.78-6.87 (3H, m), 7.52(1H, dd, J = 8.4, 2.0 Hz), 7.67 (1H, d, J = 8.4 Hz), 7.73 (1H, d, J = 2.0 Hz), 12.41-12.48 (1H, brs). |

TABLE 2-3-continued

Characterization Data for Compounds

| I-# | Chemical Structure | LCMS | ¹H NMR (400 MHz, DMSO-d₆) |
|---|---|---|---|
| 49 | 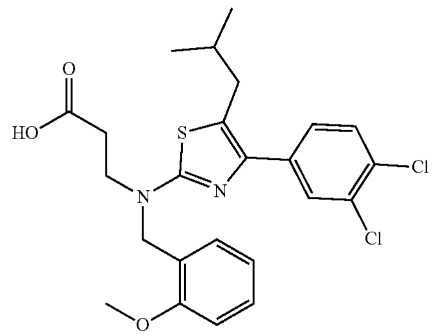 [SMILES: COc1ccccc1CN(CCC(=O)O)c1nc(-c2ccc(Cl)c(Cl)c2)c(CC(C)C)s1] | Method C, Purity is 100%, Rt = 2.074 min; MS Calcd.: 492.1; MS Found: 493.0 [M + H]⁺. | δ: 0.87 (6H, d, J = 6.8 Hz), 1.73-1.77 (1H, m), 2.60-2.67 (4H, m), 3.68 (2H, t, J = 6.8 Hz), 3.82 (3H, s), 4.58 (2H, s), 6.92 ( H, t, J = 7.2 Hz), 6.82 (1H, d, J = 8.0 Hz), 7.12 (1H, d, J = 7.2 Hz), 7.25-7.30 (1H, m), 7.50-7.53 (1H, m), 7.66 (1H, d, J = 8.4 Hz), 7.73 (1H, s), 12.17-12.48 (1H, brs). |
| 50 | 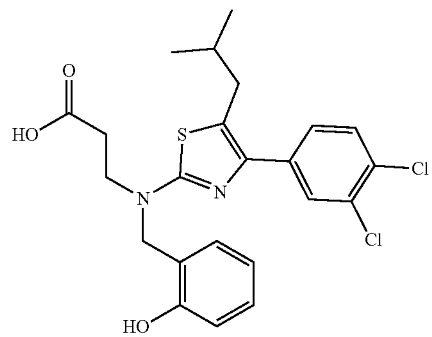 [SMILES: CC(C)Cc1sc(N(CCC(=O)O)Cc2ccccc2O)nc1-c1ccc(Cl)c(Cl)c1] | Method C, Purity is 98.3%, Rt = 1.995 min; MS Calcd.: 478.1; MS Found: 479.0 [M + H]⁺. | δ: 0.87 (6H, d, J = 6.8 Hz), 1.73-1.77 (1H, m), 2.61-2.67 (4H, m), 3.65 (2H, t, J = 7.6 Hz), 4.58 (2H, s), 6.76 (1H, t, J = 6.8 Hz), 6.82 (1H, d, J = 8.0 Hz), 7.08-7.13 (2H, m), 7.52 (1H, dd, J = 8.4, 2.0 Hz), 7.68 (1H, d, J = 8.0 Hz), 7.74 (1H, s). |
| 51 | 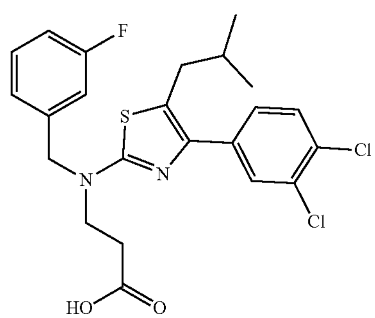 [SMILES: CC(C)Cc1sc(N(CCC(=O)O)Cc2cccc(F)c2)nc1-c1ccc(Cl)c(Cl)c1] | Method C, Purity is 100%, Rt = 2.060 min; MS Calcd.: 480.1; MS Found: 481.0 [M + H]⁺. | δ: 0.88 (6H, d, J = 6.4 Hz), 1.73-1.77 (1H, m), 2.57-2.63 (4H, m), 3.65 (2H, t, J = 7.2 Hz), 4.70 (2H, s), 7.08-7.15 (3H, m), 7.39 (1H, t, J = 7.6 Hz), 7.51 (1H, dd, J = 8.4, 2.0 Hz), 7.66 (1H, t, J = 8.4 Hz), 7.72 (2H, d, J = 2.0 Hz). |
| 52 | 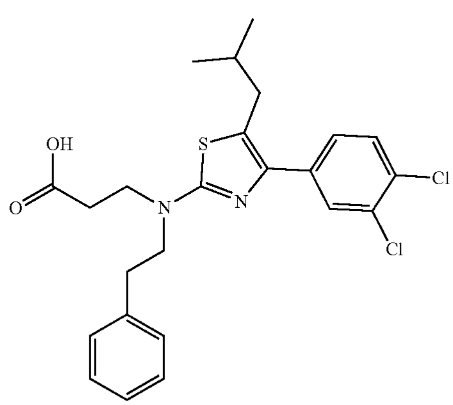 [SMILES: CC(C)Cc1sc(N(CCC(=O)O)CCc2ccccc2)nc1-c1ccc(Cl)c(Cl)c1] | Method C, Purity is 95.1%, Rt = 2.139 min; MS Calcd.: 476.1; MS Found: 477.1 [M + H]⁺. | δ: 0.87 (6H, d, J = 8.8 Hz), 1.74-1.76 (1H, m), 2.56-2.62 (4H, m), 2.90 (2H, t, J = 7.2 Hz), 3.55-3.60 (4H, m), 7.19-7.31 (5H, m), 7.51 (1H, dd, J = 8.4, 2.0 Hz), 7.66 (1H, d, J = 8.4 Hz), 7.73 (1H, d, J = 2.0 Hz), 12.33 (1H, brs). |

TABLE 2-3-continued

Characterization Data for Compounds

| I-# | Chemical Structure | LCMS | $^1$H NMR (400 MHz, DMSO-d$_6$) |
|---|---|---|---|
| 53 | 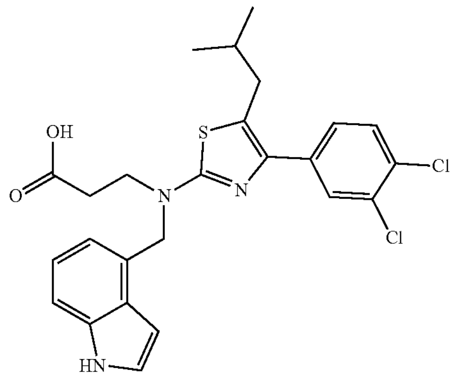 [SMILES: CC(C)Cc1sc(N(CCC(=O)O)Cc2cccc3[nH]ccc23)nc1-c1ccc(Cl)c(Cl)c1] | Method B, Purity is 96.4%, Rt = 2.090 min; MS Calcd.: 502.1; MS Found: 502.3 [M + H]$^+$. | δ: 0.86 (6H, d, J = 6.8 Hz), 1.72-1.76 (1H, m), 2.51-2.53 (2H, m), 2.61 (2H, d, J = 6.8 Hz), 3.57 (2H, t, J = 12 Hz), 4.89 (2H, s), 6.46 (1H, s), 6.88 (1H, t, J = 6.8 Hz), 7.03 (1H, t, J = 7.6 Hz), 7.30-7.33 (2H, m), 7.53 (1H, dd, J = 8.4, 2.0 Hz), 7.65 (1H, d, J = 8.4 Hz), 7.75 (1H, s), 11.18 (1H, brs). |
| 54 | 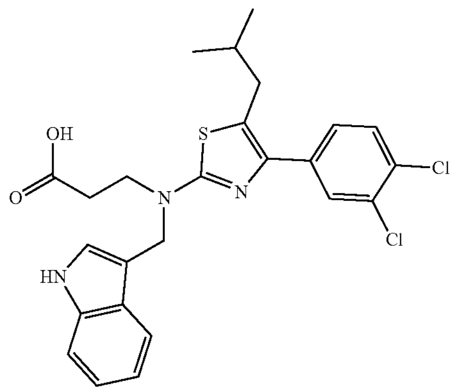 [SMILES: CC(C)Cc1sc(N(CCC(=O)O)Cc2c[nH]c3ccccc23)nc1-c1ccc(Cl)c(Cl)c1] | Method C, Purity is 94.8%, Rt = 2.126 min; MS Calcd.: 501.1; MS Found: 502.2 [M + H]$^+$. | δ: 0.88 (6H, d, J = 6.8 Hz), 1.73-1.80 (1H, m), 2.48-2.54 (2H, m), 2.63 (2H, d, J = 7.2 Hz), 3.55 (2H, t, J = 7.2 Hz), 4.74 (1H, s), 6.95 (1H, t, J = 6.8 Hz), 7.09 (1H, t, J = 1.2 Hz), 7.37 (1H, dd, J = 8.0, 2.4 Hz), 7.53-7.56 (2H, m), 7.66 (1H, d, J = 8.4 Hz), 7.77 (1H, s), 11.04 (1H, brs). |
| 55 | 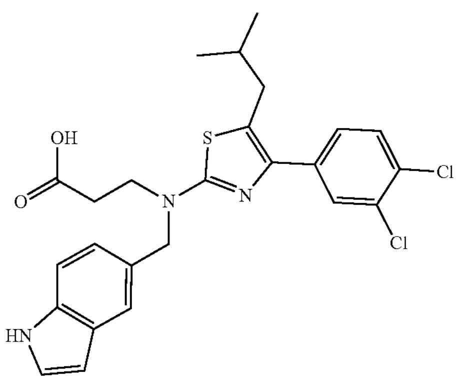 [SMILES: CC(C)Cc1sc(N(CCC(=O)O)Cc2ccc3[nH]ccc3c2)nc1-c1ccc(Cl)c(Cl)c1] | Method C, Purity is 98.4%, Rt = 2.086 min; MS Calcd.: 501.1; MS Found: 502.2 [M + H]$^+$. | δ: 0.86 (6H, d, J = 6.4 Hz), 1.69-1.71 (1H, m), 2.56-2.62 (4H, m), 3.62 (2H, t, J = 7.2 Hz), 4.67 (2H, s), 6.38 (1H, t, J = 6.0 Hz), 7.03 (1H, dd, J = 8.4, 1.2 Hz), 7.30-7.36 (2H, m), 7.47 (1H, s), 7.54 (1H, dd, J = 8.4, 2.0 Hz), 7.65 (1H, d, J = 8.4 Hz), 7.74 (1H, d, J = 2.0 Hz), 11.08 (1H, brs), 12.30 (1H, brs). |
| 56 | 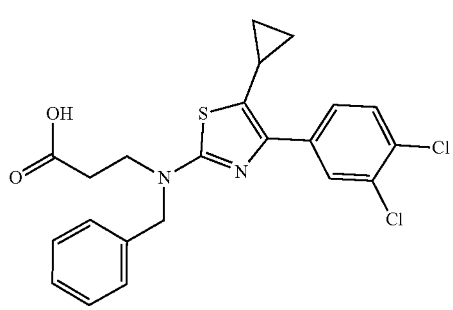 [SMILES: O=C(O)CCN(Cc1ccccc1)c1nc(-c2ccc(Cl)c(Cl)c2)c(C2CC2)s1] | Method C, Purity is 99.4%, Rt = 2.025 min; MS Calcd.: 446.1; MS Found: 447.2 [M + H]$^+$. | δ: 2.54 (2H, t, J = 7.2 Hz), 3.62 (2H, t, J = 7.2 Hz), 4.67 (2H, s), 5.08-5.15 (2H, m), 5.91-6.01 (1H, m), 7.24-7.29 (3H, m), 7.32-7.36 (2H, m), 7.53 (1H, dd, J = 8.4, 2.0 Hz), 7.65 (1H, d, J = 8.4 Hz), 7.74 (1H, d, J = 2.0 Hz). |

TABLE 2-3-continued

Characterization Data for Compounds

| I-# | Chemical Structure | LCMS | ¹H NMR (400 MHz, DMSO-d$_6$) |
|---|---|---|---|
| 57 | 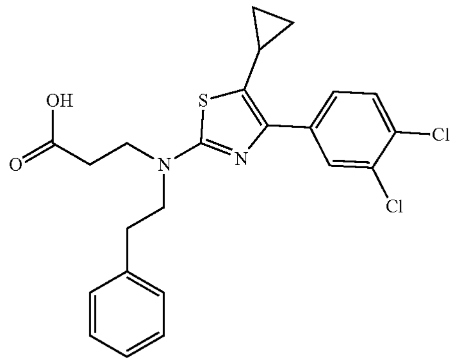 [SMILES: O=C(O)CCN(CCc1ccccc1)c1nc(-c2ccc(Cl)c(Cl)c2)c(C2CC2)s1] | Method C, Purity is 98.7%, Rt = 2.090 min; MS Calcd.: 460.1; MS Found: 461.3 [M + H]⁺. | δ: 2.51-2.53 (2H, m), 2.90 (2H, t, J = 7.6 Hz), 3.51 (2H, d, J = 6.0 Hz), 3.53-3.61 (4H, m), 5.11 (1H, s), 5.15 (1H, dd, J = 6.8, 1.6 Hz), 5.93-6.01 (1H, m), 7.20 (1H, t, J = 6.8 Hz), 7.24-7.31 (4H, m), 7.54 (1H, dd, J = 8.4, 2.0 Hz), 7.67 (1H, d, J = 8.4 Hz). |
| 58 | 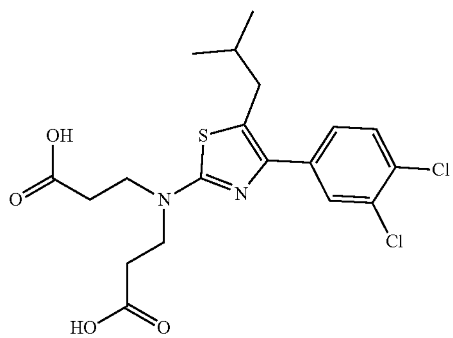 [SMILES: CC(C)Cc1sc(N(CCC(=O)O)CCC(=O)O)nc1-c1ccc(Cl)c(Cl)c1] | Method C, Purity is 97.6%, Rt = 1.563 min; MS Calcd.: 444.1; MS Found: 445.2 [M + H]⁺. | δ: 0.87 (6H, d, J = 6.4 Hz), 1.71-1.78 (1H, m), 2.43-2.45 (4H, m), 2.59 (2H, d, J = 6.8 Hz), 3.57 (4H, t, J = 12 Hz), 7.49 (1H, dd, J = 8.4, 2.0 Hz), 7.64 (1H, d, J = 8.4 Hz), 7.69 (1H, d, J = 2.0 Hz). |
| 59 | 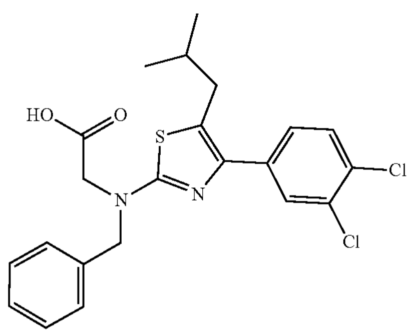 [SMILES: CC(C)Cc1sc(N(CC(=O)O)Cc2ccccc2)nc1-c1ccc(Cl)c(Cl)c1] | Method C, Purity is 100%, Rt = 2.055 min; MS Calcd.: 448.1; MS Found: 449.2 [M + H]⁺. | δ: 0.88 (6H, d, J = 6.8 Hz), 1.71-1.76 (1H, m), 2.62 (2H, d, J = 12 Hz), 3.97 (2H, brs), 4.67 (2H, s), 7.28 (1H, dd, J = 8.8, 4.0 Hz), 7.33-7.35 (4H, m), 7.52 (1H, dd, J = 8.4, 2.0 Hz), 7.66 (1H, d, J = 8.4 Hz), 7.72 (1H, d, J = 2.0 Hz). |
| 60 | 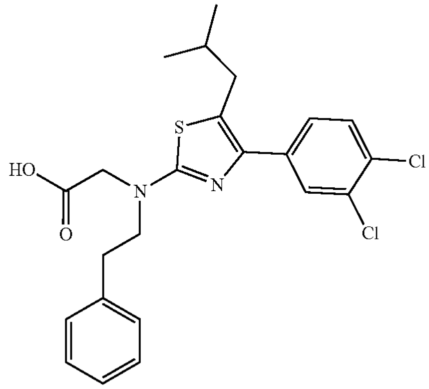 [SMILES: CC(C)Cc1sc(N(CCc2ccccc2)CC(=O)O)nc1-c1ccc(Cl)c(Cl)c1] | Method C, Purity is 100%, Rt = 2.128 min; MS Calcd.: 462.1; MS Found: 463.2 [M + H]⁺. | δ: 0.89 (6H, d, J = 6.4 Hz), 1.74-1.78 (1H, m), 2.62 (2H, d, J = 7.2 Hz), 2.93 (2H, t, J = 7.2 Hz), 3.62 (2H, t, J = 8.0 Hz), 3.96 (2H, s), 7.18-7.32 (5H, m), 7.52 (1H, dd, J = 8.4, 2.0 Hz), 7.66 (1H, d, J = 8.4 Hz), 7.73 (1H, d, J = 2.0 Hz). |

TABLE 2-3-continued

Characterization Data for Compounds

| I-# | Chemical Structure | LCMS | ¹H NMR (400 MHz, DMSO-d$_6$) |
|---|---|---|---|
| 61 | 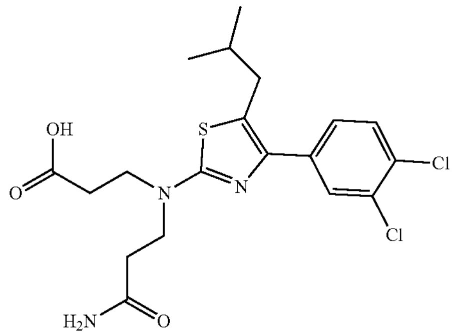 [SMILES: CC(C)Cc1sc(N(CCC(N)=O)CCC(=O)O)nc1-c1ccc(Cl)c(Cl)c1] | Method C, Purity is 100%, Rt = 1.764 min; MS Calcd.: 443.1; MS Found: 444.2 [M + H]⁺. | δ: 0.90 (6H, d, J = 6.8 Hz), 1.74-1.81 (1H, m), 2.43 (2H, t, J = 6.8 Hz), 2.62 (2H, d, J = 6.8 Hz), 3.56-3.62 (4H, m), 6.88 (1H, brs), 7.42 (1H, brs), 7.52 (1H, dd, J = 8.0, 2.0 Hz), 7.67 (1H, d, J = 8.0 Hz), 7.73 (1H, d, J = 2.0 Hz). |
| 62 | 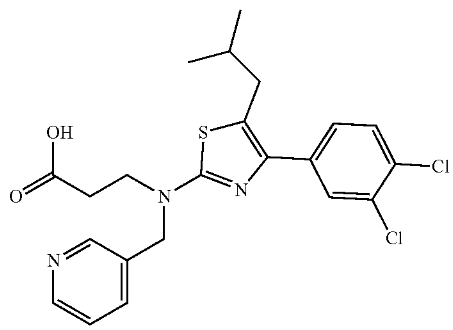 [SMILES: CC(C)Cc1sc(N(CCC(=O)O)Cc2cccnc2)nc1-c1ccc(Cl)c(Cl)c1] | Method C, Purity is 99.3%, Rt = 1.941 min; MS Calcd.: 463.1; MS Found: 464.2 [M + H]⁺. | δ: 0.86 (6H, d, J = 6.8 Hz), 1.70-1.77 (1H, m), 2.59-2.63 (4H, m), 3.63-3.67 (2H, m), 4.69 (2H, s), 7.35 (1H, dd, J = 7.6, 4.8 Hz), 7.50 (1H, dd, J = 8.4, 2.0 Hz), 7.65 (1H, d, J = 8.4 Hz), 7.69-7.71 (2H, m), 8.47 (1H, dd, J = 8.8, 1.6 Hz), 8.53 (1H, d, J = 1.6 Hz). |
| 63 | 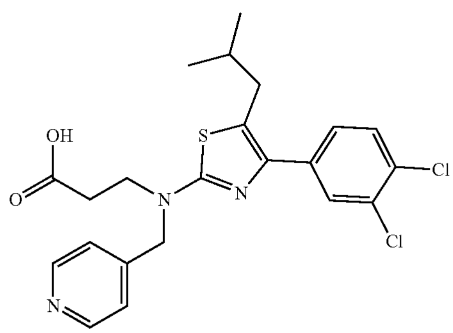 [SMILES: CC(C)Cc1sc(N(CCC(=O)O)Cc2ccncc2)nc1-c1ccc(Cl)c(Cl)c1] | Method C, Purity is 99.6%, Rt = 1.887 min; MS Calcd.: 463.1; MS Found: 464.2 [M + H]⁺. | δ: 0.88 (6H, d, J = 6.8 Hz), 1.73-1.77 (1H, m), 2.61-2.64 (1H, m), 3.66-3.70 (2H, m), 4.73 (2H, s), 7.28 (21H, d, J = 6.0 Hz), 7.50 (1H, dd, J = 8.4, 2.0 Hz), 7.66 (1H, d, J = 8.4 Hz), 7.69 (1H, d, J = 2.0 Hz), 8.52 (1H, dd, J = 4.4, 1.6 Hz),. |
| 64 | 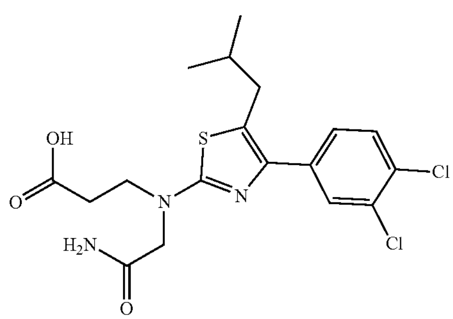 [SMILES: CC(C)Cc1sc(N(CCC(=O)O)CC(N)=O)nc1-c1ccc(Cl)c(Cl)c1] | Method C, Purity is 99.4%, Rt = 1.754 min; MS Calcd.: 429.1; MS Found: 430.2 [M + H]⁺. | δ: 0.87 (6H, d, J = 6.8 Hz), 1.72-1.76 (1H, m), 2.60 (2H, d, J = 6.8 Hz), 3.57 (2H, t, J = 6.8 Hz), 4.01 (2H, s), 7.05 (1H, brs), 7.48 (1H, dd, J = 8.4, 1.6 Hz), 7.54 (1H, brs), 7.64 (1H, d, J = 8.4 Hz), 7.69 (1H, d, J = 1.6 Hz). |

TABLE 2-3-continued

Characterization Data for Compounds

| I-# | Chemical Structure | LCMS | $^1$H NMR (400 MHz, DMSO-$d_6$) |
|---|---|---|---|
| 65 | 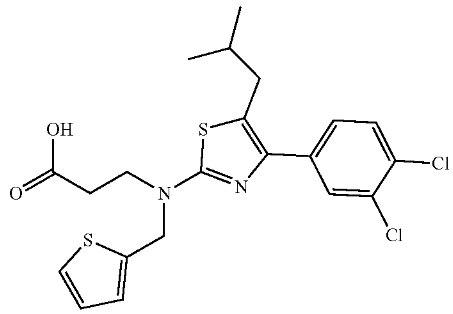 [SMILES: CC(C)Cc1sc(N(CCC(=O)O)Cc2cccs2)nc1-c1ccc(Cl)c(Cl)c1] | Method C, Purity is 98.6%, Rt = 2.028 min; MS Calcd.: 468.1; MS Found: 469.1 [M + H]$^+$. | δ: 0.87 (6H, d, J = 6.8 Hz), 1.72-1.77 (1H, m), 2.58-2.64 (4H, m), 3.57 (2H, t, J = 7.2 Hz), 4.81 (2H, s), 6.97 (1H, dd, J =5.2, 3.6 Hz), 7.11 (1H, d, J = 2.4 Hz), 7.42 (1H, dd, J = 4.8, 1.2 Hz), 7.54 (1H, dd, J = 8.4, 2.0 Hz), 7.66 (1H, d, J = 8.4 Hz), 7.77 (1H, d, J = 1.6 Hz), 12.33 (1H, brs). |
| 66 | 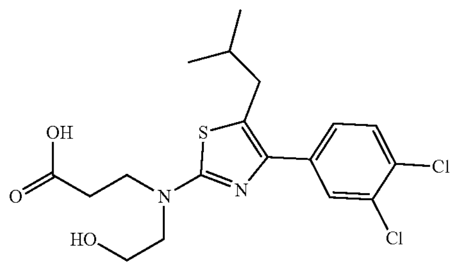 [SMILES: CC(C)Cc1sc(N(CCO)CCC(=O)O)nc1-c1ccc(Cl)c(Cl)c1] | Method C, Purity is 98.2%, Rt = 1.847 min; MS Calcd.: 416.1; MS Found: 417.2 [M + H]$^+$. | δ: 0.87 (6H, d, J = 6.8 Hz), 1.73-1.75 (1H, m), 2.53-2.60 (4H, m), 3.44 (3H, t, J = 5.6 Hz), 3.57-3.64 (4H, m), 7.49 (1H, dd, J = 8.4, 2.0 Hz), 7.64 (1H, d, J = 8.4 Hz), 7.69 (1H, d, J = 1.6 Hz). |
| 67 | 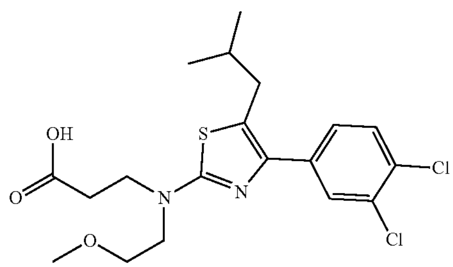 [SMILES: COCCN(CCC(=O)O)c1nc(-c2ccc(Cl)c(Cl)c2)c(CC(C)C)s1] | Method C, Purity is 99.4%, Rt = 1.964 min; MS Calcd.: 430.1; MS Found: 431.2 [M + H]$^+$. | δ: 0.87 (6H, d, J = 6.4 Hz), 1.73-1.76 (1H, m), 2.43-2.46 (2H, m), 2.59 (2H, d, J = 6.8 Hz), 3.24 (3H, s), 3.51-3.58 (6H, m), 7.48 (1H, dd, J = 8.4, 2.0 Hz), 7.64 (1H, d, J = 8.4 Hz), 7.70 (1H, d, J = 2.0 Hz). |
| 68 | 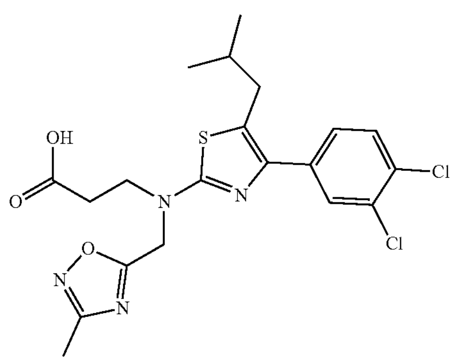 [SMILES: Cc1noc(CN(CCC(=O)O)c2nc(-c3ccc(Cl)c(Cl)c3)c(CC(C)C)s2)n1] | Method C, Purity is 99.5%, Rt = 1.951 min; MS Calcd.: 469.1; MS Found: 469.2 [M + H]$^+$. | δ: 0.87 (6H, d, J = 6.4 Hz), 1.73-1.77 (1H, m), 2.30 (3H, s), 2.60-2.63 (4H, m), 3.69 (2H, t, J = 6.8 Hz), 4.98 (2H, s), 7.44 (1H, dd, J = 8.4, 2.0 Hz), 7.61 (1H, d, J = 2.0 Hz), 7.63 (1H, d, J = 8.4 Hz). |
| 69 | 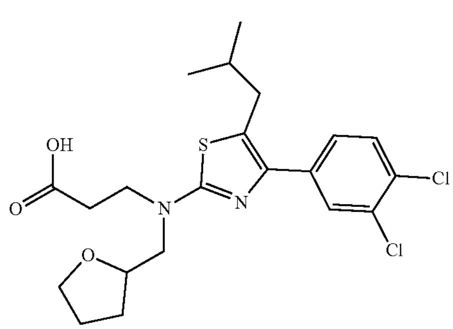 [SMILES: CC(C)Cc1sc(N(CCC(=O)O)CC2CCCO2)nc1-c1ccc(Cl)c(Cl)c1] | Method C, Purity is 99.5%, Rt = 2.011 min; MS Calcd.: 456.1; MS Found: 457.2 [M + H]$^+$. | δ: 0.87 (6H, d, J = 6.8 Hz), 1.47-1.54 (1H, m), 1.73-1.95 (4H, m), 2.52-2.60 (4H, m), 3.48-3.53 (2H, m), 3.58-3.66 (3H, m), 3.76 (1H, dd, J = 14.8, 6.8 Hz), 4.06-4.13 (1H, m), 7.49 (1H, dd, J = 8.4, 2.0 Hz), 7.64 (1H, d, J = 8.4 Hz), 7.69 (1H, d, J = 1.6 Hz). |

TABLE 2-3-continued

Characterization Data for Compounds

| I-# | Chemical Structure | LCMS | ¹H NMR (400 MHz, DMSO-d$_6$) |
|---|---|---|---|
| 70 | 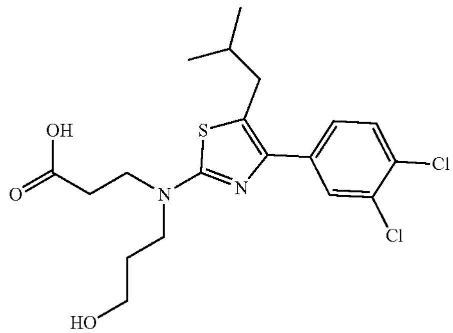 [SMILES: CC(C)Cc1sc(N(CCCO)CCC(=O)O)nc1-c1ccc(Cl)c(Cl)c1] | Method C, Purity is 97.6%, Rt = 1.846 min; MS Calcd.: 430.1; MS Found: 431.2 [M + H]⁺. | δ: 0.87 (6H, d, J = 6.4 Hz), 1.69-1.78 (3H, m), 2.48-2.54 (2H, m), 2.59 (2H, d, J = 6.8 Hz), 3.40-3.43 (5H, m), 3.58 (2H, t, J = 7.2 Hz), 7.49(1H, dd, J = 8.4, 2.0 Hz), 7.64 (1H, d, J = 8.4 Hz), 7.70 (1H, d, J = 2.0 Hz). |
| 71 | 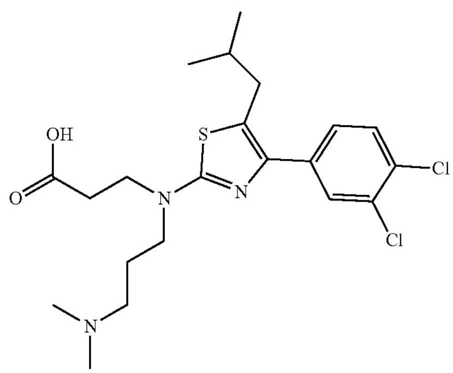 [SMILES: CC(C)Cc1sc(N(CCCN(C)C)CCC(=O)O)nc1-c1ccc(Cl)c(Cl)c1] | Method C, Purity is 99.6%, Rt = 1.904 min; MS Calcd.: 457.1; MS Found: 458.3 [M + H]⁺. | δ: 0.87 (6H, d, J = 6.4 Hz), 2.13 (6H, s), 2.23 (2H, t, J = 6.8 Hz), 2.56-2.61 (4H, m), 3.37 (2H, t, J = 7.2 Hz), 7.49 (1H, dd, J = 8.4 Hz, 2.0 Hz), 7.64 (1H, d, J = 8.4 Hz), 7.71 (1H, d, J = 2.0 Hz). |
| 72 | 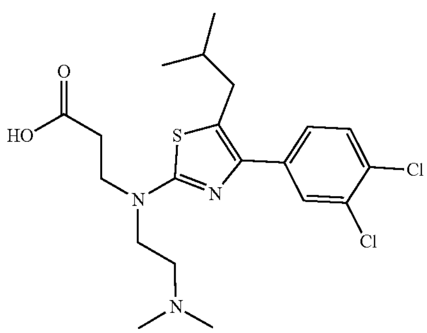 [SMILES: CC(C)Cc1sc(N(CCC(=O)O)CCN(C)C)nc1-c1ccc(Cl)c(Cl)c1] | Method C, Purity is 97.4%, Rt = 1.948 min; MS Calcd.: 443.1; MS Found: 444.3 [M + H]⁺. | δ: 0.87 (6H, d, J = 6.4 Hz), 1.72-1.78 (1H, m), 2.18 (6H, s), 2.57-2.61 (4H, m), 3.47 (3H, t, J = 6.8 Hz), 3.60 (3H, t, J = 7.2 Hz), 7.49 (1H, dd, J = 8.4, 2.0 Hz), 7.65 (1H, d, J = 8.4 Hz), 7.70 (1H, d, J = 2.0 Hz) |
| 73 | 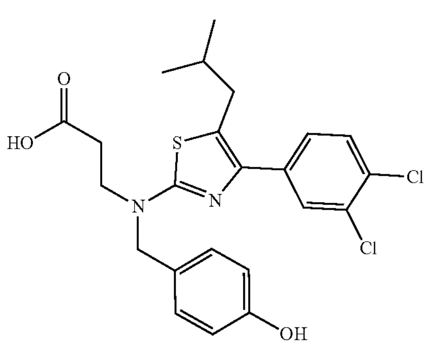 [SMILES: CC(C)Cc1sc(N(CCC(=O)O)Cc2ccc(O)cc2)nc1-c1ccc(Cl)c(Cl)c1] | Method C, Purity is 98.9%, Rt = 1.968 min; MS Calcd.: 478.1; MS Found: 479.2 [M + H]⁺. | δ: 0.86 (6H, d, J = 6.4 Hz), 1.70-1.77 (1H, m), 2.60 (2H, d, J = 7.2 Hz), 3.10-3.12 (2H, m), 3.47 (2H, t, J = 6.4 Hz), 4.50 (2H, s), 6.70 (2H, d, J = 8.4 Hz), 7.09 (1H, d, J = 8.4 Hz), 7.51 (1H, dd, J = 8.4, 2.0 Hz), 7.64 (1H, d, J = 8.4 Hz), 7.72 (1H, d, J = 2.0 Hz). |

TABLE 2-3-continued

Characterization Data for Compounds

| I-# | Chemical Structure | LCMS | ¹H NMR (400 MHz, DMSO-d$_6$) |
|---|---|---|---|
| 74 | 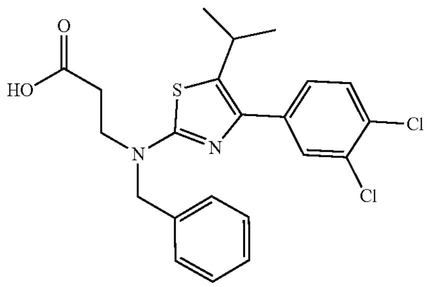 [SMILES: CC(C)c1sc(N(CCC(=O)O)Cc2ccccc2)nc1-c1ccc(Cl)c(Cl)c1] | Method C, Purity is 95.6%, Rt = 2.163 min; MS Calcd.: 448.1; MS Found: 449.3 [M + H]⁺. | δ: 1.20 (6H, d, J = 6.8 Hz), 2.60 (2H, t, J = 7.2 Hz), 3.23-3.28 (1H, m), 3.63 (2H, t, J = 7.2 Hz), 4.65 (2H, s), 7.25-7.36 (5H, m), 7.47 (1H, dd, J = 8.4, 2.0 Hz), 7.64-7.69 (2H, m), 12.34 (1H, brs). |
| 75 | 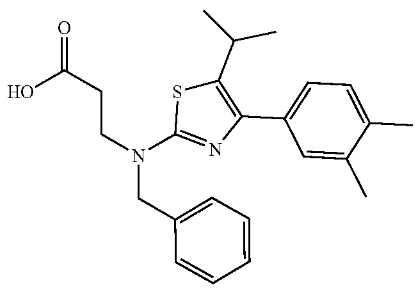 [SMILES: Cc1ccc(-c2nc(N(CCC(=O)O)Cc3ccccc3)sc2C(C)C)cc1C] | Method C, Purity is 100%, Rt = 1.981 min; MS Calcd.: 408.2; MS Found: 409.4 [M + H]⁺. | δ: 1.20 (6H, d, J = 3.2 Hz), 2.24 (6H, d, J = 2.2 Hz), 2.62 (2H, t, J = 7.2 Hz), 3.23-3.28 (1H, m), 3.63 (2H, t, J = 7.2 Hz), 4.66 (2H, s), 7.15-7.21.(2H,.m), 7.27-7.38 (6H, m), 12.33 (1H, s). |
| 76 | 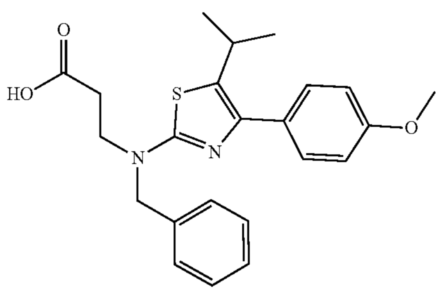 [SMILES: COc1ccc(-c2nc(N(CCC(=O)O)Cc3ccccc3)sc2C(C)C)cc1] | Method C, Purity is 99.5%, Rt = 1.824 min; MS Calcd.: 410.2; MS Found: 411.3 [M + H]⁺. | δ: 1.18 (6H, d, J = 6.8 Hz), 2.60 (2H, t, J = 7.2 Hz), 3.19-3.26 (1H, m), 3.60 (2H, t, J = 7.2 Hz), 3.75 (3H, s), 4.63 (2H, s), 6.95 (2H, d, J = 8.8 Hz), 7.24-7.36 (5H, m), 7.41 (1H, d, J = 8.8 Hz), 12.31 (1H, brs). |
| 77 | 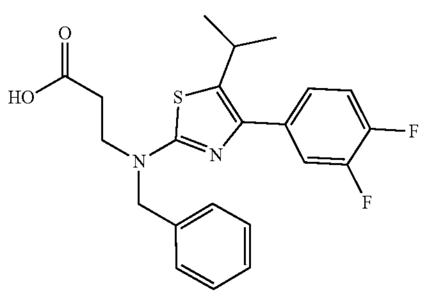 [SMILES: CC(C)c1sc(N(CCC(=O)O)Cc2ccccc2)nc1-c1ccc(F)c(F)c1] | Method C, Purity is 95.9%, Rt = 1.916 min; MS Calcd.: 416.2; MS Found: 417.3 [M + H]⁺. | δ: 1.19 (6H, d, J = 6.8 Hz), 2.60 (2H, t, J = 7.2 Hz), 3.24-3.30 (1H, m), 3.62(2H, t, J = 7.6 Hz), 4.64 (2H, s), 7.26-7.36 (6H, m), 7.41-7.50 (2H, m), 12.31 (1H, brs) |
| 78 | 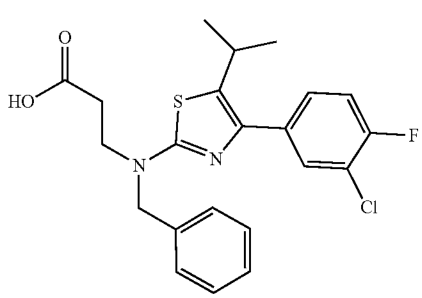 [SMILES: CC(C)c1sc(N(CCC(=O)O)Cc2ccccc2)nc1-c1ccc(F)c(Cl)c1] | Method C, Purity is 99.2%, Rt = 1.975 min; MS Calcd.: 432.1; MS Found: 433.2 [M + H]⁺. | δ: 1.19 (6 H, d, J = 6.8 Hz), 2.59 (2H, t, J = 7.6 Hz), 3.19-3.24 (1H, m), 3.62 (2H, t, J = 7.2 Hz), 4.64 (2H, s), 7.26-7.36 (5H, m), 7.43-7.48 (2H, m), 7.62 (1H, dd, J = 7.6, 2.0 Hz), 12.08-12.32 (1H, m). |

TABLE 2-3-continued

Characterization Data for Compounds

| I-# | Chemical Structure | LCMS | $^1$H NMR (400 MHz, DMSO-d$_6$) |
|---|---|---|---|
| 79 | 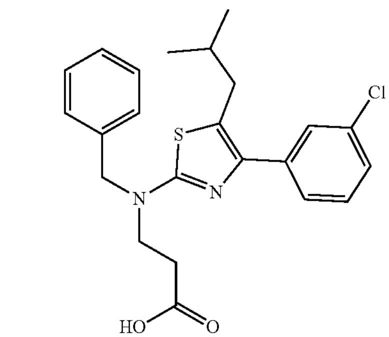 [SMILES: CC(C)Cc1sc(N(CCC(=O)O)Cc2ccccc2)nc1-c1cccc(Cl)c1] | Method C, Purity is 99.3%, Rt = 2.039 min; MS Calcd.: 428.1; MS Found: 429.3 [M + H]$^+$. | δ: 0.85 (6H, d, J = 3.4 Hz), 1.70-1.16 (1H, m), 2.48 (2H, brs), 2.59 (2H, d, J = 3.6 Hz), 3.57 (2H, t, J = 6.8 Hz), 4.65 (2H, s), 7.24-7.35 (6H, m), 7.41 (1H, t, J = 7.6 Hz), 7.47 (1H, d, J = 3.8 Hz), 7.52 (1H, s). |
| 80 | 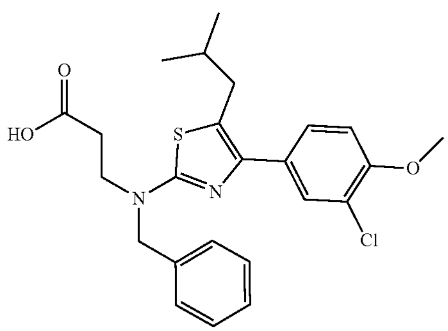 [SMILES: COc1ccc(-c2nc(N(CCC(=O)O)Cc3ccccc3)sc2CC(C)C)cc1Cl] | Method C, Purity is 100%, Rt = 1.988 min; MS Calcd.: 458.1; MS Found: 459.2 [M + H]$^+$. | δ: 0.86 (6H, d, J = 3.2 Hz), 1.69-1.76 (1H, m), 2.55-2.58 (4H, m), 3.61 (2H, t, J = 7.2 Hz), 3.85 (3H, s), 4.64 (2H, s), 7.16 (1H, d, J = 4.4 Hz), 7.23-7.35 (5H, m), 7.44 (1H, dd, J = 8.4, 2.0 Hz), 7.52 (1H, d, J = 1.0 Hz). |
| 81 | 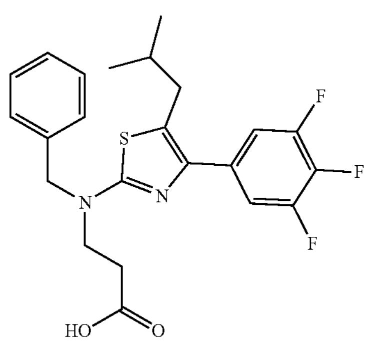 [SMILES: CC(C)Cc1sc(N(CCC(=O)O)Cc2ccccc2)nc1-c1cc(F)c(F)c(F)c1] | Method C, Purity is 87.7%, Rt = 2.043 min; MS Calcd.: 448.1; MS Found: 449.2 [M + H]$^+$. | δ: 0.85 (6H, d, J = 3.2 Hz), 1.69-1.75 (1H, m), 2.55-2.63 (4H, m), 3.62 (2H, t, J = 6.8 Hz), 4.65 (2H, s), 7.26-7.42 (7H, m). |
| 82 | 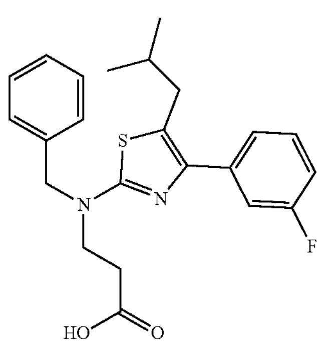 [SMILES: CC(C)Cc1sc(N(CCC(=O)O)Cc2ccccc2)nc1-c1cccc(F)c1] | Method C, Purity is 98.5%, Rt = 1.942 min; MS Calcd.: 412.2; MS Found: 413.4 [M + H]$^+$. | δ: 0.86 (6H, d, J = 6.8 Hz), 1.71-1.75 (1H, m), 2.52 (2H, t, J = 7.2 Hz), 2.61 (2H, d, J = 7.2 Hz), 3.59 (2H, t, J = 7.2 Hz), 4.65 (2H, s), 7.12 (1H, td, J = 8.4, 2.4 Hz), 7.23-7.36 (7H, m), 7.41 (1H, dd, J = 8.0, 6.4 Hz). |

TABLE 2-3-continued

Characterization Data for Compounds

| I-# | Chemical Structure | LCMS | $^1$H NMR (400 MHz, DMSO-d$_6$) |
|---|---|---|---|
| 83 | 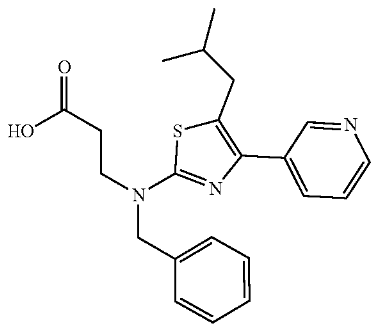 [SMILES: CC(C)Cc1sc(N(CCC(=O)O)Cc2ccccc2)nc1-c1cccnc1] | Method C, Purity is 99.4%, Rt = 1.876 min; MS Calcd.: 395.2; MS Found: 396.4 [M + H]$^+$. | δ: 0.85 (6H, d, J = 6.4 Hz), 1.70-1.75 (1H, m), 2.58-2.62 (4H, m), 3.63 (2H, t, J = 7.2 Hz), 4.66 (2H, s), 7.24-7.36 (5H, m), 7.42 (1H, dd, J = 7.6, 4.8 Hz), 7.88-7.91 (4H, m), 8.49 (1H, dd, J = 8.8, 1.6 Hz), 8.72 (1H, d, J = 1.6 Hz). |
| 84 | 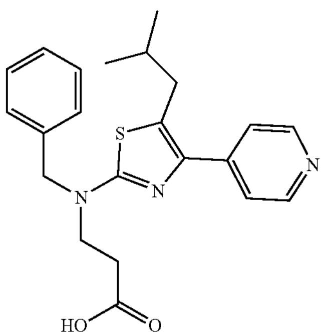 [SMILES: CC(C)Cc1sc(N(CCC(=O)O)Cc2ccccc2)nc1-c1ccncc1] | Method C, Purity is 100%, Rt = 1.666 min; MS Calcd.: 395.2; MS Found: 396.4 [M + H]$^+$. | δ: 0.87 (6H, d, J = 6.4 Hz), 1.72-1.79 (1H, m), 2.60 (2H, t, J = 12 Hz), 2.68 (2H, d, J = 12 Hz), 3.64 (2H, t, J = 12 Hz), 4.66 (2H, s), 7.24-7.36 (5H, m), 7.52 (2H, dd, J = 4.8, 1.6 Hz), 8.57 (2H, dd, J = 4.8, 1.6 Hz). |
| 85 | 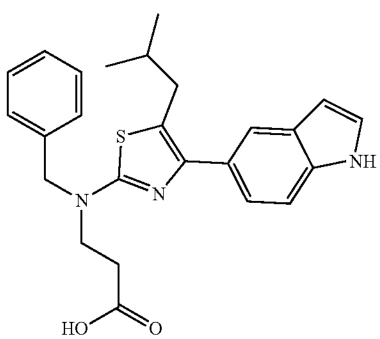 [SMILES: CC(C)Cc1sc(N(CCC(=O)O)Cc2ccccc2)nc1-c1ccc2[nH]ccc2c1] | Method C, Purity is 100%, Rt = 1.858 min; MS Calcd.: 433.1; MS Found: 434.4 [M + H]$^+$. | δ: 0.85 (6H, d, J = 6.4 Hz), 1.73-1.77 (1H, m), 2.61 (2H, d, J = 6.8 Hz), 3.60 (2 H, t, J = 12 Hz), 4.66 (2 H, s), 6.43 (1H, d, J = 2.0 Hz), 7.24-7.38 (8H, m), 7.63 (1H, s), 11.10 (1H, brs). |
| 86 | 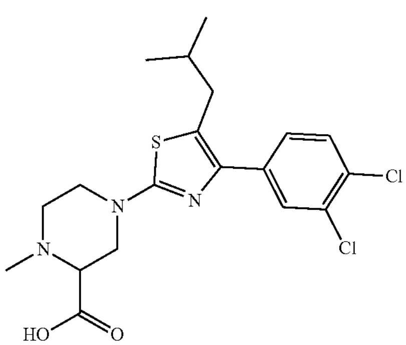 [SMILES: CC(C)Cc1sc(N2CCN(C)C(C(=O)O)C2)nc1-c1ccc(Cl)c(Cl)c1] | Method C, Purity is 100%, Rt = 1.886 min; MS Calcd.: 427.1; MS Found: 428.0 [M + H]$^+$. | δ: 0.86 (6H, d, J = 6.4 Hz), 1.73-1.76 (1H, m), 2.39 (3H, s), 2.62 (2H, d, J = 12 Hz), 3.00-3.05 (2H, m), 3.29-3.36 (2H, m), 3.52-3.55 (2H, m), 3.70-3.74 (1H, m), 7.49 (1H, dd, J = 8.4, 2.0 Hz), 7.64 (1H, d, J = 8.4 Hz), 7.71 (1H, d, J = 2.0 Hz). |

TABLE 2-3-continued

Characterization Data for Compounds

| I-# | Chemical Structure | LCMS | ¹H NMR (400 MHz, DMSO-d₆) |
|---|---|---|---|
| 87 | 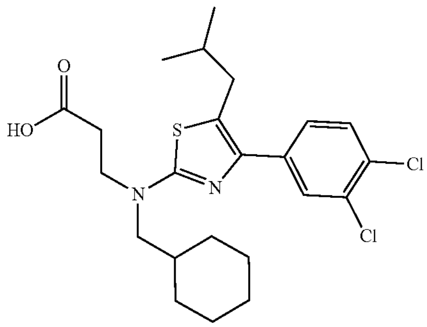 [SMILES: CC(C)Cc1sc(N(CCC(=O)O)CC2CCCCC2)nc1-c1ccc(Cl)c(Cl)c1] | Method C, Purity is 99.5%, Rt = 2.294 min; MS Calcd.: 468.1; MS Found: 469.3 [M + H]⁺. | δ: 0.86 (6H, d, J = 6.4 Hz), 0.91-0.93 (2H, m), 1.12-1.19 (3H, m), 1.61-1.67 (5H, m), 1.73 (2H, dd, J = 9.2, 6.8 Hz), 2.55-2.60 (4H, m), 3.18 (2H, d, J = 12 Hz), 3.60 (2H, t, J = 12 Hz), 7.48 (1H, dd, J = 8.4, 2.0 Hz), 7.64 (1H, d, J = 8.4 Hz), 7.71 (1H, d, J = 2.0 Hz). |
| 88 | 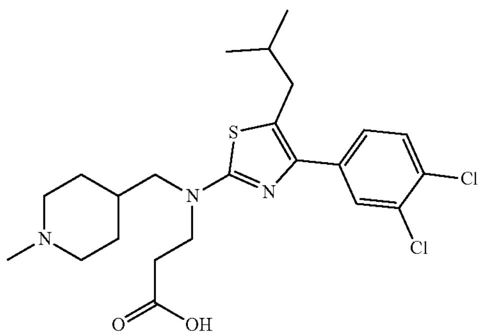 [SMILES: CC(C)Cc1sc(N(CCC(=O)O)CC2CCN(C)CC2)nc1-c1ccc(Cl)c(Cl)c1] | Method C, Purity is 100%, Rt = 1.821 min; MS Calcd.: 483.1; MS Found: 484.1 [M + H]⁺. | δ: 0.86 (6H, d, J = 6.4 Hz), 1.96-1.22 (2H, m), 1.54-1.56 (2H, m), 1.71-1.74 (2H, m), 1.84-1.86 (2H, m), 2.15 (3H, s), 2.57-2.61 (4H, m), 2.75-2.78 (2H, m), 3.61 (3H, t, J = 7.2 Hz), 7.49 (1H, dd, J = 8.4, 2.0 Hz), 7.65 (1H, d, J = 8.4 Hz), 7.70 (1H, d, J = 2.0 Hz) |
| 89 | 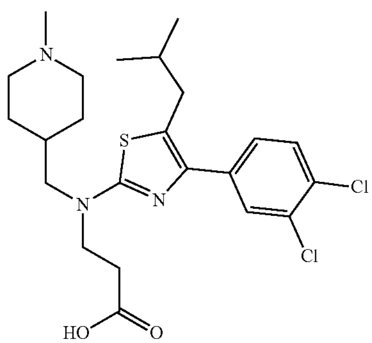 | Method B, Purity is 96.9%, Rt = 1.688 min; MS Calcd.: 463.1; MS Found: 464.0 [M + H]⁺. | δ: 2.17 (6H, s), 2.60 (1H, d, J = 7.2 Hz), 3.45 (2H, s), 3.65 (2H, t, J = 7.2 Hz), 4.66 (2H, s), 7.26-7.36 (5H, m), 7.58-7.66 (2H, m), 7.87 (1H, t, J = 2.0 Hz). |
| 90 | 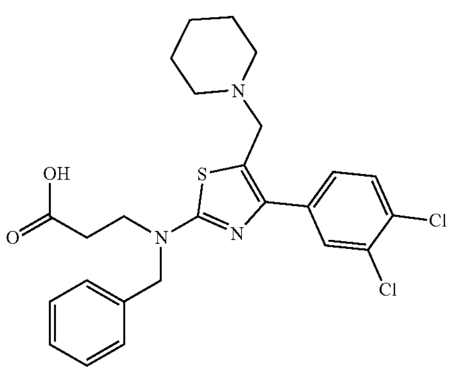 [SMILES: O=C(O)CCN(Cc1ccccc1)c1nc(-c2ccc(Cl)c(Cl)c2)c(CN2CCCCC2)s1] | Method C, Purity is 100%, Rt = 2.107 min; MS Calcd.: 418.1; MS Found: 419.2 [M + H]⁺. | δ: 1.37-1.38 (2H, m), 1.47-1.50 (3H, m), 2.32-2.38 (4H, m), 2.62 (2H, t, J = 7.2 Hz), 3.48 (2H, s), 3.66 (2H, t, J = 7.2 Hz), 4.68 (2H, s), 7.28-7.38 (5H, m), 7.61-7.68 (2H, m), 7.99 (1H, t, J = 2.0 Hz). |

TABLE 2-3-continued

Characterization Data for Compounds

| I-# | Chemical Structure | LCMS | ¹H NMR (400 MHz, DMSO-d$_6$) |
|---|---|---|---|
| 91 | 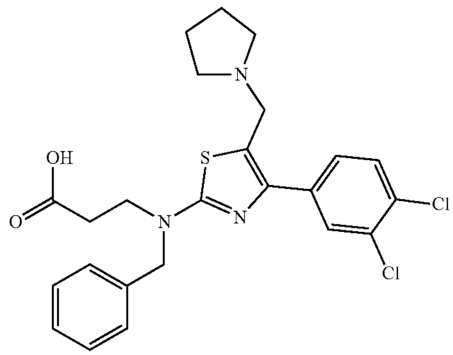 [SMILES: O=C(O)CCN(Cc1ccccc1)c1nc(-c2ccc(Cl)c(Cl)c2)c(CN2CCCC2)s1] | Method B, Purity is 97.3%, Rt = 1.728 min; MS Calcd.: 489.1; MS Found: 490.1 [M + H]$^+$. | δ: 1.81-1.91 (4H, m), 2.67 (2H, t, J = 4.0 Hz), 2.89-2.92 (2H, m), 3.63-3.72 (4H, m), 4.46-4.48 (2H, m), 4.73 (2H, s), 7.28-7.40(5H, m), 7.57-7.61 (1H, m), 7.71-7.73 (1H, m), 7.83 (1H, s). |
| 92 | 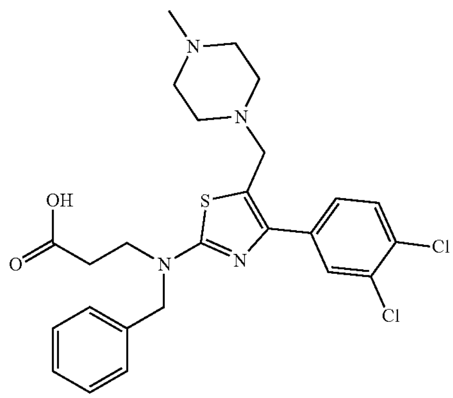 [SMILES: CN1CCN(Cc2sc(N(CCC(=O)O)Cc3ccccc3)nc2-c2ccc(Cl)c(Cl)c2)CC1] | Method B, Purity is 95.8%, Rt = 1.710 min; MS Calcd.: 418.1; MS Found: 419.1 [M + H]$^+$. | δ: 2.13 (3H, s), 2.24-2.34 (8H, m), 2.60 (2H, t, J = 7.2 Hz), 3.50 (2H, s), 3.64 (2H, t, J = 7.2 Hz), 4.66 (2H, s), 7.24-7.36 (5H, m), 7.59-7.66 (2H, m), 7.96 (1H, t, J = 2.0 Hz). |
| 93 | 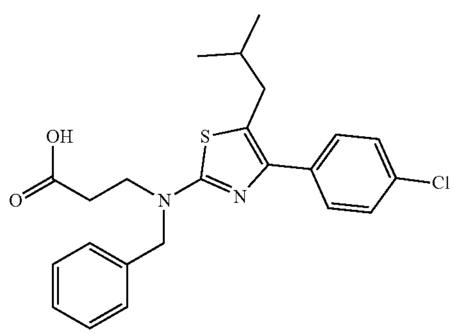 [SMILES: CC(C)Cc1sc(N(CCC(=O)O)Cc2ccccc2)nc1-c1ccc(Cl)cc1] | Method C, Purity is 93.9%, Rt = 2.045 min; MS Calcd.: 428.1; MS Found: 429.3 [M + H]$^+$. | δ: 0.85 (6H, d, J = 3.4 Hz), 1.68-1.78 (1H, m), 2.41-2.45 (2H,m), 2.58 (2H, d, J = 3.6 Hz), 3.55 (2H, t, J = 7.6 Hz), 4.66 (2H, s), 7.24-7.34 (5H, m), 7.43 (2H, d, J = 4.2 Hz), 7.53 (2H, d, J = 4.2 Hz). |
| 94 | 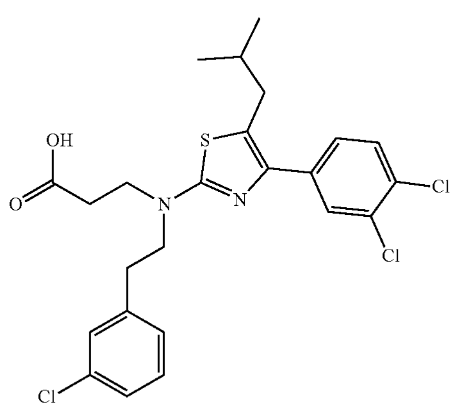 [SMILES: CC(C)Cc1sc(N(CCC(=O)O)CCc2cccc(Cl)c2)nc1-c1ccc(Cl)c(Cl)c1] | Method C, Purity is 100%, Rt = 2.237 min; MS Calcd.: 510.1; MS Found: 511.2 [M + H]$^+$. | δ: 0.89 (6H, d, J = 3.2 Hz), 1.72-1.82 (1H, m), 2.58 (2H, t, J = 12 Hz), 2.62 (2H, d, J = 3.6 Hz), 2.93 (2H, t, J = 12 Hz), 4.57-3.64 (4H, m), 7.22-7.36 (4H, m), 7.52 (1H, dd, J = 8.4, 2.0 Hz), 7.67 (1H, d, J = 4.2 Hz), 7.74 (1H, d, J = 1.0 Hz). |

TABLE 2-3-continued

Characterization Data for Compounds

| I-# | Chemical Structure | LCMS | $^1$H NMR (400 MHz, DMSO-$d_6$) |
|---|---|---|---|
| 95 | 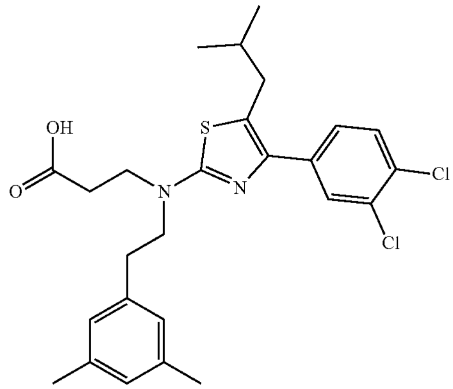 [SMILES: Cc1cc(C)cc(CCN(CCC(=O)O)c2nc(-c3ccc(Cl)c(Cl)c3)c(CC(C)C)s2)c1] | Method C, Purity is 97.2%, Rt = 2.317 min; MS Calcd.: 504.1; MS Found: 505.1 [M + H]$^+$. | δ: 0.87 (6H, d, J = 6.4 Hz), 1.74-1.77 (1H, m), 2.20 (6H, s), 2.60 (2H, d, J = 7.2 Hz), 2.77-2.81 (2H, m), 3.29-3.31 (2H, m), 3.53-3.56 (4H, m), 6.80-6.84 (3H, m), 7.50 (1H, dd, J = 8.4, 2.0 Hz), 7.65 (1H, d, J = 8.4 Hz), 7.74 (1H, d, J = 2.0 Hz). |
| 96 | 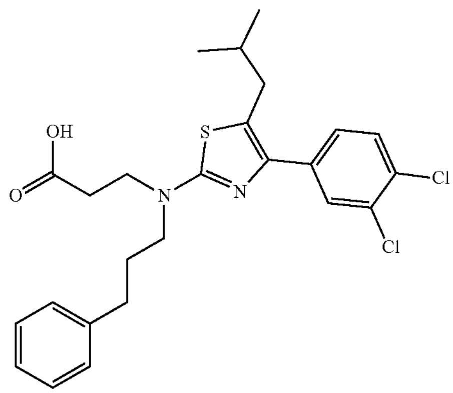 [SMILES: CC(C)Cc1sc(N(CCCc2ccccc2)CCC(=O)O)nc1-c1ccc(Cl)c(Cl)c1] | Method C, Purity is 100%, Rt = 2.265 min; MS Calcd.: 490.1; MS Found: 491.1 [M + H]$^+$. | δ: 0.87 (6H, d, J = 6.4 Hz), 1.72-1.75 (1H, m), 1.88-1.92 (2H, m), 2.56-2.60 (6H, m), 3.35-3.39 (2H, m), 3.60 (2H, t, J = 7.2 Hz), 7.16-7.28 (5H, m), 7.48 (1H, dd, J = 8.4, 2.0 Hz), 7.64 (1H, d, J = 8.4 Hz), 7.70 (1H, d, J = 2.0 Hz). |
| 97 | 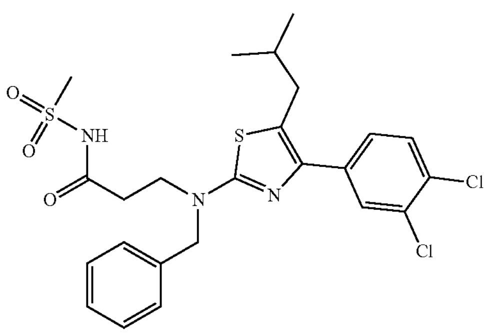 [SMILES: CC(C)Cc1sc(N(CCC(=O)NS(C)(=O)=O)Cc2ccccc2)nc1-c1ccc(Cl)c(Cl)c1] | Method C, Purity is 100%, Rt = 2.165 min; MS Calcd.: 539.1; MS Found: 540.2 [M + H]$^+$. | δ: 0.86 (6H, d, J = 6.4 Hz), 1.70-1.75 (1H, m), 2.59-2.67 (4H, m), 3.11 (3H, s), 3.66 (2H, t, J = 6.8 Hz), 4.63 (2H, s), 7.26-7.36 (5H, m), 7.51 (1H, dd, J = 8.4, 2.0 Hz), 7.65 (1H, d, J = 8.4 Hz), 7.72 (1H, d, J = 2.0 Hz), 11.80 (1H, brs). |
| 98 | 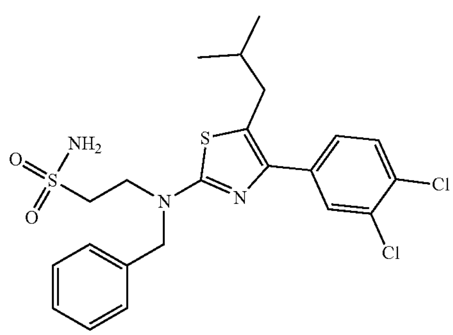 | Method C, Purity is 100%, Rt = 2.235 min; MS Calcd.: 407.1; MS Found: 408.1 [M + H]$^+$. | δ: 0.86 (6H, d, J = 6.4 Hz), 1.72-1.75 (1H, m), 2.61 (2H, d, J = 7.2 Hz), 3.34 (2H, t, J = 7.2 Hz), 3.80-3.84 (2H, m), 4.65 (2H, s), 6.97 (2H, s), 7.26-7.38 (5H, m), 7.52 (1H, dd, J = 8.4, 2.0 Hz), 7.65 (1H, d, J = 8.4 Hz), 7.74 (1H, d, J = 2.0 Hz). |

TABLE 2-3-continued

Characterization Data for Compounds

| I-# | Chemical Structure | LCMS | $^1$H NMR (400 MHz, DMSO-d$_6$) |
|---|---|---|---|
| 99 | 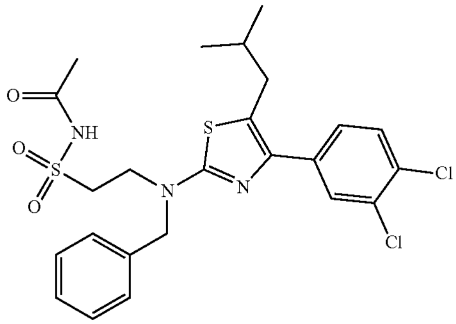 [SMILES: CC(=O)NS(=O)(=O)CCN(Cc1ccccc1)c1nc(-c2ccc(Cl)c(Cl)c2)c(CC(C)C)s1] | Method C, Purity is 100%, Rt = 2.273 min; MS Calcd.: 539.1; MS Found: 540.0 [M + H]$^+$. | δ: 0.85 (6H, d, J = 6.4 Hz), 1.70-1.74 (1H, m), 1.89 (3H, s), 2.61 (2H, d, J = 6.8 Hz), 3.76-3.80 (4H, m), 4.63 (2H, s), 7.27-7.38 (5H, m), 7.51 (1H, dd, J = 8.4, 2.0 Hz), 7.65 (1H, d, J = 8.4 Hz), 7.74 (1H, d, J = 2.0 Hz), 11.73 (1H, brs). |
| 100 | 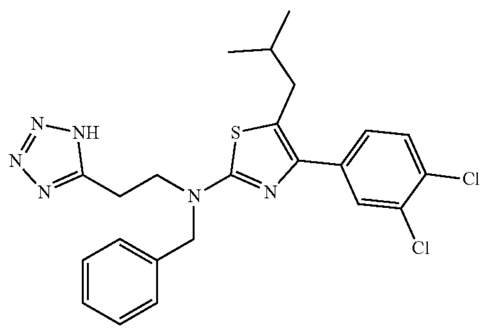 [SMILES: CC(C)Cc1sc(N(CCc2nnn[nH]2)Cc2ccccc2)nc1-c1ccc(Cl)c(Cl)c1] | Method C, Purity is 98.5%, Rt = 2.132 min; MS Calcd.: 486.1; MS Found: 487.3 [M + H]$^+$. | δ: 0.86 (6H, d, J = 6.8 Hz), 1.71-1.75 (1H, m), 2.61 (2H, d, J = 6.8 Hz), 3.28 (2H, t, J = 7.2 Hz), 3.88 (2H, t, J = 6.8 Hz), 4.62 (2H, s), 7.26-7.37 (5H, m), 7.51 (1H, dd, J = 8.4, 2.0 Hz), 7.66 (1H, d, J = 8.4 Hz), 7.71 (1H, d, J = 2.0 Hz). |
| 101 | 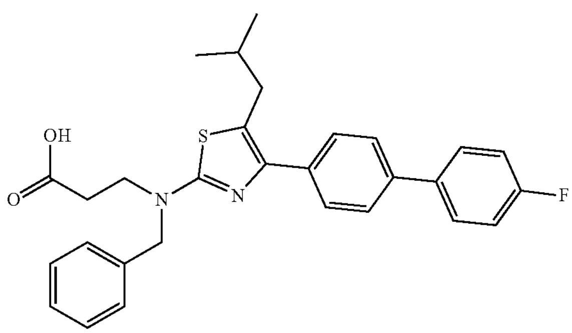 [SMILES: CC(C)Cc1sc(N(CCC(=O)O)Cc2ccccc2)nc1-c1ccc(-c2ccc(F)cc2)cc1] | Method C, Purity is 99.6%, Rt = 2.139 min; MS Calcd.: 488.2; MS Found: 489.3 [M + H]$^+$. | δ: 0.90 (6H, d, J = 3.2 Hz), 1.74-1.84 (1H, m), 2.61-2.68 (4H, m), 3.65 (2H, t, J = 7.2 Hz), 4.68 (2H, s), 7.28-7.38 (7H, m), 7.62-7.77 (6H, m), 12.32 (1H, brs). |
| 102 | 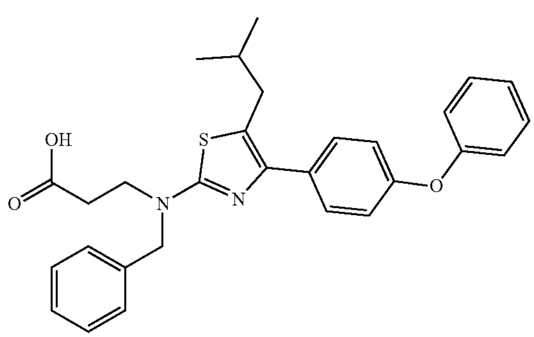 [SMILES: CC(C)Cc1sc(N(CCC(=O)O)Cc2ccccc2)nc1-c1ccc(Oc2ccccc2)cc1] | Method C, Purity is 90.0%, Rt = 2.129 min; MS Calcd.: 486.1; MS Found: 487.4 [M + H]$^+$. | δ: 0.86 (3 H, d, J = 6.4 Hz), 1.72-1.75 (1H, m), 2.60 (4H, t, J = 7.2 Hz), 3.62 (2H, t, J = 7.2 Hz), 4.64 (2H, s), 7.00-7.03 (1H, m), 7.14 (1H, t, J = 7.2 Hz), 7.26-7.41 (7H, m), 7.52 (1H, d, J = 8.4 Hz), 12.33 (1H, brs). |

TABLE 2-3-continued

Characterization Data for Compounds

| I-# | Chemical Structure | LCMS | ¹H NMR (400 MHz, DMSO-d$_6$) |
|---|---|---|---|
| 103 | 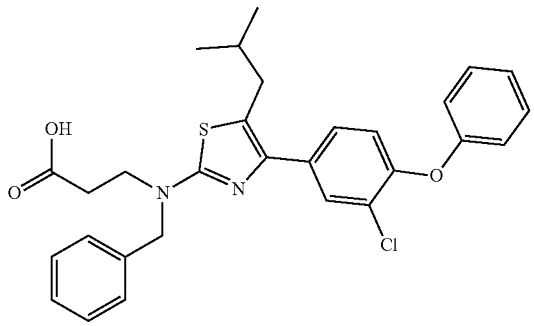 [SMILES: CC(C)Cc1sc(N(CCC(=O)O)Cc2ccccc2)nc1-c1ccc(Oc2ccccc2)c(Cl)c1] | Method C, Purity is 99.8%, Rt = 2.174 min; MS Calcd.: 520.1; MS Found: 521.3 [M + H]⁺. | δ: 0.87 (3H, d, J = 6.4 Hz), 1.73-1.76 (1H, m), 2.60 (4H, t, J = 7.2 Hz), 3.62 (2H, t, J = 7.2 Hz), 4.65 (2H, s), 6.98 (1H, d, J = 7.6 Hz), 7.07-7.15 (2H, m), 77.24-7.40 (7H, m), 7.49 (1H, dd, J = 8.4, 2.4 Hz), 7.68 (1H, s). |
| 104 | 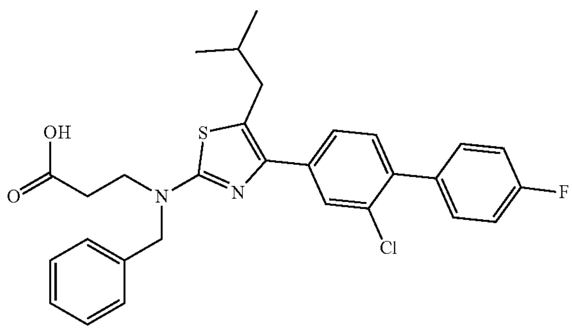 [SMILES: CC(C)Cc1sc(N(CCC(=O)O)Cc2ccccc2)nc1-c1ccc(-c2ccc(F)cc2)c(Cl)c1] | Method C, Purity is 97.2%, Rt = 2.288 min; MS Calcd.: 522.2; MS Found: 523.2 [M + H]⁺. | δ: 0.85-0.90 (6H, m), 1.71-1.81 (1H, m), 2.57-2.66 (4H, m ), 3.60- 3.66 (2H, m), 4.64-4.66 (2H, m), 7.23-7.36 (7H, m), 7.42-7.67 (5H, m), 12.38 (1H, brs). |
| 105 | 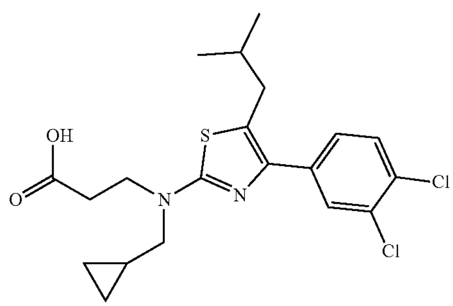 [SMILES: CC(C)Cc1sc(N(CCC(=O)O)CC2CC2)nc1-c1ccc(Cl)c(Cl)c1] | Method C, Purity is 100%, Rt = 2.068 min; MS Calcd.: 427.1; MS Found: 427.2 [M + H]⁺. | δ: 0.27-0.31 (2H, m), 0.47-0.50 (2H, m), 0.89 (6H, d, J = 6.8 Hz), 1.01-1.11 (1H, m), 1.75-1.79 (1H, m), 2.53-2.57 (2H, m), 2.61 (2H, d, J = 6.8 Hz), 3.26-3.28 (2H, m), 3.66 (2H, t, J = 6.8 Hz), 7.51 (1H, dd, J = 8.4, 2.0 Hz), 7.66 (1H, d, J = 8.4 Hz), 7.72 (1H, d, J = 2.0 Hz). |
| 106 | 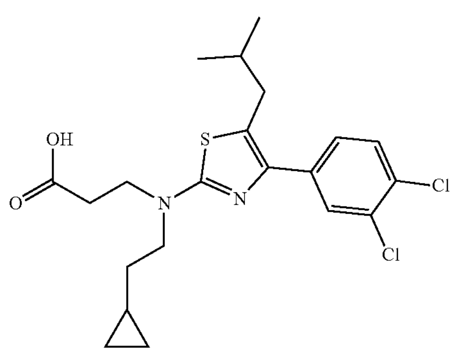 [SMILES: CC(C)Cc1sc(N(CCC(=O)O)CCC2CC2)nc1-c1ccc(Cl)c(Cl)c1] | Method C, Purity is 98.1%, Rt = 2.074 min; MS Calcd.: 440.1; MS Found: 441.1 [M + H]⁺. | δ: 0.03-0.07 (2H, m), 0.37-0.42 (2H, m), 0.63-0.66 (1H, m), 0.87 (6H, d, J = 6.8 Hz), 1.45-1.50 (2H, m), 1.73-1.77 (1H, m), 2.55 (2H, t, J = 6.8 Hz), 2.60 (2H, d, J = 6.8 Hz), 3.42 (2H, t, J = 7.2 Hz), 3.60 (2H, t, J = 6.8 Hz), 7.49 (1H, dd, J = 8.4, 2.0 Hz), 7.64 (1H, d, J = 8.4 Hz), 7.70 (1H, d, J = 2.0 Hz). |

TABLE 2-3-continued

Characterization Data for Compounds

| I-# | Chemical Structure | LCMS | $^1$H NMR (400 MHz, DMSO-$d_6$) |
|---|---|---|---|
| 107 | 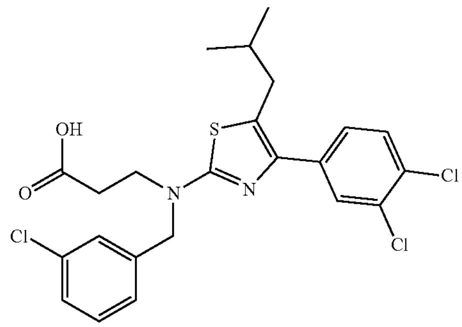 [SMILES: CC(C)Cc1sc(N(CCC(=O)O)Cc2cccc(Cl)c2)nc1-c1ccc(Cl)c(Cl)c1] | Method C, Purity is 99.4 %, Rt = 2.162 min; MS Calcd.: 496.1; MS Found: 497.2 [M + H]$^+$. | δ: 0.86 (6 H, d, J = 6.8 Hz), 1.70-1.77 (1H, m), 2.60-2.66 (4H, m), 3.69 (2H, t, J = 7.2 Hz), 4.73(2H, s), 7.24-7.34 (3H, m), 7.46-7.50 (2H, m), 7.64 (1H, d, J = 8.4 Hz), 7.69 (1H, d, J = 2.0 Hz). |
| 108 | 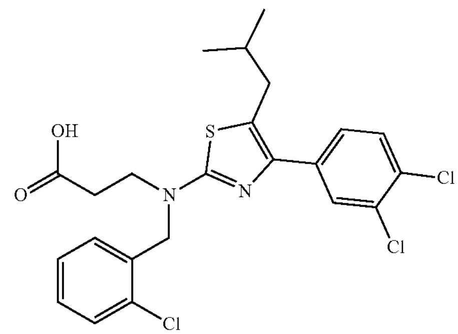 [SMILES: CC(C)Cc1sc(N(CCC(=O)O)Cc2ccccc2Cl)nc1-c1ccc(Cl)c(Cl)c1] | Method C, Purity is100%, Rt = 2.177 min; MS Calcd.: 496.1; MS Found: 497.2 [M + H]$^+$. | δ: 0.85 (6H, d, J = 6.8 Hz), 1.71-1.74 (1H, m), 2.59-2.65 (4H, m), 3.69 (2H, t, J = 6.8 Hz), 4.72 (2H, s), 7.23-7.32 (3H, m), 7.45-7.50 (2H, m), 7.64 (1H, d, J = 8.4 Hz), 7.69 (1H, d, J = 2.0 Hz). |
| 109 | 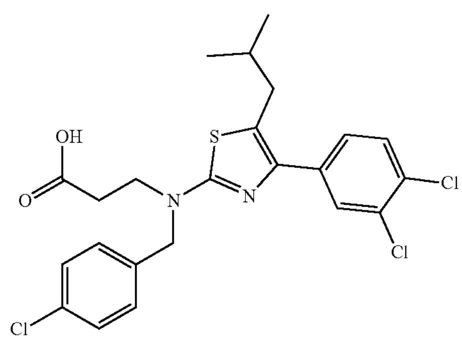 [SMILES: CC(C)Cc1sc(N(CCC(=O)O)Cc2ccc(Cl)cc2)nc1-c1ccc(Cl)c(Cl)c1] | Method C, Purity is 93.2%, Rt = 2.199 min; MS Calcd.: 496.1; MS Found: 497.2 [M + H]$^+$. | δ: 0.86 (6H, d, J = 6.4 Hz), 1.69-1.76 (1H, m), 2.59-2.62 (4H, m), 3.63 (2H, t, J = 6.8 Hz), 4.65 (2H, s), 7.31 (2H, d, J = 8.4 Hz), 7.40 (2H, d, J = 8.4 Hz), 7.50 (1H, dd, J = 8.4, 2.0 Hz), 7.65 (1H, d, J = 8.4 Hz), 7.70 (1H, d, J = 2.0 Hz), 12.34 (1H, brs). |
| 110 | 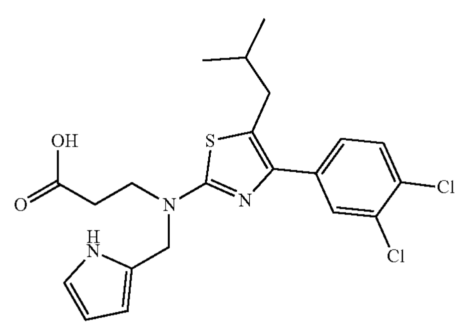 [SMILES: CC(C)Cc1sc(N(CCC(=O)O)Cc2ccc[nH]2)nc1-c1ccc(Cl)c(Cl)c1] | Method C, Purity is 98.9%, Rt = 2.031 min; MS Calcd.: 451.1; MS Found: 452.2 [M + H]$^+$. | δ: 0.89 (6H, d, J = 7.2 Hz), 1.73-1.80 (1H, m), 2.45-2.50 (2H, m), 2.62 (2H, d, J = 7.2 Hz), 3.58 (2H, t, J = 7.2 Hz), 4.52 (2H, s), 5.94 (1H, dd, J = 5.6, 2.0 Hz), 6.00 (1H, s), 6.68 (1H, d, J = 2.0 Hz), 7.53 (1H, dd, J = 8.4, 2.0 Hz), 7.67 (1H, d, J = 8.4 Hz), 7.75 (1H, d, J = 2.0 Hz), 10.89 (1H, brs). |

TABLE 2-3-continued

Characterization Data for Compounds

| I-# | Chemical Structure | LCMS | $^1$H NMR (400 MHz, DMSO-d$_6$) |
|---|---|---|---|
| 111 | 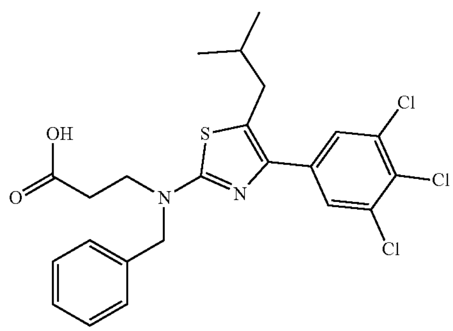 [SMILES: CC(C)Cc1sc(N(CCC(=O)O)Cc2ccccc2)nc1-c1cc(Cl)c(Cl)c(Cl)c1] | Method C, Purity is 100%, Rt = 2.219 min; MS Calcd.: 496.1; MS Found: 497.2 [M + H]$^+$. | δ: 0.87 (6H, d, J = 3.2 Hz), 1.69-1.77 (1H, m), 2.56-2.65 (4H, m), 3.63 (2H, t, J = 7.2 Hz), 4.65 (2H, s), 7.24-7.36 (5H, m), 7.71 (2H, s). |
| 112 | 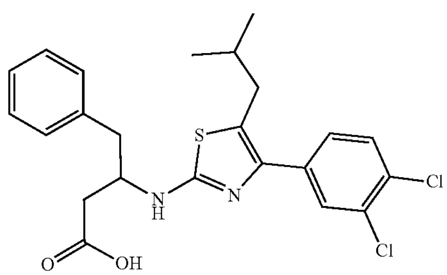 [SMILES: CC(C)Cc1sc(NC(CC(=O)O)Cc2ccccc2)nc1-c1ccc(Cl)c(Cl)c1] | Method C, Purity is 100%, Rt = 2.060 min; MS Calcd.: 462.1; MS Found: 463.2 [M + H]$^+$. | δ: 0.85 (6H, q, J = 4.8 Hz), 1.70-1.73 (1H, m), 2.39-2.47 (2H, m), 2.56 (2H, t, J = 6.8 Hz), 2.77-2.91 (2H, m), 4.10-4.13 (1H, m), 7.15-7.28 (5H, m), 7.47 (1H, d, J = 8.4, 2.4 Hz), 7.59-7.65 (2H, m), 7.69 (1H, d, J = 2.0 Hz). |
| 113 | 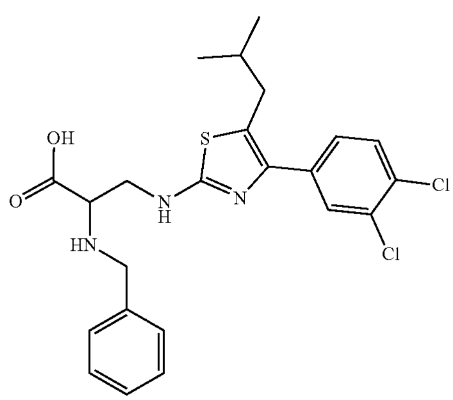 [SMILES: CC(C)Cc1sc(NCC(NCc2ccccc2)C(=O)O)nc1-c1ccc(Cl)c(Cl)c1] | Method C, Purity is 100%, Rt = 2.116 min; MS Calcd.: 477.1; MS Found: 478.1 [M + H]$^+$. | δ: 0.85 (6H, dd, J = 6.4, 4.8 Hz), 1.68-1.75 (1H, m), 2.57 (2H, d, J = 7.2 Hz), 3.46-3.55 (3H, m), 3.82 (2H, d, J = 13.2 Hz), 3.95 (1H, d, J = 13.2 Hz), 7.21-7.29 (5H, m), 7.44 (1H, dd, J = 8.4, 1.6 Hz), 7.60 (1H, d, J = 8.4 Hz), 7.66 (1H, d, J = 1.6 Hz). |
| 114 | 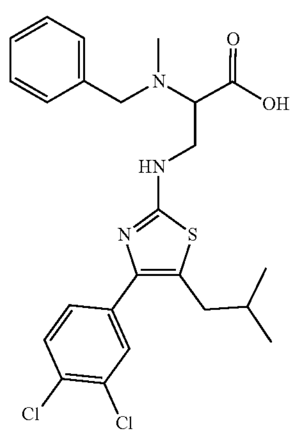 [SMILES: CC(C)Cc1sc(NCC(C(=O)O)N(C)Cc2ccccc2)nc1-c1ccc(Cl)c(Cl)c1] | Method C, Purity is 99.7%, Rt = 2.159 min; MS Calcd.: 491.1; MS Found: 492.2 [M + H]$^+$. | δ: 0.87 (6H, d, J = 6.4 Hz), 1.71-1.74 (1H, m), 2.23 (3H, s), 2.57 (2H, d, J = 7.2 Hz), 3.43-3.66 (5H, m), 3.77 (1H, d, J = 13.6 Hz), 7.15-7.22 (3H, m), 7.27 (2H, d, J = 6.8 Hz), 7.42 (1H, dd, J = 8.4, 2.0 Hz), 7.48-7.50 (1H, m), 7.60-7.62 (2H, m). |

TABLE 2-3-continued

Characterization Data for Compounds

| I-# | Chemical Structure | LCMS | ¹H NMR (400 MHz, DMSO-d₆) |
|---|---|---|---|
| 115 | 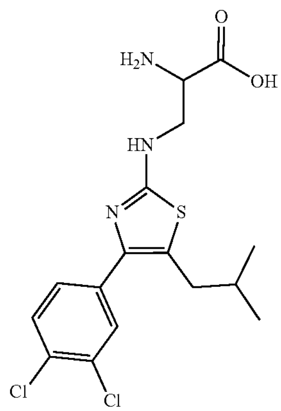 [SMILES: CC(C)Cc1sc(NCC(N)C(=O)O)nc1-c1ccc(Cl)c(Cl)c1] | Method C, Purity is 91.1%, Rt = 1.889 min; MS Calcd.: 387.1; MS Found: 388.3 [M + H]⁺. | δ: 0.86 (6H, dd, J = 6.4, 1.6 Hz), 1.71-1.74 (1H, m), 2.58 (2H, d, J = 6.8 Hz), 3.41-3.45 (2H, m), 3.61-3.66 (1H, m), 7.49 (1H, dd, J = 8.4, 2.0 Hz), 7.64 (2H, d, J = 8.4 Hz), 7.72 (1H, d, J = 2.0 Hz). |
| 116 | 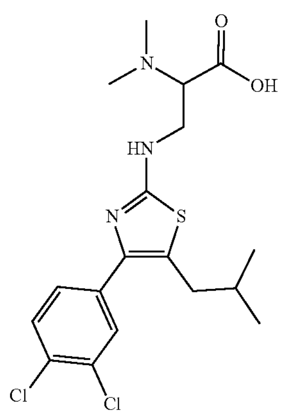 [SMILES: CC(C)Cc1sc(NCC(C(=O)O)N(C)C)nc1-c1ccc(Cl)c(Cl)c1] | Method C, Purity is 96.6%, Rt = 2.048 min; MS Calcd.: 415.1; MS Found: 416.2 [M + H]⁺. | δ: 0.87 (6H, d, J = 6.8 Hz), 1.70-1.77 (1H, m), 2.46 (6H, s), 2.59 (2H, d, J = 7.2 Hz), 3.45-3.52 (2H, m), 3.59-3.66 (1H, m), 7.50 (2H, dd, J = 8.4, 4.4 Hz), 7.64 (1H, d, J = 8.4 Hz), 7.72 (1H, d, J = 2.0 Hz). |
| 117 | 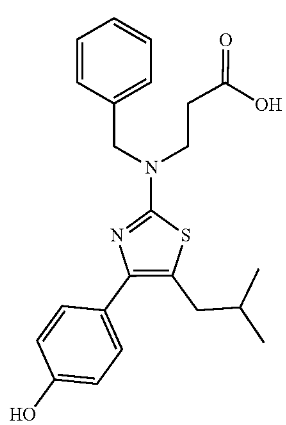 [SMILES: CC(C)Cc1sc(N(CCC(=O)O)Cc2ccccc2)nc1-c1ccc(O)cc1] | Method C, Purity is 91.7%, Rt = 1.765 min; MS Calcd.: 410.2; MS Found: 411.4 [M + H]⁺. | δ: 0.87 (6H, d, J = 6.8 Hz), 1.72-1.75 (1H, m), 2.53-2.57 (2H, m), 3.55-3.59 (4H, m), 4.66 (2H, s), 6.77 (2H, d, J = 8.4 Hz), 7.26-7.36 (7H, m). |

TABLE 2-3-continued
Characterization Data for Compounds
| I-# | Chemical Structure | LCMS | ¹H NMR (400 MHz, DMSO-d$_6$) |
|---|---|---|---|
| 118 | 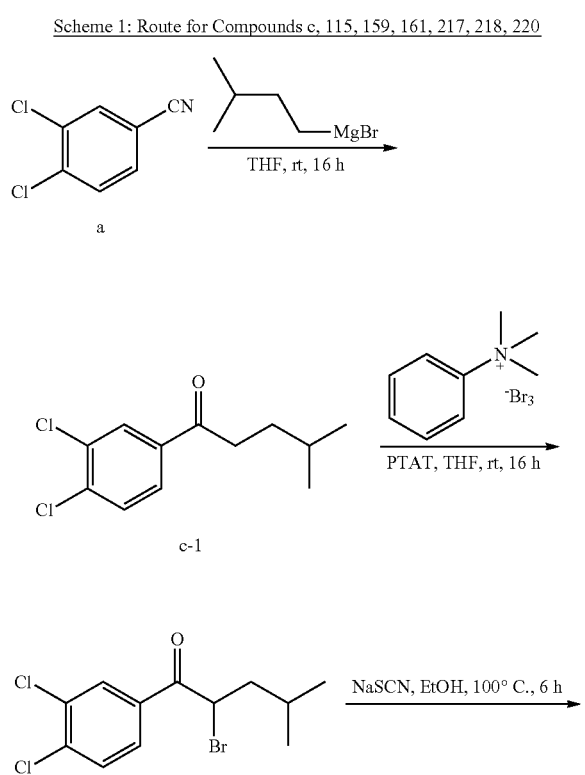 | Method C, Purity is 100%, Rt = 1.903 min; MS Calcd.: 415.2; MS Found: 416.0 [M + H]$^+$. | δ: 0.87 (6H, d, J = 6.4 Hz), 1.71-1.81 (1H, m), 2.64 (2H, d, J = 7.2 Hz), 3.09-3.15 (2H, m), 3.48-3.58 (2H, m), 3.76 (1H, dd, J = 12.4, 6.4 Hz), 3.92-3.95 (2H, m), 7.50 (1H, dd, J = 8.4, 2.8 Hz), 7.65 (1H, d, J = 8.4 Hz), 7.72 (1H, d, J = 2.0 Hz). |
Example 3. Synthesis of Compounds I-119 to I-198
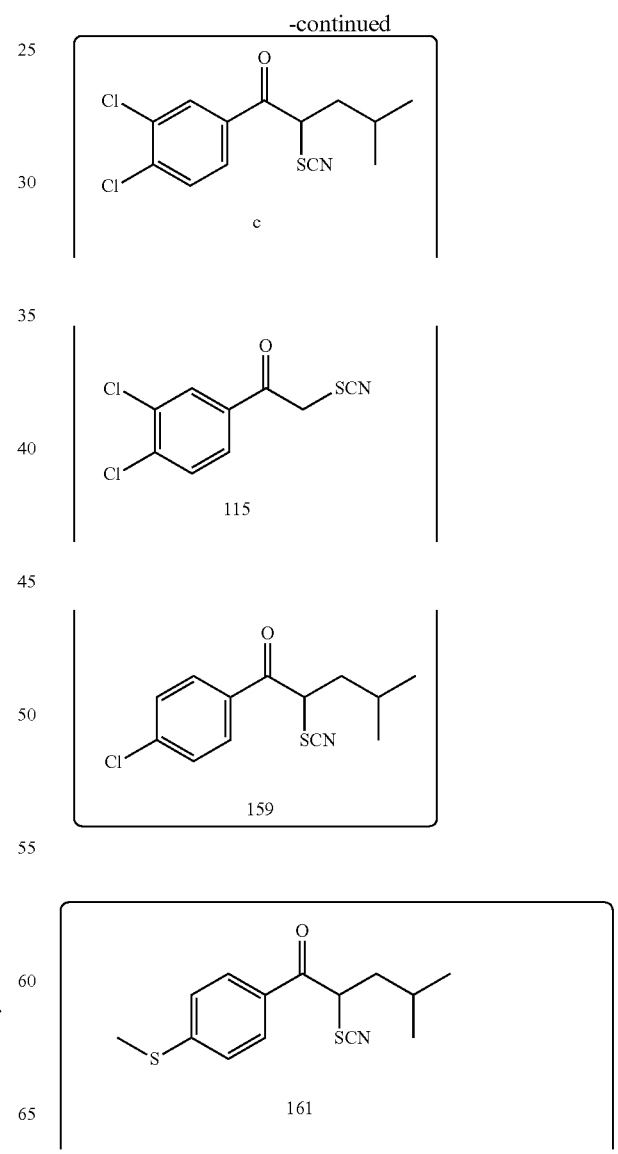

319
-continued
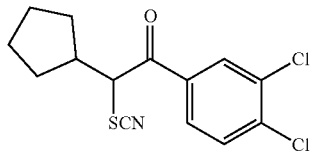
217
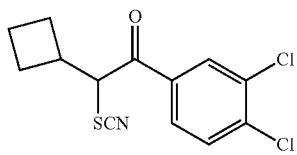
218
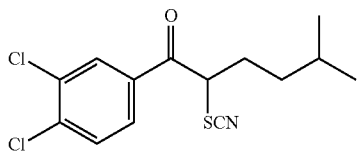
220
The same synthesis method used for other compounds 115, 159, 161, 217, 218, 220.
Scheme 2: Route for Compound 219
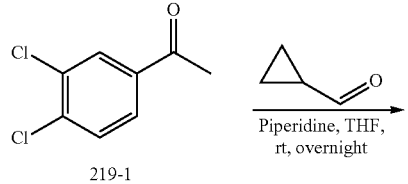
219-1
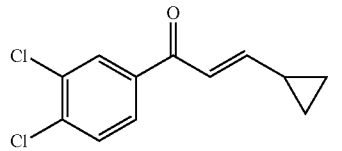
219-2
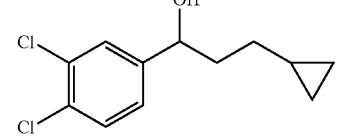
219-3
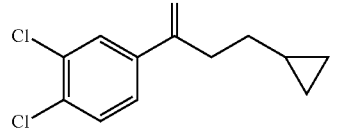
219-4
320
-continued
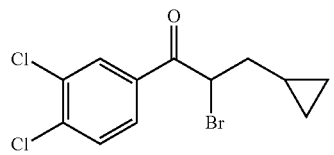
219-5
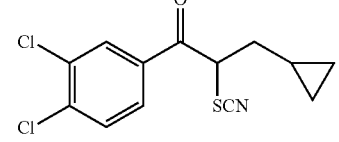
219
Scheme 3: Route for Compound b-157
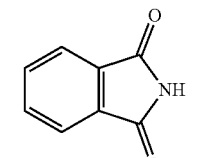
157-1
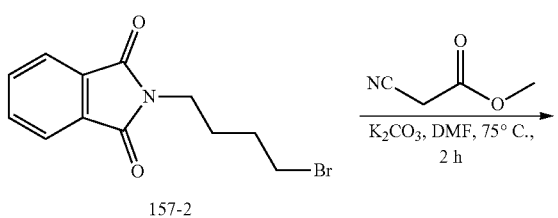
157-2
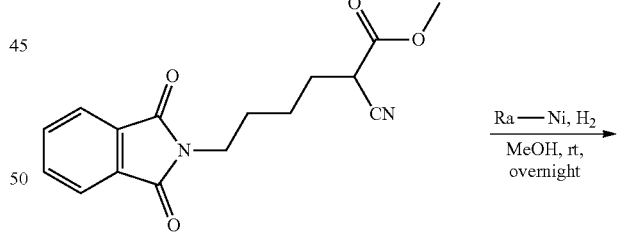
157-3
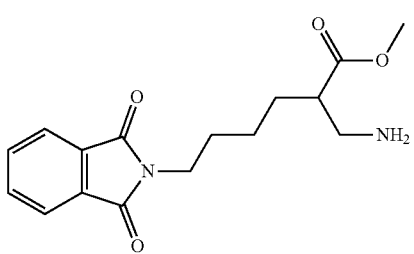 [SMILES: COC(=O)C(CN)CCCCN1C(=O)c2ccccc2C1=O]
b-157

Scheme 4: Route for Compounds b-184~b-187
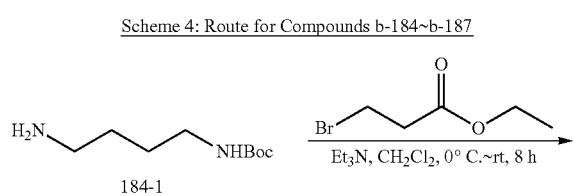
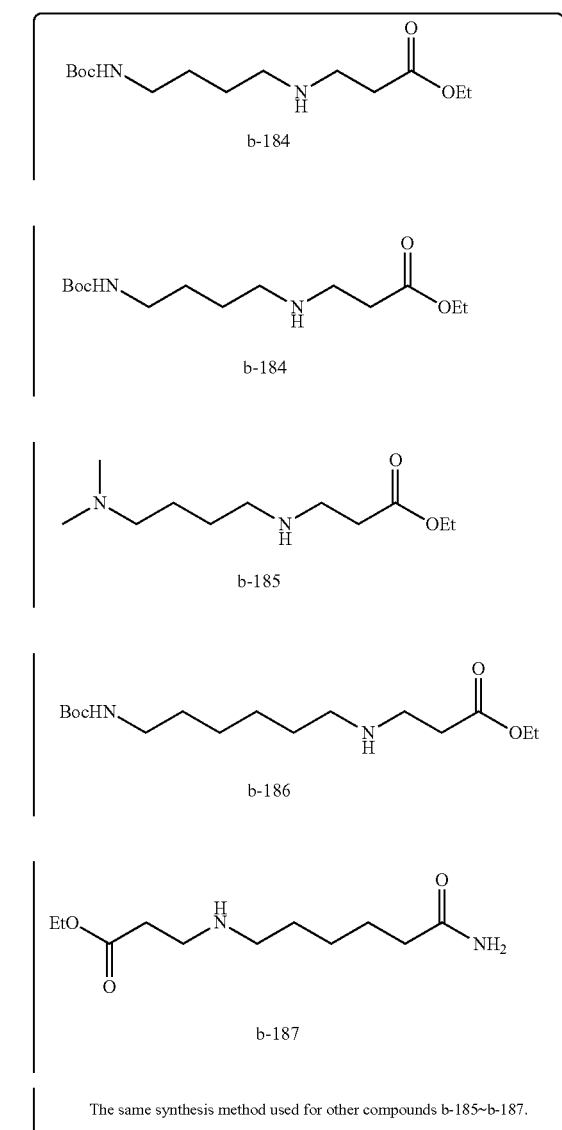
Scheme 5: Route for Compounds 1, b-188~b-196, b-198~b-201, b-203~b-205, b-211, b-212, b-214, b-215, s-1
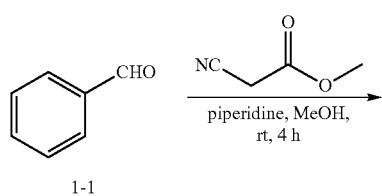
-continued
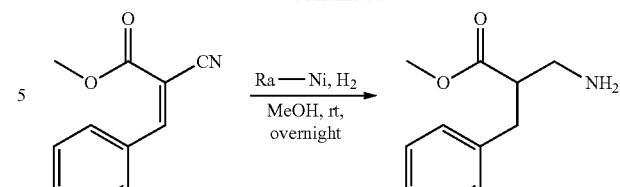
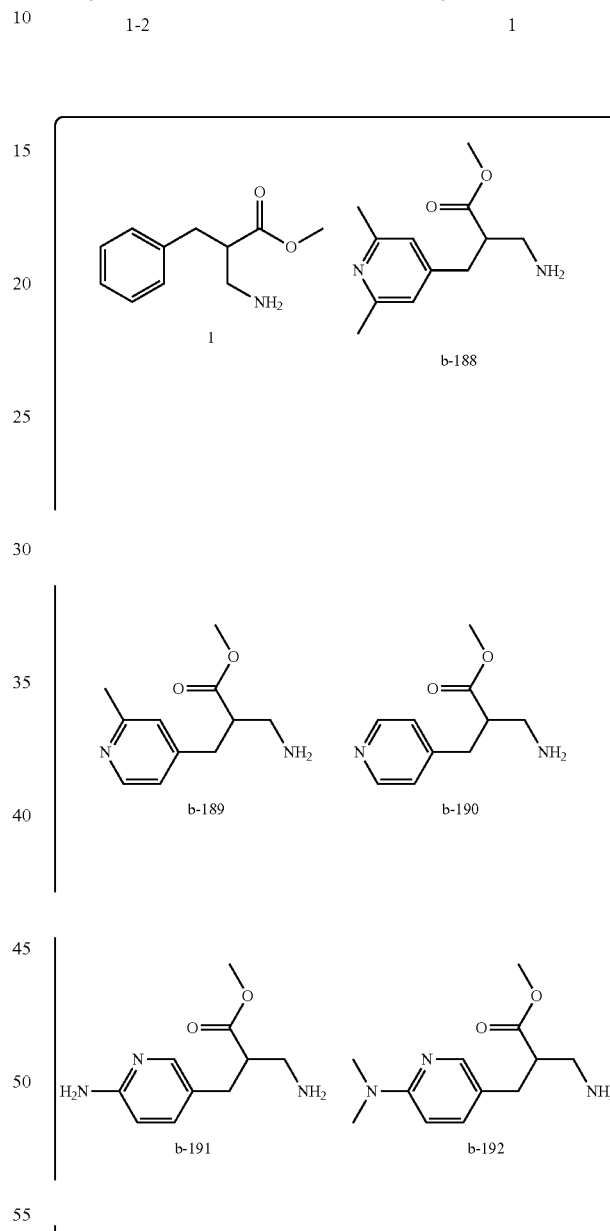
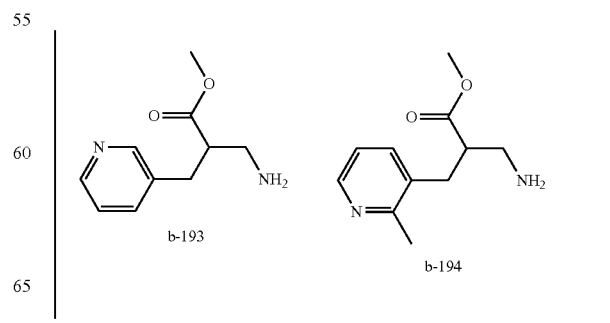

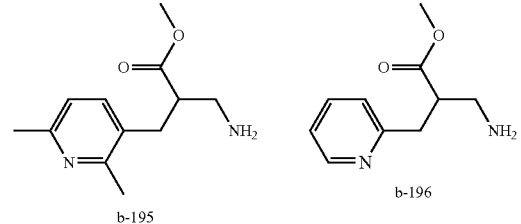
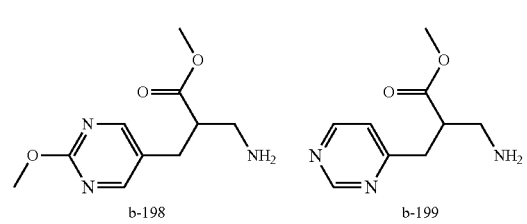
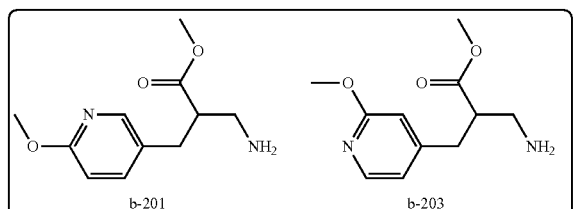
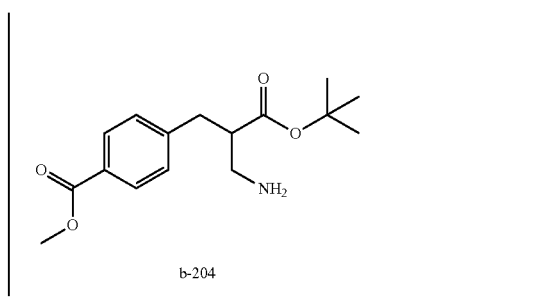
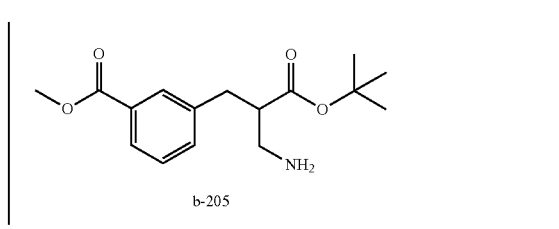
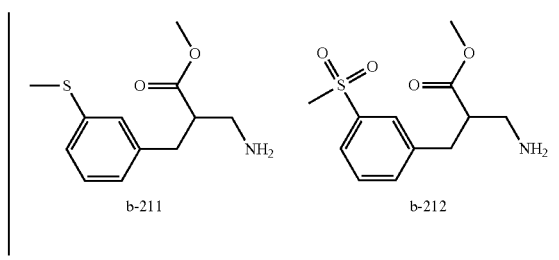
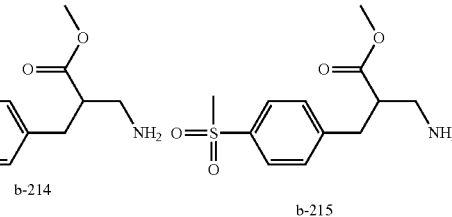
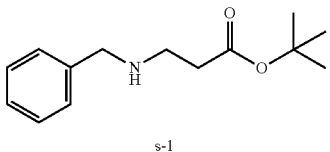
The same synthesis method used for other compounds b-188~b-196, b-198~b-201, b-203-b-205, b-211, b-212, b-214, b-215, s-1.
Scheme 6: Route for Compound b-208
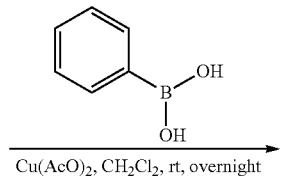
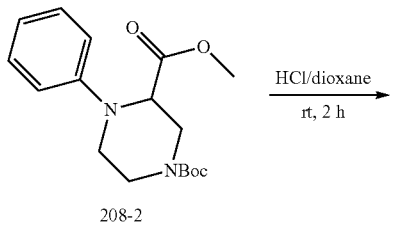
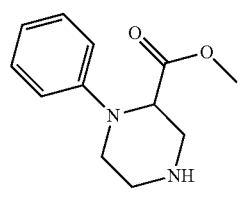

Scheme 7: Route for Compounds b-213, b-216
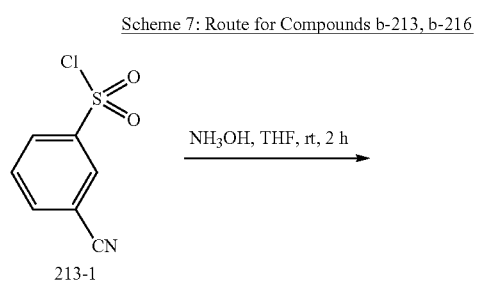
213-1
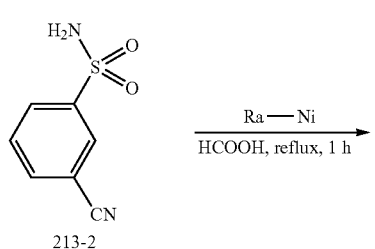
213-2
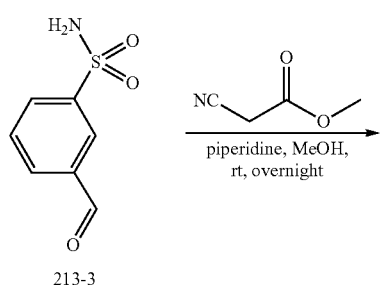
213-3
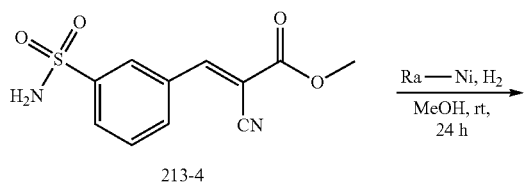
213-4
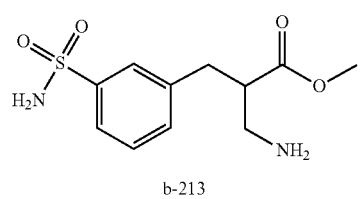
b-213
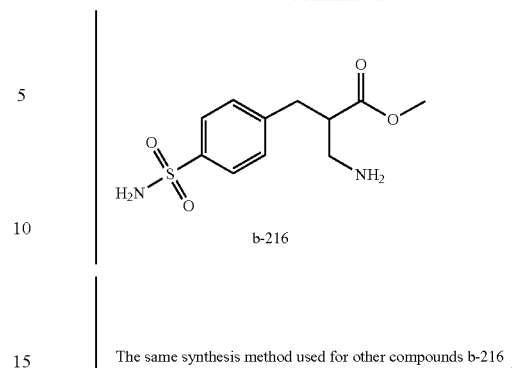
b-216
The same synthesis method used for other compounds b-216
Scheme 8: Route for Compounds b-229
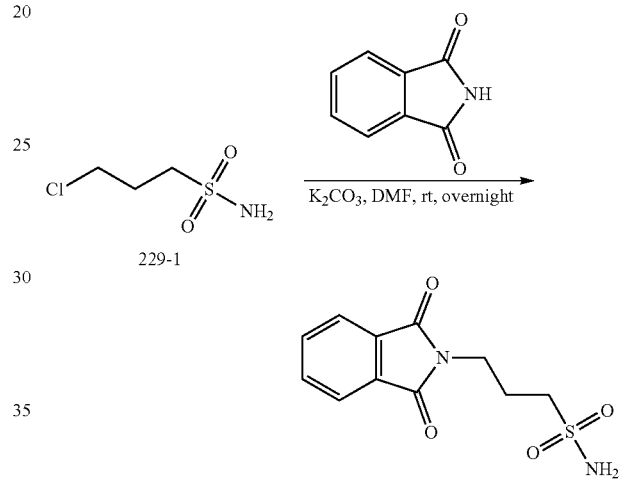
Scheme 9: Route for Compound b-233
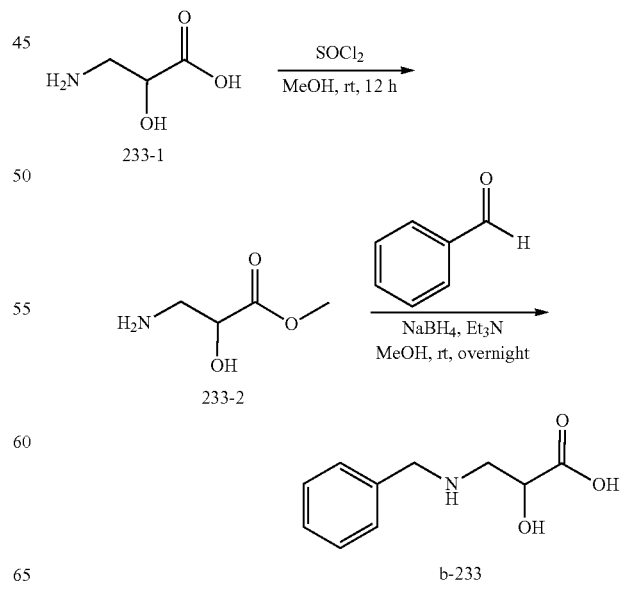

Scheme 10: Route for Compound b-235
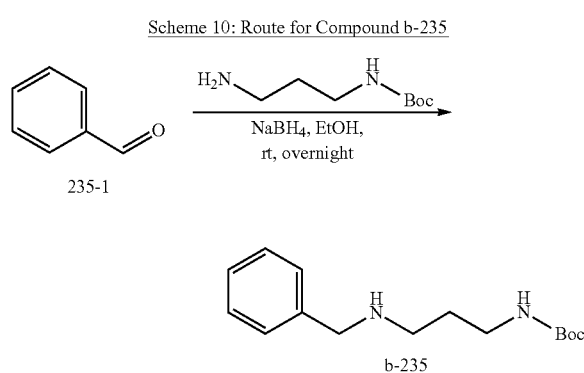
Scheme 11: Route for Compound b-242
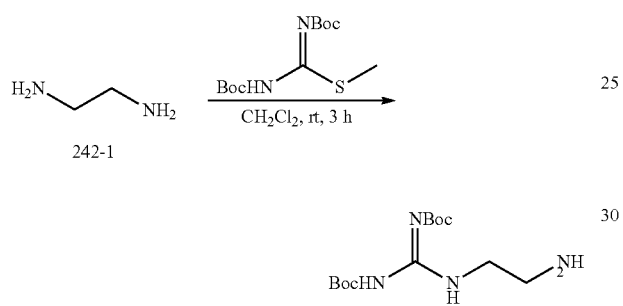
Scheme 12: Route for Compound b-243
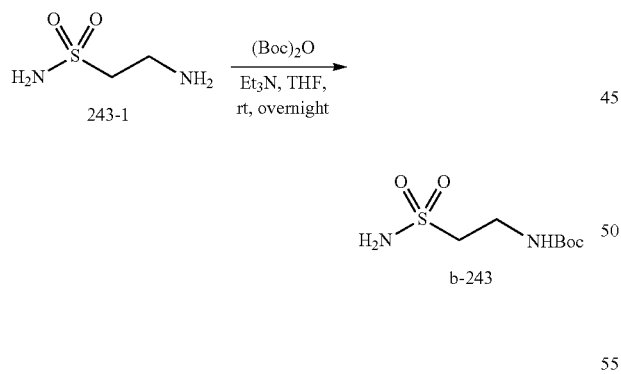
Scheme 13: Route for Compound 152-s, 227-s
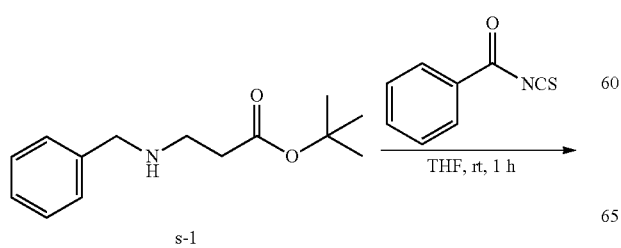
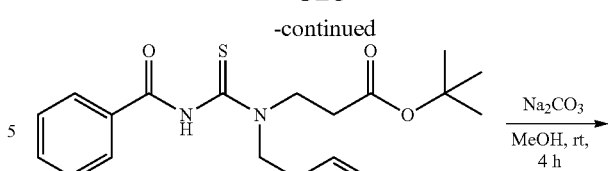
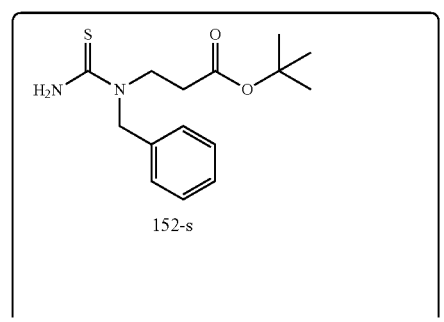
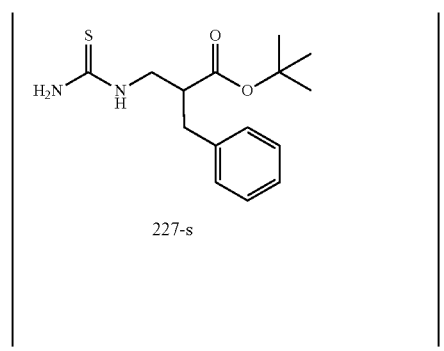
The same synthesis method used for other compounds 227-s Scheme 14: Route for Compound 178-s
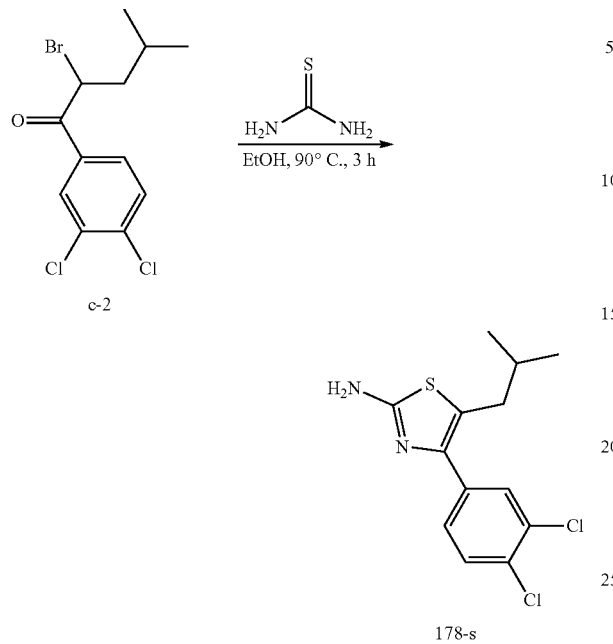
Scheme 15: Route for Compound 224-s
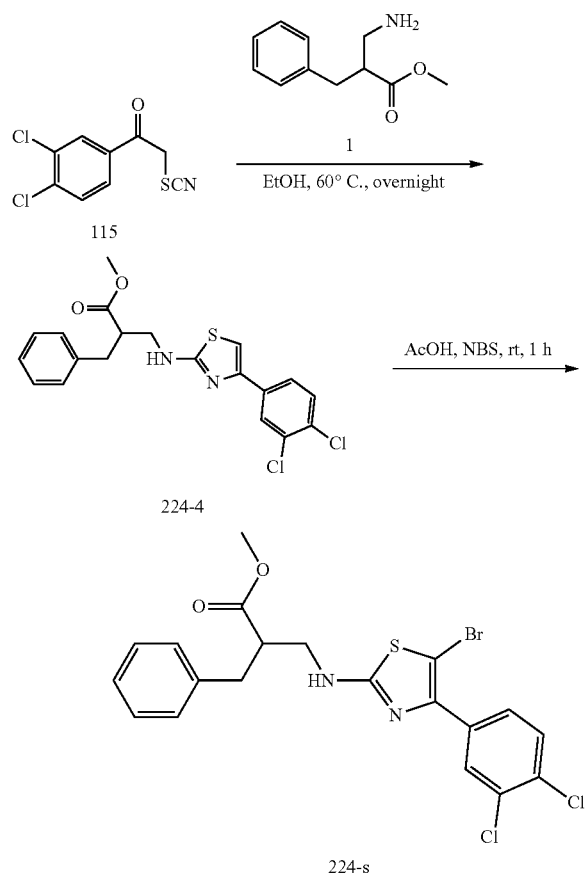
Scheme 16: Route for Compound I-119
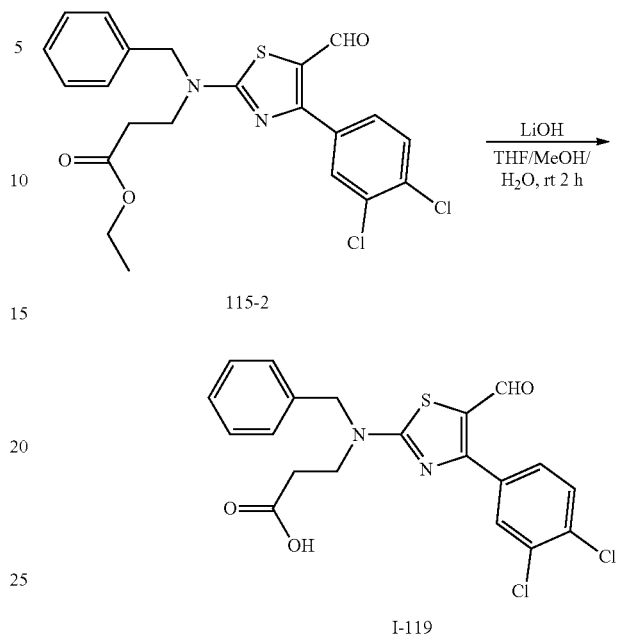
Scheme 17: Route for Compounds I-120 to I-122, I-130
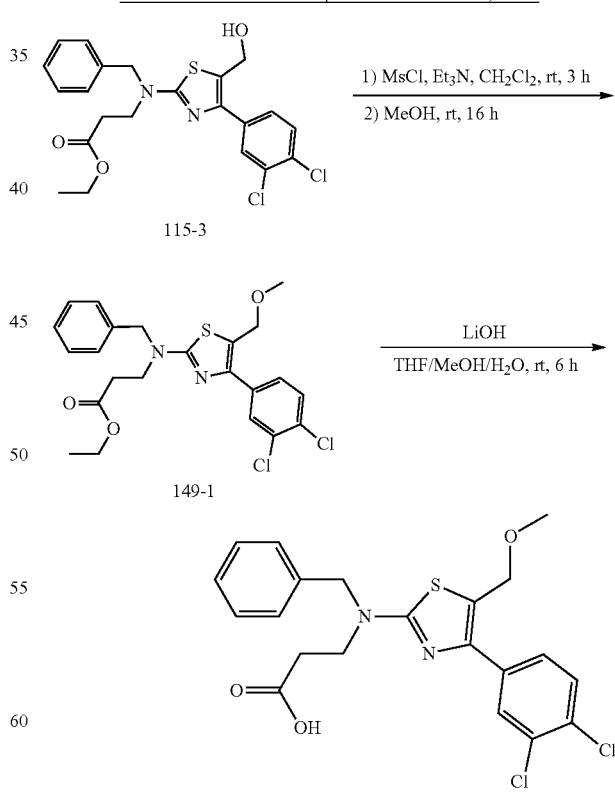
The same synthesis method used for other compounds I-121, I-122, I-130

Scheme 18: Route for Compound I-123
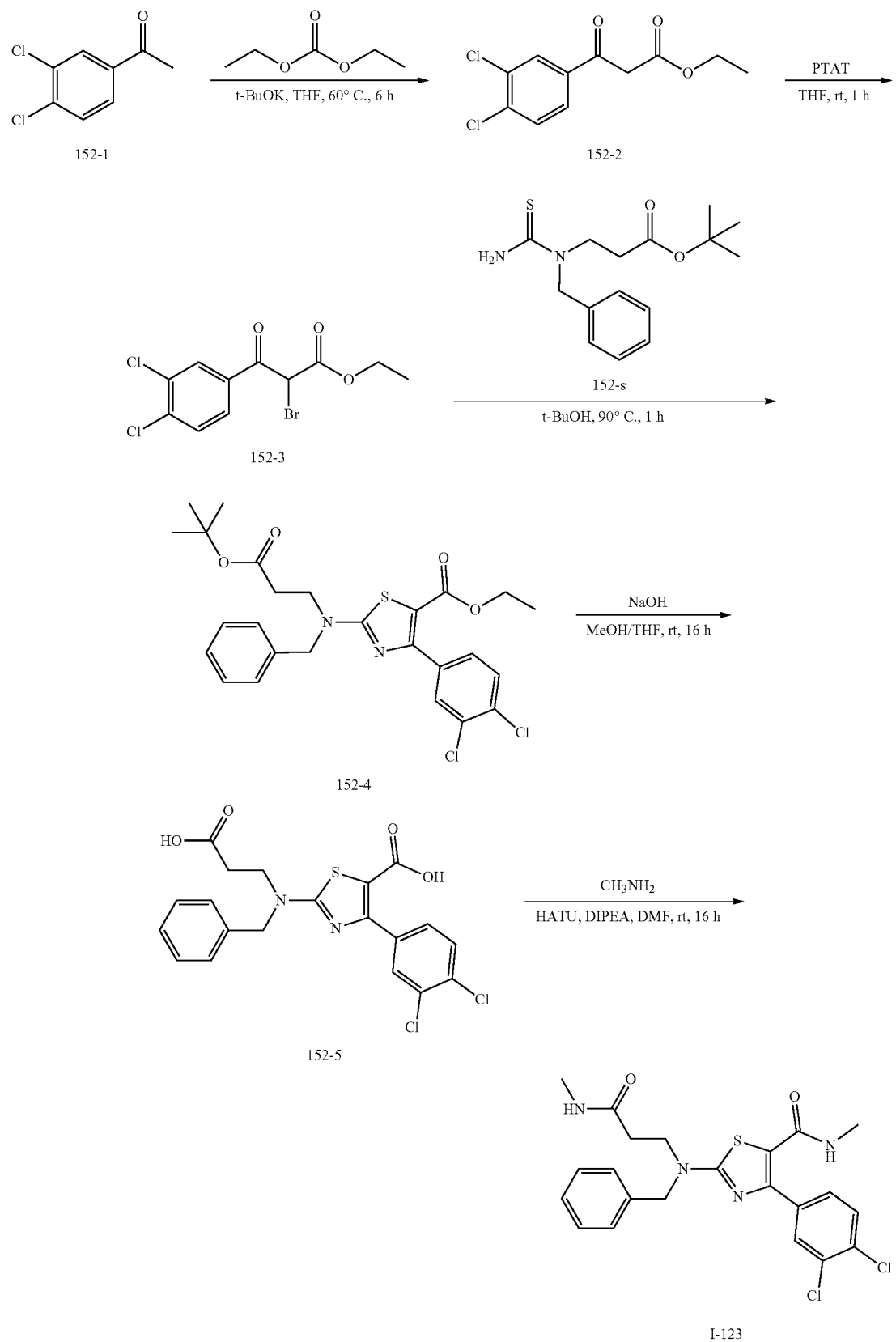

333
Scheme 19: Route for Compound I-124
334
-continued
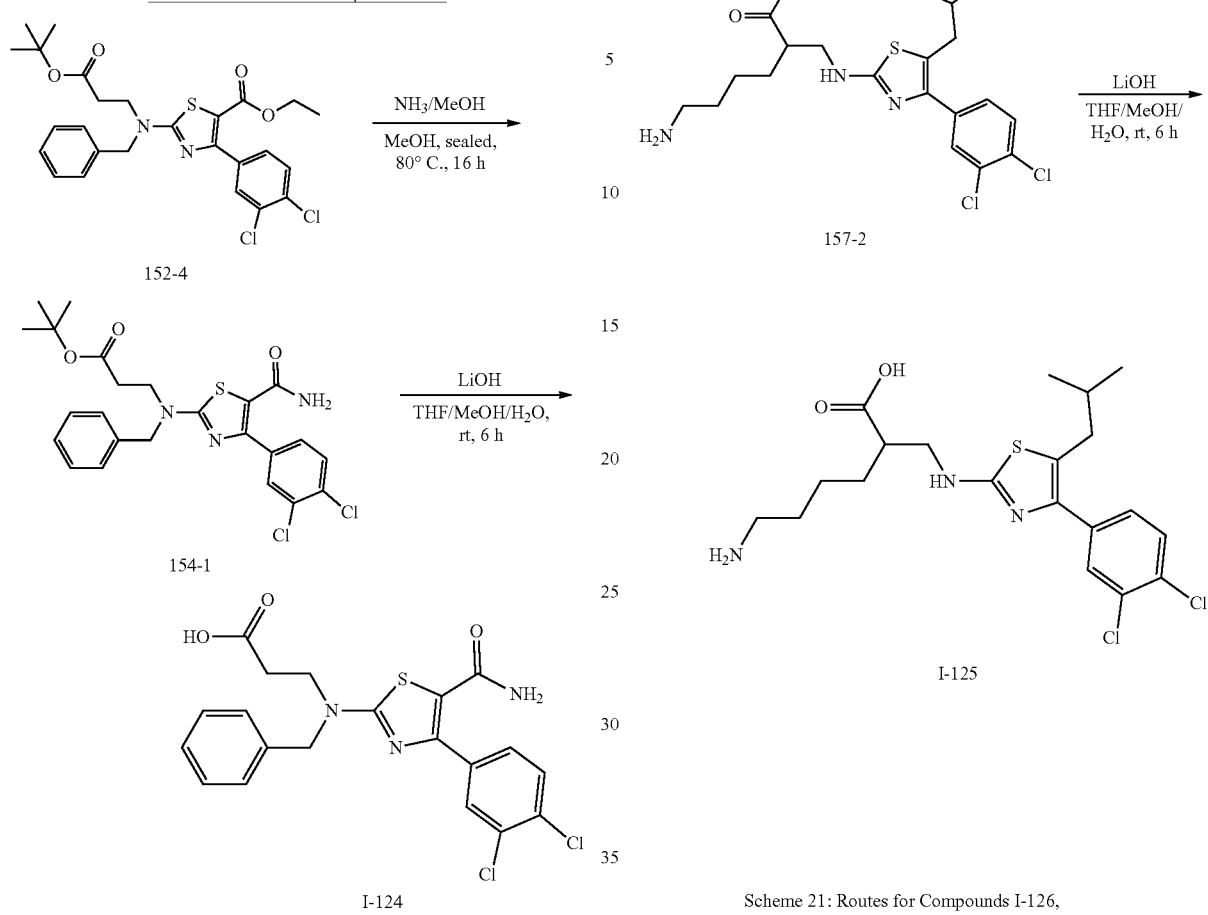
Scheme 21: Routes for Compounds I-126, I-127, I-150 to I-158, I-160, I-163, I-165, I-70, I-171 to I-180
Scheme 20: Route for Compound I-125
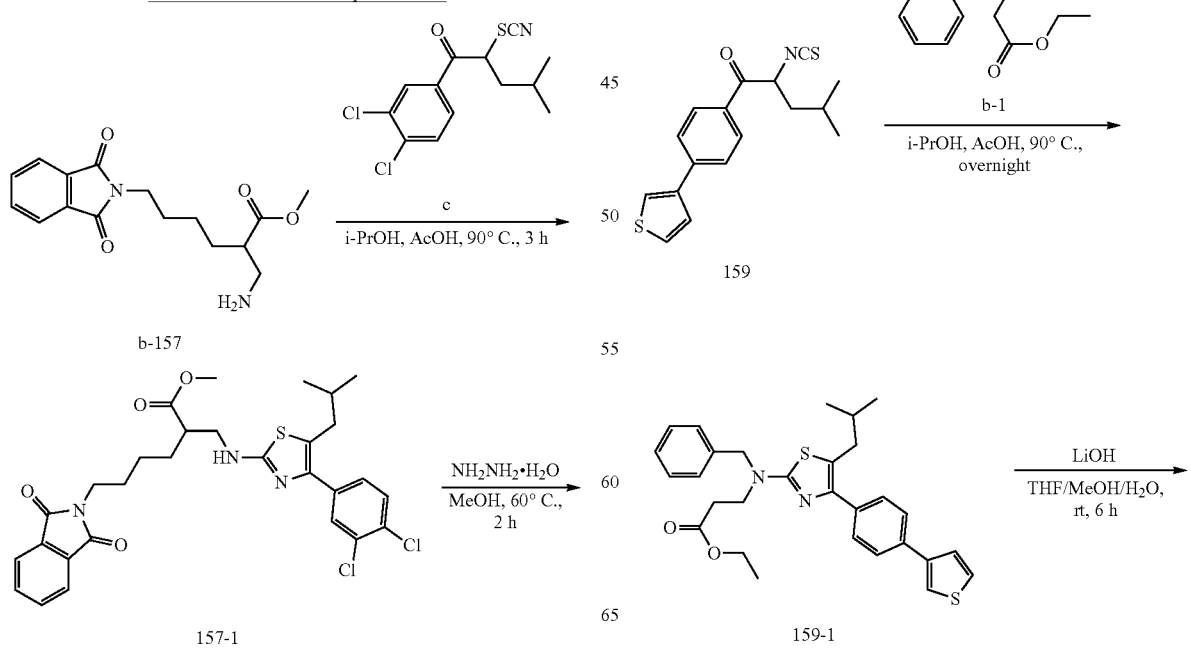

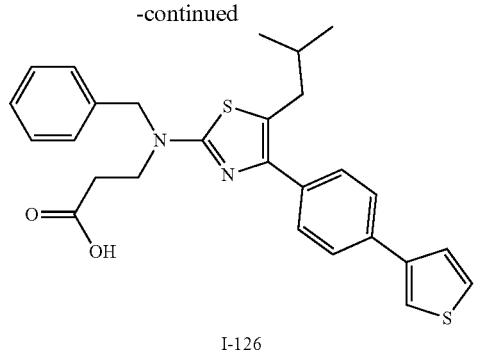
I-126
The same synthesis method used for other compounds I-127, I-150 to I-158, I-160, I-163, I-165, I-170.
Scheme 22: Route for Compound I-128
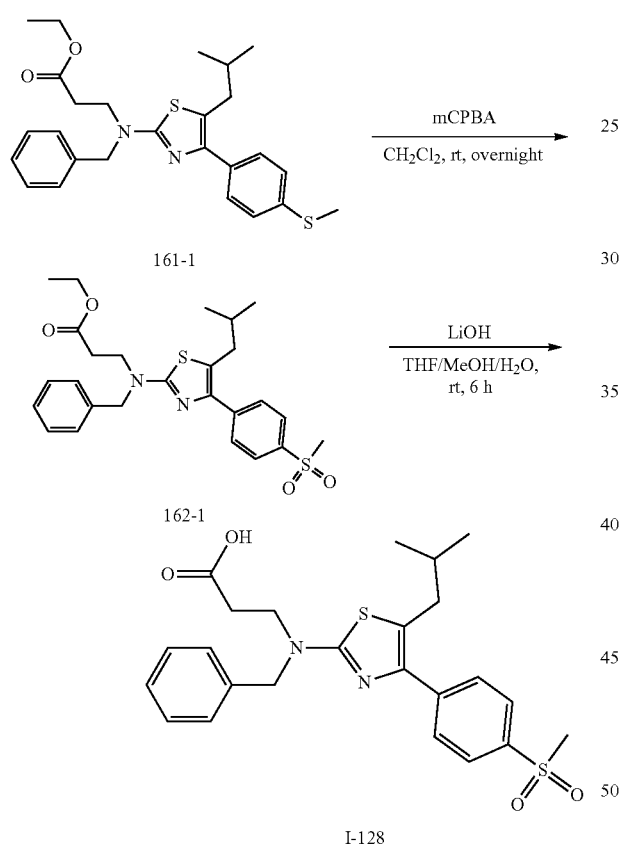
I-128
Scheme 23: Route for Compound I-129
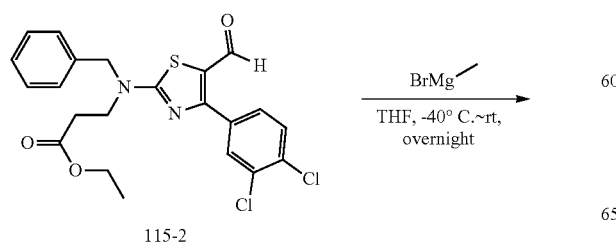
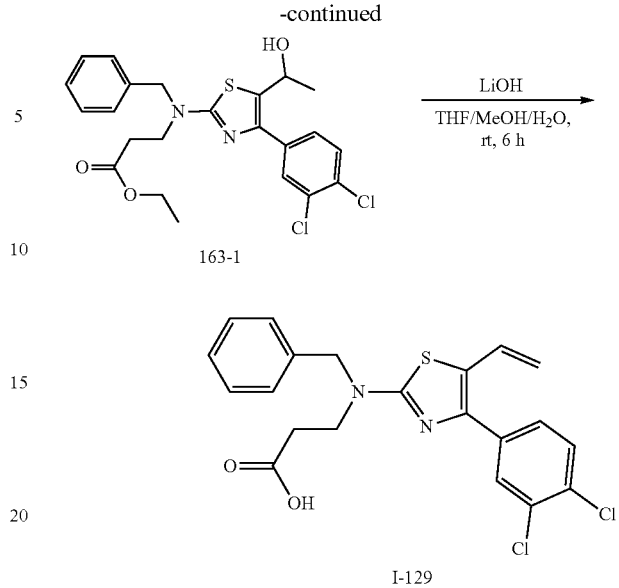
I-129
Scheme 24: Route for Compounds I-131, I-132, I-134, I-135, I-192
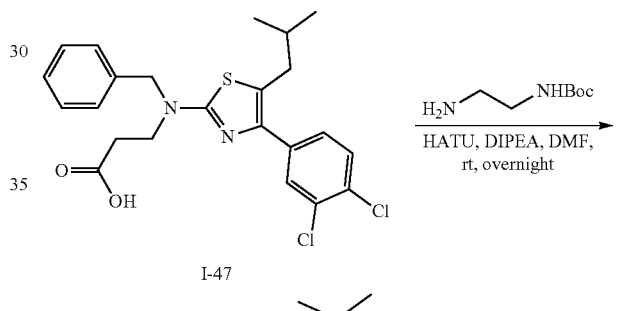
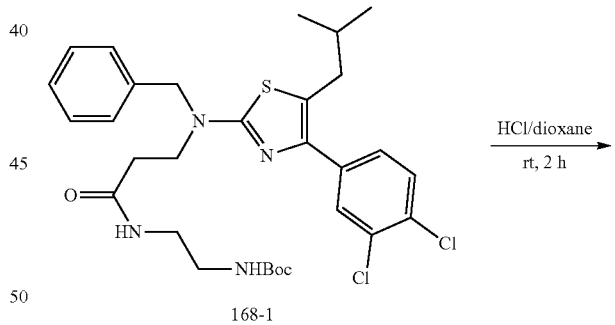
168-1
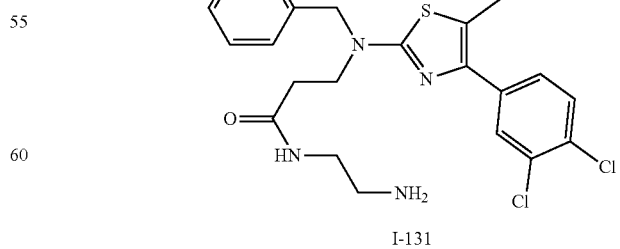
I-131
The same synthesis method used for other compounds I-132, I-134, I-135, I-192.

Scheme 25: Route for Compounds I-133, I-189, I-193 to I-195
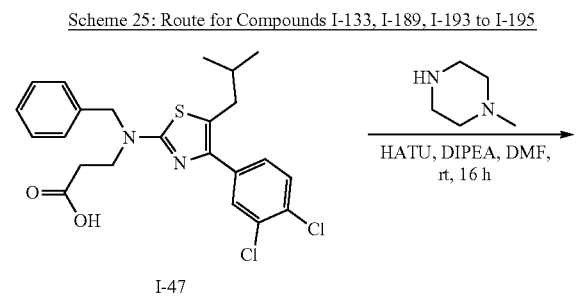
I-47
I-133
The same synthesis method used for other compounds I-189, I-193 to I-195.
Scheme 27: Route for Compound I-137, I-190
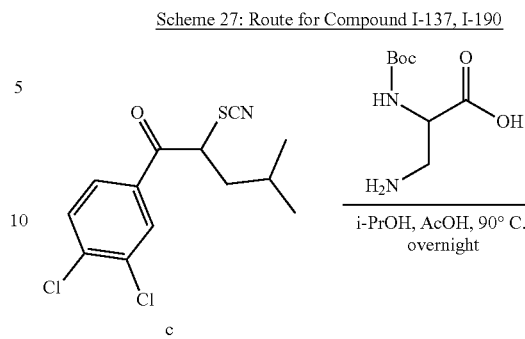
I-137
The same synthesis method used for other compounds I-190.
Scheme 26: Route for Compounds I-136, I-140
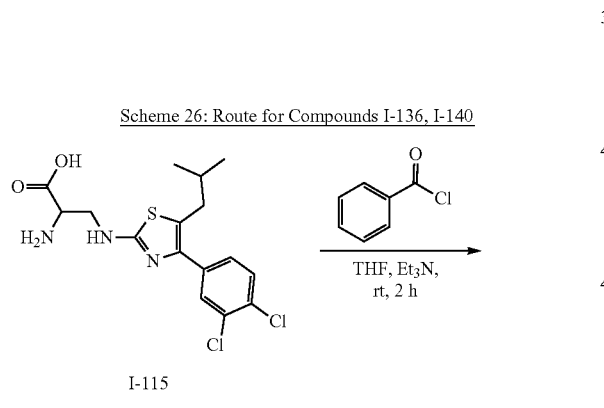
I-115
I-136
The same synthesis method used for other compounds I-140.
Scheme 28: Route for Compound I-138
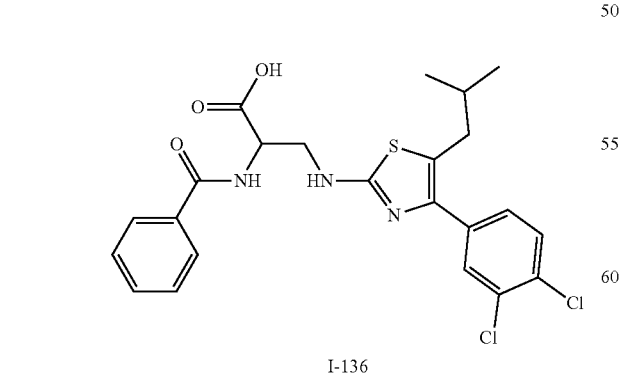
I-115
I-138

Scheme 29: Route for Compound I-139
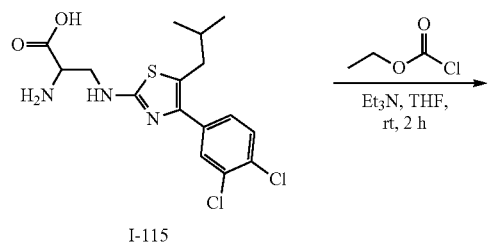
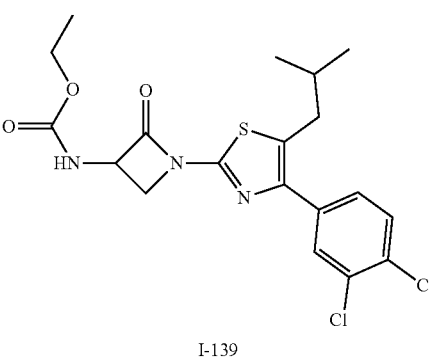
Scheme 30: Route for Compound I-141
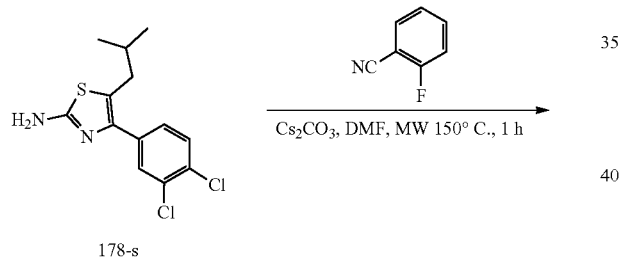
Scheme 31: Route for Compound I-142
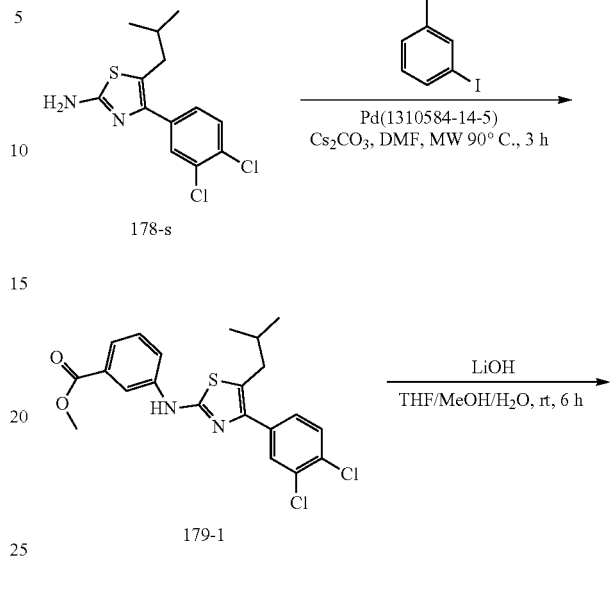
Scheme 32: Route for Compounds I-143, I-144
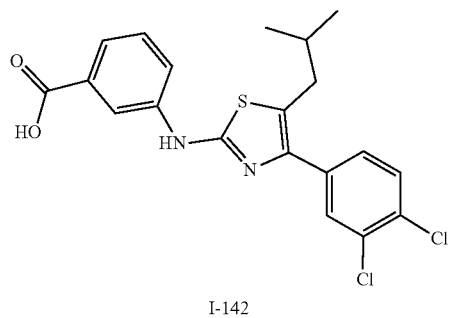
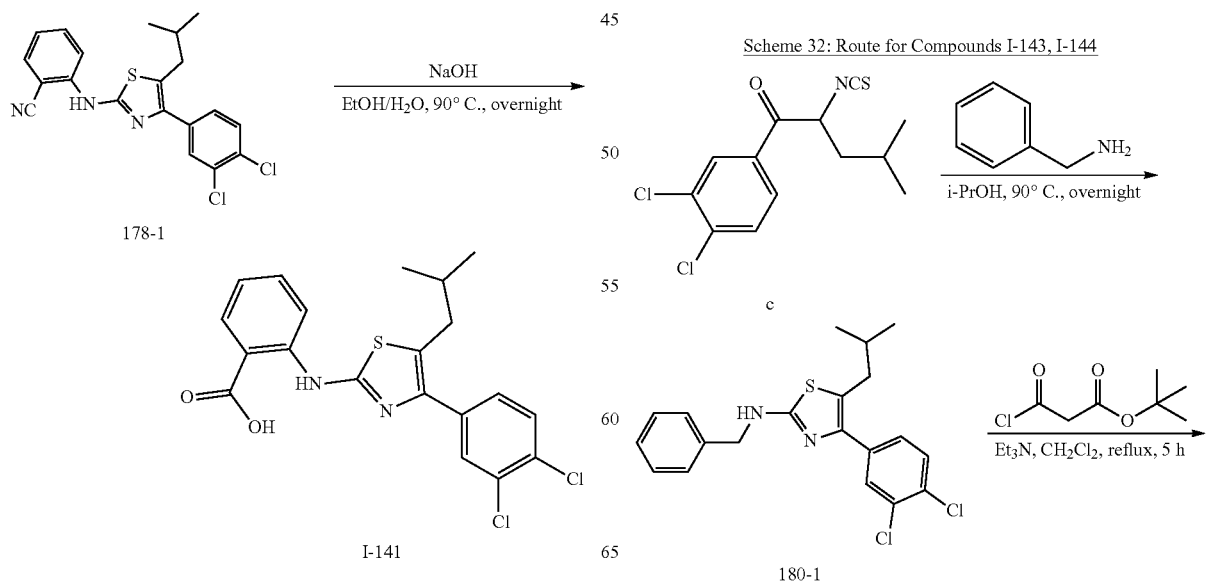

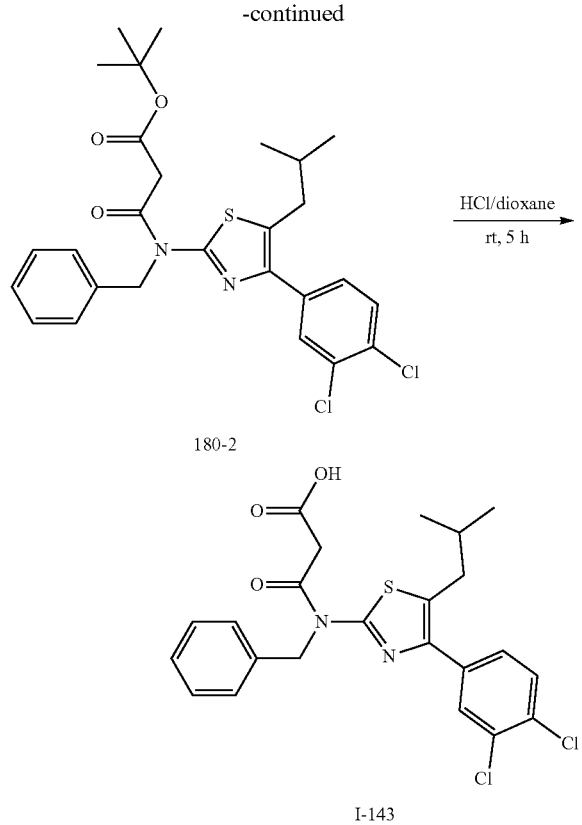
I-143
The same synthesis method used for other compounds I-144
Scheme 33: Route for Compound I-145
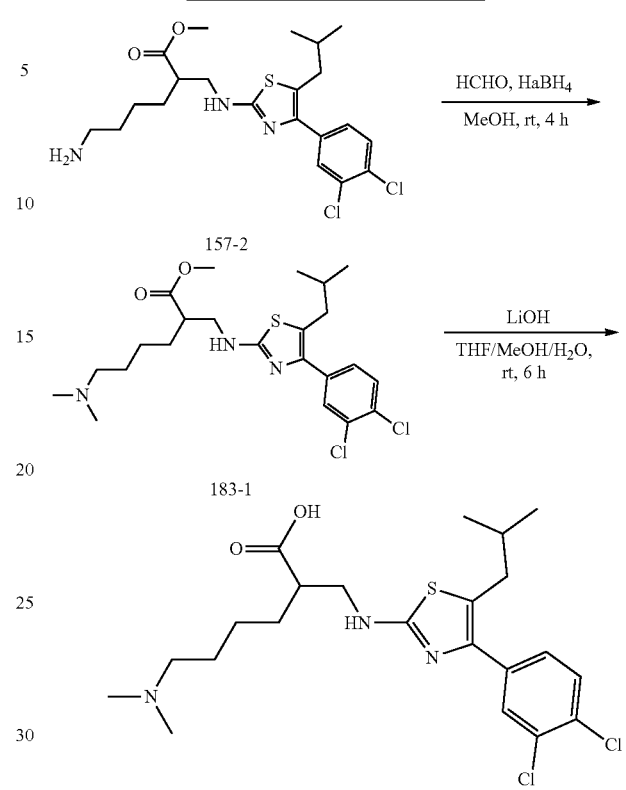
I-145
Scheme 34: Route for Compounds I-146, I-148
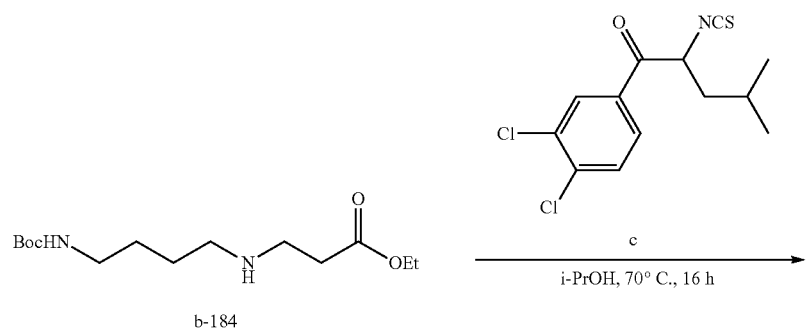
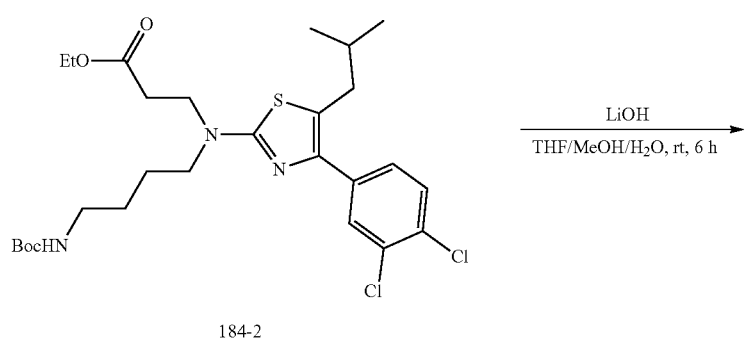

-continued
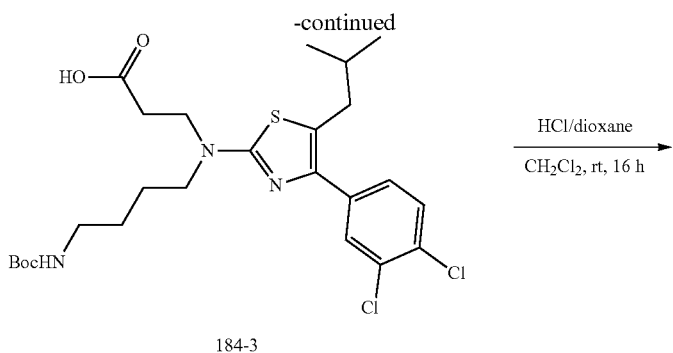
184-3
HCl/dioxane
CH₂Cl₂, rt, 16 h
I-146
The same synthesis method used for other compounds I-148.
Scheme 35: Route for Compounds I-147, I-149
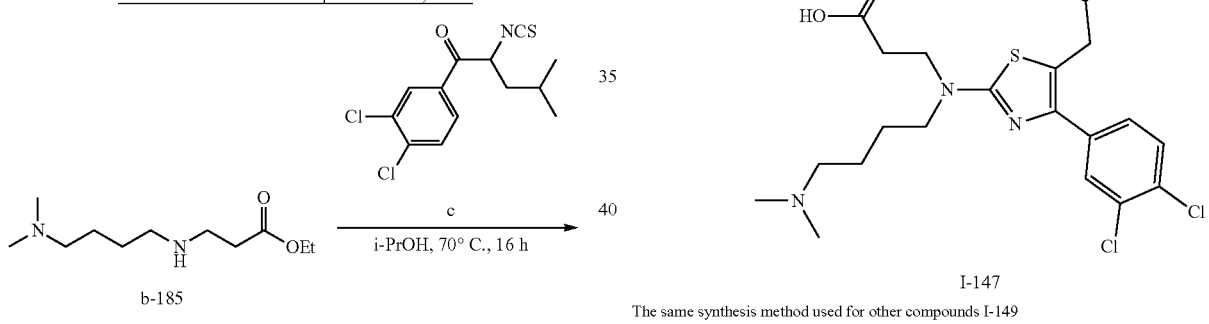
b-185
c
i-PrOH, 70° C., 16 h
I-147
The same synthesis method used for other compounds I-149
Scheme 36: Route for Compounds I-159, I-162, I-164
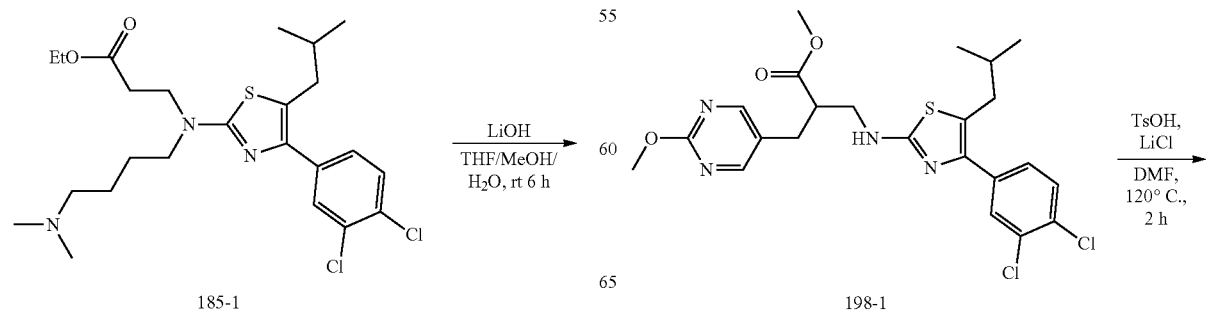
185-1
LiOH
THF/MeOH/
H₂O, rt 6 h
198-1
TsOH,
LiCl
DMF,
120° C.,
2 h 345
-continued
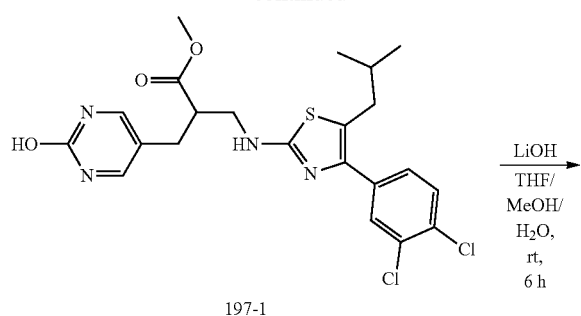
197-1
LiOH
THF/
MeOH/
H$_2$O,
rt,
6 h
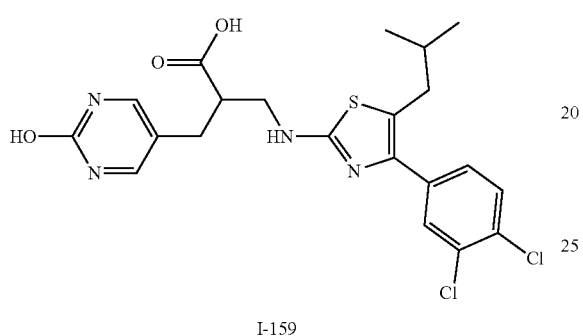
I-159
The same synthesis method used for other compounds I-162, I-164.
Scheme 37: Route for Compounds I-166 to I-167
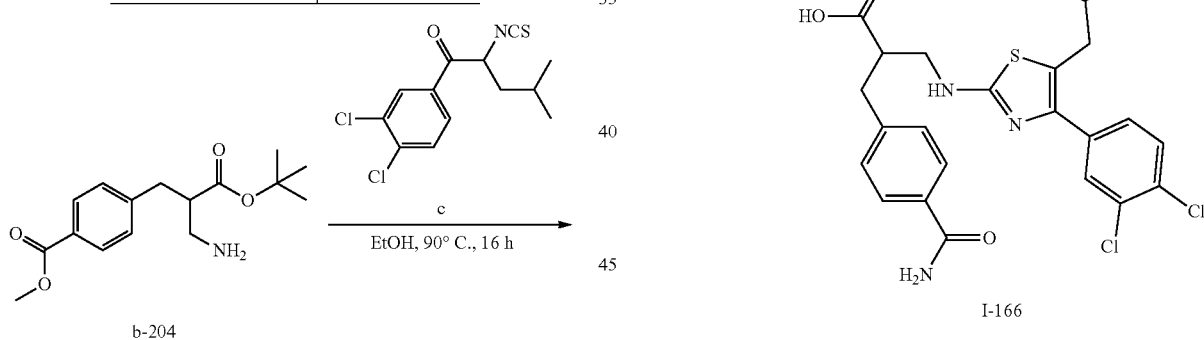
b-204
c
EtOH, 90° C., 16 h
204-1
LiOH
MeOH/
H$_2$O,
rt,
2 h
346
-continued
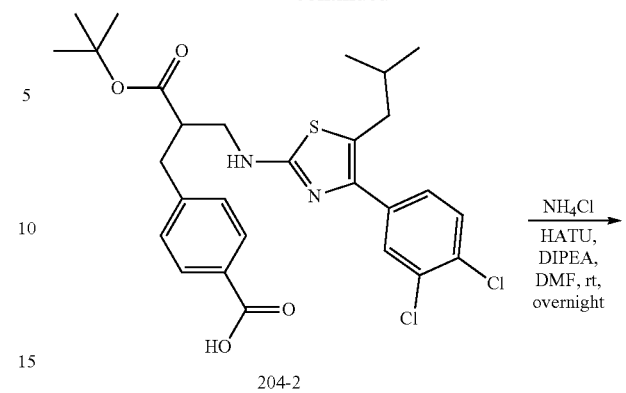
204-2
NH$_4$Cl
HATU,
DIPEA,
DMF, rt,
overnight
204-3
HCl/
dioxane
rt, 5 h
I-166
The same synthesis method used for other compounds I-167
Scheme 38: Route for Compounds I-168 to I-169
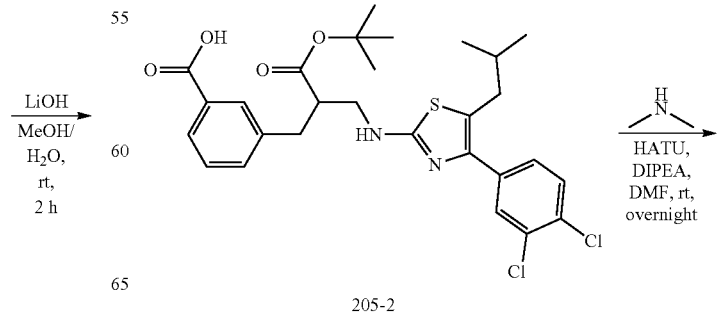
205-2
HATU,
DIPEA,
DMF, rt,
overnight
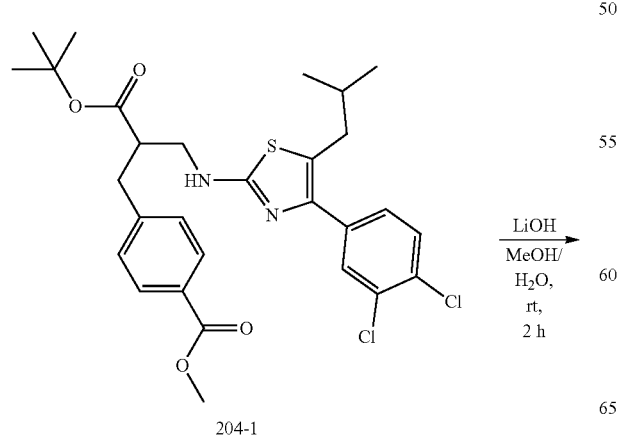

347
-continued
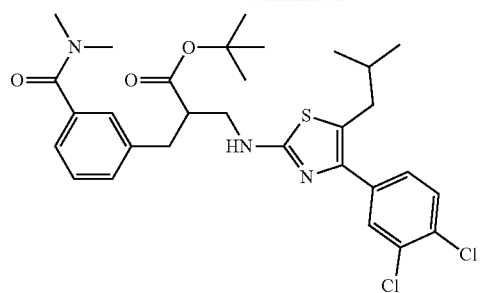
206-1
→ HCl/dioxane
rt, 5 h
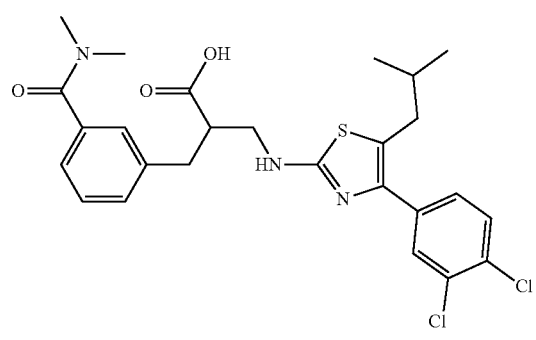
I-168
The same synthesis method used for other compounds I-169
Scheme 39: Route for Compound I-181
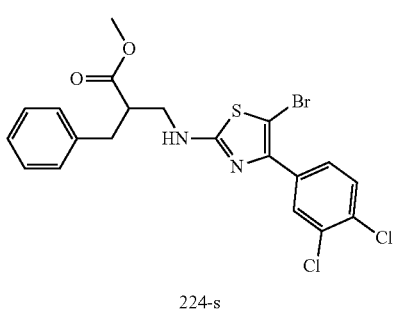
224-s
→ (Boc)₂O, DMAP
THF, rt, 2 h
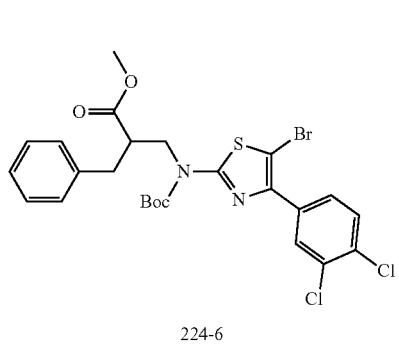
224-6
→ NaSMe
DMF, 60° C., 1 h
348
-continued
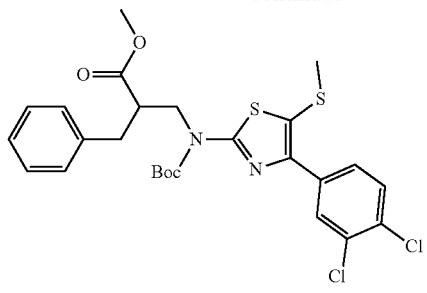
221-1
→ HCl/dioxane
rt, 5 h
(221-2 structure)
221-2
→ mCPBA
CH₂Cl₂, rt, 3 h
221-3
→ LiOH
THF/MeOH/H₂O, rt, 6 h
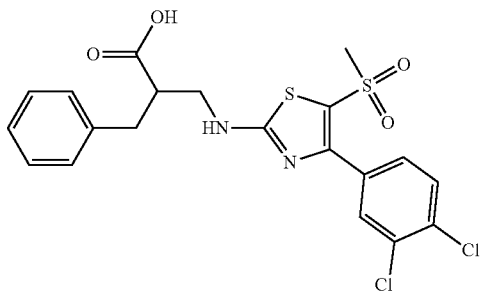
I-181

Scheme 40: Route for Compounds I-182, I-183
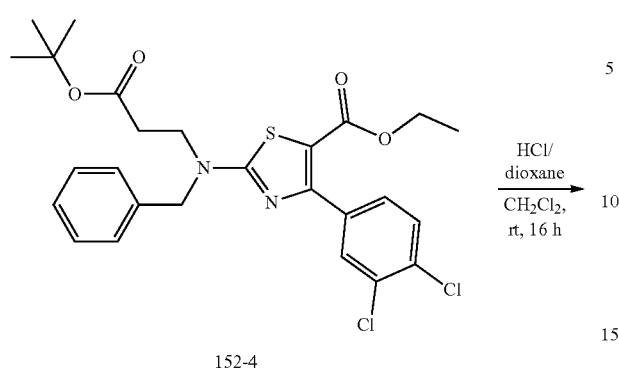
152-4
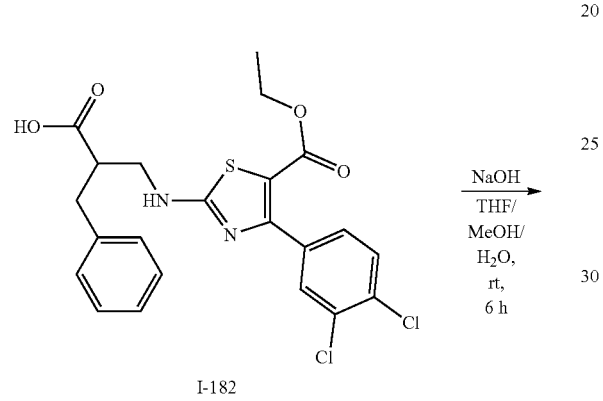
I-182
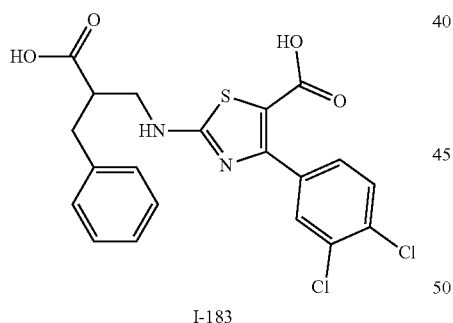
I-183
Scheme 41: Route for Compound I-184
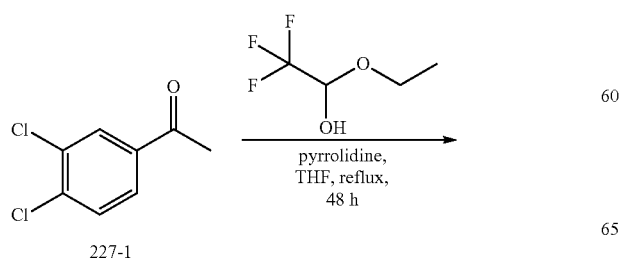
227-1
-continued
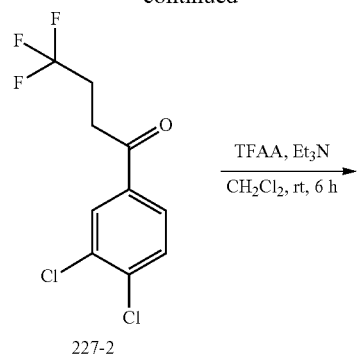
227-2
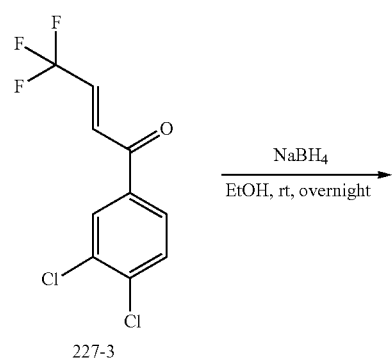
227-3
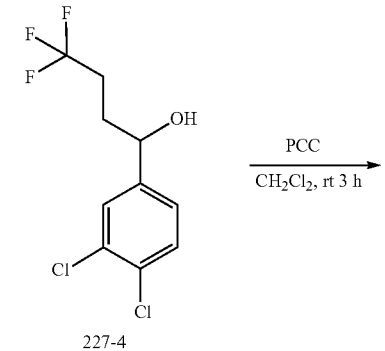
227-4
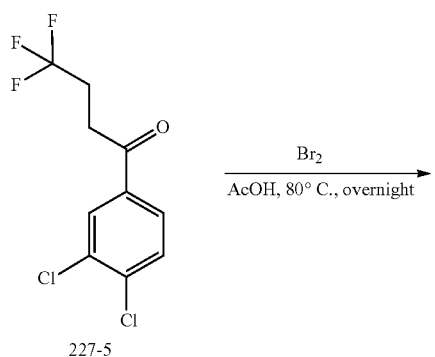
227-5

351
-continued
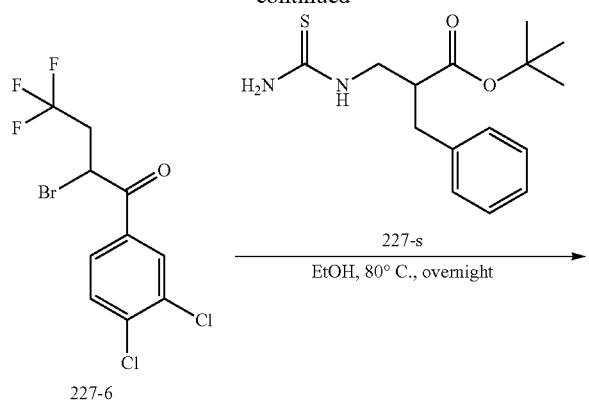
227-6
352
-continued
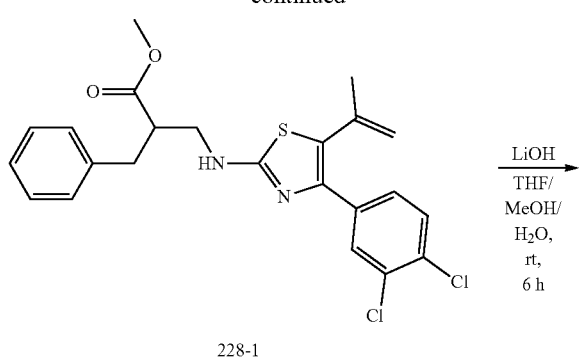
228-1
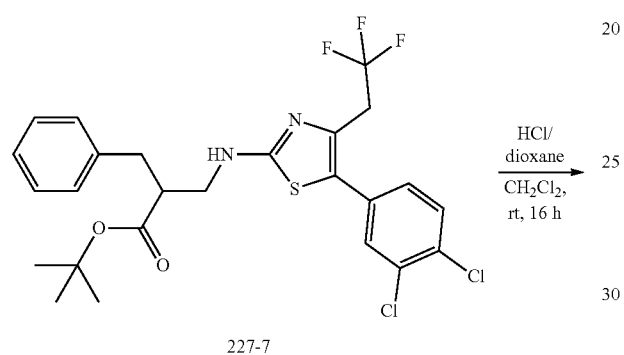
227-7
I-185
I-184
Scheme 43: Route for Compound I-186
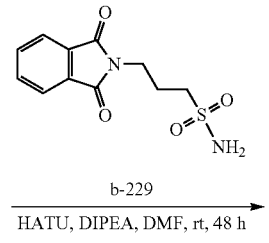
I-47
Scheme 42: Route for Compound I-185
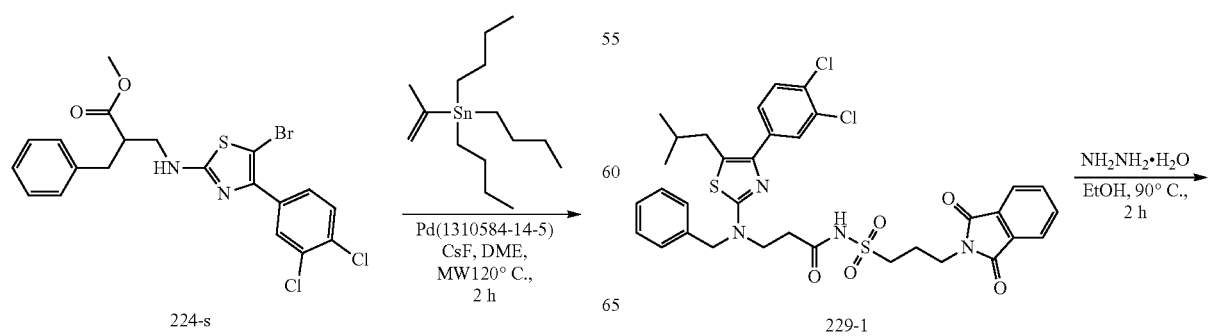
224-s
229-1

-continued
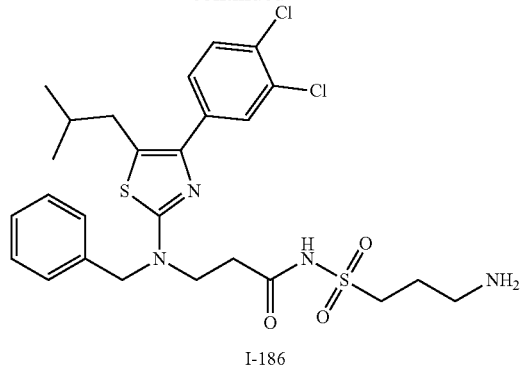
I-186
Scheme 44: Route for Compounds I-187, I-188
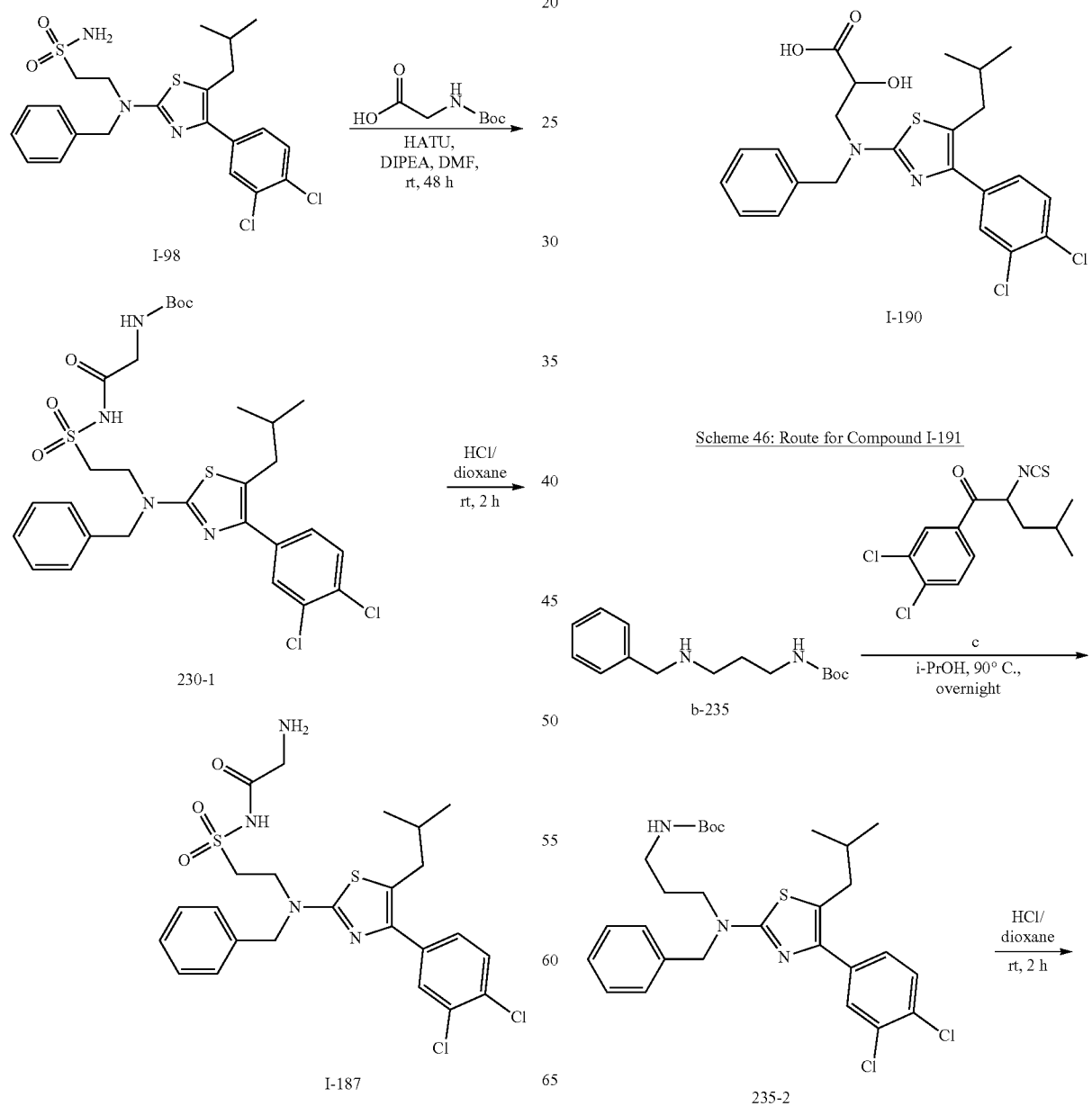
Scheme 45: Route for Compound I-190
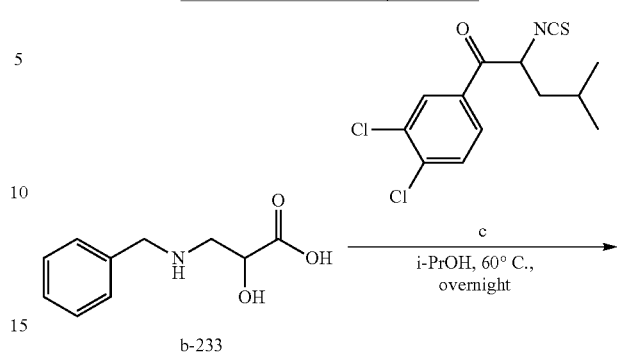
Scheme 46: Route for Compound I-191
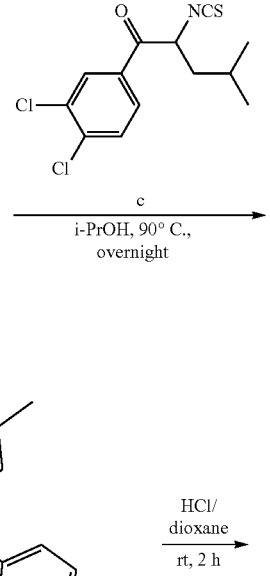

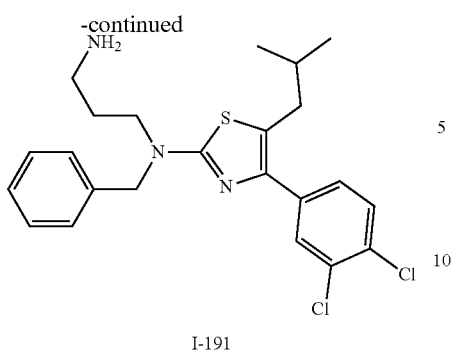
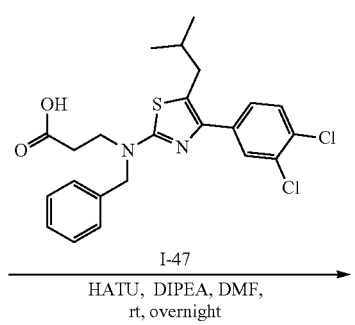
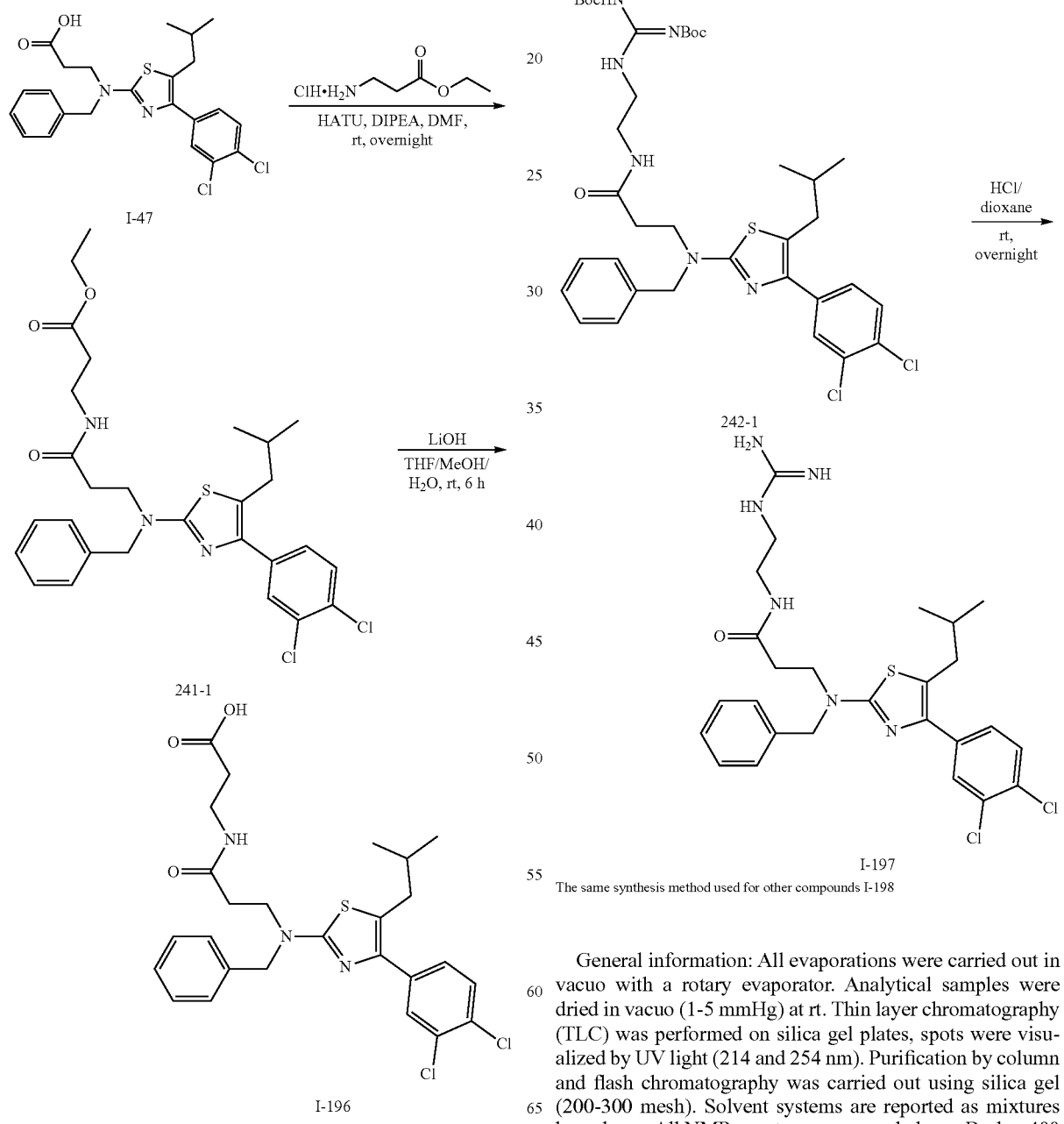

Scheme 47: Route for Compound I-196

Scheme 48: Route for Compounds I-197 to I-198

The same synthesis method used for other compounds I-198

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [CH₃CN+0.05% TFA] to 0% [water+0.05% TFA] and 100% [CH₃CN+0.05% TFA] in 0.8 min, then under this condition for 0.4 min, finally changed to 95% [water+0.05% TFA] and 5% [CH₃CN+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.)

Synthesis of 1-(3,4-dichlorophenyl)-4-methylpentan-1-one (c-1)

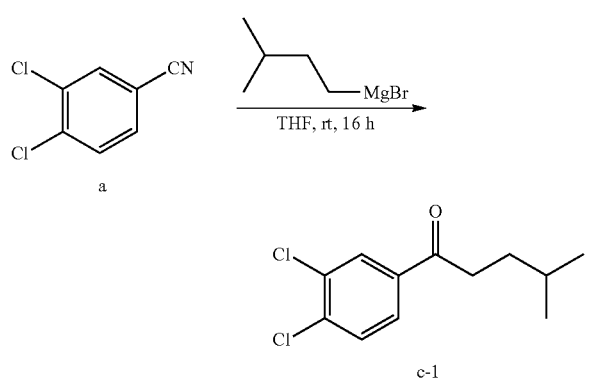

To a solution of a (25.0 g, 145 mmol) in THF (200 mL) was added isobutyl magnesium bromide (1.0 M in THF, 218 mL, 218 mmol). The reaction was stirred at room temperature for 16 h. When the reaction was completed, it was poured into aq.NH₄Cl (sat., 500 mL) and extracted with EtOAc (200 mL×3). The organic phase was combined, and washed with H₂O (100 mL) and brine (80.0 mL), then dried with anhydrous Na₂SO₄, concentrated and purified by silica gel column chromatography (petrol ether/ethyl acetate=100/1) to afford c-1 (15.0 g, 42% yield) as yellow oil.

Synthesis of 2-bromo-1-(3,4-dichlorophenyl)-4-methylpentan-1-one (c-2)

A mixture of c-1 (15.0 g, 61.2 mmol) and PTAT (34.4 g, 91.8 mmol) in THF (300 mL) was stirred at room temperature for 16 h. When the reaction was completed, it was concentrated, and the residual was dissolved in H₂O (300 mL), and then extracted with EtOAc (200 mL×3). The organic layer was combined, and washed with H₂O (100 mL×2) and Brine (100 mL), then dried by anhydrous Na₂SO₄. The solution was concentrated to give the crude product, which was used directly in next step without farther purification to afford c-2 (20.0 g, 100% yield) as brown oil.

Synthesis of 1-(3,4-dichlorophenyl)-4-methyl-2-thiocyanatopentan-1-one (c)

A mixture of c-2 (20.0 g, 61.7 mmol) and NaSCN (10.0 g, 123 mmol) in EtOH (200 mL) was stirred at 100° C. for 6 h. When the reaction was completed, it was concentrated and purified by silica gel column chromatography (petrol ether/ethyl acetate=10/1) to afford c (6.90 g, 37% yield) as a white solid.

Synthesis of (E)-3-cyclopropyl-1-(3,4-dichlorophenyl)prop-2-en-1-one (219-2)

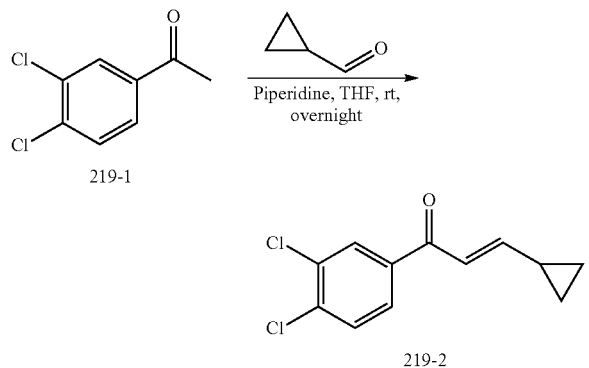

A mixture of 219-1 (1.00 g, 5.29 mmol), cyclopropanecarbaldehyde (370 mg, 5.29 mmol) and piperidine (5.0 mL) in THF (100 mL) was stirred at room temperature overnight. When the reaction was completed, it was concentrated and purified by silica gel column chromatography (petrol ether/ethyl acetate=100/1) to afford 219-2 (800 mg, 63% yield) as a yellow solid.

Synthesis of 3-cyclopropyl-1-(3,4-dichlorophenyl)propan-1-ol (219-3)

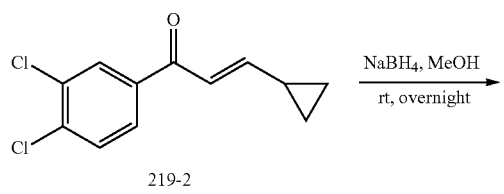

To a solution of 219-2 (800 mg, 3.32 mmol) in MeOH (50.0 mL) was added NaBH$_4$ (1.26 g, 33.2 mmol) at 0° C. The reaction was stirred at room temperature overnight. When the reaction was completed, it was concentrated, the residual was dissolved in H$_2$O (100 mL), and then extracted with EtOAc (50.0 mL×3). The organic layer was combined, and washed with H$_2$O (50.0 mL×2) and Brine (50.0 mL), then dried by anhydrous Na$_2$SO$_4$. The solution was concentrated to give the crude product, which was used directly in next step without farther purification to afford 219-3 (814 mg, 100% yield) as colorless oil.

Synthesis of 3-cyclopropyl-1-(3,4-dichlorophenyl)propan-1-one (219-4)

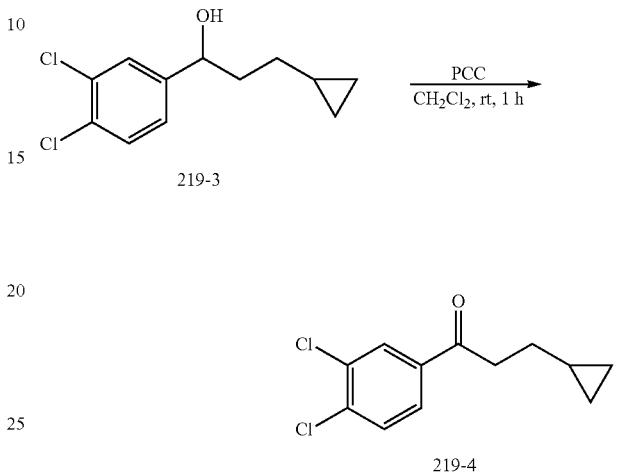

To a solution of 219-3 (814 mg, 3.32 mmol) in CH$_2$Cl$_2$ (100 mL) was added PCC (1.07 g, 4.98 mmol). The reaction was stirred at room temperature for 1 h. When the reaction was completed, it was concentrated, and purified by silica gel column chromatography (petrol ether/ethyl acetate=300/1) to afford 219-4 (400 mg, 46% yield) as a yellow solid.

Synthesis of 2-bromo-3-cyclopropyl-1-(3,4-dichlorophenyl)propan-1-one (219-5)

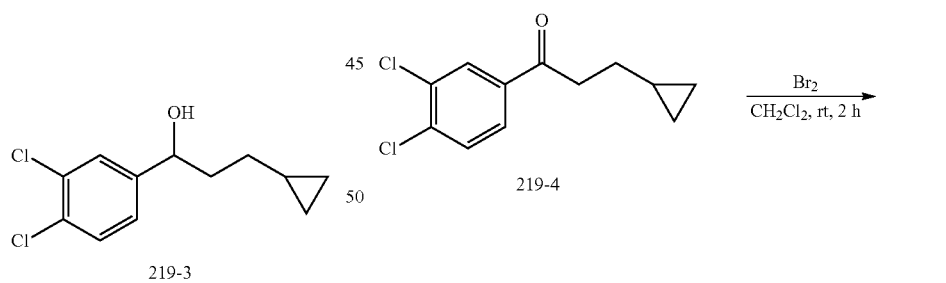

To a solution of 219-4 (400 mg, 1.65 mmol) in CH$_2$Cl$_2$ (100 mL) was added Br$_2$ (320 mg, 1.97 mmol). The reaction was stirred at room temperature for 2 h. When the reaction was completed, it was washed with H$_2$O (100 mL×2) and Brine (100 mL), and then dried by anhydrous Na₂SO₄. The solution was concentrated to give the crude product, which was used directly in next step without farther purification to afford 219-5 (530 mg, 100% yield) as yellow oil.

Synthesis of 3-cyclopropyl-1-(3,4-dichlorophenyl)-2-thiocyanatopropan-1-one (219)

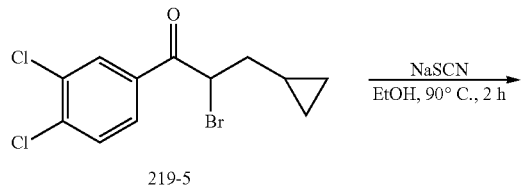

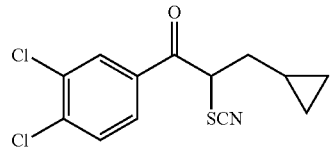

A mixture of 219-5 (530 mg, 1.65 mmol) and NaSCN (266 mg, 3.29 mmol) in EtOH (20.0 mL) was stirred at 90° C. for 2 h. When the reaction was completed, it was concentrated and purified by silica gel column chromatography (petrol ether/ethyl acetate=20/1) to afford 219 (160 mg, 3200 yield) as a yellow solid.

TABLE 3-1

Characterization Data for Compounds

| # | Chemical Structure | LCMS |
|---|---|---|
| c | (3,4-dichlorophenyl ketone with SCN and isobutyl) | Method B, Purity is 75.2%, Rt = 2.480 min; MS Calcd.: 301.0; MS Found: 324.1 [M + Na]⁺. |
| 115 | (3,4-dichlorophenyl ketone with CH₂SCN) | No MS Data. |
| 159 | (4-chlorophenyl ketone with SCN and isobutyl) | No MS Data. |
| 161 | (4-methylthiophenyl ketone with SCN and isobutyl) | Method A, Purity is 94.4%, Rt = 0.837 min; MS Calcd.: 279.1; MS Found: 280.0 [M + H]⁺. |
| 217 | (cyclopentyl, 3,4-dichlorophenyl ketone with SCN) | Method B, Purity is 67.3%, Rt = 2.176 min; MS Calcd.: 313.0; No MS Found. |
| 218 | (cyclobutyl, 3,4-dichlorophenyl ketone with SCN) | No MS Data. |

TABLE 3-1-continued

Characterization Data for Compounds

| # | Chemical Structure | LCMS |
|---|---|---|
| 219 | 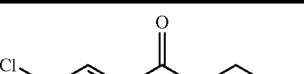 | Method B, Purity is 68.7%, Rt = 1.823 min; MS Calcd.: 299.0; No MS Found. |
| 220 | 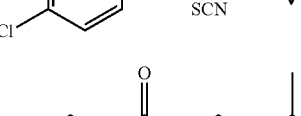 | Method B, Purity is 78.1%, Rt = 2.226 min; MS Calcd.: 315.0; MS Found: 316.0 [M + H]+. |

Synthesis of 2-(4-bromobutyl)isoindoline-1,3-dione (157-2)

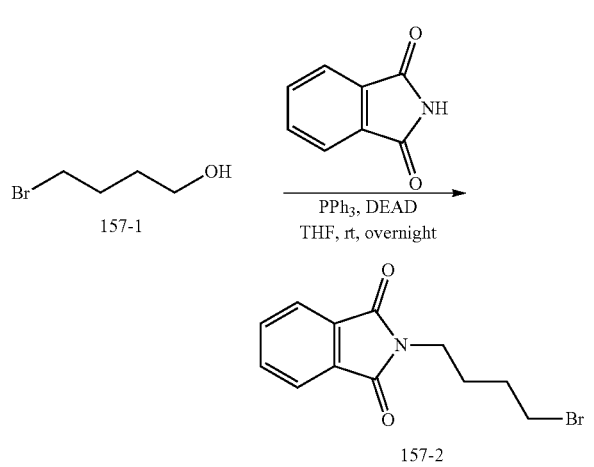

A mixture of 157-1 (1.00 g, 6.54 mmol), isoindoline-1,3-dione (1.44 g, 9.80 mmol), PPh₃ (2.57 g, 9.80 mmol) and DEAD (1.71 g, 9.80 mmol) in THF (100 mL) was stirred at room temperature overnight. When the reaction was completed, it was concentrated and purified by silica gel column chromatography (petrol ether/ethyl acetate=50/1) to afford 157-2 (700 mg, 63% yield) as a white solid.

Synthesis of methyl 2-cyano-6-(1,3-dioxoisoindolin-2-yl)hexanoate (157-3)

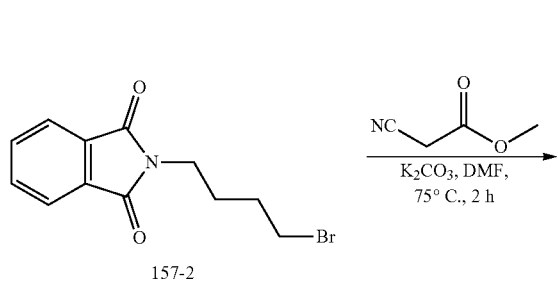

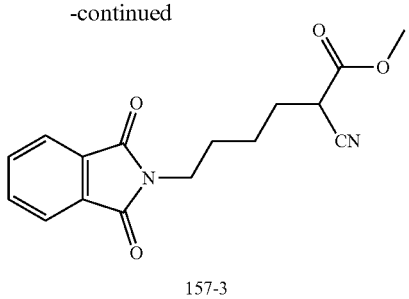

A mixture of 157-2 (500 mg, 1.78 mmol), methyl 2-cyanoacetate (351 mg, 3.55 mmol) and K₂CO₃ (368 mg, 2.67 mmol) in DMF (10.0 mL) was stirred at 75° C. for 2 h. When the reaction was completed, it was poured into H₂O (100 mL), and then extracted with EtOAc (50.0 mL×2). The organic layer was combined, and washed with H₂O (50.0 mL×2) and Brine (50.0 mL), then dried by anhydrous Na₂SO₄. The solution was concentrated and purified by silica gel column chromatography (petrol ether/ethyl acetate=20/1) to afford 157-3 (400 mg, 51% yield) as a yellow solid.

Synthesis of methyl 2-(aminomethyl)-6-(1,3-dioxoisoindolin-2-yl)hexanoate (b-157)

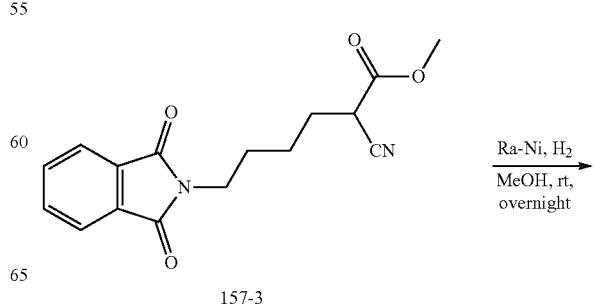

-continued

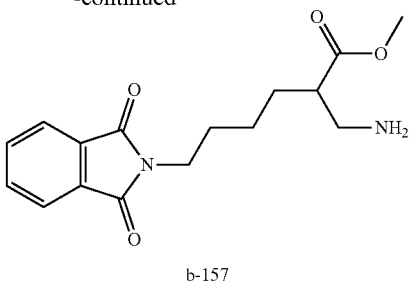

b-157

A mixture of 157-3 (400 mg, 1.32 mmol) and Raney Ni (200 mg) in MeOH (50.0 mL) was stirred under $H_2$ atmosphere at room temperature overnight. When the reaction was completed, the mixture was filtered, and the filtrate was concentrated to give a crude product, which was purified by silica gel column chromatography ($CH_2Cl_2$/MeOH=50/1) to afford b-157 (250 mg, 49% yield) as yellow oil.

Synthesis of ethyl 3-(4-(tert-butoxycarbonylamino)butylamino)propanoate (b-184)

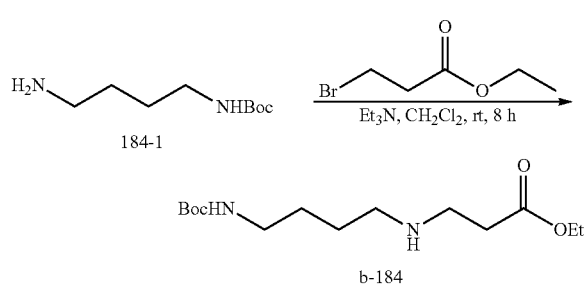

A mixture of 184-1 (1.00 g, 5.31 mmol), ethyl 3-bromopropanoate (1.15 g, 6.37 mmol) and $Et_3N$ (1.07 g, 10.6 mmol) in $CH_2Cl_2$ (100 mL) was stirred at room temperature for 8 h. When the reaction was completed, it was concentrated and purified by silica gel column chromatography (petrol ether/ethyl acetate=1/1) to afford b-184 (310 mg, 20% yield) as colorless oil.

Synthesis of (Z)-methyl 2-cyano-3-phenylacrylate (1-2)

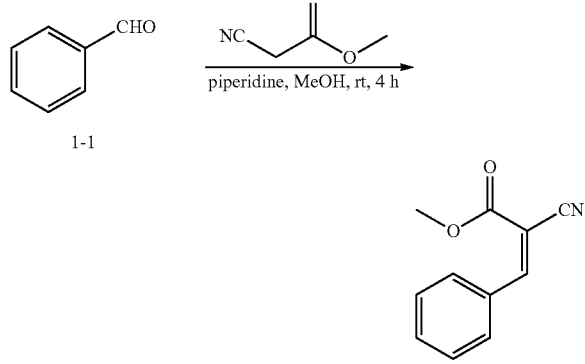

To a mixture of 1-1 (5.00 g, 47.2 mmol) an methyl 2-cyanoacetate (5.61 g, 56.6 mmol) in MeOH (100 mL) was added piperidine (5 drops). The reaction was stirred at room temperature for 4 h. When the reaction was completed, the reaction mixture was filtered, and the residue was washed with MeOH (2.0 mL×2), dried to afford 1-2 (6.50 g, 74% yield) as a white solid.

Synthesis of methyl 3-amino-2-benzylpropanoate (1)

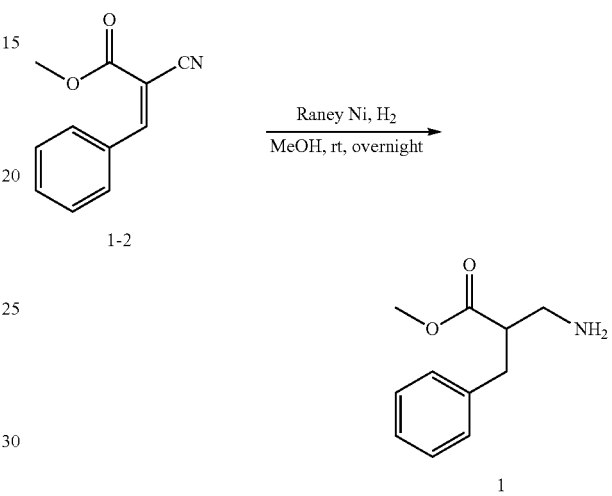

A mixture of 1-2 (6.50 g, 34.7 mmol) and Raney Ni (2.00 g) in MeOH (800 mL) was stirred under $H_2$ atmosphere at room temperature overnight. When the reaction was completed, the mixture was filtered, and the filtrate was concentrated to give a crude product, which was purified by silica gel column chromatography ($CH_2Cl_2$/MeOH=50/1) to afford 1 (550 mg, 7.5% yield) as colorless oil.

Synthesis of 1-tert-butyl 3-methyl 4-phenylpiperazine-1,3-dicarboxylate (208-2)

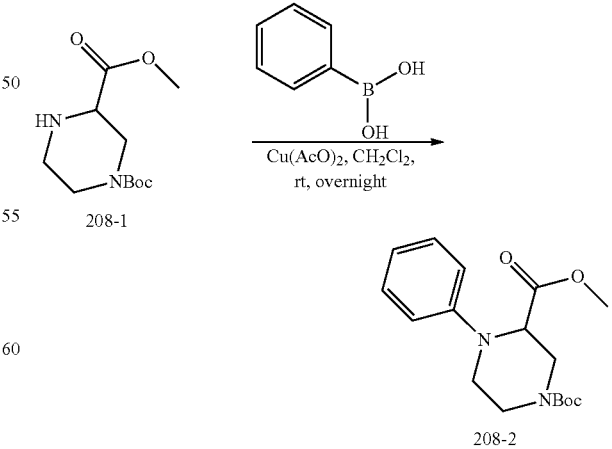

A mixture of 208-1 (1.00 g, 4.09 mmol), phenylboronic acid (749 mg, 6.14 mmol) and $Cu(AcO)_2$ (74.5 mg, 0.41 mmol) in CH$_2$Cl$_2$ (50.0 mL) was stirred at room temperature overnight. When the reaction was completed, it was concentrated and purified by silica gel column chromatography (petrol ether/ethyl acetate=20/1) to afford 208-2 (100 mg, 7.6% yield) as yellow oil.

Synthesis of methyl 1-phenylpiperazine-2-carboxylate (b-208)

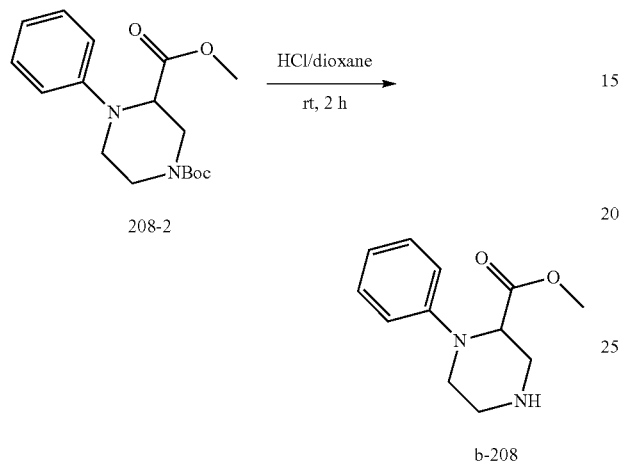

A mixture of 208-2 (100 mg, 0.31 mmol) in HCl (4.0 M in dioxane, 10.0 mL) was stirred at room temperature for 2 h. When the reaction was completed, it was concentrated, the residual was dissolved in H$_2$O (20.0 mL), and then washed with MTBE (20.0 mL×3). The aqueous layer was adjusted to pH=8 with aq. NaHCO$_3$, then extracted with EtOAc (20.0 mL×3), The organic layer was combined, and dried by anhydrous Na$_2$SO$_4$, then concentrated to afford b-208 (600 mg, 94% yield) as yellow oil.

Synthesis of 3-cyanobenzenesulfonamide (213-2)

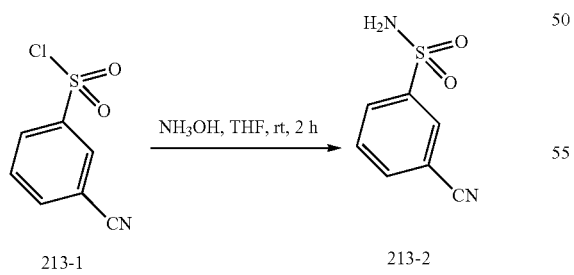

To a solution of 213-1 (2.00 g, 9.92 mmol) in THF (20.0 mL) was added NH$_3$OH (20.0 mL). The reaction was stirred at room temperature for 2 h. When the reaction was completed, it was concentrated to give the crude product, which was used directly in next step without farther purification to afford 213-2 (2.00 g, 100% yield) as a white solid.

Synthesis of 3-formylbenzenesulfonamide (213-3)

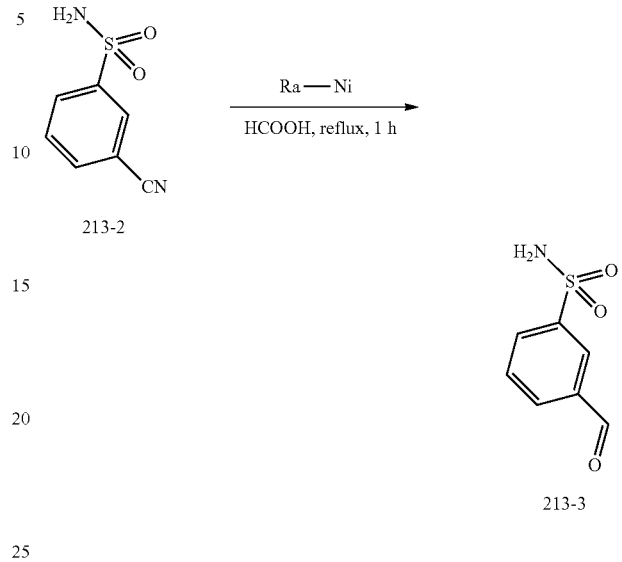

A mixture of 213-2 (2.00 g, 10.9 mmol) and Raney Ni (2.00 g) in HCOOH (800 mL) was refluxed under H$_2$ atmosphere for 1 h. When the reaction was completed, the mixture was cooled to room temperature and filtered, and the filtrate was concentrated to give a crude product, which was purified by silica gel column chromatography (petrol ether/ethyl acetate=10/1) to afford 213-3 (1.70 g, 76% yield) as a white solid.

Synthesis of (E)-methyl 2-cyano-3-(3-sulfamoylphenyl)acrylate (213-4)

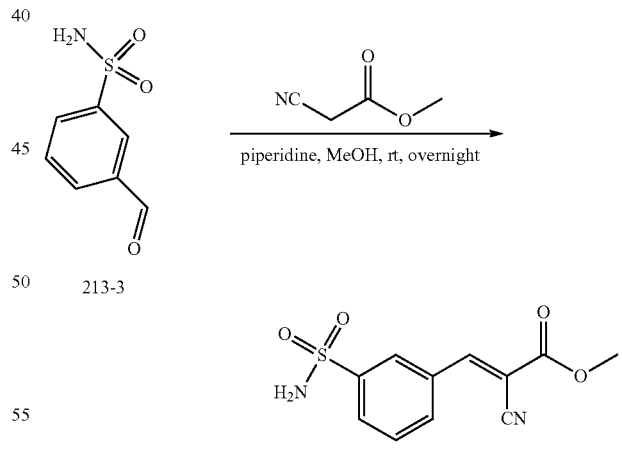

To a mixture of 213-3 (880 mg, 4.75 mmol) and methyl 2-cyanoacetate (471 mg, 4.75 mmol) in MeOH (50 mL) was added piperidine (0.3 mL). The reaction was stirred at room temperature overnight. When the reaction was completed, the reaction mixture was filtered, and the residue was washed with MeOH (2.0 mL×2), dried to afford 213-4 (1.20 g, 95% yield) as a yellow solid.

Synthesis of methyl 3-amino-2-(3-sulfamoylbenzyl)propanoate (b-213)

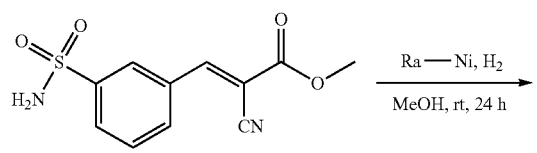

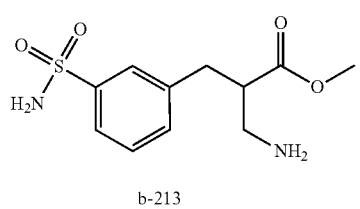

A mixture of 213-4 (1.20 g, 4.51 mmol) and Raney Ni (1.20 g) in MeOH (400 mL) was stirred under H$_2$ atmosphere at room temperature for 24 h. When the reaction was completed, the mixture was filtered, and the filtrate was concentrated to give a crude product, which was purified by silica gel column chromatography (CH$_2$Cl$_2$/MeOH=50/1) to afford b-213 (260 mg, 21% yield) as yellow oil.

Synthesis of 3-(1,3-dioxoisoindolin-2-yl)propane-1-sulfonamide (b-229)

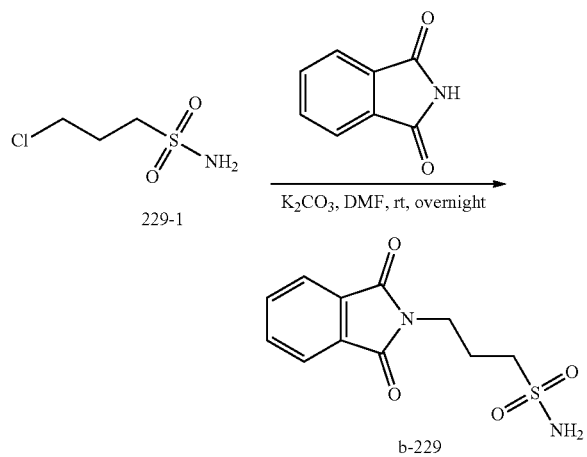

A mixture of 229-1 (400 mg, 2.54 mmol), isoindoline-1,3-dione (411 mg, 2.79 mmol) and K$_2$CO$_3$ (701 mg, 5.08 mmol) in DMF (10.0 mL) was stirred at room temperature overnight. When the reaction was completed, it was poured into H$_2$O (100 mL), and then extracted with EtOAc (50.0 mL×2). The organic layer was combined, and washed with H$_2$O (50.0 mL×2) and Brine (50.0 mL), then dried by anhydrous Na$_2$SO$_4$. The solution was concentrated and purified by silica gel column chromatography (CH$_2$Cl$_2$/MeOH=50/1) to afford b-229 (700 mg, 63% yield) as a white solid.

Synthesis of methyl 3-amino-2-hydroxypropanoate (233-2)

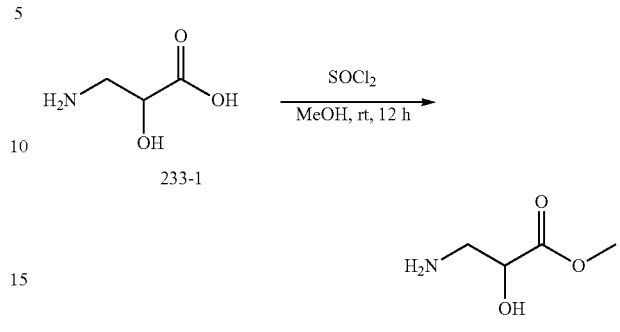

To a solution of 233-1 (1.00 g, 9.52 mmol) in MeOH (5.00 mL) was added SOCl$_2$ (2.0 mL) at 0° C. The reaction was stirred at room temperature for 12 h. When the reaction was completed, it was concentrated to afford 233-2 (1.20 g, 100% yield) as colorless oil.

Synthesis of 3-(benzylamino)-2-hydroxypropanoic acid (b-233)

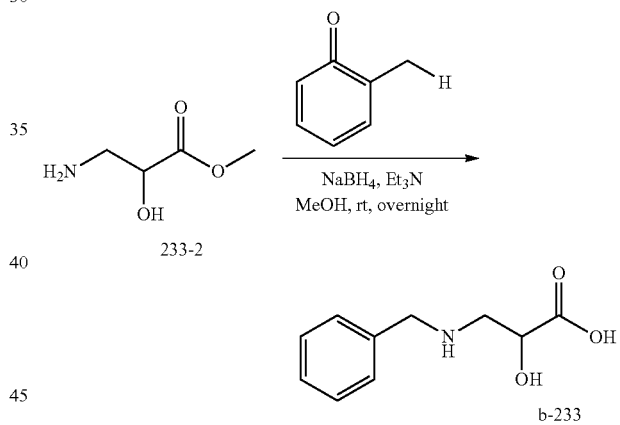

To a solution of 233-2 (1.20 g, 10.1 mmol), benzaldehyde (1.07 g, 10.1 mmol) and Et$_3$N (2.03 g, 20.1 mmol) in MeOH (50.0 mL) was added NaBH$_4$ (1.91 g, 50.4 mmol) at 0° C. The reaction was stirred at room temperature overnight. When the reaction was completed, it was concentrated and purified by silica gel column chromatography (CH$_2$Cl$_2$/MeOH=5/1) to afford 219-3 (1.00 g, 60% yield) as a white solid.

Synthesis of tert-butyl 3-(benzylamino)propylcarbamate (b-235)

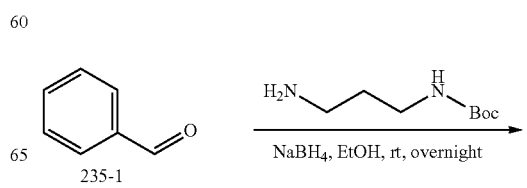

-continued

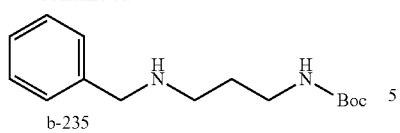
b-235

To a solution of 235-1 (1.00 g, 9.43 mmol) and tert-butyl 3-aminopropylcarbamate (1.81 g, 10.4 mmol) in EtOH (50.0 mL) was added NaBH$_4$ (358 mg, 9.43 mmol) at 0° C. The reaction was stirred at room temperature overnight. When the reaction was completed, it was concentrated and purified by silica gel column chromatography (CH$_2$Cl$_2$/MeOH=50/1) to afford b-235 (300 mg, 12% yield) as a yellow solid.

Synthesis of tert-butyl (2-aminoethylamino)(tert-butoxycarbonylamino)methylenecarbamate (b-242)

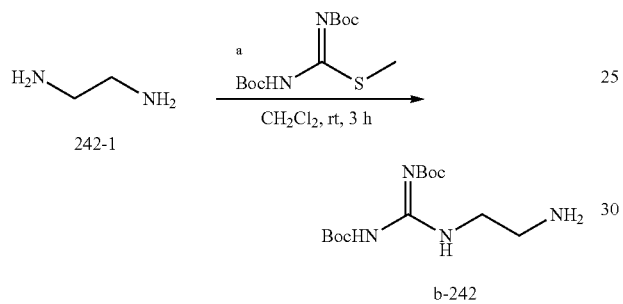

A mixture of 242-1 (60.0 mg, 1.00 mmol) and a (319 mg, 1.10 mmol) in CH$_2$Cl$_2$ (30.0 mL) was stirred at room temperature for 3 h. When the reaction was completed, the reaction mixture was filtered, and the residue was washed with CH$_2$Cl$_2$ (2.0 mL×2), dried to afford b-242 (300 mg, 90% yield) as a yellow solid.

Synthesis of tert-butyl 2-sulfamoylethylcarbamate (b-243)

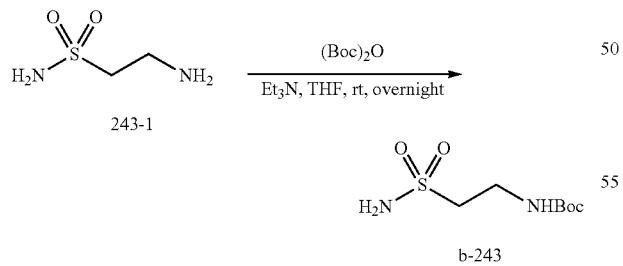

A mixture of 243-1 (200 mg, 1.61 mmol), (Boc)$_2$O (387 mg, 1.77 mmol) and Et$_3$N (325 mg, 3.22 mmol) in THF (10.0 mL) was stirred at room temperature overnight. When the reaction was completed, the reaction mixture was concentrated to give the crude product, which was used directly in next step without farther purification to afford b-243 (300 mg, 83% yield) as a yellow solid.

Synthesis of tert-butyl 3-(3-benzoylthioureido)-2-benzylpropanoate (152-2)

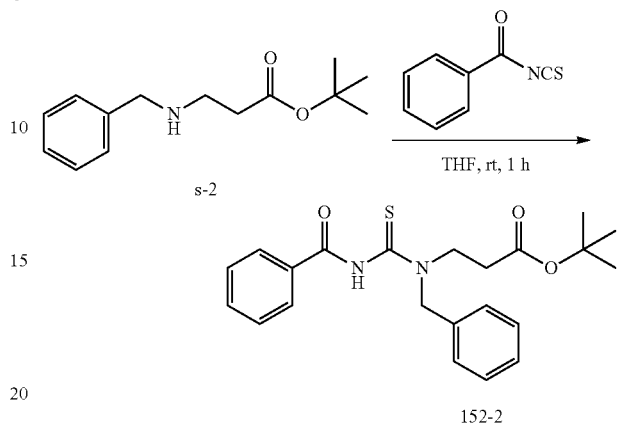

A mixture of s-2 (5.00 g, 21.2 mmol) and benzoic cyanic thioanhydride (4.19 g, 25.5 mmol) in THF (100 mL) was stirred at room temperature for 1 h. When the reaction was completed, the reaction mixture was filtered, and the residue was washed with CH$_2$Cl$_2$ (3.0 mL×2), dried to afford 152-2 (6.00 g, 71% yield) as a white solid.

Synthesis of tert-butyl 2-benzyl-3-thioureidopropanoate (152-s)

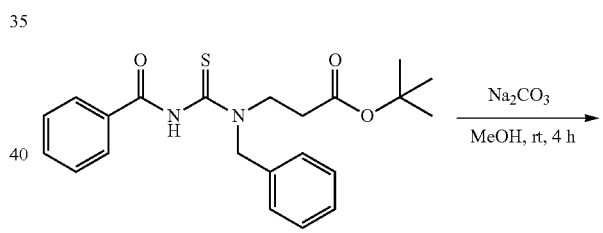

A mixture of 152-2 (6.00 g, 15.1 mmol) and Na$_2$CO$_3$ (3.19 g, 30.1 mmol) in MeOH (100 mL) was stirred at room temperature for 4 h. When the reaction was completed, the reaction mixture was filtered, and the filtrate was concentrated to give a crude product, which was purified by silica gel column chromatography (petrol ether/ethyl acetate=10/1) to afford 152-s (1.00 g, 23% yield) as a white solid.

Synthesis of 4-(3,4-dichlorophenyl)-5-isobutylthiazol-2-amine (178-s)

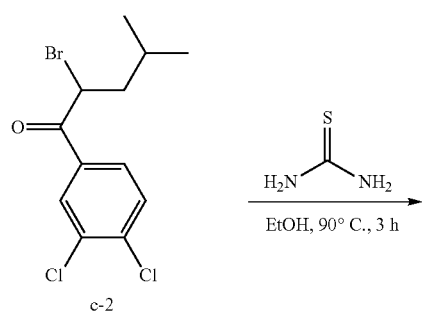

A mixture of c-2 (2.00 g, 6.17 mmol) and thiourea (564 mg, 7.41 mmol) in EtOH (50.0 mL) was stirred at 90° C. for 3 h. When the reaction was completed, it was concentrated to give a crude product, which was purified by silica gel column chromatography (petrol ether/ethyl acetate=5/1) to afford 178-s (1.20 g, 65% yield) as a white solid.

Synthesis of methyl 2-benzyl-3-(4-(3,4-dichlorophenyl)thiazol-2-ylamino)propanoate (224-4)

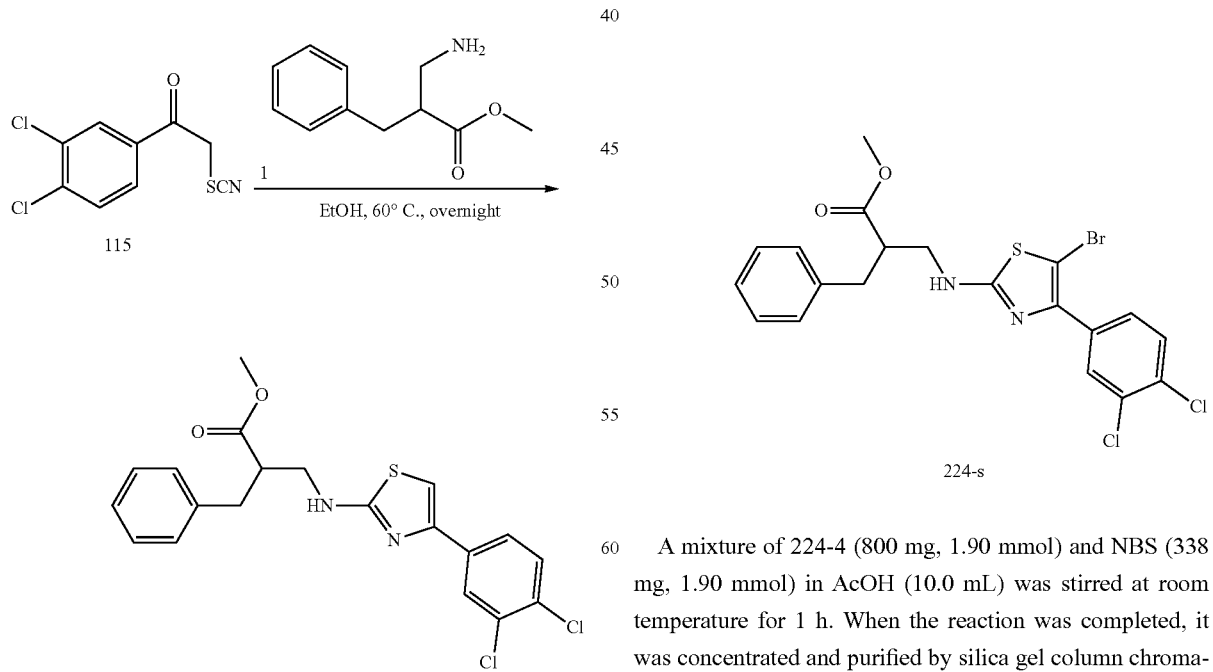

A mixture of 115 (1.00 g, 3.47 mmol) and 1 (805 mg, 4.16 mmol) in EtOH (50.0 mL) was stirred at 60° C. overnight. When the reaction was completed, it was concentrated and purified by silica gel column chromatography (petrol ether/ethyl acetate=10/1) to afford 224-4 (800 mg, 47% yield) as yellow oil.

Synthesis of methyl 2-benzyl-3-(5-bromo-4-(3,4-dichlorophenyl)thiazol-2-ylamino)propanoate (224-s)

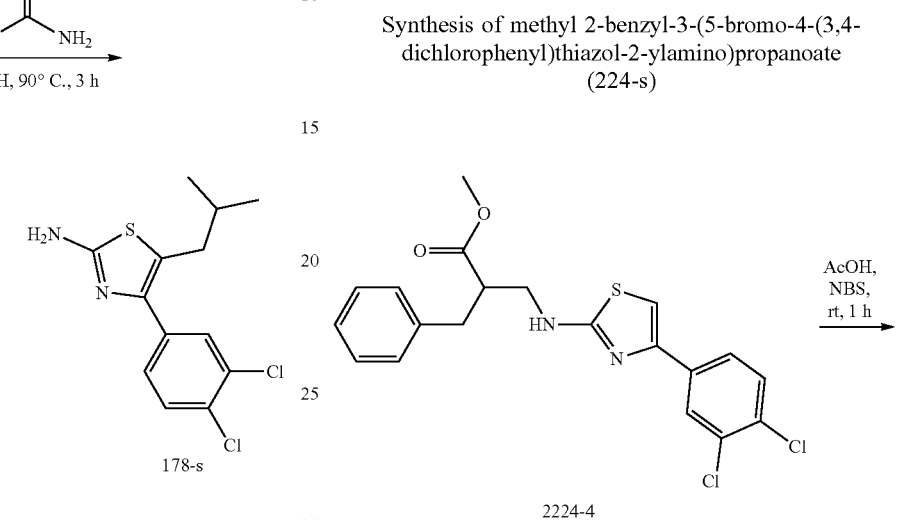

A mixture of 224-4 (800 mg, 1.90 mmol) and NBS (338 mg, 1.90 mmol) in AcOH (10.0 mL) was stirred at room temperature for 1 h. When the reaction was completed, it was concentrated and purified by silica gel column chromatography (petrol ether/ethyl acetate=10/1) to afford 224-s (600 mg, 63% yield) as colorless oil.

TABLE 3-2

Characterization Data for Compounds

| # | Chemical Structure | LCMS |
|---|---|---|
| 1 | methyl 2-(aminomethyl)-3-phenylpropanoate | Method B, Purity is 70.1%, Rt = 1.210 min; MS Calcd.: 249.1; MS Found: 194.3 [M + H]+. |
| s-1 | tert-butyl 3-(benzylamino)propanoate | Method B, Purity is 63.4%, Rt = 1.314 min; MS Calcd.: 235.2; MS Found: 236.2 [M + H]+. |
| b-157 | methyl 2-(aminomethyl)-6-(1,3-dioxoisoindolin-2-yl)hexanoate | Method B, Purity is 68.2%, Rt = 1.346 min; MS Calcd.: 304.1; MS Found: 305.2 [M + H]+. |
| b-184 | BocHN-(CH2)4-NH-CH2CH2-C(O)OEt | Method B, Purity is 75.8%, Rt = 1.302 min; MS Calcd.: 288.2; MS Found: 289.3 [M + H]+. |
| b-185 | Me2N-(CH2)3-NH-CH2CH2-C(O)OEt | Method B, Purity is 72.4%, Rt = 0.597 min; MS Calcd.: 216.2; MS Found: 217.3 [M + H]+. |
| b-186 | BocHN-(CH2)5-NH-CH2CH2-C(O)OEt | Method A, Purity is 81.1%, Rt = 1.357 min; MS Calcd.: 316.2; MS Found: 317.0 [M + H]+. |
| b-187 | EtO2C-CH2CH2-NH-(CH2)4-C(O)NH2 | Method B, Purity is 47.9%, Rt = 0.976 min; MS Calcd.: 230.2; MS Found: 231.2 [M + H]+. |
| b-188 | methyl 2-(aminomethyl)-3-(2,6-dimethylpyridin-4-yl)propanoate | Method C, Purity is 13.9%, Rt = 1.244 min; MS Calcd.: 222.1; MS Found: 223.3 [M + H]+. |
| b-189 | methyl 2-(aminomethyl)-3-(2-methylpyridin-4-yl)propanoate | Method C, Purity is 20.9%, Rt = 1.334 min; MS Calcd.: 208.1; MS Found: 209.3 [M + H]+. |

TABLE 3-2-continued

Characterization Data for Compounds

| # | Chemical Structure | LCMS |
|---|---|---|
| b-190 | 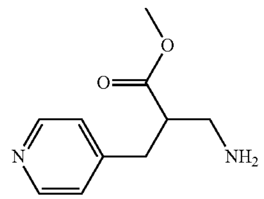 | Method C, Purity is 58.9%, Rt = 1.079 min; MS Calcd.: 194.1; MS Found: 195.3 [M + H]$^+$. |
| b-191 | 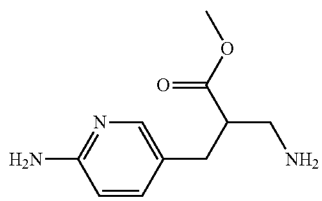 | Method C, Purity is 24.1%, Rt = 1.007 min; MS Calcd.: 209.1; MS Found: 210.3 [M + H]$^+$. |
| b-192 | 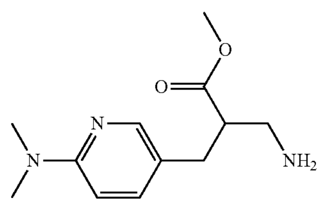 [SMILES: COC(=O)C(CN)Cc1ccc(N(C)C)nc1] | Method C, Purity is 71.5%, Rt = 1.370 min; MS Calcd.: 237.1; MS Found: 238.4 [M + H]$^+$. |
| b-193 | 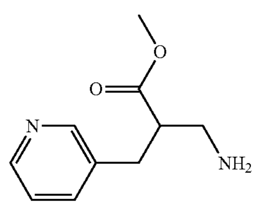 | Method C, Purity is 61.1%, Rt = 1.094 min; MS Calcd.: 194.1; MS Found: 195.2 [M + H]$^+$. |
| b-194 | 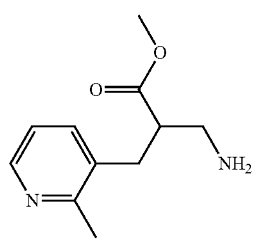 | Method C, Purity is 67.9%, Rt = 1.180 min; MS Calcd.: 208.1; MS Found: 209.3 [M + H]$^+$. |
| b-195 | 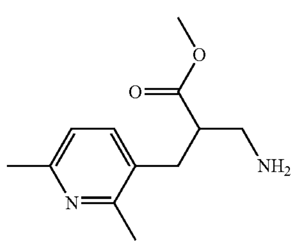 [SMILES: COC(=O)C(CN)Cc1ccc(C)nc1C] | Method C, Purity is 40.7%, Rt = 1.221 min; MS Calcd.: 222.1; MS Found: 223.3 [M + H]$^+$. |
| b-196 | 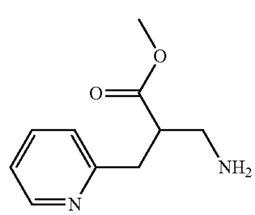 | Method A, Purity is 93.3%, Rt = 0.557 min; MS Calcd.: 194.1; No MS Found. |

TABLE 3-2-continued

Characterization Data for Compounds

| # | Chemical Structure | LCMS |
|---|---|---|
| b-198 | 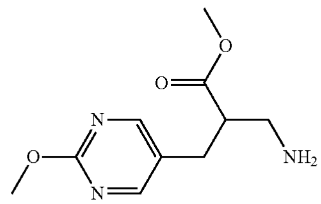 [SMILES: COC(=O)C(CN)Cc1cnc(OC)nc1] | Method C, Purity is 69.2%, Rt = 1.119 min; MS Calcd.: 225.1; MS Found: 226.3 [M + H]+. |
| b-199 | 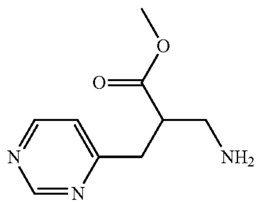 | Method C, Purity is 40.4%, Rt = 0.826 min; MS Calcd.: 195.1; MS Found: 196.3 [M + H]+. |
| b-201 | 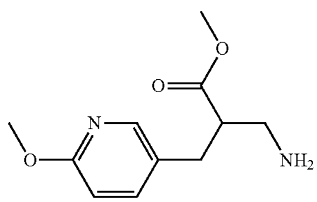 [SMILES: COC(=O)C(CN)Cc1ccc(OC)nc1] | Method C, Purity is 48.4%, Rt = 1.381 min; MS Calcd.: 224.1; MS Found: 225.3 [M + H]+. |
| b-203 | 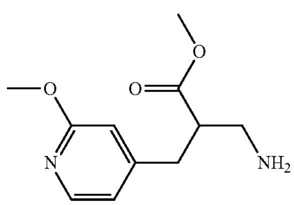 [SMILES: COC(=O)C(CN)Cc1ccnc(OC)c1] | Method C, Purity is 43.1%, Rt = 1.332 min; MS Calcd.: 224.1; MS Found: 225.2 [M + H]+. |
| b-204 | 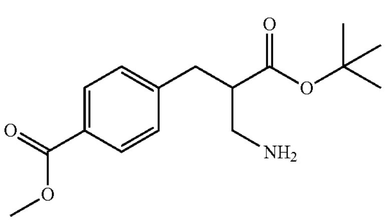 [SMILES: COC(=O)c1ccc(CC(CN)C(=O)OC(C)(C)C)cc1] | Method A, Purity is 97.1%, Rt = 0.606 min; MS Calcd.: 293.2; MS Found: 294.1 [M + H]+. |
| b-205 | 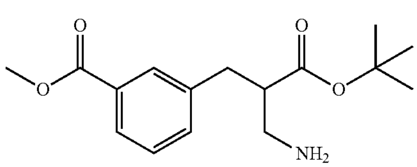 [SMILES: COC(=O)c1cccc(CC(CN)C(=O)OC(C)(C)C)c1] | Method C, Purity is 70.2%, Rt = 1.928 min; MS Calcd.: 293.2; No MS Found. |
| b-208 | 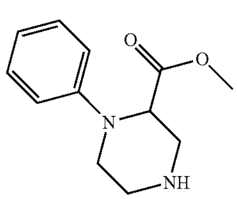 [SMILES: COC(=O)C1CNCCN1c1ccccc1] | No MS data. |

TABLE 3-2-continued

Characterization Data for Compounds

| # | Chemical Structure | LCMS |
|---|---|---|
| b-211 | 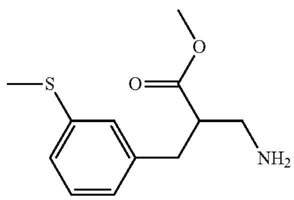 [SMILES: COC(=O)C(CN)Cc1cccc(SC)c1] | Method A, Purity is 36.2%, Rt = 0.456 min; MS Calcd.: 239.1; MS Found: 240.0 [M + H]+. |
| b-212 | 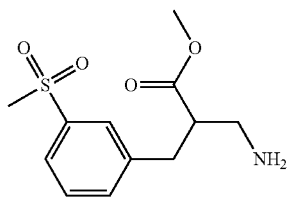 [SMILES: COC(=O)C(CN)Cc1cccc(S(C)(=O)=O)c1] | Method C, Purity is 48.4%, Rt = 1.381 min; MS Calcd.: 271.1; No MS Found. |
| b-213 | 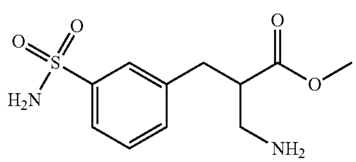 [SMILES: COC(=O)C(CN)Cc1cccc(S(N)(=O)=O)c1] | Method C, Purity is 51.7%, Rt = 1.151 min; MS Calcd.: 272.1; MS Found: 273.1 [M + H]+. |
| b-214 | 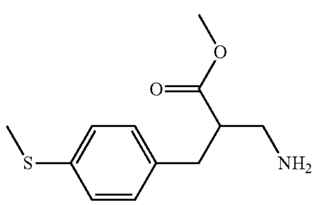 [SMILES: COC(=O)C(CN)Cc1ccc(SC)cc1] | Method A, Purity is 95.6%, Rt = 0.510 min; MS Calcd.: 239.1; MS Found: 240.0 [M + H]+. |
| b-215 | 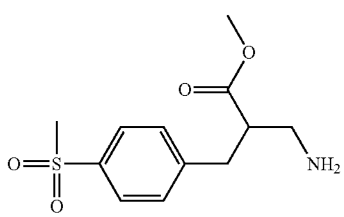 [SMILES: COC(=O)C(CN)Cc1ccc(S(C)(=O)=O)cc1] | Method A, Purity is 63.9%, Rt = 0.375 min; MS Calcd.: 271.1; MS Found: 272.0 [M + H]+. |
| b-216 | 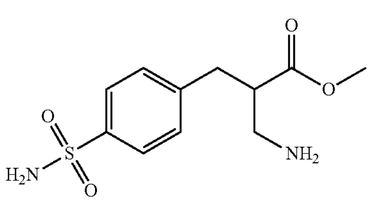 [SMILES: COC(=O)C(CN)Cc1ccc(S(N)(=O)=O)cc1] | Method B, Purity is 43.3%, Rt = 1.016 min; MS Calcd.: 272.1; MS Found: 273.1 [M + H]+. |
| b-229 | 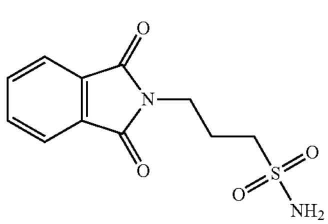 [SMILES: NS(=O)(=O)CCCN1C(=O)c2ccccc2C1=O] | Method B, Purity is 100%, Rt = 1.327 min; MS Calcd.: 268.1; MS Found: 269.2 [M + H]+. |

TABLE 3-2-continued

Characterization Data for Compounds

| # | Chemical Structure | LCMS |
|---|---|---|
| b-233 | 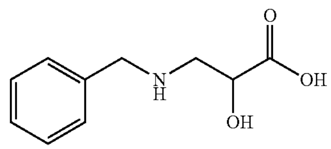 [SMILES: O=C(O)C(O)CNCc1ccccc1] | Method B, Purity is 96.0%, Rt = 0.973 min; MS Calcd.: 195.1; MS Found: 196.3 [M + H]+. |
| b-235 | 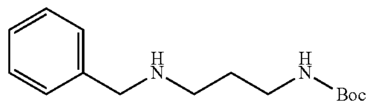 [SMILES: CC(C)(C)OC(=O)NCCCNCc1ccccc1] | Method B, Purity is 80.5%, Rt = 1.107 min; MS Calcd.: 264.2; MS Found: 265.1 [M + H]+. |
| b-242 | 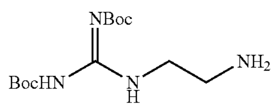 | Method C, Purity is 73.9%, Rt = 1.965 min; MS Calcd.: 302.2; MS Found: 303.5 [M + H]+. |
| b-243 | 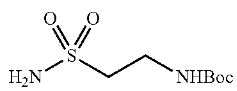 | Method A, No Purity, No Rt; MS Calcd.: 224.1; MS Found: 247.1 [M + Na]+. |
| 152-s | 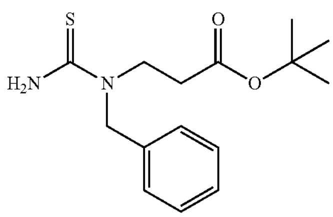 [SMILES: CC(C)(C)OC(=O)CCN(Cc1ccccc1)C(N)=S] | Method B, Purity is 94.7%, Rt = 1.813 min; MS Calcd.: 294.1; MS Found: 295.2 [M + H]+. |
| 178-s | 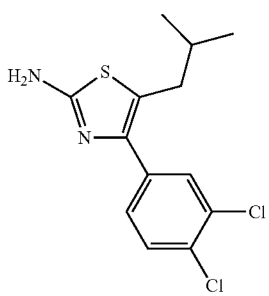 [SMILES: CC(C)Cc1sc(N)nc1-c1ccc(Cl)c(Cl)c1] | Method B, Purity is 79.8%, Rt = 1.761 min; MS Calcd.: 300.0; MS Found: 301.1 [M + H]+. |
| 224-s | 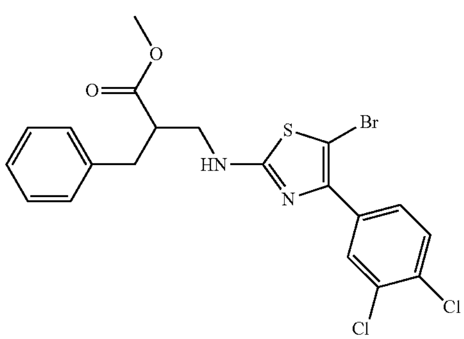 [SMILES: COC(=O)C(CNc1nc(-c2ccc(Cl)c(Cl)c2)c(Br)s1)Cc1ccccc1] | Method B, Purity is 84.5%, Rt = 2.380 min; MS Calcd.: 498.0; MS Found: 501.0 [M + H]+. |
| 227-s | 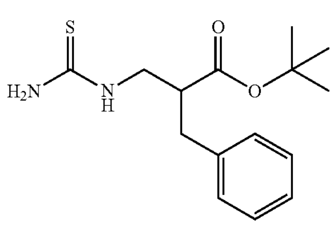 [SMILES: CC(C)(C)OC(=O)C(CNC(N)=S)Cc1ccccc1] | No MS data. |

Synthesis of 3-(benzyl(4-(3,4-dichlorophenyl)-5-formylthiazol-2-yl)amino)propanoic acid I-119)

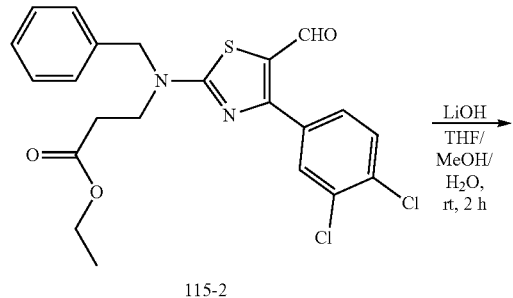

115-2

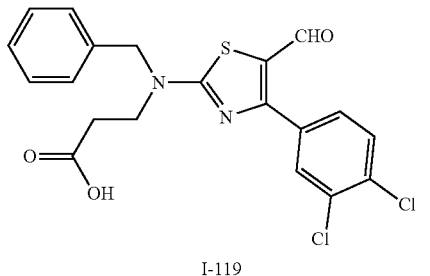

I-119

To a solution of 115-2 (80.0 mg, 0.173 mmol) in THF/MeOH/H$_2$O (v/v/v=4/1/1, 10.0 mL) was added LiOH (2.0 M in H$_2$O, 0.22 mL). The reaction was stirred at room temperature for 2 h. When the reaction was completed, the resulting reaction was concentrated, then it was diluted with H$_2$O (10 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated, the residue was purified by prep-HPLC to afford I-119 (30.0 mg, 40% yield) as a white solid.

Synthesis of ethyl 3-(benzyl(4-(3,4-dichlorophenyl)-5-(methoxymethyl)thiazol-2-yl)amino)propanoate (149-1)

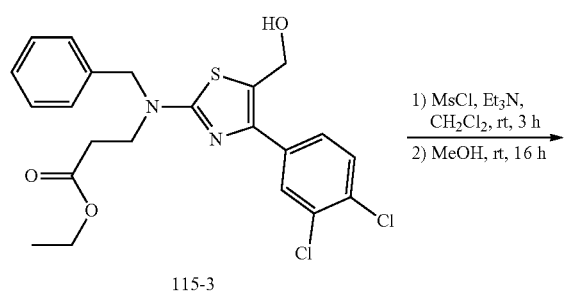

115-3

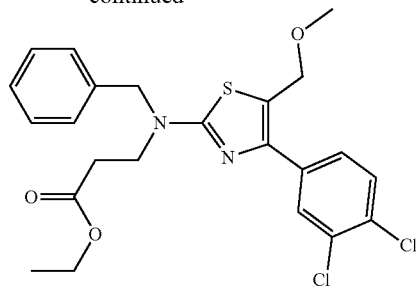

149-1

To a solution of 115-3 (250 mg, 0.54 mmol) and Et$_3$N (109 mg, 1.07 mmol) in CH$_2$Cl$_2$ (10.0 mL) was added MsCl (123 mg, 1.07 mmol). The reaction was stirred at room temperature for 3 h. When the reaction was completed, it was concentrated. The residue was solved with MeOH (10.0 mL). The reaction was stirred at room temperature for 16 h. When the reaction was completed, it was concentrated to give a crude product, which was purified by silica gel column chromatography (petrol ether/ethyl acetate=10/1) to afford 149-1 (75.0 mg, 29% yield) as yellow oil.

Synthesis of 3-(benzyl(4-(3,4-dichlorophenyl)-5-(methoxymethyl)thiazol-2-yl)amino)propanoic acid (I-120)

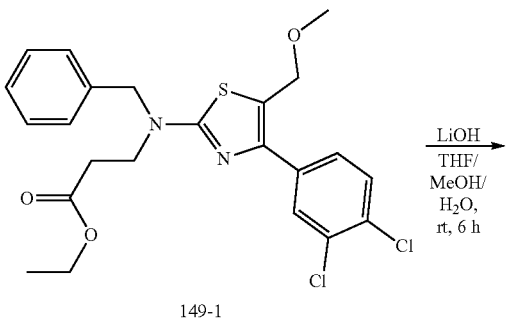

149-1

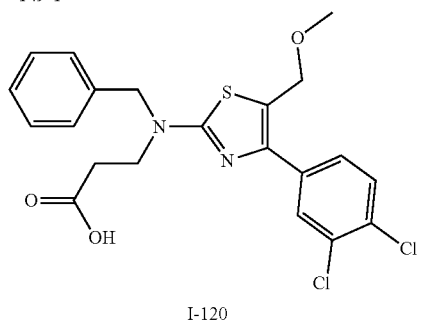

I-120

To a solution of 149-1 (75.0 mg, 0.156 mmol) in THF/MeOH/H$_2$O (v/v/v=4/1/1, 10.0 mL) was added LiOH (2.0 M in H$_2$O, 0.20 mL). The reaction was stirred at room temperature for 6 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated, the residue was purified by prep-HPLC to afford I-120 (15.0 mg, 21% yield) as a white solid.

Synthesis of ethyl 3-(3,4-dichlorophenyl)-3-oxopropanoate (152-2)

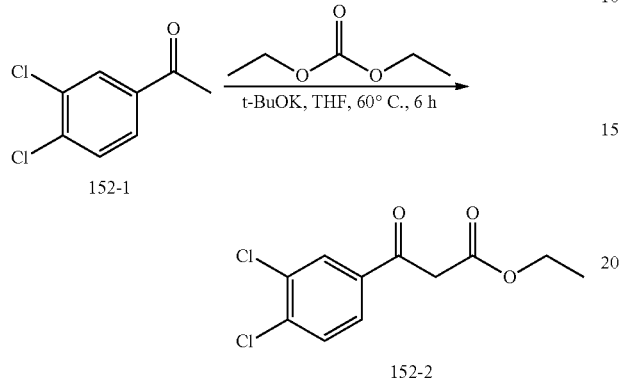

To a mixture of 152-1 (5.00 g, 26.4 mmol) and t-BuOK (1.0 M in THF, 52.9 mL, 52.9 mmol) in THF (50.0 mL) was added diethyl carbonate (4.69 g, 39.7 mmol) at room temperature. The reaction was stirred at 60° C. for 6 h. When the reaction was completed, the mixture was concentrated and purified by silica gel column chromatography (petrol ether/ethyl acetate=50/1) to afford 152-2 (3.50 g, 51% yield) as yellow oil.

Synthesis of ethyl 2-bromo-3-(3,4-dichlorophenyl)-3-oxopropanoate (152-3)

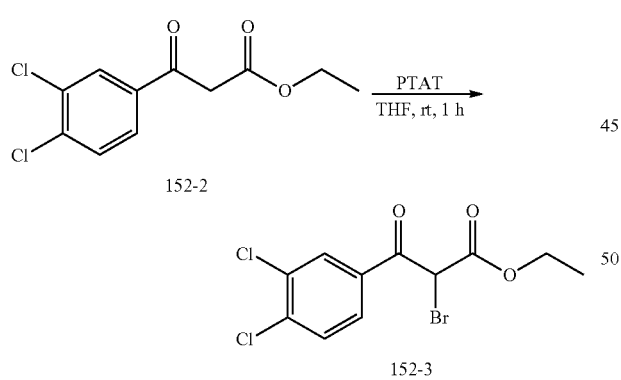

A mixture of 152-2 (1.00 g, 3.83 mmol) and PTAT (2.15 g, 5.74 mmol) in THF (100 mL) was stirred at room temperature for 1 h. When the reaction was completed, it was concentrated, and the residual was dissolved in H$_2$O (100 mL), and then extracted with EtOAc (100 mL×3). The organic layer was combined, and washed with H$_2$O (50.0 mL×2) and Brine (50.0 mL), then dried by anhydrous Na$_2$SO$_4$. The solution was concentrated and purified by silica gel column chromatography (petrol ether/ethyl acetate=50/1) to afford 152-3 (850 mg, 65% yield) as yellow oil.

Synthesis of ethyl 2-(benzyl(3-tert-butoxy-3-oxopropyl)amino)-4-(3,4-dichlorophenyl)thiazole-5-carboxylate (152-4)

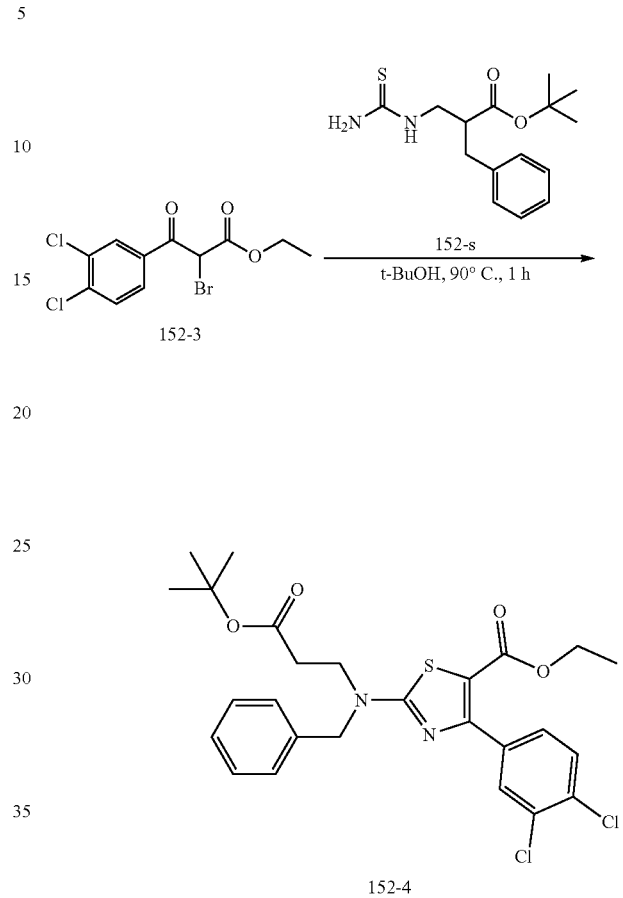

A mixture of 152-3 (500 mg, 1.47 mmol) and 152-s (433 mg, 1.47 mmol) in t-BuOH (20.0 mL) was stirred at 90° C. for 1 h. When the reaction was completed, the mixture was purified by silica gel column chromatography (petrol ether/ethyl acetate=10/1) to afford 152-4 (430 mg, 55% yield) as yellow oil.

Synthesis of 2-(benzyl(2-carboxyethyl)amino)-4-(3,4-dichlorophenyl)thiazole-5-carboxylic acid (152-5)

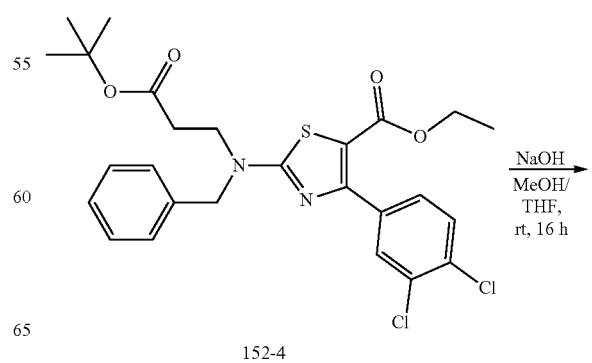

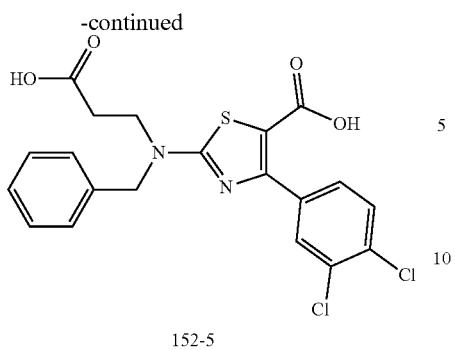

152-5

To a solution of 152-4 (80.0 mg, 0.149 mmol) in THF/MeOH (v/v/v=4/1, 5.0 mL) was added NaOH (2.0 M in H₂O, 0.37 mL). The reaction was stirred at room temperature for 16 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated to afford 152-5 (45.0 mg, 67% yield) as yellow oil.

Synthesis of 2-(benzyl(3-(methylamino)-3-oxopropyl)amino)-4-(3,4-dichlorophenyl)-N-methylthiazole-5-carboxamide (I-123)

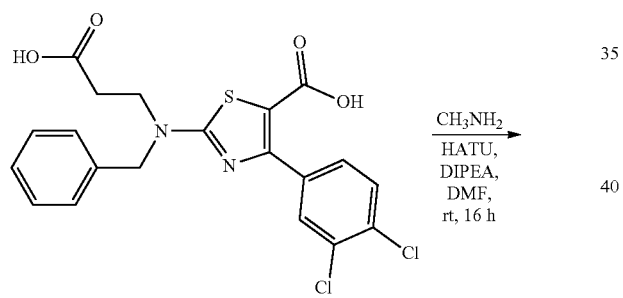

152-5

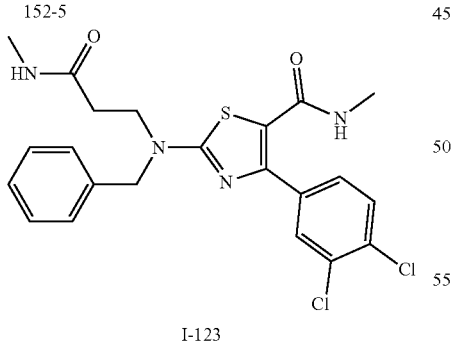

I-123

A mixture of 152-5 (10.0 mg, 0.022 mmol), methylamine (1.03 mg, 0.033 mmol), HATU (16.7 mg, 0.044 mmol) and DIPEA (8.51 mg, 0.066 mmol) in DMF (1.00 mL) was stirred at room temperature for 16 h. When the reaction was completed, poured into H₂O (10.0 mL), and then extracted with EtOAc (20.0 mL×2). The organic layer was combined, and washed with H₂O (10.0 mL×2) and Brine (10.0 mL), then dried by anhydrous Na₂SO₄. The solution was concentrated to give a crude product, which was purified by prep-HPLC to afford I-123 (3.5 mg, 26% yield) as a white solid.

Synthesis of tert-butyl 3-(benzyl(5-carbamoyl-4-(3,4-dichlorophenyl)thiazol-2-yl)amino)propanoate (154-1)

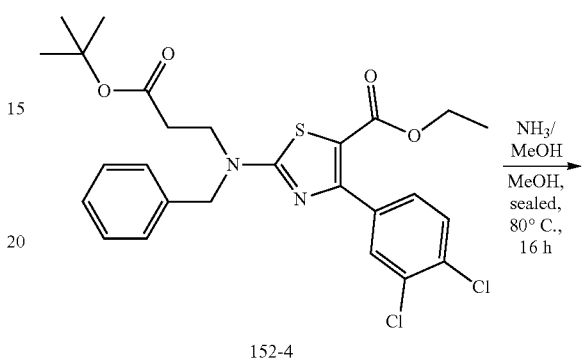

152-4

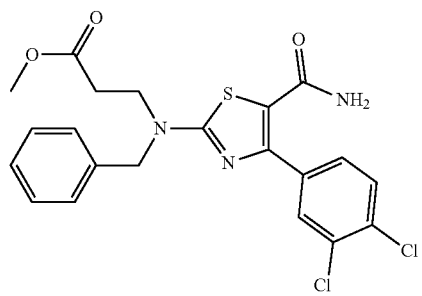

154-1

A mixture of 152-4 (70.0 mg, 0.131 mmol) and NH₃ (7.0 M in MeOH, 1.00 mL) in MeOH (1.00 mL) was stirred sealed at 80° C. for 16 h. When the reaction was completed, the mixture was concentrated and purified by prep-TLC to afford 154-1 (23.0 mg, 38% yield) as yellow oil.

Synthesis of 3-(benzyl(5-carbamoyl-4-(3,4-dichlorophenyl)thiazol-2-yl)amino)propanoic acid (I-124)

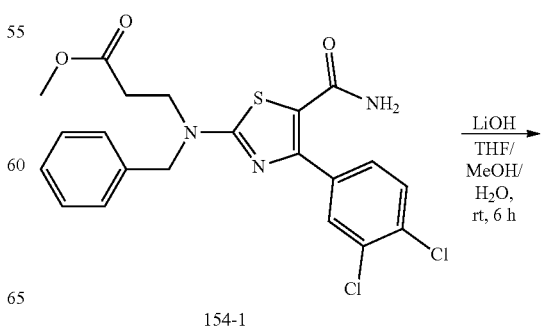

154-1

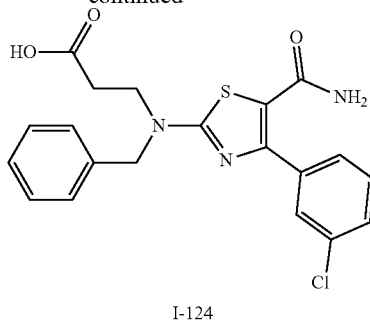

I-124

To a solution of 154-1 (23.0 mg, 0.050 mmol) in THF/MeOH/H₂O (v/v/v=4/1/1, 2.0 mL) was added LiOH (2.0 M in H₂O, 0.062 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated, the residue was purified by prep-HPLC to afford I-124 (9.0 mg, 40% yield) as a white solid.

Synthesis of methyl 2-((4-(3,4-dichlorophenyl)-5-isobutylthiazol-2-ylamino)methyl)-6-(1,3-dioxoisoindolin-2-yl)hexanoate (157-1)

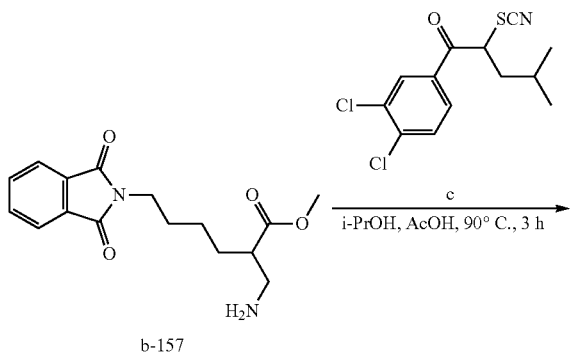

157-1

A mixture of b-157 (300 mg, 0.985 mmol), c (326 mg, 1.08 mmol) and AcOH (118 mg, 1.97 mmol) in i-PrOH (10.0 mL) was stirred at 90° C. for 3 h. When the reaction was completed, the mixture was purified by prep-TLC (petrol ether/ethyl acetate=8/1) to afford 157-1 (250 mg, 43% yield) as a yellow solid.

Synthesis of methyl 6-amino-2-((4-(3,4-dichlorophenyl)-5-isobutylthiazol-2-ylamino)methyl)hexanoate (157-2)

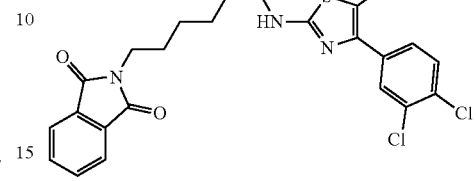

157-1

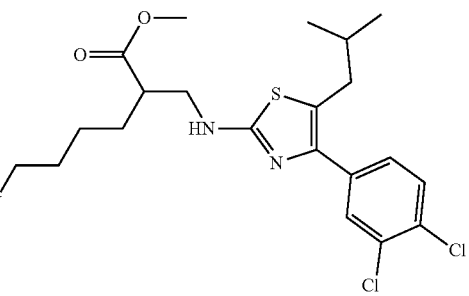

157-2

A mixture of 157-1 (250 mg, 0.425 mmol) and hydrazine hydrate (106 mg, 2.12 mmol) in MeOH (10.0 mL) was stirred at 60° C. for 2 h. When the reaction was completed, it was concentrated to give the crude product, which was purified by washed with H₂O (2.00 mL×3) to afford 157-2 (120 mg, 62% yield) as yellow oil.

Synthesis of 6-amino-2-((4-(3,4-dichlorophenyl)-5-isobutylthiazol-2-ylamino)methyl)hexanoic acid (I-125)

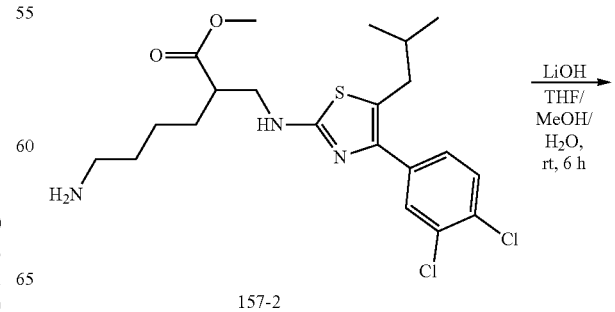

157-2

-continued

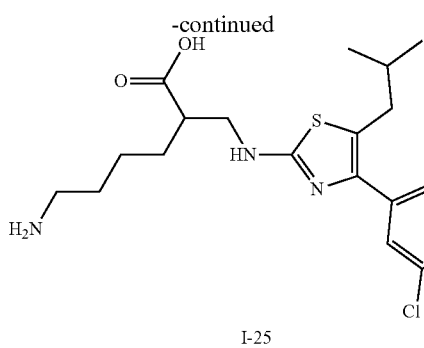

I-25

To a solution of 157-2 (120 mg, 0.050 mmol) in THF/MeOH/H₂O (v/v/v=4/1/1, 5.0 mL) was added LiOH (2.0 M in H₂O, 0.33 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated, the residue was purified by prep-HPLC to afford I-125 (30.0 mg, 26% yield) as a white solid.

Synthesis of ethyl 3-(benzyl(5-isobutyl-4-(4-(thiophen-3-yl)phenyl)thiazol-2-yl)amino)propanoate (159-1)

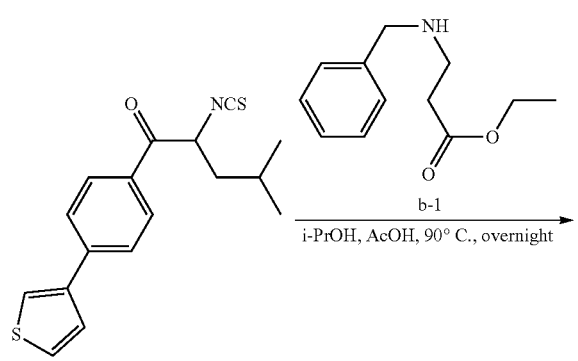

159-1

A mixture of b-1 (98.6 mg, 0.476 mmol), 159 (150 mg, 0.476 mmol) and AcOH (57.1 mg, 0.951 mmol) in i-PrOH (2.0 mL) was stirred at 90° C. overnight. When the reaction was completed, the mixture was purified by prep-TLC (petrol ether/ethyl acetate=8/1) to afford 159-1 (100 mg, 42% yield) as a yellow solid.

Synthesis of 3-(benzyl(5-isobutyl-4-(4-(thiophen-3-yl)phenyl)thiazol-2-yl)amino)propanoic acid (I-126)

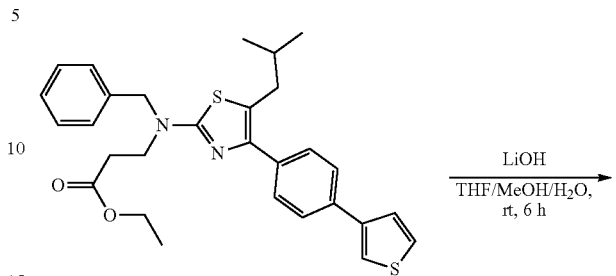

159-1

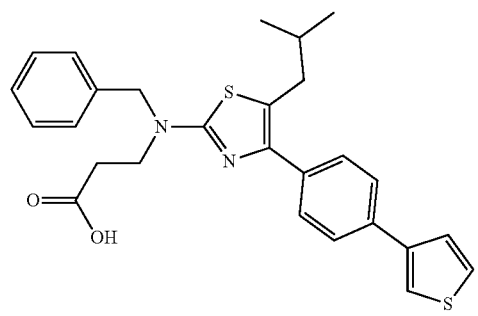

I-126

To a solution of 159-1 (100 mg, 0.198 mmol) in THF/MeOH/H₂O (v/v/v=4/1/1, 5.0 mL) was added LiOH (2.0 M in H₂O, 0.25 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated, the residue was purified by prep-HPLC to afford I-126 (16.0 mg, 17% yield) as a white solid.

Synthesis of ethyl 3-(benzyl(5-isobutyl-4-(4-(methylsulfonyl)phenyl)thiazol-2-yl)amino)propanoate (162-1)

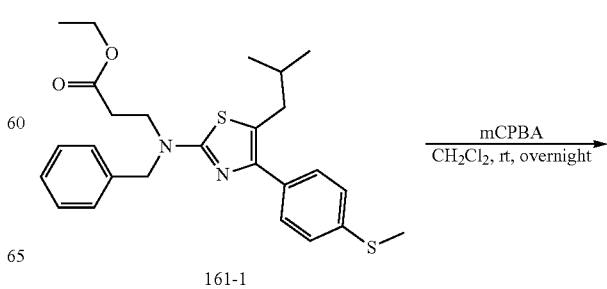

161-1

-continued

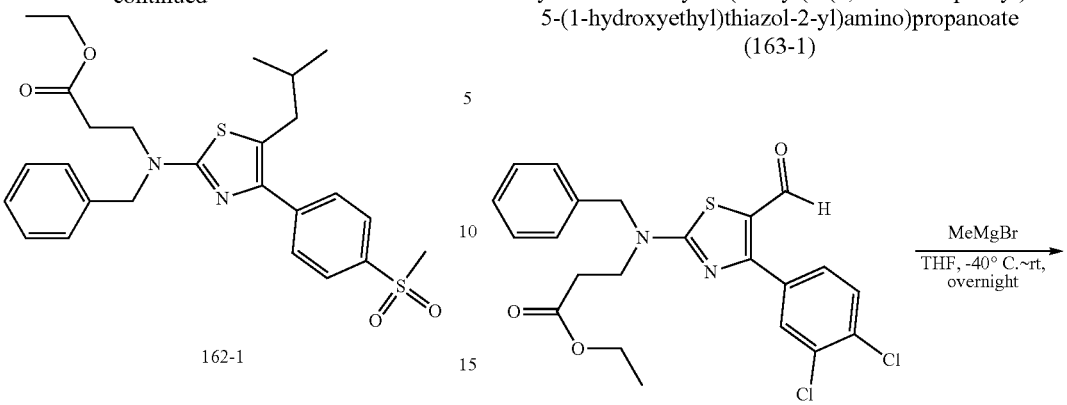

162-1

To a solution of 161-1 (500 mg, 1.07 mmol) in CH₂Cl₂ (15.0 mL) was added m-CPBA (552 mg, 3.20 mmol) at 0° C. The reaction was stirred at room temperature overnight. When the reaction was completed, the mixture was concentrated and purified by prep-TLC (CH₂Cl₂/MeOH=100/1) to afford 162-1 (200 mg, 37% yield) as a white solid.

Synthesis of 3-(benzyl(5-isobutyl-4-(4-(methylsulfonyl)phenyl)thiazol-2-yl)amino)propanoic acid (I-128)

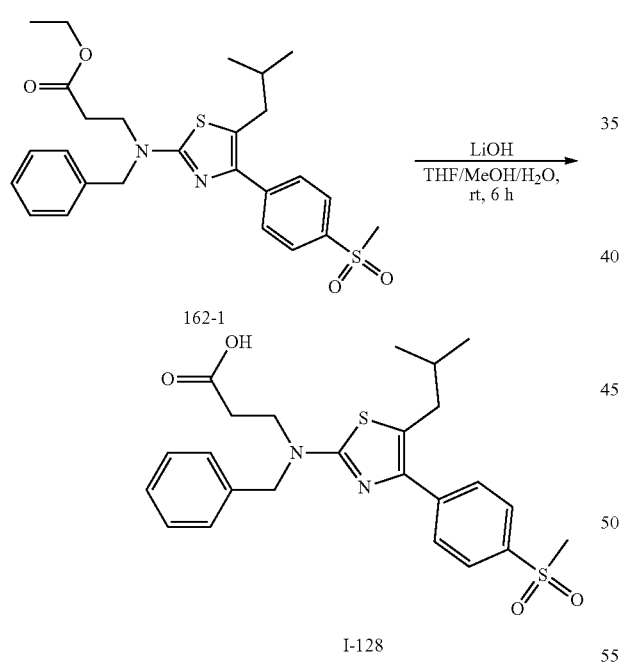

To a solution of 162-1 (200 mg, 0.399 mmol) in THF/MeOH/H₂O (v/v/v=4/1/1, 10.0 mL) was added LiOH (2.0 M in H₂O, 0.50 mL). The reaction was stirred at room temperature for 6 h. When the reaction was completed, the resulting reaction was concentrated, then it was diluted with H₂O (10.0 mL) and adjusted pH to 4-5 with aq.HCl (1.0 M). The mixture was extracted with EtOAc (40.0 mL×2), and the combined organic phase washed with brine (30.0 mL), dried by anhydrous Na₂SO₄, concentrated and purified by prep-HPLC to afford I-128 (50.0 mg, 26% yield) as a white solid.

Synthesis of ethyl 3-(benzyl(4-(3,4-dichlorophenyl)-5-(1-hydroxyethyl)thiazol-2-yl)amino)propanoate (163-1)

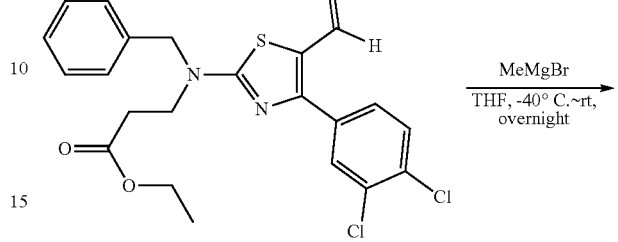

115-2

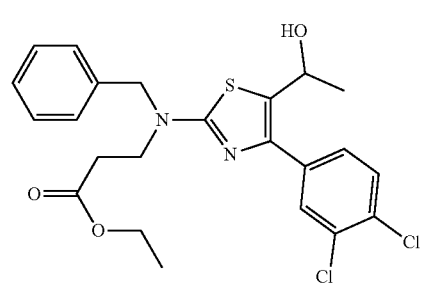

163-1

To a solution of 115-2 (350 mg, 0.755 mmol) in THF (20.0 mL) was added methylmagnesium bromide (1.0 M in THF, 1.13 mL, 1.13 mmol) at −40° C. The reaction was stirred at room temperature overnight. When the reaction was completed, it was quenched with aq.NH₄Cl (20.0 mL), and then extracted with EtOAc (100 mL×2). The organic layer was combined, and washed with H₂O (60.0 mL×2) and Brine (80.0 mL), then dried by anhydrous Na₂SO₄. The solution was concentrated to give the crude product, which was purified by prep-TLC (petrol ether/ethyl acetate=8/1) to afford 163-1 (80.0 mg, 22% yield) as a yellow solid.

Synthesis of 3-(benzyl(4-(3,4-dichlorophenyl)-5-vinylthiazol-2-yl)amino)propanoic acid (I-129)

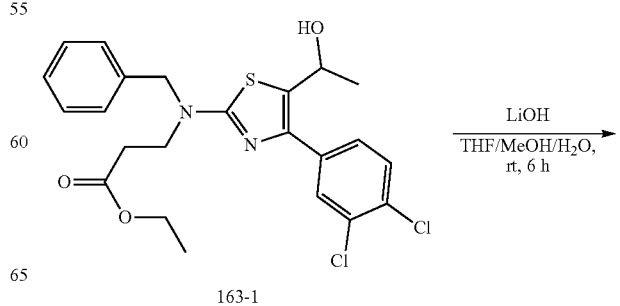

163-1

397

-continued

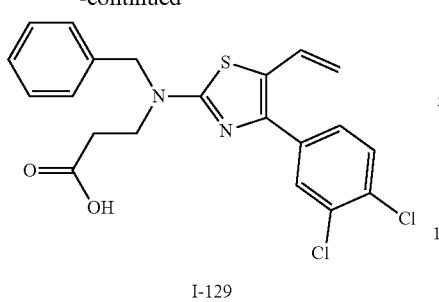

I-129

To a solution of 163-1 (80.0 mg, 0.167 mmol) in THF/MeOH/H₂O (v/v/v=4/1/1, 5.0 mL) was added LiOH (2.0 M in H₂O, 0.21 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, concentrated and purified by prep-HPLC to afford I-129 (12.0 mg, 17% yield) as a white solid.

Synthesis of tert-butyl 2-(3-(benzyl(4-(3,4-dichlorophenyl)-5-isobutylthiazol-2-yl)amino) propanamido) ethylcarbamate (168-1)

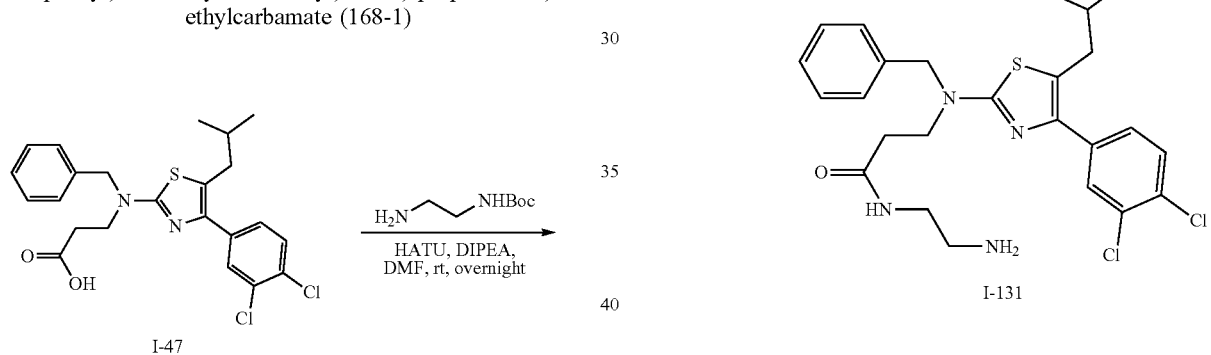

A mixture of I-47 (250 mg, 0.539 mmol), tert-butyl 2-aminoethylcarbamate (130 mg, 0.809 mmol), HATU (410 mg, 1.08 mmol) and DIPEA (209 mg, 1.62 mmol) in DMF (5.00 mL) was stirred at room temperature overnight. When the reaction was completed, poured into H₂O (100 mL), and then extracted with EtOAc (200 mL×2). The organic layer was combined, and washed with H₂O (100 mL×2) and Brine (100 mL), then dried by anhydrous Na₂SO₄. The solution was concentrated to give a crude product, which was used directly in next step without farther purification to afford 168-1 (200 mg, 61% yield) as a yellow solid.

398

Synthesis of N-(2-aminoethyl)-3-(benzyl(4-(3,4-dichlorophenyl)-5-isobutylthiazol-2-yl)amino)propanamide (I-131)

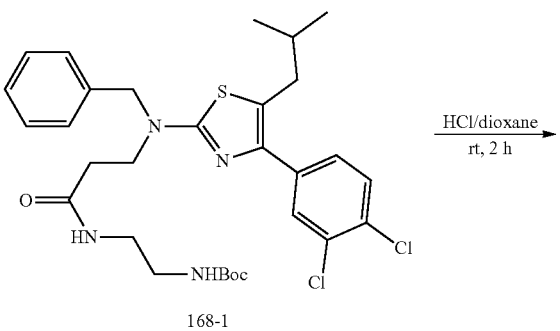

I-131

A mixture of 168-1 (200 mg, 0.330 mmol) in HCl (4.0 M in dioxane, 5.00 mL) was stirred at room temperature for 2 h. When the reaction was completed, it was concentrated to give a crude product, which was purified by prep-HPLC to afford I-131 (60.0 mg, 36% yield) as a white solid.

Synthesis of 3-(benzyl(4-(3,4-dichlorophenyl)-5-isobutylthiazol-2-yl)amino)-1-(4-methylpiperazin-1-yl)propan-1-one (I-133)

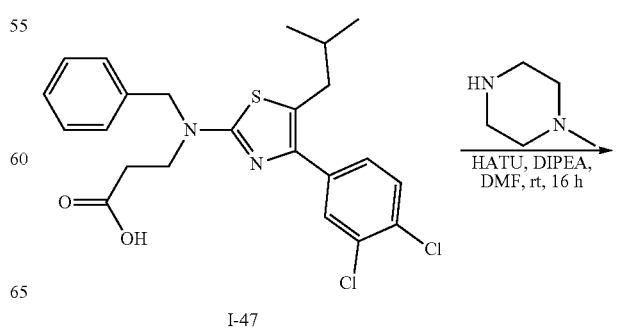

I-47

-continued

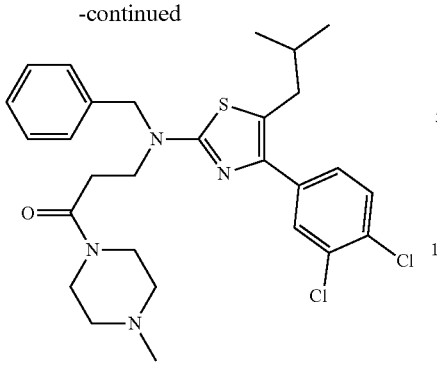

I-133

A mixture of I-47 (150 mg, 0.324 mmol), 1-methylpiperazine (48.6 mg, 0.486 mmol), HATU (246 mg, 0.648 mmol) and DIPEA (125 mg, 0.972 mmol) in DMF (5.00 mL) was stirred at room temperature for 16 h. When the reaction was completed, it was poured into $H_2O$ (100 mL), and then extracted with EtOAc (200 mL×2). The organic layer was combined, and washed with $H_2O$ (100 mL×2) and Brine (100 mL), then dried by anhydrous $Na_2SO_4$. The solution was concentrated to give a crude product, which was purified by prep-HPLC to afford I-133 (75 mg, 42% yield) as a white solid.

Synthesis of 2-benzamido-3-(4-(3,4-dichlorophenyl)-5-isobutylthiazol-2-ylamino)propanoic acid (I-136)

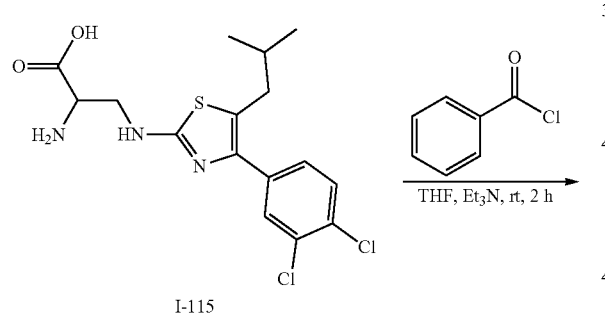

To a mixture of I-115 (200 mg, 0.515 mmol) and $Et_3N$ (156 mg, 1.55 mmol) in THF (10.0 mL) was added benzoyl chloride (145 mg, 1.03 mmol) at 0° C., The reaction was stirred at room temperature for 2 h. When the reaction was completed, it was concentrated and purified by prep-HPLC to afford I-136 (25 mg, 9.9% yield) as a white solid.

Synthesis of 2-(tert-butoxycarbonylamino)-3-(4-(3,4-dichlorophenyl)-5-isobutylthiazol-2-ylamino) propanoic acid (I-137)

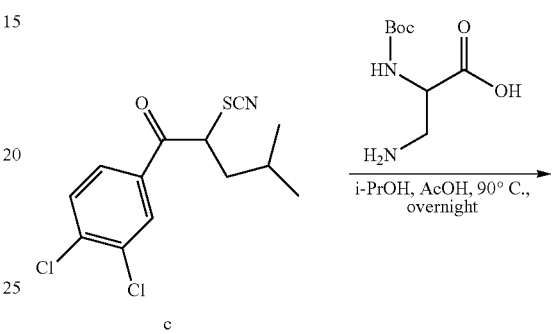

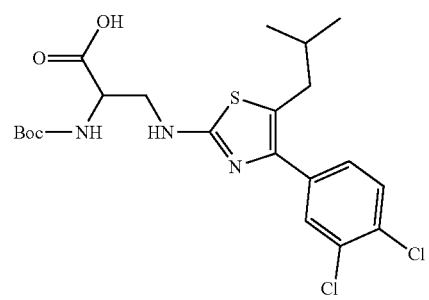

I-137

A mixture of c (500 mg, 1.66 mmol), 3-amino-2-(tert-butoxycarbonylamino)propanoic acid (407 mg, 1.99 mmol) and AcOH (199 mg, 3.32 mmol) in i-PrOH (20.0 mL) was stirred at 90° C. overnight. When the reaction was completed, the mixture was purified by prep-HPLC to afford I-137 (96.0 mg, 12% yield) as a white solid.

Synthesis of 2-(benzyloxycarbonylamino)-3-(4-(3,4-dichlorophenyl)-5-isobutylthiazol-2-ylamino) propanoic acid (I-138)

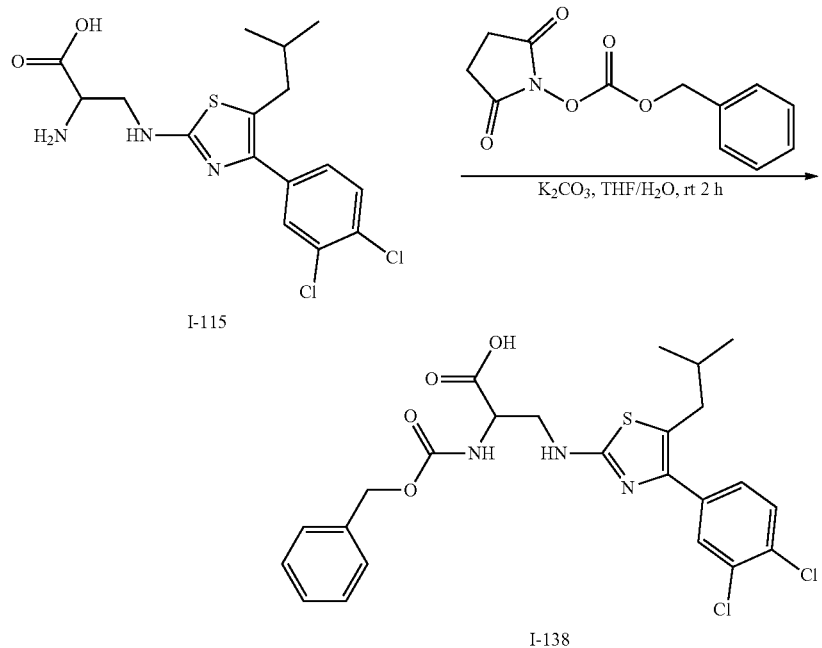

To a mixture of I-115 (200 mg, 0.515 mmol) and K₂CO₃ (214 mg, 1.55 mmol) in THF/H₂O (v/v=4/1, 10.0 mL) was added benzyl 2,5-dioxopyrrolidin-1-yl carbonate (257 mg, 1.03 mmol) at 0° C., The reaction was stirred at room temperature for 2 h. When the reaction was completed, it was concentrated and purified by prep-HPLC to afford I-138 (65.0 mg, 24% yield) as a white solid.

Synthesis of ethyl 1-(4-(3,4-dichlorophenyl)-5-isobutylthiazol-2-yl)-2-oxoazetidin-3-ylcarbamate (I-139)

To a mixture of I-115 (300 mg, 0.773 mmol) and Et₃N (234 mg, 2.32 mmol) in THF (10.0 mL) was added ethyl carbonochloridate (168 mg, 1.55 mmol) at 0° C., The reaction was stirred at room temperature for 2 h. When the reaction was completed, it was concentrated and purified by prep-HPLC to afford I-139 (50.0 mg, 15% yield) as a white solid.

Synthesis of 2-(4-(3,4-dichlorophenyl)-5-isobutylthiazol-2-ylamino)benzonitrile (178-1)

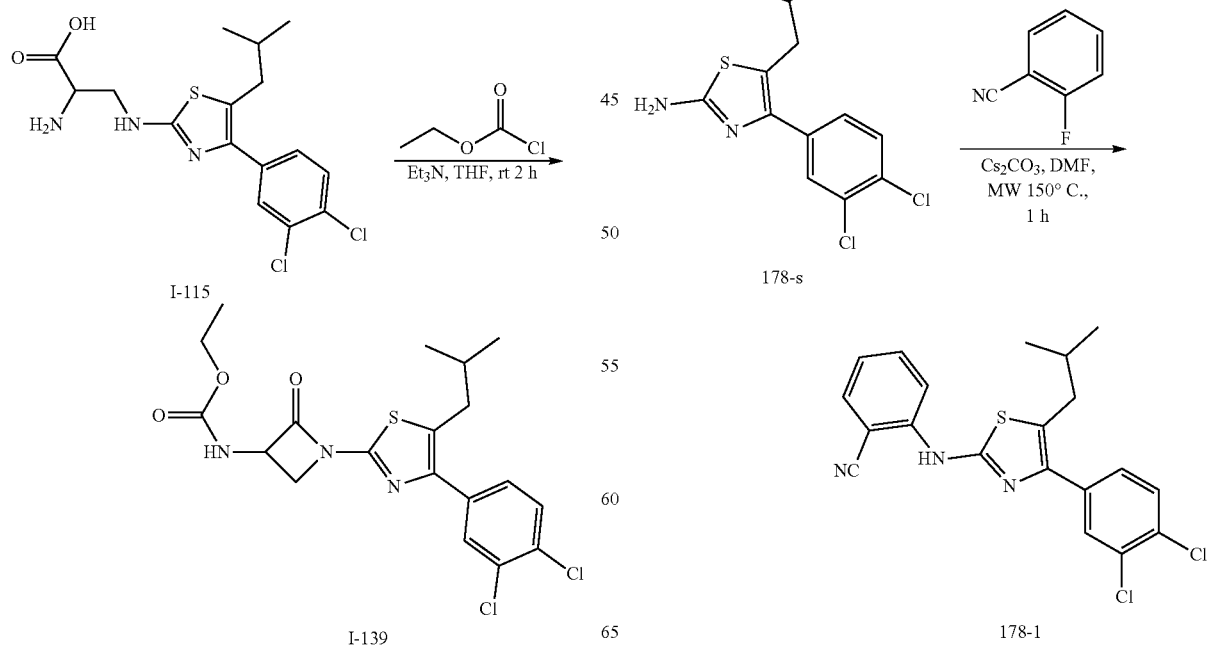

A mixture of 178-s (500 mg, 1.66 mmol), 2-fluorobenzonitrile (241 mg, 1.99 mmol) and Cs₂CO₃ (1.08 g, 3.32 mmol) in DMF (10.0 mL) was stirred at 150° C. under microwave for 1 h. When the reaction was completed, it was poured into H₂O (100 mL), and then extracted with EtOAc (100 mL×2). The organic layer was combined, and washed with H₂O (50.0 mL×2) and Brine (50.0 mL), then dried by anhydrous Na₂SO₄. The solution was concentrated and purified by silica gel column chromatography (petrol ether/ethyl acetate=10/1) to afford 178-1 (220 mg, 33% yield) as a yellow solid.

Synthesis of 2-(4-(3,4-dichlorophenyl)-5-isobutylthiazol-2-ylamino)benzoic acid (I-141)

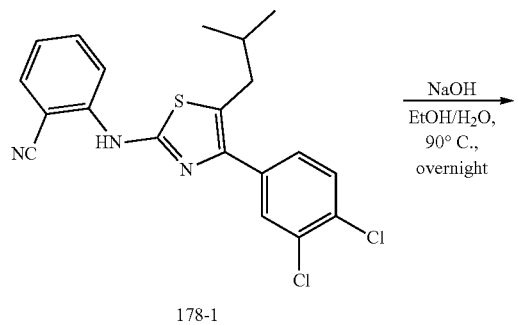

A mixture of 178-1 (100 mg, 0.25 mmol) and NaOH (5.0 M in H₂O, 0.25 mL, 1.24 mmol) in EtOH/H₂O (2.00 mL) was stirred at 90° C. overnight. When the reaction was completed, the mixture was purified by prep-HPLC to afford I-141 (15.0 mg, 14% yield) as a yellow solid.

Synthesis of methyl 3-(4-(3,4-dichlorophenyl)-5-isobutylthiazol-2-ylamino)benzoate (179-1)

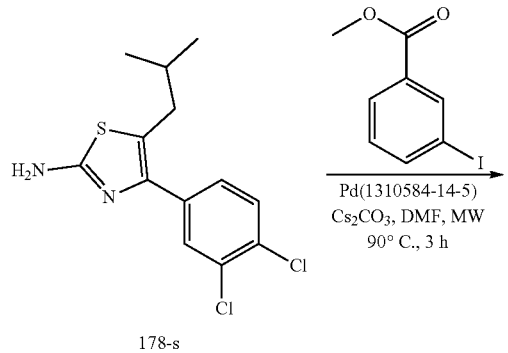

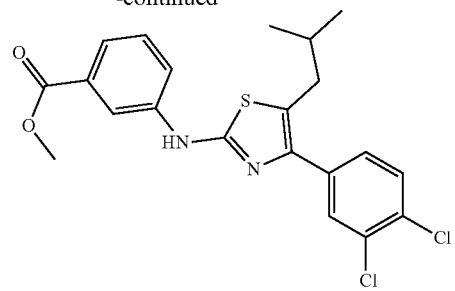

A mixture of 178-s (300 mg, 0.996 mmol), methyl 3-iodobenzoate (313 mg, 1.20 mmol), Pd catalyst (CAS: 1310584-14-5, 15.7 mg, 0.199 mmol) and Cs₂CO₃ (649 mg, 1.99 mmol) in DMF (5.0 mL) was stirred at 90° C. under microwave for 3 h. When the reaction was completed, it was poured into H₂O (80.0 mL), and then extracted with EtOAc (100 mL×2). The organic layer was combined, and washed with H₂O (50.0 mL×2) and Brine (50.0 mL), then dried by anhydrous Na₂SO₄. The solution was concentrated and purified by silica gel column chromatography (petrol ether/ethyl acetate=10/1) to afford 179-1 (58.0 mg, 13% yield) as a yellow solid.

Synthesis of 3-(4-(3,4-dichlorophenyl)-5-isobutylthiazol-2-ylamino)benzoic acid (I-142)

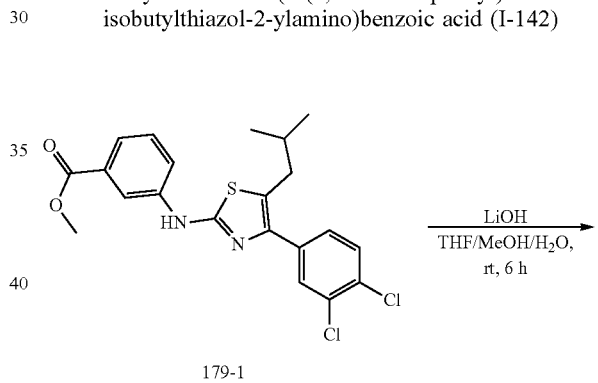

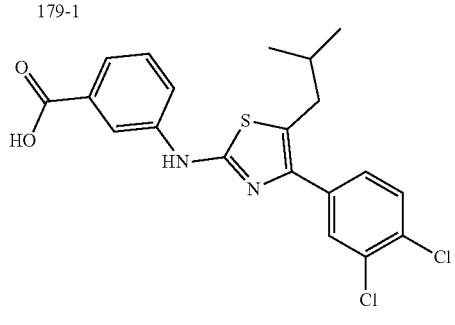

To a solution of 179-1 (58.0 mg, 0.133 mmol) in THF/MeOH/H₂O (v/v/v=4/1/1, 5.0 mL) was added LiOH (2.0 M in H₂O, 0.17 mL). The reaction was stirred at room temperature for 6 h. When the reaction was completed, the resulting reaction was concentrated, then it was diluted with H₂O (10.0 mL) and adjusted pH to 4-5 with aq.HCl (1.0 M). The mixture was extracted with EtOAc (40.0 mL×2), and the combined organic phase washed with brine (30.0 mL), dried by anhydrous Na₂SO₄, concentrated and purified by prep-HPLC to afford I-142 (10.0 mg, 18% yield) as a white solid.

Synthesis of N-benzyl-4-(3,4-dichlorophenyl)-5-isobutylthiazol-2-amine (180-1)

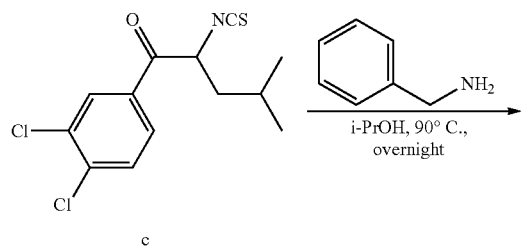

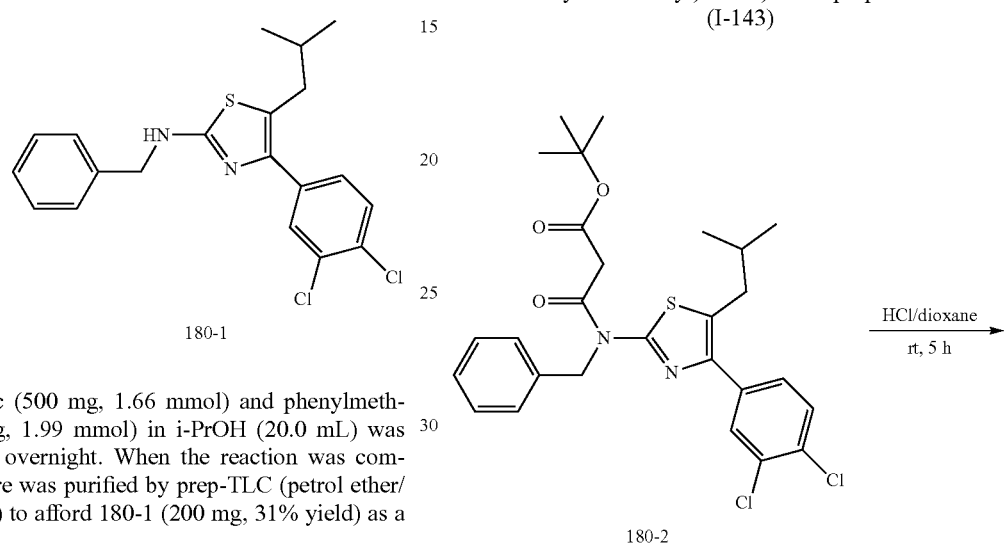

A mixture of c (500 mg, 1.66 mmol) and phenylmethanamine (214 mg, 1.99 mmol) in i-PrOH (20.0 mL) was stirred at 90° C. overnight. When the reaction was completed, the mixture was purified by prep-TLC (petrol ether/ethyl acetate=8/1) to afford 180-1 (200 mg, 31% yield) as a yellow solid.

Synthesis of tert-butyl 3-(benzyl(4-(3,4-dichlorophenyl)-5-isobutylthiazol-2-yl)amino)-3-oxopropanoate (180-2)

To a mixture of 180-1 (200 mg, 0.511 mmol) and Et₃N (103 mg, 1.02 mmol) in CH₂Cl2 (10.0 mL) was added tert-butyl 3-chloro-3-oxopropanoate (137 mg, 0.767 mmol) at 0° C., The reaction was refluxed for 5 h. When the reaction was completed, it was concentrated and purified by prep-TLC (petrol ether/ethyl acetate=8/1) to afford 180-2 (100 mg, 37% yield) as a yellow solid.

Synthesis of 3-(benzyl(4-(3,4-dichlorophenyl)-5-isobutylthiazol-2-yl)amino)-3-oxopropanoic acid (I-143)

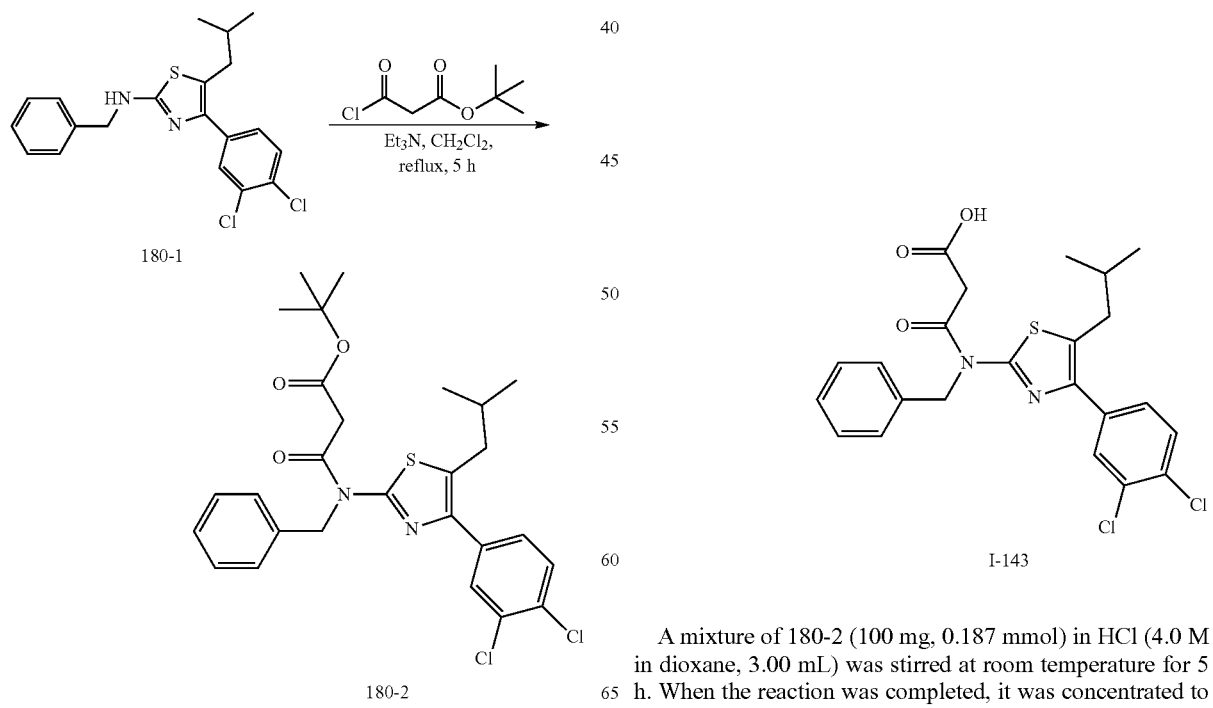

A mixture of 180-2 (100 mg, 0.187 mmol) in HCl (4.0 M in dioxane, 3.00 mL) was stirred at room temperature for 5 h. When the reaction was completed, it was concentrated to give a crude product, which was purified by prep-HPLC to afford I-143 (32.0 mg, 36% yield) as a white solid.

Synthesis of methyl 2-((4-(3,4-dichlorophenyl)-5-isobutylthiazol-2-ylamino)methyl)-6-(dimethylamino)hexanoate (183-1)

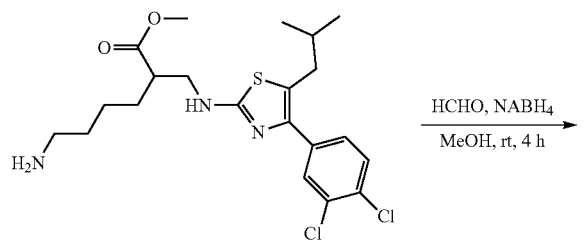

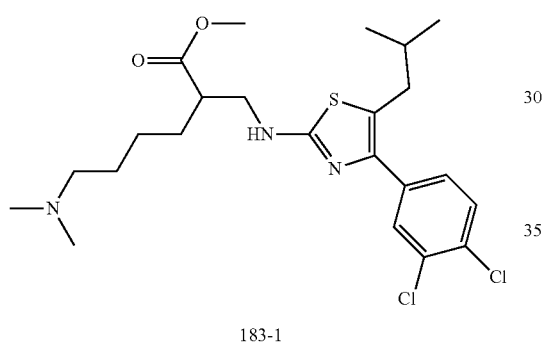

To a solution of 157-2 (200 mg, 0.436 mmol) and formaldehyde (37% in H₂O, 74.4 mg, 0.916 mmol) in MeOH (50.0 mL) was added NaBH₄ (33.1 mg, 0.872 mmol) at 0° C. The reaction was stirred at room temperature for 4 h. When the reaction was completed, it was concentrated and purified by prep-TLC (petrol ether/ethyl acetate=8/1) to afford 183-1 (100 mg, 47% yield) as a yellow solid.

Synthesis of 2-((4-(3,4-dichlorophenyl)-5-isobutylthiazol-2-ylamino)methyl)-6-(dimethylamino) hexanoic acid (I-145)

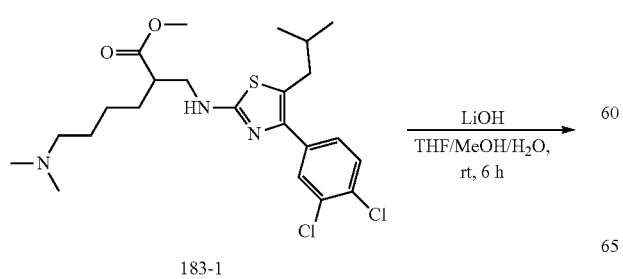

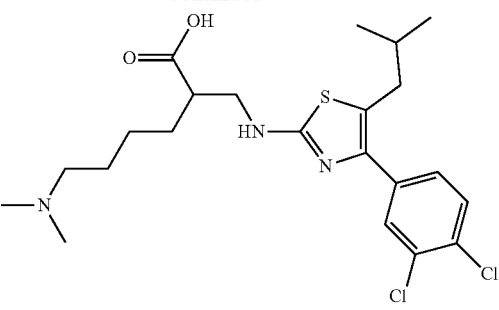

To a solution of 183-1 (100 mg, 0.206 mmol) in THF/MeOH/H₂O (v/v/v=4/1/1, 10.0 mL) was added LiOH (2.0 M in H₂O, 0.26 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated to give a crude product, which was purified by prep-HPLC to afford I-145 (20.0 mg, 21% yield) as a white solid.

Synthesis of ethyl 3-((4-(tert-butoxycarbonylamino)butyl)(4-(3,4-dichlorophenyl)-5-isobutylthiazol-2-yl)amino)propanoate (184-2)

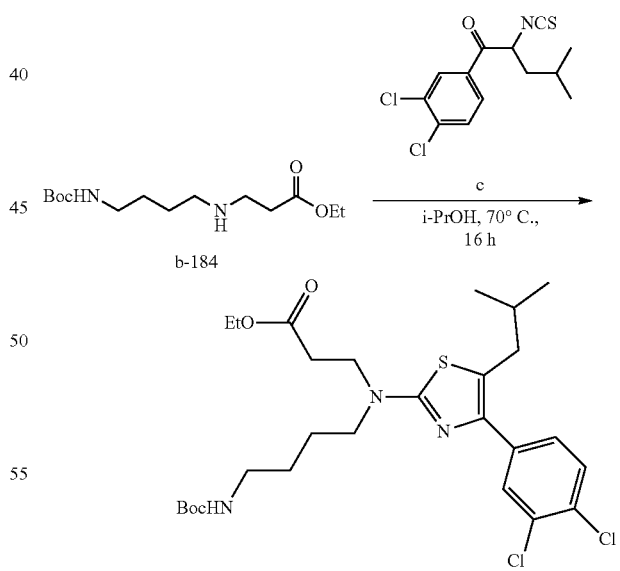

A mixture of c (324 mg, 1.07 mmol) and b-184 (310 mg, 1.07 mmol) in i-PrOH (10.0 mL) was stirred at 70° C. for 16 h. When the reaction was completed, the mixture was purified by prep-TLC (petrol ether/ethyl acetate=8/1) to afford 184-2 (180 mg, 29% yield) as a yellow solid.

Synthesis of 3-((4-(tert-butoxycarbonylamino)butyl)(4-(3,4-dichlorophenyl)-5-isobutylthiazol-2-yl)amino)propanoic acid (184-3)

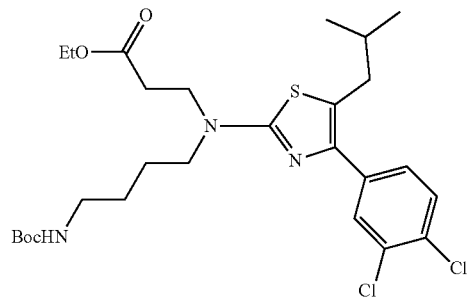

184-2

LiOH
THF/MeOH/H₂O,
rt, 6 h

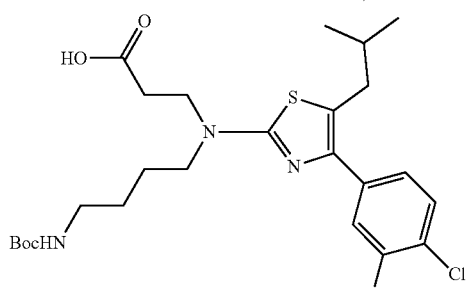

184-3

To a solution of 184-2 (180 mg, 0.314 mmol) in THF/MeOH/H₂O (v/v/v=4/1/1, 10.0 mL) was added LiOH (2.0 M in H₂O, 0.39 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated to give a crude product, which was used directly in next step without farther purification to afford 184-3 (180 mg, 100% yield) as a white solid.

Synthesis of 3-((4-aminobutyl)(4-(3,4-dichlorophenyl)-5-isobutylthiazol-2-yl)amino)propanoic acid (I-146)

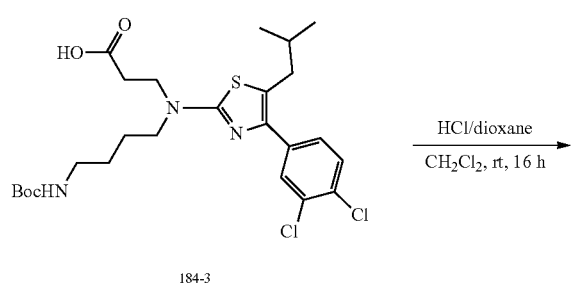

184-3

HCl/dioxane
CH₂Cl₂, rt, 16 h

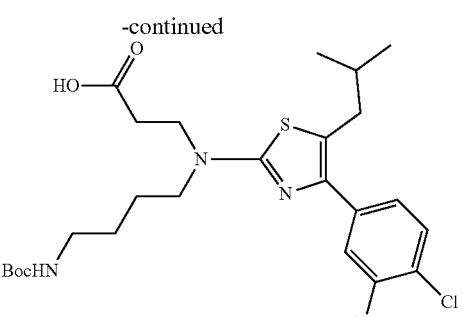

I-146

A mixture of 184-3 (180 mg, 0.331 mmol) and HCl (4.0 M in dioxane, 5.00 mL) in CH₂Cl₂ (10.0 mL) was stirred at room temperature for 16 h. When the reaction was completed, it was concentrated to give a crude product, which was purified by prep-HPLC to afford I-146 (20.0 mg, 14% yield) as a white solid.

Synthesis of ethyl 3-((4-(3,4-dichlorophenyl)-5-isobutylthiazol-2-yl)(4-(dimethylamino)butyl)amino)propanoate (185-1)

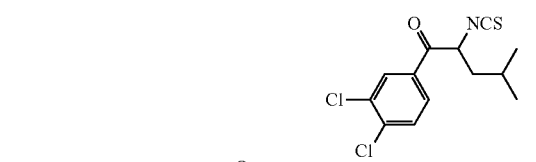

b-185 c
i-PrOH, 70° C.,
16 h

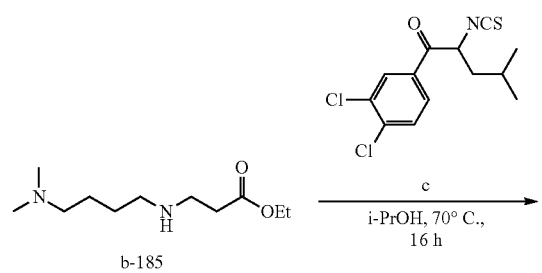

185-1

A mixture of c (181 mg, 0.601 mmol) and b-185 (130 mg, 0.601 mmol) in i-PrOH (5.0 mL) was stirred at 70° C. for 16 h. When the reaction was completed, the mixture was purified by prep-TLC (CH₂Cl₂/MeOH=80/1) to afford 185-1 (30.0 mg, 10% yield) as a yellow solid.

411

Synthesis of 3-((4-(3,4-dichlorophenyl)-5-isobutylthiazol-2-yl)(4-(dimethylamino)butyl)amino)propanoic acid (I-147)

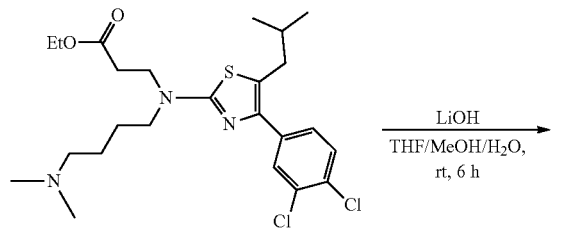

185-1

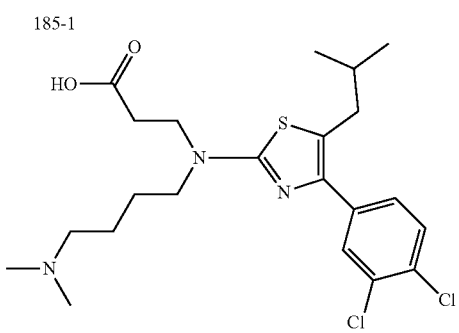

I-147

To a solution of 185-1 (30.0 mg, 0.0599 mmol) in THF/MeOH/H$_2$O (v/v/v=4/1/1, 1.0 mL) was added LiOH (2.0 M in H$_2$O, 0.07 mL). The reaction was stirred at room temperature for 4 h. When the reaction was completed, the resulting reaction was concentrated, then it was diluted with H$_2$O (5.0 mL) and adjusted pH to 4-5 with HCl (1.0 M). The mixture was extracted with EtOAc (20.0 mL×2), and the combined organic phase washed with brine (10.0 mL), dried by anhydrous Na$_2$SO$_4$, and concentrated to give a crude product, which was purified by prep-HPLC to afford I-147 (3.20 mg, 11% yield) as a white solid.

Synthesis of methyl 3-(4-(3,4-dichlorophenyl)-5-isobutylthiazol-2-ylamino)-2-((2-hydroxypyrimidin-5-yl)methyl)propanoate (197-1)

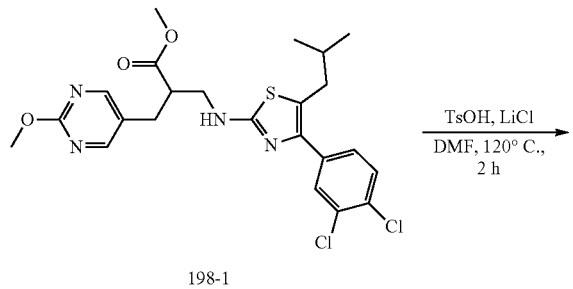

198-1

412

-continued

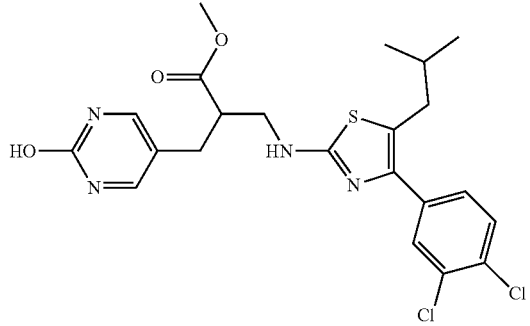

197-1

A mixture of 198-1 (150 mg, 0.294 mmol), TsOH (254 mg, 1.47 mmol) and LiCl (62.3 mg, 1.47 mmol) in DMF (5.0 mL) was stirred at 120° C. for 2 h. When the reaction was completed, it was poured into H$_2$O (80.0 mL), and then extracted with EtOAc (100 mL×2). The organic layer was combined, and washed with H$_2$O (50.0 mL×2) and Brine (50.0 mL), then dried by anhydrous Na$_2$SO$_4$. The solution was concentrated to give a crude product, which was used directly in next step without farther purification to afford 197-1 (150 mg, 100% yield) as yellow oil.

Synthesis of 3-(4-(3,4-dichlorophenyl)-5-isobutylthiazol-2-ylamino)-2-((2-hydroxypyrimidin-5-yl)methyl)propanoic acid (I-159)

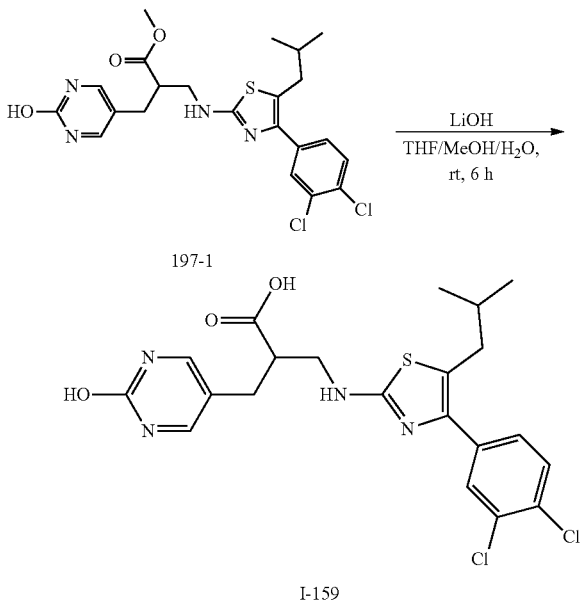

I-159

To a solution of 197-1 (150 mg, 0.303 mmol) in THF/MeOH/H$_2$O (v/v/v=4/1/1, 5.0 mL) was added LiOH (2.0 M in H$_2$O, 0.38 mL). The reaction was stirred at room temperature for 6 h. When the reaction was completed, the resulting reaction was concentrated, then it was diluted with H$_2$O (5.0 mL) and adjusted pH to 4-5 with HCl (1.0 M). The mixture was extracted with EtOAc (20.0 mL×2), and the combined organic phase washed with brine (10.0 mL), dried by anhydrous Na$_2$SO$_4$, and concentrated to give a crude product, which was purified by prep-HPLC to afford I-159 (70.0 mg, 48% yield) as a white solid.

Synthesis of methyl 4-(3-tert-butoxy-2-((4-(3,4-dichlorophenyl)-5-isobutylthiazol-2-ylamino)methyl)-3-oxopropyl)benzoate (204-1)

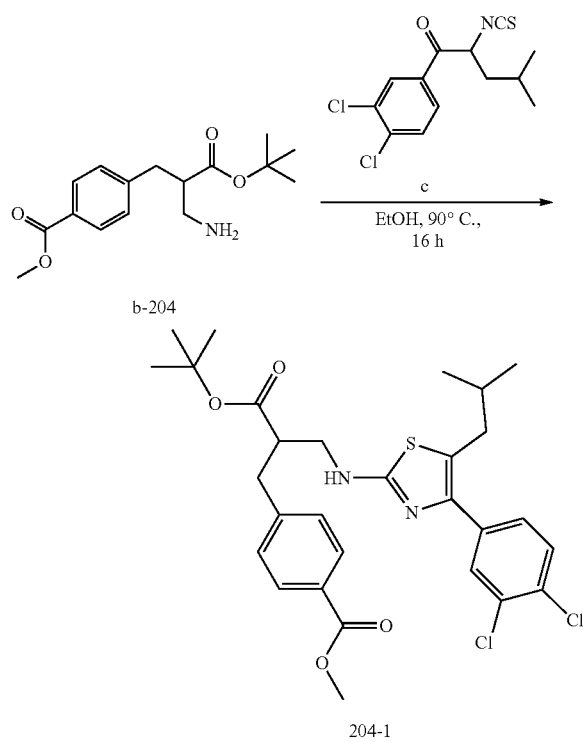

A mixture of c (462 mg, 1.53 mmol) and b-204 (450 mg, 1.53 mmol) in EtOH (15 mL) was stirred at 90° C. for 16 h. When the reaction was completed, the mixture was purified by prep-TLC (petrol ether/ethyl acetate=2/1) to afford 204-1 (400 mg, 45% yield) as a yellow solid.

Synthesis of 4-(3-tert-butoxy-2-((4-(3,4-dichlorophenyl)-5-isobutylthiazol-2-ylamino)methyl)-3-oxopropyl)benzoic acid (204-2)

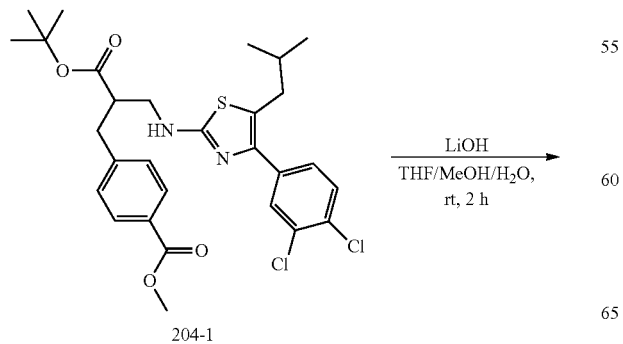

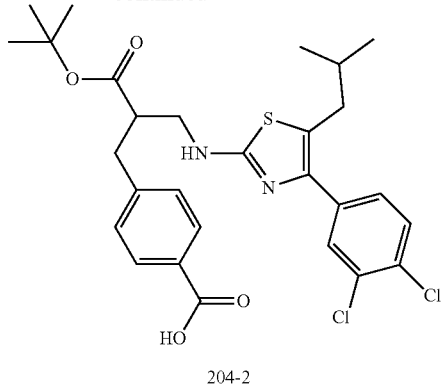

To a solution of 204-1 (400 mg, 0.0599 mmol) in MeOH/H$_2$O (v/v=1/1, 20.0 mL) was added LiOH (2.0 M in H$_2$O, 0.07 mL). The reaction was stirred at room temperature for 2 h. When the reaction was completed, the resulting reaction was concentrated, then it was diluted with H$_2$O (20.0 mL) and adjusted pH to 4-5 with HCl (1.0 M). The mixture was extracted with EtOAc (30.0 mL×2), and the combined organic phase washed with brine (20.0 mL), dried by anhydrous Na$_2$SO$_4$, and concentrated to give a crude product, which was used directly in next step without farther purification to afford 204-2 (300 mg, 77% yield) as a yellow solid.

Synthesis of tert-butyl 2-(4-carbamoylbenzyl)-3-(4-(3,4-dichlorophenyl)-5-isobutylthiazol-2-ylamino)propanoate (204-3)

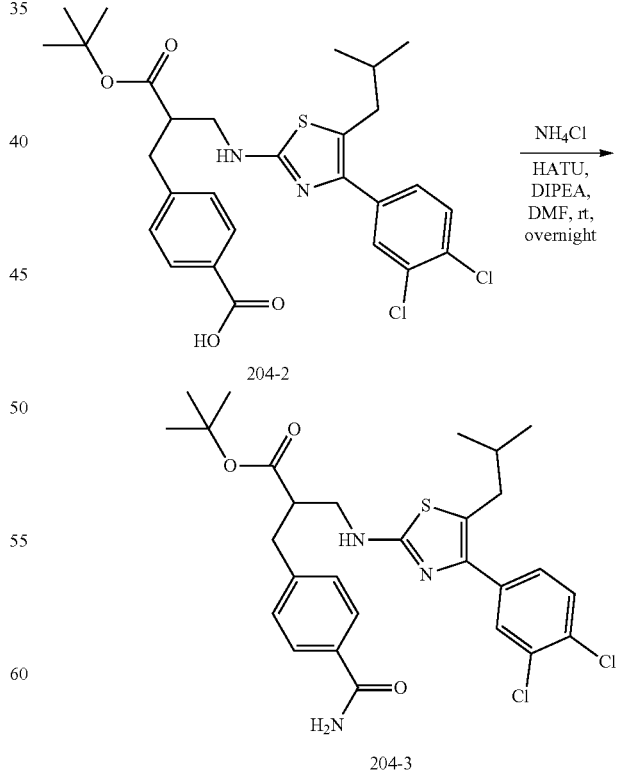

A mixture of 204-2 (130 mg, 0.231 mmol), NH$_4$Cl (18.5 mg, 0.346 mmol), HATU (176 mg, 0.462 mmol) and DIPEA (89.4 mg, 0.693 mmol) in DMF (3.00 mL) was stirred at room temperature overnight. When the reaction was completed, it was poured into H₂O (50.0 mL), and then extracted with EtOAc (100 mL×2). The organic layer was combined, and washed with H₂O (50.0 mL×2) and Brine (50.0 mL), then dried by anhydrous Na₂SO₄. The solution was concentrated to give a crude product, which was purified by prep-TLC (petrol ether/ethyl acetate=1/1) to afford 204-3 (70.0 mg, 54% yield) as a white solid.

Synthesis of 2-(4-carbamoylbenzyl)-3-(4-(3,4-dichlorophenyl)-5-isobutylthiazol-2-ylamino)propanoic acid (I-166)

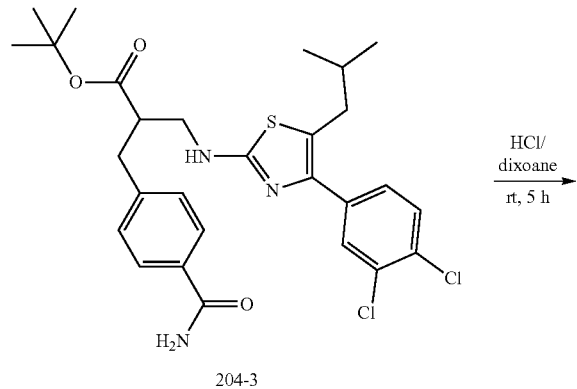

204-3

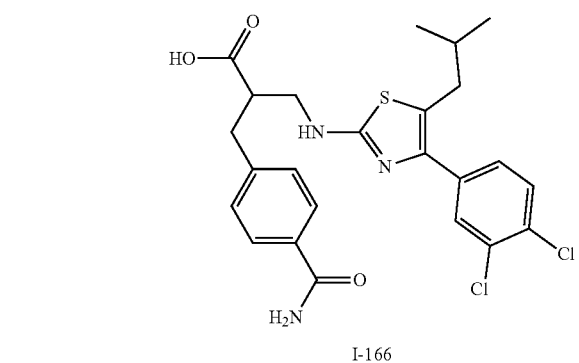

I-166

A mixture of 204-3 (70.0 mg, 0.124 mmol) in HCl (4.0 M in dioxane, 3.00 mL) was stirred at room temperature for 5 h. When the reaction was completed, it was concentrated to give a crude product, which was purified by prep-HPLC to afford I-166 (20.0 mg, 32% yield) as a white solid.

Synthesis of tert-butyl 3-(4-(3,4-dichlorophenyl)-5-isobutylthiazol-2-ylamino)-2-(3-(dimethylcarbamoyl)benzyl)propanoate (206-1)

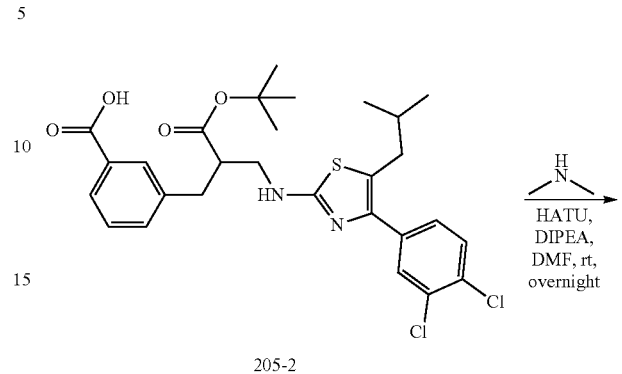

205-2

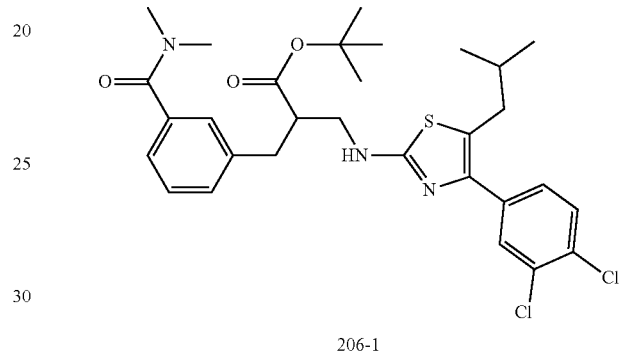

206-1

A mixture of 205-2 (200 mg, 0.355 mmol), dimethylamine (24.0 mg, 0.533 mmol), HATU (270 mg, 0.710 mmol) and DIPEA (137 mg, 1.07 mmol) in DMF (5.00 mL) was stirred at room temperature overnight. When the reaction was completed, it was poured into H₂O (100 mL), and then extracted with EtOAc (200 mL×2). The organic layer was combined, and washed with H₂O (80.0 mL×2) and Brine (50.0 mL), then dried by anhydrous Na₂SO₄. The solution was concentrated to give a crude product, which was used directly in next step without farther purification to afford 206-1 (200 mg, 95% yield) as a yellow solid.

Synthesis of 3-(4-(3,4-dichlorophenyl)-5-isobutylthiazol-2-ylamino)-2-(3-(dimethylcarbamoyl)benzyl)propanoic acid (I-168)

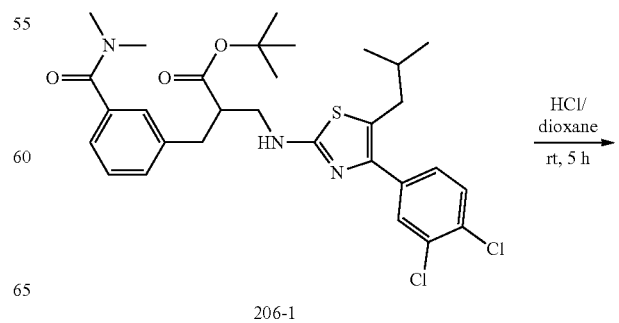

206-1

417
-continued

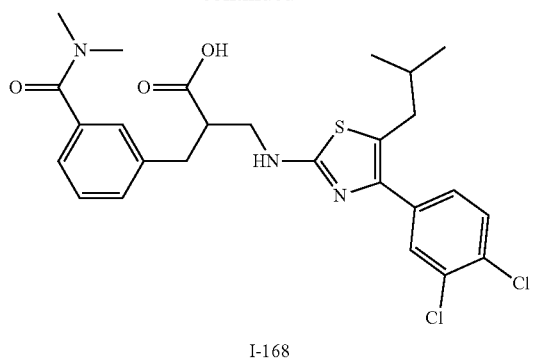

I-168

A mixture of 206-1 (200 mg, 0.339 mmol) in HCl (4.0 M in dioxane, 5.0 mL) was stirred at room temperature for 5 h. When the reaction was completed, it was concentrated to give a crude product, which was purified by prep-HPLC to afford I-168 (30.0 mg, 17% yield) as a white solid.

Synthesis of methyl 2-benzyl-3-((5-bromo-4-(3,4-dichlorophenyl)thiazol-2-yl)(tert-butoxycarbonyl)amino)propanoate (224-6)

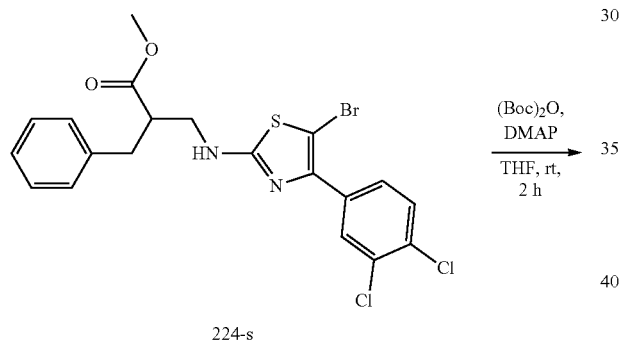

224-s

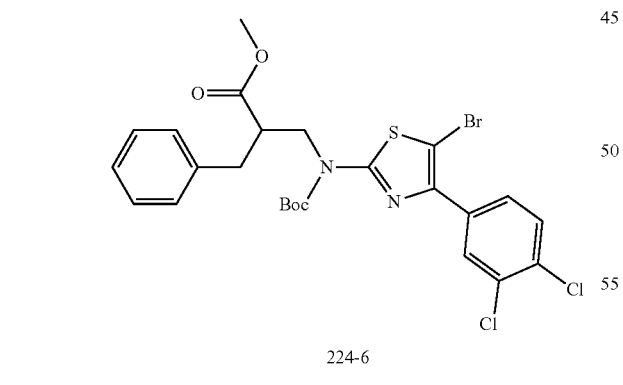

224-6

A mixture of 224-s (1.0 g, 2.00 mmol), (Boc)₂O (458 mg, 2.10 mmol) and DMAP (366 mg, 3.00 mmol) in THF (20.0 mL) was stirred at room temperature for 2 h. When the reaction was completed, it was concentrated to give a crude product, which was purified by prep-TLC (petrol ether/ethyl acetate=6/1) to afford 224-6 (700 mg, 58% yield) as a yellow solid.

418

Synthesis of methyl 2-benzyl-3-(tert-butoxycarbonyl(4-(3,4-dichlorophenyl)-5-(methylthio)thiazol-2-yl)amino)propanoate (221-1)

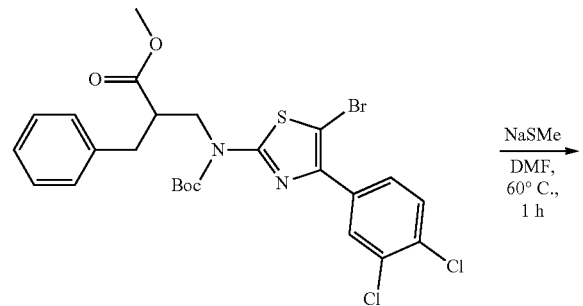

224-6

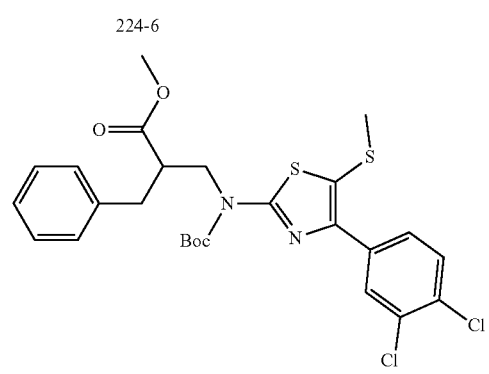

221-1

A mixture of 224-6 (200 mg, 0.333 mmol) and NaSMe (28.0 mg, 0.400 mmol) in DMF (2.0 mL) was stirred at 60° C. for 1 h. When the reaction was completed, it was poured into H₂O (100 mL), and then extracted with EtOAc (200 mL×2). The organic layer was combined, and washed with H₂O (80.0 mL×2) and Brine (50.0 mL), then dried by anhydrous Na₂SO₄. The solution was concentrated and purified by prep-TLC (petrol ether/ethyl acetate=5/1) to afford 221-1 (100 mg, 53% yield) as yellow oil.

Synthesis of methyl 2-benzyl-3-(4-(3,4-dichlorophenyl)-5-(methylthio)thiazol-2-ylamino)propanoate (221-2)

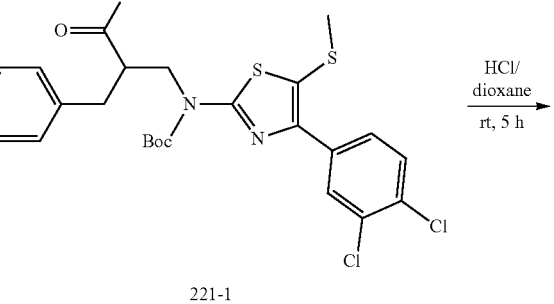

221-1

-continued

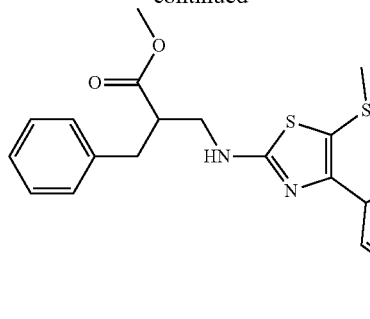

221-2

A mixture of 221-1 (100 mg, 0.176 mmol) in HCl (4.0 M in dioxane, 3.0 mL) was stirred at room temperature for 5 h. When the reaction was completed, it was concentrated to give a crude product, which was used directly in next step without farther purification to afford 221-2 (90.0 mg, 100% yield) as a white solid.

Synthesis of methyl 2-benzyl-3-(4-(3,4-dichlorophenyl)-5-(methylsulfonyl)thiazol-2-ylamino)

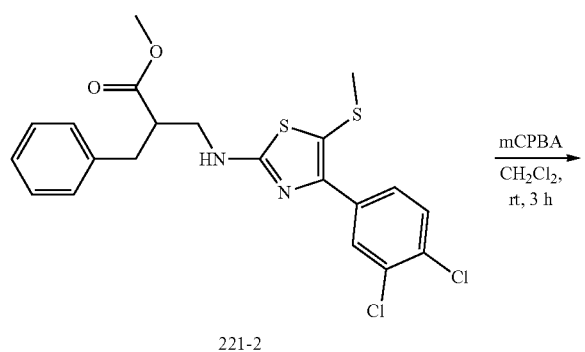

To a solution of 221-2 (90.0 mg, 0.193 mmol) in CH$_2$Cl$_2$ (10.0 mL) was added mCPBA (83.1 mg, 0.481 mmol) at 0° C. The reaction was stirred at room temperature for 3 h. When the reaction was completed, the mixture was concentrated and purified by prep-TLC (CH$_2$Cl$_2$/MeOH=80/1) to afford 221-3 (60.0 mg, 62% yield) as a white solid.

Synthesis of 2-benzyl-3-(4-(3,4-dichlorophenyl)-5-(methylsulfonyl)thiazol-2-ylamino)propanoic acid (I-181)

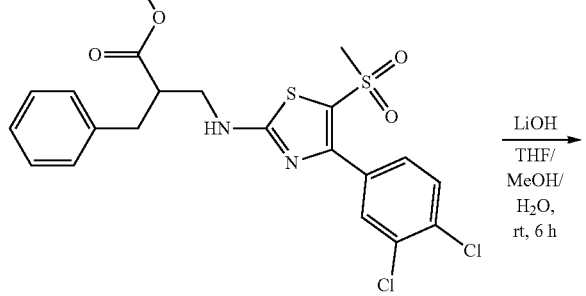

221-3

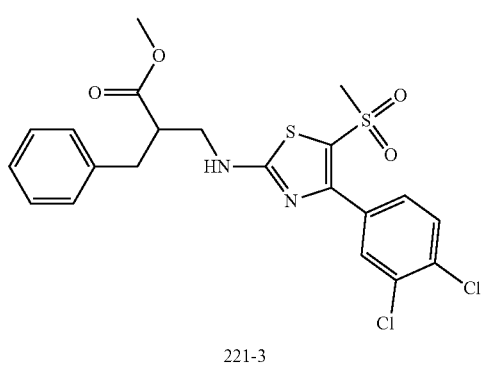

I-181

To a solution of 221-3 (60.0 mg, 0.120 mmol) in THF/MeOH/H$_2$O (v/v/v=4/1/1, 5.0 mL) was added LiOH (2.0 M in H$_2$O, 0.15 mL). The reaction was stirred at room temperature for 6 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated, the residue was purified by prep-HPLC to afford I-181 (7.00 mg, 12% yield) as a white solid.

Synthesis of 2-benzyl-3-(4-(3,4-dichlorophenyl)-5-(ethoxycarbonyl)thiazol-2-ylamino)propanoic acid (I-182)

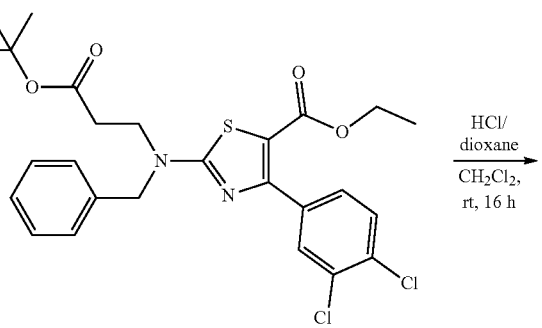

152-4

421

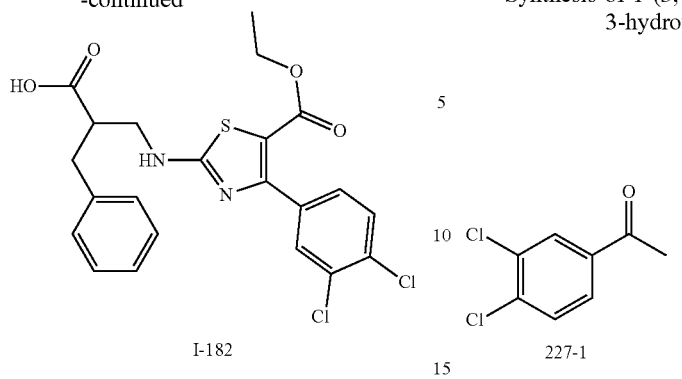

I-182

A mixture of 152-4 (250 mg, 0.467 mmol) and HCl (4.0 M in dioxane, 2.0 mL) in CH₂Cl₂ (10.0 mL) was stirred at room temperature for 16 h. When the reaction was completed, it was concentrated to give a crude product, which was purified by prep-HPLC to afford I-182 (125 mg, 56% yield) as a white solid.

Synthesis of 2-(2-carboxy-3-phenylpropylamino)-4-(3,4-dichlorophenyl)thiazole-5-carboxylic acid (I-183)

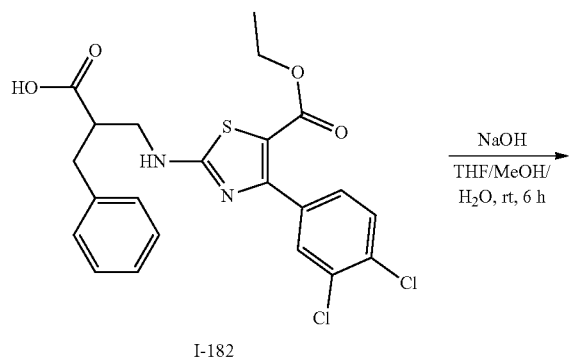

To a solution of I-182 (50.0 mg, 0.104 mmol) in THF/MeOH/H₂O (v/v/v=4/1/1, 2.0 mL) was added NaOH (2.0 M in H₂O, 0.13 mL). The reaction was stirred at room temperature for 6 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, and concentrated, the residue was purified by silica gel column chromatography (EtOAc) to afford I-183 (38.0 mg, 81% yield) as a white solid.

422

Synthesis of 1-(3,4-dichlorophenyl)-4,4,4-trifluoro-3-hydroxybutan-1-one (227-2)

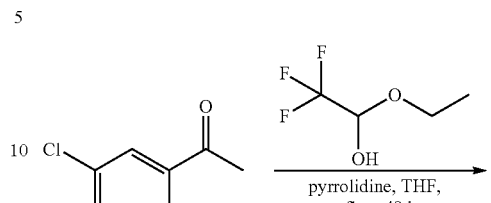

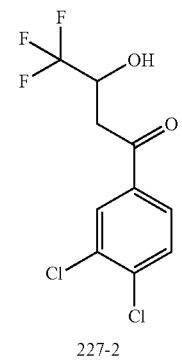

227-2

To a mixture of 227-1 (2.60 g, 13.8 mmol) and pyrrolidine (687 mg, 9.66 mmol) in THF (50.0 mL) was added 1-ethoxy-2,2,2-trifluoroethanol (1.99 g, 13.8 mmol). The reaction was refluxed for 48 h. When the reaction was completed, it was concentrated and purified by silica gel column chromatography (petrol ether/ethyl acetate=30/1) to afford 227-2 (2.50 g, 63% yield) as colorless oil.

Synthesis of (E)-1-(3,4-dichlorophenyl)-4,4,4-trifluorobut-2-en-1-one (227-3)

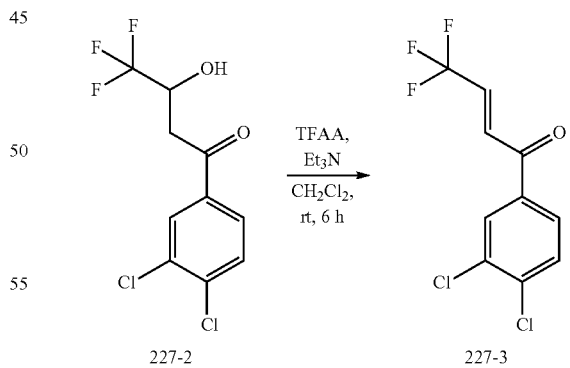

To a mixture of 227-2 (2.40 g, 8.36 mmol) in CH₂Cl₂ (50.0 mL) was added TFAA (3.51 g, 16.7 mmol) and Et₃N (2.53 g, 25.1 mmol) at 0° C. The reaction was stirred at room temperature for 6 h. When the reaction was completed, it was concentrated and purified by silica gel column chromatography (petrol ether/ethyl acetate=50/1) to afford 227-3 (2.00 g, 63% yield) as yellow oil.

Synthesis of 1-(3,4-dichlorophenyl)-4,4,4-trifluorobutan-1-ol (227-4)

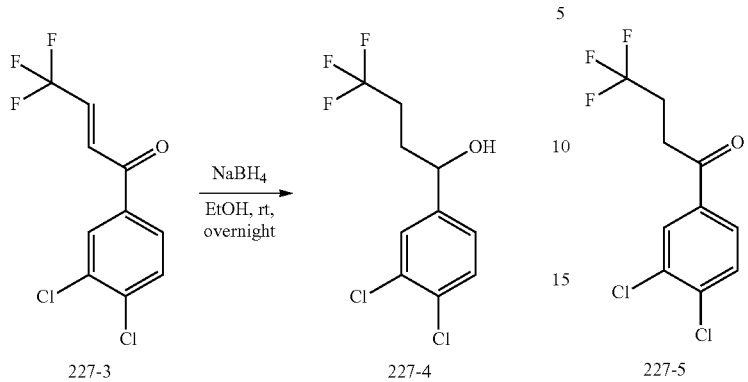

A mixture of 227-3 (2.00 g, 7.43 mmol) and NaBH₄ (2.82 g, 74.3 mmol) in EtOH (50.0 mL) was stirred at room temperature overnight. When the reaction was completed, it was concentrated and the residue was solved with EtOAc (100 mL), which was washed with H₂O (50.0 mL×2) and Brine (30.0 mL). The organic layer was dried by anhydrous Na₂SO₄, and concentrated to give a crude product, which was used directly in next step without farther purification to afford 227-4 (2.00 g, 99% yield) as colorless oil.

Synthesis of 1-(3,4-dichlorophenyl)-4,4,4-trifluorobutan-1-one (227-5)

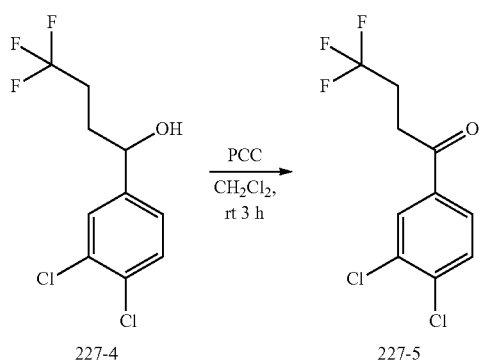

To a solution of 227-4 (2.00 g, 7.32 mmol) in CH₂Cl₂ (150 mL) was added PCC (2.37 g, 11.0 mmol). The reaction was stirred at room temperature for 3 h. When the reaction was completed, it was concentrated, and purified by silica gel column chromatography (petrol ether/ethyl acetate=100/1) to afford 227-5 (1.30 g, 65% yield) as yellow oil.

Synthesis of 2-bromo-1-(3,4-dichlorophenyl)-4,4,4-trifluorobutan-1-one (227-6)

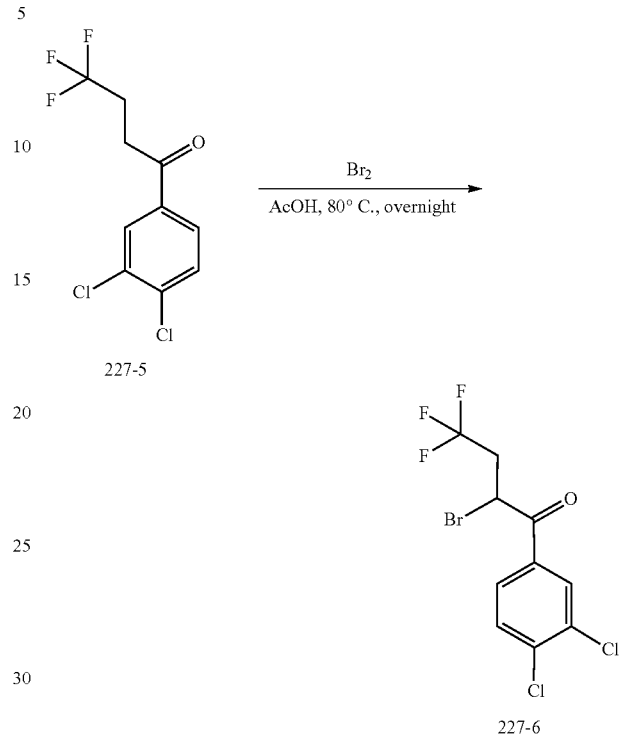

A mixture of 227-5 (1.00 g, 3.69 mmol) and Br₂ (619 mg 3.87 mmol) in AcOH (10.0 mL) was stirred at 80° C. overnight. When the reaction was completed, it was concentrated and the residue was solved with EtOAc (150 mL), which was washed with H₂O (80.0 mL×2) and Brine (50.0 mL). The organic layer was dried by anhydrous Na₂SO₄, and concentrated to give a crude product, which was purified by silica gel column chromatography (petrol ether/ethyl acetate=100/1) to afford 227-6 (720 mg, 56% yield) as yellow oil.

Synthesis of tert-butyl 2-benzyl-3-(5-(3,4-dichlorophenyl)-4-(2,2,2-trifluoroethyl)thiazol-2-ylamino) propanoate (227-7)

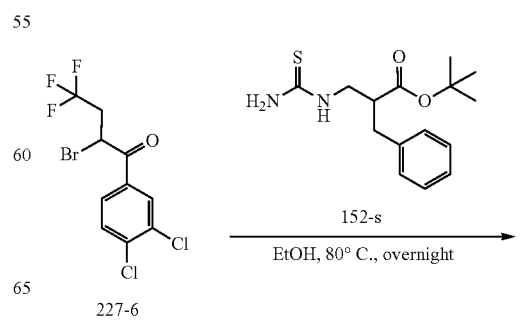

426

Synthesis of methyl 2-benzyl-3-(4-(3,4-dichlorophenyl)-5-(prop-1-en-2-yl)thiazol-2-ylamino)propanoate (228-1)

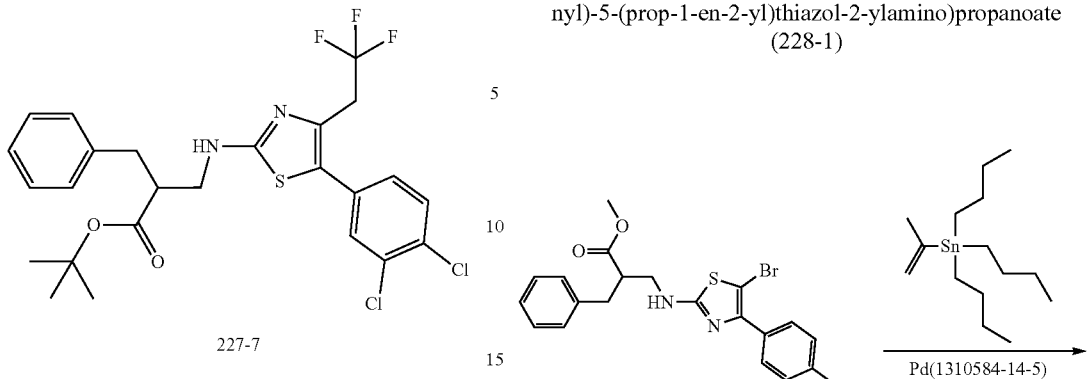

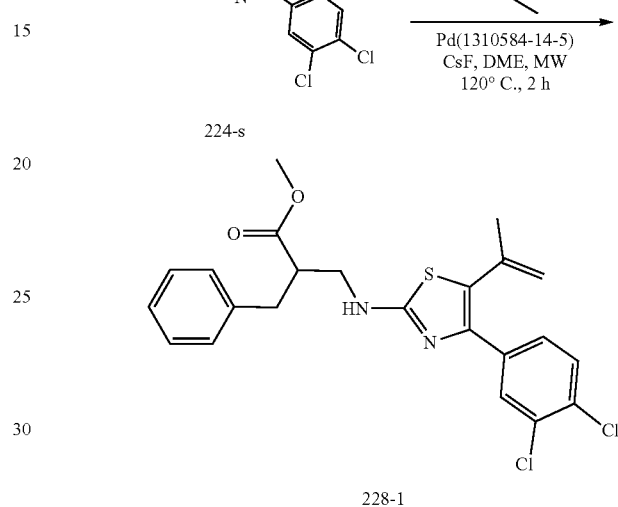

A mixture of 224-s (200 mg, 0.400 mmol), tributyl(prop-1-en-2-yl)stannane (199 mg, 0.600 mmol), Pd catalyst (CAS: 1310584-14-5, 62.9 mg, 0.080 mmol) and CsF (122 mg, 0.800 mmol) in DME (5.0 mL) was stirred at 120° C. under microwave for 2 h. When the reaction was completed, it was poured into H₂O (80 mL), and then extracted with EtOAc (100 mL×2). The organic layer was combined, and washed with H₂O (50.0 mL×2) and Brine (50.0 mL), then dried by anhydrous Na₂SO₄. The solution was concentrated and purified by silica gel column chromatography (petrol ether/ethyl acetate=10/1) to afford 228-1 (55.0 mg, 30% yield) as a yellow solid Synthesis of 2-benzyl-3-(4-(3,4-dichlorophenyl)-5-(prop-1-en-2-yl)thiazol-2-ylamino)propanoic acid (I-185)

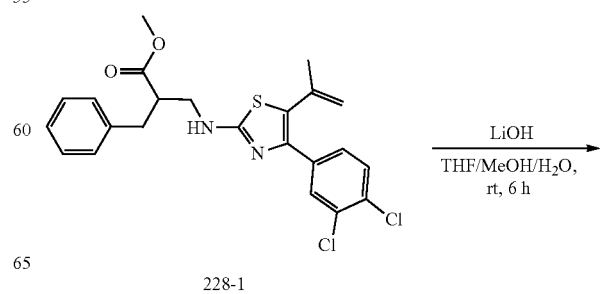

425

-continued

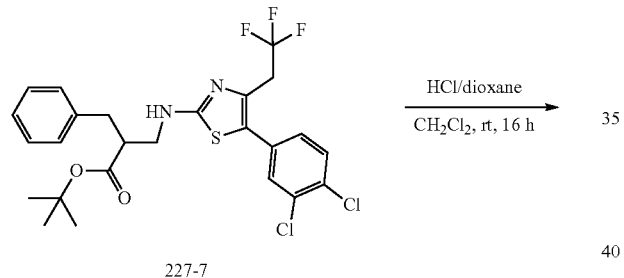

227-7

A mixture of 227-6 (250 mg, 0.713 mmol) and 152-s (210 mg, 0.713 mmol) in EtOH (2.0 mL) was stirred at 80° C. overnight. When the reaction was completed, the mixture was concentrated to give a crude product, which was used directly in next step without farther purification to afford 227-7 (300 mg, 77% yield) as yellow oil.

Synthesis of 2-benzyl-3-(4-(3,4-dichlorophenyl)-5-(2,2,2-trifluoroethyl)thiazol-2-ylamino)propanoic acid (I-184)

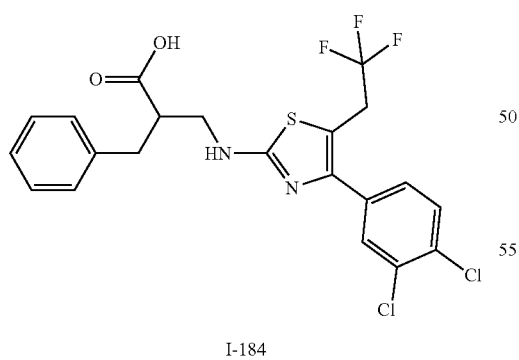

A mixture of 227-7 (300 mg, 0.550 mmol) and HCl (4.0 M in dioxane, 5.0 mL) in CH₂Cl₂ (10.0 mL) was stirred at room temperature for 16 h. When the reaction was completed, it was concentrated to give a crude product, which was purified by prep-HPLC to afford I-184 (55.0 mg, 20% yield) as a white solid.

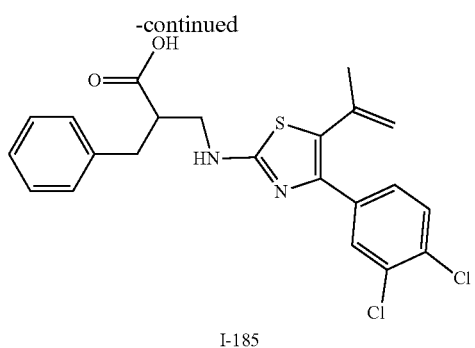

I-185

To a solution of 228-1 (55.0 mg, 0.119 mmol) in THF/MeOH/H$_2$O (v/v/v=4/1/1, 2.0 mL) was added LiOH (2.0 M in H$_2$O, 0.15 mL). The reaction was stirred at room temperature for 6 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated, the residue was purified by prep-HPLC to afford I-185 (10.0 mg, 19% yield) as a white solid.

Synthesis of 3-(benzyl(4-(3,4-dichlorophenyl)-5-isobutylthiazol-2-yl)amino)-N-(3-(1,3-dioxoisoindolin-2-yl)propylsulfonyl)propanamide (229-1)

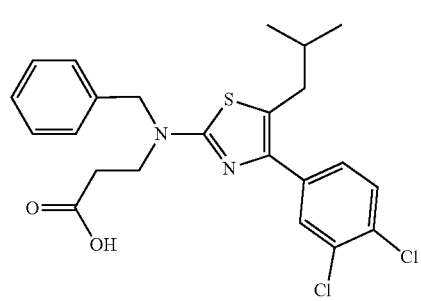

I-47

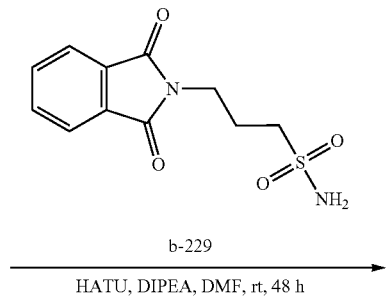

b-229

HATU, DIPEA, DMF, rt, 48 h

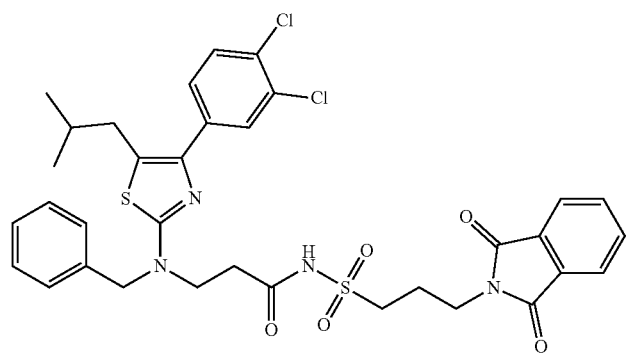

229-1

A mixture of I-47 (294 mg, 0.634 mmol), b-229 (170 mg, 0.634 mmol), HATU (482 mg, 1.27 mmol) and DIPEA (245 mg, 1.90 mmol) in DMF (5.00 mL) was stirred at room temperature for 48 h. When the reaction was completed, it was poured into H$_2$O (100 mL), and then extracted with EtOAc (200 mL×2). The organic layer was combined, and washed with H$_2$O (80.0 mL×2) and Brine (50.0 mL), then dried by anhydrous Na$_2$SO$_4$. The solution was concentrated to give a crude product, which was purified by silica gel column chromatography (CH$_2$Cl$_2$/MeOH=100/1) to afford 229-1 (45.0 mg, 10% yield) as a yellow solid.

A mixture of 229-1 (45.0 mg, 0.063 mmol) and hydrazine hydrate (6.31 mg, 0.126 mmol) in EtOH (2.0 mL) was stirred at 90° C. for 2 h. When the reaction was completed, it was concentrated to give the crude product, which was purified by prep-HPLC to afford I-186 (4.0 mg, 11% yield) as a white solid.

Synthesis of tert-butyl 2-(2-(benzyl(4-(3,4-dichlorophenyl)-5-isobutylthiazol-2-yl)amino)ethylsulfonamido)-2-oxoethylcarbamate (230-1)

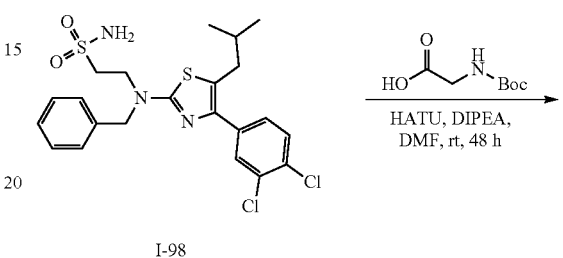

Synthesis of N-(3-aminopropylsulfonyl)-3-(benzyl (4-(3,4-dichlorophenyl)-5-isobutylthiazol-2-yl) amino)propanamide (I-186)

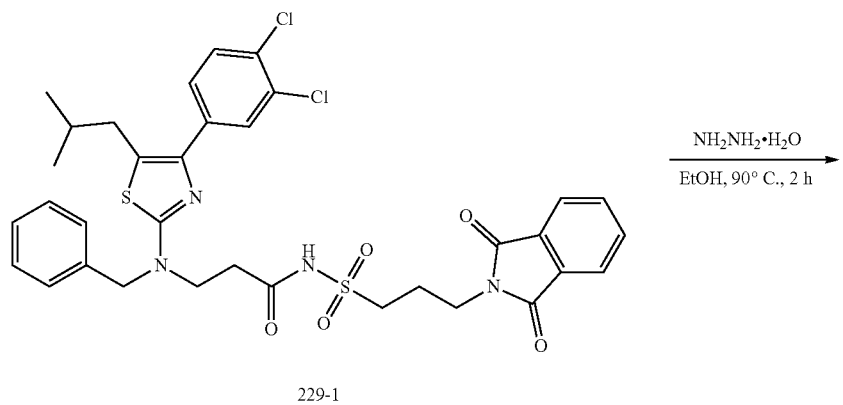

229-1

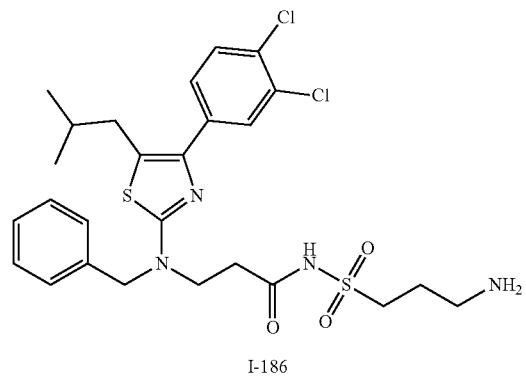

I-186

-continued

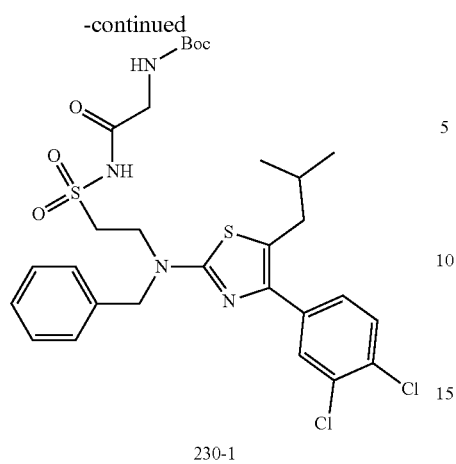

230-1

-continued

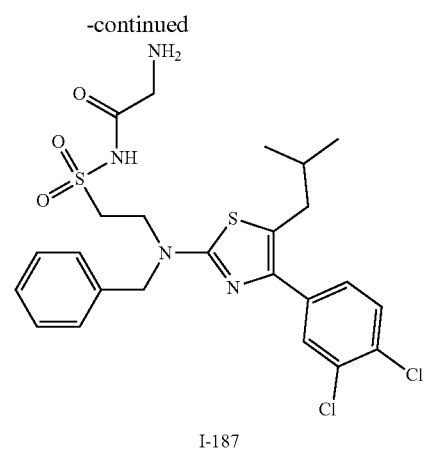

I-187

A mixture of 230-1 (200 mg, 0.305 mmol) in HCl (4.0 M in dioxane, 3.0 mL) was stirred at room temperature for 2 h. When the reaction was completed, it was concentrated to give a crude product, which was purified by prep-HPLC to afford I-187 (100 mg, 59% yield) as a white solid.

A mixture of I-98 (200 mg, 0.401 mmol), 2-(tert-butoxycarbonylamino)acetic acid (84.3 mg, 0.481 mmol), HATU (305 mg, 0.802 mmol) and DIPEA (155 mg, 1.20 mmol) in DMF (5.00 mL) was stirred at room temperature for 48 h. When the reaction was completed, it was poured into H$_2$O (100 mL), and then extracted with EtOAc (200 mL×2). The organic layer was combined, and washed with H$_2$O (80.0 mL×2) and Brine (50.0 mL), then dried by anhydrous Na$_2$SO$_4$. The solution was concentrated to give a crude product, which was used directly in next step without farther purification to afford 230-1 (200 mg, 76% yield) as a yellow solid.

Synthesis of 3-(benzyl(4-(3,4-dichlorophenyl)-5-isobutylthiazol-2-yl)amino)-2-hydroxypropanoic acid (I-190)

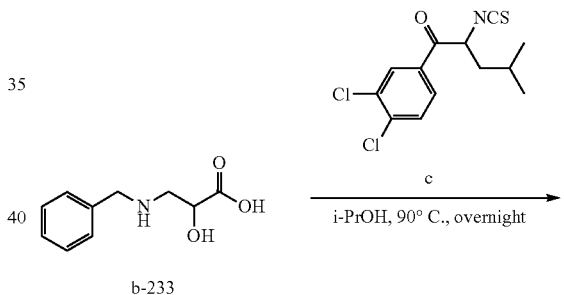

b-233

Synthesis of 2-amino-N-(2-(benzyl(4-(3,4-dichlorophenyl)-5-isobutylthiazol-2-yl)amino)ethylsulfonyl) acetamide (I-187)

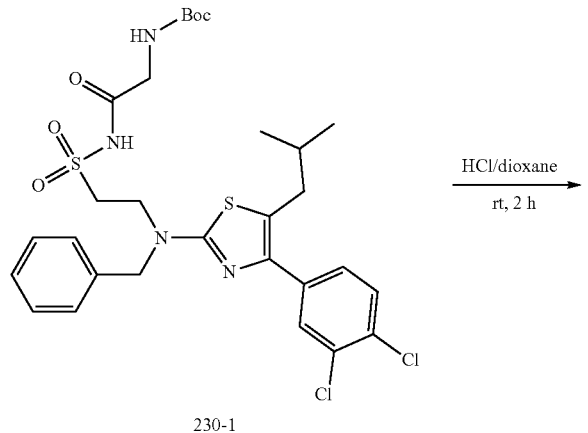

230-1

HCl/dioxane
rt, 2 h

I-190

A mixture of c (771 mg, 2.56 mmol) and b-233 (500 mg, 2.56 mmol) in i-PrOH (15.0 mL) was stirred at 90° C. overnight. When the reaction was completed, the mixture was purified by prep-HPLC to afford I-190 (200 mg, 16% yield) as a white solid.

433

Synthesis of tert-butyl 3-(benzyl(4-(3,4-dichlorophenyl)-5-isobutylthiazol-2-yl)amino)propylcarbamate (235-2)

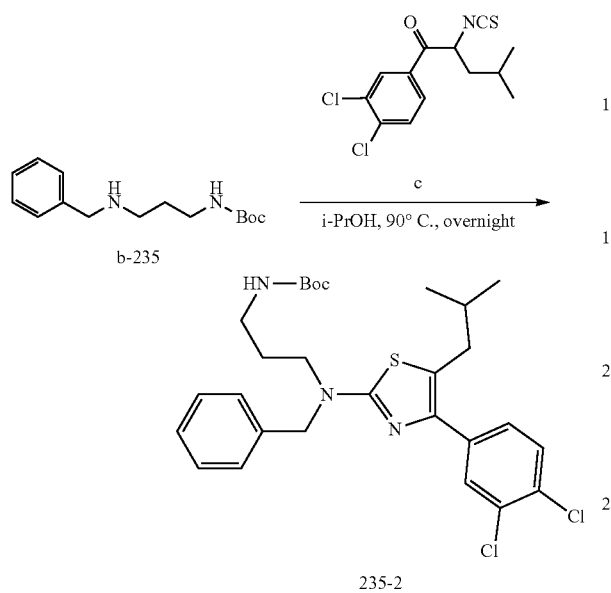

A mixture of c (228 mg, 0.757 mmol) and b-235 (200 mg, 0.757 mmol) in i-PrOH (5.0 mL) was stirred at 90° C. overnight. When the reaction was completed, the mixture was purified by prep-TLC (CH₂Cl₂/MeOH=100/1) to afford 235-2 (80.0 mg, 19% yield) as a white solid.

434

Synthesis of N¹-benzyl-N¹-(4-(3,4-dichlorophenyl)-5-isobutylthiazol-2-yl)propane-1,3-diamine (I-191)

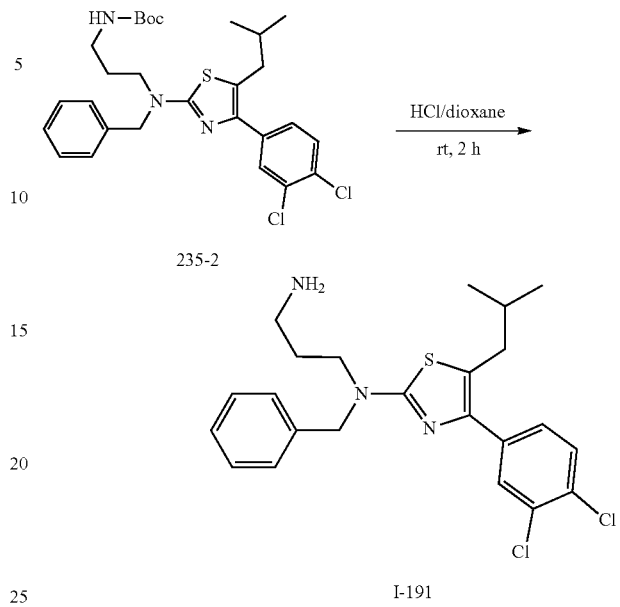

A mixture of 235-2 (80.0 mg, 0.146 mmol) in HCl (4.0 M in dioxane, 3.0 mL) was stirred at room temperature for 2 h. When the reaction was completed, it was concentrated to give a crude product, which was purified by prep-HPLC to afford I-191 (10.0 mg, 15% yield) as a white solid.

Synthesis of ethyl 3-(3-(benzyl(4-(3,4-dichlorophenyl)-5-isobutylthiazol-2-yl)amino) propanamido) propanoate (241-1)

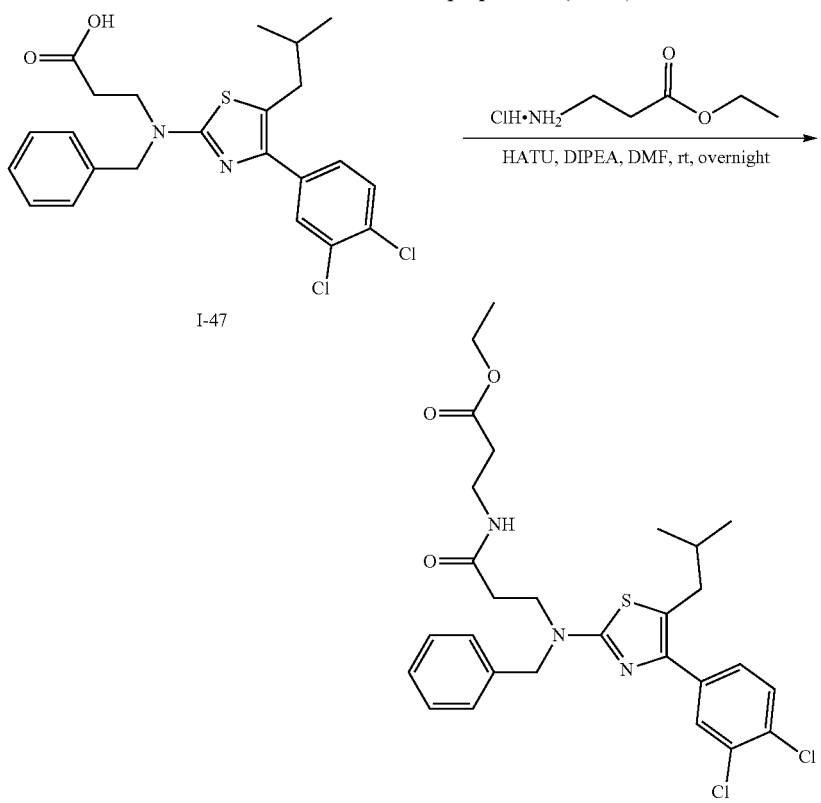

A mixture of I-47 (150 mg, 0.324 mmol), ethyl 3-aminopropanoate hydrochloride (59.8 mg, 0.389 mmol), HATU (246 mg, 0.648 mmol) and DIPEA (125 mg, 0.972 mmol) in DMF (2.00 mL) was stirred at room temperature overnight. When the reaction was completed, it was poured into H$_2$O (50.0 mL), and then extracted with EtOAc (80.0 mL×2). The organic layer was combined, and washed with H$_2$O (50.0 mL×2) and Brine (50.0 mL), then dried by anhydrous Na$_2$SO$_4$. The solution was concentrated to give a crude product, which was used directly in next step without farther purification to afford 241-1 (30.0 mg, 16% yield) as a yellow solid.

Synthesis of 3-(3-(benzyl(4-(3,4-dichlorophenyl)-5-isobutylthiazol-2-yl)amino) propanamido)propanoic acid (I-196)

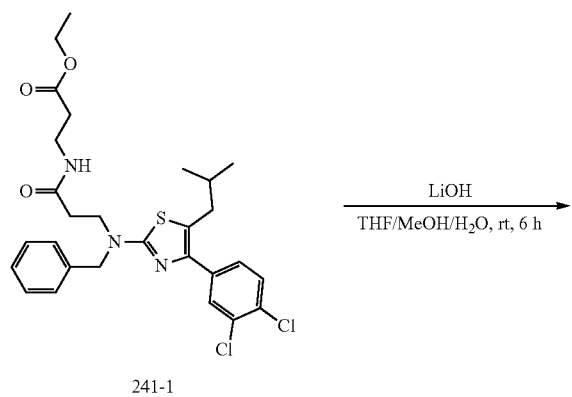

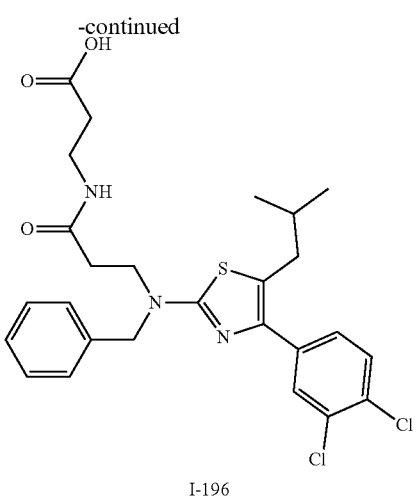

I-196

To a solution of 241-1 (30.0 mg, 0.0533 mmol) in THF/MeOH/H$_2$O (v/v/v=4/1/1, 1.0 mL) was added LiOH (2.0 M in H$_2$O, 0.067 mL). The reaction was stirred at room temperature for 6 h. When the reaction was completed, the resulting reaction was concentrated, then it was diluted with H$_2$O (5.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-196 (10.0 mg, 35% yield) as a white solid.

Synthesis of tert-butyl 2-(4-(3,4-dichlorophenyl)-5-isobutylthiazol-2-yl)-14,14-dimethyl-5,12-dioxo-1-phenyl-13-oxa-2,6,9,11-tetraazapentadecan-10-ylidenecarbamate (242-1)

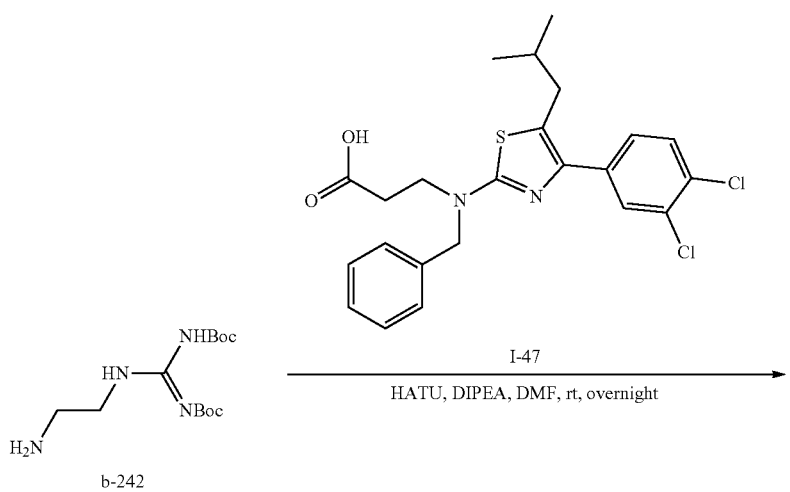

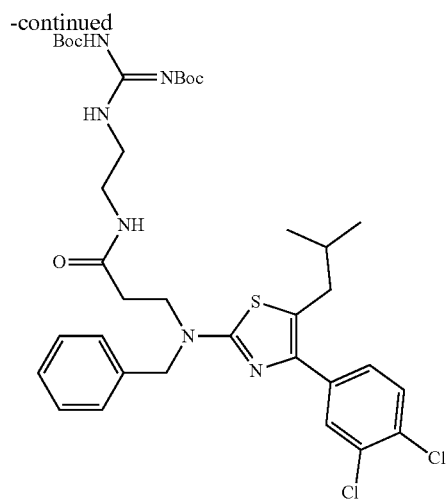

242-1

A mixture of I-47 (230 mg, 0.496 mmol), b-242 (150 mg, 0.496 mmol), HATU (377 mg, 0.992 mmol) and DIPEA (192 mg, 1.49 mmol) in DMF (10.0 mL) was stirred at room temperature overnight. When the reaction was completed, it was poured into H₂O (150 mL), and then extracted with EtOAc (100 mL×2). The organic layer was combined, and washed with H₂O (100 mL×2) and Brine (50 mL), then dried by anhydrous Na₂SO₄. The solution was concentrated to give a crude product, which was used directly in next step without farther purification to afford 241-1 (300 mg, 81% yield) as a yellow solid.

Synthesis of 3-(benzyl(4-(3,4-dichlorophenyl)-5-isobutylthiazol-2-yl)amino)-N-(2-guanidinoethyl)propanamide (I-197)

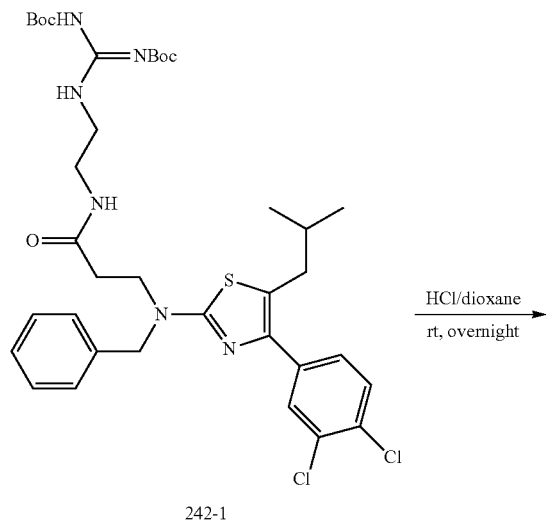

242-1

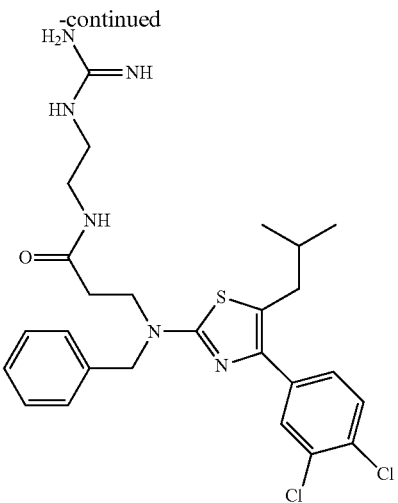

I-197

A mixture of 242-1 (300 mg, 0.401 mmol) in HCl (4.0 M in dioxane, 10.0 mL) was stirred at room temperature overnight. When the reaction was completed, it was concentrated to give a crude product, which was purified by prep-HPLC to afford I-197 (100 mg, 4600 yield) as a white solid.

TABLE 3-3

| I-# | Chemical Structure | LCMS | $^1$H NMR (400 MHz, d$_6$-DMSO) |
|---|---|---|---|
| 119 | 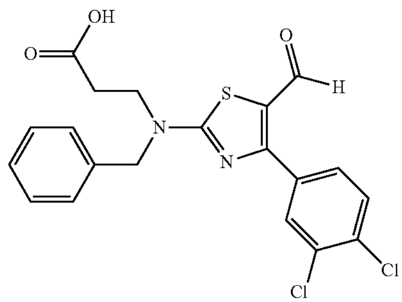 [SMILES: O=Cc1sc(N(CCC(=O)O)Cc2ccccc2)nc1-c1ccc(Cl)c(Cl)c1] | Method C, Purity is 97.0%, Rt = 1.806 min; MS Calcd.: 434.1; MS Found: 435.2 [M + H]$^+$. | δ: 2.65-2.68 (2H, m), 3.77-3.85 (2H, m), 4.78-4.86 (2H, m), 7.28-7.38 (5H, m), 7.73-7.77 (2H, m), 8.00 (1H, s), 9.62 (1H, s), 12.44 (1H, brs). |
| 120 | 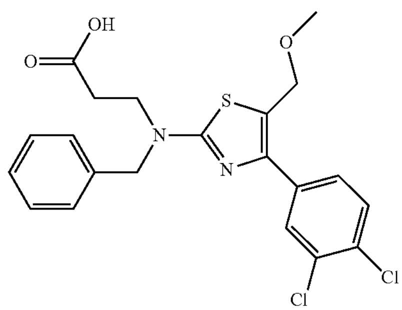 [SMILES: COCc1sc(N(CCC(=O)O)Cc2ccccc2)nc1-c1ccc(Cl)c(Cl)c1] | Method C, Purity is 97.6%, Rt = 1.905 min; MS Calcd.: 450.1; MS Found: 451.2 [M + H]$^+$. | δ: 2.53 (2H, t, J = 7.6 Hz), 3.28 (3H, s), 3.64 (2H, t, J = 7.6 Hz), 4.41 (2H, s), 4.69 (2H, s), 7.23-7.35 (5H, m), 7.56 (1H, dd, J = 8.4, 2.0 Hz), 7.67 (1H, d, J = 8.4 Hz), 7.78 (1H, d, J = 2.0 Hz). |
| 121 | 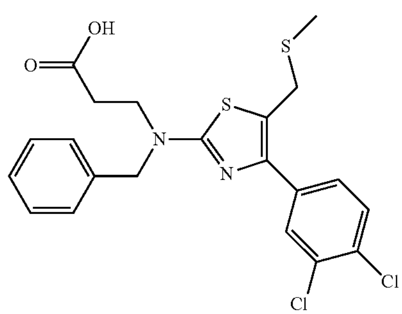 [SMILES: CSCc1sc(N(CCC(=O)O)Cc2ccccc2)nc1-c1ccc(Cl)c(Cl)c1] | Method B, Purity is 97.4%, Rt = 2.138 min; MS Calcd.: 466.1; MS Found: 467.0 [M + H]$^+$. | δ: 2.05 (3H, s), 2.61 (2H, t, J = 7.2 Hz), 3.66 (2H, t, J = 7.2 Hz), 3.89 (2H, s), 4.67 (2H, s), 7.27-7.36 (5H, m), 7.59 (1H, dd, J = 8.4, 2.0 Hz), 7.68 (1H, d, J = 8.0 Hz), 7.81 (1H, d, J = 2.0 Hz), 12.38 (1H, brs). |
| 122 | 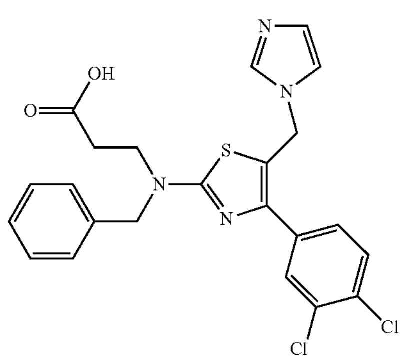 [SMILES: O=C(O)CCN(Cc1ccccc1)c1nc(-c2ccc(Cl)c(Cl)c2)c(Cn2ccnc2)s1] | Method C, Purity is 99.3%, Rt = 1.748 min; MS Calcd.: 486.1; MS Found: 419.2 [M − C$_3$H$_3$N$_2$]$^+$. | δ: 2.56 (2H, t, J = 6.8 Hz), 3.62 (3H, t, J = 6.8 Hz), 4.65 (2H, s), 5.34 (2H, s), 6.87 (1H, s), 7.07 (1H, s), 7.25-7.35 (5H, m), 7.54 (1H, dd, J = 8.4, 2.0 Hz), 7.62 (1H, s), 7.66-7.70 (1H, m), 7.74 (1H, d, J = 2.0 Hz). |

TABLE 3-3-continued

Characterization Data for Compounds

| I-# | Chemical Structure | LCMS | $^1$H NMR (400 MHz, $d_6$-DMSO) |
|---|---|---|---|
| 123 | 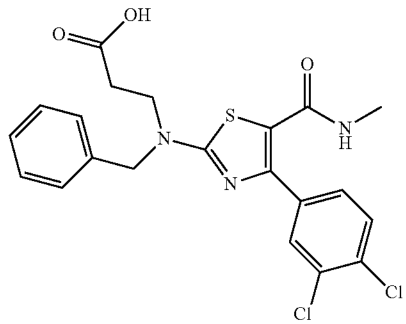 | Method C, Purity is 100%, Rt = 2.110 min; MS Calcd.: 476.1; MS Found: 477.2 [M + H]$^+$. | δ: 2.54 (3H, t, J = 4.8 Hz), 2.60 (3H, t, J = 4.4 Hz), 3.30-3.32 (2H, m), 3.69 (2H, t, J = 6.8 Hz), 4.67 (2H, s), 7.27-7.29 (3H, m), 7.33-7.37 (2H, m), 7.57-7.64 (2H, m), 7.83-7.90 (2H, m), 8.51 (1H, s). |
| 124 | 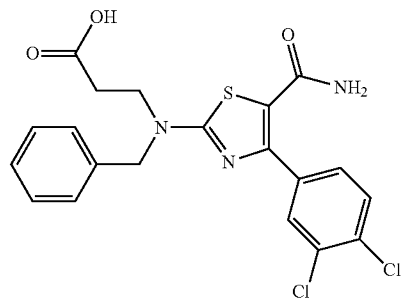 [SMILES: NC(=O)c1sc(N(CCC(=O)O)Cc2ccccc2)nc1-c1ccc(Cl)c(Cl)c1] | Method C, Purity is 100%, Rt = 2.624 min; MS Calcd.: 505.1; MS Found: 506.2 [M + H]$^+$. | δ: 2.42-2.45 (2H, m), 3.61 (2H, t, J = 7.2 Hz), 4.64 (2H, s), 6.88 (1H, s), 7.25-7.30 (5H, m), 7.44 (1H, s), 7.50 (1H, d, J = 8.4 Hz), 8.18-8.21 (1H, m), 8.72 (1H, s). |
| 125 | 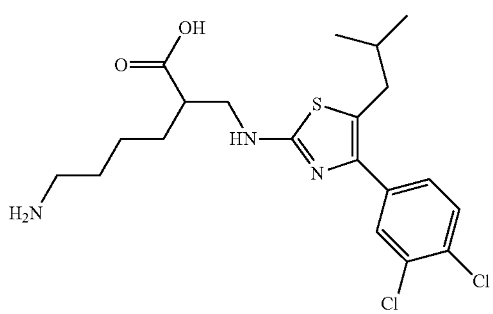 [SMILES: CC(C)Cc1sc(NCC(CCCCN)C(=O)O)nc1-c1ccc(Cl)c(Cl)c1] | Method C, Purity is 98.1%, Rt = 1.860 min; MS Calcd.: 443.1; MS Found: 444.3 [M + H]$^+$. | δ: 0.85 (6H, d, J = 6.4 Hz), 1.33-1.45 (6H, m), 1.70-1.74 (1H, m), 2.27 (1H, s), 2.56 (2H, d, J = 7.2 Hz), 2.65-2.87 (2H, m), 3.13-3.16 (2H, m), 3.23-3.25 (3H, m), 7.47 (1H, dd, J = 8.4, 2.0 Hz), 7.55 (1H, brs), 7.62 (1H, d, J = 8.4 Hz), 7.69 (1H, d, J = 2.0 Hz). |
| 126 | 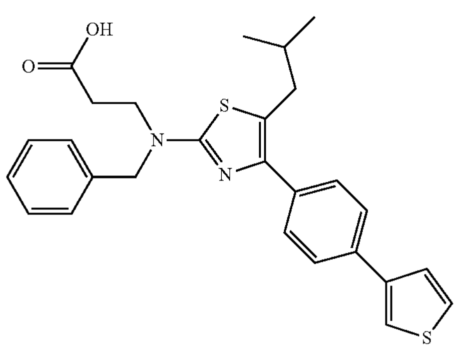 [SMILES: CC(C)Cc1sc(N(CCC(=O)O)Cc2ccccc2)nc1-c1ccc(-c2ccsc2)cc1] | Method C, Purity is 100%, Rt = 2.087 min; MS Calcd.: 476.2; MS Found: 477.3 [M + H]$^+$. | δ: 0.87 (6H, d, J = 3.4 Hz), 1.73-1.80 (1H, m), 2.44 (2H, brs), 2.62 (2H, d, J = 6.4 Hz), 3.56 (2H, t, J = 5.6 Hz), 4.67 (2H, s), 7.24-7.34 (5H, m), 7.54-7.56 (3H, m), 7.61-7.63 (1H, m), 7.72 (2H, d, J = 6.8 Hz), 7.86 (1H, s). |
| 127 | 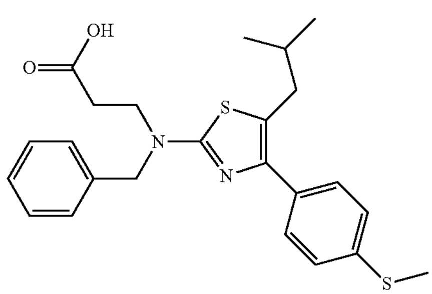 [SMILES: CSc1ccc(-c2nc(N(CCC(=O)O)Cc3ccccc3)sc2CC(C)C)cc1] | Method C, Purity is 100%, Rt = 2.034 min; MS Calcd.: 440.1; MS Found: 441.4 [M + H]$^+$. | δ: 0.86 (6H, d, J = 6.8 Hz), 1.67-1.76 (1H, m), 2.49 (3H, s), 2.57-2.62 (4H, m), 3.62 (2H, t, J = 7.2 Hz), 4.63 (2H, s), 7.23-7.35 (7H, m), 7.46 (2H, dd, J = 6.8, 2.0 Hz), 12.33 (1H, brs). |

TABLE 3-3-continued

Characterization Data for Compounds

| I-# | Chemical Structure | LCMS | ¹H NMR (400 MHz, d₆-DMSO) |
|---|---|---|---|
| 128 | 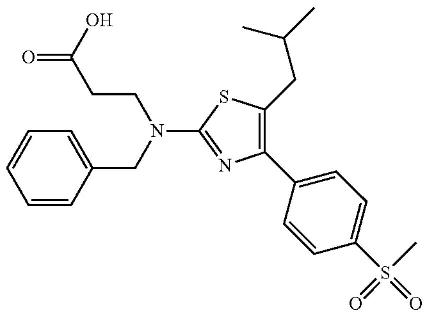 [SMILES: CC(C)Cc1sc(N(CCC(=O)O)Cc2ccccc2)nc1-c1ccc(S(C)(=O)=O)cc1] | Method C, Purity is 99.9%, Rt = 1.771 min; MS Calcd.: 472.2; MS Found: 473.4 [M + H]⁺. | δ: 0.86 (6H, d, J = 6.8 Hz), 1.73-1.77 (1H, m), 2.56 (2H, t, J = 7.2 Hz), 2.65 (2H, d, J = 7.2 Hz), 3.21 (3H, s), 3.62 (2H, t, J = 7.2 Hz), 4.66 (2H, s), 7.24-7.36 (5H, m), 7.78 (2H, d, J = 8.8 Hz), 7.93 (2H, d, J = 8.4 Hz). |
| 129 | 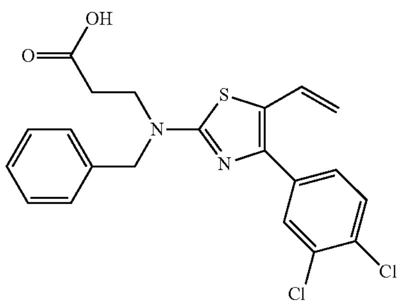 [SMILES: C=Cc1sc(N(CCC(=O)O)Cc2ccccc2)nc1-c1ccc(Cl)c(Cl)c1] | Method C, Purity is 81.2%, Rt = 2.008 min; MS Calcd.: 432.1; MS Found: 433.3 [M + H]⁺. | δ: 2.56-2.67 (2H, m), 3.68 (2H, dd, J = 14.4, 6.8 Hz), 4.74 (2H, brs), 5.09-5.23 (1H, m), 7.28-7.39 (5H, m), 7.52 (1H, t, J = 6.0 Hz), 7.69-7.74 (2H, m). |
| 130 | 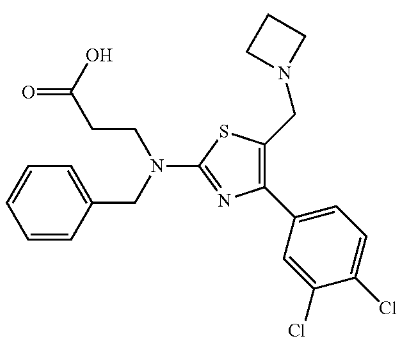 [SMILES: O=C(O)CCN(Cc1ccccc1)c1nc(-c2ccc(Cl)c(Cl)c2)c(CN2CCC2)s1] | Method C, Purity is 97.8%, Rt = 1.885 min; MS Calcd.: 475.1; MS Found: 419.2 [M − C₃H₆N]⁺. | δ: 1.95 (2H, t, J = 7.2 Hz), 2.60 (2H, t, J = 7.2 Hz), 3.14 (4H, t, J = 7.2 Hz), 3.63-3.67 (4H, m), 4.68 (2H, s), 7.28-7.37 (5H, m), 7.59 (1H, dd, J = 8.4, 2.0 Hz), 7.67 (1H, d, J = 8.4 Hz), 7.83 (1H, d, J = 2.0 Hz). |
| 131 | 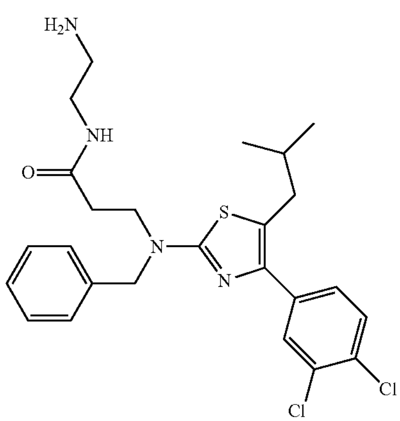 [SMILES: CC(C)Cc1sc(N(CCC(=O)NCCN)Cc2ccccc2)nc1-c1ccc(Cl)c(Cl)c1] | Method B, Purity is 93.8%, Rt = 1.926 min; MS Calcd.: 504.2; MS Found: 505.1 [M + H]⁺. | d₄-MeOD; δ: 0.90 (6H, d, J = 6.4 Hz), 1.77-1.81 (1H, m), 2.59-2.62 (4H, m), 2.70 (2H, t, J = 6.4 Hz), 3.22 (2H, t, J = 6.4 Hz), 3.78 (2H, t, J = 7.2 Hz), 4.67 (2H, s), 7.26-7.35 (5H, m), 7.45 (1H, d, J = 1.0 Hz), 7.47-7.69 (1H, m), 7.70 (1H, s). |

TABLE 3-3-continued

Characterization Data for Compounds

| I-# | Chemical Structure | LCMS | ¹H NMR (400 MHz, d₆-DMSO) |
|---|---|---|---|
| 132 | 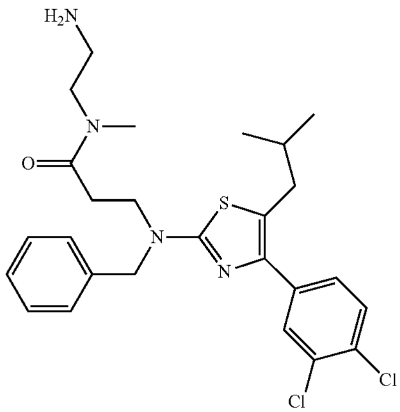 [SMILES: CC(C)Cc1sc(N(CCC(=O)N(C)CCN)Cc2ccccc2)nc1-c1ccc(Cl)c(Cl)c1] | Method B, Purity is 98.6%, Rt = 2.003 min; MS Calcd.: 518.2; MS Found: 519.2 [M + H]⁺. | d₄-MeOD; δ: 0.90 (6H, d, J = 6.4 Hz), 1.77-1.81 (1H, m), 2.62 (2H, d, J = 7.2 Hz), 2.72-2.80 (4H, m), 2.88 (1H, s), 3.01 (2H, s), 3.37-3.43 (2H, m), 3.78 (2H, t, J = 6.8 Hz), 4.68 (2H, brs), 7.27-7.34 (5H, m), 7.47 (1H, dd, J = 3.6, 1.6 Hz), 7.54 (1H, dd, J = 8.4, 2.4 Hz), 7.69 (1H, s). |
| 133 | 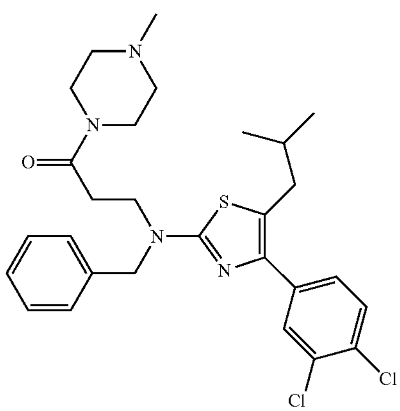 [SMILES: CC(C)Cc1sc(N(CCC(=O)N2CCN(C)CC2)Cc2ccccc2)nc1-c1ccc(Cl)c(Cl)c1] | Purity is 100%, Rt = 1.956 min; MS Calcd.: 544.1; MS Found: 545.2 [M + H]⁺. | δ: 0.85 (6H, d, J = 6.8 Hz), 1.69-1.74 (1H, m), 1.69 (3H, m), 2.17-2.21 (4H, m), 2.60 (2H, dd, J = 7.2 Hz), 2.64-2.69 (2H, q, J = 5.2 Hz), 3.38 (4H, t, J = 5.2 Hz), 3.62 (1H, t, J = 7.2 Hz), 4.64 (2H, s), 7.24-7.36 (5H, m), 7.49 (1H, dd, J = 6.8, 2.0 Hz), 7.64 (1H, d, J = 8.4 Hz), 7.71 (1 H, d, J = 2.0 Hz). |
| 134 | 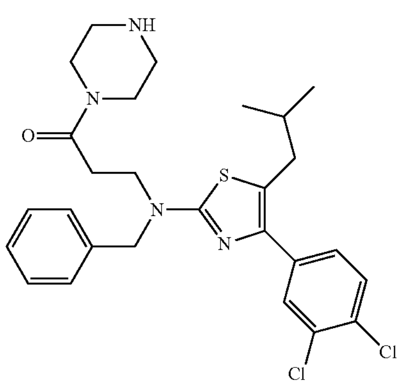 [SMILES: CC(C)Cc1sc(N(CCC(=O)N2CCNCC2)Cc2ccccc2)nc1-c1ccc(Cl)c(Cl)c1] | Method B, Purity is 99.2%, Rt = 1.920 min; MS Calcd.: 530.1; MS Found: 531.2 [M + H]⁺. | δ: 0.85 (6H, d, J = 6.4 Hz), 1.69-1.76 (1H, m), 2.54-2.61 (6H, m), 2.64-2.68 (2H, m), 3.30 (4H, s), 3.62 (2H, t, J = 7.6 Hz), 4.64 (2H, s), 7.23-7.35 (5H, m), 7.50 (1H, dd, J = 6.8, 2.0 Hz), 7.64 (1H, d, J = 8.4 Hz), 7.71 (1H, d, J = 2.0 Hz). |

TABLE 3-3-continued

Characterization Data for Compounds

| I-# | Chemical Structure | LCMS | $^1$H NMR (400 MHz, $d_6$-DMSO) |
|---|---|---|---|
| 135 | 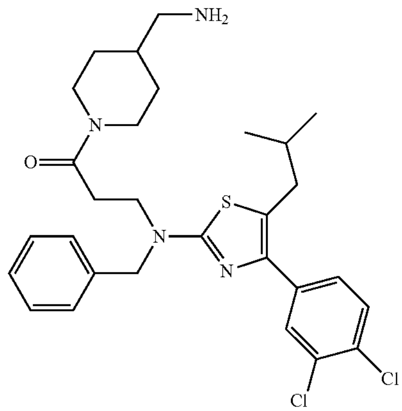 [SMILES: CC(C)Cc1sc(N(CCC(=O)N2CCC(CN)CC2)Cc2ccccc2)nc1-c1ccc(Cl)c(Cl)c1] | Method B, Purity is 98.8%, Rt = 1.881 min; MS Calcd.: 558.2; MS Found: 559.1 [M + H]$^+$. | δ: 0.86 (6H, d, J = 6.4 Hz), 0.90-1.01 (2H, m), 1.65-1.75 (4H, m), 2.57-2.61 (4H, m), 2.64-2.70 (2H, m), 2.90 (1H, t, J = 12.8 Hz), 3.60-3.62 (2H, m), 3.85 (1H, d, J = 13.2 Hz), 4.32 (1H, d, J = 12.8 Hz), 4.65 (2H, s), 7.24-7.36 (5H, m), 7.50 (1H, dd, J = 8.4, 2.0 Hz), 7.65 (1H, d, J = 8.4 Hz), 7.71 (1H, d, J = 2.0 Hz), 8.38 (1H, brs). |
| 136 | 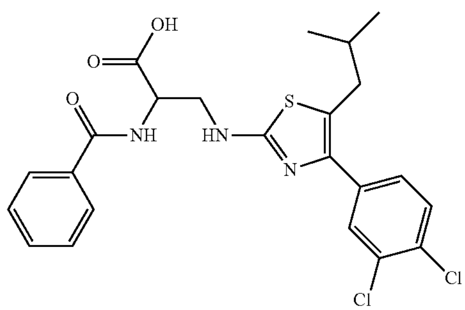 [SMILES: CC(C)Cc1sc(NCC(NC(=O)c2ccccc2)C(=O)O)nc1-c1ccc(Cl)c(Cl)c1] | Method B, Purity is 93.1%, Rt = 1.972 min; MS Calcd.: 491.1; MS Found: 492.1 [M + H]$^+$. | δ: 0.84 (6H, d, J = 6.4 Hz), 1.68-1.73 (1H, m), 2.57 (2H, d, J = 7.2 Hz), 3.65-3.72 (1H, m), 3.81-3.84 (1H, m), 4.62-4.67 (1H, m), 7.29 (2H, t, J = 6.8 Hz), 7.45-7.51 (2H, m), 7.64-7.66 (1H, m), 7.73 (3H, dd, J = 5.2, 2.8 Hz), 7.80 (1H, brs), 8.85 (1H, d, J = 7.2 Hz). |
| 137 | 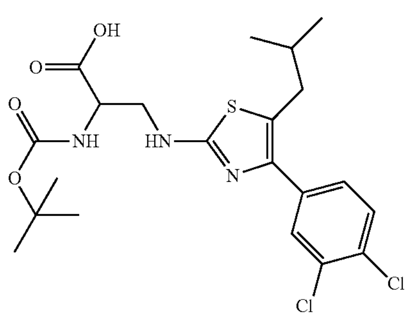 [SMILES: CC(C)Cc1sc(NCC(NC(=O)OC(C)(C)C)C(=O)O)nc1-c1ccc(Cl)c(Cl)c1] | Method C, Purity is 99.8%, Rt = 2.049 min; MS Calcd.: 487.1; MS Found: 488.2 [M + H]$^+$. | δ: 0.86 (6H, dd, J = 6.4, 2.4 Hz), 1.33 (9H, s), 1.68-1.76 (1H, m), 2.58 (2H, d, J = 7.2 Hz), 3.53-3.59 (3H, m), 4.09-4.12 (1H, m), 7.04 (1H, d, J = 6.4 Hz), 7.49 (1H, dd, J = 8.4, 2.0 Hz), 7.63 (2H, d, J = 8.4 Hz), 7.71 (1H, d, J = 2.0 Hz). |
| 138 | 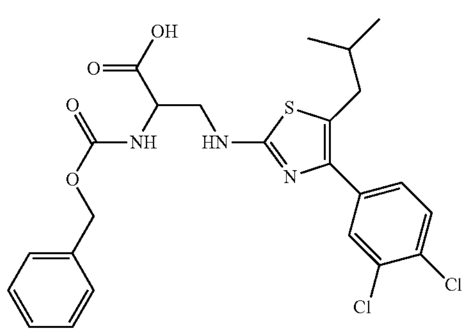 [SMILES: CC(C)Cc1sc(NCC(NC(=O)OCc2ccccc2)C(=O)O)nc1-c1ccc(Cl)c(Cl)c1] | Method C, Purity is 98.8%, Rt = 2.067 min; MS Calcd.: 521.1; MS Found: 522.2 [M + H]$^+$. | δ: 0.88 (6H, d, J = 6.4 Hz), 1.72-1.76 (1H, m), 2.59 (2H, d, J = 7.2 Hz), 3.51-3.61 (3H, m), 4.13-4.15 (1H, m), 5.02 (2H, s), 7.26-7.37 (5H, m), 7.44-7.51 (2H, m), 7.58 (1H, d, J = 8.4 Hz), 7.65 (1H, brs), 7.73 (1H, d, J = 1.6 Hz). |

TABLE 3-3-continued

Characterization Data for Compounds

| I-# | Chemical Structure | LCMS | ¹H NMR (400 MHz, d₆-DMSO) |
|---|---|---|---|
| 139 | 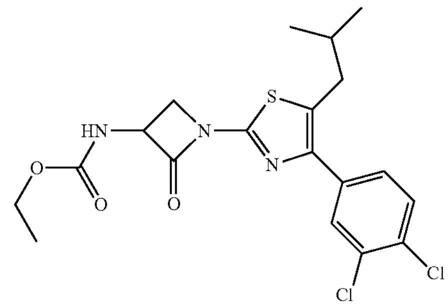 [SMILES: CCOC(=O)NC1CN(c2nc(-c3ccc(Cl)c(Cl)c3)c(CC(C)C)s2)C1=O] | Method C, Purity is 92.6%, Rt = 2.354 min; MS Calcd.: 441.1; MS Found: 442.3 [M + H]⁺. | δ: 0.81 (6H, dd, J = 14.8, 6.8 Hz), 1.13 (3H, t, J = 7.2 Hz), 1.64-1.71 (1H, m), 2.11 (2H, d, J = 7.2 Hz), 3.53 (1H, dd, J = 14.8, 13.6 Hz), 3.63-3.69 (1H, m), 3.97 (2H, q, J = 7.2 Hz), 4.32-4.40 (1H, m), 7.27 (1H, dd, J = 8.0, 2.0 Hz), 7.41 (1H, d, J = 8.4 Hz), 7.57 (1H, d, J = 2.0 Hz), 7.66 (1H, d, J = 8.4 Hz). |
| 140 | 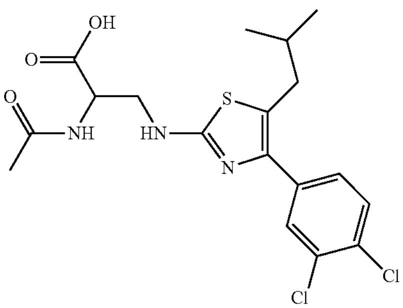 [SMILES: CC(=O)NC(CNc1nc(-c2ccc(Cl)c(Cl)c2)c(CC(C)C)s1)C(=O)O] | Method C, Purity is 98.3%, Rt = 1.821 min; MS Calcd.: 429.1; MS Found: 430.2 [M + H]⁺. | δ: 0.87-0.89 (6H, m), 1.71-1.83 (1H, m), 1.83 (3H, s), 2.60 (2H, d, J = 6.8 Hz), 3.50-3.54 (3H, m), 4.23-4.28 (1H, m), 7.49-7.56 (2H, m), 7.65 (1H, d, J = 8.4 Hz), 7.73 (1H, d, J = 2.0 Hz), 7.96 (1H, d, J = 7.2 Hz). |
| 141 | 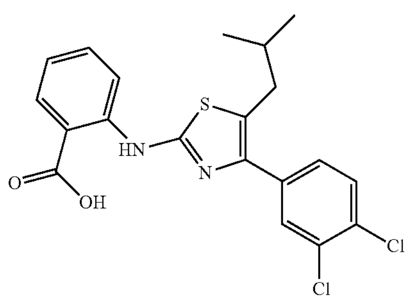 [SMILES: CC(C)Cc1sc(Nc2ccccc2C(=O)O)nc1-c1ccc(Cl)c(Cl)c1] | Method C, Purity is 98.7%, Rt = 2.104 min; MS Calcd.: 420.0; MS Found: 421.2 [M + H]⁺. | δ: 0.89 (6H, d, J = 6.4 Hz), 1.76-1.83 (1H, m), 2.68 (2H, d, J = 7.2 Hz), 6.87 (1H, t, J = 7.2 Hz), 7.37 (1H, t, J = 8.0 Hz), 7.58 (1H, dd, J = 8.0, 2.0 Hz), 7.70 (1H, d, J = 8.4 Hz), 7.78 (1H, d, J = 2.0 Hz), 7.95 (1H, dd, J = 8.0, 1.6 Hz), 8.26 (1H, d, J = 8.4 Hz), 13.99 (1H, brs). |
| 142 | 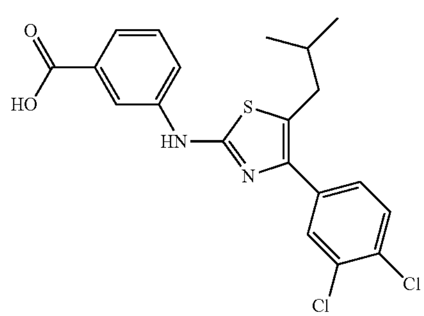 | Method C, Purity is 97.4%, Rt = 2.138 min; MS Calcd.: 466.1; MS Found: 467.0 [M + H]⁺. | δ: 0.89 (6H, d, J = 6.8 Hz), 1.76-1.83 (1H, m), 2.70 (2H, d, J = 7.2 Hz), 7.39 (1H, t, J = 7.2 Hz), 7.47-7.50 (1H, m), 7.59 (1H, dd, J = 8.4, 2.0 Hz), 7.69 (1H, d, J = 8.4 Hz), 7.81-7.84 (2H, m), 8.28 (1H, s), 10.34 (1H, s), 12.90 (1H, brs). |
| 143 | 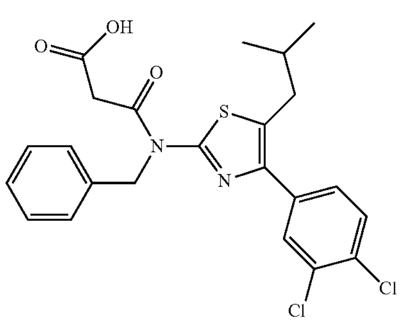 [SMILES: CC(C)Cc1sc(N(Cc2ccccc2)C(=O)CC(=O)O)nc1-c1ccc(Cl)c(Cl)c1] | Method B, Purity is 100%, Rt = 2.287 min; MS Calcd.: 476.1; MS Found: 477.1 [M + H]⁺. | δ: 0.86 (6H, d, J = 10.4 Hz), 1.82-1.97 (1H, m), 2.75 (2H, d, J = 6.8 Hz), 3.63 (2H, s), 5.47 (2H, s), 7.22-7.35 (5H, m), 7.50 (1H, dd, J = 8.4, 2.0Hz), 7.67 (2H, dd, J = 9.2, 5.2 Hz), 13.02 (1H, brs). |

TABLE 3-3-continued

Characterization Data for Compounds

| I-# | Chemical Structure | LCMS | $^1$H NMR (400 MHz, d$_6$-DMSO) |
|---|---|---|---|
| 144 | 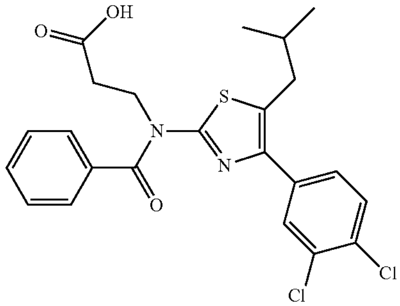 [SMILES: CC(C)Cc1sc(N(CCC(=O)O)C(=O)c2ccccc2)nc1-c1ccc(Cl)c(Cl)c1] | Method C, Purity is 96.5%, Rt = 1.953 min; MS Calcd.: 476.1; MS Found: 477.2 [M + H]$^+$. | δ: 0.91 (6H, d, J = 6.4 Hz), 1.85-1.91 (1H, m), 2.74-2.81 (4H, m), 4.22 (2H, t, J = 7.2 Hz ), 7.53-7.63 (5H, m), 7.73 (2H, d, J = 8.4 Hz), 7.83 (1H, s), 12.34 (1H, brs). |
| 145 | 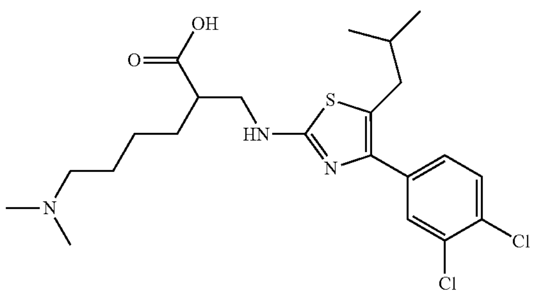 [SMILES: CC(C)Cc1sc(NCC(CCCCN(C)C)C(=O)O)nc1-c1ccc(Cl)c(Cl)c1] | Method C, Purity is 99.0%, Rt = 1.931 min; MS Calcd.: 471.2; MS Found: 472.3 [M + H]$^+$. | δ: 0.88 (6H, d, J = 6.4 Hz), 1.26-1.39 (4H, m), 1.46-1.51 (2H, m), 1.72-1.76 (1H, m), 2.08 (6H, s), 2.14-2.17 (2H, m), 2.54-2.60 (3H, m), 3.25-3.29 (1H, m), 3.33-3.38 (1H, m), 7.50 (1H, dd, J = 8.4, 2.0 Hz), 7.64 (1H, d, J = 8.4 Hz), 7.72 (1H, d, J = 1.6 Hz). |
| 146 | 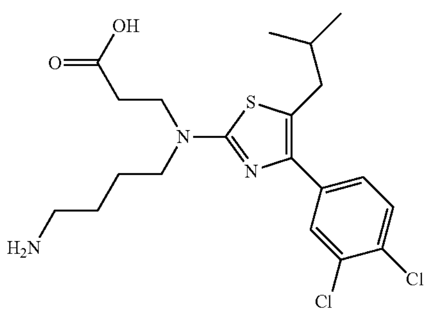 [SMILES: CC(C)Cc1sc(N(CCCCN)CCC(=O)O)nc1-c1ccc(Cl)c(Cl)c1] | Method B, Purity is 100%, Rt = 1.734 min; MS Calcd.: 443.1; MS Found: 444.1 [M + H]$^+$. | δ: 0.87 (6H, d, J = 6.8 Hz), 1.48-1.53 (2H, m), 1.67-1.76 (3H, m), 2.34 (2H, s), 2.58-2.60 (2H, m), 2.74-2.76 (2H, m), 3.34-3.39 (2H, m), 3.56-3.58 (2H, m), 7.48 (1H, d, J = 8.0 Hz), 7.63 (1H, d, J = 8.4 Hz), 7.69 (1H, s), 8.41 (2H, brs). |
| 147 | 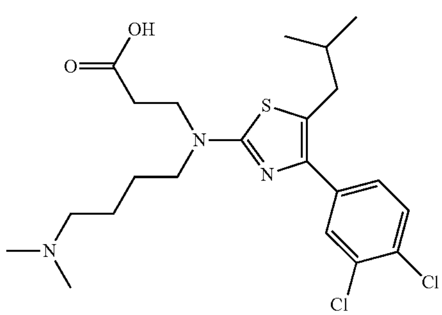 [SMILES: CC(C)Cc1sc(N(CCCCN(C)C)CCC(=O)O)nc1-c1ccc(Cl)c(Cl)c1] | Method C, Purity is 100%, Rt = 1.945 min; MS Calcd.: 471.2; MS Found: 472.2 [M + H]$^+$. | δ: 0.85 (6H, dd, J = 8.4, 6.4 Hz), 1.34-1.38 (2H, m), 1.54-1.58 (2H, m), 1.73-1.75 (1H, m), 1.95-1.98 (1H, m), 2.09 (6H, s), 2.19 (3H, t, J = 7.2 Hz), 2.58 (2H, d, J = 7.2 Hz), 3.37-3.42 (4H, m), 7.48 (1H, dd, J = 8.4, 2.0 Hz), 7.63 (1H, d, J = 8.4 Hz), 7.70 (1H, d, J = 2.0 Hz). |
| 148 | 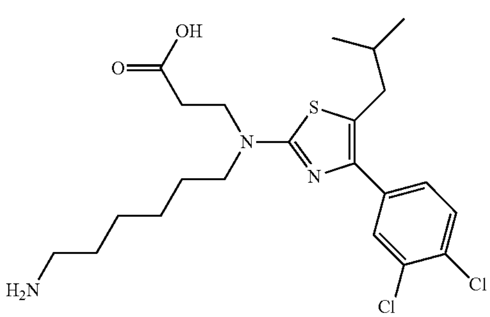 [SMILES: CC(C)Cc1sc(N(CCCCCCN)CCC(=O)O)nc1-c1ccc(Cl)c(Cl)c1] | Method C, Purity is 99.0%, Rt = 1.993 min; MS Calcd.: 471.1; MS Found: 472.3 [M + H]$^+$. | δ: 0.88 (6H, d, J = 6.4 Hz), 1.30-1.34 (4H, m), 1.56-1.58 (4H, m), 1.72-1.79 (1H, m), 2.54-2.76 (6H, m), 3.58-3.68 (4H, m), 7.51 (1H, dd, J = 8.4, 1.2 Hz), 7.67 (1H, d, J = 8.4 Hz), 7.72 (1H, s), 8.12 (1H, brs). |

TABLE 3-3-continued

Characterization Data for Compounds

| I-# | Chemical Structure | LCMS | ¹H NMR (400 MHz, d₆-DMSO) |
|---|---|---|---|
| 149 | 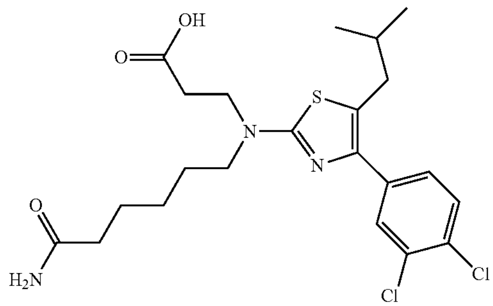 [SMILES: CC(C)Cc1sc(N(CCCCCC(N)=O)CCC(=O)O)nc1-c1ccc(Cl)c(Cl)c1] | Method C, Purity is 95.5%, Rt = 1.828 min; MS Calcd.: 485.1; MS Found: 486.4 [M + H]⁺. | δ: 0.87 (6H, d, J = 6.4 Hz), 1.19-1.27 (2H, m), 1.45-1.58 (4H, m), 1.71-1.76 (1H, m), 2.02 (2H, t, J = 7.2 Hz), 2.21 (2H, t, J = 7.2 Hz), 2.57-2.75 (4H, m), 3.48 (2H, t, J = 7.2 Hz), 4.14 (1H, t, J = 6.8 Hz), 6.64 (1H, s), 7.36 (1H, s), 7.49 (1H, dd, J = 8.4, 1.6 Hz), 7.63 (1H, d, J = 8.4 Hz), 7.68 (1H, d, J = 1.6 Hz). |
| 150 | 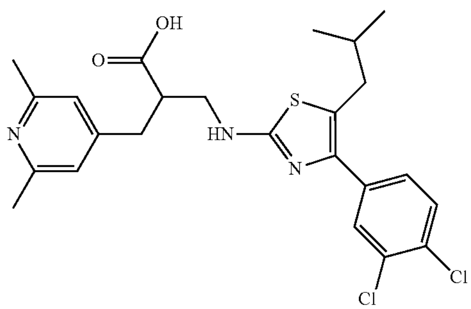 [SMILES: Cc1cc(CC(CNc2nc(-c3ccc(Cl)c(Cl)c3)c(CC(C)C)s2)C(=O)O)cc(C)n1] | Method C, Purity is 98.0%, Rt = 1.894 min; MS Calcd.: 491.1; MS Found: 492.2 [M + H]⁺. | δ: 0.87 (6H, d, J = 6.8 Hz), 1.68-1.78 (1H, m), 2.31 (6H, s), 2.42-2.55 (2H, m), 2.57-2.59 (2H, d, J = 7.2 Hz), 2.86-2.91 (1H, m), 3.09-3.19 (2H, m), 6.85 (2H, s), 7.45-7.47 (1H, dd, J = 8.4, 2.0 Hz), 7.60 (1H, s), 7.63 (1H, d, J = 8.4 Hz), 7.68 (1H, d, J = 1.6 Hz). |
| 151 | 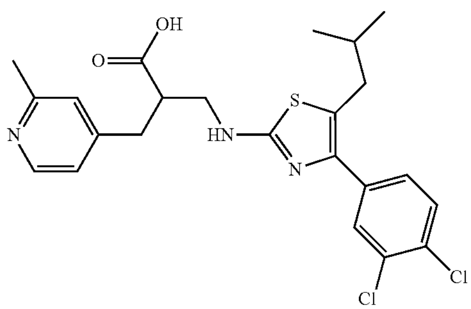 [SMILES: Cc1cc(CC(CNc2nc(-c3ccc(Cl)c(Cl)c3)c(CC(C)C)s2)C(=O)O)ccn1] | Method C, Purity is 100%, Rt = 1.995 min; MS Calcd.: 477.1; MS Found: 478.2 [M + H]⁺. | δ: 0.85 (6H, d, J = 6.8 Hz), 1.68-1.73 (1H, m), 2.47 (3H, s), 2.56-2.65 (4H, m), 2.84-2.88 (1H, m), 3.18-3.23 (2H, m), 7.00 (1H, d, J = 5.2 Hz), 7.05 (1H, s), 7.60 (2H, q, J = 2.0 Hz), 7.61-7.68 (3H, m), 8.23 (1H, d, J = 5.2 Hz). |
| 152 | 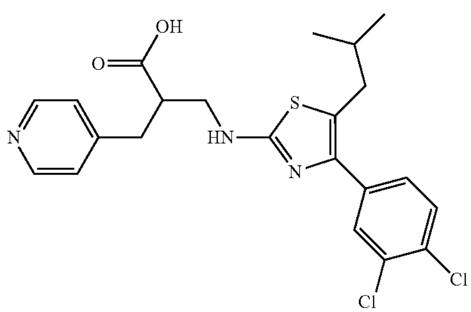 | Method C, Purity is 100%, Rt = 1.94 min; MS Calcd.: 464.4; MS Found: 465.2 [M + H]⁺. | δ: 0.85 (6H, d, J = 6.4 Hz), 1.68-1.74 (1H, m), 2.56 (2H, d, J = 7.2 Hz), 2.69-2.92 (3H, m), 3.20-3.30 (2H, m), 7.22 (2H, J = 6.0 Hz), 7.44-7.46 (2H, m), 7.61-7.68 (3H, m), 8.38 (2H, J = 2.0 Hz). |
| 153 | 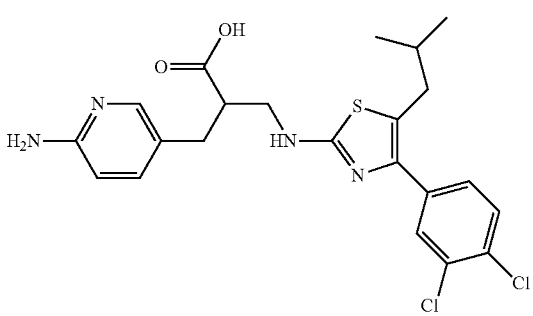 [SMILES: CC(C)Cc1sc(NCC(Cc2ccc(N)nc2)C(=O)O)nc1-c1ccc(Cl)c(Cl)c1] | Method C, Purity is 96.2%, Rt = 1.932 min; MS Calcd.: 478.1; MS Found: 479.0 [M + H]⁺. | δ: 0.87 (6H, d, J = 6.4 Hz), 1.70-1.79 (1H, m), 2.44-2.47 (2H, m), 2.58 (2H, d, J = 7.2 Hz), 2.70-2.75 (1H, m), 3.08-3.16 (2H, m), 5.60 (2H, s), 6.33 (1H, d, J = 8.4 Hz), 7.23 (1H, dd, J = 8.4, 2.4 Hz), 7.48 (1H, dd, J = 8.4, 2.0 Hz), 7.63-7.70 (4H, m). |

TABLE 3-3-continued

Characterization Data for Compounds

| I-# | Chemical Structure | LCMS | $^1$H NMR (400 MHz, d$_6$-DMSO) |
|---|---|---|---|
| 154 | 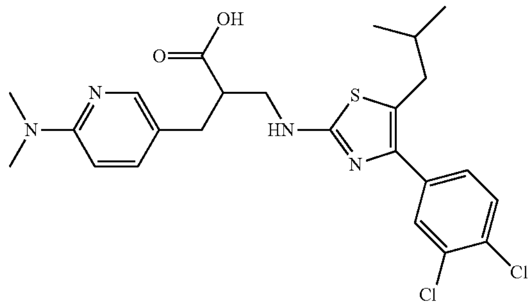 | Method C, Purity is 97.2%, Rt = 1.973 min; MS Calcd.: 506.1; MS Found: 507.2 [M + H]$^+$. | δ: 0.85 (6H, d, J = 6.8 Hz), 1.66-1.76 (1H, m), 2.47-2.53 (2H, m), 2.55-2.57 (2H, d, J = 7.2 Hz), 2.71-2.77 (1H, m), 2.93 (6H, s), 3.09-3.19 (2H, m), 6.49 (1H, d, J = 8.4 Hz), 7.34 (1H, dd, J = 8.8, 2.4 Hz), 7.45 (1H, dd, J = 8.4, 2.0 Hz), 7.60-7.67 (3H, m), 7.86-7.87 (1H, d, J = 2.4 Hz). |
| 155 | 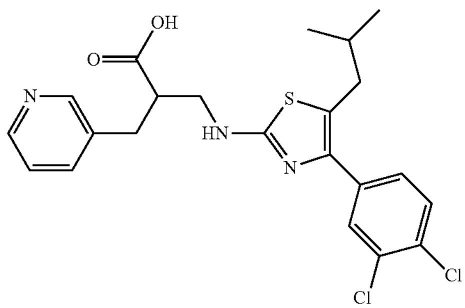 [SMILES: CC(C)Cc1sc(NCC(Cc2cccnc2)C(=O)O)nc1-c1ccc(Cl)c(Cl)c1] | Method C, Purity is 100%, Rt = 1.977 min; MS Calcd.: 464.4; MS Found: 465.2 [M + H]$^+$. | δ: 0.87 (6H, d, J = 6.4 Hz), 1.70-1.77 (1H, m), 1.68-1.75 (1H, m), 1.97-2.02 (1H, m), 2.58-2.67 (2H, m), 2.90-3.16 (4H, m), 7.18-7.20 (2H, m), 7.22-7.25 (1H, m), 7.46-7.49 (1H, m), 7.62-7.68 (4H, m), 8.33-8.39 (2H, m). |
| 156 | 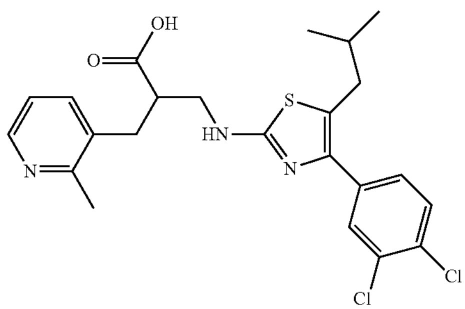 [SMILES: Cc1ncccc1CC(CNc1nc(-c2ccc(Cl)c(Cl)c2)c(CC(C)C)s1)C(=O)O] | Method C, Purity is 98.5%, Rt = 1.847 min; MS Calcd.: 477.1; MS Found: 478.2 [M + H]$^+$. | δ: 0.85 (6H, d, J = 6.8 Hz), 1.70-1.73 (1H, m), 2.42 (3H, s), 2.57(2H, d, J = 6.8 Hz), 2.73-2.87 (3H, m), 3.36 (2H, s), 7.08 (1H, dd, J = 4.8, 4.6 Hz), 7.45 (1H, dd, J = 8.4, 2.0 Hz), 7.50-7.52 (1H, m), 7.62-7.76 (3H, m), 8.23 (1H, d, J = 3.6 Hz). |
| 157 | 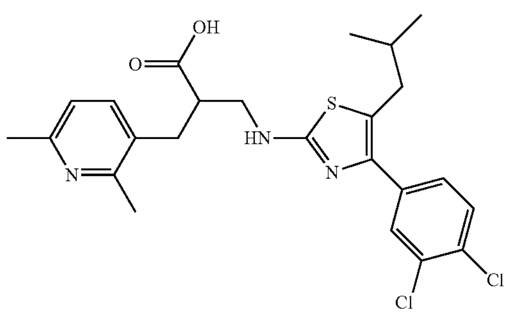 [SMILES: Cc1ccc(CC(CNc2nc(-c3ccc(Cl)c(Cl)c3)c(CC(C)C)s2)C(=O)O)c(C)n1] | Method C, Purity is 97.5%, Rt = 2.069 min; MS Calcd.: 491.1; MS Found: 492.2 [M + H]$^+$. | δ: 0.87 (6H, d, J = 6.8 Hz), 1.70-1.76 (1H, m), 2.36 (6H, d, J = 16.8 Hz), 2.58 (2H, d, J = 4.2 Hz), 2.66-2.69 (1H, m), 2.76-2.87 (2H, m), 3.24-3.28 (2H, m), 6.91-6.93 (1H, d, J = 8.0 Hz), 7.39-7.41 (1H, d, J = 7.6 Hz), 7.46 (1H, dd, J = 8.4, 2.0 Hz), 7.64 (1H, d, J = 8.4 Hz), 7.70 (1H, d, J = 2.0 Hz). |
| 158 | 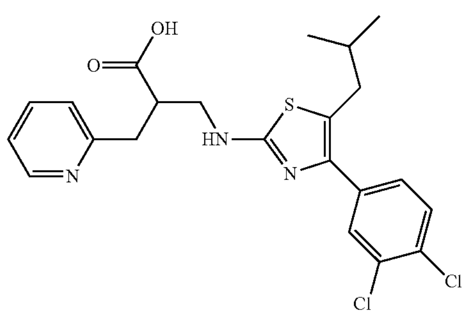 [SMILES: CC(C)Cc1sc(NCC(Cc2ccccn2)C(=O)O)nc1-c1ccc(Cl)c(Cl)c1] | Method C, Purity is 97.3%, Rt = 1.841 min; MS Calcd.: 463.1; MS Found: 464.1 [M + H]$^+$. | δ: 0.87 (6H, d, J = 6.4 Hz), 1.71-1.74 (1H, m), 2.58 (2H, d, J = 6.8 Hz), 2.85-2.88 (1H, m), 3.03-3.08 (2H, m), 3.29-3.30 (2H, m), 7.16-7.19 (1H, m), 7.45 (1H, dd, J = 8.4, 2.0 Hz), 7.50-7.52 (1H, m), 7.62-7.76 (3H, m), 8.23 (1H, d, J = 3.6 Hz). |

TABLE 3-3-continued

Characterization Data for Compounds

| I-# | Chemical Structure | LCMS | ¹H NMR (400 MHz, d₆-DMSO) |
|---|---|---|---|
| 159 | 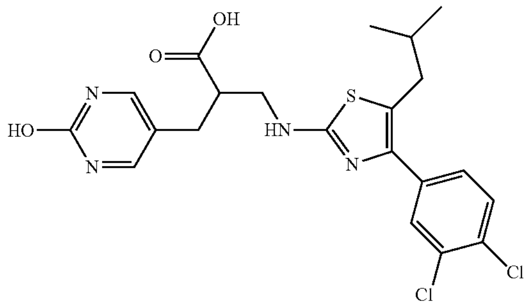 [SMILES: CC(C)Cc1sc(NCC(Cc2cnc(O)nc2)C(=O)O)nc1-c1ccc(Cl)c(Cl)c1] | Method C, Purity is 99.4%, Rt = 1.761 min; MS Calcd.: 480.1; MS Found: 481.3 [M + H]⁺. | δ: 0.88 (6H, d, J = 6.4 Hz), 1.69-1.77 (1H, m), 2.52-2.60 (4H, m), 3.19-3.33 (2H, m), 7.49 (1H, dd, J = 8.4, 2.0 Hz), 7.63-7.70 (3H, m), 8.07 (1H, s). |
| 160 | 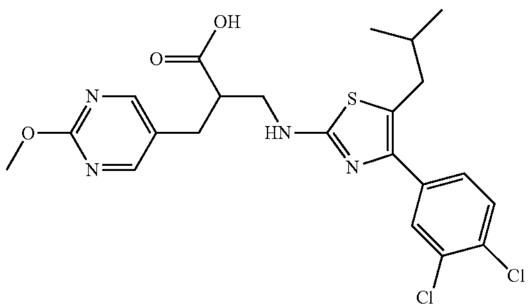 [SMILES: COc1ncc(CC(CNc2nc(-c3ccc(Cl)c(Cl)c3)c(CC(C)C)s2)C(=O)O)cn1] | Method C, Purity is 99.7%, Rt = 1.896 min; MS Calcd.: 494.1; MS Found: 495.2 [M + H]⁺. | δ: 0.85 (6H, d, J = 6.4 Hz), 1.66-1.75 (1H, m), 2.56 (2H, d, J = 7.2 Hz), 2.67-2.80 (3H, m), 3.20-3.33 (2H, m), 3.83 (3H, s), 7.46 (1H, dd, J = 5.2, 1.2 Hz), 7.47 (1H, dd, J = 8.4, 2.0 Hz), 7.60-7.67 (3H, m), 8.40 (2H, s). |
| 161 | 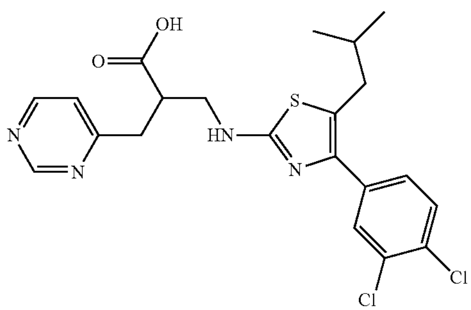 [SMILES: CC(C)Cc1sc(NCC(Cc2ccncn2)C(=O)O)nc1-c1ccc(Cl)c(Cl)c1] | Method C, Purity is 98.0%, Rt = 1.906 min; MS Calcd.: 464.1; MS Found: 465.0 [M + H]⁺. | δ: 0.85 (6H, d, J = 6.8 Hz), 1.67-1.74 (1H, m), 2.55 (2H, d, J = 7.2 Hz), 2.71-2.83 (2H, m), 3.04-3.07 (1H, m), 3.20-3.31 (2H, m), 7.38-7.45 (2H, m), 7.60-7.66 (3H, m), 8.56 (1H, d, J = 5.2 Hz), 8.99 (1H, d, J = 1.2 Hz). |
| 162 | 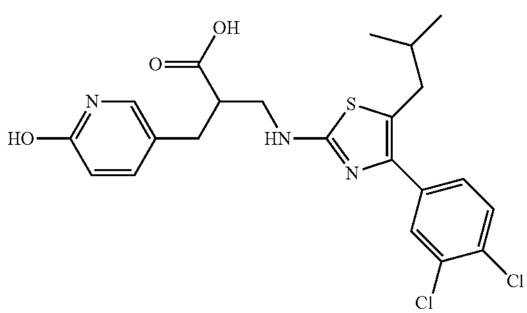 [SMILES: CC(C)Cc1sc(NCC(Cc2ccc(O)nc2)C(=O)O)nc1-c1ccc(Cl)c(Cl)c1] | Method C, Purity is 99.5%, Rt = 1.839 min; MS Calcd.: 479.1; MS Found: 480.2 [M + H]⁺. | δ: 0.85 (6H, d, J = 6.4 Hz), 1.66-1.77 (1H, m), 2.45-2.51 (2H, m), 2.55-2.60 (3H, m), 2.63-2.70 (1H, m), 3.20-3.33 (2H, m), 6.21 (1H, d, J = 9.2 Hz), 7.12 (1H, d, J = 1.6 Hz), 7.31 (1H, dd, J = 9.2, 2.4 Hz), 7.46 (1H, dd, J = 8.4, 2.0 Hz), 7.62 (2H, d, J = 8.4 Hz), 7.69 (1H, d, J = 2.0 Hz). |
| 163 | 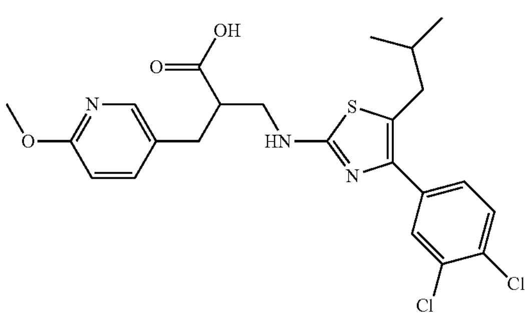 [SMILES: COc1ccc(CC(CNc2nc(-c3ccc(Cl)c(Cl)c3)c(CC(C)C)s2)C(=O)O)cn1] | Method C, Purity is 99.3%, Rt = 1.969 min; MS Calcd.: 493.1; MS Found: 494.2 [M + H]⁺. | δ: 0.88 (6H, d, J = 6.8 Hz), 1.70-1.77 (1H, m), 2.59 (2H, d, J = 7.2 Hz), 2.70-2.75 (1H, m), 2.78-2.82 (2H, m), 3.24-3.33 (2H, m), 3.79 (3H, s), 6.71 (1H, d, J = 8.4 Hz), 7.48 (1H, dd, J = 8.4, 2.0 Hz), 7.56 (1H, dd, J = 8.4, 2.4 Hz), 7.65 (1H, d, J = 8.4 Hz), 7.70 (2H, d, J = 2.0 Hz), 7.98 (1H, d, J = 2.0 Hz). |

TABLE 3-3-continued

Characterization Data for Compounds

| I-# | Chemical Structure | LCMS | ¹H NMR (400 MHz, d₆-DMSO) |
|---|---|---|---|
| 164 | 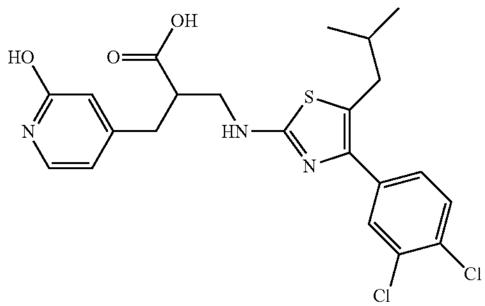 [SMILES: CC(C)Cc1sc(NCC(Cc2ccnc(O)c2)C(=O)O)nc1-c1ccc(Cl)c(Cl)c1] | Method C, Purity is 96.3%, Rt = 1.765 min; MS Calcd.: 479.1; MS Found: 480.2 [M + H]⁺. | δ: 0.85 (6H, d, J = 6.8 Hz), 1.66-1.75 (1H, m), 2.47-2.52 (1H, m), 2.56 (2H, d, J = 7.2 Hz), 2.67-2.73 (2H, m), 3.20-3.31 (2H, m), 6.04 (1H, dd, J = 6.8, 1.6 Hz), 6.11 (1H, s), 7.19 (1H, d, J = 6.8 Hz), 7.47 (1H, dd, J = 8.8, 2.4 Hz), 7.61-7.67 (3H, m). |
| 165 | 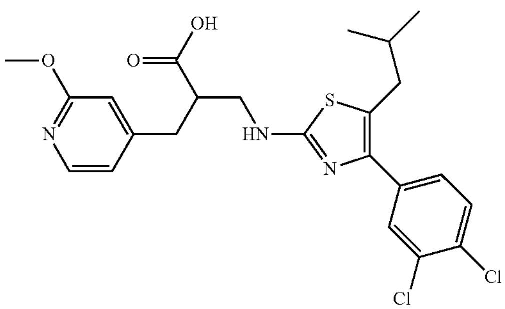 [SMILES: COc1cc(CC(CNc2nc(-c3ccc(Cl)c(Cl)c3)c(CC(C)C)s2)C(=O)O)ccn1] | Method C, Purity is 99.1%, Rt = 1.945 min; MS Calcd.: 493.1; MS Found: 494.2 [M + H]⁺. | δ: 0.87 (6H, d, J = 6.4 Hz), 1.68-1.78 (1H, m), 2.58 (2H, d, J = 7.2 Hz), 2.66-2.71 (1H, m), 2.74-2.81 (1H, m), 2.84-2.89 (1H, m), 3.21-3.33 (2H, m), 3.78 (3H, s), 6.64 (1H, s), 6.84 (1H, dd, J = 5.2, 1.2 Hz), 7.47 (1H, dd, J = 8.4, 2.0 Hz), 7.62-7.69 (3H, m),.00 (1H, d, J = 5.2 Hz). |
| 166 | 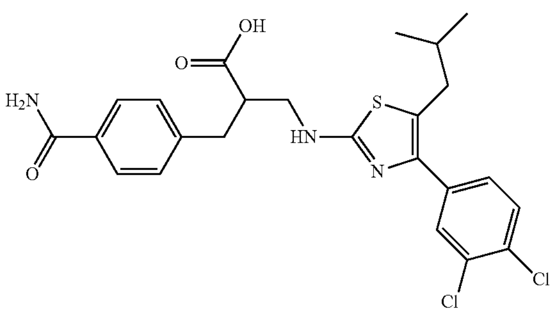 [SMILES: CC(C)Cc1sc(NCC(Cc2ccc(C(N)=O)cc2)C(=O)O)nc1-c1ccc(Cl)c(Cl)c1] | Method C, Purity is 100%, Rt = 1.953 min; MS Calcd.: 505.1; MS Found: 506.2 [M + H]⁺. | δ: 0.87 (6H, d, J = 6.4 Hz), 1.70-1.74 (1H, m), 2.58 (2H, d, J = 7.2 Hz), 2.77-2.93 (3H, m), 3.25-3.38 (2H, m), 5.60 (2H, s), 7.25 (3H, m), 7.43 (1H, dd, J = 2.4, 2.0 Hz), 7.62-7.87 (5H, m), 8.39 (1H, s). |
| 167 | 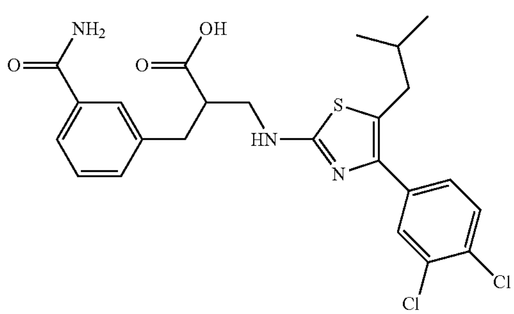 [SMILES: CC(C)Cc1sc(NCC(Cc2cccc(C(N)=O)c2)C(=O)O)nc1-c1ccc(Cl)c(Cl)c1] | Method B, Purity is 100%, Rt = 1.793 min; MS Calcd.: 506.4; MS Found: 507.1 [M + H]⁺. | δ: 0.85 (6H, d, J = 6.4 Hz), 1.68-1.75 (1H, m), 2.57 (2H, d, J = 7.2 Hz), 2.80-2.83 (4H, m), 3.25-3.50 (2H, m), 7.31-7.46 (4H, m), 7.61-7.95 (6H, m). |
| 168 | 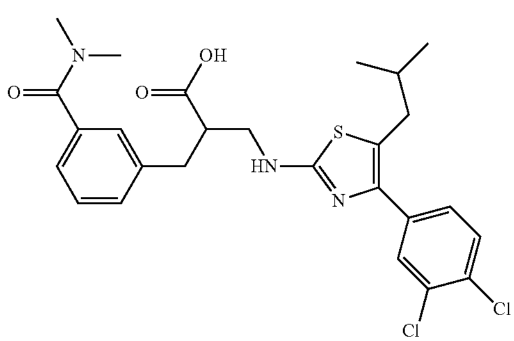 [SMILES: CC(C)Cc1sc(NCC(Cc2cccc(C(=O)N(C)C)c2)C(=O)O)nc1-c1ccc(Cl)c(Cl)c1] | Method B, Purity is 100%, Rt = 1.865 min; MS Calcd.: 534.5; MS Found: 535.2 [M + H]⁺. | δ: 0.85 (6H, d, J = 6.4 Hz), 1.68-1.75 (1H, m), 2.50 (2H, d, J = 3.2 Hz), 2.82-2.92 (8H, m), 3.25-3.50 (2H, m), 7.18-7.20 (2H, m), 7.27-7.31 (2H, m), 7.46 (1H, s), 7.62-7.68 (3H, m). |

TABLE 3-3-continued

Characterization Data for Compounds

| I-# | Chemical Structure | LCMS | $^{1}$H NMR (400 MHz, d$_{6}$-DMSO) |
|---|---|---|---|
| 169 | 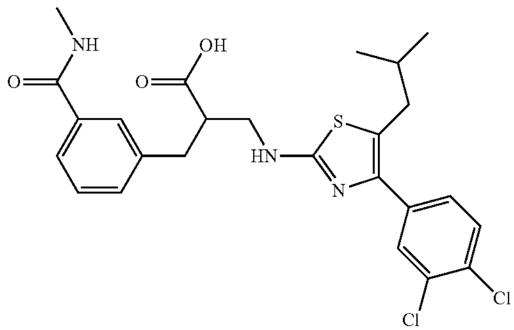 [SMILES: CNC(=O)c1cccc(CC(CNc2nc(-c3ccc(Cl)c(Cl)c3)c(CC(C)C)s2)C(=O)O)c1] | Method B, Purity is 100%, Rt = 1.837 min; MS Calcd.: 520.5; MS Found: 521.1 [M + H]$^{+}$. | δ: 0.86 (6H, d, J = 6.4 Hz), 1.67-1.75 (1H, m), 2.49 (2H, d, J = 3.2 Hz), 2.73 (3H, d, J = 4.4 Hz), 2.80-2.99 (8H, m), 3.38-3.42 (2H, m), 7.18-7.20 (2H, m), 7.32-7.33 (2H, m), 7.34-7.43 (1H, m), 7.61-7.67 (5H, m), 8.36-8.37 (1H, m). |
| 170 | 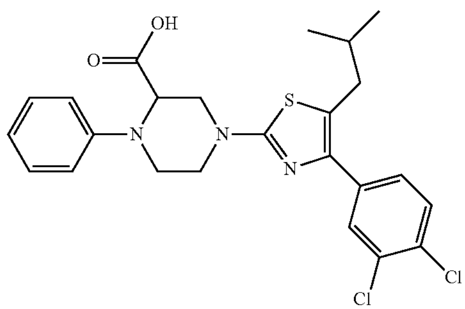 [SMILES: CC(C)Cc1sc(N2CCN(c3ccccc3)C(C(=O)O)C2)nc1-c1ccc(Cl)c(Cl)c1] | Method B, Purity is 100%, Rt = 2.205 min; MS Calcd.: 489.1; MS Found: 490.1 [M + H]$^{+}$. | δ: 0.90 (6H, t, J = 6.2 Hz), 1.73-1.81 (1H, m), 2.63-2.68 (2H, m), 3.08-3.14 (1H, m), 3.24-3.28 (2H, m), 3.52-3.70 (2H, m), 3.93 (2H, d, J = 12.8 Hz), 4.26 (1H, d, J = 12.4 Hz), 6.57 (1H, t, J = 7.2 Hz), 6.74 (2H, d, J = 8.4 Hz), 7.10 (1H, t, J = 8.0 Hz), 7.53 (1H, dd, J = 8.4, 2.0 Hz), 7.66 (1H, d, J = 8.4 Hz), 7.75 (1H, d, J = 2.0 Hz). |
| 171 | 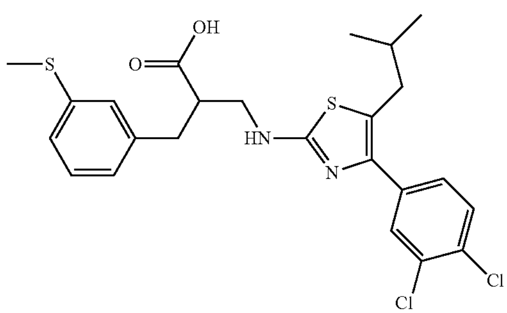 | Method C, Purity is 100%, Rt = 2.117 min; MS Calcd.: 508.1; MS Found: 509.2 [M + H]$^{+}$. | δ: 0.86 (6H, d, J = 6.4 Hz), 1.69-1.74 (1H, m), 2.37 (3H, d, J = 7.6 Hz), 2.70 (2H, d, J = 4.8 Hz), 2.72-2.74 (1H, m), 2.84-2.88 (2H, m), 3.27-3.30 (2H, m), 6.96 (1H, d, J = 7.6 Hz), 7.04 (1H, s), 7.06 (1H, s), 7.18 (1H, t, J = 8.0, 7.6 Hz), 7.45 (1H, dd, J = 6.0, 2.0 Hz), 7.62-7.68 (4H, m). |
| 172 | 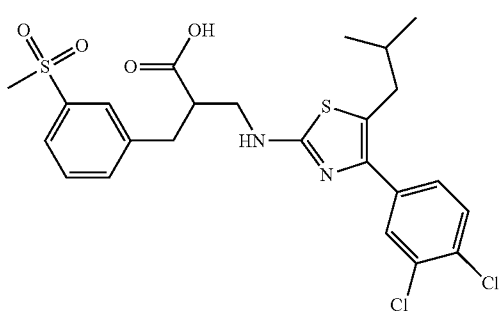 [SMILES: CC(C)Cc1sc(NCC(Cc2cccc(S(C)(=O)=O)c2)C(=O)O)nc1-c1ccc(Cl)c(Cl)c1] | Method B, Purity is 100%, Rt = 1.880 min; MS Calcd.: 540.1; MS Found: 541.2 [M + H]$^{+}$. | δ: 0.86 (6H, d, J = 6.4 Hz), 1.69-1.76 (1H, m), 2.58 (2H, d, J = 7.2 Hz), 2.94-3.02 (3H, m), 3.15 (3H, s), 3.37-3.46 (2H, m), 7.45-7.76 (8H, m), 12.49 (1H, brs). |

TABLE 3-3-continued

Characterization Data for Compounds

| I-# | Chemical Structure | LCMS | $^1$H NMR (400 MHz, $d_6$-DMSO) |
|---|---|---|---|
| 173 | 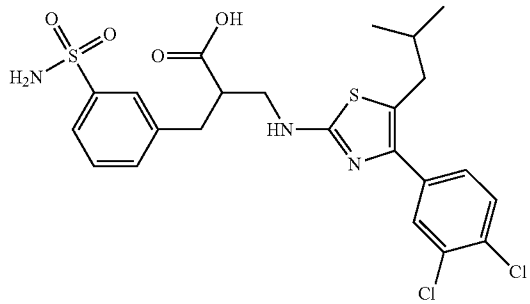 [SMILES: CC(C)Cc1sc(NCC(Cc2cccc(S(N)(=O)=O)c2)C(=O)O)nc1-c1ccc(Cl)c(Cl)c1] | Method B, Purity is 97.0%, Rt = 1.835 min; MS Calcd.: 541.1; MS Found: 542.1 [M + H]$^+$. | δ: 0.87 (6H, d, J = 6.4 Hz), 1.68-1.78 (1H, m), 2.31-2.38 (1H, m), 2.58 (2H, d, J = 6.8 Hz), 2.65-2.70 (1H, m), 3.01-3.06 (1H, m), 3.14 (2H, s), 7.26 (2H, s), 7.38-7.49 (3H, m), 7.60-7.64 (2H, m), 7.68-7.69 (2H, m), 7.75 (1H, s). |
| 174 | 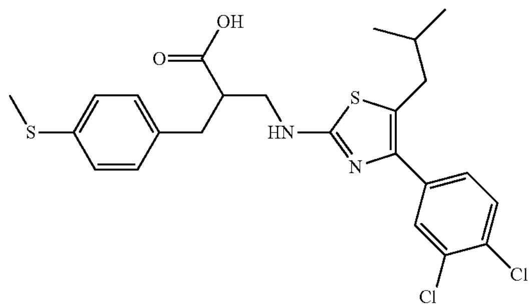 [SMILES: CSc1ccc(CC(CNc2nc(-c3ccc(Cl)c(Cl)c3)c(CC(C)C)s2)C(=O)O)cc1] | Method C, Purity is 100%, Rt = 2.221 min; MS Calcd.: 508.1; MS Found: 509.0 [M + H]$^+$. | δ: 0.88 (6H, d, J = 6.8 Hz), 1.69-1.78 (1H, m), 2.43 (3H, s), 2.60 (2H, d, J = 7.2 Hz), 2.72-2.74 (1H, m), 2.82-2.89 (2H, m), 3.27-3.33 (2H, m), 7.16 (4H, s), 7.18 (1H, t, J = 8.0, 7.6 Hz), 7.45 (1H, dd, J = 6.0, 2.0 Hz), 7.64-7.71 (3H, m). |
| 175 | 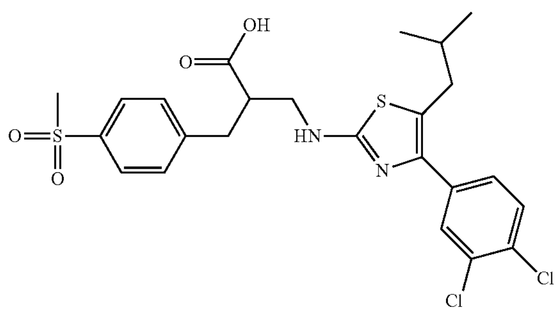 [SMILES: CC(C)Cc1sc(NCC(Cc2ccc(S(C)(=O)=O)cc2)C(=O)O)nc1-c1ccc(Cl)c(Cl)c1] | Method C, Purity is 98.5%, Rt = 2.026 min; MS Calcd.: 540.1; MS Found: 541.1 [M + H]$^+$. | δ: 0.88 (6H, d, J = 6.4 Hz), 1.70-1.77 (1H, m), 2.48-2.49 (1H, m), 2.43 (3H, s), 2.58 (2H, d, J = 7.2 Hz), 2.71-2.76 (1H, m), 303-3.06 (1H, m), 3.08-3.17 (5H, m), 7.46-7.50 (3H, m), 7.76 (2H, d, J = 8.4 Hz). |
| 176 | 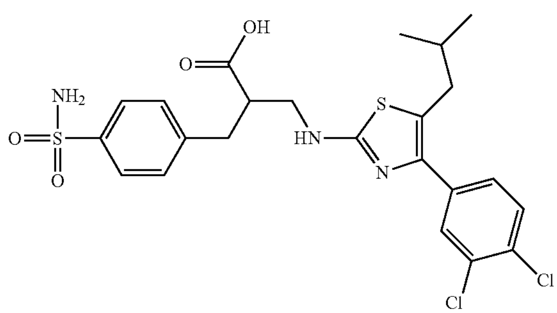 [SMILES: CC(C)Cc1sc(NCC(Cc2ccc(S(N)(=O)=O)cc2)C(=O)O)nc1-c1ccc(Cl)c(Cl)c1] | Method B, Purity is 94.6%, Rt = 1.817 min; MS Calcd.: 541.1; MS Found: 542.1 [M + H]$^+$. | δ: 0.88 (6H, d, J = 6.4 Hz), 0.92 (1H, t, J = 7.2 Hz), 1.68-1.77 (1H, m), 1.96-2.02 (1H, m), 2.39-2.44 (1H, m), 2.59 (2H, d, J = 7.2 Hz), 2.70-2.77 (1H, m), 2.76-3.02 (1H, m), 7.25 (2H, s), 7.39 (2H, d, J = 8.4 Hz), 7.48 (1H, dd, J = 8.4, 2.0 Hz), 7.63-7.71 (5H, m). |
| 177 | 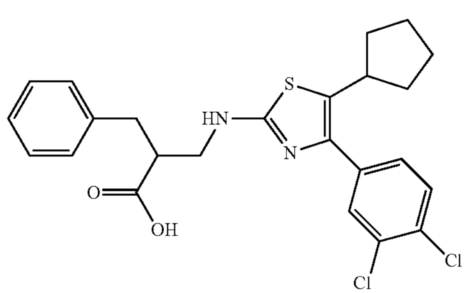 [SMILES: O=C(O)C(CNc1nc(-c2ccc(Cl)c(Cl)c2)c(C2CCCC2)s1)Cc1ccccc1] | Method C, Purity is 98.9%, Rt = 2.091 min; MS Calcd.: 474.1; MS Found: 475.2 [M + H]$^+$. | δ: 1.45 (2H, brs), 1.60 (2H, brs), 1.71 (2H, brs), 2.04 (2H, brs), 2.83 (2H, dd, J = 8.4, 7.6 Hz), 3.00 (1H, d, J = 2.4 Hz), 3.24 (1H, d, J = 8.0 Hz ), 3.34-3.40 (2H, m), 7.20-7.30 (5H, m), 7.45 (1H, dd, J = 8.4, 2.0 Hz), 7.65-7.71 (3H, m), 12.32 (1H, s). |

TABLE 3-3-continued

Characterization Data for Compounds

| I-# | Chemical Structure | LCMS | $^1$H NMR (400 MHz, d$_6$-DMSO) |
|---|---|---|---|
| 178 | 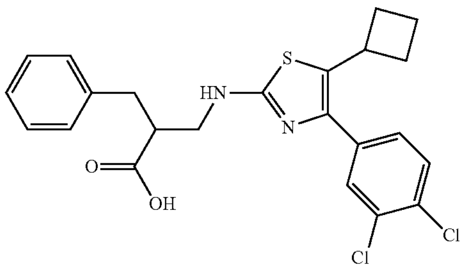 [SMILES: O=C(O)C(CNc1nc(-c2ccc(Cl)c(Cl)c2)c(C2CCC2)s1)Cc1ccccc1] | Method C, Purity is 99.7%, Rt = 2.047 min; MS Calcd.: 460.2; MS Found: 461.3 [M + H]$^+$. | δ: 1.75-1.77 (1H, m), 1.86-1.99 (3H, m), 2.31-2.35 (2H, m), 2.72-2.74 (1H, m), 2.87-2.89 (2H, m), 3.25-3.28 (2H, m), 3.66-3.70 (1H, m), 7.16-7.27 (5H, m), 7.38 (1H, dd, J = 8.4, 2.0 Hz), 7.63 (2H, dd, J = 4.8, 2.8 Hz), 7.75 (1H, brs). |
| 179 | 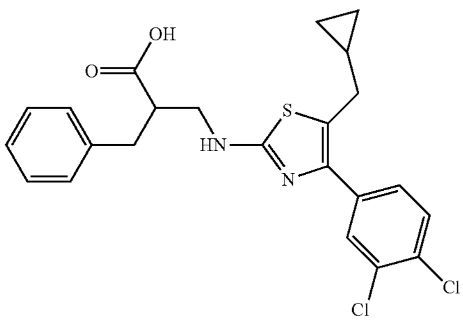 [SMILES: O=C(O)C(CNc1nc(-c2ccc(Cl)c(Cl)c2)c(CC2CC2)s1)Cc1ccccc1] | Method C, Purity is 99.6%, Rt = 2.011 min; MS Calcd.: 460.1; MS Found: 461.3 [M + H]$^+$. | δ: 0.16 (2H, dd, J = 10.0, 5.2 Hz), 0.46-0.50 (2H, m), 0.92 (1H, t, J = 6.8 Hz), 2.62-2.69 (4H, m), 2.91 (1H, t, J = 6.4 Hz), 3.21-3.24 (2H, m), 7.12-7.25 (5H, m), 7.46 (1H, dd, J = 8.4, 2.0 Hz), 7.61 (1H, d, J = 8.4 Hz), 7.70 (1H, d, J = 2.0 Hz). |
| 180 | 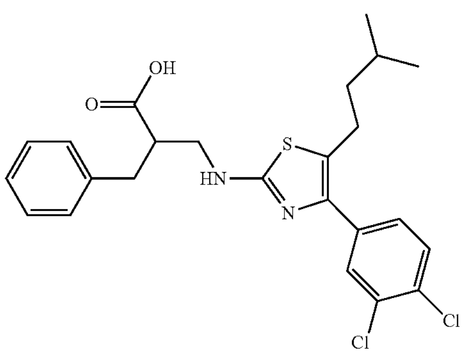 [SMILES: CC(C)CCc1sc(NCC(Cc2ccccc2)C(=O)O)nc1-c1ccc(Cl)c(Cl)c1] | Method C, Purity is 100%, Rt = 2.132 min; MS Calcd.: 476.1; MS Found: 477.2 [M + H]$^+$. | δ: 0.85 (6H, d, J = 6.4 Hz), 1.40-1.46 (2H, m), 1.53-1.60 (1H, m), 2.69-2.78 (3H, m), 2.86-2.91 (2H, m), 3.24-3.38 (2H, m), 7.16-7.28 (5H, m), 7.48 (1H, dd, J = 8.4, 2.0 Hz), 7.64-7.71 (3H, m). |
| 181 | 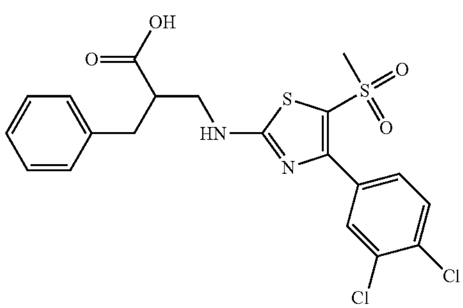 [SMILES: CS(=O)(=O)c1sc(NCC(Cc2ccccc2)C(=O)O)nc1-c1ccc(Cl)c(Cl)c1] | Method C, Purity is 99.1%, Rt = 1.721 min; MS Calcd.: 484.0; MS Found: 485.2 [M + H]$^+$. | δ: 2.64-2.66 (2H, m), 2.94-2.96 (1H, m), 3.11 (3H, s), 3.27-3.29 (2H, m), 7.15-7.24 (5H, m), 7.65-7.71 (2H, m), 7.89 (1H, d, J = 2.0 Hz). |
| 182 | 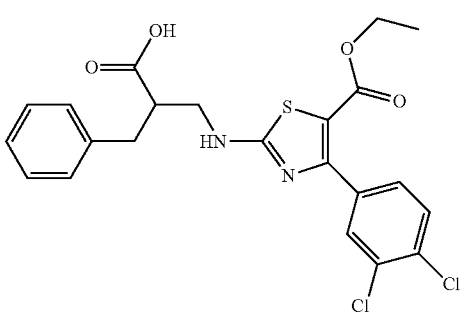 [SMILES: CCOC(=O)c1sc(NCC(Cc2ccccc2)C(=O)O)nc1-c1ccc(Cl)c(Cl)c1] | Method B, Purity is 100%, Rt = 2.096 min; MS Calcd.: 477.1; MS Found: 478.8 [M + H]$^+$. | δ: 1.15 (3H, t, J = 6.8 Hz), 2.75-2.98 (3H, m), 3.41-3.45 (2H, m), 4.10 (2H, q, J = 7.2 Hz), 7.16-7.28 (5H, m), 7.61-7.66 (2H, m), 7.91 (1H, d, J = 1.6 Hz), 8.64 (1H, m), 12.43 (1H, brs). |

TABLE 3-3-continued

Characterization Data for Compounds

| I-# | Chemical Structure | LCMS | ¹H NMR (400 MHz, d₆-DMSO) |
|---|---|---|---|
| 183 | 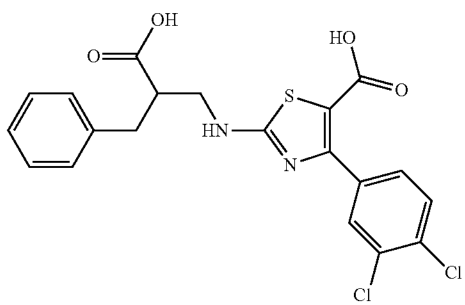 [SMILES: O=C(O)c1sc(NCC(Cc2ccccc2)C(=O)O)nc1-c1ccc(Cl)c(Cl)c1] | Method B, Purity is 95.7%, Rt = 1.831 min; MS Calcd.: 450.1; MS Found: 451.2 [M + H]⁺. | δ: 2.48-3.00 (3H, m), 3.37-3.48 (2H, m), 7.16-7.28 (5H, m), 7.61-7.67 (2H, m), 7.91 (1H, d, J = 1.2 Hz), 8.53 (1H, m), 12.44-12.50 (2H, brs). |
| 184 | 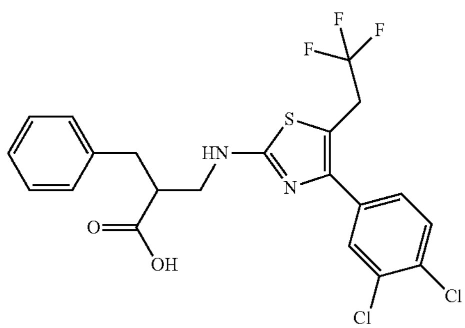 [SMILES: O=C(O)C(CNc1nc(-c2ccc(Cl)c(Cl)c2)c(CC(F)(F)F)s1)Cc1ccccc1] | Method C, Purity is 100%, Rt = 1.933 min; MS Calcd.: 488.0; MS Found: 489.2 [M + H]⁺. | δ: 2.77-2.98 (3H, m), 3.38-3.39 (2H, m), 3.80 (2H, q, J = 10.4 Hz), 7.18-7.30 (5H, m), 7.49 (1H, dd, J = 8.4, 2.0 Hz), 7.71 (2H, dd, J = 5.6, 2.0 Hz), 7.99 (1H, brs). |
| 185 | 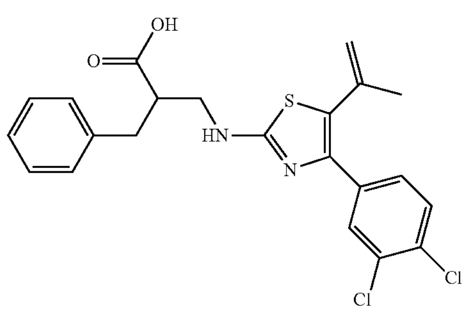 [SMILES: C=C(C)c1sc(NCC(Cc2ccccc2)C(=O)O)nc1-c1ccc(Cl)c(Cl)c1] | Method C, Purity is 98.5%, Rt = 1.990 min; MS Calcd.: 446.1; MS Found: 447.2 [M + H]⁺. | δ: 1.87 (3H, s), 2.76-2.99 (3H, m), 3.36-3.43 (2H, m), 5.05 (1H, s), 5.15 (1H, t, J = 1.2 Hz), 7.18-7.30 (5H, m), 7.49 (1H, dd, J = 8.4, 2.0 Hz), 7.63 (1H, d, J = 8.4 Hz), 7.74 (1H, d, J = 2.0 Hz), 7.88 (1H, brs). |
| 186 | 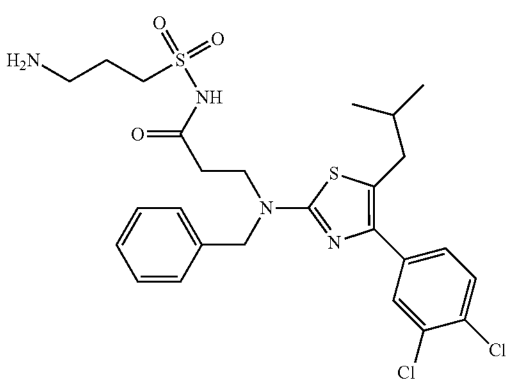 [SMILES: CC(C)Cc1sc(N(CCC(=O)NS(=O)(=O)CCCN)Cc2ccccc2)nc1-c1ccc(Cl)c(Cl)c1] | Method C, Purity is 99.0%, Rt = 2.255 min; MS Calcd.: 583.0; MS Found: 584.2 [M + H]⁺. | δ: 0.87 (6H, d, J = 6.4 Hz), 1.74-1.78 (3H, m), 2.25-2.31 (2H, m), 2.56-2.65 (2H, m), 2.77 (2H, t, J = 12 Hz), 2.99 (2H, t, J = 12 Hz), 3.50-3.53 (2H, m), 4.69 (2H, s), 7.24-7.34 (5H, m), 7.49-7.52 (1H, m), 7.63 (1H, d, J = 8.4 Hz), 7.70 (1 H, s). |

TABLE 3-3-continued

Characterization Data for Compounds

| I-# | Chemical Structure | LCMS | ¹H NMR (400 MHz, d₆-DMSO) |
|---|---|---|---|
| 187 | 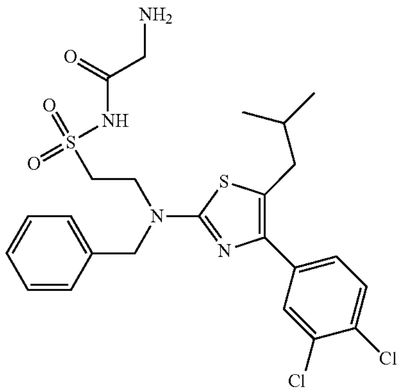 [SMILES: CC(C)Cc1sc(N(CCS(=O)(=O)NC(=O)CN)Cc2ccccc2)nc1-c1ccc(Cl)c(Cl)c1] | Method C, Purity is 90.8%, Rt = 2.286 min; MS Calcd.: 554.1; MS Found: 555.2 [M + H]⁺. | δ: 0.87 (6H, d, J = 6.4 Hz), 1.73-1.76 (1H, m), 2.62 (2H, d, J = 12 Hz), 3.22 (2H, s), 3.35-3.37 (2H, m), 3.70 (2H, t, J = 6.8 Hz), 4.66 (2H, s), 7.27-7.37 (5H, m), 7.51-7.58 (3H, m), 7.65 (1H, d, J = 8.4 Hz), 7.73 (1H, d, J = 1.6 Hz). |
| 188 | 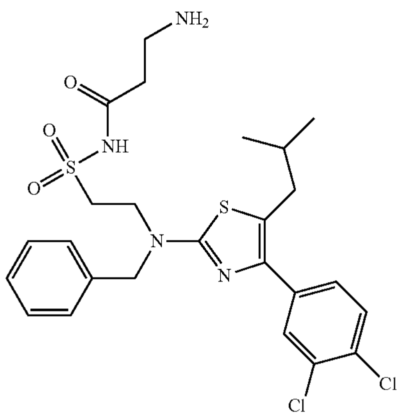 [SMILES: CC(C)Cc1sc(N(CCS(=O)(=O)NC(=O)CCN)Cc2ccccc2)nc1-c1ccc(Cl)c(Cl)c1] | Method C, Purity is 100%, Rt = 2.300 min; MS Calcd.: 568.1; MS Found: 569.2 [M + H]⁺ | δ: 0.88 (6H, d, J = 6.8 Hz), 1.73-1.76 (1H, m), 2.25 (2H, t, J = 6.4 Hz), 2.62 (2H, d, J = 6.8 Hz), 2.85 (2H, t, J = 6.8 Hz), 3.31-3.35 (2H, m), 3.62-3.66 (2H, m), 4.65 (2H, s), 7.25-7.37 (5H, m), 7.51-7.56 (4H, m), 7.66 (1H, d, J = 8.4 Hz), 7.73 (1H, d, J = 2.0 Hz). |
| 189 | 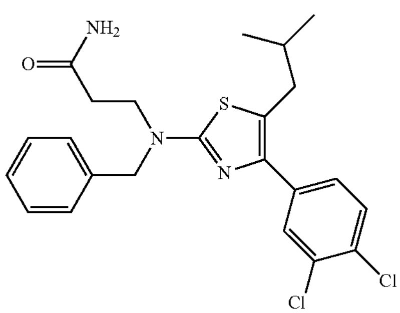 [SMILES: CC(C)Cc1sc(N(CCC(N)=O)Cc2ccccc2)nc1-c1ccc(Cl)c(Cl)c1] | Method C, Purity is 98.0%, Rt = 2.704 min; MS Calcd.: 461.1; MS Found: 462.2 [M + H]⁺. | d₄-MeOD; δ: 0.93 (6H, d, J = 6.8 Hz), 1.80-1.84 (1H, m), 2.62-2.65 (4H, m), 3.79 (2H, t, J = 7.2 Hz), 4.72 (2H, s), 7.29-7.36 (5H, m), 7.48 (1H, dd, J = 8.4, 1.6 Hz), 7.55 (1H, d, J = 8.4 Hz), 7.71 (1H, d, J = 2.0 Hz). |
| 190 | 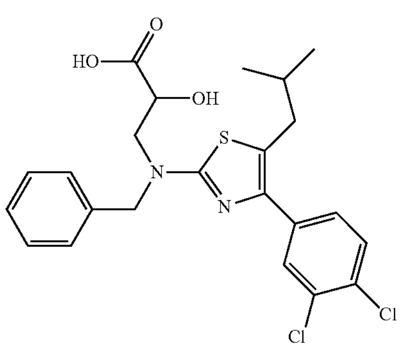 [SMILES: CC(C)Cc1sc(N(Cc2ccccc2)CC(O)C(=O)O)nc1-c1ccc(Cl)c(Cl)c1] | Method B, Purity is 99.3%, Rt = 2.157 min; MS Calcd.: 478.4; MS Found: 479.1 [M + H]⁺. | δ: 0.88 (6H, dd, J = 6.4, 2.0 Hz), 1.73-1.76 (1H, m), 2.61-2.67 (2H, m), 3.51 (1H, dd, J = 14.4, 8.4 Hz), 3.82 (1H, dd, J = 14.4, 4.0 Hz), 4.45 (1H, q, J = 4.0 Hz), 4.75 (2H, s), 7.27-7.37 (5H, m), 7.52 (1H, dd, J = 8.4, 2.4 Hz), 7.66 (1H, d, J = 8.4 Hz), 7.73 (1H, d, J = 2.0 Hz), 12.68 (1H, brs). |

TABLE 3-3-continued

Characterization Data for Compounds

| I-# | Chemical Structure | LCMS | ¹H NMR (400 MHz, d₆-DMSO) |
|---|---|---|---|
| 191 | 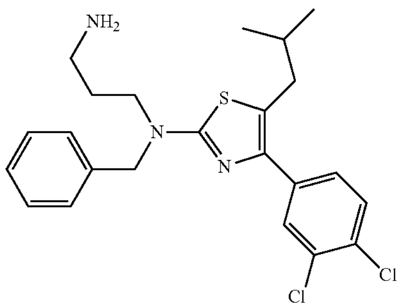 [SMILES: CC(C)Cc1sc(N(CCCN)Cc2ccccc2)nc1-c1ccc(Cl)c(Cl)c1] | Method B, Purity is 100%, Rt = 2.098 min; MS Calcd.: 447.1; MS Found: 448.2 [M + H]⁺. | δ: 0.86 (6H, d, J = 6.4 Hz), 1.71-1.75 (1H, m), 1.82 (2H, t, J = 6.4 Hz), 2.60 (2H, d, J = 7.2 Hz), 2.69 (2H, t, J = 6.8 Hz), 3.50 (2H, t, J = 6.8 Hz), 4.63 (2H, s), 7.24-7.36 (5H, m), 7.51 (1H, dd, J = 8.4, 2.0 Hz), 7.64 (1H, d, J = 8.4 Hz), 7.72 (1H, d, J = 2.0 Hz), 8.41 (1H, s). |
| 192 | 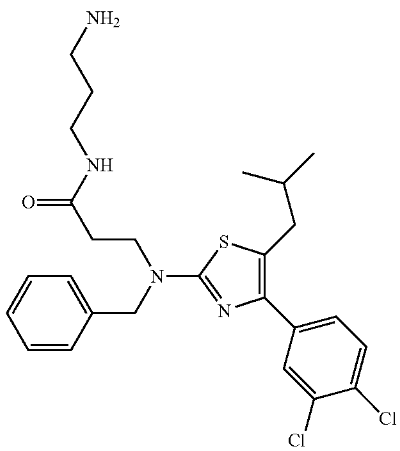 [SMILES: CC(C)Cc1sc(N(CCC(=O)NCCCN)Cc2ccccc2)nc1-c1ccc(Cl)c(Cl)c1] | Method B, Purity is 100%, Rt = 1.697 min; MS Calcd.: 518.1; MS Found: 519.2 [M + H]⁺. | δ: 0.86 (6H, d, J = 6.4 Hz), 1.71-1.75 (1H, m), 1.21-1.23 (2H, m), 1.46 (2H, dd, J = 13.6, 6.8 Hz), 1.72-1.75 (1H, m), 2.53 (2H, t, J = 6.8 Hz), 2.60 (2H, d, J = 6.8 Hz), 3.06 (2H, dd, J = 8.4, 6.8 Hz), 3.63 (2H, t, J = 6.8 Hz), 4.62 (2H, s), 7.26-7.35 (5H, m), 7.51 (1H, dd, J = 8.4, 2.0 Hz), 7.65 (1H, d, J = 8.4 Hz), 7.72 (1H, d, J = 1.6 Hz), 7.95-7.96 (1H, m). |
| 193 | 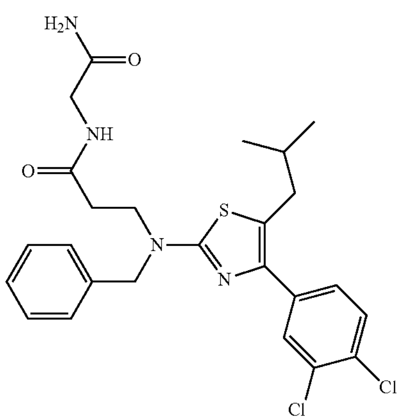 [SMILES: CC(C)Cc1sc(N(CCC(=O)NCC(N)=O)Cc2ccccc2)nc1-c1ccc(Cl)c(Cl)c1] | Method C, Purity is 100%, Rt = 2.549 min; MS Calcd.: 518.1; MS Found: 519.2 [M + H]⁺. | δ: 0.86 (6H, d, J = 6.4 Hz), 1.72-1.75 (1H, m), 2.55 (2H, t, J = 6.8 Hz), 2.60 (2H, d, J = 7.2 Hz), 3.60-3.65 (2H, m), 4.64 (2H, s), 7.00 (1H, s), 7.23-7.35 (6H, m), 7.51 (1H, dd, J = 8.4, 2.0 Hz), 7.64 (1H, d, J = 8.4 Hz), 7.72 (1H, d, J = 2.0 Hz), 8.16 (1H, t, J = 6.0 Hz). |

TABLE 3-3-continued

Characterization Data for Compounds

| I-# | Chemical Structure | LCMS | ¹H NMR (400 MHz, d₆-DMSO) |
|---|---|---|---|
| 194 | 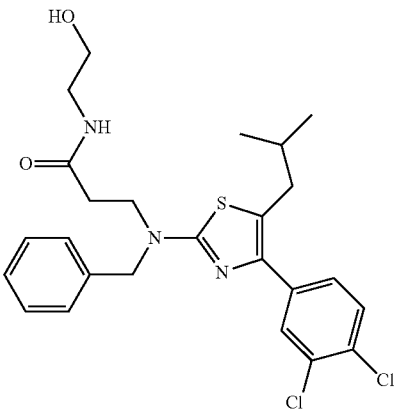 [SMILES: CC(C)Cc1sc(N(CCC(=O)NCCO)Cc2ccccc2)nc1-c1ccc(Cl)c(Cl)c1] | Method C, Purity is 100%, Rt = 1.564 min; MS Calcd.: 450.0; MS Found: 449.2 [M + H]⁺. | δ: 0.88 (6H, d, J = 6.4 Hz), 1.72-1.79 (1H, m), 2.50-2.51 (2H, m), 2.62 (2H, d, J = 7.2 Hz), 3.07-3.12 (2H, m), 3.35-3.38 (2H, m), 3.64 (2H, t, J = 6.8 Hz), 4.65 (3H, s), 7.25-7.30 (3 H, m), 7.33-7.37 (2H, m), 7.52 (1H, dd, J = 8.4, 2.4 Hz), 7.66 (1H, d, J = 8.4 Hz), 7.74 (1H, d, J = 2.0 Hz), 7.79-8.00 (1H, m). |
| 195 | 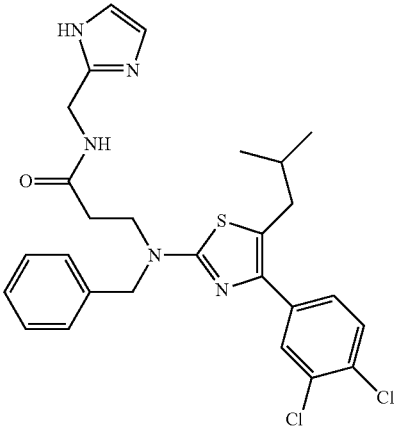 [SMILES: CC(C)Cc1sc(N(CCC(=O)NCc2ncc[nH]2)Cc2ccccc2)nc1-c1ccc(Cl)c(Cl)c1] | Method C, Purity is 99.8%, Rt = 2.599 min; MS Calcd.: 541.2; MS Found: 542.3 [M + H]⁺. | δ: 0.86 (6H, d, J = 6.4 Hz), 1.71-1.75 (1H, m), 2.54-2.61 (4H, m), 3.65 (2H, t, J = 6.8 Hz), 4.23 (2H, d, J = 5.6 Hz), 4.61 (2H, s), 6.78 (1H, s), 6.98 (1H, s), 7.23-7.27 (3H, m), 7.31-7.35 (2H, m), 7.50 (1H, dd, J = 8.4, 2.0 Hz), 7.63-7.66 (1H, m), 7.72 (1H, d, J = 2.0 Hz), 8.42-8.45 (1H, m), 11.76 (1H, brs). |
| 196 | 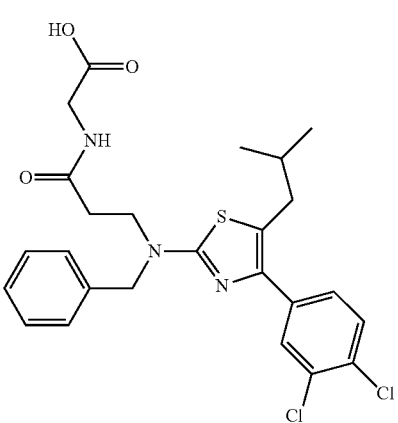 [SMILES: CC(C)Cc1sc(N(CCC(=O)NCC(=O)O)Cc2ccccc2)nc1-c1ccc(Cl)c(Cl)c1] | Method C, Purity is 97.2%, Rt = 2.070 min; MS Calcd.: 519.1; MS Found: 520.2 [M + H]⁺. | δ: 0.86 (6H, d, J = 6.4 Hz), 1.71-1.75 (1H, m), 2.48-2.54 (2H, m), 2.60 (2H, d, J = 7.2 Hz), 3.45-3.47 (2H, m), 3.60 (2H, t, J = 6.8 Hz), 4.64 (2H, s), 7.22-7.34 (5H, m), 7.51 (1H, dd, J = 8.4, 2.0 Hz), 7.64 (1H, d, J = 8.4 Hz), 7.71 (1H, d, J = 2.0 Hz), 7.77 (1H, brs). |

TABLE 3-3-continued

Characterization Data for Compounds

| I-# | Chemical Structure | LCMS | $^1$H NMR (400 MHz, $d_6$-DMSO) |
|---|---|---|---|
| 197 | 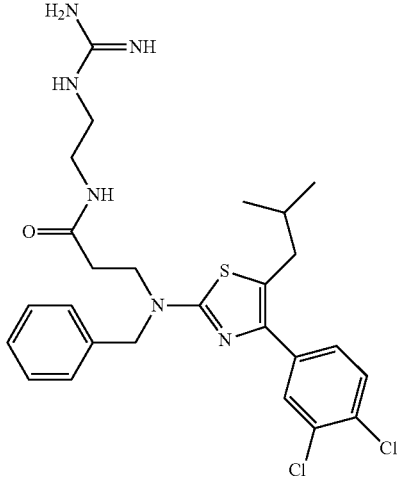 [SMILES: CC(C)Cc1sc(N(CCC(=O)NCCNC(=N)N)Cc2ccccc2)nc1-c1ccc(Cl)c(Cl)c1] | Method B, Purity is 91.8%, Rt = 1.970 min; MS Calcd.: 546.2; MS Found: 547.3 [M + H]$^+$. | δ: 0.86 (6H, d, J = 6.8 Hz), 1.69-1.75 (1H, m), 2.48-2.52 (2H, m), 2.61 (2H, d, J = 6.8 Hz), 3.14 (4H, s), 3.65 (2H, t, J = 6.8 Hz), 4.63 (2H, s), 7.24-7.28 (2H, m), 7.27-7.36 (6H, m), 7.49-7.52 (2H, m), 7.65 (1H, d, J = 8.4 Hz), 7.72 (1H, d, J = 2.0 Hz), 8.14 (1H, brs). |
| 198 | 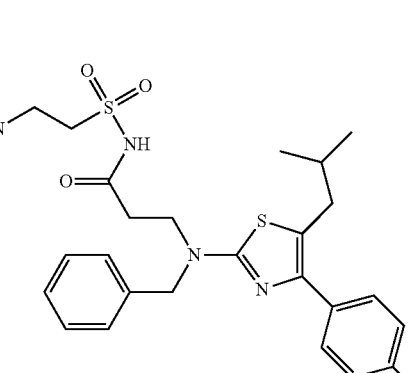 | Method C, Purity is 94.4%, Rt = 2.260 min; MS Calcd.: 568.1; MS Found: 569.2 [M + H]$^+$. | δ: 0.87 (6H, d, J = 6.4 Hz), 1.73-1.77 (1H, m), 2.34 (2H, t, J = 12 Hz), 2.61 (2H, d, J = 12 Hz), 3.02 (2H, t, J = 6.8 Hz), 3.20 (2H, t, J = 6.8 Hz), 3.53 (2H, t, J = 12 Hz), 4.69 (2H, s), 7.22-7.35 (5H, m), 7.51 (1H, dd, J = 8.4, 2.0 Hz), 7.64 (1H, d, J = 8.4 Hz), 7.70 (1H, d, J = 2.0 Hz), 7.75 (1H, brs). |

Example 4. Synthesis of Compounds I-199 to I-285

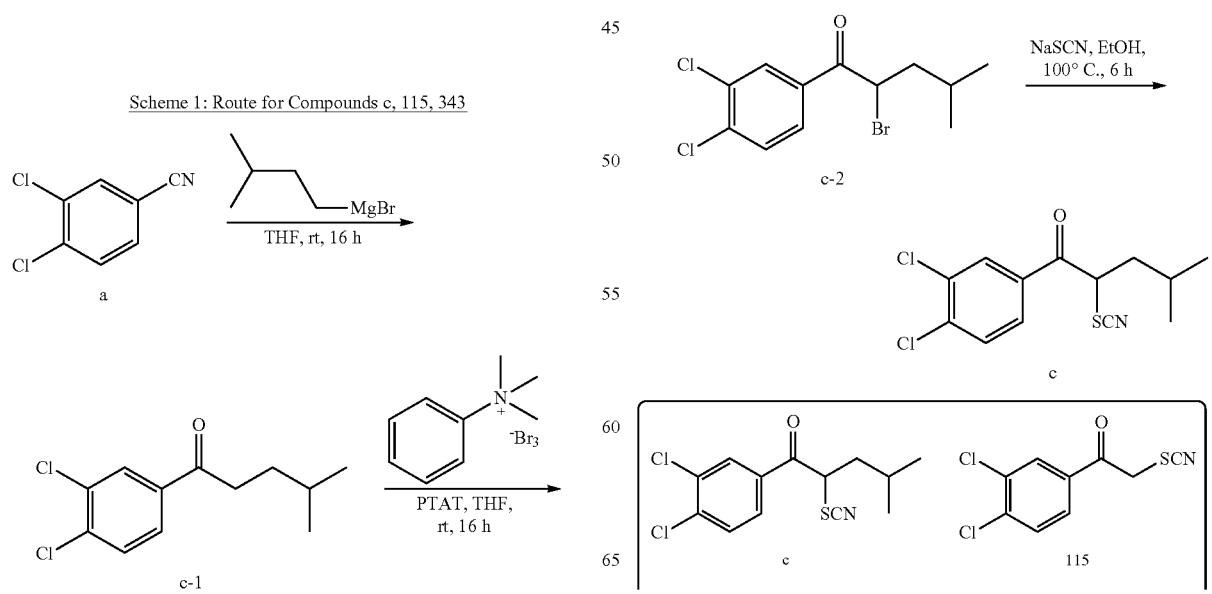

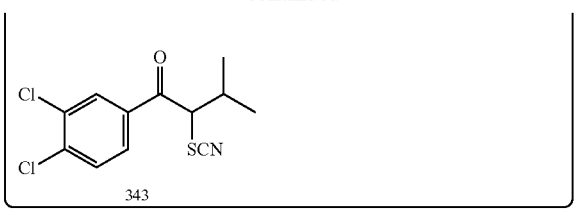
343
The same synthesis method used for other compounds 115, 343.
Scheme 2: Route for Compound 346
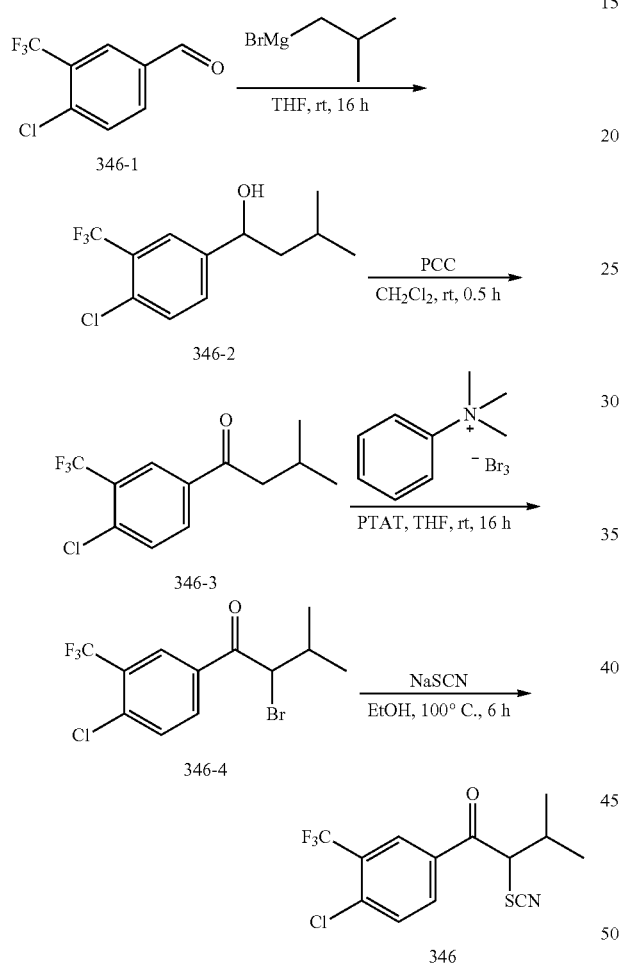
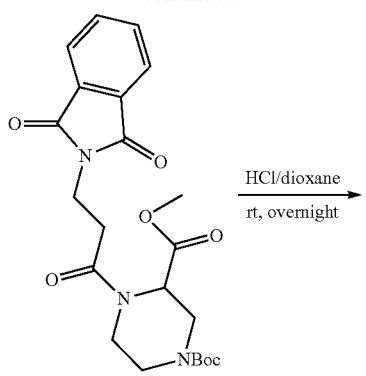
244-2
b-244
Scheme 4: Route for Compound b-250
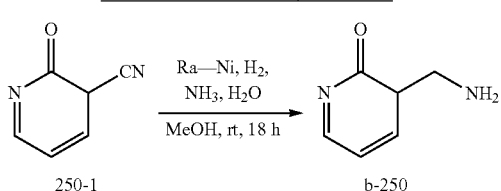
250-1          b-250
Scheme 3: Route for Compound b-244
Scheme 5: Route for Compound b-257
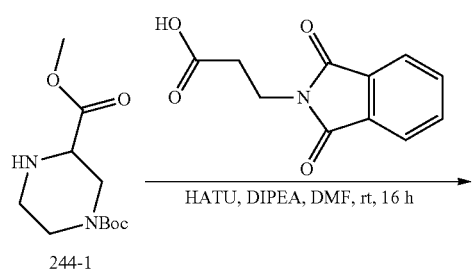
244-1
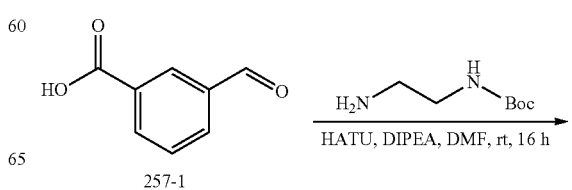
257-1

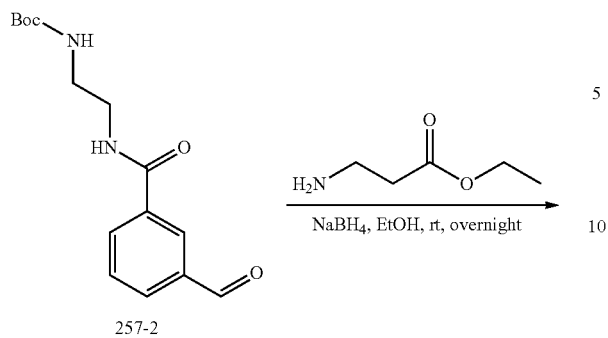
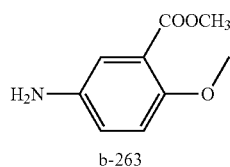
b-263
Scheme 8: Route for Compound b-264
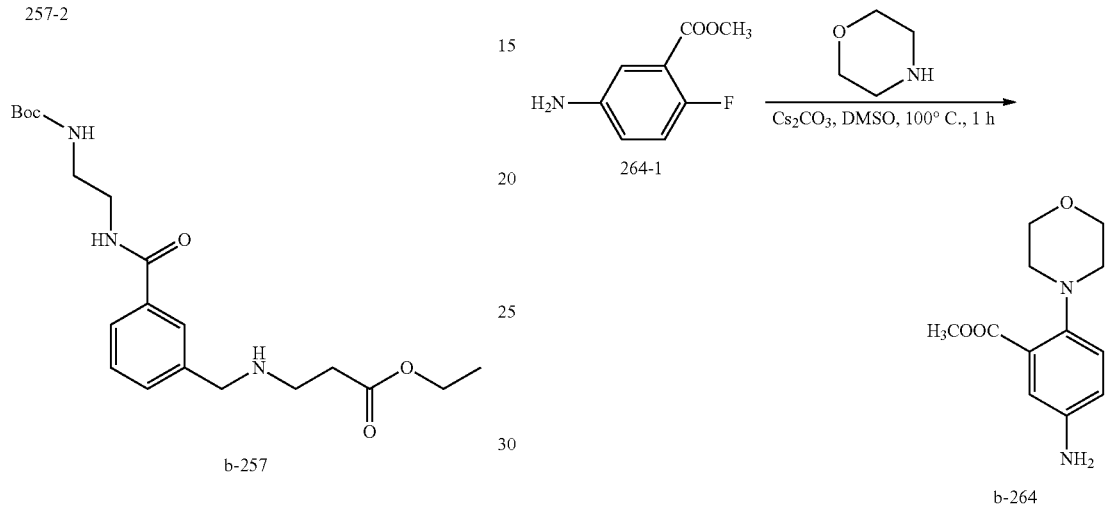
Scheme 6: Route for Compound b-260
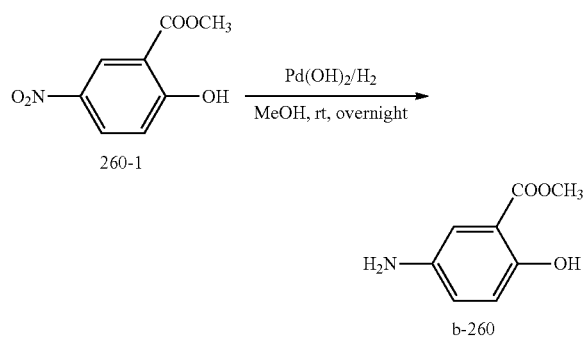
Scheme 9: Route for Compounds b-268, b-269, b-299, b-309, b-348, b-357, b-358, b-380
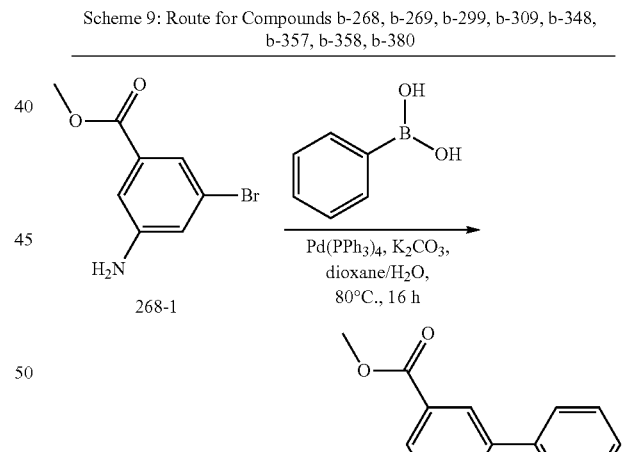
Scheme 7: Route for Compound b-263
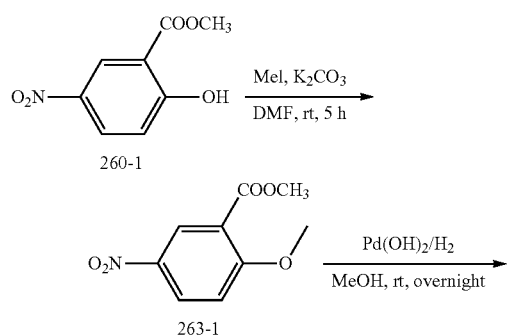
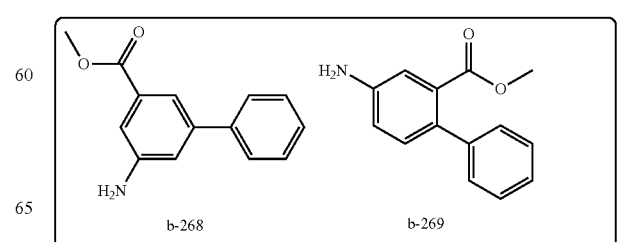

-continued
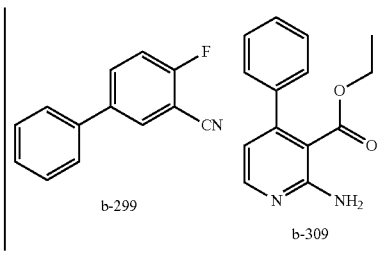
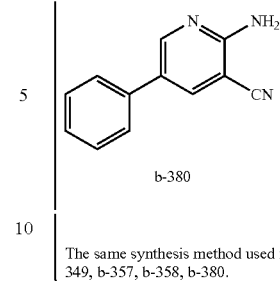
The same synthesis method used for other compounds b-269, b-299, b-309, b-348, b-349, b-357, b-358, b-380.
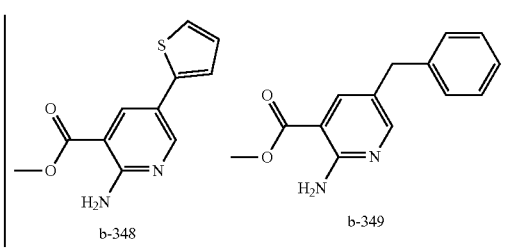
Scheme 10: Route for Compound b-270
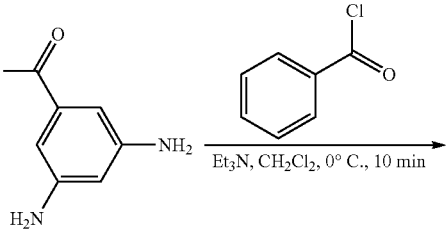
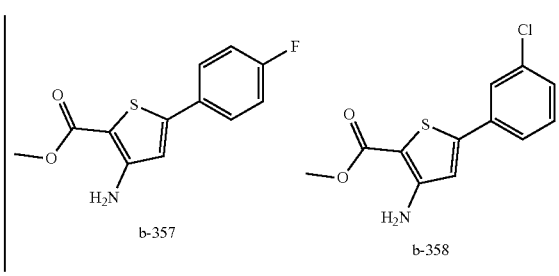
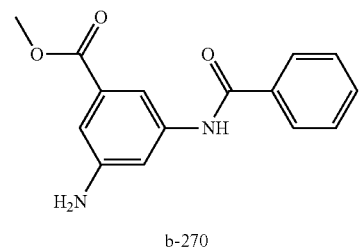
Scheme 11: Route for Compounds b-288, b-289
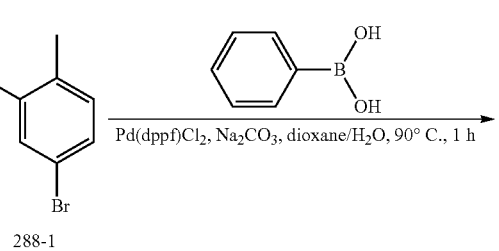
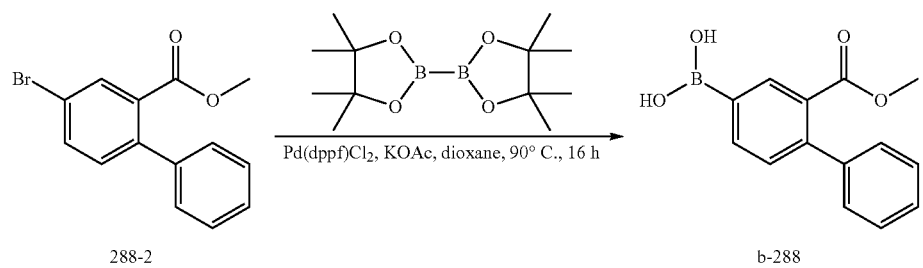

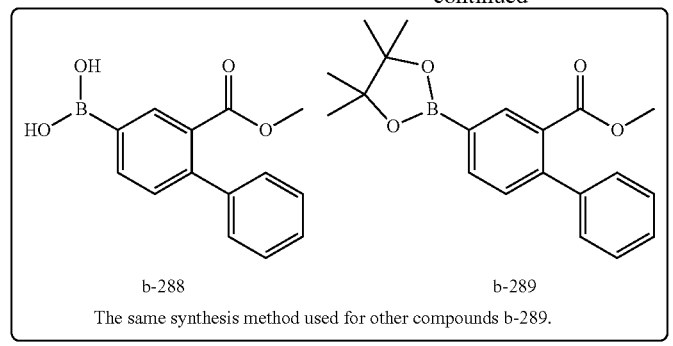
b-288  b-289
The same synthesis method used for other compounds b-289.
Scheme 12: Route for Compound b-290
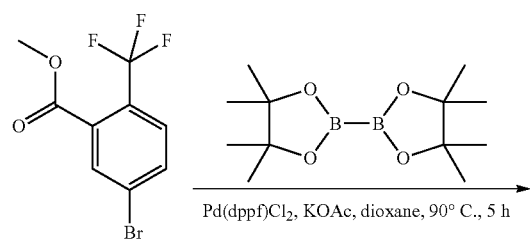
Scheme 13: Route for Compound b-291
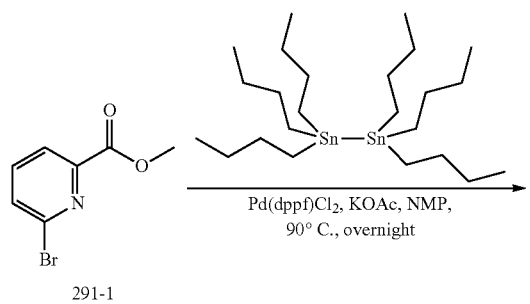
Scheme 14: Route for Compound b-292
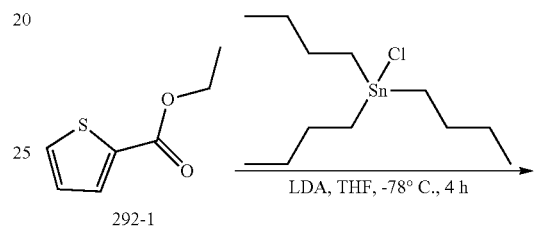
Scheme 15: Route for Compound b-294
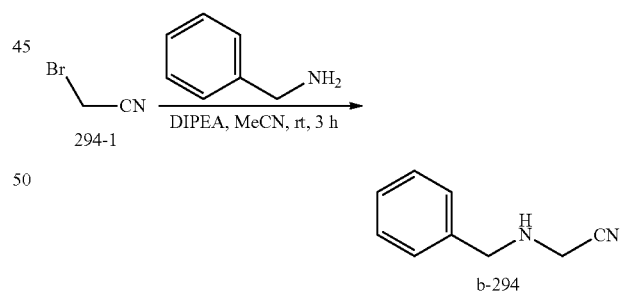
Scheme 16: Route for Compound b-295
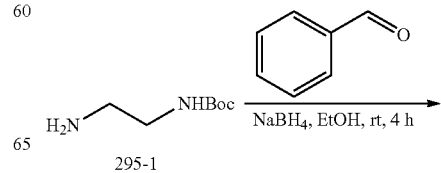

-continued
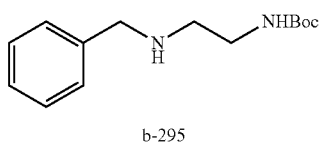
b-295
Scheme 17: Route for Compound b-300
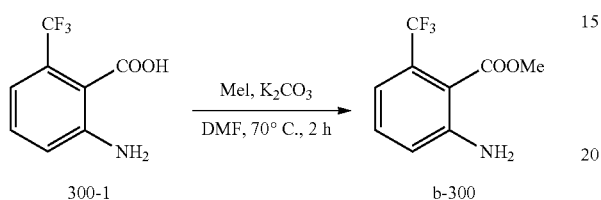
Scheme 18: Route for Compound b-301
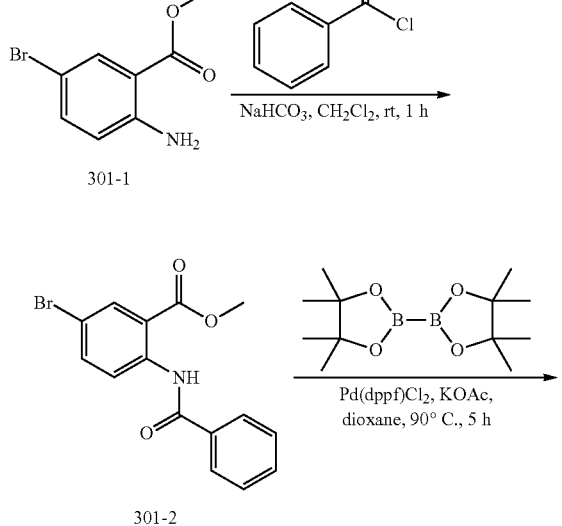
Scheme 19: Route for Compound b-287
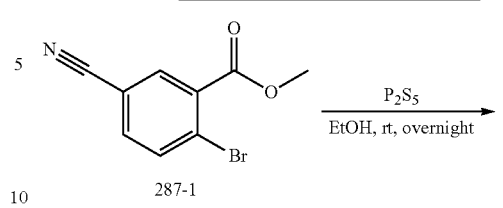
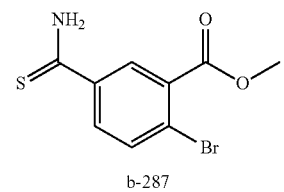
b-287
Scheme 20: Route for Compounds b-302, b-306
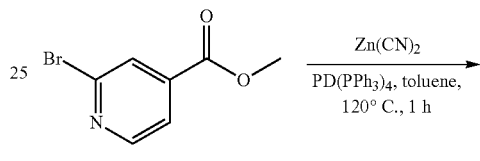
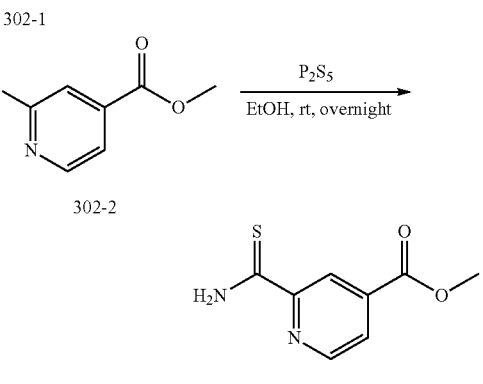
The same synthesis method used for other compounds b-306.
Scheme 21: Route for Compound b-310
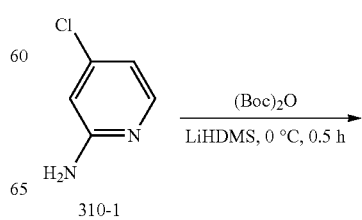
310-1

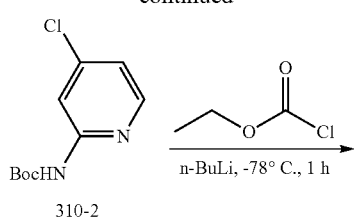
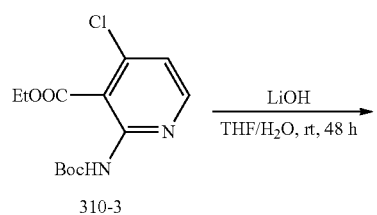
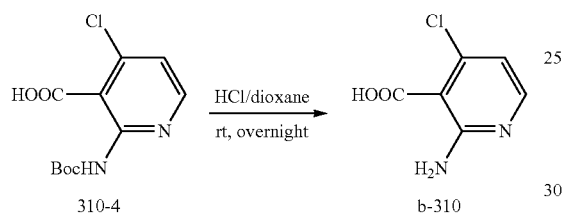
Scheme 22: Route for Compound b-313
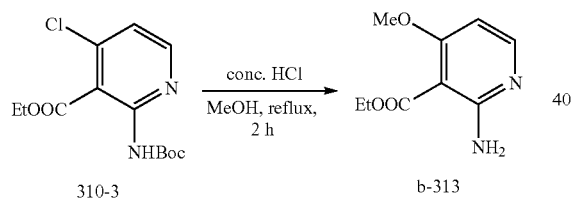
Scheme 23: Route for Compound b-332
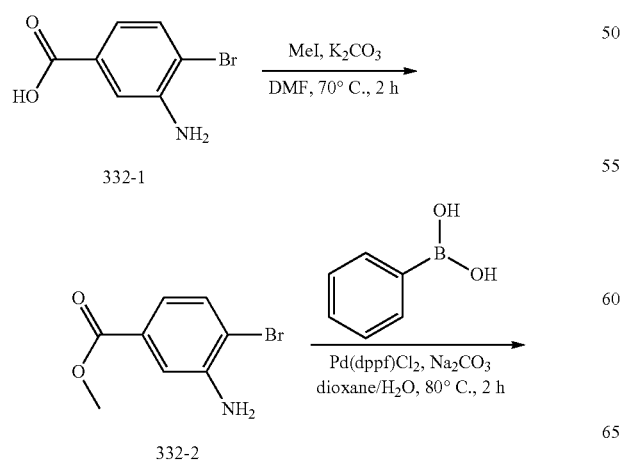
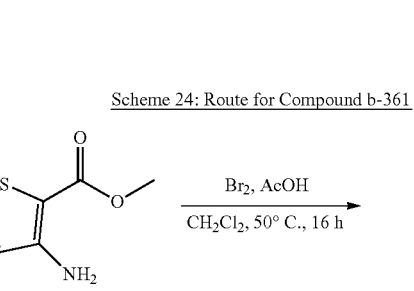
Scheme 24: Route for Compound b-361
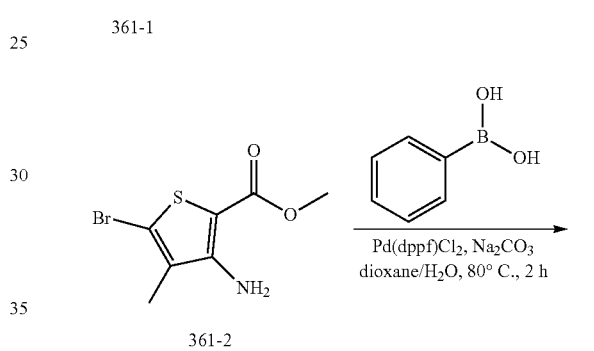
Scheme 25: Route for Compound b-372
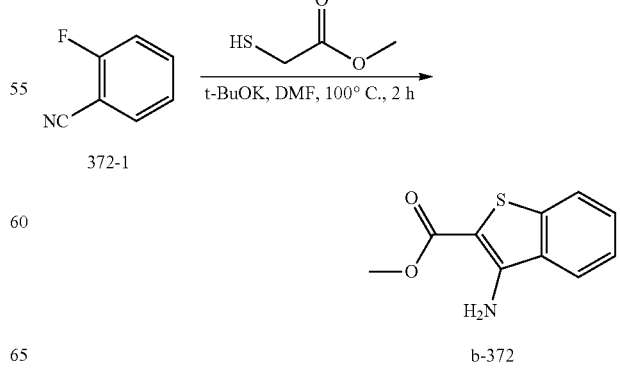

Scheme 26: Route for Compound b-378
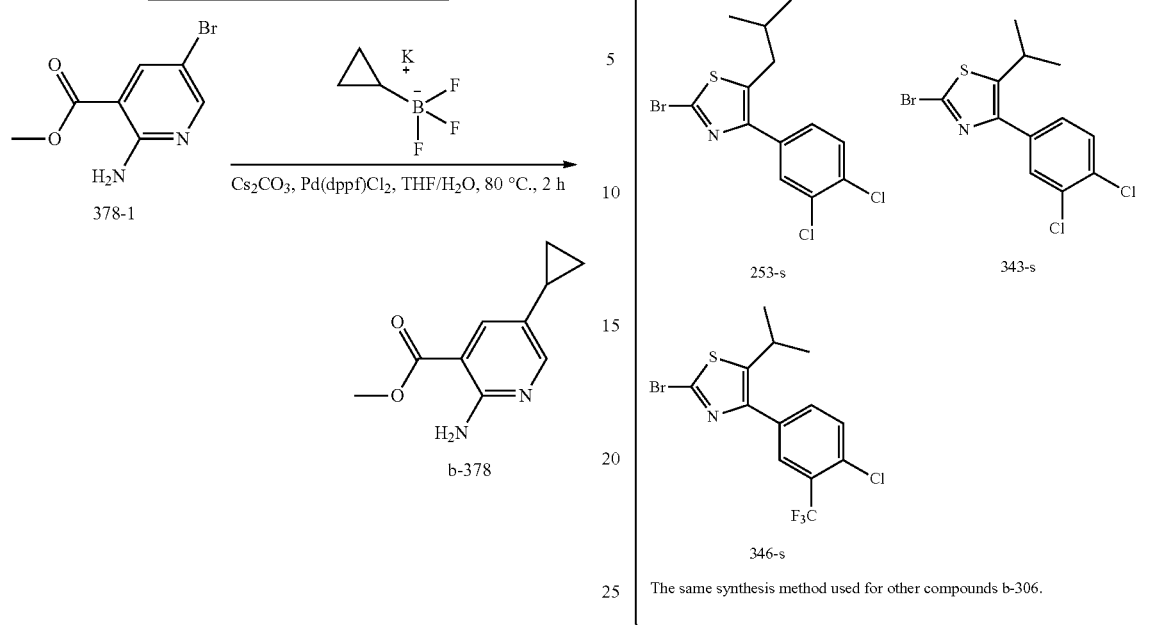
Scheme 27: Route for Compounds 253-s, 343-s
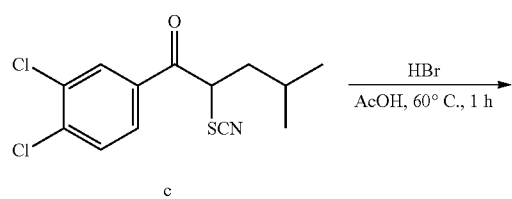
Scheme 28: Route for Compound 316-s
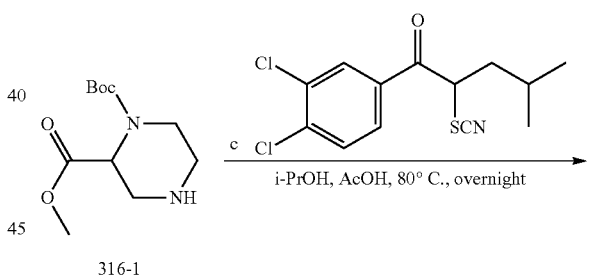
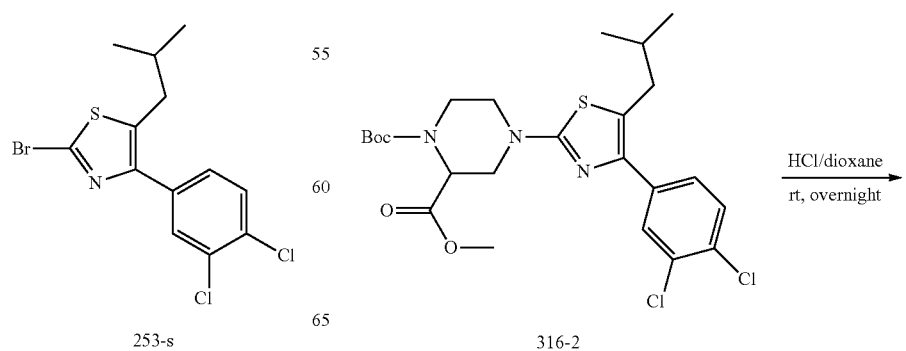

-continued
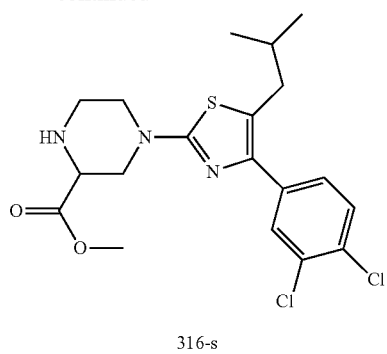
316-s
Scheme 29: Route for Compounds 344-s, 356-s, 366-s
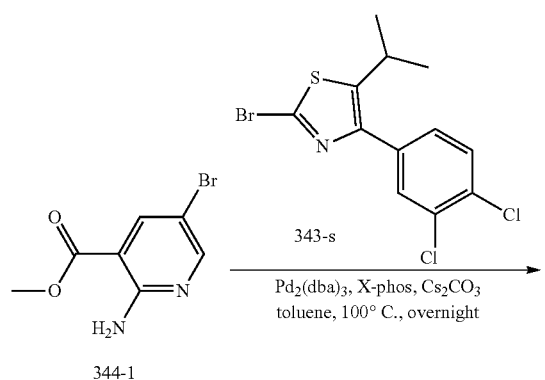
344-1      343-s
Pd$_2$(dba)$_3$, X-phos, Cs$_2$CO$_3$
toluene, 100° C., overnight
-continued
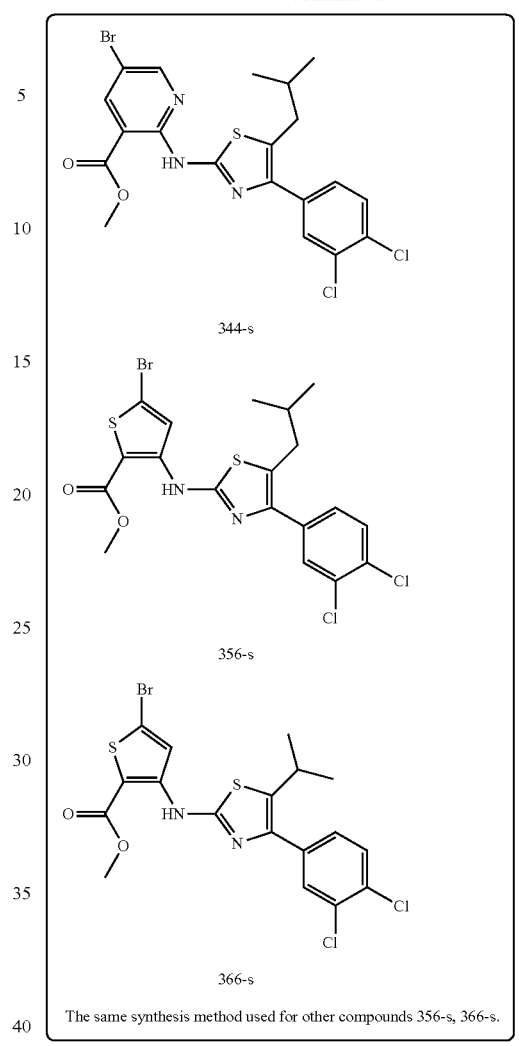
344-s
356-s
366-s
The same synthesis method used for other compounds 356-s, 366-s.
Scheme 30: Route for Compound I-199
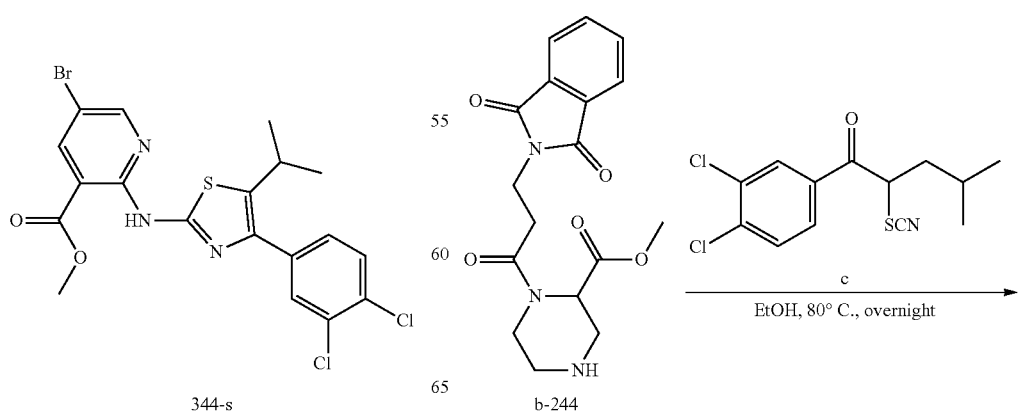
344-s     b-244
c
EtOH, 80° C., overnight 493
-continued
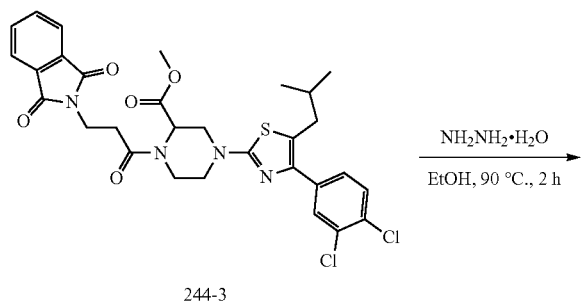
244-3
NH$_2$NH$_2$·H$_2$O
EtOH, 90 °C., 2 h
→
494
-continued
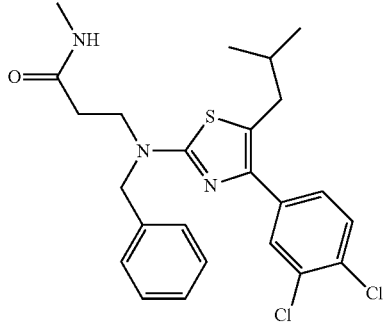
I-200
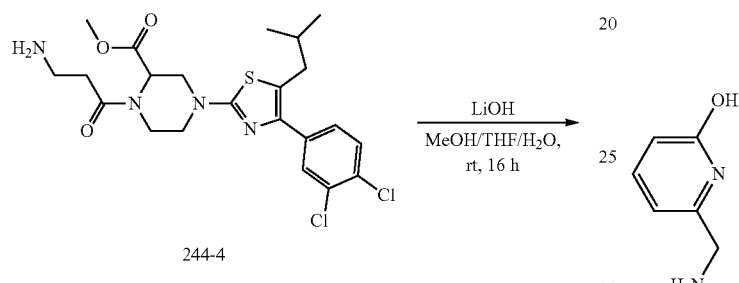
244-4
LiOH
MeOH/THF/H$_2$O,
rt, 16 h
→
Scheme 32: Route for Compounds I-201, I-202
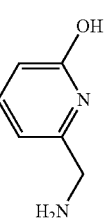
249-1
EtOH, 80° C., overnight
→
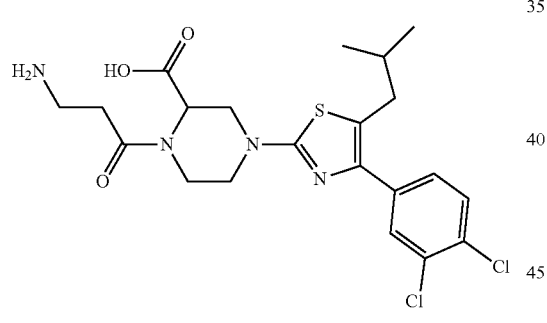
I-199
Scheme 31: Route for Compound I-200
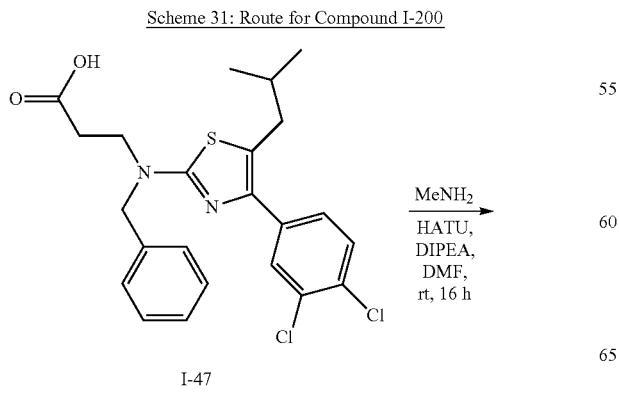
I-47
MeNH$_2$
HATU,
DIPEA,
DMF,
rt, 16 h
→
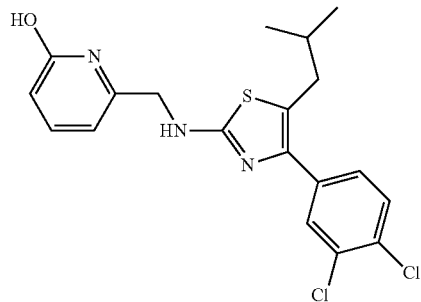
I-201
The same synthesis method used for other compound I-202

495
Scheme 33: Route for Compounds I-203, I-225 to I-227, I-237, I-265 to I-268, I-270, I-273, I-278
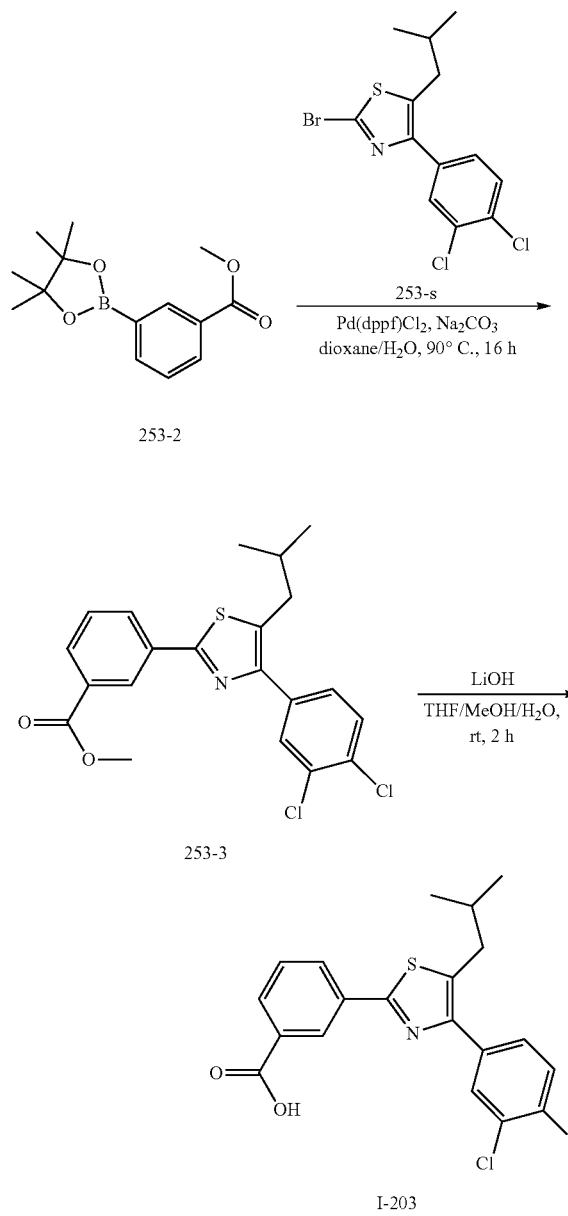
The same synthesis method used for other compound I-203, I-225 to I-227, I-237, I-265 to I-268, I-270, I-273, I-278.
Scheme 34: Route for Compound I-204
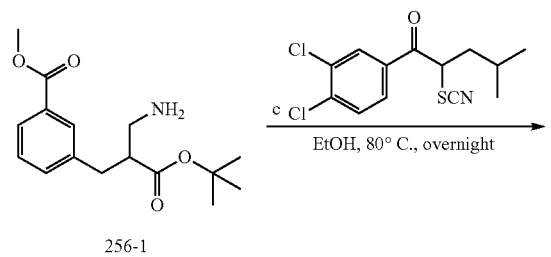
496
-continued
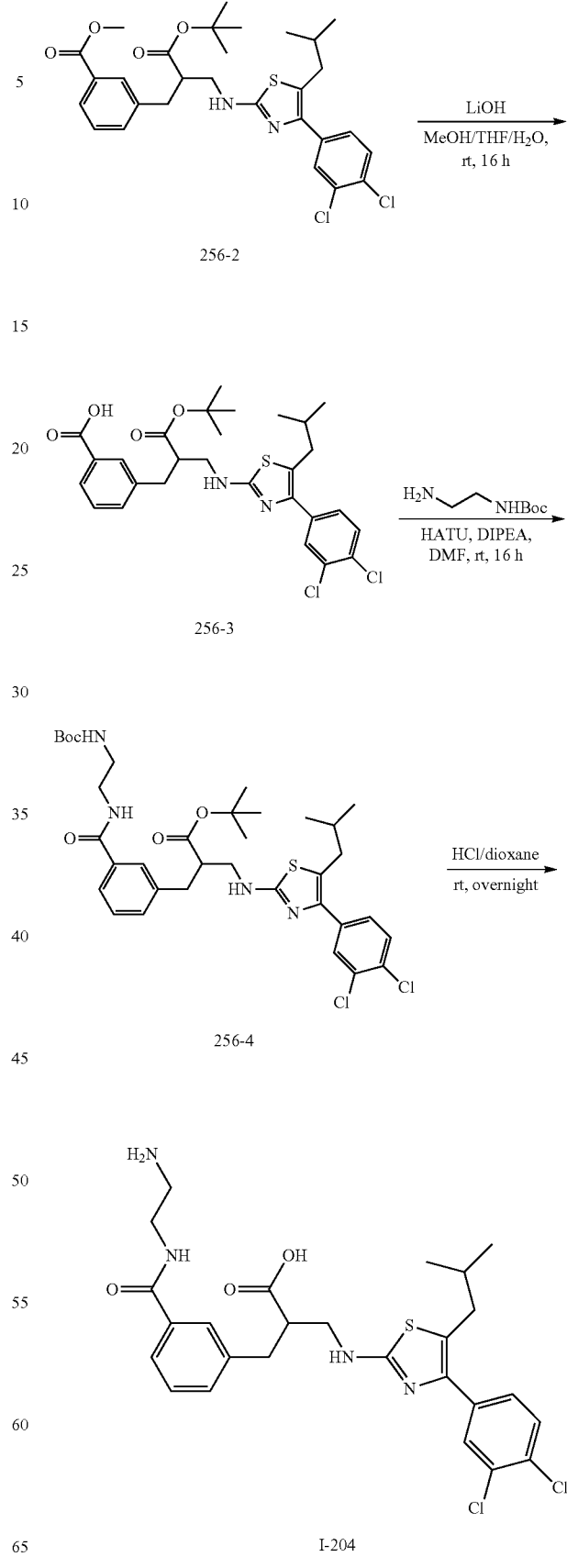

Scheme 35: Route for Compound I-205
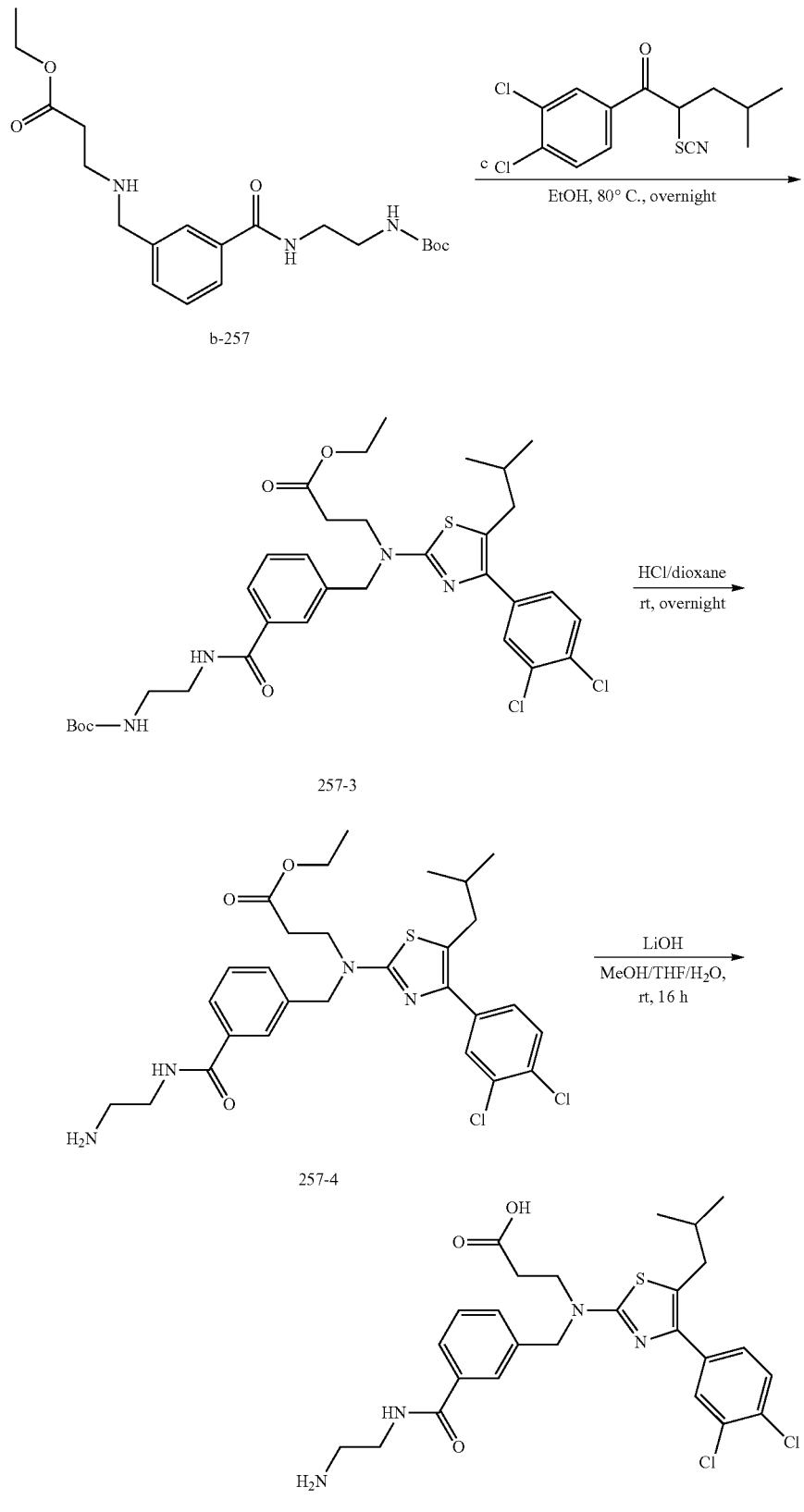

Scheme 36: Route for Compound I-206
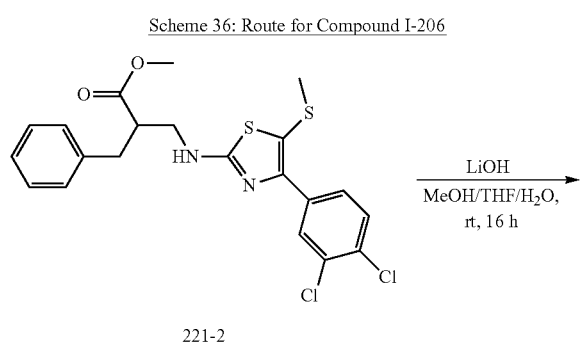
221-2
I-206
Scheme 37: Route for Compounds I-207 to I-208 to I-214, I-217, I-219, I-220, I-222, I-236, I-241, I-243, I-254, to I-256, I-258, I-261, I-264, I-274, I-280, I-281, I-283
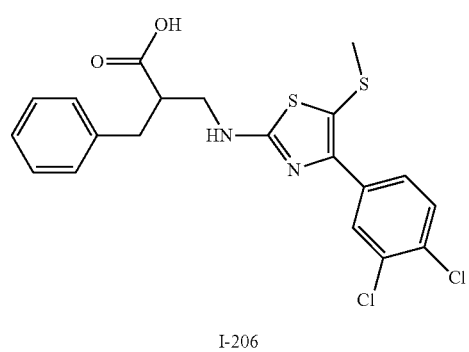
253-s
b-260
260-2
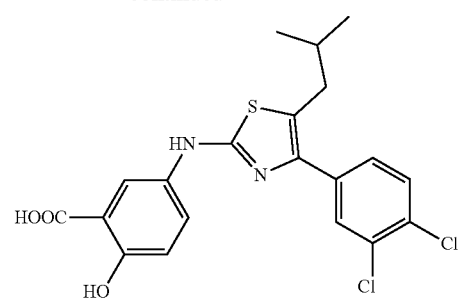
I-207
The same synthesis method is used for other compounds to I-208 to I-214, I-217, I-219, -220, I-222, I-236, I-241, I-243, I-254, to I-256, I-258, I-261, I-264, I-274, I-280, I-281, I-283.
Scheme 38: Route for Compounds I-215, I-216
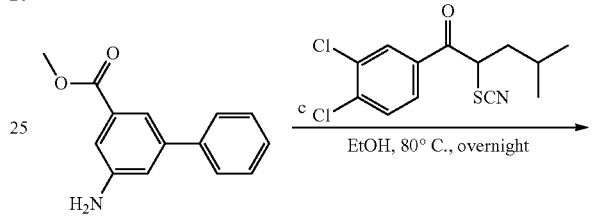
b-268
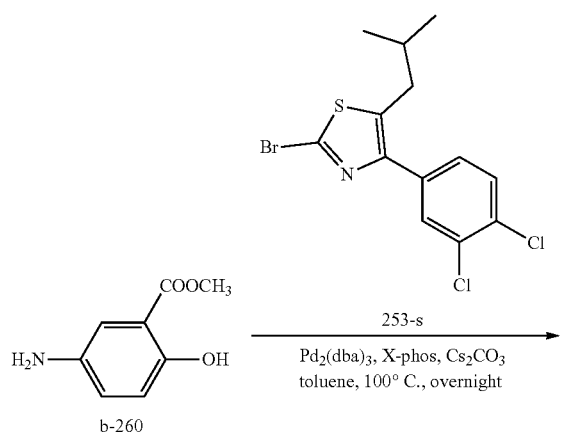
268-2
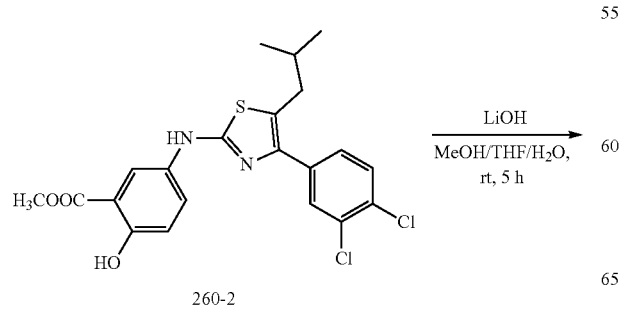
I-215
The same synthesis method used for other compound I-216

Scheme 39: Route for Compound I-218
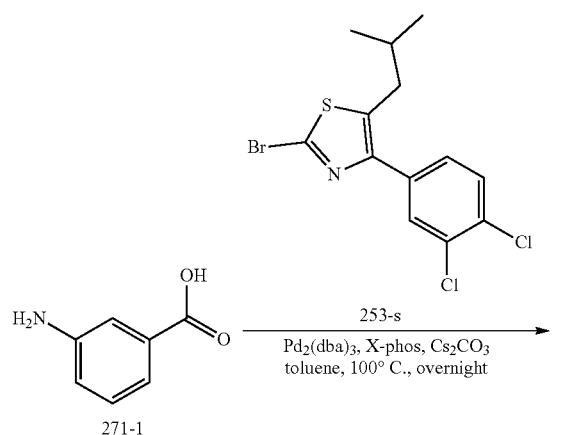
Scheme 40: Route for Compounds I-221, I-229, I-239, I-242
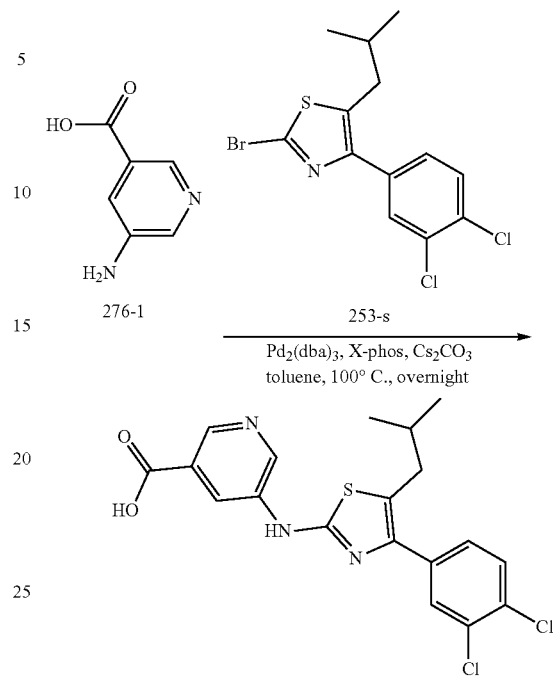
The same synthesis method used for other compounds I-229, I-239, I-242.
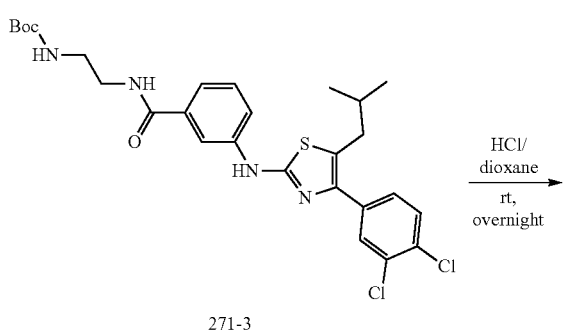
Scheme 41: Route for Compound I-223
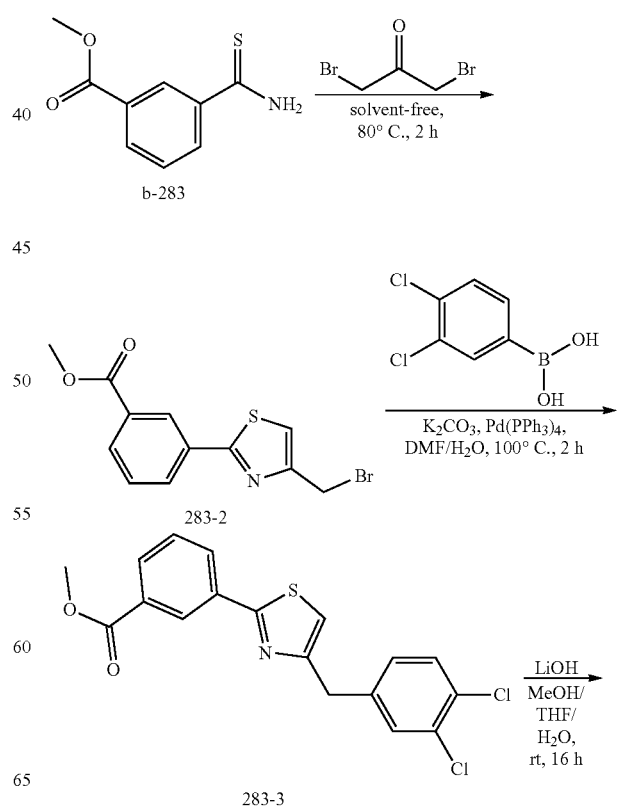

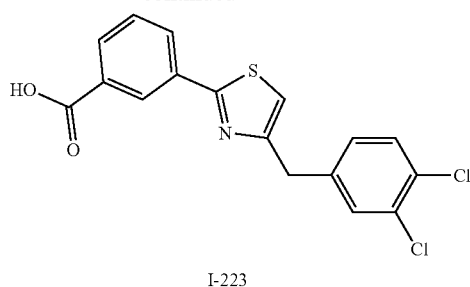
I-223
Scheme 42: Route for Compounds I-224, I-238, I-240
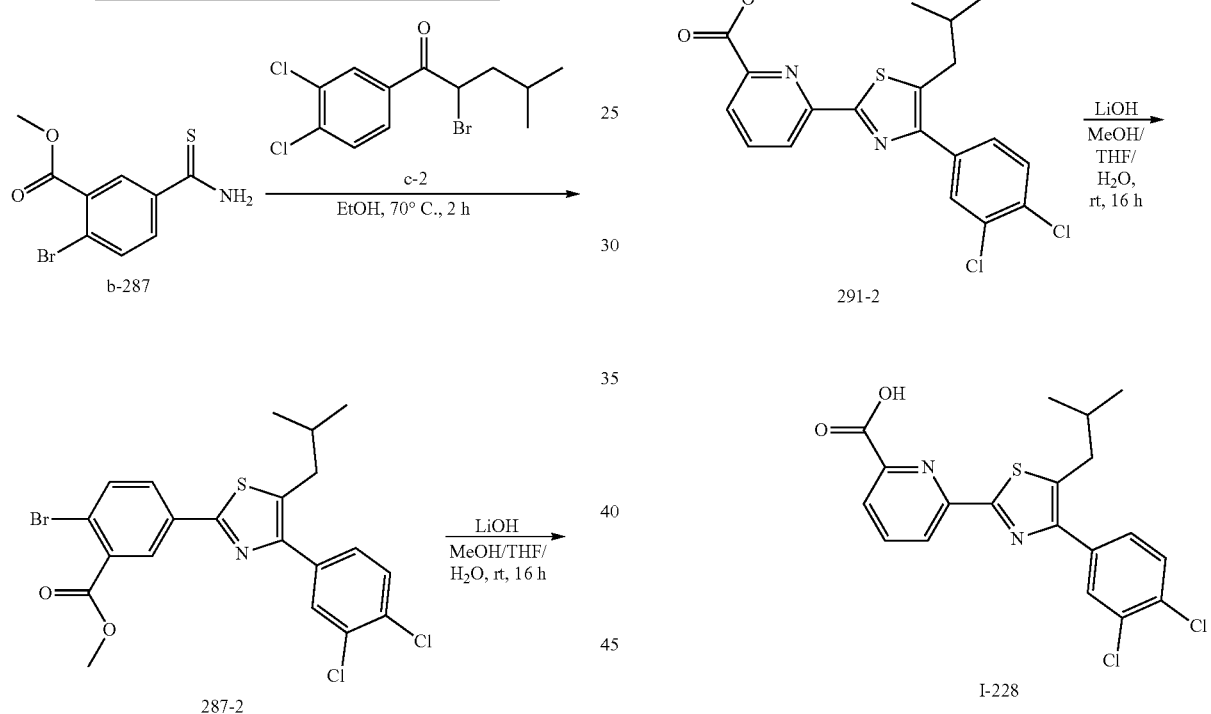
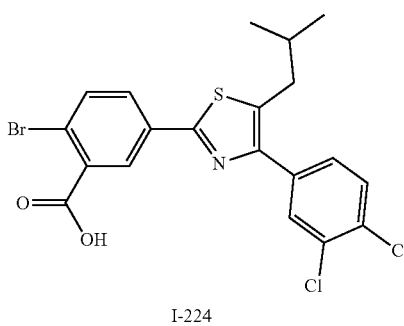
I-224
The same synthesis method used for other compounds I-238, I-240.
Scheme 43: Route for Compounds I-228, I-229
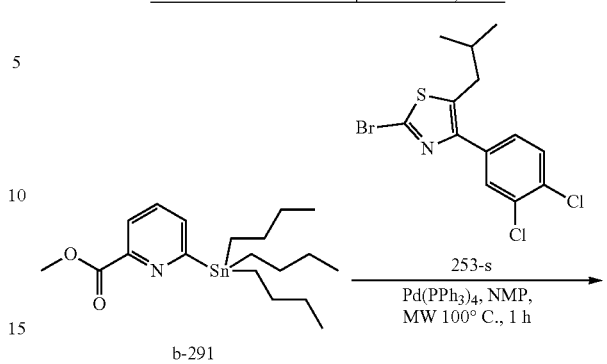
The same synthesis method used for other compoud I-229.
Scheme 44: Route for Compound I-230
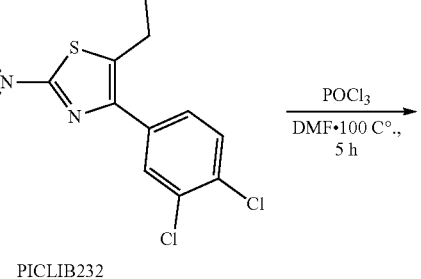
PICLIB232

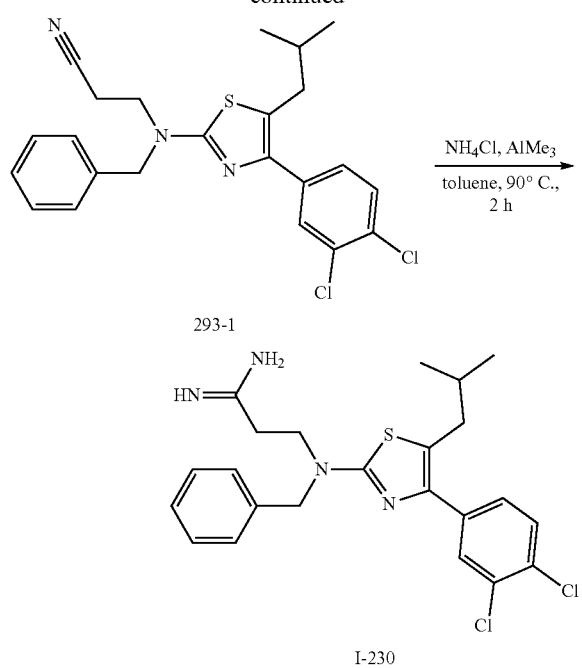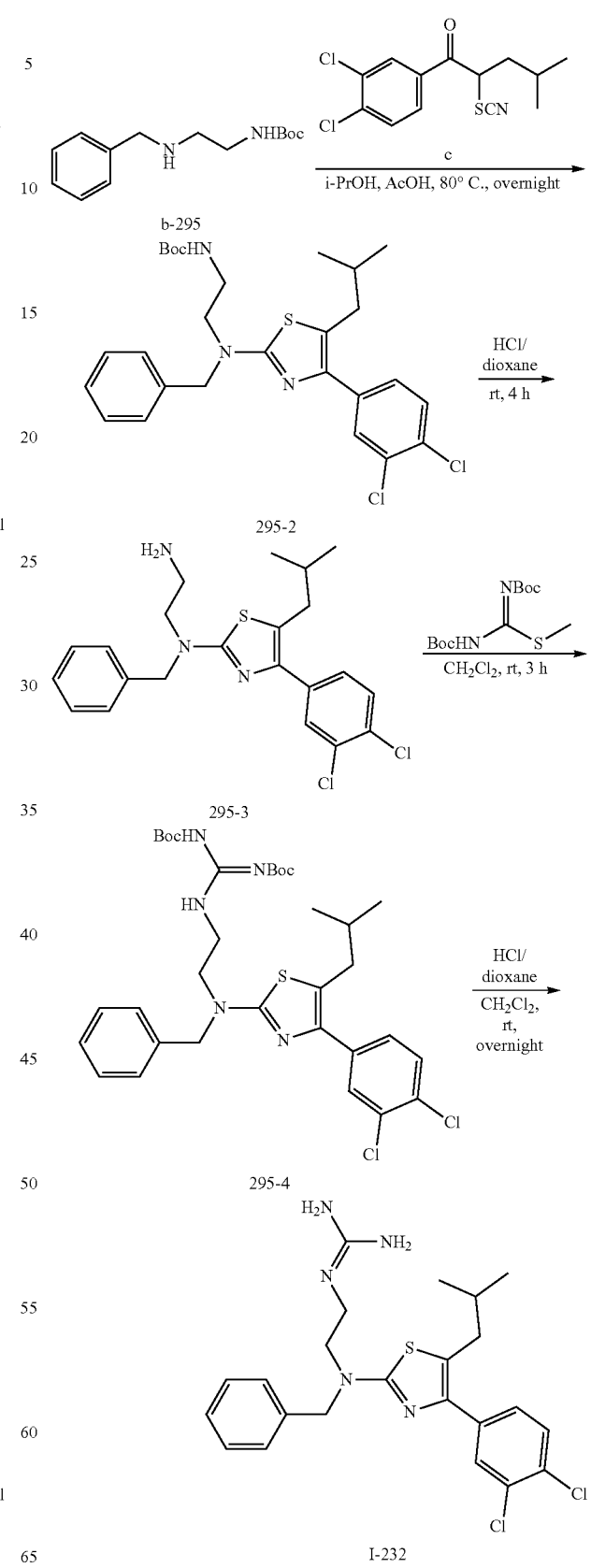

Scheme 47: Route for Compounds I-234, I-235
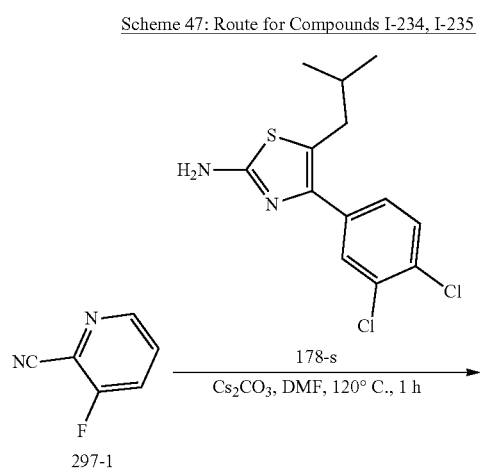
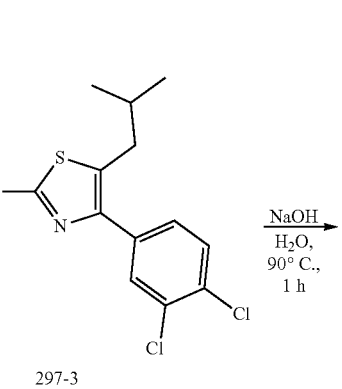
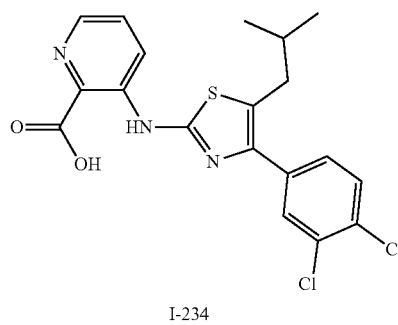
Scheme 48: Route for Compound I-244
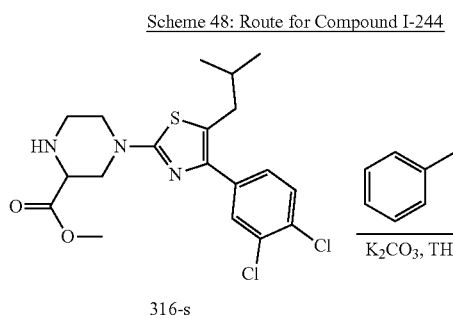
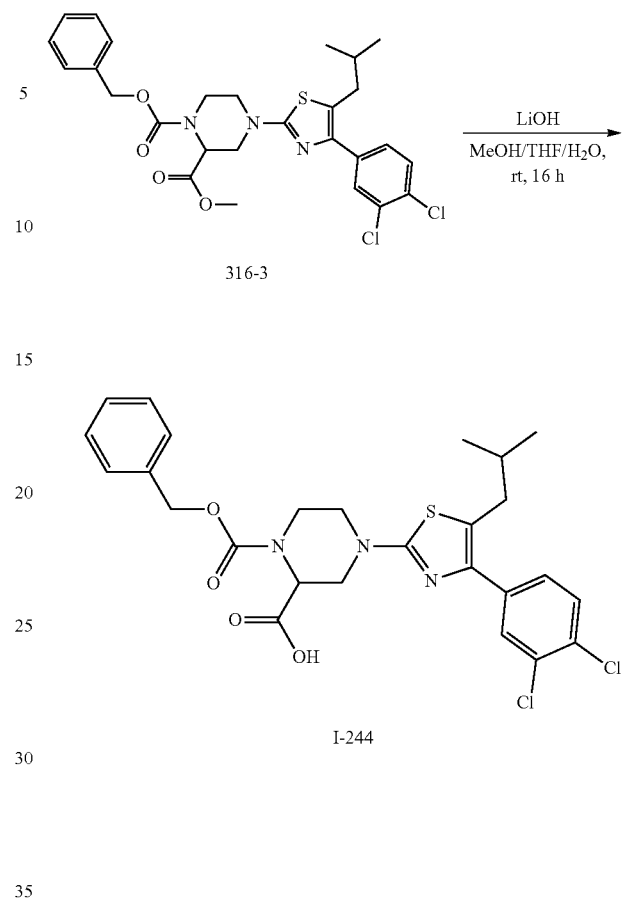
Scheme 49: Route for Compound I-245
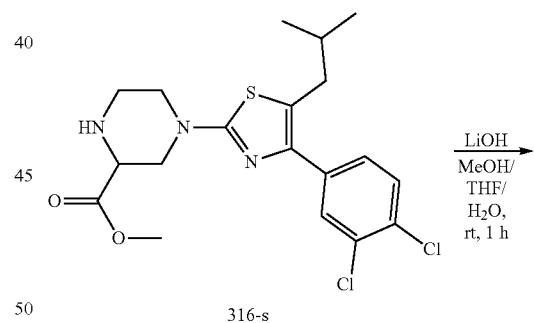
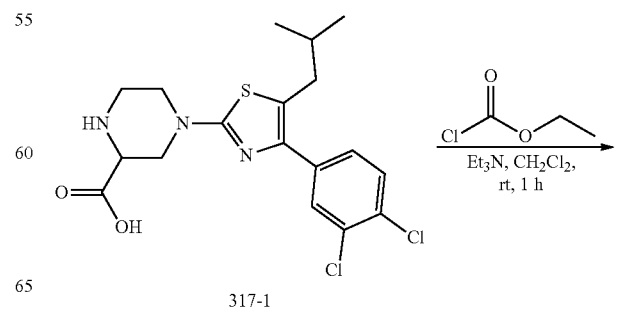

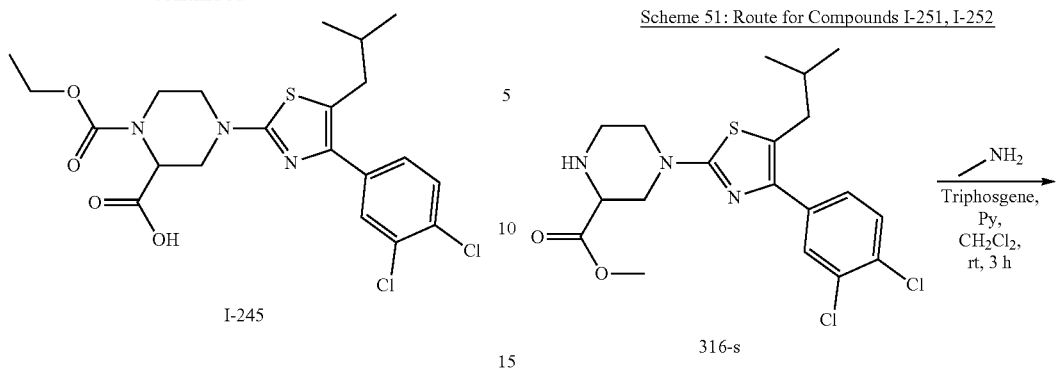
I-245
Scheme 50: Route for Compounds I-246 to I-250
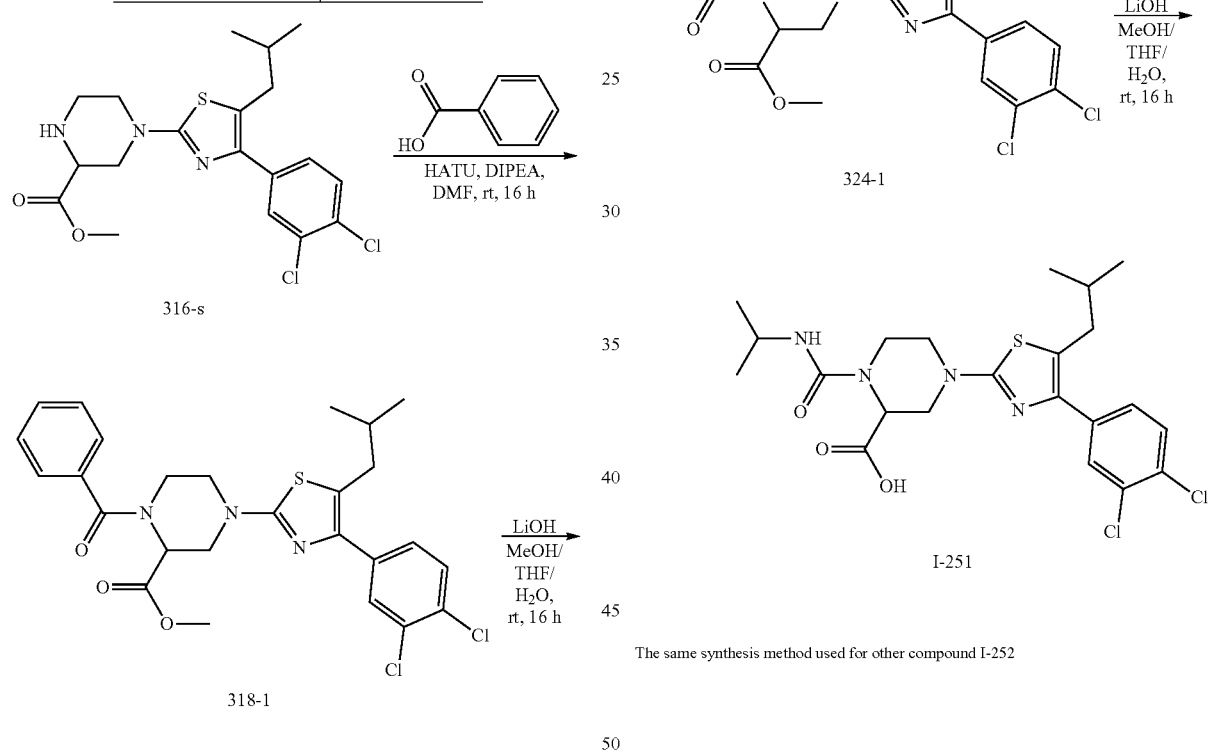
I-246
The same synthesis method used for other compounds I-247 to I-250.
Scheme 51: Route for Compounds I-251, I-252
316-s
324-1
I-251
The same synthesis method used for other compound I-252
Scheme 52: Route for Compound I-253
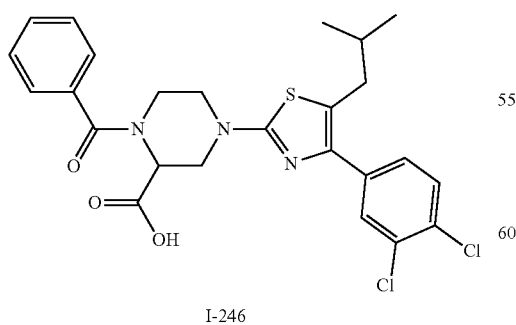
316-s

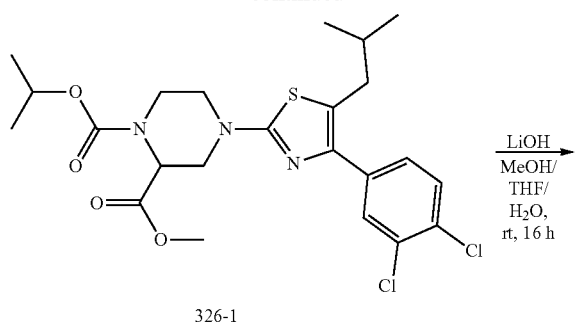
326-1
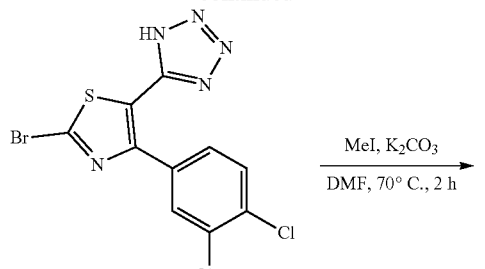
341-4
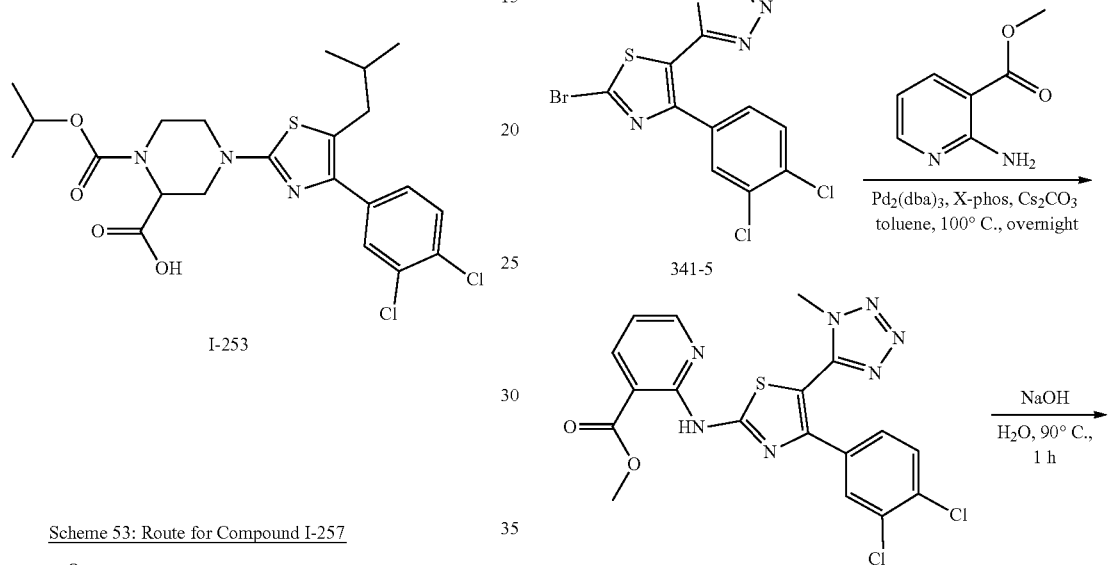
Scheme 53: Route for Compound I-257
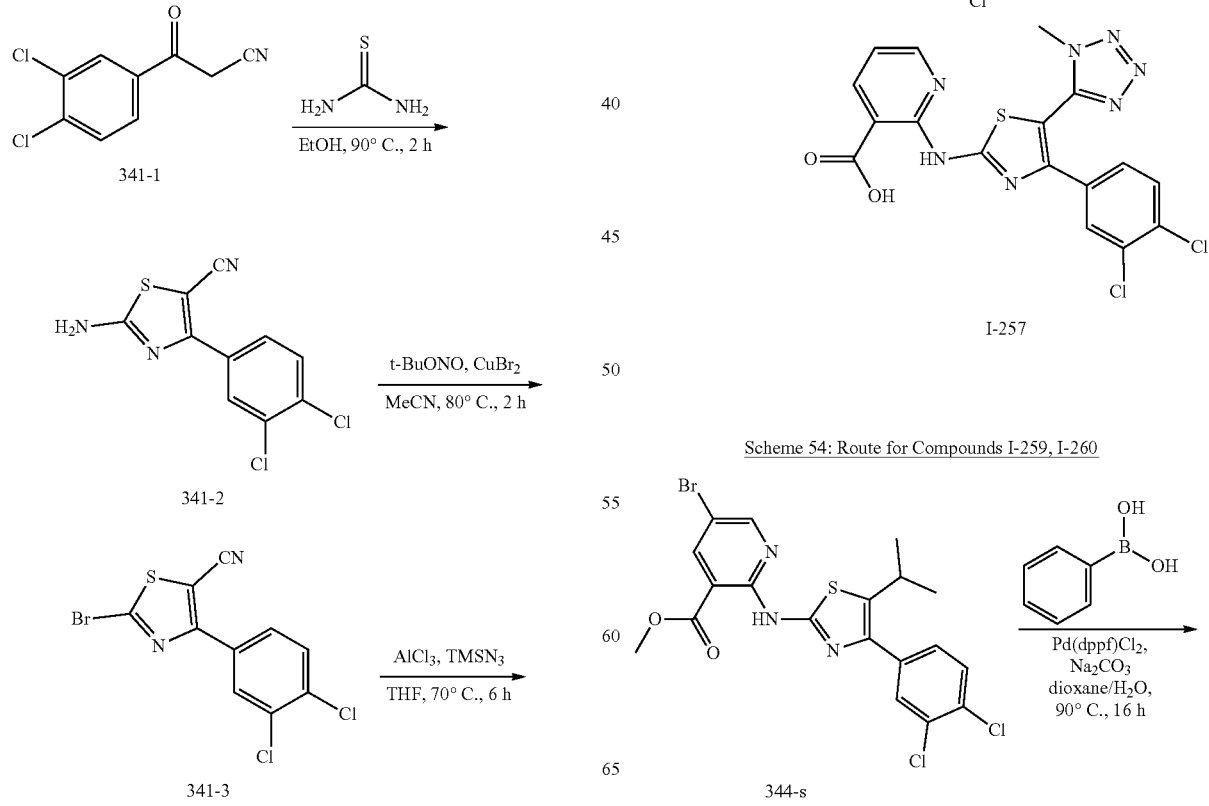

513
-continued
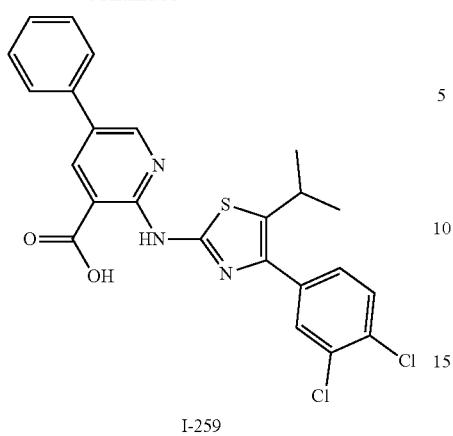
I-259
The same synthesis method used for other compound I-260
514
-continued
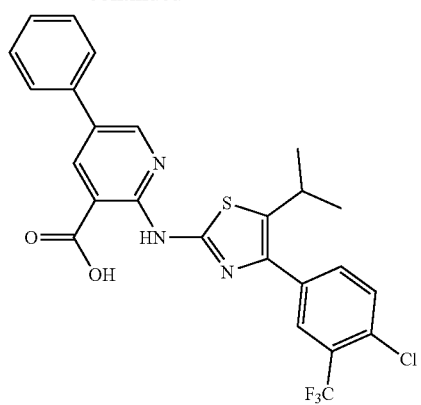
I-262
Scheme 55: Route for Compound I-262
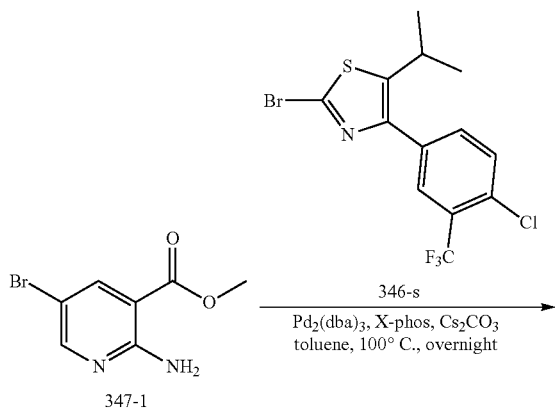
Scheme 56: Rotue for Compounds I-269, I-271, I-272, I-275
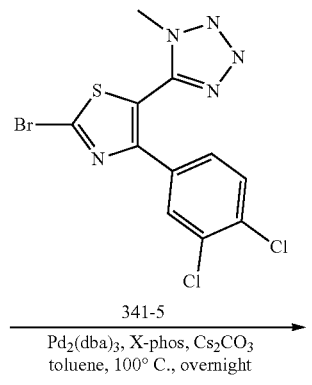
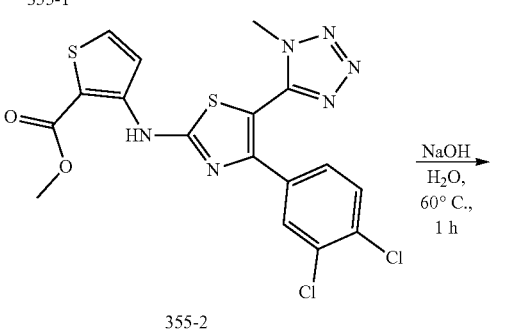
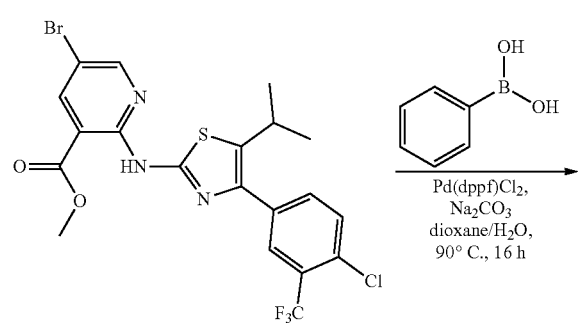
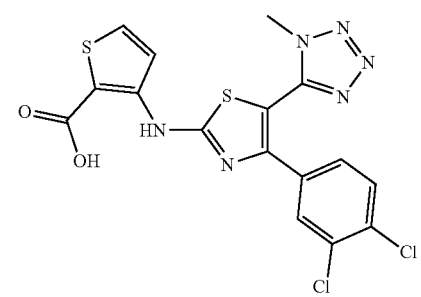
I-269
The same synthesis method used for other compounds I-271, I-272, I-275.

Scheme 57: Route for Compounds I-276, I-277
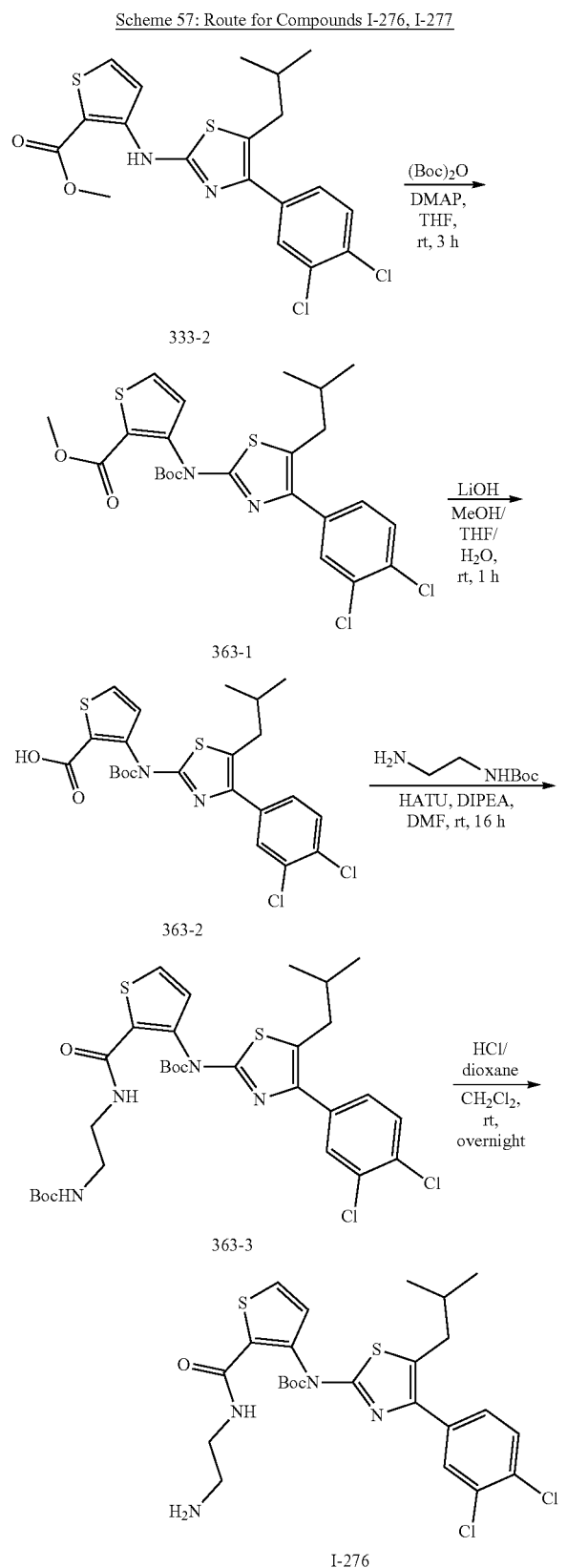
The same synthesis method used for other compound I-277
Scheme 58: Route for Compound I-279
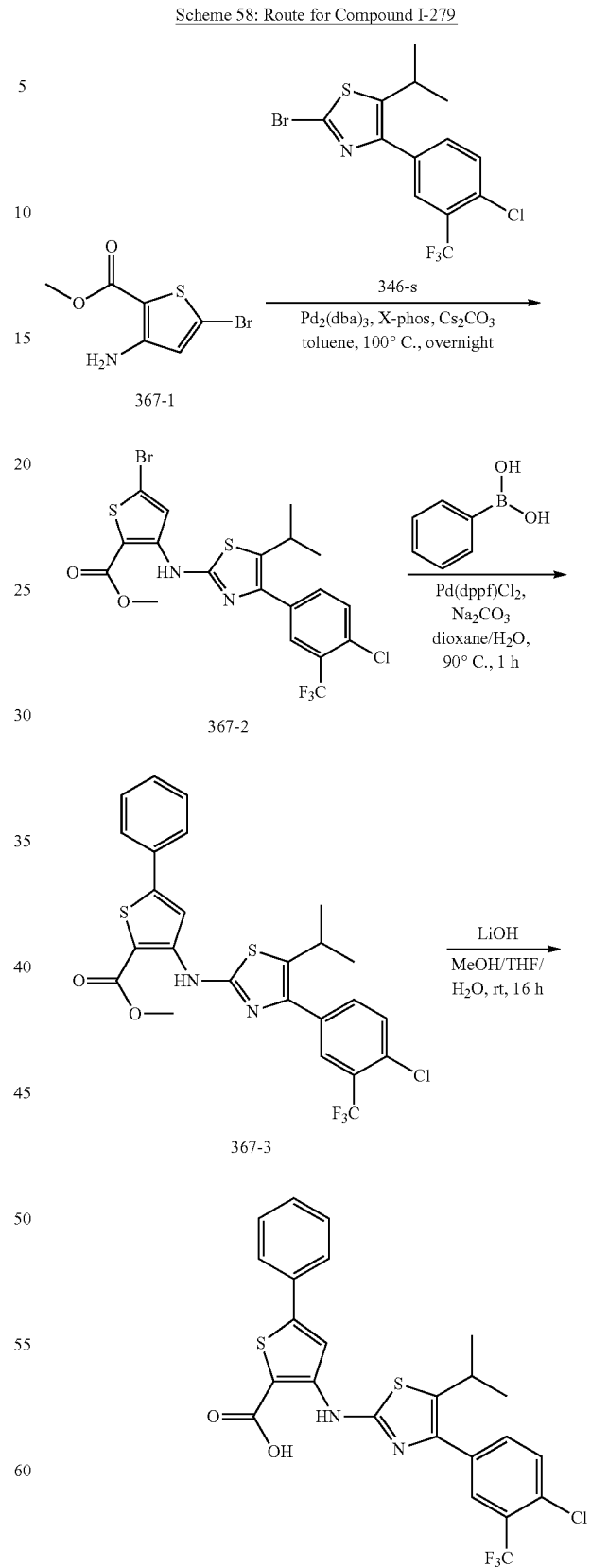

Scheme 59: Route for Compound I-282

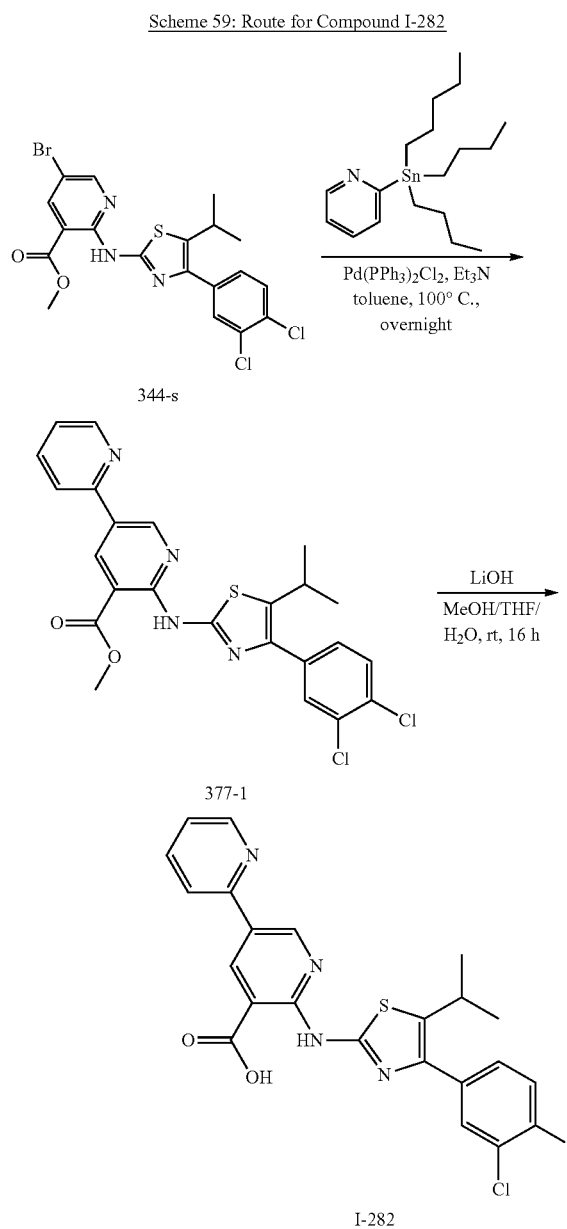

Scheme 60: route for compounds I-284, I-285

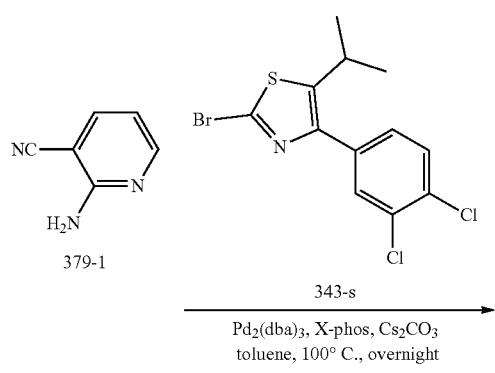

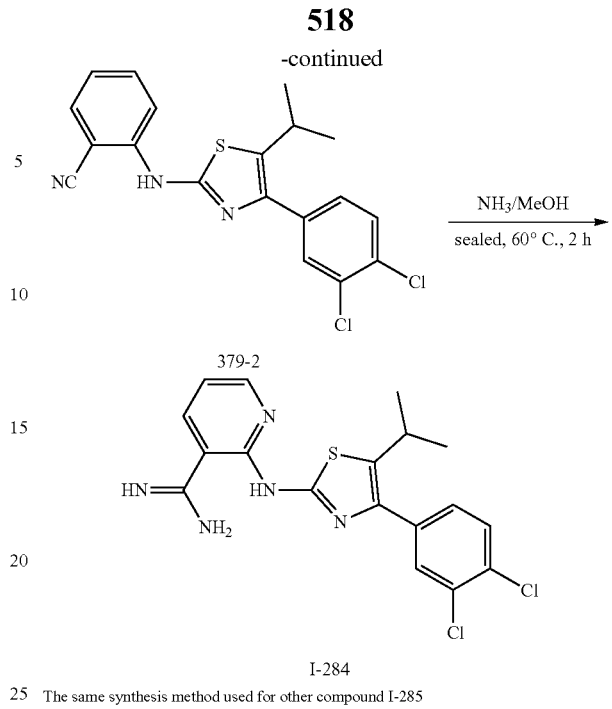

I-284

The same synthesis method used for other compound I-285

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [$CH_3CN$+0.05% TFA] to 0% [water+0.05% TFA] and 100% [$CH_3CN$+0.05% TFA] in 0.8 min, then under this condition for 0.4 min, finally changed to 95% [water+0.05% TFA] and 5% [$CH_3CN$+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, Synthesis of 1-(3,4-dichlorophenyl)-4-methylpentan-1-one (c-1)

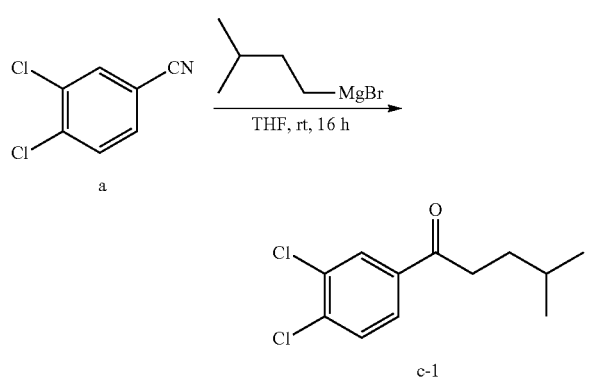

To a solution of a (25.0 g, 145 mmol) in THF (200 mL) was added isobutyl magnesium bromide (1.0 M in THF, 218 mL, 218 mmol). The reaction was stirred at room temperature for 16 h. When the reaction was completed, it was poured into aq.NH$_4$Cl (sat., 500 mL) and extracted with EtOAc (200 mL×3). The organic phase was combined, and washed with H$_2$O (100 mL) and brine (80.0 mL), then dried with anhydrous Na$_2$SO$_4$, concentrated and purified by silica gel column chromatography (petrol ether/ethyl acetate=100/1) to afford c-1 (15.0 g, 42% yield) as yellow oil.

Synthesis of 2-bromo-1-(3,4-dichlorophenyl)-4-methylpentan-1-one (c-2)

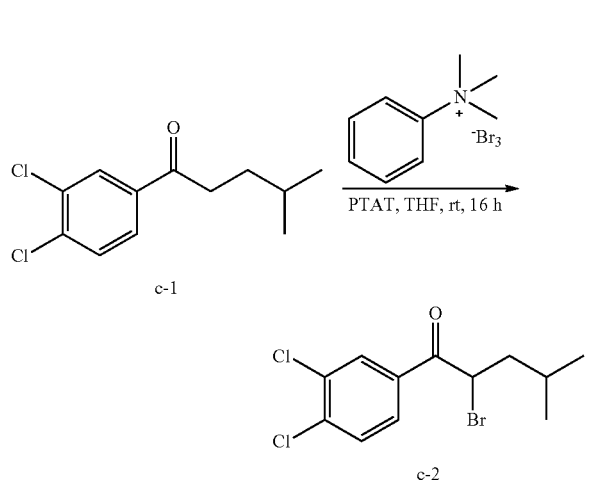

A mixture of c-1 (15.0 g, 61.2 mmol) and PTAT (34.4 g, 91.8 mmol) in THF (300 mL) was stirred at room temperature for 16 h. When the reaction was completed, it was concentrated, and the residual was dissolved in H$_2$O (300 mL), and then extracted with EtOAc (200 mL×3). The organic layer was combined, and washed with H$_2$O (100 mL×2) and Brine (100 mL), then dried by anhydrous Na$_2$SO$_4$. The solution was concentrated to give the crude product, which was used directly in next step without farther purification to afford c-2 (20.0 g, 100% yield) as brown oil.

Synthesis of 1-(3,4-dichlorophenyl)-4-methyl-2-thiocyanatopentan-1-one (c)

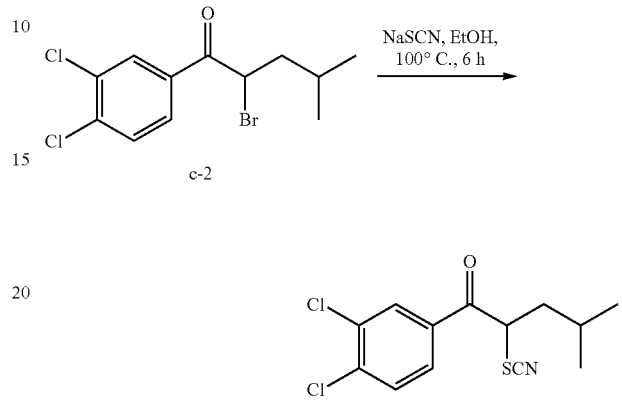

A mixture of c-2 (20.0 g, 61.7 mmol) and NaSCN (10.0 g, 123 mmol) in EtOH (200 mL) was stirred at 100° C. for 6 h. When the reaction was completed, it was concentrated and purified by silica gel column chromatography (petrol ether/ethyl acetate=10/1) to afford c (6.90 g, 37% yield) as a white solid.

Synthesis of 1-(4-chloro-3-(trifluoromethyl)phenyl)-3-methylbutan-1-ol (346-2)

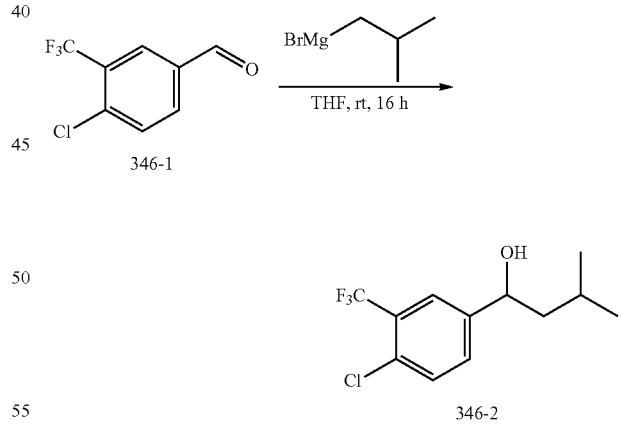

To a solution of 346-1 (14.0 g, 67.1 mmol) in THF (200 mL) was added isobutylmagnesium bromide (1.0 Min THF, 101 mL, 101 mmol). The reaction was stirred at room temperature for 16 h. When the reaction was completed, it was poured into aq.NH$_4$Cl (sat., 500 mL) and extracted with EtOAc (200 mL×3). The organic phase was combined, and washed with H$_2$O (100 mL) and brine (80.0 mL), then dried with anhydrous Na$_2$SO$_4$, concentrated to give the crude product, which was used directly in next step without farther purification to afford 346-2 (15.0 g, 84% yield) as yellow oil.

Synthesis of 1-(4-chloro-3-(trifluoromethyl)phenyl)-3-methylbutan-1-one (346-3)

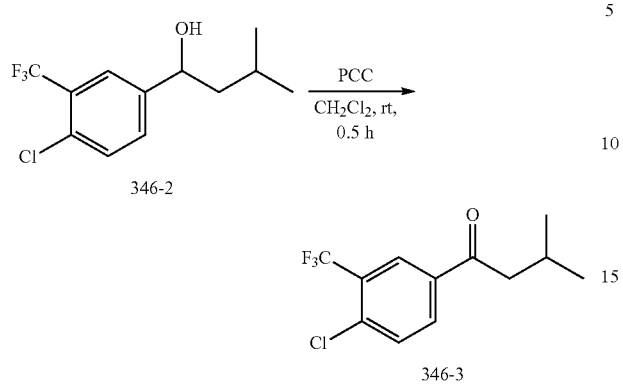

To a solution of 346-2 (15.0 g, 56.2 mmol) in CH$_2$Cl$_2$ (200 mL) was added PCC (18.2 g, 84.4 mmol). The reaction was stirred at room temperature for 0.5 h. When the reaction was completed, it was concentrated, and purified by silica gel column chromatography (petrol ether/ethyl acetate=100/1) to afford 346-3 (4.00 g, 27% yield) as a yellow solid.

Synthesis of 2-bromo-1-(4-chloro-3-(trifluoromethyl)phenyl)-3-methylbutan-1-one (346-4)

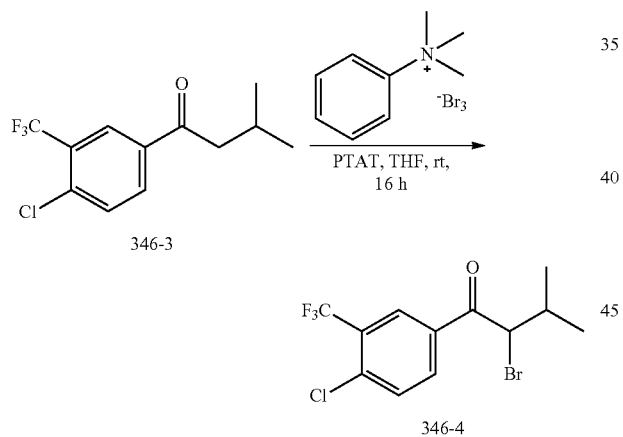

A mixture of 346-3 (4.00 g, 15.1 mmol) and PTAT (8.50 g, 22.7 mmol) in THF (100 mL) was stirred at room temperature for 16 h. When the reaction was completed, it was concentrated, and the residual was dissolved in H$_2$O (200 mL), and then extracted with EtOAc (100 mL×3). The organic layer was combined, and washed with H$_2$O (100 mL×2) and Brine (100 mL), then dried by anhydrous Na$_2$SO$_4$. The solution was concentrated to give the crude product, which was used directly in next step without farther purification to afford 346-4 (5.00 g, 96% yield) as brown oil.

Synthesis of 1-(4-chloro-3-(trifluoromethyl)phenyl)-3-methyl-2-thiocyanatobutan-1-one (346)

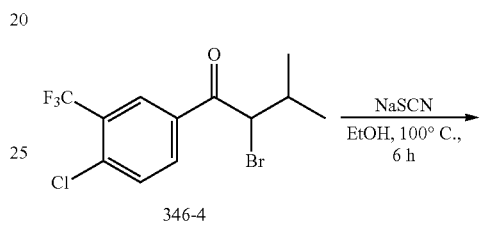

A mixture of 346-4 (5.00 g, 14.6 mmol) and NaSCN (2.36 g, 29.1 mmol) in EtOH (100 mL) was stirred at 100° C. for 6 h. When the reaction was completed, it was concentrated and purified by silica gel column chromatography (petrol ether/ethyl acetate=20/1) to afford 346 (4.60 g, 98% yield) as a yellow solid.

TABLE 4-1

Characterization Data for Compounds

| # | Chemical Structure | LCMS |
|---|---|---|
| c | 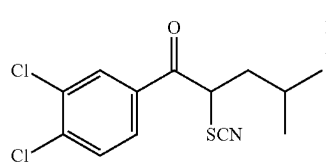 | Method B, Purity is 75.2%, Rt = 2.480 min; MS Calcd.: 301.0; MS Found: 324.1 [M + Na]$^+$. |

TABLE 4-1-continued

Characterization Data for Compounds

| # | Chemical Structure | LCMS |
|---|---|---|
| 115 | ![structure] | No MS Data. |
| 343 | ![structure] | Method A, Purity is 87.1%, Rt = 0.865 min; MS Calcd.: 287.0; MS Found: 288.1 [M + H]$^+$. |
| 346 | ![structure] | Method B, Purity is 31.3%, Rt = 1.699 min; MS Calcd.: 321.0; MS Found: 322.1 [M + H]$^+$. |

Synthesis of 1-tert-butyl 3-methyl 4-(3-(1,3-dioxoisoindolin-2-yl)propanoyl) piperazine-1,3-dicarboxylate (244-2)

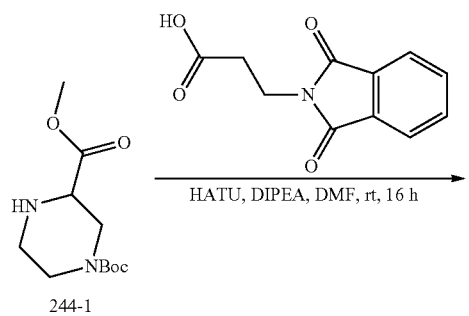

A mixture of 244-1 (178 mg, 0.729 mmol), 3-(1,3-dioxoisoindolin-2-yl)propanoic acid (192 mg, 0.874 mmol), HATU (554 mg, 1.46 mmol) and DIPEA (188 mg, 1.46 mmol) in DMF (10.0 mL) was stirred at room temperature for 16 h. When the reaction was completed, it was poured into H$_2$O (150 mL), and then extracted with EtOAc (100 mL×2). The organic layer was combined, and washed with H$_2$O (100 mL×2) and Brine (50 mL), then dried by anhydrous Na$_2$SO$_4$. The solution was concentrated and purified by silica gel column chromatography (petrol ether/ethyl acetate=1/1) to afford 244-2 (270 mg, 83% yield) as a white solid.

Synthesis of methyl 1-(3-(1,3-dioxoisoindolin-2-yl)propanoyl)piperazine-2-carboxylate (b-244)

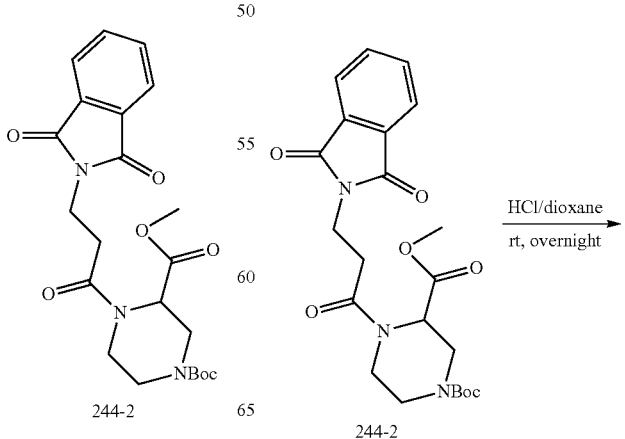

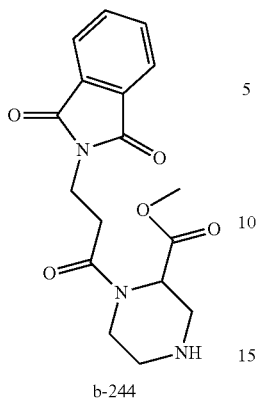

b-244

A mixture of 244-2 (270 mg, 0.606 mmol) in HCl (4.0 M in dioxane, 5.00 mL) was stirred at room temperature overnight. When the reaction was completed, it was filtered and the solid was dried to afford b-244 (160 mg, 76% yield) as a yellow solid.

Synthesis of 3-(aminomethyl)pyridin-2(3H)-one (b-250)

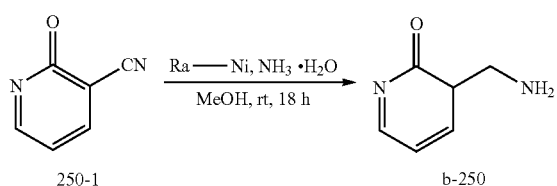

A mixture of 250-1 (1.00 g, 8.33 mmol), $NH_3 \cdot H_2O$ (W/W=28%, 1.04 g) and Raney Ni (1.00 g) in MeOH (200 mL) was stirred under $H_2$ atmosphere at room temperature for 18 h. When the reaction was completed, the mixture was filtered, and the filtrate was concentrated to give a crude product, which was purified by silica gel column chromatography ($CH_2Cl_2$/MeOH=80/1) to afford b-250 (470 mg, 45% yield) as yellow oil.

Synthesis of tert-butyl 2-(3-formylbenzamido)ethylcarbamate (257-2)

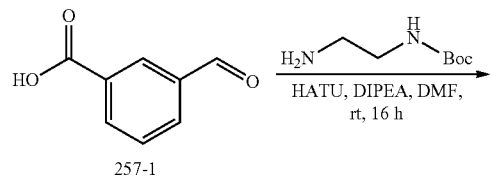

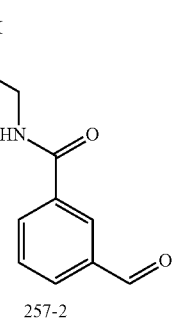

257-2

A mixture of 257-1 (1.00 g, 6.66 mmol), tert-butyl 2-aminoethylcarbamate (1.28 g, 7.99 mmol), HATU (5.06 g, 13.3 mmol) and DIPEA (2.58 g, 20.0 mmol) in DMF (20.0 mL) was stirred at room temperature for 16 h. When the reaction was completed, it was poured into $H_2O$ (250 mL), and then extracted with EtOAc (200 mL×2). The organic layer was combined, and washed with $H_2O$ (150 mL×2) and Brine (100 mL), then dried by anhydrous $Na_2SO_4$. The solution was concentrated and purified by silica gel column chromatography (petrol ether/ethyl acetate=1/1) to afford 257-2 (2.00 g, 100% yield) as brown oil.

Synthesis of ethyl 3-(3-(2-(tert-butoxycarbonylamino)ethylcarbamoyl)benzylamino)propanoate (b-257)

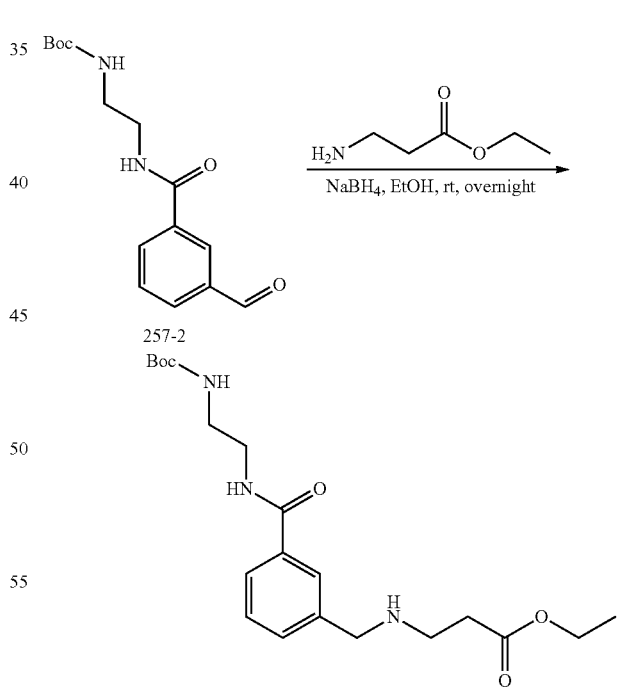

b-257

To a solution of 257-2 (2.00 g, 6.84 mmol) and ethyl 3-aminopropanoate (962 mg, 8.21 mmol) in EtOH (50.0 mL) was added $NaBH_4$ (517 mg, 13.7 mmol) at 0° C. The reaction was stirred at room temperature overnight. When the reaction was completed, it was concentrated and purified by silica gel column chromatography (CH$_2$Cl$_2$/MeOH=100/1) to afford b-257 (2.40 g, 89% yield) as a yellow solid.

Synthesis of methyl 5-amino-2-hydroxybenzoate (b-260)

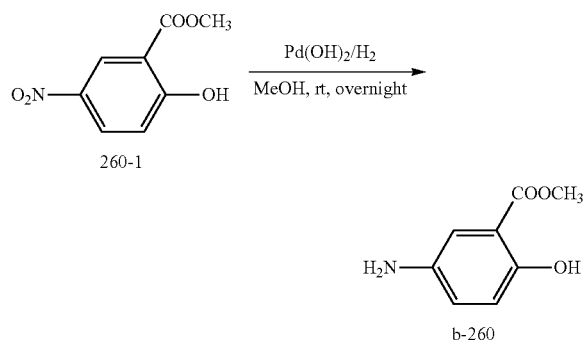

A mixture of 260-1 (300 mg, 1.52 mmol) and Pd(OH)$_2$ (200 mg) in MeOH (50 mL) was stirred under H$_2$ atmosphere at room temperature overnight. When the reaction was completed, the mixture was filtered, and the filtrate was concentrated to give a crude product, which was purified by silica gel column chromatography (CH$_2$Cl$_2$/MeOH=20/1) to afford b-260 (200 mg, 79% yield) as yellow oil.

Synthesis of methyl 2-methoxy-5-nitrobenzoate (263-1)

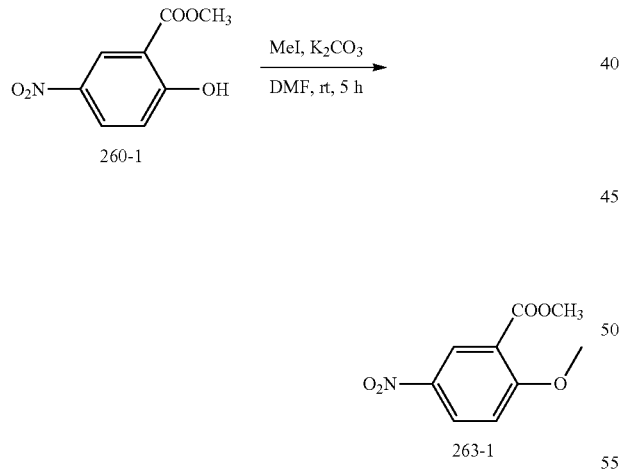

A mixture of 260-1 (500 mg, 2.54 mmol), MeI (432 mg, 3.04 mmol) and K$_2$CO$_3$ (700 mg, 5.07 mmol) in DMF (10 mL) was stirred at room temperature for 5 h. When the reaction was completed, it was poured into H$_2$O (150 mL), and then extracted with EtOAc (100 mL×2). The organic layer was combined, and washed with H$_2$O (80 mL×2) and Brine (50 mL), then dried by anhydrous Na$_2$SO$_4$. The solution was concentrated and purified by silica gel column chromatography (petrol ether/ethyl acetate=5/1) to afford 263-1 (400 mg, 75% yield) as yellow oil.

Synthesis of methyl 5-amino-2-methoxybenzoate (b-263)

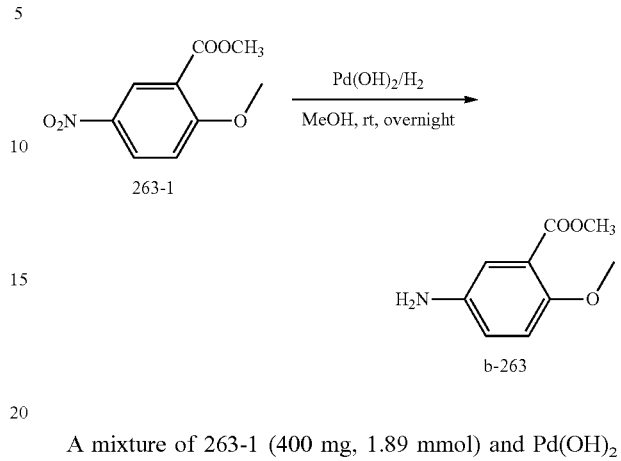

A mixture of 263-1 (400 mg, 1.89 mmol) and Pd(OH)$_2$ (200 mg) in MeOH (50 mL) was stirred under H$_2$ atmosphere at room temperature overnight. When the reaction was completed, the mixture was filtered, and the filtrate was concentrated to give a crude product, which was purified by silica gel column chromatography (CH$_2$Cl$_2$/MeOH=50/1) to afford b-263 (350 mg, 100% yield) as yellow oil.

Synthesis of methyl 5-amino-2-morpholinobenzoate (b-264)

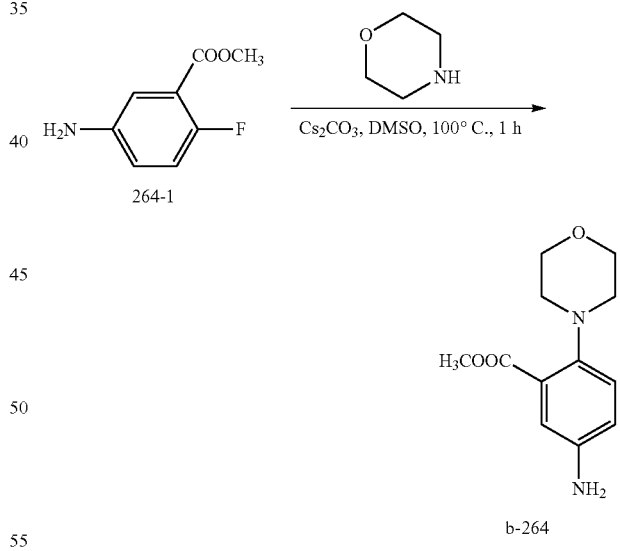

A mixture of 264-1 (250 mg, 1.48 mmol), morpholine (155 mg, 1.77 mmol) and Cs$_2$CO$_3$ (964 mg, 2.96 mmol) in DMSO (10.0 mL) was stirred at 100° C. for 1 h. When the reaction was completed, it was poured into H$_2$O (100 mL), and then extracted with EtOAc (50.0 mL×2). The organic layer was combined, and washed with H$_2$O (50.0 mL×2) and Brine (50.0 mL), then dried by anhydrous Na$_2$SO$_4$. The solution was concentrated and purified by silica gel column chromatography (CH$_2$Cl$_2$/MeOH=50/1) to afford b-264 (150 mg, 43% yield) as yellow oil.

Synthesis of methyl 5-aminobiphenyl-3-carboxylate (b-268)

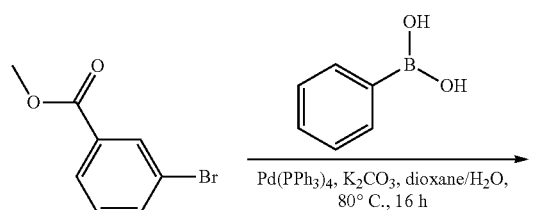

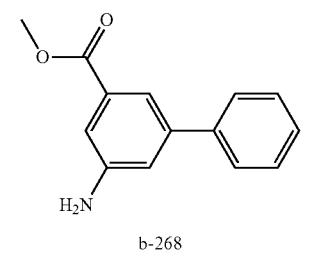

A mixture of 268-1 (150 mg, 0.652 mmol), phenylboronic acid (119 mg, 0.978 mmol), Pd(PPH$_3$)$_4$ (15.1 mg, 0.0131 mmol) and K$_2$CO$_3$ (180 mg, 1.30 mmol) in dioxane/H$_2$O (v/v=5/1, 10.0 mL) was stirred under N$_2$ atmosphere at 80° C. for 16 h. When the reaction was completed, it was concentrated and purified by silica gel column chromatography (CH$_2$Cl$_2$/MeOH=80/1) to afford b-268 (145 mg, 98% yield) as a yellow solid.

Synthesis of methyl 3-amino-5-benzamidobenzoate (b-270)

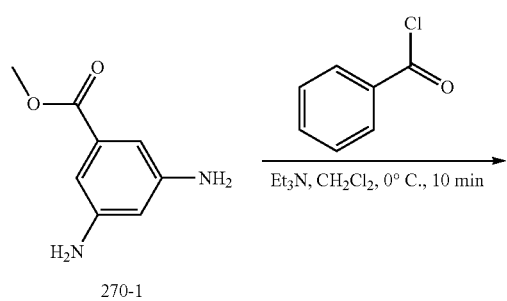

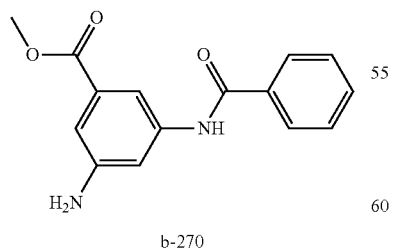

A mixture of 270-1 (500 mg, 3.01 mmol), benzoyl chloride (58 mg, 3.61 mmol) and Et$_3$N (607 mg, 6.01 mmol) in CH$_2$Cl$_2$ (50 mL) was stirred at 0° C. for 10 min. When the reaction was completed, it was concentrated and purified by silica gel column chromatography (CH$_2$Cl$_2$/MeOH=80/1) to afford b-270 (300 mg, 37% yield) as a yellow solid.

Synthesis of methyl 4-bromobiphenyl-2-carboxylate (288-2)

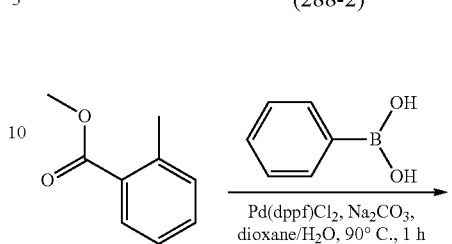

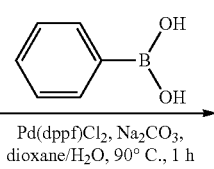

A mixture of 288-1 (1.00 g, 2.93 mmol), phenylboronic acid (536 mg, 4.40 mmol), Pd(dppf)Cl$_2$ (107 mg, 0.147 mmol) and Na$_2$CO$_3$ (622 mg, 5.87 mmol) in dioxane/H$_2$O (v/v=5/1, 20.0 mL) was stirred under N$_2$ atmosphere at 90° C. for 1 h. When the reaction was completed, it was concentrated and purified by silica gel column chromatography (petrol ether/ethyl acetate=100/1) to afford 288-2 (400 mg, 47% yield) as a yellow solid.

Synthesis of 2-(methoxycarbonyl)biphenyl-4-ylboronic acid (b-288)

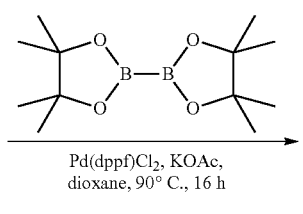

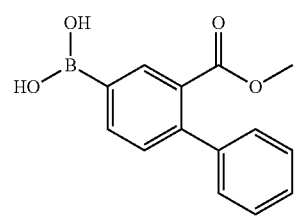

A mixture of 288-2 (200 mg, 0.687 mmol), 4,4,4',4',5,5,5',5'-octamethyl-2,2'-bi(1,3,2-dioxaborolane) (262 mg, 1.03 mmol), Pd(dppf)Cl$_2$ (100 mg, 0.137 mmol) and KOAc (135 mg, 1.37 mmol) in dioxane (10.0 mL) was stirred under N₂ atmosphere at 90° C. for 16 h. When the reaction was completed, it was concentrated and purified by prep-HPLC to afford b-288 (100 mg, 57% yield) as yellow oil.

Synthesis of methyl 5-(4,4,5,5-tetramethyl-1,3,2-dioxaborolan-2-yl)-2-(trifluoromethyl)benzoate (b-290)

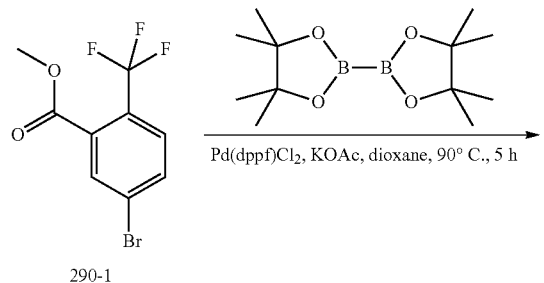

A mixture of 290-1 (100 mg, 0.353 mmol), 4,4,4',4',5,5,5',5'-octamethyl-2,2'-bi(1,3,2-dioxaborolane) (135 mg, 0.530 mmol), Pd(dppf)Cl₂ (12.9 mg, 0.018 mmol) and KOAc (69.3 mg, 0.706 mmol) in dioxane (5.0 mL) was stirred under N₂ atmosphere at 90° C. for 5 h. When the reaction was completed, it was concentrated and purified by silica gel column chromatography (petrol ether/ethyl acetate=50/1) to afford b-290 (100 mg, 86% yield) as yellow oil.

Synthesis of methyl 6-(tributylstannyl)picolinate (b-291)

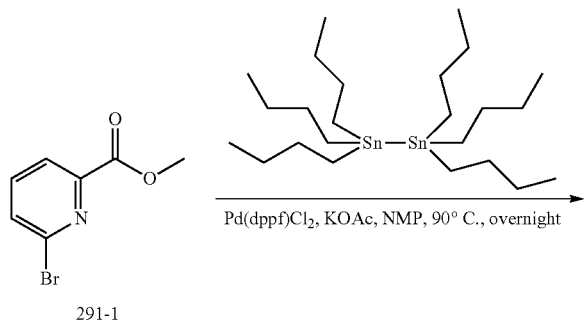

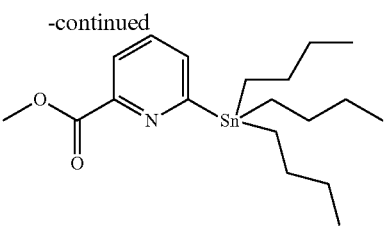

A mixture of 291-1 (1.00 g, 4.63 mmol), 1,1,1,2,2,2-hexabutyldistannane (4.03 g, 6.94 mmol), Pd(dppf)Cl₂ (169 mg, 0.231 mmol) and KOAc (90.9 mg, 0.926 mmol) in NMP (20.0 mL) was stirred under N₂ atmosphere at 90° C. overnight. When the reaction was completed, it was poured into H₂O (250 mL), and then extracted with EtOAc (150 mL×2). The organic layer was combined, and washed with H₂O (100 mL×2) and Brine (100 mL), then dried by anhydrous Na₂SO₄. The solution was concentrated and purified by silica gel column chromatography (petrol ether/ethyl acetate=100/1) to afford b-291 (500 mg, 25% yield) as yellow oil.

Synthesis of ethyl 5-(tributylstannyl)thiophene-2-carboxylate (b-292)

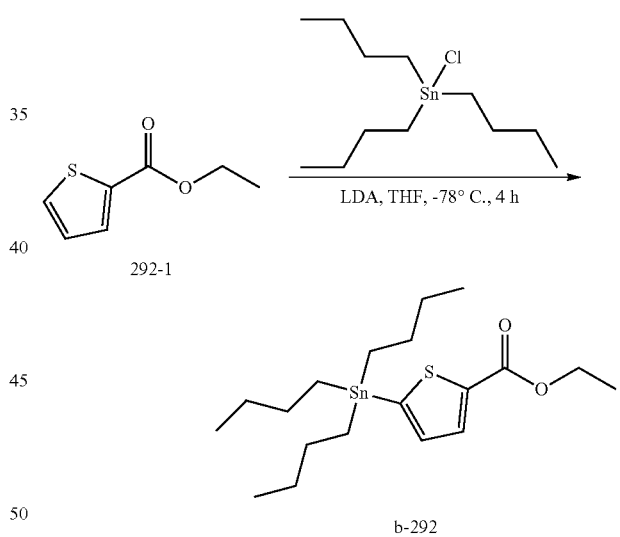

To a solution of 292-1 (1.00 g, 6.40 mmol) in THF (50.0 mL) was added LDA (1.0 M in THF, 9.60 mL, 9.60 mmol) at −78° C. The reaction was stirred at −78° C. for 0.5 h, and then tributylchlorostannane (2.50 g, 7.68 mmol) was added into the reaction. The mixture was stirred at −78° C. for 4 h. When the reaction was completed, it was quenched with aq.NH₄Cl (50.0 mL), and then extracted with EtOAc (100 mL×2). The organic layer was combined, and washed with H₂O (50 mL×2) and Brine (50 mL), then dried by anhydrous Na₂SO₄. The solution was concentrated and purified by silica gel column chromatography (petrol ether) to afford b-292 (1.30 g, 46% yield) as colorless oil.

Synthesis of 2-(benzylamino)acetonitrile (b-294)

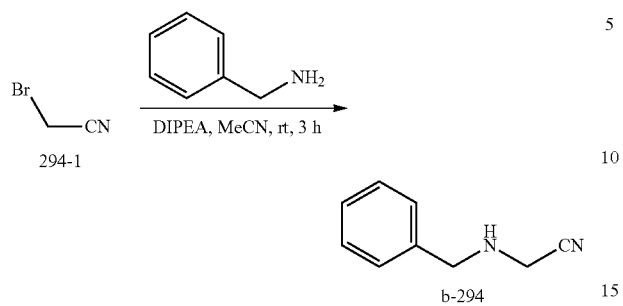

A mixture of 294-1 (1.00 g, 8.34 mmol), phenylmethanamine (983 mg, 9.17 mmol) and DIPEA (2.15 g, 16.7 mmol) in MeCN (100 mL) was stirred at room temperature for 3 h. When the reaction was completed, it was concentrated and purified by silica gel column chromatography (CH$_2$Cl$_2$/MeOH=100/1) to afford b-294 (1.10 g, 90% yield) as brown oil.

Synthesis of tert-butyl 2-(benzylamino)ethylcarbamate (b-295)

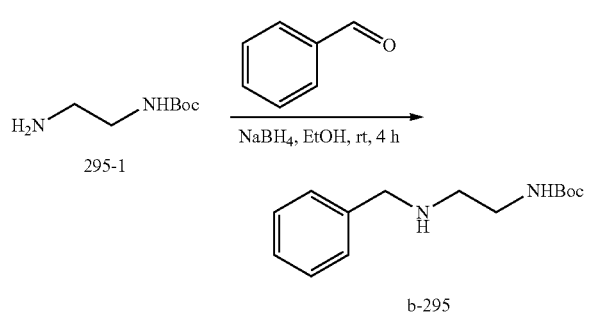

To a solution of 295-1 (500 mg, 3.12 mmol) and benzaldehyde (331 mg, 3.12 mmol) in EtOH (50.0 mL) was added NaBH$_4$ (177 mg, 4.68 mmol) at 0° C. The reaction was stirred at room temperature for 4 h. When the reaction was completed, it was concentrated and purified by silica gel column chromatography (petrol ether/ethyl acetate=1/1) to afford b-295 (550 mg, 70% yield) as colorless oil.

Synthesis of methyl 2-amino-6-(trifluoromethyl)benzoate (b-300)

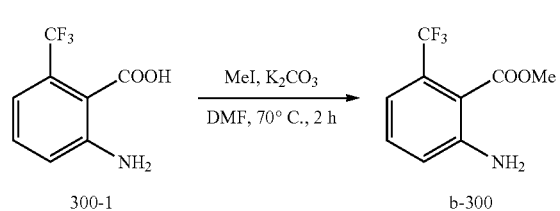 [SMILES: Nc1cccc(C(F)(F)F)c1C(=O)O ; COC(=O)c1c(N)cccc1C(F)(F)F]

A mixture of 300-1 (500 mg, 2.44 mmol), MeI (415 mg, 2.92 mmol) and K$_2$CO$_3$ (673 mg, 4.87 mmol) in DMF (20 mL) was stirred at 70° C. for 2 h. When the reaction was completed, it was poured into H$_2$O (250 mL), and then extracted with EtOAc (150 mL×2). The organic layer was combined, and washed with H$_2$O (100 mL×2) and Brine (100 mL), then dried by anhydrous Na$_2$SO$_4$. The solution was concentrated and purified by silica gel column chromatography (petrol ether/ethyl acetate=5/1) to afford b-300 (450 mg, 84% yield) as a yellow solid.

Synthesis of methyl 2-benzamido-5-bromobenzoate (301-2)

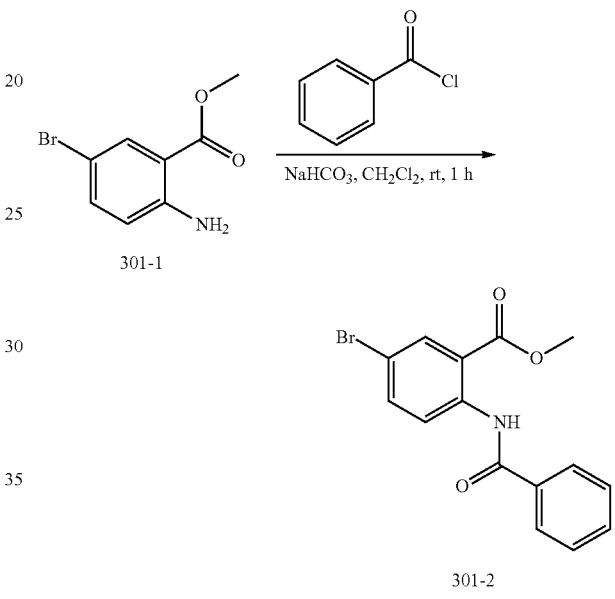

A mixture of 301-1 (1.00 g, 4.35 mmol), benzoyl chloride (733 mg, 5.22 mmol) and NaHCO$_3$ (921 mg, 8.69 mmol) in CH$_2$Cl$_2$ (100 mL) was stirred at room temperature for 1 h. When the reaction was completed, it was concentrated and purified by silica gel column chromatography (petrol ether/ethyl acetate=20/1) to afford 301-2 (1.36 g, 94% yield) as a gray solid.

Synthesis of methyl 2-benzamido-5-(4,4,5,5-tetramethyl-1,3,2-dioxaborolan-2-yl)benzoate (b-301)

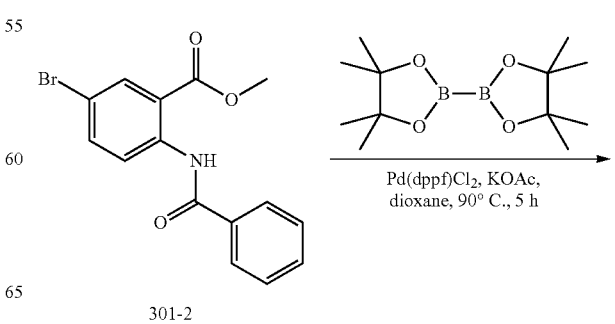

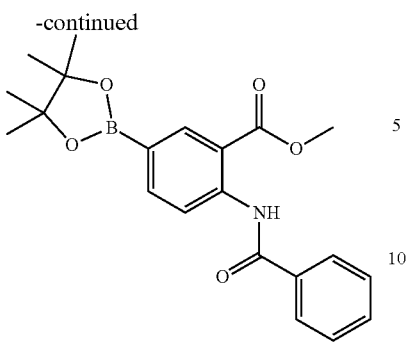

b-301

A mixture of 301-2 (1.16 g, 3.47 mmol), 4,4,4',4',5,5,5',5'-octamethyl-2,2'-bi(1,3,2-dioxaborolane) (1.32 g, 5.21 mmol), Pd(dppf)Cl$_2$ (127 mg, 0.174 mmol) and KOAc (681 mg, 6.94 mmol) in dioxane (20.0 mL) was stirred under N$_2$ atmosphere at 90° C. for 5 h. When the reaction was completed, it was concentrated and purified by silica gel column chromatography (petrol ether/ethyl acetate=20/1) to afford b-301 (1.36 g, 100% yield) as a yellow solid.

Synthesis of methyl 2-bromo-5-carbamothioylbenzoate (b-287)

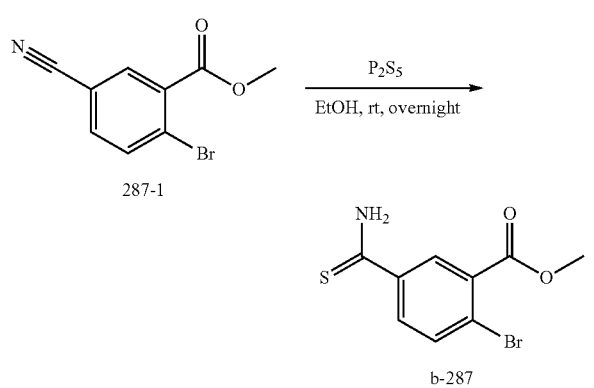

A mixture of 287-1 (200 mg, 0.833 mmol) and P$_2$S$_5$ (222 mg, 1.00 mmol) in EtOH (10.0 mL) was stirred at room temperature overnight. When the reaction was completed, it was concentrated to give a crude product, which was purified by silica gel column chromatography (petrol ether/ethyl acetate=20/1) to afford b-287 (200 mg, 88% yield) as a yellow solid.

Synthesis of methyl 2-cyanoisonicotinate (302-2)

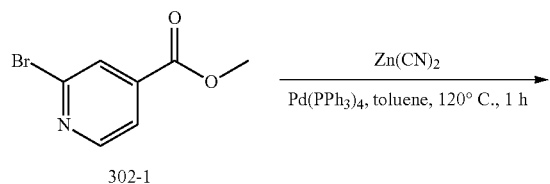

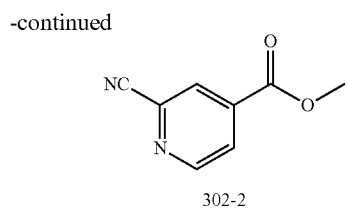

302-2

A mixture of 302-1 (1.70 g, 7.87 mmol), Zn(CN)$_2$ (462 mg, 3.93 mmol) and Pd(PPH$_3$)$_4$ (182 mg, 0.157 mmol) in toluene (100 mL) was stirred under N$_2$ atmosphere at 120° C. for 1 h. When the reaction was completed, it was concentrated and purified by silica gel column chromatography (petrol ether/ethyl acetate=10/1) to afford 302-2 (1.00 g, 78% yield) as a yellow solid.

Synthesis of methyl 2-carbamothioylisonicotinate (b-302)

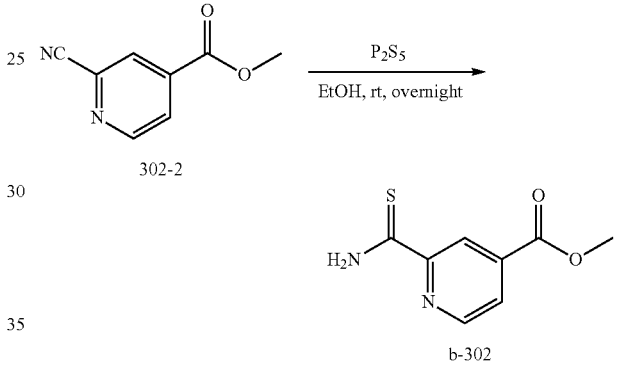

A mixture of 302-2 (1.00 g, 6.17 mmol) and P$_2$S$_5$ (1.64 g, 7.400 mmol) in EtOH (100 mL) was stirred at room temperature overnight. When the reaction was completed, it was concentrated to give a crude product, which was purified by silica gel column chromatography (petrol ether/ethyl acetate=10/1) to afford b-302 (400 mg, 33% yield) as a yellow solid.

Synthesis of tert-butyl 4-chloropyridin-2-ylcarbamate (310-2)

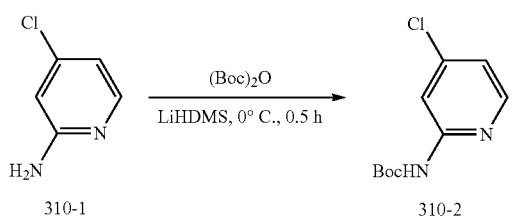

To a solution of 310-1 (5.00 g, 38.9 mmol) in THF (100 mL) was added LiHDMS (1.0 M in hexane, 92.7 mL, 92.7 mmol) at 0° C. The reaction was stirred at 0° C. for 10 min, and then (Boc)$_2$O (10.2 g, 46.7 mmol) was added into the reaction. The mixture was stirred at 0° C. for 0.5 h. When the reaction was completed, it was quenched with aq.NH$_4$Cl (200 mL), and then extracted with EtOAc (200 mL×2). The

Synthesis of ethyl 2-(tert-butoxycarbonylamino)-4-chloronicotinate (310-3)

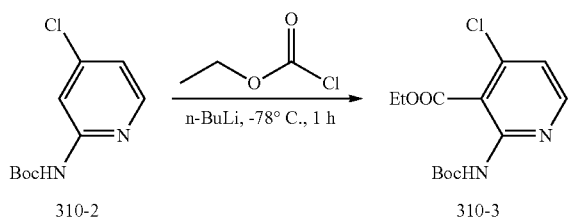

To a solution of 310-2 (3.00 g, 13.1 mmol) in THF (100 mL) was added n-BuLi (2.0 M in THF, 16.4 mL, 32.8 mmol) at −78° C. The reaction was stirred at −78° C. for 30 min, and then ethyl carbonochloridate (2.14 g, 19.7 mmol) was added into the reaction. The mixture was stirred at −78° C. for 1 h. When the reaction was completed, it was quenched with aq.NH$_4$Cl (100 mL), and then extracted with EtOAc (200 mL×2). The organic layer was combined, and washed with H$_2$O (100 mL×2) and Brine (100 mL), then dried by anhydrous Na$_2$SO$_4$. The solution was concentrated and purified by silica gel column chromatography (petrol ether/ethyl acetate=20/1) to afford 310-3 (2.10 g, 53% yield) as an orange solid.

Synthesis of 2-(tert-butoxycarbonylamino)-4-chloronicotinic acid (310-4)

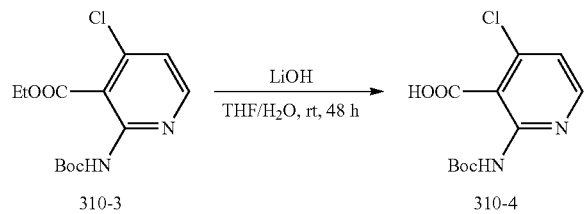 [SMILES: CCOC(=O)c1c(Cl)ccnc1NC(=O)OC(C)(C)C ; "LiOH" ; CC(C)(C)OC(=O)Nc1nccc(Cl)c1C(=O)O]

To a solution of 310-3 (200 mg, 0.665 mmol) in THF/H$_2$O (v/v=4/1, 5.00 mL) was added LiOH (2.0 M in H$_2$O, 0.83 mL). The reaction was stirred at room temperature for 48 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated to give a crude product, which was used directly in next step without farther purification to afford 310-4 (100 mg, 55% yield) as a white solid.

Synthesis of 2-amino-4-chloronicotinic acid (b-310)

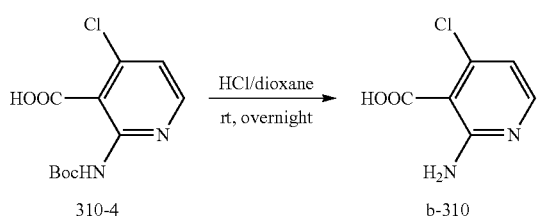 [SMILES: CC(C)(C)OC(=O)Nc1nccc(Cl)c1C(=O)O ; "HCl/dioxane" ; Nc1nccc(Cl)c1C(=O)O]

A mixture of 310-4 (100 mg, 0.366 mmol) in HCl (4.0 M in dioxane, 2.0 mL) was stirred at room temperature overnight. When the reaction was completed, it was concentrated to give a crude product, which was used directly in next step without farther purification to afford b-310 (80.0 mg, 100% yield) as a white solid.

Synthesis of ethyl 2-amino-4-methoxynicotinate (b-313)

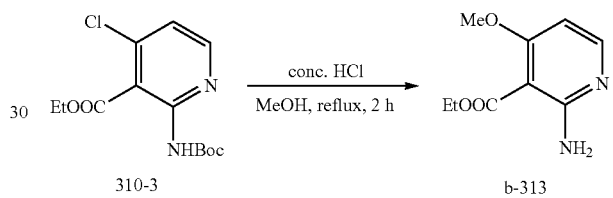

A mixture of 310-3 (200 mg, 0.665 mmol) and conc. HCl (2.0 mL) in MeOH (5.0 mL) was refluxed for 2 h. When the reaction was completed, it was concentrated to give a crude product, which was used directly in next step without farther purification to afford b-313 (160 mg, 100% yield) as a yellow solid.

Synthesis of methyl 3-amino-4-bromobenzoate (332-2)

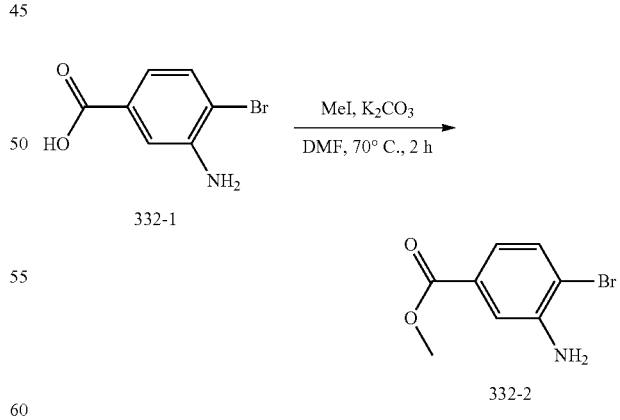

A mixture of 332-1 (1.00 g, 4.63 mmol), MeI (788 mg, 5.55 mmol) and K$_2$CO$_3$ (1.28 g, 9.26 mmol) in DMF (20 mL) was stirred at 70° C. for 2 h. When the reaction was completed, it was poured into H$_2$O (250 mL), and then extracted with EtOAc (150 mL×2). The organic layer was combined, and washed with H$_2$O (100 mL×2) and Brine (100 mL), then dried by anhydrous Na₂SO₄. The solution was concentrated and purified by silica gel column chromatography (petrol ether/ethyl acetate=10/1) to afford 332-2 (800 mg, 75% yield) as a yellow solid.

Synthesis of 2-(benzyl(2-carboxyethyl)amino)-4-(3,4-dichlorophenyl)thiazole-5-carboxylic acid (b-332)

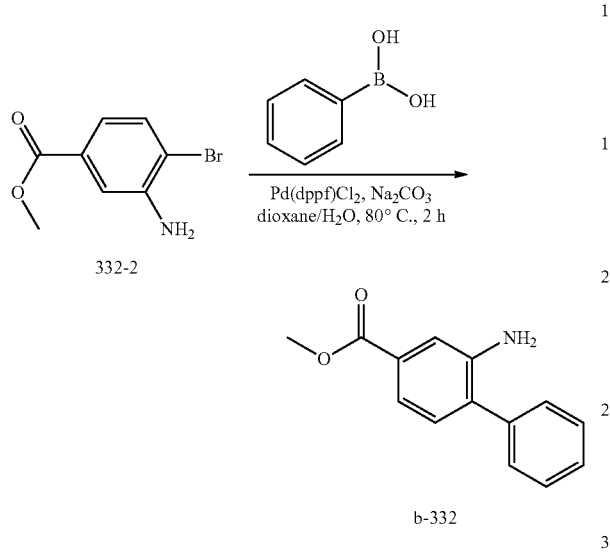

A mixture of 332-2 (800 mg, 3.48 mmol), phenylboronic acid (636 mg, 5.22 mmol), Pd(dppf)Cl₂ (127 mg, 0.174 mmol) and Na₂CO₃ (738 mg, 6.96 mmol) in dioxane/H₂O (v/v=5/1, 20.0 mL) was stirred under N₂ atmosphere at 80° C. for 2 h. When the reaction was completed, it was concentrated and purified by silica gel column chromatography (petrol ether/ethyl acetate=10/1) to afford b-332 (700 mg, 89% yield) as a yellow solid.

Synthesis of methyl 3-amino-5-bromo-4-methylthiophene-2-carboxylate (361-2)

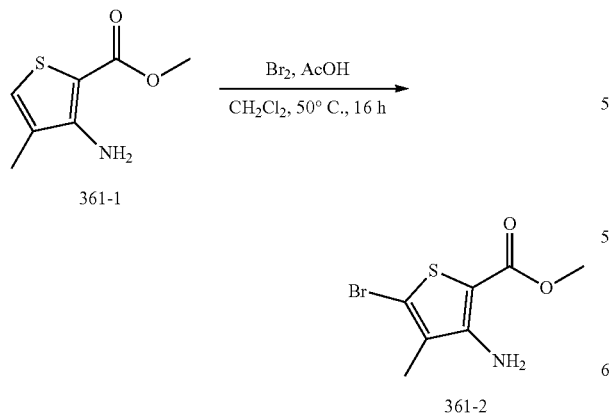

To a solution of 361-1 (2.00 g, 11.7 mmol) and AcOH (20 mL) in CH₂Cl₂ (100 mL) was added Br₂ (1.96 g, 12.3 mmol). The reaction was stirred at 50° C. for 16 h. When the reaction was completed, it was washed with H₂O (100 mL×2) and Brine (100 mL), and then dried by anhydrous Na₂SO₄. The solution was concentrated to give the crude product, which was purified by silica gel column chromatography (petrol ether/ethyl acetate=50/1) to afford 361-2 (600 mg, 21% yield) as yellow oil.

Synthesis of methyl 3-amino-4-methyl-5-phenylthiophene-2-carboxylate (b-361)

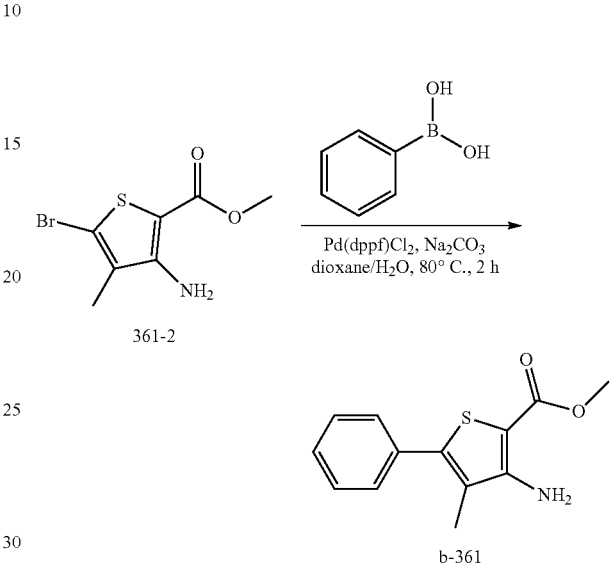

A mixture of 361-2 (600 mg, 2.40 mmol), phenylboronic acid (439 mg, 3.60 mmol), Pd(dppf)Cl₂ (87.7 mg, 0.120 mmol) and Na₂CO₃ (509 mg, 4.80 mmol) in dioxane/H₂O (v/v=5/1, 20.0 mL) was stirred under N₂ atmosphere at 80° C. for 2 h. When the reaction was completed, it was concentrated and purified by silica gel column chromatography (petrol ether/ethyl acetate=50/1) to afford b-361 (200 mg, 34% yield) as a yellow solid.

Synthesis of methyl 3-aminobenzo[b]thiophene-2-carboxylate (b-372)

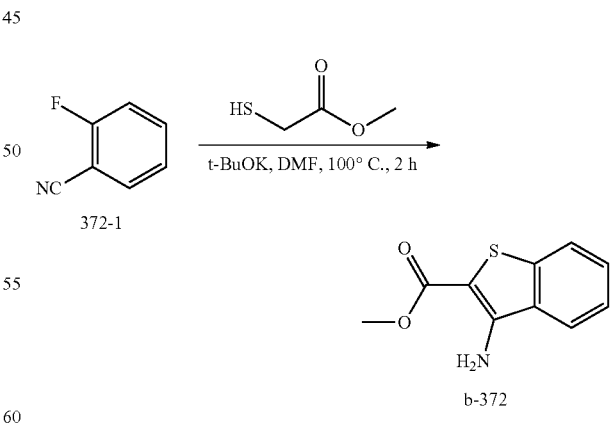

A mixture of 372-1 (1.00 g, 8.26 mmol), methyl 2-mercaptoacetate (1.05 g, 9.91 mmol) and t-BuOK (1.85 g, 16.5 mmol) in DMF (10.0 mL) was stirred at 100° C. for 2 h. When the reaction was completed, it was poured into H₂O (100 mL), and then extracted with EtOAc (50.0 mL×2). The organic layer was combined, and washed with H₂O (50.0 mL×2) and Brine (50.0 mL), then dried by anhydrous Na₂SO₄. The solution was concentrated and purified by silica gel column chromatography (CH₂Cl₂/MeOH=150/1) to afford b-372 (1.20 g, 70% yield) as a yellow solid.

Synthesis of methyl 2-amino-5-cyclopropylnicotinate (b-378)

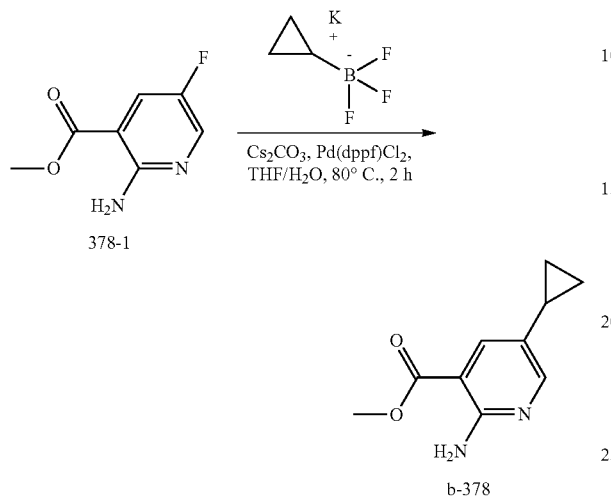

A mixture of 378-1 (1.00 g, 4.33 mmol), potassium cyclopropyltrifluoroborate (961 mg, 6.49 mmol), Pd(dppf)Cl₂ (158 mg, 0.216 mmol) and Cs₂CO₃ (2.82 g, 8.66 mmol) in THF/H₂O (v/v=5/1, 50.0 mL) was stirred under N₂ atmosphere at 80° C. for 2 h. When the reaction was completed, it was concentrated and purified by silica gel column chromatography (petrol ether/ethyl acetate=10/1) to afford b-378 (190 mg, 23% yield) as a yellow solid.

Synthesis of 2-bromo-4-(3,4-dichlorophenyl)-5-isobutylthiazole (253-s)

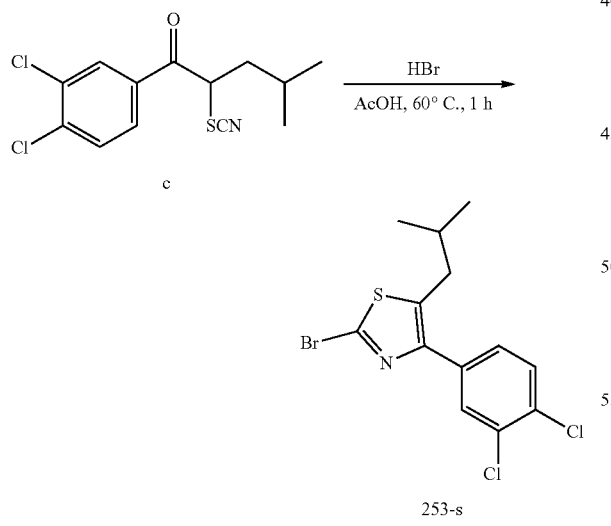

A mixture of c (3.10 g, 10.3 mmol) in HBr (2.0 M in AcOH, 20.0 mL) was stirred at 60° C. for 1 h. When the reaction was completed, it was concentrated and purified by silica gel column chromatography (petrol ether/ethyl acetate=10/1) to afford 253-s (3.30 g, 88% yield) as a yellow solid.

Synthesis of 1-tert-butyl 2-methyl 4-(4-(3,4-dichlorophenyl)-5-isobutylthiazol-2-yl)piperazine-1,2-dicarboxylate (316-2)

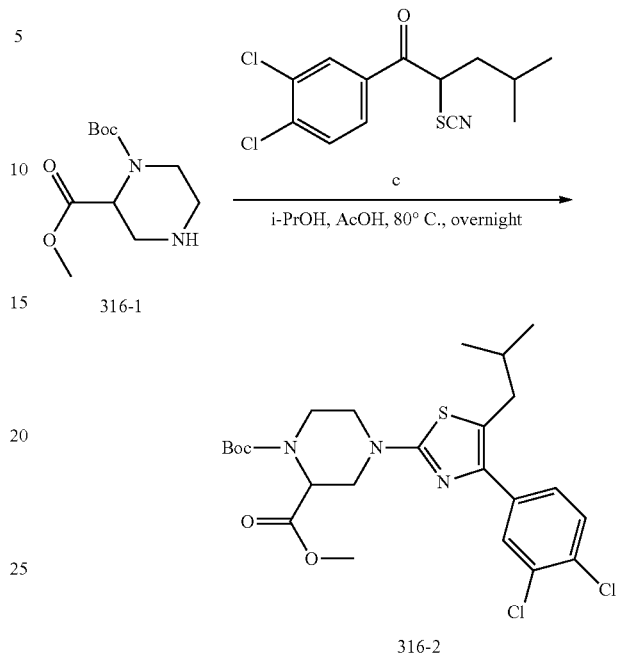

A mixture of 316-1 (1.00 g, 4.09 mmol), AcOH (491 mg, 8.19 mmol) and c (1.24 g, 4.09 mmol) in i-PrOH (10.0 mL) was stirred at 80° C. overnight. When the reaction was completed, the mixture was purified by silica gel column chromatography (petrol ether/ethyl acetate=10/1) to afford 316-2 (2.00 g, 92% yield) as a yellow solid.

Synthesis of methyl 4-(4-(3,4-dichlorophenyl)-5-isobutylthiazol-2-yl)piperazine-2-carboxylate (316-s)

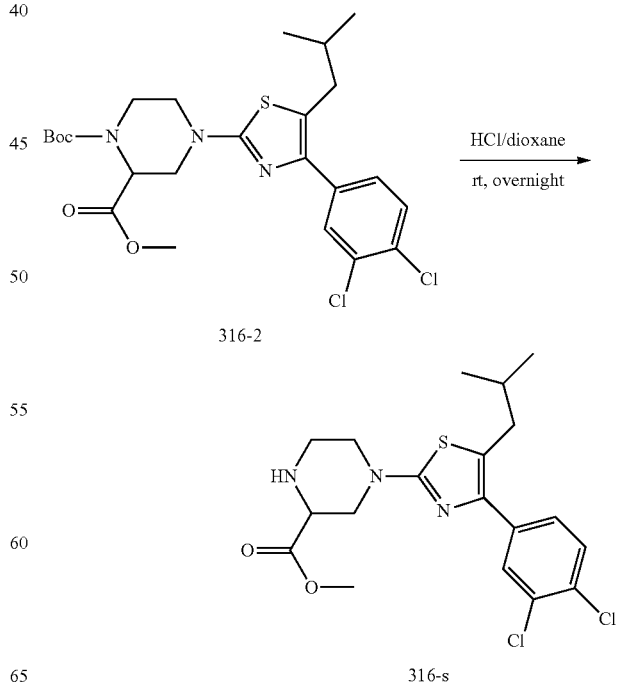

543

A mixture of 316-2 (2.00 g, 0.401 mmol) in HCl (4.0 M in dioxane, 30.0 mL) was stirred at room temperature overnight. When the reaction was completed, it was filtered and the solid was dried to afford 316-s (1.20 g, 74% yield) as a white solid.

Synthesis of methyl 5-bromo-2-(4-(3,4-dichlorophenyl)-5-isopropylthiazol-2-ylamino)nicotinate (344-s)

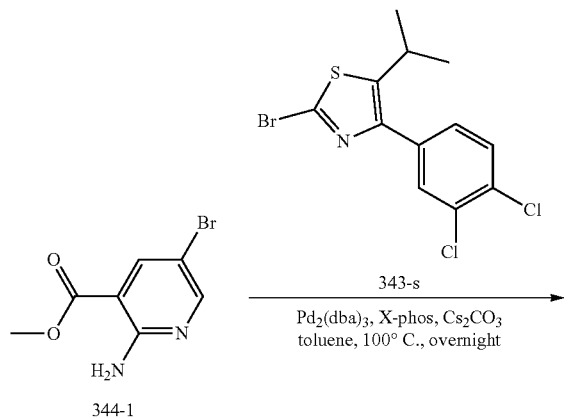

544

-continued

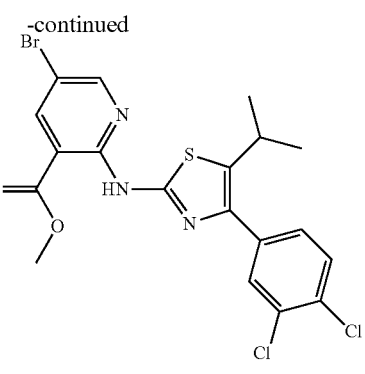

344-s

A mixture of 344-1 (500 mg, 2.16 mmol), 343-s (760 mg, 2.16 mmol), Pd$_2$(dba)$_3$ (40.3 mg, 0.0432 mmol), X-phos (31.3 mg, 0.0541 mmol) and Cs$_2$CO$_3$ (1.41 g, 4.33 mmol) in toluene (20.0 mL) was stirred under N$_2$ atmosphere at 100° C. overnight. When the reaction was completed, it was concentrated and purified by silica gel column chromatography (petrol ether/ethyl acetate=50/1) to afford 344-s (420 mg, 3900 yield) as a yellow solid.

Scheme 2: Characterization Data for Compounds

| # | Chemical Structure | LCMS |
|---|---|---|
| b-244 | 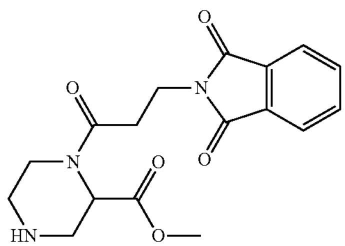 [SMILES: COC(=O)C1CNCCN1C(=O)CCN1C(=O)c2ccccc2C1=O] | Method C, Purity is 84.1%, Rt = 1.474 min; MS Calcd.: 345.1; MS Found: 346.3 [M + H]$^+$. |
| b-250 | 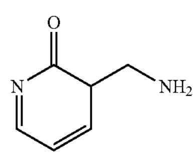 | Method C, Purity is 85.9%, Rt = 0.387 min; MS Calcd.: 124.1; MS Found: 125.3 [M + H]$^+$. |
| b-257 | 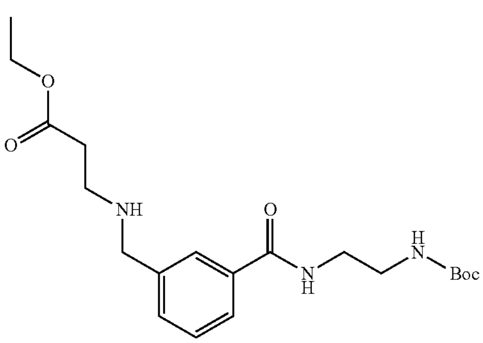 [SMILES: CCOC(=O)CCNCc1cccc(C(=O)NCCNC(=O)OC(C)(C)C)c1] | Method C, Purity is 73.9%, Rt = 1.843 min; MS Calcd.: 393.2; MS Found: 394.3 [M + H]$^+$. |
| b-260 | 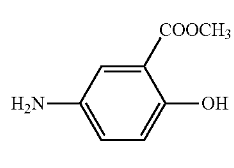 [SMILES: COC(=O)c1cc(N)ccc1O] | Method A, Purity is 98.5%, Rt = 0.340 min; MS Calcd.: 167.1; MS Found: 168.4 [M + H]$^+$. |

-continued

Scheme 2: Characterization Data for Compounds

| # | Chemical Structure | LCMS |
|---|---|---|
| b-263 | 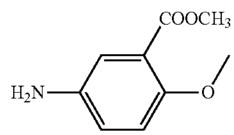 | Method A, Purity is 98.5%, Rt = 0.303 min; MS Calcd.: 181.1; MS Found: 182.4 [M + H]+. |
| b-264 | 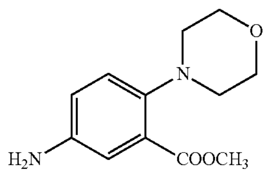 | Method A, Purity is 81.3%, Rt = 0.430 min; MS Calcd.: 236.1; MS Found: 237.4 [M + H]+. |
| b-268 | 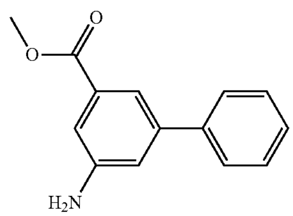 [SMILES: COC(=O)c1cc(N)cc(-c2ccccc2)c1] | Method A, Purity is 99.3%, Rt = 0.641 min; MS Calcd.: 227.1; MS Found: 228.4 [M + H]+. |
| b-269 | 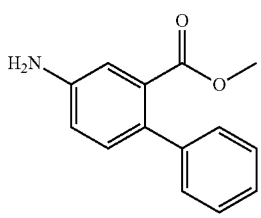 [SMILES: COC(=O)c1cc(N)ccc1-c1ccccc1] | Method C, Purity is 98.0%, Rt = 1.752 min; MS Calcd.: 227.1; MS Found: 228.3 [M + H]+. |
| b-270 | 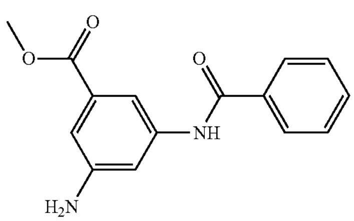 [SMILES: COC(=O)c1cc(N)cc(NC(=O)c2ccccc2)c1] | Method A, Purity is 51.5%, Rt = 0.525 min; MS Calcd.: 270.1; MS Found: 271.2 [M + H]+. |
| b-287 | 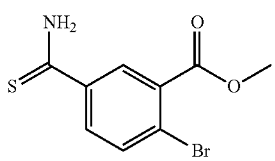 | Method B, Purity is 98.5%, Rt = 1.612 min; MS Calcd.: 273.0; MS Found: 274.0 [M + H]+. |
| b-288 | 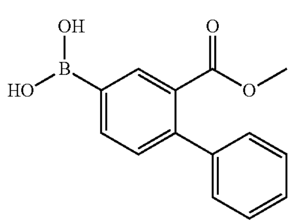 [SMILES: COC(=O)c1cc(B(O)O)ccc1-c1ccccc1] | Method B, Purity is 79.3%, Rt = 1.646 min; MS Calcd.: 256.1; MS Found: 257.2 [M + H]+. |

Scheme 2: Characterization Data for Compounds

| # | Chemical Structure | LCMS |
|---|---|---|
| b-289 | 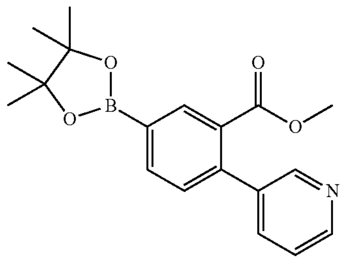 [SMILES: COC(=O)c1cc(B2OC(C)(C)C(C)(C)O2)ccc1-c1cccnc1] | Method B, Purity is 35.8%, Rt = 1.618 min; MS Calcd.: 339.2; MS Found: 340.3 [M + H]+. |
| b-290 | 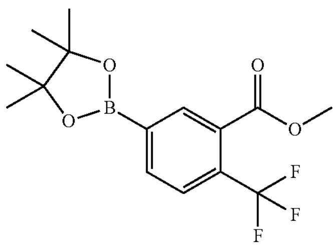 | Method C, Purity is 69.4%, Rt = 2.407 min; MS Calcd.: 330.1; No MS Found. |
| b-291 | 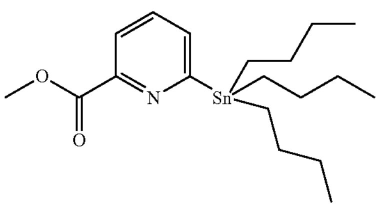 [SMILES: CCC[CH2][Sn]([CH2]CCC)([CH2]CCC)[c]1cccc(C(=O)OC)n1] | Method B, Purity is 90.8%, Rt = 2.128 min; MS Calcd.: 427.2; MS Found: 428.2 [M + H]+. |
| b-292 | 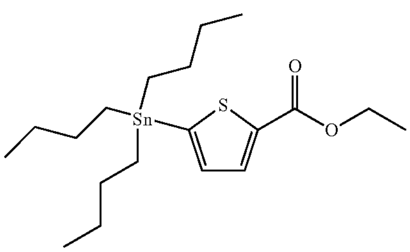 [SMILES: CCC[CH2][Sn]([CH2]CCC)([CH2]CCC)[c]1ccc(C(=O)OCC)s1] | $^1$H NMR (400 MHz, CDCl$_3$) δ: 0.86-0.91 (9H, m), 1.10-1.15 (5H, m), 1.30-1.39 (10H, m), 1.51-1.59 (6H, m), 4.34 (2H, q, J = 7.6 Hz), 7.14 (1H, d, J = 3.2 Hz), 7.87 (1H, d, J = 3.2 Hz). |
| b-294 | 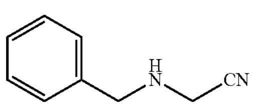 [SMILES: N#CCNCc1ccccc1] | Method B, Purity is 54.6%, Rt = 0.985 min; MS Calcd.: 146.1; MS Found: 147.3 [M + H]+. |
| b-295 | 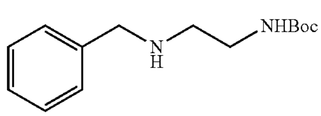 [SMILES: CC(C)(C)OC(=O)NCCNCc1ccccc1] | Method B Purity is 48.1%, Rt = 1.512 min; MS Calcd.: 250.2; MS Found: 251.3 [M + H]+. |
| b-299 | 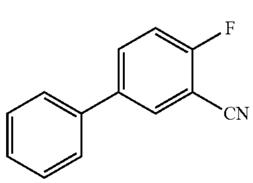 [SMILES: N#Cc1cc(-c2ccccc2)ccc1F] | Method C, Purity is 97.8%, Rt = 2.245 min; MS Calcd.: 222.1; No MS Found. |

-continued

Scheme 2: Characterization Data for Compounds

| # | Chemical Structure | LCMS |
|---|---|---|
| b-300 | (2-amino-6-(trifluoromethyl)phenyl methyl ester with CF$_3$, COOMe, NH$_2$ substituents) | Method B, Purity is 90.1%, Rt = 1.768 min; MS Calcd.: 219.1; MS Found: 220.1 [M + H]$^+$. |
| b-301 | (methyl 2-benzamido-5-(4,4,5,5-tetramethyl-1,3,2-dioxaborolan-2-yl)benzoate) | Method C, Purity is 80.6%, Rt = 2.302 min; MS Calcd.: 381.2; MS Found: 382.2 [M + H]$^+$. |
| b-302 | (methyl 2-carbamothioylisonicotinate) | Method B, Purity is 88.7%, Rt = 1.488 min; MS Calcd.: 196.0; MS Found: 197.1 [M + H]$^+$. |
| b-306 | (methyl 2-carbamothioyl-5-fluoroisonicotinate) | Method B, Purity is 72.2%, Rt = 1.523 min; MS Calcd.: 214.0; MS Found: 215.1 [M + H]$^+$. |
| b-309 | (ethyl 3-amino-5-phenylisonicotinate) | Method B, Purity is 92.1%, Rt = 1.459 min; MS Calcd.: 242.1; MS Found: 243.3 [M + H]$^+$. |
| b-310 | (2-amino-4-chloronicotinic acid) | No MS data. |
| b-313 | (ethyl 2-amino-4-methoxynicotinate) | No MS data. |

-continued

Scheme 2: Characterization Data for Compounds

| # | Chemical Structure | LCMS |
|---|---|---|
| b-332 | 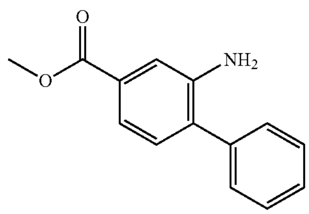 [SMILES: COC(=O)c1ccc(-c2ccccc2)c(N)c1] | Method A, Purity is 99.5%, Rt = 0.707 min; MS Calcd.: 227.1; MS Found: 228.4 [M + H]⁺. |
| b-348 | 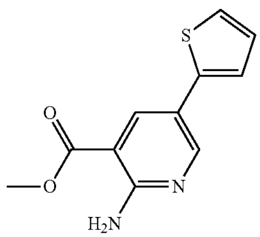 [SMILES: COC(=O)c1cc(-c2cccs2)cnc1N] | Method C, Purity is 81.1%, Rt = 2.308 min; MS Calcd.: 234.1; MS Found: 235.0 [M + H]⁺. |
| b-349 | 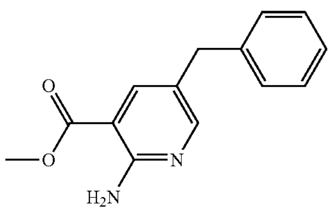 [SMILES: COC(=O)c1cc(Cc2ccccc2)cnc1N] | Method B, Purity is 69.9%, Rt = 1.475 min; MS Calcd.: 242.1; MS Found: 243.3 [M + H]⁺. |
| b-357 | 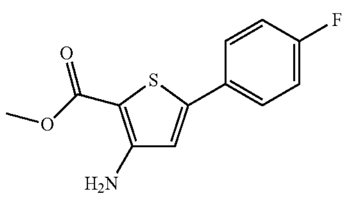 | Method C, Purity is 51.7%, Rt = 1.151 min; MS Calcd.: 272.1; MS Found: 273.1 [M + H]⁺. |
| b-358 | 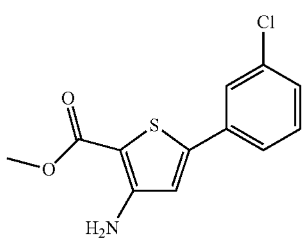 | Method A, Purity is 95.6%, Rt = 0.510 min; MS Calcd.: 239.1; MS Found: 240.0 [M + H]⁺. |
| b-361 | 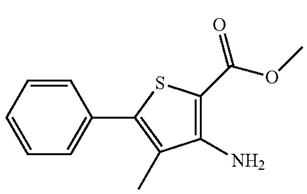 [SMILES: COC(=O)c1sc(-c2ccccc2)c(C)c1N] | Method B, Purity is 75.1%, Rt = 2.559 min; MS Calcd.: 247.1; MS Found: 248.2 [M + H]⁺. |
| b-372 | 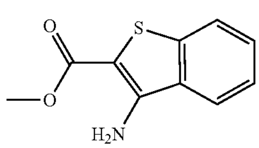 | Method A, Purity is 100%, Rt = 0.696 min; MS Calcd.: 207.0; MS Found: 208.3 [M + H]⁺. |

Scheme 2: Characterization Data for Compounds
| # | Chemical Structure | LCMS |
|---|---|---|
| b-378 | 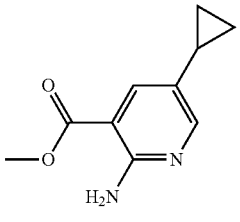 | Method A, Purity is 82.4%, Rt = 0.426 min; MS Calcd.: 192.1; MS Found: 193.4 [M + H]$^+$. |
| b-380 | 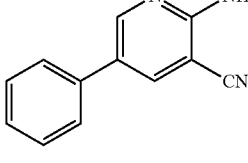 | Method A, Purity is 85.8%, Rt = 0.595 min; MS Calcd.: 195.1; MS Found: 196.3 [M + H]$^+$. |
| 253-s | 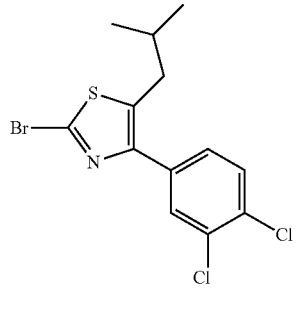 [SMILES: CC(C)Cc1sc(Br)nc1-c1ccc(Cl)c(Cl)c1] | Method B, Purity is 96.3%, Rt = 2.508 min; MS Calcd.: 363.0; MS Found: 364.0 [M + H]$^+$. |
| 316-s | 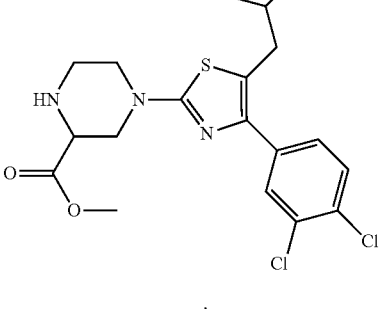 | Method B, Purity is 93.4%, Rt = 1.951 min; MS Calcd.: 427.1; MS Found: 428.1 [M + H]$^+$. |
| 343-s | 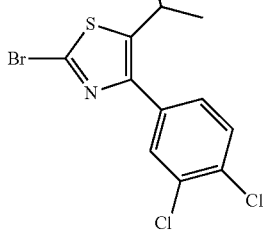 | Method A, Purity is 91.2%, Rt = 1.055 min; MS Calcd.: 349.0; MS Found: 350.0 [M + H]$^+$. |

Scheme 2: Characterization Data for Compounds

| # | Chemical Structure | LCMS |
|---|---|---|
| 344-s | 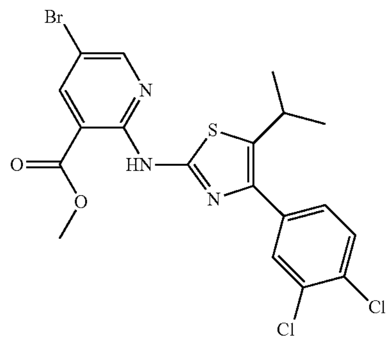 [SMILES: COC(=O)c1cc(Br)cnc1Nc1nc(-c2ccc(Cl)c(Cl)c2)c(C(C)C)s1] | Method B, Purity is 83.8%, Rt = 2.577 min; MS Calcd.: 499.0; MS Found: 500.0 [M + H]⁺. |
| 346-s | 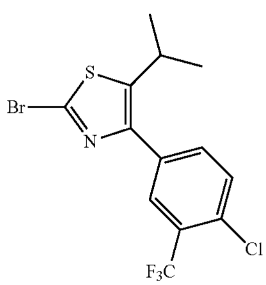 [SMILES: CC(C)c1sc(Br)nc1-c1ccc(Cl)c(C(F)(F)F)c1] | Method B, Purity is 94.3%, Rt = 2.406 min; MS Calcd.: 383.0; MS Found: 384.0 [M + H]⁺. |
| 356-s | 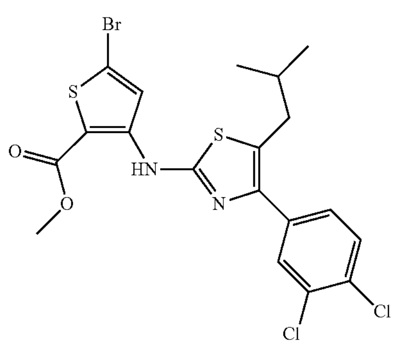 | Method B, Purity is 84.8%, Rt = 2.916 min; MS Calcd.: 498.0; No MS Found. |
| 366-s | 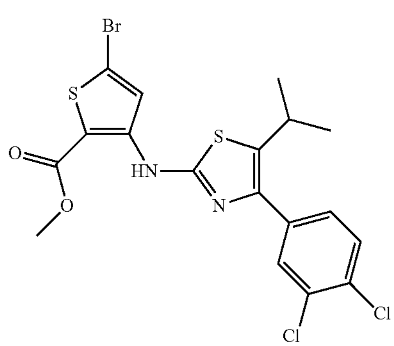 [SMILES: COC(=O)c1sc(Br)cc1Nc1nc(-c2ccc(Cl)c(Cl)c2)c(C(C)C)s1] | No MS data. |

Synthesis of methyl 4-(4-(3,4-dichlorophenyl)-5-isobutylthiazol-2-yl)-1-(3-(1,3-dioxoisoindolin-2-yl)propanoyl)piperazine-2-carboxylate (244-3)

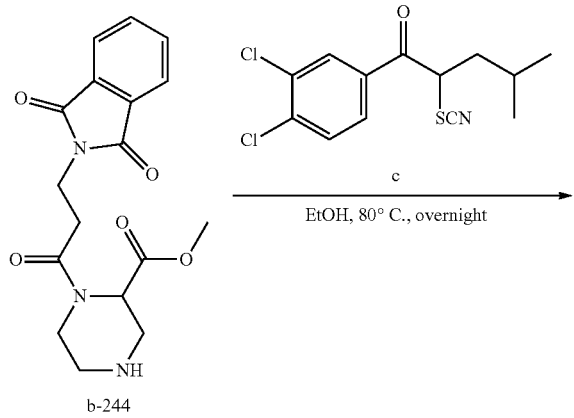

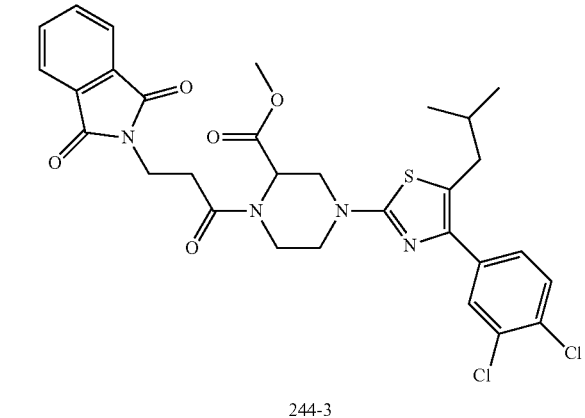

A mixture of b-244 (160 mg, 0.463 mmol) and c (140 mg, 0.463 mmol) in EtOH (5.0 mL) was stirred at 80° C. overnight. When the reaction was completed, the mixture was concentrated and purified by silica gel column chromatography (petrol ether/ethyl acetate=5/1) to afford 244-3 (200 mg, 69% yield) as yellow oil.

Synthesis of methyl 1-(3-aminopropanoyl)-4-(4-(3,4-dichlorophenyl)-5-isobutylthiazol-2-yl)piperazine-2-carboxylate (244-4)

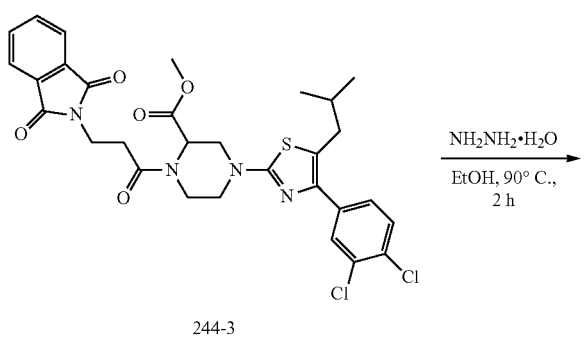

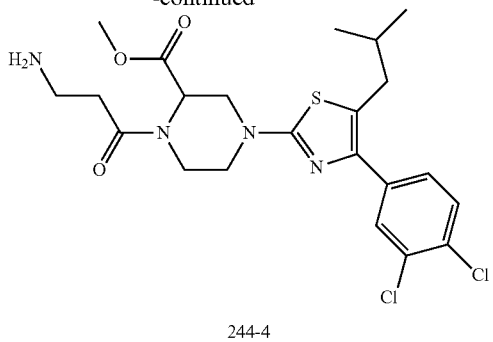

A mixture of 244-3 (200 mg, 0.318 mmol) and hydrazine hydrate (31.8 mg, 0.635 mmol) in EtOH (5.0 mL) was stirred at 90° C. for 2 h. When the reaction was completed, it was concentrated to give the crude product, which was used directly in next step without farther purification to afford 244-4 (150 mg, 95% yield) as yellow oil.

Synthesis of 1-(3-aminopropanoyl)-4-(4-(3,4-dichlorophenyl)-5-isobutylthiazol-2-yl)piperazine-2-carboxylic acid (I-199)

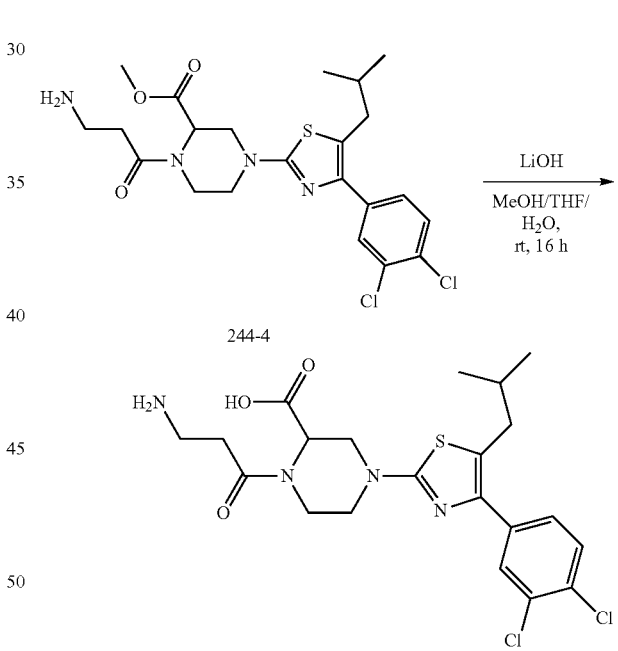

To a solution of 244-4 (150 mg, 0.300 mmol) in THF/MeOH/H$_2$O (v/v/v=4/1/1, 5.0 mL) was added LiOH (2.0 M in H$_2$O, 0.375 mL). The reaction was stirred at room temperature for 16 h. When the reaction was completed, the resulting reaction was concentrated, then it was diluted with H$_2$O (5.0 mL) and adjusted pH to 4-5 with HCl (1.0 M). The mixture was extracted with EtOAc (30.0 mL×2), and the combined organic phase washed with brine (10.0 mL), dried by anhydrous Na$_2$SO$_4$, and concentrated, the residue was purified by prep-HPLC to afford I-199 (10.0 mg, 6.9% yield) as a yellow solid.

Synthesis of 3-(benzyl(4-(3,4-dichlorophenyl)-5-isobutylthiazol-2-yl)amino)-N-methylpropanamide (I-200)

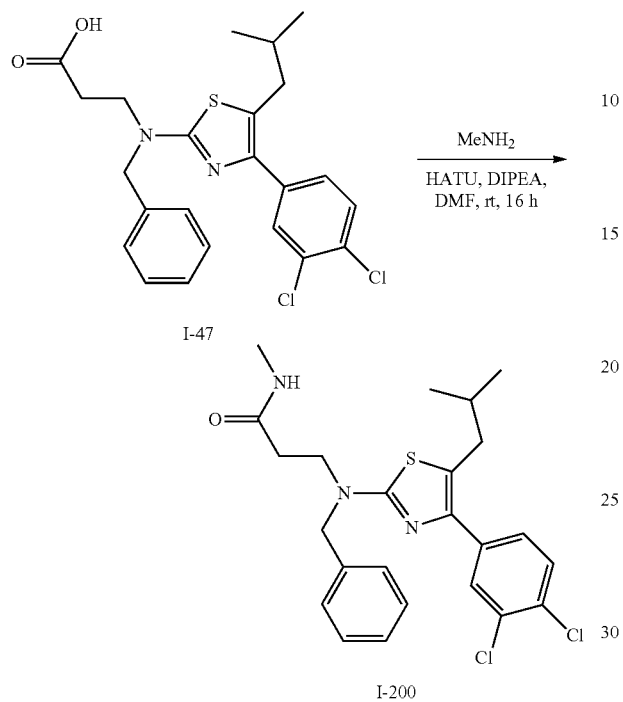

A mixture of I-47 (100 mg, 0.216 mmol), methylamine (8.04 mg, 0.259 mmol), HATU (164 mg, 0.432 mmol) and DIPEA (83.5 mg, 0.647 mmol) in DMF (2.00 mL) was stirred at room temperature for 16 h. When the reaction was completed, poured into H₂O (20.0 mL), and then extracted with EtOAc (30.0 mL×2). The organic layer was combined, and washed with H₂O (20.0 mL×2) and Brine (20.0 mL), then dried by anhydrous Na₂SO₄. The solution was concentrated to give a crude product, which was purified by prep-HPLC to afford I-200 (10.0 mg, 9.7% yield) as a white solid.

Synthesis of 6-((4-(3,4-dichlorophenyl)-5-isobutylthiazol-2-ylamino)methyl)pyridin-2-ol (I-201)

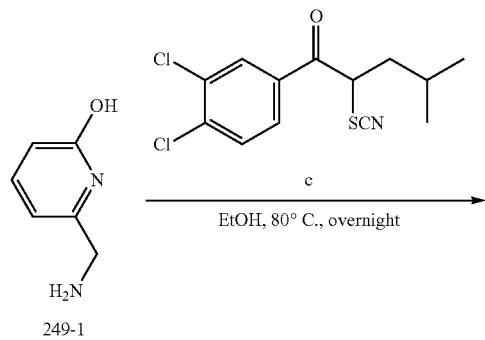

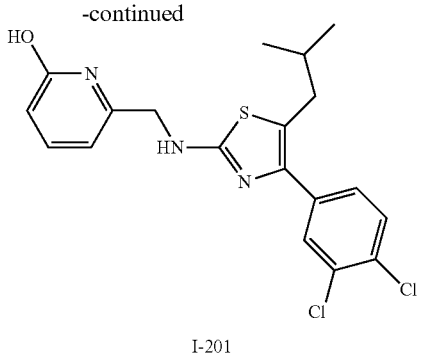

A mixture of 249-1 (28.0 mg, 0.226 mmol) and c (68.2 mg, 0.226 mmol) in EtOH (2.0 mL) was stirred at 80° C. overnight. When the reaction was completed, the mixture was purified by prep-HPLC to afford I-201 (15.0 mg, 16% yield) as a white solid.

Synthesis of methyl 3-(4-(3,4-dichlorophenyl)-5-isobutylthiazol-2-yl)benzoate (253-3)

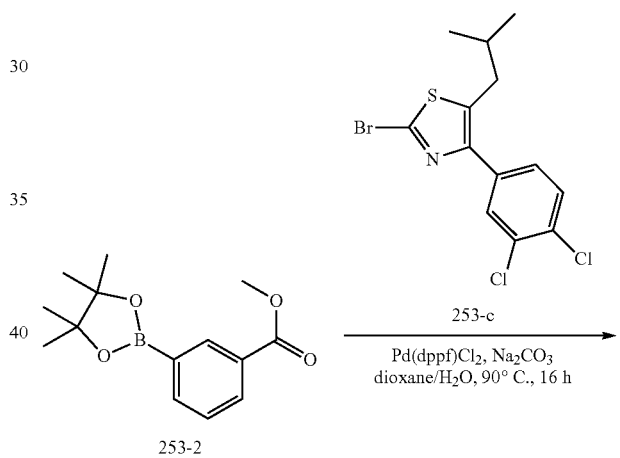

A mixture of 253-2 (100 mg, 0.382 mmol), 253-s (139 mg, 0.382 mmol), Pd(dppf)Cl₂ (13.9 mg, 0.0191 mmol) and Na₂CO₃ (80.9 mg, 0.763 mmol) in dioxane/H₂O (v/v=5/1, 2.0 mL) was stirred under N₂ atmosphere at 90° C. for 16 h. When the reaction was completed, it was concentrated and purified by silica gel column chromatography (petrol ether/ethyl acetate=10/1) to afford 253-3 (80 mg, 50% yield) as a yellow solid.

561

Synthesis of 3-(4-(3,4-dichlorophenyl)-5-isobutylthiazol-2-yl)benzoic acid (I-203)

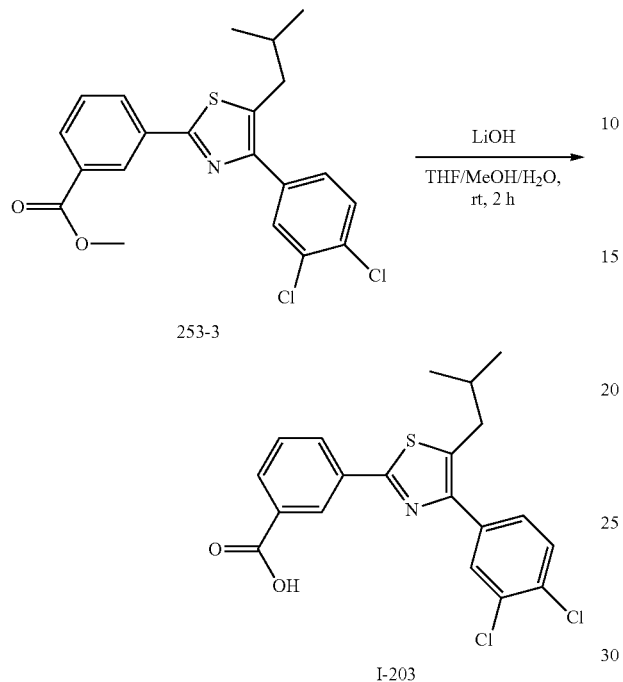

To a solution of 253-3 (80.0 mg, 0.190 mmol) in THF/MeOH/H₂O (v/v/v=4/1/1, 1.0 mL) was added LiOH (2.0 M in H₂O, 0.238 mL). The reaction was stirred at room temperature for 2 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by recrystallization to afford I-203 (30.0 mg, 39% yield) as a white solid.

Synthesis of methyl 3-(3-tert-butoxy-2-((4-(3,4-dichlorophenyl)-5-isobutylthiazol-2-ylamino)methyl)-3-oxopropyl)benzoate (256-2)

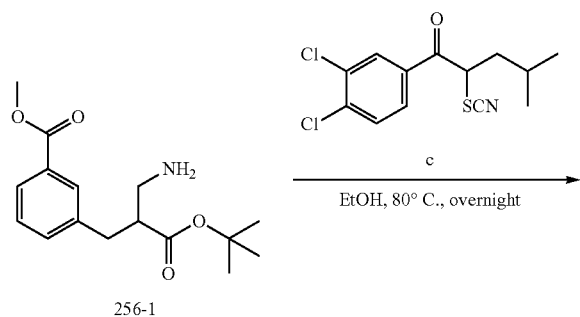

562

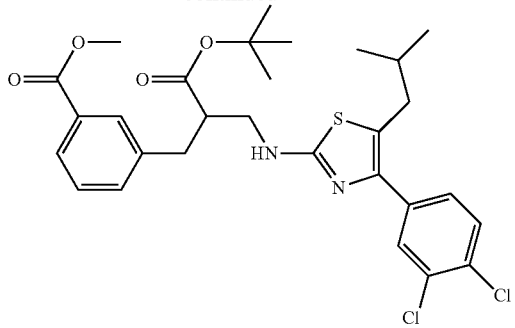

A mixture of 256-1 (1.00 g, 3.41 mmol) and c (1.03 g, 3.41 mmol) in EtOH (20.0 mL) was stirred at 80° C. overnight. When the reaction was completed, the mixture was purified by silica gel column chromatography (petrol ether/ethyl acetate=10/1) to afford 256-2 (900 mg, 46% yield) as a white solid.

Synthesis of 3-(3-tert-butoxy-2-((4-(3,4-dichlorophenyl)-5-isobutylthiazol-2-ylamino)methyl)-3-oxopropyl)benzoic acid (256-3)

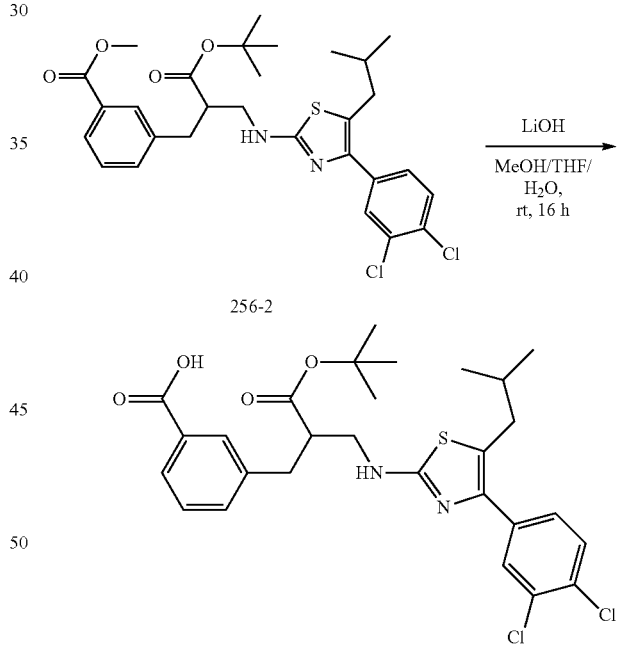

To a solution of 256-2 (900 mg, 1.56 mmol) in THF/MeOH/H₂O (v/v/v=4/1/1, 10.0 mL) was added LiOH (2.0 M in H₂O, 1.95 mL). The reaction was stirred at room temperature for 16 h. When the reaction was completed, the resulting reaction was concentrated, then it was diluted with H₂O (30.0 mL) and adjusted pH to 4-5 with HCl (1.0 M). The mixture was extracted with EtOAc (50.0 mL×2), and the combined organic phase washed with brine (30.0 mL), dried by anhydrous Na₂SO₄, and concentrated to afford 256-3 (700 mg, 80% yield) as a yellow solid.

563

Synthesis of tert-butyl 2-(3-(2-(tert-butoxycarbonylamino)ethylcarbamoyl)benzyl)-3-(4-(3,4-dichlorophenyl)-5-isobutylthiazol-2-ylamino)propanoate (256-4)

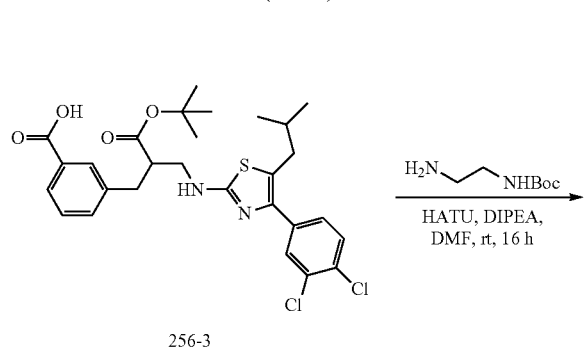

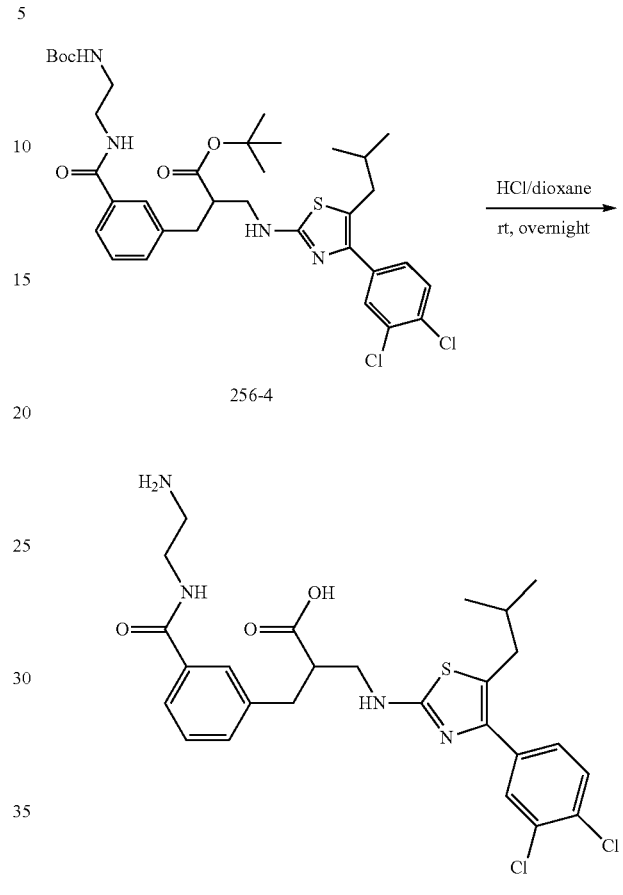

A mixture of 256-3 (100 mg, 0.177 mmol), tert-butyl 2-aminoethylcarbamate (34.1 mg, 0.213 mmol), HATU (135 mg, 0.355 mmol) and DIPEA (68.7 mg, 0.532 mmol) in DMF (2.0 mL) was stirred at room temperature for 16 h. When the reaction was completed, it was poured into H$_2$O (30 mL), and then extracted with EtOAc (50 mL×2). The organic layer was combined, and washed with H$_2$O (30 mL×2) and Brine (50 mL), then dried by anhydrous Na$_2$SO$_4$. The solution was concentrated to give a crude product, which was used directly in next step without farther purification to afford 256-4 (100 mg, 80% yield) as a yellow solid.

564

Synthesis of ethyl 2-(3-(2-aminoethylcarbamoyl)benzyl)-3-(4-(3,4-dichlorophenyl)-5-isobutylthiazol-2-ylamino)propanoic acid (I-204)

A mixture of 256-4 (100 mg, 0.142 mmol) in HCl (4.0 M in dioxane, 5.0 mL) was stirred at room temperature overnight. When the reaction was completed, it was concentrated to give a crude product, which was purified by prep-HPLC to afford I-204 (20.0 mg, 26% yield) as a white solid.

Synthesis of ethyl 3-((3-(2-(tert-butoxycarbonylamino)ethylcarbamoyl)benzyl)(4-(3,4-dichlorophenyl)-5-isobutylthiazol-2-yl)amino)propanoate (257-3)

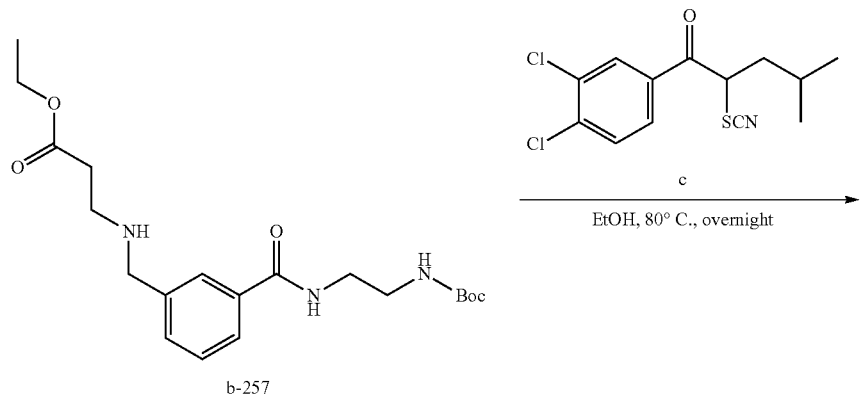

-continued

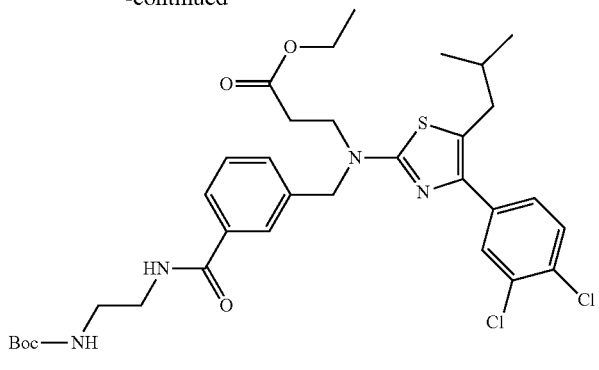
257-3

A mixture of b-257 (400 mg, 1.02 mmol) and c (307 mg, 1.02 mmol) in EtOH (10.0 mL) was stirred at 80° C. overnight. When the reaction was completed, the mixture was purified by prep-HPLC to afford 257-3 (180 mg, 26% yield) as yellow oil.

Synthesis of ethyl 3-((3-(2-aminoethylcarbamoyl)benzyl)(4-(3,4-dichlorophenyl)-5-isobutylthiazol-2-yl)amino)propanoate (257-4)

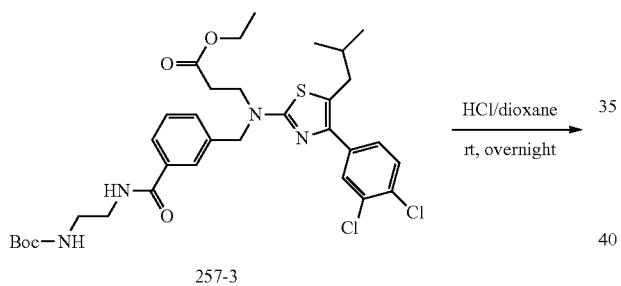
257-3

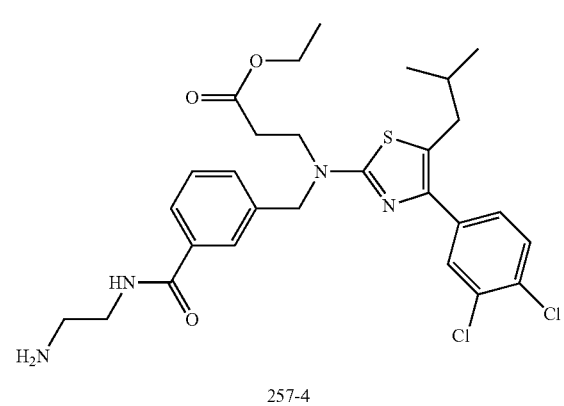
257-4

A mixture of 257-3 (180 mg, 0.401 mmol) in HCl (4.0 M in dioxane, 10.0 mL) was stirred at room temperature overnight. When the reaction was completed, it was filtered and the solid was dried to afford 257-4 (60.0 mg, 39% yield) as a white solid.

Synthesis of 3-((3-(2-aminoethylcarbamoyl)benzyl)(4-(3,4-dichlorophenyl)-5-isobutylthiazol-2-yl)amino)propanoic acid (I-205)

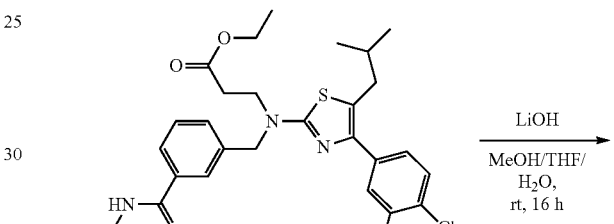
257-4

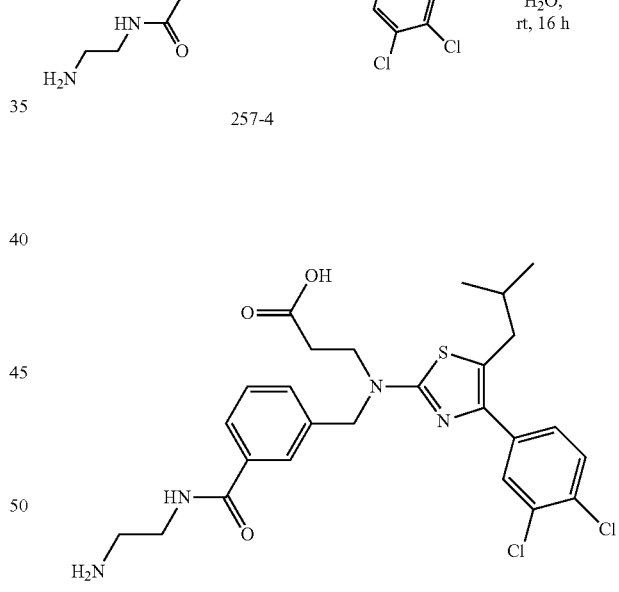
I-205

To a solution of 241-1 (60.0 mg, 0.104 mmol) in THF/MeOH/H$_2$O (v/v/v=4/1/1, 1.0 mL) was added LiOH (2.0 M in H$_2$O, 0.130 mL). The reaction was stirred at room temperature for 16 h. When the reaction was completed, the resulting reaction was concentrated, then it was diluted with H$_2$O (5.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-205 (20.0 mg, 35% yield) as a white solid.

567

Synthesis of 2-benzyl-3-(4-(3,4-dichlorophenyl)-5-(methylthio)thiazol-2-ylamino)propanoic acid (I-206)

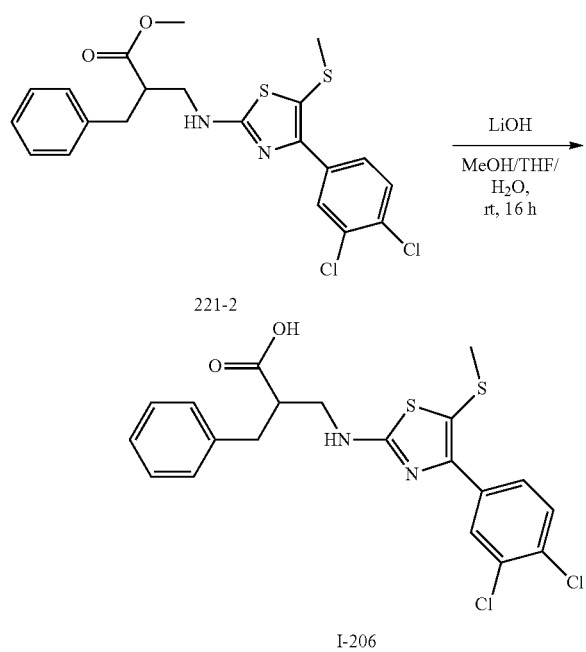

To a solution of 221-2 (100 mg, 0.214 mmol) in THF/MeOH/H₂O (v/v/v=4/1/1, 3.0 mL) was added LiOH (2.0 M in H₂O, 0.267 mL). The reaction was stirred at room temperature for 16 h. When the reaction was completed, the resulting reaction was concentrated, then it was diluted with H₂O (10.0 mL) and adjusted pH to 4-5 with HCl (1.0 M). The mixture was extracted with EtOAc (40.0 mL×2), and the combined organic phase washed with brine (30.0 mL), dried by anhydrous Na₂SO₄, concentrated and purified by prep-HPLC to afford I-206 (20.0 mg, 21% yield) as a white solid.

Synthesis of methyl 5-(4-(3,4-dichlorophenyl)-5-isobutylthiazol-2-ylamino)-2-hydroxybenzoate (260-2)

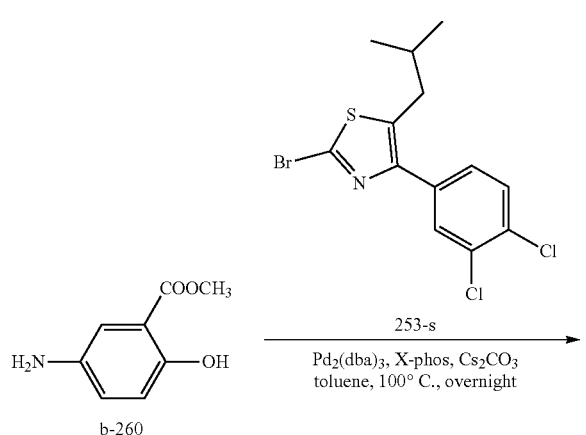

568

-continued

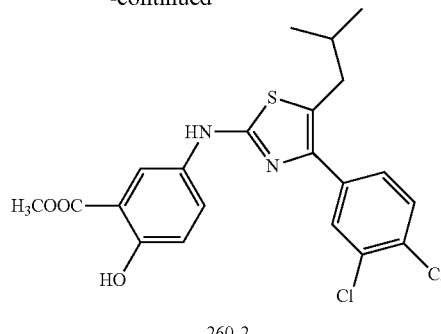

260-2

A mixture of b-260 (200 mg, 1.20 mmol), 253-s (437 mg, 1.20 mmol), Pd₂(dba)₃ (22.3 mg, 0.0239 mmol), X-phos (17.3 mg, 0.0299 mmol) and Cs₂CO₃ (780 mg, 2.39 mmol) in toluene (20.0 mL) was stirred under N₂ atmosphere at 100° C. overnight. When the reaction was completed, it was concentrated and purified by silica gel column chromatography (petrol ether/ethyl acetate=5/1) to afford 260-2 (220 mg, 41% yield) as a yellow solid.

Synthesis of 5-(4-(3,4-dichlorophenyl)-5-isobutylthiazol-2-ylamino)-2-hydroxybenzoic acid (I-207)

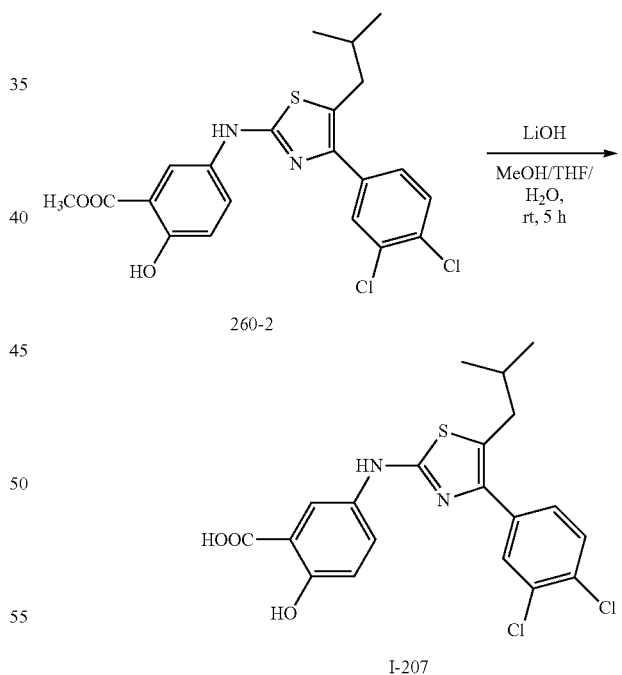

To a solution of 260-2 (220 mg, 0.487 mmol) in THF/MeOH/H₂O (v/v/v=4/1/1, 2.0 mL) was added LiOH (2.0 M in H₂O, 0.609 mL). The reaction was stirred at room temperature for 5 h. When the reaction was completed, the resulting reaction was concentrated, then it was diluted with H₂O (15.0 mL) and adjusted pH to 4-5 with HCl (1.0 M). The mixture was extracted with EtOAc (30.0 mL×2), and the combined organic phase washed with brine (10.0 mL), dried by anhydrous Na₂SO₄, and concentrated, the residue was purified by prep-HPLC to afford I-207 (5.00 mg, 2.3% yield) as a white solid.

Synthesis of methyl 5-(4-(3,4-dichlorophenyl)-5-isobutylthiazol-2-ylamino)biphenyl-3-carboxylate (268-2)

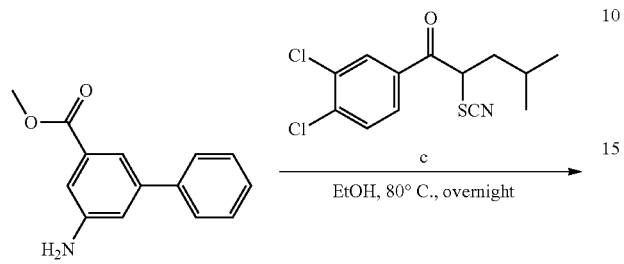

A mixture of b-268 (145 mg, 0.638 mmol) and c (193 mg, 0.638 mmol) in EtOH (2.0 mL) was stirred at 80° C. overnight. When the reaction was completed, the mixture was purified by prep-TLC (petrol ether/ethyl acetate=10/1) to afford 268-2 (200 mg, 61% yield) as a yellow solid.

Synthesis of 5-(4-(3,4-dichlorophenyl)-5-isobutylthiazol-2-ylamino)biphenyl-3-carboxylic acid (I-215)

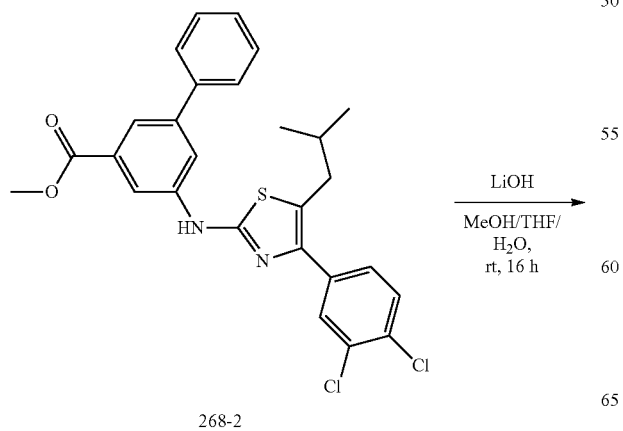

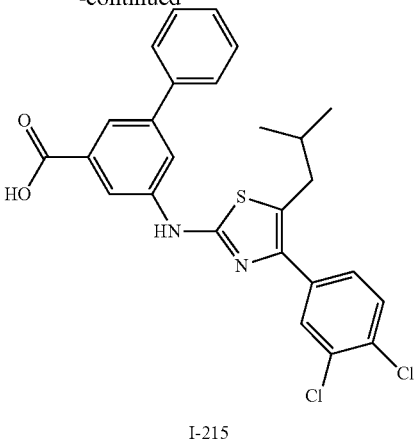

To a solution of 268-2 (200 mg, 0.391 mmol) in THF/MeOH/H₂O (v/v/v=4/1/1, 1.0 mL) was added LiOH (2.0 M in H₂O, 0.489 mL). The reaction was stirred at room temperature for 16 h. When the reaction was completed, the resulting reaction was concentrated, then it was diluted with H₂O (10.0 mL) and adjusted pH to 4-5 with HCl (1.0 M). The mixture was extracted with EtOAc (20.0 mL×2), and the combined organic phase washed with brine (10.0 mL), dried by anhydrous Na₂SO₄, and concentrated, the residue was purified by recrystallization to afford I-215 (110 mg, 57% yield) as a white solid.

Synthesis of 3-(4-(3,4-dichlorophenyl)-5-isobutylthiazol-2-ylamino)benzoic acid (271-2)

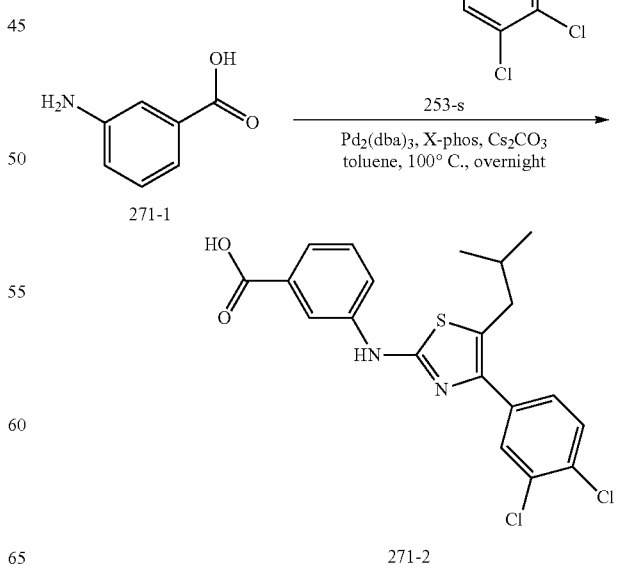

571

A mixture of 271-1 (200 mg, 1.46 mmol), 253-s (532 mg, 1.46 mmol), Pd₂(dba)₃ (27.1 mg, 0.0291 mmol), X-phos (21.1 mg, 0.0364 mmol) and Cs₂CO₃ (949 mg, 2.91 mmol) in toluene (30.0 mL) was stirred under N₂ atmosphere at 100° C. overnight. When the reaction was completed, it was concentrated and purified by silica gel column chromatography (CH₂Cl₂/MeOH=50/1) to afford 271-2 (150 mg, 24% yield) as a yellow solid.

Synthesis of tert-butyl 2-(3-(4-(3,4-dichlorophenyl)-5-isobutylthiazol-2-ylamino)benzamido)ethylcarbamate (271-3)

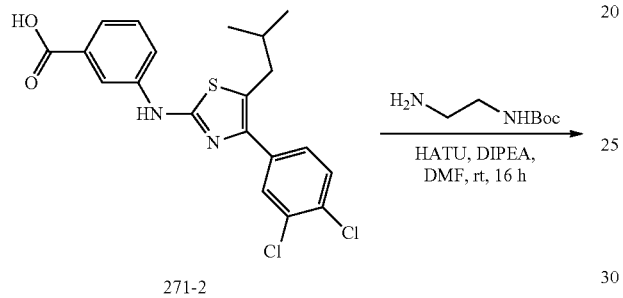

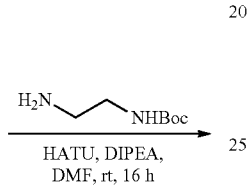

271-2

A mixture of 271-2 (150 mg, 0.356 mmol), tert-butyl 2-aminoethylcarbamate (68.4 mg, 0.427 mmol), HATU (271 mg, 0.712 mmol) and DIPEA (138 mg, 1.07 mmol) in DMF (2.0 mL) was stirred at room temperature for 16 h. When the reaction was completed, it was poured into H₂O (50 mL), and then extracted with EtOAc (50 mL×2). The organic layer was combined, and washed with H₂O (30 mL×2) and Brine (30 mL), then dried by anhydrous Na₂SO₄. The solution was concentrated and purified by prep-TLC (petrol ether/ethyl acetate=5/1) to afford 271-3 (80.0 mg, 40% yield) as a yellow solid.

572

Synthesis of N-(2-aminoethyl)-3-(4-(3,4-dichlorophenyl)-5-isobutylthiazol-2-ylamino)benzamide (I-218)

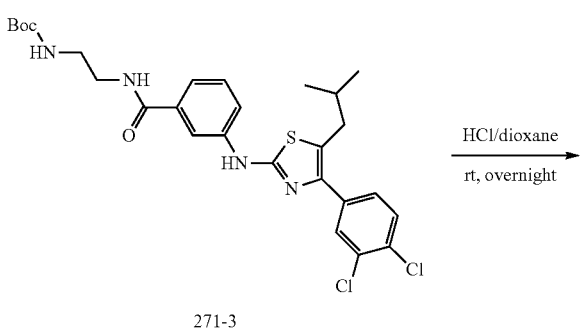

271-3

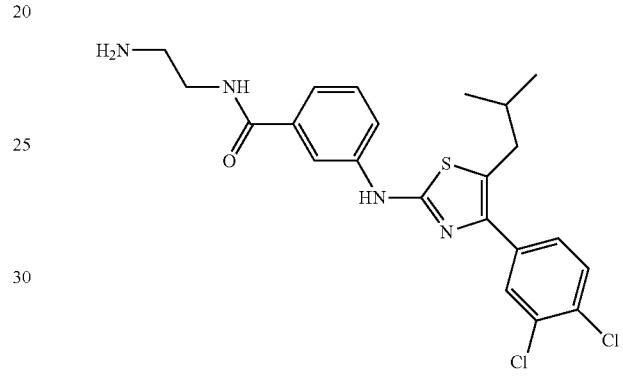

I-218

A mixture of 271-3 (80.0 mg, 0.142 mmol) in HCl (4.0 M in dioxane, 5.0 mL) was stirred at room temperature overnight. When the reaction was completed, it was concentrated to give a crude product, which was purified by prep-HPLC to afford I-218 (10.0 mg, 15% yield) as a white solid.

Synthesis of 5-(4-(3,4-dichlorophenyl)-5-isobutylthiazol-2-ylamino)nicotinic acid (I-221)

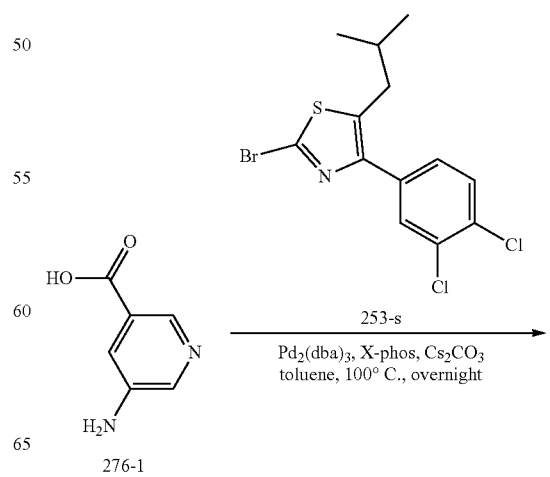

276-1

573

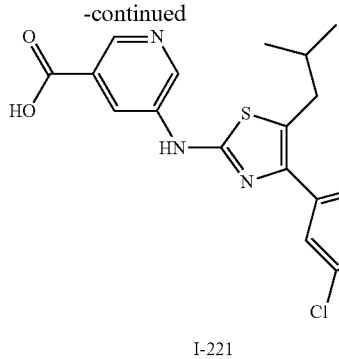

I-221

A mixture of 276-1 (41.6 mg, 0.301 mmol), 253-s (100 mg, 0.274 mmol), Pd$_2$(dba)$_3$ (51.2 mg, 0.0548 mmol), X-phos (39.6 mg, 0.0685 mmol) and Cs$_2$CO$_3$ (179 mg, 0.548 mmol) in toluene (2.0 mL) was stirred under N$_2$ atmosphere at 100° C. overnight. When the reaction was completed, it was concentrated and purified by prep-HPLC to afford I-221 (8.00 mg, 6.9% yield) as a white solid.

Synthesis of methyl 3-(4-(bromomethyl)thiazol-2-yl)benzoate (283-2)

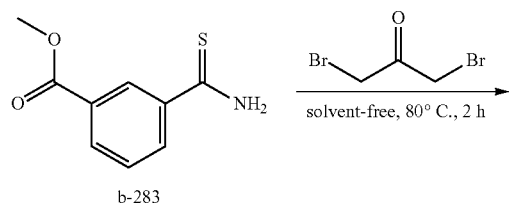

b-283

A mixture of b-283 (550 mg, 2.56 mmol) and 1,3-dibromopropan-2-one (10 mL) was stirred without solvent at 80° C. for 2 h. When the reaction was completed, the mixture was solved with EtOAc (150 mL) then washed with H$_2$O (50 mL×2) and Brine (50 mL), then dried by anhydrous Na$_2$SO$_4$. The organic layer was concentrated and purified by silica gel column chromatography (petrol ether/ethyl acetate=10/1) to afford 283-2 (680 mg, 77% yield) as a yellow solid.

574

Synthesis of methyl 3-(4-(3,4-dichlorobenzyl)thiazol-2-yl)benzoate (283-3)

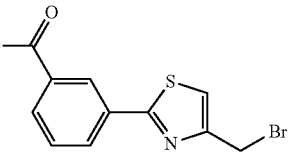 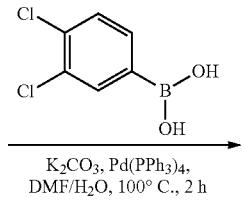

283-2

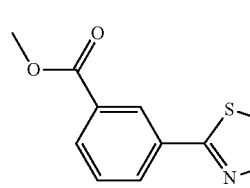

283-3

A mixture of 283-2 (680 mg, 2.18 mmol), 3,4-dichlorophenylboronic acid (623 mg, 3.27 mmol), Pd(PPh$_3$)$_4$ (50.4 mg, 0.0436 mmol) and K$_2$CO$_3$ (601 mg, 4.36 mmol) in DMF/H$_2$O (v/v=10/1, 22.0 mL) was stirred under N$_2$ atmosphere at 100° C. for 2 h. When the reaction was completed, it was poured into H$_2$O (200 mL), and then extracted with EtOAc (150 mL×2). The organic layer was combined, and washed with H$_2$O (80 mL×2) and Brine (80 mL), then dried by anhydrous Na$_2$SO$_4$. The solution was concentrated and purified by silica gel column chromatography (petrol ether/ethyl acetate=10/1) to afford 283-3 (255 mg, 31% yield) as yellow oil.

Synthesis of 3-(4-(3,4-dichlorobenzyl)thiazol-2-yl)benzoic acid (I-223)

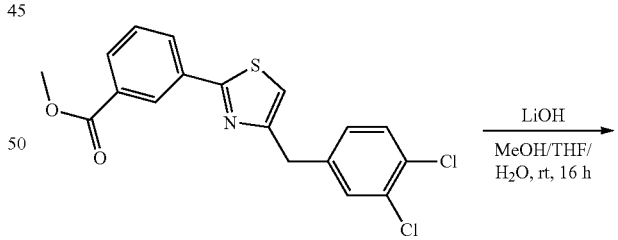

283-3

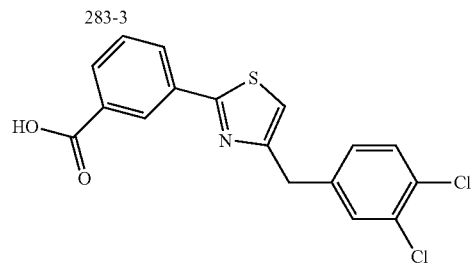

I-223

To a solution of 283-3 (55.0 mg, 0.145 mmol) in THF/MeOH/H₂O (v/v/v=4/1/1, 2.0 mL) was added LiOH (2.0 M in H₂O, 0.182 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-223 (26.0 mg, 49% yield) as a white solid.

Synthesis of methyl 2-bromo-5-(4-(3,4-dichlorophenyl)-5-isobutylthiazol-2-yl)benzoate (287-2)

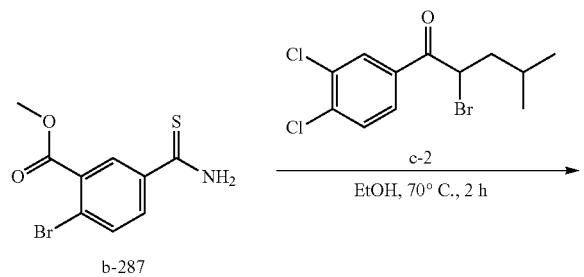

b-287

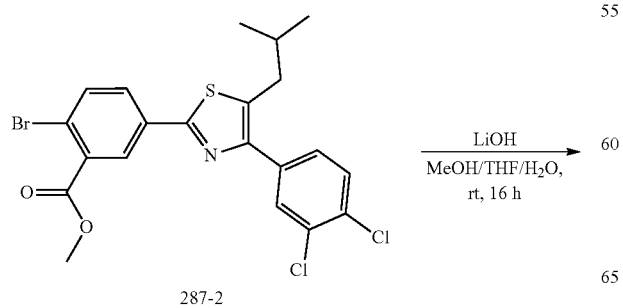

287-2

A mixture of b-287 (200 mg, 0.730 mmol) and c-2 (248 mg, 0.766 mmol) in EtOH (5.0 mL) was stirred at 70° C. for 2 h. When the reaction was completed, the mixture was purified by prep-TLC (petrol ether/ethyl acetate=8/1) to afford 287-2 (100 mg, 27% yield) as colorless oil.

Synthesis of 2-bromo-5-(4-(3,4-dichlorophenyl)-5-isobutylthiazol-2-yl)benzoic acid (I-224)

287-2

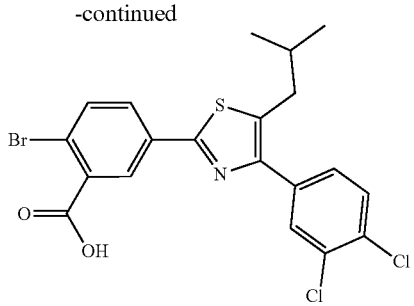

I-224

To a solution of 287-2 (100 mg, 0.200 mmol) in THF/MeOH/H₂O (v/v/v=4/1/1, 2.0 mL) was added LiOH (2.0 M in H₂O, 0.250 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-224 (60.0 mg, 62% yield) as a white solid.

Synthesis of methyl 6-(4-(3,4-dichlorophenyl)-5-isobutylthiazol-2-yl)picolinate (291-2)

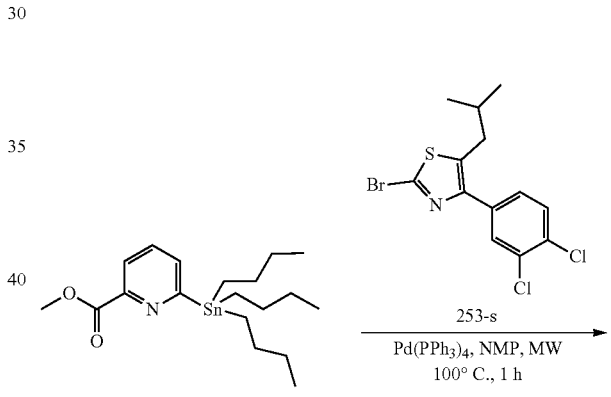

291-2

A mixture of b-291 (390 mg, 0.915 mmol), 253-s (400 mg, 1.10 mmol) and Pd(PPh₃)₄ (21.2 mg, 0.0183 mmol) in NMP (5.0 mL) was stirred under N₂ atmosphere at 100° C. under microwave for 1 h. When the reaction was completed, it was poured into H₂O (80 mL), and then extracted with EtOAc (80 mL×2). The organic layer was combined, and washed with H₂O (50 mL×2) and Brine (50 mL), then dried by anhydrous Na₂SO₄. The solution was concentrated and purified by silica gel column chromatography (petrol ether/ethyl acetate=10/1) to afford 291-2 (300 mg, 65% yield) as yellow oil.

Synthesis of 6-(4-(3,4-dichlorophenyl)-5-isobutylthiazol-2-yl)picolinic acid (I-228)

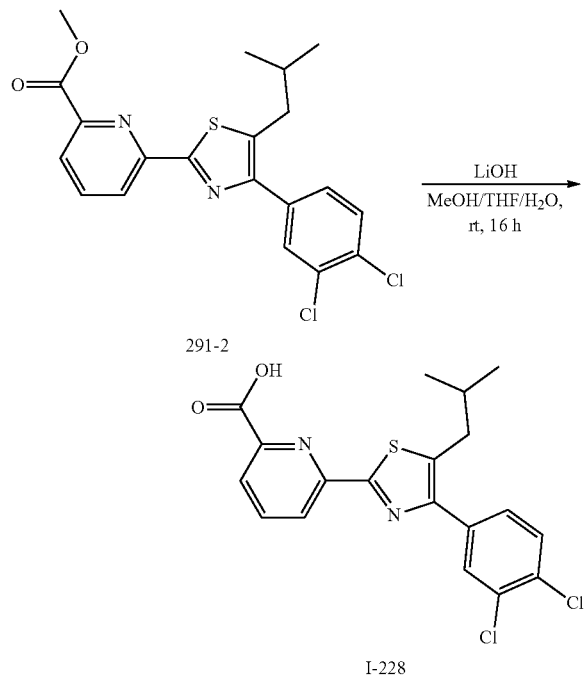

To a solution of 291-2 (300 mg, 0.712 mmol) in THF/MeOH/H₂O (v/v/v=4/1/1, 5.0 mL) was added LiOH (2.0 M in H₂O, 0.890 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-228 (50.0 mg, 17% yield) as a white solid.

Synthesis of 3-(benzyl(4-(3,4-dichlorophenyl)-5-isobutylthiazol-2-yl)amino)propanenitrile (293-1)

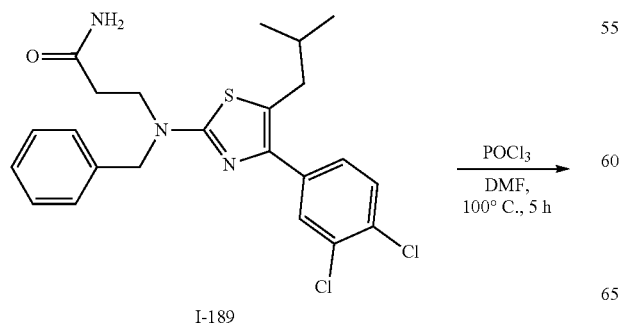

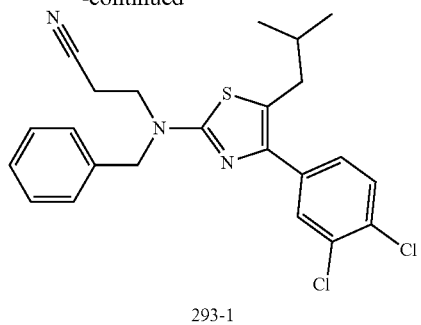

To a solution of I-189 (120 mg, 0.259 mmol) in DMF (1.0 mL) was added POCl₃ (0.20 mL). The reaction was stirred at 100° C. for 5 h. When the reaction was completed, it was poured into H₂O (30 mL), and then extracted with EtOAc (50 mL×2). The organic layer was combined, and washed with H₂O (30 mL×2) and Brine (30 mL), then dried by anhydrous Na₂SO₄. The solution was concentrated and purified by silica gel column chromatography (petrol ether/ethyl acetate=10/1) to afford 293-1 (40.0 mg, 35% yield) as a yellow solid.

Synthesis of 3-(benzyl(4-(3,4-dichlorophenyl)-5-isobutylthiazol-2-yl)amino)propanimidamide (I-230)

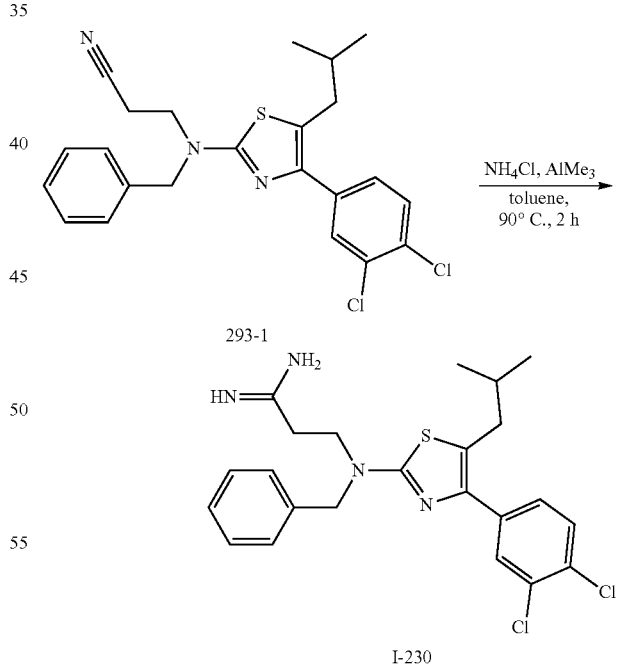

To a solution of 293-1 (40.0 mg, 0.090 mmol) and NH₄Cl (9.63 mg, 0.180 mmol) in toluene (1.0 mL) was added AlMe₃ (1.0 M in toluene, 0.45 mL, 0.450 mmol). The reaction was stirred at 90° C. for 2 h. When the reaction was completed, it was concentrated and purified by prep-HPLC to afford I-230 (10.0 mg, 24% yield) as a white solid.

Synthesis of 2-(benzyl(4-(3,4-dichlorophenyl)-5-isobutylthiazol-2-yl)amino)acetonitrile (294-2)

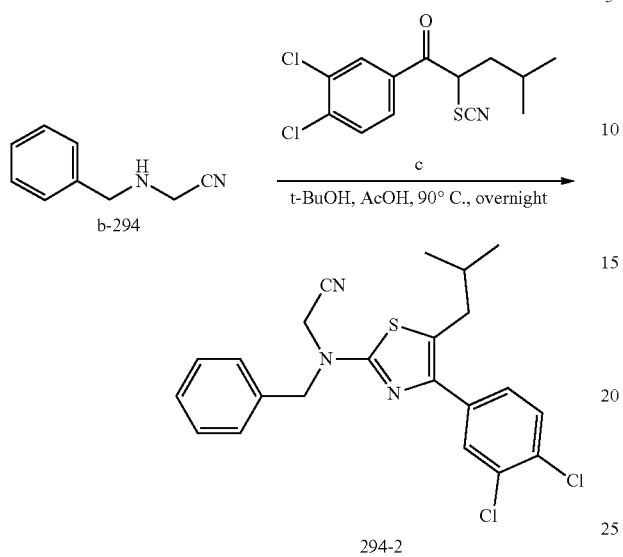

A mixture of b-294 (600 mg, 4.10 mmol), c (1.24 g, 4.10 mmol) and AcOH (492 mg, 8.20 mmol) in t-BuOH (5.0 mL) was stirred at 90° C. overnight. When the reaction was completed, the mixture was purified by prep-TLC (petrol ether/ethyl acetate=10/1) to afford 294-2 (1.10 g, 62% yield) as a yellow solid.

Synthesis of 2-(benzyl(4-(3,4-dichlorophenyl)-5-isobutylthiazol-2-yl)amino)acetimidamide (I-231)

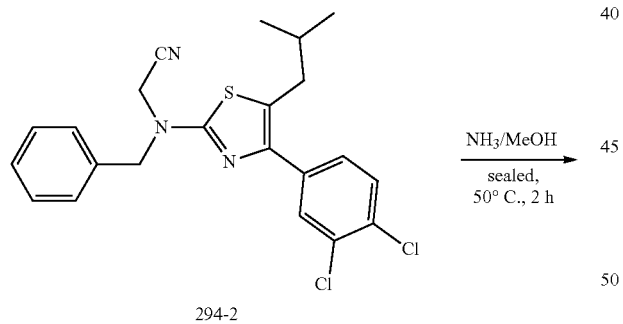

A mixture of 294-2 (50.0 mg, 0.116 mmol) in $NH_3$ (7.0 M in MeOH, 3.0 mL) was stirred sealed at 50° C. for 2 h. When the reaction was completed, it was concentrated to give a crude product, which was purified by prep-HPLC to afford I-231 (18.0 mg, 35% yield) as an off-white solid.

Synthesis of tert-butyl 2-(benzyl(4-(3,4-dichlorophenyl)-5-isobutylthiazol-2-yl)amino)ethylcarbamate (295-2)

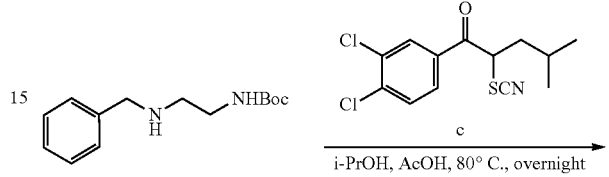

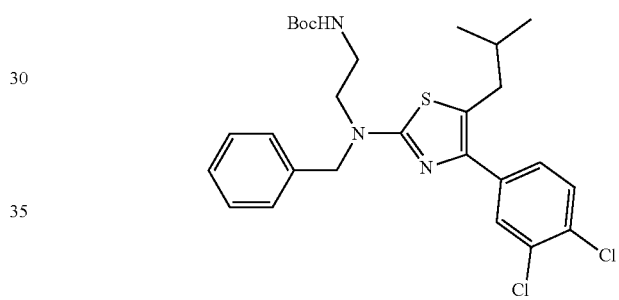

A mixture of b-295 (550 mg, 2.20 mmol), c (664 mg, 2.20 mmol) and AcOH (264 mg, 4.39 mmol) in i-PrOH (5.0 mL) was stirred at 80° C. overnight. When the reaction was completed, the mixture was purified by silica gel column chromatography (petrol ether/ethyl acetate=10/1) to afford 295-2 (350 mg, 30% yield) as a yellow solid.

Synthesis of $N^1$-benzyl-$N^1$-(4-(3,4-dichlorophenyl)-5-isobutylthiazol-2-yl)ethane-1,2-diamine (295-3)

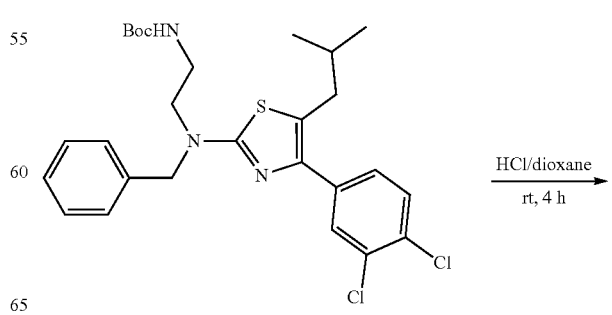

581

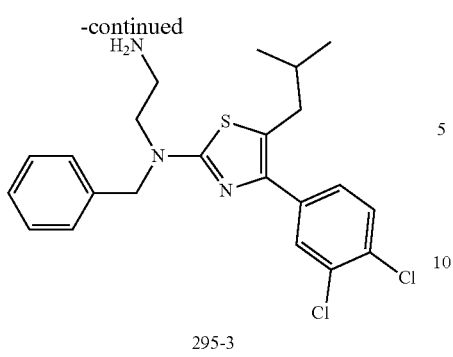

295-3

A mixture of 295-2 (350 mg, 0.655 mmol) in HCl (4.0 M in dioxane, 5.0 mL) was stirred at room temperature for 4 h. When the reaction was completed, it was filtered and the solid was dried to afford 295-3 (270 mg, 95% yield) as a white solid.

Synthesis of tert-butyl 2-(4-(3,4-dichlorophenyl)-5-isobutylthiazol-2-yl)-10,10-dimethyl-8-oxo-1-phenyl-9-oxa-2,5,7-triazaundecan-6-ylidenecarbamate (295-4)

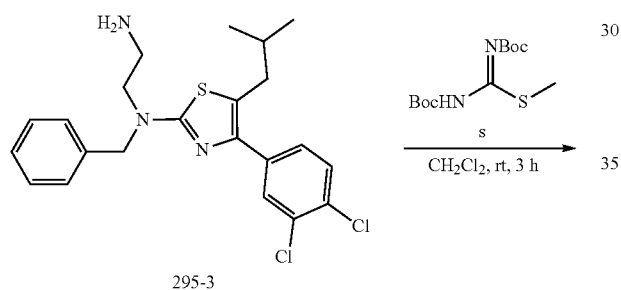

A mixture of 295-3 (270 mg, 0.622 mmol) and s (199 mg, 0.684 mmol) in $CH_2Cl_2$ (10.0 mL) was stirred at room temperature for 3 h. When the reaction was completed, the reaction mixture was filtered, and the residue was washed with $CH_2Cl_2$ (2.0 mL×2), dried to afford 295-4 (310 mg, 74% yield) as a yellow solid.

582

Synthesis of 2-(2-(benzyl(4-(3,4-dichlorophenyl)-5-isobutylthiazol-2-yl)amino)ethyl)guanidine (I-232)

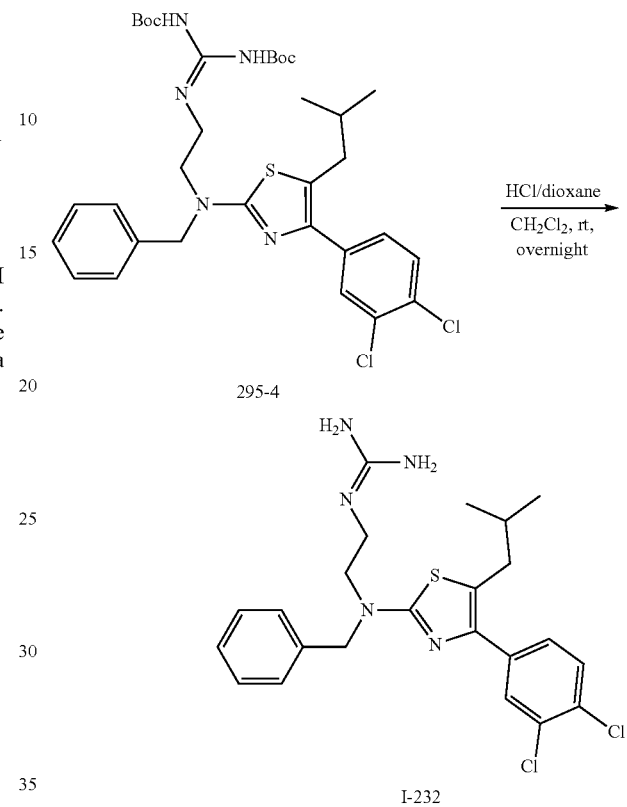

A mixture of 295-4 (310 mg, 0.655 mmol) and HCl (4.0 M in dioxane, 2.0 mL) in $CH_2Cl_2$ (5.0 mL) was stirred at room temperature overnight. When the reaction was completed, it was filtered and the solid was purified by washing with EtOAc (2.0 mL×3) to afford I-232 (120 mg, 55% yield) as a white solid.

Synthesis of 3-(4-(3,4-dichlorophenyl)-5-isobutylthiazol-2-ylamino)picolinonitrile (297-3)

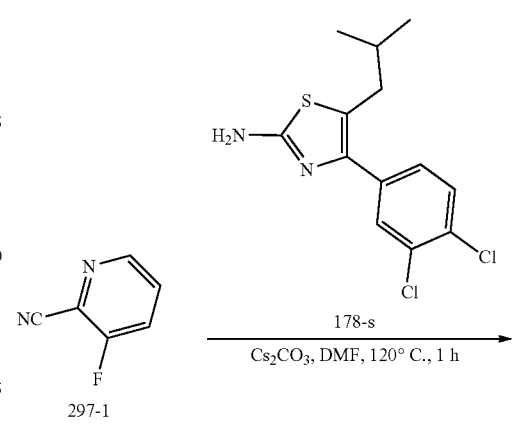

583

-continued

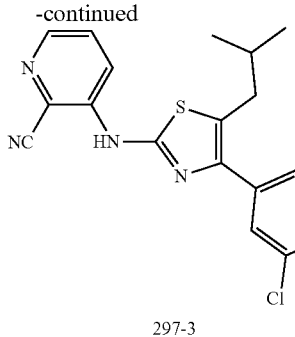
297-3

A mixture of 297-1 (300 mg, 2.46 mmol), 178-s (617 mg, 2.05 mmol) and Cs$_2$CO$_3$ (1.33 g, 4.10 mmol) in DMF (8.0 mL) was stirred at 120° C. for 1 h. When the reaction was completed, it was poured into H$_2$O (100 mL), and then extracted with EtOAc (100 mL×2). The organic layer was combined, and washed with H$_2$O (50.0 mL×2) and Brine (50.0 mL), then dried by anhydrous Na$_2$SO$_4$. The solution was concentrated and purified by silica gel column chromatography (petrol ether/ethyl acetate=10/1) to afford 297-3 (100 mg, 12% yield) as a yellow solid.

Synthesis of 3-(4-(3,4-dichlorophenyl)-5-isobutylthiazol-2-ylamino)picolinic acid (I-234)

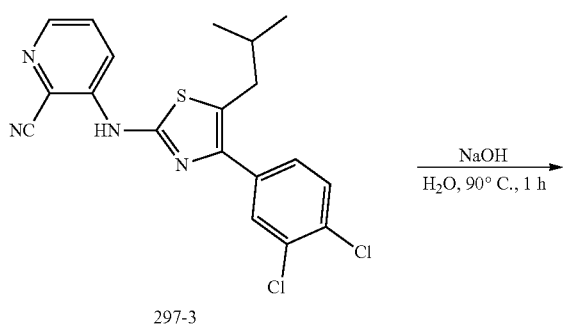

To a solution of 297-3 (100 mg, 0.248 mmol) in H$_2$O (1.0 mL) was added NaOH (5.0 M in H$_2$O, 0.248 mL). The reaction was stirred at 90° C. for 1 h. When the reaction was completed, the resulting reaction was concentrated, then it was diluted with H$_2$O (10.0 mL) and adjusted pH to 4-5 with HCl (1.0 M). The mixture was extracted with EtOAc (40.0 mL×2), and the combined organic phase washed with brine (30.0 mL), dried by anhydrous Na$_2$SO$_4$, and concentrated, the residue was purified by prep-HPLC to afford I-234 (30.0 mg, 29% yield) as a white solid.

584

Synthesis of 1-benzyl 2-methyl 4-(4-(3,4-dichlorophenyl)-5-isobutylthiazol-2-yl)piperazine-1,2-dicarboxylate (316-3)

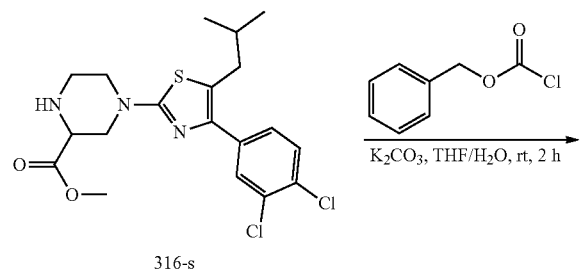

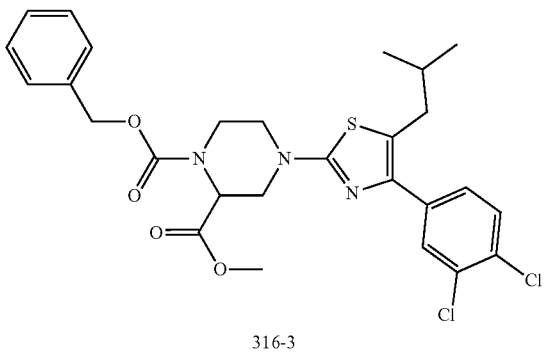

To a mixture of 316-s (180 mg, 0.420 mmol) and K$_2$CO$_3$ (116 mg, 0.840 mmol) in THF/H$_2$O (v/v=5/1, 10.0 mL) was added benzyl carbonochloridate (86.0 mg, 0.504 mmol). The reaction was stirred at room temperature for 2 h. When the reaction was completed, it was concentrated and purified by prep-TLC (petrol ether/ethyl acetate=10/1) to afford 316-3 (120 mg, 51% yield) as yellow oil.

Synthesis of 1-(benzyloxycarbonyl)-4-(4-(3,4-dichlorophenyl)-5-isobutylthiazol-2-yl)piperazine-2-carboxylic acid (I-244)

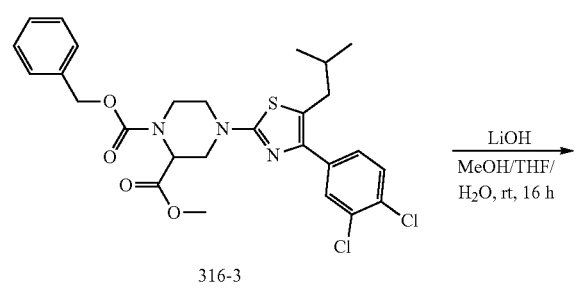

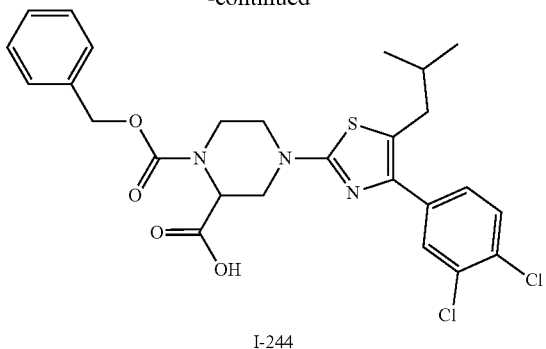

I-244

To a solution of 316-3 (120 mg, 0.213 mmol) in THF/MeOH/H₂O (v/v/v=4/1/1, 1.0 mL) was added LiOH (2.0 M in H₂O, 0.267 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-244 (40.0 mg, 34% yield) as a white solid.

Synthesis of 4-(4-(3,4-dichlorophenyl)-5-isobutylthiazol-2-yl)piperazine-2-carboxylic acid (317-1)

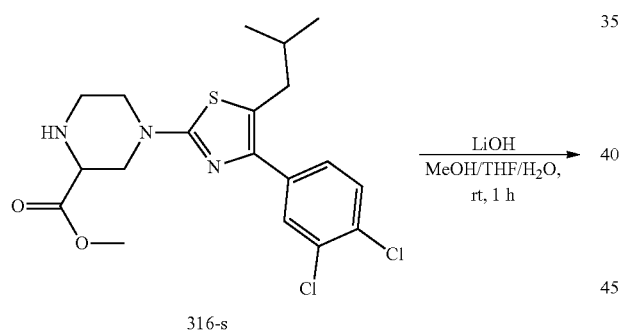

To a solution of 316-s (200 mg, 0.467 mmol) in THF/MeOH/H₂O (v/v/v=4/1/1, 5.0 mL) was added LiOH (2.0 M in H₂O, 0.584 mL). The reaction was stirred at room temperature for 1 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by recrystallization to afford 317-1 (150 mg, 78% yield) as a yellow solid.

Synthesis of 4-(4-(3,4-dichlorophenyl)-5-isobutylthiazol-2-yl)-1-(ethoxycarbonyl)piperazine-2-carboxylic acid (I-245)

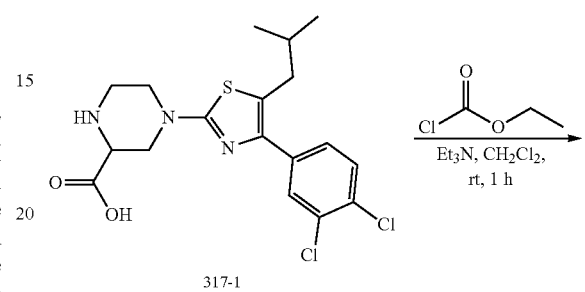

I-245

To a mixture of 317-1 (150 mg, 0.362 mmol) and Et₃N (73.1 mg, 0.724 mmol) in CH₂Cl₂ (5.0 mL) was added ethyl carbonochloridate (47.1 mg, 0.434 mmol). The reaction was stirred at room temperature for 1 h. When the reaction was completed, it was concentrated and purified by prep-HPLC to afford I-245 (25.0 mg, 14% yield) as a white solid.

Synthesis of methyl 1-benzoyl-4-(4-(3,4-dichlorophenyl)-5-isobutylthiazol-2-yl)piperazine-2-carboxylate (318-1)

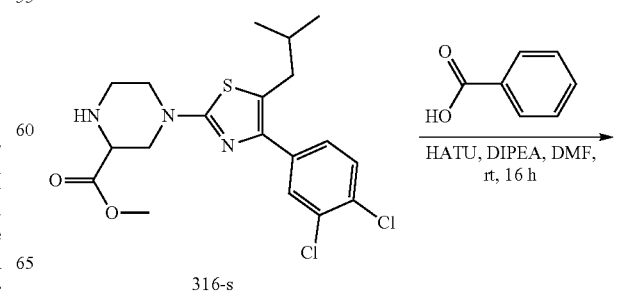

587

-continued

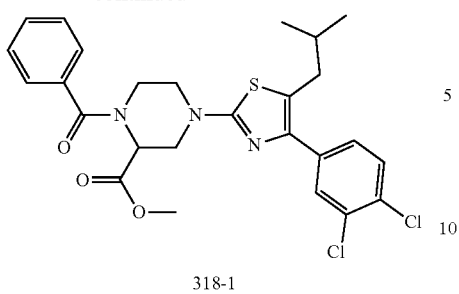

318-1

A mixture of 316-s (200 mg, 0.467 mmol), benzoic acid (68.4 mg, 0.560 mmol), HATU (355 mg, 0.934 mmol) and DIPEA (181 mg, 1.40 mmol) in DMF (5.0 mL) was stirred at room temperature for 16 h. When the reaction was completed, it was poured into H₂O (100 mL), and then extracted with EtOAc (100 mL×2). The organic layer was combined, and washed with H₂O (80 mL×2) and Brine (50 mL), then dried by anhydrous Na₂SO₄. The solution was concentrated to give a crude product, which was purified by prep-TLC (petrol ether/ethyl acetate=10/1) to afford 318-1 (70.0 mg, 28% yield) as a yellow solid.

Synthesis of 1-benzoyl-4-(4-(3,4-dichlorophenyl)-5-isobutylthiazol-2-yl)piperazine-2-carboxylic acid (I-246)

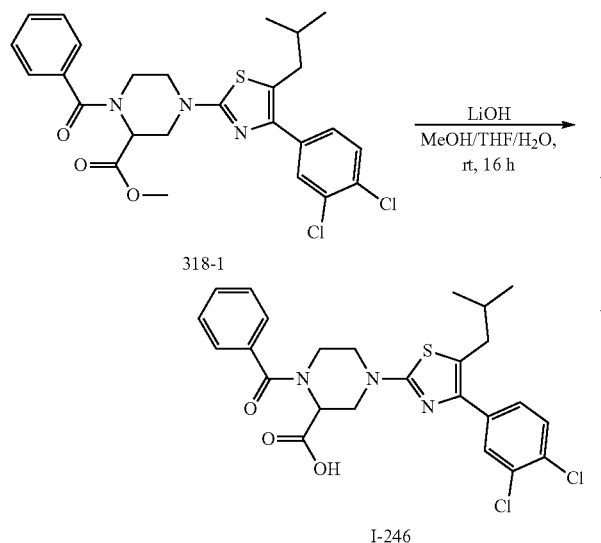

To a solution of 318-1 (70.0 mg, 0.131 mmol) in THF/MeOH/H₂O (v/v/v=4/1/1, 1.0 mL) was added LiOH (2.0 M in H₂O, 0.164 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-246 (30.0 mg, 44% yield) as a white solid.

588

Synthesis of methyl 4-(4-(3,4-dichlorophenyl)-5-isobutylthiazol-2-yl)-1-(methylcarbamoyl)piperazine-2-carboxylate (324-1)

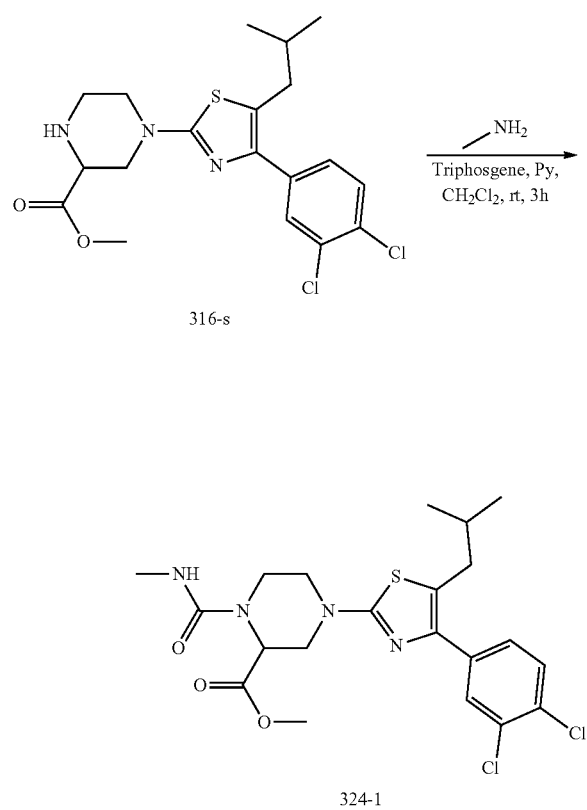

A mixture of 316-s (80.0 mg, 0.187 mmol), methanamine (8.70 mg, 0.280 mmol), Triphosgene (66.6 mg, 0.224 mmol) and pyridine (44.3 mg, 0.561 mmol) in CH₂Cl₂ (5.0 mL) was stirred at room temperature for 3 h. When the reaction was completed, it was washed with H₂O (10 mL×2) and Brine (10 mL) then dried by anhydrous Na₂SO₄. The solution was concentrated to give a crude product, which was purified by prep-TLC (petrol ether/ethyl acetate=8/1) to afford 324-1 (40.0 mg, 44% yield) as yellow oil.

Synthesis of 4-(4-(3,4-dichlorophenyl)-5-isobutylthiazol-2-yl)-1-(methylcarbamoyl)piperazine-2-carboxylic acid (I-251)

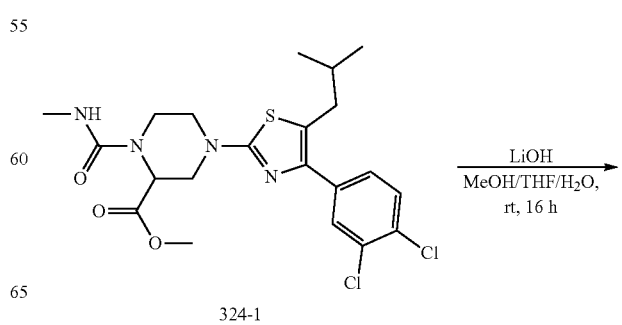

324-1

-continued

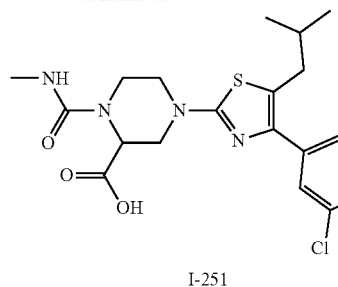

I-251

To a solution of 324-1 (40.0 mg, 0.0824 mmol) in THF/MeOH/H₂O (v/v/v=4/1/1, 1.0 mL) was added LiOH (2.0 M in H₂O, 0.103 mL). The reaction was stirred at room temperature for 16 h. When the reaction was completed, the resulting reaction was concentrated, then it was diluted with H₂O (5.0 mL) and adjusted pH to 6-7 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-251 (25.0 mg, 64% yield) as a white solid.

Synthesis of 1-isopropyl 2-methyl 4-(4-(3,4-dichlorophenyl)-5-isobutylthiazol-2-yl)piperazine-1,2-dicarboxylate (326-1)

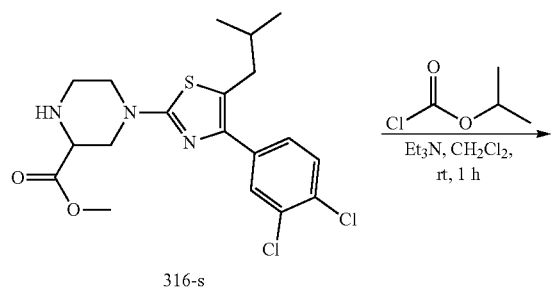

316-s

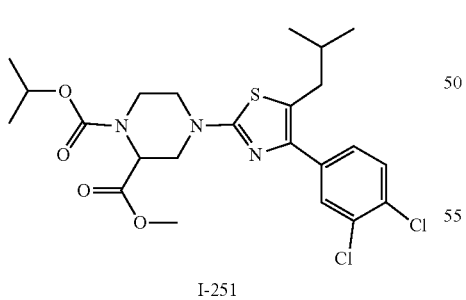

I-251

To a mixture of 316-s (50.0 mg, 0.117 mmol) and Et₃N (23.6 mg, 0.234 mmol) in CH₂Cl₂ (5.0 mL) was added isopropyl carbonochloridate (17.2 mg, 0.140 mmol). The reaction was stirred at room temperature for 1 h. When the reaction was completed, it was concentrated and purified by prep-TLC (petrol ether/ethyl acetate=8/1) to afford 326-1 (50.0 mg, 83% yield) as a yellow solid.

Synthesis of 4-(4-(3,4-dichlorophenyl)-5-isobutylthiazol-2-yl)-1-(isopropoxycarbonyl)piperazine-2-carboxylic acid (I-253)

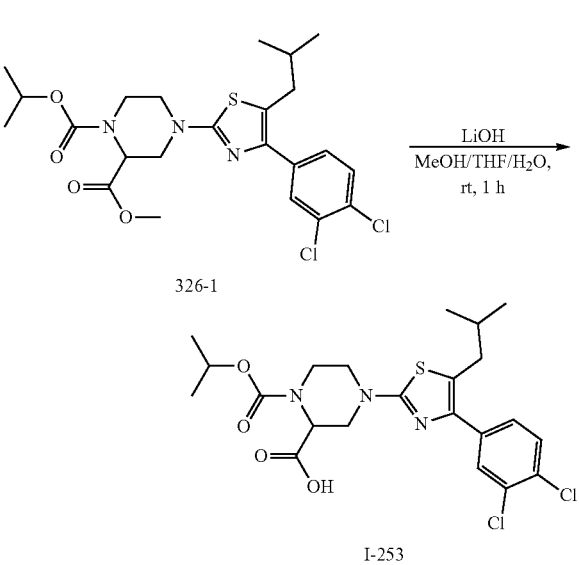 [SMILES: COC(=O)C1CN(c2nc(-c3ccc(Cl)c(Cl)c3)c(CC(C)C)s2)CCN1C(=O)OC(C)C ; "LiOH" ; CC(C)Cc1sc(N2CCN(C(=O)OC(C)C)C(C(=O)O)C2)nc1-c1ccc(Cl)c(Cl)c1]

To a solution of 326-1 (50.0 mg, 0.0972 mmol) in THF/MeOH/H₂O (v/v/v=4/1/1, 1.0 mL) was added LiOH (2.0 M in H₂O, 0.121 mL). The reaction was stirred at room temperature for 1 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-253 (30.0 mg, 62% yield) as a white solid.

Synthesis of 2-amino-4-(3,4-dichlorophenyl)thiazole-5-carbonitrile (341-2)

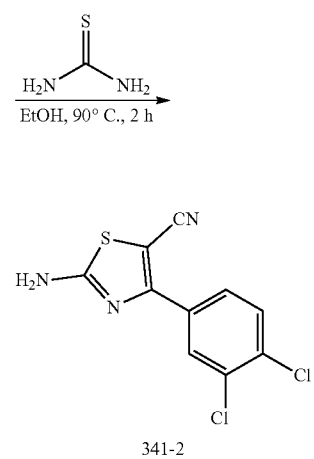

A mixture of 341-1 (1.00 g, 4.67 mmol) and thiourea (427 mg, 5.61 mmol) in EtOH (50.0 mL) was stirred at 90° C. for 2 h. When the reaction was completed, it was concentrated to give a crude product, which was purified by silica gel column chromatography (petrol ether/ethyl acetate=5/1) to afford 341-2 (1.10 g, 87% yield) as a white solid.

Synthesis of 2-bromo-4-(3,4-dichlorophenyl)thiazole-5-carbonitrile (341-3)

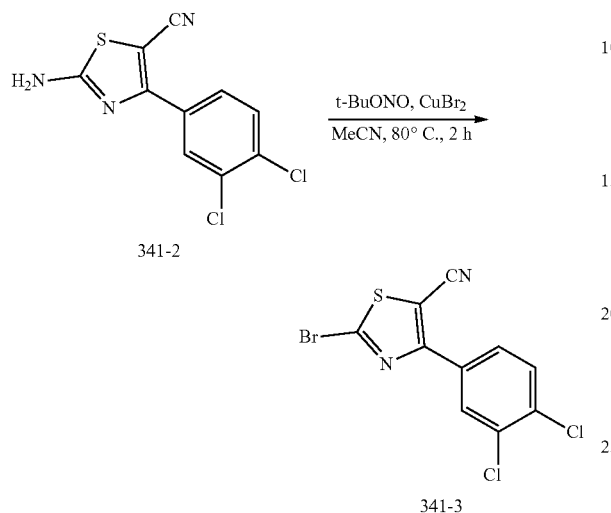

A mixture of 341-2 (900 mg, 3.33 mmol), tert-Butyl nitrite (412 mg, 4.00 mmol) and CuBr$_2$ (446 mg, 2.00 mmol) in MeCN (20.0 mL) was stirred at 80° C. for 2 h. When the reaction was completed, it was poured into H$_2$O (100 mL), and then extracted with EtOAc (200 mL×2). The organic layer was combined, and washed with H$_2$O (80.0 mL×2) and Brine (50.0 mL), then dried by anhydrous Na$_2$SO$_4$. The solution was concentrated and purified by silica gel column chromatography (petrol ether/ethyl acetate=20/1) to afford 341-3 (950 mg, 85% yield) as a yellow solid.

Synthesis of 2-bromo-4-(3,4-dichlorophenyl)-5-(1H-tetrazol-5-yl)thiazole (341-4)

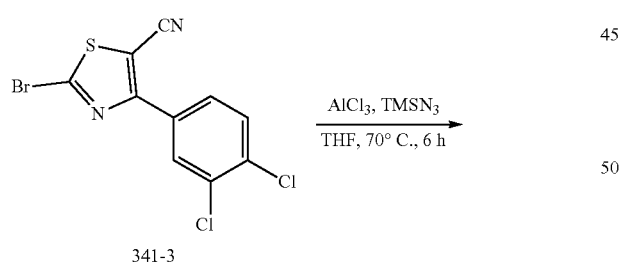

A mixture of 341-3 (1.00 g, 2.99 mmol), TMSN$_3$ (1.72 g, 15.0 mmol) and AlCl$_3$ (397 mg, 2.99 mmol) in THF (100 mL) was stirred at 70° C. for 6 h. When the reaction was completed, it was concentrated and purified by silica gel column chromatography (petrol ether/ethyl acetate=5/1) to afford 341-4 (1.00 g, 89% yield) as a yellow solid.

Synthesis of 2-bromo-4-(3,4-dichlorophenyl)-5-(1-methyl-1H-tetrazol-5-yl)thiazole (341-5)

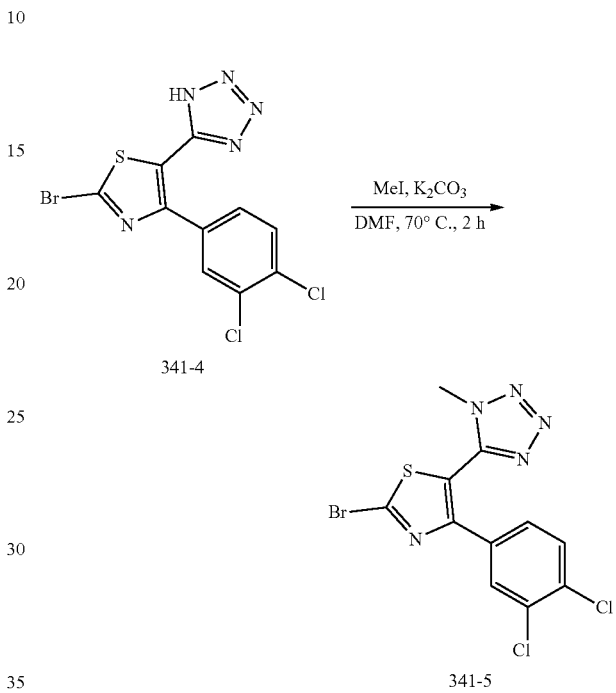

A mixture of 341-4 (600 mg, 1.59 mmol), MeI (271 mg, 1.91 mmol) and K$_2$CO$_3$ (439 mg, 3.18 mmol) in DMF (5 mL) was stirred at 70° C. for 2 h. When the reaction was completed, it was poured into H$_2$O (100 mL), and then extracted with EtOAc (100 mL×2). The organic layer was combined, and washed with H$_2$O (80 mL×2) and Brine (80 mL), then dried by anhydrous Na$_2$SO$_4$. The solution was concentrated and purified by silica gel column chromatography (petrol ether/ethyl acetate=10/1) to afford 341-5 (500 mg, 80% yield) as an off-white solid.

Synthesis of methyl 2-(4-(3,4-dichlorophenyl)-5-(1-methyl-1H-tetrazol-5-yl)thiazol-2-ylamino)nicotinate (341-6)

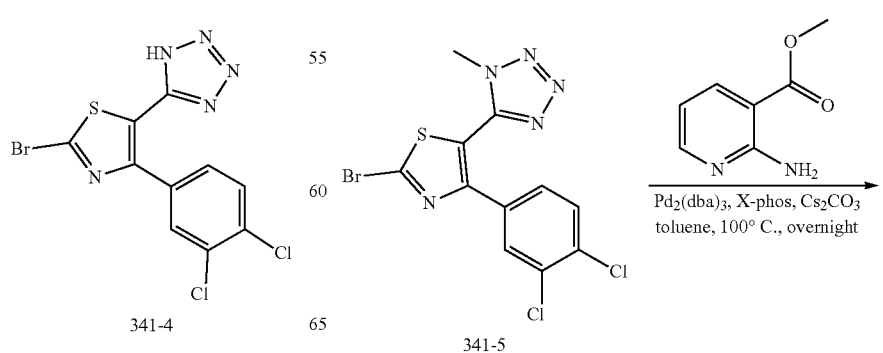

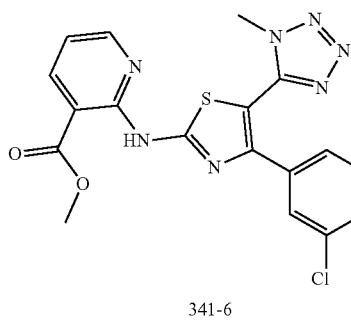

341-6

A mixture of 341-5 (100 mg, 0.256 mmol), methyl 2-aminonicotinate (46.7 mg, 0.307 mmol), Pd$_2$(dba)$_3$ (47.6 mg, 0.0511 mmol), X-phos (36.9 mg, 0.0639 mmol) and Cs$_2$CO$_3$ (167 mg, 0.511 mmol) in toluene (20.0 mL) was stirred under N$_2$ atmosphere at 100° C. overnight. When the reaction was completed, it was concentrated and purified by washing with EtOAc (3.0 mL×3) to afford 341-6 (60.0 mg, 51% yield) as a yellow solid.

Synthesis of 2-(4-(3,4-dichlorophenyl)-5-(1-methyl-1H-tetrazol-5-yl)thiazol-2-ylamino)nicotinic acid (I-257)

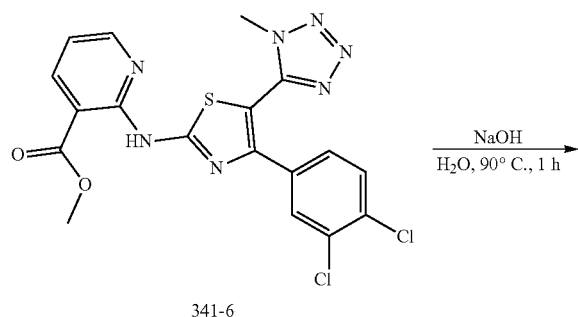

To a solution of 341-6 (60.0 mg, 0.130 mmol) in H$_2$O (1.0 mL) was added NaOH (5.0 M in H$_2$O, 0.130 mL). The reaction was stirred at 90° C. for 1 h. When the reaction was completed, the resulting reaction was adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-257 (30.0 mg, 52% yield) as a white solid.

Synthesis of 2-(4-(3,4-dichlorophenyl)-5-isopropylthiazol-2-ylamino)-5-phenylnicotinic acid (I-259)

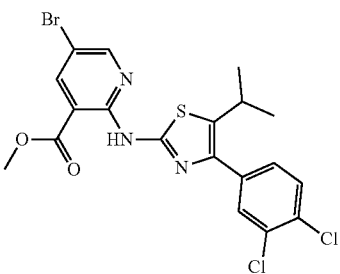 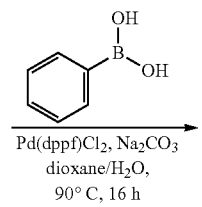

344-s

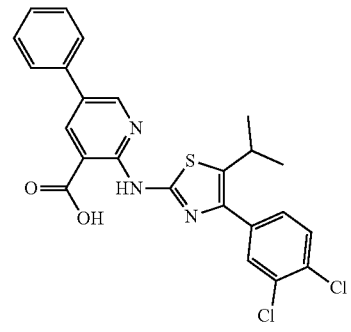

I-259

A mixture of 344-s (200 mg, 0.399 mmol), phenylboronic acid (73.0 mg, 0.599 mmol), Pd(dppf)Cl$_2$ (58.3 mg, 0.0798 mmol) and Na$_2$CO$_3$ (84.6 mg, 0.798 mmol) in dioxane/H$_2$O (v/v=5/1, 20.0 mL) was stirred under N$_2$ atmosphere at 90° C. for 16 h. When the reaction was completed, it was concentrated and purified by prep-HPLC to afford I-259 (20.0 mg, 10% yield) as a white solid.

Synthesis of methyl 5-bromo-2-(4-(4-chloro-3-(trifluoromethyl)phenyl)-5-isopropylthiazol-2-ylamino)nicotinate (347-2)

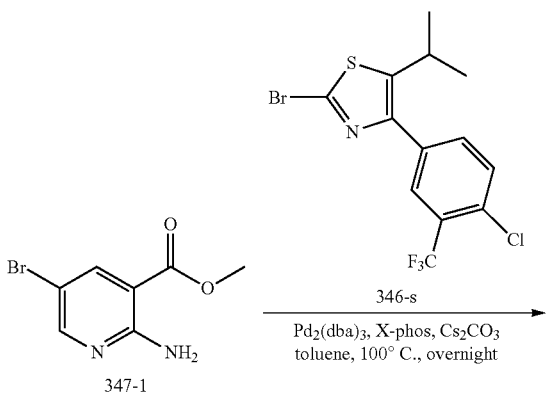

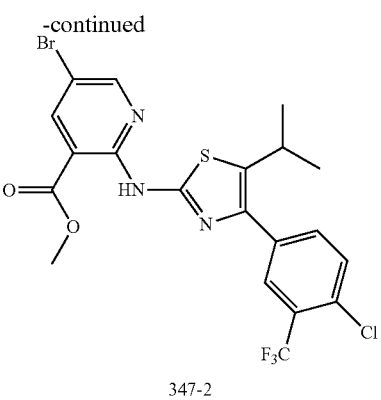

347-2

A mixture of 347-1 (200 mg, 0.866 mmol), 346-s (333 mg, 0.866 mmol), Pd$_2$(dba)$_3$ (16.1 mg, 0.0173 mmol), X-phos (12.5 mg, 0.0217 mmol) and Cs$_2$CO$_3$ (564 mg, 1.73 mmol) in toluene (10.0 mL) was stirred under N$_2$ atmosphere at 100° C. overnight. When the reaction was completed, it was concentrated and purified by silica gel column chromatography (petrol ether/ethyl acetate=50/1) to afford 347-2 (200 mg, 43% yield) as a yellow solid.

Synthesis of 2-(4-(4-chloro-3-(trifluoromethyl)phenyl)-5-isopropylthiazol-2-ylamino)-5-phenylnicotinic acid (I-262)

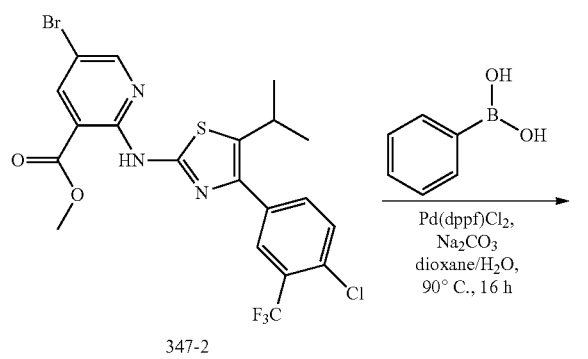

I-262

A mixture of 347-2 (100 mg, 0.187 mmol), phenylboronic acid (34.2 mg, 0.280 mmol), Pd(dppf)Cl$_2$ (27.3 mg, 0.0374 mmol) and Na$_2$CO$_3$ (39.6 mg, 0.374 mmol) in dioxane/H$_2$O (v/v=5/1, 5.0 mL) was stirred under N$_2$ atmosphere at 90° C. for 16 h. When the reaction was completed, it was concentrated and purified by prep-HPLC to afford I-262 (20.0 mg, 21% yield) as a white solid.

Synthesis of methyl 3-(4-(3,4-dichlorophenyl)-5-(1-methyl-1H-tetrazol-5-yl)thiazol-2-ylamino)thiophene-2-carboxylate (355-2)

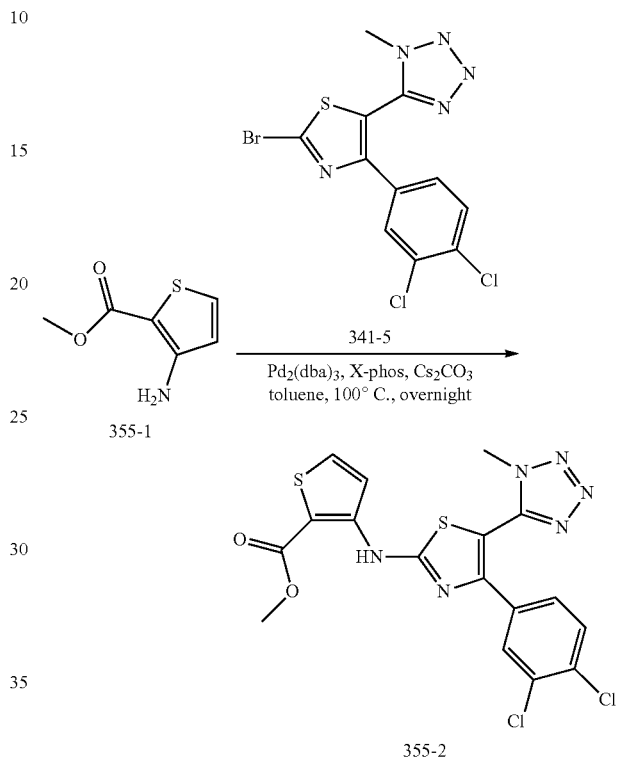

355-2

A mixture of 355-1 (48.2 mg, 0.307 mmol), 341-5 (100 mg, 0.256 mmol), Pd$_2$(dba)$_3$ (47.6 mg, 0.0511 mmol), X-phos (36.9 mg, 0.0639 mmol) and Cs$_2$CO$_3$ (167 mg, 0.511 mmol) in toluene (10.0 mL) was stirred under N$_2$ atmosphere at 100° C. overnight. When the reaction was completed, it was concentrated and purified by washing with EtOAc (3.0 mL×3) to afford 355-2 (100 mg, 84% yield) as a yellow solid.

Synthesis of 3-(4-(3,4-dichlorophenyl)-5-(1-methyl-1H-tetrazol-5-yl)thiazol-2-ylamino)thiophene-2-carboxylic acid (I-269)

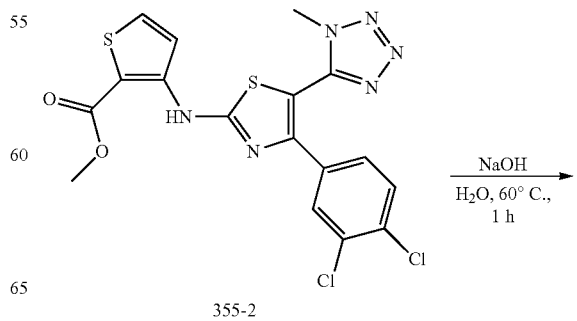

355-2

-continued

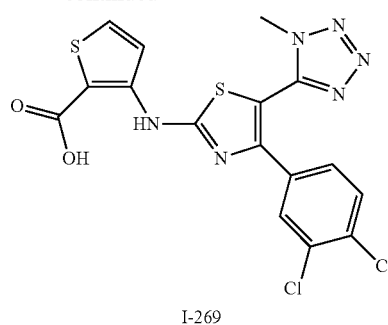

I-269

To a solution of 355-2 (100 mg, 0.214 mmol) in H₂O (1.0 mL) was added NaOH (5.0 M in H₂O, 0.267 mL). The reaction was stirred at 60° C. for 1 h. When the reaction was completed, the resulting reaction was adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-269 (20.0 mg, 21% yield) as a white solid.

Synthesis of methyl 3-(tert-butoxycarbonyl(4-(3,4-dichlorophenyl)-5-isobutylthiazol-2-yl)amino)thiophene-2-carboxylate (363-1)

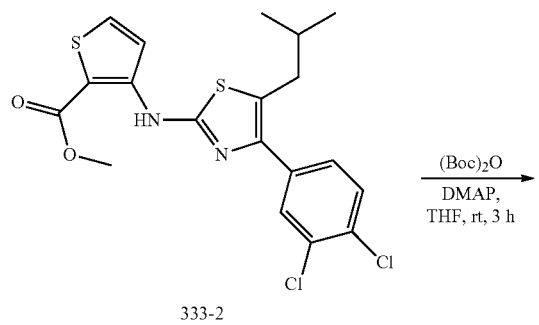

A mixture of 333-2 (1.30 g, 2.95 mmol), (Boc)₂O (669 mg, 3.09 mmol) and DMAP (378 mg, 3.09 mmol) in THF (50.0 mL) was stirred at room temperature for 3 h. When the reaction was completed, it was concentrated to give a crude product, which was purified by silica gel column chromatography (petrol ether/ethyl acetate=10/1) to afford 363-1 (1.10 g, 69% yield) as a white solid.

Synthesis of 3-(tert-butoxycarbonyl(4-(3,4-dichlorophenyl)-5-isobutylthiazol-2-yl)amino)thiophene-2-carboxylic acid (363-2)

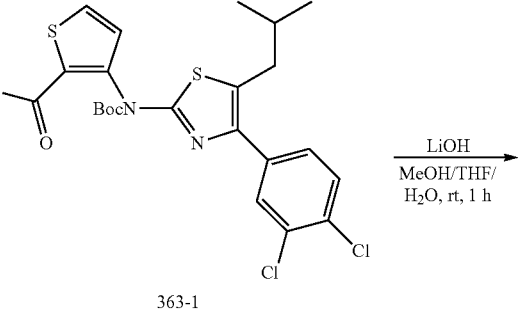

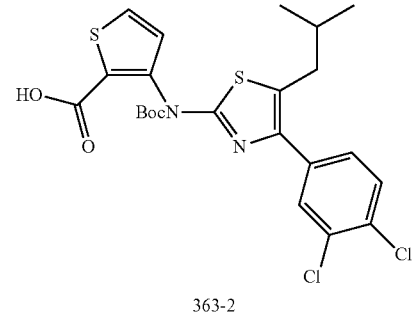

363-2

To a solution of 363-1 (1.10 g, 2.03 mmol) in THF/MeOH/H₂O (v/v/v=4/1/1, 10.0 mL) was added LiOH (2.0 M in H₂O, 2.54 mL). The reaction was stirred at room temperature for 1 h. When the reaction was completed, the resulting reaction was concentrated, then it was diluted with H₂O (50.0 mL) and adjusted pH to 6-7 with HCl (1.0 M). The mixture was extracted with EtOAc (100.0 mL×2), and the combined organic phase washed with brine (50.0 mL), dried by anhydrous Na₂SO₄, and concentrated, the residue was purified by prep-HPLC to afford 363-2 (800 mg, 75% yield) as a white solid.

Synthesis of tert-butyl 2-(2-(3-tert-butylureido)ethylcarbamoyl)thiophen-3-yl(4-(3,4-dichlorophenyl)-5-isobutylthiazol-2-yl)carbamate (363-3)

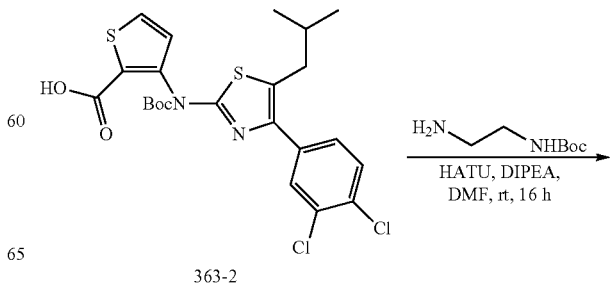

599

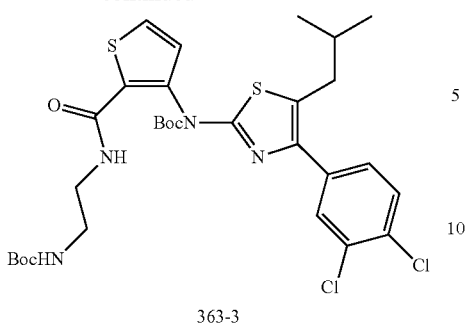

363-3

A mixture of 363-2 (200 mg, 0.379 mmol), tert-butyl 2-aminoethylcarbamate (72.9 mg, 0.455 mmol), HATU (288 mg, 0.758 mmol) and DIPEA (147 mg, 1.14 mmol) in DMF (5.0 mL) was stirred at room temperature for 16 h. When the reaction was completed, it was poured into H$_2$O (100 mL), and then extracted with EtOAc (100 mL×2). The organic layer was combined, and washed with H$_2$O (100 mL×2) and Brine (50 mL), then dried by anhydrous Na$_2$SO$_4$. The solution was concentrated to give a crude product, which was purified by prep-TLC (CH$_2$Cl$_2$/MeOH=100/1) to afford 363-3 (140 mg, 55% yield) as a yellow solid.

Synthesis of N-(2-aminoethyl)-3-(4-(3,4-dichlorophenyl)-5-isobutylthiazol-2-ylamino)thiophene-2-carboxamide (I-276)

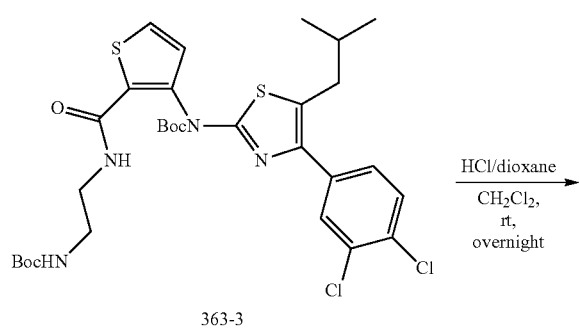

A mixture of 363-3 (140 mg, 0.209 mmol) in HCl (4.0 M in dioxane, 5.0 mL) was stirred at room temperature overnight. When the reaction was completed, it was concentrated to give a crude product, which was purified by recrystallization to afford I-276 (70.0 mg, 71% yield) as a yellow solid.

600

Synthesis of methyl 5-bromo-3-(4-(4-chloro-3-(trifluoromethyl)phenyl)-5-isopropylthiazol-2-ylamino)thiophene-2-carboxylate (367-2)

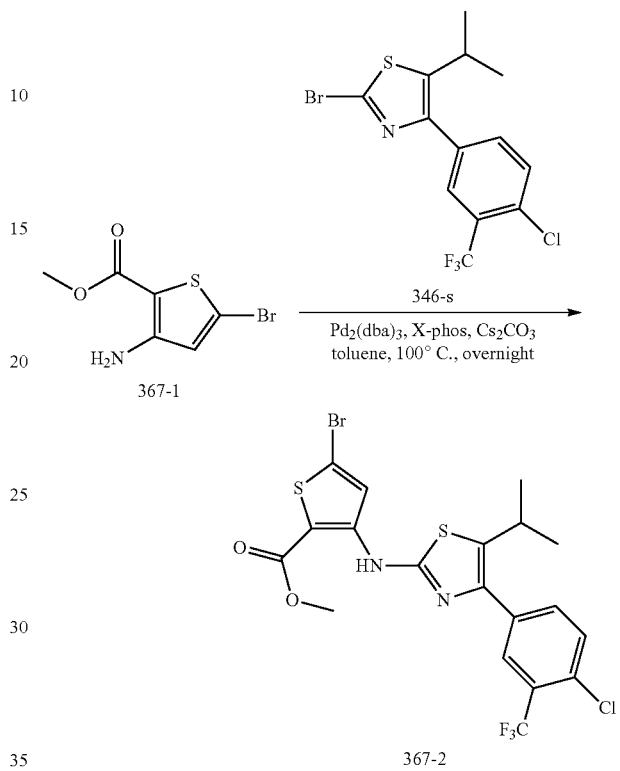

A mixture of 367-1 (368 mg, 1.56 mmol), 346-s (500 mg, 1.30 mmol), Pd$_2$(dba)$_3$ (242 mg, 0.260 mmol), X-phos (188 mg, 0.325 mmol) and Cs$_2$CO$_3$ (847 mg, 2.60 mmol) in toluene (50.0 mL) was stirred under N$_2$ atmosphere at 100° C. overnight. When the reaction was completed, it was concentrated and purified by silica gel column chromatography (petrol ether/ethyl acetate=20/1) to afford 367-2 (300 mg, 43% yield) as a yellow solid.

Synthesis of methyl 3-(4-(4-chloro-3-(trifluoromethyl)phenyl)-5-isopropylthiazol-2-ylamino)-5-phenylthiophene-2-carboxylate (367-3)

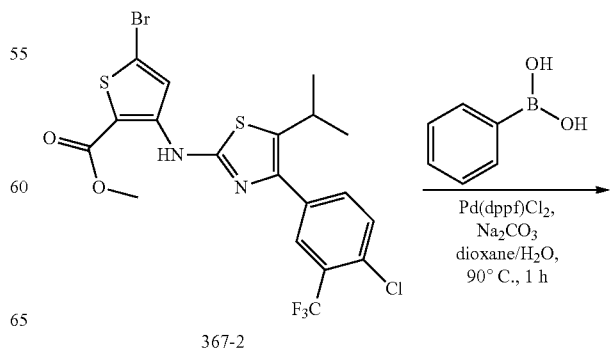

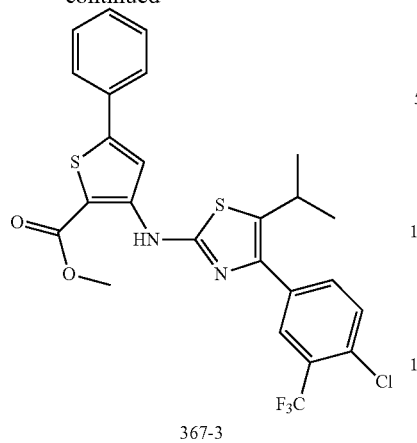

367-3

A mixture of 367-2 (100 mg, 0.185 mmol), phenylboronic acid (33.9 mg, 0.278 mmol), Pd(dppf)Cl₂ (27.0 mg, 0.037 mmol) and Na₂CO₃ (39.2 mg, 0.371 mmol) in dioxane/H₂O (v/v=5/1, 2.0 mL) was stirred under N₂ atmosphere at 90° C. for 1 h. When the reaction was completed, it was concentrated and purified by prep-TLC (petrol ether/ethyl acetate=8/1) to afford 367-3 (80.0 mg, 80% yield) as a yellow solid.

Synthesis of 3-(4-(4-chloro-3-(trifluoromethyl)phenyl)-5-isopropylthiazol-2-ylamino)-5-phenylthiophene-2-carboxylic acid (I-279)

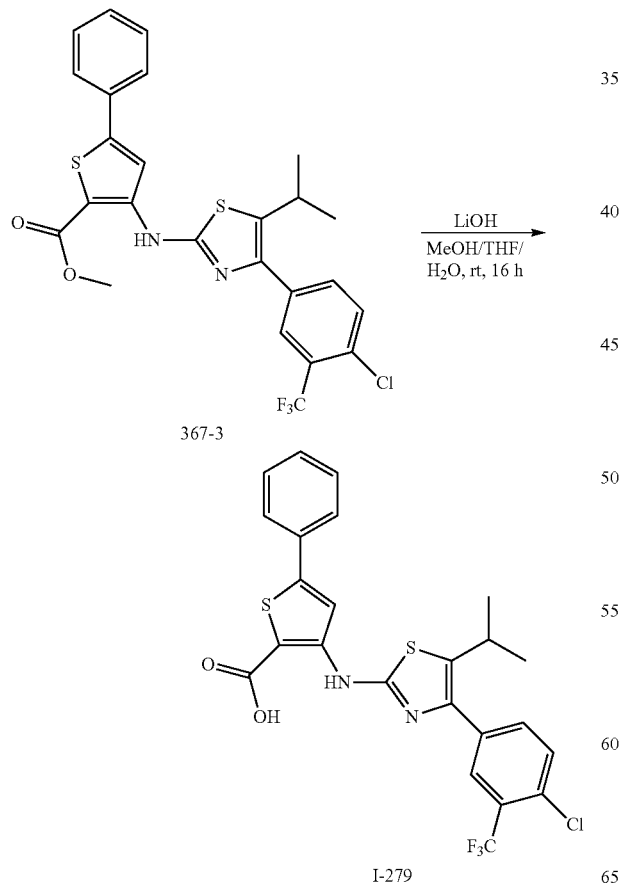

To a solution of 367-3 (80.0 mg, 0.149 mmol) in THF/MeOH/H₂O (v/v/v=4/1/1, 1.0 mL) was added LiOH (2.0 M in H₂O, 0.186 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-279 (5.0 mg, 6.4% yield) as a yellow solid.

Synthesis of methyl 6'-(4-(3,4-dichlorophenyl)-5-isopropylthiazol-2-ylamino)-2,3'-bipyridine-5'-carboxylate (377-1)

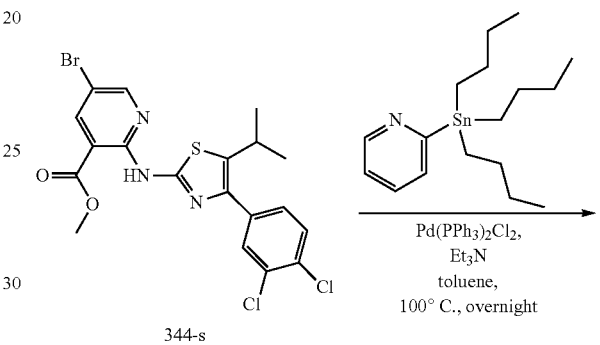

344-s 377-1

A mixture of 344-s (100 mg, 0.200 mmol), 2-(tributylstannyl)pyridine (110 mg, 0.299 mmol), Pd(PPh₃)₂Cl₂ (28.0 mg, 0.0399 mmol) and Et₃N (40.3 mg, 0.399 mmol) in toluene (10.0 mL) was stirred under N₂ atmosphere at 100° C. overnight. When the reaction was completed, it was concentrated and purified by prep-TLC (CH₂Cl₂/MeOH=100/1) to afford 377-1 (50.0 mg, 50% yield) as a yellow solid.

603

Synthesis of 6'-(4-(3,4-dichlorophenyl)-5-isopropylthiazol-2-ylamino)-2,3'-bipyridine-5'-carboxylic acid (I-282)

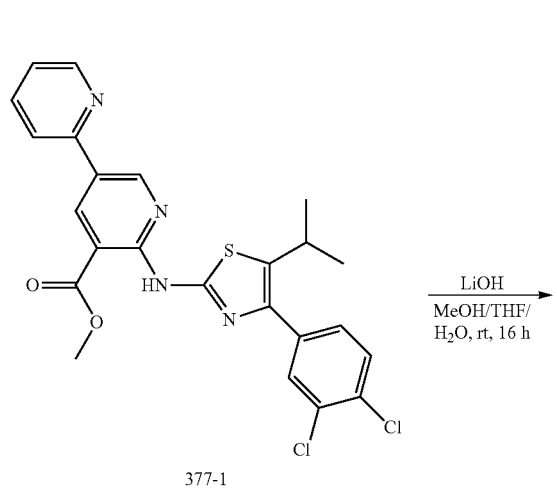

To a solution of 377-1 (50.0 mg, 0.100 mmol) in THF/MeOH/H₂O v/v/v 4/1/1, 1.0 mL) was added LiOH (2.0 M in H₂O, 0.125 mL). The reaction was stirred at room temperature for 16 h. When the reaction was completed, the resulting reaction was concentrated, then it was diluted with H₂O (5.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-282 (20.0 mg, 41% yield) as a white solid.

604

Synthesis of 2-(4-(3,4-dichlorophenyl)-5-isopropylthiazol-2-ylamino)nicotinonitrile (379-2)

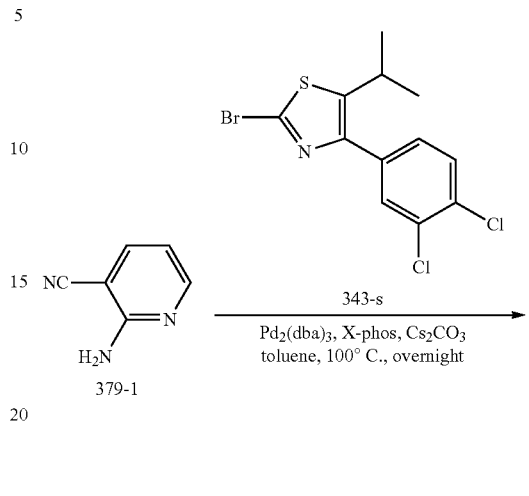

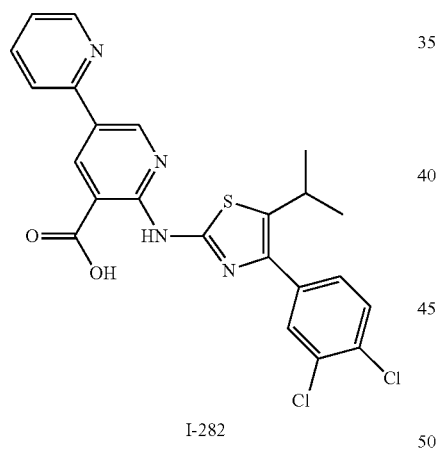

A mixture of 379-1 (61.1 mg, 0.513 mmol), 343-s (150 mg, 0.427 mmol), Pd₂(dba)₃ (79.5 mg, 0.0854 mmol), X-phos (61.7 mg, 0.107 mmol) and Cs₂CO₃ (278 mg, 0.854 mmol) in toluene (5.0 mL) was stirred under N₂ atmosphere at 100° C. overnight. When the reaction was completed, it was concentrated and purified by silica gel column chromatography (petrol ether/ethyl acetate=8/1) to afford 379-2 (120 mg, 72% yield) as a yellow solid.

Synthesis of 2-(4-(3,4-dichlorophenyl)-5-isopropylthiazol-2-ylamino)nicotinimidamide (I-284)

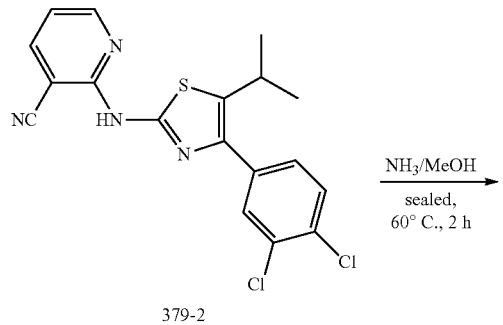

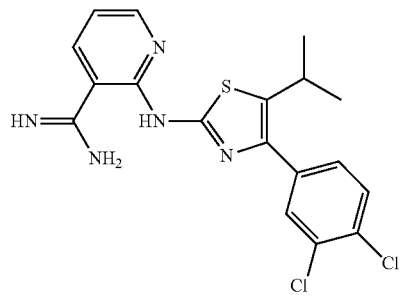

A mixture of 379-2 (120 mg, 0.131 mmol) and NH$_3$ (7.0 M in MeOH, 1.00 mL) was stirred sealed at 60° C. for 2 h. When the reaction was completed, the mixture was concentrated and purified by prep-HPLC to afford I-284 (70.0 mg, 56% yield) as a white solid.

Characterization Data for Additional Exemplary Compounds

| I-# | Chemical Structure | LCMS | $^1$H NMR (400 MHz, d$_6$-DMSO) |
|---|---|---|---|
| 199 | 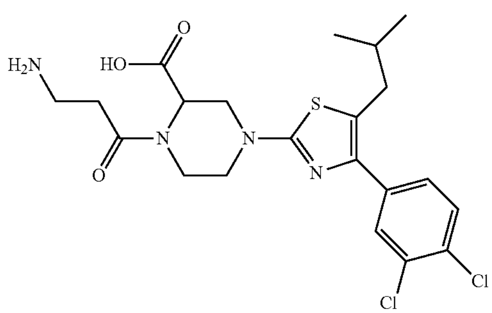 [SMILES: CC(C)Cc1sc(N2CCN(C(=O)CCN)C(C(=O)O)C2)nc1-c1ccc(Cl)c(Cl)c1] | Method C, Purity is 95.5%, Rt = 2.002 min; MS Calcd.: 484.1; MS Found: 485.1 [M + H]$^+$. | δ: 0.79-0.86 (6H, m), 1.70-1.77 (1H, m), 2.60-2.62 (4H, d, J = 7.2 Hz), 2.77-3.17 (5H, m), 3.74-3.89 (2H, m), 4.15-4.28 (2H, m), 7.47-7.49 (1H, d, J = 8.4 Hz), 7.63-7.65 (1H, d, J = 8.4 Hz), 7.70 (1H, s). |
| 200 | 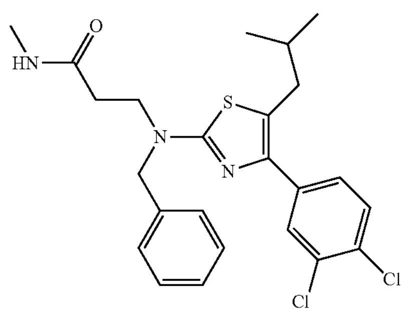 [SMILES: CNC(=O)CCN(Cc1ccccc1)c1nc(-c2ccc(Cl)c(Cl)c2)c(CC(C)C)s1] | Method C, Purity is 100%, Rt = 2.906 min; MS Calcd.: 475.1; MS Found: 476.0 [M + H]$^+$. | δ: 0.88 (6H, d, J = 6.4 Hz), 1.72-1.75 (1H, m), 2.44-2.61 (7H, m), 2.43 (3H, s), 3.62 (2H, t, J = 6.4, 6.4 Hz), 2.71-2.76 (1H, m), 4.6 (1H, s), 7.26-7.35 (5H, m), 7.51 (1H, d, J = 8.8 Hz), 7.62-7.73 (2H, m), 7.88 (1H, d, J = 10.8 Hz). |
| 201 | 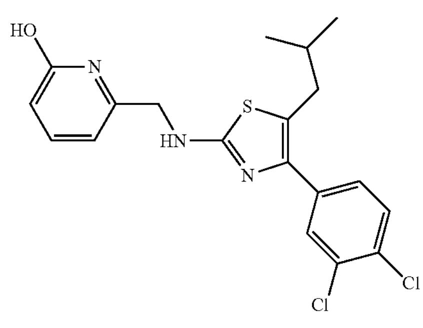 [SMILES: CC(C)Cc1sc(NCc2cccc(O)n2)nc1-c1ccc(Cl)c(Cl)c1] | Method C, Purity is 100%, Rt = 2.443 min; MS Calcd.: 407.1; MS Found: 408.0 [M + H]$^+$. | δ: 0.88 (6H, d, J = 6.4 Hz), 1.71-1.79 (1H, m), 2.62-2.67 (2H, m), 4.30 (2H, brs), 5.95-6.20 (2H, m), 3.29-3.30 (2H, m), 7.29-7.39 (1H, m), 7.44-7.46 (1H, dd, J = 2.0, 2.0 Hz), 7.48-7.53 (1H, m), 7.63-7.76 (2H, m), 11.74 (1H, brs). |

-continued

| I-# | Chemical Structure | LCMS | ¹H NMR (400 MHz, d₆-DMSO) |
|---|---|---|---|
| 202 | 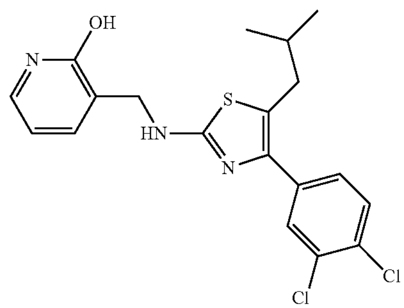 [SMILES: CC(C)Cc1sc(NCc2cccnc2O)nc1-c1ccc(Cl)c(Cl)c1] | Method C, Purity is 100%, Rt = 2.298 min; MS Calcd.: 407.1; MS Found: 408.0 [M + H]⁺. | δ: 0.87 (6H, d, J = 6.4 Hz), 1.71-1.77 (1H, m), 2.59 (2H, d, J = 6.8 Hz), 4.20 (2H, d, J = 5.6 Hz), 6.17 (1H, t, J = 6.8 Hz), 7.30 (1H, dd, J = 2.0, 2.0 Hz), 7.38 (1H, dd, J = 1.2, 0.8 Hz), 7.48 (1H, d, J = 2.0 Hz), 7.50 (1H, d, J = 2.0 Hz), 7.64-7.66 (1H, m), 7.83 (1H, t, J = 5.6 Hz). |
| 203 | 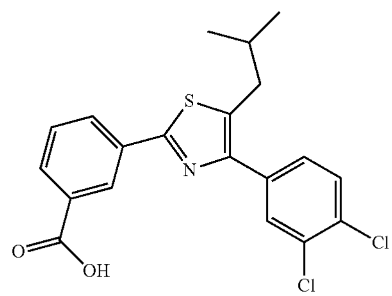 [SMILES: CC(C)Cc1sc(-c2cccc(C(=O)O)c2)nc1-c1ccc(Cl)c(Cl)c1] | Method B, Purity is 97.1%, Rt = 2.363 min; MS Calcd.: 405.1; MS Found: 406.1 [M + H]⁺. | δ: 0.90 (6H, d, J = 6.4 Hz), 1.85-1.92 (1H, m), 2.86 (2H, d, J = 7.2 Hz), 7.61-7.67 (2H, m), 7.74 (1H, d, J = 8.4 Hz), 7.89 (1H, d, J = 2.0 Hz), 8.01-8.03 (1H, m), 8.16 (1H, d, J = 8.0 Hz), 8.44 (1H, t, J = 1.6 Hz), 13.29 (1H, brs). |
| 204 | 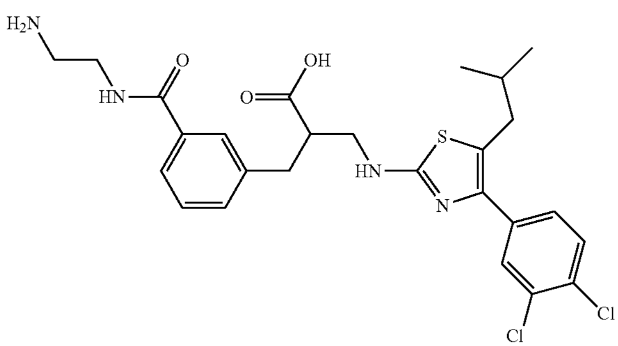 [SMILES: CC(C)Cc1sc(NCC(Cc2cccc(C(=O)NCCN)c2)C(=O)O)nc1-c1ccc(Cl)c(Cl)c1] | Method C, Purity is 100%, Rt = 2.035 min; MS Calcd.: 549.5; MS Found: 550.2 [M + H]⁺. | δ: 0.84 (6H, d, J = 6.4 Hz), 1.65-1.75 (1H, m), 2.54 (2H, d, J = 6.8 Hz), 2.55-2.77 (4H, m), 2.96-3.33 (4H, m), 7.23-7.43 (3H, m), 7.59-7.78 (5H, m), 8.90 (1H, brs). |
| 205 | 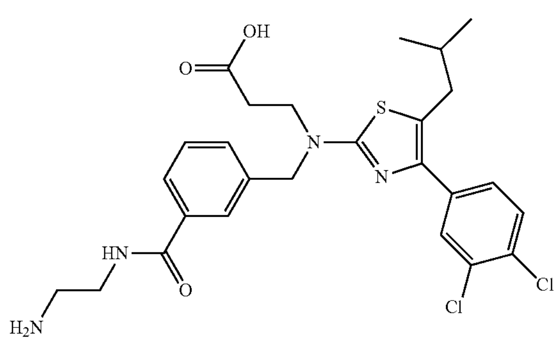 [SMILES: CC(C)Cc1sc(N(CCC(=O)O)Cc2cccc(C(=O)NCCN)c2)nc1-c1ccc(Cl)c(Cl)c1] | Method C, Purity is 100%, Rt = 2.157 min; MS Calcd.: 548.1; MS Found: 549.2 [M + H]⁺. | δ: 0.85 (6H, d, J = 6.4 Hz), 1.69-1.76 (1H, m), 2.26 (2H, s), 2.57-2.59 (2H, d, J = 7.2 Hz), 2.87 (1H, m), 3.24 (2H, m), 3.69 (2H, m), 4.64 (1H, s), 7.35-7.39 (1H, t, J = 15.2, 7.6 Hz), 7.45-7.47 (2H, dd, J = 8.0, 1.6 Hz), 7.61-7.66 (3H, m), 7.93 (1H, s), 9.09 (1H, s). |

-continued

Characterization Data for Additional Exemplary Compounds

| I-# | Chemical Structure | LCMS | $^1$H NMR (400 MHz, d$_6$-DMSO) |
|---|---|---|---|
| 206 | 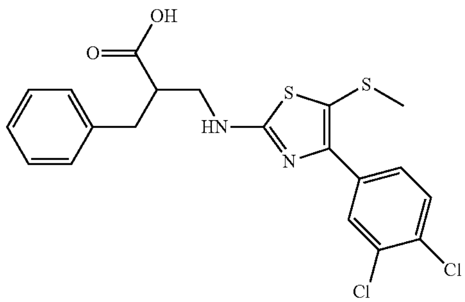 [SMILES: CSc1sc(NCC(Cc2ccccc2)C(=O)O)nc1-c1ccc(Cl)c(Cl)c1] | Method C, Purity is 100%, Rt = 2.051 min; MS Calcd.: 453.4; MS Found: 454.0 [M + H]$^+$. | δ: 2.33-2.34 (4H, m), 2.66-2.80 (2H, m), 2.88-2.94 (2H, m), 7.17-7.30 (5H, m), 7.67-7.69 (1H, m), 7.89-7.92 (1H, m), 8.10-8.14 (2H, m). |
| 207 | 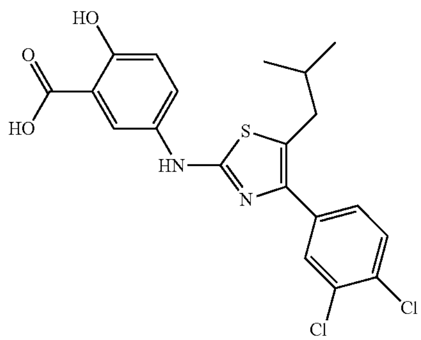 [SMILES: CC(C)Cc1sc(Nc2ccc(O)c(C(=O)O)c2)nc1-c1ccc(Cl)c(Cl)c1] | Method B, Purity is 98.7%, Rt = 2.206 min; MS Calcd.: 436.0; MS Found: 437.0 [M + H]$^+$. | δ: 0.90 (6H, d, J = 6.4 Hz), 1.77-1.80 (1H, m), 2.65 (2H, d, J = 6.8 Hz), 6.73-6.77 (1H, m), 7.51-7.58 (2H, m), 7.68-7.70 (2H, m), 7.80 (1H, s), 7.95-7.97 (1H, m), 9.79-9.81 (1H, m). |
| 208 | 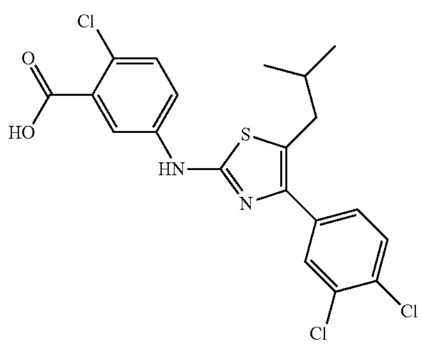 [SMILES: CC(C)Cc1sc(Nc2ccc(Cl)c(C(=O)O)c2)nc1-c1ccc(Cl)c(Cl)c1] | Method C, Purity is 100%, Rt = 2.033 min; MS Calcd.: 454.0; MS Found: 455.0 [M + H]$^+$. | δ: 0.87 (6H, d, J = 6.4 Hz), 1.76-1.79 (1H, m), 2.65 (2H, d, J = 7.2 Hz), 7.11 (1H, d, J = 8.4 Hz), 7.33 (1H, d, J = 2.8 Hz), 7.49-7.56 (2H, m), 7.68 (1H, d, J = 8.4 Hz), 7.75 (1H, d, J = 2.0 Hz), 10.11 (1H, s). |
| 209 | 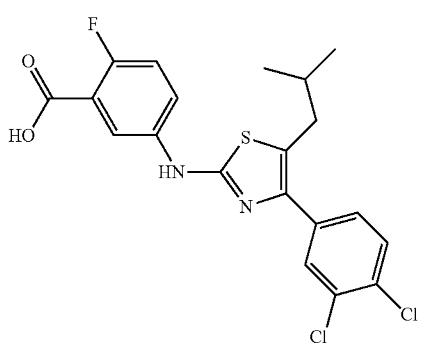 [SMILES: CC(C)Cc1sc(Nc2ccc(F)c(C(=O)O)c2)nc1-c1ccc(Cl)c(Cl)c1] | Method C, Purity is 100%, Rt = 2.028 min; MS Calcd.: 438.0; MS Found: 439.0 [M + H]$^+$. | δ: 0.87 (6H, d, J = 6.4 Hz), 1.76-1.79 (1H, m), 2.68 (2H, d, J = 7.2 Hz), 7.22 (1H, t, J = 10.0 Hz), 7.56-7.58 (1H, m), 7.68 (1H, d, J = 8.4 Hz), 7.77-7.82 (2H, m), 8.14-8.18 (1H, m), 10.30 (1H, s). |

-continued

Characterization Data for Additional Exemplary Compounds

| I-# | Chemical Structure | LCMS | $^1$H NMR (400 MHz, $d_6$-DMSO) |
|---|---|---|---|
| 210 | 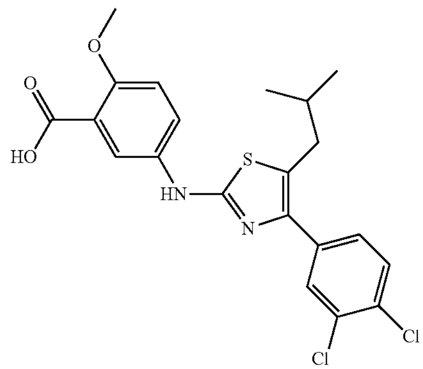 [SMILES: COc1ccc(Nc2nc(-c3ccc(Cl)c(Cl)c3)c(CC(C)C)s2)cc1C(=O)O] | Method B, Purity is 100%, Rt = 2.186 min; MS Calcd.: 450.0; MS Found: 451.0 [M + H]$^+$. | δ: 0.91 (6H, d, J = 6.8 Hz), 1.78-1.82 (1H, m), 2.68 (2H, d, J = 7.2 Hz), 3.78 (3H, s), 7.11 (1H, d, J = 9.2 Hz), 7.58 (1H, d, J = 8.8 Hz), 7.70 (1H, d J = 8.4 Hz), 7.79-7.82 (2H, m), 7.94 (1H, s), 10.09 (1H, s), 12.58 (1H, brs). |
| 211 | 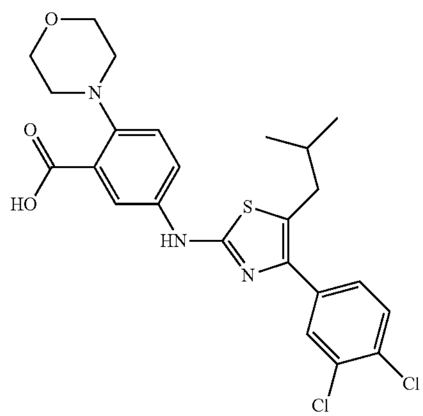 [SMILES: CC(C)Cc1sc(Nc2ccc(N3CCOCC3)c(C(=O)O)c2)nc1-c1ccc(Cl)c(Cl)c1] | Method B, Purity is 100%, Rt = 2.171 min; MS Calcd.: 505.1; MS Found: 506.0 [M + H]$^+$. | δ: 0.91 (6H, d, J = 6.8 Hz), 1.79-1.83 (1H, m), 2.72 (2H, d, J = 7.2 Hz), 3.04-3.05 (3H, s), 7.11 (1H, d, J = 9.2 Hz), 7.58 (1H, d, J = 8.8 Hz), 7.70 (1H, d J = 8.4 Hz), 7.79-7.82 (2H, m), 7.94 (1H, s), 10.09 (1H, s), 12.58 (1H, brs). |
| 212 | 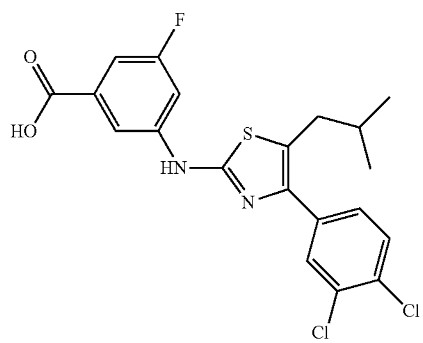 [SMILES: CC(C)Cc1sc(Nc2cc(F)cc(C(=O)O)c2)nc1-c1ccc(Cl)c(Cl)c1] | Method C, Purity is 97.8%, Rt = 2.060 min; MS Calcd.: 438.0; MS Found: 439.2 [M + H]$^+$. | δ: 0.89 (6H, d, J = 6.4 Hz), 1.74-1.85 (1H, m), 2.70 (2H, d, J = 7.2 Hz), 7.15-7.18 (1H, m), 7.58 (1H, dd, J = 8.4, 2.4 Hz), 7.71 (1H, d, J = 8.0 Hz), 7.82 (1H, d, J = 2.0 Hz), 7.88-7.92 (2H, m), 10.63 (1H, brs). |
| 213 | 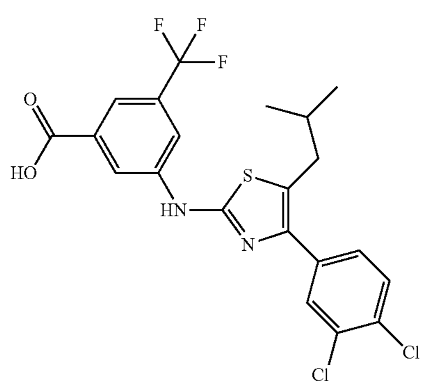 [SMILES: CC(C)Cc1sc(Nc2cc(C(=O)O)cc(C(F)(F)F)c2)nc1-c1ccc(Cl)c(Cl)c1] | Method C, Purity is 97.7%, Rt = 1.875 min; MS Calcd.: 488.0; MS Found: 489.2 [M + H]$^+$. | δ: 0.92 (6H, d, J = 6.4 Hz), 1.79-1.86 (1H, m), 2.75 (2H, d, J = 6.8 Hz), 7.61 (1H, d, J = 8.4 Hz), 7.71-7.73 (2H, m), 7.87 (1H, s), 8.83 (1H, s), 8.48 (1H, s), 10.76 (1H, s). |

-continued

Characterization Data for Additional Exemplary Compounds

| I-# | Chemical Structure | LCMS | ¹H NMR (400 MHz, d₆-DMSO) |
|---|---|---|---|
| 214 | 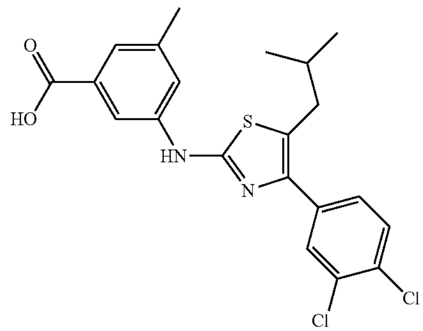 [SMILES: Cc1cc(Nc2nc(-c3ccc(Cl)c(Cl)c3)c(CC(C)C)s2)cc(C(=O)O)c1] | Method C, Purity is 100%, Rt = 2.161 min; MS Calcd.: 434.0; MS Found: 435.0 [M + H]⁺. | δ: 0.89 (6H, d, J = 6.4 Hz), 1.76-1.82 (1H, m), 2.31 (1H, s), 2.69 (2H, d, J = 7.2 Hz), 7.32 (1H, s), 7.59 (2H, d, J = 7.2 Hz), 7.69 (2H, d, J = 8.4 Hz), 7.84 (1H, s), 8.07 (1H,s), 10.26 (1H, s). |
| 215 | 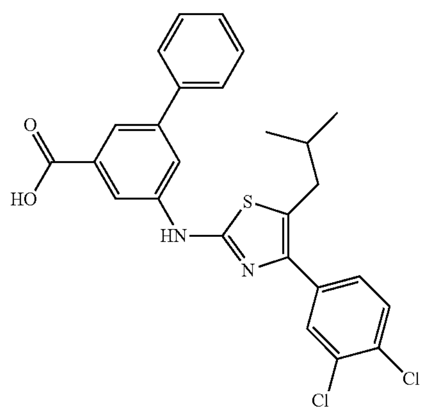 [SMILES: CC(C)Cc1sc(Nc2cc(C(=O)O)cc(-c3ccccc3)c2)nc1-c1ccc(Cl)c(Cl)c1] | Method C, Purity is 98.9%, Rt = 2.216 min; MS Calcd.: 496.0; MS Found: 497.0 [M + H]⁺. | δ: 0.90 (6H, d, J = 6.8 Hz),1.77-1.84 (1H, m), 2.73 (2H, d, J = 6.8 Hz), 7.39 (1H, dd, J = 14.8, 7.2 Hz), 7.49 (2H, dd, J = 15.2, 8.0 Hz), 7.60 (1H, dd, J = 8.4, 2.0 Hz), 7.68 (1H, dd, J = 14.8, 6.8 Hz), 7.75 (1H, s), 7.93 (1H, d, J = 2.0 Hz), 7.83 (1H, s), 8.12 (1H, s), 8.45-8.45 (1H, m), 10.49 (1H, s), 13.05 (1H, s). |
| 216 | 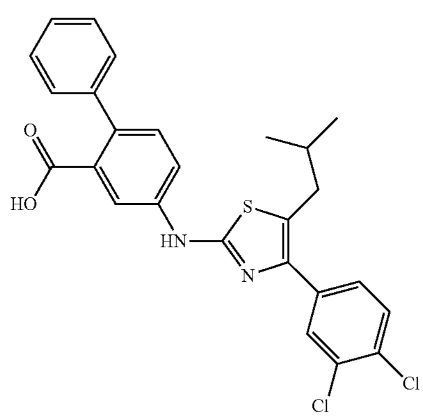 [SMILES: CC(C)Cc1sc(Nc2ccc(-c3ccccc3)c(C(=O)O)c2)nc1-c1ccc(Cl)c(Cl)c1] | Method C, Purity is 96.8%, Rt = 1.839 min; MS Calcd.: 496.0; MS Found: 497.0 [M + H]⁺. | δ: 0.92 (6H, d, J = 6.4 Hz), 1.79-1.85 (1H, m), 2.72 (2H, d, J = 7.2 Hz), 7.28-7.39 (6H, m), 7.61 (1H, d, J = 8.4 Hz), 7.71 (1H, d, J = 8.4 Hz), 7.80 (1H, d, J = 8.4 Hz), 7.83 (1H, s), 8.00 (1H, s), 10.42 (1H, s). |

-continued

Characterization Data for Additional Exemplary Compounds

| I-# | Chemical Structure | LCMS | $^1$H NMR (400 MHz, d$_6$-DMSO) |
|---|---|---|---|
| 217 | 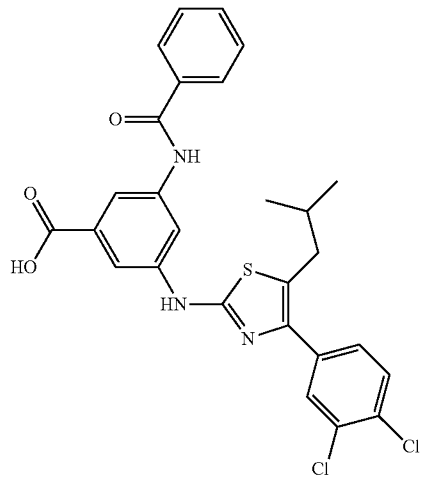 [SMILES: CC(C)Cc1sc(Nc2cc(NC(=O)c3ccccc3)cc(C(=O)O)c2)nc1-c1ccc(Cl)c(Cl)c1] | Method B, Purity is 96.9%, Rt = 2.230 min; MS Calcd.: 539.1; MS Found: 540.2 [M + H]$^+$. | δ: 0.93 (6H, d, J = 6.4 Hz), 1.82-1.85 (1H, m), 2.75 (2H, d, J = 6.8 Hz), 7.53-7.63 (3H, m), 7.66-7.71 (2H, m), 7.88 (1H, s), 8.01-8.05 (4H, m), 8.67 (1H, s), 10.41 (2H, d, J = 10.8 Hz), 12.94 (1H, brs). |
| 218 | 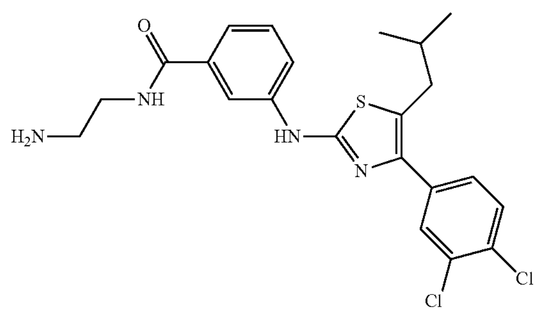 [SMILES: CC(C)Cc1sc(Nc2cccc(C(=O)NCCN)c2)nc1-c1ccc(Cl)c(Cl)c1] | Method C, Purity is 97.9%, Rt = 2.319 min; MS Calcd.: 462.1; MS Found: 463.0 [M + H]$^+$. | δ: 0.91 (6H, d, J = 6.4 Hz), 1.79-1.83 (1H, m), 2.65-2.72 (4H, m), 3.22-3.24 (2H, m), 7.37-7.39 (2H, m), 7.61 (1H, dd, J = 8.4, 2.0 Hz), 7.71 (1H, d, J = 8.4 Hz), 7.79-7.84 (2H, m), 8.06 (1H, s), 8.36 (1H, s), 10.32 (1H, brs). |
| 219 | 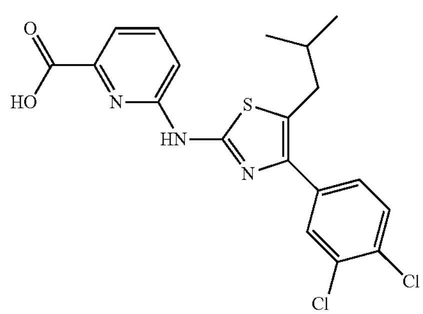 [SMILES: CC(C)Cc1sc(Nc2cccc(C(=O)O)n2)nc1-c1ccc(Cl)c(Cl)c1] | Method C, Purity is 97.8%, Rt = 2.007 min; MS Calcd.: 421.0; MS Found: 422.2 [M + H]$^+$. | δ: 0.92 (6H, d, J = 6.4 Hz), 1.84-1.91 (1H, m), 2.74 (2H, d J = 6.8 Hz), 7.22-7.24 (2H, m), 7.41 (1H, s), 7.59 (1H, d, J = 8.4 Hz), 7.70 (1H, d, J = 8.4 Hz), 7.83 (1H, s), 8.23 (1H, d, J = 9.2 Hz). |
| 220 | 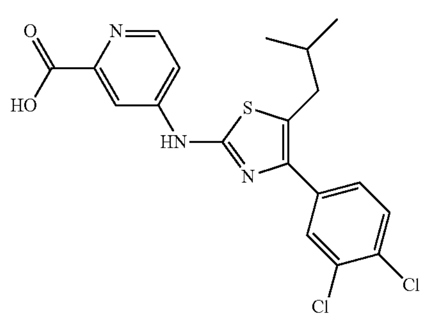 [SMILES: CC(C)Cc1sc(Nc2ccnc(C(=O)O)c2)nc1-c1ccc(Cl)c(Cl)c1] | Method B, Purity is 99.0%, Rt = 1.886 min; MS Calcd.: 421.0; MS Found: 422.0 [M + H]$^+$. | δ: 0.91 (6H, d, J = 6.4 Hz), 1.84 (1H, t, J = J = 6.8 Hz), 2.79 (2H, d, J = 6.8 Hz), 7.63 (1H, d, J = 8.4 Hz), 7.75 (1H, d, J = 8.4 Hz), 7.86 (1H, s), 8.01 (1H, d, J = 5.2 Hz), 8.36 (1H, brs), 8.50 (1H, d, J = 5.2 Hz), 11.63 (1H, brs). |

-continued

| I-# | Chemical Structure | LCMS | ¹H NMR (400 MHz, d₆-DMSO) |
|---|---|---|---|
| 221 | 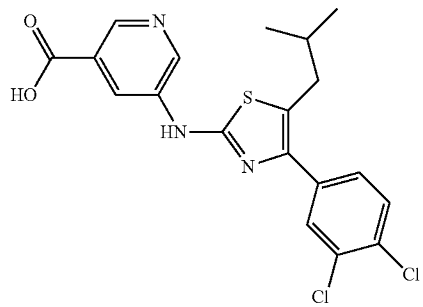 [SMILES: CC(C)Cc1sc(Nc2cncc(C(=O)O)c2)nc1-c1ccc(Cl)c(Cl)c1] | Method C, Purity is 99.6%, Rt = 1.903 min; MS Calcd.: 421.0; MS Found: 422.2 [M + H]⁺. | δ: 0.92 (6H, d, J = 6.4 Hz), 1.81-1.84 (1H, m), 2.74 (2H, d J = 7.2 Hz), 7.61 (1H, dd, J = 8.4, 2.0 Hz), 7.73 (1H, d, J = 8.4 Hz), 7.86 (1H, d, J = 2.0 Hz), 8.63 (1H, d, J = 1.6 Hz), 8.67 (1H, brs), 8.95 (1H, d, J = 2.8 Hz), 10.59 (1H, brs). |
| 222 | 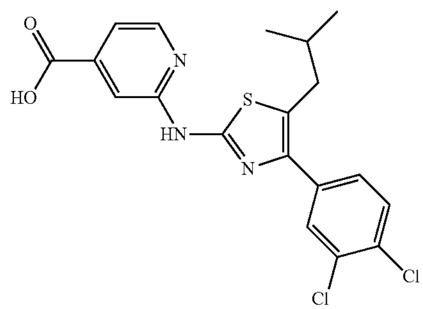 [SMILES: CC(C)Cc1sc(Nc2cc(C(=O)O)ccn2)nc1-c1ccc(Cl)c(Cl)c1] | Method C, Purity is 95.7%, Rt = 1.863 min; MS Calcd.: 421.0; MS Found: 422.2 [M + H]⁺. | δ: 0.90 (6H, d, J = 6.4 Hz), 1.80-1.85 (1H, m), 2.74 (2H, d J = 7.2 Hz), 7.19-7.20 (1H, m), 7.53-7.59 (2H, m), 7.69 (1H, d, J = 8.4 Hz), 7.78-7.81 (2H, m), 11.46 (1H, brs). |
| 223 | 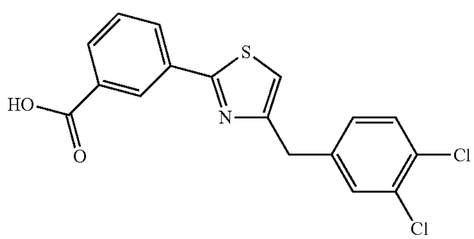 [SMILES: O=C(O)c1cccc(-c2nc(Cc3ccc(Cl)c(Cl)c3)cs2)c1] | Method B, Purity is 97.8%, Rt = 2.059 min; MS Calcd.: 362.9; MS Found: 364.1 [M + H]⁺. | δ: 4.15 (2H, s), 7.31 (1H, dd, J = 8.0, 2.0 Hz), 7.47 (1H, s), 7.55-7.62 (3H, m), 7.98-8.01 (1H, m), 8.09-8.12 (1H, m), 8.41 (1H, t, J = 1.8 Hz), 13.22 (1H, brs). |
| 224 | 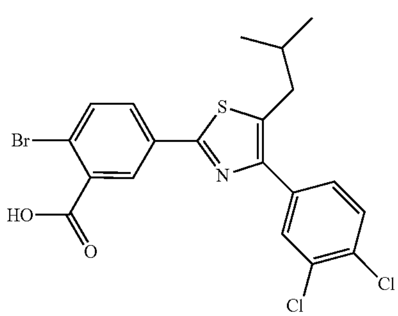 [SMILES: CC(C)Cc1sc(-c2ccc(Br)c(C(=O)O)c2)nc1-c1ccc(Cl)c(Cl)c1] | Method B, Purity is 100%, Rt = 2.392 min; MS Calcd.: 485.2; MS Found: 486.0 [M + H]⁺. | δ: 0.92 (6H, d, J = 6.8 Hz), 1.86-1.92 (1H, m), 2.88 (2H, d, J = 6.8 Hz), 7.66-7.98 (5H, m), 8.24 (1H, m). |
| 225 | 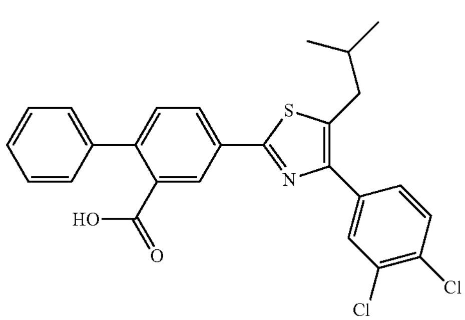 | Method C, Purity is 100%, Rt = 2.141 min; MS Calcd.: 481.1; MS Found: 482.3 [M + H]⁺. | δ: 0.93 (6H, d, J = 6.4 Hz), 1.87-1.94 (1H, m), 2.89 (2H, d J = 7.2 Hz), 7.34-7.44 (5H, m), 7.48 (1H, d, J = 8.0 Hz), 7.69 (1H, s), 7.77 (1H, d, J = 8.4 Hz), 7.92 (1H, d, J = 2.0 Hz), 8.02 (1H, dd, J = 8.0, 2.0 Hz), 8.12 (1H, d, J = 1.2 Hz). |

-continued

Characterization Data for Additional Exemplary Compounds

| I-# | Chemical Structure | LCMS | ¹H NMR (400 MHz, d₆-DMSO) |
|---|---|---|---|
| 226 | 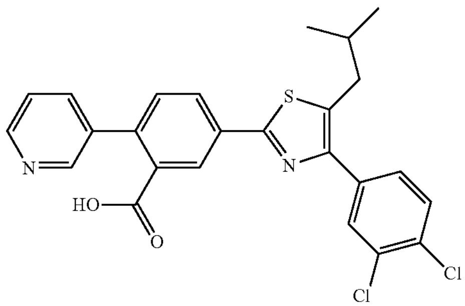 [SMILES: CC(C)Cc1sc(-c2ccc(-c3ccccc3)c(C(=O)O)c2)nc1-c1ccc(Cl)c(Cl)c1] | Method C, Purity is 99.0%, Rt = 2.023 min; MS Calcd.: 482.1; MS Found: 483.2 [M + H]⁺. | δ: 0.92 (6H, d, J = 6.4 Hz), 1.88-1.92 (1H, m), 2.89 (2H, d, J = 6.8 Hz), 7.47 (1H, s), 7.56 (1H, d, J = 8.0 Hz), 7.68 (1H, dd, J = 8.4, 2.0 Hz), 7.75-7.81 (2H, m), 7.92 (1H, d, J = 2.0 Hz), 8.16 (1H, dd, J = 8.0, 2.0 Hz), 8.37 (1H, d, J = 1.6 Hz), 8.58 (2H, brs), 13.16 (1H, brs). |
| 227 | 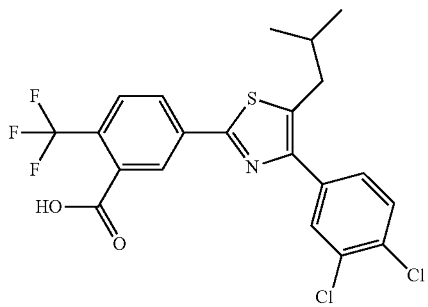 [SMILES: CC(C)Cc1sc(-c2ccc(C(F)(F)F)c(C(=O)O)c2)nc1-c1ccc(Cl)c(Cl)c1] | Method B, Purity is 97.6%, Rt = 2.367 min; MS Calcd.: 474.1; MS Found: 475.0 [M + H]⁺. | (CDCl₃) δ: 0.99 (6H, d, J = 6.8 Hz), 1.93-2.00 (1H, m), 2.84 (2H, d, J = 7.2 Hz), 7.48-7.56 (2H, m), 7.78 (1H, d, J = 2.0 Hz), 7.86 (1H, d, J = 8.4 Hz), 8.20 (1H, d, J = 8.4 Hz), 8.52 (1H, s). |
| 228 | 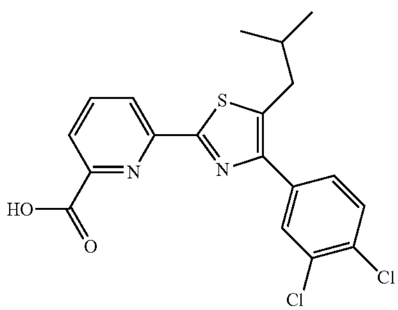 [SMILES: CC(C)Cc1sc(-c2cccc(C(=O)O)n2)nc1-c1ccc(Cl)c(Cl)c1] | Method B, Purity is 93.3%, Rt = 2.290 min; MS Calcd.: 406.0; MS Found: 407.1 [M + H]⁺. | δ: 0.91 (6H, d, J = 6.4 Hz), 1.89-1.97 (1H, m), 2.88 (2H, d, J = 7.2 Hz), 7.67 (1H, dd, J = 8.0, 1.6 Hz), 7.75 (1H, d, J = 8.4 Hz), 7.92 (1H, d, J = 2.0 Hz), 8.07-8.13 (2H, m), 8.34 (1H, dd, J = 7.2, 1.6 Hz), 13.57 (1H, brs). |
| 229 | 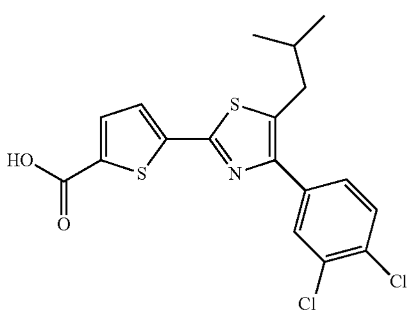 [SMILES: CC(C)Cc1sc(-c2ccc(C(=O)O)s2)nc1-c1ccc(Cl)c(Cl)c1] | Method B, Purity is 98.6%, Rt = 2.235 min; MS Calcd.: 411.2; MS Found: 412.1 [M + H]⁺. | δ: 0.89 (6H, d, J = 6.4 Hz), 1.81-1.89 (1H, m), 2.84 (2H, d, J = 7.2 Hz), 7.60 (1H, dd, J = 7.2, 2.0 Hz), 7.66 (1H, d, J = 4.0 Hz), 7.70 (1H, d, J = 4.0 Hz), 7.74 (1H, d, J = 8.4 Hz), 7.83 (1H, d, J = 2.0 Hz), 13.37 (1H, brs). |
| 230 | 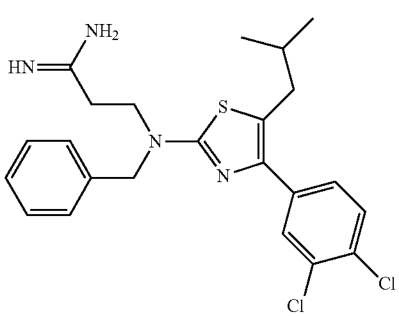 | Method B, Purity is 94.8%, Rt = 2.243 min; MS Calcd.: 460.1; MS Found: 461.2 [M + H]⁺. | δ: 0.87 (6H, d, J = 6.4 Hz), 1.79-1.83 (1H, m), 2.62 (2H, d, J = 6.8 Hz), 2.75-2.78 (2H, m) 3.84 (2H, t, J = 6.4 Hz), 4.65 (1H, s), 7.29-7.37 (5H, m,), 7.54-7.57 (1H, m), 7.66 (1H, d, J = 8.4 Hz), 7.77 (1H, d J = 2.0 Hz), 8.41-8.82 (2H, m), 10.51 (1H, brs). |

-continued

Characterization Data for Additional Exemplary Compounds

| I-# | Chemical Structure | LCMS | $^1$H NMR (400 MHz, d$_6$-DMSO) |
|---|---|---|---|
| 231 | 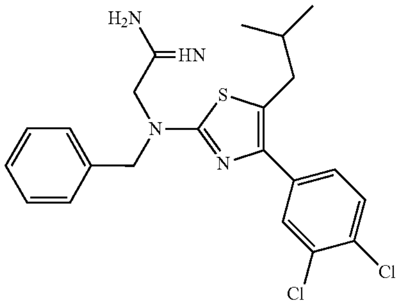 [SMILES: CC(C)Cc1sc(N(CC(=N)N)Cc2ccccc2)nc1-c1ccc(Cl)c(Cl)c1] | Method B, Purity is 98.1%, Rt = 2.081 min; MS Calcd.: 446.1; MS Found: 447.1 [M + H]$^+$. | δ: 0.88 (6H, d, J = 6.4 Hz), 1.72-1.79 (1H, m), 2.66 (2H, d, J = 7.2 Hz), 4.47 (2H, s), 4.68 (2H, s), 7.30-7.33 (3H, m), 7.37-7.40 (2H, m), 7.52 (1H, dd, J = 8.4, 2.0 Hz), 7.68 (1H, d, J = 8.4 Hz), 7.75 (1H, d, J = 2.0 Hz), 8.84-8.94 (3H, m). |
| 232 | 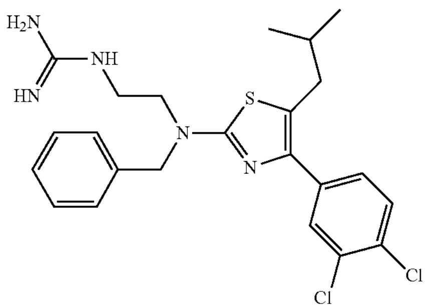 [SMILES: CC(C)Cc1sc(N(CCNC(=N)N)Cc2ccccc2)nc1-c1ccc(Cl)c(Cl)c1] | Method B, Purity is 100%, Rt = 2.190 min; MS Calcd.: 475.2; MS Found: 476.2 [M + H]$^+$. | δ: 0.84 (6H, d, J = 6.8 Hz), 1.70-1.73 (1H, m), 2.58 (2H, d, J = 7.2 Hz), 3.43-3.46 (2H, m), 3.56-3.60 (2H, m), 4.69 (2H, s), 5.16 (4H, brs), 7.25-7.30 (3H, m), 7.33-7.37 (2H, m), 7.51 (1H, dd, J = 8.4, 2.0 Hz), 7.66 (1H, d, J = 8.4 Hz), 7.73 (1H, d, J = 2.0 Hz), 7.82-7.86 (1H, m). |
| 233 | 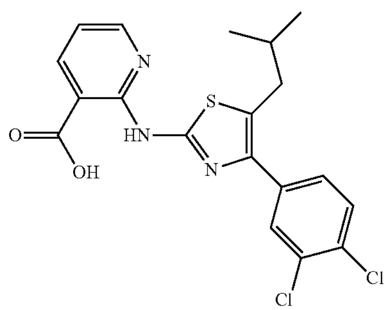 [SMILES: CC(C)Cc1sc(Nc2ncccc2C(=O)O)nc1-c1ccc(Cl)c(Cl)c1] | Method B, Purity is 98.2%, Rt = 2.287 min; MS Calcd.: 421.1; MS Found: 422.0 [M + H]$^+$. | δ: 0.92 (6H, d, J = 6.8 Hz), 1.84-1.91 (1H, m), 2.77 (2H, d, J = 7.2 Hz), 7.10 (1H, q, J = 4.8 Hz), 7.59-7.62 (1H, m), 7.70 (1H, d, J = 8.4 Hz), 7.82 (1H, d, J = 2.0 Hz), 8.36 (1H, dd, J = 8.4, 2.0 Hz), 8.57-8.59 (1H, m), 11.55 (1H, brs), 14.12 (1H, brs). |
| 234 | 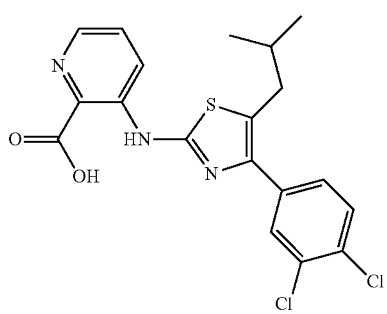 [SMILES: CC(C)Cc1sc(Nc2cccnc2C(=O)O)nc1-c1ccc(Cl)c(Cl)c1] | Method B, Purity is 100%, Rt = 2.122 min; MS Calcd.: 421.0; MS Found: 422.1 [M + H]$^+$. | δ: 0.91 (6H, d, J = 6.4 Hz), 1.82 (1H, d, J = 6.4 Hz), 2.72 (2H, d, J = 7.2 Hz), 7.61 (2H, dd, J = 8.4, 2.0 Hz), 7.72 (1H, d, J = 8.4 Hz), 7.81 (1H, d, J = 2.0 Hz), 8.23 (1H, brs), 8.92 (1H, d, J = 8.4 Hz), 13.88 (1H, brs). |

-continued

Characterization Data for Additional Exemplary Compounds

| I-# | Chemical Structure | LCMS | $^1$H NMR (400 MHz, d$_6$-DMSO) |
|---|---|---|---|
| 235 | 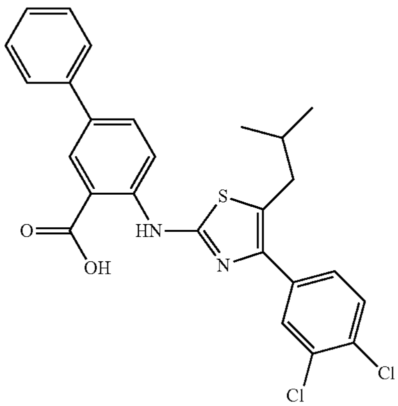 [SMILES: CC(C)Cc1sc(Nc2ccc(-c3ccccc3)cc2C(=O)O)nc1-c1ccc(Cl)c(Cl)c1] | Method C, Purity is 96.9%, Rt = 2.344 min; MS Calcd.: 496.0; MS Found: 497.2 [M + H]$^+$. | δ: 0.89 (6H, d, J = 6.4 Hz), 1.77-1.83 (1H, m), 2.70 (2H, d, J = 6.8 Hz), 7.29 (1H, t, J = 7.2 Hz), 7.42 (2H, t, J = 8.0 Hz), 7.58-7.63 (3H, m), 7.70 (1H, t, J = 8.4 Hz), 7.75-7.80 (2H, m), 8.28 (1H, s), 8.41 (1H, d, J = 8.8 Hz), 13.48 (1H, s). |
| 236 | 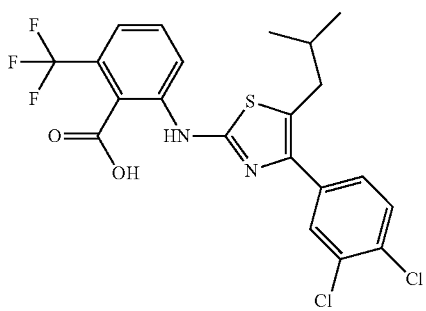 [SMILES: CC(C)Cc1sc(Nc2cccc(C(F)(F)F)c2C(=O)O)nc1-c1ccc(Cl)c(Cl)c1] | Method B, Purity is 99.6%, Rt = 2.326 min; MS Calcd.: 488.0; MS Found: 489.1 [M + H]$^+$. | δ: 0.88 (6H, d, J = 6.4 Hz), 1.73-1.79 (1H, m), 2.62 (2H, d, J = 6.8 Hz), 7.44-7.72 (5H, m), 8.31 (1H, m), 9.66 (1H, s). |
| 237 | 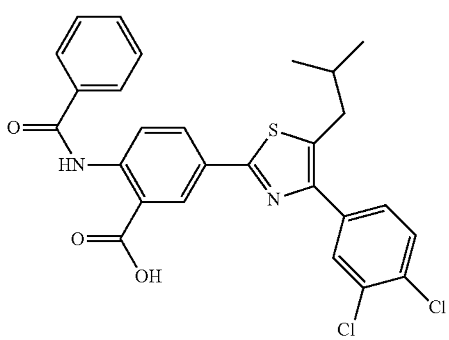 [SMILES: CC(C)Cc1sc(-c2ccc(NC(=O)c3ccccc3)c(C(=O)O)c2)nc1-c1ccc(Cl)c(Cl)c1] | Method C, Purity is 100%, Rt = 2.225 min; MS Calcd.: 524.0; MS Found: 495.0 [M + H]$^+$. | δ: 0.90 (6H, d, J = 6.8 Hz), 1.84-1.91 (1H, m), 2.85 (2H, d, J = 7.2 Hz), 7.56-7.66 (1H, m), 7.74 (1H, d, J = 8.4 Hz), 7.88 (1H, d, J = 2.0 Hz), 7.96-7.98 (1H, m), 8.16 (1H, dd, J = 8.8, 2.4 Hz), 8.56 (1H, d, J = 2.4 Hz), 8.82 (1H, d, J = 8.8 Hz), 12.78 (1H, s). |
| 238 | 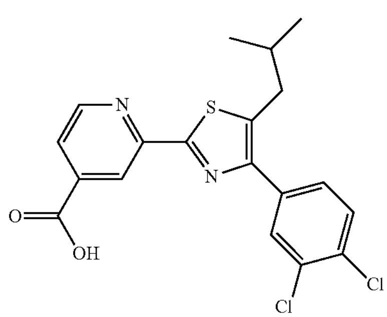 [SMILES: CC(C)Cc1sc(-c2cc(C(=O)O)ccn2)nc1-c1ccc(Cl)c(Cl)c1] | Method B, Purity is 97.9%, Rt = 2.315 min; MS Calcd.: 406.0; MS Found: 407.0 [M + H]$^+$. | δ: 0.90 (6H, d, J = 6.8 Hz), 1.80-1.89 (1H, m), 2.88 (2H, d, J = 6.8 Hz), 7.68 (1H, dd, J = 8.4, 2.0 Hz), 7.75 (1H, d, J = 8.4 Hz), 7.87-7.91 (2H, m), 8.49 (1H, s), 8.80 (1H, d, J = 4.8 Hz), 13.45 (1H, brs). |

| I-# | Chemical Structure | LCMS | ¹H NMR (400 MHz, d₆-DMSO) |
|---|---|---|---|
| 239 | 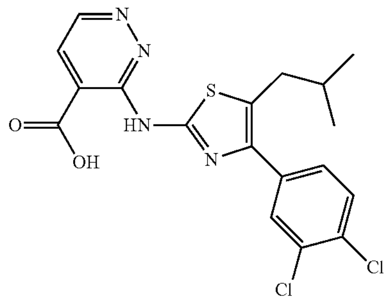 [SMILES: CC(C)Cc1sc(Nc2nnccc2C(=O)O)nc1-c1ccc(Cl)c(Cl)c1] | Method B, Purity is 97.8%, Rt = 2.148 min; MS Calcd.: 422.0; MS Found: 423.1 [M + H]⁺. | δ: 0.92 (6H, d, J = 6.4 Hz), 1.88-1.91 (1H, m), 2.79 (2H, d, J = 6.8 Hz), 7.61 (1H, dd, J = 8.4, 2.0 Hz), 7.71 (1H, d, J = 8.4 Hz), 7.84 (1H, d, J = 2.0 Hz), 8.02 (1H, d, J = 5.2 Hz), 9.03 (1H, d, J = 4.8 Hz), 11.86 (1H, brs). |
| 240 | 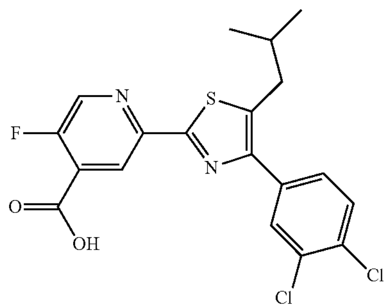 [SMILES: CC(C)Cc1sc(-c2cc(C(=O)O)c(F)cn2)nc1-c1ccc(Cl)c(Cl)c1] | Method C, Purity is 95.8%, Rt = 1.997 min; MS Calcd.: 424.0; MS Found: 425.0 [M + H]⁺. | δ: 0.89 (6H, d, J = 6.8 Hz), 1.84-1.91 (1H, m), 2.87 (2H, d J = 7.2 Hz), 7.66 (1H, dd, J = 8.4, 2.0 Hz), 7.74 (1H, d, J = 8.4 Hz), 7.89 (1H, d, J = 2.0 Hz), 8.41 (1H, d, J = 1.6 Hz), 8.78 (1H, d, J = 2.0 Hz). |
| 241 | 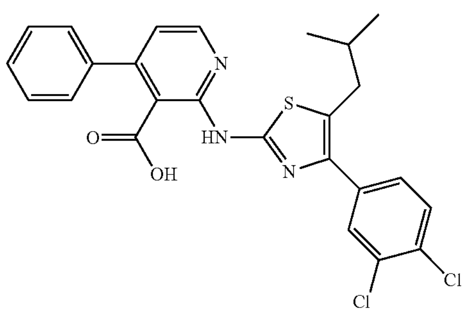 [SMILES: CC(C)Cc1sc(Nc2nccc(-c3ccccc3)c2C(=O)O)nc1-c1ccc(Cl)c(Cl)c1] | Method B, Purity is 100%, Rt = 2.456 min; MS Calcd.: 497.2; MS Found: 498.2 [M + H]⁺. | δ: 0.92 (6H, d, J = 6.4 Hz), 1.85-1.92 (1H, m), 2.77 (2H, d, J = 6.8 Hz), 6.99 (1H, d, J = 5.2 Hz), 7.37-7.48 (5H, m), 7.59-7.62 (1H, m), 7.70 (1H, d, J = 8.4 Hz), 7.83 (1H, d, J = 2.0 Hz), 8.49 (1H, d, J = 5.2 Hz), 10.92 (1H, m), 13.67 (1H, brs). |
| 242 | 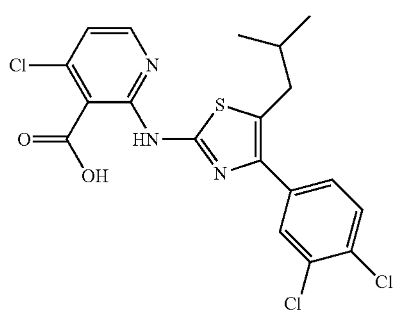 [SMILES: CC(C)Cc1sc(Nc2nccc(Cl)c2C(=O)O)nc1-c1ccc(Cl)c(Cl)c1] | Method B, Purity is 97.8%, Rt = 2.393 min; MS Calcd.: 455.0; MS Found: 456.0 [M + H]⁺. | δ: 0.89 (6H, d, J = 6.4 Hz), 1.83-1.86 (1H, m), 2.72 (2H, d J = 6.8 Hz), 7.15 (1H, d, J = 5.2 Hz), 7.57 (1H, d, J = 8.4 Hz), 7.69 (1H, d, J = 8.4 Hz), 7.80 (1H, d, J = 1.2 Hz), 8.36 (1H, d, J = 5.6 Hz). |
| 243 | 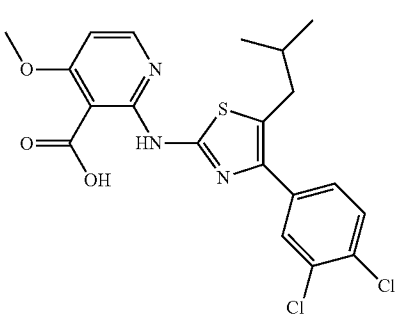 [SMILES: COc1ccnc(Nc2nc(-c3ccc(Cl)c(Cl)c3)c(CC(C)C)s2)c1C(=O)O] | Method B, Purity is 100%, Rt = 2.227 min; MS Calcd.: 451.1; MS Found: 452.0 [M + H]⁺. | δ: 0.89 (6H, d, J = 6.8 Hz), 1.81-1.87 (1H, m), 2.65 (2H, d, J = 7.2 Hz), 3.90 (3H, s), 6.82 (1H, m), 7.55-7.78 (3H, m), 8.33 (1H, d, J = 6.0 Hz). |

-continued

Characterization Data for Additional Exemplary Compounds

| I-# | Chemical Structure | LCMS | ¹H NMR (400 MHz, d₆-DMSO) |
|---|---|---|---|
| 244 | 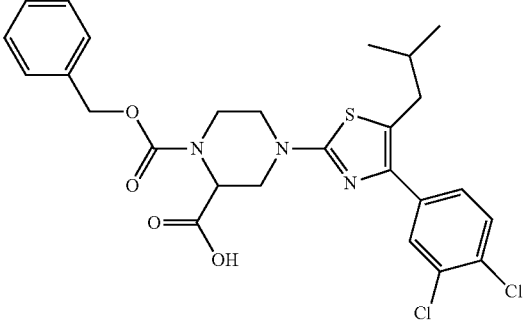 [SMILES: CC(C)Cc1sc(N2CCN(C(=O)OCc3ccccc3)C(C(=O)O)C2)nc1-c1ccc(Cl)c(Cl)c1] | Method C, Purity is 98.1%, Rt = 2.174 min; MS Calcd.: 547.1; MS Found: 548.2 [M + H]⁺. | δ: 0.86 (6H, dd, J = 6.4, 3.2 Hz), 1.72-1.76 (1H, m), 2.61 (2H, d, J = 7.2 Hz), 2.92-2.95 (1H, m), 3.18 (2H, dd, J = 12.4, 4.4 Hz), 3.84-3.89 (2H, m), 4.26 (1H, t, J = 13.6 Hz), 4.56 (1H, s), 5.09 (2H, d, J = 12.8 Hz), 7.28-7.37 (5H, m), 7.48 (1H, dd, J = 8.4, 2.0 Hz), 7.64 (1H, d, J = 8.4 Hz), 7.70 (1H, d, J = 2.0 Hz). |
| 245 | 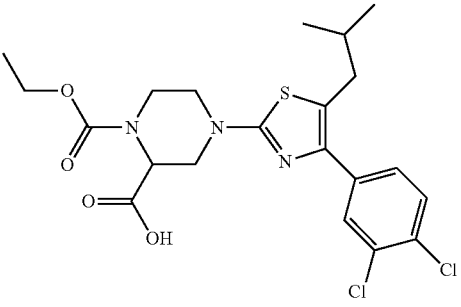 [SMILES: CCOC(=O)N1CCN(c2nc(-c3ccc(Cl)c(Cl)c3)c(CC(C)C)s2)CC1C(=O)O] | Method C, Purity is 100%, Rt = 1.972 min; MS Calcd.: 485.1; MS Found: 486.1 [M + H]⁺. | δ: 0.86-0.89 (6H, m), 1.18 (3H, dt, J = 21.2, 7.2 Hz), 1.73-1.79 (1H, m), 2.64 (2H, d J = 7.2 Hz), 2.90-2.96 (1H, m), 3.17 (2H, dd, J = 12.4, 4.4 Hz), 3.84 (2H, d, J = 12.4 Hz), 4.01-4.09 (1H, m), 4.26 (1H, t, J = 11.2 Hz), 4.52 (1H, d, J = 28.4 Hz), 7.50 (1H, dd, J = 8.4, 2.0 Hz), 7.66 (1H, d, J = 8.4 Hz), 7.72 (1H, d, J = 2.0 Hz). |
| 246 | 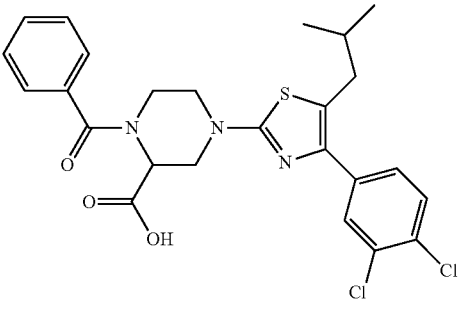 [SMILES: CC(C)Cc1sc(N2CCN(C(=O)c3ccccc3)C(C(=O)O)C2)nc1-c1ccc(Cl)c(Cl)c1] | Method B, Purity is 100%, Rt = 2.164 min; MS Calcd.: 517.0; MS Found: 518.1 [M + H]⁺. | δ: 0.86 (6H, d, J = 6.4 Hz), 1.71-1.78 (1H, m), 2.60-2.65 (2H, m), 2.96-3.01 (1H, m), 3.13-3.20 (1H, m), 3.43-3.50 (1H, m), 3.74-5.11 (4H, m), 7.23 (1H, brs), 7.39-7.40 (3H, m), 7.46-7.50 (2H, m), 7.65 (1H, d, J = 8.4 Hz), 7.71 (1H, d, J = 1.6 Hz). |
| 247 | 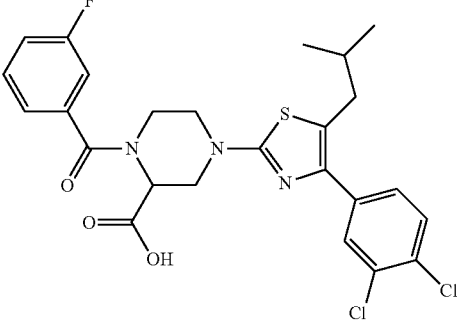 | Method C, Purity is 97.8%, Rt = 2.007 min; MS Calcd.: 421.0; MS Found: 422.2 [M + H]⁺. | δ: 0.86 (6H, d, J = 6.4 Hz), 1.71-1.77 (1H, m), 2.64 (2H, d, J = 7.2 Hz), 3.04-3.13 (1.4H, m), 3.37-3.44 (1H, m), 3.56-3.60 (0.6H, m), 3.72-3.75 (0.6H, m), 3.96-3.98 (0.4H, m), 4.15-4.19 (0.4H, m), 4.35-4.39 (1.4H, m), 5.21-5.22 (0.6H, m), 7.19-7.34 (3H, m), 7.48-7.54 (2H, m), 7.65 (1H, d, J = 8.4 Hz), 7.71 (1H, d, J = 2.0 Hz), 13.35 (1H, brs). |

Characterization Data for Additional Exemplary Compounds

| I-# | Chemical Structure | LCMS | ¹H NMR (400 MHz, d₆-DMSO) |
|---|---|---|---|
| 248 | 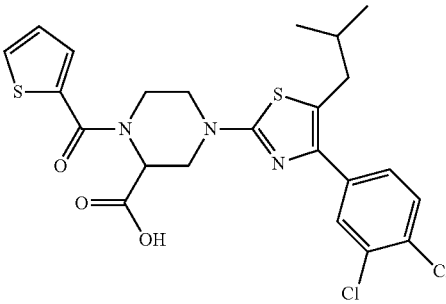 | Method C, Purity is 95.0%, Rt = 2.039 min; MS Calcd.: 523.1; MS Found: 524.2 [M + H]⁺. | δ: 0.86 (6H, d, J = 6.4 Hz), 1.71-1.78 (1H, m), 2.62 (2H, d, J = 7.2 Hz), 2.97-2.99 (2H, m), 3.63-3.65 (1H, m), 3.86-3.88 (1H, m), 4.15-4.30 (2H, m), 4.70-5.06 (1H, m), 7.11 (1H, brs), 7.39-7.51 (2H, m), 7.65 (1H, d, J = 8.4 Hz), 7.71-7.76 (2H, m). |
| 249 | 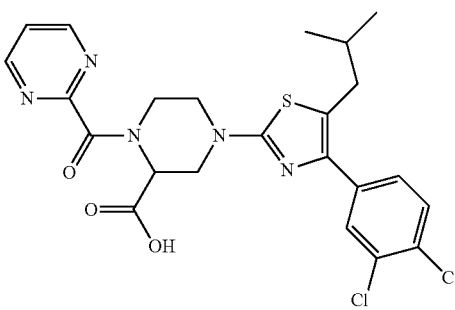 | Method C, Purity is 100%, Rt = 1.886 min; MS Calcd.: 519.0; MS Found: 520.2 [M + H]⁺. | δ: 0.87 (6H, s), 1.73-1.77 (1H, m), 2.64 (2H, m), 3.00-3.08 (2H, m), 3.75-4.19 (2H, m), 4.37-4.49 (2H, m), 5.27 (1H, s), 7.50-7.78 (4H, m), 8.93 (1H, s), 13.31 (1H, s). |
| 250 | 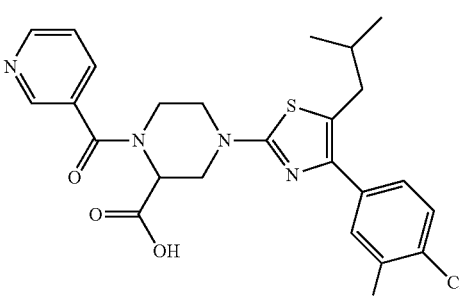 | Method C, Purity is 100%, Rt = 1.911 min; MS Calcd.: 518.0; MS Found: 519.2 [M + H]⁺. | δ: 0.86 (6H, d, J = 6.4 Hz),1.71-1.78 (1H, m), 2.63 (2H, d, J = 7.2 Hz), 3.05-3.05 (2H, m), 3.38-3.77 (2H, m), 3.97-4.42 (2H, m), 5.23 (1H, s), 7.48-7.53 (2H, m), 7.65 (1H, d, J = 8.4 Hz), 7.71 (1H, d, J = 2.0 Hz), 7.78-7.87 (1H, m), 8.57-8.68 (2H, m), 13.28 (1H, s). |
| 251 | 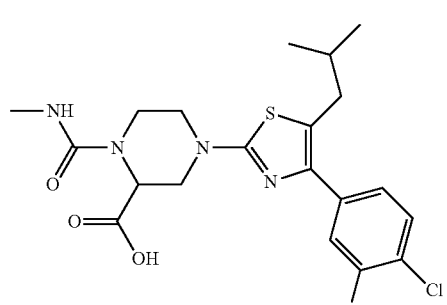 | Method C, Purity is 94.4%, Rt = 1.898 min; MS Calcd.: 470.1; MS Found: 471.2 [M + H]⁺. | δ: 0.87 (6H, d, J = 6.8 Hz), 1.74-1.77 (1H, m), 2.52 (3H, d, J = 4.0 Hz), 2.61 (2H, d, J = 6.8 Hz), 3.01-3.04 (1H, m), 3.22-3.25 (1H, m), 3.75-3.80 (2H, m), 4.16-4.23 (2H, m), 6.40 (1H, d, J = 4.0 Hz), 7.48-7.51 (1H, m), 7.64 (1H, d, J = 8.4 Hz), 7.70 (1H, d, J = 2.0 Hz). |
| 252 | 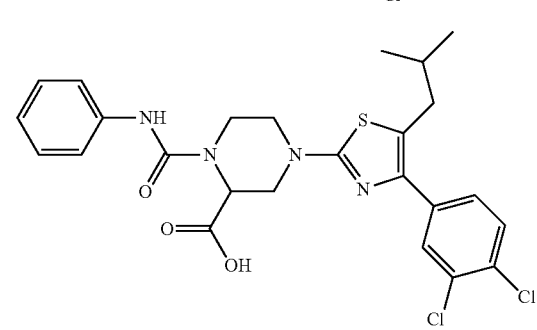 | Method C, Purity is 94.3%, Rt = 2.053 min; MS Calcd.: 532.1; MS Found: 533.2 [M + H]⁺. | δ: 0.88-0.92 (6H, m), 1.74-1.81 (1H, m), 2.64-2.67 (2H, m), 3.02-3.08 (1H, m), 3.20-3.24 (2H, m), 3.83 (1H, d, J = 11.6 Hz), 4.01 (1H, d, J = 12.8 Hz), 4.25 (1H, d, J = 12.4 Hz), 4.66 (1H, s), 6.91 (1H, t, J = 7.2 Hz), 7.22 (2H, dd, J = 8.4, 7.6 Hz), 7.44-7.53 (3H, m), 7.66-7.74 (1H, m), 7.74 (1H, s), 9.08 (1H, s). |

-continued

Characterization Data for Additional Exemplary Compounds

| I-# | Chemical Structure | LCMS | $^1$H NMR (400 MHz, d$_6$-DMSO) |
|---|---|---|---|
| 253 | 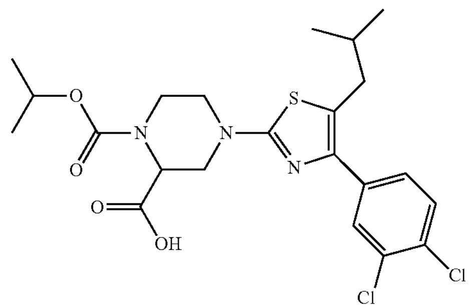 [SMILES: CC(C)Cc1sc(N2CCN(C(=O)OC(C)C)C(C(=O)O)C2)nc1-c1ccc(Cl)c(Cl)c1] | Method C, Purity is 100.0%, Rt = 2.021 min; MS Calcd.: 499.1; MS Found: 500.0 [M + H]$^+$. | δ: 0.85-0.87 (6H, m), 1.11-1.20 (6H, m), 1.71-1.76 (1H, m), 2.62 (2H, d, J = 6.8 Hz), 2.91-2.97 (1H, m), 3.12-3.20 (2H, m), 3.81-3.96 (2H, m), 4.24 (1H, dd, J = 14.4, 13.6 Hz), 4.57 (1H, d, J = 28.4 Hz), 4.78 (1H, d, J = 3.2 Hz), 7.47-7.49 (1H, m), 7.65 (1H, d, J = 8.4 Hz), 7.70 (1H, d, J = 2.0 Hz). |
| 254 | 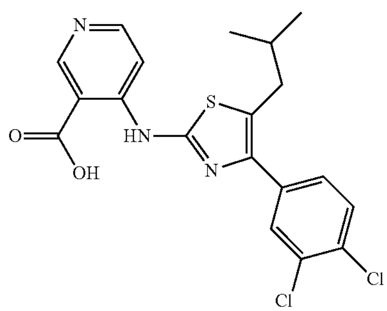 [SMILES: CC(C)Cc1sc(Nc2ccncc2C(=O)O)nc1-c1ccc(Cl)c(Cl)c1] | Method C, Purity is 100%, Rt = 1.995 min; MS Calcd.: 421.0; MS Found: 421.8 [M + H]$^+$. | δ: 0.91 (6H, d, J = 6.8 Hz), 1.79-1.86 (1H, m), 2.71-2.73 (2H, d, J = 7.2 Hz), 7.60-7.82 (3H, m), 8.13-8.31 (2H, m), 8.88 (1H, m). |
| 255 | 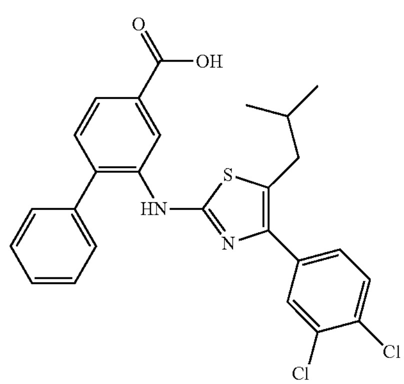 [SMILES: CC(C)Cc1sc(Nc2cc(C(=O)O)ccc2-c2ccccc2)nc1-c1ccc(Cl)c(Cl)c1] | Method C, Purity is 100%, Rt = 2.134 min; MS Calcd.: 496.1; MS Found: 497.0 [M + H]$^+$. | δ: 0.82-0.85 (6H, m), 1.67-1.75 (1H, m), 2.57 (2H, d J = 6.8 Hz), 7.37-7.47 (5H, m), 7.62-7.66 (2H, m), 7.70-7.73 (1H, m), 8.08 (1H, d, J = 1.6 Hz). |
| 256 | 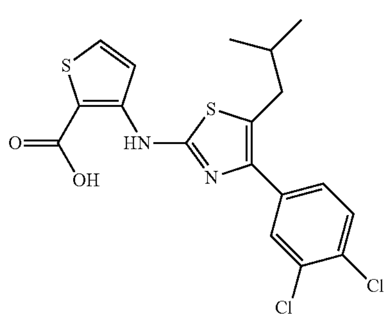 [SMILES: CC(C)Cc1sc(Nc2ccsc2C(=O)O)nc1-c1ccc(Cl)c(Cl)c1] | Method C, Purity is 96.6%, Rt = 2.137 min; MS Calcd.: 427.1; MS Found: 427.2 [M + H]$^+$. | δ: 0.88 (6H, d, J = 6.4 Hz), 1.77-1.81 (1H, m), 2.70 (2H, d, J = 7.2 Hz), 7.57 (1H, dd, J = 8.4, 2.0 Hz), 7.69 (1H, d, J = 8.4 Hz), 7.77 (1H, d, J = 2.0 Hz), 7.84 (1H, d, J = 5.6 Hz), 8.01 (1H, d, J = 1.6 Hz), 10.23 (1H, s), 13.16 (1H, brs). |

-continued

Characterization Data for Additional Exemplary Compounds

| I-# | Chemical Structure | LCMS | $^1$H NMR (400 MHz, d$_6$-DMSO) |
|---|---|---|---|
| 257 | 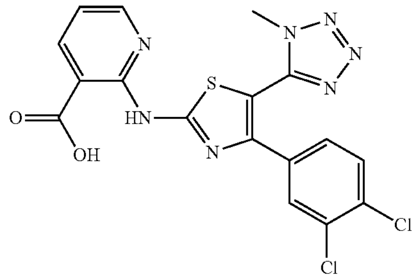 [SMILES: Cn1nnnc1-c1sc(Nc2ncccc2C(=O)O)nc1-c1ccc(Cl)c(Cl)c1] | Method C, Purity is 100%, Rt = 1.789 min; MS Calcd.: 447.1; MS Found: 448.0 [M + H]$^+$. | δ: 4.38 (3H, s), 6.95-7.16 (2H, m), 7.67 (1H, d, J = 8.4 Hz), 7.76-7.79 (1H, m), 8.06 (1H, d, J = 2.0 Hz), 8.36-8.38 (1H, m), 8.58-8.60 (1H, m), 12.8 (1H, brs). |
| 258 | 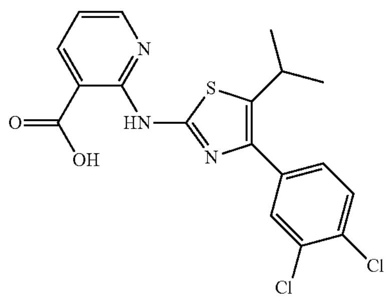 [SMILES: CC(C)c1sc(Nc2ncccc2C(=O)O)nc1-c1ccc(Cl)c(Cl)c1] | Method B, Purity is 97.3%, Rt = 2.218 min; MS Calcd.: 407.0; MS Found: 408.1 [M + H]$^+$. | δ: 1.31 (6H, d, J = 6.8 Hz), 3.34-3.39 (1H, m), 7.08 (1H, dd, J = 8.4, 2.0 Hz), 7.54 (1H, dd, J = 7.6, 4.8 Hz), 7.69 (1H, d, J = 8.4 Hz), 7.77 (1H, d, J = 2.0 Hz), 8.33 (1H, dd, J = 7.6, 2.0 Hz), 8.57 (1H, dd, J = 4.8, 1.6 Hz), 11.57 (1H, brs). |
| 259 | 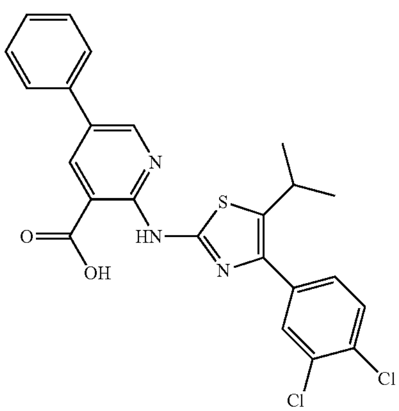 [SMILES: CC(C)c1sc(Nc2ncc(-c3ccccc3)cc2C(=O)O)nc1-c1ccc(Cl)c(Cl)c1] | Method C, Purity is 100%, Rt = 2.253 min; MS Calcd.: 483.0; MS Found: 483.8 [M + H]$^+$. | δ: 1.32 (6H, d, J = 6.8 Hz), 3.36-3.39 (1H, m), 7.37 (1H, t, J = 7.2 Hz), 7.47 (2H, t, J = 7.6 Hz), 7.55 (1H, dd, J = 6.4, 2.0 Hz), 7.68-7.73 (3H, m), 7.77 (1H, d, J = 1.6 Hz), 8.53 (1H, d, J = 2.4 Hz), 8.82 (1H, s). |
| 260 | 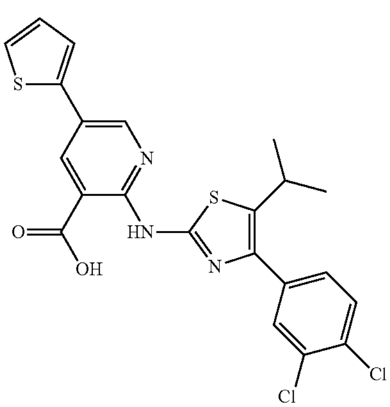 [SMILES: CC(C)c1sc(Nc2ncc(-c3cccs3)cc2C(=O)O)nc1-c1ccc(Cl)c(Cl)c1] | Method C, Purity is 90.0%, Rt = 2.262 min; MS Calcd.: 489.0; MS Found: 489.7 [M + H]$^+$. | δ: 1.32 (6H, d, J = 6.8 Hz), 3.36-3.41 (1H, m), 7.15-7.17 (1H, m), 7.54 (1H, dd, J = 6.0, 2.4 Hz), 7.59 (1H, dd, J = 4.0, 1.2 Hz), 7.63 (1H, dd, J = 2.8, 0.8 Hz), 7.69 (1H, d, J = 8.4 Hz), 7.77 (1H, d, J = 2.0 Hz), 8.44 (1H, d, J = 2.4 Hz), 8.93 (1H, d, J = 2.4 Hz), 11.72 (1H, s). |

-continued

Characterization Data for Additional Exemplary Compounds

| I-# | Chemical Structure | LCMS | $^1$H NMR (400 MHz, d$_6$-DMSO) |
|---|---|---|---|
| 261 | 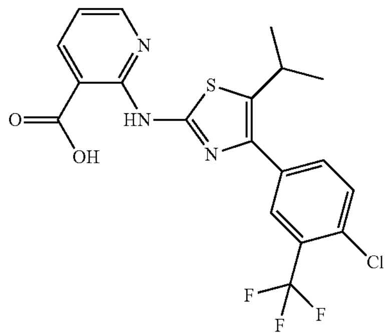 [SMILES: CC(C)c1sc(Nc2ncccc2C(=O)O)nc1-c1ccc(Cl)c(C(F)(F)F)c1] | Method B, Purity is 91.2%, Rt = 2.236 min; MS Calcd.: 441.0; MS Found: 442.1 [M + H]$^+$. | δ: 1.33 (6H, d, J = 5.2 Hz), 3.31-3.39 (1H, m), 7.07-7.11 (1H, m), 7.78-7.87 (2H, m), 7.96 (1H, s), 8.32-8.36 (1H, m), 8.57-8.58 (1H, m), 11.56 (1H, s), 14.09 (1H, brs). |
| 262 | 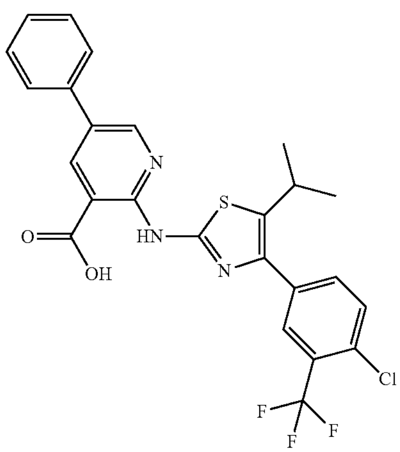 [SMILES: CC(C)c1sc(Nc2ncc(-c3ccccc3)cc2C(=O)O)nc1-c1ccc(Cl)c(C(F)(F)F)c1] | Method B, Purity is 94.3%, Rt = 2.394 min; MS Calcd.: 517.1; MS Found: 518.2 [M + H]$^+$. | δ: 1.34 (6H, d, J = 6.8 Hz), 3.38 (1H, m), 7.39-7.50 (3H, m), 7.74-7.97 (5H, m), 8.54 (1H, s), 8.93 (1H, s). |
| 263 | 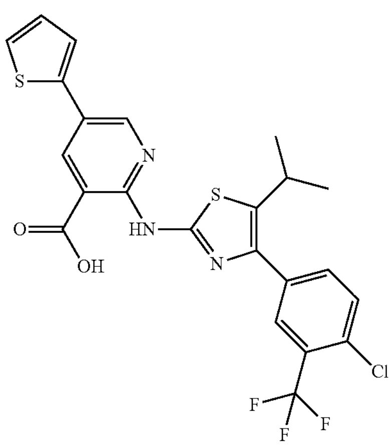 [SMILES: CC(C)c1sc(Nc2ncc(-c3cccs3)cc2C(=O)O)nc1-c1ccc(Cl)c(C(F)(F)F)c1] | Method B, Purity is 100%, Rt = 2.421 min; MS Calcd.: 523.0; MS Found: 524.0 [M + H]$^+$. | δ: 1.36 (6H, d, J = 6.8 Hz), 3.34 (1H, m), 7.15-7.17 (1H, m), 7.53-7.55 (2H, m), 7.80-8.00 (3H, m), 8.42 (1H, s), 8.71 (1H, s). |

-continued

Characterization Data for Additional Exemplary Compounds

| I-# | Chemical Structure | LCMS | $^1$H NMR (400 MHz, d$_6$-DMSO) |
|---|---|---|---|
| 264 | 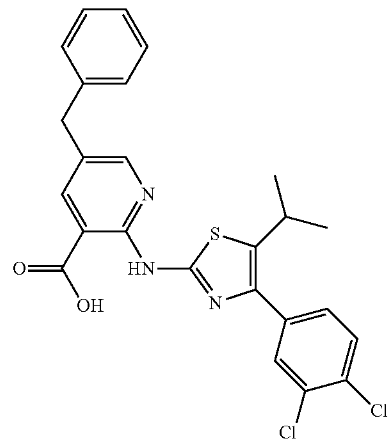 [SMILES: CC(C)c1sc(Nc2ncc(Cc3ccccc3)cc2C(=O)O)nc1-c1ccc(Cl)c(Cl)c1] | Method C, Purity is 95.3%, Rt = 2.272 min; MS Calcd.: 497.2; MS Found: 498.2 [M + H]$^+$. | δ: 1.30 (6H, d, J = 6.8 Hz), 3.24-3.32 (1H, m), 3.97 (2H, s), 7.19-7.30 (5H, m), 7.52-7.54 (1H, m), 7.67-7.69 (1H, m), 7.76 (1H, s), 8.17 (1H, s), 8.51 (1H, s), 11.40 (1H, brs), 14.09 (1H, brs). |
| 265 | 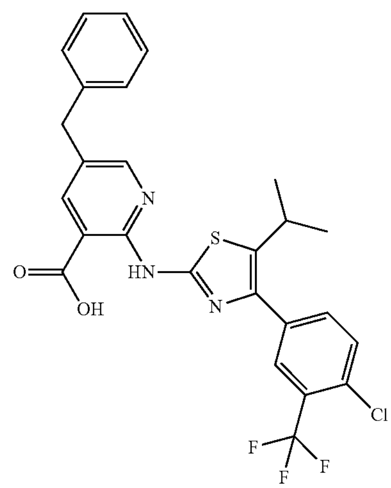 [SMILES: CC(C)c1sc(Nc2ncc(Cc3ccccc3)cc2C(=O)O)nc1-c1ccc(Cl)c(C(F)(F)F)c1] | Method C, Purity is 98.8%, Rt = 2.249 min; MS Calcd.: 531.1; MS Found: 532.2 [M + H]$^+$. | δ: 1.34 (6H, d, J = 6.8 Hz), 2.51-2.50 (1H, m), 3.97 (2H, s), 7.19-7.35 (5H, m), 7.79 (1H, d, J = 8.4 Hz), 7.86-7.88 (1H, m), 7.98 (1H, d, J = 1.6 Hz), 8.15 (1H, d, J = 2.0 Hz), 8.43-8.44 (1H, m), 12.40 (1H, brs). |
| 266 | 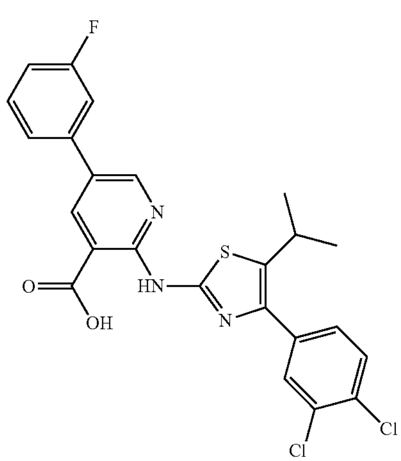 [SMILES: CC(C)c1sc(Nc2ncc(-c3cccc(F)c3)cc2C(=O)O)nc1-c1ccc(Cl)c(Cl)c1] | Method C, Purity is 96.7%, Rt = 2.261 min; MS Calcd.: 501.1; MS Found: 502.0 [M + H]$^+$. | δ: 1.32 (6H, d, J = 6.8 Hz), 3.35-3.40 (1H, m), 7.14-7.18 (1H, m), 7.48-7.56 (4H, m), 7.68 (1H, d, J = 8.4 Hz), 7.76 (1H, d, J = 2.0 Hz), 8.12 (1H, s), 8.53 (1H, d, J = 2.0 Hz), 8.73 (1H, brs). |

Characterization Data for Additional Exemplary Compounds

| I-# | Chemical Structure | LCMS | ¹H NMR (400 MHz, d₆-DMSO) |
|---|---|---|---|
| 267 | 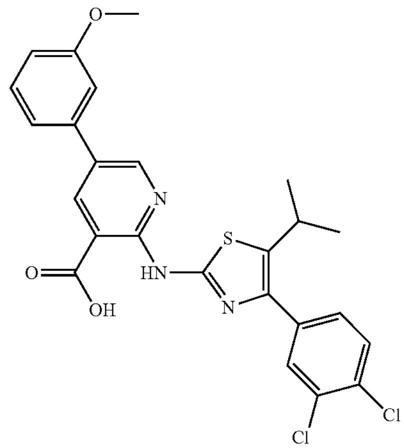 [SMILES: COc1cccc(-c2cnc(Nc3nc(-c4ccc(Cl)c(Cl)c4)c(C(C)C)s3)c(C(=O)O)c2)c1] | Method C, Purity is 99.4%, Rt = 2.242 min; MS Calcd.: 513.1; MS Found: 514.0 [M + H]⁺. | δ: 1.32 (6H, d, J = 6.8 Hz), 3.35-3.38 (1H, m), 3.82 (3H, brs), 6.92 (1H, dd, J = 8.4, 2.0 Hz), 7.23-7.25 (2H, m), 7.37 (1H, t, J = 8.4 Hz), 7.55 (1H, dd, J = 8.4, 2.0 Hz), 7.76 (1H, d, J = 2.0 Hz), 8.52 (1H, d, J = 2.0 Hz), 8.71 (1H, brs). |
| 268 | 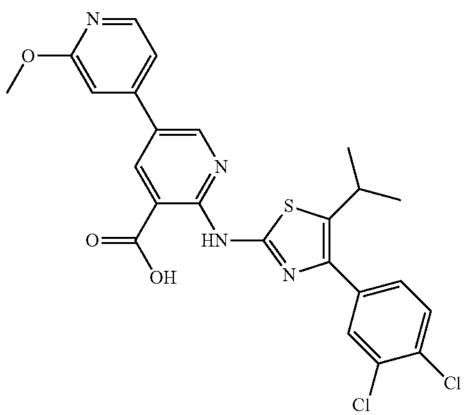 [SMILES: COc1cc(-c2cnc(Nc3nc(-c4ccc(Cl)c(Cl)c4)c(C(C)C)s3)c(C(=O)O)c2)ccn1] | Method B, Purity is 100%, Rt = 2.300 min; MS Calcd.: 514.1; MS Found: 515.2 [M + H]⁺. | δ: 1.31 (6H, d, J = 6.4 Hz), 3.35-3.38 (1H, m), 3.88 (1H, s), 7.12 (1H, s), 7.33-7.35 (1H, m), 7.54 (1H, dd, J = 8.4, 2.0 Hz), 7.68 (1H, d, J = 8.4 Hz), 7.76 (1H, d, J = 1.6 Hz), 8.19 (1H, d, J = 5.2 Hz), 8.58 (1H, s), 8.79 (1H, d, J = 2.0 Hz), 14.28 (1H, brs). |
| 269 | 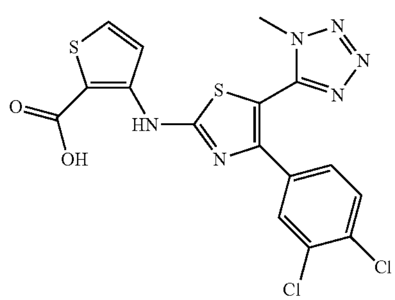 [SMILES: Cn1nnnc1-c1sc(Nc2ccsc2C(=O)O)nc1-c1ccc(Cl)c(Cl)c1] | Method C, Purity is 100%, Rt = 1.846 min; MS Calcd.: 452.0; MS Found: 453.0 [M + H]⁺. | δ: 4.37 (3H, s), 7.11 (1H, brs), 7.68-7.78 (3H, m), 8.02-8.04 (2H, m), 11.29 (1H, brs). |
| 270 | 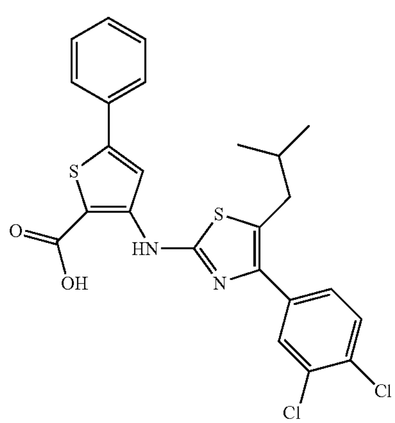 [SMILES: CC(C)Cc1sc(Nc2cc(-c3ccccc3)sc2C(=O)O)nc1-c1ccc(Cl)c(Cl)c1] | Method C, Purity is 98.7%, Rt = 2.410 min; MS Calcd.: 502.1; MS Found: 503.2 [M + H]⁺. | δ: 0.92 (6H, d, J = 6.4 Hz), 1.82-1.86 (1H, m), 2.75 (2H, d, J = 7.2 Hz), 7.42-7.50 (2H, m), 7.62-7.74 (4H, m), 7.92 (1H, d, J = 1.6 Hz), 8.40 (1H, s), 10.67 (1H, s). |

-continued

Characterization Data for Additional Exemplary Compounds

| I-# | Chemical Structure | LCMS | ¹H NMR (400 MHz, d₆-DMSO) |
|---|---|---|---|
| 271 | 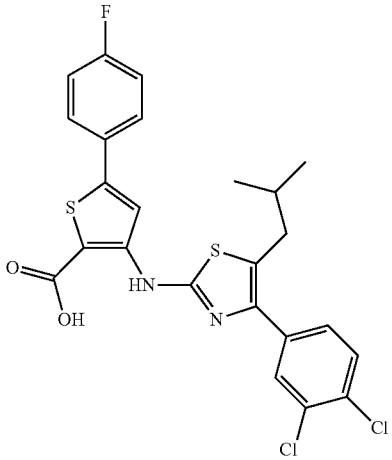 [SMILES: CC(C)Cc1sc(Nc2cc(-c3ccc(F)cc3)sc2C(=O)O)nc1-c1ccc(Cl)c(Cl)c1] | Method C, Purity is 100%, Rt = 2.266 min; MS Calcd.: 520.1; MS Found: 521.2 [M + H]⁺. | δ: 0.92 (6H, d, J = 6.4 Hz), 1.81-1.83 (1H, m), 2.73 (2H, d, J = 7.2 Hz), 7.07-7.09 (2H, m), 7.30 (1H, t, J = 8.4 Hz), 7.63 (1H, d, J = 8.4 Hz), 7.69-7.74 (3H, m), 7.89 (1H, s), 8.20 (1H, s). |
| 272 | 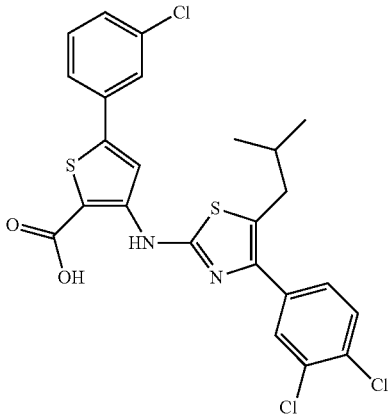 [SMILES: CC(C)Cc1sc(Nc2cc(-c3cccc(Cl)c3)sc2C(=O)O)nc1-c1ccc(Cl)c(Cl)c1] | Method C, Purity is 100%, Rt = 2.363 min; MS Calcd.: 536.1; MS Found: 537.1 [M + H]⁺. | δ: 0.93 (6H, d, J = 6.4 Hz), 1.80-1.87 (1H, m), 2.76 (2H, d, J = 7.2 Hz), 7.50-7.54 (2H, m), 7.63 (1H, dd, J = 8.6, 1.6 Hz), 7.67-7.69 (1H, m), 7.71 (1H, d, J = 8.4 Hz), 7.77 (1H, s), 7.94 (1H, d, J = 1.6 Hz), 8.49 (1H, s), 10.36 (1H, s), 13.35 (1H, brs). |
| 273 | 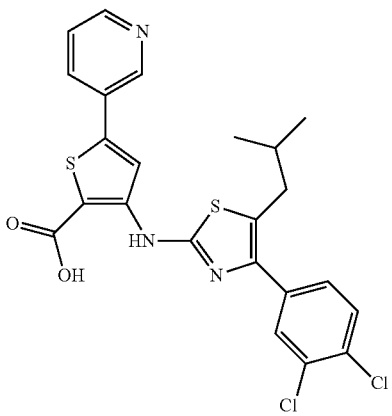 | Method C, Purity is 95.8%, Rt = 2.068 min; MS Calcd.: 503.2; MS Found: 504.0 [M + H]⁺. | δ: 0.90 (6H, d, J = 6.8 Hz), 1.78-1.83 (1H, m), 2.72 (2H, d, J = 7.2 Hz), 7.47-7.50 (1H, m), 7.62-7.65 (1H, m), 7.71-7.73 (1H, m), 7.89 (1H, s), 8.04-8.07 (1H, m), 8.35 (1H, s), 8.55-8.57 (1H, m), 8.90 (1H, s), 11.52 (1H, brs). |

-continued

Characterization Data for Additional Exemplary Compounds

| I-# | Chemical Structure | LCMS | ¹H NMR (400 MHz, d₆-DMSO) |
|---|---|---|---|
| 274 | 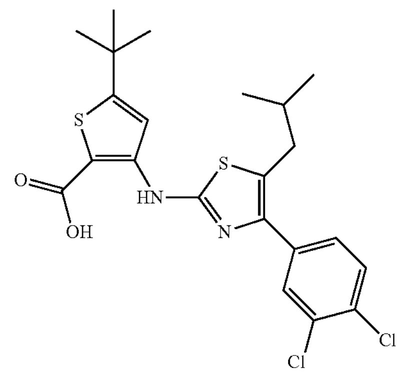 [SMILES: CC(C)Cc1sc(Nc2cc(C(C)(C)C)sc2C(=O)O)nc1-c1ccc(Cl)c(Cl)c1] | Method C, Purity is 99.6%, Rt = 2.302 min; MS Calcd.: 482.1; MS Found: 483.2 [M + H]⁺. | δ: 0.90 (6H, d, J = 6.8 Hz), 1.34 (9H, s), 1.78-1.82 (1H, m), 2.73 (2H, d J = 6.8 Hz), 7.11 (1H, brs), 7.58 (1H, dd, J = 8.4, 2.0 Hz), 7.69 (1H, d, J = 8.4 Hz), 7.86 (1H, d, J = 2.0 Hz), 7.90 (1H, s), 10.63 (1H, brs). |
| 275 | 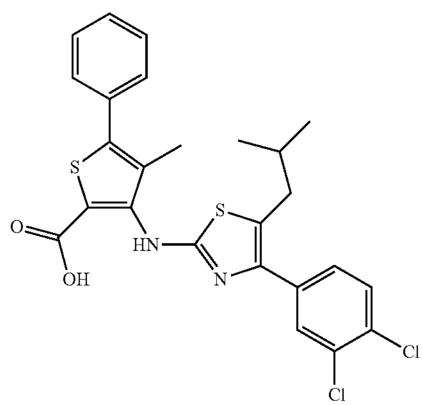 [SMILES: Cc1c(-c2ccccc2)sc(C(=O)O)c1Nc1nc(-c2ccc(Cl)c(Cl)c2)c(CC(C)C)s1] | Method C, Purity is 97.5%, Rt = 2.273 min; MS Calcd.: 516.0; MS Found: 517.1 [M + H]⁺. | δ: 0.88 (6H, d, J = 6.8 Hz), 1.76-1.79 (1H, m), 2.12 (3H, s), 2.66 (2H, d, J = 7.2 Hz), 6.07 (1H, s), 7.34 (1H, dd, J = 6.0, 3.6 Hz), 7.42-7.45 (4H, m), 7.53 (1H, dd, J = 8.0, 2.0 Hz), 7.66 (1H, d, J = 8.0 Hz), 7.72 (1H, d, J = 2.0 Hz), 11.23 (1H, brs). |
| 276 | 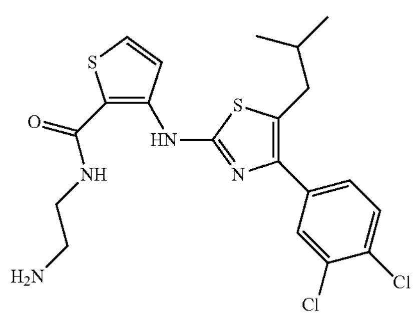 [SMILES: CC(C)Cc1sc(Nc2ccsc2C(=O)NCCN)nc1-c1ccc(Cl)c(Cl)c1] | Method B, Purity is 98.9%, Rt = 2.252 min; MS Calcd.: 468.1; MS Found: 469.1 [M + H]⁺. | δ: 0.91 (6H, d, J = 6.4 Hz), 1.77-1.84 (1H, m), 2.72 (2H, d J = 7.2 Hz), 2.98 (2H, dd, J = 12.4, 5.6 Hz), 3.08-3.10 (1H, m), 3.51 (2H, dd, J = 11.6, 5.6 Hz), 7.59 (1H, dd, J = 8.0, 2.0 Hz), 7.72 (1H, d, J = 8.4 Hz), 7.79-7.81 (2H, m), 7.98 (1H, d, J = 5.6 Hz), 8.06 (2H, brs), 8.42 (1H, t, J = 5.2 Hz). |
| 277 | 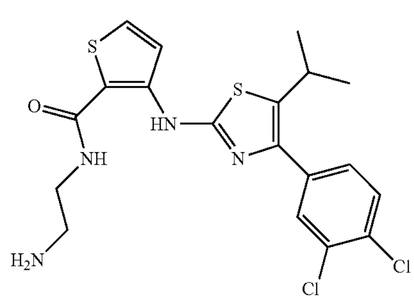 [SMILES: CC(C)c1sc(Nc2ccsc2C(=O)NCCN)nc1-c1ccc(Cl)c(Cl)c1] | Method C, Purity is 97.5%, Rt = 2.106 min; MS Calcd.: 454.1; MS Found: 455.0 [M + H]⁺. | δ: 1.28 (6H, d, J = 6.8 Hz), 2.98 (2H, dd, J = 11.6, 5.6 Hz), 3.31-3.38 (1H, m), 3.50 (2H, dd, J = 11.6, 6.0 Hz), 7.56 (1H, dd, J = 8.4, 2.0 Hz), 7.73 (1H, d, J = 8.4 Hz), 7.78 (2H, dd, J = 8.4, 2.0 Hz), 7.96 (1H, d, J = 5.2 Hz), 8.03 (2H, brs), 8.41 (1H, t, J = 5.2 Hz). |

-continued

Characterization Data for Additional Exemplary Compounds

| I-# | Chemical Structure | LCMS | ¹H NMR (400 MHz, d$_6$-DMSO) |
|---|---|---|---|
| 278 | 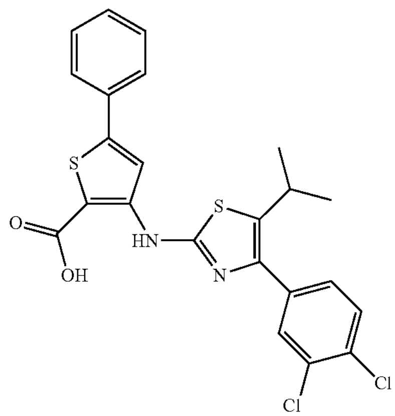 [SMILES: CC(C)c1sc(Nc2cc(-c3ccccc3)sc2C(=O)O)nc1-c1ccc(Cl)c(Cl)c1] | Method C, Purity is 88.8%, Rt = 2.241 min; MS Calcd.: 488.1; MS Found: 489.2 [M + H]⁺. | δ: 1.31 (6H, d, J = 6.4 Hz), 3.40-3.42 (1H, m), 7.42-7.51 (3H, m), 7.59 (1H, dd, J = 8.0, 1.6 Hz), 7.70-7.74 (3H, m), 7.88 (1H, d, J = 2.0 Hz), 8.42 (1H, s), 10.29 (1H, s), 13.30 (1H, brs). |
| 279 | 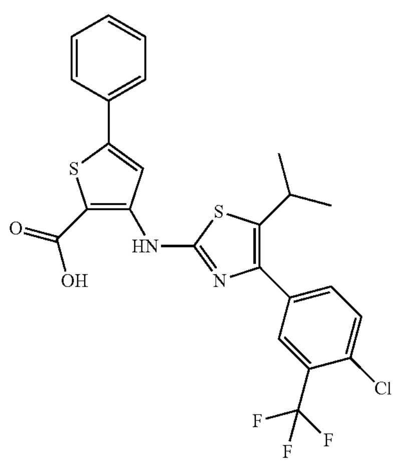 [SMILES: CC(C)c1sc(Nc2cc(-c3ccccc3)sc2C(=O)O)nc1-c1ccc(Cl)c(C(F)(F)F)c1] | Method C, Purity is 98.1%, Rt = 2.204 min; MS Calcd.: 522.0; MS Found: 523.1 [M + H]⁺. | δ: 1.31 (6H, d, J = 6.8 Hz), 3.38-3.41 (1H, m), 7.12 (2H, brs), 7.35 (1H, d, J = 7.6 Hz), 7.42 (2H, t, J = 7.6 Hz), 7.62 (2H, d, J = 7.2 Hz), 7.82 (1H, d, J = 8.4 Hz), 7.91 (1H, dd, J = 8.4, 2.0 Hz), 8.13 (1H, d, J = 1.6 Hz), 8.20 (1H, s). |
| 280 | 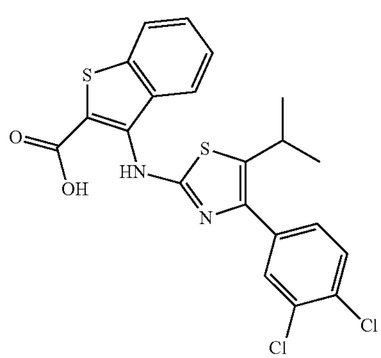 [SMILES: CC(C)c1sc(Nc2c(C(=O)O)sc3ccccc23)nc1-c1ccc(Cl)c(Cl)c1] | Method B, Purity is 96.1%, Rt = 2.299 min; MS Calcd.: 462.0; MS Found: 463.0 [M + H]⁺. | δ: 1.25 (6H, d, J = 6.8 Hz), 3.27-3.34 (1H, m), 7.40-7.47 (2H, m), 7.53-7.57 (1H, m), 7.61-7.66 (2H, m), 7.84 (1H, d, J = 8.0 Hz), 8.01 (1H, d, J = 8.0 Hz). |

-continued

Characterization Data for Additional Exemplary Compounds

| I-# | Chemical Structure | LCMS | $^1$H NMR (400 MHz, d$_6$-DMSO) |
|---|---|---|---|
| 281 | 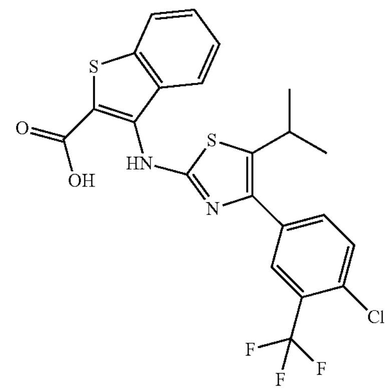 [SMILES: CC(C)c1sc(Nc2c(C(=O)O)sc3ccccc23)nc1-c1ccc(Cl)c(C(F)(F)F)c1] | Method B, Purity is 99.1%, Rt = 2.286 min; MS Calcd.: 496.0; MS Found: 497.1 [M + H]$^+$. | δ: 1.27 (6H, d, J = 6.4 Hz), 3.27-3.33 (1H, m), 7.41-7.45 (1H, m), 7.52-7.56 (1H, m), 7.73 (2H, s), 7.84 (2H, d, J = 8.8 Hz), 8.00 (1H, d, J = 8.0 Hz), 10.09 (1H, s), 13.46 (1H, brs). |
| 282 | 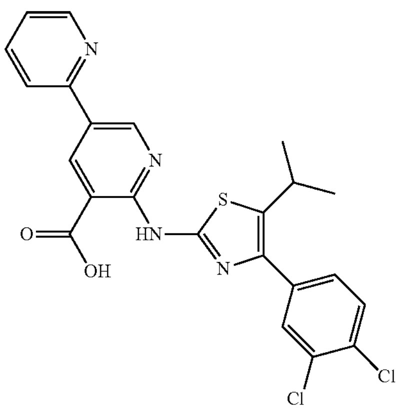 [SMILES: CC(C)c1sc(Nc2ncc(-c3ccccn3)cc2C(=O)O)nc1-c1ccc(Cl)c(Cl)c1] | Method C, Purity is 100%, Rt = 2.086 min; MS Calcd.: 484.1; MS Found: 484.8 [M + H]$^+$. | δ: 1.34 (6H, d, J = 6.4 Hz), 3.46 (1H, m), 7.35-7.90 (5H, m), 8.06-8.08 (1H, m), 8.67 (1H, s), 9.00-9.16 (2H, m). |
| 283 | 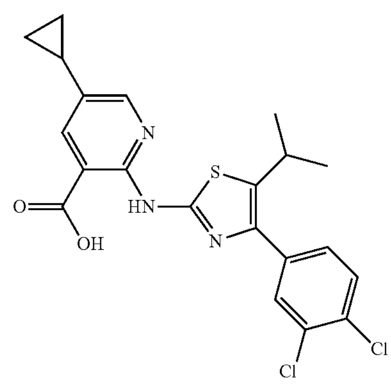 [SMILES: CC(C)c1sc(Nc2ncc(C3CC3)cc2C(=O)O)nc1-c1ccc(Cl)c(Cl)c1] | Method B, Purity is 100%, Rt = 2.306 min; MS Calcd.: 447.1; MS Found: 448.1 [M + H]$^+$. | δ: 0.74-0.78 (2H, m), 0.95-1.00 (2H, m), 1.33 (6H, d, J = 6.8 Hz), 1.97-2.08 (1H, m), 3.35-3.41 (1H, m), 7.56 (1H, dd, J = 8.0, 1.6 Hz), 7.71 (1H, d, J = 8.4 Hz), 7.78 (1H, d, J = 2.0 Hz), 8.01 (1H, d, J = 2.4 Hz), 8.42 (1H, d, J = 2.4 Hz), 11.41 (1H, s), 14.09 (1H, brs). |
| 284 | 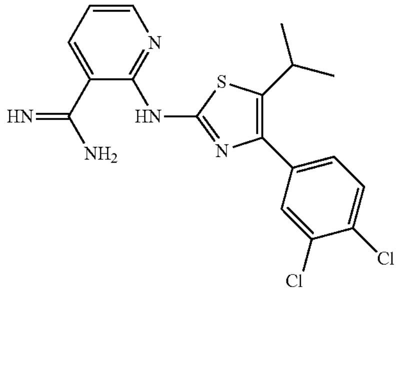 [SMILES: CC(C)c1sc(Nc2ncccc2C(=N)N)nc1-c1ccc(Cl)c(Cl)c1] | Method C, Purity is 98.5%, Rt = 2.880 min; MS Calcd.: 405.1; MS Found: 406.2 [M + H]$^+$. | δ: 1.28 (6H, d, J = 6.8 Hz), 3.31-3.34 (1H, m), 6.80-6.83 (1H, m), 7.49-7.51 (1H, m), 7.65 (1H, d, J = 8.4 Hz), 7.73 (1H, d, J = 1.6 Hz), 8.15-8.17 (1H, m), 8.37-8.38 (1H, m), 9.31 (3H, brs). |

Characterization Data for Additional Exemplary Compounds

| I-# | Chemical Structure | LCMS | $^1$H NMR (400 MHz, $d_6$-DMSO) |
|---|---|---|---|
| 285 | 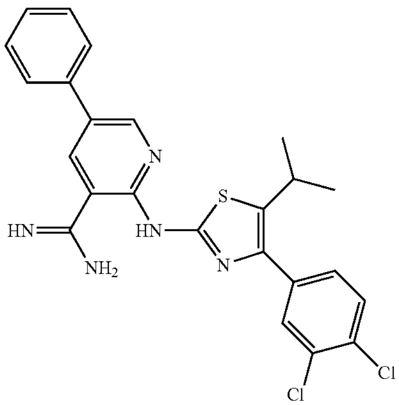 [SMILES: CC(C)c1sc(Nc2ncc(-c3ccccc3)cc2C(=N)N)nc1-c1ccc(Cl)c(Cl)c1] | Method C, Purity is 92.3%, Rt = 2.492 min; MS Calcd.: 481.1; MS Found: 482.0 [M + H]$^+$. | δ: 1.29-1.33 (6H, m), 3.33-3.37 (1H, m), 7.34-7.36 (1H, m), 7.46-7.54 (3H, m), 7.67-7.69 (1H, m), 7.76-7.81 (3H, m), 8.51 (1H, d, J = 2.4 Hz), 8.77 (1H, d, J = 2.4 Hz), 9.31 (3H, brs). |

Example 5. Compound Testing in Human eIF4E/4G2 Binding Assay

Human eIF4E (aa 28-217) with a C-terminal His-tag was expressed in *E. coli* in inclusion bodies. The protein was solubilized with 8 M urea and purified under denaturing conditions using nickel-charged HisTrap HP columns (GE Healthcare). The purified protein was then refolded by diluting in 20 mM Hepes pH 7.0, 0.5 M NaCl, 1 mM DTT, 1 mM EDTA, 0.5 M arginine plus 6 M urea, and then dialyzing overnight into the same buffer without the urea. The protein was further dialyzed into 20 mM Hepes, pH 6.5, 50 mM NaCl, 1 mM EDTA, 1 mM DTT, and concentrated using Hitrap SP sepharose FF columns (GE Healthcare). The concentrated protein was dialyzed into 20 mM Hepes, pH 7.0, 0.5M NaCl, 5 mM DTT and 10% glycerol, and stored at −80° C. until use.

Test compounds (3.43 mM stock in DMSO) were diluted 2-fold in series in DMSO (10 concentration points). Compound solutions (1.2 μl/well) were added into black 384-well polypropylene microplates (Matrix, Thermal Scientific). Twenty-two microliters per well of Assay Buffer (50 mM NaPi, pH 6.5, 50 mM KCl, 1 mM DTT and 0.5 mg/ml gamma globulin) and eight microliters per well of 82.5 nM purified eIF4E in Assay Buffer were added. The samples were incubated at room temperature (20-23° C.) for 4 hours. Biotin labeled 4G2 peptide (Ac-Lys-Gln-Tyr-Asp-Arg-Glu-Phe-Leu-Leu-Asp-Phe-Gln-Phe-Met-Pro-Lys(Aha-Bio)-NH2, 1.75 μM stock in DMSO) was diluted to 0.14 μM in Assay Buffer (without DTT) and 5 μl/well was added. The samples were incubated at room temperature for 20 min. Five microliters per well of 6.4 nM Eu-streptavidin (Eu-SA, Perkin Elmer) and 80 nM Allophycocyanin (APC)-anti His antibody (Columbia Biosciences) in Assay Buffer (without DTT) were then added and the samples were incubated at room temperature for 20 min.

Assay signals were monitored by reading excitation at 340 nm and emission fluorescence at 615 nm and 665 nm on an Envision reader (Perkin Elmer). Normalized TR-FRET (time-resolved fluorescence resonance energy transfer) assay signal (Rn) was calculated by the formula:

$$Rn = [(A - Ba - C \times D)/(D - Bd)] \times (Dc - Bd)$$

Where A is the fluorescence intensity of the sample at 665 nm,
D is the fluorescence intensity of the sample at 615 nm,
Ba and Bd are plate backgrounds at 665 nm and 615 nm, respectively,
Dc is the fluorescence intensity of 0.78 nM Eu-SA in the assay buffer at 615 nm The cross-talk factor (C) is determined by the following formula:

$$C = (Ac - Ba)/(Dc - Bd)$$

Where Ac is the fluorescence intensity of 0.78 nM Eu-SA in the assay buffer at 665 nm.

IC50 values were calculated using xLFit program (IDBS). Table 2 below lists EC50 of some compounds, wherein A represents EC50≤1 uM; B represents 1 uM<EC50≤10 uM; and C represents EC50>10 uM.

TABLE 2

IC50 of Certain Exemplary Compounds.

| Comp. No. | IC50 | Comp. No. | IC50 | Comp. No. | IC50 |
|---|---|---|---|---|---|
| I-1 | A | I-97 | B | I-195 | C |
| I-2 | A | I-98 | C | I-196 | B |
| I-3 | A | I-99 | B | I-197 | B |
| I-4 | B | I-100 | A | I-198 | C |
| I-5 | B | I-101 | A | I-199 | C |
| I-6 | A | I-103 | A | I-200 | C |
| I-7 | A | I-104 | A | I-201 | C |
| I-8 | B | I-105 | B | I-202 | C |
| I-9 | B | I-106 | B | I-203 | B |
| I-10 | B | I-107 | A | I-204 | C |
| I-11 | B | I-108 | A | I-205 | C |
| I-12 | B | I-109 | B | I-206 | B |
| I-13 | B | I-110 | B | I-207 | B |
| I-14 | B | I-111 | A | I-208 | A |
| I-15 | B | I-114 | B | I-209 | A |
| I-16 | B | I-115 | C | I-210 | A |
| I-17 | A | I-116 | C | I-211 | C |
| I-18 | A | I-117 | B | I-212 | A |
| I-19 | A | I-119 | B | I-213 | A |
| I-20 | A | I-120 | B | I-214 | B |
| I-21 | B | I-121 | B | I-215 | A |
| I-22 | B | I-122 | B | I-216 | A |
| I-23 | A | I-124 | C | I-217 | A |
| I-24 | B | I-125 | C | I-218 | C |
| I-25 | A | I-126 | A | I-219 | B |

TABLE 2-continued

IC50 of Certain Exemplary Compounds.

| Comp. No. | IC50 | Comp. No. | IC50 | Comp. No. | IC50 | Comp. No. | IC50 | Comp. No. | IC50 | Comp. No. | IC50 |
|---|---|---|---|---|---|---|---|---|---|---|---|
| I-26 | B | I-127 | B | I-220 | B | I-64 | B | I-165 | B | I-258 | A |
| I-27 | A | I-128 | C | I-221 | B | I-65 | A | I-166 | B | I-259 | A |
| I-28 | C | I-129 | B | I-222 | B | I-66 | B | I-167 | B | I-260 | A |
| I-29 | B | I-130 | C | I-223 | B | I-67 | B | I-168 | B | I-261 | A |
| I-30 | B | I-131 | B | I-224 | B | I-68 | B | I-169 | B | I-262 | A |
| I-31 | C | I-132 | B | I-225 | A | I-69 | B | I-170 | B | I-263 | A |
| I-32 | B | I-133 | C | I-226 | A | I-70 | B | I-171 | A | I-264 | A |
| I-33 | B | I-134 | B | I-227 | B | I-71 | C | I-172 | B | I-265 | A |
| I-34 | B | I-135 | B | I-228 | B | I-72 | C | I-173 | B | I-266 | A |
| I-35 | B | I-136 | B | I-229 | A | I-73 | B | I-174 | A | I-267 | A |
| I-36 | B | I-137 | B | I-230 | C | I-74 | A | I-175 | B | I-268 | A |
| I-37 | B | I-138 | A | I-231 | C | I-75 | B | I-176 | B | I-269 | B |
| I-38 | B | I-139 | B | I-232 | B | I-76 | C | I-177 | A | I-270 | A |
| I-39 | B | I-140 | C | I-233 | A | I-77 | B | I-178 | B | I-271 | A |
| I-40 | B | I-141 | B | I-234 | B | I-78 | B | I-179 | B | I-272 | A |
| I-41 | B | I-142 | A | I-235 | A | I-79 | B | I-180 | A | I-273 | A |
| I-42 | B | I-143 | C | I-236 | A | I-80 | B | I-181 | C | I-274 | A |
| I-43 | B | I-144 | B | I-237 | A | I-81 | B | I-182 | B | I-275 | A |
| I-44 | B | I-145 | C | I-238 | B | I-82 | B | I-183 | C | I-276 | B |
| I-45 | B | I-146 | C | I-239 | B | I-83 | C | I-184 | B | I-277 | B |
| I-46 | B | I-147 | B | I-240 | B | I-84 | C | I-185 | B | I-278 | A |
| I-47 | A | I-148 | C | I-241 | A | I-85 | B | I-186 | C | I-279 | A |
| I-48 | A | I-149 | C | I-242 | A | I-86 | C | I-187 | C | I-280 | A |
| I-49 | A | I-150 | B | I-243 | A | I-87 | A | I-188 | C | I-281 | A |
| I-50 | B | I-151 | B | I-244 | A | I-88 | C | I-189 | C | I-282 | A |
| I-51 | A | I-152 | B | I-245 | B | I-89 | C | I-190 | A | I-283 | A |
| I-52 | A | I-153 | C | I-246 | B | I-90 | C | I-191 | B | I-284 | C |
| I-53 | B | I-154 | B | I-247 | A | I-93 | B | I-192 | B | I-285 | C |
| I-54 | B | I-155 | B | I-248 | A | I-94 | A | I-193 | C | I-286 | C |
| I-55 | A | I-156 | B | I-249 | B | I-96 | A | I-194 | C | I-287 | C |
| I-56 | B | I-157 | B | I-250 | B | | | | | I-288 | C |
| I-57 | A | I-158 | B | I-251 | B | I-309 | A | I-310 | A | I-320 | A |
| I-58 | C | I-159 | B | I-252 | A | I-321 | A | I-322 | A | I-323 | A |
| I-59 | A | I-160 | C | I-253 | B | I-324 | A | I-325 | A | I-326 | A |
| I-60 | A | I-161 | B | I-254 | B | I-327 | A | I-329 | A | I-330 | A |
| I-61 | C | I-162 | B | I-255 | B | I-331 | A | I-332 | A | I-333 | A |
| I-62 | B | I-163 | B | I-256 | A | | | | | | |
| I-63 | B | I-164 | B | I-257 | A | | | | | | |

Example 6. Synthesis of Compounds I-289 to I-319

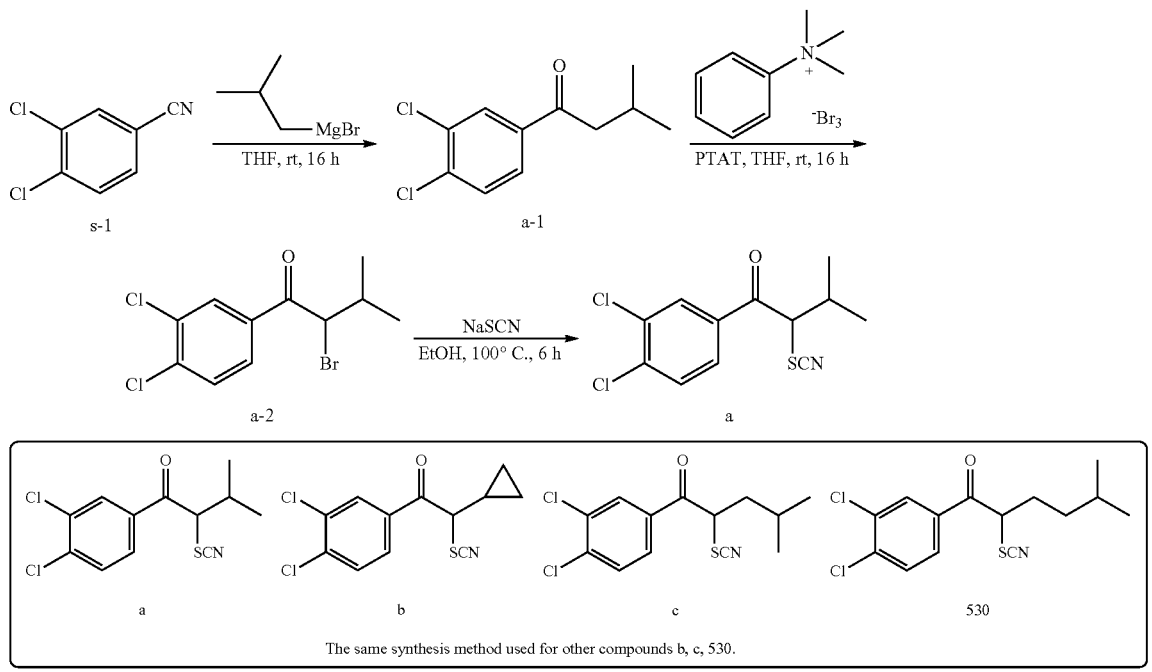

Scheme 1: Route for Compounds a, b, c, 530

The same synthesis method used for other compounds b, c, 530.

Scheme 2: Route for Compound 595
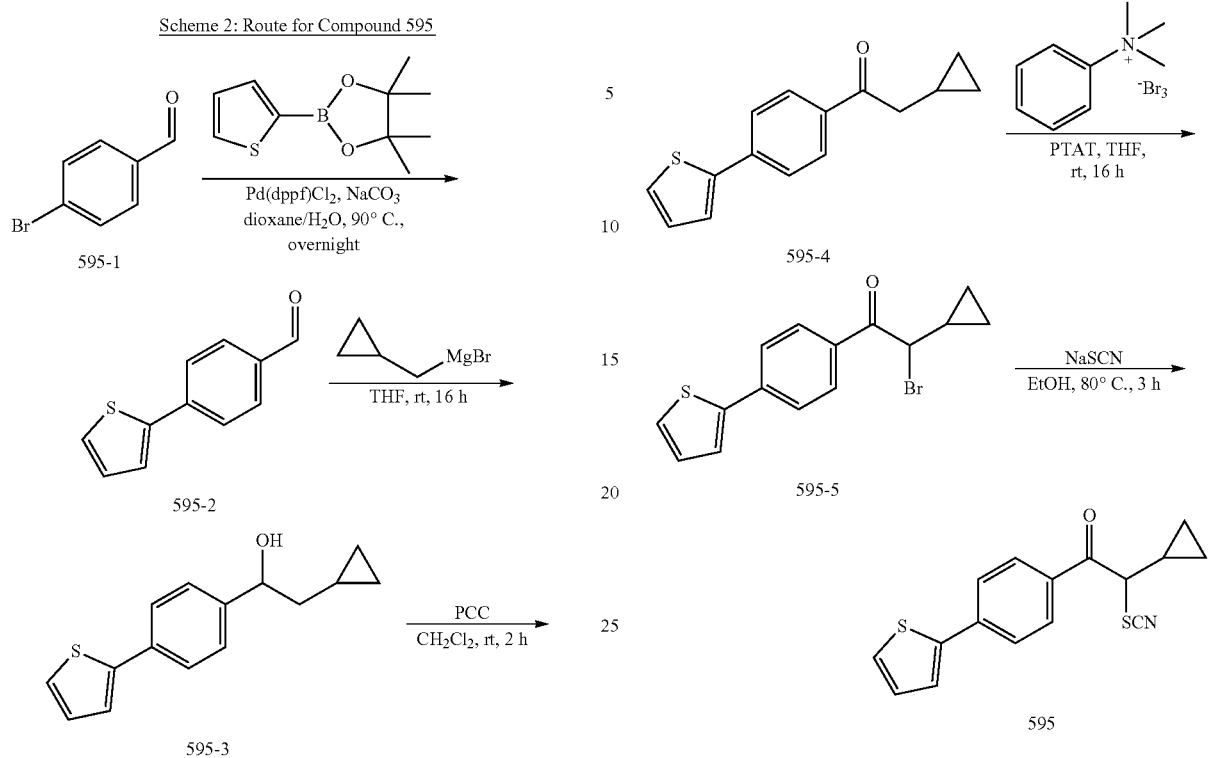
Scheme 3: Route for Compounds 604, 661, 664, 667, 671, 672
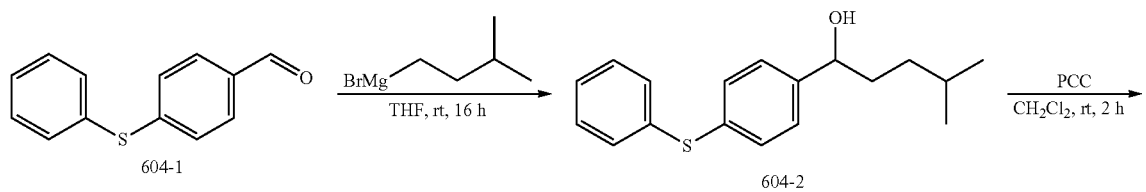
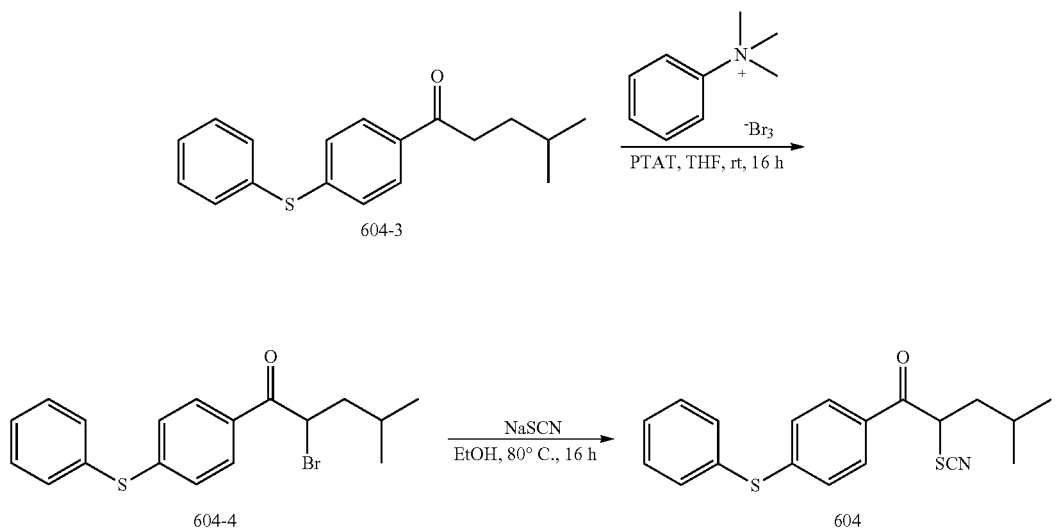

-continued
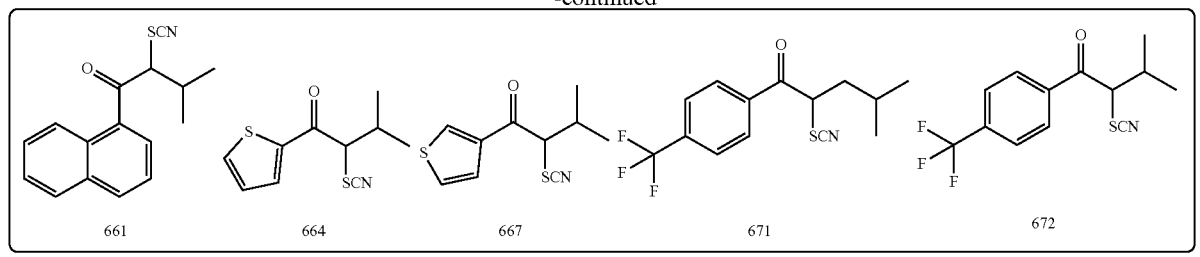
Scheme 4: Route for Compound 611
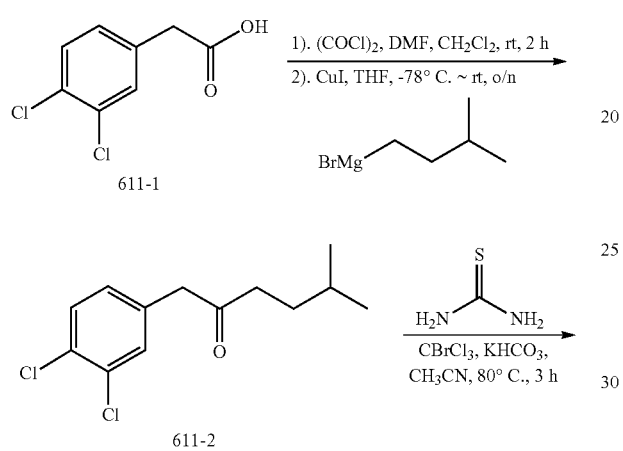
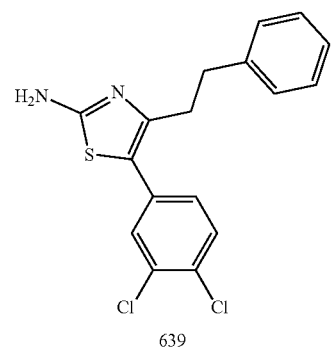
Scheme 6: Route for Compound 634
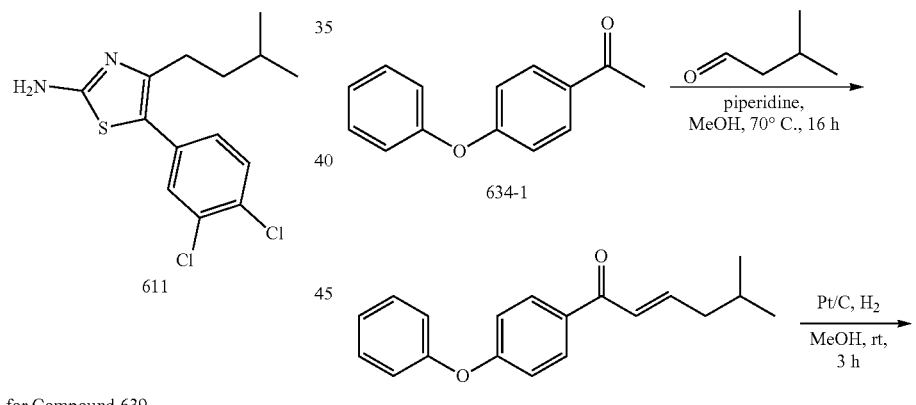
Scheme 5: Route for Compound 639
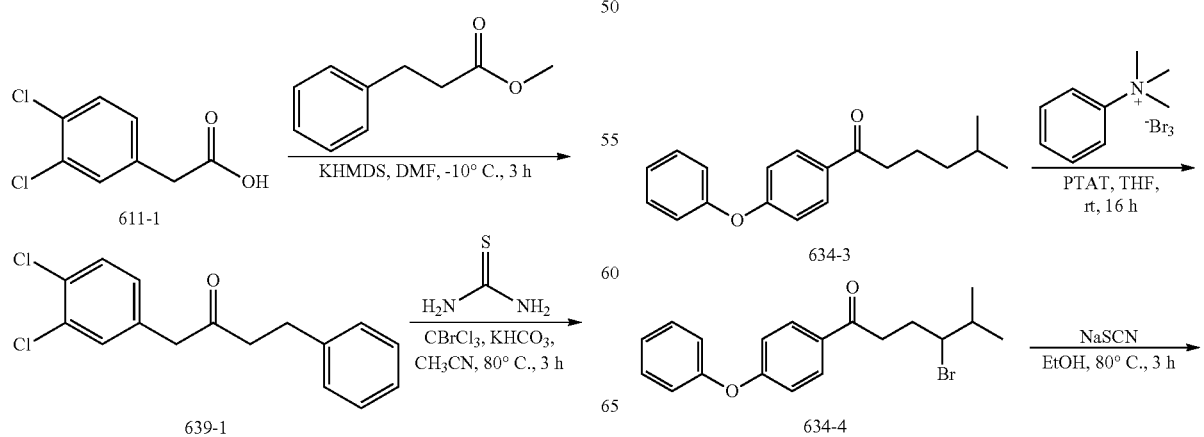

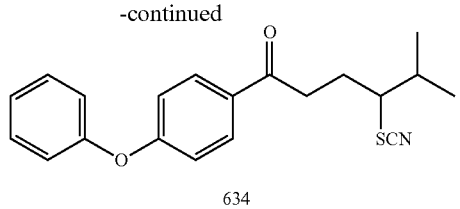
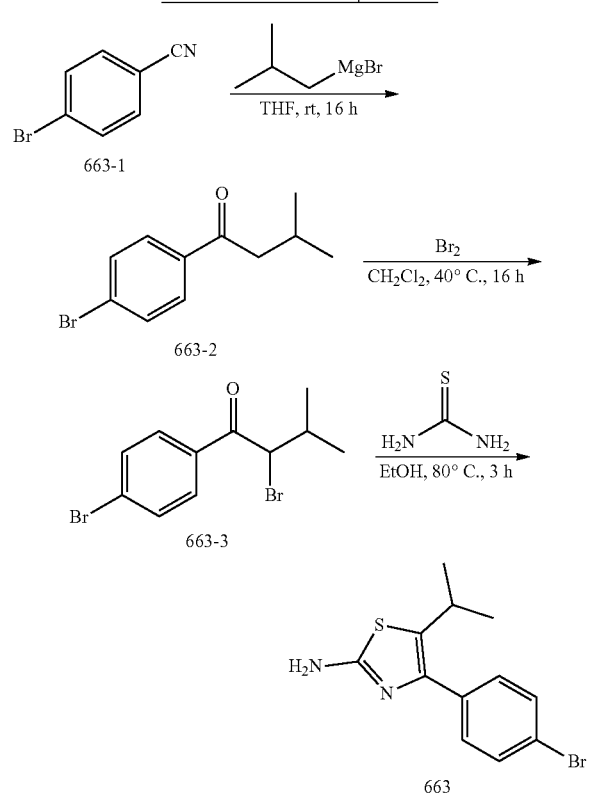
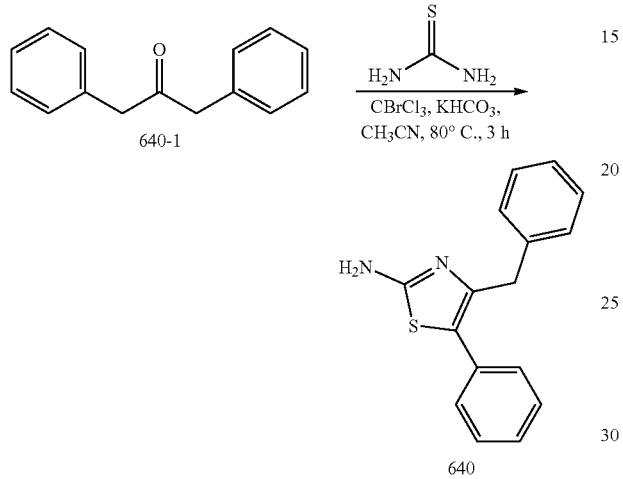
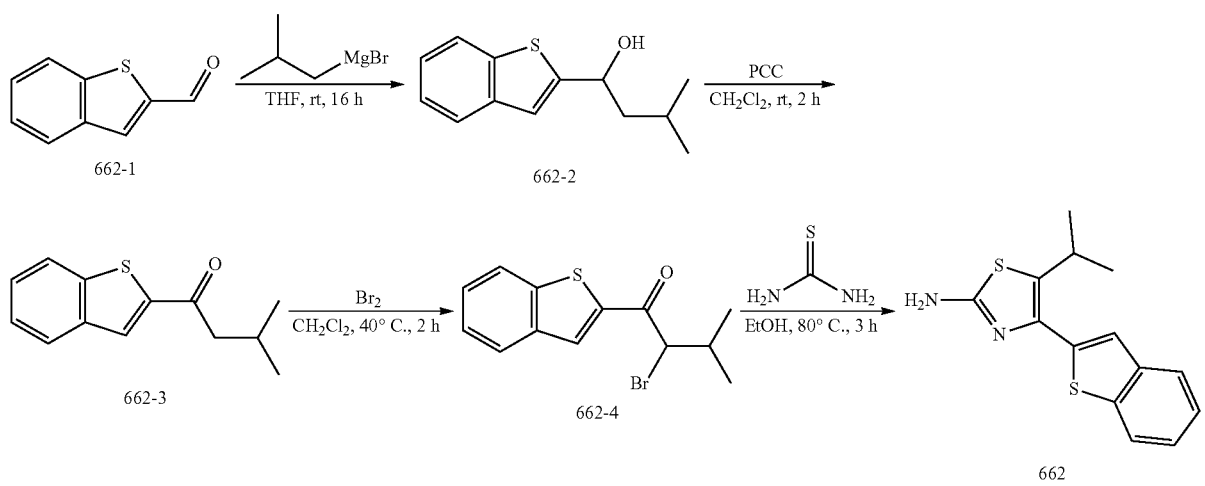
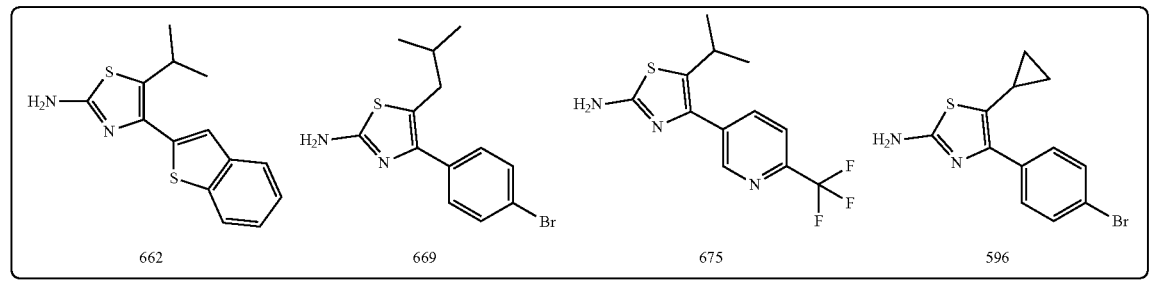

Scheme 10: Route for Compound 613
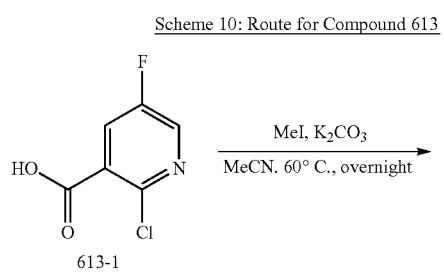
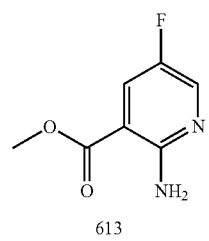
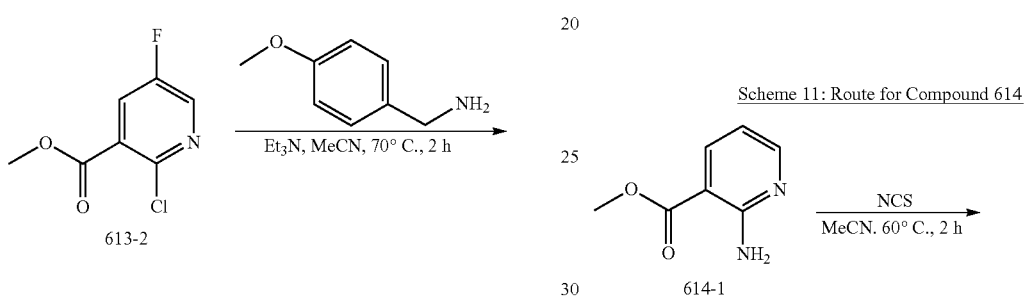
Scheme 11: Route for Compound 614
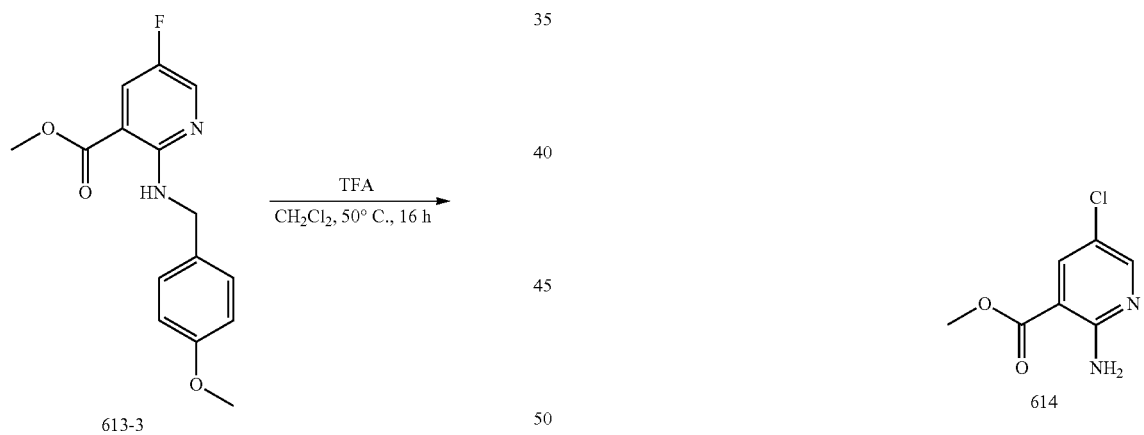
Scheme 12: Route for Compounds 595-s, 596-s, 614-s, 634-s, 661-s, 664-s, 667-s, 671-s, 672-s
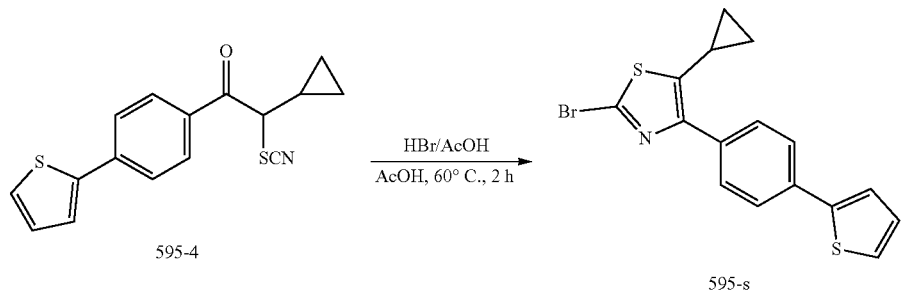

-continued
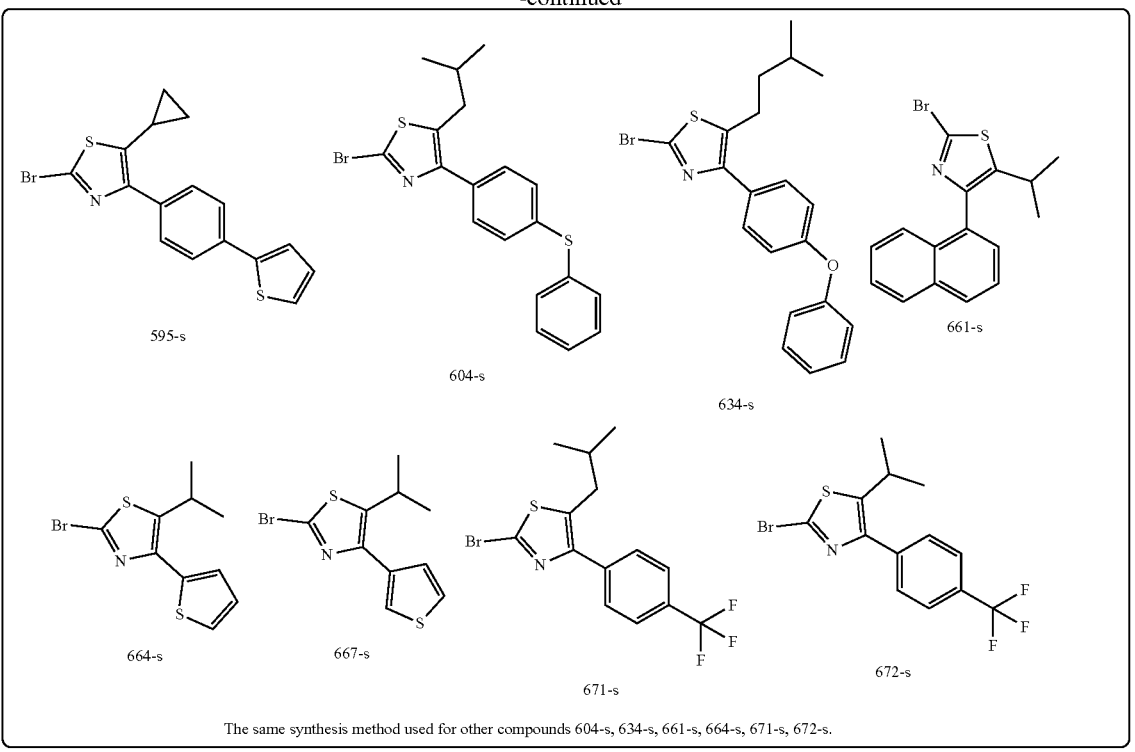
The same synthesis method used for other compounds 604-s, 634-s, 661-s, 664-s, 671-s, 672-s.
Scheme 13: Route for Compound 611-s
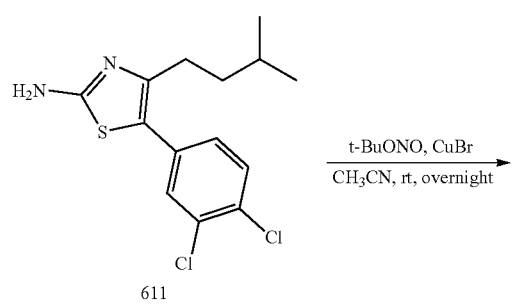
Scheme 14: Route for Compounds 596-s, 663-s, 669-s
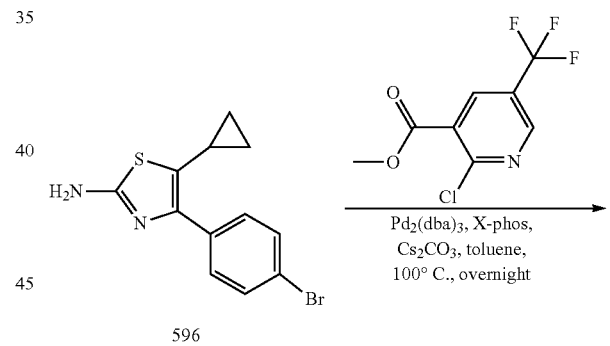

-continued
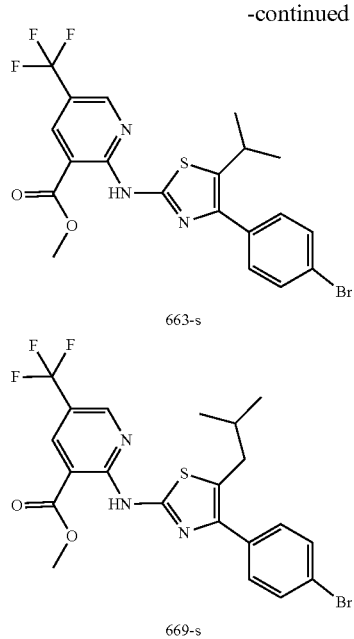
The same synthesis method used for other compounds 663-s, 669-s
Scheme 15: Route for Compound 624-s
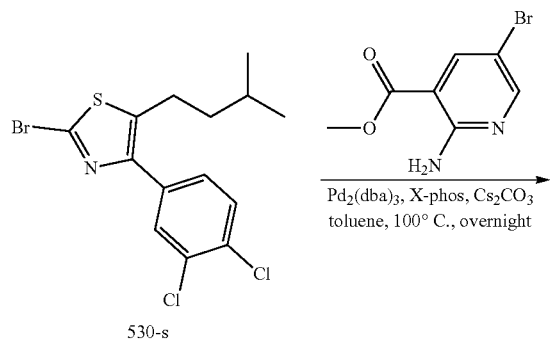
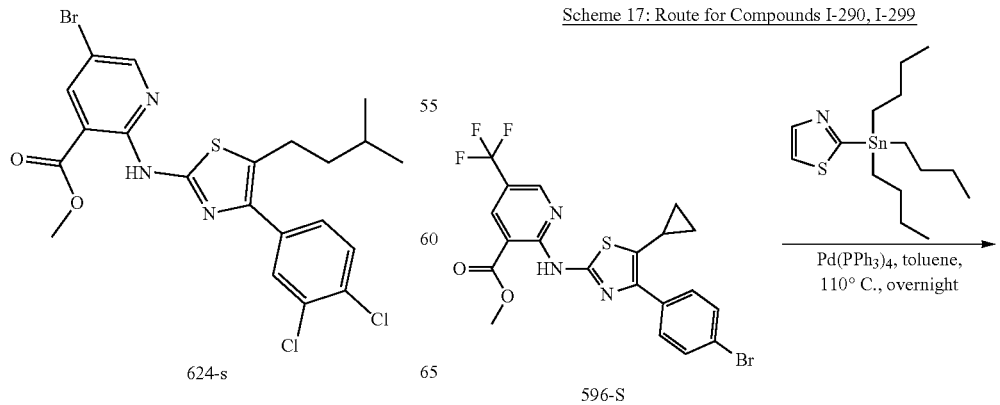
Scheme 16: Route for Compounds I-289, I-294, I-298, I-301 to I-304, I-308, I-311, I-314, I-315, I-317, I-318
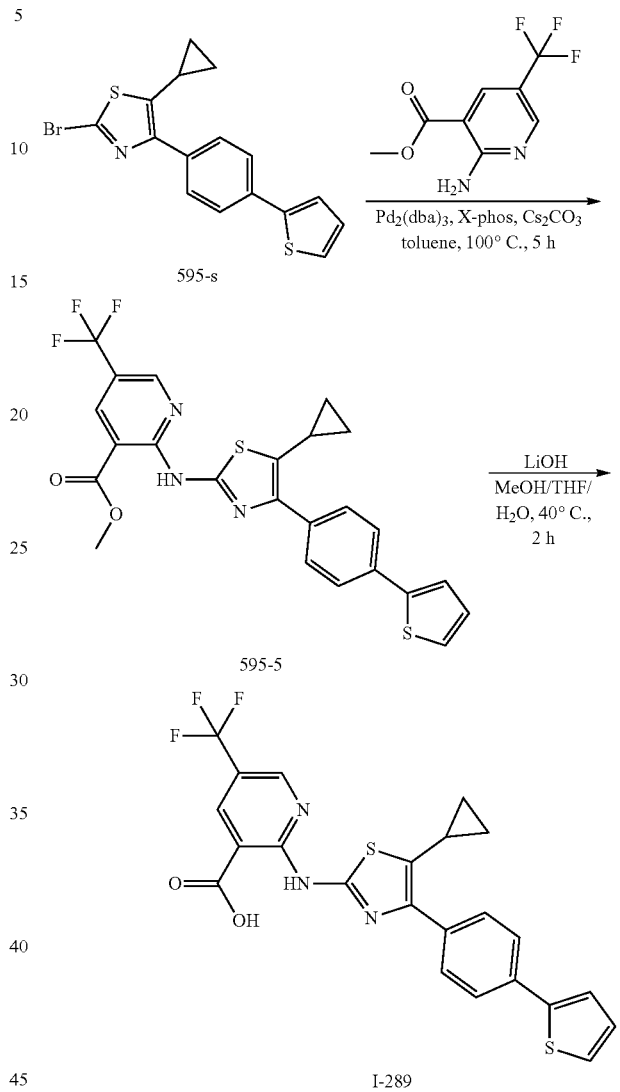
The same synthesis method used for other compounds I-294, I-298, I-301 to I-304, I-308, I-311, I-314, I-315, I-317, I-318
Scheme 17: Route for Compounds I-290, I-299

665
-continued
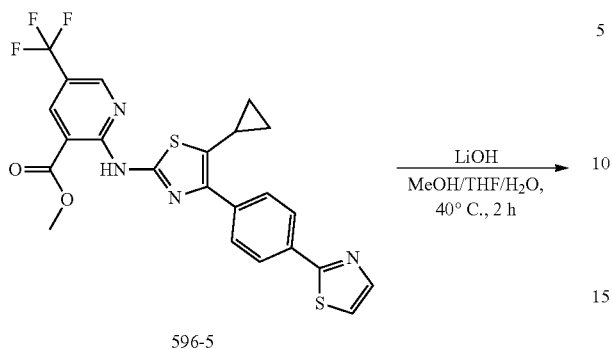
596-5
→ LiOH
MeOH/THF/H₂O,
40° C., 2 h
666
-continued
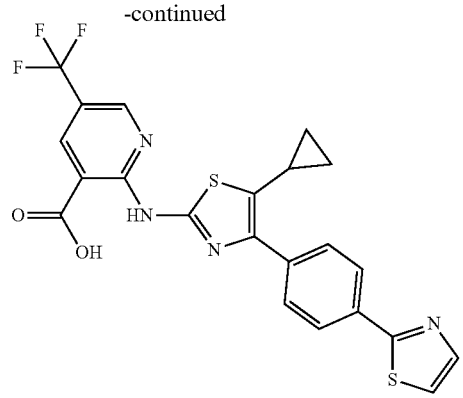
I-290
The same synthesis method used for other compounds I-299.
Scheme 18: Route for Compound I-291
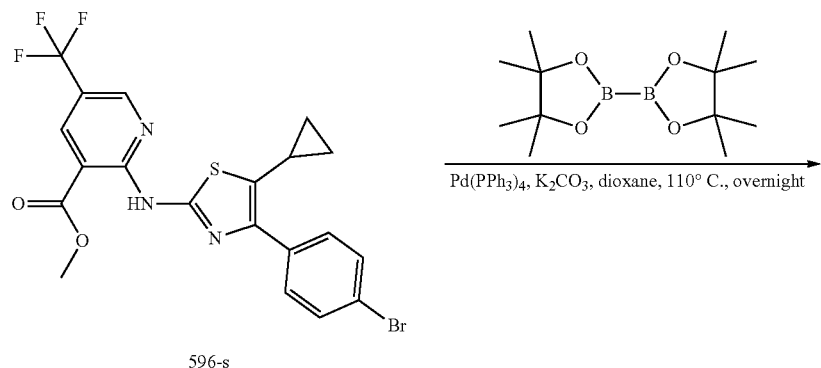
596-s
Pd(PPh₃)₄, K₂CO₃, dioxane, 110° C., overnight
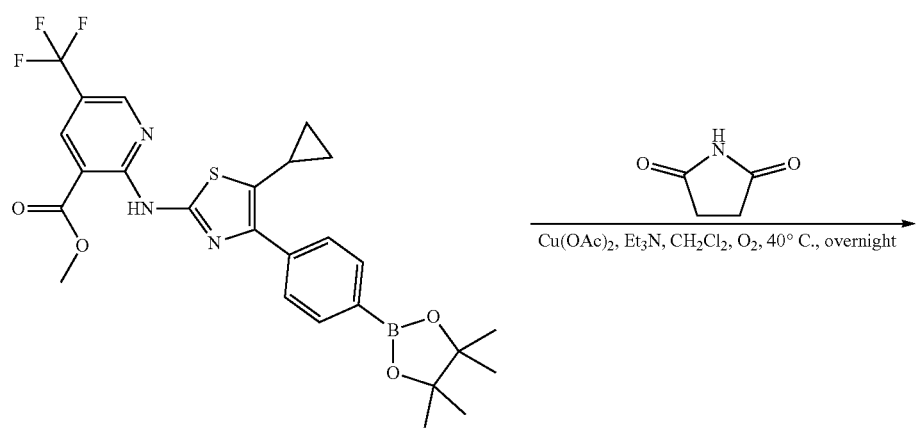
598-1
Cu(OAc)₂, Et₃N, CH₂Cl₂, O₂, 40° C., overnight -continued
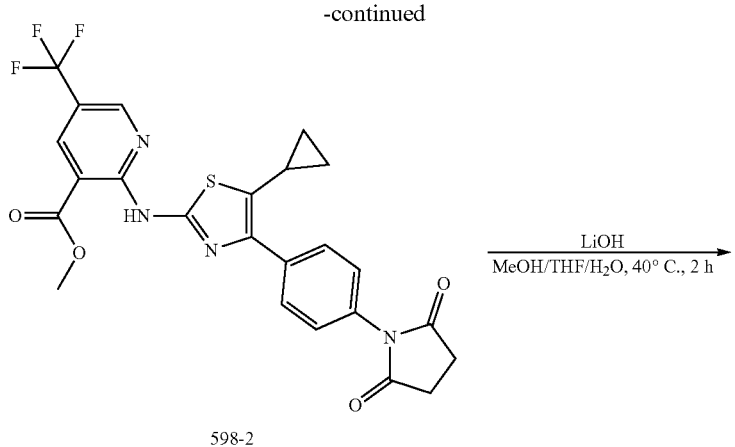
598-2
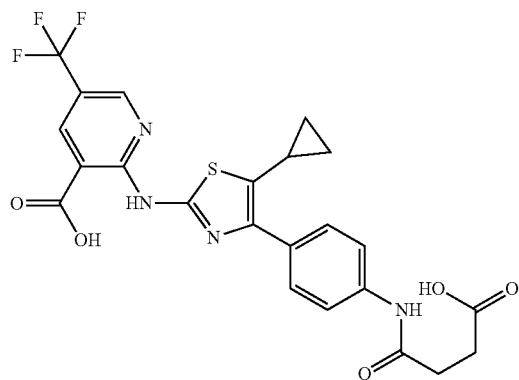
I-291
Scheme 19: Route for Compounds I-295, I-296
-continued
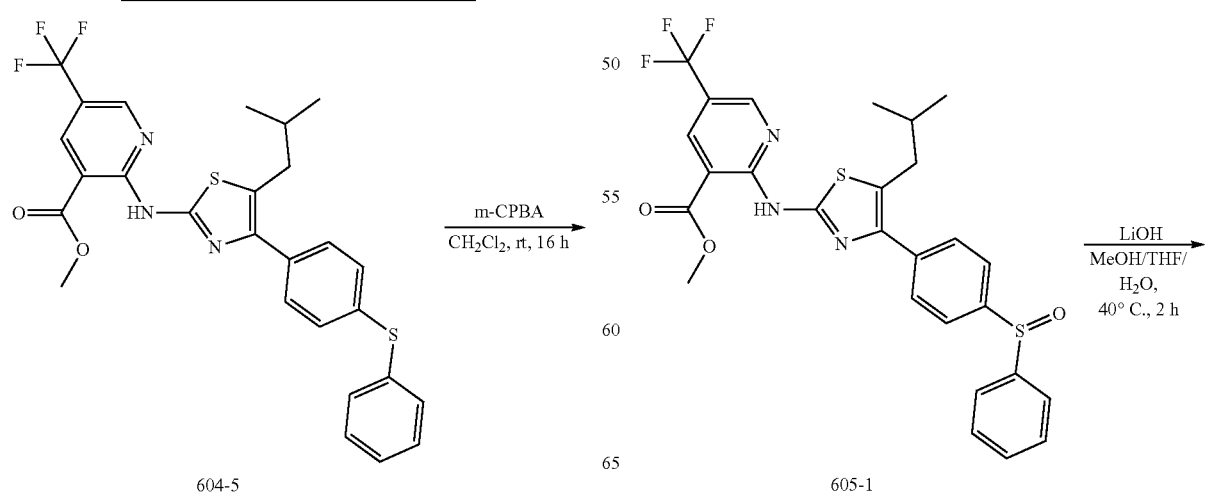
604-5
605-1

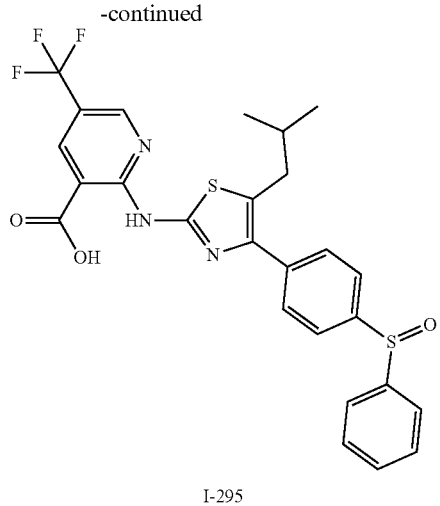
I-295
The same synthesis method used for other compounds I-296.
Scheme 20 Route for Compound I-297
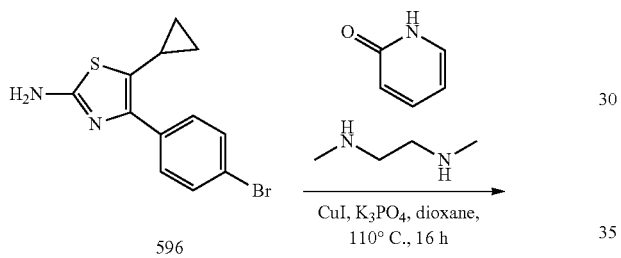
596
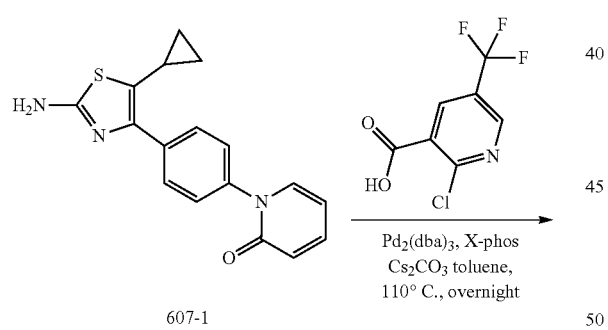
607-1
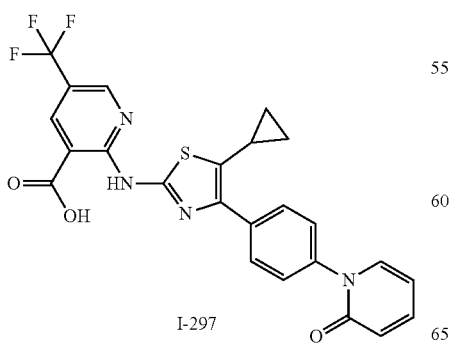
I-297
Scheme 21: Route for Compound 300
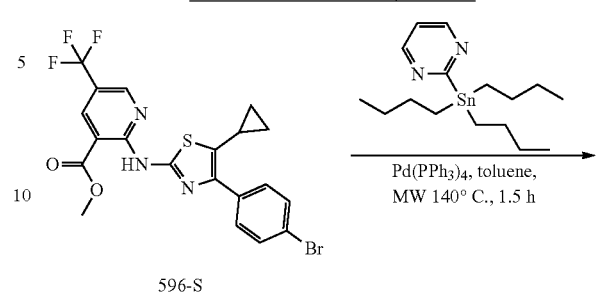
596-S
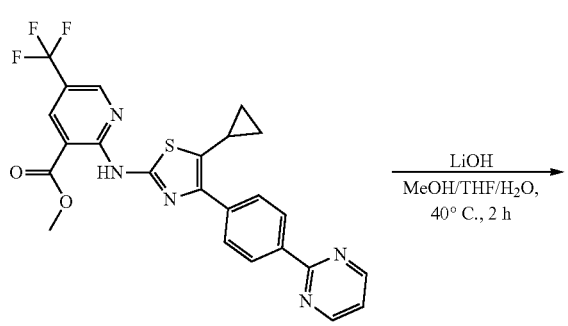
610-2
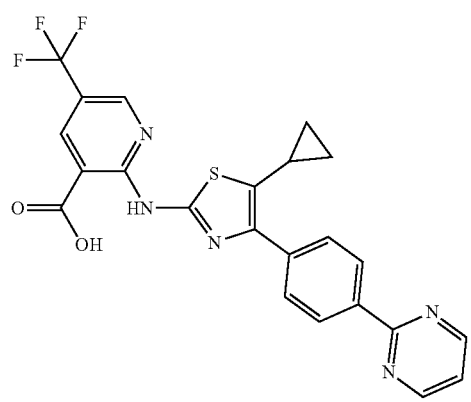
I-300
Scheme 22: Route for Compound I-312
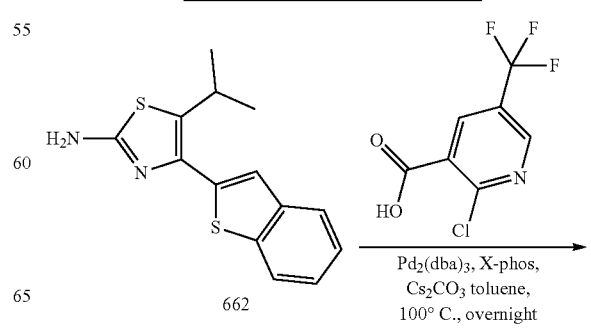
662

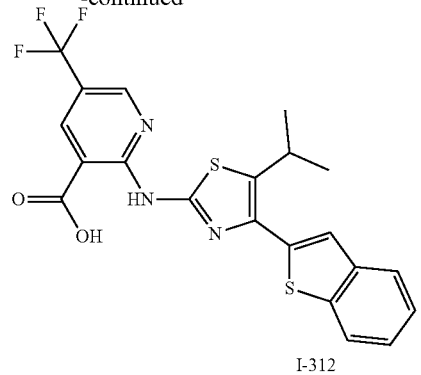

I-312

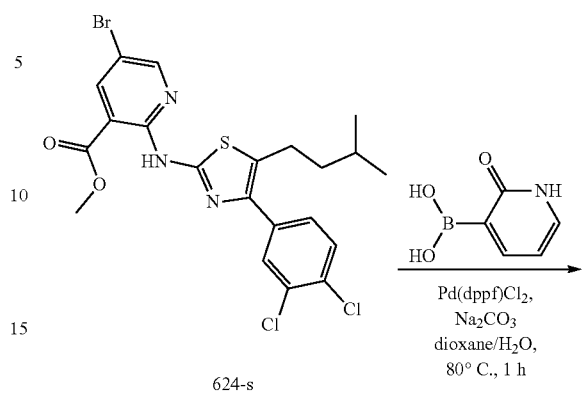

Scheme 24 Route for Compounds I-305 to I-307, I-313, I-316

624-s

Pd(dppf)Cl$_2$, Na$_2$CO$_3$
dioxane/H$_2$O,
80° C., 1 h

Scheme 23 Route for Compounds I-309, I-310, I-319

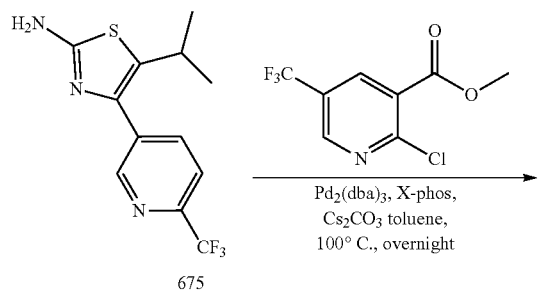

675

Pd$_2$(dba)$_3$, X-phos,
Cs$_2$CO$_3$ toluene,
100° C., overnight

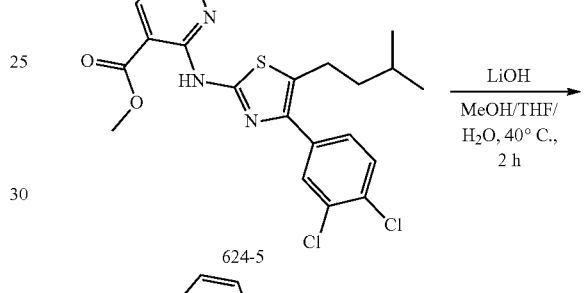

624-5

LiOH
MeOH/THF/
H$_2$O, 40° C.,
2 h

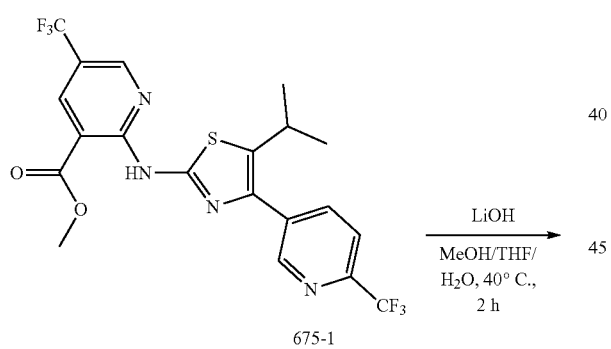

675-1

LiOH
MeOH/THF/
H$_2$O, 40° C.,
2 h

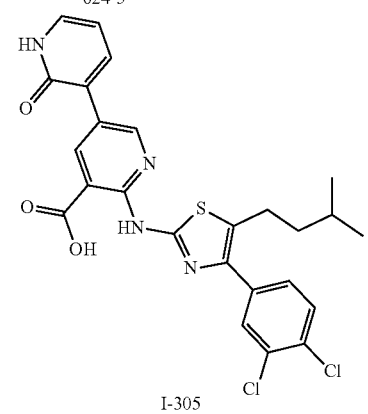

I-305

The same synthesis method used for other compounds I-306, I-307, I-313, I-36

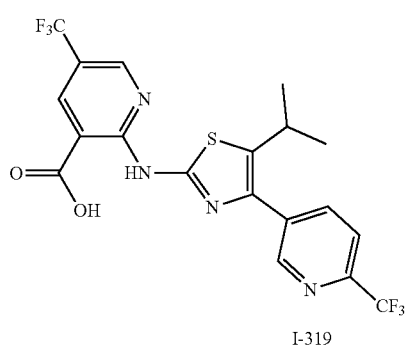

I-319

The same synthesis method used for other compounds I-309, I-310

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.)

Method D (Agilent LCMS 1200-6120, Column: Waters X-Bridge C18 (50 mm×4.6 mm×3.5 m); Column Temperature: 45° C.; Flow Rate: 2.3 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.75 min, then under this condition for 0.8 min, finally changed to 95% [water+10 mM NH$_4$HCO$_3$] and 5% [CH$_3$CN] in 0.1 min and under this condition for 0.1 min.)

Synthesis of 1-(3,4-dichlorophenyl)-3-methylbutan-1-one (a-1)

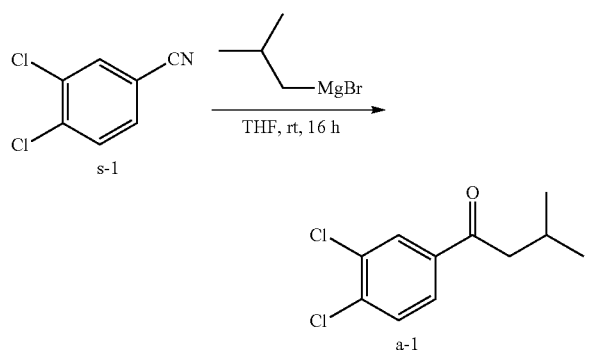

To a solution of s-1 (10.0 g, 58.1 mmol) in THF (100 m was added isobutyl magnesium bromide (1.0 M in THF, 87.1 mL, 87.1 mmol). The reaction was stirred at room temperature for 16 h. When the reaction was completed, it was poured into aq.NH$_4$Cl (sat., 500 mL) and extracted with EtOAc (100 mL×3). The organic phase was combined, and washed with H$_2$O (100 mL) and brine (80 mL), then dried with anhydrous Na$_2$SO$_4$, concentrated and purified by silica gel column chromatography (petrol ether/ethyl acetate=20/1) to afford a-1 (7.50 g, 55.8% yield) as yellow oil.

Synthesis of 2-bromo-1-(3,4-dichlorophenyl)-3-methylbutan-1-one (a-2)

A mixture of a-1 (7.50 g, 32.5 mmol) and PTAT (18.3 g, 48.7 mmol) in THF (150 mL) was stirred at room temperature overnight. When the reaction was completed, it was concentrated, and the residual was dissolved in H$_2$O (100 mL), and then extracted with EtOAc (100 mL×2). The organic layer was combined, and washed with H$_2$O (60 mL×2) and Brine (80 mL), then dried by anhydrous Na$_2$SO$_4$. The solution was concentrated to give the crude product, which was used directly in next step without farther purification to afford a-2 (10.1 g, 100% yield) as brown oil.

Synthesis of 1-(3,4-dichlorophenyl)-3-methyl-2-thiocyanatobutan-1-one (a)

A mixture of a-2 (10.1 g, 32.5 mmol) and NaSCN (5.26 g, 64.9 mmol) in EtOH (100.0 mL) was stirred at 100° C. for 6 h. When the reaction was completed, it was concentrated and purified by silica gel column chromatography (petrol ether/ethyl acetate=10/1) to afford a (5.32 g, 57.0% yield) as a white solid.

Synthesis of 4-(thiophen-2-yl)benzaldehyde (595-2)

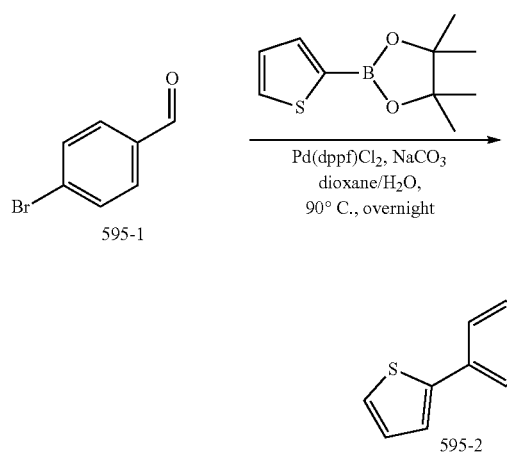

A mixture of 595-1 (1.50 g, 8.11 mmol), 4,4,5,5-tetramethyl-2-(thiophen-2-yl)-1,3,2-dioxaborolane (2.04 g, 9.73 mmol), Pd(dppf)Cl$_2$ (593 mg, 0.811 mmol) and Na$_2$CO$_3$ (1.72 g, 16.2 mmol) in dioxane/H$_2$O (v/v=10/1, 22.0 mL) was stirred under N$_2$ atmosphere at 90° C. overnight. When the reaction was completed, it was concentrated and purified by silica gel column chromatography (petrol ether/ethyl acetate=50/1) to afford 595-2 (1.70 g, 100% yield) as a white solid.

Synthesis of 2-cyclopropyl-1-(4-(thiophen-2-yl)phenyl)ethanol (595-3)

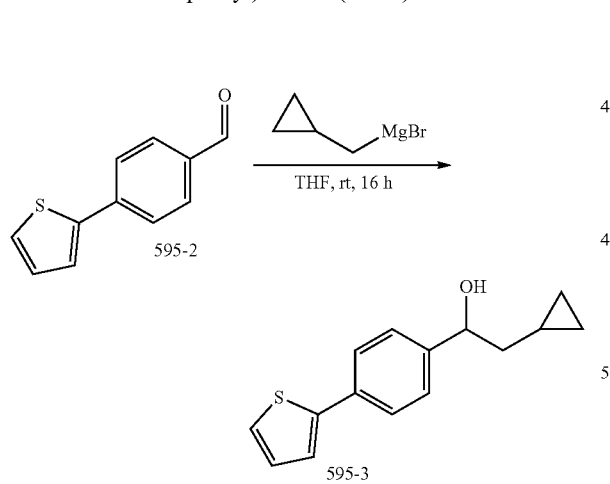

To a solution of 595-2 (1.70 g, 9.03 mmol) in THF (20.0 mL) was added (cyclopropylmethyl) magnesium bromide (1.0 M in THF, 13.5 mL, 13.5 mmol). The reaction was stirred at room temperature for 16 h. When the reaction was completed, it was poured into aq.NH$_4$Cl (sat., 50.0 mL) and extracted with EtOAc (80.0 mL×3). The organic phase was combined, and washed with H$_2$O (50.0 mL) and brine (50.0 mL), dried with anhydrous Na$_2$SO$_4$, concentrated to give the crude product, which was used directly in next step without farther purification to afford 595-3 (1.50 g, 68.0% yield) as yellow oil.

Synthesis of 2-cyclopropyl-1-(4-(thiophen-2-yl)phenyl)ethanone (595-4)

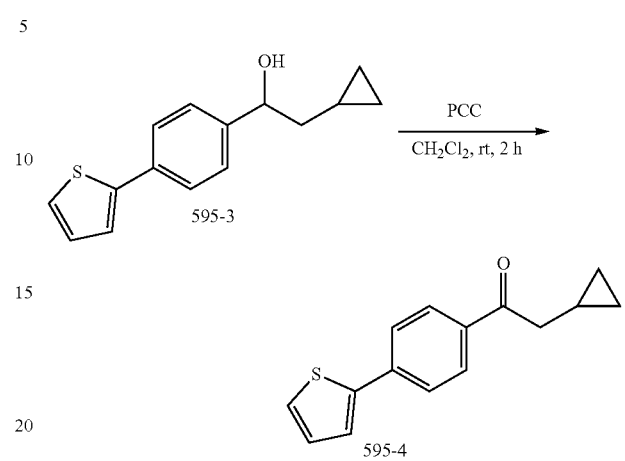

To a solution of 595-3 (1.50 g, 6.14 mmol) in CH$_2$Cl$_2$ (20.0 mL) was added PCC (2.65 g, 12.3 mmol). The reaction was stirred at room temperature for 2 h. When the reaction was completed, it was concentrated, and purified by silica gel column chromatography (petrol ether/ethyl acetate=50/1) to afford 595-4 (1.35 g, 90.7% yield) as a white solid.

Synthesis of 2-bromo-2-cyclopropyl-1-(4-(thiophen-2-yl)phenyl)ethanone (595-5)

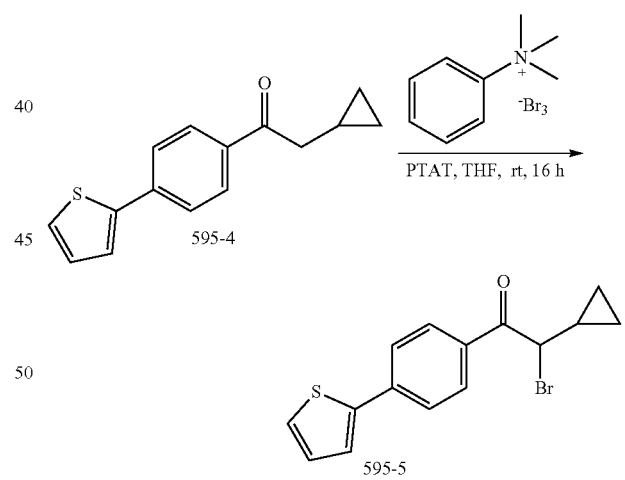

A mixture of 595-4 (1.35 g, 5.57 mmol) and PTAT (3.13 g, 8.36 mmol) in THF (20.0 mL) was stirred at room temperature for 16 h. When the reaction was completed, it was concentrated, and the residual was dissolved in H$_2$O (30.0 mL), and then extracted with EtOAc (50.0 mL×2). The organic layer was combined, and washed with H$_2$O (30.0 mL×2) and Brine (50.0 mL), then dried by anhydrous Na$_2$SO$_4$. The solution was concentrated to give the crude product, which was used directly in next step without farther purification to afford 595-5 (1.90 g, 100% yield) as yellow oil.

Synthesis of 2-cyclopropyl-2-thiocyanato-1-(4-(thiophen-2-yl)phenyl)ethanone (595)

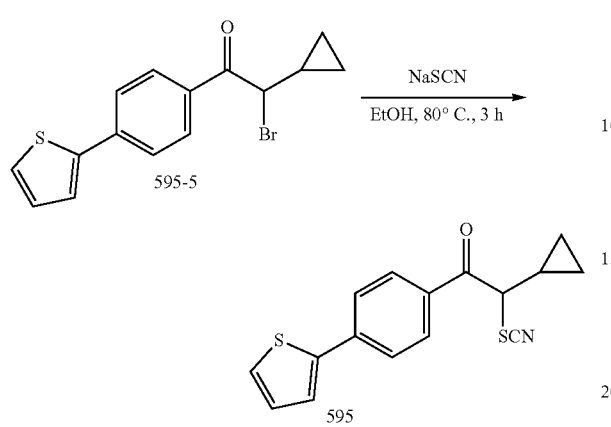

A mixture of 595-5 (1.90 g, 5.91 mmol) and NaSCN (959 mg, 11.8 mmol) in EtOH (20.0 mL) was stirred at 80° C. for 3 h. When the reaction was completed, it was concentrated and purified by silica gel column chromatography (petrol ether/ethyl acetate=10/1) to afford 595 (1.50 g, 84.7% yield) as a yellow solid.

Synthesis of 4-methyl-1-(4-(phenylthio)phenyl)pentan-1-ol (604-2)

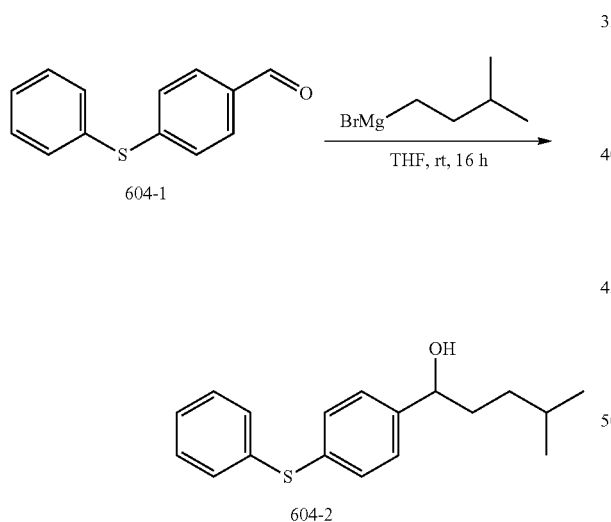

To a solution of 604-1 (5.0 g, 23.3 mmol) in THF (30.0 mL) was added isopentyl magnesium bromide (1.0 M in THF, 35.0 mL, 35.0 mmol). The reaction was stirred at room temperature for 16 h. When the reaction was completed, it was poured into aq.NH$_4$Cl (sat., 50.0 mL) and extracted with EtOAc (80.0 mL×3). The organic phase was combined, and washed with H$_2$O (50.0 mL) and brine (50.0 mL), then dried with anhydrous Na$_2$SO$_4$, concentrated to give the crude product, which was used directly in next step without farther purification to afford 604-2 (3.80 g, 56.9% yield) as colorless oil.

Synthesis of 4-methyl-1-(4-(phenylthio)phenyl)pentan-1-one (604-3)

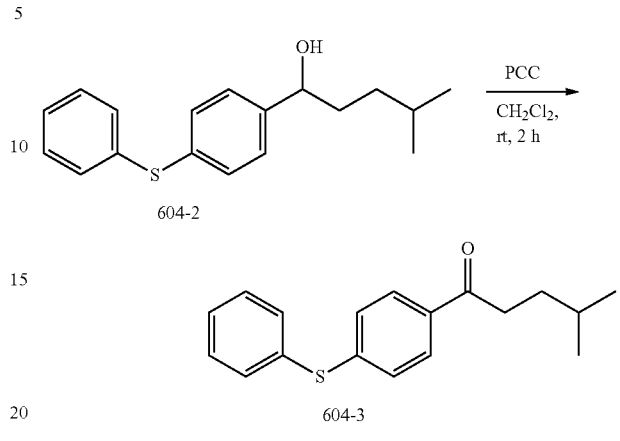

To a solution of 604-2 (3.80 g, 13.3 mmol) in CH$_2$Cl$_2$ (10.0 mL) was added PCC (5.72 g, 26.5 mmol). The reaction was stirred at room temperature for 2 h. When the reaction was completed, it was concentrated, and purified by silica gel column chromatography (petrol ether/ethyl acetate=50/1) to afford 604-3 (2.50 g, 66.3% yield) as yellow oil.

Synthesis of 2-bromo-4-methyl-1-(4-(phenylthio)phenyl)pentan-1-one (604-4)

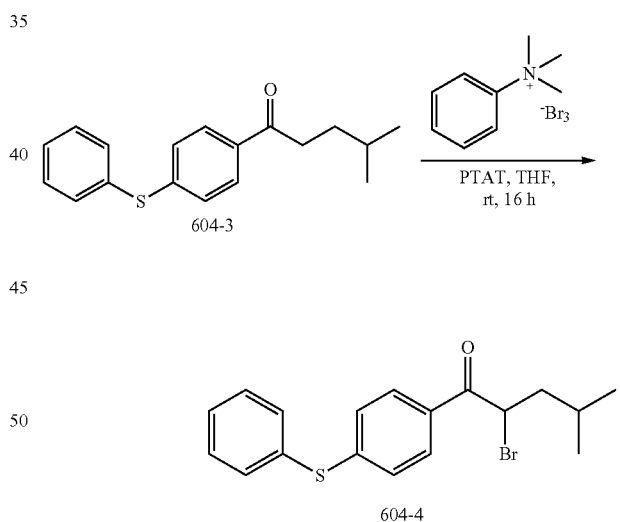

A mixture of 604-3 (2.50 g, 8.79 mmol) and PTAT (4.94 g, 13.2 mmol) in THF (30.0 mL) was stirred at room temperature for 16 h. When the reaction was completed, it was concentrated, and the residual was dissolved in H$_2$O (30.0 mL), and then extracted with EtOAc (50.0 mL×2). The organic layer was combined, and washed with H$_2$O (30.0 mL×2) and Brine (50.0 mL), then dried by anhydrous Na$_2$SO$_4$. The solution was concentrated to give the crude product, which was used directly in next step without farther purification to afford 604-4 (2.20 g, 68.9% yield) as yellow oil.

Synthesis of 4-methyl-1-(4-(phenylthio)phenyl)-2-thiocyanatopentan-1-one (604)

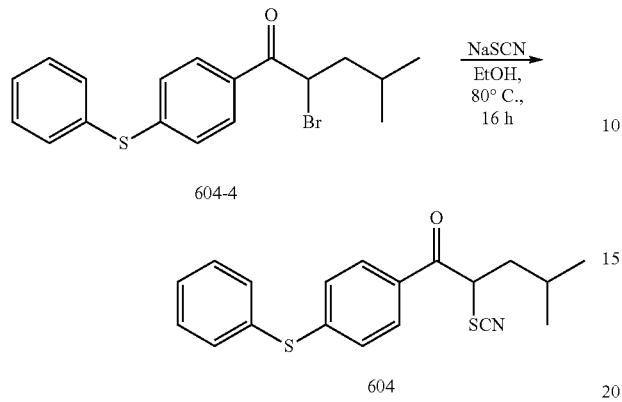

A mixture of 604-4 (2.20 g, 6.06 mmol) and NaSCN (982 mg, 12.1 mmol) in EtOH (15.0 mL) was stirred at 80° C. for 16 h. When the reaction was completed, it was concentrated and purified by silica gel column chromatography (petrol ether/ethyl acetate=10/1) to afford 604 (1.40 g, 67.7% yield) as a yellow solid.

Synthesis of 1-(3,4-dichlorophenyl)-5-methylhexan-2-one (611-2)

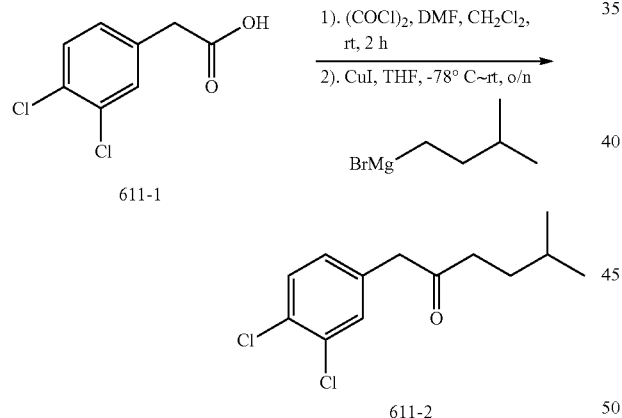

To a solution of 611-1 (5.0 g, 24.4 mmol) and $(COCl)_2$ (3.40 g, 26.8 mmol) in $CH_2Cl2$ (20.0 mL) was added DMF (2 drops). The reaction was stirred at room temperature for 2 h. When the reaction was completed, it was concentrated and solvent with THF (20.0 mL). The solution was added into the mixture of isopentyl magnesium bromide (1.0 M in THF, 36.6 mL, 36.6 mmol) and CuI (697 mg, 3.66 mmol) in THF (10.0 mL) at −78° C. The reaction was stirred at room temperature overnight. When the reaction was completed, it was poured into aq.$NH_4Cl$ (sat., 80.0 mL) and extracted with EtOAc (100 mL×3). The organic phase was combined, and washed with $H_2O$ (50.0 mL) and brine (80.0 mL), then dried with anhydrous $Na_2SO_4$, concentrated and purified by silica gel column chromatography (petrol ether/ethyl acetate=50/1) to afford 611-2 (2.70 g, 42.7% yield) as yellow oil.

Synthesis of 5-(3,4-dichlorophenyl)-4-isopentylthiazol-2-amine (611)

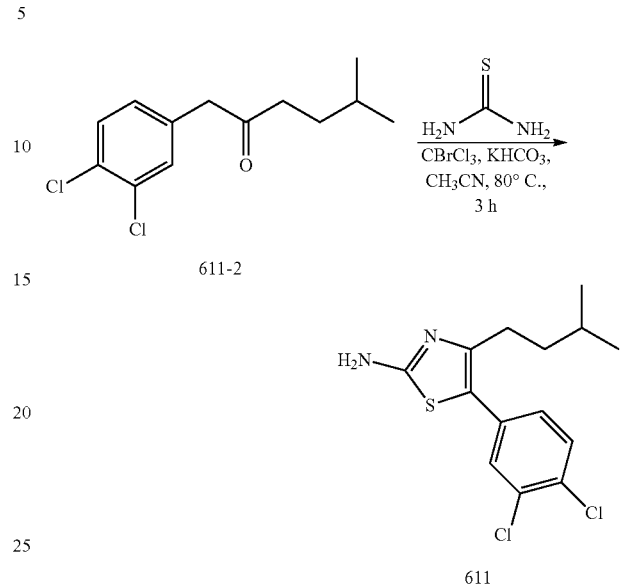

A mixture of 611-2 (2.70 g, 10.4 mmol), thiourea (1.59 g, 20.8 mmol), $CBrCl_3$ (2.0 mL) and $KHCO_3$ (2.09 g, 20.8 mmol) in $CH_3CN$ (15.0 mL) was stirred at 80° C. for 3 h. When the reaction was completed, it was concentrated and purified by silica gel column chromatography (petrol ether/ethyl acetate=3/1) to afford 611 (1.70 g, 51.8% yield) as a yellow solid.

Synthesis of 1-(3,4-dichlorophenyl)-3-methylbutan-2-one (615-1)

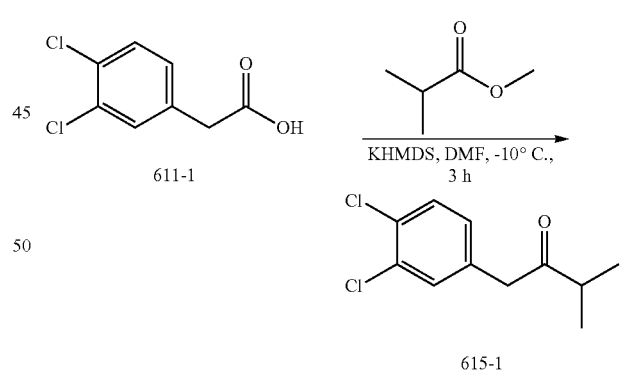

To a solution of 611-1 (1.30 g, 6.34 mmol) and methyl isobutyrate (648 mg, 6.34 mmol) in DMF (12.0 mL) was added KHDMS (1.0 M in THF, 25.0 mL) at −10° C. The reaction was stirred at room temperature for 3 h. When the reaction was completed, it was quenched with aq.$NH_4Cl$ (sat., 80.0 mL) and extracted with EtOAc (100 mL×2), and the combined organic phase washed with brine (100 mL), dried by anhydrous $Na_2SO_4$, concentrated and purified by silica gel column chromatography (petrol ether/ethyl acetate=50/1) to afford 615-1 (900 mg, 61.4% yield) as yellow oil.

681

Synthesis of (E)-5-methyl-1-(4-phenoxyphenyl)hex-2-en-1-one (634-2)

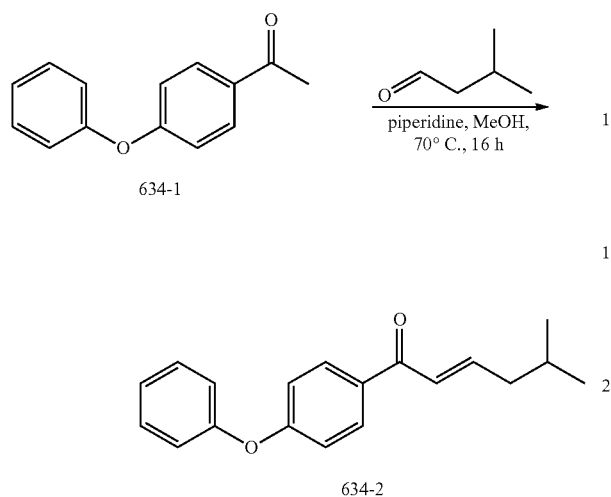

A mixture of 634-1 (5.0 g, 26.5 mmol), 3-methylbutanal (5.0 mL) and piperidine (0.5 mL) in MeOH (20.0 mL) was stirred at 70° C. for 16 h. When the reaction was completed, it was concentrated and purified by silica gel column chromatography (petrol ether/ethyl acetate=50/1) to afford 634-2 (1.20 g, 18.2% yield) as yellow oil.

Synthesis of 5-methyl-1-(4-phenoxyphenyl)hexan-1-one (634-3)

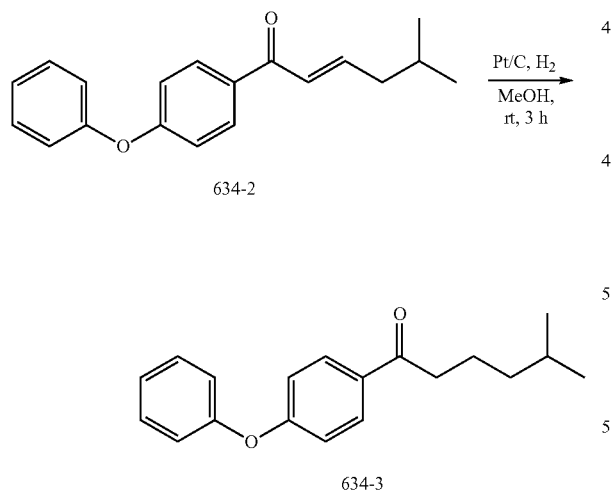

A mixture of 634-2 (1.20 g, 4.28 mmol) and Pt/C (120 mg) in MeOH (30.0 mL) was stirred under $H_2$ atmosphere at room temperature for 3 h. When the reaction was completed, it was filtered and the filtrate was concentrated to give a crude product, which was purified by silica gel column chromatography (petrol ether/ethyl acetate=20/1) to afford 634-3 (0.85 g, 70.3% yield) as colorless oil.

682

Synthesis of 2-bromo-5-methyl-1-(4-phenoxyphenyl)hexan-1-one (634-4)

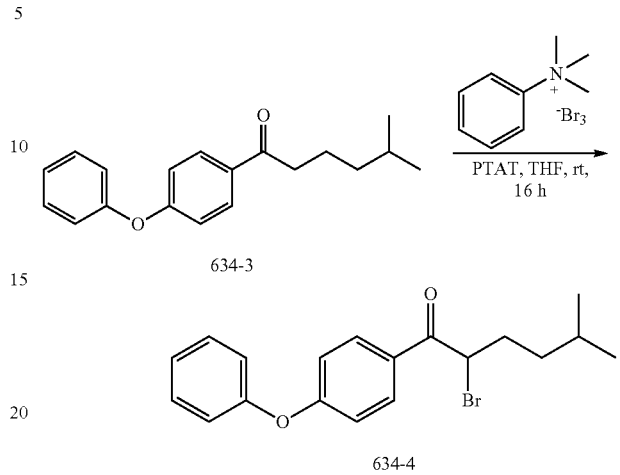

A mixture of 634-3 (0.85 g, 3.01 mmol) and PTAT (1.69 g, 4.52 mmol) in THF (20.0 mL) was stirred at room temperature for 16 h. When the reaction was completed, it was concentrated, and the residual was dissolved in $H_2O$ (50.0 mL), and then extracted with EtOAc (80.0 mL×2). The organic layer was combined, and washed with $H_2O$ (30.0 mL×2) and Brine (50.0 mL), then dried by anhydrous $Na_2SO_4$. The solution was concentrated to give the crude product, which was used directly in next step without farther purification to afford 634-4 (1.20 g, 100% yield) as yellow oil.

Synthesis of 5-methyl-1-(4-phenoxyphenyl)-2-thiocyanatohexan-1-one (634)

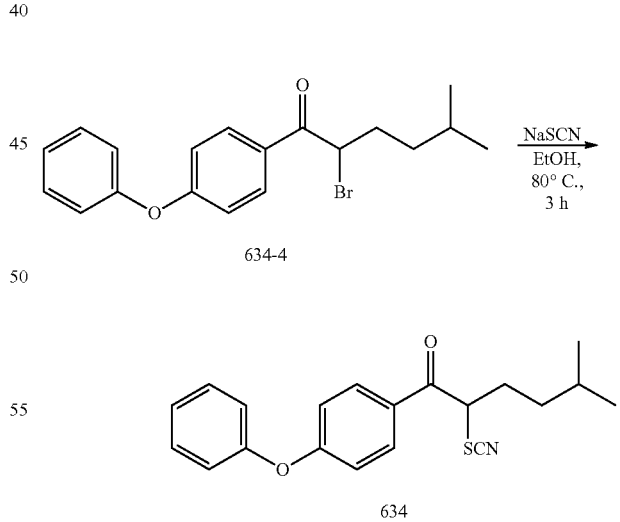

A mixture of 634-4 (1.20 g, 3.32 mmol) and NaSCN (539 mg, 6.64 mmol) in EtOH (20.0 mL) was stirred at 80° C. for 3 h. When the reaction was completed, it was concentrated and purified by silica gel column chromatography (petrol ether/ethyl acetate=10/1) to afford 634 (800 mg, 71.0% yield) as a yellow solid.

Synthesis of 4-benzyl-5-phenylthiazol-2-amine (640)

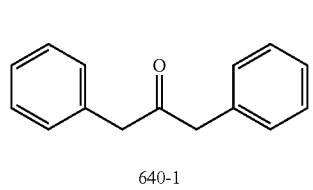 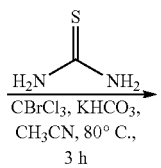

A mixture of 640-1 (900 mg, 3.89 mmol), thiourea (593 mg, 7.79 mmol), CBrCl₃ (1.50 mL) and KHCO₃ (780 mg, 7.79 mmol) in CH₃CN (10.0 mL) was stirred at 80° C. for 3 h. When the reaction was completed, it was concentrated and purified by silica gel column chromatography (petrol ether/ethyl acetate=3/1) to afford 640 (500 mg, 44.7% yield) as a yellow solid.

Synthesis of 1-(benzo[b]thiophen-2-yl)-3-methylbutan-1-ol (662-2)

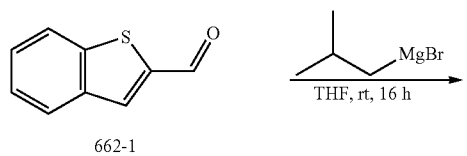

To a solution of 662-1 (2.0 g, 12.3 mmol) in THF (20.0 mL) was added isobutyl magnesium bromide (1.0 M in THF, 18.5 mL, 18.5 mmol). The reaction was stirred at room temperature for 16 h. When the reaction was completed, it was poured into aq.NH₄Cl (sat., 50.0 mL) and extracted with EtOAc (80.0 mL×3). The organic phase was combined, and washed with H₂O (50.0 mL) and brine (80.0 mL), then dried with anhydrous Na₂SO₄, concentrated and purified by silica gel column chromatography (petrol ether/ethyl acetate=10/1) to afford 662-2 (1.60 g, 58.9% yield) as a yellow solid.

Synthesis of 1-(benzo[b]thiophen-2-yl)-3-methylbutan-1-one (662-3)

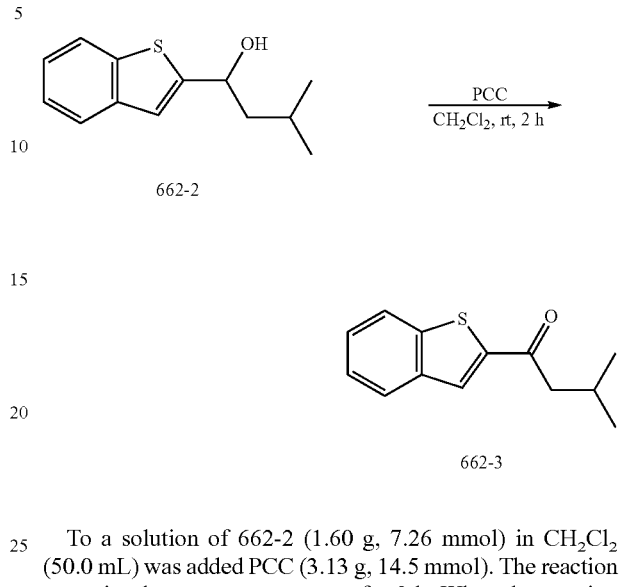

To a solution of 662-2 (1.60 g, 7.26 mmol) in CH₂Cl₂ (50.0 mL) was added PCC (3.13 g, 14.5 mmol). The reaction was stirred at room temperature for 2 h. When the reaction was completed, it was concentrated, and purified by silica gel column chromatography (petrol ether/ethyl acetate=50/1) to afford 662-3 (1.40 g, 88.3% yield) as yellow oil.

Synthesis of 1-(benzo[b]thiophen-2-yl)-2-bromo-3-methylbutan-1-one (662-4)

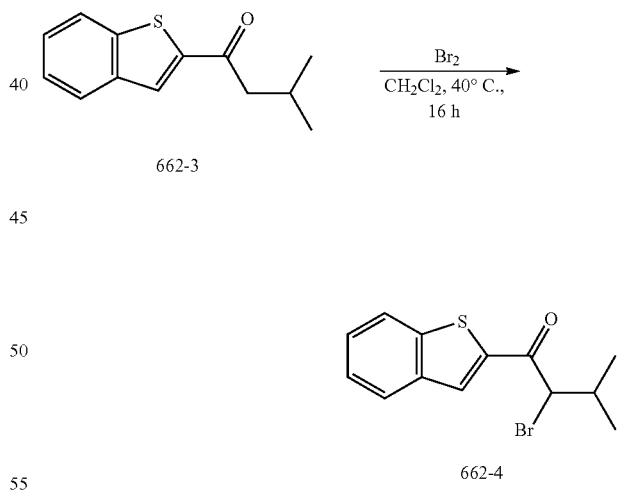

A mixture of 662-3 (1.40 g, 6.41 mmol) and Br₂ (1.13 g, 7.05 mmol) in CH₂Cl₂ (50.0 mL) was stirred at 40° C. for 16 h. When the reaction was completed, it was concentrated, and the residual was dissolved in H₂O (50.0 mL), and then extracted with EtOAc (100 mL×2). The organic layer was combined, and washed with H₂O (60.0 mL×2) and Brine (80.0 mL), then dried by anhydrous Na₂SO₄. The solution was concentrated to give the crude product, which was used directly in next step without farther purification to afford 662-4 (1.50 g, 78.7% yield) as brown oil.

685

Synthesis of 4-(benzo[b]thiophen-2-yl)-5-isopropylthiazol-2-amine (662)

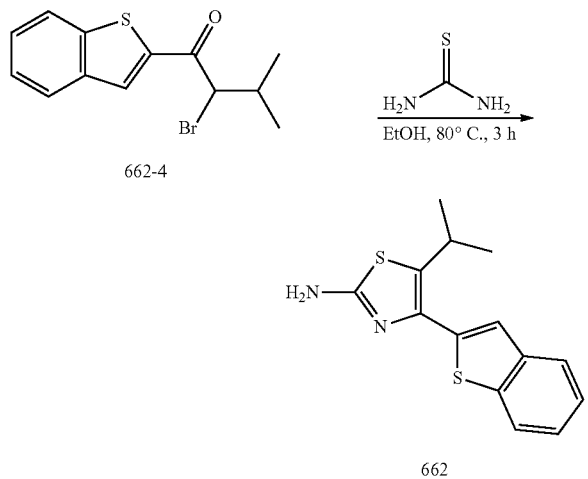

A mixture of 662-4 (1.50 g, 5.05 mmol) and thiourea (768 mg, 10.1 mmol) in EtOH (20.0 mL) was stirred at 80° C. for 3 h. When the reaction was completed, it was concentrated and purified by silica gel column chromatography (petrol ether/ethyl acetate=3/1) to afford 662 (500 mg, 36.1% yield) as a yellow solid.

Synthesis of 1-(4-bromophenyl)-3-methylbutan-1-one (663-2)

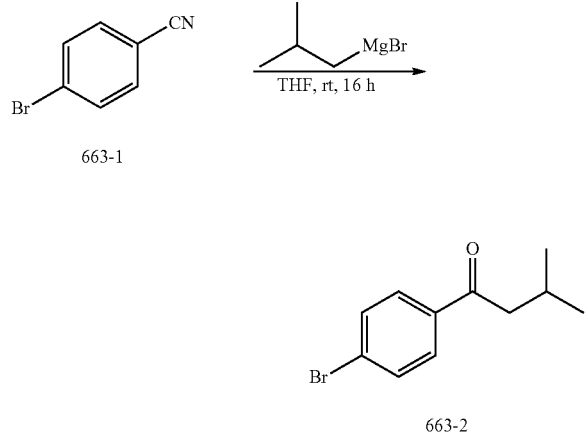

To a solution of 663-1 (5.0 g, 27.5 mmol) in THF (20.0 mL) was added isobutyl magnesium bromide (1.0 M in THF, 41.2 mL, 41.2 mmol). The reaction was stirred at room temperature for 16 h. When the reaction was completed, it was poured into aq.NH$_4$Cl (sat., 80.0 mL) and extracted with EtOAc (100 mL×3). The organic phase was combined, and washed with H$_2$O (50.0 mL) and brine (80.0 mL), then dried with anhydrous Na$_2$SO$_4$, concentrated and purified by silica gel column chromatography (petrol ether/ethyl acetate=5/1) to afford 663-2 (2.0 g, 30.2% yield) as yellow oil.

686

Synthesis of 2-bromo-1-(4-bromophenyl)-3-methylbutan-1-one (663-3)

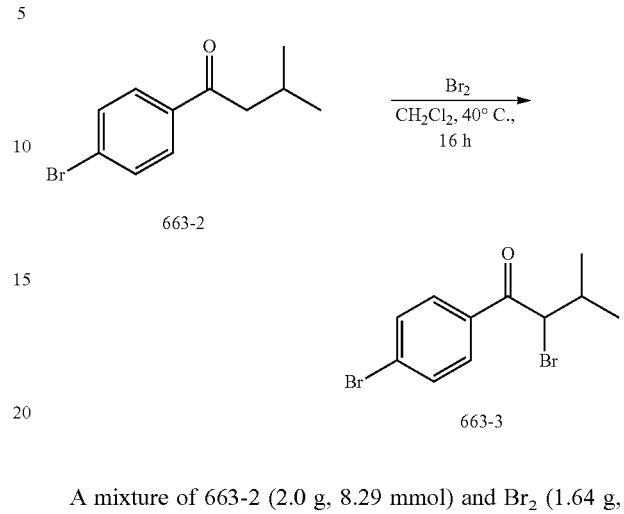

A mixture of 663-2 (2.0 g, 8.29 mmol) and Br$_2$ (1.64 g, 9.12 mmol) in CH$_2$Cl$_2$ (100 mL) was stirred at 40° C. for 16 h. When the reaction was completed, it was concentrated, and the residual was dissolved in H$_2$O (50.0 mL), and then extracted with EtOAc (100 mL×2). The organic layer was combined, and washed with H$_2$O (60.0 mL×2) and Brine (80.0 mL), then dried by anhydrous Na$_2$SO$_4$. The solution was concentrated to give the crude product, which was used directly in next step without farther purification to afford 663-3 (2.0 g, 75.3% yield) as brown oil.

Synthesis of 4-(4-bromophenyl)-5-isopropylthiazol-2-amine (663)

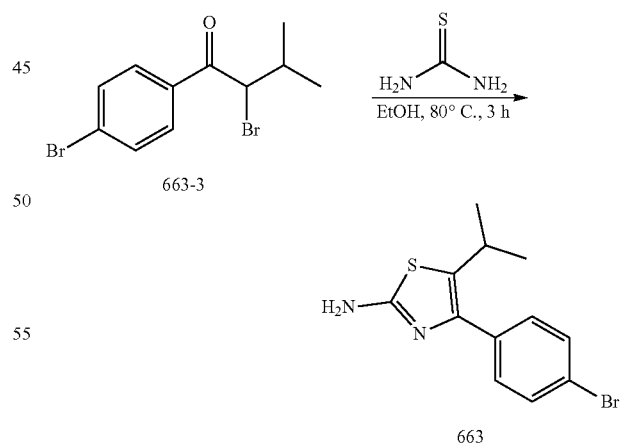

A mixture of 663-3 (2.0 g, 6.25 mmol) and thiourea (9.51 mg, 12.5 mmol) in EtOH (50.0 mL) was stirred at 80° C. for 3 h. When the reaction was completed, it was concentrated and purified by silica gel column chromatography (petrol ether/ethyl acetate=3/1) to afford 663 (1.50 g, 80.8% yield) as a yellow solid.

Synthesis of methyl 2-chloro-5-fluoronicotinate (613-2)

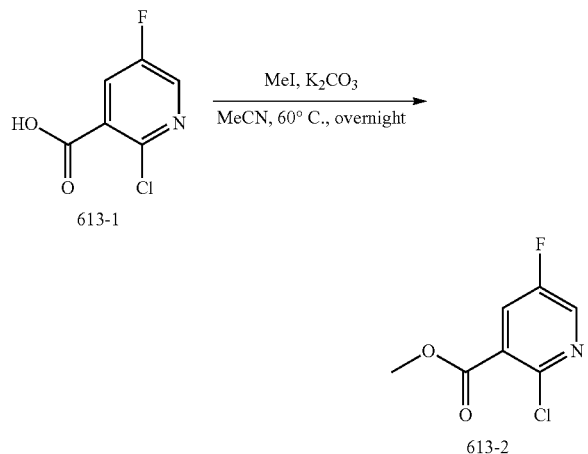

A mixture of 613-1 (500 mg, 2.85 mmol), CH₃I (606 mg, 4.27 mmol) and K₂CO₃ (788 mg, 5.71 mmol) in CH₃CN (10.0 mL) was stirred at 60° C. overnight. When the reaction was completed, it was concentrated and purified by silica gel column chromatography (petrol ether/ethyl acetate=20/1) to afford 613-2 (450 mg, 83.3% yield) as colorless oil.

Synthesis of methyl 5-fluoro-2-(4-methoxybenzylamino)nicotinate (613-3)

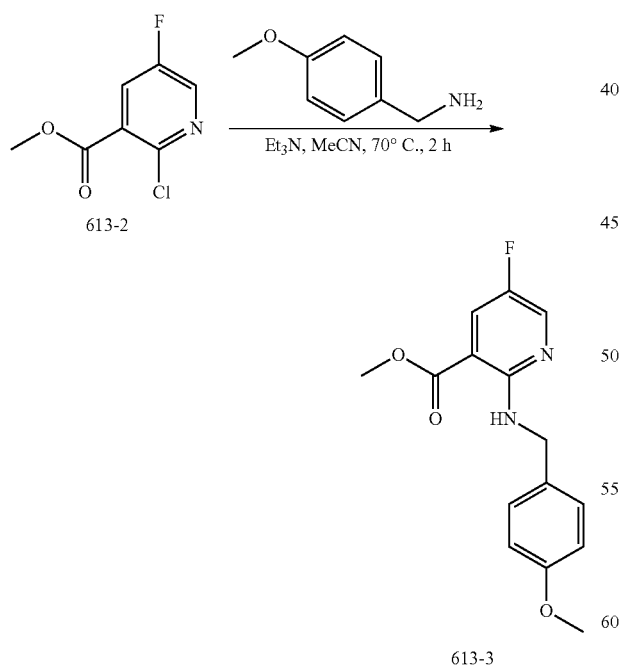

A mixture of 613-2 (400 mg, 2.11 mmol), (4-methoxyphenyl)methanamine (347 mg, 2.53 mmol) and Et₃N (426 mg, 4.22 mmol) in MeCN (30.0 mL) was stirred at 70° C. for 2 h. When the reaction was completed, it was concentrated and purified by silica gel column chromatography (petrol ether/ethyl acetate=20/1) to afford 613-3 (100 mg, 16.3% yield) as a white solid.

Synthesis of methyl 2-amino-5-fluoronicotinate (613)

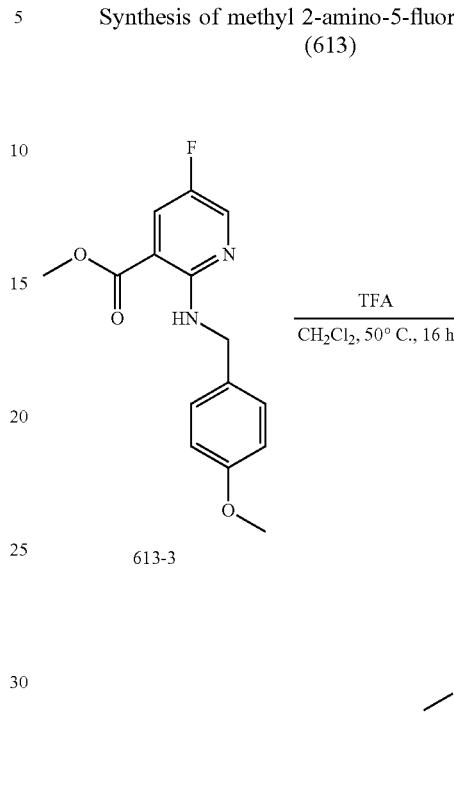

A mixture of 613-3 (100 mg, 0.344 mmol) and TFA (2.0 mL) in CH₂Cl₂ (2.0 mL) was stirred at 50° C. for 16 h. When the reaction was completed, it was concentrated and purified by silica gel column chromatography (petrol ether/ethyl acetate=3/1) to afford 613 (75.0 mg, 100% yield) as a white solid.

Synthesis of methyl 2-amino-5-chloronicotinate (614)

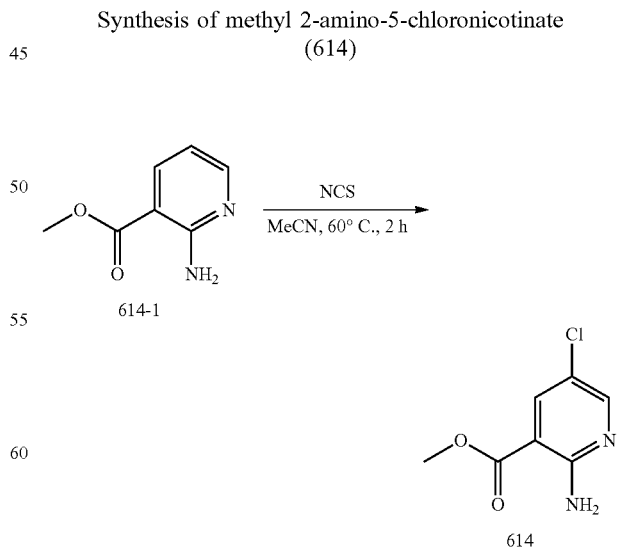

A mixture of 614-1 (300 mg, 1.97 mmol) and NCS (316 mg, 2.37 mmol) in MeCN (10.0 mL) was stirred at 60° C.

for 2 h. When the reaction was completed, it was concentrated to give a crude product, which was purified by silica gel column chromatography (petrol ether/ethyl acetate=10/1) to afford 614 (200 mg, 54.4% yield) as colorless oil.

Synthesis of 2-bromo-5-cyclopropyl-4-(4-(thiophen-2-yl)phenyl)thiazole (595-s)

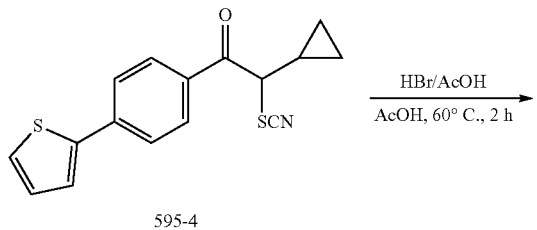

595-4

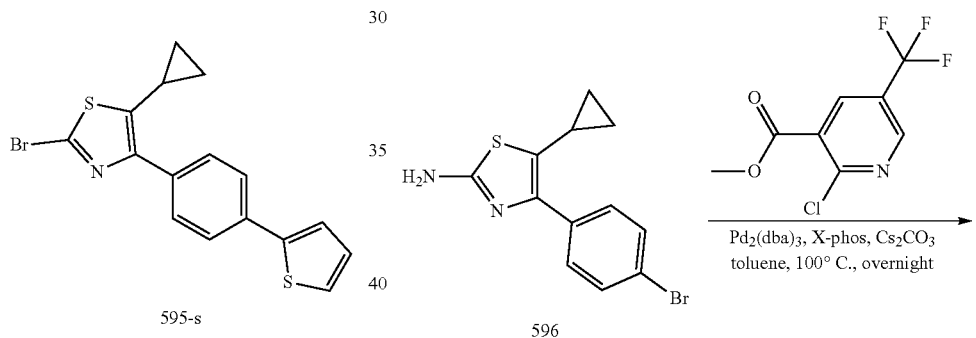

595-s

A mixture of 595-4 (1.50 g, 5.00 mmol) and HBr (2.0 M in AcOH, 5.0 mL) in AcOH (2.0 mL) was stirred at 60° C. for 2 h. When the reaction was completed, it was concentrated and purified by silica gel column chromatography (petrol ether/ethyl acetate=10/1) to afford 595-s (600 mg, 33.1% yield) as yellow oil.

Synthesis of 2-bromo-5-(3,4-dichlorophenyl)-4-isopentylthiazole (611-s)

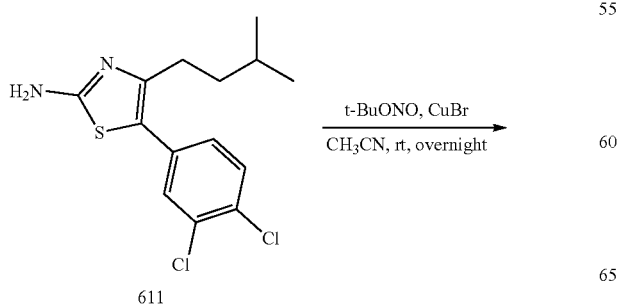

611

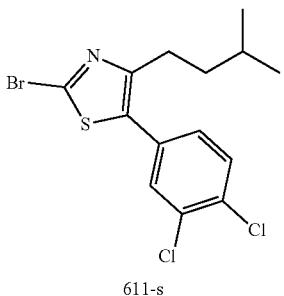

611-s

A mixture of 611 (1.10 g, 3.49 mmol), t-BuONO (720 mg, 6.98 mmol) and CuBr (1.00 g, 6.98 mmol) in $CH_3CN$ (20.0 mL) was stirred at room temperature overnight. When the reaction was completed, it was concentrated to give a crude product, which was purified by silica gel column chromatography (petrol ether/ethyl acetate=10/1) to afford 611-s (1.10 g, 83.2% yield) as a yellow solid.

Synthesis of methyl 2-(4-(4-bromophenyl)-5-cyclopropylthiazol-2-ylamino)-5-(trifluoromethyl)nicotinate (596-s)

596

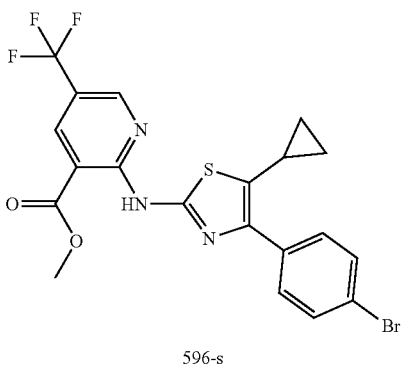

596-s

A mixture of 596 (2.0 g, 6.78 mmol), methyl 2-chloro-5-(trifluoromethyl)nicotinate (1.95 g, 8.13 mmol), Pd$_2$(dba)$_3$ (315 mg, 0.339 mmol), X-phos (294 mg, 0.509 mmol) and Cs$_2$CO$_3$ (4.42 g, 13.6 mmol) in toluene (50.0 mL) was stirred under N$_2$ atmosphere at 100° C. overnight. When the reaction was completed, it was concentrated and purified by silica gel column chromatography (petrol ether/ethyl acetate=50/1) to afford 596-s (1.30 g, 38.5% yield) as a yellow solid.

Synthesis of methyl 5-bromo-2-(4-(3,4-dichlorophenyl)-5-isopentylthiazol-2-ylamino)nicotinate (624-s)

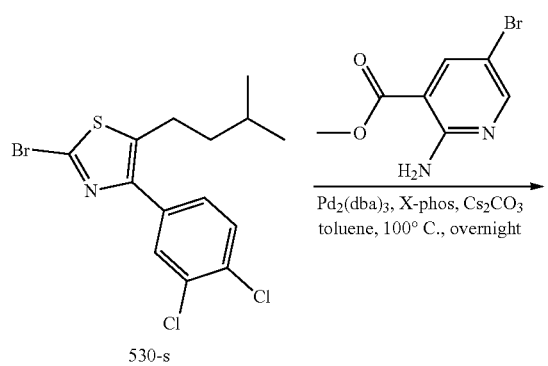

530-s

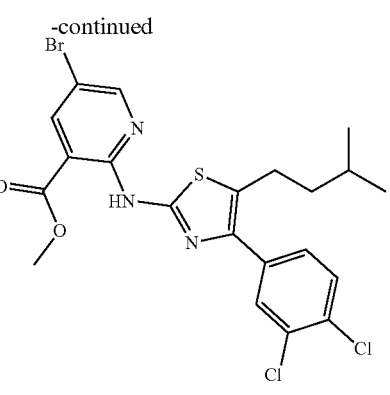

624-s

A mixture of 530-s (500 mg, 1.32 mmol), methyl 2-amino-5-bromonicotinate (366 mg, 1.58 mmol), Pd$_2$(dba)$_3$ (61.4 mg, 0.066 mmol), X-phos (57.2 mg, 0.099 mmol) and Cs$_2$CO$_3$ (860 mg, 2.64 mmol) in toluene (10.0 mL) was stirred under N$_2$ atmosphere at 100° C. overnight. When the reaction was completed, it was concentrated and purified by silica gel column chromatography (petrol ether/ethyl acetate=50/1) to afford 624-s (200 mg, 28.7% yield) as a yellow solid.

TABLE 6-1

Characterization Data for Compounds

| # | Chemical Structure | LCMS |
|---|---|---|
| a | 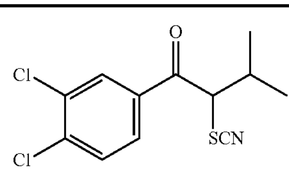 | Method A, Purity is 87.1%, Rt = 0.865 min; MS Calcd.: 287.0; MS Found: 288.1 [M + H]$^+$. |
| b | 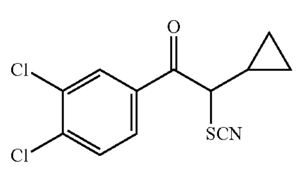 | Method B, Purity is 100%, Rt = 2.053 min; MS Calcd.: 284.98; No MS Found. |
| c | 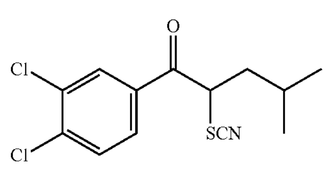 | Method B, Purity is 75.2%, Rt = 2.480 min; MS Calcd.: 301.0; MS Found: 324.1 [M + Na]$^+$. |
| 530 | 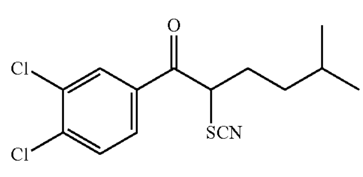 | $^1$H NMR (400 MHz, d$_6$-DMSO) δ: 0.88 (6H, dd, J = 8.4, 6.8 Hz), 1.28-1.35 (2H, m), 1.59 (1H, dt, J = 13.2, 6.8 Hz), 1.83-1.93 (1H, m), 2.03-2.13 (1H, m), 5.22 (1H, dd, J = 8.4, 5.2 Hz), 7.87 (1H, d, J = 8.4 Hz), 8.03 (1H, dd, J = 8.4, 2.0 Hz), 8.35 (1H, d, J = 2.0 Hz). |

TABLE 6-1-continued

Characterization Data for Compounds

| # | Chemical Structure | LCMS |
|---|---|---|
| 595 | 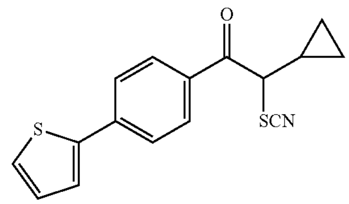 | Method A, Purity is 53.3%, Rt = 0.835 min; MS Calcd.: 299.0; MS Found: 300.2 [M + H]$^+$. |
| 604 | 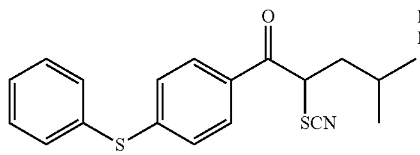 | Method B, Purity is 89.0%, Rt = 2.218 min; MS Calcd.: 341.1; MS Found: 342.0 [M + H]$^+$. |
| 661 | 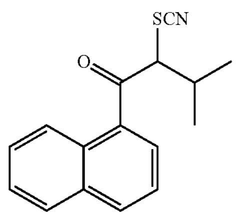 | Method A, Purity is 80.9%, Rt = 0.882 min; MS Calcd.: 269.0; MS Found: 292.0 [M + Na]$^+$. |
| 664 | 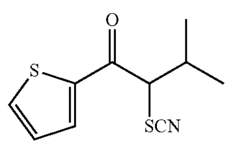 | Method B, Purity is 88.2%, Rt = 1.812 min; MS Calcd.: 225.0; MS Found: 226.1 [M + H]$^+$. |
| 667 | 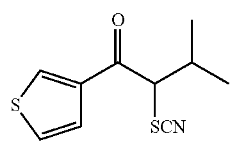 | Method B, Purity is 89.2%, Rt = 1.838 min; MS Calcd.: 225.0; MS Found: 226.1 [M + H]$^+$. |
| 672 | 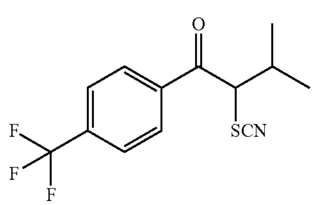 | Method A, Purity is 97.8%, Rt = 0.818 min; MS Calcd.: 287.1; MS Found: 288.1 [M + H]$^+$. |
| 611 | 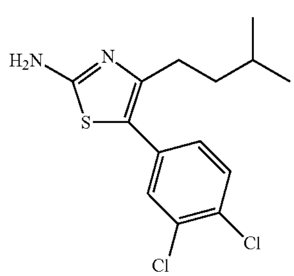 [SMILES: CC(C)CCc1nc(N)sc1-c1ccc(Cl)c(Cl)c1] | Method A, Purity is 100%, Rt = 0.744 min; MS Calcd.: 314.0; MS Found: 315.2 [M + H]$^+$. |

TABLE 6-1-continued
Characterization Data for Compounds
| # | Chemical Structure | LCMS |
|---|---|---|
| 615 | 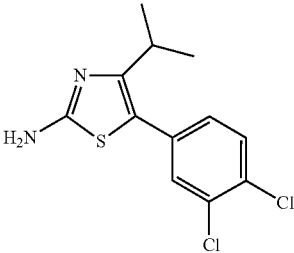 [SMILES: CC(C)c1nc(N)sc1-c1ccc(Cl)c(Cl)c1] | Method C, Purity is 85.4%, Rt = 2.085 min; MS Calcd.: 286.0; MS Found: 287.0 [M + H]$^+$. |
| 639 | 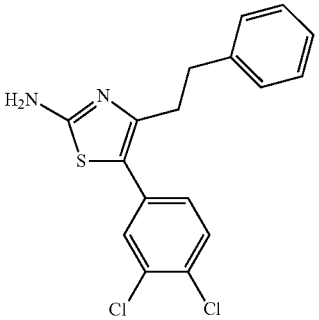 [SMILES: Nc1nc(CCc2ccccc2)c(-c2ccc(Cl)c(Cl)c2)s1] | Method C, Purity is 92.2%, Rt = 2.156 min; MS Calcd.: 348.0; MS Found: 349.0 [M + H]$^+$. |
| 640 | 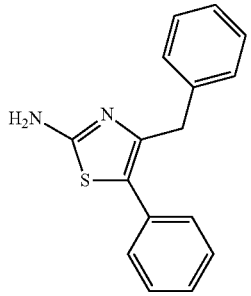 [SMILES: Nc1nc(Cc2ccccc2)c(-c2ccccc2)s1] | Method C, Purity is 100%, Rt = 1.888 min; MS Calcd.: 266.1; MS Found: 267.0 [M + H]$^+$. |
| 675 | 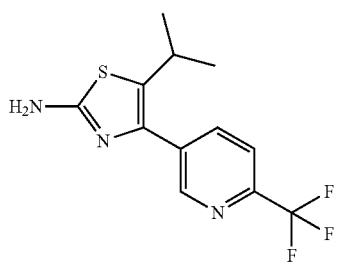 [SMILES: CC(C)c1sc(N)nc1-c1ccc(C(F)(F)F)nc1] | Method C, Purity is 92.0%, Rt = 1.860 min; MS Calcd.: 287.1; MS Found: 288.2 [M + H]$^+$. |
| 595-s | 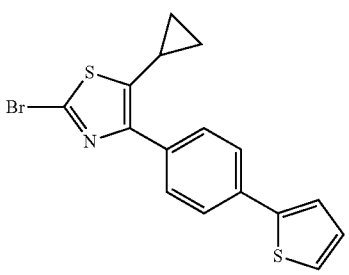 [SMILES: Brc1nc(-c2ccc(-c3cccs3)cc2)c(C2CC2)s1] | Method A, Purity is 59.1%, Rt = 0.999 min; MS Calcd.: 361.0; MS Found: 362.0 [M + H]$^+$. |

TABLE 6-1-continued

Characterization Data for Compounds

| # | Chemical Structure | LCMS |
|---|---|---|
| 604-s | 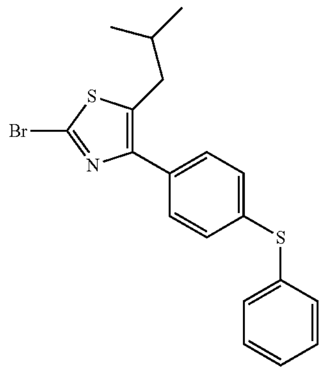 [SMILES: CC(C)Cc1sc(Br)nc1-c1ccc(Sc2ccccc2)cc1] | $^1$H NMR (400 MHz, CDCl$_3$) δ: 0.97 (6H, d, J = 6.4 Hz), 2.77 (2H, d, J = 7.2 Hz), 4.00 (3H, s), 7.10 (1H, d, J = 16.0 Hz), 7.31 (2H, dt, J = 8.4, 1.6 Hz), 7.36-7.43 (6H, m), 7.57 (2H, dd, J = 6.4, 2.0 Hz), 7.61-7.64 (1H, m), 7.75 (1H, d, J = 16.0 Hz), 8.51 (1H, d, J = 2.4 Hz), 8.77 (1H, d, J =2.4 Hz), 11.43 (1H, s). |
| 611-s | 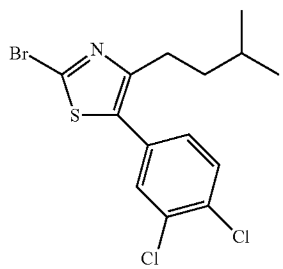 [SMILES: CC(C)CCc1nc(Br)sc1-c1ccc(Cl)c(Cl)c1] | Method A, Purity is 91.3%, Rt = 1.103 min; MS Calcd.: 376.9; MS Found: 378.0 [M + H]$^+$. |
| 634-s | 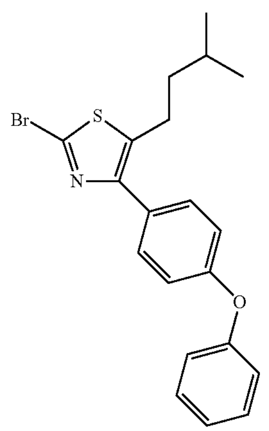 [SMILES: CC(C)CCc1sc(Br)nc1-c1ccc(Oc2ccccc2)cc1] | Method B, Purity is 93.2%, Rt = 2.499 min; MS Calcd.: 401.0; MS Found: 402.0 [M + H]$^+$. |
| 661-s | 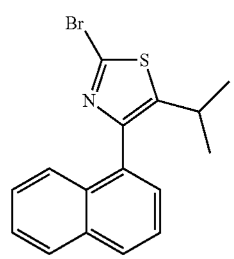 [SMILES: CC(C)c1sc(Br)nc1-c1cccc2ccccc12] | Method B, Purity is 74.0%, Rt = 2.293 min; MS Calcd.: 331.0; MS Found: 331.9 [M + H]$^+$. |
| 664-s | 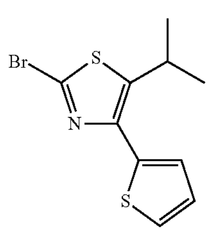 | Method C, Purity is 93.1%, Rt = 2.322 min; MS Calcd.: 286.9; MS Found: 288.0 [M + H]$^+$. |

TABLE 6-1-continued

Characterization Data for Compounds

| # | Chemical Structure | LCMS |
|---|---|---|
| 667-s | 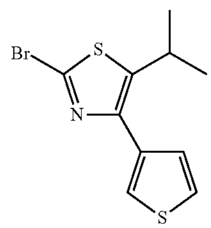 | Method B, Purity is 86.4%, Rt = 2.212 min; MS Calcd.: 286.9; MS Found: 288.0 [M + H]⁺. |
| 671-s | 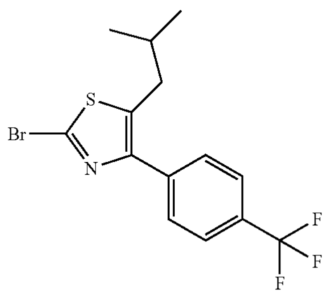 [SMILES: CC(C)Cc1sc(Br)nc1-c1ccc(C(F)(F)F)cc1] | ¹H NMR (400 MHz, CDCl₃) δ: 0.95 (6H, d, J = 6.8 Hz), 1.85-1.89 (1H, m), 2.78 (2H, d, J = 7.2 Hz), 7.69 (4H, s). |
| 613 | 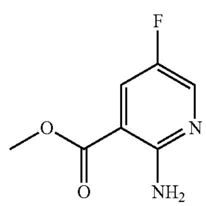 | Method A, Purity is 100%, Rt = 0.452 min; MS Calcd.: 170.1; MS Found: 171.3 [M + H]⁺. |
| 614 | 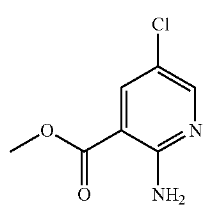 | Method B, Purity is 90.0%, Rt = 1.544 min; MS Calcd.: 186.0; MS Found: 187.1 [M + H]⁺. |
| 625-s | 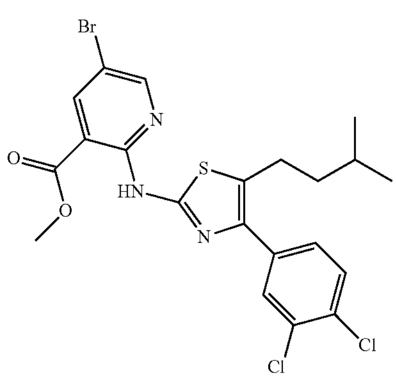 [SMILES: COC(=O)c1cc(Br)cnc1Nc1nc(-c2ccc(Cl)c(Cl)c2)c(CCC(C)C)s1] | Method D, Purity is 93.1%, Rt = 2.647 min; MS Calcd.: 527.0; MS Found: 527.7 [M + H]⁺. |

TABLE 6-1-continued

Characterization Data for Compounds

| # | Chemical Structure | LCMS |
|---|---|---|
| 669-s | (structure) | Method A, Purity is 92.1%, Rt = 1.079 min; MS Calcd.: 513.0; MS Found: 514.0 [M + H]+. |

Synthesis of methyl 2-(5-cyclopropyl-4-(4-(thiophen-2-yl)phenyl)thiazol-2-ylamino)-5-(trifluoromethyl)nicotinate (595-5)

Synthesis of 2-(5-cyclopropyl-4-(4-(thiophen-2-yl)phenyl)thiazol-2-ylamino)-5-(trifluoromethyl)nicotinic acid (I-289)

A mixture of 595-s (200 mg, 0.552 mmol), methyl 2-amino-5-(trifluoromethyl)nicotinate (146 mg, 0.662 mmol), Pd$_2$(dba)$_3$ (51.3 mg, 0.0552 mmol), X-phos (47.9 mg, 0.0828 mmol) and Cs$_2$CO$_3$ (360 mg, 1.10 mmol) in toluene (3.0 mL) was stirred under N$_2$ atmosphere at 100° C. for 5 h. When the reaction was completed, it was concentrated and purified by silica gel column chromatography (petrol ether/ethyl acetate=20/1) to afford 595-6 (150 mg, 54.2% yield) as a yellow solid.

To a solution of 595-6 (150 mg, 0.299 mmol) in THF/MeOH/H$_2$O (v/v/v=4/1/1, 2.0 mL) was added LiOH (2.0 M in H$_2$O, 1.0 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-289 (5.0 mg, 3.43% yield) as a yellow solid.

The synthesis of methyl 2-(5-cyclopropyl-4-(4-(thiazol-2-yl)phenyl)thiazol-2-ylamino)-5-(trifluoromethyl)nicotinate (596-5)

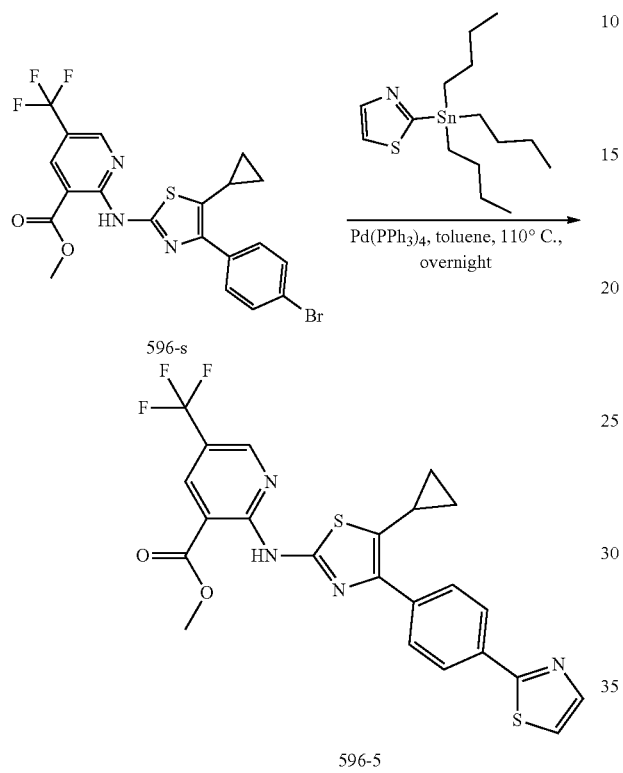

A mixture of 596-s (200 mg, 0.401 mmol), 2-(tributylstannyl)thiazole (300 mg, 0.803 mmol) and Pd(PPh$_3$)$_4$ (46.3 mg, 0.0401 mmol) in toluene (3.0 mL) was stirred under N$_2$ atmosphere at 110° C. overnight. When the reaction was completed, it was concentrated and purified by silica gel column chromatography (petrol ether/ethyl acetate=10/1) to afford 596-5 (90.0 mg, 44.6% yield) as a yellow solid.

Synthesis of 2-(5-cyclopropyl-4-(4-(thiazol-2-yl)phenyl)thiazol-2-ylamino)-5-(trifluoromethyl)nicotinic acid (I-290)

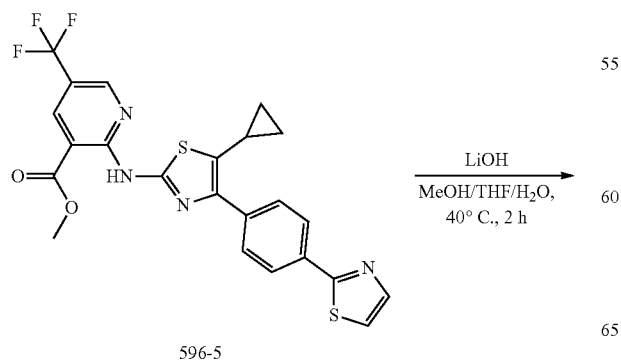

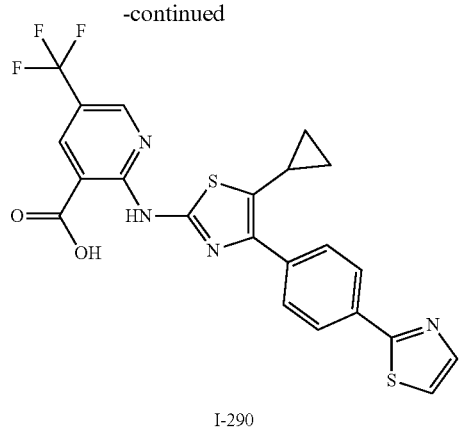

I-290

To a solution of 596-5 (90.0 mg, 0.179 mmol) in THF/MeOH/H$_2$O (v/v/v=4/1/1, 2.0 mL) was added LiOH (2.0 M in H$_2$O, 0.50 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-290 (12.0 mg, 13.7% yield) as a yellow solid.

Synthesis of methyl 2-(5-cyclopropyl-4-(4-(4,4,5,5-tetramethyl-1,3,2-dioxaborolan-2-yl)phenyl)thiazol-2-ylamino)-5-(trifluoromethyl)nicotinate (598-1)

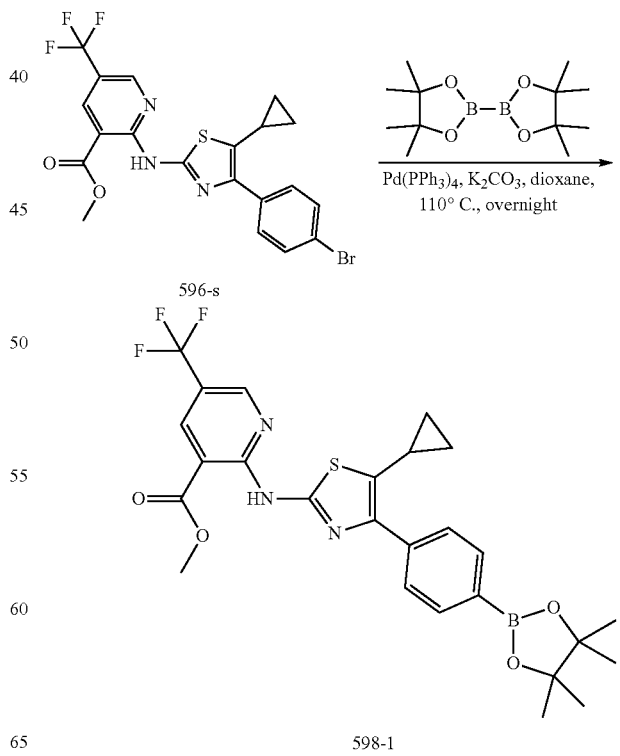

A mixture of 596-s (500 mg, 1.00 mmol), B$_2$(Pin)$_2$ (382 mg, 1.51 mmol), Pd(PPh$_3$)$_4$ (116 mg, 0.10 mmol) and K$_2$CO$_3$ (277 mg, 2.01 mmol) in dioxane (10.0 mL) was stirred under N$_2$ atmosphere at 110° C. overnight. When the reaction was completed, it was concentrated and purified by silica gel column chromatography (petrol ether/ethyl acetate=20/1) to afford 598-1 (250 mg, 45.7% yield) as a yellow solid.

Synthesis of methyl 2-(5-cyclopropyl-4-(4-(2,5-dioxopyrrolidin-1-yl)phenyl)thiazol-2-ylamino)-5-(trifluoromethyl)nicotinate (598-2)

A mixture of 598-1 (250 mg, 0.458 mmol), pyrrolidine-2,5-dione (68.1 mg, 0.688 mmol), Cu(OAc)$_2$ (167 mg, 0.917 mmol) and Et$_3$N (92.6 mg, 0.917 mmol) in CH$_2$Cl$_2$ (10.0 mL) was stirred under O$_2$ atmosphere at 40° C. overnight. When the reaction was completed, it was concentrated and purified by silica gel column chromatography (petrol ether/ethyl acetate=10/1) to afford 598-2 (50.0 mg, 21.1% yield) as a yellow solid.

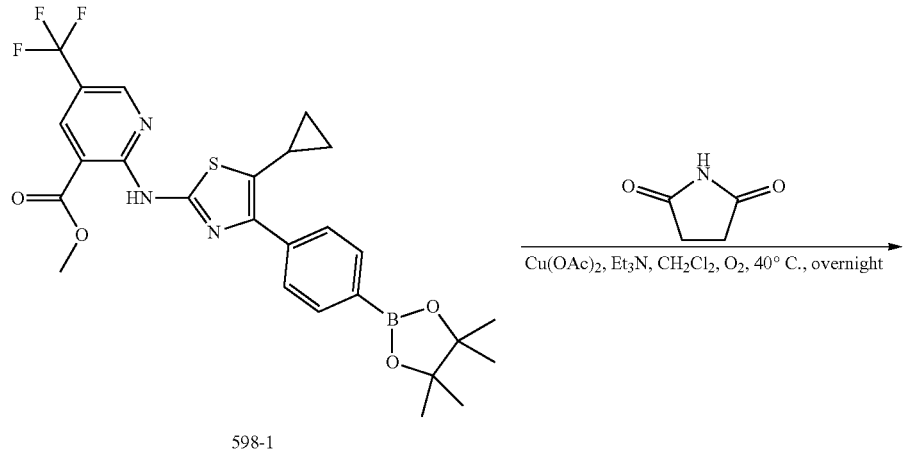

598-1

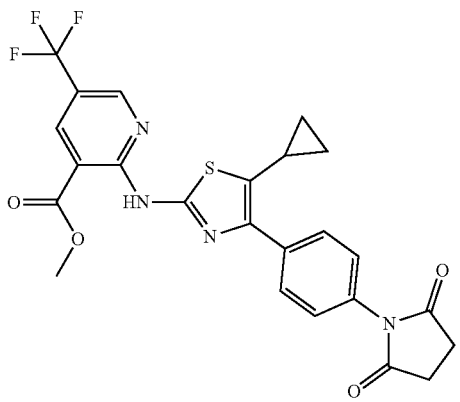

598-2

Synthesis of 2-(4-(4-(3-carboxypropanamido)phenyl)-5-cyclopropylthiazol-2-ylamino)-5-(trifluoromethyl)nicotinic acid (I-291)

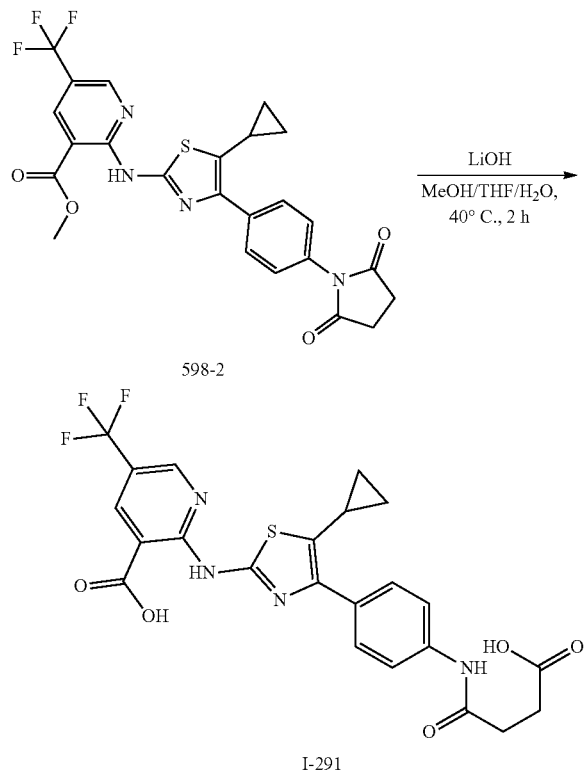

To a solution of 598-2 (50.0 mg, 0.0968 mmol) in THF/MeOH/H$_2$O (v/v/v=4/1/1, 2.0 mL) was added LiOH (2.0 M in H$_2$O, 0.50 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-291 (30.0 mg, 59.5% yield) as a yellow solid.

Synthesis of methyl 2-(5-isobutyl-4-(4-(phenylsulfinyl)phenyl)thiazol-2-ylamino)-5-(trifluoromethyl)nicotinate (605-1)

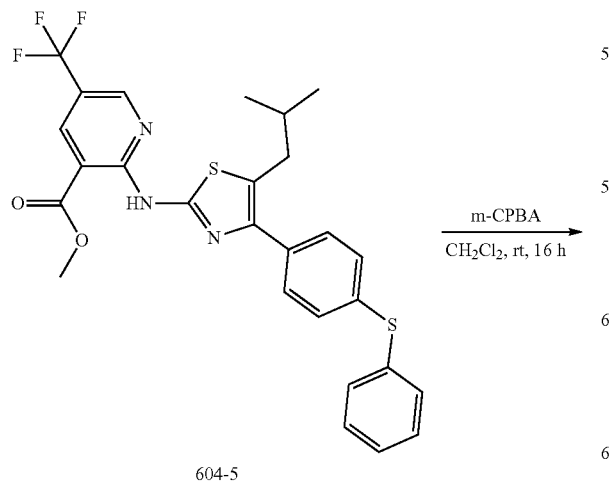

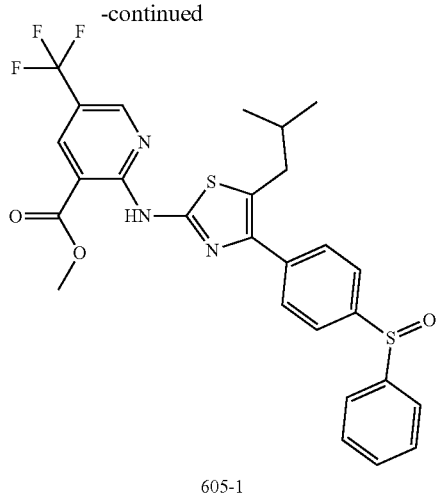

To a solution of 604-5 (200 mg, 0.368 mmol) in CH$_2$Cl$_2$ (30.0 mL) was added m-CPBA (76.2 mg, 0.441 mmol). The reaction was stirred at room temperature for 16 h. When the reaction was completed, it was washed with H$_2$O (15.0 mL×2) and the organic phase washed with brine (10.0 mL), dried by anhydrous Na$_2$SO$_4$, and concentrated, the residue was purified by silica gel column chromatography (petrol ether/ethyl acetate=10/1) to afford 605-1 (100 mg, 48.6% yield) as a yellow solid.

Synthesis of 2-(5-isobutyl-4-(4-(phenylsulfinyl)phenyl)thiazol-2-ylamino)-5-(trifluoromethyl)nicotinic acid (I-295)

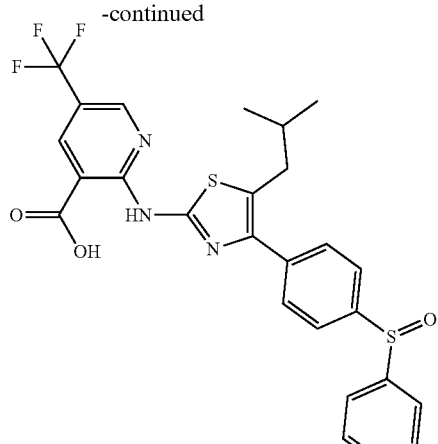

I-295

To a solution of 605-1 (100 mg, 0.179 mmol) in THF/MeOH/H₂O (v/v/v=4/1/1, 2.0 mL) was added LiOH (2.0 M in H₂O, 0.50 mL). The reaction was stirred at 40° C. for 2 h. When the reaction was completed, the resulting reaction was concentrated, then it was diluted with H₂O (15.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-295 (35.0 mg, 35.9% yield) as a white solid.

Synthesis of 1-(4-(2-amino-5-cyclopropylthiazol-4-yl)phenyl)pyridin-2(1H)-one (607-1)

A mixture of 596 (300 mg, 1.02 mmol), pyridin-2(1H)-one (116 mg, 1.22 mmol), N1,N2-dimethylethane-1,2-diamine (13.4 mg, 0.152 mmol), CuI (19.4 mg, 0.102 mmol) and K₃PO₄ (433 mg, 2.04 mmol) in dioxane (10.0 mL) was stirred under N₂ atmosphere at 110° C. for 16 h. When the reaction was completed, it was concentrated and purified by silica gel column chromatography (petrol ether/ethyl acetate=1/1) to afford 607-1 (70.0 mg, 22.2% yield) as a yellow solid.

Synthesis of 2-(5-cyclopropyl-4-(4-(2-oxopyridin-1(2H)-yl)phenyl)thiazol-2-ylamino)-5-(trifluoromethyl)nicotinic acid (I-297)

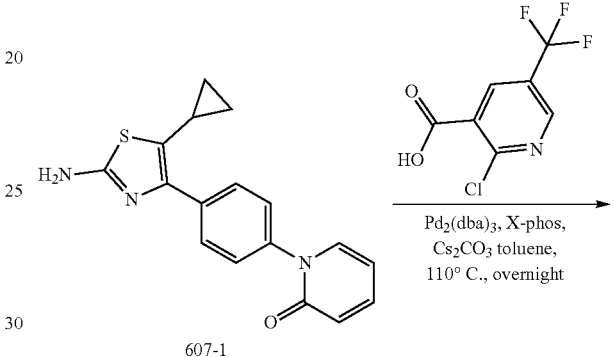

607-1

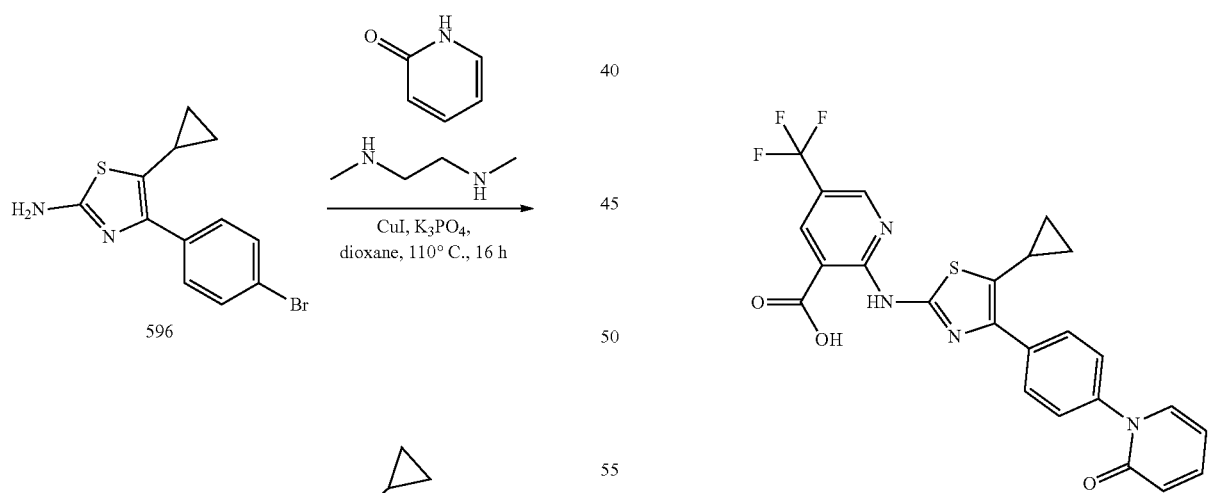

I-297

A mixture of 607-1 (70.0 mg, 0.226 mmol), 2-chloro-5-(trifluoromethyl)nicotinic acid (61.2 mg, 0.272 mmol), Pd₂(dba)₃ (21.0 mg, 0.0226 mmol), X-phos (19.6 mg, 0.0339 mmol) and Cs₂CO₃ (147 mg, 0.452 mmol) in toluene (2.0 mL) was stirred under N₂ atmosphere at 110° C. overnight. When the reaction was completed, it was concentrated and purified by prep-HPLC to afford I-297 (5.0 mg, 4.43% yield) as a yellow solid.

Synthesis of methyl 2-(5-cyclopropyl-4-(4-(pyrimidin-2-yl)phenyl)thiazol-2-ylamino)-5-(trifluoromethyl)nicotinate (610-2)

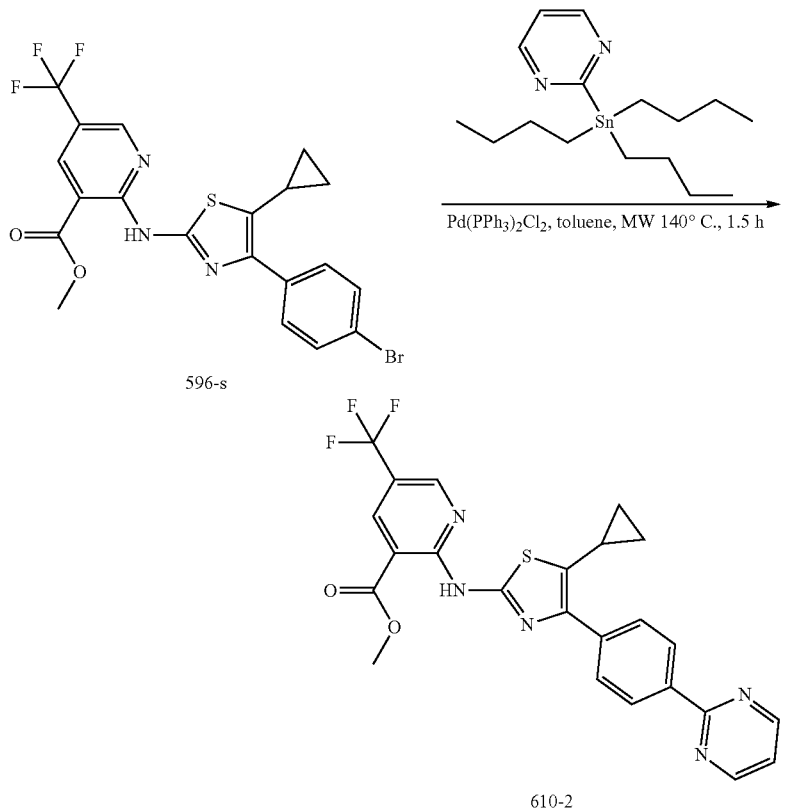

A mixture of 596-s (180 mg, 0.361 mmol), 2-(tributylstannyl)pyrimidine (200 mg, 0.542 mmol) and Pd(PPh$_3$)$_2$Cl$_2$ (25.3 mg, 0.0361 mmol) in toluene (3.0 mL) was stirred under N$_2$ atmosphere at 140° C. under microwave for 1.5 h. When the reaction was completed, it was concentrated and purified by silica gel column chromatography (petrol ether/ethyl acetate=10/1) to afford 610-2 (70.0 mg, 39.0% yield) as a yellow solid.

Synthesis of 2-(5-cyclopropyl-4-(4-(pyrimidin-2-yl)phenyl)thiazol-2-ylamino)-5-(trifluoromethyl)nicotinic acid (I-300)

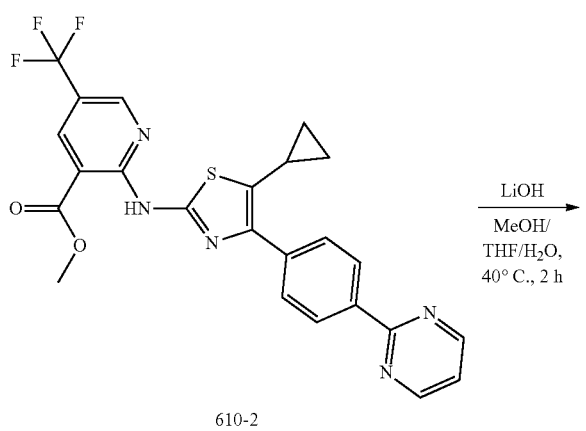

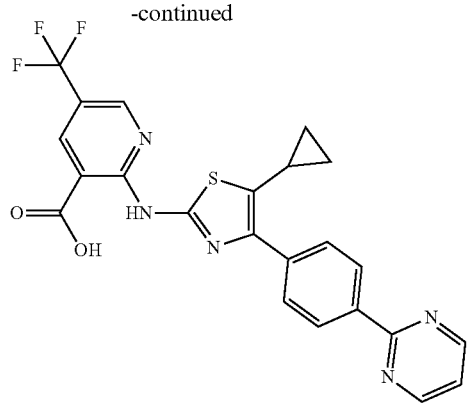

To a solution of 610-2 (70.0 mg, 0.141 mmol) in THF/MeOH/H$_2$O (v/v/v=4/1/1, 2.0 mL) was added LiOH (2.0 M in H$_2$O, 0.50 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-300 (9.0 mg, 13.2% yield) as a yellow solid.

713
Synthesis of methyl 2-(4-(3,4-dichlorophenyl)-5-isopentylthiazol-2-ylamino)-5-(2-oxo-1,2-dihydropyridin-3-yl)nicotinate (624-5)

714
The synthesis of 2-(4-(3,4-dichlorophenyl)-5-isopentylthiazol-2-ylamino)-5-(2-oxo-1,2-dihydropyridin-3-yl)nicotinic acid (I-305)

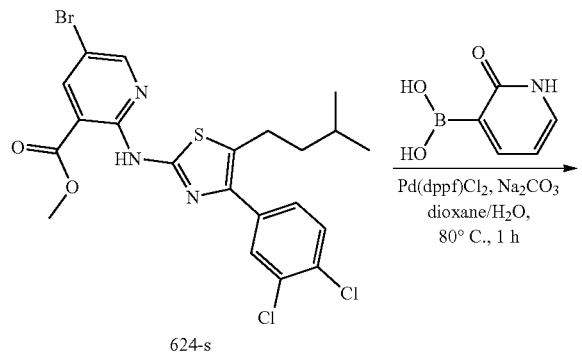
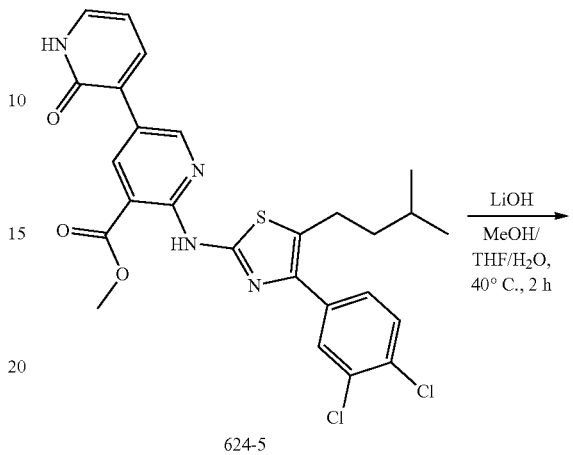
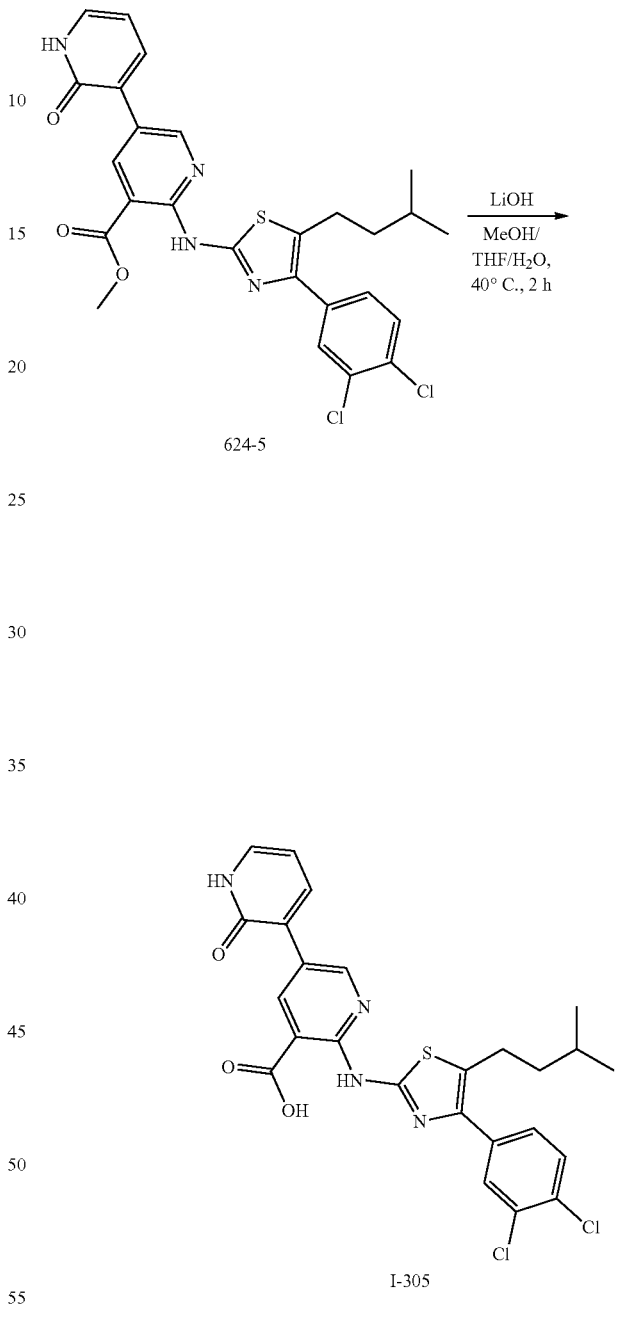

A mixture of 624-s (50.0 mg, 0.0945 mmol), 2-oxo-1,2-dihydropyridin-3-ylboronic acid (19.7 mg, 0.142 mmol), Pd(dppf)Cl$_2$ (6.92 mg, 0.00945 mmol) and Na$_2$CO$_3$ (20.0 mg, 0.189 mmol) in dioxane/H$_2$O (v/v=5/1, 2.0 mL) was stirred under N$_2$ atmosphere at 80° C. for 1 h. When the reaction was completed, it was concentrated and purified by silica gel column chromatography (petrol ether/ethyl acetate=5/1) to afford 624-5 (20.0 mg, 39.0% yield) as a brown solid.

To a solution of 624-5 (20.0 mg, 0.0368 mmol) in THF/MeOH/H$_2$O (v/v/v=4/1/1, 2.0 mL) was added LiOH (2.0 M in H$_2$O, 0.50 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-305 (10.0 mg, 51.3% yield) as a yellow solid.

TABLE 6-2

| I# | Chemical Structure | LCMS | ¹H NMR (400 MHz, d₆-DMSO) |
|---|---|---|---|
| 289 | 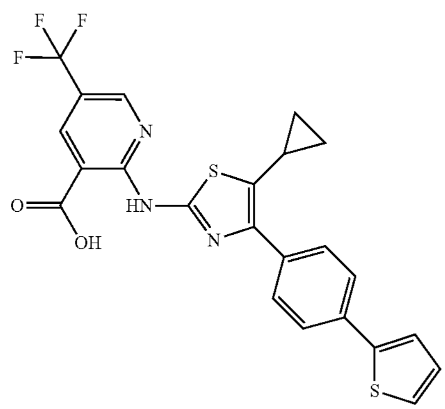 [SMILES: O=C(O)c1cc(C(F)(F)F)cnc1Nc1nc(-c2ccc(-c3cccs3)cc2)c(C2CC2)s1] | Method C, Purity is 96.0%, Rt = 2.103 min; MS Calcd.: 487.0; MS Found: 487.8 [M + H]⁺. | δ: 3.69 (2H, d, J = 6.0 Hz), 5.17-5.22 (2H, m), 6.04-6.14 (1H, m), 7.15-7.18 (1H, m), 7.58 (2H, d, J = 4.4 Hz), 7.68-7.76 (4H, m), 8.48 (1H, d, J = 2.0 Hz), 8.89 (1H, d, J = 1.2 Hz). |
| 290 | 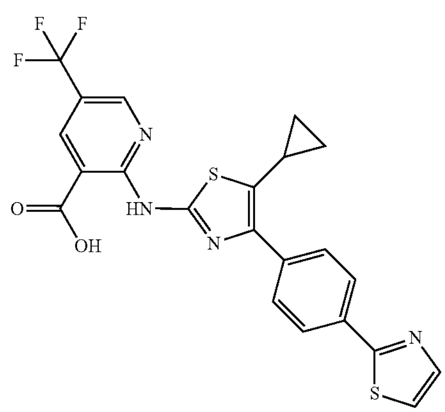 [SMILES: O=C(O)c1cc(C(F)(F)F)cnc1Nc1nc(-c2ccc(-c3nccs3)cc2)c(C2CC2)s1] | Method C, Purity is 92.9%, Rt = 1.840 min; MS Calcd.: 488.0; MS Found: 489.0 [M + H]⁺. | δ: 1.89 (3H, q, J = 1.2 Hz), 6.06-6.12 (1H, m), 6.70 (1H, dd, J = 15.6, 2.0 Hz), 7.76 (2H, d, J = 8.4 Hz ), 7.83 (1H, d, J = 2.4 Hz), 7.97 (1H, d, J = 2.4 Hz), 8.06 (2H, d, J = 8.4 Hz), 8.51 (1H, d, J = 2.4 Hz), 8.95 (1H, s), 12.33 (1H, brs). |
| 291 | 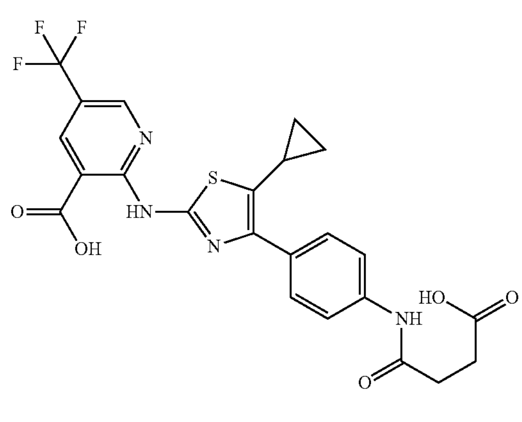 [SMILES: O=C(O)CCC(=O)Nc1ccc(-c2nc(Nc3ncc(C(F)(F)F)cc3C(=O)O)sc2C2CC2)cc1] | Method C, Purity is 96.1%, Rt = 1.424 min; MS Calcd.: 520.0; MS Found: 521.0 [M + H]⁺. | δ: 2.56 (4H, dd, J = 14.0, 5.2 Hz), 3.63 (2H, d, J = 6.0 Hz), 5.15-5.20 (2H, m), 6.03-6.08 (1H, m), 7.55 (2H, d, J = 8.4 Hz), 7.66 (2H, d, J = 8.8 Hz), 8.45 (1H, d, J = 1.6 Hz), 8.72 (1H, s), 10.08 (1H, s), 12.04 (1H, brs), 14.10 (1H, brs). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 294 | 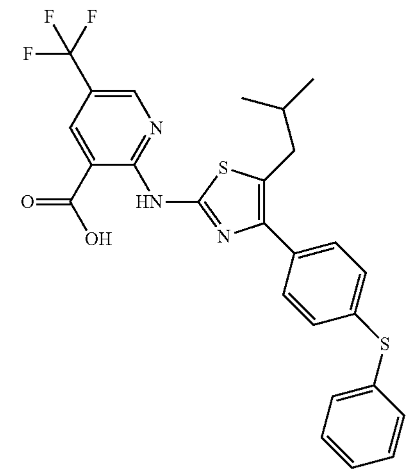 [SMILES: CC(C)Cc1sc(Nc2ncc(C(F)(F)F)cc2C(=O)O)nc1-c1ccc(Sc2ccccc2)cc1] | Method C, Purity is 96.6%, Rt = 2.229 min; MS Calcd.: 529.1; MS Found: 529.8 [M + H]$^+$. | δ: 0.91 (6H, d, J = 6.8), 1.84-1.92 (1H, m), 2.77 (2H, d, J = 7.2 Hz), 7.33-7.44 (7H, m), 7.62 (2H, d, J = 8.4 Hz), 8.50 (1H, d, J = 2.4 Hz), 8.95 (1H, d, J = 1.2 Hz), 11.88 (1H, brs). |
| 295 | 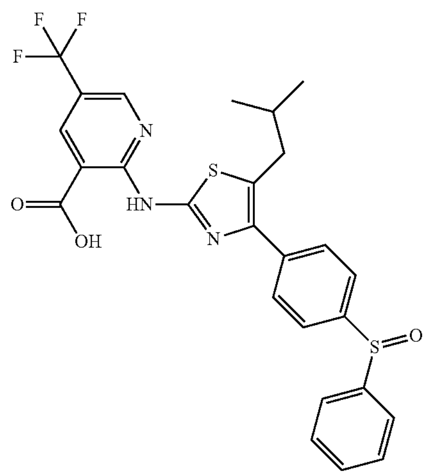 [SMILES: CC(C)Cc1sc(Nc2ncc(C(F)(F)F)cc2C(=O)O)nc1-c1ccc(S(=O)c2ccccc2)cc1] | Method C, Purity is 97.6%, Rt = 1.169 min; MS Calcd.: 545.1; MS Found: 546.0 [M + H]$^+$.m), | δ: 0.90 (6H, d, J = 6.4 Hz), 1.85-1.88 (1H, m), 2.78 (2H, d, J = 7.2 Hz), 7.53-7.59 (3H, m), 7.74-7.81 (6H, m), 8.50 (1H, d, J = 2.4 Hz), 8.95 (1H, d, J = 1.6 Hz), 11.85 (1H, brs). |
| 296 | 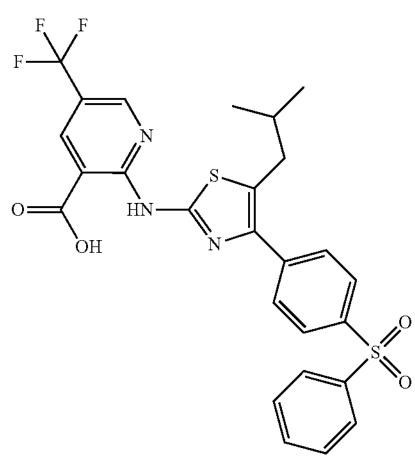 [SMILES: CC(C)Cc1sc(Nc2ncc(C(F)(F)F)cc2C(=O)O)nc1-c1ccc(S(=O)(=O)c2ccccc2)cc1] | Method C, Purity is 93.8%, Rt = 2.062 min; MS Calcd.: 561.1; MS Found: 561.7 [M + H]$^+$.8.4 Hz), | δ: 0.90 (6H, d, J = 6.4 Hz), 1.85-1.90 (1H, m), 2.80 (2H, d, J = 7.2 Hz), 7.63-7.74 (3H, m), 7.87 (2H, d, J = 8.4 Hz), 7.98-8.04 (4H, m), 8.50 (1H, d, J = 2.0 Hz), 8.95 (1H, d, J = 1.6 Hz), 11.97 (1H, brs). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 297 | 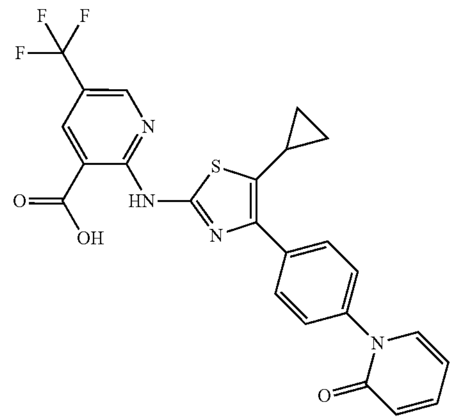 [SMILES: O=C(O)c1cc(C(F)(F)F)cnc1Nc1nc(-c2ccc(-n3ccccc3=O)cc2)c(C2CC2)s1] | Method C, Purity is 98.1%, Rt = 1.685 min; MS Calcd.: 498.1; MS Found: 499.0 [M + H]$^+$. | δ: 3.70 (2H, d, J = 6.0 Hz), 5.18-5.23 (2H, m), 6.07-6.14 (1H, m), 6.34 (1H, t, J = 6.8 Hz), 6.51 (1H, d, J = 8.4 Hz), 7.47-7.55 (4H, m), 7.71 (1H, dd, J = 11.2, 6.8 Hz), 7.77 (2H, d, J = 8.4 Hz), 8.43 (1H, brs), 8.75 (1H, brs). |
| 298 | 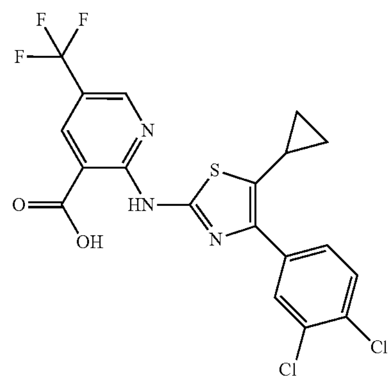 [SMILES: O=C(O)c1cc(C(F)(F)F)cnc1Nc1nc(-c2ccc(Cl)c(Cl)c2)c(C2CC2)s1] | Method B, Purity is 98.1%, Rt = 1.685 min; MS Calcd.: 473.0; MS Found: 473.9 [M + H]$^+$. | δ: 3.68 (2H, d, J = 6.0 Hz), 5.15-5.21 (2H, m), 6.01-6.12 (1H, m), 7.61 (1H, dd, J = 8.4, 2.0 Hz), 7.70 (1H, d, J = 8.4 Hz), 7.82 (1H, d, J = 1.6 Hz), 8.49 (1H, d, J = 2.4 Hz), 8.94 (1H, d, J = 1.6 Hz), 11.87 (1H, brs). |
| 299 | 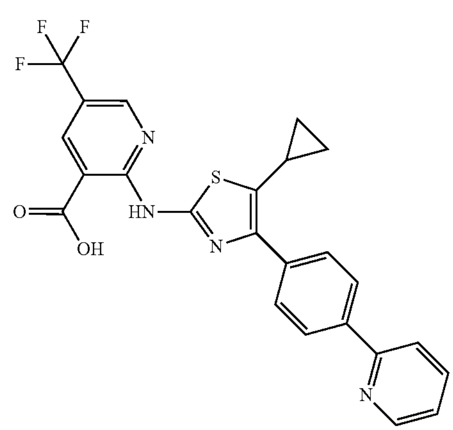 | Method C, Purity is 83.0%, Rt = 1.771 min; MS Calcd.: 482.1; MS Found: 483.1 [M + H]$^+$. | δ: 3.73 (2H, d, J = 6.4 Hz), 5.26-5.16 (2H, m), 6.16-6.04 (1H, m), 7.43-7.34 (1H, m), 7.78 (2H, d, J = 8.4 Hz), 7.95-7.87 (1H, m), 8.11 (1H, d, J = 7.6 Hz), 8.19 (1H, d, J = 8.4 Hz), 8.51 (1H, d, J = 2.0 Hz), 8.70 (1H, d, J = 4.0 Hz), 8.95 (1H, s). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 300 | 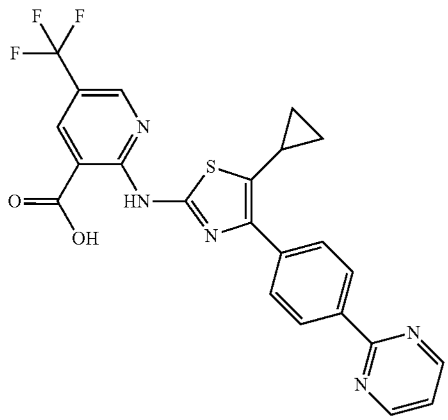 [SMILES: O=C(O)c1cc(C(F)(F)F)cnc1Nc1nc(-c2ccc(-c3ncccn3)cc2)c(C2CC2)s1] | Method C, Purity is 94.8%, Rt = 1.931 min; MS Calcd.: 483.1; MS Found: 483.8 [M + H]$^+$. | δ: 3.74 (2H, d, J = 6.4 Hz), 5.27-5.17 (2H, m), 6.16-6.04 (1H, m), 7.47 (1H, t, J = 5.0 Hz), 7.82 (2H, d, J = 8.4 Hz), 8.54-8.45 (3H, m), 8.99-8.91 (3H, m). |
| 301 | 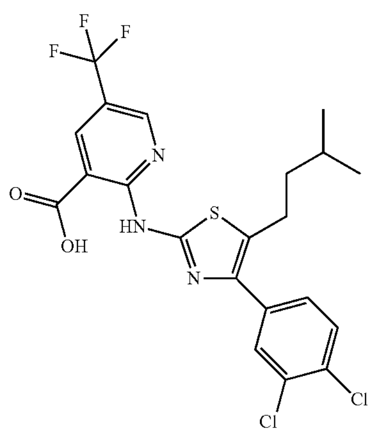 [SMILES: CC(C)CCc1sc(Nc2ncc(C(F)(F)F)cc2C(=O)O)nc1-c1ccc(Cl)c(Cl)c1] | Method C, Purity is 98.5%, Rt = 2.243 min; MS Calcd.: 503.0; MS Found: 503.7 [M + H]$^+$. | δ: 0.90 (6H, d, J = 6.4 Hz), 1.52-1.56 (3H, m), 2.90 (2H, t, J = 7.6 Hz), 7.61 (1H, dd, J = 8.4, 2.0 Hz), 7.72 (1H, d, J = 8.4 Hz), 7.82 (1H, d, J = 1.6 Hz), 8.50 (1H, d, J = 1.6 Hz), 8.95 (1H, d, J = 1.2 Hz), 11.86 (1H, brs). |
| 302 | 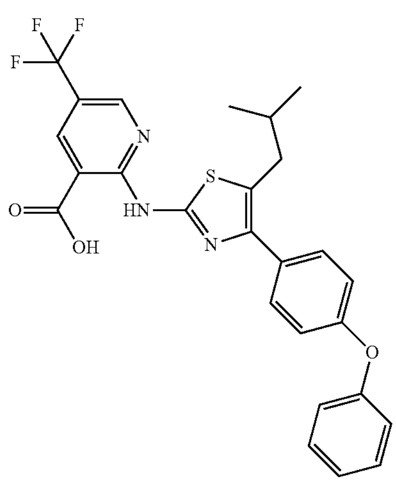 | Method C, Purity is 92.1%, Rt = 2.195 min; MS Calcd.: 513.0; MS Found: 513.8 [M + H]$^+$. | δ: 0.92 (6H, d, J = 6.8 Hz), 1.85-1.92 (1H, m), 2.77 (2H, d, J = 7.2 Hz), 7.06-7.07 (4H, m), 7.18 (1H, t, J = 7.2 Hz), 7.43 (2H, q, J = 8.0 Hz), 7.62 (2H, t, J = 8.8 Hz), 8.50 (1H, d, J = 2.4 Hz), 8.96 (1H, d, J = 1.2 Hz), 11.82 (1H, brs). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 303 | 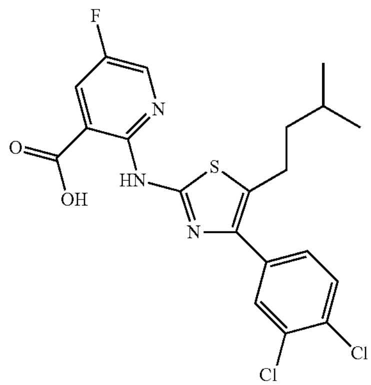 [SMILES: CC(C)CCc1sc(Nc2ncc(F)cc2C(=O)O)nc1-c1ccc(Cl)c(Cl)c1] | Method C, Purity is 100%, Rt = 2.150 min; MS Calcd.: 453.1; MS Found: 453.7 [M + H]$^+$. | δ: 0.89 (2H, d, J = 6.4 Hz), 1.54-1.65 (3H, m), 2.86-2.90 (2H, m), 7.59-7.62 (1H, m), 7.70-7.72 (1H, m), 7.81 (1H, m), 8.19-8.22 (1H, m), 8.62 (1H, s), 11.77 (1H, brs). |
| 304 | 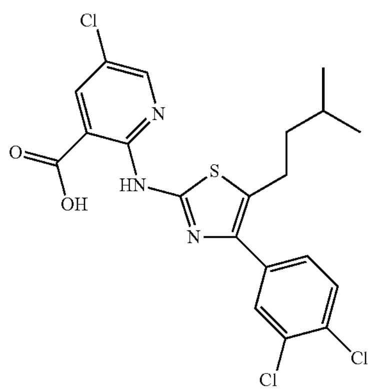 [SMILES: CC(C)CCc1sc(Nc2ncc(Cl)cc2C(=O)O)nc1-c1ccc(Cl)c(Cl)c1] | Method C, Purity is 97.3%, Rt = 2.201 min; MS Calcd.: 469.0; MS Found: 469.8 [M + H]$^+$. | δ: 0.89 (2H, d, J = 6.4 Hz), 1.52-1.65 (3H, m), 2.86-2.90 (2H, m), 7.60-7.62 (1H, m), 7.70-7.72 (1H, m), 7.81 (1H, s), 8.28 (1H, m), 8.57 (1H, m), 12.20 (1H, brs). |
| 305 | 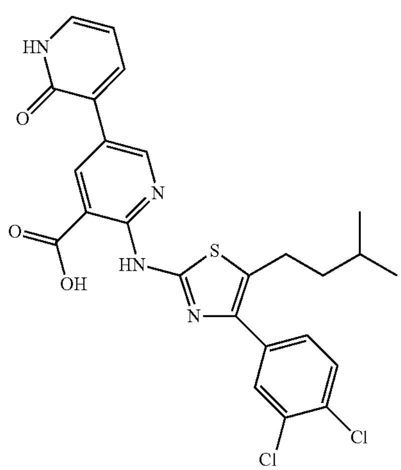 [SMILES: CC(C)CCc1sc(Nc2ncc(-c3ccc[nH]c3=O)cc2C(=O)O)nc1-c1ccc(Cl)c(Cl)c1] | Method C, Purity is 93.2%, Rt = 2.064 min; MS Calcd.: 528.1; MS Found: 529.1 [M + H]$^+$. | δ: 0.90 (6H, d, J = 6.4 Hz), 1.55-1.63 (3H, m), 2.90 (2H, t, J = 8.0 Hz), 6.34 (1H, t, J = 6.4 Hz), 7.44 (1H, d, J = 4.0 Hz), 7.62 (1H, dd, J = 8.4, 2.0 Hz), 7.71 (1H, d, J = 8.4 Hz), 7.83-7.86 (2H, m), 8.80 (1H, d, J = 2.4 Hz), 8.92 (1H, d, J = 2.0 Hz), 11.95 (1H, brs). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 306 | 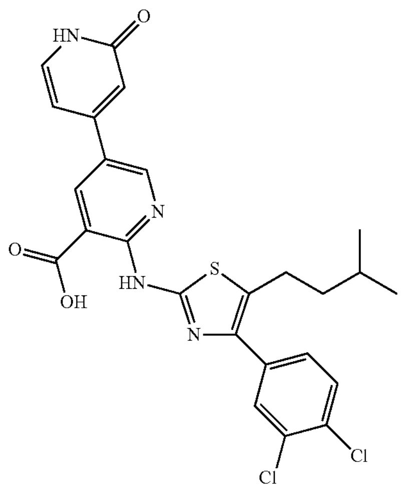 [SMILES: CC(C)CCc1sc(Nc2ncc(-c3cc[nH]c(=O)c3)cc2C(=O)O)nc1-c1ccc(Cl)c(Cl)c1] | Method C, Purity is 88.0%, Rt = 2.012 min; MS Calcd.: 528.1; MS Found: 529.0 [M + H]$^+$. | δ: 0.90 (3H, s), 0.92 (3H, s), 1.68-1.52 (3H, m), 2.89 (2H, t, J = 8.2 Hz), 6.62-6.53 (2H, m), 7.45 (1H, d, J = 6.4 Hz), 7.62 (1H, dd, J = 8.4, 2.0 Hz), 7.70 (1H, d, J = 8.4 Hz), 7.83 (1H, d, J = 2.0 Hz), 8.47 (1H, d, J = 2.4 Hz), 8.69 (1H, d, J = 2.0 Hz), 11.57 (1H, brs). |
| 307 | 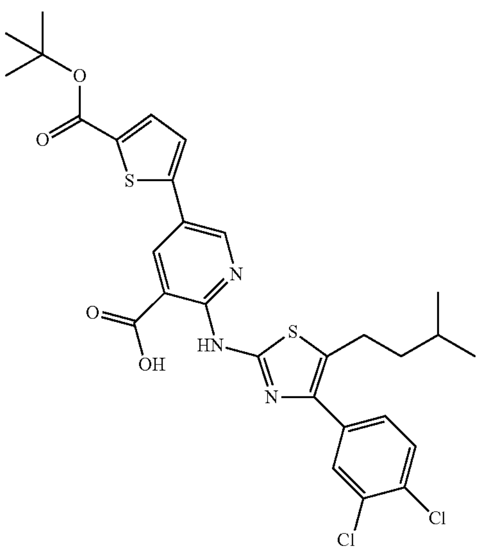 [SMILES: CC(C)CCc1sc(Nc2ncc(-c3ccc(C(=O)OC(C)(C)C)s3)cc2C(=O)O)nc1-c1ccc(Cl)c(Cl)c1] | Method C, Purity is 92.1%, Rt = 1.933 min; MS Calcd.: 617.1; MS Found: 618.0 [M + H]$^+$. | δ: 0.90 (3H, s), 0.92 (3H, s), 1.55 (9H, s), 1.68-1.56 (3H, m), 2.90 (2H, t, J = 7.8 Hz), 7.62 (1H, dd, J = 8.4, 2.0 Hz), 7.75-7.67 (3H, m), 7.83 (1H, d, J = 2.0 Hz), 8.52 (1H, d, J = 2.4 Hz), 8.99 (1H, d, J = 2.4 Hz), 11.74 (1H, brs). |
| 308 | 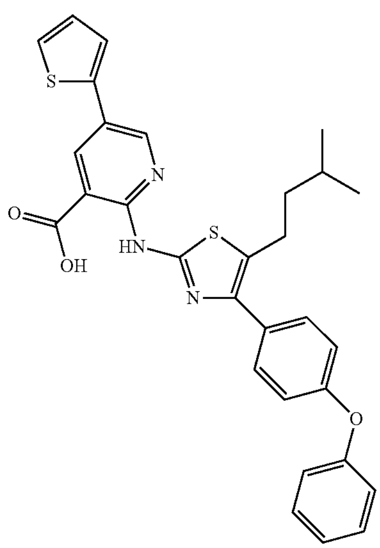 [SMILES: CC(C)CCc1sc(Nc2ncc(-c3cccs3)cc2C(=O)O)nc1-c1ccc(Oc2ccccc2)cc1] | Method C, Purity is 95.2%, Rt = 2.297 min; MS Calcd.: 541.1; MS Found: 542.3 [M + H]$^+$. | δ: 0.89 (6H, d, J = 6.4 Hz), 1.53-1.62 (3H, m), 2.87 (2H, t, J = 8.0 Hz), 7.06-7.09 (4H, m), 7.16-7.20 (2H, m), 7.41-7.45 (2H, m), 7.60-7.64 (4H, m), 8.45 (1H, d, J = 2.4 Hz), 8.93 (1H, d, J = 2.8 Hz), 11.50 (1H, brs), 14.45 (0.5 H, brs). |

TABLE 6-2-continued

Characterization Data for Additional Exemplary Compounds

| I# | Chemical Structure | LCMS | $^1$H NMR (400 MHz, $d_6$-DMSO) |
|---|---|---|---|
| 309 | 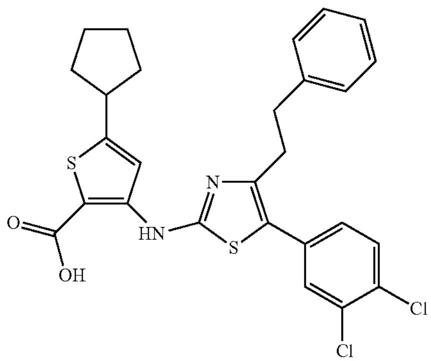 [SMILES: O=C(O)c1sc(C2CCCC2)cc1Nc1nc(CCc2ccccc2)c(-c2ccc(Cl)c(Cl)c2)s1] | Method C, Purity is 85.3%, Rt = 1.987 min; MS Calcd.: 542.1; MS Found: 543.0 [M + H]$^+$. | δ: 1.56-1.66 (4H, m), 1.73-1.76 (2H, m), 2.04-2.07 (2H, m), 2.49-2.51 (3H, m), 2.84-2.87 (2H, m), 3.03 (1H, t, J = 7.6 Hz), 7.14-7.31 (7H, m), 7.54 (1H, s), 7.59 (1H, d, J = 8.4 Hz), 12.72 (1H, s). |
| 310 | 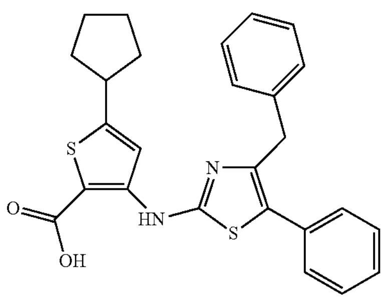 [SMILES: O=C(O)c1sc(C2CCCC2)cc1Nc1nc(Cc2ccccc2)c(-c2ccccc2)s1] | Method C, Purity is 90.1%, Rt = 1.817 min; MS Calcd.: 460.1; MS Found: 461.0 [M + H]$^+$. | δ: 1.50-1.66 (6H, m), 2.01-2.04 (2H, m), 3.13 (1H, t, J = 8.4 Hz), 3.96 (2H, s), 7.20-7.35 (6H, m), 7.42-7.46 (5H, m), 12.52 (1H, s). |
| 311 | 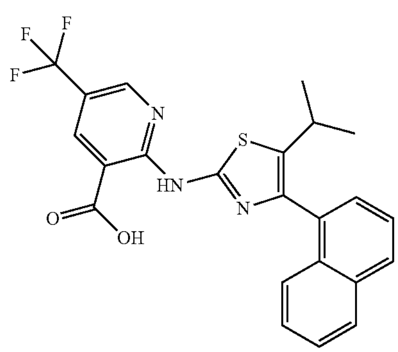 [SMILES: CC(C)c1sc(Nc2ncc(C(F)(F)F)cc2C(=O)O)nc1-c1cccc2ccccc12] | Method C, Purity is 97.5%, Rt = 1.913 min; MS Calcd.: 457.1; MS Found: 457.9 [M + H]$^+$. | δ: 1.21 (6H, d, J = 6.8 Hz), 2.90-2.94 (1H, m), 7.50-7.68 (5H, m), 8.01 (2H, d, J = 8.0 Hz), 8.50 (1H, d, J = 2.4 Hz), 8.97 (1H, s), 12.51 (1H, brs). |
| 312 | 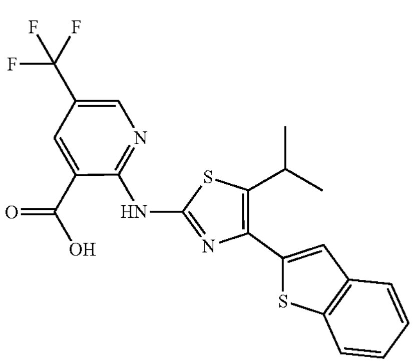 [SMILES: CC(C)c1sc(Nc2ncc(C(F)(F)F)cc2C(=O)O)nc1-c1cc2ccccc2s1] | Method C, Purity is 92.8%, Rt = 2.114 min; MS Calcd.: 463.0; MS Found: 464.0 [M + H]$^+$. | δ: 1.41 (6H, d, J = 6.8 Hz), 3.71-3.75 (1H, m), 7.34-7.40 (2H, m), 7.68 (1H, s), 7.92 (1H, dd, J = 25.2, 7.2 Hz), 8.40 (1H, d, J = 2.4 Hz), 8.66 (1H, d, J = 1.2 Hz), 15.07 (1H, brs). |

TABLE 6-2-continued

Characterization Data for Additional Exemplary Compounds

| I# | Chemical Structure | LCMS | $^1$H NMR (400 MHz, d$_6$-DMSO) |
|---|---|---|---|
| 313 | 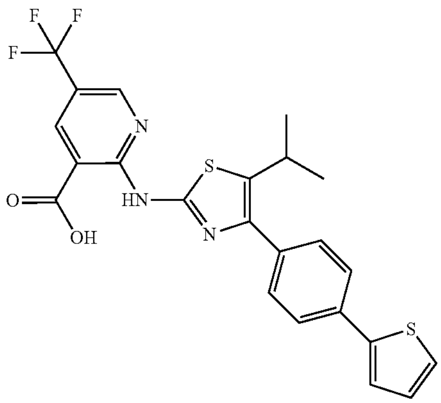 [SMILES: CC(C)c1sc(Nc2ncc(C(F)(F)F)cc2C(=O)O)nc1-c1ccc(-c2cccs2)cc1] | Method C, Purity is 90.9%, Rt = 2.152 min; MS Calcd.: 489.1; MS Found: 490.1 [M + H]$^+$. | δ: 1.35 (6H, d, J = 6.8 Hz), 3.43-3.47 (1H, m), 7.17 (1H, t, J = 4.4 Hz), 7.58 (2H, d, J = 4.4 Hz), 7.63 (2H, d, J = 8.4 Hz), 7.74 (2H, d, J = 8.4 Hz), 8.38 (1H, d, J = 2.4 Hz), 8.65 (1H, d, J = 1.6 Hz), 15.00 (1H, s). |
| 314 | 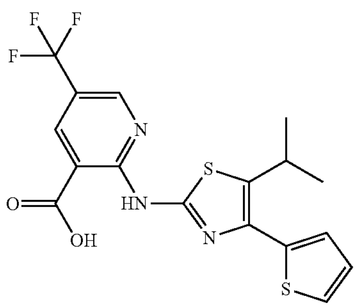 [SMILES: CC(C)c1sc(Nc2ncc(C(F)(F)F)cc2C(=O)O)nc1-c1cccs1] | Method C, Purity is 97.1%, Rt = 1.822 min; MS Calcd.: 413.0; MS Found: 413.9 [M + H]$^+$. | δ: 1.36 (3H, s), 1.37 (3H, s), 3.65-3.55 (1H, m), 7.15 (1H, dd, J = 5.0, 3.8 Hz), 7.37 (1H, d, J = 2.8 Hz), 7.57 (1H, d, J = 4.8 Hz), 8.50 (1H, d, J = 2.4 Hz), 8.97 (1H, d, J = 1.2 Hz), 11.95 (1H, brs). |
| 315 | 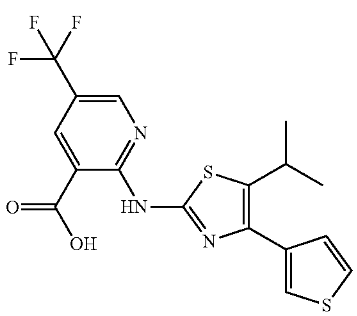 [SMILES: CC(C)c1sc(Nc2ncc(C(F)(F)F)cc2C(=O)O)nc1-c1ccsc1] | Method C, Purity is 95.8%, Rt = 1.968 min; MS Calcd.: 413.1; MS Found: 414.1 [M + H]$^+$. | δ: 1.32 (6H, d, J = 6.8 Hz), 3.47-3.51 (1H, m), 7.42 (1H, dd, J = 4.8, 1.2 Hz), 7.61 (1H, dd, J = 4.8, 2.8 Hz), 7.66 (1H, d, J = 2.0 Hz), 8.39 (1H, d, J = 2.0 Hz), 8.65 (1H, s), 14.78 (1H, brs). |
| 316 | 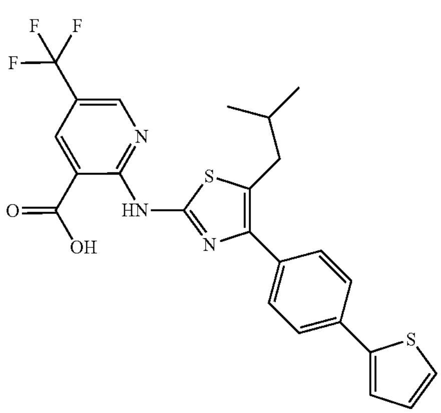 [SMILES: CC(C)Cc1sc(Nc2ncc(C(F)(F)F)cc2C(=O)O)nc1-c1ccc(-c2cccs2)cc1] | Method C, Purity is 97.6%, Rt = 2.221 min; MS Calcd.: 503.1; MS Found: 504.1 [M + H]$^+$. | δ: 0.94 (6H, d, J = 6.4 Hz), 1.89-1.92 (1H, m), 2.83 (2H, d, J = 7.2 Hz), 7.171 (1H, t, J = 4.4 Hz), 7.584 (2H, d, J = 4.0 Hz), 7.67 (2H, d, J = 8.0 Hz), 7.75 (2H, d, J = 8.4 Hz), 8.50 (1H, s), 8.92 (1H, s), 12.35 (1H, s). |

TABLE 6-2-continued

Characterization Data for Additional Exemplary Compounds

| I# | Chemical Structure | LCMS | ¹H NMR (400 MHz, d₆-DMSO) |
|---|---|---|---|
| 317 | 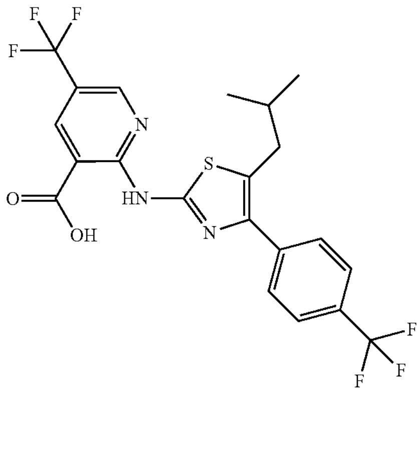 [SMILES: CC(C)Cc1sc(Nc2ncc(C(F)(F)F)cc2C(=O)O)nc1-c1ccc(C(F)(F)F)cc1] | Method C, Purity is 96.3%, Rt = 2.166 min; MS Calcd.: 489.0; MS Found: 489.8 [M + H]⁺. | δ: 0.92 (6H, d, J = 6.4 Hz), 1.87-1.90 (1H, m), 2.82 (2H, d, J = 6.8 Hz), 7.83 (4H, q, J = 8.4 Hz), 8.51 (1H, d, J = 2.0 Hz), 8.97 (1H, d, J = 1.6 Hz), 11.89 (0.5H, brs). |
| 318 | 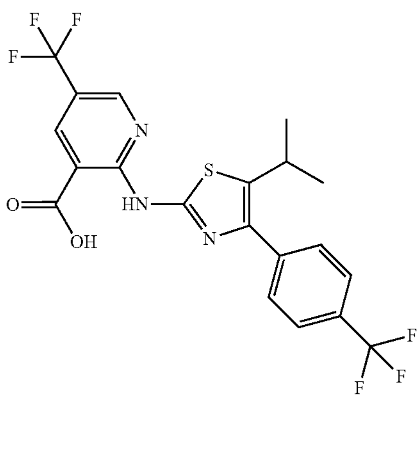 [SMILES: CC(C)c1sc(Nc2ncc(C(F)(F)F)cc2C(=O)O)nc1-c1ccc(C(F)(F)F)cc1] | Method C, Purity is 100%, Rt = 1.920 min; MS Calcd.: 475.1; MS Found: 475.9 [M + H]⁺. | δ: 1.35 (6H, d, J = 6.8 Hz), 3.41-3.48 (1H, m), 7.82 (4H, s), 8.52 (1H, s), 8.99 (1H, s), 11.85 (1H, brs). |
| 319 | 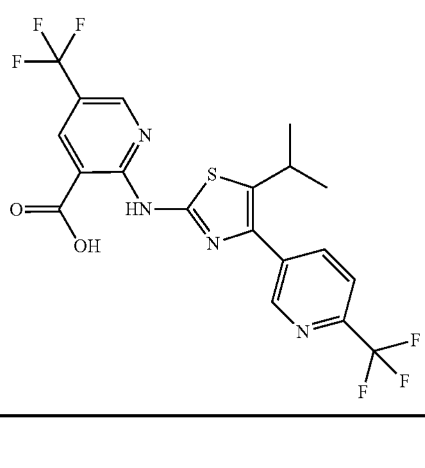 | Method C, Purity is 99.2%, Rt = 2.015 min; MS Calcd.: 476.1; MS Found: 476.9 [M + H]⁺. | δ: 1.36 (3H, s), 1.37 (3H, s), 3.48-3.40 (1H, m), 8.00 (1H, d, J = 8.0 Hz), 8.27 (1H, dd, J = 8.2, 1.8 Hz), 8.52 (1H, d, J = 2.4 Hz), 9.03-8.94 (2H, m), 11.93 (1H, brs). |

Example 7. Synthesis of Compounds I-320 to I-333
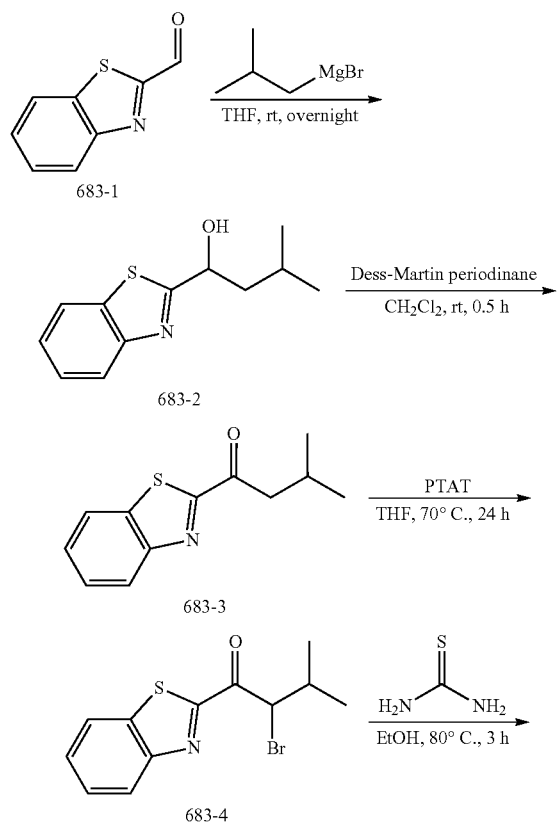
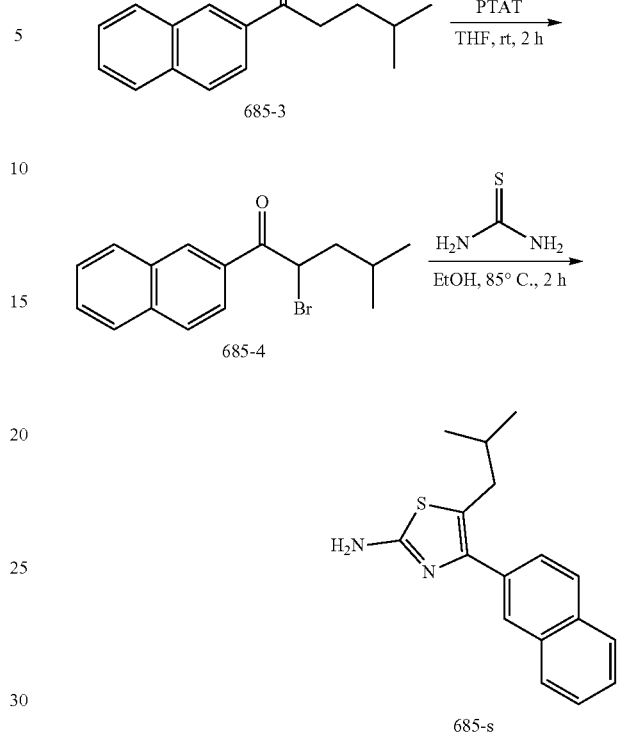
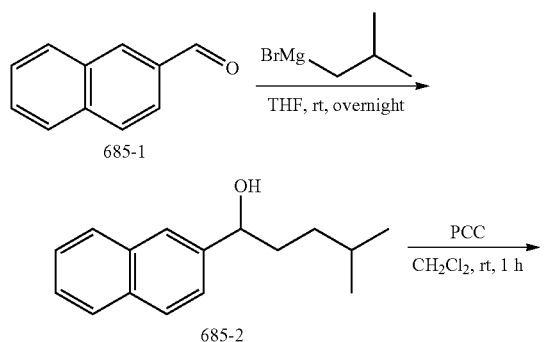
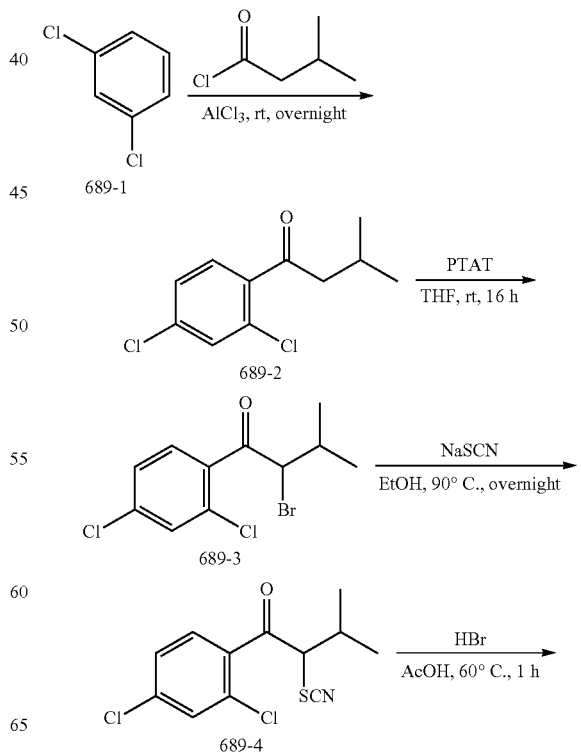

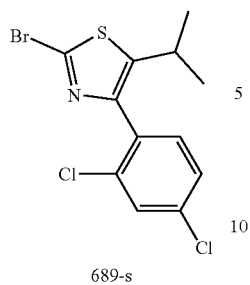
689-s
Scheme 5: Route for Compound 711-s
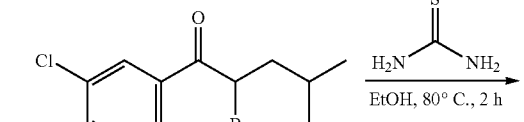
568-5
Scheme 4: Route for Compounds 709-s
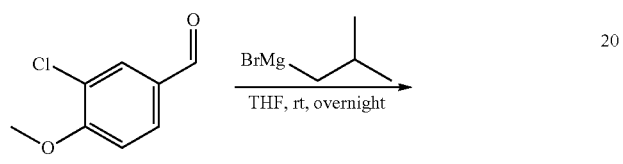
568-2
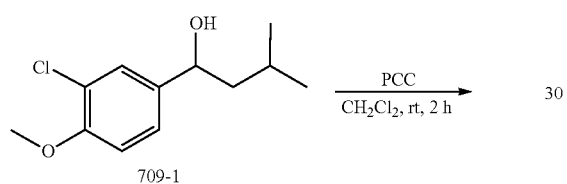
709-1
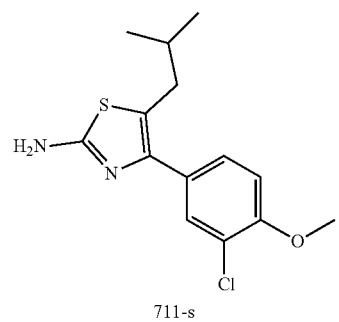
711-s
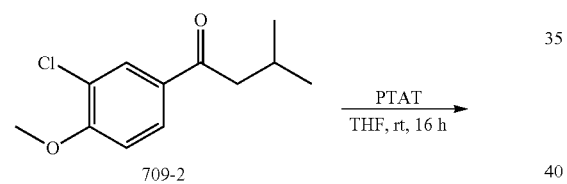
709-2
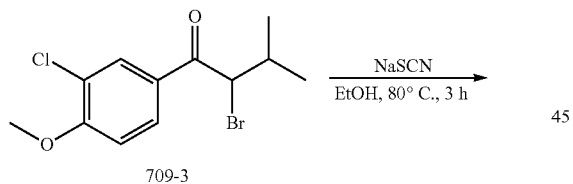
709-3
Scheme 6: Route for Compound 714-s~719-s
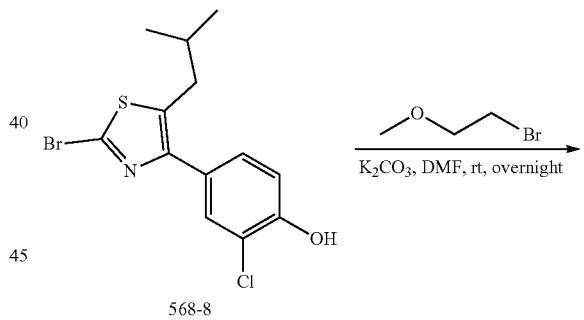
568-8
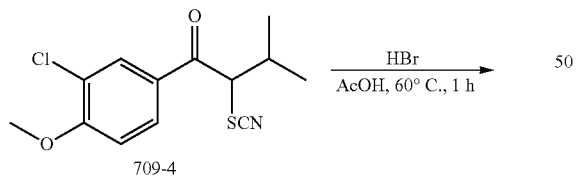
709-4
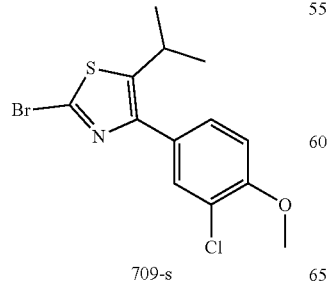
709-s
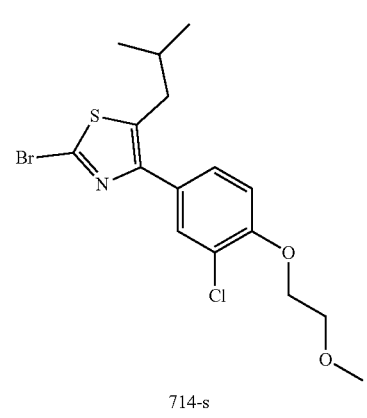
714-s

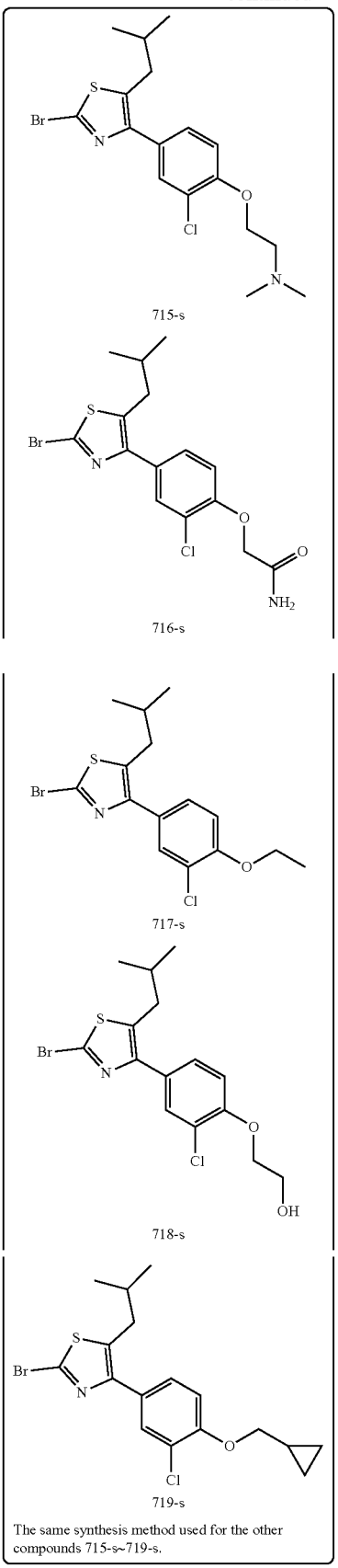 [SMILES: CC(C)Cc1sc(Br)nc1-c1ccc(OCCN(C)C)c(Cl)c1 ; CC(C)Cc1sc(Br)nc1-c1ccc(OCC(N)=O)c(Cl)c1 ; CCOc1ccc(-c2nc(Br)sc2CC(C)C)cc1Cl ; CC(C)Cc1sc(Br)nc1-c1ccc(OCCO)c(Cl)c1 ; CC(C)Cc1sc(Br)nc1-c1ccc(OCC2CC2)c(Cl)c1]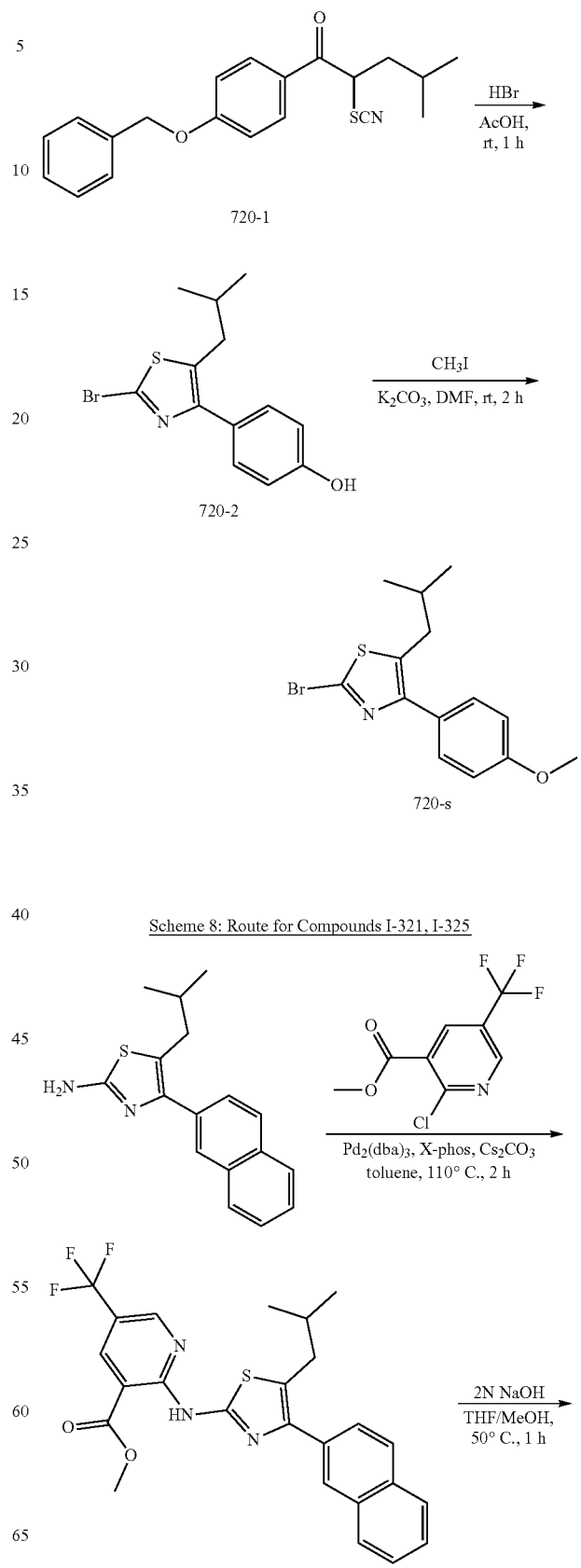

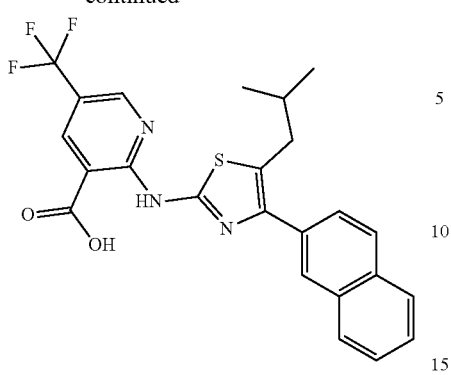
The same synthesis method used for compound I-325.
Scheme 9: Route for Compound I-320
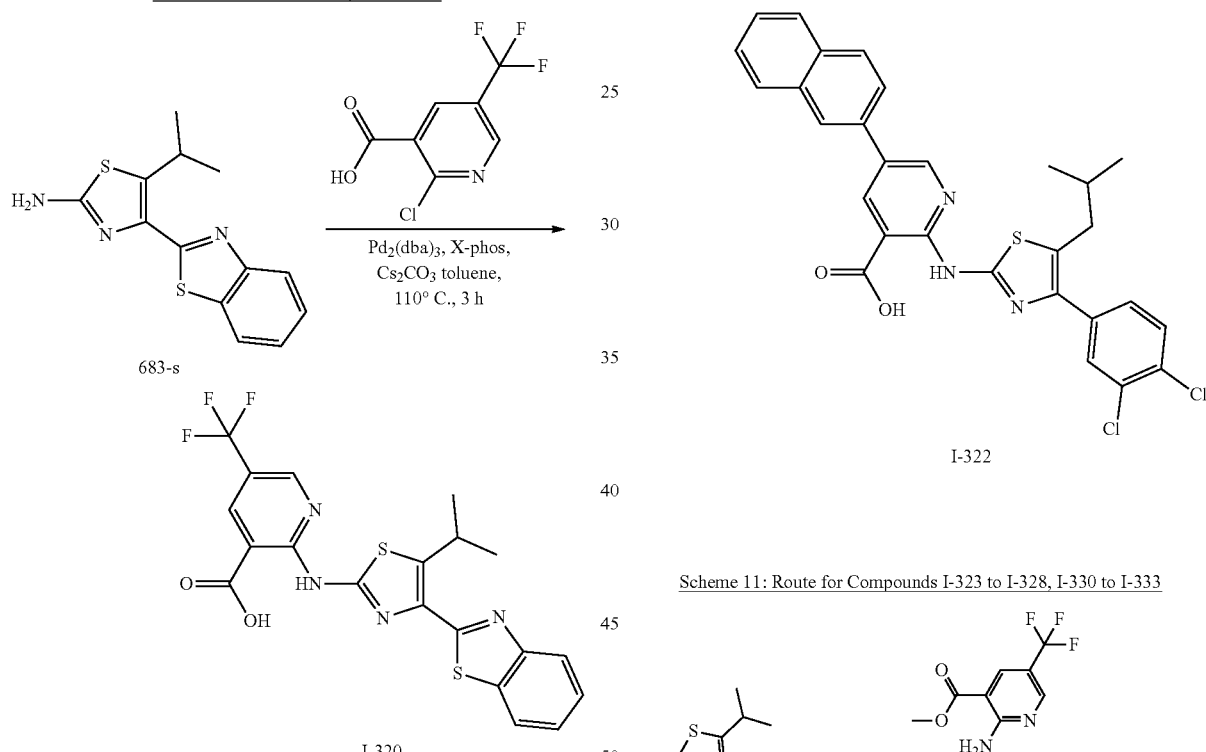
Scheme 10: Route for Compound I-322
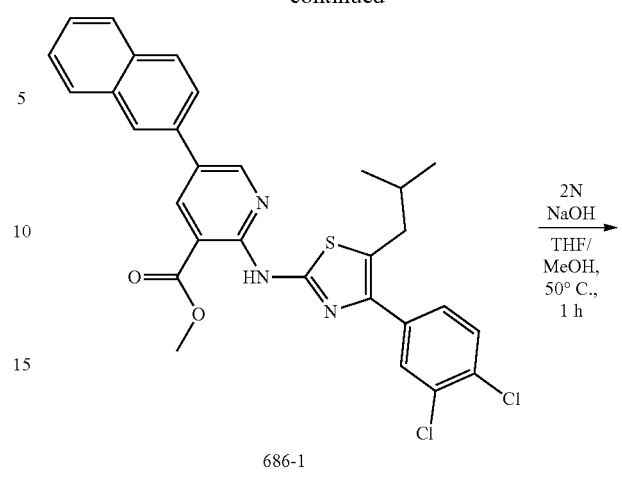
Scheme 11: Route for Compounds I-323 to I-328, I-330 to I-333
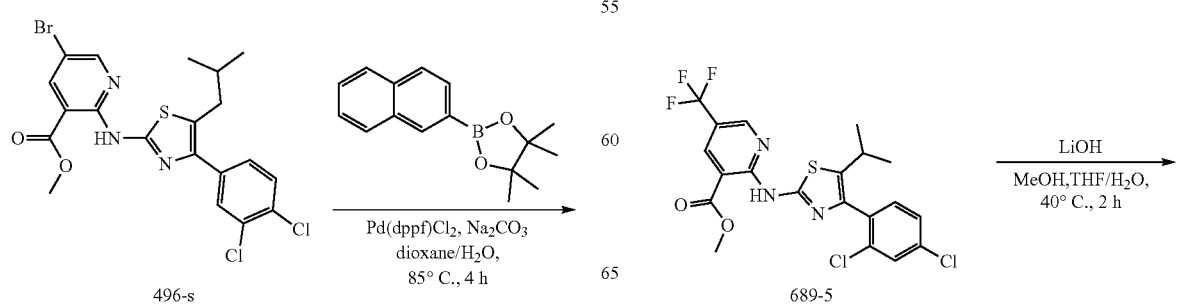

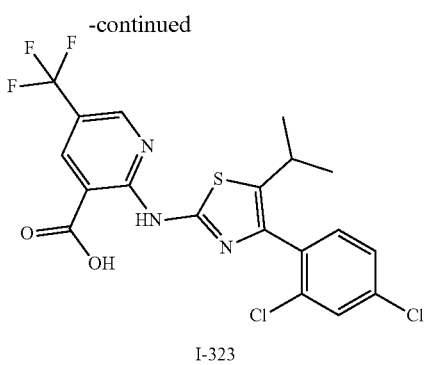

I-323

The same synthesis method used for other compounds I-324 to I-328, I-330 to I-333.

Scheme 12: Route for Compound I-329

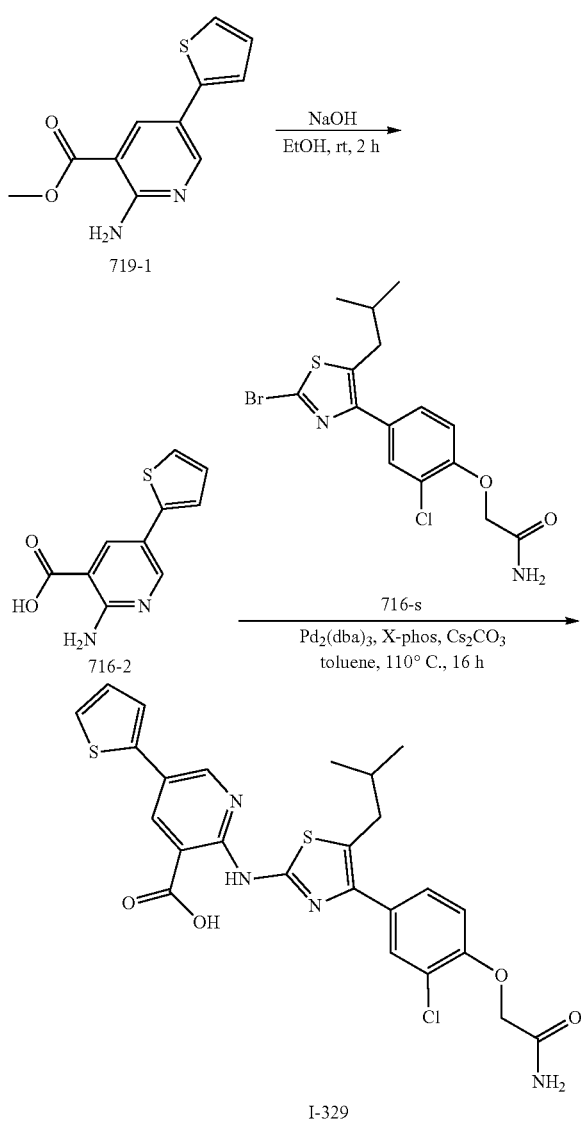

I-329

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on an Agilent 1200 series 6110 or 6120 mass spectrometer with electrospray ionization and excepted as otherwise indicated, the general LCMS condition was as follows:

Method A (Agilent LCMS 1200-6110, Column: Waters X-Bridge C18 (50 mm×4.6 mm×3.5 m); Column Temperature: 40° C.; Flow Rate: 3.0 mL/min; mobile phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05% TFA] in 0.01 min).

Method B (Agilent LCMS 1200-6110, Column: Waters X-Bridge C18 (50 mm×4.6 mm×3.5 m); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min.).

Method C (Agilent LCMS 1200-6120, Column: Waters X-Bridge C18 (50 mm×4.6 mm×3.5 m); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.)

Method D (Agilent LCMS 1200-6120, Column: Waters X-Bridge C18 (50 mm×4.6 mm×3.5 m); Column Temperature: 45° C.; Flow Rate: 2.3 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.75 min, then under this condition for 0.8 min, finally changed to 95% [water+10 mM NH$_4$HCO$_3$] and 5% [CH$_3$CN] in 0.1 min and under this condition for 0.1 min.)

The synthesis of 1-(benzo[d]thiazol-2-yl)-3-methylbutan-1-ol (683-2)

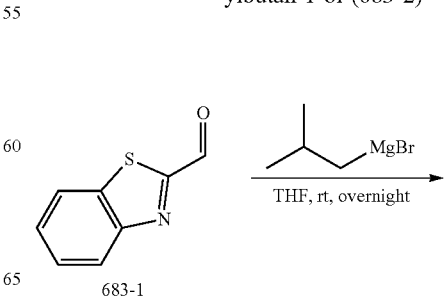

683-1

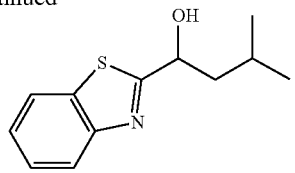

683-2

To a solution of 683-1 (2.0 g, 12.3 mmol) in THF (20.0 mL) was added isobutylmagnesium bromide (1.0 M in THF, 18.4 mL, 18.4 mmol). The reaction was stirred at room temperature overnight. When the reaction was completed, it was poured into aq.NH$_4$Cl (sat., 100 mL) and extracted with EtOAc (80.0 mL×3). The organic phase was combined, and washed with H$_2$O (50.0 mL) and brine (50.0 mL), then dried with anhydrous Na$_2$SO$_4$, concentrated and purified by silica gel column chromatography (petrol ether/ethyl acetate=1/1) to afford 683-2 (930 mg, 34.3% yield) as yellow oil.

The synthesis of 1-(benzo[d]thiazol-2-yl)-3-methylbutan-1-one (683-3)

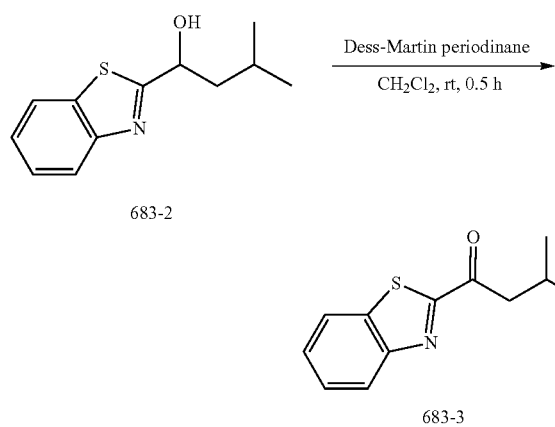

To a solution of 683-2 (800 mg, 3.62 mmol) in CH$_2$Cl$_2$ (20.0 mL) was added Dess-Martin periodinane (3.07 g, 7.24 mmol). The reaction was stirred at room temperature for 0.5 h. When the reaction was completed, it was concentrated, and purified by silica gel column chromatography (petrol ether/ethyl acetate=10/1) to afford 683-3 (630 mg, 79.5% yield) as a yellow solid.

Synthesis of 1-(benzo[d]thiazol-2-yl)-2-bromo-3-methylbutan-1-one (683-4)

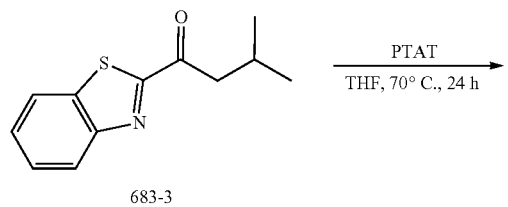

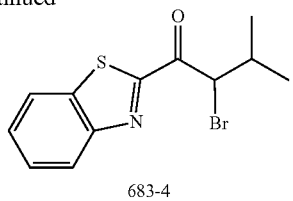

683-4

A mixture of 683-3 (600 mg, 2.74 mmol) and PTAT (1.54 g, 4.11 mmol) in THF (20.0 mL) was stirred at 70° C. for 24 h. When the reaction was completed, it was concentrated, and the residual was dissolved in H$_2$O (50.0 mL), and then extracted with EtOAc (80.0 mL×2). The organic layer was combined, and washed with H$_2$O (30.0 mL×2) and Brine (50.0 mL), then dried by anhydrous Na$_2$SO$_4$. The solution was concentrated to give the crude product, which was used directly in next step without farther purification to afford 683-4 (800 mg, 98.3% yield) as brown oil.

Synthesis of 4-(benzo[d]thiazol-2-yl)-5-isopropylthiazol-2-amine (683-s)

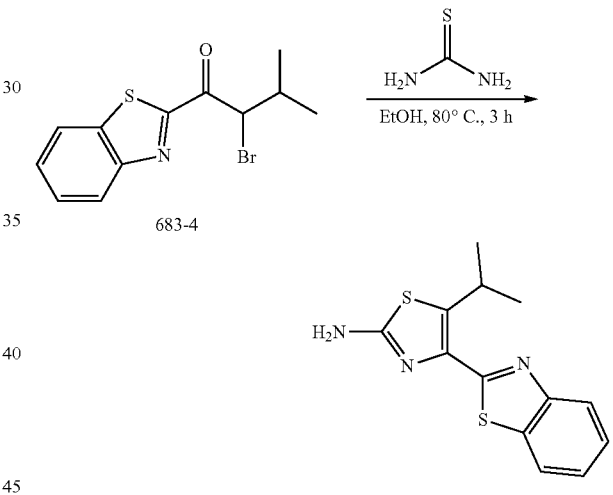

A mixture of 683-4 (800 mg, 2.69 mmol) an thiourea (409 mg, 5.39 mmol) in EtOH (10.0 mL) was stirred at 80° C. for 3 h. When the reaction was completed, it was concentrated and purified by silica gel column chromatography (petrol ether/ethyl acetate=3/1) to afford 683-s (50.0 mg, 6.75% yield) as a yellow solid.

Synthesis of 4-methyl-1-(naphthalen-2-yl)pentan-1-ol (685-2)

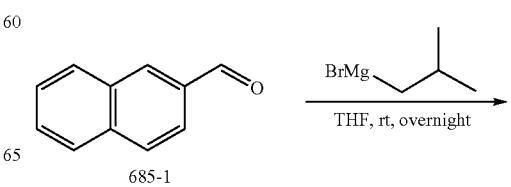

745

-continued

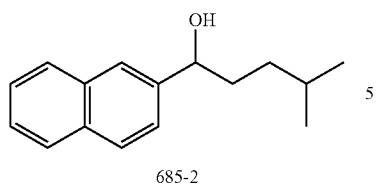

685-2

To a solution of 685-1 (2.0 g, 12.8 mmol) in THF (20.0 mL) was added isobutylmagnesium bromide (1.0 M in THF, 19.2 mL, 19.2 mmol). The reaction was stirred at room temperature overnight. When the reaction was completed, it was poured into aq.NH₄Cl (sat., 50.0 mL) and extracted with EtOAc (80.0 mL×3). The organic phase was combined, and washed with H₂O (50.0 mL) and brine (80.0 mL), then dried with anhydrous Na₂SO₄, concentrated to give the crude product, which was used directly in next step without farther purification to afford 685-2 (2.50 g, 85.5% yield) as yellow oil.

Synthesis of 4-methyl-1-(naphthalen-2-yl)pentan-1-one (685-3)

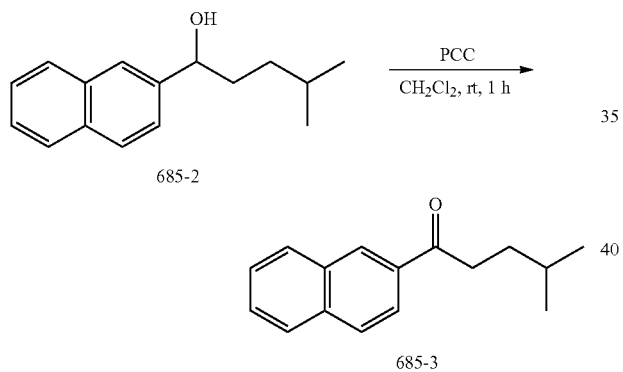

To a solution of 685-2 (2.50 g, 11.0 mmol) in CH₂Cl₂ (100 mL) was added PCC (4.73 g, 21.9 mmol). The reaction was stirred at room temperature for 1 h. When the reaction was completed, it was concentrated, and purified by silica gel column chromatography (petrol ether/ethyl acetate=50/1) to afford 685-3 (2.20 g, 88.8% yield) as a yellow solid.

Synthesis of 2-bromo-4-methyl-1-(naphthalen-2-yl) pentan-1-one (685-4)

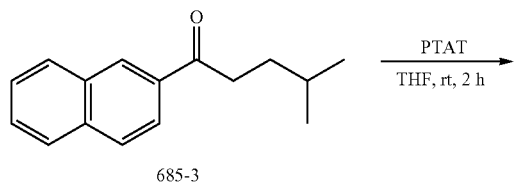

746

-continued

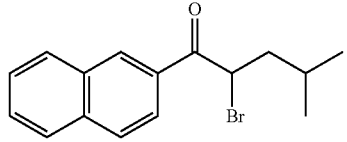

685-4

A mixture of 685-3 (2.20 g, 9.73 mmol) and PTAT (5.48 g, 14.6 mmol) in THF (100 mL) was stirred at room temperature for 2 h. When the reaction was completed, it was concentrated, and the residual was dissolved in H₂O (50.0 mL), and then extracted with EtOAc (80.0 mL×2). The organic layer was combined, and washed with H₂O (30.0 mL×2) and Brine (50.0 mL), then dried by anhydrous Na₂SO₄. The solution was concentrated to give the crude product, which was used directly in next step without farther purification to afford 685-4 (2.90 g, 98.0% yield) as yellow oil.

Synthesis of 5-isobutyl-4-(naphthalen-2-yl)thiazol-2-amine (685-s)

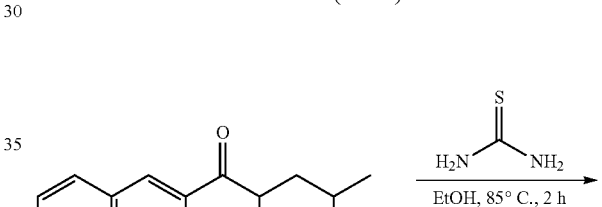

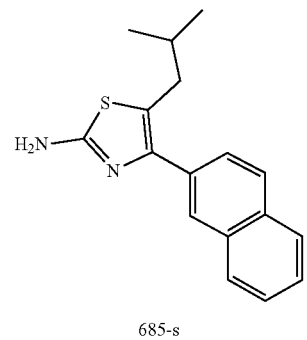

685-s

A mixture of 685-4 (2.90 g, 9.54 mmol) and thiourea (1.45 g, 19.1 mmol) in EtOH (50.0 mL) was stirred at 85° C. for 2 h. When the reaction was completed, it was concentrated and purified by silica gel column chromatography (petrol ether/ethyl acetate=3/1) to afford 685-s (1.0 g, 37.2% yield) as a yellow solid.

Synthesis of 1-(2,4-dichlorophenyl)-3-methylbutan-1-one (689-2)

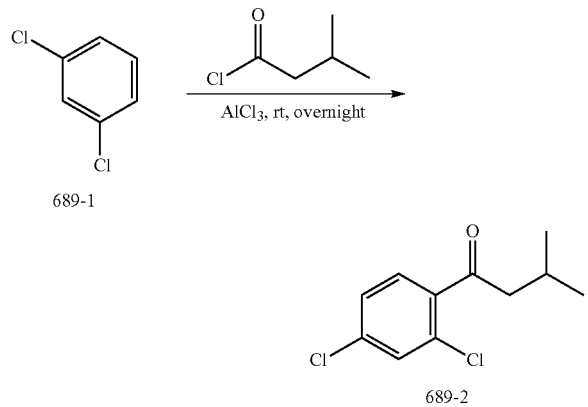

A mixture of 689-1 (10.0 mL), 3-methylbutanoyl chloride (2.0 g, 16.6 mmol) and AlCl$_3$ (2.65 g, 19.9 mmol) was stirred at room temperature overnight. When the reaction was completed, it was solved with EtOAc (200 mL). The organic phase was combined and washed with H$_2$O (80.0 mL) and brine (50.0 mL), then dried with anhydrous Na$_2$SO$_4$, concentrated and purified by silica gel column chromatography (petrol ether/ethyl acetate=20/1) to afford 689-2 (1.50 g, 39.3% yield) as yellow oil.

Synthesis of 2-bromo-1-(2,4-dichlorophenyl)-3-methylbutan-1-one (689-3)

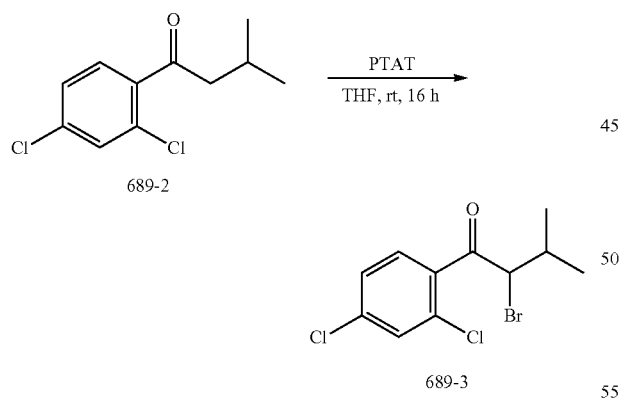

A mixture of 689-2 (1.50 g, 6.52 mmol) and PTAT (3.67 g, 9.78 mmol) in THF (80.0 mL) was stirred at room temperature for 16 h. When the reaction was completed, it was concentrated, and the residual was dissolved in H$_2$O (50.0 mL), and then extracted with EtOAc (80.0 mL×2). The organic layer was combined, and washed with H$_2$O (30.0 mL×2) and Brine (50.0 mL), then dried by anhydrous Na$_2$SO$_4$. The solution was concentrated to give the crude product, which was used directly in next step without farther purification to afford 689-3 (2.0 g, 100% yield) as yellow oil.

Synthesis of 1-(2,4-dichlorophenyl)-3-methyl-2-thiocyanatobutan-1-one (689-4)

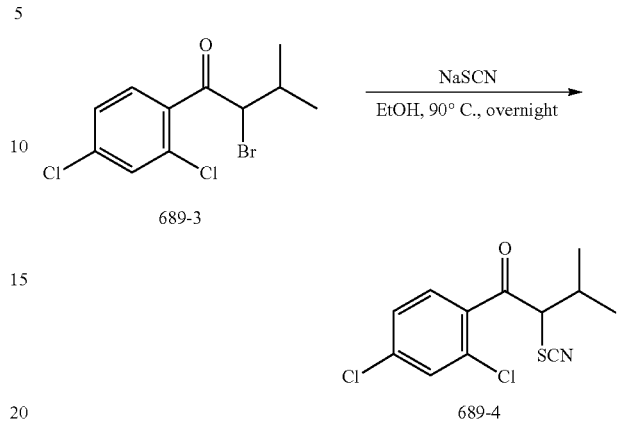

A mixture of 689-3 (2.0 g, 6.49 mmol) and NaSCN (1.05 g, 13.0 mmol) in EtOH (50.0 mL) was stirred at 90° C. overnight. When the reaction was completed, it was concentrated and purified by silica gel column chromatography (petrol ether/ethyl acetate=3/1) to afford 689-4 (1.40 g, 75.1% yield) as a yellow solid.

Synthesis of 2-bromo-4-(2,4-dichlorophenyl)-5-isopropylthiazole (689-s)

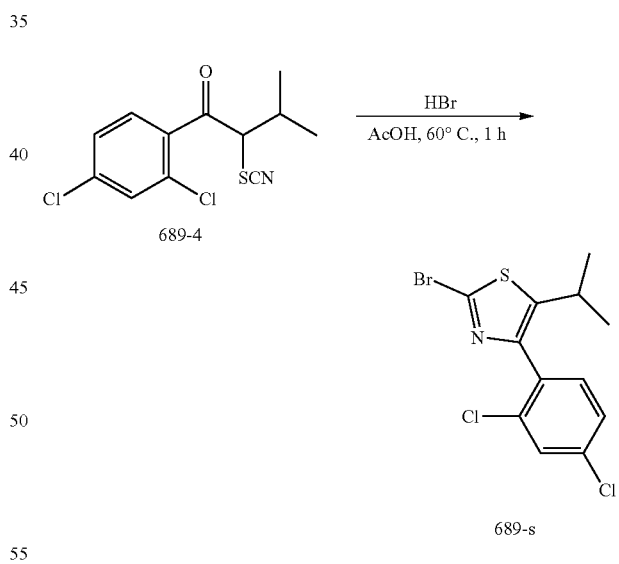

A mixture of 689-4 (1.40 g, 4.88 mmol) and HBr (2.0 M in AcOH, 5.0 mL) in AcOH (10.0 mL) was stirred at 60° C. for 1 h. When the reaction was completed, it was poured into H$_2$O (100 mL) and extracted with EtOAc (100 mL×3). The organic phase was combined, and washed with H$_2$O (80.0 mL) and brine (80.0 mL), then dried with anhydrous Na$_2$SO$_4$, concentrated and purified by silica gel column chromatography (petrol ether/ethyl acetate=10/1) to afford 689-s (1.20 g, 70.5% yield) as yellow oil.

Synthesis of 1-(3-chloro-4-methoxyphenyl)-3-methylbutan-1-ol (709-1)

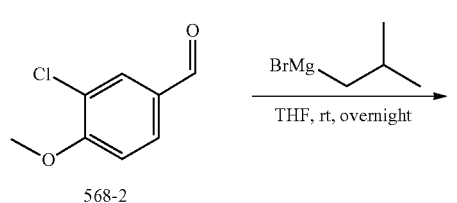

To a solution of 568-2 (4.40 g, 25.9 mmol) in THF (30.0 mL) was added isobutylmagnesium bromide (1.0 M in THF, 38.8 mL, 38.8 mmol). The reaction was stirred at room temperature overnight. When the reaction was completed, it was poured into aq.NH$_4$Cl (sat., 100 mL) and extracted with EtOAc (80.0 mL×3). The organic phase was combined, and washed with H$_2$O (50.0 mL) and brine (80.0 mL), then dried with anhydrous Na$_2$SO$_4$, concentrated to give the crude product, which was used directly in next step without farther purification to afford 709-1 (5.0 g, 84.7% yield) as yellow oil.

Synthesis of 1-(3-chloro-4-methoxyphenyl)-3-methylbutan-1-one (709-2)

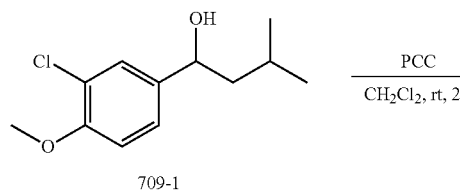

To a solution of 709-1 (5.0 g, 21.9 mmol) in CH$_2$Cl$_2$ (200 mL) was added PCC (9.45 g, 43.9 mmol). The reaction was stirred at room temperature for 2 h. When the reaction was completed, it was concentrated and purified by silica gel column chromatography (petrol ether/ethyl acetate=50/1) to afford 709-2 (4.20 g, 84.7% yield) as yellow oil.

Synthesis of 5-bromo-4-isopropylthiazol-2-amine (709-3)

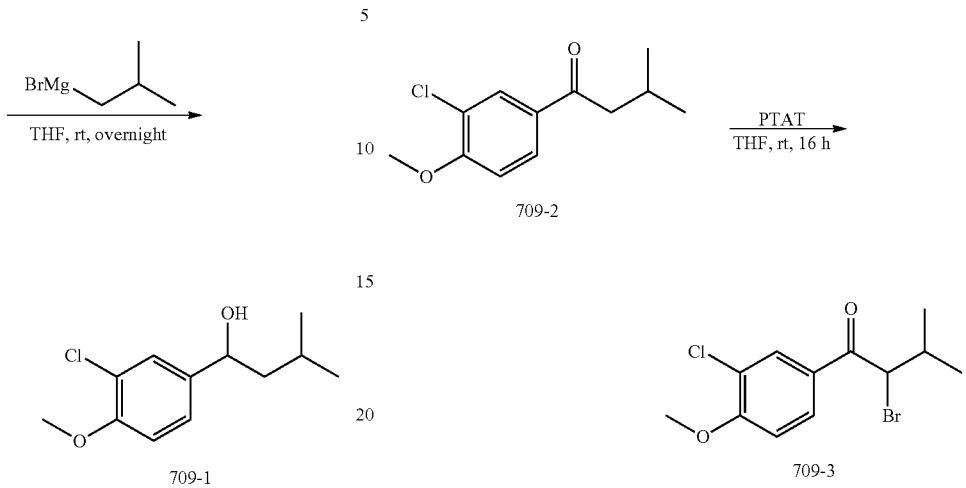

A mixture of 709-2 (4.20 g, 18.6 mmol) and PTAT (10.5 g, 27.9 mmol) in THF (100 mL) was stirred at room temperature for 16 h. When the reaction was completed, it was concentrated, and the residual was dissolved in H$_2$O (80.0 mL), and then extracted with EtOAc (80.0 mL×2). The organic layer was combined, and washed with H$_2$O (50.0 mL×2) and Brine (50.0 mL), then dried by anhydrous Na$_2$SO$_4$. The solution was concentrated and purified by silica gel column chromatography (petrol ether/ethyl acetate=50/1) to afford 709-3 (4.0 g, 70.8% yield) as yellow oil.

Synthesis of 1-(3-chloro-4-methoxyphenyl)-3-methyl-2-thiocyanatobutan-1-one (709-4)

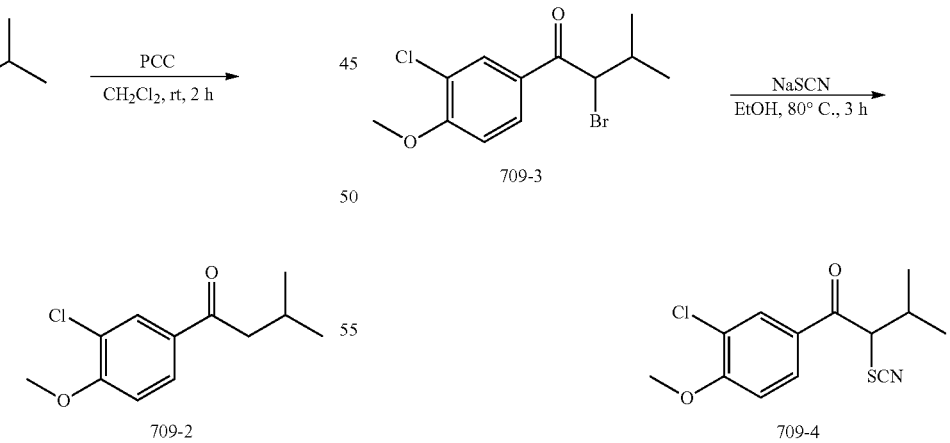

A mixture of 709-3 (4.0 g, 13.2 mmol) and NaSCN (2.13 g, 26.3 mmol) in EtOH (80.0 mL) was stirred at 80° C. for 3 h. When the reaction was completed, it was concentrated and purified by silica gel column chromatography (petrol ether/ethyl acetate=3/1) to afford 709-4 (3.0 g, 80.6% yield) as a yellow solid.

751

Synthesis of 2-bromo-4-(3-chloro-4-methoxyphenyl)-5-isopropylthiazole (709-s)

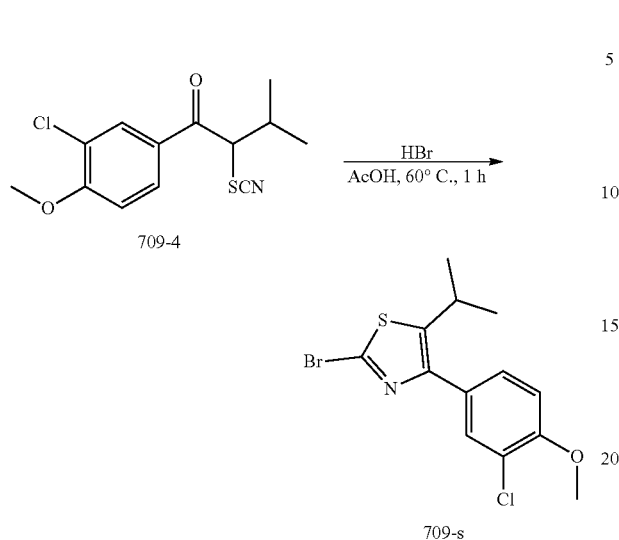

A mixture of 709-4 (1.50 g, 5.30 mmol) and HBr (2.0 M in AcOH, 5.0 mL) in AcOH (10.0 mL) was stirred at 60° C. for 1 h. When the reaction was completed, it was poured into H$_2$O (100 mL) and extracted with EtOAc (80.0 mL×3). The organic phase was combined, and washed with H$_2$O (50.0 mL) and brine (80.0 mL), then dried with anhydrous Na$_2$SO$_4$, concentrated and purified by silica gel column chromatography (petrol ether/ethyl acetate=10/1) to afford 709-s (600 mg, 32.8% yield) as yellow oil.

Synthesis of 4-(3-chloro-4-methoxyphenyl)-5-isobutylthiazol-2-amine (711-s)

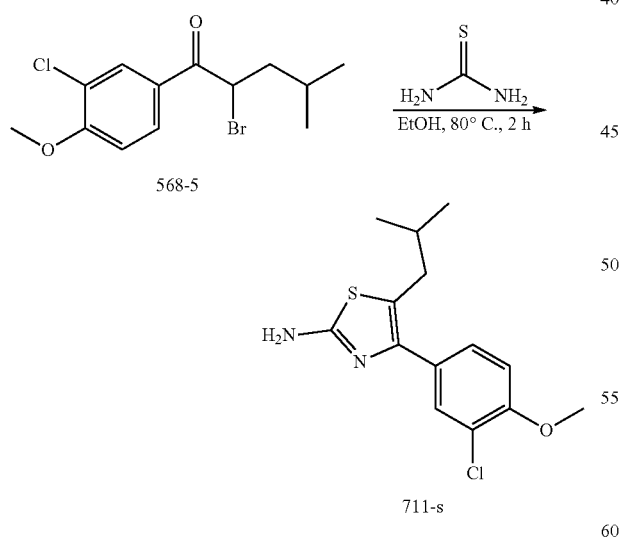

A mixture of 568-5 (1.0 g, 3.14 mmol) and thiourea (478 mg, 6.29 mmol) in EtOH (20.0 mL) was stirred at 80° C. for 2 h. When the reaction was completed, it was concentrated and purified by silica gel column chromatography (petrol ether/ethyl acetate=3/1) to afford 711-s (700 mg, 75.2% yield) as a yellow solid.

752

Synthesis of 2-bromo-4-(3-chloro-4-(2-methoxyethoxy)phenyl)-5-isobutylthiazole (714-s)

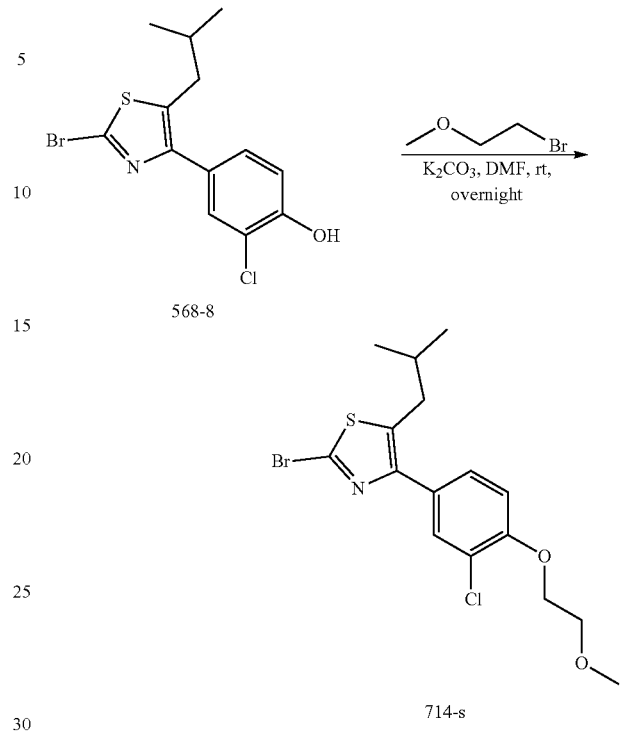

A mixture of 568-8 (250 mg, 0.725 mmol), 1-bromo-2-methoxyethane (201 mg, 1.45 mmol) and K$_2$CO$_3$ (138 mg, 1.45 mmol) in DMF (3.0 mL) was stirred at room temperature overnight. When the reaction was completed, it was poured into H$_2$O (50.0 mL) and extracted with EtOAc (80.0 mL×3). The organic phase was combined, and washed with H$_2$O (50.0 mL) and brine (50.0 mL), then dried with anhydrous Na$_2$SO$_4$, concentrated to give the crude product, which was used directly in next step without farther purification to afford 714-s (300 mg, 100% yield) as colorless oil.

Synthesis of 4-(2-bromo-5-isobutylthiazol-4-yl)phenol (720-2)

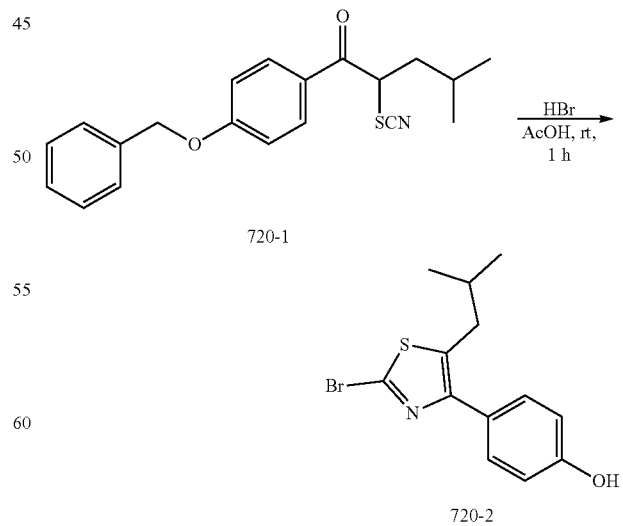

A mixture of 720-1 (350 mg, 1.03 mmol) and HBr (2.0 M in AcOH, 2.0 mL) in AcOH (3.0 mL) was stirred at room temperature for 1 h. When the reaction was completed, it was poured into H₂O (50.0 mL) and extracted with EtOAc (80.0 mL×3). The organic phase was combined, and washed with H₂O (50.0 mL) and brine (50.0 mL), then dried with anhydrous Na₂SO₄, concentrated and purified by silica gel column chromatography (petrol ether/ethyl acetate=1/1) to afford 720-2 (170 mg, 52.9% yield) as yellow oil.

Synthesis of 2-bromo-5-isobutyl-4-(4-methoxyphenyl)thiazole (720-s)

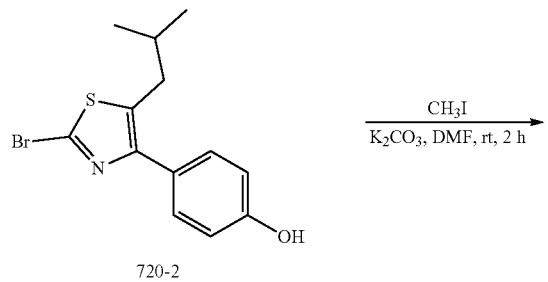

720-2

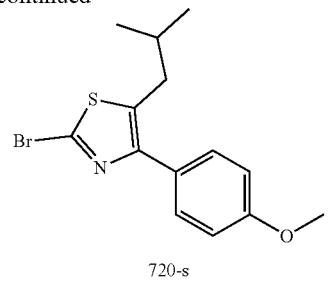

720-s

A mixture of 720-2 (170 mg, 0.547 mmol), CH₃I (116 mg, 0.820 mmol) and K₂CO₃ (151 mg, 1.09 mmol) in DMF (3.0 mL) was stirred at room temperature for 2 h. When the reaction was completed, it was poured into H₂O (50.0 mL) and extracted with EtOAc (80.0 mL×3). The organic phase was combined, and washed with H₂O (50.0 mL) and brine (80.0 mL), then dried with anhydrous Na₂SO₄, concentrated to give the crude product, which was used directly in next step without farther purification to afford 720-s (150 mg, 84.4% yield) as colorless oil.

TABLE 7-1

Characterization Data for Compounds

| # | Chemical Structure | LCMS |
|---|---|---|
| 685-s | 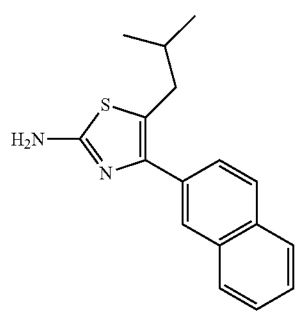 [SMILES: CC(C)Cc1sc(N)nc1-c1ccc2ccccc2c1] | Method A, Purity is 86.6%, Rt = 0.659 min; MS Calcd.: 282.1; MS Found: 283.1 [M + H]⁺. |
| 709-s | 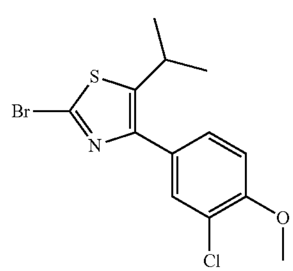 [SMILES: COc1ccc(-c2nc(Br)sc2C(C)C)cc1Cl] | Method B, Purity is 39.7%, Rt = 2.286 min; MS Calcd.: 345.0; MS Found: 345.9 [M + H]⁺. |
| 711-s | 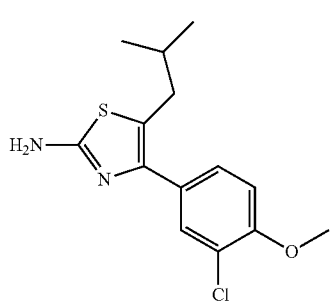 [SMILES: COc1ccc(-c2nc(N)sc2CC(C)C)cc1Cl] | Method A, Purity is 84.6%, Rt = 0.642 min; MS Calcd.: 296.1; MS Found: 297.0 [M + Na]⁺. |

TABLE 7-1-continued
Characterization Data for Compounds
| # | Chemical Structure | LCMS |
|---|---|---|
| 714-s | 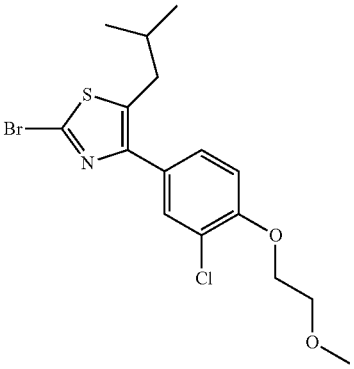 [SMILES: COCCOc1ccc(-c2nc(Br)sc2CC(C)C)cc1Cl] | Method A, Purity is 90.1%, Rt = 0.968 min; MS Calcd.: 403.0; MS Found: 403.8 [M + H]⁺. |
| 715-s | 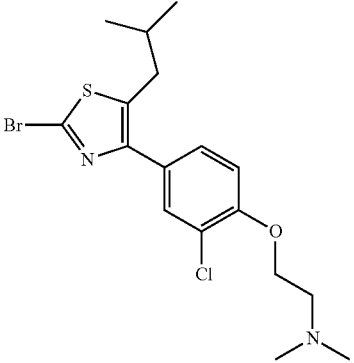 [SMILES: CC(C)Cc1sc(Br)nc1-c1ccc(OCCN(C)C)c(Cl)c1] | Method A, Purity is 86.8%, Rt = 0.703 min; MS Calcd.: 416.0; MS Found: 416.8 [M + H]⁺. |
| 716-s | 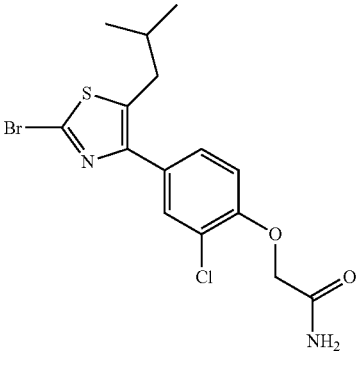 [SMILES: CC(C)Cc1sc(Br)nc1-c1ccc(OCC(N)=O)c(Cl)c1] | Method B, Purity is 92.0%, Rt = 2.046 min; MS Calcd.: 402.0; MS Found: 402.9 [M + H]⁺. |
| 718-s | 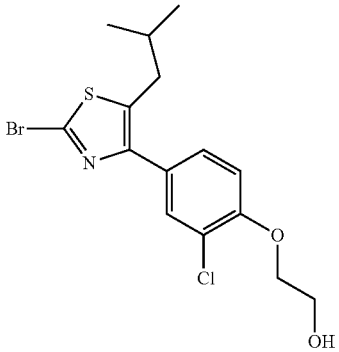 [SMILES: CC(C)Cc1sc(Br)nc1-c1ccc(OCCO)c(Cl)c1] | Method B, Purity is 100%, Rt = 2.135 min; MS Calcd.: 389.0; MS Found: 389.8 [M + H]⁺. |

TABLE 7-1-continued

Characterization Data for Compounds

| # | Chemical Structure | LCMS |
|---|---|---|
| 719-s | 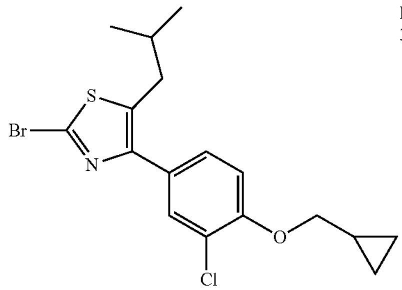 | Method A, Purity is 95.3%, Rt = 1.034 min; MS Calcd.: 399.0; MS Found: 400.0 [M + H]⁺. |
| 720-s | 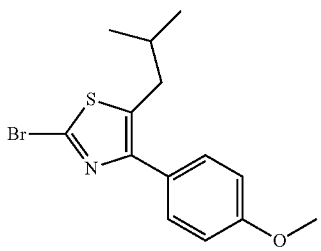 [SMILES: COc1ccc(-c2nc(Br)sc2CC(C)C)cc1] | Method A, Purity is 94.5%, Rt = 0.949 min; MS Calcd.: 325.0; MS Found: 326.0 [M + H]⁺. |

Synthesis of 2-(4-(benzo[d]thiazol-2-yl)-5-isopropylthiazol-2-ylamino)-5-(trifluoromethyl)nicotinic acid (I-320)

A mixture of 683-s (50.0 mg, 0.182 mmol), 2-chloro-5-(trifluoromethyl)nicotinic acid (49.2 mg, 0.218 mmol), Pd$_2$(dba)$_3$ (16.9 mg, 0.0182 mmol), X-phos (158 mg, 0.0273 mmol) and Cs$_2$CO$_3$ (88.9 mg, 0.273 mmol) in toluene (3.0 mL) was stirred under N$_2$ atmosphere at 110° C. for 3 h.

When the reaction was completed, it was concentrated and purified by prep-HPLC to afford I-320 (10.0 mg, 11.9% yield) as a yellow solid.

Synthesis of methyl 2-(4-(3,4-dichlorophenyl)-5-isobutylthiazol-2-ylamino)-5-(naphthalen-2-yl)nicotinate 686-1

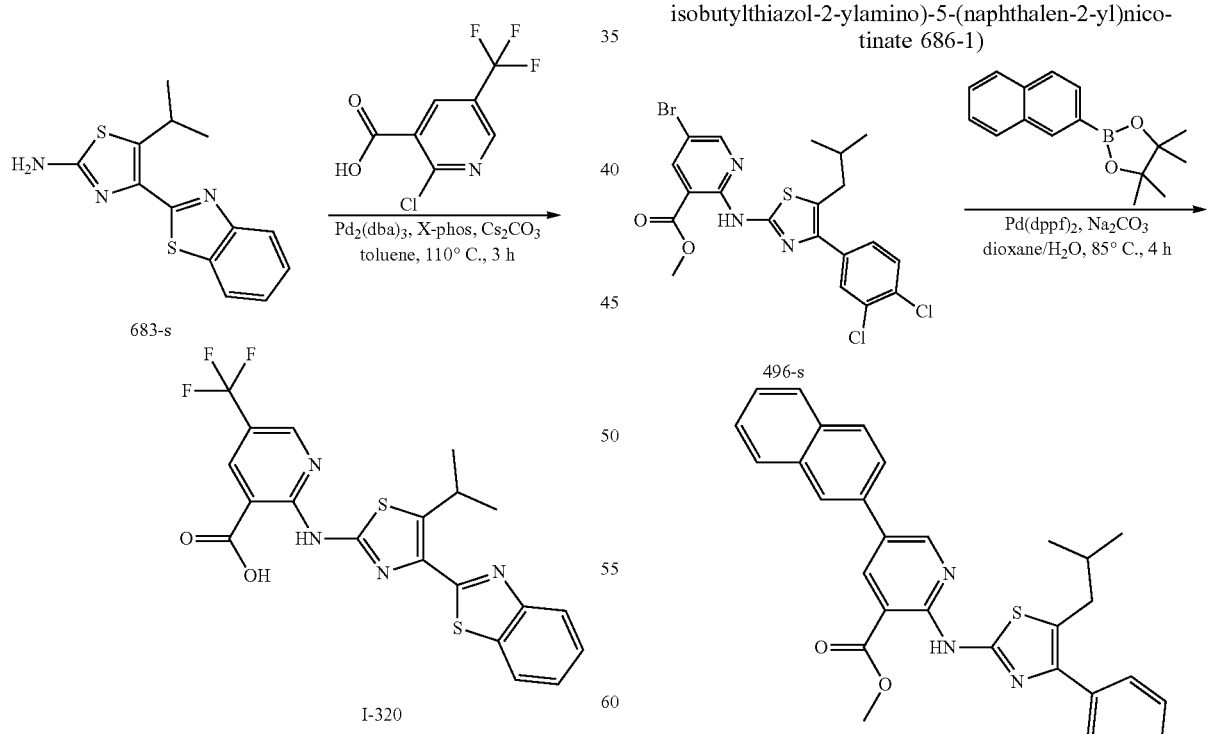

A mixture of 496-s (150 mg, 0.292 mmol), 4,4,5,5-tetramethyl-2-(naphthalen-2-yl)-1,3,2-dioxaborolane (111 mg, 0.439 mmol), Pd(dppf)Cl₂ (21.3 mg, 0.0292 mmol) and Na₂CO₃ (61.9 mg, 0.584 mmol) in dioxane/H₂O (v/v=5/1, 5.0 mL) was stirred under N₂ atmosphere at 85° C. for 4 h. When the reaction was completed, it was concentrated and purified by silica gel column chromatography (petrol ether/ethyl acetate=8/1) to afford 686-1 (80.0 mg, 48.9% yield) as a yellow solid.

Synthesis of 2-(4-(3,4-dichlorophenyl)-5-isobutylthiazol-2-ylamino)-5-(naphthalen-2-yl)nicotinic acid (I-322)

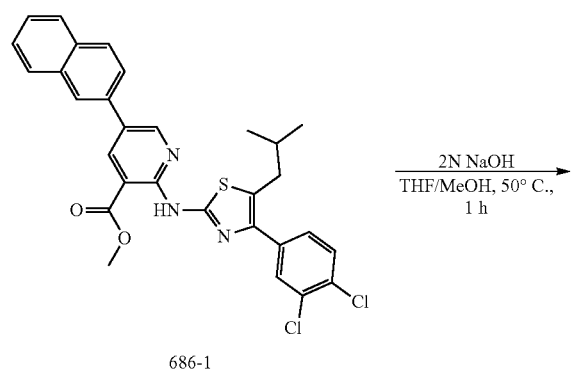

686-1

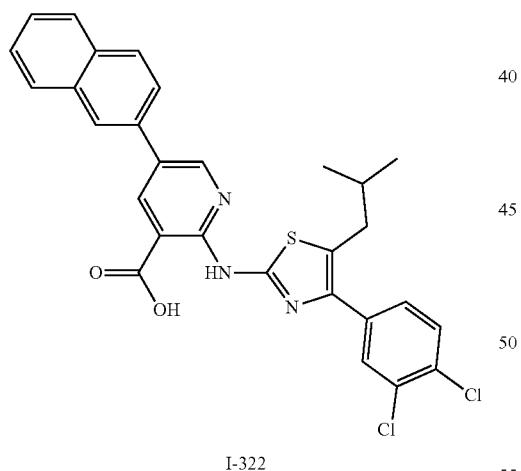

I-322

To a solution of 686-1 (80.0 mg, 0.142 mmol) in THF/MeOH (v/v=4/1, 5.0 mL) was added NaOH (2.0 M in H₂O, 1.0 mL). The reaction was stirred at 50° C. for 1 h. When the reaction was completed, the resulting reaction was concentrated, then it was diluted with H₂O (15.0 mL) and adjusted pH to 4-5 with HCl (1.0 M). The mixture was extracted with EtOAc (10.0 mL×2), and the combined organic phase washed with brine (10.0 mL), dried by anhydrous Na₂SO₄, and concentrated, the residue was purified by prep-HPLC to afford I-322 (30.0 mg, 38.5% yield) as a yellow solid.

Synthesis of methyl 2-(4-(2,4-dichlorophenyl)-5-isopropylthiazol-2-ylamino)-5-(trifluoromethyl)nicotinate (689-5)

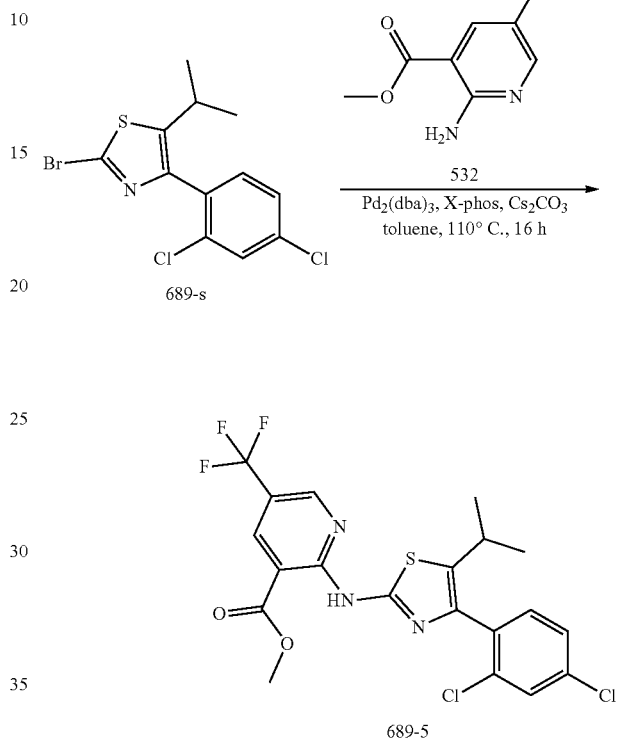

A mixture of 689-s (200 mg, 0.573 mmol), 532 (151 mg, 0.688 mmol), Pd₂(dba)₃ (53.3 mg, 0.0573 mmol), X-phos (49.7 mg, 0.0860 mmol) and Cs₂CO₃ (280 mg, 0.860 mmol) in toluene (5.0 mL) was stirred under N₂ atmosphere at 110° C. for 16 h. When the reaction was completed, it was concentrated and purified by silica gel column chromatography (petrol ether/ethyl acetate=8/1) to afford 689-5 (120 mg, 42.8% yield) as a yellow solid.

Synthesis of 2-(4-(2,4-dichlorophenyl)-5-isopropylthiazol-2-ylamino)-5-(trifluoromethyl)nicotinic acid (I-323)

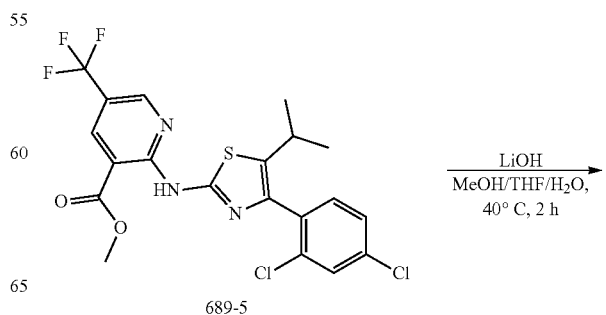

689-5

-continued

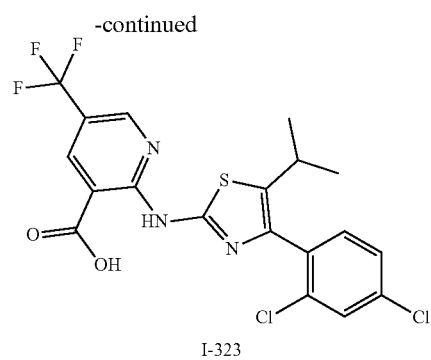

I-323

To a solution of 689-5 (120 mg, 0.245 mmol) in THF/MeOH/H$_2$O (v/v/v=4/1/1, 5.0 mL) was added LiOH (2.0 M in H$_2$O, 2.0 mL). The reaction was stirred at 40° C. for 2 h. When the reaction was completed, the resulting reaction was concentrated, then it was diluted with H$_2$O (15.0 mL) and adjusted pH to 4-5 with HCl (1.0 M). The mixture was extracted with EtOAc (10.0 mL×2), and the combined organic phase washed with brine (10.0 mL), dried by anhydrous Na$_2$SO$_4$, and concentrated, the residue was purified by prep-HPLC to afford I-323 (30.0 mg, 25.7% yield) as a yellow solid.

Synthesis of 2-amino-5-(thiophen-2-yl)nicotinic acid (716-2)

To a solution of 716-1 (200 mg, 0.854 mmol) in EtOH (5.0 mL) was added NaOH (2.0 M in H$_2$O, 1.0 mL). The reaction was stirred at room temperature for 2 h. When the reaction was completed, the resulting reaction was concentrated and purified by prep-HPLC to afford 716-2 (160 mg, 85.1% yield) as a yellow solid.

Synthesis of 2-(4-(4-(2-amino-2-oxoethoxy)-3-chlorophenyl)-5-isobutylthiazol-2-ylamino)-5-(thiophen-2-yl)nicotinic acid (I-329)

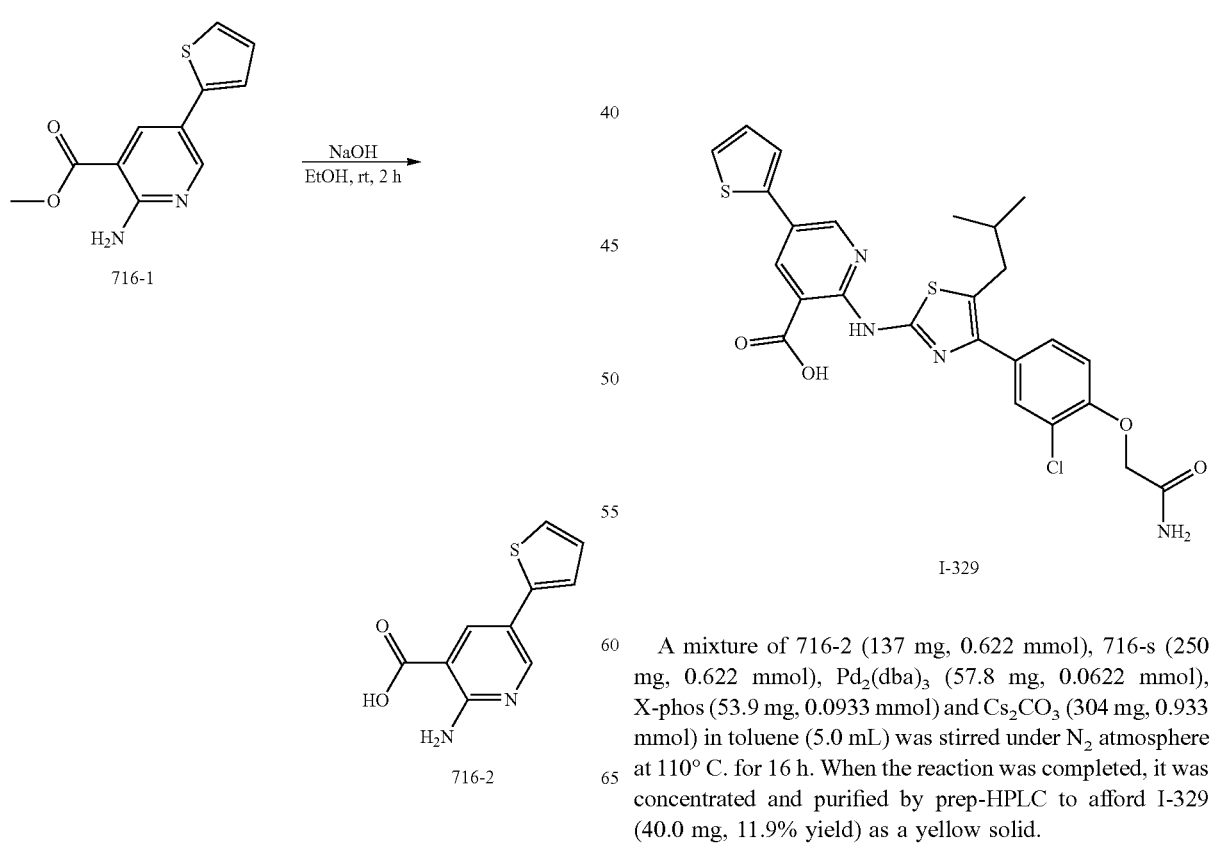

A mixture of 716-2 (137 mg, 0.622 mmol), 716-s (250 mg, 0.622 mmol), Pd$_2$(dba)$_3$ (57.8 mg, 0.0622 mmol), X-phos (53.9 mg, 0.0933 mmol) and Cs$_2$CO$_3$ (304 mg, 0.933 mmol) in toluene (5.0 mL) was stirred under N$_2$ atmosphere at 110° C. for 16 h. When the reaction was completed, it was concentrated and purified by prep-HPLC to afford I-329 (40.0 mg, 11.9% yield) as a yellow solid.

Characterization Data for Additional Exemplary Compounds

| I# | Chemical Structure | LCMS | ¹H NMR (400 MHz, d₆-DMSO) |
|---|---|---|---|
| 320 | 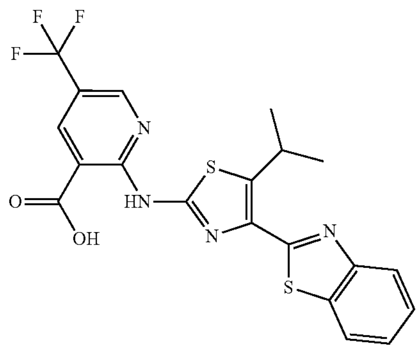 [SMILES: CC(C)c1sc(Nc2ncc(C(F)(F)F)cc2C(=O)O)nc1-c1nc2ccccc2s1] | Method C, Purity is 88.0%, Rt = 2.144 min; MS Calcd.: 464.1; MS Found: 464.9 [M + H]⁺. | δ: 1.40 (6H, d, J = 6.8 Hz), 4.55 (1H, t, J = 6.8 Hz), 5.16-5.28 (4H, m), 7.41-7.46 (1H, m), 7.50-7.54 (1H, m), 8.20 (1H, d, J = 8.0 Hz), 8.12 (1H, d, J = 8.0 Hz), 8.39 (1H, d, J = 2.4 Hz), 8.67-8.68 (1H, m), 15.38 (1H, brs). |
| 321 | 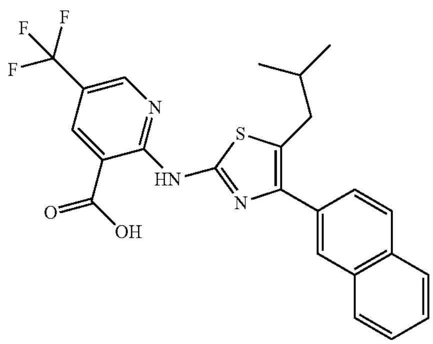 [SMILES: CC(C)Cc1sc(Nc2ncc(C(F)(F)F)cc2C(=O)O)nc1-c1ccc2ccccc2c1] | Method C, Purity is 95.2%, Rt = 2.169 min; MS Calcd.: 471.1; MS Found: 471.9 [M + H]⁺. | δ: 0.98 (3H, s), 0.99 (3H, s), 1.92-2.04 (1H, m), 2.94 (2H, d, J = 7.2 Hz), 7.58-7.64 (2H, m), 7.84 (1H, dd, J = 8.8, 1.6 Hz), 7.99-8.11 (3H, m), 8.20 (1H, s), 8.58 (1H, d, J = 2.4 Hz), 9.04 (1H, d, J = 1.6 Hz), 11.93 (1H, brs). |
| 322 | 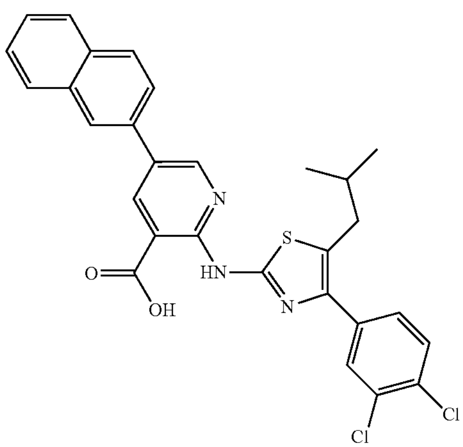 [SMILES: CC(C)Cc1sc(Nc2ncc(-c3ccc4ccccc4c3)cc2C(=O)O)nc1-c1ccc(Cl)c(Cl)c1] | Method C, Purity is 93.2%, Rt = 2.086 min; MS Calcd.: 547.1; MS Found: 548.3 [M + H]⁺. | δ: 0.94 (3H, s), 0.95 (3H, s), 1.87-1.94 (1H, m), 2.80 (2H, d, J = 7.2 Hz), 7.52-7.60 (2H, m), 7.63 (1H, dd, J = 8.4, 2.0 Hz), 7.72 (1H, d, J = 8.4 Hz), 7.84 (1H, d, J = 2.0 Hz), 7.92-7.99 (2H, m), 8.00-8.07 (2H, m), 8.35 (1H, s), 8.72 (1H, d, J = 2.4 Hz), 9.05 (1H, d, J = 2.0 Hz). |
| 323 | 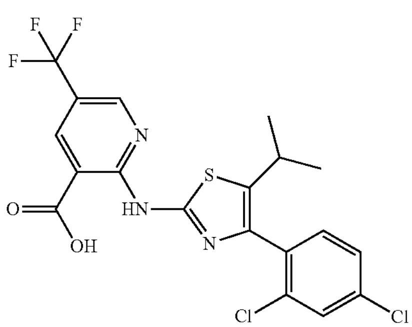 [SMILES: CC(C)c1sc(Nc2ncc(C(F)(F)F)cc2C(=O)O)nc1-c1ccc(Cl)cc1Cl] | Method C, Purity is 99.0%, Rt = 1.963 min; MS Calcd.: 475.0; MS Found: 475.9 [M + H]⁺. | δ: 1.22 (6H, d, J = 7.2 Hz), 2.85-2.89 (1H, m), 7.44-7.53 (2H, m), 7.76 (1H, d, J = 2.0 Hz), 8.45 (1H, d, J = 2.4 Hz), 8.81 (1H, s), 13.64 (1H, s). |

| I# | Chemical Structure | LCMS | ¹H NMR (400 MHz, d₆-DMSO) |
|---|---|---|---|
| 324 | 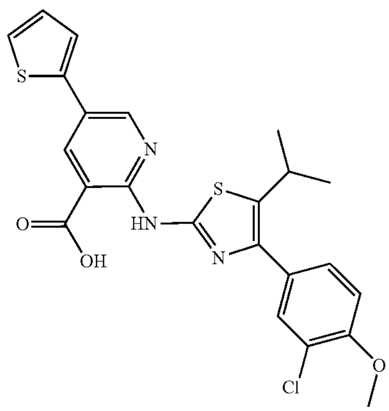 [SMILES: COc1ccc(-c2nc(Nc3ncc(-c4cccs4)cc3C(=O)O)sc2C(C)C)cc1Cl] | Method C, Purity is 100%, Rt = 1.920 min; MS Calcd.: 485.1; MS Found: 486.0 [M + H]⁺. | δ: 1.33 (6H, d, J = 6.4 Hz), 3.26-3.29 (1H, m), 3.91 (3H, s), 7.19-7.25 (2H, m), 7.50 (1H, d, J = 8.0 Hz), 7.60-7.65 (3H, m), 8.47 (1H, s), 8.97 (1H, s), 11.54 (1H, brs). |
| 325 | 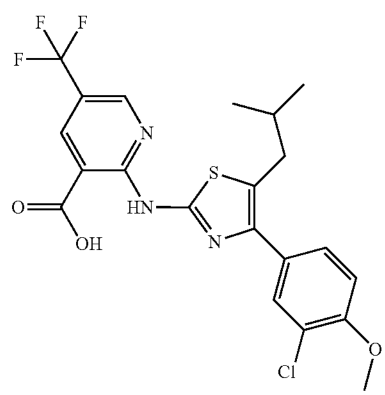 [SMILES: COc1ccc(-c2nc(Nc3ncc(C(F)(F)F)cc3C(=O)O)sc2CC(C)C)cc1Cl] | Method C, Purity is 97.4%, Rt = 2.117 min; MS Calcd.: 485.1; MS Found: 486.0 [M + H]⁺. | δ: 0.91 (3H, s), 0.93 (3H, s), 1.81-1.92 (1H, m), 2.75 (2H, d, J = 7.2 Hz), 3.91 (3H, s), 7.23 (1H, d, J = 8.8 Hz), 7.54 (1H, dd, J = 8.6, 2.0 Hz), 7.63 (1H, d, J = 2.0 Hz), 8.50 (1H, d, J = 2.4 Hz), 8.96 (1H, d, J = 1.6 Hz), 11.84 (1H, brs). |
| 326 | 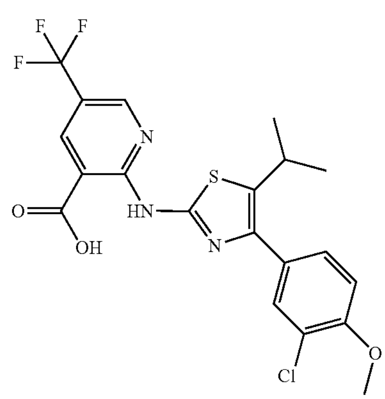 [SMILES: COc1ccc(-c2nc(Nc3ncc(C(F)(F)F)cc3C(=O)O)sc2C(C)C)cc1Cl] | Method C, Purity is 100%, Rt = 1.911 min; MS Calcd.: 471.1; MS Found: 472.0 [M + H]⁺. | δ: 1.32 (6H, d, J = 6.4 Hz), 3.36-3.39 (1H, m), 3.91 (3H, s), 7.23 (2H, d, J = 8.8 Hz), 7.51 (1H, d, J = 8.4 Hz), 7.59 (1H, s), 8.50 (1H, s), 8.98 (1H, s), 11.85 (1H, brs). |

Characterization Data for Additional Exemplary Compounds

| I# | Chemical Structure | LCMS | $^1$H NMR (400 MHz, d$_6$-DMSO) |
|---|---|---|---|
| 327 | 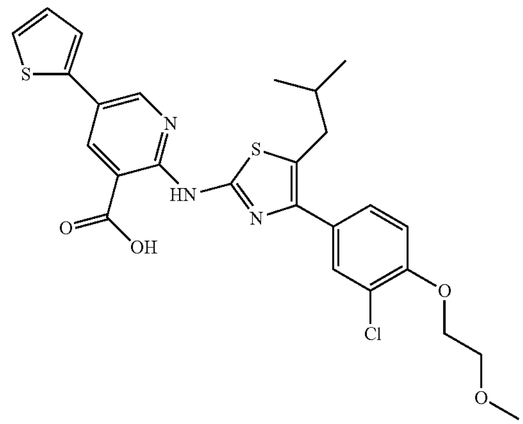 [SMILES: COCCOc1ccc(-c2nc(Nc3ncc(-c4cccs4)cc3C(=O)O)sc2CC(C)C)cc1Cl] | Method C, Purity is 96.9%, Rt = 1.963 min; MS Calcd.: 543.0; MS Found: 544.0 [M + H]$^+$. | δ: 0.93 (6H, d, J = 6.4 Hz), 1.86-1.89 (1H, m), 2.73 (2H, d, J = 7.2 Hz), 3.35 (3H, s), 3.72 (2H, t, J = 4.4 Hz), 4.23 (2H, t, J = 4.4 Hz), 7.17-7.24 (2H, m), 7.49-7.52 (1H, m), 7.60-7.63 (3H, m), 8.45 (1H, d, J = 2.4 Hz), 8.92 (1H, d, J = 2.4 Hz), 11.53 (1H, s), 14.29 (1H, s). |
| 328 | 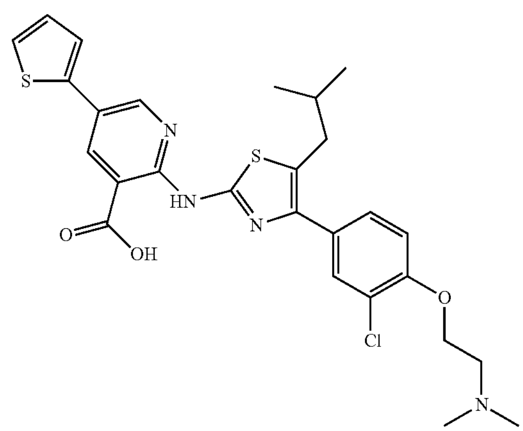 [SMILES: CC(C)Cc1sc(Nc2ncc(-c3cccs3)cc2C(=O)O)nc1-c1ccc(OCCN(C)C)c(Cl)c1] | Method C, Purity is 97.6%, Rt = 1.918 min; MS Calcd.: 556.1; MS Found: 557.0 [M + H]$^+$. | δ: 0.91 (6H, d, J = 6.4 Hz), 1.85-1.88 (1H, m), 2.71 (2H, d, J = 6.8 Hz), 2.92 (6H, s), 3.58 (2H, d, J = 4.0 Hz), 4.49 (2H, t, J =4.0 Hz), 7.16 (1H, t, J = 4.4 Hz), 7.28 (1H, t, J = 8.8 Hz), 7.53-7.57 (3H, m), 7.65 (1H, d, J = 2.0 Hz), 8.43 (1H, d, J = 2.4 Hz), 8.75 (1H, d, J = 2.4 Hz), 13.36 (1H, brs). |
| 329 | 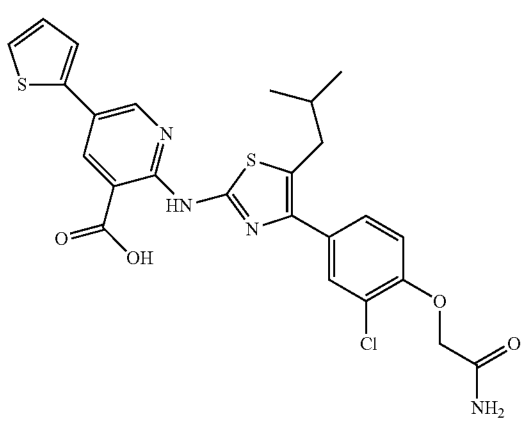 [SMILES: CC(C)Cc1sc(Nc2ncc(-c3cccs3)cc2C(=O)O)nc1-c1ccc(OCC(N)=O)c(Cl)c1] | Method C, Purity is 91.5%, Rt = 1.790 min; MS Calcd.: 542.1; MS Found: 542.9 [M + H]$^+$. | δ: 0.93 (6H, d, J = 6.4 Hz), 1.87-1.90 (1H, m), 2.72 (2H, d, J = 6.8 Hz), 4.61 (2H, s), 7.07-7.16 (2H, m), 7.41 (1H, d, J = 11.2 Hz), 7.50-7.54 (4H, m), 7.65 (1H, d, J = 2.0 Hz), 8.63 (1H, d, J = 2.8 Hz), 14.68 (1H, brs). |

| I# | Chemical Structure | LCMS | $^1$H NMR (400 MHz, d$_6$-DMSO) |
|---|---|---|---|
| 330 | 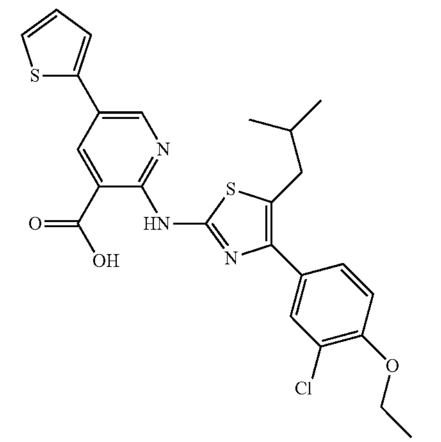 [SMILES: CCOc1ccc(-c2nc(Nc3ncc(-c4cccs4)cc3C(=O)O)sc2CC(C)C)cc1Cl] | Method C, Purity is 96.1%, Rt = 2.190 min; MS Calcd.: 513.0; MS Found: 513.8 [M + H]$^+$. | δ: 0.93 (6H, d, J = 6.8 Hz), 1.39 (3H, t, J = 6.8 Hz), 1.86-1.91 (1H, m), 2.73 (2H, d, J = 6.8 Hz), 4.16 (2H, q, J = 6.8 Hz), 7.17-7.22 (2H, m), 7.51 (1H, dq, J = 8.4, 2.0 Hz), 7.60-7.64 (3H, m), 8.45 (1H, d, J = 2.4 Hz), 8.92 (1H, d, J = 2.4 Hz), 11.65 (1H, brs), 14.35 (1H, brs). |
| 331 | 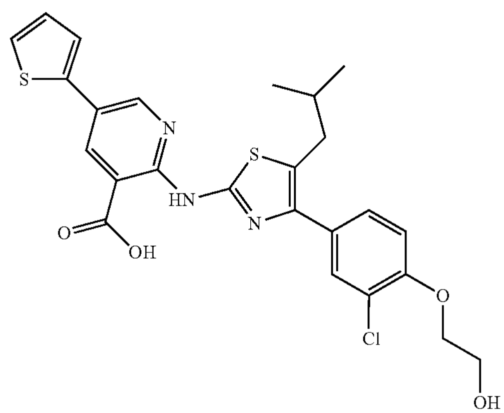 [SMILES: CC(C)Cc1sc(Nc2ncc(-c3cccs3)cc2C(=O)O)nc1-c1ccc(OCCO)c(Cl)c1] | Method C, Purity is 90.6%, Rt = 1.997 min; MS Calcd.: 529.0; MS Found: 529.8 [M + H]$^+$. | δ: 0.93 (6H, d, J = 6.8 Hz), 1.92-1.95 (1H, m), 2.74 (2H, d, J = 6.8 Hz), 3.77 (2H, t, J = 4.8 Hz), 4.13 (2H, t, J = 4.8 Hz), 7.17-7.25 (2H, m), 7.51 (1H, dq, J = 8.6, 2.0 Hz), 7.60-7.65 (3H, m), 8.46 (1H, d, J = 2.4 Hz), 8.93 (1H, d, J = 2.0 Hz), 11.56 (1H, brs), 14.33 (1H, brs). |
| 332 | 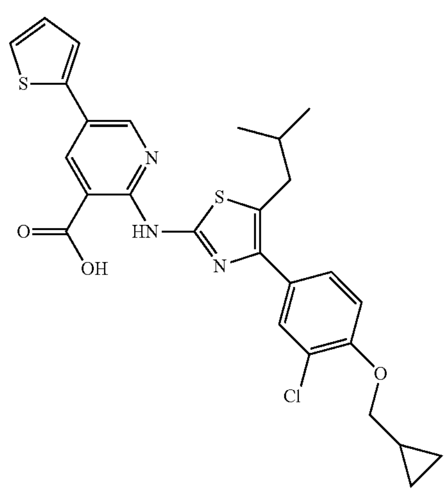 [SMILES: CC(C)Cc1sc(Nc2ncc(-c3cccs3)cc2C(=O)O)nc1-c1ccc(OCC2CC2)c(Cl)c1] | Method C, Purity is 100%, Rt = 2.237 min; MS Calcd.: 539.1; MS Found: 539.8 [M + H]$^+$. | δ: 0.36-0.40 (2H, m), 0.58-0.63 (2H, m), 0.93 (6H, d, J = 6.4 Hz), 1.26-1.30 (1H, m), 1.84-1.91 (1H, m), 2.72 (2H, d, J = 6.8 Hz), 3.96 (2H, d, J = 7.2 Hz), 7.13-7.19 (2H, m), 7.49-7.53 (3H, m), 7.62 (1H, d, J = 2.0 Hz), 8.39 (1H, d, J = 2.4 Hz), 8.62 (1H, d, J = 2.4 Hz), 14.64 (1H, s). |

Characterization Data for Additional Exemplary Compounds

| I# | Chemical Structure | LCMS | ¹H NMR (400 MHz, $d_6$-DMSO) |
|---|---|---|---|
| 333 | 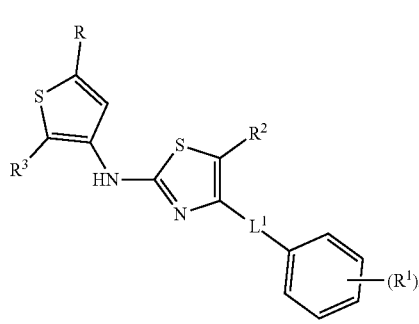 | Method C, Purity is 100%, Rt = 1.915 min; MS Calcd.: 465.1; MS Found: 466.0 $[M + H]^+$. | δ: 0.92 (6H, d, J = 6.8 Hz), 1.84-1.90 (1H, m), 2.73 (2H, d, J = 6.8 Hz), 3.80 (3H, s), 7.01 (2H, d, J = 8.8 Hz), 7.17 (1H, dd, J = 4.8, 4.0 Hz), 7.53 (2H, d, J = 8.8 Hz), 7.57-7.60 (2H, m), 8.44 (1H, d, J = 2.4 Hz), 8.83 (1H, brs). |

While a number of embodiments of this invention are described, it is apparent that the basic examples may be altered to provide other embodiments that utilize the compounds and methods of this invention. Therefore, it will be appreciated that the scope of this invention is to be defined by the specification and appended claims rather than by the specific embodiments that have been represented by way of example.

The invention claimed is:
1. A compound of formula V:

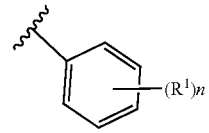

(V)

or a pharmacutically salt thereof, wherein:
each $R$ is independently halogen, R, -N(R)$_2$, -OR, -SR, -C(O)OR, or -S(O)$_2$R;
n is 0, 1, 2, 3, 4, or 5;
$L^1$ is a bond, or an optionally substituted $C_{1-8}$ bivalent straight or branched hydrocarbon chain, wherein 1, 2, 3, or 4 methylene units of the hydrocarbon chain are optionally and independently replaced with —O-, -S-, —N(R)-, or -S(O)$_2$-;
$R^2$ is halogen, R, -OR, -SR, -C(O)R, -C(O)OR, -C(O)N(R)$_2$, -S(O)$_2$R, -S(O)$_2$OR, or -S(O)$_2$N(R)$_2$;
$R^3$ is —CN, -C(O)R, -C(O)OR, -C(O)N(R)$_2$, -N(R)-C(O)-R, -N(R)-C(O)-OR, -S(O)$_2$-N(R)$_2$, -S(O)$_2$-N(R)-C(O)R, -C(O)-N(R)-S(O)$_2$R, -C(=NR)-N(R)$_2$, -N(R)-C(=NR)-N(R)$_2$, or a 5-6 membered monocyclic heteroaromatic ring having 1-4 heteroatoms independently selected from nitrogen, oxygen, and sulfur; and R is hydrogen, optionally substituted —$C_{1-6}$ aliphatic, or an optionally substituted ring selected from phenyl, a 5-6 membered monocyclic heteroaromatic ring having 1-4 heteroatoms independently selected from nitrogen, oxygen, and sulfur, a 3-6 membered monocyclic, saturated or partially unsaturated, carbocyclic ring, or a 3-6 membered monocyclic, saturated or partially unsaturated, heterocyclic ring having 1-4 heteroatoms independently selected from nitrogen, oxygen, and sulfur.

2. The compound of claim 1, wherein

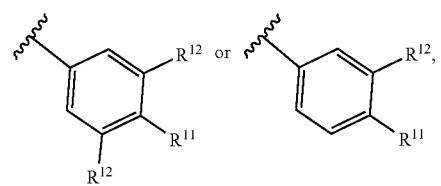

wherein each of $R^{11}$ and $R^{12}$ is independently halogen, R, —N(R)$_2$, —OR, —SR, —C(O)OR, or —S(O)$_2$R.

3. The compound of claim 2, wherein at least one of $R^{12}$ is not hydrogen.

4. The compound of claim 1, wherein $L^1$ is a bond.

5. The compound of claim 1, wherein $R^2$ is not hydrogen.

6. The compound of claim 5, wherein $R^2$ is optionally substituted —$C_{1-6}$ aliphatic.

7. The compound of claim 1, wherein $R^2$ is H,

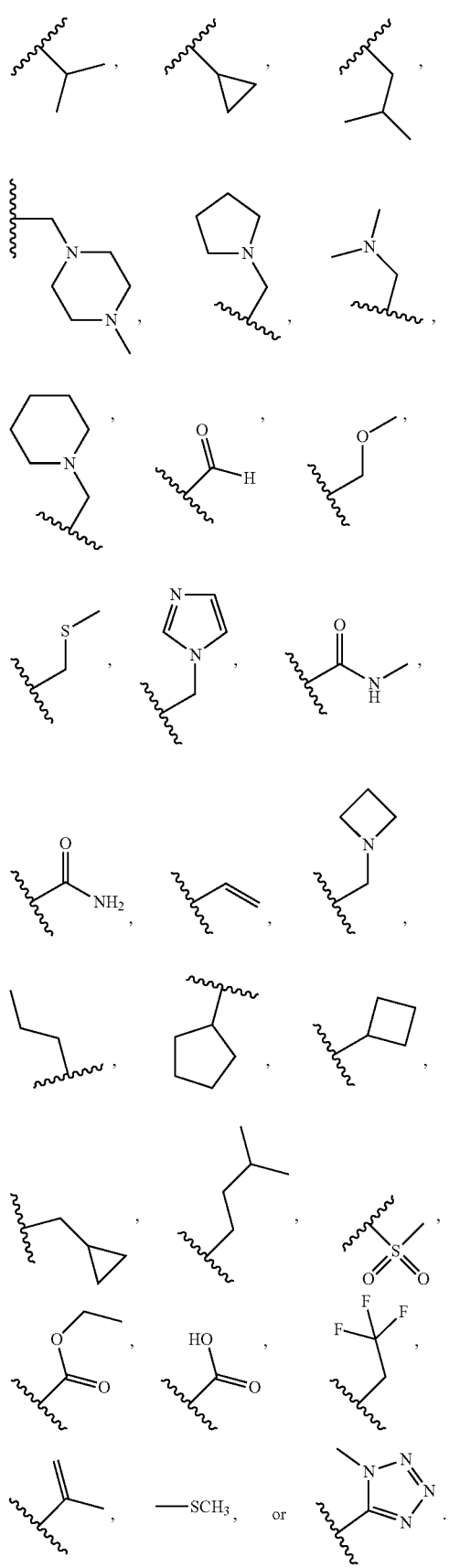
8. The compound of claim 1, wherein R³ is —COOH, —CN,
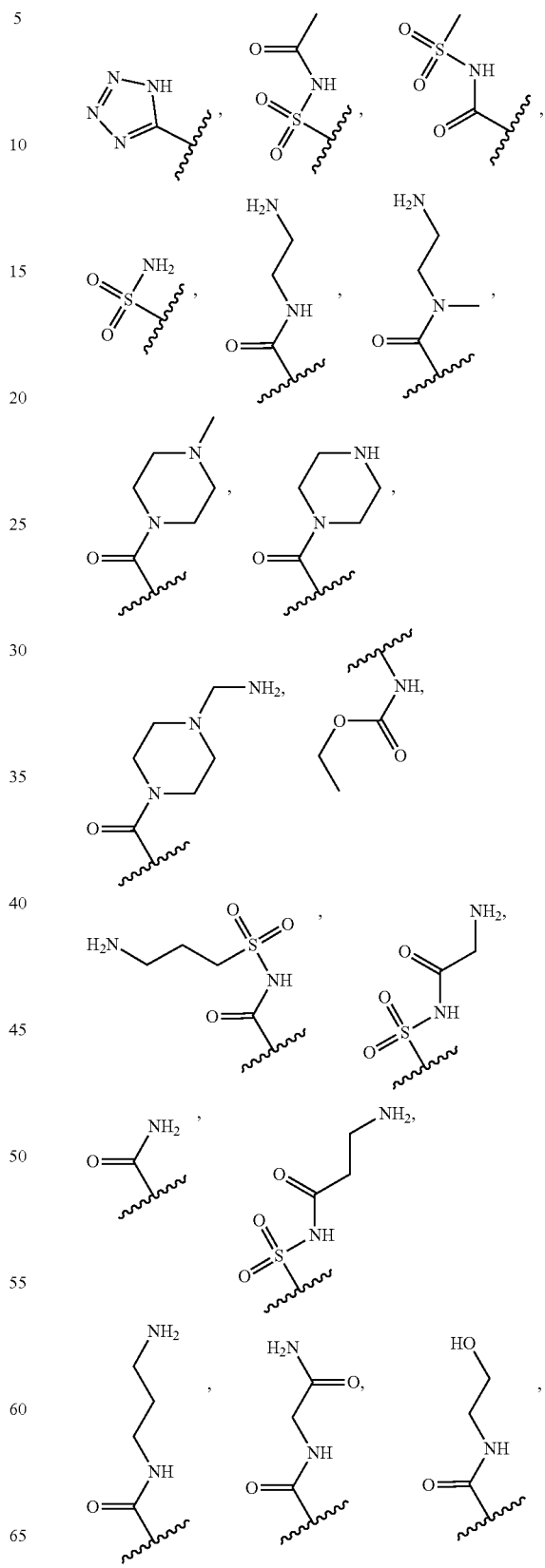

-continued

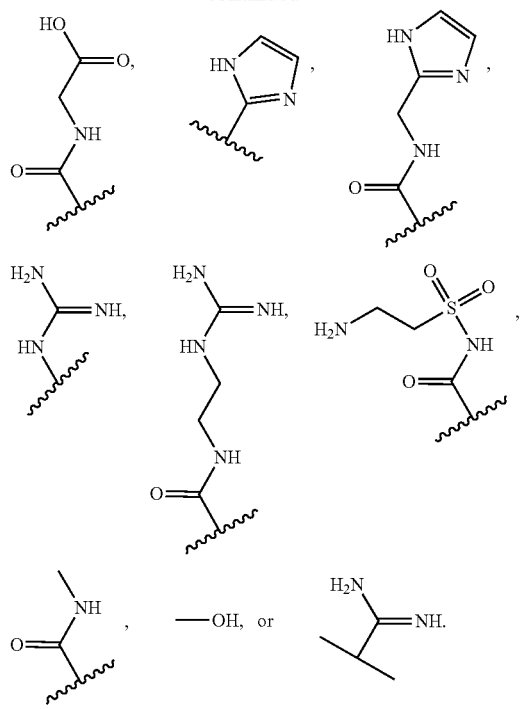

9. The compound of claim 1, wherein $L^1$ is a bond, or an optionally substituted $C_{1-8}$ bivalent straight or branched hydrocarbon chain, wherein 1, 2, 3, or 4 methylene units of the hydrocarbon chain are optionally and independently replaced with —O—, —S—, —N(R)—, or —S(O)$_2$—, wherein R is hydrogen or optionally substituted —$C_{1-6}$ aliphatic.

10. The compound of claim 1, wherein the compound is of Formulae V-a to V-d:

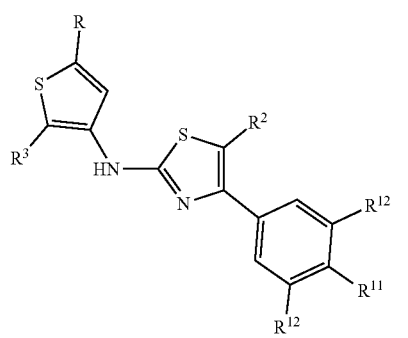

(V-a)

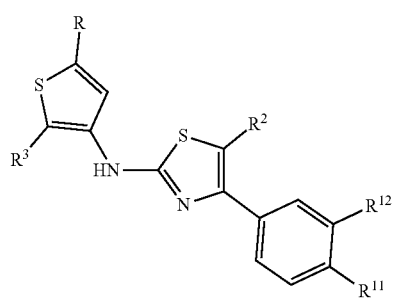

(V-b)

-continued

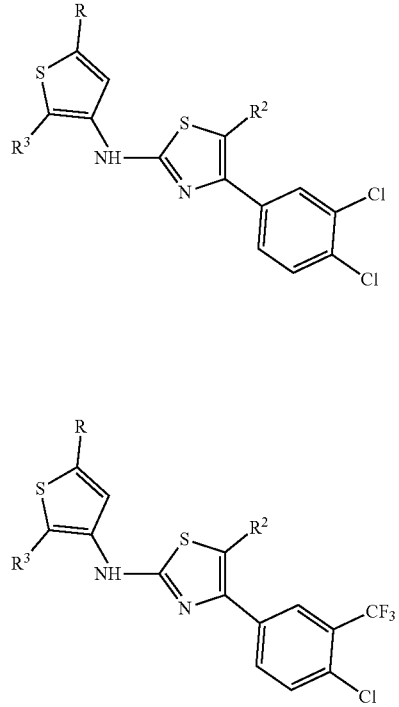

(V-c)

(V-d)

or a pharmaceutically acceptable salt thereof, wherein each of $R^{11}$ and $R^{12}$ is independently halogen, R, —N(R)$_2$, —OR, —SR, —C(O)OR, or —S(O)$_2$R.

11. The compound of claim 1, or a pharmaceutically acceptable salt thereof, selected from:

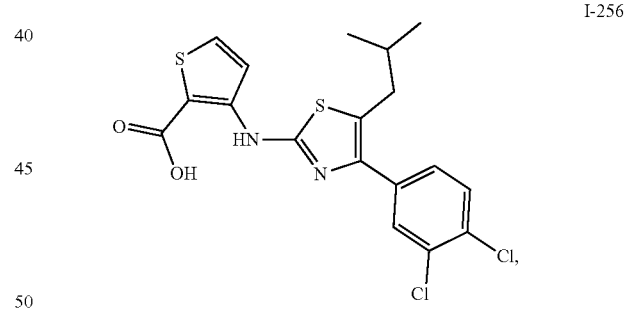

I-256

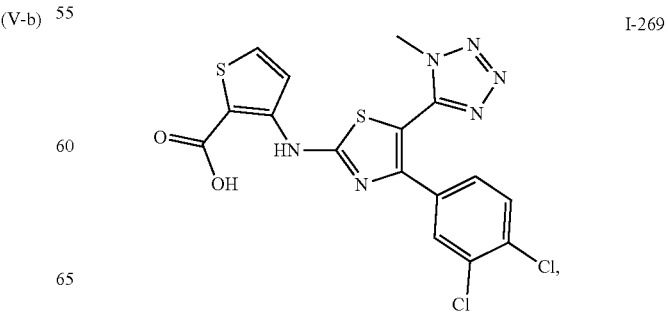

I-269

I-270
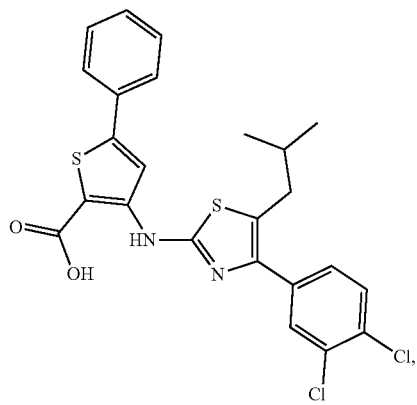
I-274
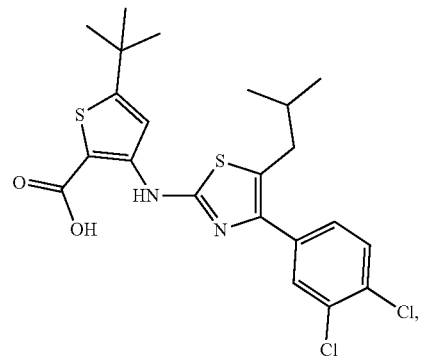
I-271
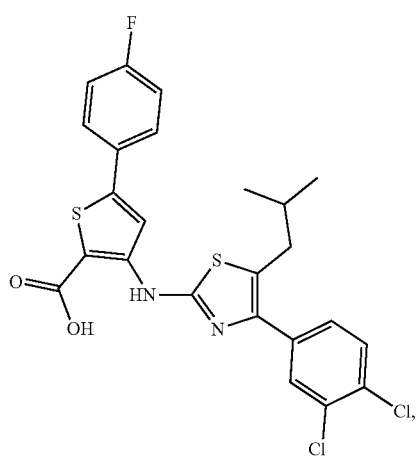
I-276
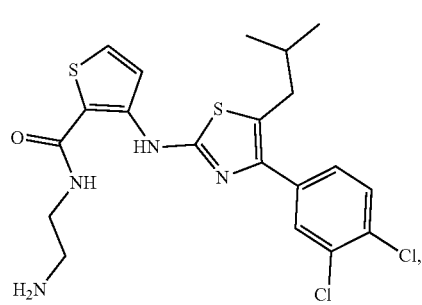
I-272
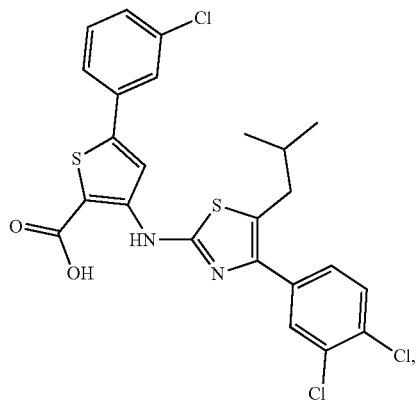
I-277
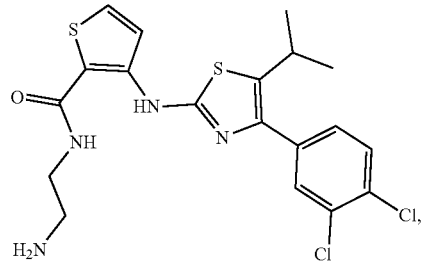
I-273
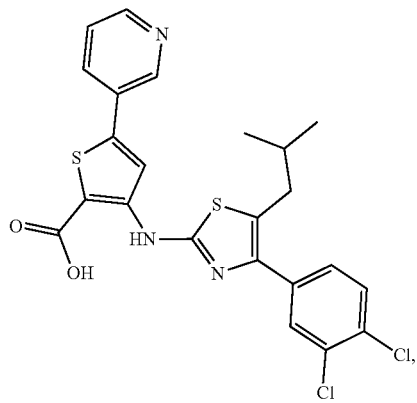
I-278
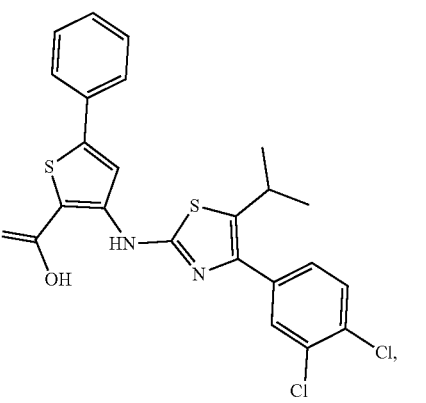
and -continued

I-279

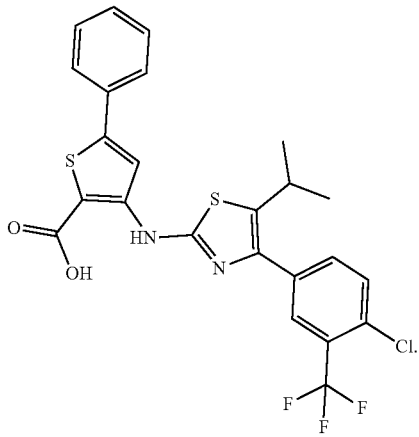

12. A pharmaceutical composition comprising the compound of claim 1, or a pharmaceutically acceptable salt thereof, and a pharmaceutically acceptable carrier, adjuvant, or vehicle.

13. The compound of claim 1, wherein $R^1$ is optionally substituted —$C_{1-6}$ alkyl.

14. The compound of claim 1, wherein

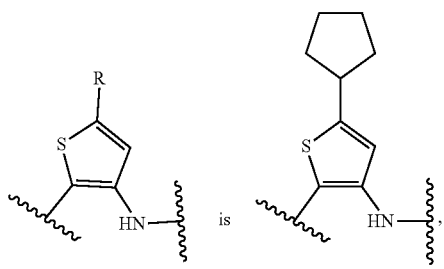 is

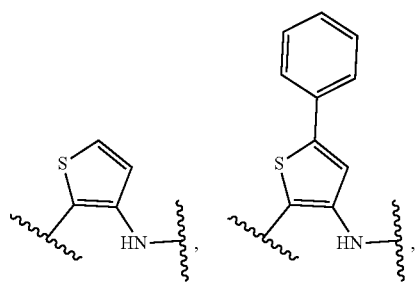

-continued

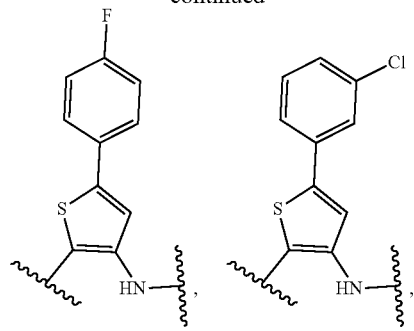

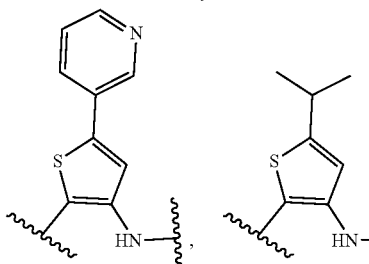

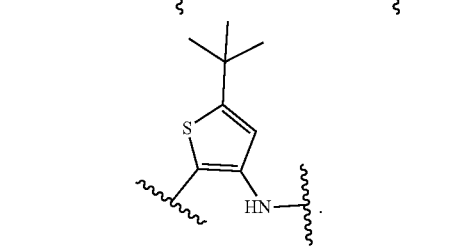

15. The compound of claim 1, wherein $R^3$ is —C(O)OR.

16. The compound of claim 1, wherein each $R^1$ is independently halogen, R, —N(R)$_2$, —OR, —SR, —C(O)OR, or —S(O)$_2$R, wherein R is hydrogen or optionally substituted —$C_{1-6}$ aliphatic.

17. The compound of claim 1, wherein $R^2$ is halogen, R, —OR, —SR, —C(O)R, —C(O)OR, —C(O)N(R)$_2$, —S(O)$_2$R, —S(O)$_2$OR, or —S(O)$_2$N(R)$_2$, wherein R is hydrogen or optionally substituted —$C_{1-6}$ aliphatic.

18. The compound of claim 1, wherein $R^3$ is —CN, —C(O)R, —C(O)OR, —C(O)N(R)$_2$, —N(R)—C(O)—R, —N(R)—C(O)—OR, —S(O)$_2$—N(R)$_2$, —S(O)$_2$—N(R)—C(O)R, —C(O)—N(R)—S(O)$_2$R, —C(=NR)—N(R)$_2$, —N(R)—C(=NR)—N(R)$_2$, or a 5-6 membered monocyclic heteroaromatic ring having 1-4 heteroatoms independently selected from nitrogen, oxygen, and sulfur, wherein R is hydrogen or optionally substituted —$C_{1-6}$ aliphatic.

19. The compound of claim 2, wherein each of $R^{11}$ and $R^{12}$ is independently halogen, R, —N(R)$_2$, —OR, —SR, —C(O)OR, or —S(O)$_2$R, wherein R is hydrogen or optionally substituted —$C_{1-6}$ aliphatic.

20. The compound of claim 10, wherein each of $R^{11}$ and $R^{12}$ is independently halogen, R, —N(R)$_2$, —OR, —SR, —C(O)OR, or —S(O)$_2$R, wherein R is hydrogen or optionally substituted —$C_{1-6}$ aliphatic.

21. The compound of claim 15, wherein R is hydrogen or optionally substituted —$C_{1-6}$ aliphatic.

* * * * *